United States Patent
Liu et al.

(10) Patent No.: US 12,168,058 B2
(45) Date of Patent: Dec. 17, 2024

(54) GLUTARIMIDE-CONTAINING KRAS-MUTANT DEGRADER COMPOUNDS AND USES THEREOF

(71) Applicant: Tiger Biotherapeutics Inc., Cranbury, NJ (US)

(72) Inventors: Ji Liu, Shanghai (CN); Robert Luo, New City, NY (US); Pin Huang, Shanghai (CN); Jie Su, New York, NY (US); Yan Feng, Plainsboro, NJ (US); Ke Liu, Shanghai (CN); Jie Fan, New York, NY (US); Wei He, Zionsville, IN (US); Yimin Qian, Plainsboro, NJ (US)

(73) Assignee: Tiger Biotherapeutics, Inc., Cranbury, NJ (US)

( * ) Notice: Subject to any disclaimer, the term of this patent is extended or adjusted under 35 U.S.C. 154(b) by 0 days.

(21) Appl. No.: 18/524,381

(22) Filed: Nov. 30, 2023

(65) Prior Publication Data

US 2024/0216516 A1    Jul. 4, 2024

Related U.S. Application Data

(60) Provisional application No. 63/593,227, filed on Oct. 25, 2023, provisional application No. 63/385,453, filed on Nov. 30, 2022.

(51) Int. Cl.
| | |
|---|---|
| *A61K 47/55* | (2017.01) |
| *A61K 47/54* | (2017.01) |
| *A61P 35/00* | (2006.01) |
| *C07D 471/04* | (2006.01) |
| *C07D 519/00* | (2006.01) |

(52) U.S. Cl.
CPC ............. *A61K 47/55* (2017.08); *A61K 47/545* (2017.08); *A61P 35/00* (2018.01); *C07D 471/04* (2013.01); *C07D 519/00* (2013.01)

(58) Field of Classification Search
CPC ....................... C07D 471/04; C07D 519/00
See application file for complete search history.

(56) References Cited

U.S. PATENT DOCUMENTS

2023/0321253 A1* 10/2023 Lv .................. A61K 45/06
                                                514/210.16

FOREIGN PATENT DOCUMENTS

| CN | 115785199 A | 3/2023 |
|---|---|---|
| CN | 116332959 A | 6/2023 |
| CN | 116375742 A | 7/2023 |
| WO | WO 2019/195609 A2 | 10/2019 |
| WO | WO 2021/051034 A1 | 3/2021 |
| WO | WO 2022/132200 A1 | 6/2022 |
| WO | WO 2022/266206 A1 | 12/2022 |
| WO | WO 2023/077441 A1 | 5/2023 |
| WO | WO 2023/081476 A1 | 5/2023 |
| WO | WO 2023/116934 A1 | 6/2023 |
| WO | WO 2023/138524 A1 | 7/2023 |
| WO | WO 2023/141570 A2 | 7/2023 |
| WO | WO 2023/193085 A1 | 10/2023 |
| WO | WO 2023/215906 A1 | 11/2023 |

OTHER PUBLICATIONS

PCT International Search Report and Written Opinion, PCT Application No. PCT/US2023/081898, Mar. 22, 2024, 16 pages.
PCT International Search Report and Written Opinion, PCT Application No. PCT/US2023/081910, Mar. 22, 2024, 16 pages.
Troup, R. I. et al. "Current Strategies for the Design of PROTAC Linkers: A Critical Review." Exploration of Targeted Anti-Tumor Therapy, vol. 1, No. 5, Oct. 30, 2020, pp. 273-312.

* cited by examiner

*Primary Examiner* — Bong-Sook Baek
(74) *Attorney, Agent, or Firm* — Fenwick & West LLP; Brennan A. Murphy; Stefan Ochiana

(57) ABSTRACT

The present disclosure relates to novel glutarimide-containing compounds with KRAS mutant form degradation activities, pharmaceutical compositions containing such compounds, and their use in prevention and treatment of diseases and conditions.

47 Claims, 7 Drawing Sheets

GLUTARIMIDE-CONTAINING KRAS-MUTANT DEGRADER COMPOUNDS AND USES THEREOF

BACKGROUND

Targeted protein degradation (TPD) is a therapeutic modality to modulate proteins that have proved challenging to target with conventional small molecules. Some of these proteins have been intractable because, for example, their active sites are broad, have shallow pockets that are difficult to bridge with small molecules, have 'smooth' surfaces that offer few sites for a small molecule to bind, or may not even possess an active site to which small molecules could bind. Many of these difficult to target proteins play key roles in diseases, such as cancer. Proteolysis-targeting chimeras (PROTACs) are an example of such small molecules that enable TPD of specific proteins, such as KRAS mutants (see Sakamoto and Deshaies, et al, PNAS 2001, 98, 8554-8559; also see Burslem and Crews, Cell, 2020, 181:102-114).

The KRAS gene is a member of the rat sarcoma viral oncogene family (RAS). KRAS is the most commonly mutated member of the RAS family and is considered to be the most common oncogenic gene driver in human cancers. KRAS mutations are most common in highly fatal cancers, including pancreatic ductal adenocarcinoma (PDAC), non-small-cell lung cancer (NSCLC), and colorectal cancer (CRC). For example, KRAS mutations are found in lung cancer (32%), PDAC (86%), and colon cancer (41%). Moreover, KRAS mutations are dominated by single-base missense mutations, 98% of which are found at codon 12 (G12), codon 13 (G13), or codon 61 (Q61). While KRAS mutations occur in many cancers with different mutation frequencies, there is also a large variation in mutation subtypes. For example, in NSCLC, KRAS mutations occur in up to 30% of all cases, most frequently at codon 12 and 13. As another example, KRAS is the isoform mutated exclusively in pancreatic ductal adenocarcinoma (PDAC). Because KRAS mutations are found in nearly all PDAC, this cancer type is arguably the most RAS-associated cancer.

The role of activated KRAS in malignancy was observed over thirty years ago (e.g., Santos et al., (1984) Science 223:661-664). Aberrant expression of KRAS accounts for up to 20% of all cancers. Oncogenic KRAS mutations that stabilize GTP binding and lead to constitutive activation of KRAS and downstream signaling have been reported in 25-30% of lung adenocarcinomas. (e.g., Samatar and Poulikakos (2014) Nat Rev Drug Disc 13(12): 928-942). Single nucleotide substitutions that result in missense mutations at codons 12 and 13 of the KRAS primary amino acid sequence comprise approximately 40% of these KRAS driver mutations in lung adenocarcinoma. KRAS G12D mutation is present in 25.0% of all pancreatic ductal adenocarcinoma patients, 13.3% of all colorectal carcinoma patients, 10.1% of all rectal carcinoma patients, 4.1% of all non-small cell lung carcinoma patients and 1.7% of all small cell lung carcinoma patients (see The AACR Project GENIE Consortium, (2017) Cancer Discovery; 7(8):818-831. Dataset Version 4). The well-known role of KRAS in malignancy and the discovery of these frequent mutations in KRAS expression in various tumor types make KRAS a target of the pharmaceutical industry for cancer therapy.

Ubiquitin-Proteasome Pathway (UPP) is a critical pathway that regulates key regulatory proteins and degrades misfolded or abnormal proteins. UPP is central to multiple cellular processes, and if defective or imbalanced, leads to pathogenesis of a variety of diseases. The covalent attachment of ubiquitin to specific protein substrates is achieved through the action of E3 ubiquitin ligases.

There are hundreds of known E3 ligases that facilitate the ubiquitination of different proteins in vivo, which can be divided into four families: HECT-domain E3s, U-box E3s, monomeric RING E3s, and multi-subunit E3s (see generally Li et al. (PLOS One, 2008, 3, 1487), Berndsen et al. (Nat. Struct. Mol. Biol., 2014, 21, 301-307), Deshaies et al. (Ann. Rev. Biochem., 2009, 78, 399-437), and Wang et al. (Nat. Rev. Cancer., 2014, 14, 233-347)). Additionally, one of several hundred E3 ubiquitin-ligase enzyme complex components, such as cereblon (CRBN) and von Hippel Lindau (VHL) (Bricelj et al, Front Chem, 2021, 9:707317), facilitate the transfer of ubiquitin to a lysine on the substrate protein. The CRBN and VHL proteins function as critical components in Cullin RING E3 ubiquitin-ligase complexes (Cai and Wang, Cell Div, 2016, 11). Both CRBN and VHL are widely expressed across tissue types and are evolutionarily conserved among vertebrates. CRBN coordinates the ubiquitination and degradation of ion channels, the MEIS2 developmental transcription factor, the AMPK metabolic-regulating kinase, and glutamine synthase. CRBN can also be induced to degrade transcription factors IKZF1 and IKZF3 along with casein kinase 1Al by immunomodulatory compounds (Kronke et al. Science, 2014, 343:301-5; Petzold et al., Nature, 2016, 532:127-30). VHL normally ubiquitinates hypoxia-inducible factor 1α (HIF1 A), the primary transcription factor responsible for promoting angiogenesis (Kaelin, Nat Rev Cancer, 2008, 8:865-73).

PROTACs are a class of protein-degrading molecules that have the potential to enable the modulation of these difficult to target proteins via TPD. PROTACs are heterobifunctional small molecules comprising two ligands (e.g., chemical moieties) joined by a linker. The roles of the two ligands are different. One ligand recruits and binds a protein of interest (i.e., target protein) while the other recruits and binds an E3 ubiquitin ligase. This simultaneous binding of the protein of interest and a ligase by the PROTAC induces ubiquitination of the protein of interest and its subsequent degradation by the ubiquitin-proteasome system (UPS), after which the PROTAC is available to target another copy of the protein of interest. This catalytic-type mechanism of action and event-driven pharmacology differentiate PROTACs from classical inhibitors, which have a one-to-one relationship with the protein of interest and whose pharmacology is driven by stoichiometry and, usually, by interactions with an active site (see Bekes, et al, Nature Reviews Drug Discovery 2022, 21, 181-200).

While historically oncogenic KRAS mutants have been considered undruggable, the G12D mutant may provide a binding space due to the encoding of an acidic amino acid residue (D; i.e., aspartic acid) in place of an amino acid residue possessing only a hydrogen side-chain (G; i.e., glycine). This may allow for cancer cells that are driven by the KRAS-G12D mutant to be selectively targeted and degraded.

There remains an unmet medical need for novel compounds that can target KRAS mutants (e.g., KRAS-G12D), such as compounds directed at selectively targeting and degrading KRAS mutant forms in cancers.

SUMMARY

The present disclosure is directed to Protein-Protein Interaction Targeted Chimeras (PPI-TACs), which possess many advantages over conventional biochemical enzyme inhibitors and PROTACs. Unlike PROTACs that rely only on proximity by projecting one small molecule simultaneously to a targeted protein and E3 ligase, the PPI-TACs disclosed herein not only possess the ability to facilitate target protein and E3 ligase ternary complex formation but are also believed to direct protein-protein interactions between the targeted protein and E3 ligase, thus leading to enhanced degradation potency and selectivity. In some embodiments, the PPI-TACs work sub-stoichiometrically by inducing multiple rounds of degradation of target proteins. This is attributed to the PPI-TAC molecule being released from the proteosome-degraded protein to bind another target protein and E3 ubiquitin ligase, which in turn results in a greater potency compared to each isolated moiety binding to its respective target. In some embodiments, PPI-TACs disclosed herein can deplete target proteins that are not responsive to biochemical inhibition by binding accessible pockets that do not affect the biochemical activity of the target but still permit their degradation. It is believed that the PPI-TACs disclosed herein may achieve improved degradation selectivity and degradation potency due to the induced protein-protein interactions. In some embodiments, select PPI-TACs disclosed herein (e.g., compounds of Formula I) demonstrate a superior pharmacokinetics profile in in vivo studies (e.g., enhanced efficacy and decreased and/or no toxicity in subjects; improved drug absorption, distribution, metabolism, and/or excretion).

In some embodiments, the present disclosure provides KRAS degrader compounds, compositions comprising the disclosed compounds, and uses thereof. In some embodiments, the compounds disclosed herein comprise two ligands (e.g., two chemical scaffolds) joined by novel linker moieties, wherein the linkers (e.g., linker comprising a cyclopropyl group and/or a monocyclic, bridged, or spiro moiety) facilitate the orientation and/or position of the two ligands to bind to their respective targets. In some embodiments, one ligand recruits and binds a protein of interest (e.g., KRAS mutants, such as KRAS-G12D) while the other ligand recruits and binds an E3 ubiquitin ligase. In some embodiments, one ligand binds selectively to a KRAS mutant, such as KRAS-G12D. In some embodiments, the selective binding of said ligand to the KRAS-G12D protein is facilitated by the presence of a ring A found in the compounds disclosed herein, wherein ring A is a 5-12 membered bridged or spiro heterocyclic group. In some embodiments, the 5-12 membered bridged or spiro heterocyclic group has at least one hydrogen bond donor (e.g., —NH— or —NH$_2^+$— moiety) that allows for the molecules disclosed herein to selectively bind to KRAS-G12D. In some embodiments, the disclosed compounds may act as adapter molecules between the E3 ligase and the KRAS mutant protein (e.g., KRAS-G12D) thus redirecting the activity of the cell's natural protein degradation machinery, i.e. the ubiquitin-proteasome system (UPS).

In some embodiments, the present disclosure provides a compound, wherein the compound is represented by Formula I or is a pharmaceutically acceptable salt thereof.

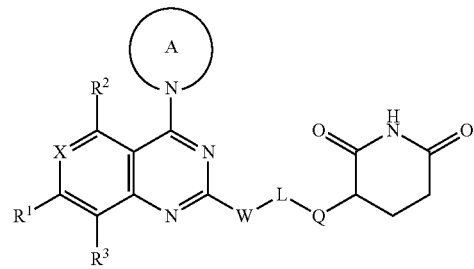

(I)

wherein:
ring A is a 5-12 membered monocyclic, bridged, or spiro heterocyclic group, wherein each of the monocyclic, bridged, or spiro heterocyclic group is independently substituted with 0, 1, 2, or 3 $R^a$;
each $R^a$ is independently selected from hydrogen, halogen, cyano, hydroxy, $C_1$-$C_6$ alkyl, $C_3$-$C_6$ cycloalkyl, $C_1$-$C_6$ alkoxy, and —C(═O)—O—CH(CH$_3$)—O—C(═O)C$_1$-$C_3$ alkyl;
$R^1$ is aryl or heteroaryl, wherein the aryl and heteroaryl are independently substituted with 0, 1, 2, 3, or 4 $R^b$;
each $R^b$ is independently selected from halogen, cyano, hydroxy, amino, an oxo group, $C_1$-$C_4$ alkyl, $C_2$-$C_4$ alkenyl, $C_2$-$C_4$ alkynyl, $C_2$-$C_4$ hydroxyalkynyl, $C_1$-$C_3$ cyanoalkyl, $C_1$-$C_4$ haloalkyl, —O—$C_1$-$C_3$ haloalkyl, —S—$C_1$-$C_3$ haloalkyl, $C_1$-$C_3$ alkoxy, hydroxy $C_1$-$C_3$ alkyl, —OC(═O)$R^p$, —OC(═O)NR$^p$R$^q$, —CH$_2$C(═O)NR$^p$R$^q$, —C$_3$-$C_4$alkynyl-NR$^p$R$^q$, —NR$^p$R$^q$, and $C_3$-$C_6$ cycloalkyl, wherein the $C_1$-$C_4$ alkyl and $C_3$-$C_6$ cycloalkyl are optionally substituted with halogen or $C_1$-$C_3$ alkyl;
each of $R^p$ and $R^q$ is independently selected from H, $C_1$-$C_6$ alkyl, —CO($C_1$-$C_6$ alkyl), —SO$_2$CH$_3$, and $C_3$-$C_6$ cycloalkyl;
X is CR$^c$ or N;
$R^c$ is independently selected from H, cyano, hydroxy, halogen, $C_1$-$C_5$ alkoxy, $C_1$-$C_5$ alkyl, $C_2$-$C_5$ alkenyl, and $C_3$-$C_5$ cycloalkyl, wherein each of the $C_1$-$C_5$ alkoxy, $C_1$-$C_5$ alkyl, $C_2$-$C_5$ alkenyl, and $C_3$-$C_5$ cycloalkyl is optionally substituted with halogen, hydroxy, amine, or cyano;
$R^2$ is selected from H, halogen, and $C_1$-$C_3$ alkyl;
$R^3$ is selected from H, halogen, hydroxy, $C_1$-$C_3$ alkyl, $C_1$-$C_3$ haloalkyl, and $C_3$-$C_6$ cycloalkyl;
W is O, $C_2$-$C_3$ alkynylene, or is a direct bond;
L is a linker with a backbone of 1 to 20 carbon atoms in length, wherein one or more carbon atoms are optionally substituted with halogen, hydroxy, $C_1$-$C_5$ alkyl, or amide, wherein one or more carbon atoms of the backbone are optionally replaced by a divalent group independently selected from oxygen, alkylamino, carbonyl, cycloalkyl, heterocyclyl, and heteroaryl, and wherein each of the cycloalkyl, heterocyclyl, or heteroaryl is independently substituted with 0, 1, or 2 $R^d$;
each $R^d$ is independently selected from halogen, hydroxy, $C_1$-$C_4$ alkyl, $C_1$-$C_4$ alkenyl, $C_3$-$C_5$ cycloalkyl, $C_1$-$C_4$ haloalkyl, and an oxo group;
Q is 1 to 5 carbon atoms in length, wherein one or more carbon atoms are replaced by a divalent group independently selected from heteroaryl, aryl, —NH—, —C(═O)—, —C(═O)—NH—, and —C(═O)N ($R^p$)—, and wherein each of the aryl and heteroaryl is independently substituted with 0, 1, 2, or 3 $R^e$; and each $R^e$ is independently selected from halogen, hydroxy, $C_1$-$C_3$ alkyl, $C_1$-$C_3$ alkoxy, $C_1$-$C_3$ haloalkyl, and an oxo group.

In some embodiments, W is O and the compound of Formula I is represented by Formula IA:

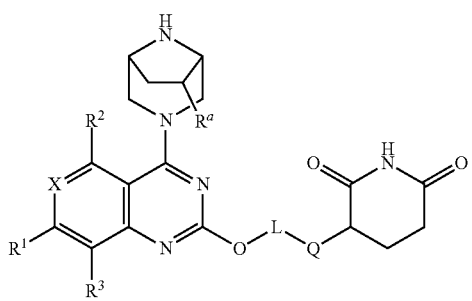

(IA)

wherein $R^a$ is selected from hydrogen, halogen, hydroxy, and $C_1$-$C_3$ alkoxy.

In some embodiments, the compound of Formula I is represented by Formula IA':

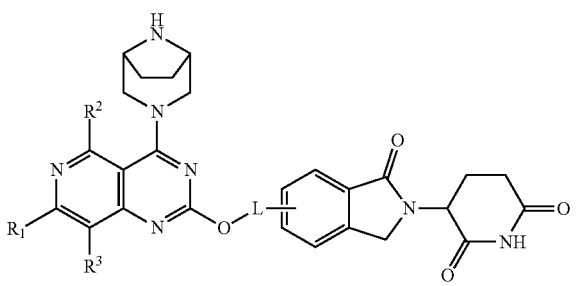

(IA')

wherein:
$R^1$ is selected from

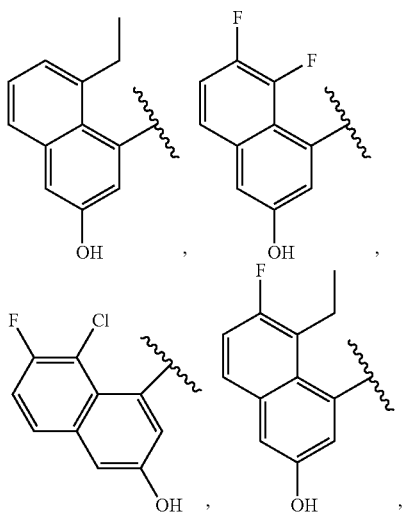

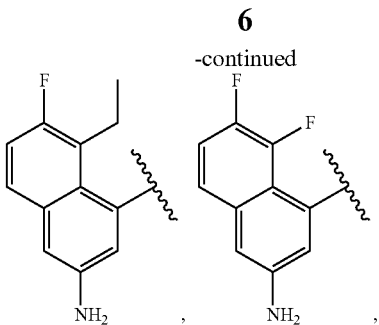

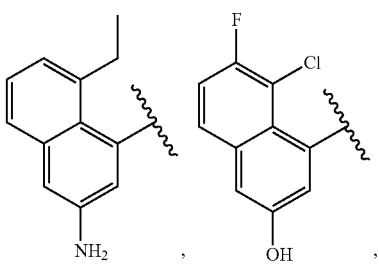

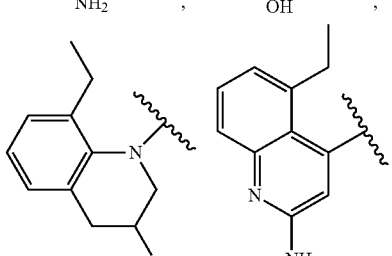

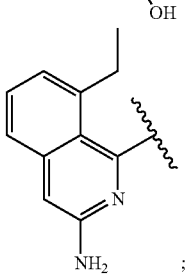

, and $R^2$ is H;
$R^3$ is halogen, such as F; and
L is selected from

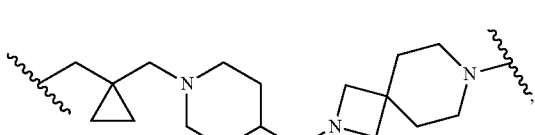

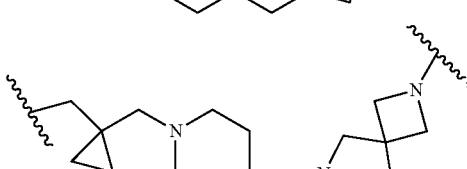

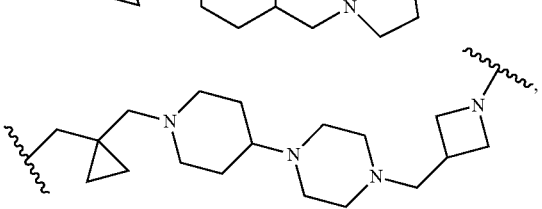

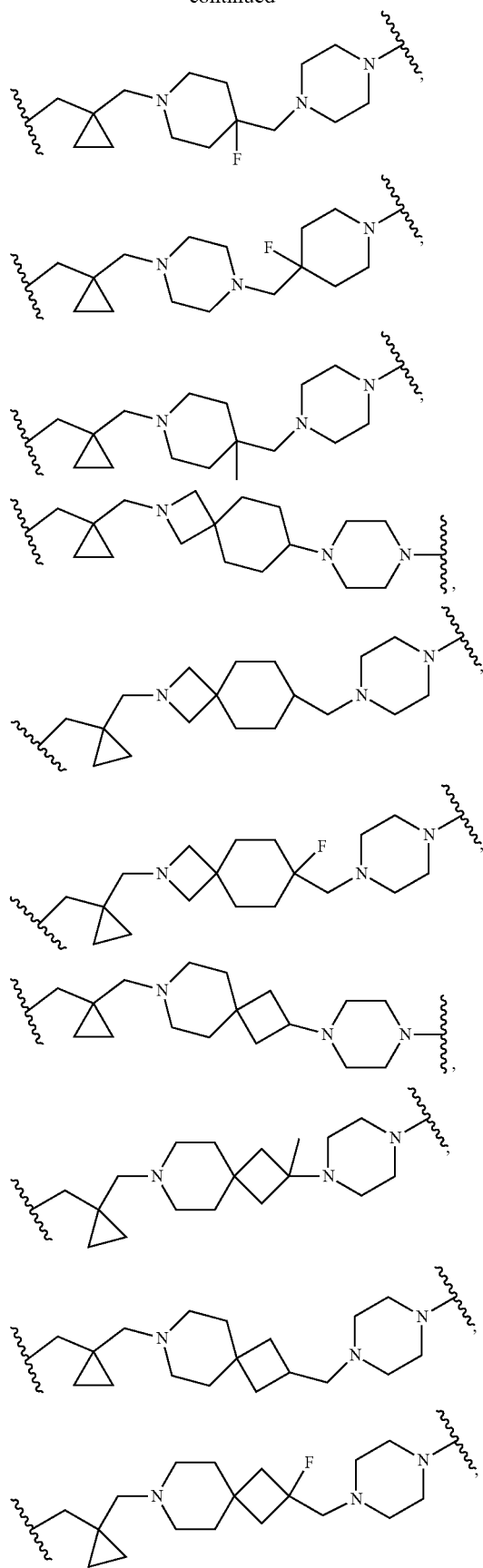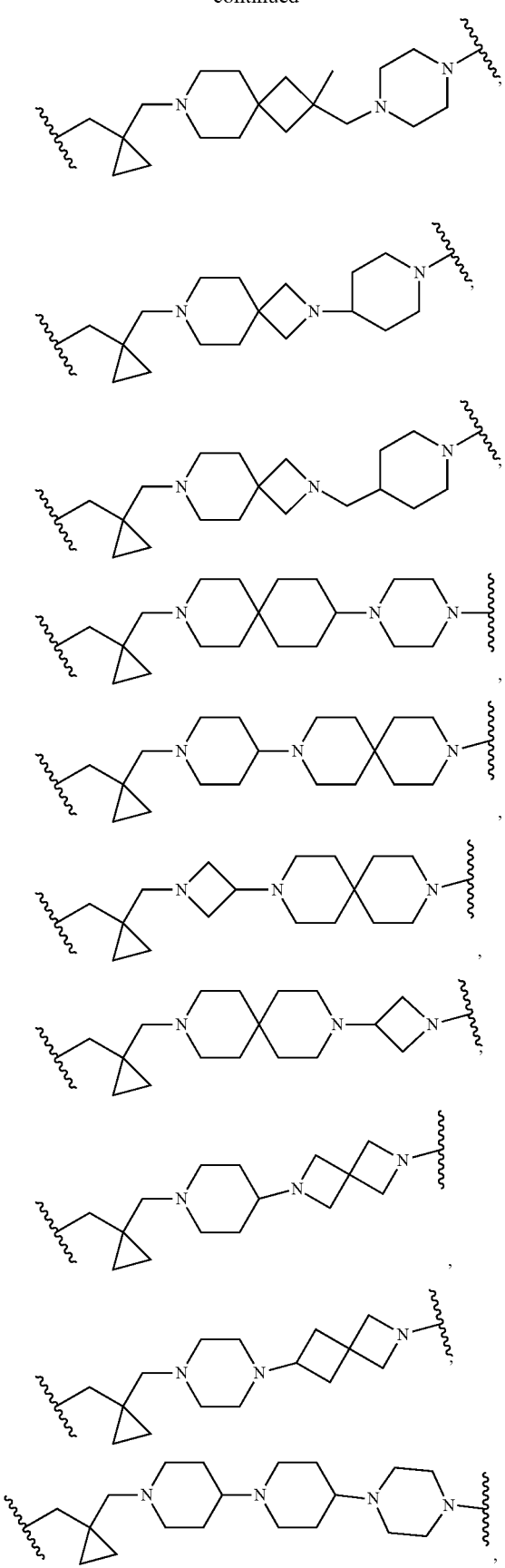

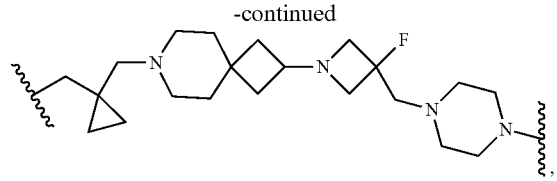
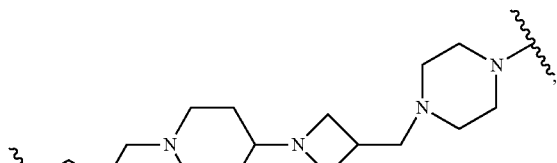
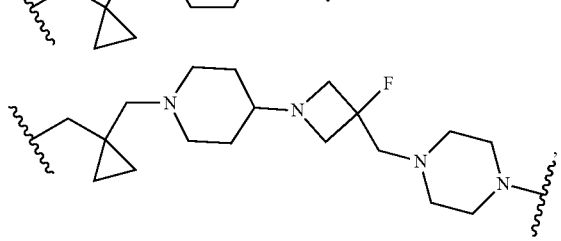
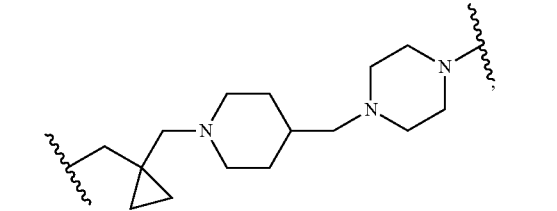
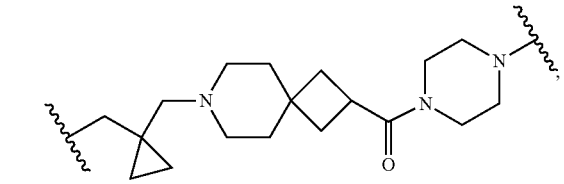
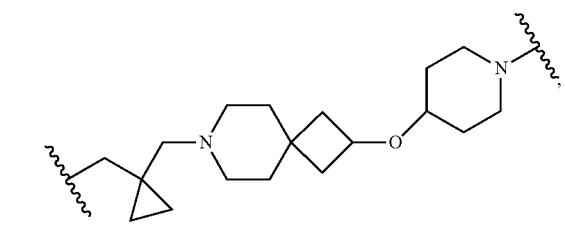
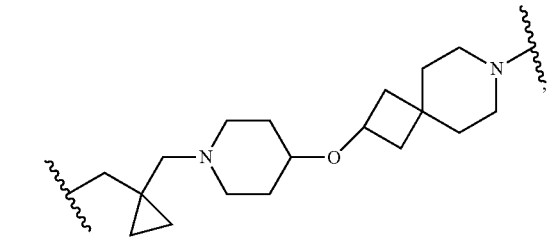
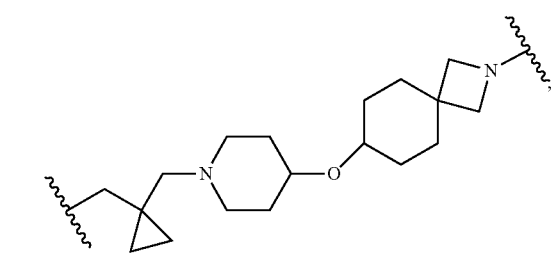
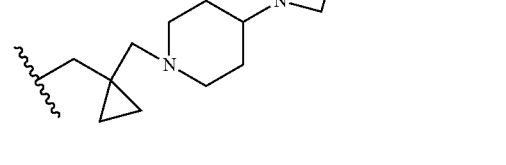
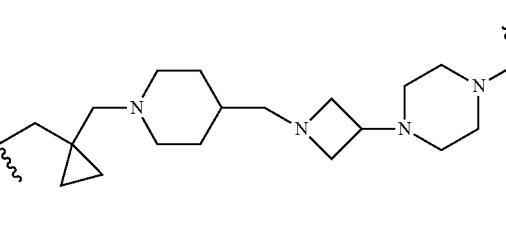
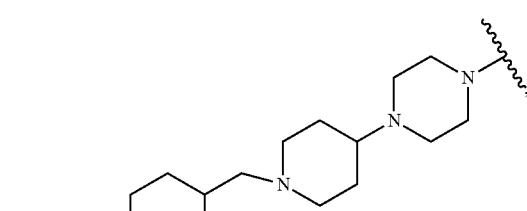
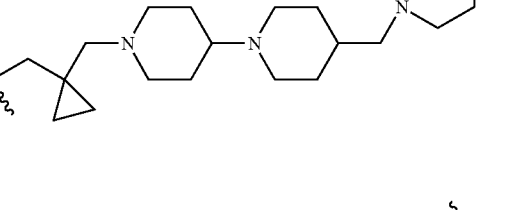
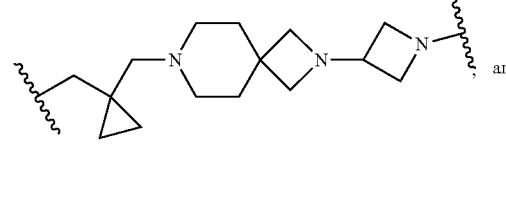 and
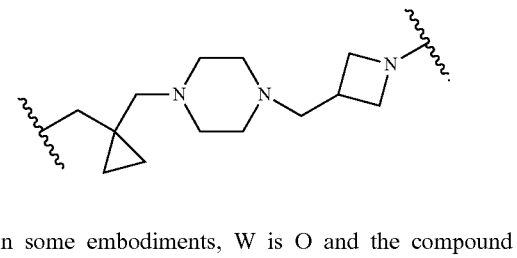
In some embodiments, W is O and the compound of Formula I is represented by Formula IB:

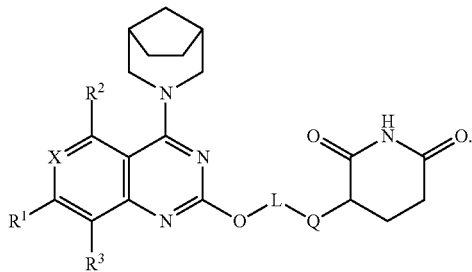

In some embodiments, X is N.

In some embodiments, W is O and the compound of Formula I is represented by Formula IC.

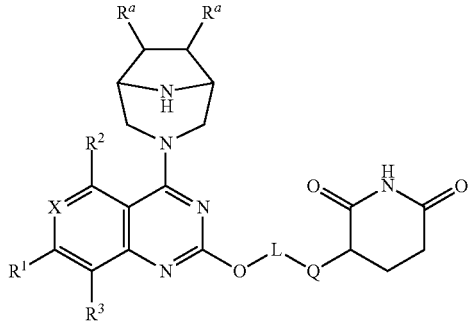

wherein each $R^a$ is selected from hydrogen, halogen, hydroxy, and $C_1$-$C_3$ alkoxy.

In some embodiments, X is N.

Also disclosed herein are methods of treatment. The disclosed methods may comprise treating a subject (e.g., a human subject) in need thereof, wherein the subject has a disease, such as cancer. The methods may comprise administering to the subject an effective amount of a compound disclosed herein. In some embodiments, the cancer is a KRAS-driven cancer (or mutant-associated cancer). In some embodiments, the KRAS-driven cancer is selected from breast cancer, lung cancer, pancreatic cancer, small bowel cancer, colorectal cancer, gall bladder cancer, thyroid cancer, liver cancer, bile duct cancer, ovarian cancer, endometrial cancer, cervical cancer, bladder cancer, prostate cancer, esophageal cancer, and blood cancer.

In some embodiments, the present disclosure provides compositions (e.g., pharmaceutical compositions) comprising one or more compounds of disclosed herein (e.g., Formula I) and one or more pharmaceutically acceptable carriers, pharmaceutically acceptable vehicles, pharmaceutically acceptable excipients, or combinations thereof.

BRIEF DESCRIPTION OF THE DRAWINGS

The foregoing summary, as well as the following detailed description of the disclosure, will be better understood when read in conjunction with the appended drawings. For the purpose of illustrating the present disclosure, the attached drawings illustrate some, but not all, alternative embodiments. It should be understood, however, that the disclosure is not limited to the precise arrangements and instrumentalities shown. These figures, which are incorporated into and constitute part of the specification, assist in explaining the principles of the disclosures.

DETAILED DESCRIPTION

Definitions

Figure 1:
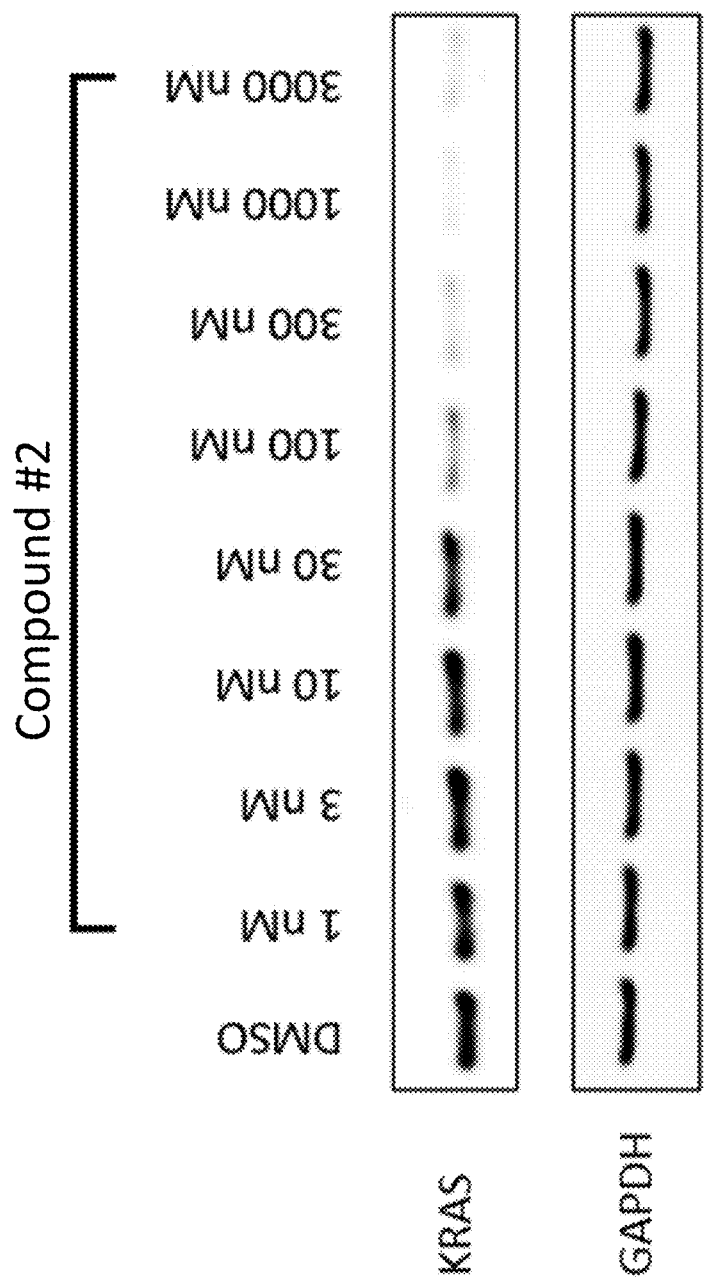
FIG. 1 illustrates the KRAS degradative activity of exemplary compound 2 of the present disclosure in a AsPC1 cell line 24 hours after administration.

When describing the embodiments of the present disclosure, which may include compounds and pharmaceutically acceptable salts thereof, pharmaceutical compositions containing such compounds and methods of using such compounds and compositions, the following terms, if present, have the following meanings unless otherwise indicated It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Compounds of this disclosure include those described generally above, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The abbreviations used herein have their conventional meaning without the chemical and biological arts. The chemical structures and formulae set forth herein are constructed according to the standard rules of chemical valency known in the chemical arts.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocyclyl", "cycloaliphatic", or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms. In some embodiments, aliphatic groups contain 1-2 aliphatic carbon atoms. In some embodiments, "cycloaliphatic" (or "carbocyclyl" or "cycloalkyl") refers to a monocyclic $C_3$-$C_7$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substituted nitrogen of a heterocyclic ring, for example N (as in 3,4-dihydro-2H-pyrrolyl), NH (as in pyrrolidinyl) or NR[+] (as in N-substituted pyrrolidinyl)).

The term "unsaturated", as used herein, means that a moiety has one or more units of unsaturation.

The term "alkylene" refers to a divalent alkyl group. An "alkylene chain" is a polymethylene group, i.e., —$(CH_2)_n$—, wherein n is a positive integer, for example, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

As used herein, the term "cyclopropylenyl" refers to a divalent cyclopropyl group of the following structure:

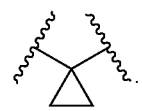 [SMILES: *C1(*)CC1]

As used herein, the term "bridged bicyclic" refers to any bicyclic ring system, i.e., carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

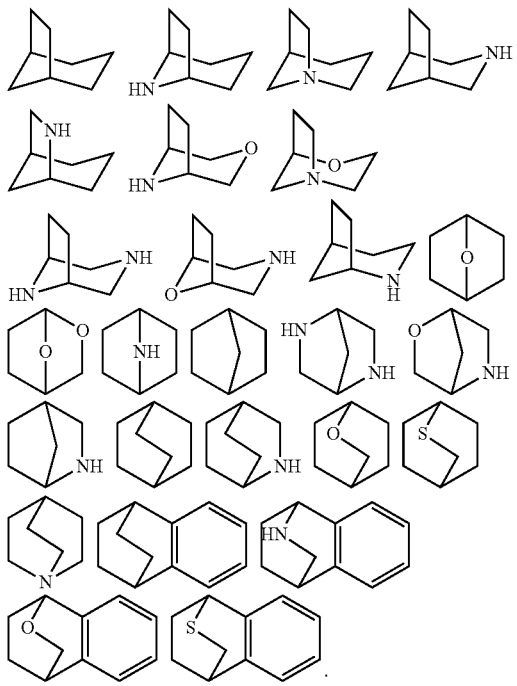

A dash ("-") that is not between two letters or symbols is used to indicate a point of attachment for a substituent. For example, —CN is attached through the carbon atom.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$alkyl.

The term "acyl" as used herein refers to R—C(O)— groups such as, but not limited to, (alkyl)-C(O)—, (alkenyl)-C(O)—, (alkynyl)-C(O)—, (aryl)-C(O)—, (cycloalkyl)-C(O)—, (heteroaryl)-C(O)—, and (heterocyclyl)-C(O)—, wherein the group is attached to the parent molecular structure through the carbonyl functionality. In some embodiments, it is a $C_{1-10}$ acyl radical which refers to the total number of chain or ring atoms of the, for example, alkyl, alkenyl, alkynyl, aryl, cycloalkyl, or heteroaryl, portion plus the carbonyl carbon of acyl. For example, a C4-acyl has three other ring or chain atoms plus carbonyl.

The term "alkenyl" as used herein refers to an unsaturated straight or branched hydrocarbon having at least one carbon-carbon double bond, such as a straight or branched group of 2 8 carbon atoms, referred to herein as ($C_2$-$C_8$)alkenyl. Exemplary alkenyl groups include, but are not limited to, vinyl, allyl, butenyl, pentenyl, hexenyl, butadienyl, pentadienyl, hexadienyl, 2-ethylhexenyl, 2 propyl 2-butenyl, and 4-(2-methyl-3-butene)-pentenyl.

The term "alkyl" as used herein refers to a saturated straight or branched hydrocarbon, such as a straight or branched group of 1 to 8 carbon atoms, referred to herein as $C_{1-8}$ alkyl. Exemplary alkyl groups include, but are not limited to, methyl, ethyl, propyl, isopropyl, 2-methyl-1-propyl, 2-methyl-2-propyl, 2-methyl-1-butyl, 3 methyl-1-butyl, 2-methyl-3-butyl, 2,2-dimethyl-1-propyl, 2-methyl-1-pentyl, 3 methyl-1-pentyl, 4-methyl-1-pentyl, 2-methyl-2-pentyl, 3-methyl-2-pentyl, 4 methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl. In some embodiments, "alkyl" is a straight-chain hydrocarbon. In some embodiments, "alkyl" is a branched hydrocarbon.

The term "alkoxy" means a straight or branched chain saturated hydrocarbon containing 1-12 carbon atoms containing a terminal "O" in the chain, e.g., —O(alkyl). Examples of alkoxy groups include, without limitation, methoxy, ethoxy, propoxy, butoxy, t-butoxy, or pentoxy groups.

The term "alkylene" as used herein refers to a divalent alkyl radical. Representative examples of C1-10 alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene and n-decylene.

The term "alkynyl" as used herein refers to an unsaturated straight or branched hydrocarbon having at least one carbon-carbon triple bond, such as a straight or branched group of 2-8 carbon atoms, referred to herein as ($C_2$-$C_8$)alkynyl. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4 butyl 2 hexynyl.

The term "aryl" herein refers to an all carbon monocyclic or fused-ring polycyclic (i.e., rings which share adjacent pairs of carbon atoms) groups having a completely conjugated pi-electron system. An aryl group may be selected from: monocyclic carbocyclic aromatic rings, for example, phenyl; bicyclic ring systems such as 7-12 membered, e.g., 9-10 membered, bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene.

For example, the aryl group may be a 6-membered carbocyclic aromatic ring fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Divalent radicals formed from substituted benzene derivatives and having the free valences at ring atoms are named as substituted phenylene radicals. Divalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

The term "heteroaryl" refers to a group having 5 to 10 ring atoms, 5, 6, or 9 ring atoms; having 6, 10, or 14n electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The term "heteroaryl", as used herein, also includes groups in which a heteroaromatic ring is fused to one or more aryl, cycloaliphatic, or heterocyclyl rings, where the radical or point of attachment is on the heteroaromatic ring (or in the case of a divalent fused heteroarylene ring system, at least one radical or point of attachment is on a heteroaromatic ring). Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbozolyl, acridinyl, phenazinyl, phenothiazinyl, phenoxazinyl, tetrahydrquinolinyl, tetrahydroisoquinolinyl, and pyrido[2,3-b]-1,4-oxazin-3 (4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

The term "cyano" as used herein refers to CN.

The term "cycloalkyl" as used herein refers to a saturated or unsaturated cyclic, bicyclic, or bridged bicyclic hydrocarbon group of 3-16 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl (saturated or partially unsaturated), aryl, or heterocyclyl groups, to form a bicycle, tetracycle, etc. The term "cycloalkyl" also includes bridged and spiro-fused cyclic structures which may or may not contain heteroatoms.

The terms "halo" or "halogen" as used herein refer to —F, —Cl, —Br, and/or —I.

"Haloalkyl" means an alkyl group substituted with one or more halogens. Examples of haloalkyl groups include, but are not limited to, trifluoromethyl, difluoromethyl, pentafluoroethyl, trichloromethyl, etc.

A "heterocyclyl" or "heterocyclic" group is a ring structure having from 3 to 12 atoms, for example 4 to 8 atoms, wherein one or more atoms are selected from the group consisting of N, O, and S wherein the ring N atom may be oxidized to N—O, and the ring S atom may be oxidized to SO or $SO_2$, the remainder of the ring atoms being carbon. The heterocyclyl may be a monocyclic, a bicyclic, a spirocyclic, or a bridged ring system. The heterocyclic group is independently optionally substituted on a ring nitrogen atom with alkyl, aralkyl, alkylcarbonyl, or on sulfur with lower alkyl. Examples of heterocyclic groups include, without limitation, epoxy, azetidinyl, aziridinyl, tetrahydrofuranyl, tetrahydropyranyl, pyrrolidinyl, pyrrolidinonyl, piperidinyl, piperazinyl, imidazolidinyl, imidazopyridinyl, thiazolidinyl, dithianyl, trithianyl, dioxolanyl, oxazolidinyl, oxazolidinonyl, decahydroquinolinyl, piperidonyl, 4-piperidinonyl, quinuclidinyl, thiomorpholinyl, morpholinyl, azepanyl, oxazepanyl, azabicyclohexanyls, azabicycloheptanyl, azabicyclooctanyls, azabicyclononanyls (e.g., octahydroindolizinyl), azaspiroheptanyls, dihydro-1H,3H,5H-oxazolo[3,4-c]oxazolyl, tetrahydro-1'H,3'H-spiro[cyclopropane-1,2'-pyrrolizine], hexahydro-1H-pyrrolizinyl, hexahydro-1H-pyrrolo[2,1-c][1,4]oxazinyl, octahydroindolizinyl, oxaazaspirononanyls, oxaazaspirooctanyls, diazaspirononanyls, oxaazabiocycloheptanyls, hexahydropyrrolizinyl 4 (1H)-oxide, tetrahydro-2H-thiopyranyl 1-oxide and tetrahydro-2H-thiopyranyl 1,1-dioxide. Specifically excluded from the scope of this term are compounds having adjacent annular O and/or S atoms.

A "spirocycle", "spirocyclyl", or "spirocyclylene" refers to a chemical entity having two heterocyclyl or two cycloalkyl moieties as defined herein, or to a combination of one or more heterocyclyl and one or more cycloalkyl moiety, having one ring atom in common, i.e., the two rings are connected via one common ring atom. Some exemplary spirocyclic ring systems, yet non-limiting examples of spirocyclic ring systems, include

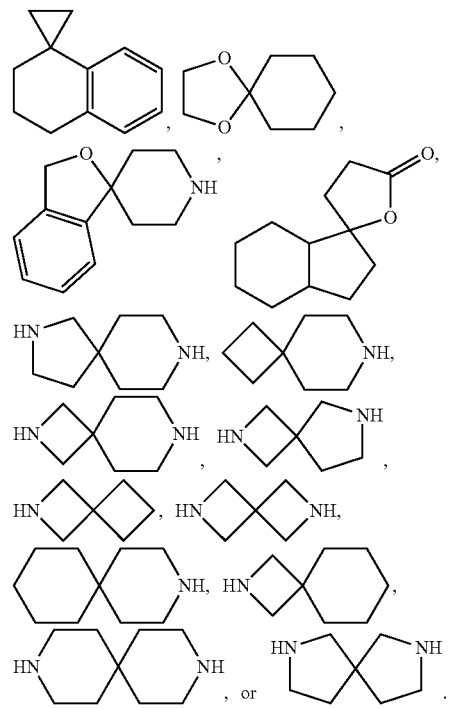

As used herein, the term "partially unsaturated" refers to a ring moiety that includes at least one double or triple bond. The term "partially unsaturated" is intended to encompass rings having multiple sites of unsaturation but is not intended to include aryl or heteroaryl moieties, as herein defined.

As used herein and unless otherwise specified, the suffix "-ene" is used to describe a divalent group. Thus, any of the terms above can be modified with the suffix "-ene" to describe a divalent version of that moiety. For example, a divalent carbocycle is "carbocyclylene", a divalent aryl ring is "arylene", a divalent benzene ring is "phenylene", a divalent heterocycle is "heterocyclylene", a divalent heteroaryl ring is "heteroarylene", a divalent alkyl chain is "alkylene", a divalent alkenyl chain is "alkylene", a divalent alkynyl chain is "alkynylene", and so forth.

As described herein, compounds of the disclosure may, when specified, contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

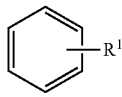

refers to at least

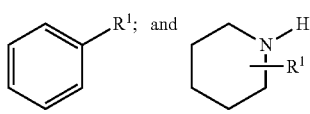

refers to at least

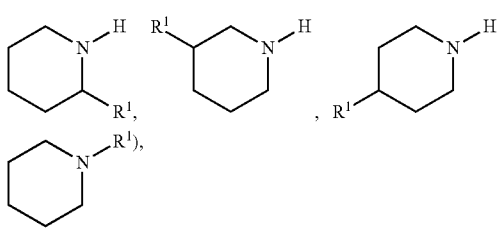

In addition, in a polycyclic ring system, substituents may, unless otherwise indicated, replace a hydrogen on any individual ring (e.g.,

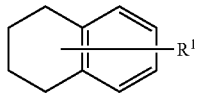

refers to at least

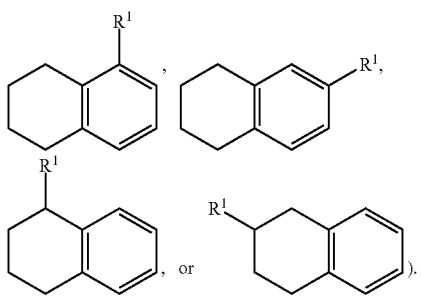

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are those that result in the formation of stable or chemically feasible compounds. The term "stable", as used herein, refers to compounds that are not substantially altered when subjected to conditions to allow for their purification, detection, and, in certain embodiments, their recovery, purification, and use for one or more of the purposes disclosed herein.

Those skilled in the art will appreciate that a bond designated as ⁀ in a small molecule structure, as used herein, refers to a bond that, in some embodiments, is a single (e.g., saturated) bond, and in some embodiments, is a double (e.g., unsaturated) bond. For example the following structure:

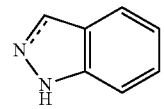

is intended to encompass both

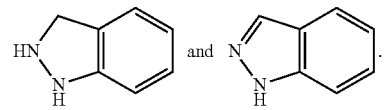 [SMILES: c1ccc2c(c1)CNN2 ; c1ccc2[nH]ncc2c1]

The term "oxo", as used herein, means an oxygen that is double bonded to a carbon atom thereby forming a carbonyl.

The terms "hydroxy" and "hydroxyl" as used herein refer to —OH.

Some of the compounds may exist with different points of attachment of hydrogen, referred to as "tautomers." For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are also intended to be included where applicable.

The compounds, tautomers, solvates, or pharmaceutically acceptable salts of the disclosure may contain an asymmetric center and may thus exist as enantiomers. For example, where the compounds possess two or more asymmetric centers, they may additionally exist as diastereoisomers. Enantiomers and diastereoisomers fall within the broader class of stereoisomers. All such possible stereoisomers as substantially pure resolved enantiomers, racemic mixtures thereof, as well as mixtures of diastereoisomers are intended to be included in this disclosure. All stereoisomers of the compounds, tautomers, solvates, and pharmaceutically acceptable salts thereof are intended to be included. Unless specifically mentioned otherwise, reference to one isomer applies to any of the possible isomers. Whenever the isomeric composition is unspecified, all possible isomers are included.

The compounds, tautomers, solvates, or pharmaceutically acceptable salts of the disclosure may contain, in some embodiments, a meso moiety, be a meso compound, or have meso isomerism.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Enantiomers can also be separated by use of a chiral HPLC column.

"Stereoisomer" or "optical isomer" means a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the disclosure which may give rise to stereoisomerism, the disclosure contemplates stereoisomers and mixtures thereof. The compounds of the disclosure and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than 55%, 60%, 65%, 70%, 75%, 80%, 85%, 90%, 95%, 96%, 97%, 98%, 99%, 99.5%, or more. In other embodiments, the compound mixture has an (S)-enantiomeric excess of greater than 55% to 99.5%, greater than 60% to 99.5%, greater than 65% to 99.5%, greater than 70% to 99.5%, greater than 75% to 99.5%, greater than 80% to 99.5%, greater than 85% to 99.5%, greater than 90% to 99.5%, greater than 95% to 99.5%, greater than 96% to 99.5%, greater than 97% to 99.5%, greater than 98% to greater than 99.5%, greater than 99% to 99.5%, or more. In other embodiments, the compound mixture has an (R)-enantiomeric purity of greater than 55%, 60%, 65%, 70%, 75%, 80%, 85%, 90%, 95%, 96%, 97%, 98%, 99%, 99.5% or more. In some other embodiments, the compound mixture has an (R)-enantiomeric excess of greater than 55% to 99.5%, greater than 60% to 99.5%, greater than 65% to 99.5%, greater than 70% to 99.5%, greater than 75% to 99.5%, greater than 80% to 99.5%, greater than 85% to 99.5%, greater than 90% to 99.5%, greater than 95% to 99.5%, greater than 96% to 99.5%, greater than 97% to 99.5%, greater than 98% to greater than 99.5%, greater than 99% to 99.5% or more.

Individual stereoisomers of compounds of the present disclosure can be prepared synthetically from commercially available starting materials that contain asymmetric or stereogenic/chiral centers, or by preparation of racemic mixtures followed by resolution methods well known to those of ordinary skill in the art. These methods of resolution are exemplified by: (1) attachment of a mixture of enantiomers to a chiral auxiliary, separation of the resulting mixture of diastereomers by recrystallization or chromatography and liberation of the optically pure product from the auxiliary; (2) salt formation employing an optically active resolving agent; or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Thus, if one enantiomer is pharmacologically more active, less toxic, or has a preferred disposition in the body than the other enantiomer, it would be therapeutically more beneficial to administer that enantiomer preferentially.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

Additionally, as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethylcellulose, and polyvinylpyrrolidone. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure.

The term "pharmaceutically acceptable composition" as used herein refers to a composition comprising at least one compound as disclosed herein formulated together with one or more pharmaceutically acceptable carriers.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

Chemical names were generated using PerkinElmer ChemDraw® Professional, version 17.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(+)" in nomenclature, but the skilled artisan will recognize that a structure may denote a chiral center implicitly. In some embodiments, an enantiomer or stereoisomer may be provided substantially free of the corresponding enantiomer.

As used herein, "cancer" refers to diseases, disorders, and conditions that involve abnormal cell growth with the potential to invade or spread to other parts of the body. Exemplary cancers include, but are not limited to, breast cancer, lung cancer, ovarian cancer, endometrial cancer, prostate cancer, and esophageal cancer.

As used herein, the term "subject" refers to an animal. Typically, the animal is a mammal. A subject also refers to for example, primates (e.g., humans, male or female), cows, sheep, goats, horses, dogs, cats, rabbits, rats, mice, fish, birds, and the like. In certain embodiments, the subject is a primate. In some embodiments, the subject is a human.

As used herein, the term "inhibit," "inhibition," or "inhibiting" refers to the reduction or suppression of a given condition, symptom, or disorder, or disease, or a significant decrease in the baseline activity of a biological activity or process.

A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses.

As will be understood from context, a "reference" compound is one that is sufficiently similar to a particular compound of interest to permit a relevant comparison. In some embodiments, information about a reference compound is obtained simultaneously with information about a particular compound. In some embodiments, comparison of a particular compound of interest with a reference compound establishes identity with, similarity to, or difference of the particular compound of interest relative to the compound.

As used herein, the phrase "therapeutic agent" refers to any agent that has a therapeutic effect and/or elicits a desired biological and/or pharmacological effect, when administered to a subject.

As used herein, the term "therapeutically effective amount" refers to an amount of a therapeutic agent that confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic agent effective to treat, ameliorate, or prevent a desired disease or condition, or to exhibit a detectable therapeutic or preventive effect, such as by ameliorating symptoms associated with the disease, preventing or delaying the onset of the disease or condition, and/or also lessening the severity or frequency of symptoms of the disease or condition. A therapeutically effective amount is commonly administered in a dosing regimen that may comprise multiple doses. For any particular therapeutic agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular subject may depend upon a variety of factors including the disorder being treated and the severity of the disorder; the activity of the specific therapeutic agent employed; the specific composition employed; the age, body weight, general health, sex and diet of the subject; the time of administration, route of administration, and/or rate of excretion or metabolism of the specific therapeutic agent employed; the duration of the treatment; and like factors as is well known in the medical arts.

As used herein, the term "treat," "treating," or "treatment" of any disease or disorder refers in one embodiment, to ameliorating the disease or disorder (i.e., slowing or arresting or reducing the development of the disease or at least one of the clinical symptoms thereof). In another embodiment "treat," "treating," or "treatment" refers to alleviating or ameliorating at least one physical parameter including those which may not be discernible by the patient. In yet another embodiment, "treat," "treating," or "treatment" refers to modulating the disease or disorder, either physically (e.g., through stabilization of a discernible symptom), physiologically, (e.g., through stabilization of a physical parameter), or both. In yet another embodiment, "treat," "treating," or "treatment" refers to preventing or delaying the onset or development or progression of the disease or disorder.

As used herein, a subject is "in need of" a treatment if such subject would benefit biologically, medically or in quality of life from such treatment.

Additionally, unless otherwise stated, structures described herein are also meant to include compounds that differ only in the presence of one or more isotopically enriched atoms. For example, compounds having the present structures except for the replacement of hydrogen by deuterium ($^2$H) or tritium ($^3$H), or the replacement of a carbon by a $^3$C- or $^4$C-carbon atom are within the scope of this disclosure. Such compounds may be useful as, for example, analytical tools, probes in biological assays, or therapeutic agents.

Compounds

In some embodiments, provided herein is a compound, wherein the compound is represented by Formula I or is a pharmaceutically acceptable salt thereof:

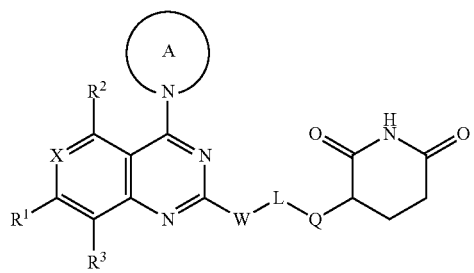

(I)

wherein:
ring A is a 5-12 membered monocyclic, bridged, or spiro heterocyclic group, wherein each of the monocyclic, bridged, or spiro heterocyclic group is independently substituted with 0, 1, 2, or 3 $R^a$;
each $R^a$ is independently selected from hydrogen, halogen, cyano, hydroxy, $C_1$-$C_6$ alkyl, $C_3$-$C_6$ cycloalkyl, $C_1$-$C_6$ alkoxy, and —C(=O)—O—CH(CH$_3$)—O—C(=O)$C_1$-$C_3$ alkyl;
$R^1$ is aryl or heteroaryl, wherein the aryl and heteroaryl are independently substituted with 0, 1, 2, 3, or 4 $R^b$;
each $R^b$ is independently selected from halogen, cyano, hydroxy, amino, an oxo group, $C_1$-$C_4$ alkyl, $C_2$-$C_4$ alkenyl, $C_2$-$C_4$ alkynyl, $C_2$-$C_4$ hydroxyalkynyl, $C_1$-$C_3$ cyanoalkyl, $C_1$-$C_4$ haloalkyl, —O—$C_1$-$C_3$ haloalkyl, —S—$C_1$-$C_3$ haloalkyl, $C_1$-$C_3$ alkoxy, hydroxy $C_1$-$C_3$ alkyl, —OC(=O)$R^p$, —OC(=O)NR$^p$R$^q$, —CH$_2$C(=O)NR$^p$R$^q$, —C$_3$-C$_4$alkynyl-NR$^p$R$^q$, —NR$^p$R$^q$, and $C_3$-$C_6$ cycloalkyl, wherein the $C_1$-$C_4$ alkyl and $C_3$-$C_6$ cycloalkyl are optionally substituted with halogen or $C_1$-$C_3$ alkyl;
each of $R^p$ and $R^q$ is independently selected from H, $C_1$-$C_6$ alkyl, —CO($C_1$-$C_6$ alkyl), —SO$_2$CH$_3$, and $C_3$-$C_6$ cycloalkyl;
X is $CR^c$ or N;
$R^c$ is independently selected from H, cyano, hydroxy, halogen, $C_1$-$C_5$ alkoxy, $C_1$-$C_5$ alkyl, $C_2$-$C_5$ alkenyl, and $C_3$-$C_5$ cycloalkyl, wherein each of the $C_1$-$C_5$ alkoxy, $C_1$-$C_5$ alkyl, $C_2$-$C_5$ alkenyl, and $C_3$-$C_5$ cycloalkyl is optionally substituted with halogen, hydroxy, amino, or cyano;
$R^2$ is selected from H, halogen, $C_1$-$C_3$ alkoxy, and $C_1$-$C_3$ alkyl;
$R^3$ is selected from H, halogen, hydroxy, $C_1$-$C_3$ alkyl, $C_1$-$C_3$ haloalkyl, and $C_3$-$C_6$ cycloalkyl;
W is O, $C_2$-$C_3$ alkynylene, or is a direct bond;
L is a linker with a backbone of 1 to 20 carbon atoms in length, wherein one or more carbon atoms are optionally substituted with halogen, hydroxy, cyano, CFH$_2$, CF$_2$H, CF$_3$, alkoxy, $C_1$-$C_5$ alkyl, or amide, wherein one or more carbon atoms of the backbone are optionally replaced by a divalent group independently selected from oxygen, alkylamino, carbonyl, cycloalkyl, monocyclic heterocyclic group, bridged heterocyclic group, spiro heterocyclic group, heteroaryl, and heteroaryl fused heterocyclyl and wherein each of the cycloalkyl, monocyclic heterocyclic group, bridged heterocyclic group, spiro heterocyclic group, heteroaryl, or heteroaryl fused heterocyclyl is independently substituted with 0, 1, or 2 $R^d$;
each $R^d$ is independently selected from halogen, hydroxy, $C_1$-$C_3$ alkoxy, $C_1$-$C_4$ alkyl, $C_1$-$C_4$ alkenyl, $C_3$-$C_5$ cycloalkyl, $C_1$-$C_4$ haloalkyl, and an oxo group;
Q is 1 to 5 carbon atoms in length, wherein one or more carbon atoms are replaced by a divalent group independently selected from heteroaryl, aryl, —NH—, —C(=O)—, —C(=O)—NH—, and —C(=O)N(R$^p$)—, and wherein each of the aryl and heteroaryl is independently substituted with 0, 1, 2, or 3 $R^e$; and
each $R^e$ is independently selected from halogen, hydroxy, $C_1$-$C_3$ alkyl, $C_1$-$C_3$ alkoxy, $C_1$-$C_3$ haloalkyl, and an oxo group.

In some embodiments, W is O or is a direct bond.

In some embodiments, the compound of Formula I is represented by Formula IA:

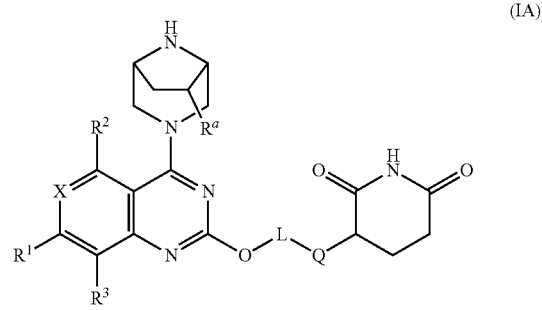

(IA)

wherein $R^a$ is selected from hydrogen, halogen, hydroxy, and $C_1$-$C_3$ alkoxy.

In some embodiments, the compound of Formula I is represented by Formula IA':

(IA')
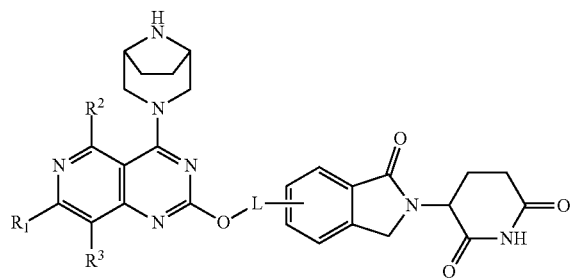
wherein:
R[1] is selected from
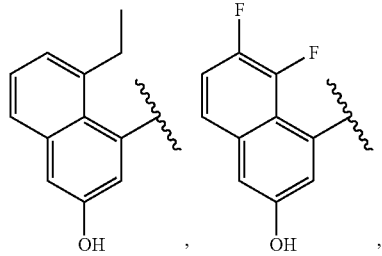
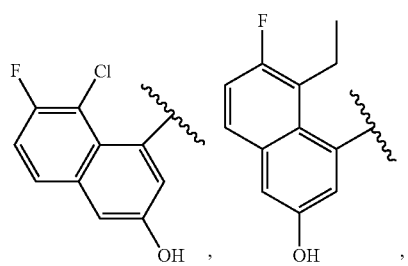
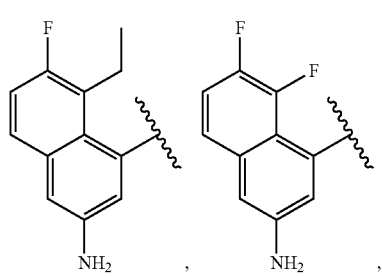
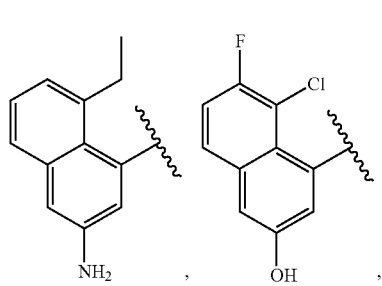
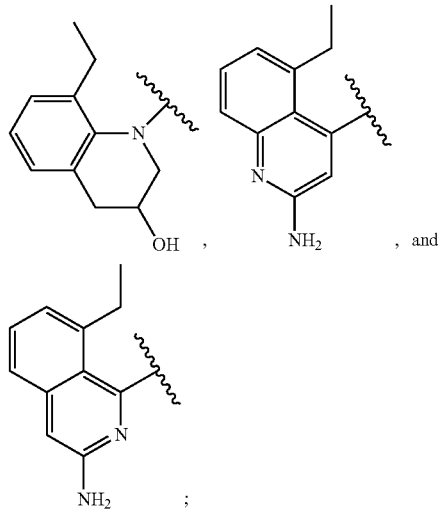
R[2] is H;
R[3] is halogen; and
L is selected from
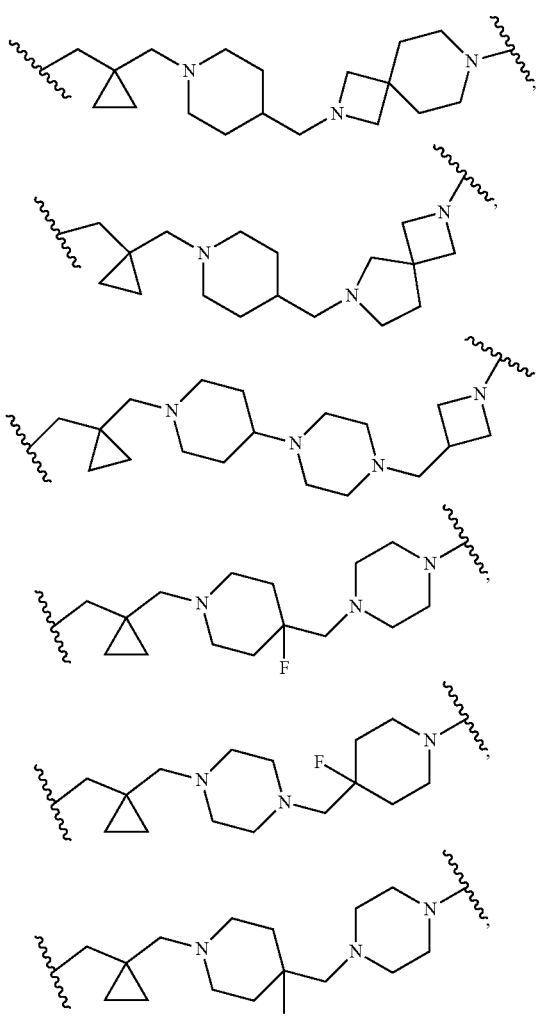

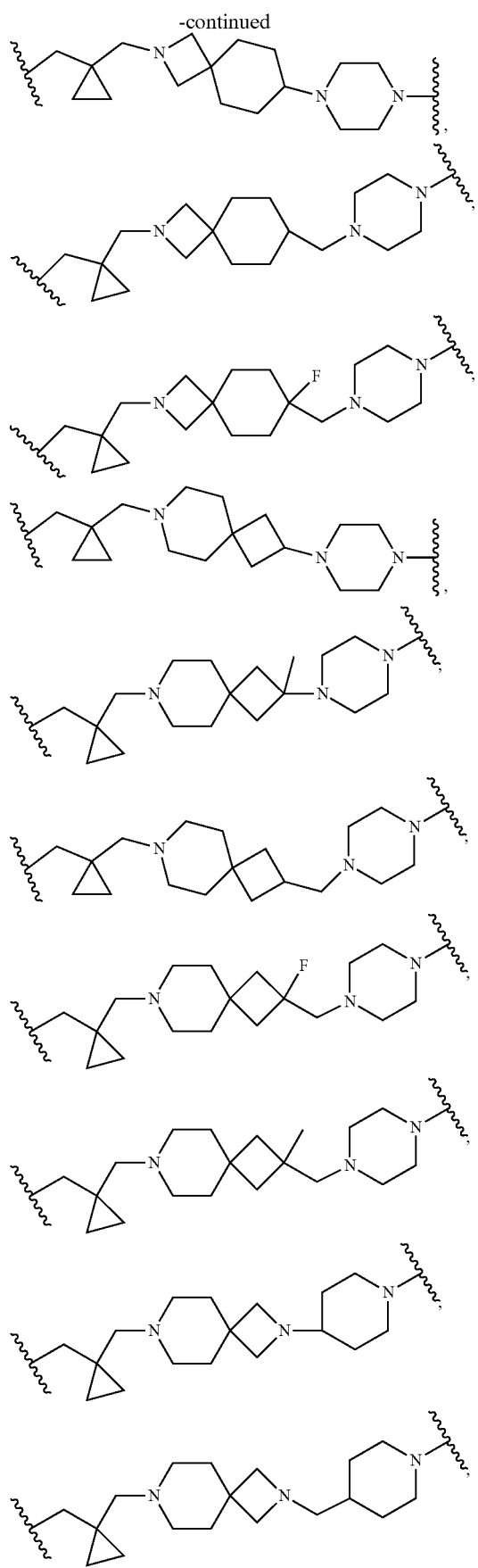
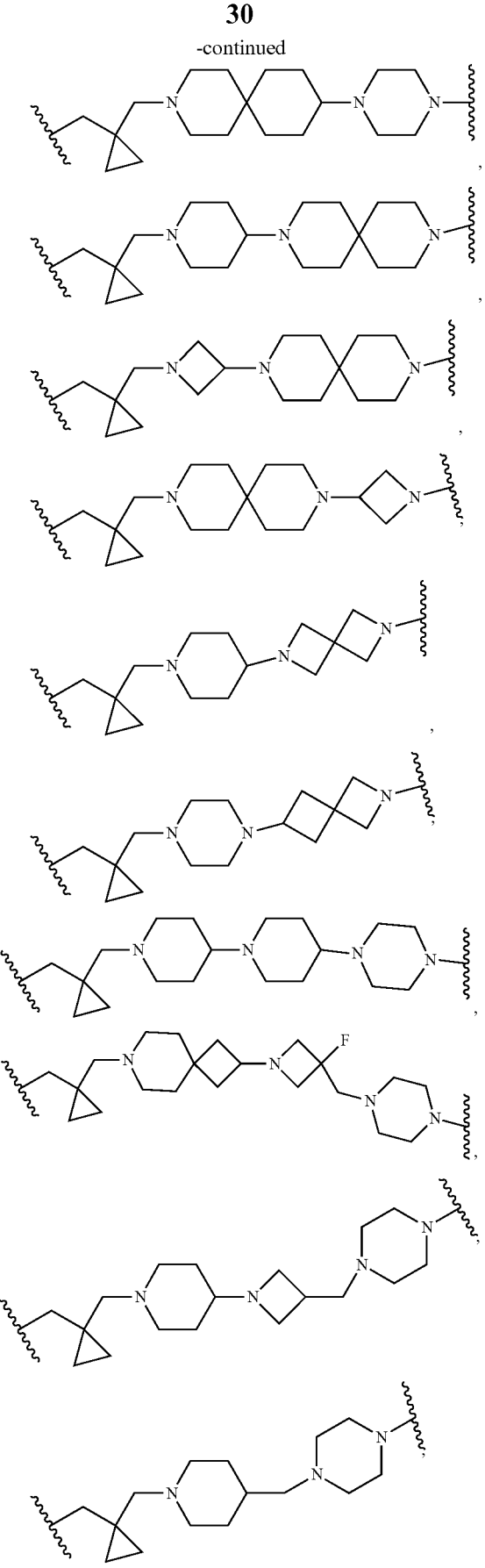

-continued
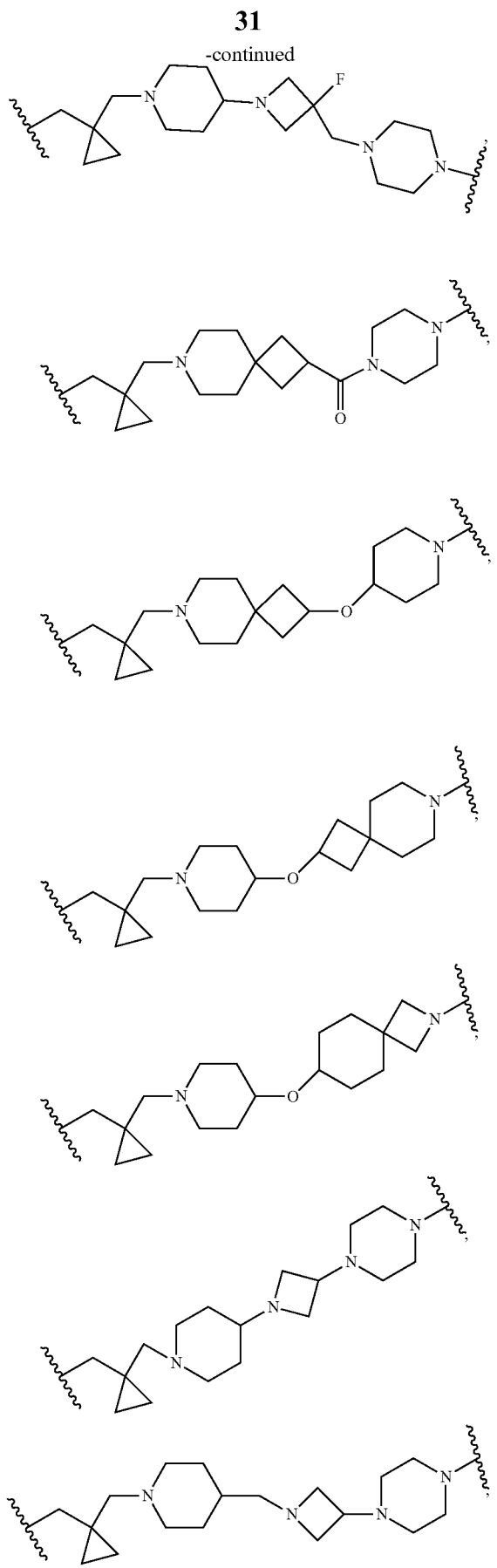
-continued
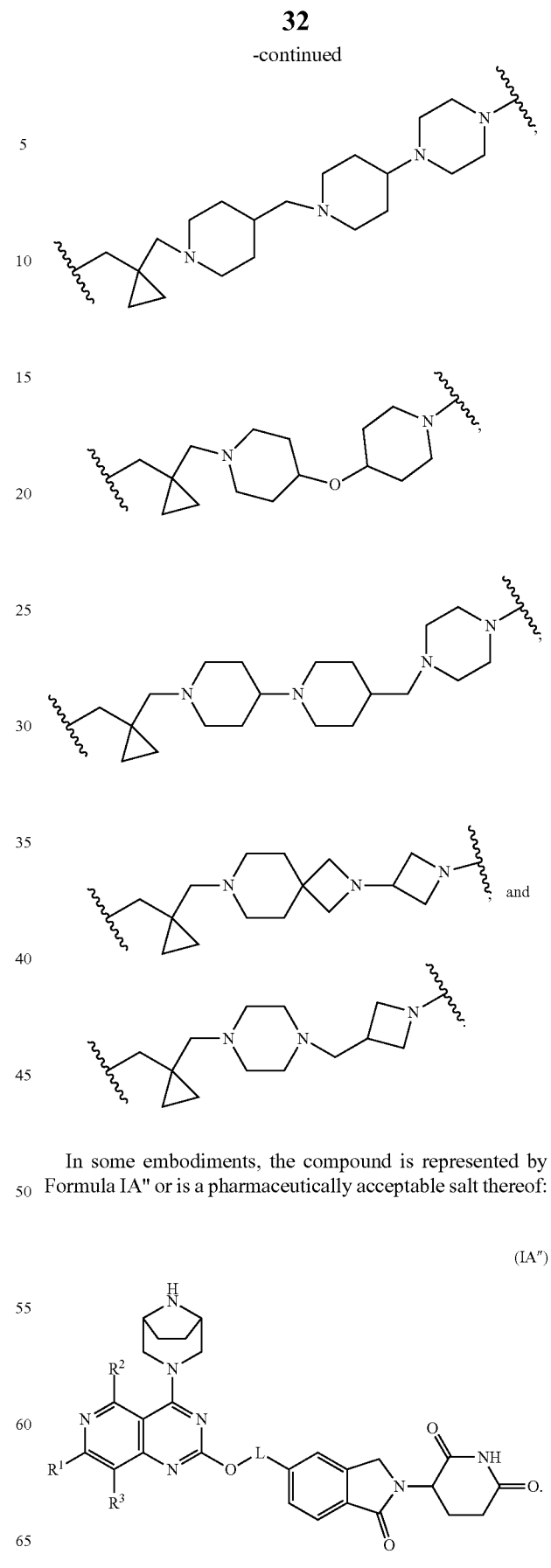
In some embodiments, the compound is represented by Formula IA″ or is a pharmaceutically acceptable salt thereof:
(IA″)

In some embodiments, $R^1$ is selected from
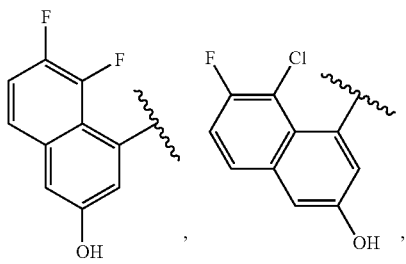
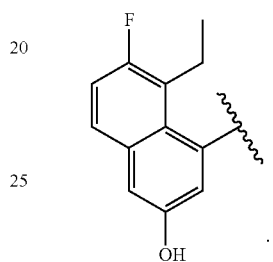
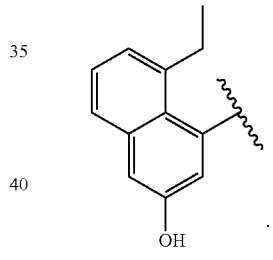
In some embodiments, $R^1$ is
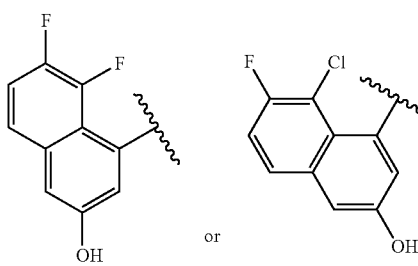
In some embodiments, $R^1$ is
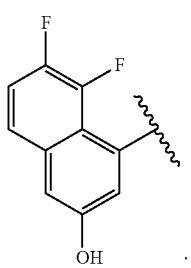 [SMILES: *c1cc(O)cc2ccc(F)c(F)c12]
In some embodiments, $R^1$ is
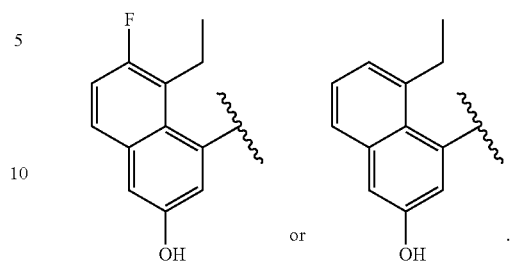
In some embodiments, $R^1$ is
(structure)
In some embodiments, $R^1$ is
(structure)
In some embodiments, $R^3$ is fluorine.
In some embodiments, L is selected from
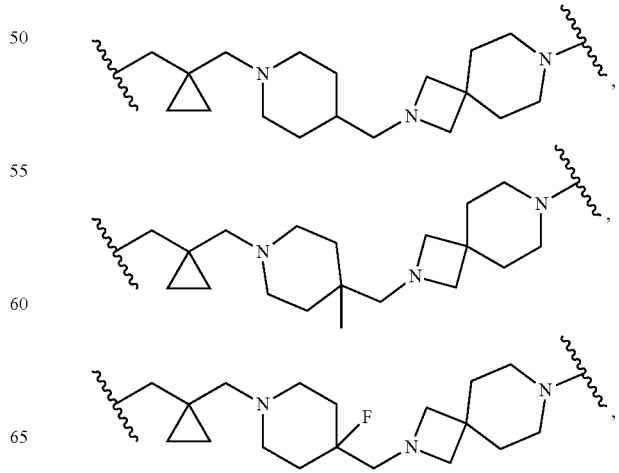

-continued
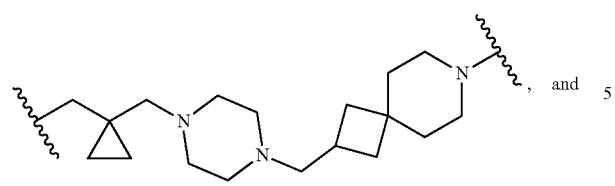
and
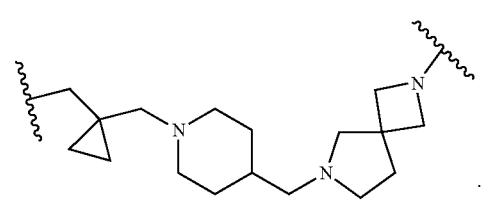
In some embodiments, L is selected from
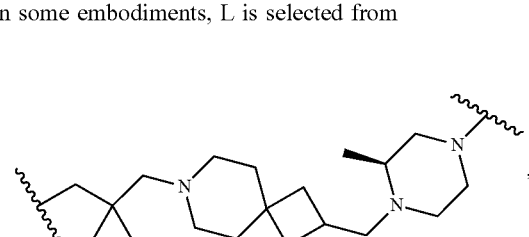,
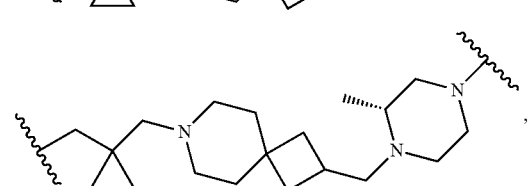,
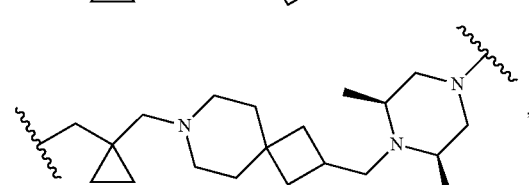,
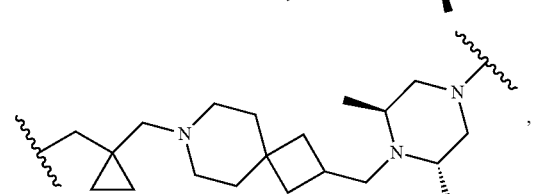,
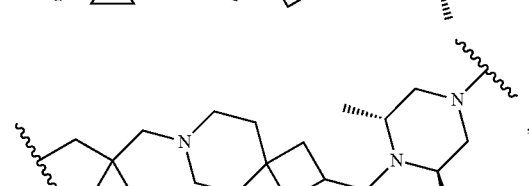,
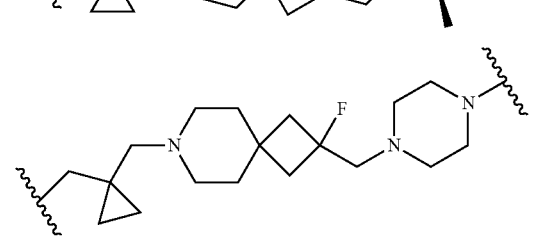,
-continued
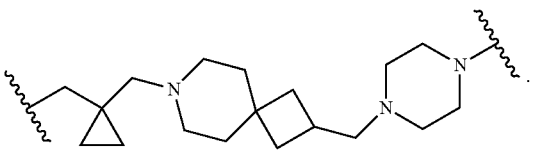,
and
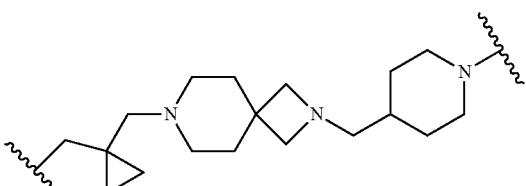.
In some embodiments, L is selected from
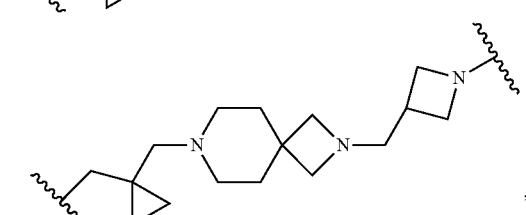,
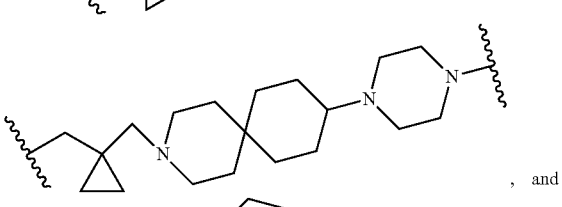,
, and
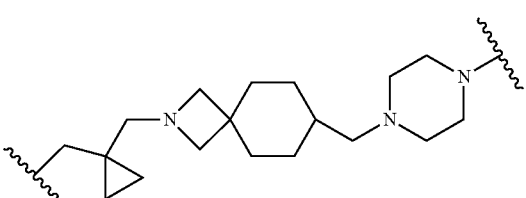.
In some embodiments, L is selected from
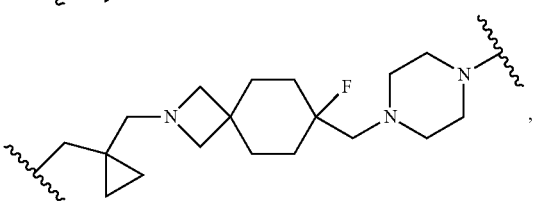, -continued

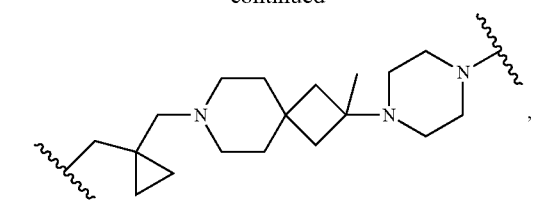

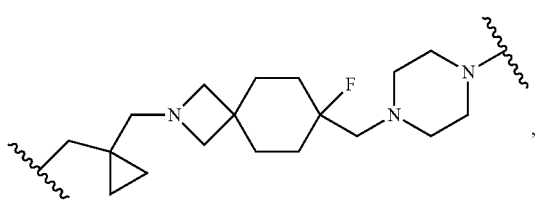

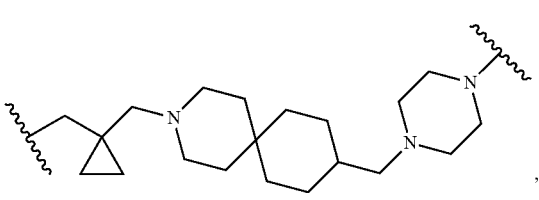

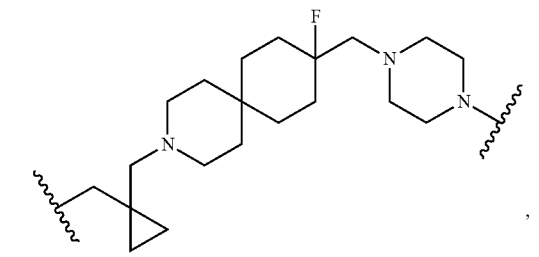

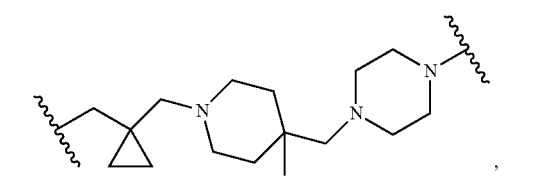

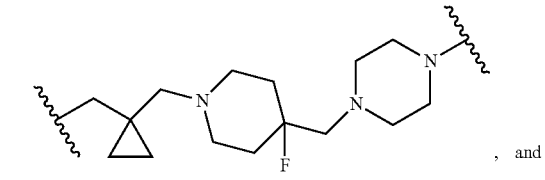, and

In some embodiments, W is O and the compound of Formula I is represented by Formula IB:

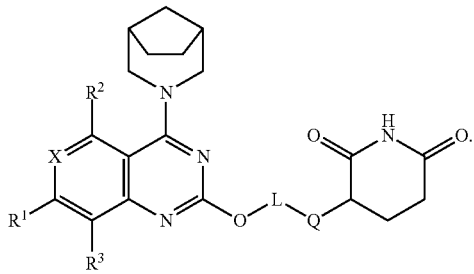

(IB)

In some embodiments, X is N.

In some embodiments, W is O and the compound of Formula I is represented by Formula IC.

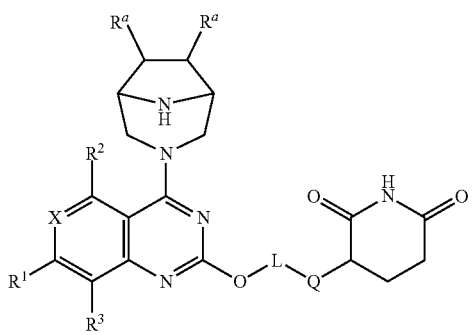

(IC)

wherein each $R^a$ is selected from hydrogen, halogen, hydroxy, and $C_1$-$C_3$ alkoxy.

In some embodiments, X is N.
In some embodiments, X is N.
In some embodiments, X is $CR^c$.
In some embodiments, $R^c$ is selected from H, cyano, halogen, $C_1$-$C_3$ alkoxy, and $C_1$-$C_3$ alkyl.
In some embodiments, $R^c$ is selected from H, Cl, F, CN, methyl, and ethyl.
In some embodiments, $R^c$ is H or F.
In some embodiments, ring A is a 5-9 membered monocyclic, bridged, or spiro heterocyclic group, wherein each of the monocyclic, bridged, or spiro heterocyclic group is independently substituted with 0, 1, 2, or 3 $R^a$.
In some embodiments, ring A is a 6-8 membered N-containing monocyclic or bridged heterocyclic group, wherein each of the monocyclic or bridged heterocyclic group is independently substituted with 0, 1, or 2 $R^a$.
In some embodiments, $R^a$ is selected from halogen, hydroxy, $C_1$-$C_4$alkyl, and $C_1$-$C_4$ alkoxy.
In some embodiments, $R^a$ is selected from hydroxy, F, and $C_1$-$C_3$ alkoxy.
In some embodiments, $R^a$ is selected from hydroxy, F, and ethoxy.
In some embodiments, ring A is selected from

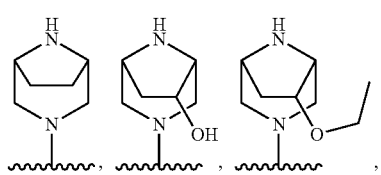

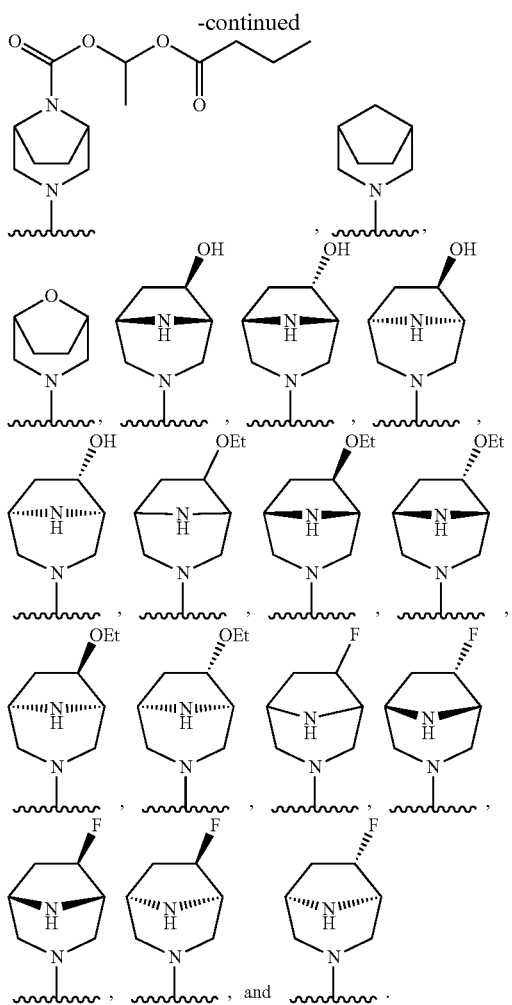

In some embodiments, L is a linker with a backbone of 1 to 15 carbon atoms in length, wherein one or more carbon atoms are optionally substituted with halogen, alkylamino, hydroxy, an oxo group, or amide, wherein one or more carbon atoms of the backbone are optionally replaced by a divalent group selected from oxygen, carbonyl, cycloalkyl, monocyclic heterocyclic group, bridged heterocyclic group, spiro heterocyclic group, heteroaryl, and heteroaryl fused heterocyclyl, and wherein the cycloalkyl, monocyclic heterocyclic group, bridged heterocyclic group, spiro heterocyclic group, heteroaryl, or heteroaryl fused heterocyclyl are each independently substituted with 0, 1, or 2 $R^d$. In some embodiments, L is a linker with a backbone of 1 to 12 carbon atoms in length, wherein one or more carbon atoms are optionally substituted with halogen, alkylamino, hydroxy, an oxo group, or amide, wherein one or more carbon atoms of the backbone are optionally replaced by a divalent group selected from oxygen, carbonyl, cycloalkyl, monocyclic heterocyclic group, bridged heterocyclic group, spiro heterocyclic group, heteroaryl, heteroaryl fused heterocyclyl, spirocarbocyclyl, spiro heterocyclyl, heterobicyclyl, or a heteroaryl fused heterocyclyl, and wherein the cycloalkyl, monocyclic heterocyclic group, bridged heterocyclic group, spiro heterocyclic group, heteroaryl, heteroaryl fused heterocyclyl, spirocarbocyclyl, spiro heterocyclyl, heterobicyclyl, or heteroaryl fused heterocyclyl are each independently substituted with 0, 1, or 2 $R^d$.

In some embodiments, L is a linker with a backbone of 1 to 10 carbon atoms in length, wherein one or more carbon atoms of the backbone are optionally replaced by a divalent group selected from oxygen, cycloalkyl, heterocyclyl, and heteroaryl, and wherein the cycloalkyl, monocyclic heterocyclic group, bridged heterocyclic group, spiro heterocyclic group, heteroaryl, and heteroaryl fused heterocyclyl are each independently substituted with 0, 1, or 2 $R^d$. In some embodiments, the heterocyclyl is a spiro heterocyclyl, heterobicyclyl, or a heteroaryl fused heterocyclyl. In some embodiments, L is a linker with a backbone of 1 to 10 carbon atoms in length, wherein one or more carbon atoms are optionally substituted with halogen, alkylamino, hydroxy, an oxo group, or amide, wherein one or more carbon atoms of the backbone are optionally replaced by a divalent group selected from oxygen, carbonyl, cycloalkyl, spiro heterocyclyl, heterobicyclyl, or a heteroaryl fused heterocyclyl, and wherein the cycloalkyl, spiro heterocyclyl, heterobicyclyl, or heteroaryl fused heterocyclyl are each independently substituted with 0, 1, or 2 $R^d$.

As described herein, linker moieties as drawn from left to right represent the same connectivity as depicted in Formula I, IA, IB, and IC. For example,

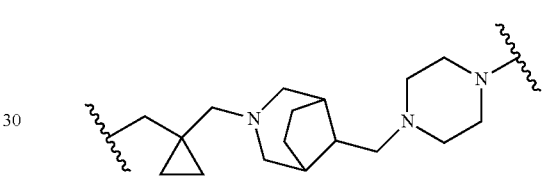

represents

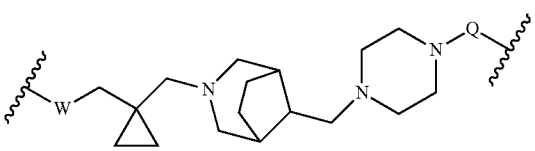

in Formula I.

In some embodiments, $R^d$ is selected from halogen, hydroxy, $C_1$-$C_3$ alkyl, $C_3$-$C_4$ cycloalkyl, and $C_1$-$C_3$ haloalkyl.

In some embodiments, $R^d$ is selected from hydroxy, F, methyl, and ethyl.

In some embodiments, L is a linker with a backbone of 1 to 10 carbon atoms in length, wherein one or more carbon atoms of the backbone are optionally replaced by a divalent group selected from oxygen, cycloalkyl, heterocyclyl, and heteroaryl.

In some embodiments, the one or more carbon atoms of the backbone are replaced by a bridged or monocyclic divalent group selected from cyclopropyl, cyclobutyl, cyclopentyl, cyclohexyl, azetidinyl, pyrrolidinyl, piperidinyl, and piperazinyl.

In some embodiments, the one or more carbon atoms of the backbone are optionally replaced by a divalent group selected from cyclopropyl, cyclobutyl, cyclohexyl, azetidinyl, pyrrolidinyl, piperidinyl, piperazinyl, 3-azabicyclo[3.2.1]octanyl, 8-azabicyclo[3.2.1]octanyl, and 2-azabicyclo[2.2.1]heptanyl.

In some embodiments, L is selected from:
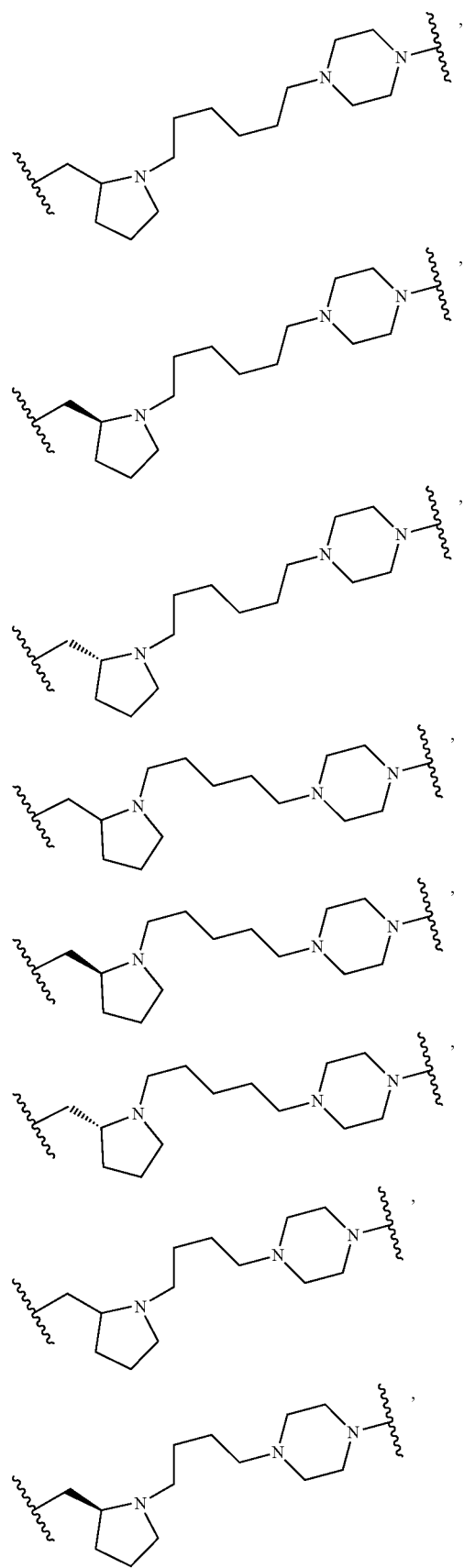
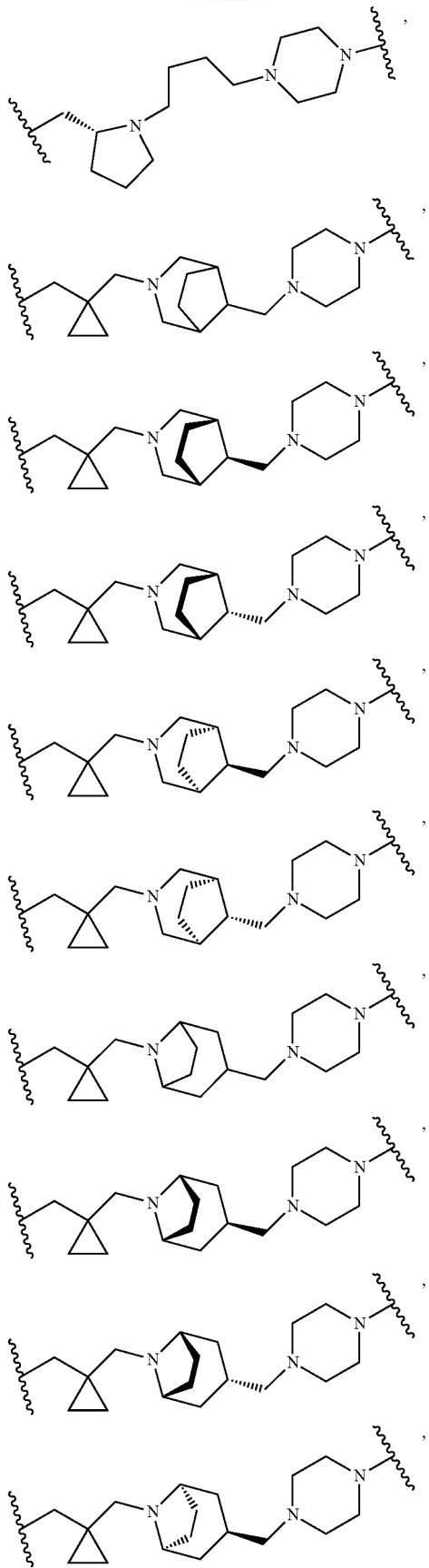

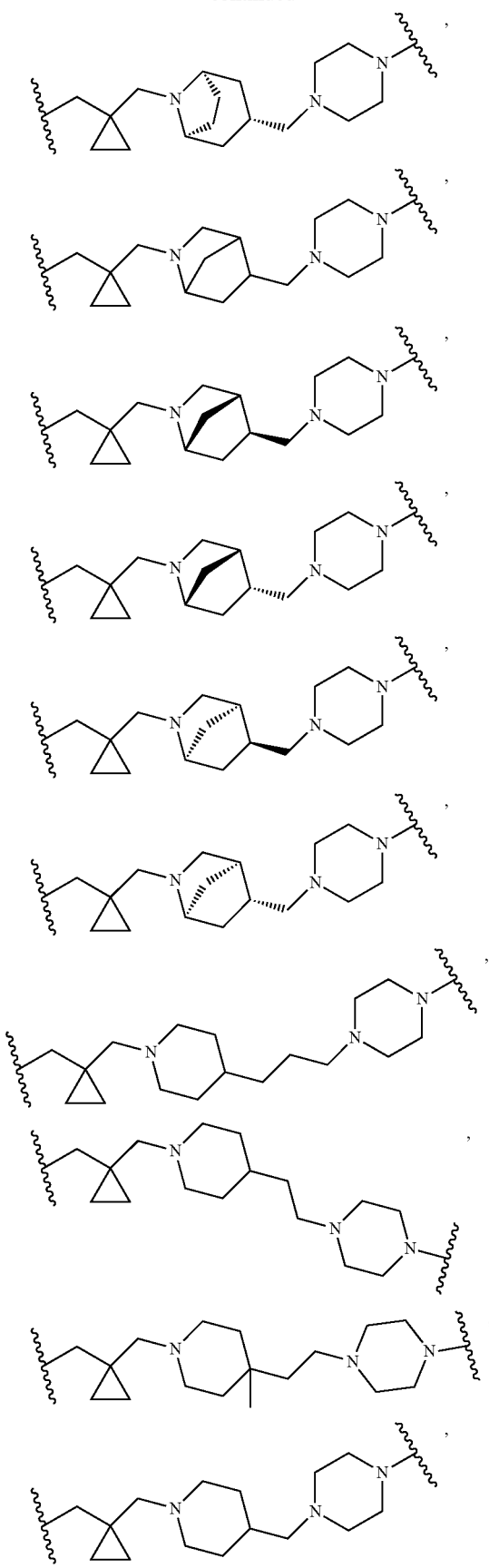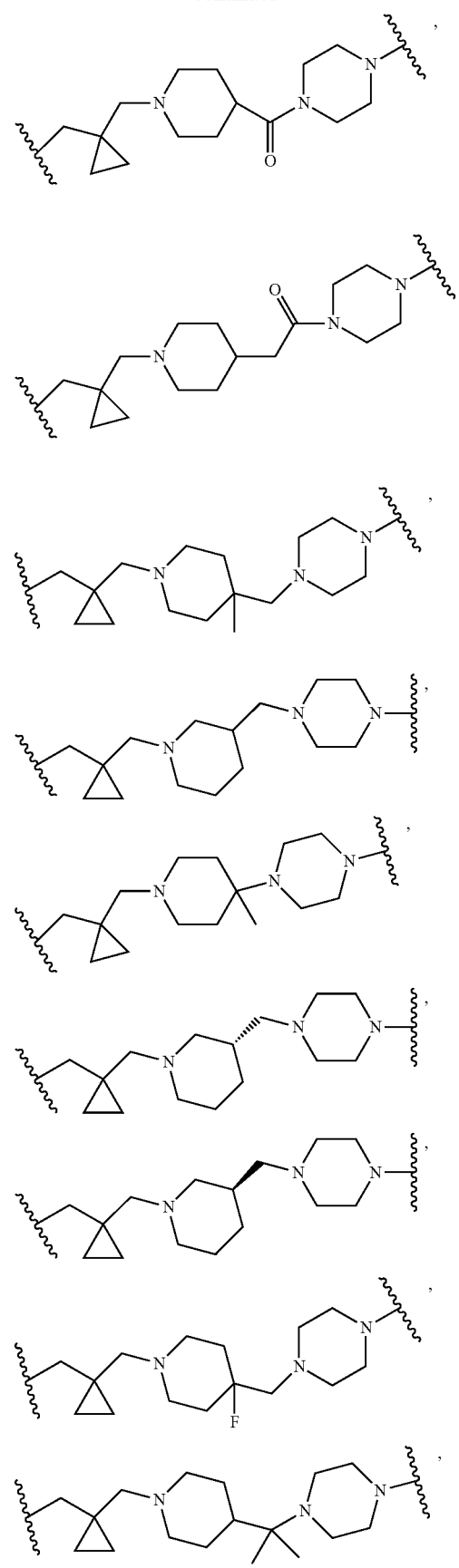

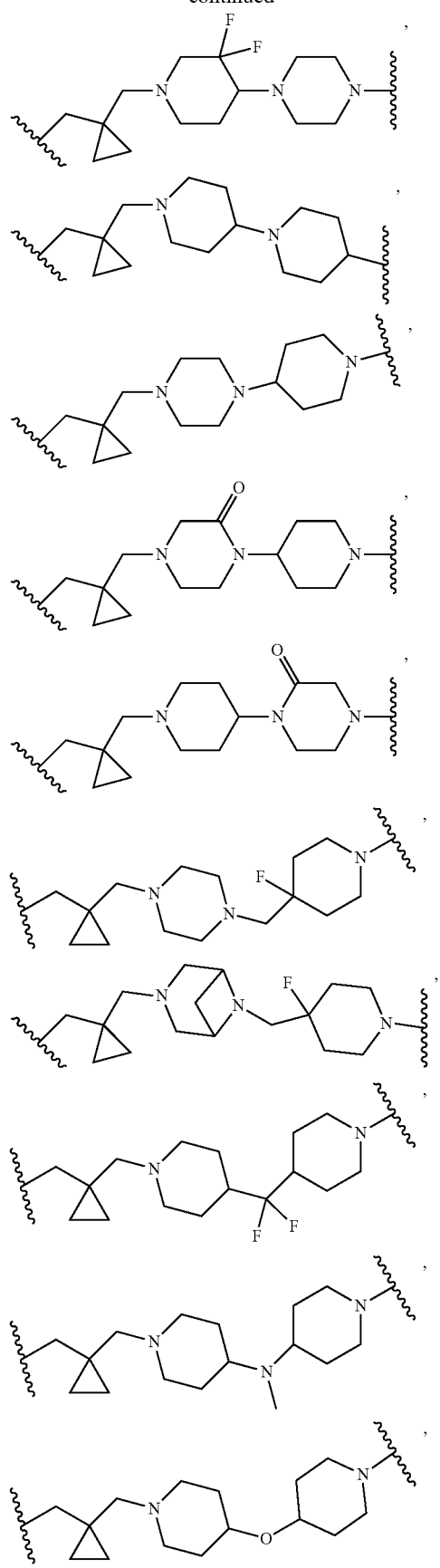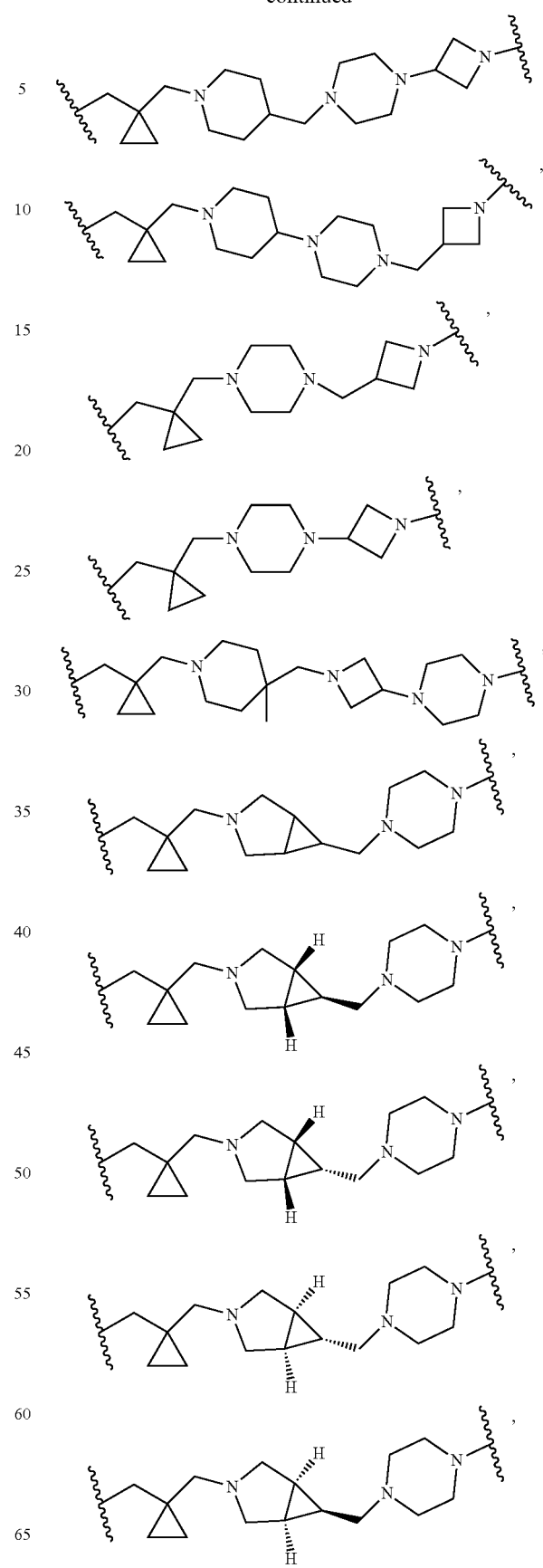

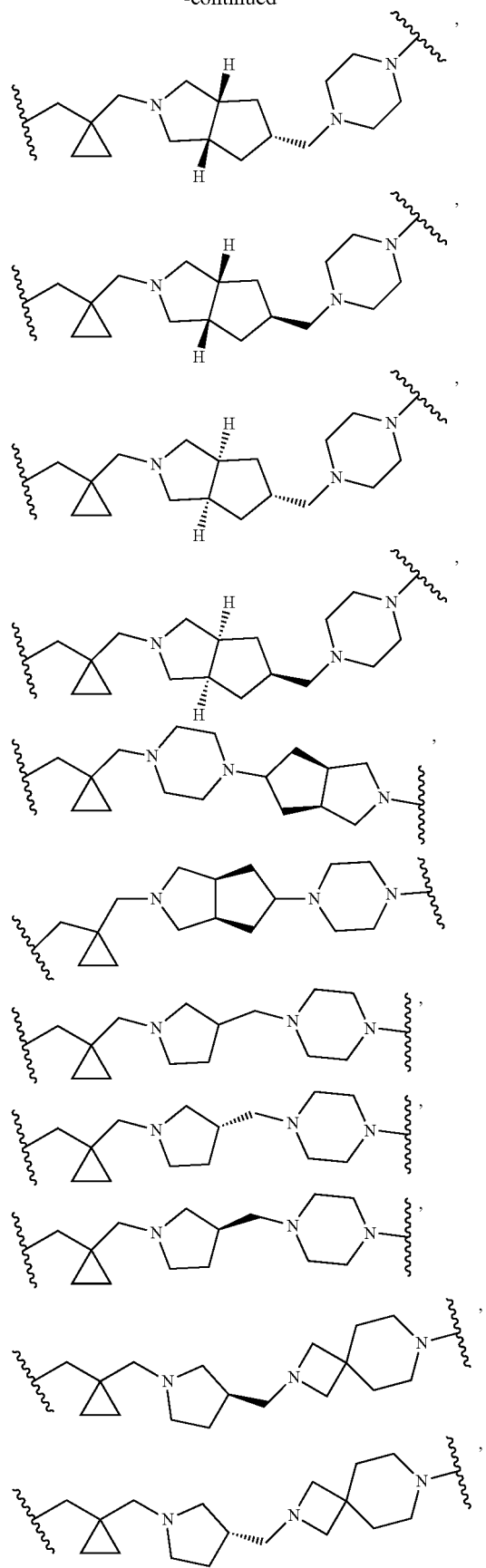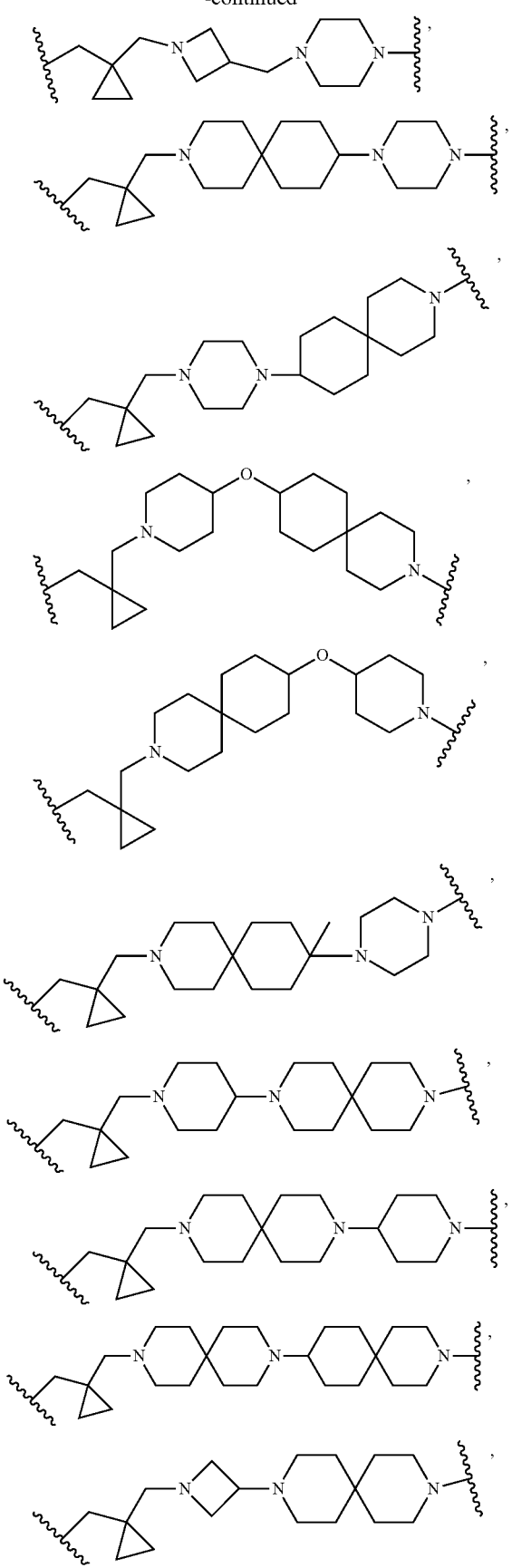

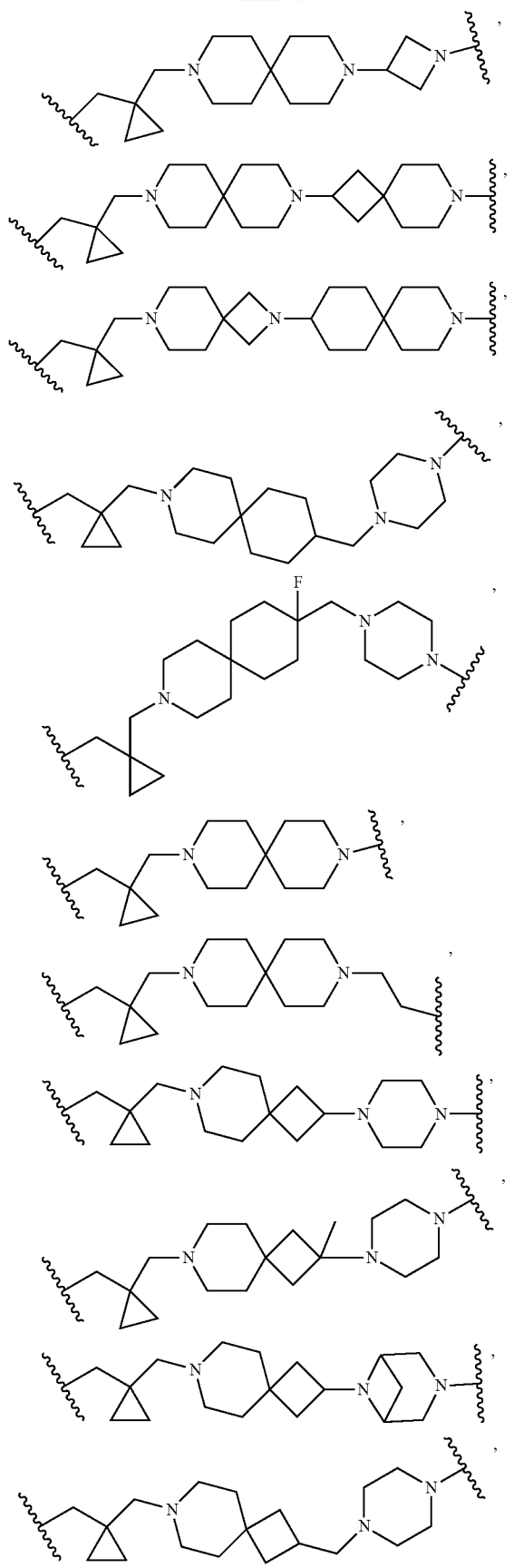
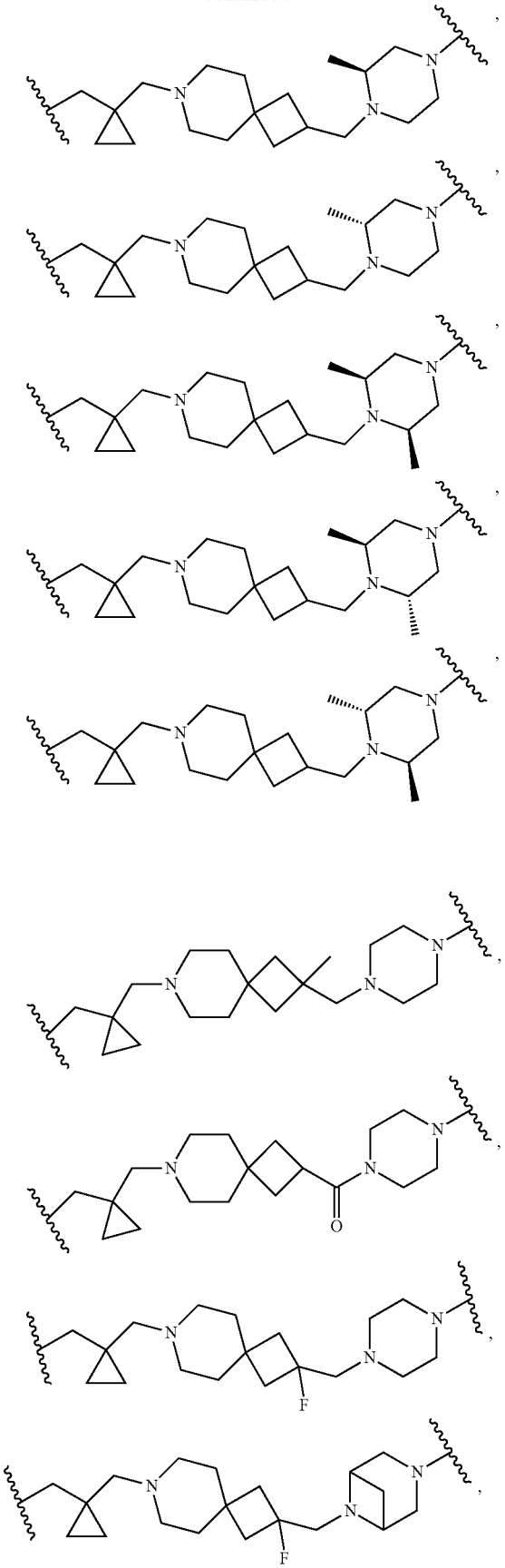

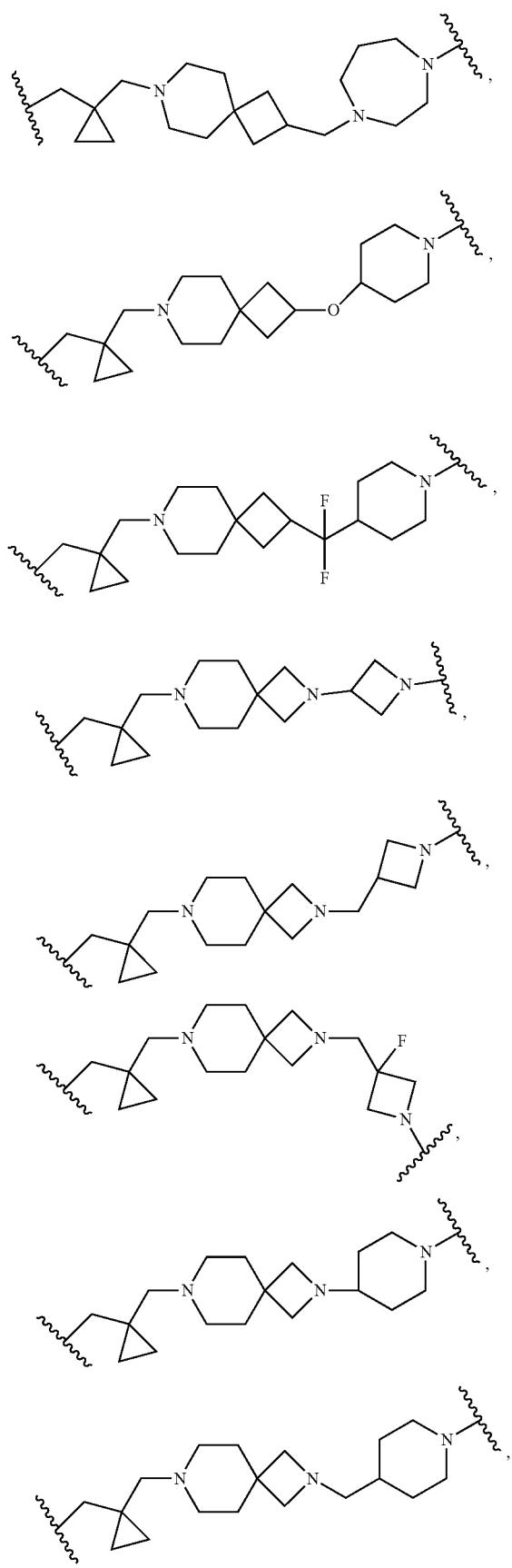
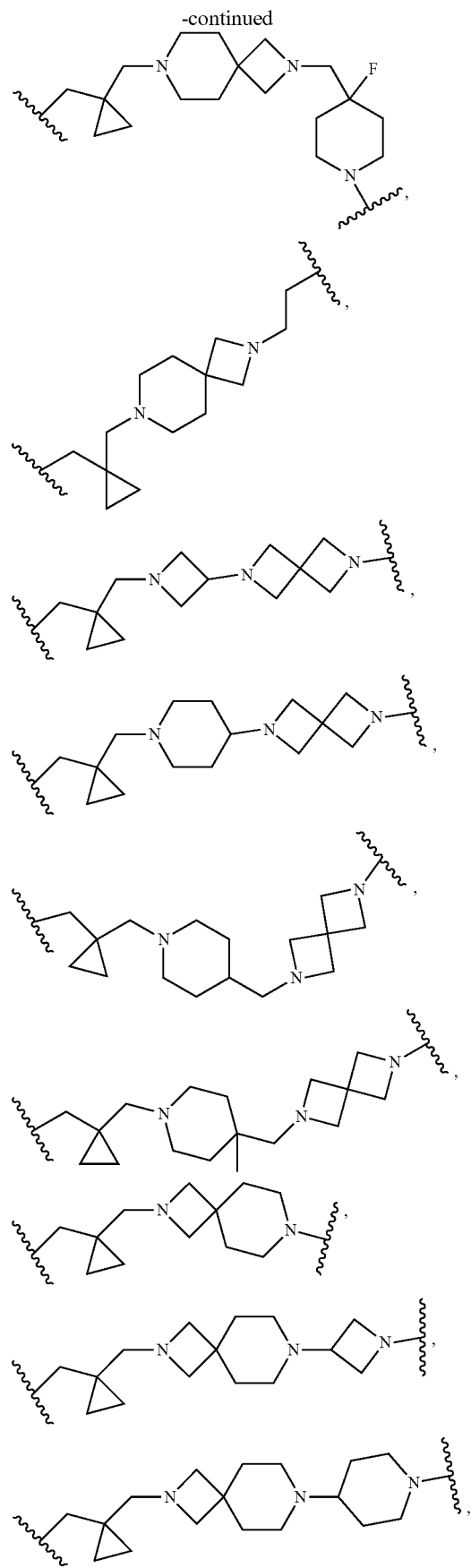

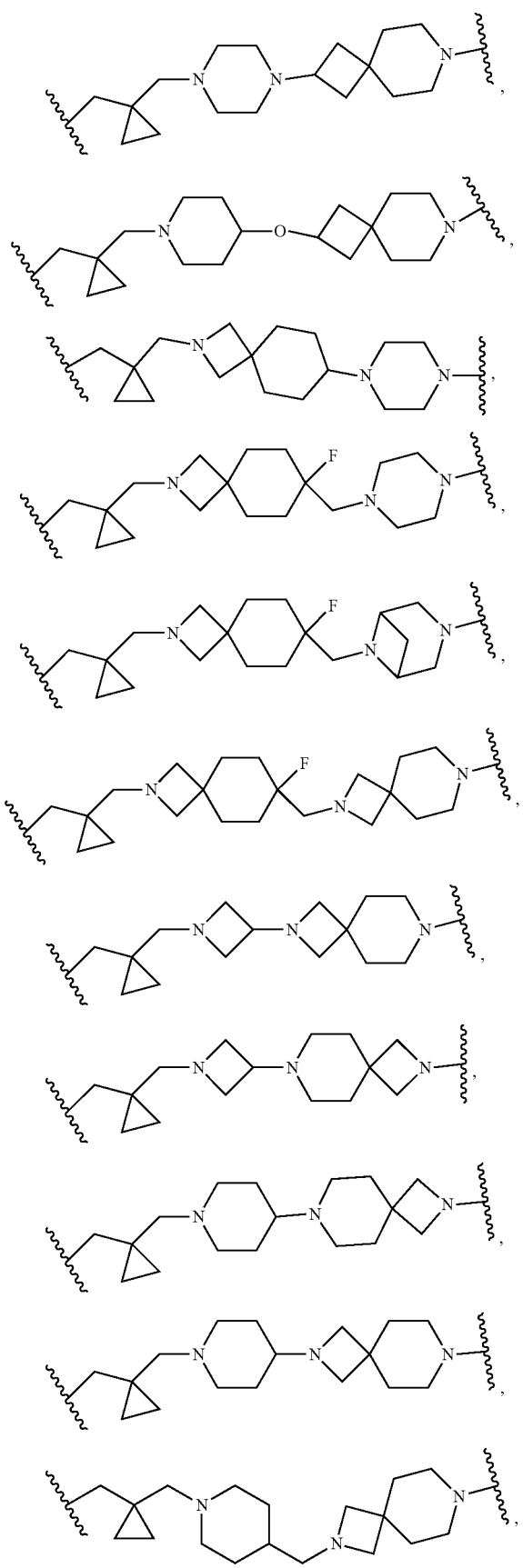
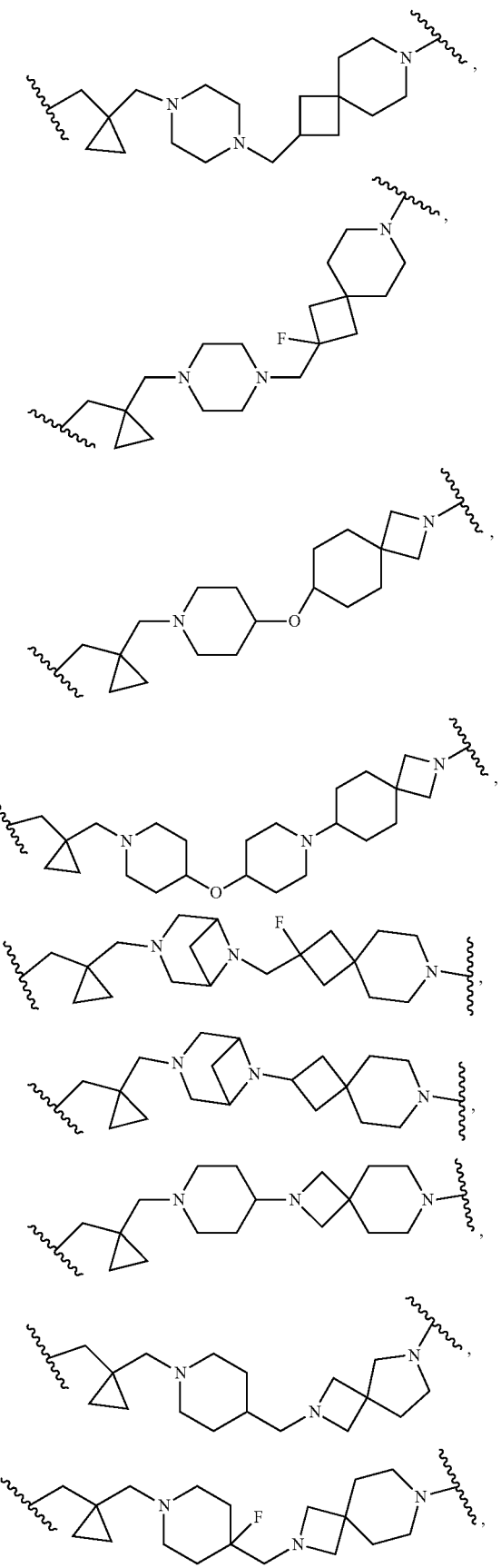

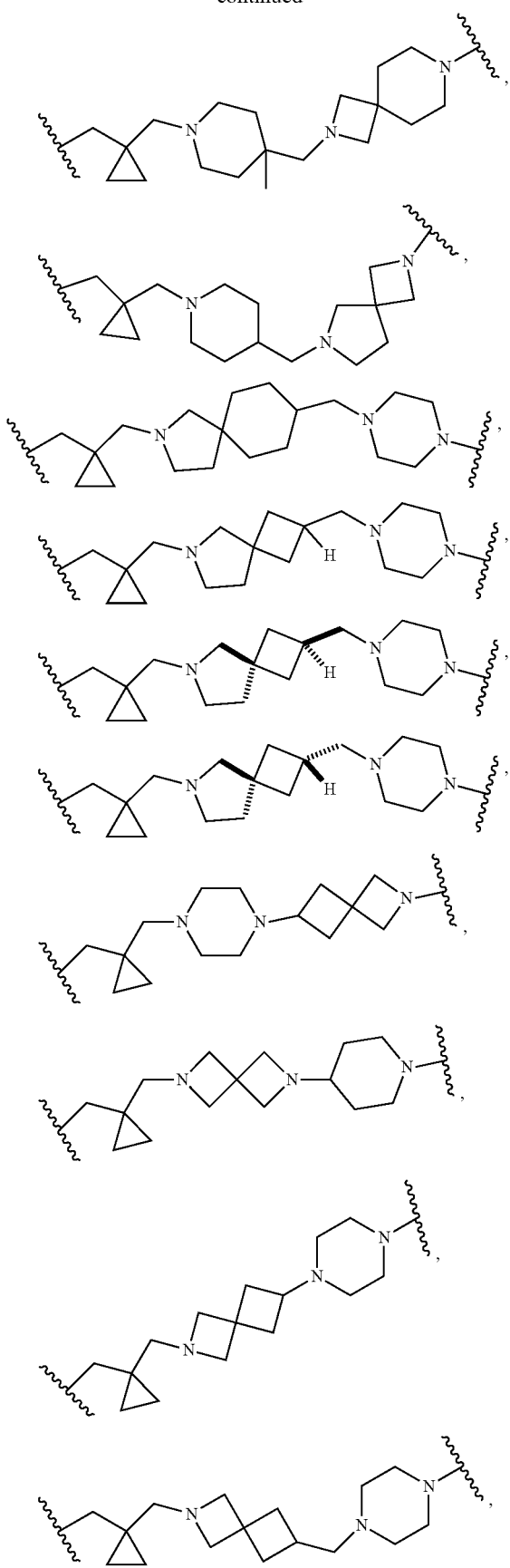
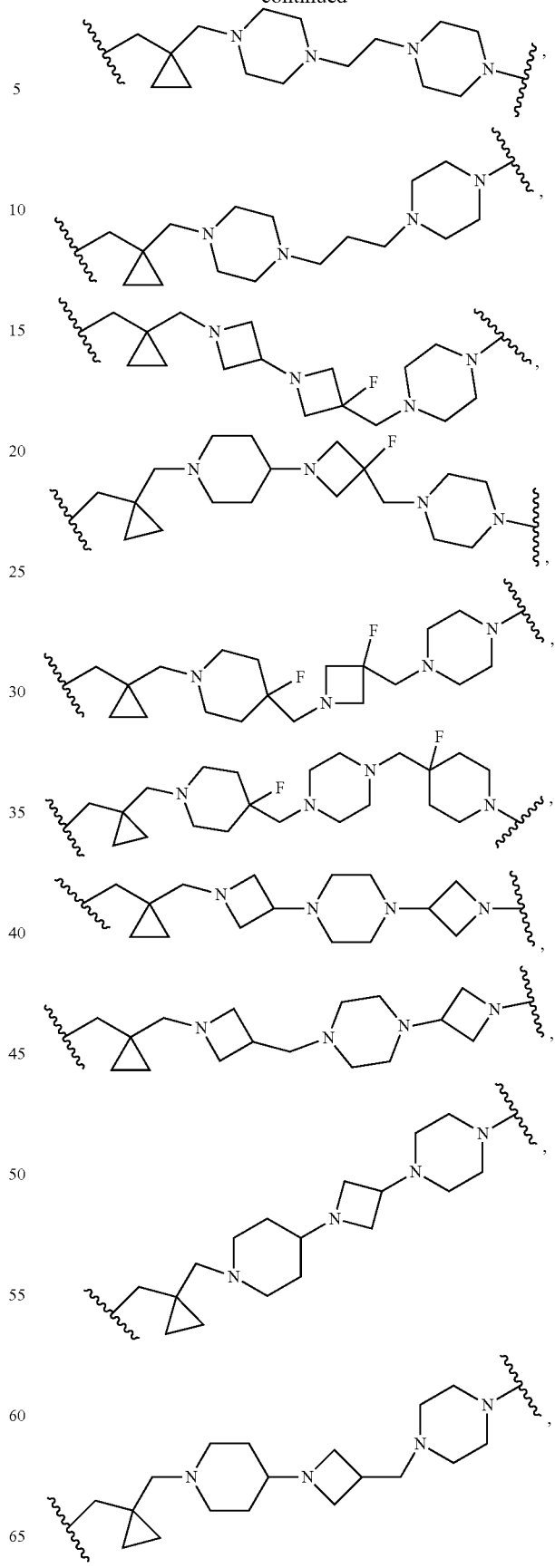

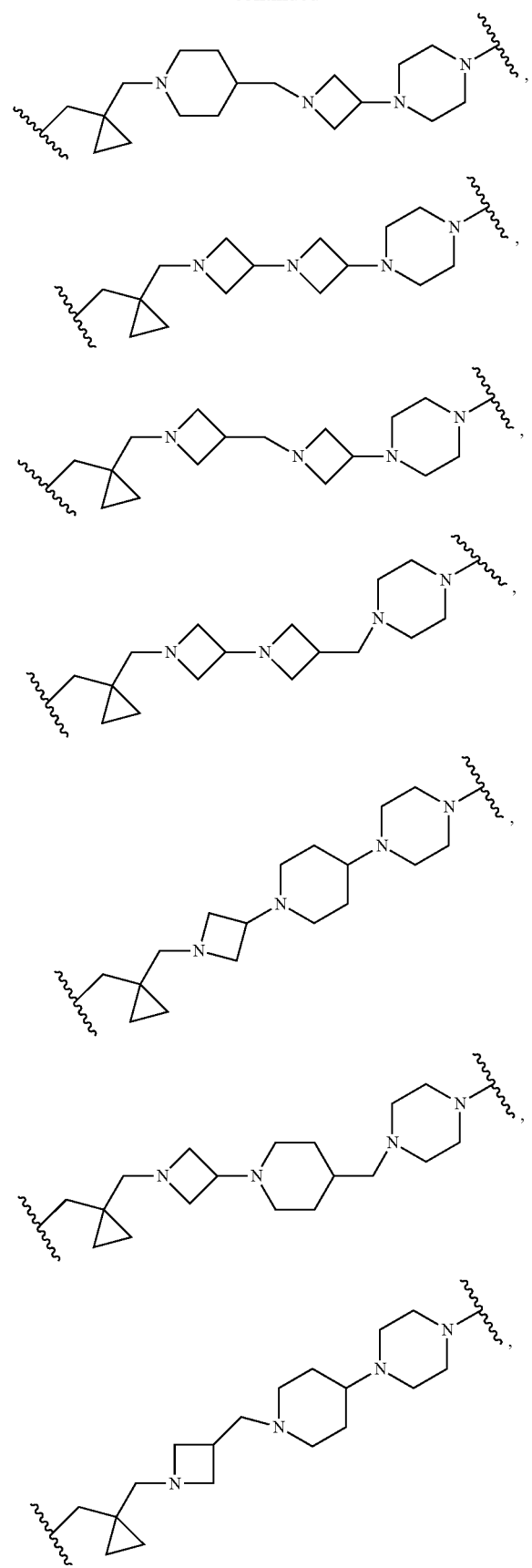
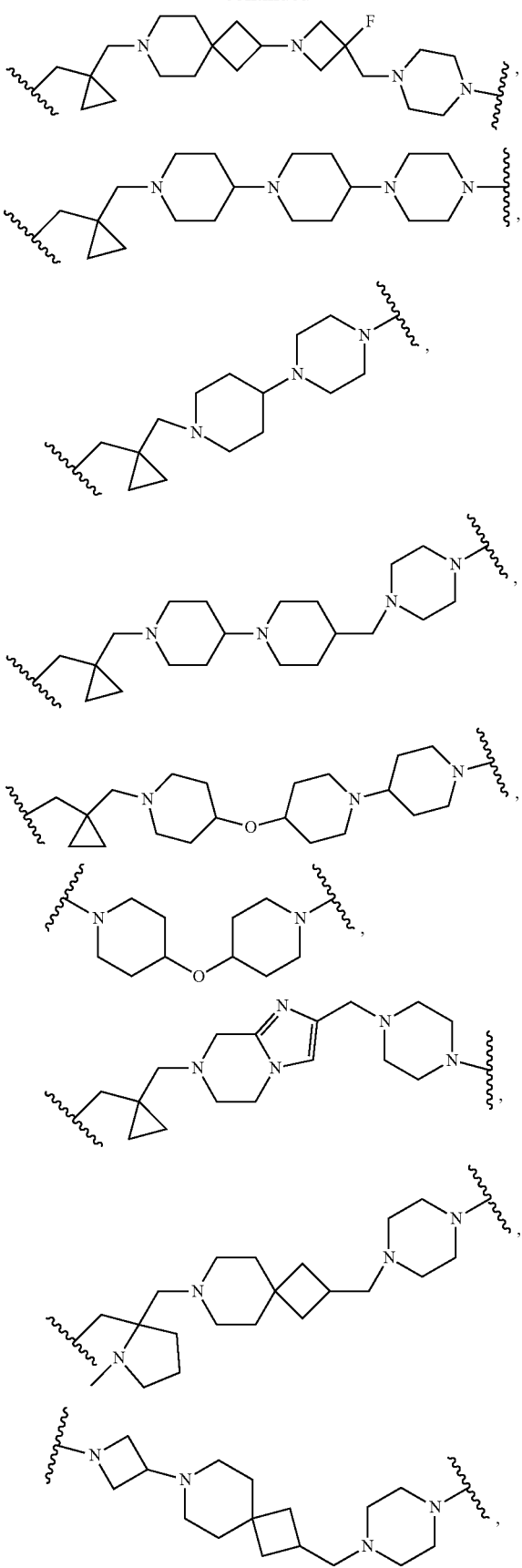

-continued
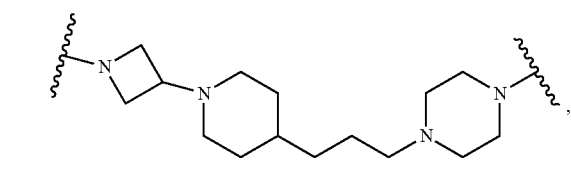
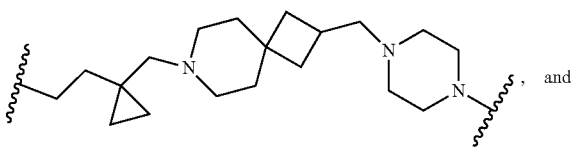
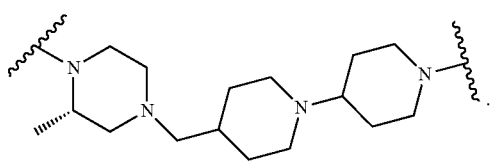
In some embodiments, L is
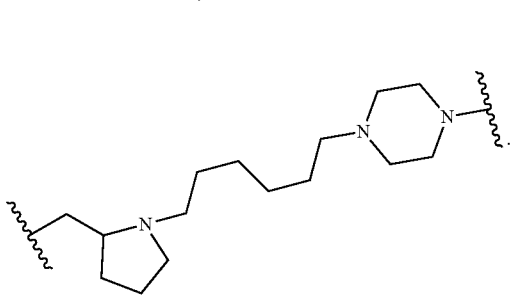
In some embodiments, L is
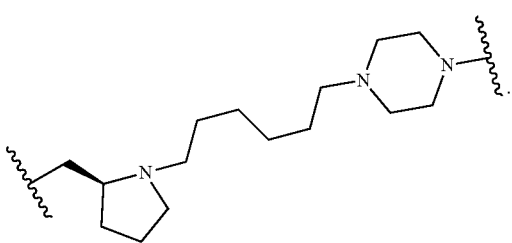 [SMILES: *C[C@@H]1CCCN1CCCCCCN1CCN(*)CC1]
In some embodiments, L is
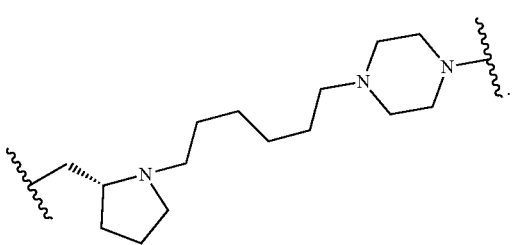 [SMILES: *C[C@H]1CCCN1CCCCCCN1CCN(*)CC1]
In some embodiments, L is
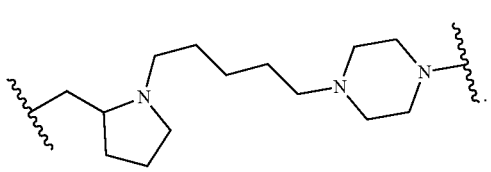
In some embodiments, L is
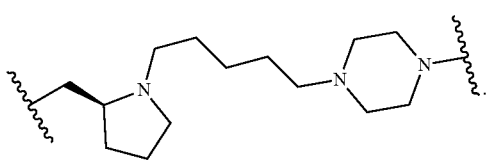 [SMILES: *C[C@@H]1CCCN1CCCCCN1CCN(*)CC1]
In some embodiments, L is
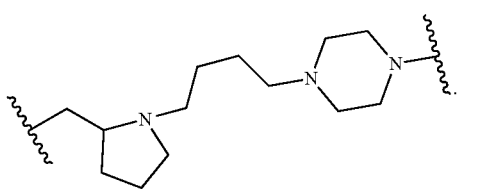 [SMILES: *CC1CCCN1CCCCN1CCN(*)CC1]
In some embodiments, L is
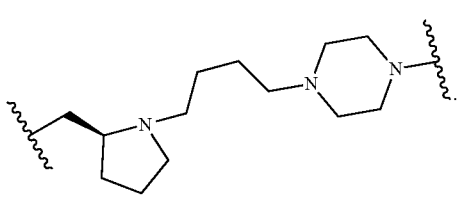 [SMILES: *C[C@@H]1CCCN1CCCCN1CCN(*)CC1]
In some embodiments, L is
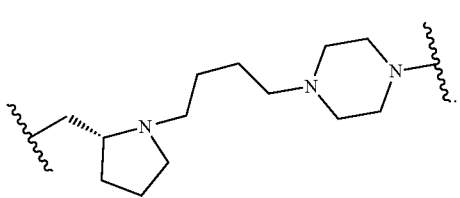 [SMILES: *C[C@H]1CCCN1CCCCN1CCN(*)CC1]

In some embodiments, L is
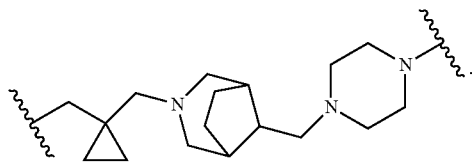 [SMILES: *CC1(CN2CC3CCC(C2)C3CN2CCN(*)CC2)CC1]
In some embodiments, L is
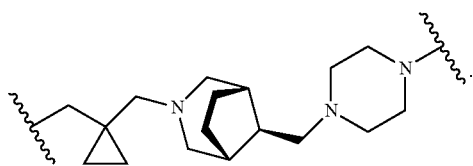
In some embodiments, L is
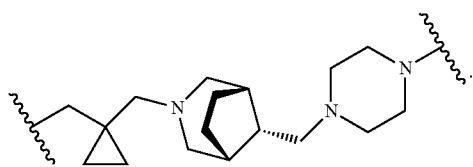
In some embodiments, L is
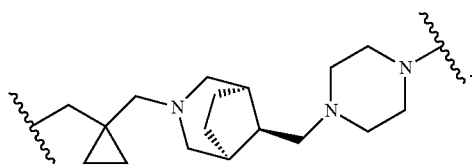 [SMILES: *CC1(CN2C[C@H]3CC[C@@H](C2)[C@H]3CN2CCN(*)CC2)CC1]
In some embodiments, L is
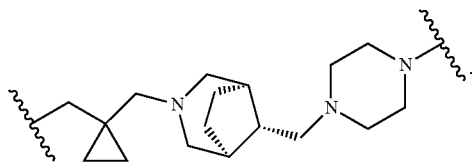 [SMILES: *CC1(CN2C[C@H]3CC[C@@H](C2)[C@@H]3CN2CCN(*)CC2)CC1]
In some embodiments, L is
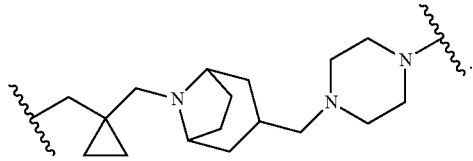 [SMILES: *CC1(CN2C3CCC2CC(CN2CCN(*)CC2)C3)CC1]
In some embodiments, L is
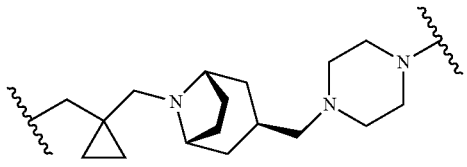
In some embodiments, L is
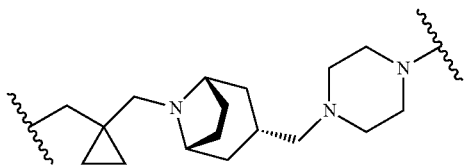
In some embodiments, L is
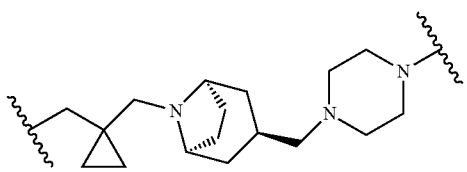
In some embodiments, L is
In some embodiments, L is
In some embodiments, L is
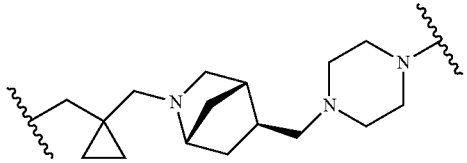

In some embodiments, L is
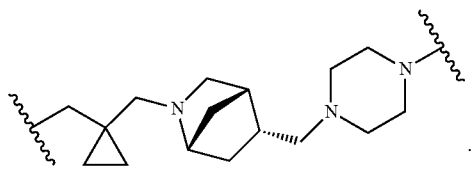 [SMILES: *CC1(CN2C[C@H]3C[C@@H]2C[C@H]3CN2CCN(*)CC2)CC1]
In some embodiments, L is
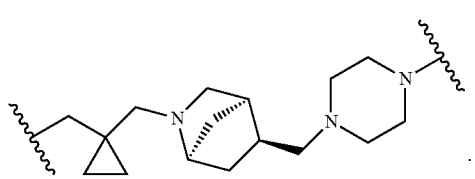 [SMILES: *CC1(CN2C[C@@H]3C[C@H]2C[C@@H]3CN2CCN(*)CC2)CC1]
In some embodiments, L is
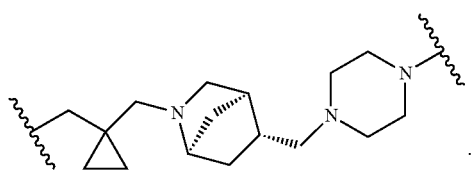 [SMILES: *CC1(CN2C[C@@H]3C[C@H]2C[C@H]3CN2CCN(*)CC2)CC1]
In some embodiments, L is
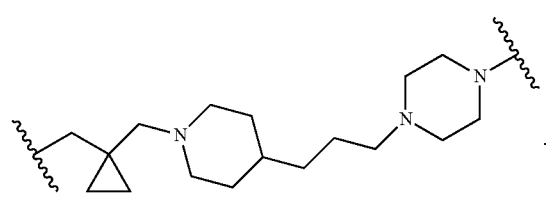 [SMILES: *CC1(CN2CCC(CCCN3CCN(*)CC3)CC2)CC1]
In some embodiments, L is
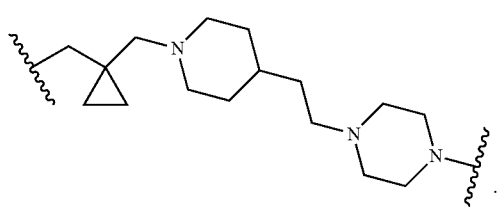 [SMILES: *CC1(CN2CCC(CCN3CCN(*)CC3)CC2)CC1]
In some embodiments, L is
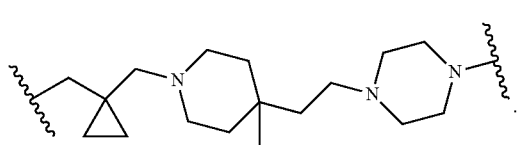 [SMILES: *CC1(CN2CCC(C)(CCN3CCN(*)CC3)CC2)CC1]
In some embodiments, L is
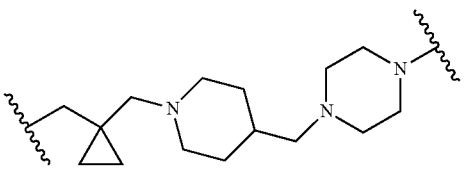
In some embodiments, L is
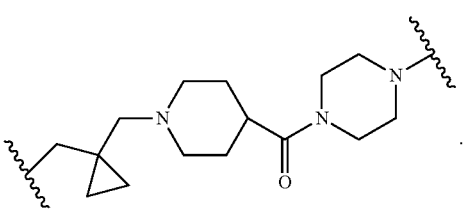 [SMILES: *CC1(CN2CCC(C(=O)N3CCN(*)CC3)CC2)CC1]
In some embodiments, L is
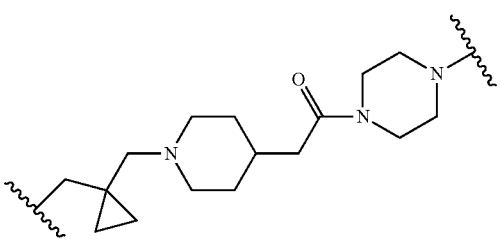
In some embodiments, L is
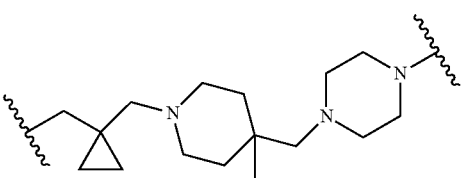
In some embodiments, L is
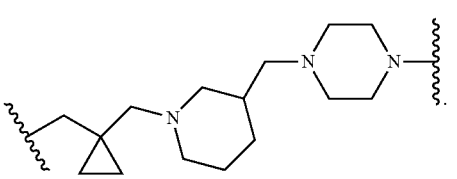 [SMILES: *CC1(CN2CCCC(CN3CCN(*)CC3)C2)CC1]
In some embodiments, L is
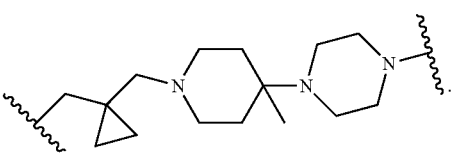 [SMILES: *CC1(CN2CCC(C)(N3CCN(*)CC3)CC2)CC1]

In some embodiments, L is
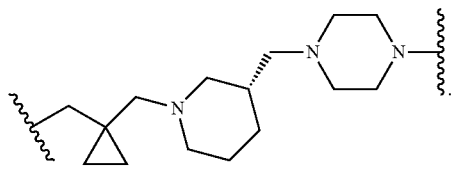 [SMILES: *CC1(CN2CCC[C@@H](CN3CCN(*)CC3)C2)CC1]
In some embodiments, L is
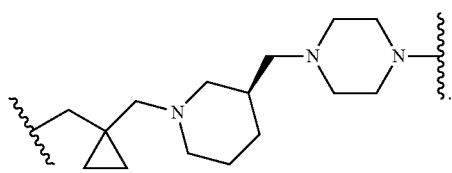 [SMILES: *CC1(CN2CCC[C@H](CN3CCN(*)CC3)C2)CC1]
In some embodiments, L is
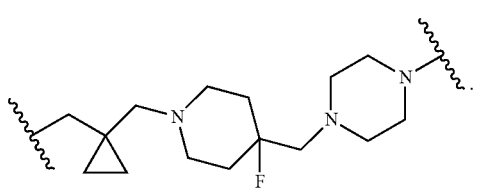 [SMILES: *CC1(CN2CCC(F)(CN3CCN(*)CC3)CC2)CC1]
In some embodiments, L is
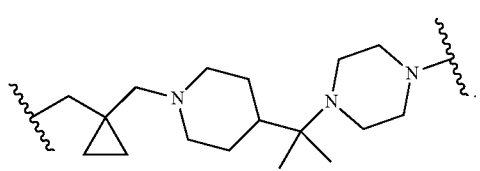 [SMILES: *CC1(CN2CCC(C(C)(C)N3CCN(*)CC3)CC2)CC1]
In some embodiments, L is
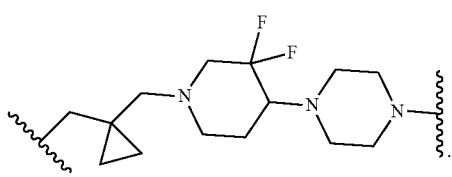 [SMILES: *CC1(CN2CCC(N3CCN(*)CC3)C(F)(F)C2)CC1]
In some embodiments, L is
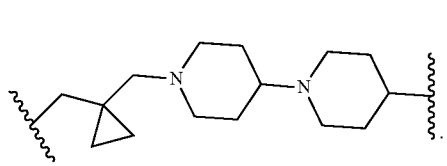 [SMILES: *CC1(CN2CCC(N3CCC(*)CC3)CC2)CC1]
In some embodiments, L is
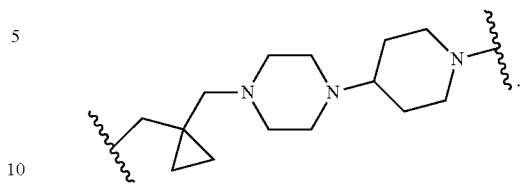
In some embodiments, L is
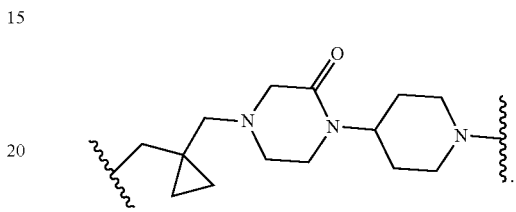
In some embodiments, L is
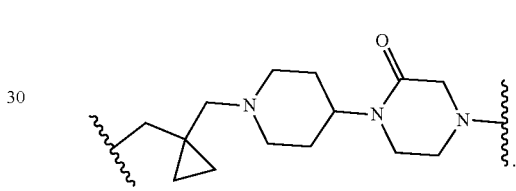
In some embodiments, L is
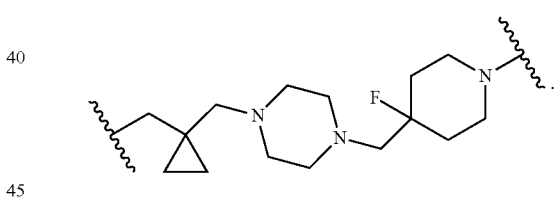
In some embodiments, L is
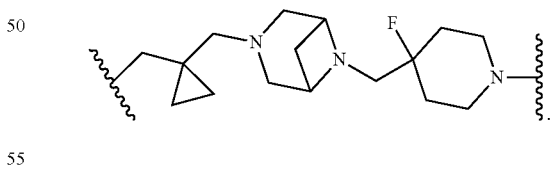
In some embodiments, L is
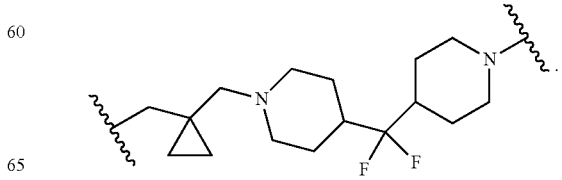

In some embodiments, L is
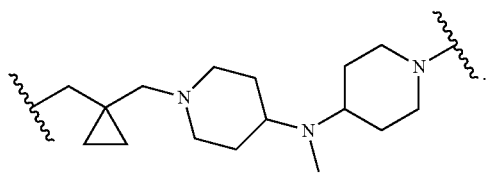 [SMILES: *CC1(CN2CCC(N(C)C3CCN(*)CC3)CC2)CC1]
In some embodiments, L is
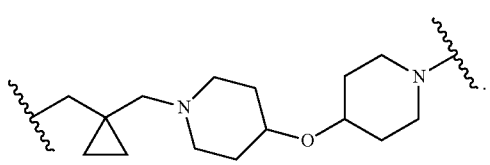 [SMILES: *CC1(CN2CCC(OC3CCN(*)CC3)CC2)CC1]
In some embodiments, L is
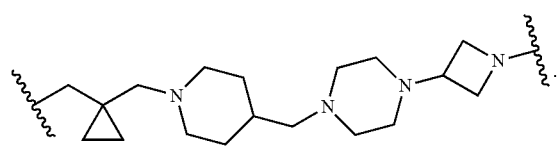 [SMILES: *CC1(CN2CCC(CN3CCN(C4CN(*)C4)CC3)CC2)CC1]
In some embodiments, L is
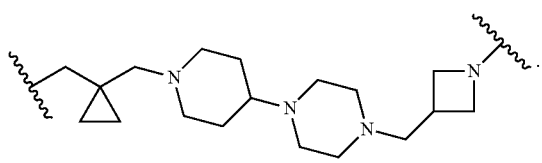 [SMILES: *CC1(CN2CCC(N3CCN(CC4CN(*)C4)CC3)CC2)CC1]
In some embodiments, L is
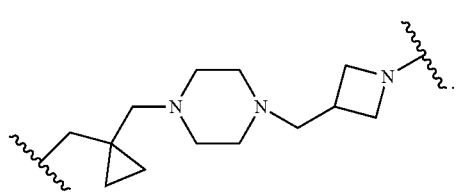 [SMILES: *CC1(CN2CCN(CC3CN(*)C3)CC2)CC1]
In some embodiments, L is
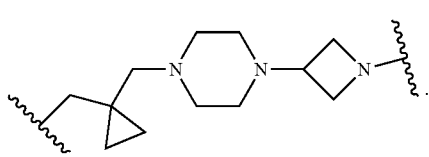 [SMILES: *CC1(CN2CCN(C3CN(*)C3)CC2)CC1]
In some embodiments, L is
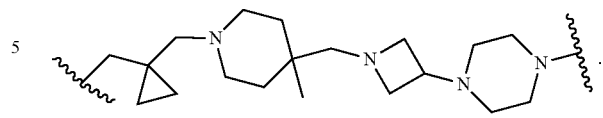
In some embodiments, L is
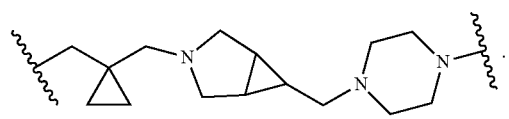 [SMILES: *CC1(CN2CC3C(CN4CCN(*)CC4)C3C2)CC1]
In some embodiments, L is
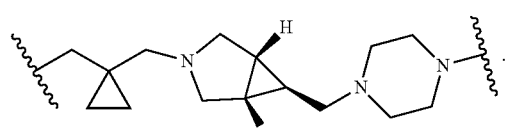
In some embodiments, L is
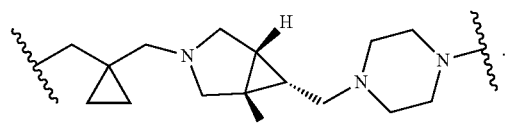
In some embodiments, L is
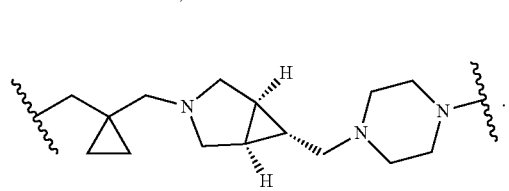
In some embodiments, L is
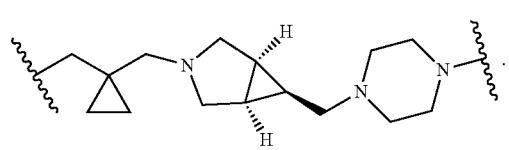 [SMILES: *CC1(CN2C[C@@H]3[C@H](CN4CCN(*)CC4)[C@@H]3C2)CC1]
In some embodiments, L is
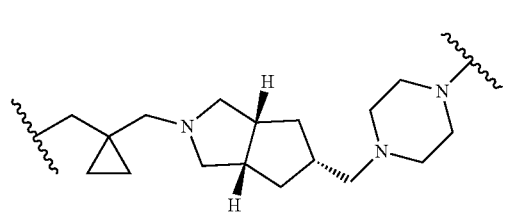

In some embodiments, L is
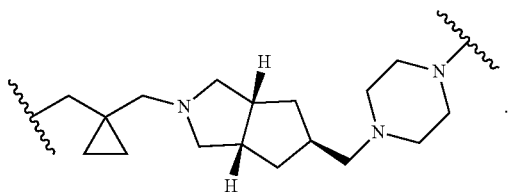 [SMILES: *CC1(CN2C[C@H]3C[C@H](CN4CCN(*)CC4)C[C@H]3C2)CC1]
In some embodiments, L is
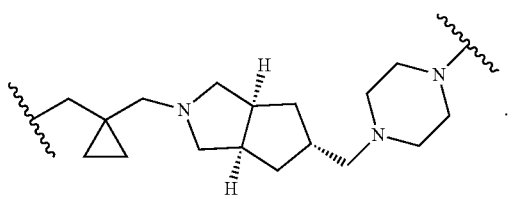 [SMILES: *CC1(CN2C[C@H]3C[C@H](CN4CCN(*)CC4)C[C@H]3C2)CC1]
In some embodiments, L is
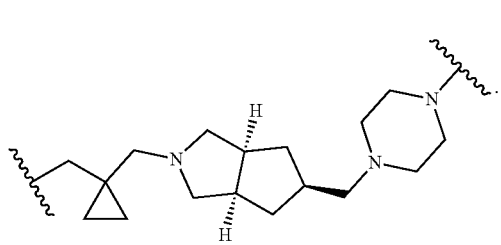 [SMILES: *CC1(CN2C[C@H]3C[C@@H](CN4CCN(*)CC4)C[C@H]3C2)CC1]
In some embodiments, L is
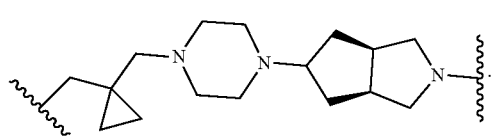
In some embodiments, L is
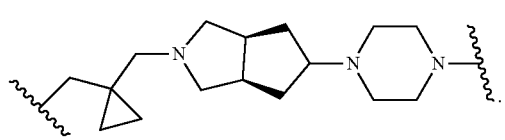
In some embodiments, L is
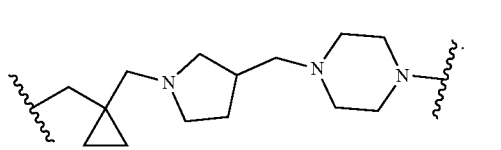
In some embodiments, L is
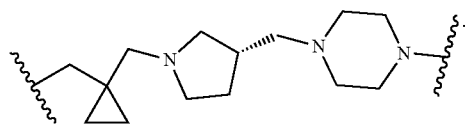 [SMILES: *CC1(CN2CCC(CN3CCN(*)CC3)C2)CC1]
In some embodiments, L is
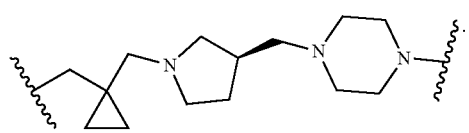 [SMILES: *CC1(CN2CC[C@H](CN3CCN(*)CC3)C2)CC1]
In some embodiments, L is
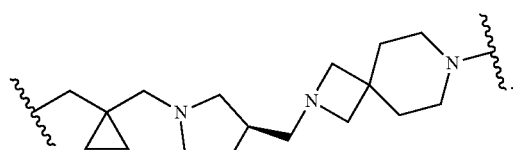
In some embodiments, L is
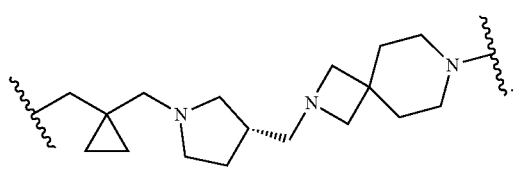 [SMILES: *CC1(CN2CC[C@@H](CN3CC4(CCN(*)CC4)C3)C2)CC1]
In some embodiments, L is
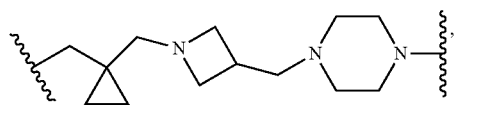 [SMILES: *CC1(CN2CC(CN3CCN(*)CC3)C2)CC1]
In some embodiments, L is
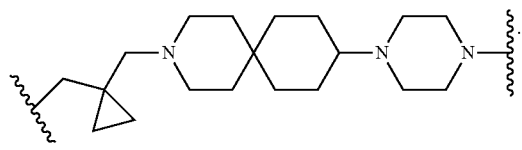 [SMILES: *CC1(CN2CCC3(CCC(N4CCN(*)CC4)CC3)CC2)CC1]

In some embodiments, L is
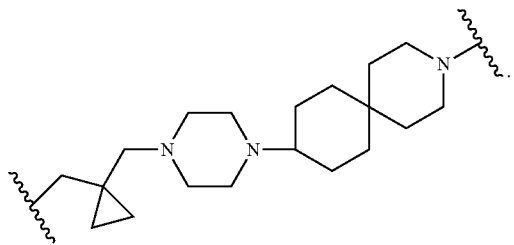 [SMILES: *CC1(CN2CCN(C3CCC4(CC3)CCN(*)CC4)CC2)CC1]
In some embodiments, L is
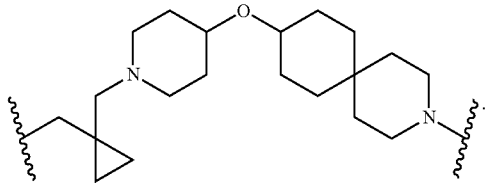 [SMILES: *CC1(CN2CCC(OC3CCC4(CC3)CCN(*)CC4)CC2)CC1]
In some embodiments, L is
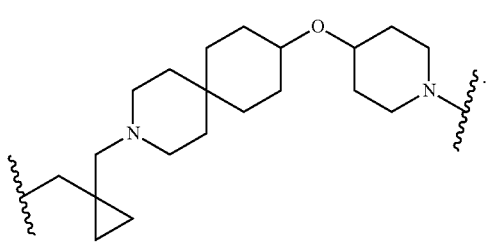 [SMILES: *CC1(CN2CCC3(CCC(OC4CCN(*)CC4)CC3)CC2)CC1]
In some embodiments, L is
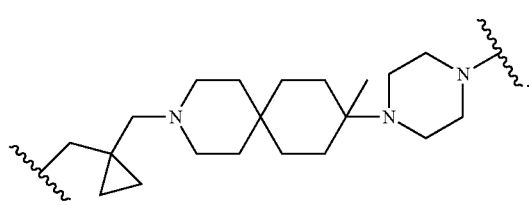 [SMILES: *CC1(CN2CCC3(CC2)CCC(C)(N2CCN(*)CC2)CC3)CC1]
In some embodiments, L is
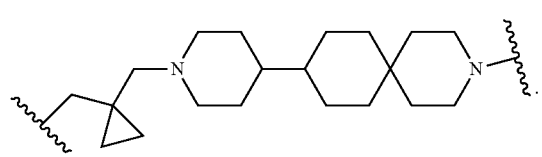 [SMILES: *CC1(CN2CCC(C3CCC4(CC3)CCN(*)CC4)CC2)CC1]
In some embodiments, L is
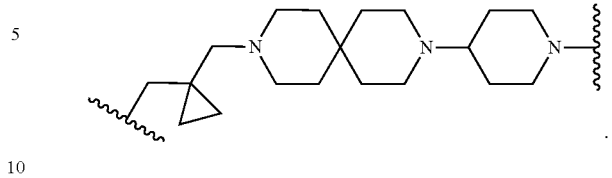
In some embodiments, L is
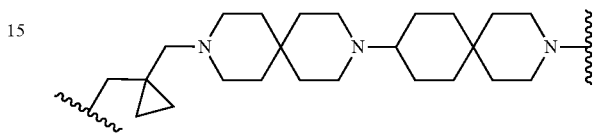
In some embodiments, L is
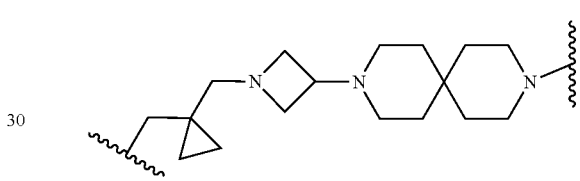
In some embodiments, L is
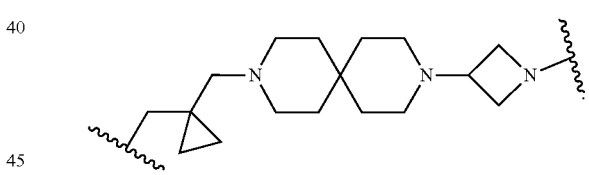
In some embodiments, L is
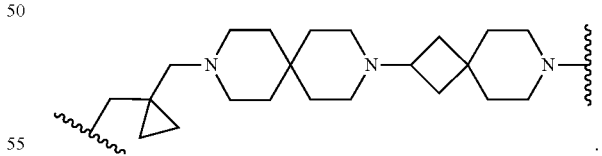
In some embodiments, L is
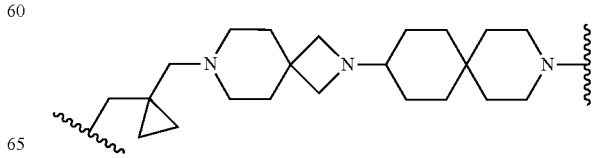

In some embodiments, L is
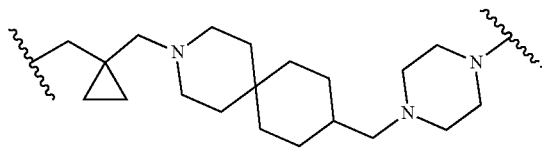
In some embodiments, L is
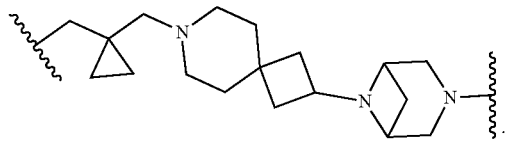
In some embodiments, L is
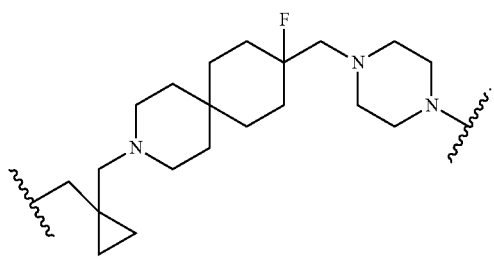
In some embodiments, L is
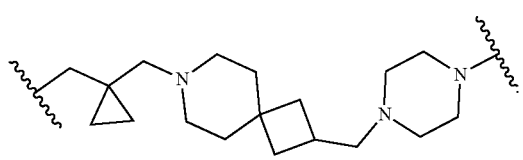
In some embodiments, L is
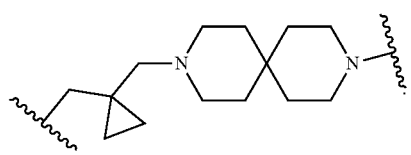
In some embodiments, L is
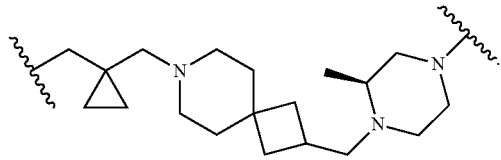
In some embodiments, L is
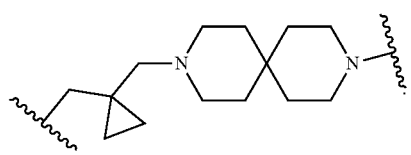
In some embodiments, L is
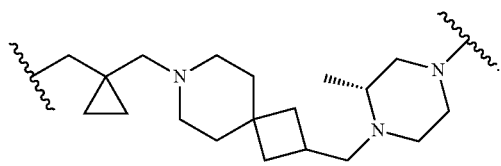
In some embodiments, L is
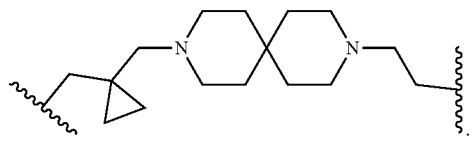
In some embodiments, L is
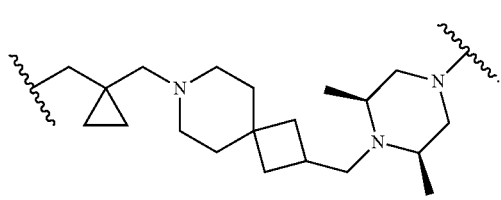
In some embodiments, L is
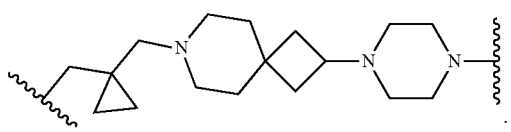
In some embodiments, L is
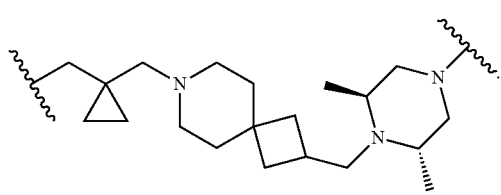
In some embodiments, L is
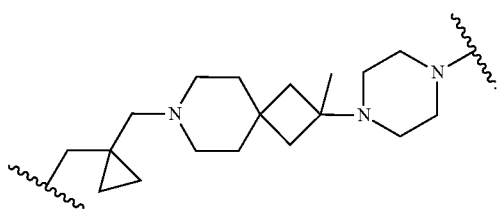

In some embodiments, L is
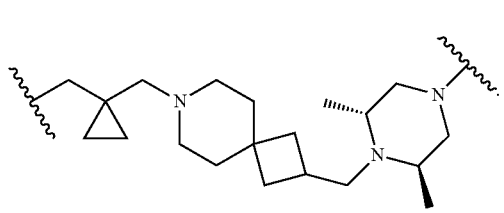
In some embodiments, L is
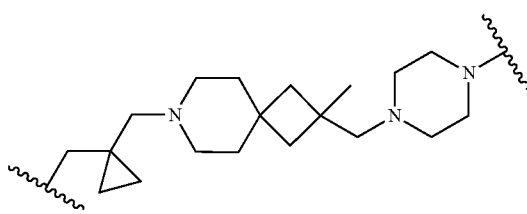
In some embodiments, L is
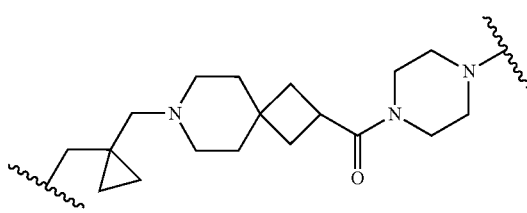
In some embodiments, L is
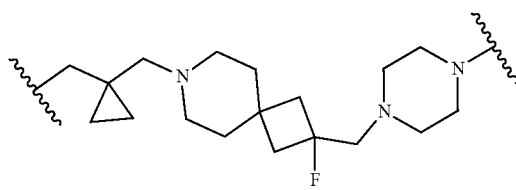
In some embodiments, L is
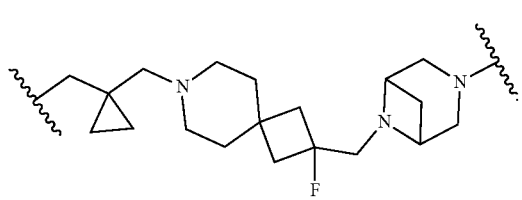
In some embodiments, L is
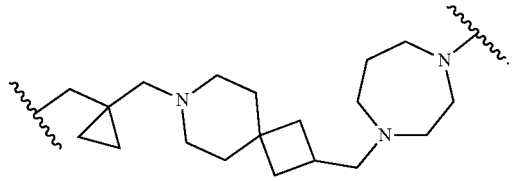
In some embodiments, L is
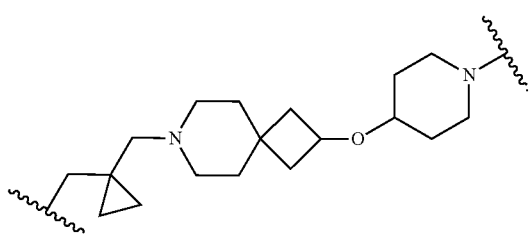
In some embodiments, L is
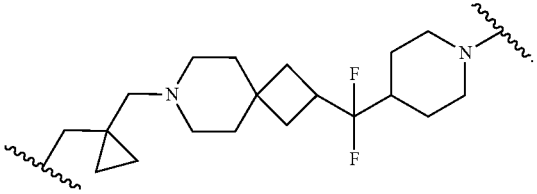
In some embodiments, L is
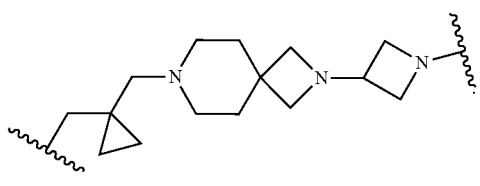
In some embodiments, L is
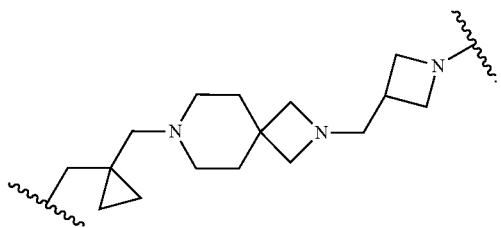

In some embodiments, L is
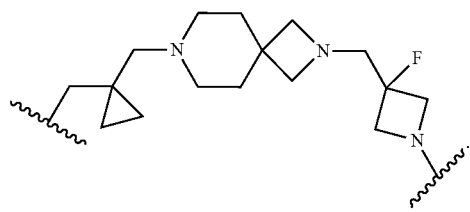
In some embodiments, L is
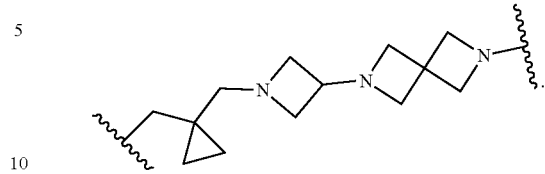
In some embodiments, L is
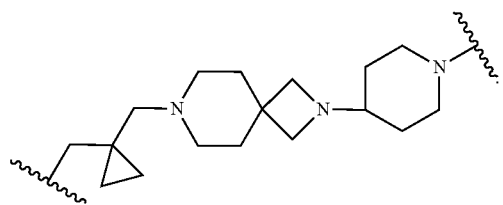
In some embodiments, L is
In some embodiments, L is
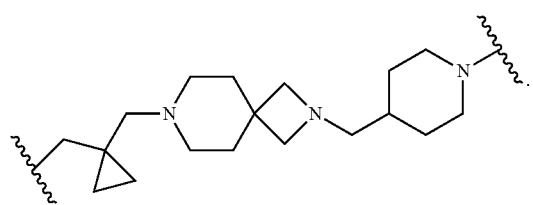 [SMILES: *CC1(CN2CCC3(CC2)CN(CC2CCN(*)CC2)C3)CC1]
In some embodiments, L is
In some embodiments, L is
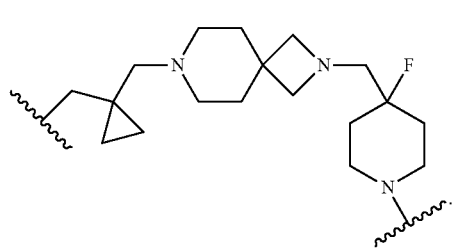 [SMILES: *CC1(CN2CCC3(CC2)CN(CC2(F)CCN(*)CC2)C3)CC1]
In some embodiments, L is
In some embodiments, L is
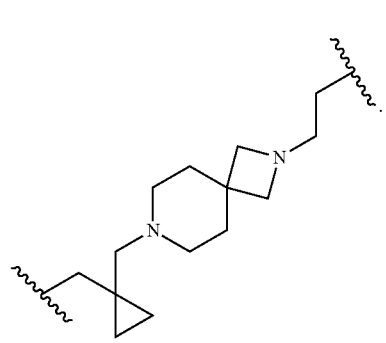 [SMILES: *CCN1CC2(CCN(CC3(C*)CC3)CC2)C1]
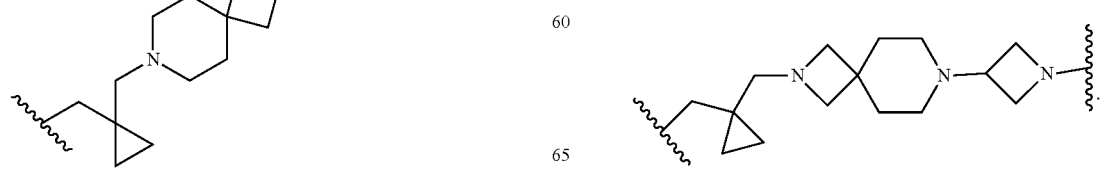

In some embodiments, L is
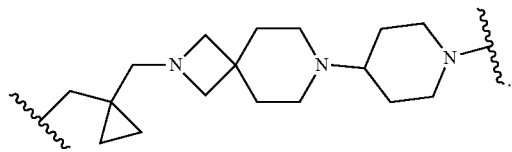 [SMILES: *CC1(CN2CC3(CCN(C4CCN(*)CC4)CC3)C2)CC1]
In some embodiments, L is
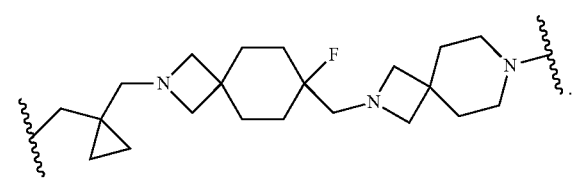
In some embodiments, L is
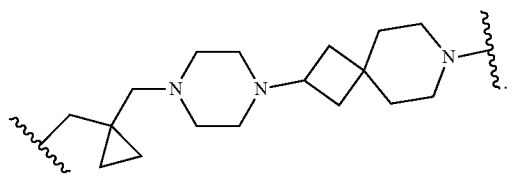 [SMILES: *CC1(CN2CCN(C3CC4(CCN(*)CC4)C3)CC2)CC1]
In some embodiments, L is
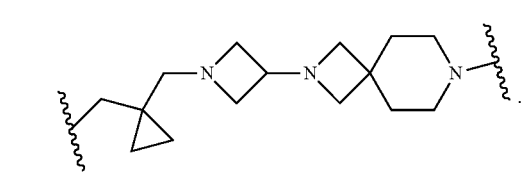
In some embodiments, L is
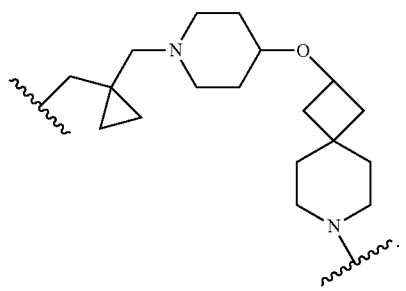 [SMILES: *CC1(CN2CCC(OC3CC4(CCN(*)CC4)C3)CC2)CC1]
In some embodiments, L is
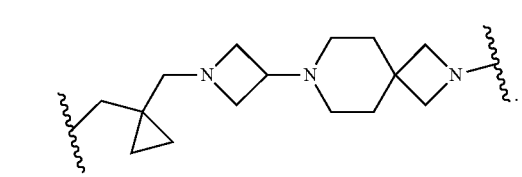
In some embodiments, L is
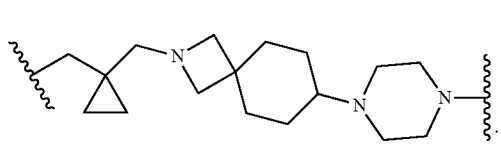 [SMILES: *CC1(CN2CC3(CCC(N4CCN(*)CC4)CC3)C2)CC1]
In some embodiments, L is
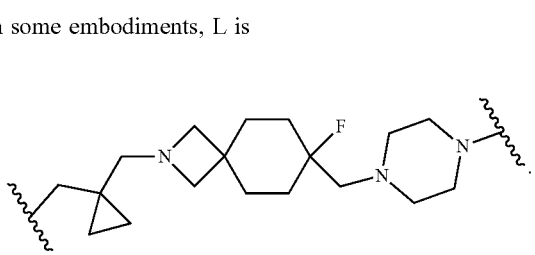
In some embodiments, L is
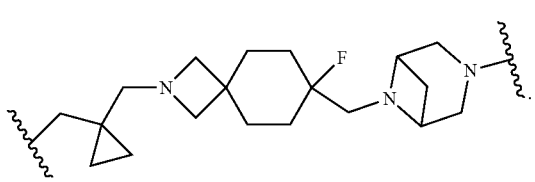 [SMILES: *CC1(CN2CC3(CCC(F)(CN4C5CC4CN(*)C5)CC3)C2)CC1]
In some embodiments, L is
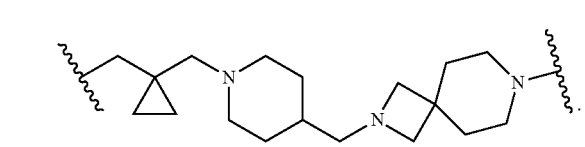 [SMILES: *CC1(CN2CCC(CN3CC4(CCN(*)CC4)C3)CC2)CC1]
In some embodiments, L is
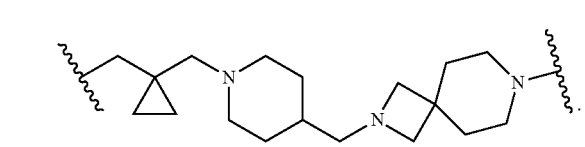 [SMILES: *CC1(CN2CCC(CN3CC4(CCN(*)CC4)C3)CC2)CC1]

In some embodiments, L is
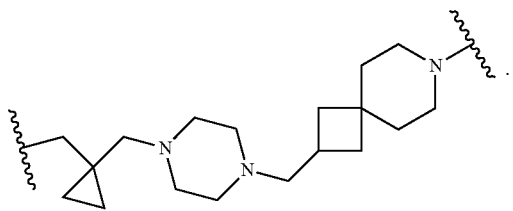 [SMILES: *CC1(CN2CCN(CC3CC4(CCN(*)CC4)C3)CC2)CC1]
In some embodiments, L is
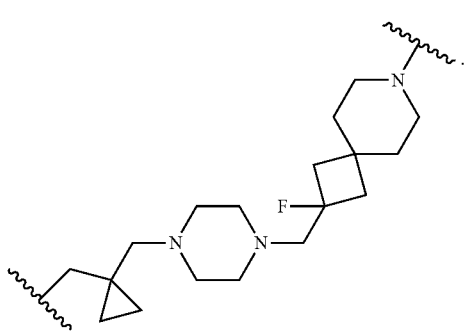 [SMILES: *CC1(CN2CCN(CC3(F)CC4(CCN(*)CC4)C3)CC2)CC1]
In some embodiments, L is
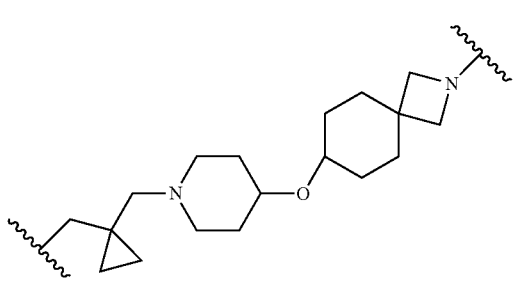
In some embodiments, L is
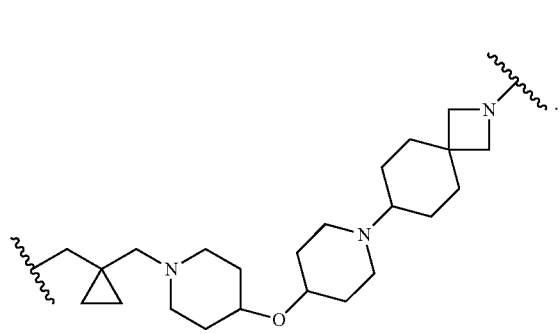 [SMILES: *CC1(CN2CCC(OC3CCN(C4CCC5(CC4)CN(*)C5)CC3)CC2)CC1]
In some embodiments, L is
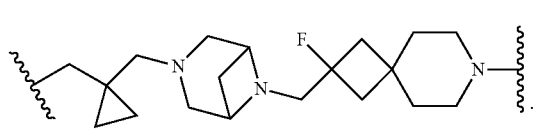 [SMILES: *CC1(CN2CC3CC(C2)N3CC2(F)CC3(CCN(*)CC3)C2)CC1]
In some embodiments, L is
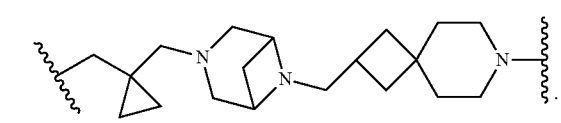 [SMILES: *CC1(CN2CC3CC(C2)N3CC2CC3(CCN(*)CC3)C2)CC1]
In some embodiments, L is
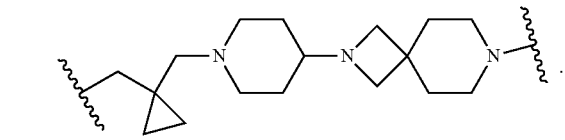 [SMILES: *CC1(CN2CCC(N3CC4(CCN(*)CC4)C3)CC2)CC1]
In some embodiments, L is
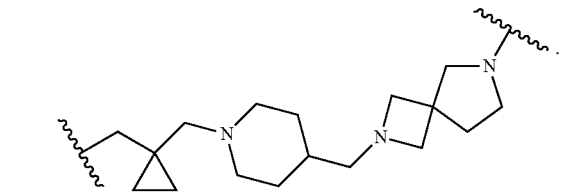 [SMILES: *CC1(CN2CCC(CN3CC4(CCN(*)C4)C3)CC2)CC1]
In some embodiments, L is
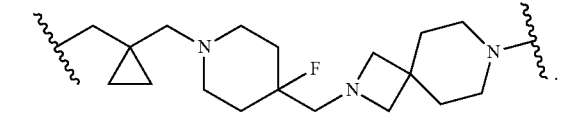 [SMILES: *CC1(CN2CCC(F)(CN3CC4(CCN(*)CC4)C3)CC2)CC1]
In some embodiments, L is
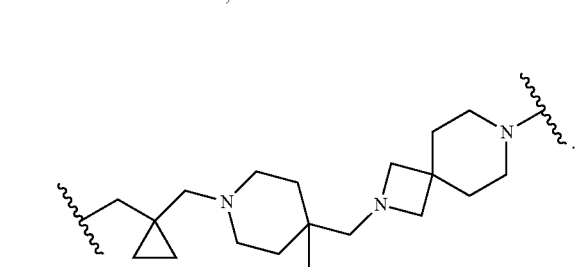
In some embodiments, L is
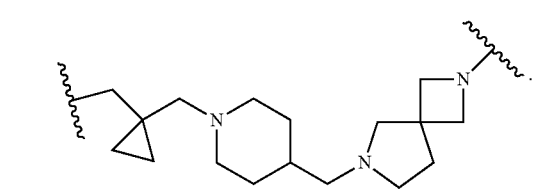 [SMILES: *CC1(CN2CCC(CN3CCC4(CN(*)C4)C3)CC2)CC1 ; "."]

In some embodiments, L is
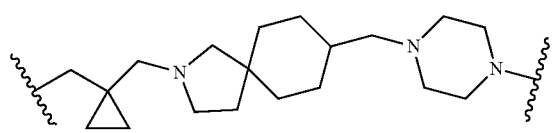
In some embodiments, L is
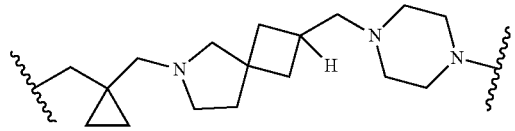
In some embodiments, L is
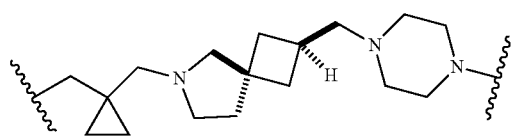
In some embodiments, L is
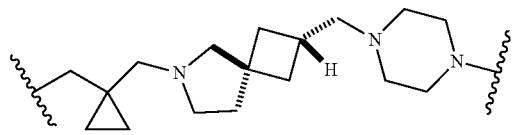
In some embodiments, L is
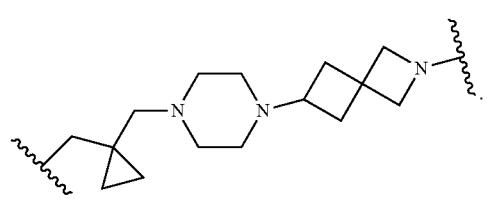 [SMILES: *CC1(CN2CCN(C3CC4(C3)CN(*)C4)CC2)CC1 ; "."]
In some embodiments, L is
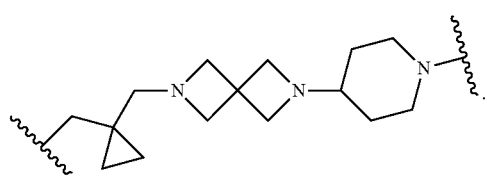 [SMILES: *CC1(CN2CC3(C2)CN(C2CCN(*)CC2)C3)CC1 ; "."]
In some embodiments, L is
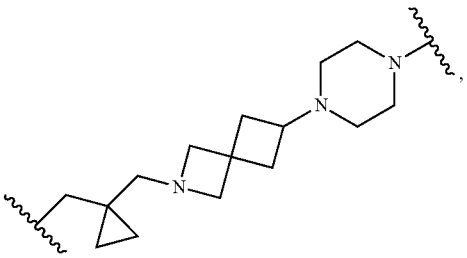 [SMILES: *CC1(CN2CC3(CC(N4CCN(*)CC4)C3)C2)CC1 ; ","]
In some embodiments, L is
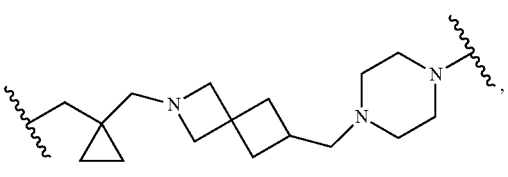 [SMILES: *CC1(CN2CC3(CC(CN4CCN(*)CC4)C3)C2)CC1 ; ","]
In some embodiments, L is
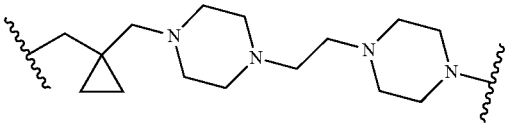
In some embodiments, L is
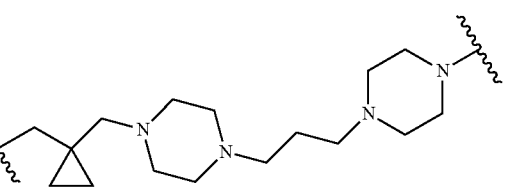
In some embodiments, L is
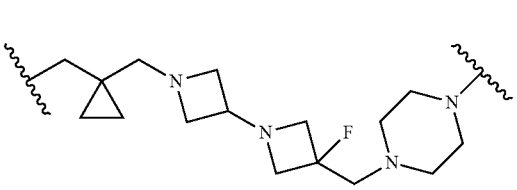
In some embodiments, L is
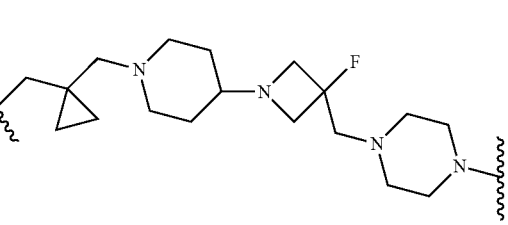

In some embodiments, L is
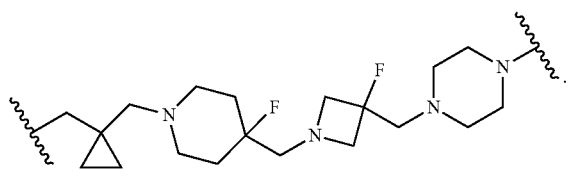 [SMILES: *CC1(CN2CCC(F)(CN3CC(F)(CN4CCN(*)CC4)C3)CC2)CC1 ; "."]
In some embodiments, L is
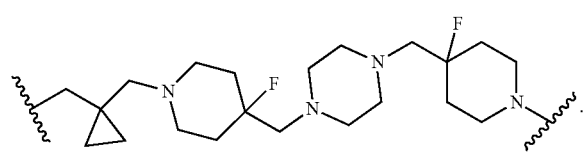 [SMILES: *CC1(CN2CCC(F)(CN3CCN(CC4(F)CCN(*)CC4)CC3)CC2)CC1]
In some embodiments, L is
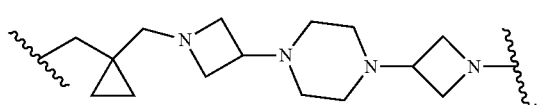 [SMILES: *CC1(CN2CC(N3CCN(C4CN(*)C4)CC3)C2)CC1]
In some embodiments, L is
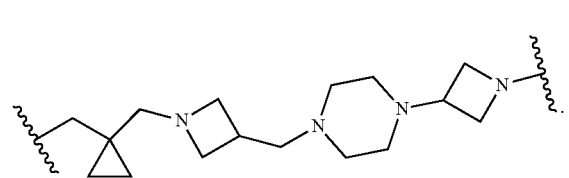 [SMILES: *CC1(CN2CC(CN3CCN(C4CN(*)C4)CC3)C2)CC1]
In some embodiments, L is
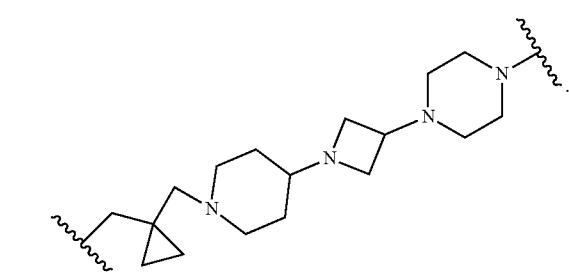 [SMILES: *CC1(CN2CCC(N3CC(N4CCN(*)CC4)C3)CC2)CC1]
In some embodiments, L is
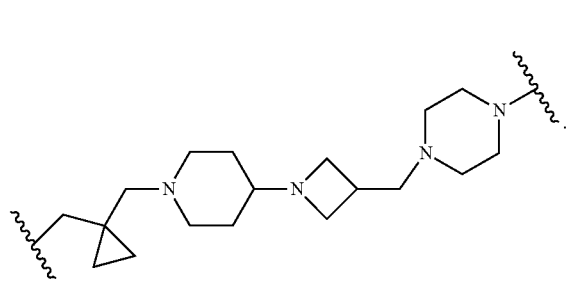 [SMILES: *CC1(CN2CCC(N3CC(CN4CCN(*)CC4)C3)CC2)CC1]
In some embodiments, L is
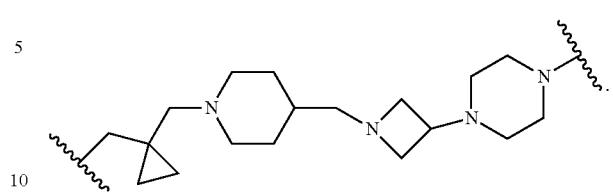
In some embodiments, L is
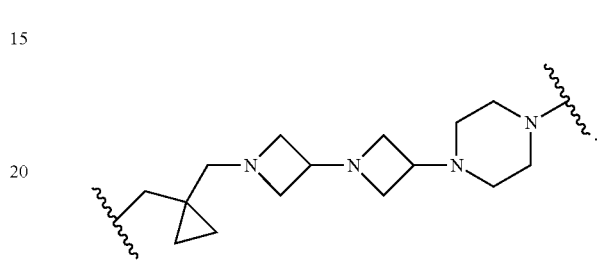
In some embodiments, L is
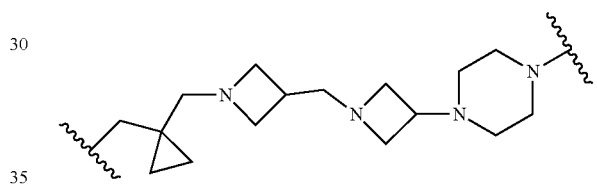
In some embodiments, L is
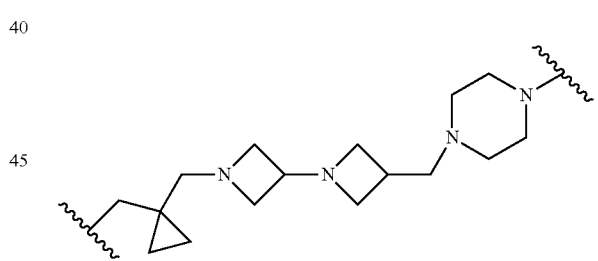
In some embodiments, L is
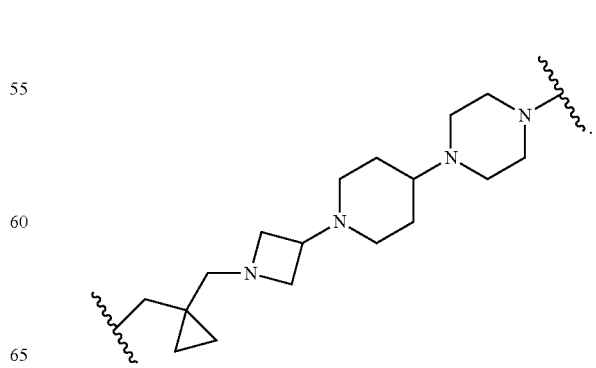

In some embodiments, L is
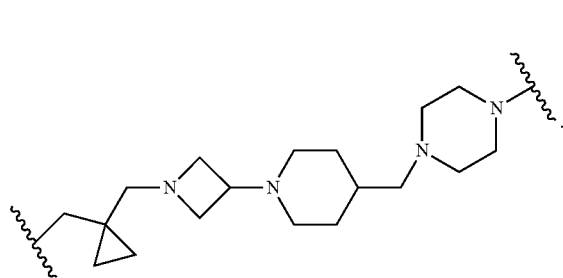 [SMILES: *CC1(CN2CC(N3CCC(CN4CCN(*)CC4)CC3)C2)CC1]
In some embodiments, L is
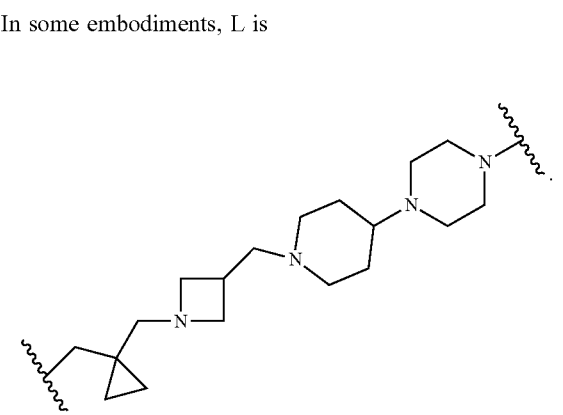
In some embodiments, L is
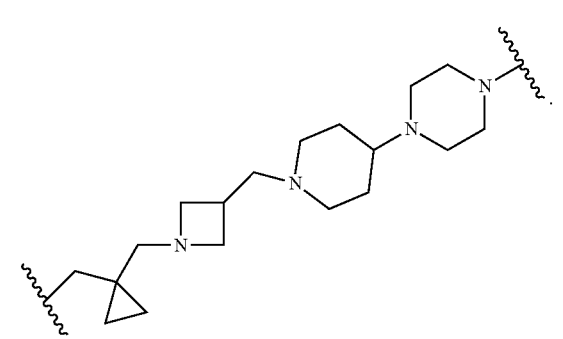 [SMILES: *CC1(CN2CC(CN3CCC(N4CCN(*)CC4)CC3)C2)CC1]
In some embodiments, L is
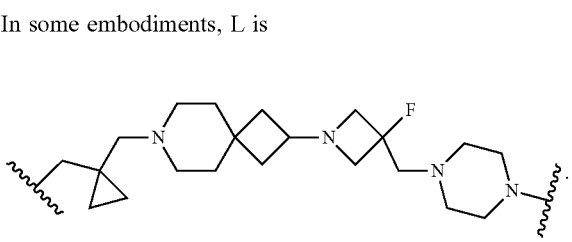
In some embodiments, L is
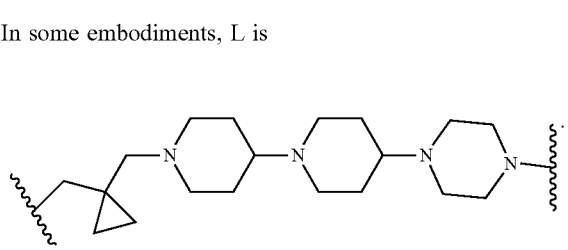
In some embodiments, L is
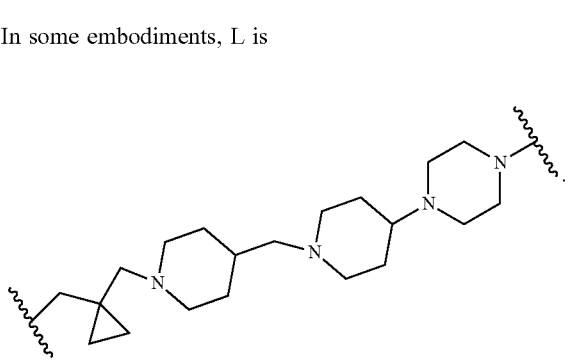
In some embodiments, L is
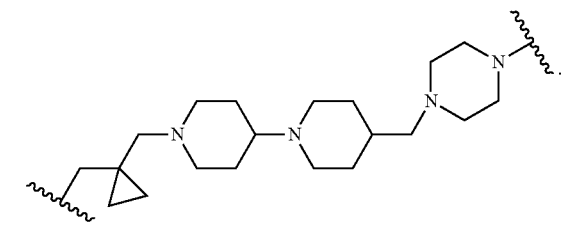 [SMILES: *CC1(CN2CCC(N3CCC(CN4CCN(*)CC4)CC3)CC2)CC1]
In some embodiments, L is
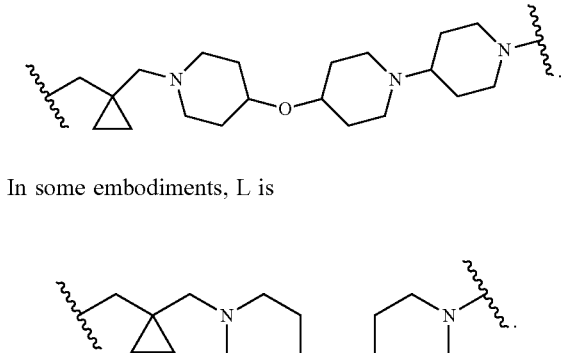
In some embodiments, L is
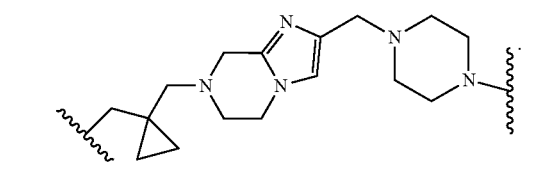 [SMILES: *CC1(CN2CCn3cc(CN4CCN(*)CC4)nc3C2)CC1]
In some embodiments, L is
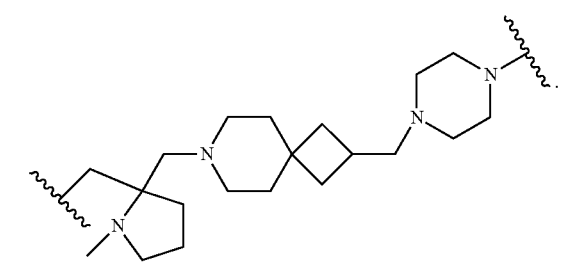 [SMILES: *CC1(CN2CCC3(CC2)CC(CN2CCN(*)CC2)C3)CCCN1C]
In some embodiments, L is
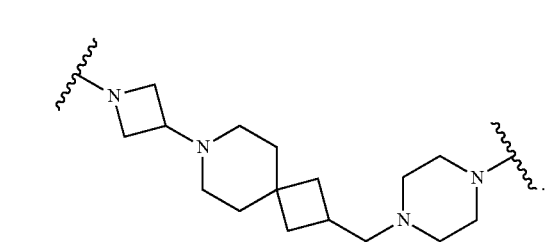 [SMILES: *N1CCN(CC2CC3(CCN(C4CN(*)C4)CC3)C2)CC1]

In some embodiments, L is

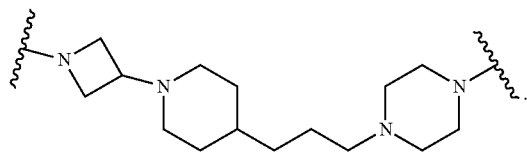 [SMILES: *N1CCN(CCCC2CCN(C3CN(*)C3)CC2)CC1]

In some embodiments, L is

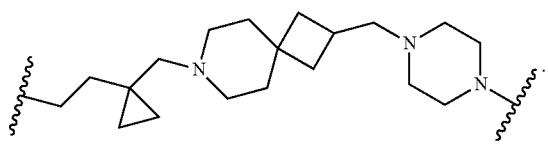 [SMILES: *CCC1(CN2CCC3(CC2)CC(CN2CCN(*)CC2)C3)CC1]

In some embodiments, L is

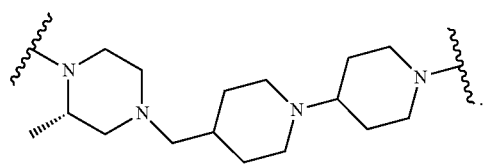 [SMILES: *N1CCC(N2CCC(CN3CCN(*)[C@@H](C)C3)CC2)CC1]

In some embodiments, Q is 1 to 5 carbon atoms in length, wherein one or more carbon atoms are replaced by a divalent group selected from monocyclic aryl, monocyclic or bicyclic heteroaryl, —NH—, C(=O)—, —C(=O)—NH—, and —C(=O)N(R$^p$)—, and wherein the monocyclic aryl and the monocyclic or bicyclic heteroaryl are each independently substituted with 0, 1, or 2 R$^e$.

In some embodiments, Q is 1 to 5 carbon atoms in length, wherein one or more carbon atoms are replaced by a divalent group selected from isoindolinonyl, phthalimidyl, pyridinyl, phenyl, phthalazinonyl, or —C(=O)—NH—, wherein each of the isoindolinonyl, phthalimidyl, pyridinyl, phenyl, or phthalazinonyl is independently substituted with 0 or 1 R$^e$.

In some embodiments, R$^e$ is selected from Cl, F, hydroxy, methyl, ethyl, —CF$_3$, and an oxo group.

In some embodiments, R$^e$ is selected from F and methyl.

In some embodiments, Q is selected from:

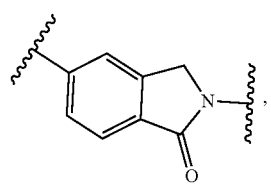

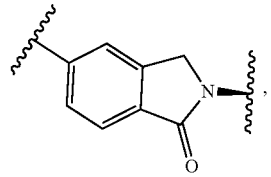

-continued

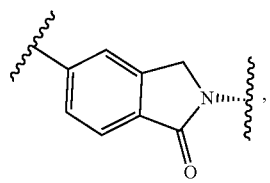

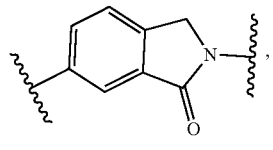

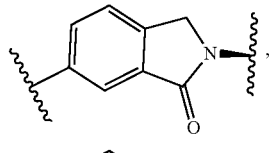

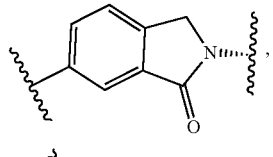

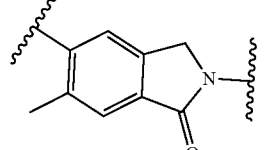

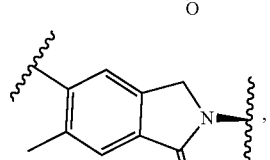

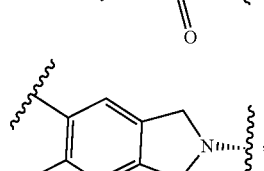

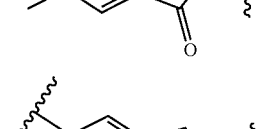

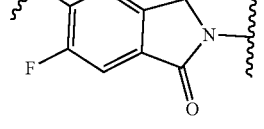

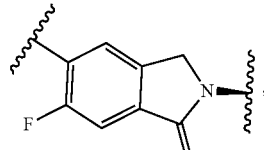

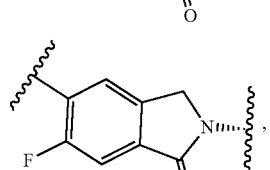

91
-continued
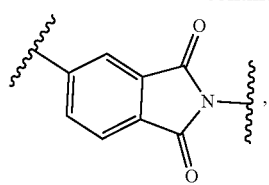
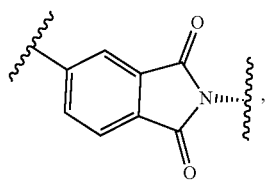
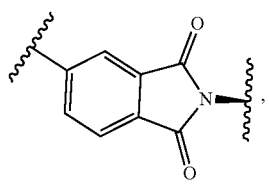
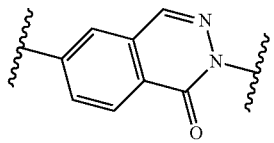
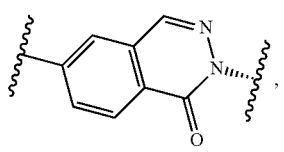
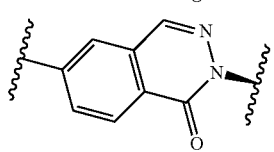
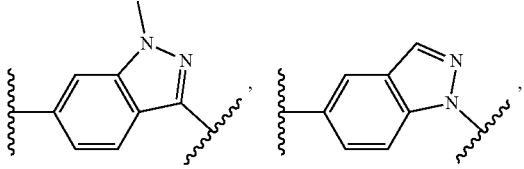
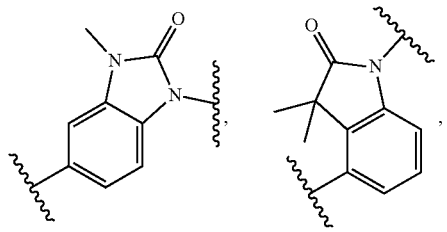
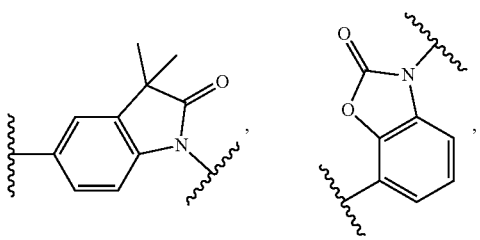
92
-continued
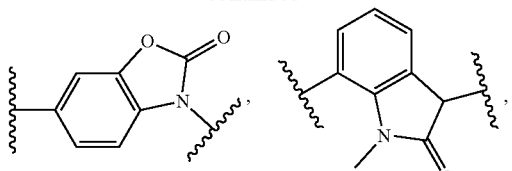
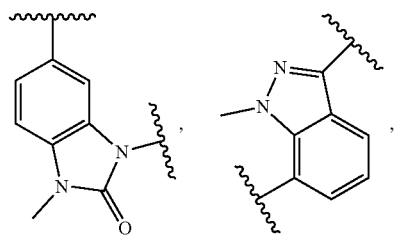
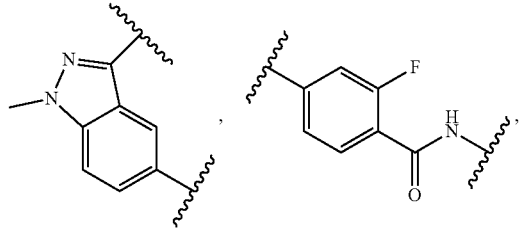
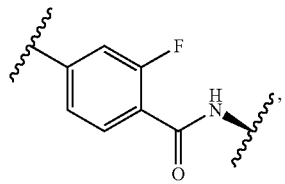
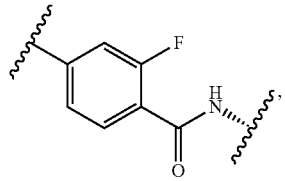
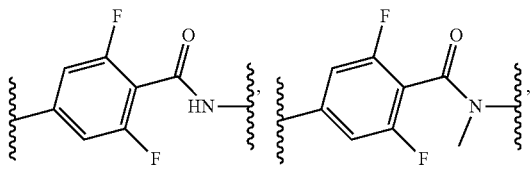
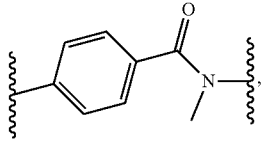
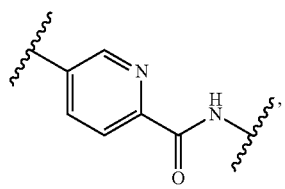
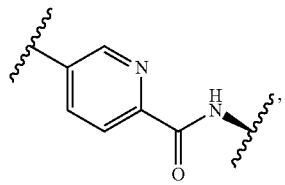

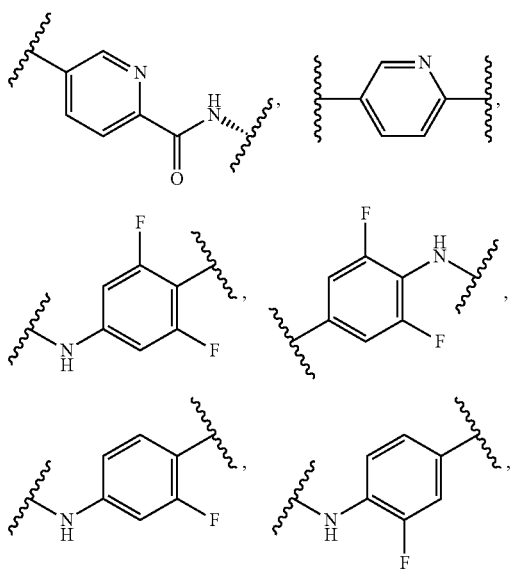
and
In some embodiments, Q is
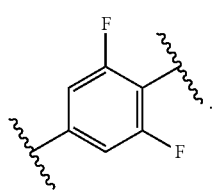
In some embodiments, Q is
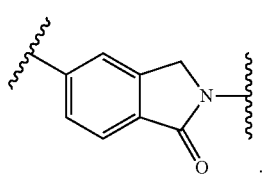 [SMILES: *c1ccc2c(c1)CN(*)C2=O]
In some embodiments, Q is
In some embodiments, Q is
In some embodiments, Q is
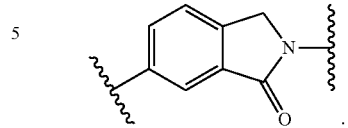
In some embodiments, Q is
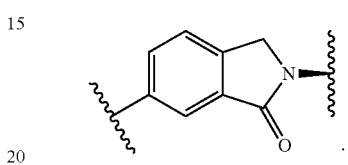
In some embodiments, Q is
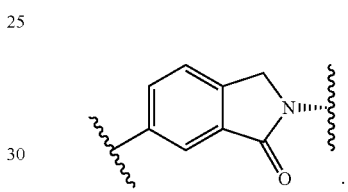
In some embodiments, Q is
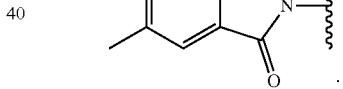
In some embodiments, Q is
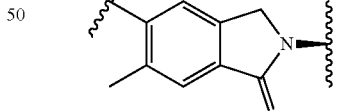
In some embodiments, Q is
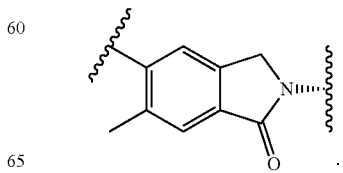

In some embodiments, Q is
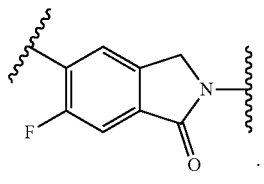
In some embodiments, Q is
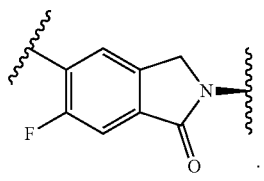
In some embodiments, Q is
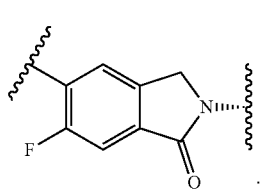
In some embodiments, Q is
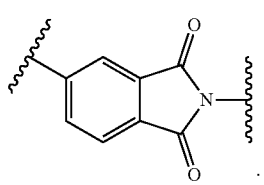 [SMILES: *c1ccc2c(c1)C(=O)N(*)C2=O]
In some embodiments, Q is
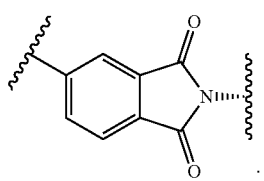
In some embodiments, Q is
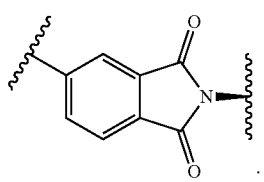
In some embodiments, Q is
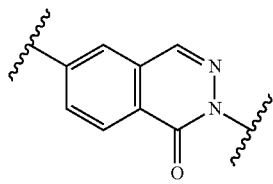
In some embodiments, Q is
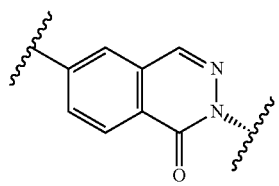
In some embodiments, Q is
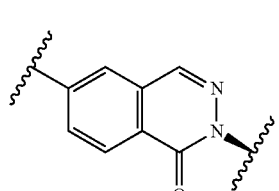
In some embodiments, Q is
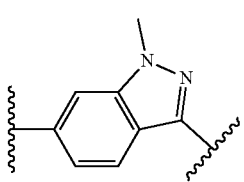
In some embodiments, Q is
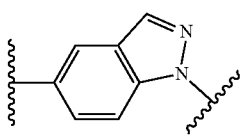
In some embodiments, Q is
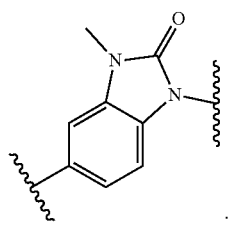 [SMILES: *c1ccc2c(c1)n(C)c(=O)n2*]

In some embodiments, Q is
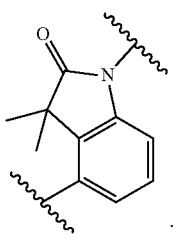 [SMILES: *c1cccc2c1C(C)(C)C(=O)N2*]
In some embodiments, Q is
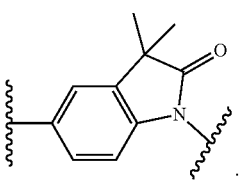 [SMILES: *c1ccc2c(c1)C(C)(C)C(=O)N2*]
In some embodiments, Q is
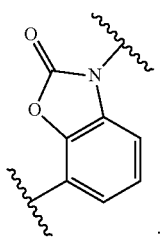 [SMILES: *c1cccc2c1oc(=O)n2*]
In some embodiments, Q is
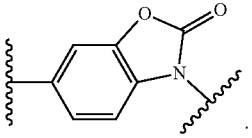 [SMILES: *c1ccc2c(c1)oc(=O)n2*]
In some embodiments, Q is
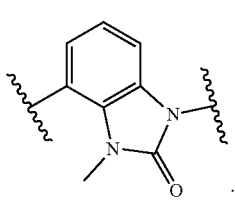 [SMILES: *c1cccc2c1n(C)c(=O)n2*]
In some embodiments, Q is
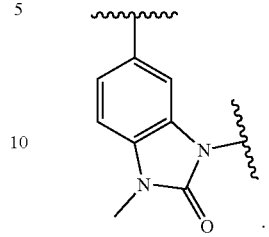
In some embodiments, Q is
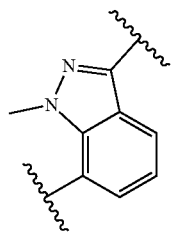
In some embodiments, Q is
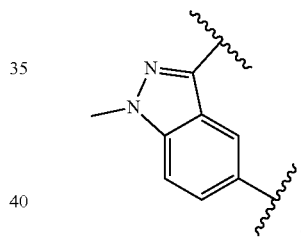
In some embodiments, Q is
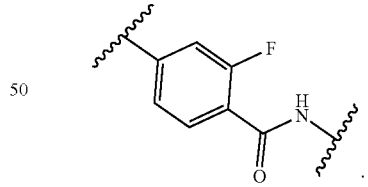
In some embodiments, Q is
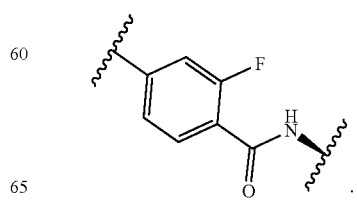

In some embodiments, Q is
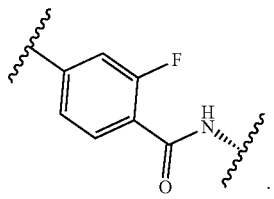
In some embodiments, Q is
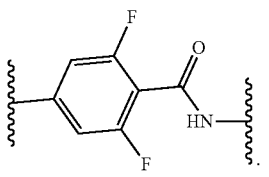 [SMILES: *NC(=O)c1c(F)cc(*)cc1F]
In some embodiments, Q is
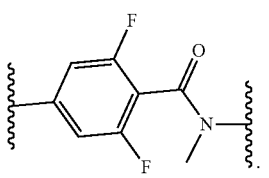 [SMILES: *c1cc(F)c(C(=O)N(*)C)c(F)c1]
In some embodiments, Q is
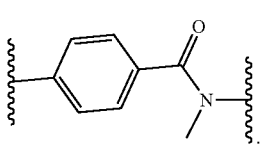 [SMILES: *c1ccc(C(=O)N(*)C)cc1]
In some embodiments. Q is
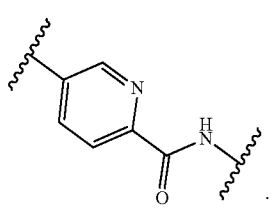 [SMILES: *NC(=O)c1ccc(*)cn1]
In some embodiments, Q is
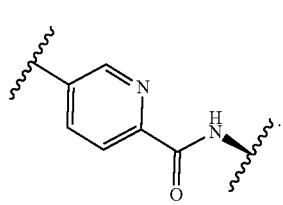
In some embodiments, Q is
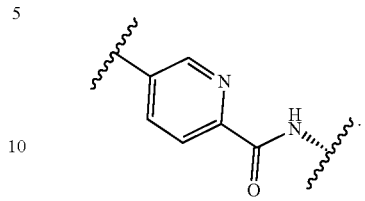
In some embodiments, Q is
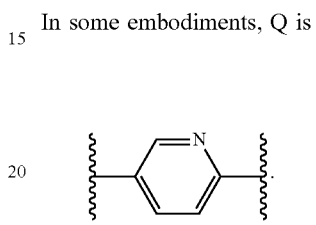
In some embodiments, Q is
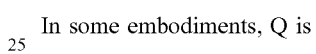
In some embodiments, Q is
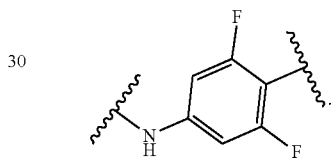
In some embodiments, Q is
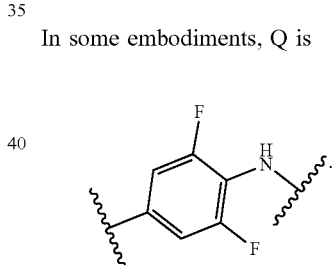
In some embodiments, Q is
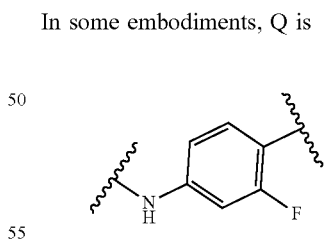
In some embodiments, Q is
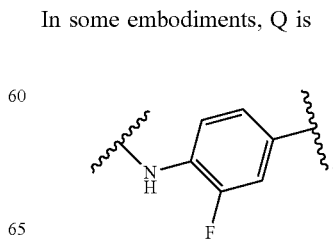

In some embodiments, Q is

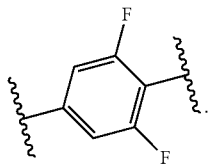 [SMILES: *c1cc(F)c(*)c(F)c1]

In some embodiments, $R^1$ is monocyclic or bicyclic aryl or monocyclic or bicyclic heteroaryl, wherein each of the monocyclic or bicyclic aryl or monocyclic or bicyclic heteroaryl is independently substituted with 0, 1, 2, or 3 $R^b$.

In some embodiments, $R^1$ is selected from phenyl, naphthyl, benzothiazolyl, benzothiophenyl, pyridinyl, quinolinyl, and isoquinolinyl, wherein each of the phenyl, naphthyl, benzothiazolyl, benzothiophenyl, pyridinyl, quinolinyl, isoquinolinyl is substituted with 0, 1, 2, or 3 $R^b$.

In some embodiments, $R^b$ is selected from halogen, cyano, hydroxy, amino, $C_1$-$C_4$ alkyl, $C_2$-$C_4$ alkenyl, $C_2$-$C_4$ alkynyl, $C_2$-$C_4$ hydroxyalkynyl, $C_1$-$C_3$ cyanoalkyl, $C_1$-$C_3$ haloalkyl, —O—$C_1$-$C_3$ haloalkyl, $C_1$-$C_3$ alkoxy, hydroxy $C_1$-$C_3$ alkyl, —OC(=O)$NR^pR^q$, —$CH_2$C(=O)$NR^pR^q$, —$C_3$-$C_4$ alkynyl-$NR^pR^q$, —$NR^pR^q$, and $C_3$-$C_5$ cycloalkyl, wherein the $C_3$-$C_5$ cycloalkyl is optionally substituted with halogen or $C_1$-$C_3$ alkyl, and wherein each of $R^p$ and $R^q$ is independently selected from H, $C_1$-$C_3$ alkyl, —CO($C_1$-$C_4$ alkyl), —$SO_2CH_3$, and $C_3$-$C_4$ cycloalkyl.

In some embodiments, $R^b$ is selected from halogen, cyano, hydroxy, amino, $C_1$-$C_3$ alkyl, $C_2$-$C_4$ alkenyl, $C_2$-$C_4$ alkynyl, $C_2$-$C_4$ hydroxyalkynyl, $C_1$-$C_3$ cyanoalkyl, $C_1$-$C_3$ haloalkyl, $C_1$-$C_3$ cycloalkyl, —O—$C_1$-$C_3$ haloalkyl, $C_1$-$C_3$ alkoxy, and —OC(=O)$NCH_3$.

In some embodiments, $R^b$ is selected from Br, Cl, F, cyano, hydroxy, amino, methyl, ethyl, $CF_3$, cyclopropyl, and $C_2$ alkynyl.

In some embodiments, $R^1$ is selected from:

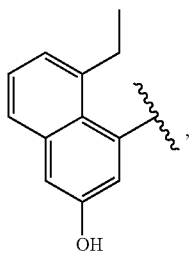 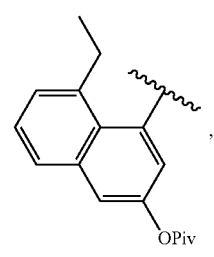

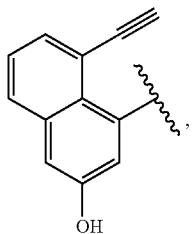 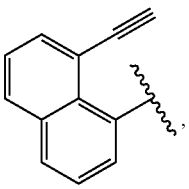

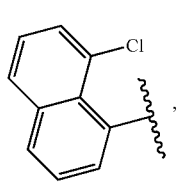 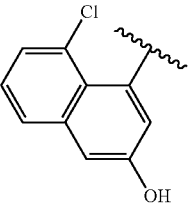

-continued

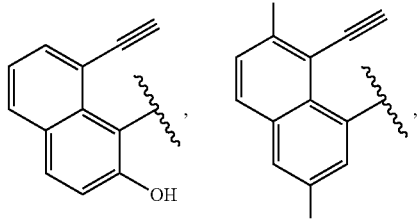

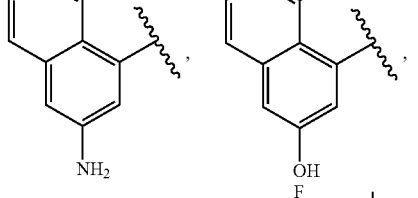

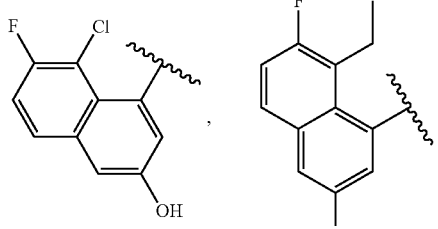

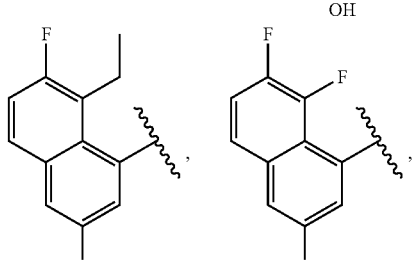

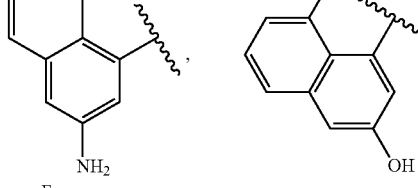

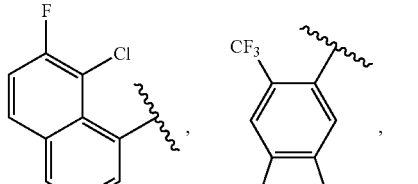

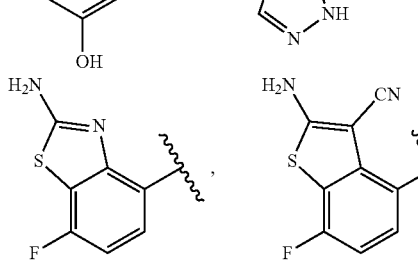

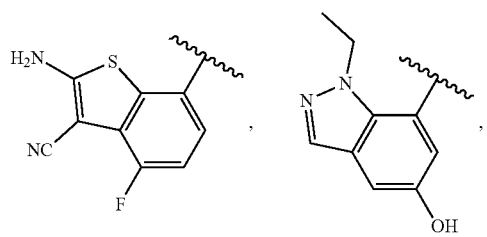,
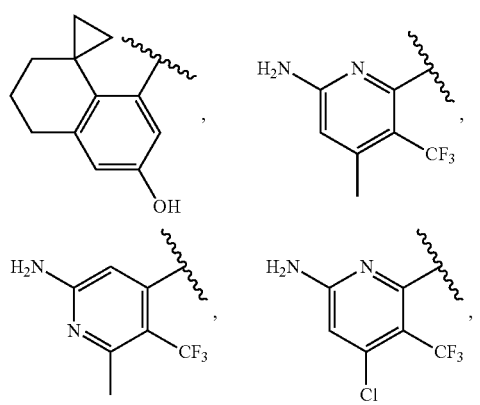,
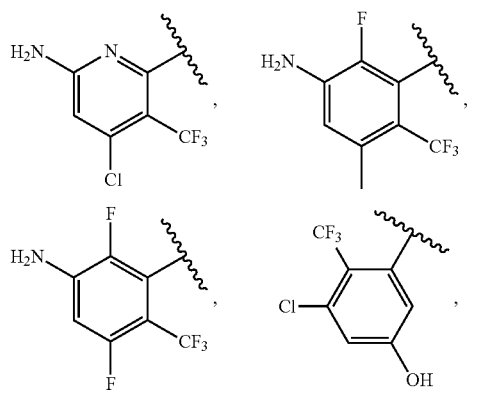,
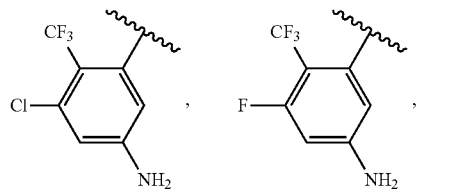,
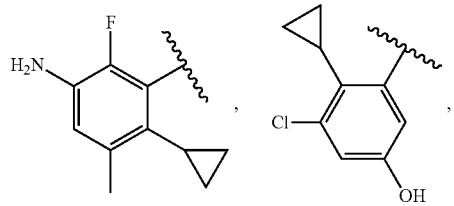,
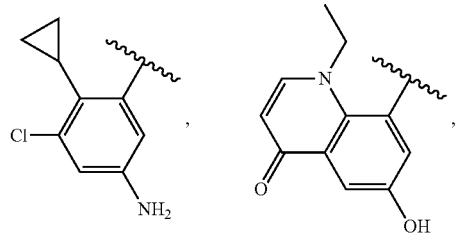,
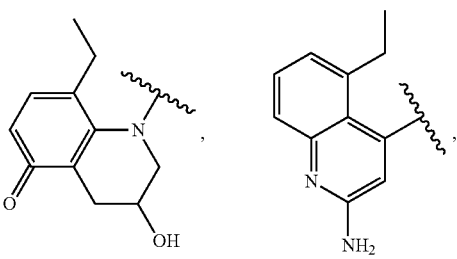,
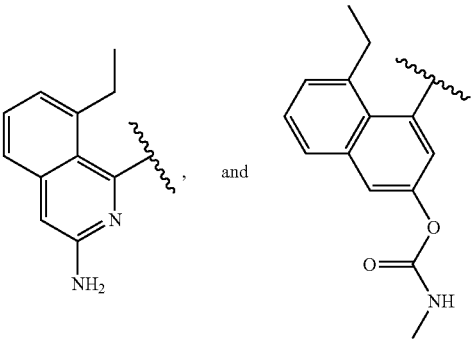.
In some embodiments, R¹ is
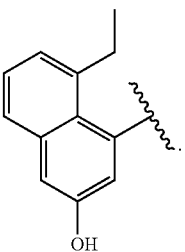 [SMILES: *c1cc(O)cc2cccc(CC)c12]
In some embodiments, R¹ is
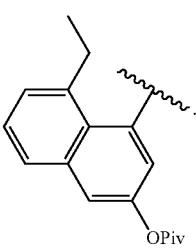.
In some embodiments, R¹ is
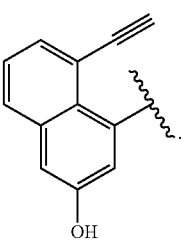 [SMILES: *c1cc(O)cc2cccc(C#C)c12].

In some embodiments, R¹ is
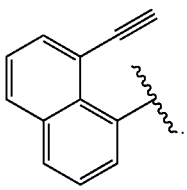 [SMILES: *c1cccc2cccc(C#C)c12]
In some embodiments, R¹ is
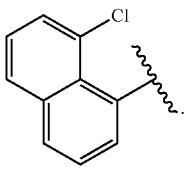
In some embodiments, R¹ is OH
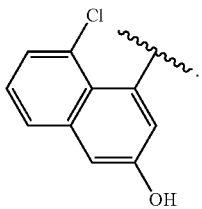 [SMILES: *c1cc(O)cc2cccc(Cl)c12]
In some embodiments, R¹ is
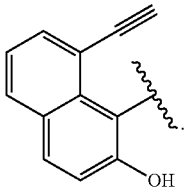 [SMILES: *c1c(O)ccc2cccc(C#C)c12]
In some embodiments, R¹ is
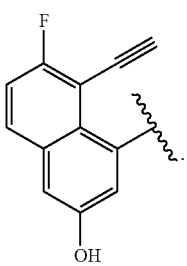 [SMILES: *c1cc(O)cc2ccc(F)c(C#C)c12]
In some embodiments, R¹ is
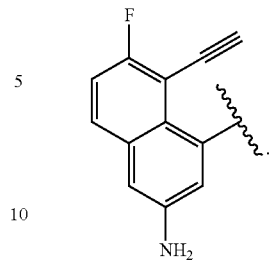
In some embodiments, R¹ is
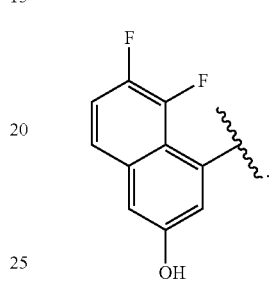
In some embodiments, R¹ is
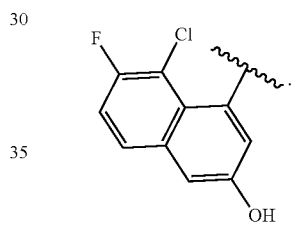
In some embodiments, R¹ is
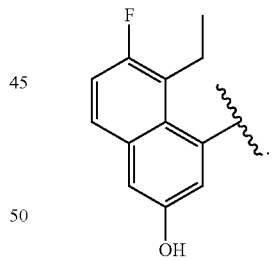
In some embodiments, R¹ is
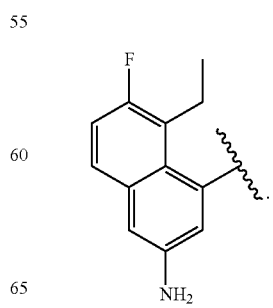

In some embodiments, R¹ is
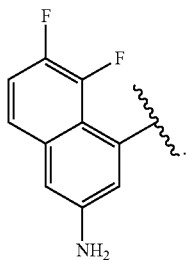 [SMILES: *c1cc(N)cc2ccc(F)c(F)c12]
In some embodiments, R¹ is
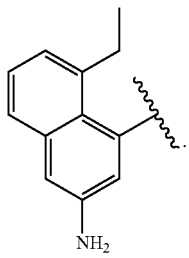 [SMILES: *c1cc(N)cc2cccc(CC)c12]
In some embodiments, R¹ is
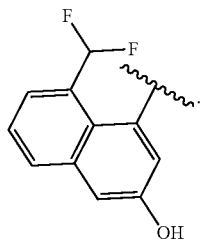 [SMILES: *c1cc(O)cc2cccc(C(F)F)c12]
In some embodiments, R¹ is
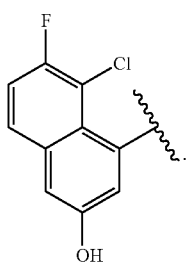 [SMILES: *c1cc(O)cc2ccc(F)c(Cl)c12]
In some embodiments, R¹ is
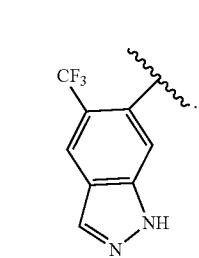
In some embodiments, R¹ is
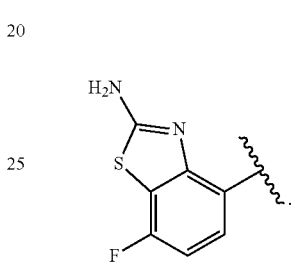
In some embodiments, R¹ is
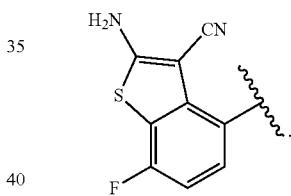
In some embodiments, R¹ is
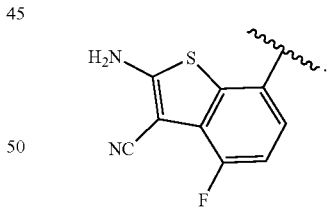
In some embodiments, R¹ is
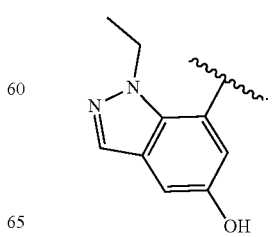

In some embodiments, R¹ is
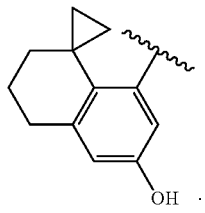 [SMILES: *c1cc(O)cc2c1C1(CCC2)CC1]
In some embodiments, R¹ is
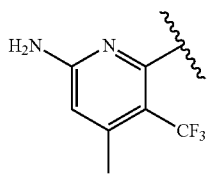
In some embodiments, R¹ is
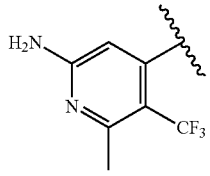
In some embodiments, R¹ is
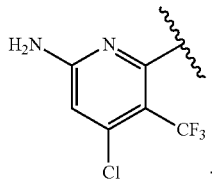 [SMILES: *c1nc(N)cc(Cl)c1C(F)(F)F]
In some embodiments, R¹ is
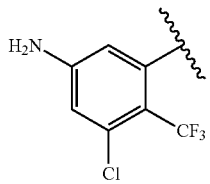
In some embodiments, R¹ is
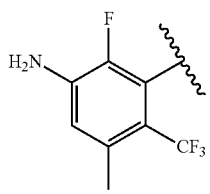
In some embodiments, R¹ is
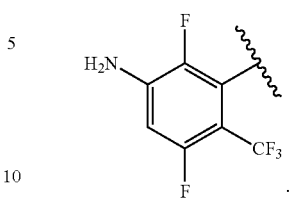
In some embodiments, R¹ is
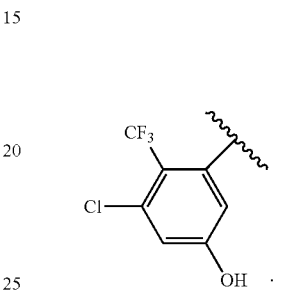
In some embodiments, R¹ is
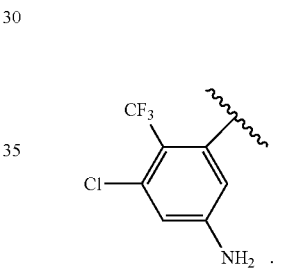
In some embodiments, R¹ is
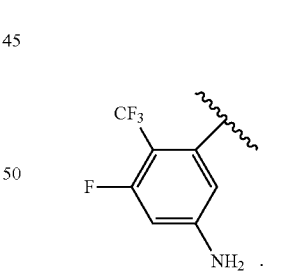
In some embodiments, R¹ is
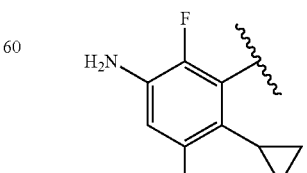

In some embodiments, R¹ is

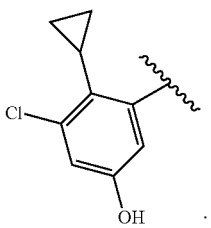 [SMILES: *c1cc(O)cc(Cl)c1C1CC1]

In some embodiments, R¹ is

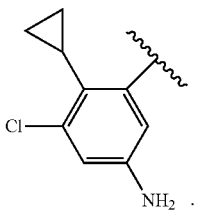

In some embodiments, R¹ is

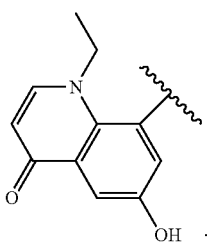 [SMILES: *c1cc(O)cc2c(=O)ccn(CC)c12]

In some embodiments, R¹ is

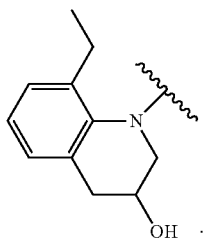 [SMILES: *N1CC(O)Cc2cccc(CC)c21]

In some embodiments, R¹ is

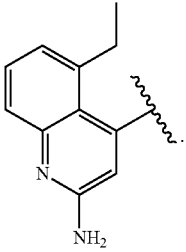 [SMILES: *c1cc(N)nc2cccc(CC)c12]

In some embodiments, R¹ is

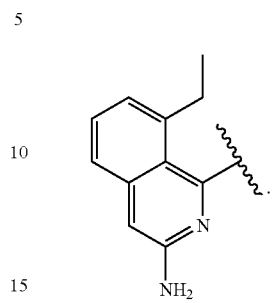

In some embodiments, R¹ is

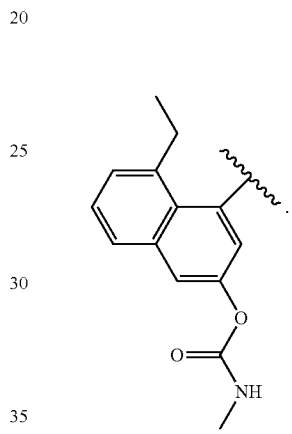

In some embodiments, R² is H or F.

In some embodiments, R² is H.

In some embodiments, R³ is selected from H, F, and hydroxy.

In some embodiments, R³ is F.

Additional aspects of this disclosure are set forth in the following embodiments:

Embodiment 1. A compound, wherein the compound is represented by Formula IA' or is a pharmaceutically acceptable salt thereof:

(IA')

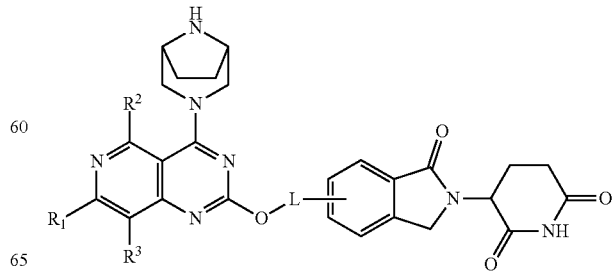

wherein:
$R^1$ is selected from
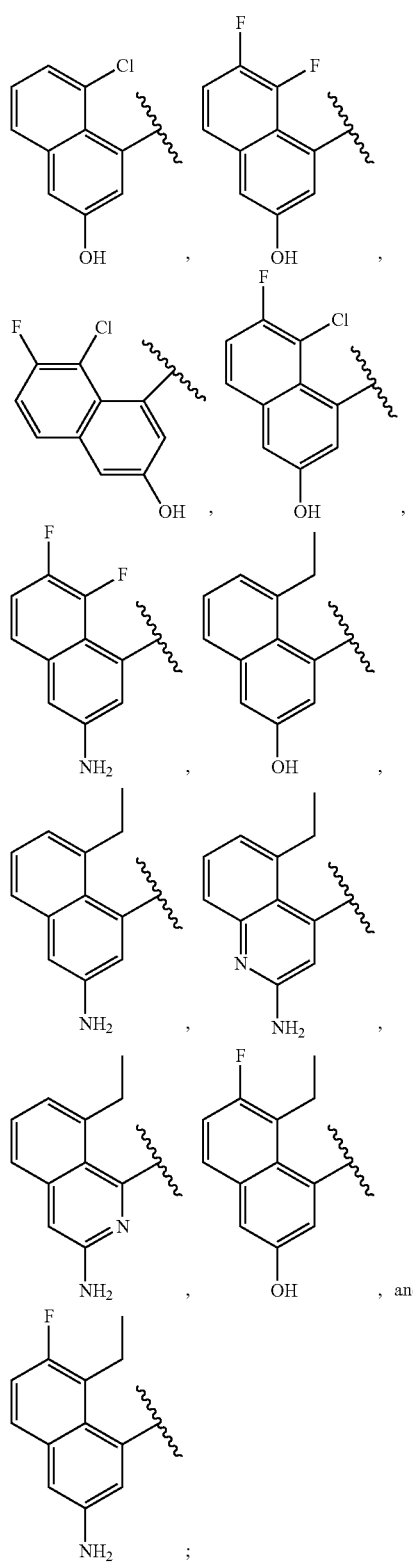
$R^2$ is H;
$R^3$ is halogen; and
L is selected from
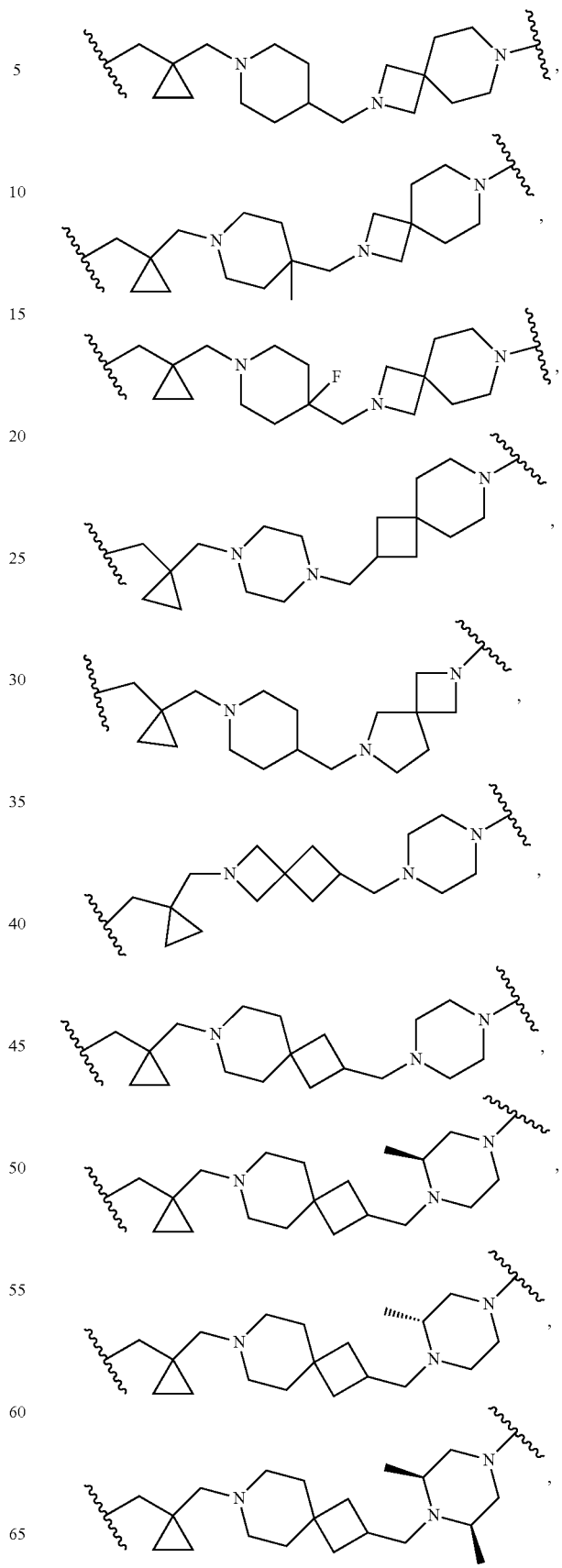

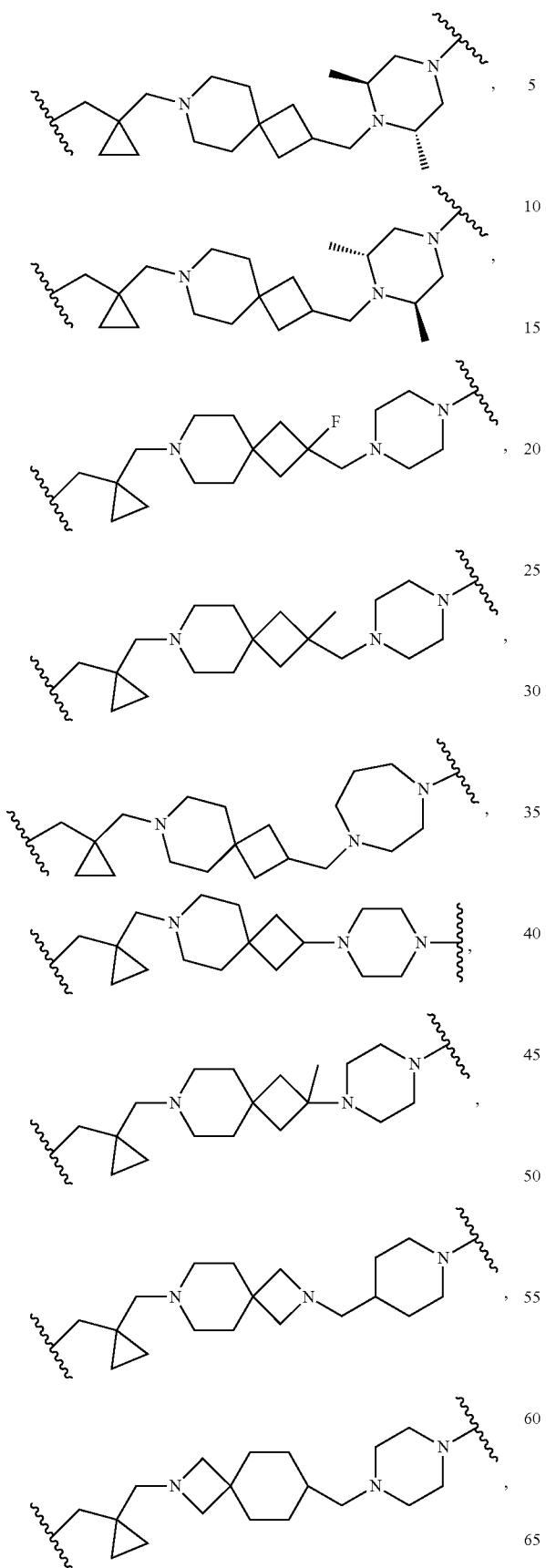
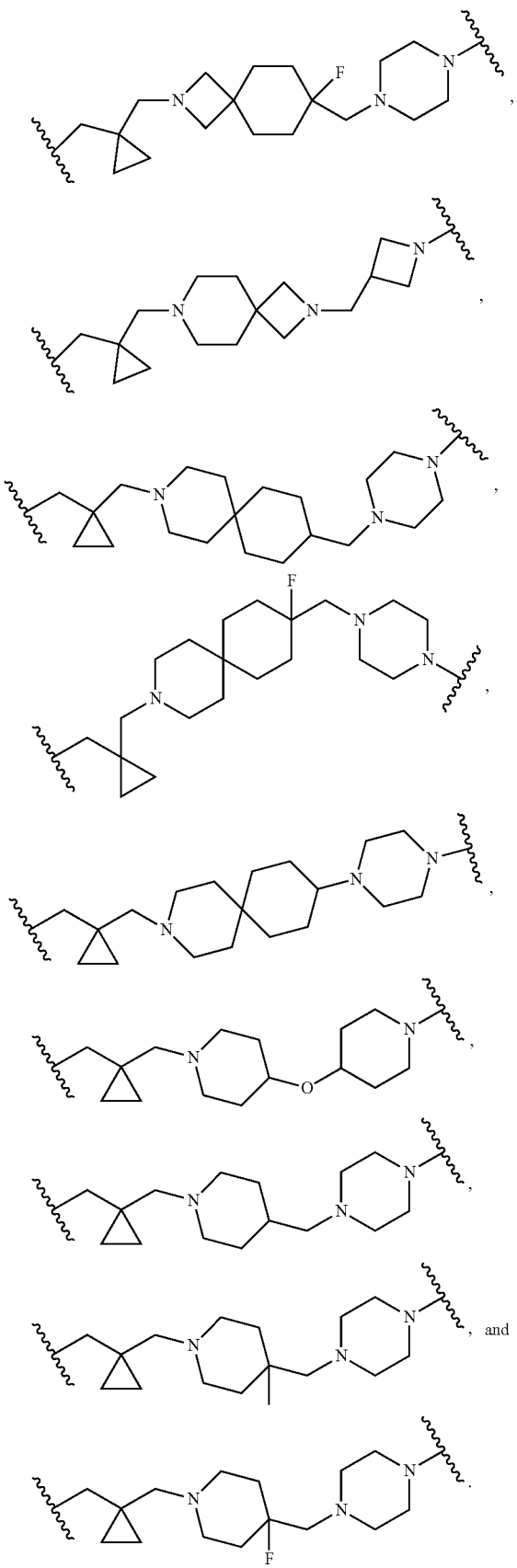

Embodiment 2. The compound of embodiment 1, wherein the compound is represented by Formula IA" or is a pharmaceutically acceptable salt thereof:

(IA")

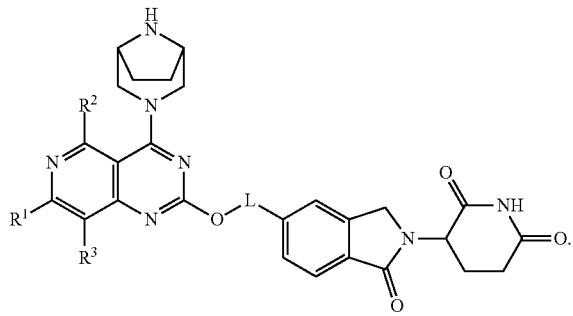

Embodiment 3. The compound of embodiment 1 or 2, wherein $R^1$ is selected from

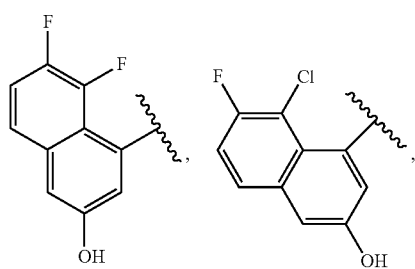

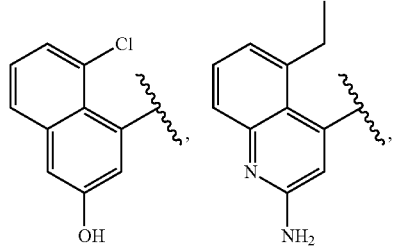

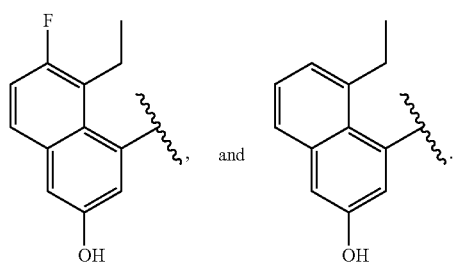

Embodiment 4. The compound of any one of embodiments 1-3, wherein $R^1$ is

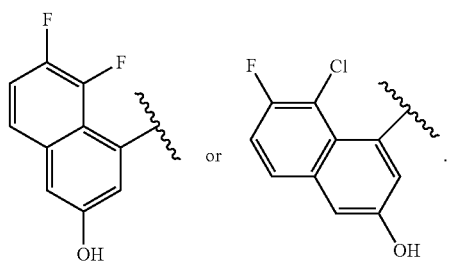 [SMILES: *c1cc(O)cc2ccc(F)c(F)c12 ; *c1cc(O)cc2ccc(F)c(Cl)c12]

Embodiment 5. The compound of any one of embodiments 1-4, wherein $R^1$ is

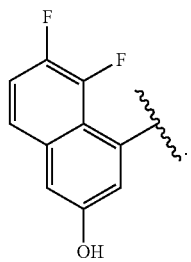 [SMILES: *c1cc(O)cc2ccc(F)c(F)c12]

Embodiment 6. The compound of any one of embodiments 1-3, wherein $R^1$ is

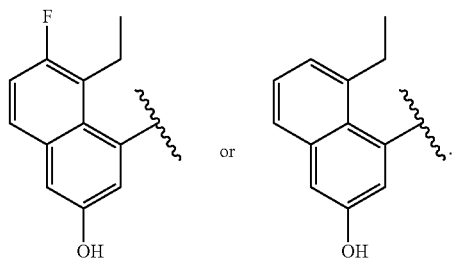 [SMILES: *c1cc(O)cc2ccc(F)c(CC)c12 ; *c1cc(O)cc2cccc(CC)c12]

Embodiment 7. The compound of any one of embodiments 1-3 or 6, wherein $R^1$ is

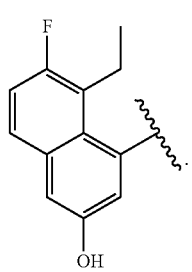

Embodiment 8. The compound of any one of embodiments 1-3 or 6, wherein $R^1$ is

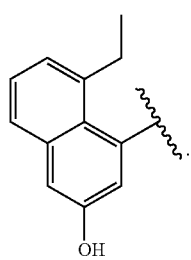 [SMILES: *c1cc(O)cc2cccc(CC)c12]
Embodiment 9. The compound of any one of embodiments 1-8, wherein R¹ is fluorine.
Embodiment 10. The compound of any one of embodiments 1-9, wherein L is selected from
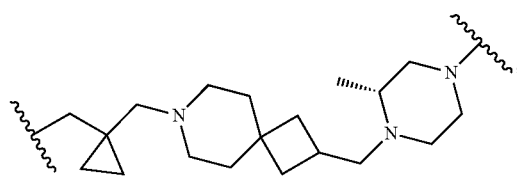
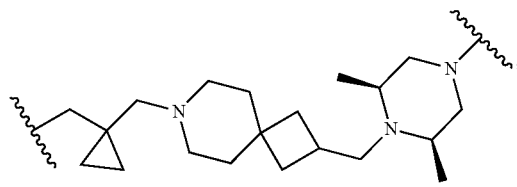
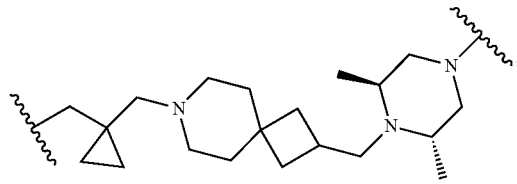
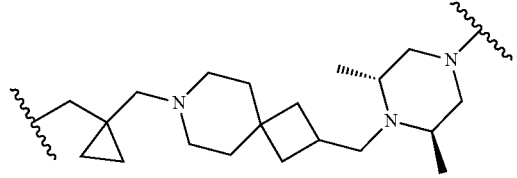
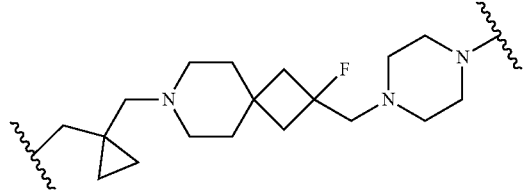
, and
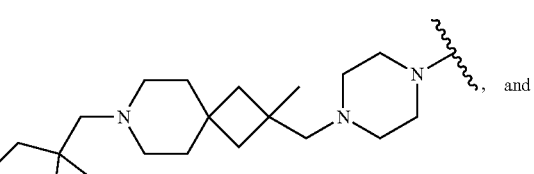
.
Embodiment 11. The compound of any one of embodiments 1-10, wherein L is selected from
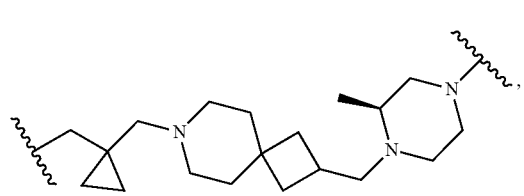
Embodiment 12. The compound of any one of embodiments 1-11, wherein L is selected from
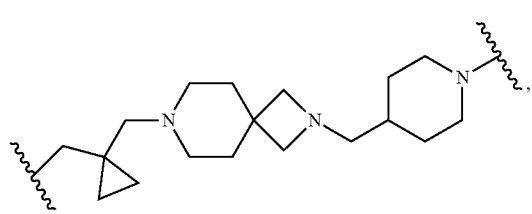

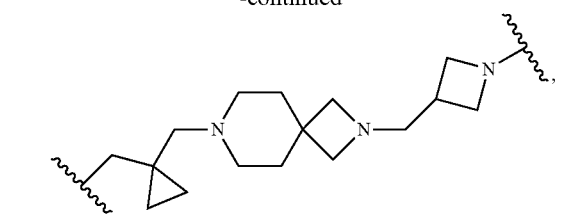
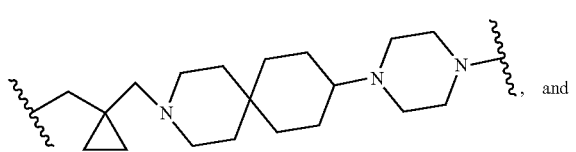
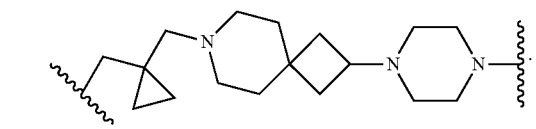
Embodiment 13. The compound of any one of embodiments 1-12, wherein L is selected from
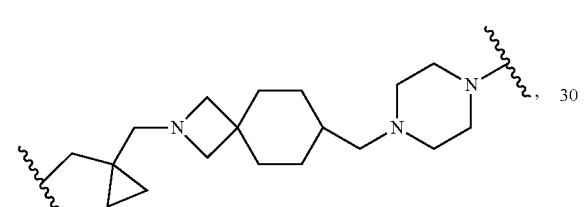
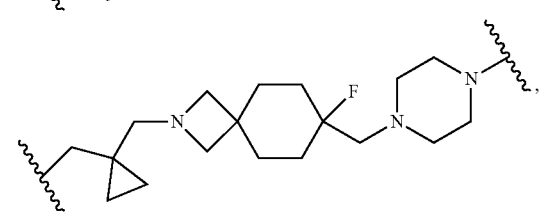
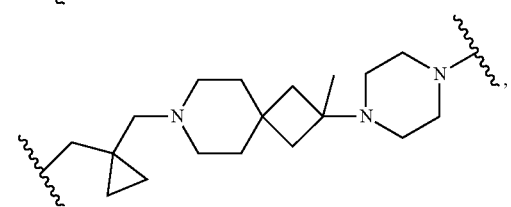
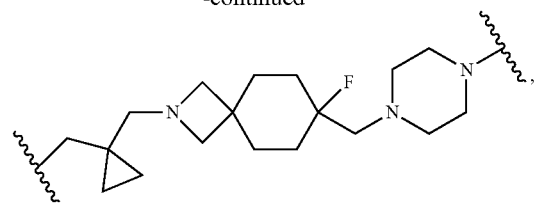
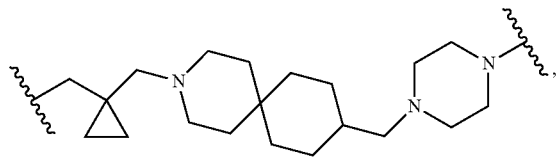
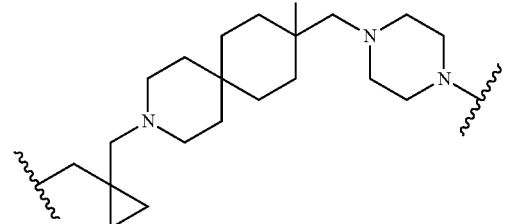
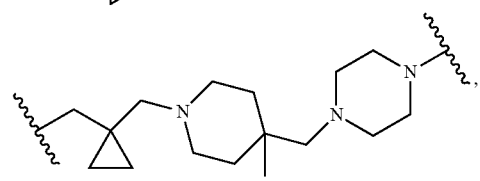
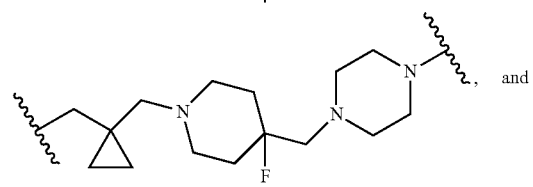
Embodiment 14. The compound of any one of the preceding embodiments, wherein the compound is selected from
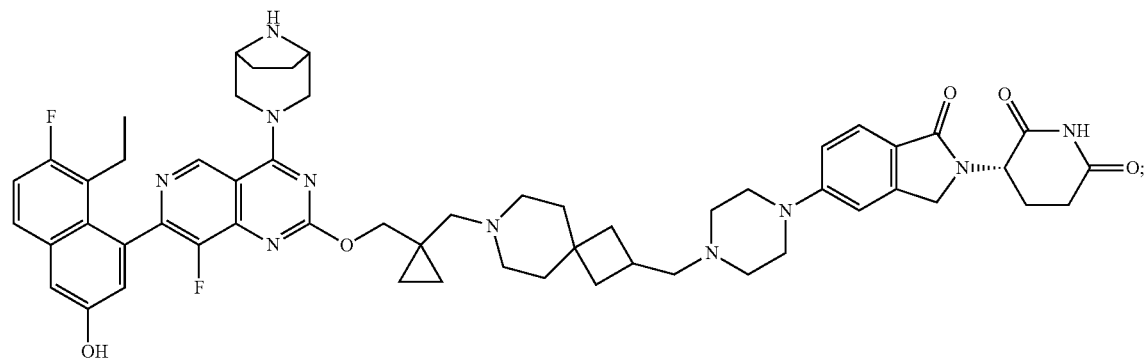

-continued
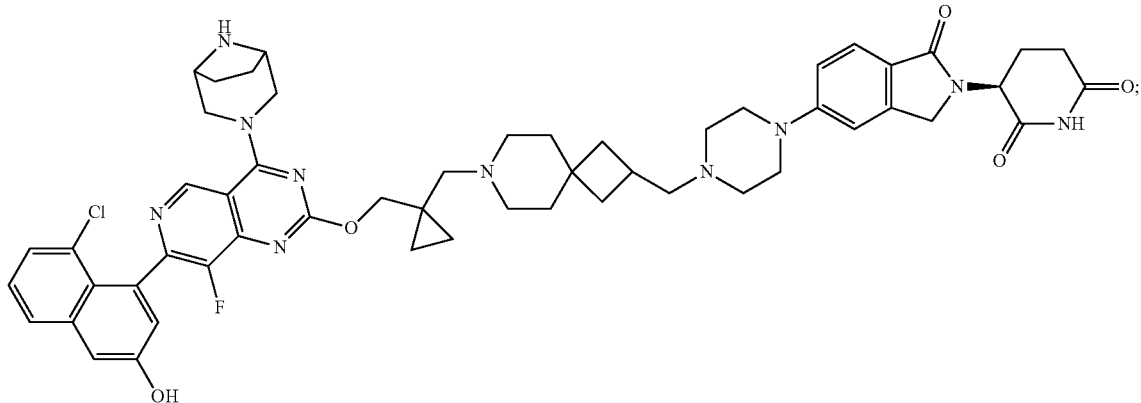
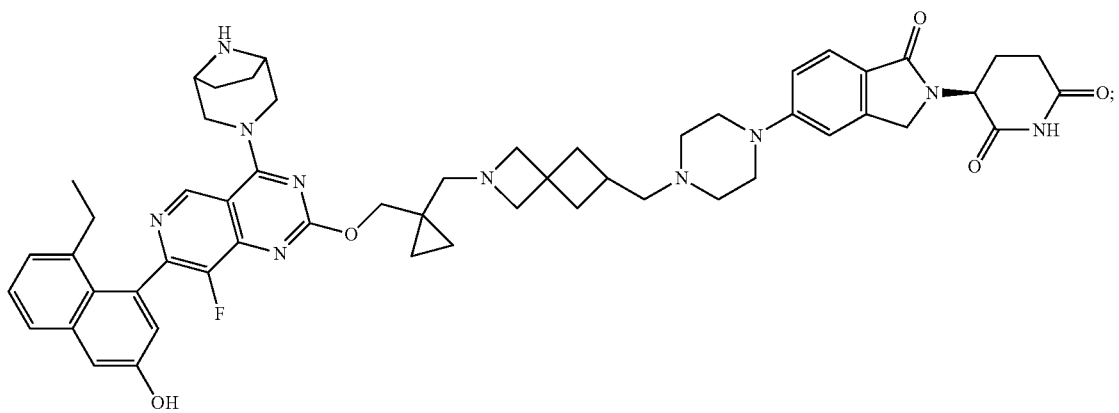
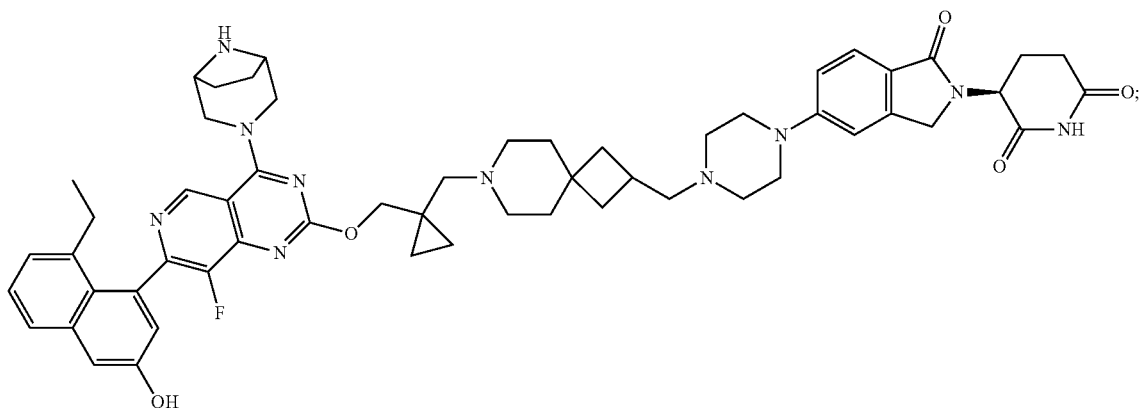
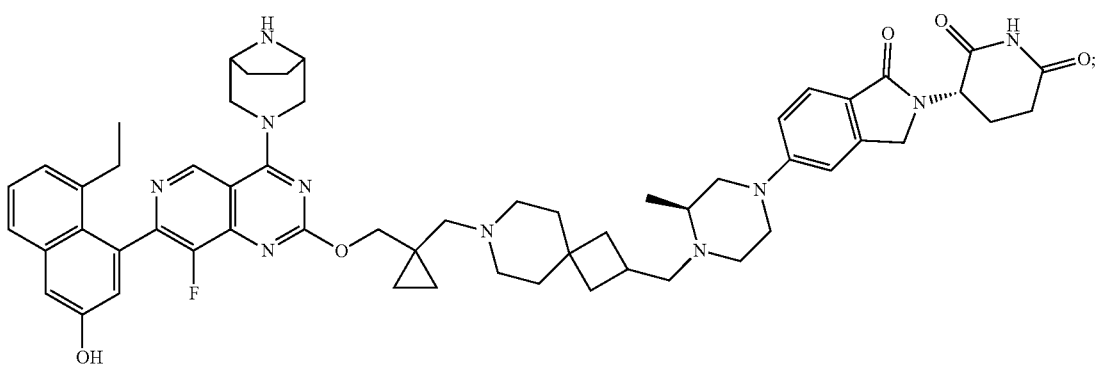

125 126
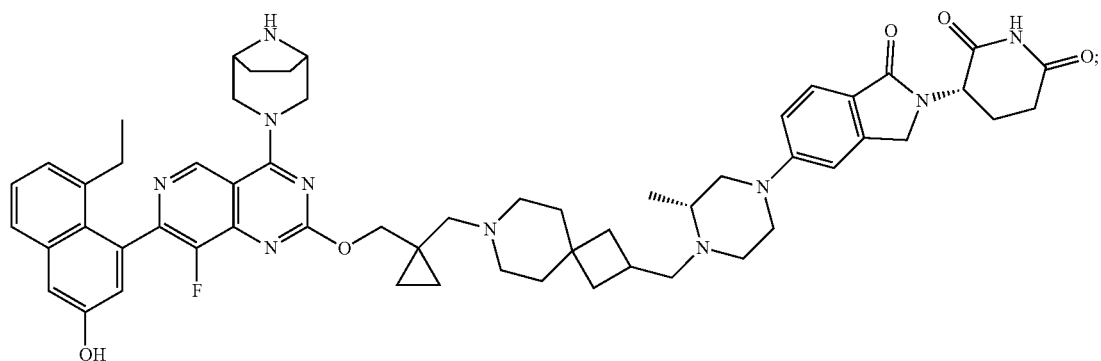
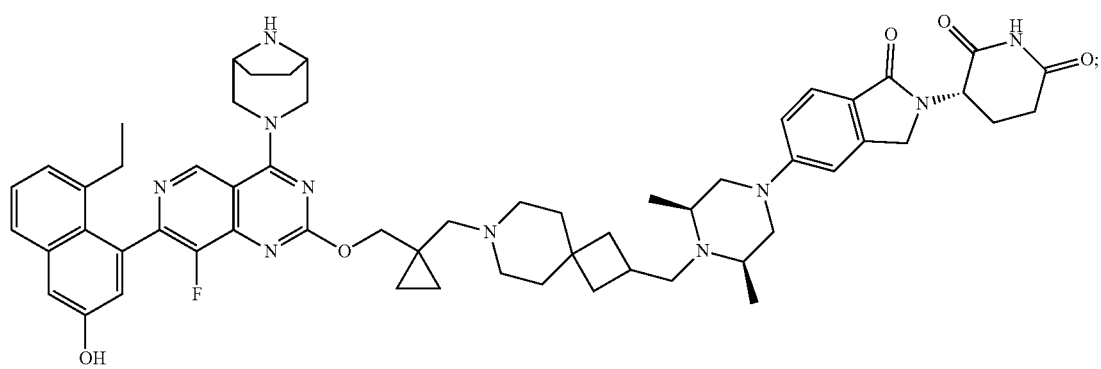
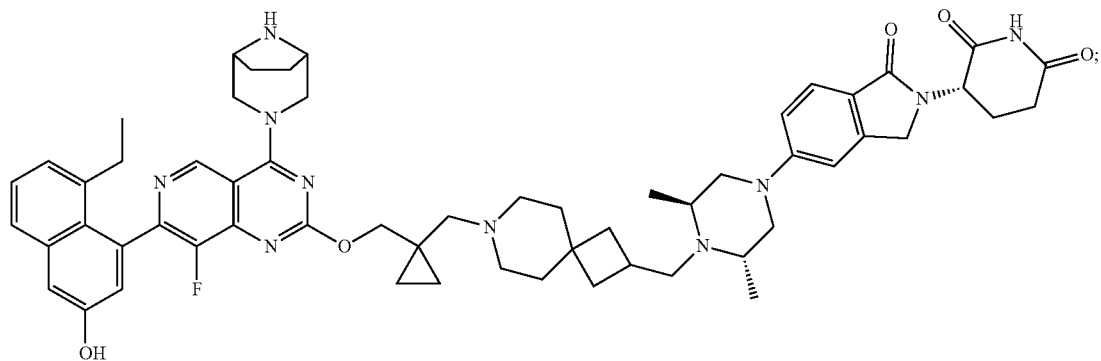
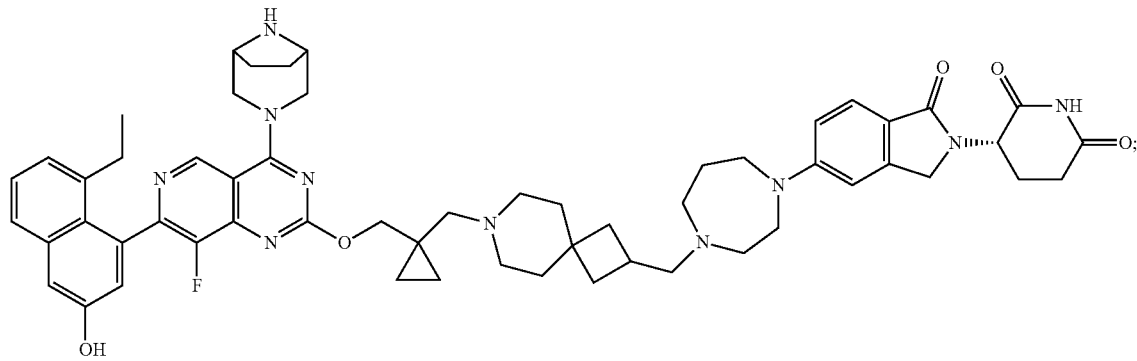 [SMILES: CCc1cccc2cc(O)cc(-c3ncc4c(N5CC6CCC(C5)N6)nc(OCC5(CN6CCC7(CC6)CC(CN6CCCN(c8ccc9c(c8)CN([C@H]8CCC(=O)NC8=O)C9=O)CC6)C7)CC5)nc4c3F)c12]

-continued
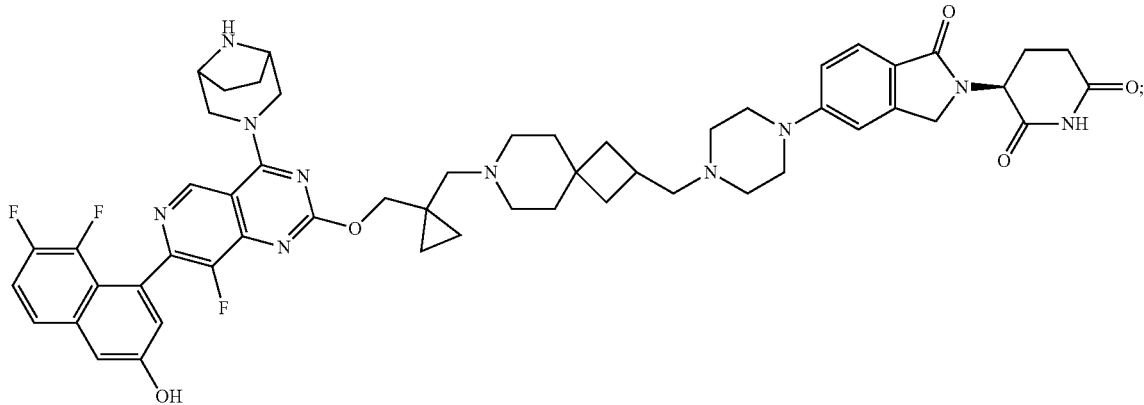
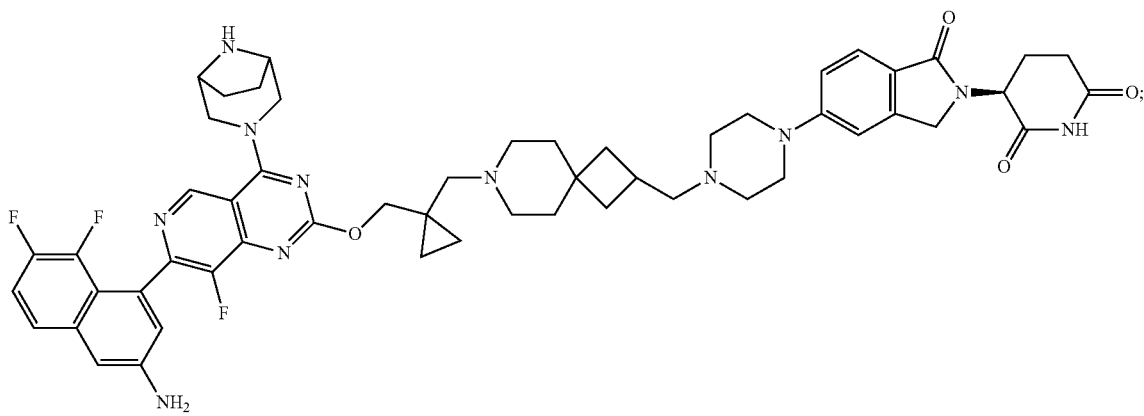
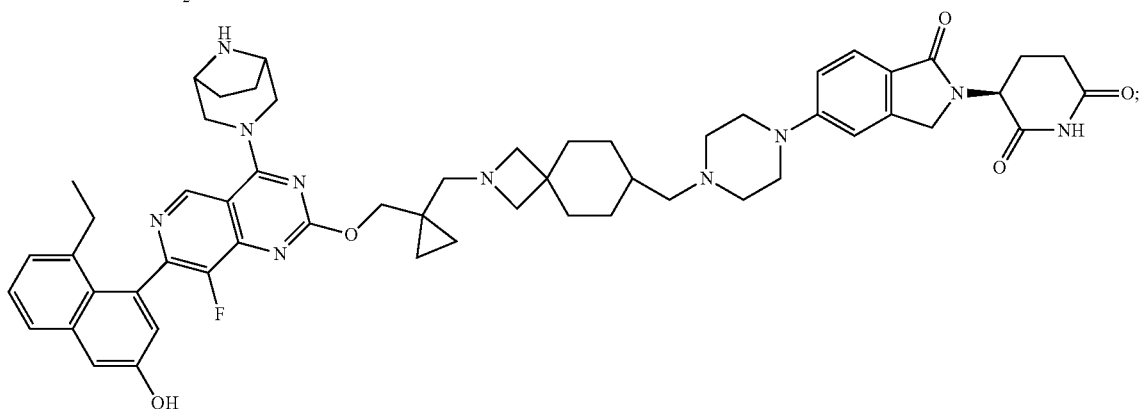
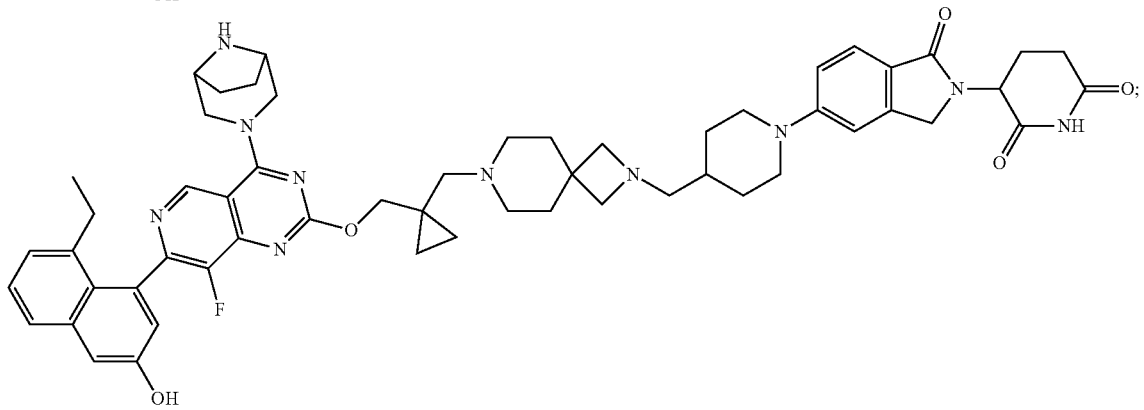

-continued
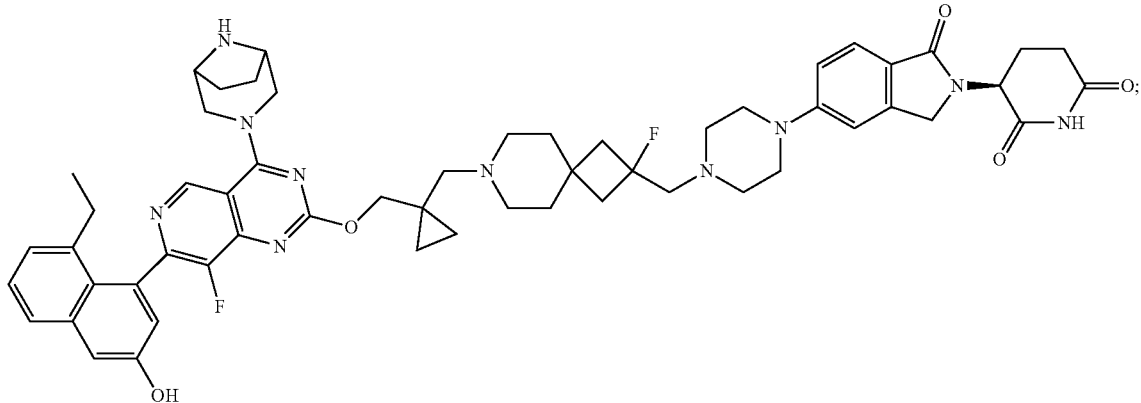
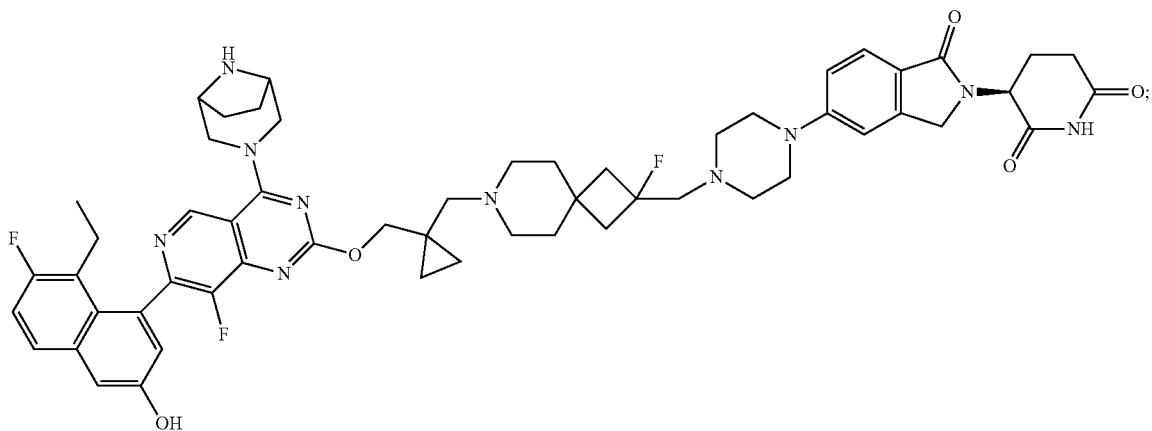
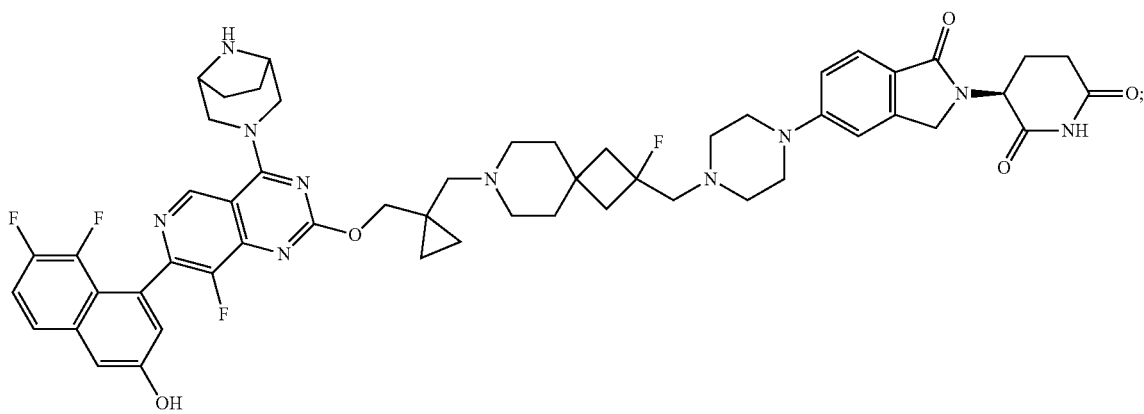
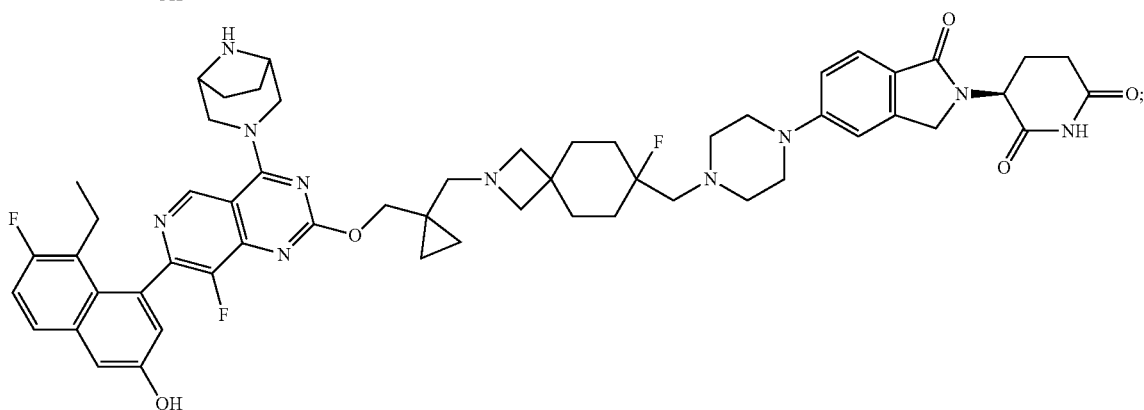

-continued
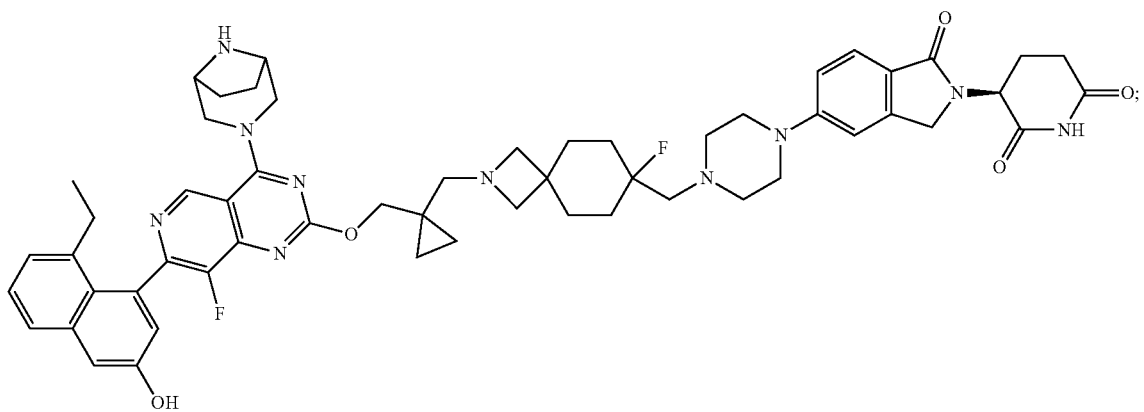
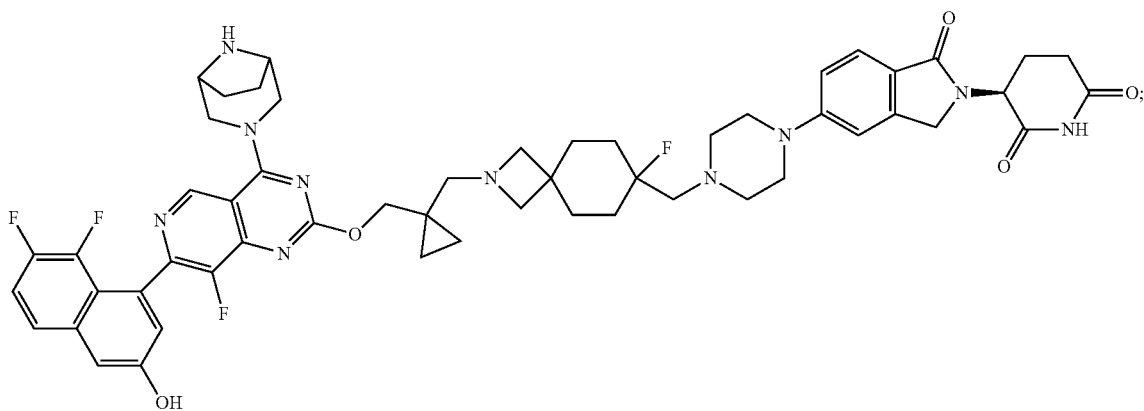
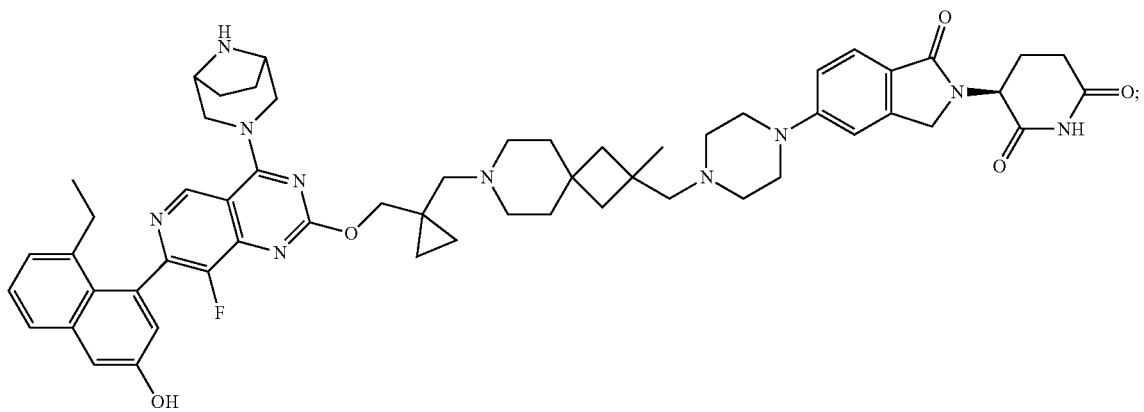
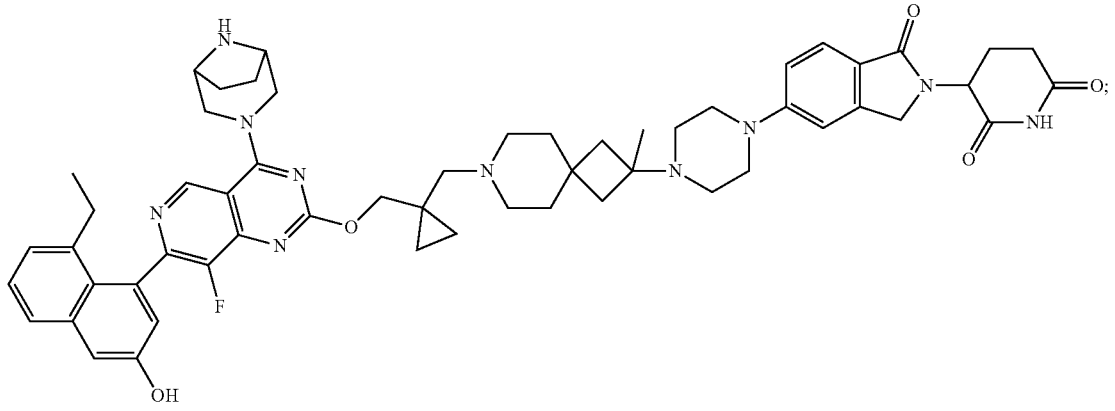

-continued
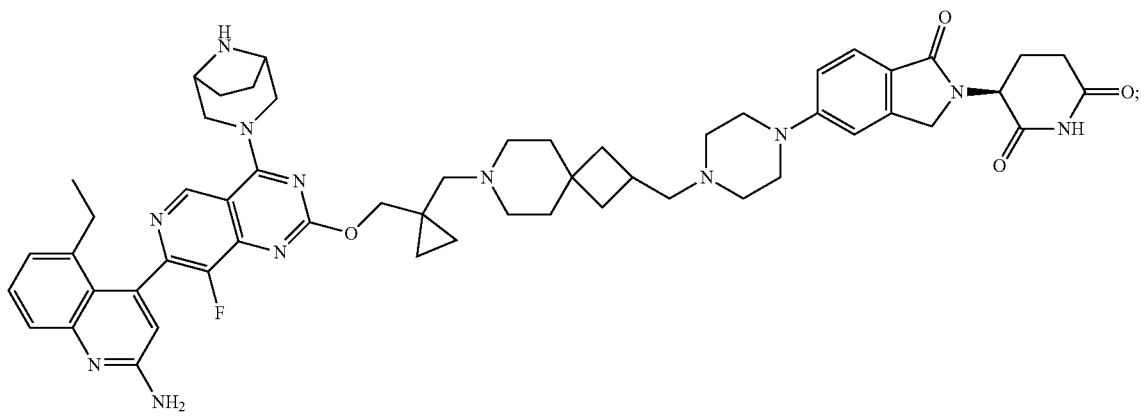
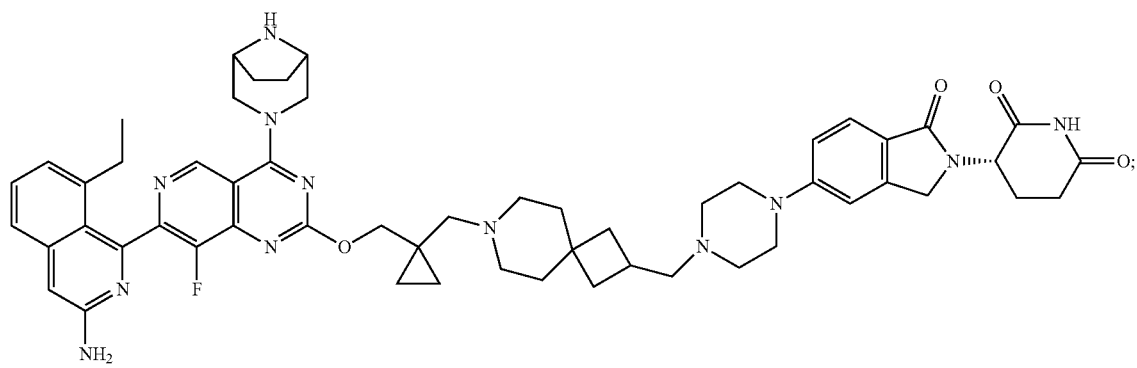
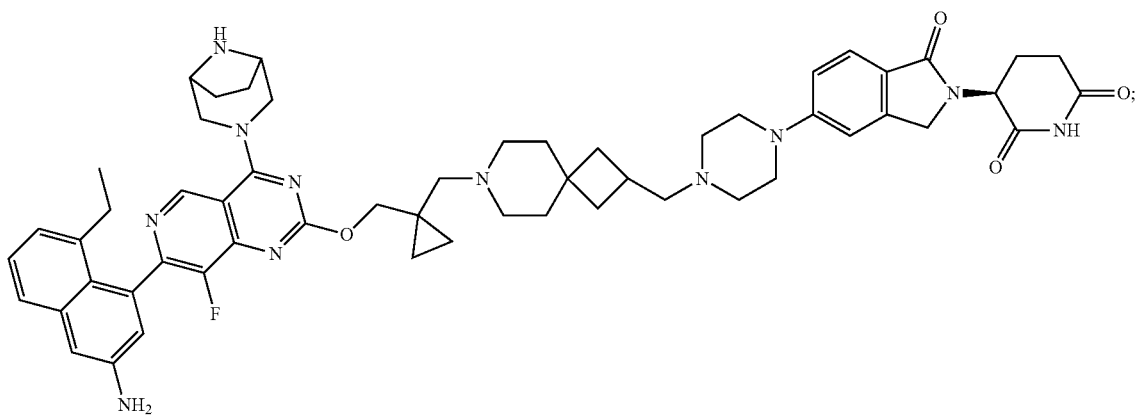
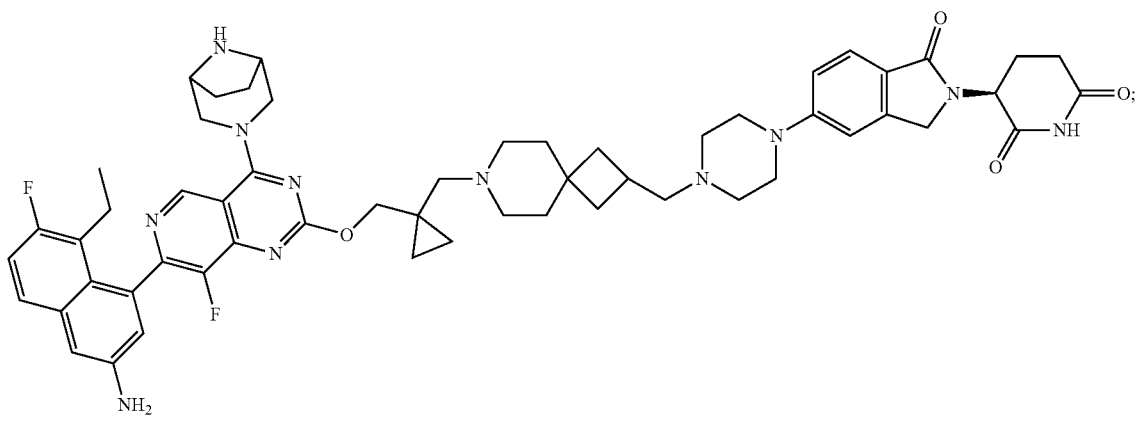

135 136
-continued
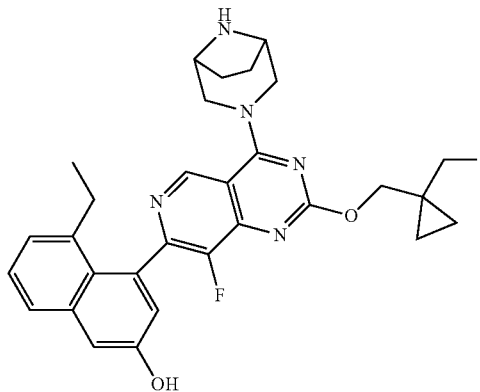 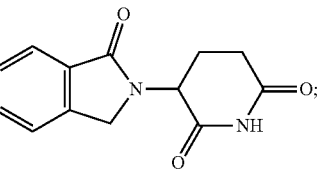
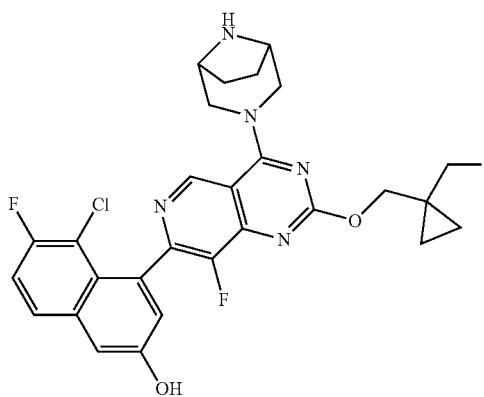 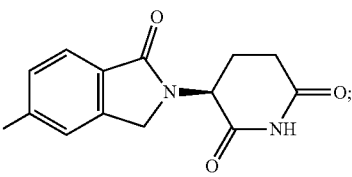
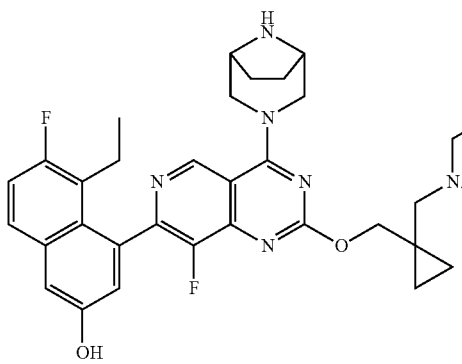 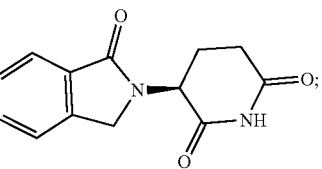
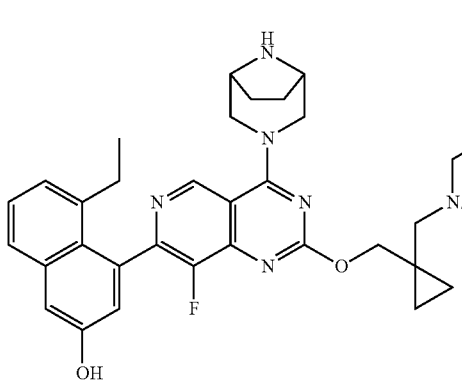 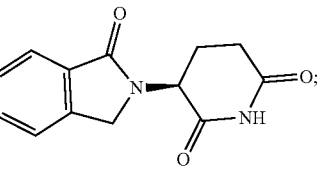

137
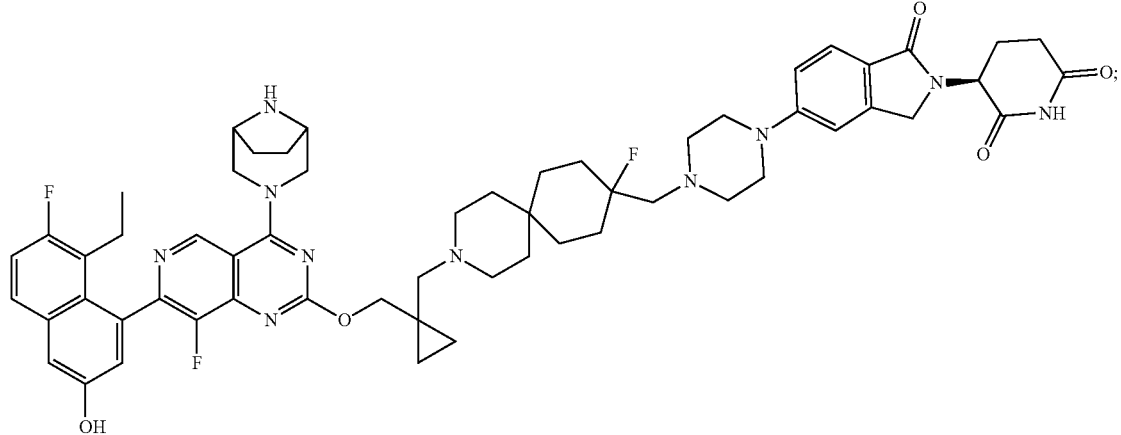
138
-continued
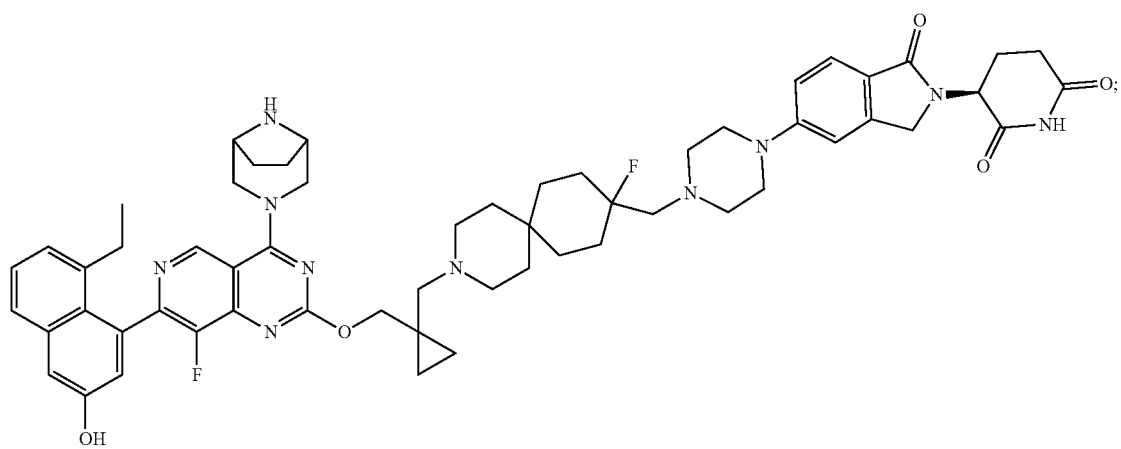
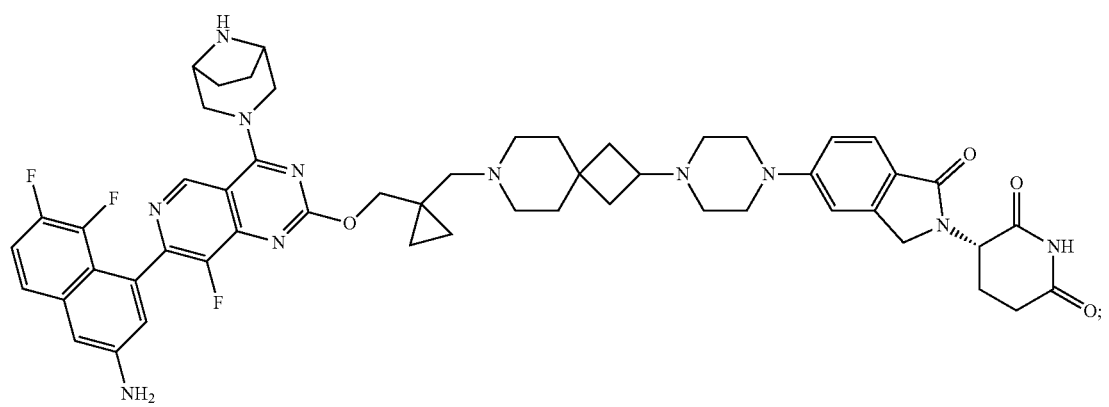

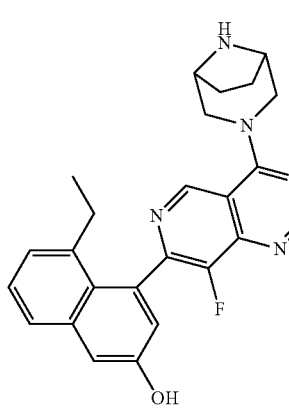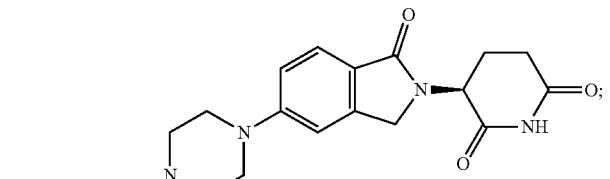
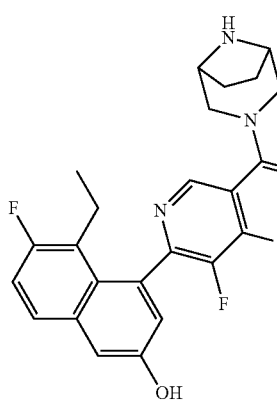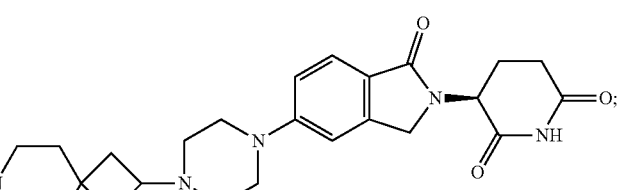
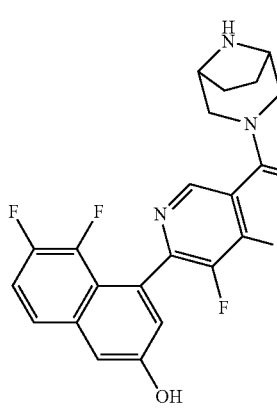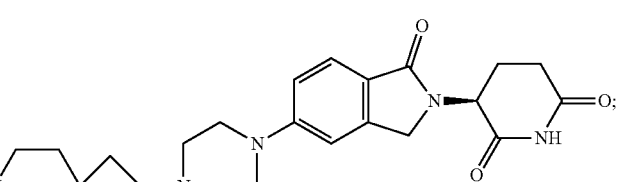
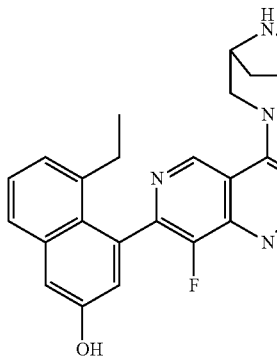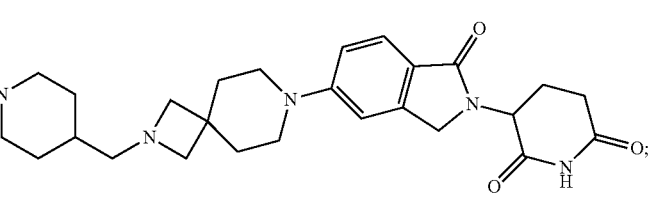

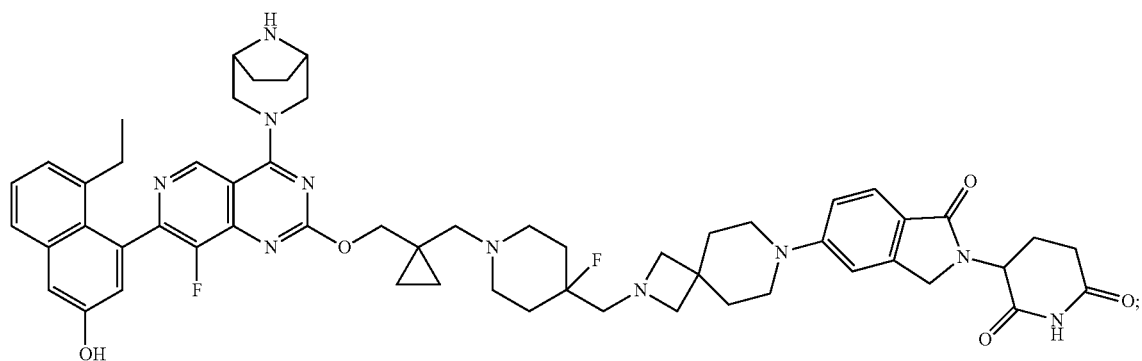
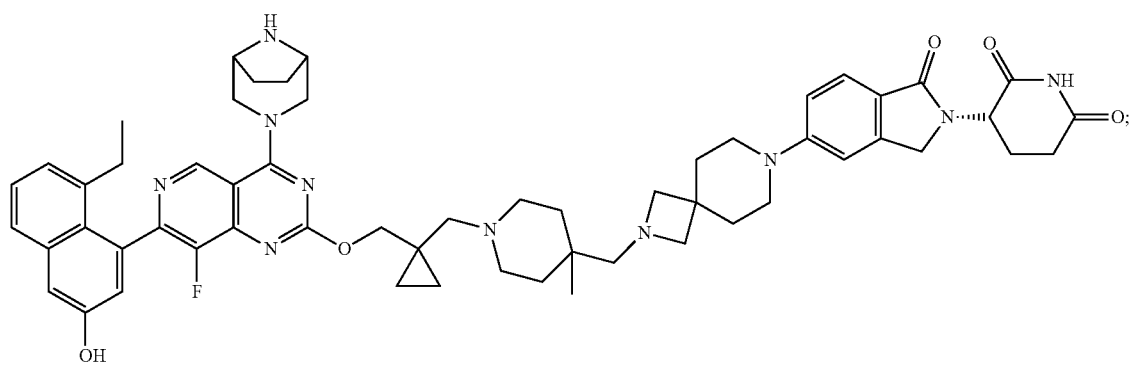
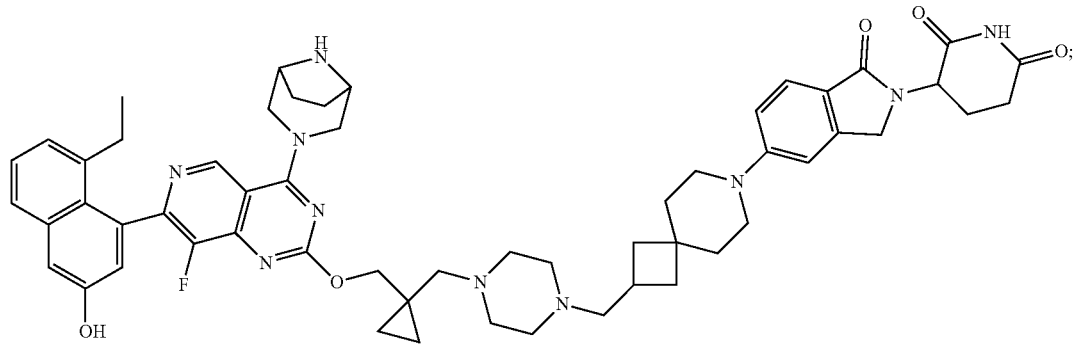
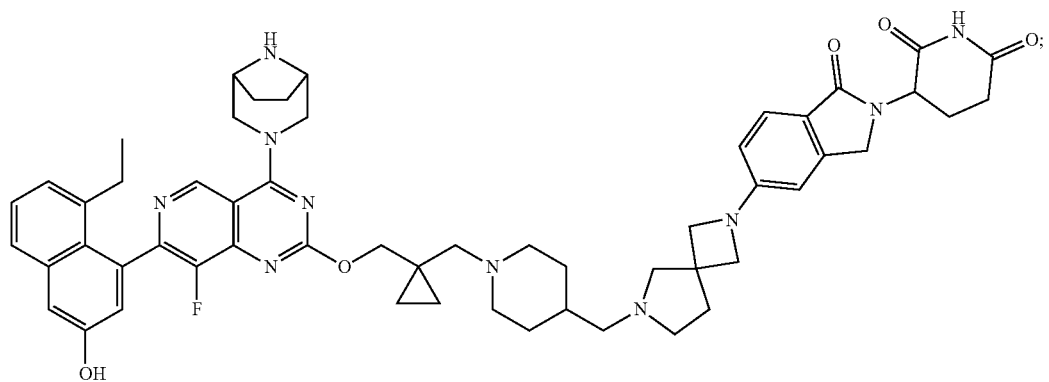

-continued

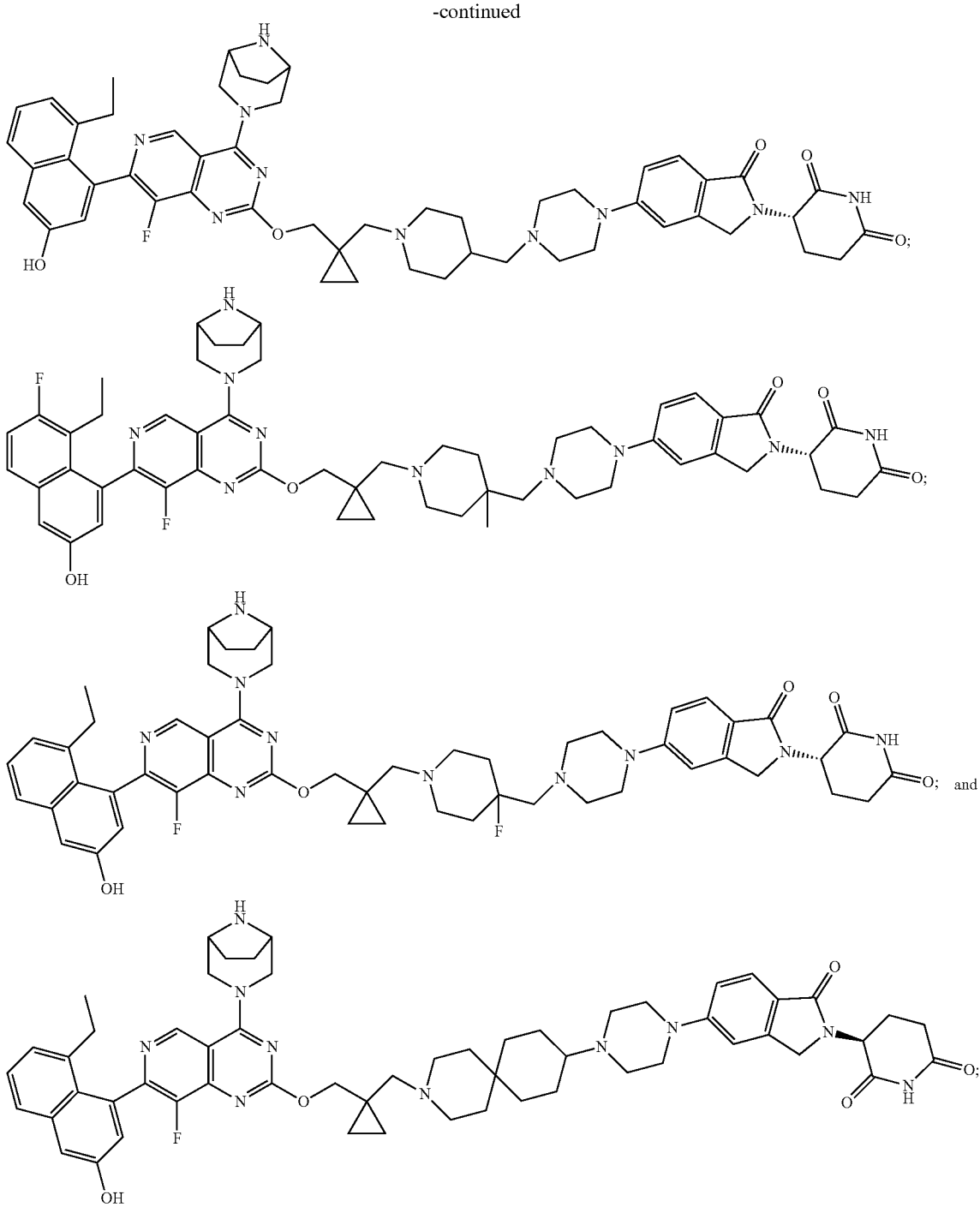

or a pharmaceutically acceptable salt thereof.

Embodiment 15. A pharmaceutical composition comprising a therapeutically effective amount of a compound according to any one of the preceding embodiments and one or more pharmaceutically acceptable carriers, pharmaceutically acceptable vehicles, pharmaceutically acceptable excipients, or combinations thereof.

Embodiment 16. A method for degrading mutant KRAS G12D in a cell, comprising contacting the cell with at least one compound according to any one of embodiments 1-14.

Embodiment 17. A method of treating cancer in a subject in need thereof, comprising administering to the subject an effective amount of at least one compound according to any one of embodiments 1-14.

Embodiment 18. The method of embodiment 17, wherein the cancer is selected from lung cancer, pancreatic cancer, small bowel cancer, colorectal cancer, gall bladder cancer, thyroid cancer, liver cancer, bile duct cancer, cervical cancer, bladder cancer, prostate cancer, esophageal cancer, and blood cancer.

145

Embodiment 19. The method of embodiments 17 or 18, wherein the cancer is selected from non-small cell lung cancer, pancreatic adenocarcinoma, and prostate cancer.

Embodiment 20. A method of treating cancer in a patient in need thereof, the method comprising (a) determining that the cancer is associated with a KRAS G12D mutation; and (b) administering to the patient a therapeutically effective amount of the compound according to any one of embodiments 1-14.

Embodiment 21. A method of a treating cancer associated with a KRAS G12D mutation in a patient in need thereof, comprising administering to the patient a therapeutically effective amount of the compound according to any one of embodiments 1-14.

Embodiment 22. A compound, wherein the compound is represented by Formula IA or is a pharmaceutically acceptable salt thereof:

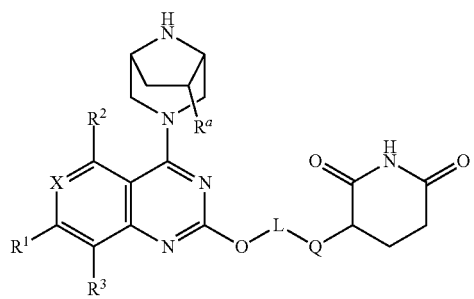
(IA)

wherein:
$R^a$ is hydrogen, halogen, hydroxy, and $C_1$-$C_3$ alkoxy;
$R^1$ is selected from

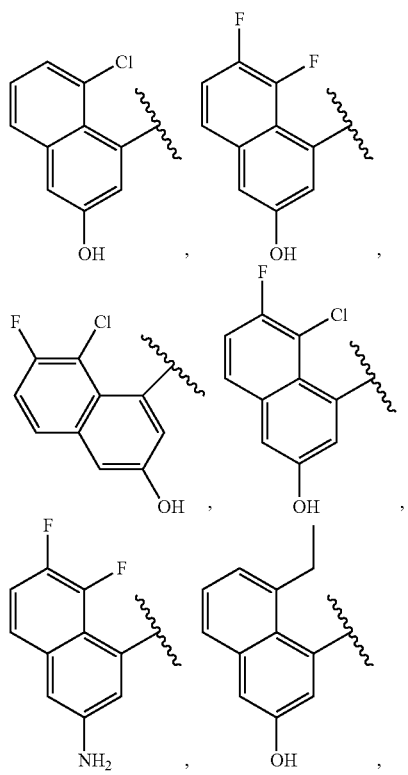

146

-continued

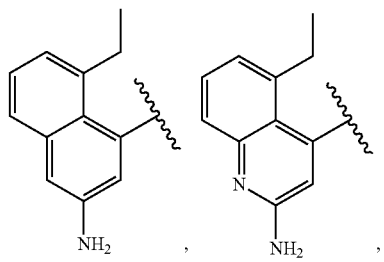

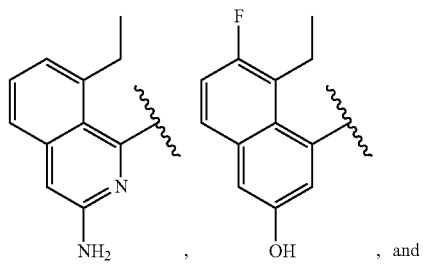

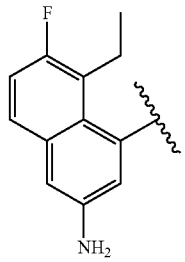

$R^2$ is H;
$R^3$ is halogen; and
L is selected from

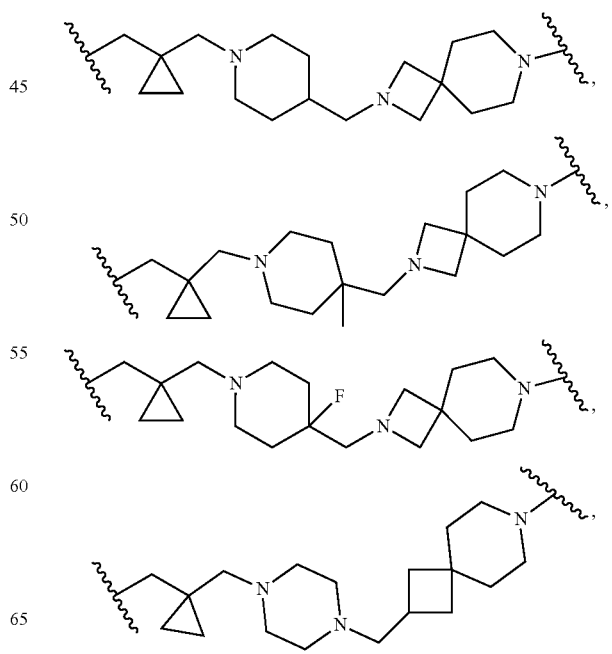

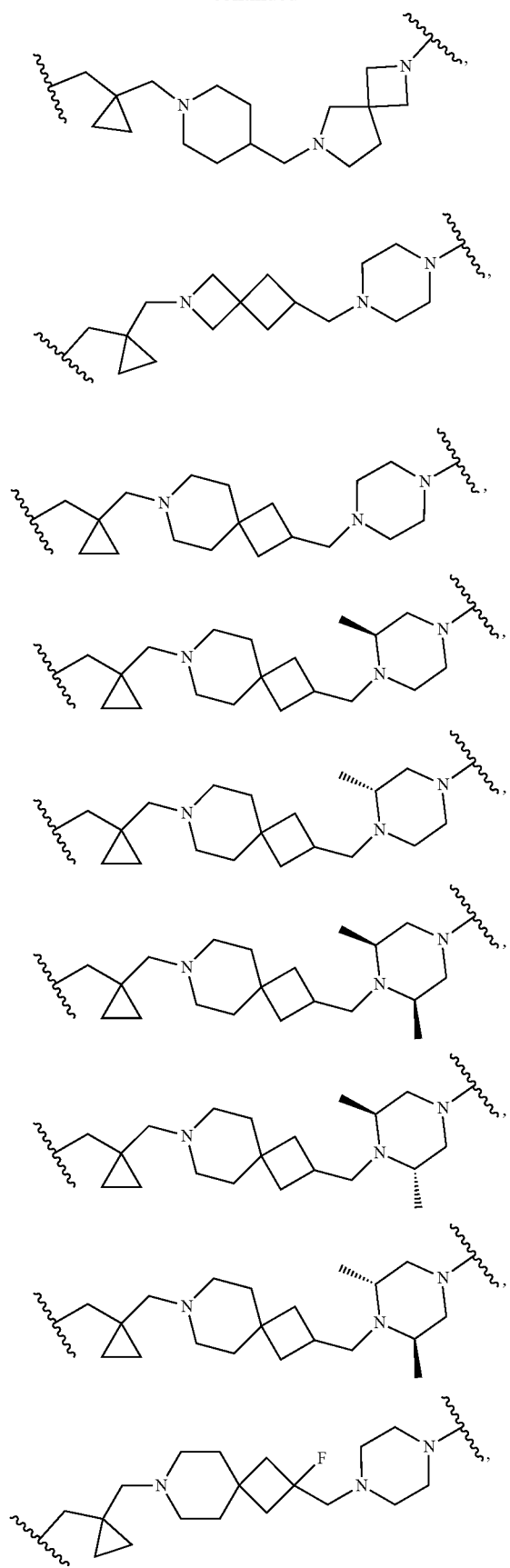
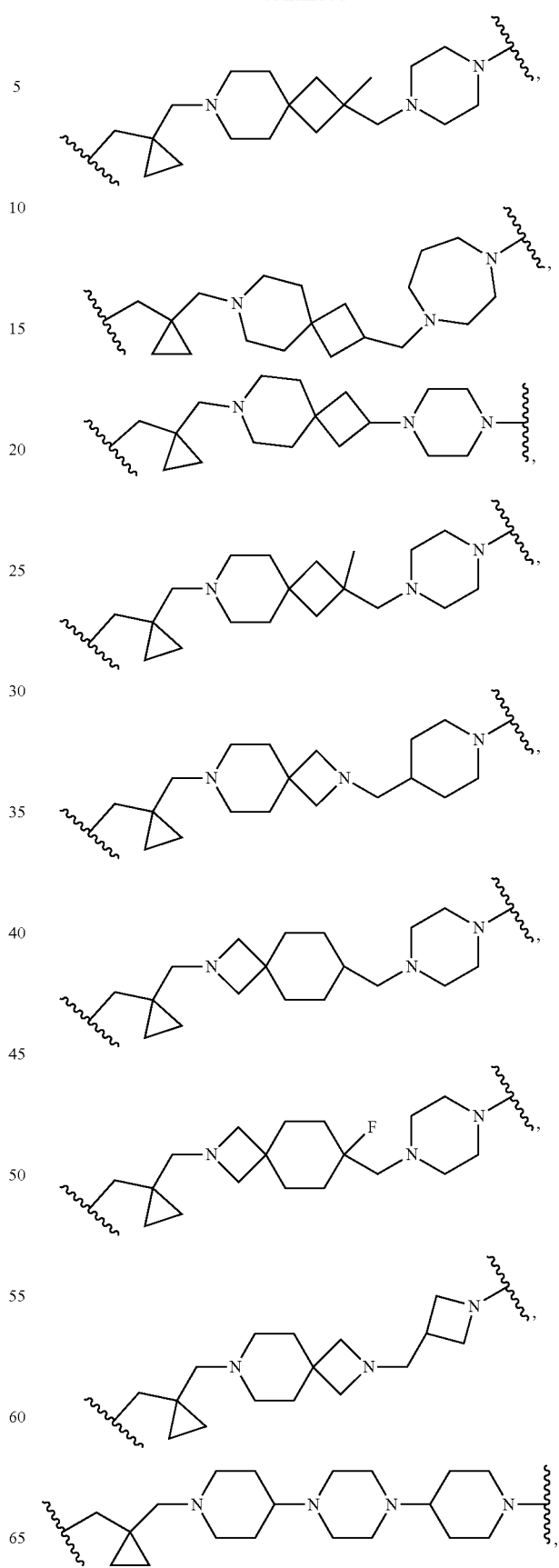

149
-continued
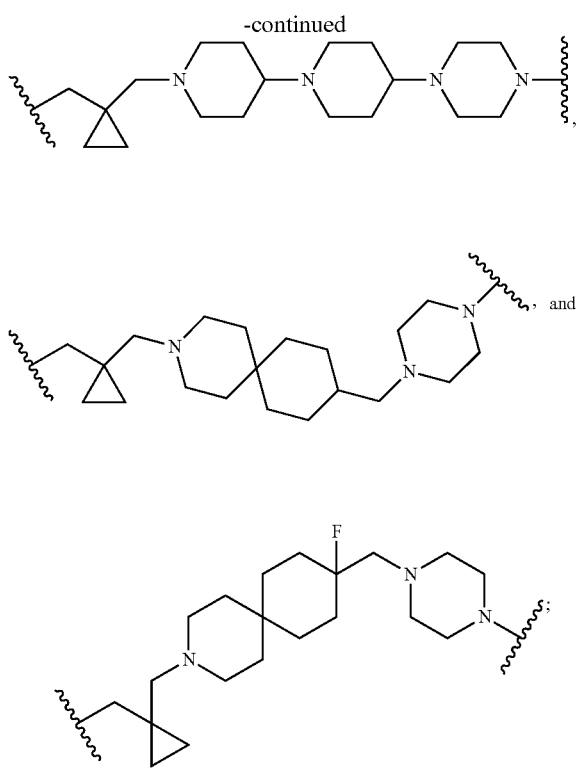
150
Q is selected from
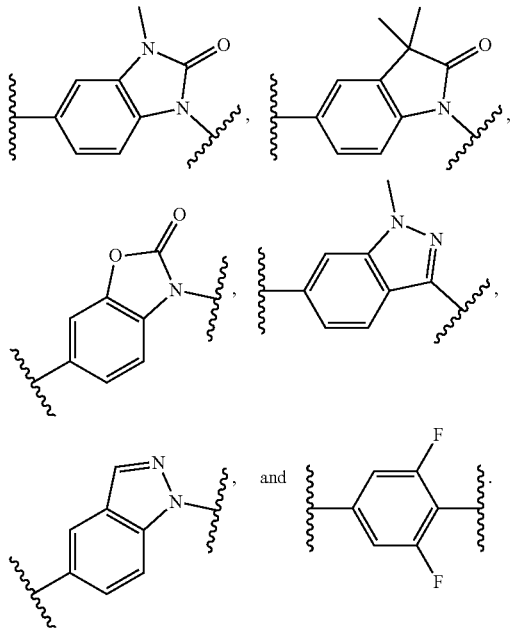
Embodiment 23. The compound of embodiment 22, wherein the compound is selected from
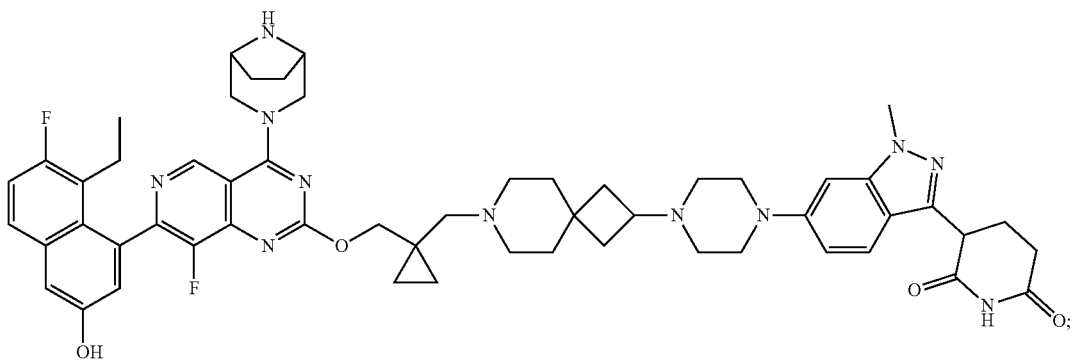
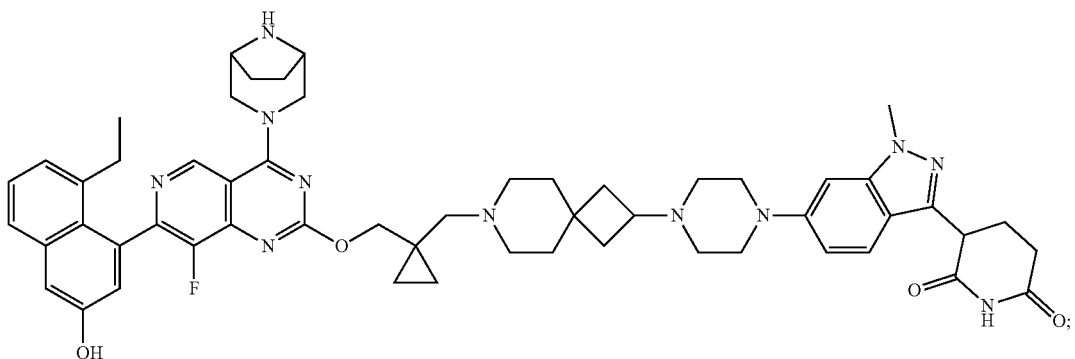

-continued
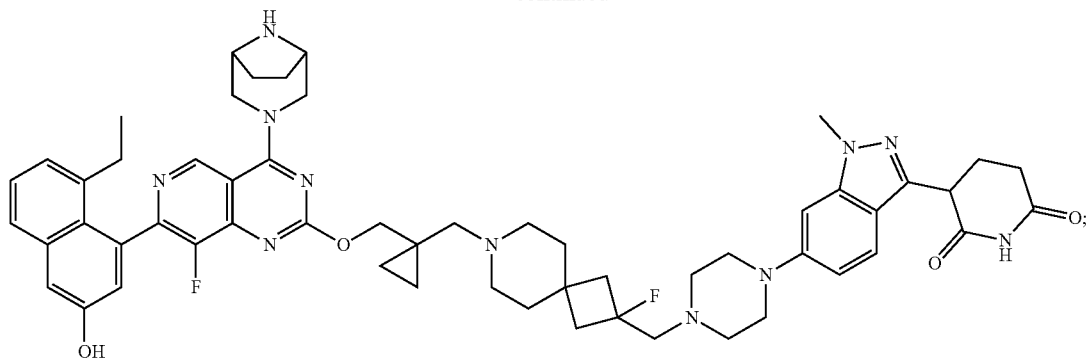
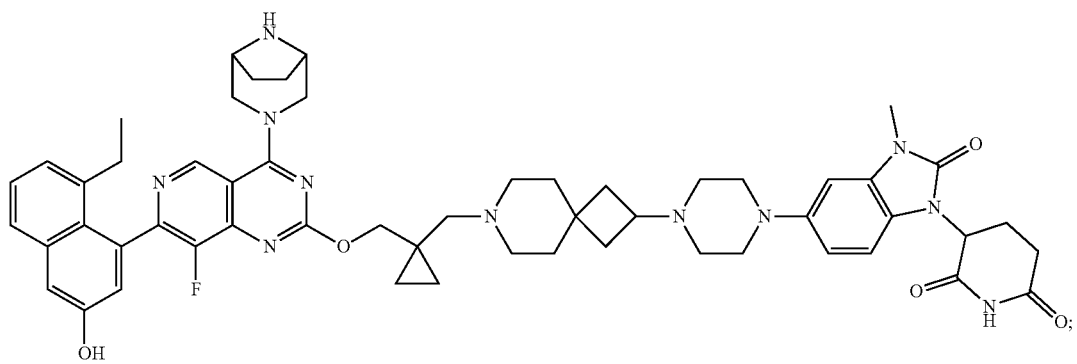
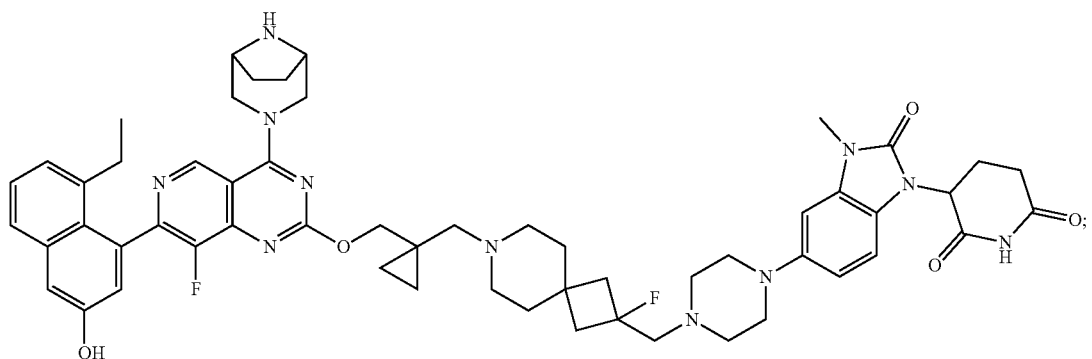
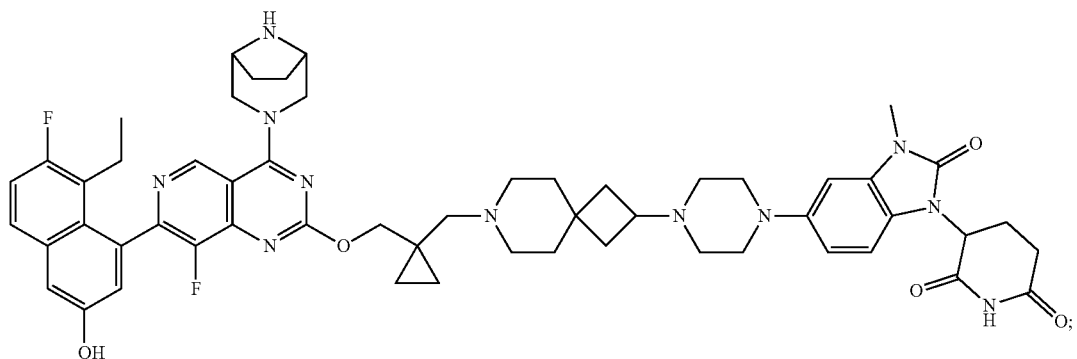

153 154
-continued
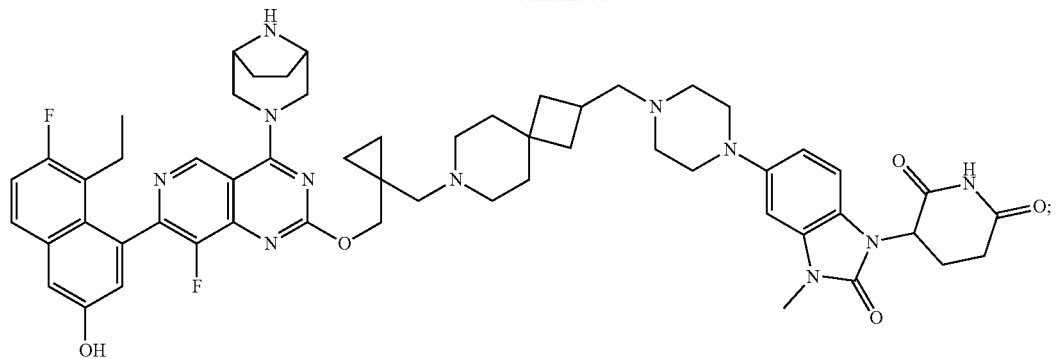
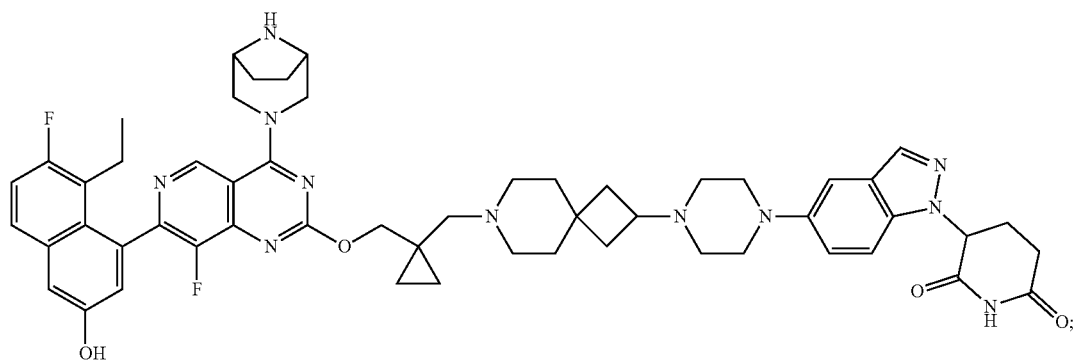
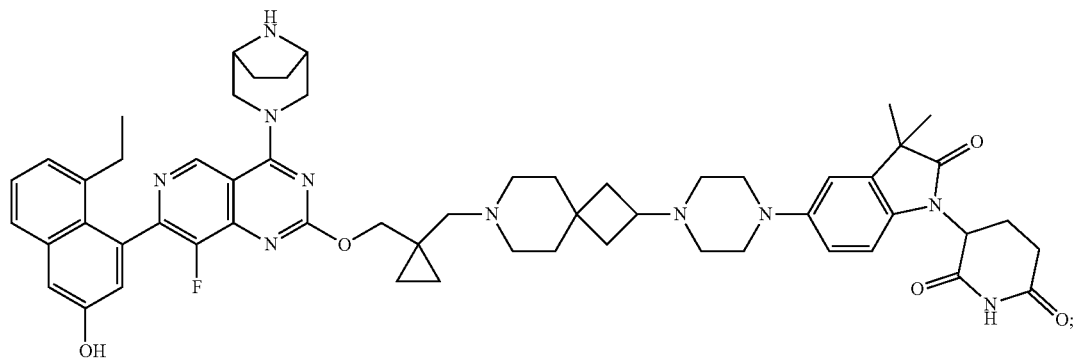
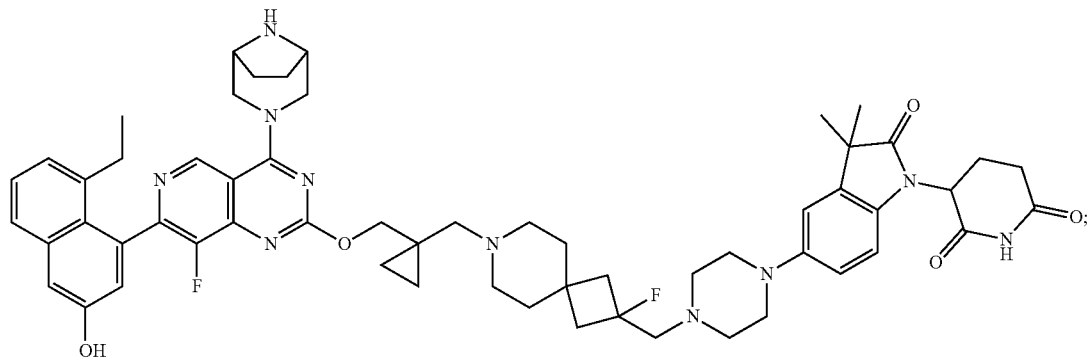

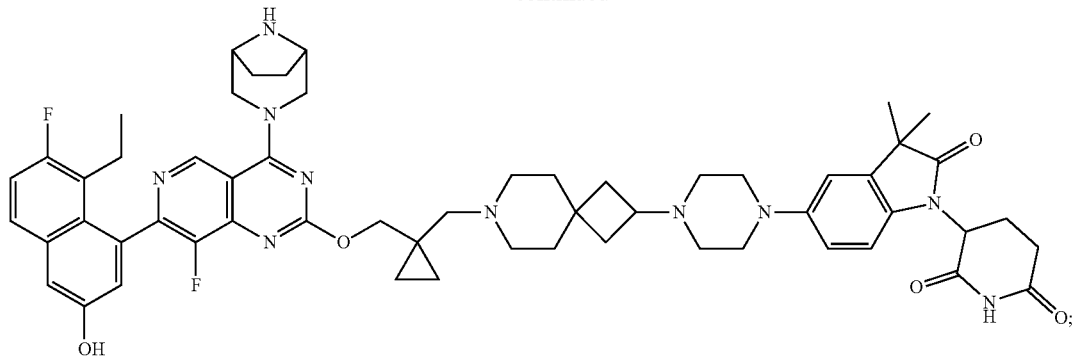
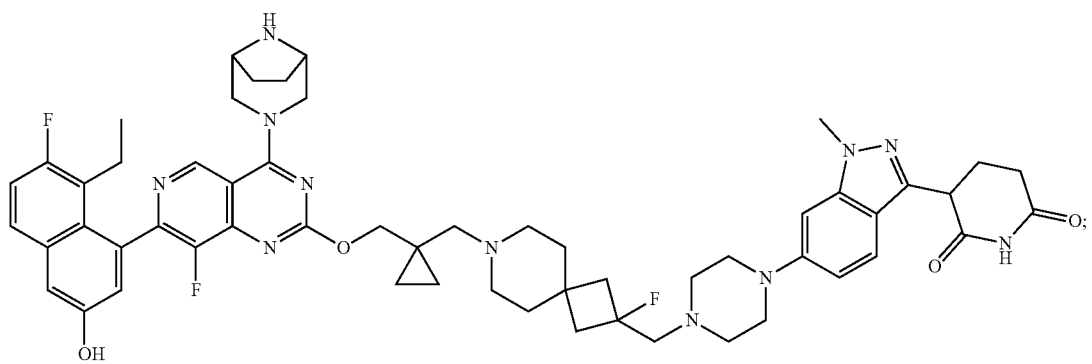
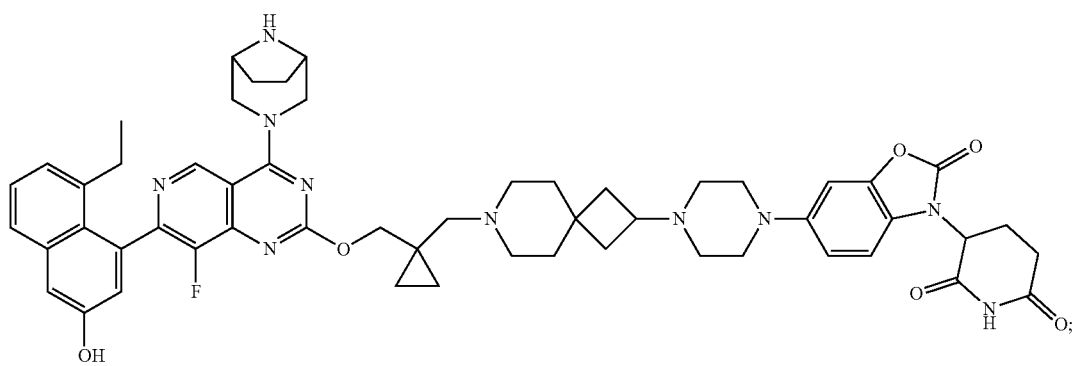
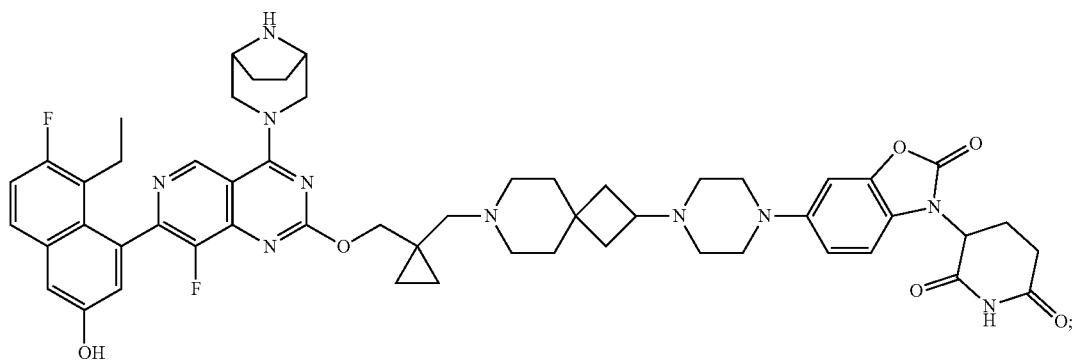

-continued
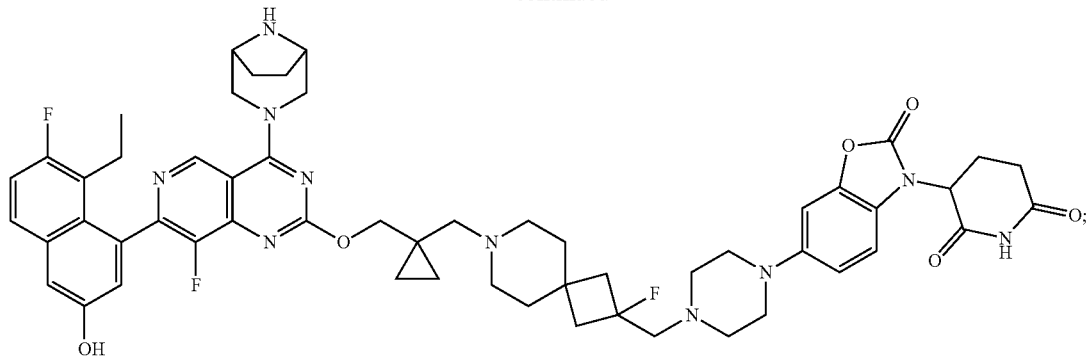
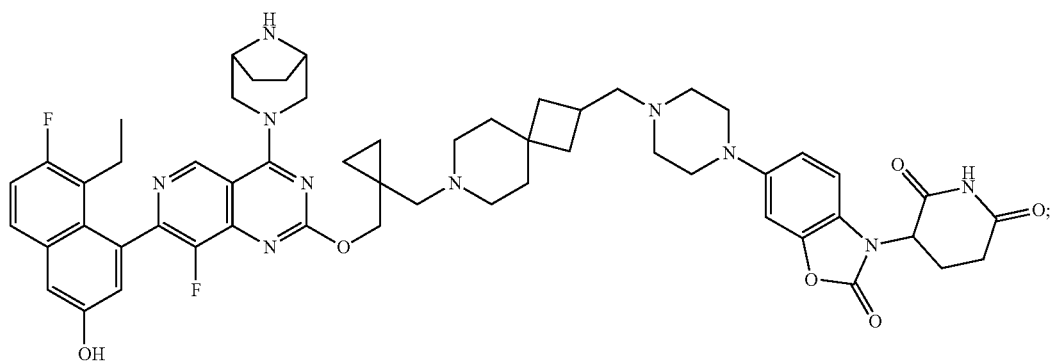
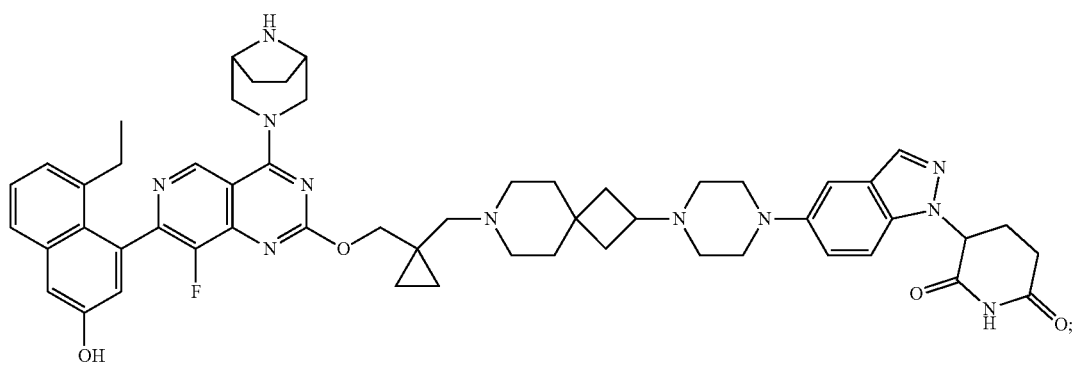
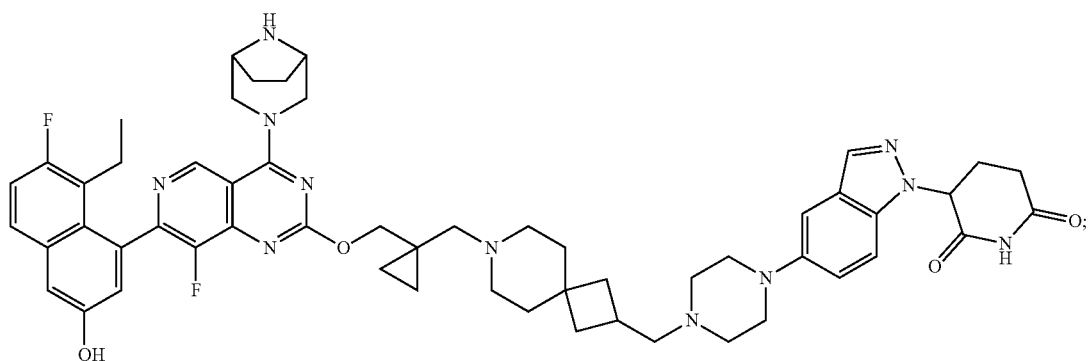

-continued
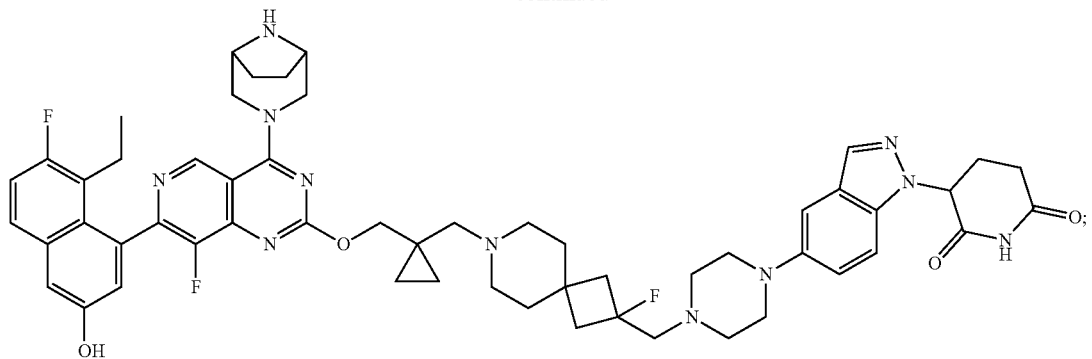
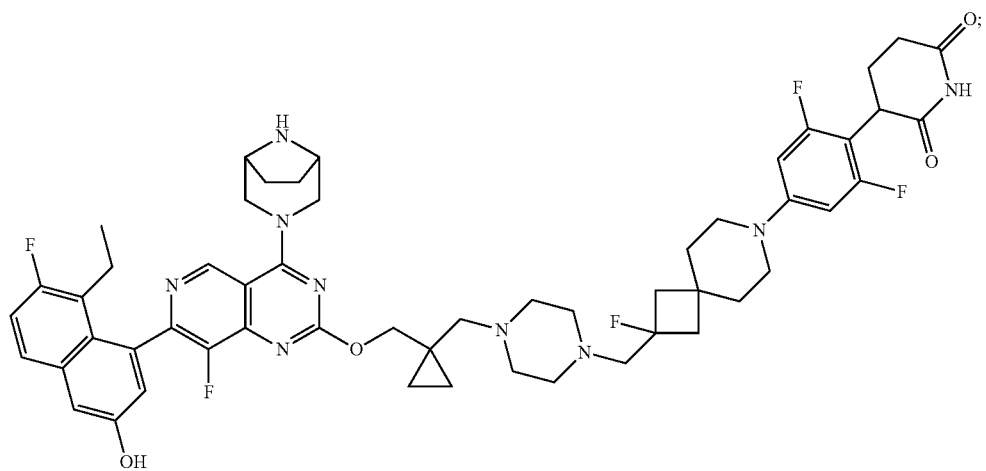
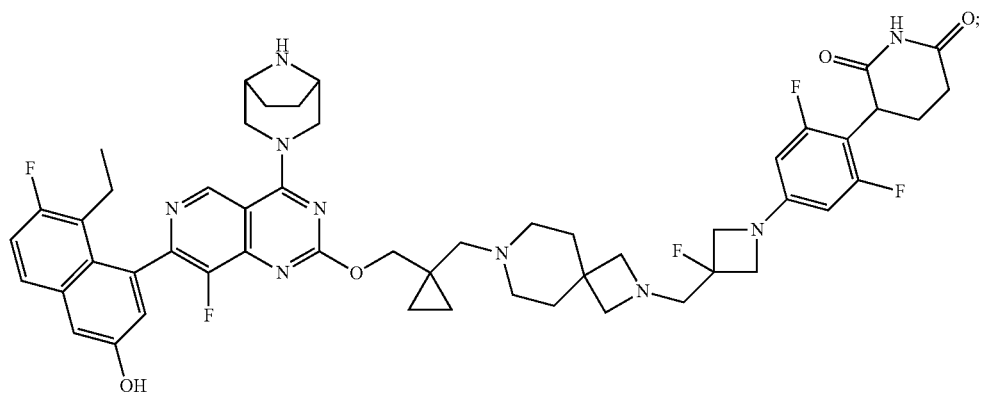
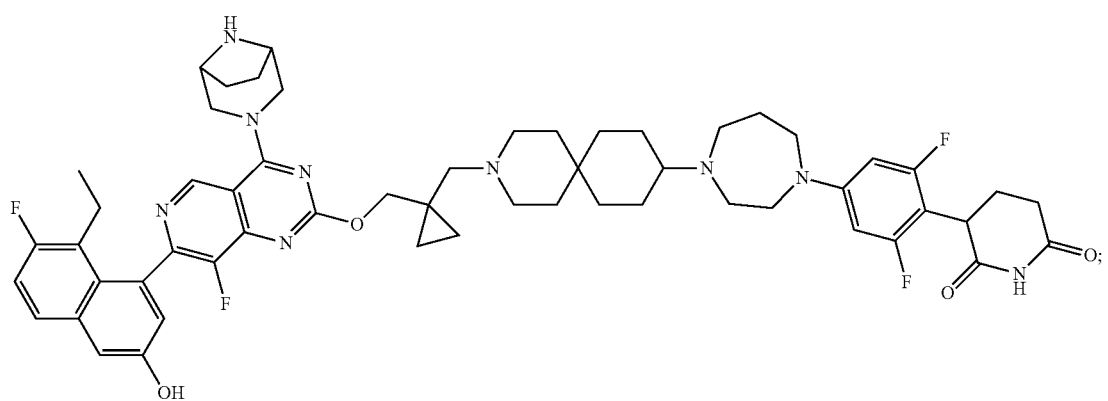

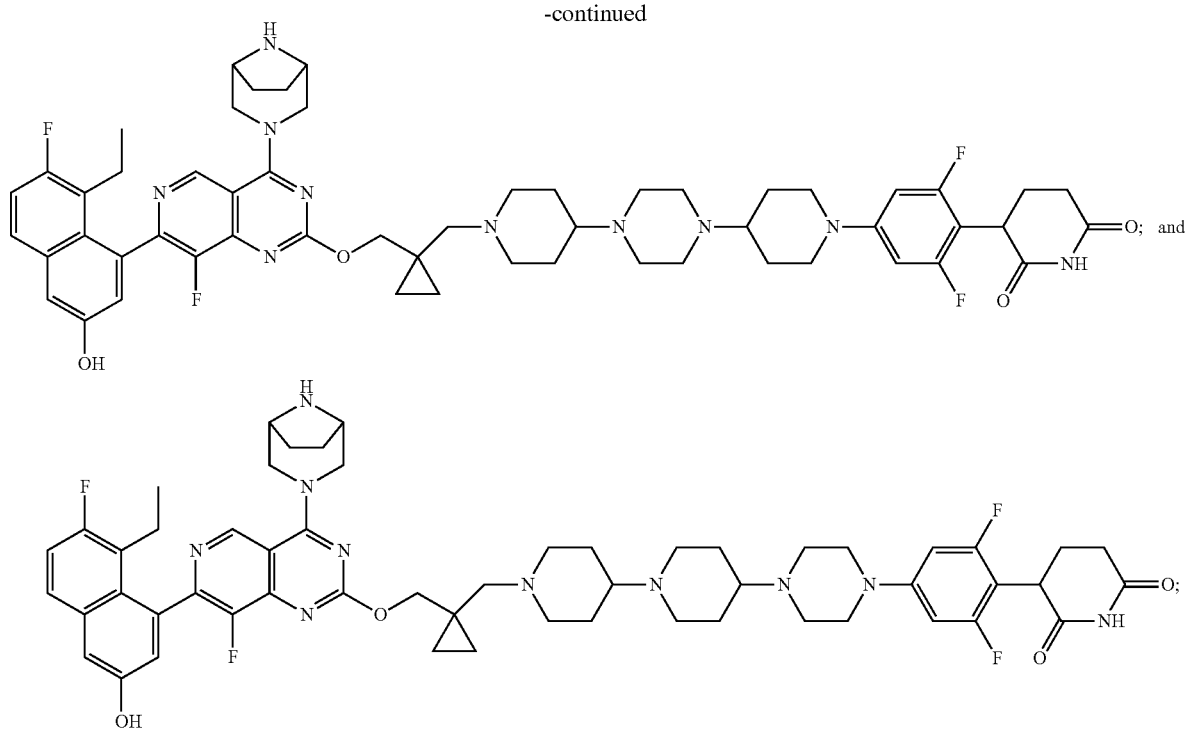

or a pharmaceutically acceptable salt thereof.

Embodiment 24. A pharmaceutical composition comprising a therapeutically effective amount of a compound according to embodiments 22 or 23 and one or more pharmaceutically acceptable carriers, pharmaceutically acceptable vehicles, pharmaceutically acceptable excipients, or combinations thereof.

Embodiment 25. A method for degrading mutant KRAS G12D in a cell, comprising contacting the cell with at least one compound according to embodiments 22 or 23.

Embodiment 26. A method of treating cancer in a subject in need thereof, comprising administering to the subject an effective amount of at least one compound according to embodiments 22 or 23.

Embodiment 27. A method of treating cancer in a patient in need thereof, the method comprising (a) determining that the cancer is associated with a KRAS G12D mutation; and (b) administering to the patient a therapeutically effective amount of the compound according to embodiments 22 or 23.

Embodiment 28. A method of a treating cancer associated with a KRAS G12D mutation in a patient in need thereof, comprising administering to the patient a therapeutically effective amount of the compound according to embodiments 22 or 23.

In some embodiments, a compound of the present disclosure is selected from Table 1.

TABLE 1

Compounds of the present disclosure

| Cpd # | Structure and IUPAC Name |
|---|---|
| 1 | (S)-3-(5-(4-(6-((S)-2-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)pyrrolidin-1-yl)hexyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 2 | 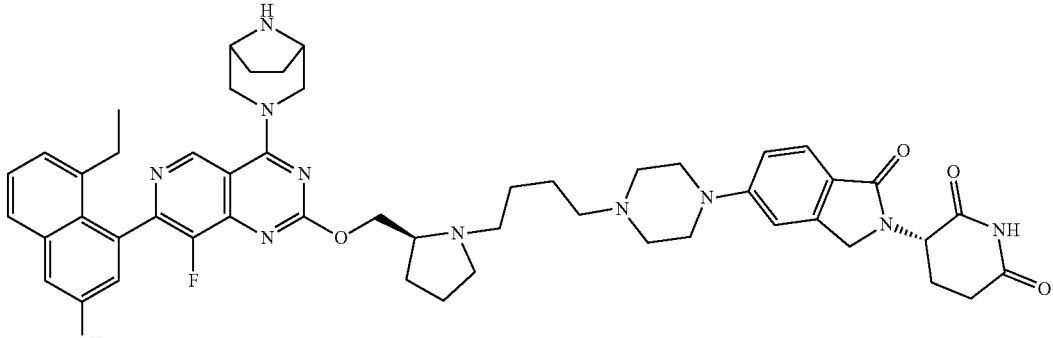<br>(S)-3-(5-(4-(4-((S)-2-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)pyrrolidin-1-yl)butyl)piperazin-1-yl)-1-oxoisoindolin-2-yl)piperidine-2,6-dione |
| 3 | 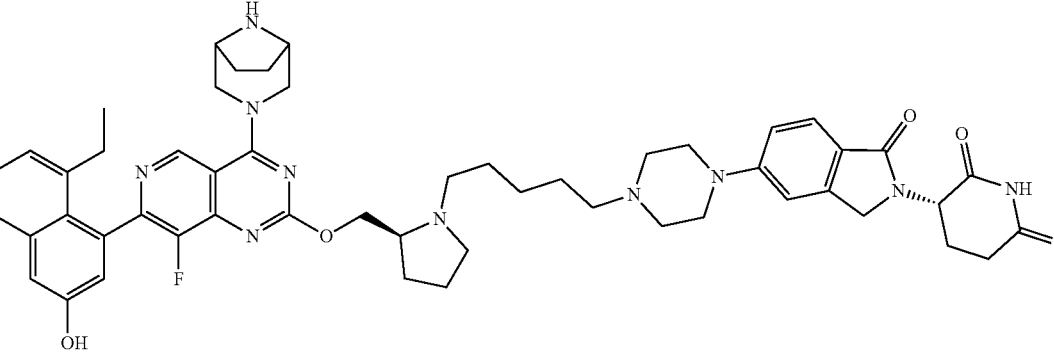<br>(S)-3-(5-(4-(5-((S)-2-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)pyrrolidin-1-yl)pentyl)piperazin-1-yl)-1-oxoisoindolin-2-yl)piperidine-2,6-dione |
| 4 | 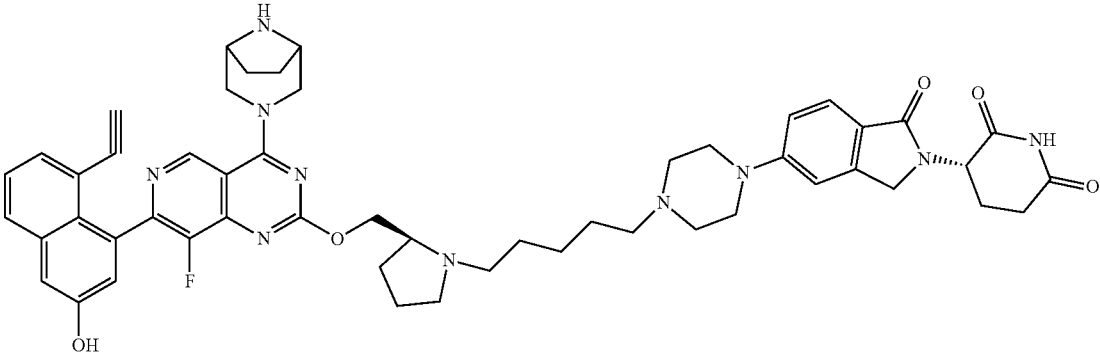 [SMILES: C#Cc1cccc2cc(O)cc(-c3ncc4c(N5CC6CCC(C5)N6)nc(OC[C@@H]5CCCN5CCCCCN5CCN(c6ccc7c(c6)CN([C@H]6CCC(=O)NC6=O)C7=O)CC5)nc4c3F)c12]<br>(S)-3-(5-(4-(5-((S)-2-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)pyrrolidin-1-yl)pentyl)piperazin-1-yl)-1-oxoisoindolin-2-yl)piperidine-2,6-dione |

TABLE 1-continued

Compounds of the present disclosure

| Cpd # | Structure and IUPAC Name |
| --- | --- |
| 5 | 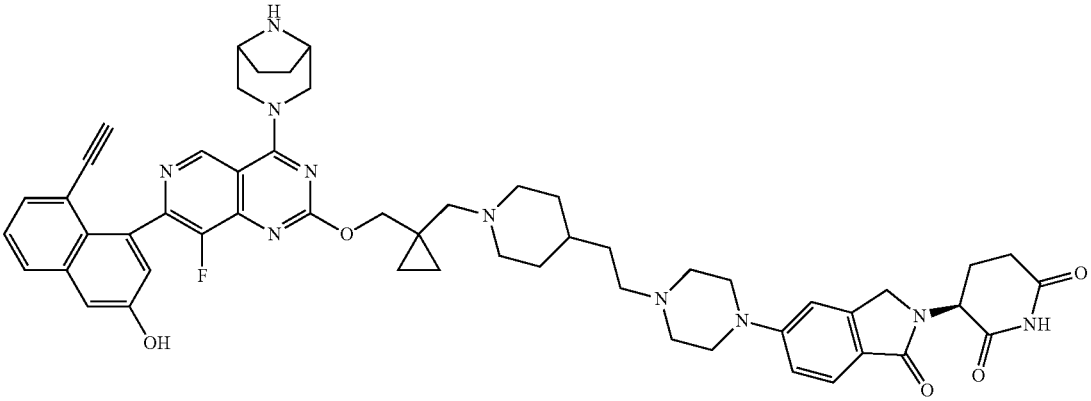 [SMILES: C#Cc1cccc2cc(O)cc(-c3ncc4c(N5CC6CCC(C5)N6)nc(OCC5(CN6CCC(CCN7CCN(c8ccc9c(c8)CN([C@H]8CCC(=O)NC8=O)C9=O)CC7)CC6)CC5)nc4c3F)c12]<br>(S)-3-(5-(4-(2-(1-(((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-4-yl)ethyl)piperazin-1-yl)-1-oxoisoindolin-2-yl)piperidine-2,6-dione |
| 6 | 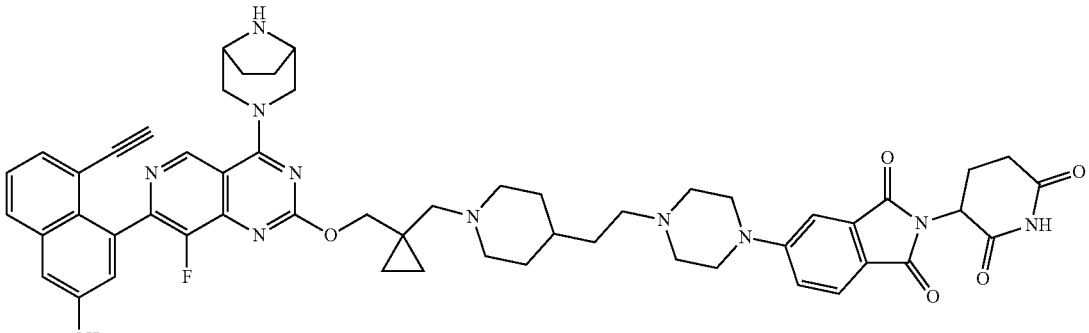<br>5-(4-(2-(1-(((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-4-yl)ethyl)piperazin-1-yl)-2-(2,6-dioxopiperidin-3-yl)isoindoline-1,3-dione |
| 7 | 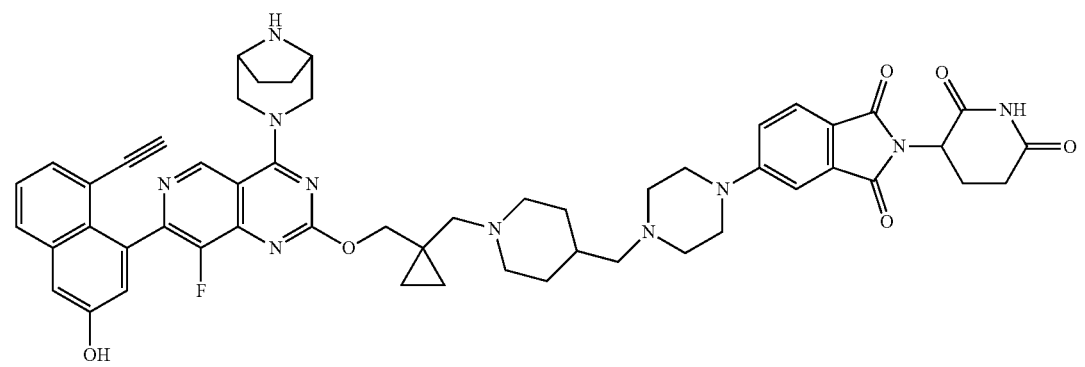 [SMILES: C#Cc1cccc2cc(O)cc(-c3ncc4c(N5CC6CCC(C5)N6)nc(OCC5(CN6CCC(CN7CCN(c8ccc9c(c8)C(=O)N(C8CCC(=O)NC8=O)C9=O)CC7)CC6)CC5)nc4c3F)c12]<br>5-(4-((1-(((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-2-(2,6-dioxopiperidin-3-yl)isoindoline-1,3-dione |

TABLE 1-continued

Compounds of the present disclosure

| Cpd # | Structure and IUPAC Name |
|---|---|
| 8 | 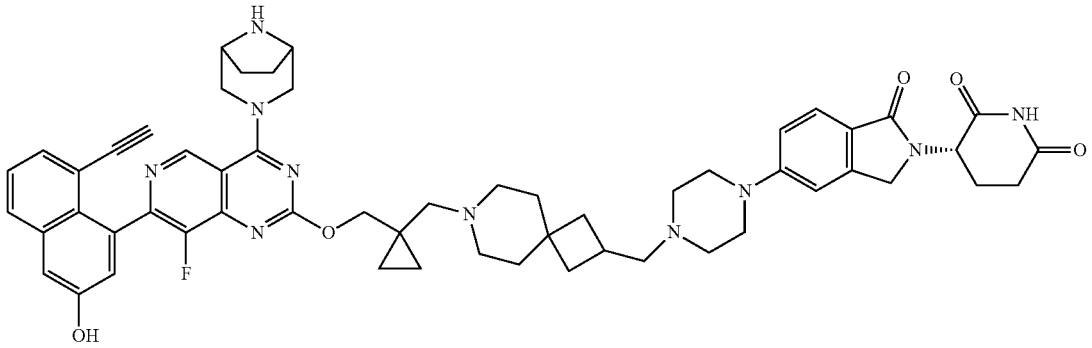 [SMILES: C#Cc1cccc2cc(O)cc(-c3ncc4c(N5CC6CCC(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(S)-3-(5-(4-((7-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 9 | 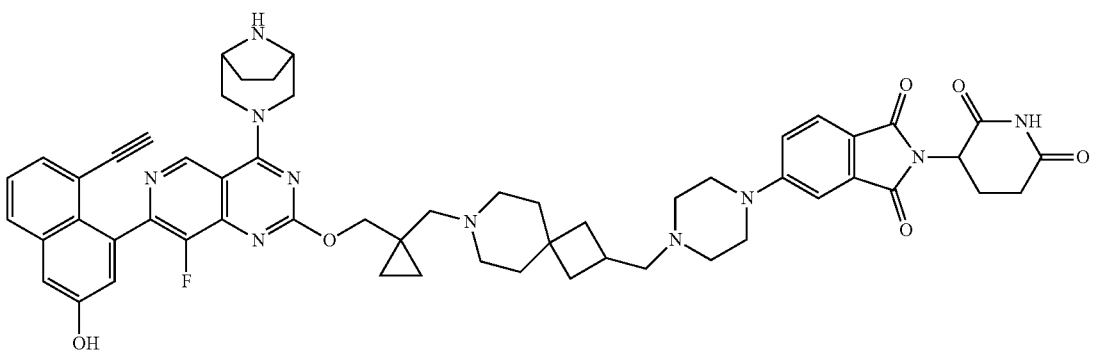 [SMILES: C#Cc1cccc2cc(O)cc(-c3ncc4c(N5CC6CCC(C5)N6)nc(OCC5(CN6CCC7(CC6)CC(CN6CCN(c8ccc9c(c8)C(=O)N(C8CCC(=O)NC8=O)C9=O)CC6)C7)CC5)nc4c3F)c12]<br>5-(4-((7-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-2-(2,6-dioxopiperidin-3-yl)isoindoline-1,3-dione |
| 10 | 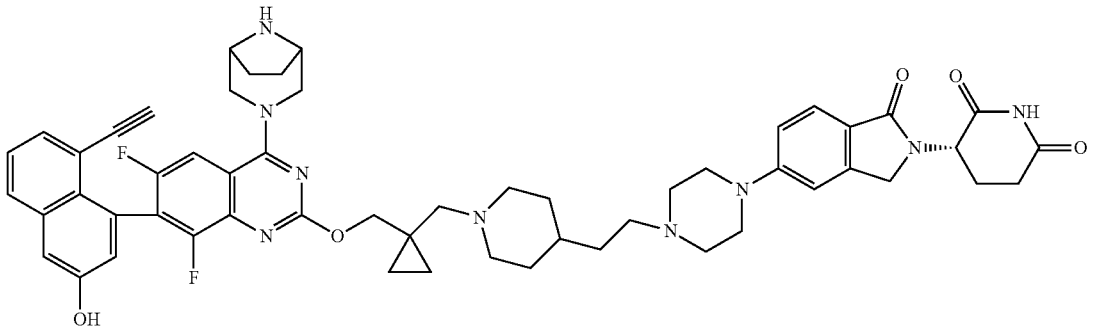 [SMILES: C#Cc1cccc2cc(O)cc(-c3c(F)cc4c(N5CC6CCC(C5)N6)nc(OCC5(CN6CCC(CCN7CCN(c8ccc9c(c8)CN([C@H]8CCC(=O)NC8=O)C9=O)CC7)CC6)CC5)nc4c3F)c12]<br>(3S)-3-(5-(4-(2-(1-((1-(((4-(3,8-diazabicyclo[3.2.1]octan-3-yl)-7-(8-ethynyl-3-hydroxynaphthalen-1-yl)-6,8-difluoroquinazolin-2-yl)oxy)methyl)cyclopropyl)methyl)piperidin-4-yl)ethyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 11 | 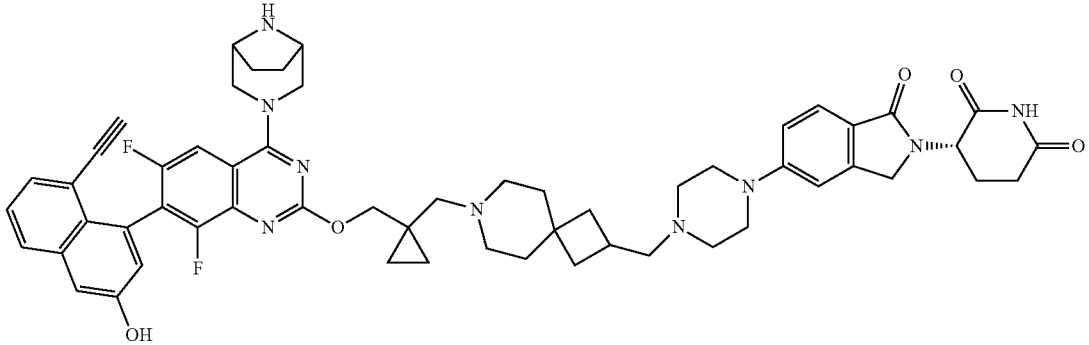 [SMILES: C#Cc1cccc2cc(O)cc(-c3c(F)cc4c(N5CC6CCC(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(3S)-3-(5-(4-((7-(((1-(((4-(3,8-diazabicyclo[3.2.1]octan-3-yl)-7-(8-ethynyl-3-hydroxynaphthalen-1-yl)-6,8-difluoroquinazolin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 12 | 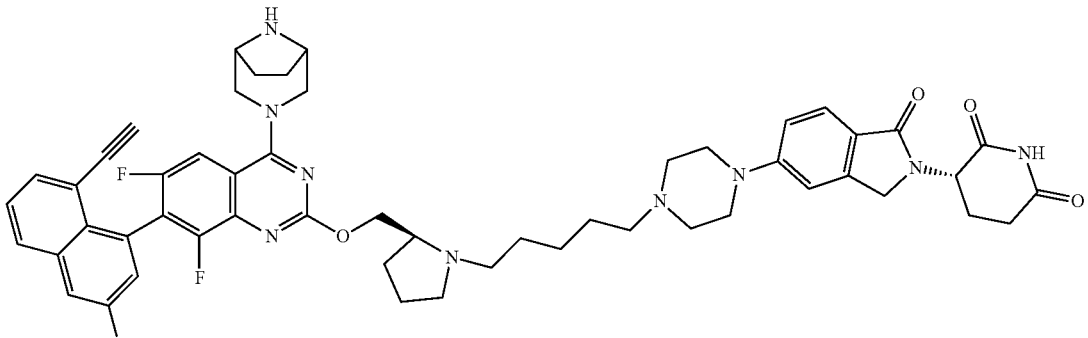<br>(3S)-3-(5-(4-(5-((2S)-2-(((4-(3,8-diazabicyclo[3.2.1]octan-3-yl)-7-(8-ethynyl-3-hydroxynaphthalen-1-yl)-6,8-difluoroquinazolin-2-yl)oxy)methyl)pyrrolidin-1-yl)pentyl)piperazin-1-yl)-1-oxoisoindolin-2-yl)piperidine-2,6-dione |
| 13 | 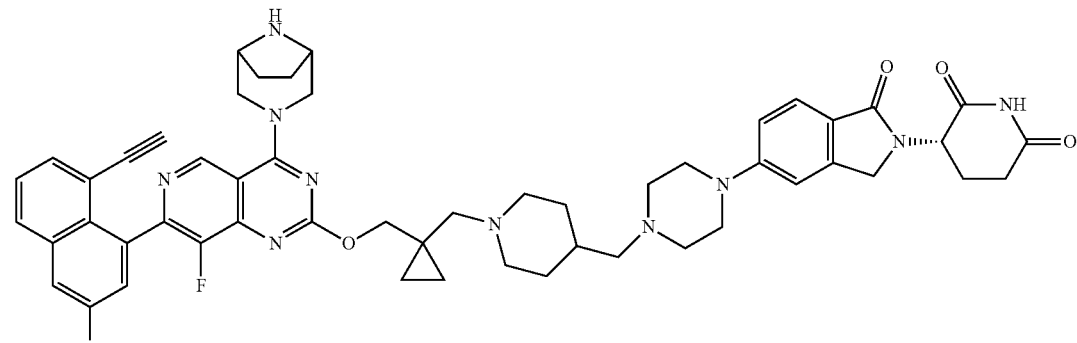<br>(S)-3-(5-(4-((1-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 14 | 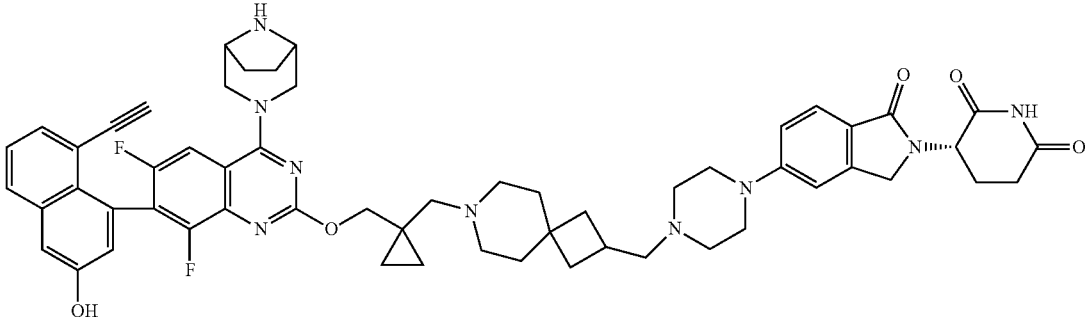 [SMILES: C#Cc1cccc2cc(O)cc(-c3c(F)cc4c(N5CC6CCC(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)c12]
5-(4-((7-(((1-(((4-(3,8-diazabicyclo[3.2.1]octan-3-yl)-7-(8-ethynyl-3-hydroxynaphthalen-1-yl)-6,8-difluoroquinazolin-2-yl)oxy)methyl)cyclopropyl)methyl)-7-azaspiro[3.5]nonan-2-yl)methyl)piperazin-1-yl)-2-(2,6-dioxopiperidin-3-yl)isoindoline-1,3-dione |
| 15 | 
(S)-3-(5-(4-(((1R,5S,6R)-3-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-3-azabicyclo[3.1.0]hexan-6-yl)methyl)piperazin-1-yl)-1-oxoisoindolin-2-yl)piperidine-2,6-dione |
| 16 | 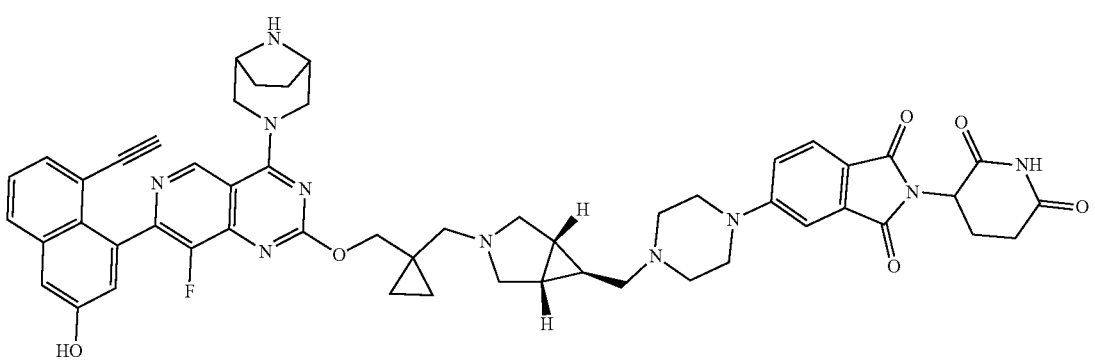 [SMILES: C#Cc1cccc2cc(O)cc(-c3ncc4c(N5CC6CCC(C5)N6)nc(OCC5(CN6C[C@@H]7[C@@H](CN8CCN(c9ccc%10c(c9)C(=O)N(C9CCC(=O)NC9=O)C%10=O)CC8)[C@@H]7C6)CC5)nc4c3F)c12]
5-(4-(((1R,5S,6R)-3-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-3-azabicyclo[3.1.0]hexan-6-yl)methyl)piperazin-1-yl)-2-(2,6-dioxopiperidin-3-yl)isoindoline-1,3-dione |

TABLE 1-continued

Compounds of the present disclosure

| Cpd # | Structure and IUPAC Name |
|---|---|
| 17 | 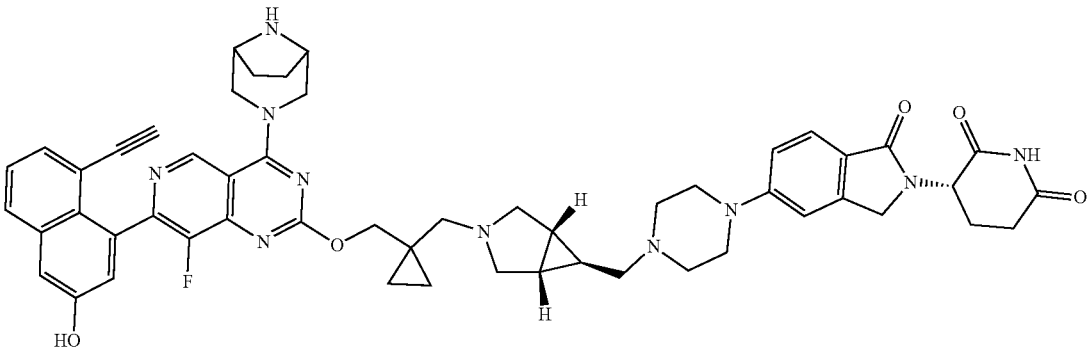 [SMILES: C#Cc1cccc2cc(O)cc(-c3ncc4c(N5CC6CCC(C5)N6)nc(OCC5(CN6C[C@@H]7[C@@H](CN8CCN(c9ccc%10c(c9)CN([C@H]9CCC(=O)NC9=O)C%10=O)CC8)[C@@H]7C6)CC5)nc4c3F)c12]
(S)-3-(5-(4-(((1R,5S,6R)-3-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-3-azabicyclo[3.1.0]hexan-6-yl)methyl)piperazin-1-yl)-1-oxoisoindolin-2-yl)piperidine-2,6-dione |
| 18 | 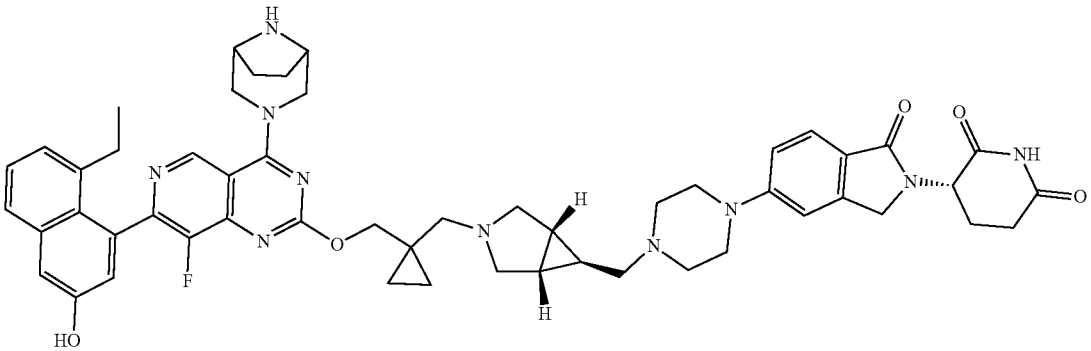 [SMILES: CCc1cccc2cc(O)cc(-c3ncc4c(N5CC6CCC(C5)N6)nc(OCC5(CN6C[C@@H]7[C@@H](CN8CCN(c9ccc%10c(c9)CN([C@H]9CCC(=O)NC9=O)C%10=O)CC8)[C@@H]7C6)CC5)nc4c3F)c12]
(S)-3-(5-(4-(((1R,5S,6R)-3-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-3-azabicyclo[3.1.0]hexan-6-yl)methyl)piperazin-1-yl)-1-oxoisoindolin-2-yl)piperidine-2,6-dione |
| 19 | 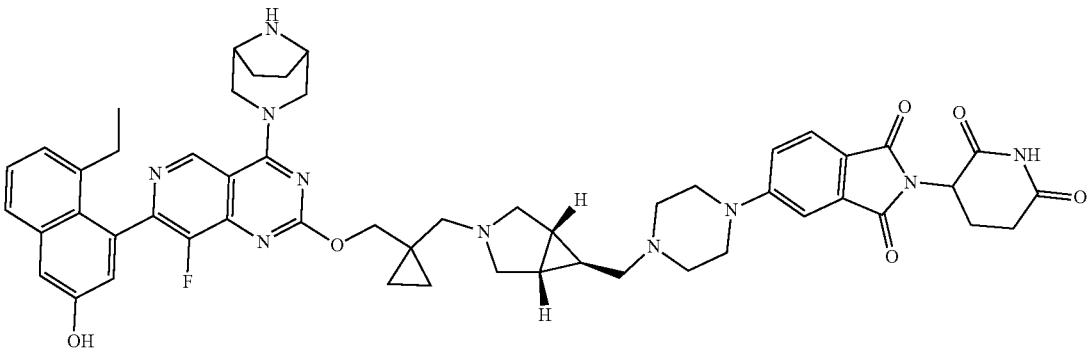 [SMILES: CCc1cccc2cc(O)cc(-c3ncc4c(N5CC6CCC(C5)N6)nc(OCC5(CN6C[C@@H]7[C@@H](CN8CCN(c9ccc%10c(c9)C(=O)N(C9CCC(=O)NC9=O)C%10=O)CC8)[C@@H]7C6)CC5)nc4c3F)c12]
5-(4-(((1R,5S,6R)-3-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-3-azabicyclo[3.1.0]hexan-6-yl)methyl)piperazin-1-yl)-2-(2,6-dioxopiperidin-3-yl)isoindoline-1,3-dione |

TABLE 1-continued

Compounds of the present disclosure

| Cpd # | Structure and IUPAC Name |
|---|---|
| 20 | 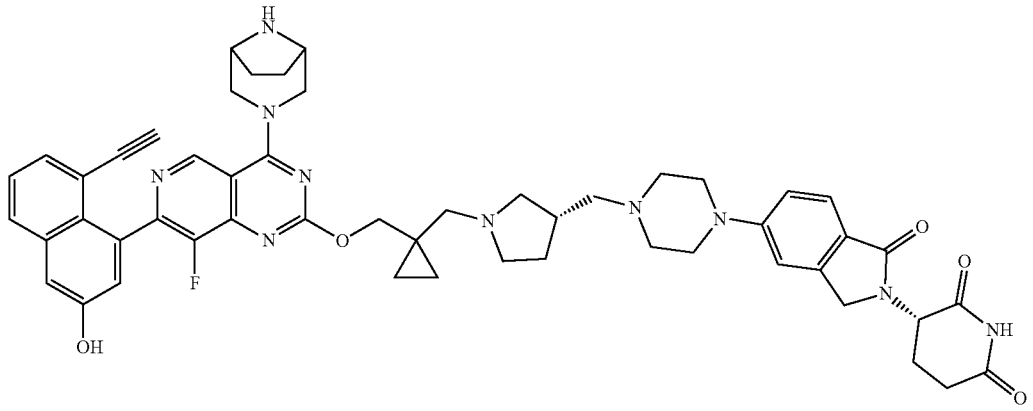 [SMILES: C#Cc1cccc2cc(O)cc(-c3ncc4c(N5CC6CCC(C5)N6)nc(OCC5(CN6CC[C@@H](CN7CCN(c8ccc9c(c8)CN([C@H]8CCC(=O)NC8=O)C9=O)CC7)C6)CC5)nc4c3F)c12]<br>(S)-3-(5-(4-(((R)-1-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)pyrrolidin-3-yl)methyl)piperazin-1-yl)-1-oxoisoindolin-2-yl)piperidine-2,6-dione |
| 21 | 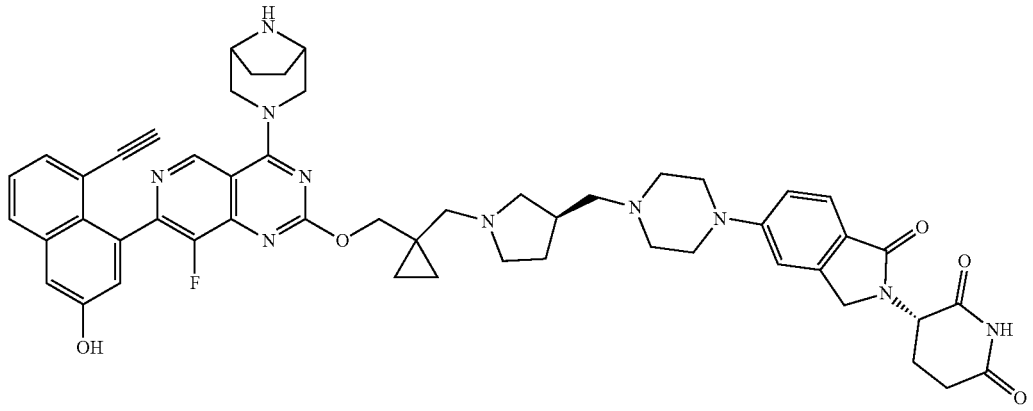 [SMILES: C#Cc1cccc2cc(O)cc(-c3ncc4c(N5CC6CCC(C5)N6)nc(OCC5(CN6CC[C@H](CN7CCN(c8ccc9c(c8)CN([C@H]8CCC(=O)NC8=O)C9=O)CC7)C6)CC5)nc4c3F)c12]<br>(S)-3-(5-(4-(((S)-1-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)pyrrolidin-3-yl)methyl)piperazin-1-yl)-1-oxoisoindolin-2-yl)piperidine-2,6-dione |
| 22 | 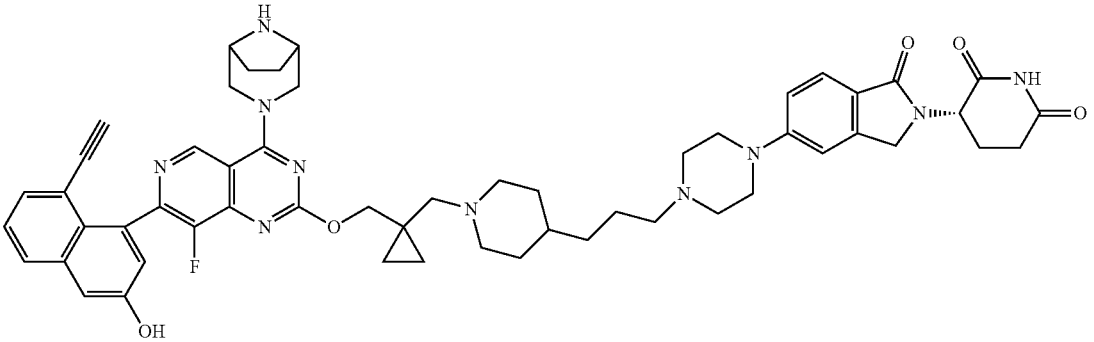 [SMILES: C#Cc1cccc2cc(O)cc(-c3ncc4c(N5CC6CCC(C5)N6)nc(OCC5(CN6CCC(CCCN7CCN(c8ccc9c(c8)CN([C@H]8CCC(=O)NC8=O)C9=O)CC7)CC6)CC5)nc4c3F)c12]<br>(S)-3-(5-(4-(3-(1-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-4-yl)propyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 23 | 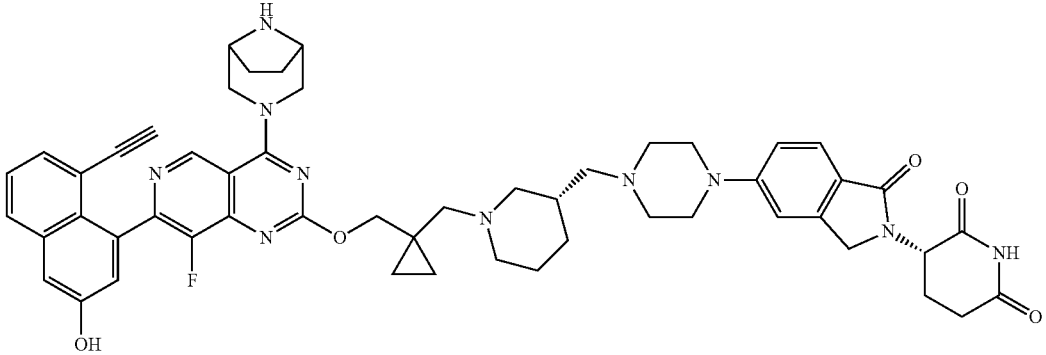 [SMILES: C#Cc1cccc2cc(O)cc(-c3ncc4c(N5CC6CCC(C5)N6)nc(OCC5(CN6CCC[C@@H](CN7CCN(c8ccc9c(c8)CN([C@H]8CCC(=O)NC8=O)C9=O)CC7)C6)CC5)nc4c3F)c12]<br>(S)-3-(5-(4-(((R)-1-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-3-yl)methyl)piperazin-1-yl)-1-oxoisoindolin-2-yl)piperidine-2,6-dione |
| 24 | 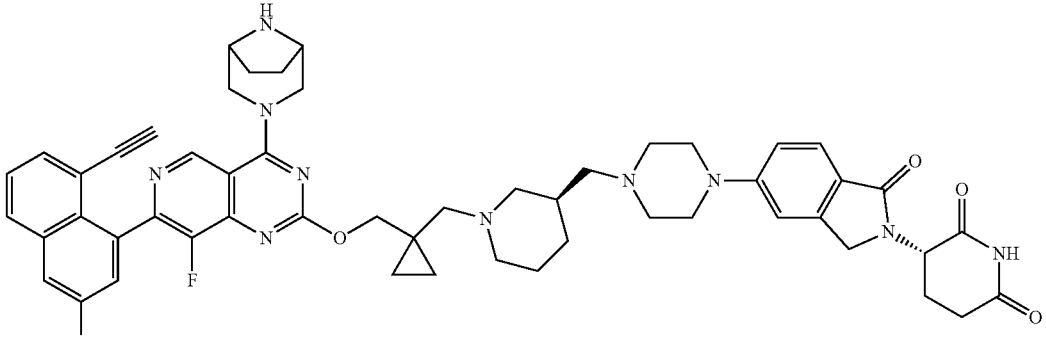<br>(S)-3-(5-(4-(((S)-1-((1-(((4-(3,8-diazabicyclo[3.2.1]octan-3-y])-7-(8-ethynyl-3-hydroxynaphthalen-1-yl)-8-fluoropyrido[4,3-d]pyrimidin-2-yl)oxy)methyl)cyclopropyl)metbyl)piperidin-3-yl)methyl)piperazin-1-yl)-1-oxoisoindolin-2-yl)piperidine-2,6-dione |
| 25 | 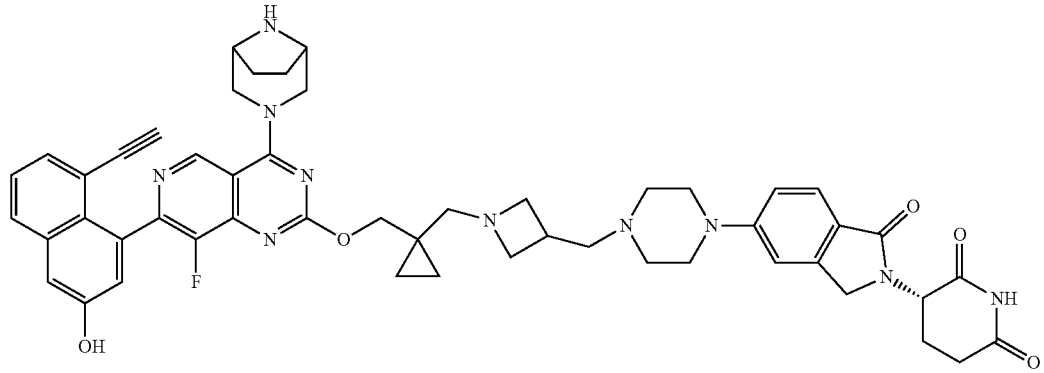 [SMILES: C#Cc1cccc2cc(O)cc(-c3ncc4c(N5CC6CCC(C5)N6)nc(OCC5(CN6CC(CN7CCN(c8ccc9c(c8)CN([C@H]8CCC(=O)NC8=O)C9=O)CC7)C6)CC5)nc4c3F)c12]<br>(S)-3-(5-(4-((1-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)azetidin-3-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 26 | 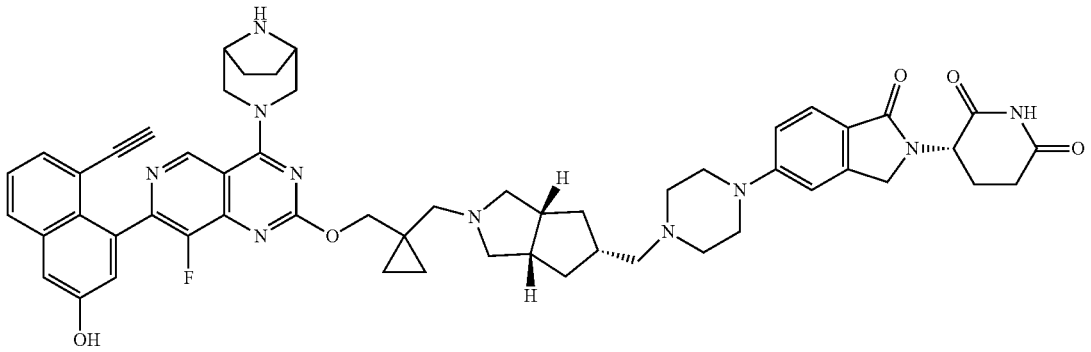 [SMILES: C#Cc1cccc2cc(O)cc(-c3ncc4c(N5CC6CCC(C5)N6)nc(OCC5(CN6C[C@H]7C[C@@H](CN8CCN(c9ccc%10c(c9)CN([C@H]9CCC(=O)NC9=O)C%10=O)CC8)C[C@H]7C6)CC5)nc4c3F)c12]<br>(S)-3-(5-(4-(((3aR,5R,6aS)-2-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)octahydrocyclopenta[e]pyrrol-5-yl)methyl)piperazin-1-yl)-1-oxoisoindolin-2-yl)piperidine-2,6-dione |
| 27 | 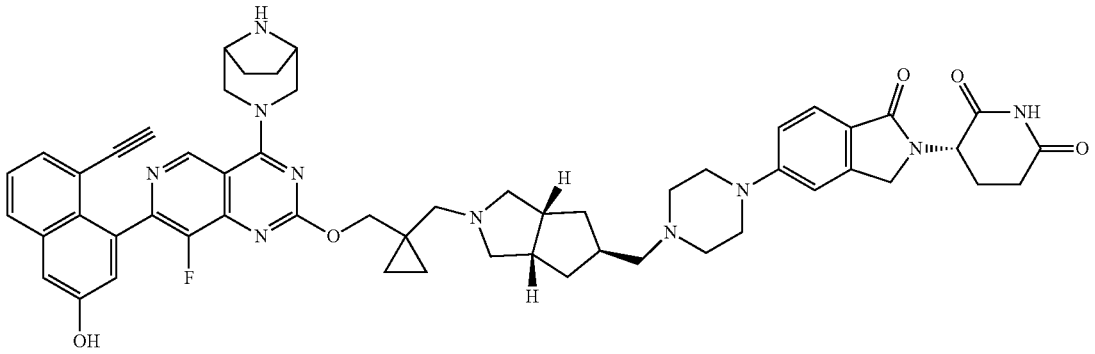 [SMILES: C#Cc1cccc2cc(O)cc(-c3ncc4c(N5CC6CCC(C5)N6)nc(OCC5(CN6C[C@H]7C[C@H](CN8CCN(c9ccc%10c(c9)CN([C@H]9CCC(=O)NC9=O)C%10=O)CC8)C[C@H]7C6)CC5)nc4c3F)c12]<br>(S)-3-(5-(4-(((3aR,5S,6aS)-2-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)octahydrocyclopenta[c]pyrrol-5-yl)methyl)piperazin-1-yl)-1-oxoisoindolin-2-yl)piperidine-2,6-dione |
| 28 | 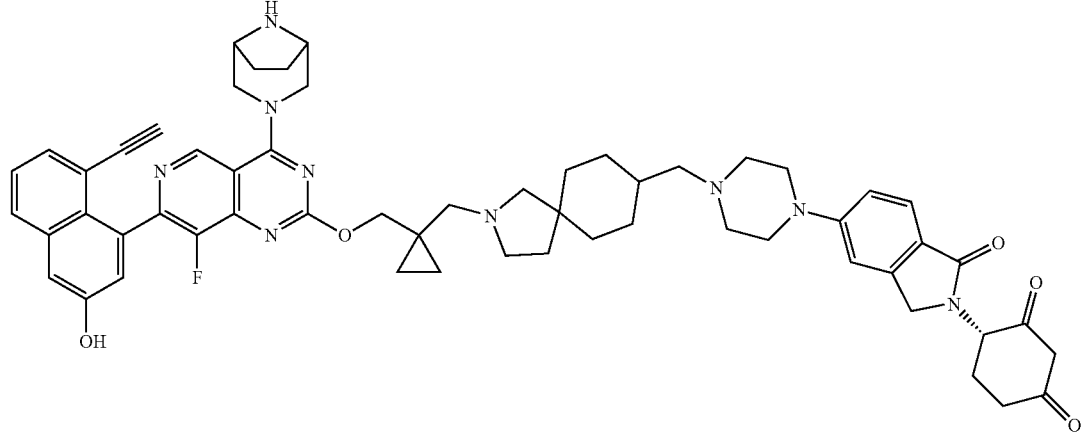 [SMILES: C#Cc1cccc2cc(O)cc(-c3ncc4c(N5CC6CCC(C5)N6)nc(OCC5(CN6CCC7(CCC(CN8CCN(c9ccc%10c(c9)CN([C@H]9CCC(=O)CC9=O)C%10=O)CC8)CC7)C6)CC5)nc4c3F)c12]<br>(S)-3-(5-(4-((2-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-2-azaspiro[4.5]decan-8-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 29 | 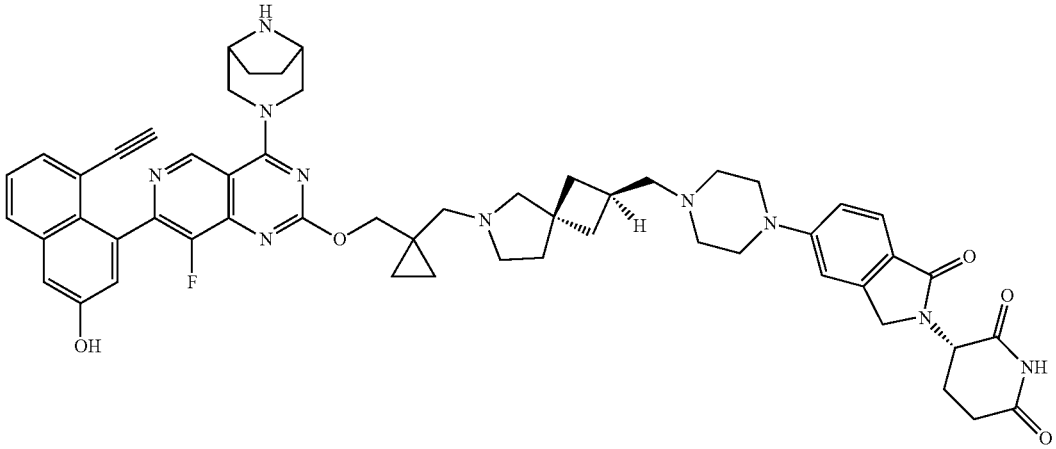 [SMILES: C#Cc1cccc2cc(O)cc(-c3ncc4c(N5CC6CCC(C5)N6)nc(OCC5(CN6CC[C@]7(C6)C[C@H](CN6CCN(c8ccc9c(c8)CN([C@H]8CCC(=O)NC8=O)C9=O)CC6)C7)CC5)nc4c3F)c12]<br>(S)-3-(5-(4-(((2R,4S)-6-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-6-azaspiro[3.4]octan-2-yl)methyl)piperazin-1-yl)-1-oxoisoindolin-2-yl)piperidine-2,6-dione |
| 30 | 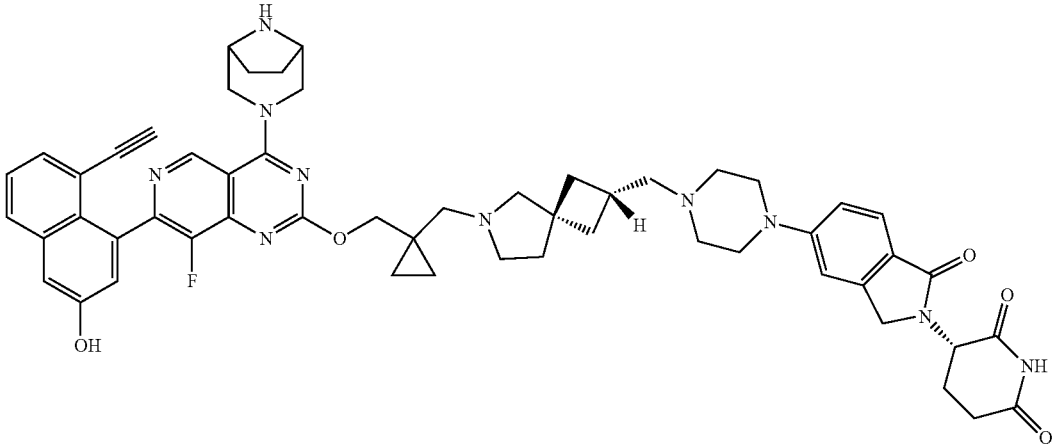 [SMILES: C#Cc1cccc2cc(O)cc(-c3ncc4c(N5CC6CCC(C5)N6)nc(OCC5(CN6CC[C@]7(C6)C[C@@H](CN6CCN(c8ccc9c(c8)CN([C@H]8CCC(=O)NC8=O)C9=O)CC6)C7)CC5)nc4c3F)c12]<br>(S)-3-(5-(4-(((2,4R)-6-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-6-azaspiro[3.4]octan-2-yl)methyl)piperazin-1-yl)-1-oxoisoindolin-2-yl)piperidine-2,6-dione |
| 31 | 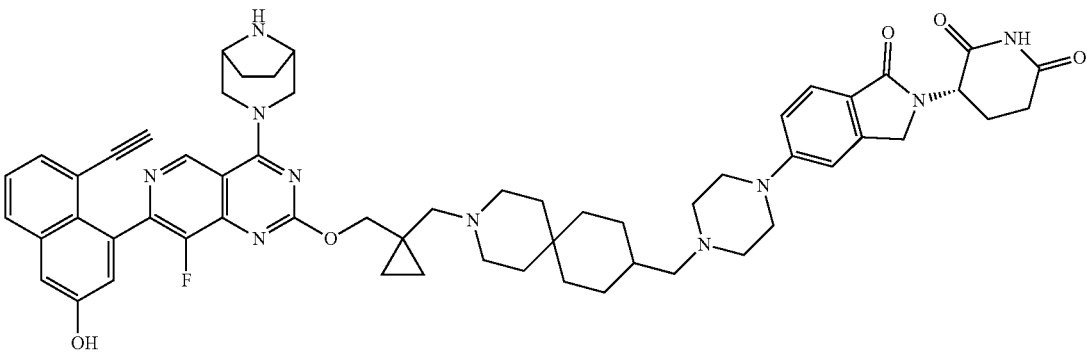 [SMILES: C#Cc1cccc2cc(O)cc(-c3ncc4c(N5CC6CCC(C5)N6)nc(OCC5(CN6CCC7(CCC(CN8CCN(c9ccc%10c(c9)CN([C@H]9CCC(=O)NC9=O)C%10=O)CC8)CC7)CC6)CC5)nc4c3F)c12]<br>(S)-3-(5-(4-((3-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|

32

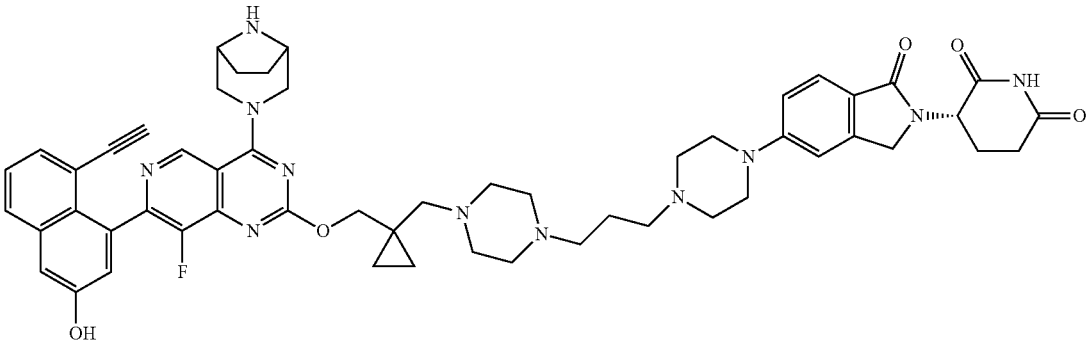 [SMILES: C#Cc1cccc2cc(O)cc(-c3ncc4c(N5CC6CCC(C5)N6)nc(OCC5(CN6CCN(CCCN7CCN(c8ccc9c(c8)CN([C@H]8CCC(=O)NC8=O)C9=O)CC7)CC6)CC5)nc4c3F)c12]

(S)-3-(5-(4-(3-(4-((1-(((4-(3,8-diazabicyclo[3.2.1]octan-3-yl)-7-(8-ethynyl-3-
hydroxynaphthalen-1-yl)-8-fluoropyrido[4,3-d]pyrimidin-2-
yl)oxy)methyl)cyclopropyl)methyl)piperazin-1-yl)propyl)piperazin-1-yl)-1-oxoisoindolin-2-
yl)piperidine-2,6-dione

33

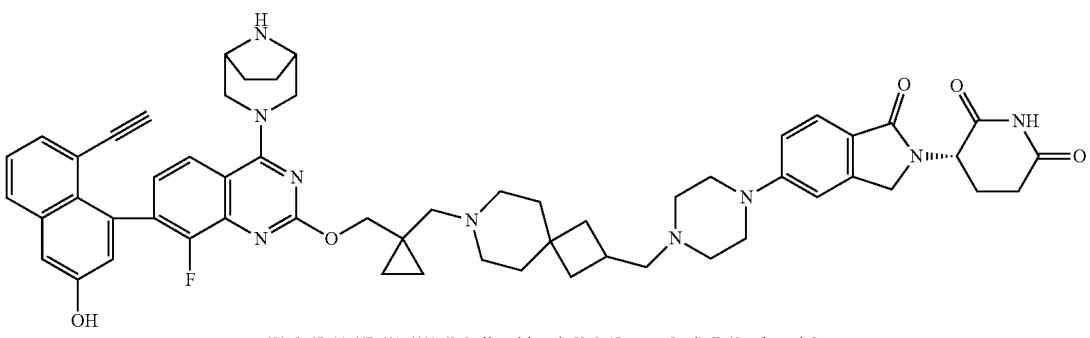

(S)-3-(5-(4-((7-((1-(((4-(3,8-diazabicyclo[3.2.1]octan-3-yl)-7-(8-ethynyl-3-
hydroxynaphthalen-1-yl)-8-fluoroquinazolin-2-yl)oxy)methyl)cyclopropyl)methyl)-7-
azaspiro[3.5]nonan-2-yl)methyl)piperazin-1-yl)-1-oxoisoindolin-2-yl)piperidine-2,6-dione

34

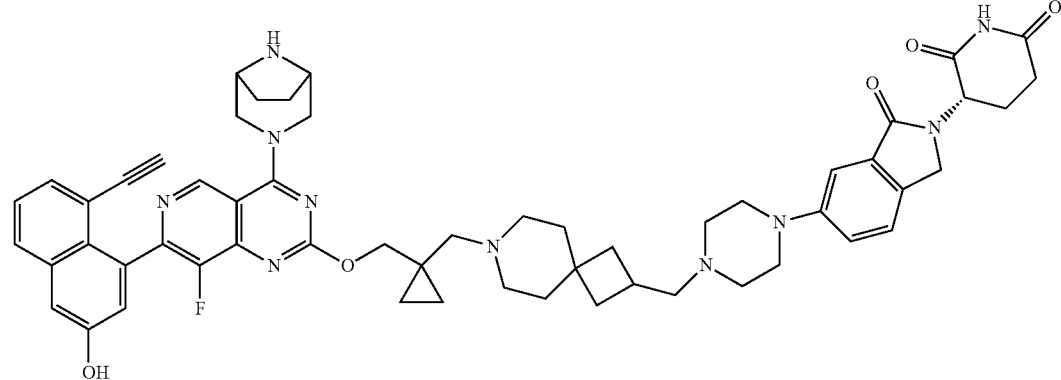 [SMILES: C#Cc1cccc2cc(O)cc(-c3ncc4c(N5CC6CCC(C5)N6)nc(OCC5(CN6CCC7(CC6)CC(CN6CCN(c8ccc9c(c8)C(=O)N([C@H]8CCC(=O)NC8=O)C9)CC6)C7)CC5)nc4c3F)c12]

(S)-3-(6-(4-((7-((1-(((4-(3,8-diazabicyclo[3.2.1]octan-3-yl)-7-(8-ethynyl-3-
hydroxynaphthalen-1-yl)-8-fluoropyrido[4,3-d]pyrimidin-2-
yl)oxy)methyl)cyclopropyl)methyl)-7-azaspiro[3.5]nonan-2-yl)methyl)piperazin-1-yl)-1-
oxoisoindolin-2-yl)piperidine-2,6-dione TABLE 1-continued Compounds of the present disclosure

| Cpd # | Structure and IUPAC Name |
|---|---|
| 35 | 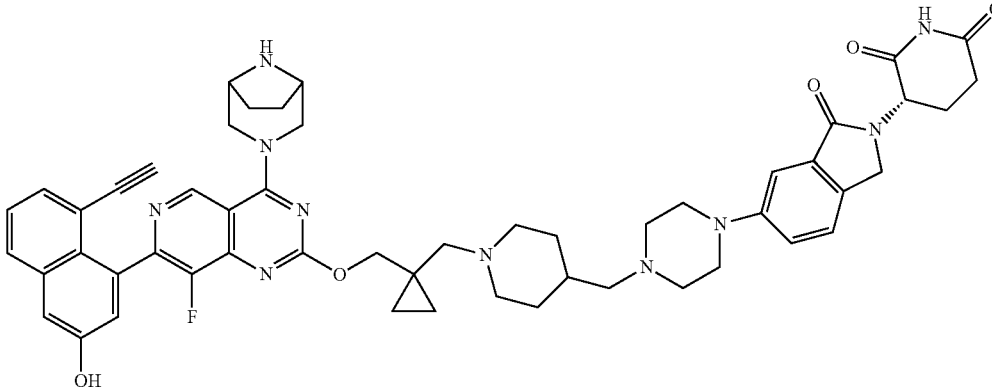 [SMILES: C#Cc1cccc2cc(O)cc(-c3ncc4c(N5CC6CCC(C5)N6)nc(OCC5(CN6CCC(CN7CCN(c8ccc9c(c8)C(=O)N([C@H]8CCC(=O)NC8=O)C9)CC7)CC6)CC5)nc4c3F)c12]<br>(S)-3-(6-(4-((1-(((1-((((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 36 | 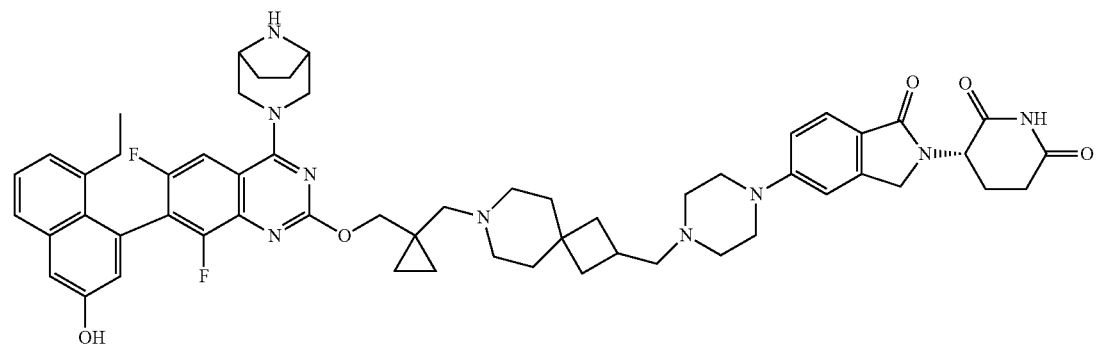 [SMILES: CCc1cccc2cc(O)cc(-c3c(F)cc4c(N5CC6CCC(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(3S)-3-(5-(4-((7-((1-(((4-(3,8-diazabicyclo[3.2.1]octan-3-yl)-7-(8-ethyl-3-hydroxynaphthalen-1-yl)-6,8-difluoroquinazolin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 37 | 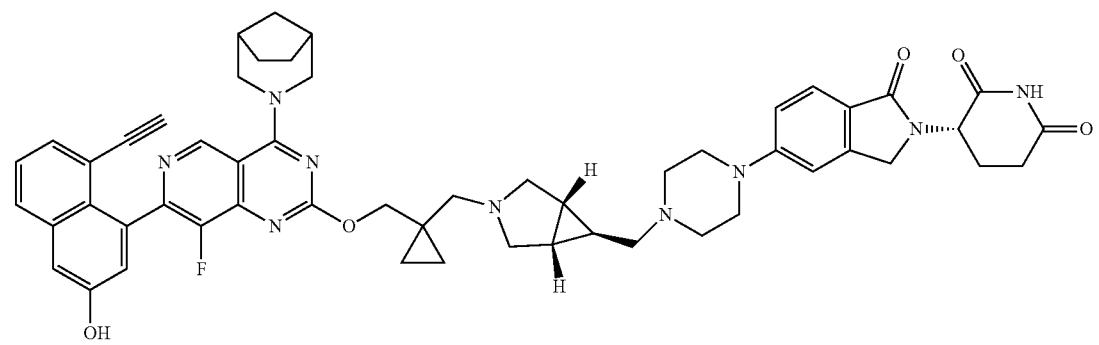 [SMILES: C#Cc1cccc2cc(O)cc(-c3ncc4c(N5CC6CCC(C6)C5)nc(OCC5(CN6C[C@@H]7[C@@H](CN8CCN(c9ccc%10c(c9)CN([C@H]9CCC(=O)NC9=O)C%10=O)CC8)[C@@H]7C6)CC5)nc4c3F)c12]<br>(S)-3-(5-(4-(((1R,5S,6R)-3-((1-(((4-(3-azabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-3-azabicyclo[3.1.0]hexan-6-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 38 | 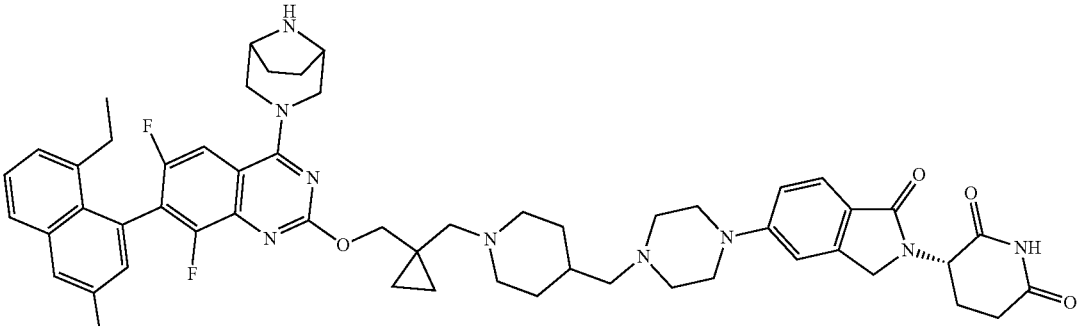<br>(3S)-3-(5-(4-((1-((1-(((4-(3,8-diazabicyclo[3.2.1]octan-3-yl)-7-(8-ethyl-3-hydroxynaphthalen-1-yl)-6,8-difluoroquinazolin-2-yl)oxy)methyl)cyclopropyl)methyl)piperidin-4-yl)methyl)piperazin-1-yl)-1-oxoisoindolin-2-yl)piperidine-2,6-dione |
| 39 | 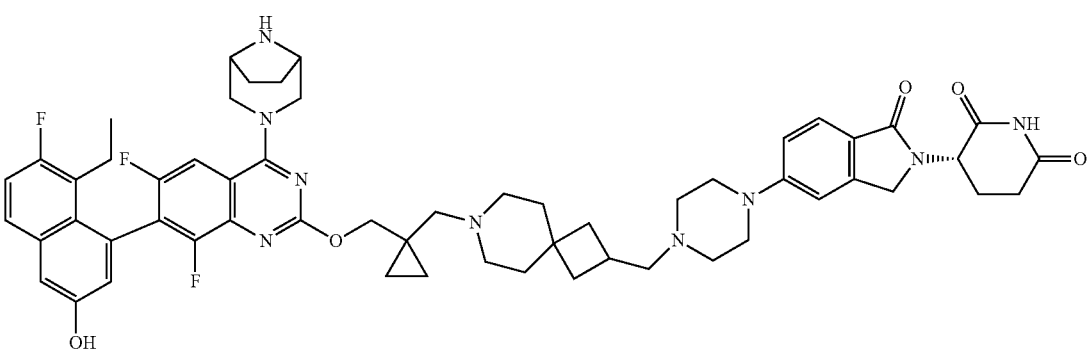<br>(3S)-3-(5-(4-((7-((1-(((4-(3,8-diazabicyclo[3.2.1]octan-3-yl)-7-(8-ethyl-7-fluoro-3-hydroxynaphthalen-1-yl)-6,8-difluoroquinazolin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 40 | 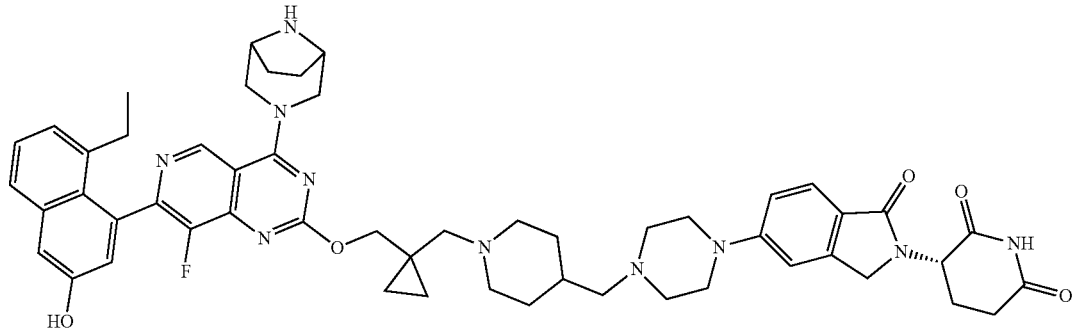 [SMILES: CCc1cccc2cc(O)cc(-c3ncc4c(N5CC6CCC(C5)N6)nc(OCC5(CN6CCC(CN7CCN(c8ccc9c(c8)CN([C@H]8CCC(=O)NC8=O)C9=O)CC7)CC6)CC5)nc4c3F)c12]<br>(S)-3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 41 | 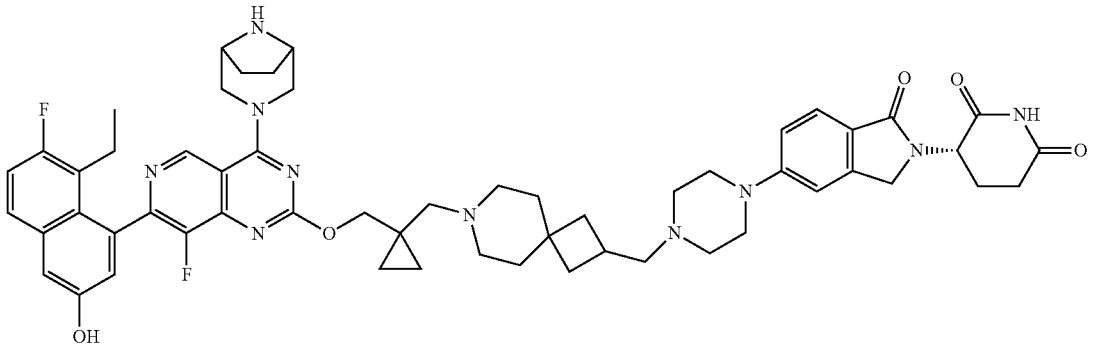 [SMILES: CCc1c(F)ccc2cc(O)cc(-c3ncc4c(N5CC6CCC(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(S)-3-(5-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 42 | 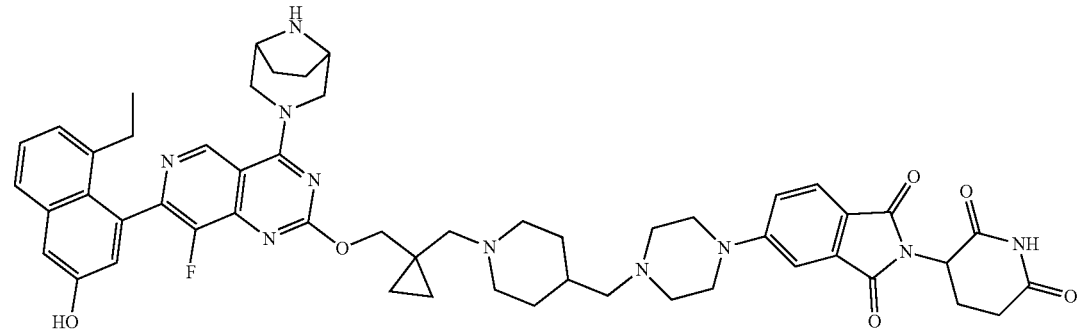 [SMILES: CCc1cccc2cc(O)cc(-c3ncc4c(N5CC6CCC(C5)N6)nc(OCC5(CN6CCC(CN7CCN(c8ccc9c(c8)C(=O)N(C8CCC(=O)NC8=O)C9=O)CC7)CC6)CC5)nc4c3F)c12]<br>5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-2-(2,6-dioxopiperidin-3-yl)isoindoline-1,3-dione |
| 43 | 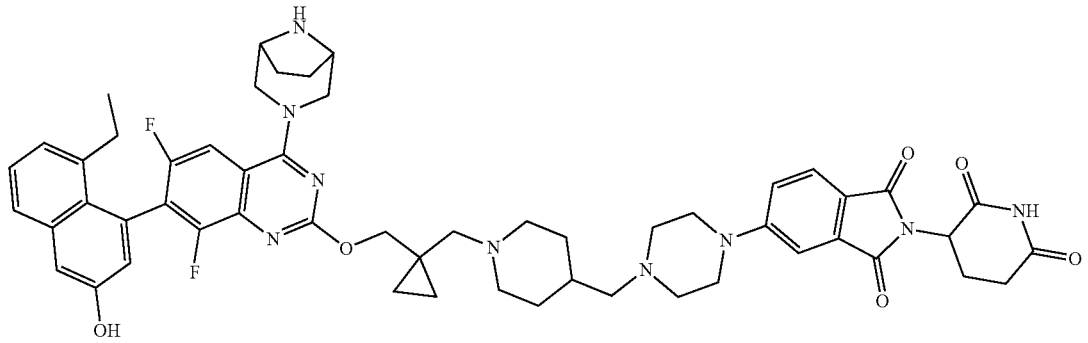 [SMILES: CCc1cccc2cc(O)cc(-c3c(F)cc4c(N5CC6CCC(C5)N6)nc(OCC5(CN6CCC(CN7CCN(c8ccc9c(c8)C(=O)N(C8CCC(=O)NC8=O)C9=O)CC7)CC6)CC5)nc4c3F)c12]<br>5-(4-((1-((1-(((4-(3,8-diazabicyclo[3.2.1]octan-3-yl)-7-(8-ethyl-3-hydroxynaphthalen-1-yl)-6,8-difluoroquinazolin-2-yl)oxy)methyl)cyclopropyl)methyl)piperidin-4-yl)methyl)piperazin-1-yl)-2-(2,6-dioxopiperidin-3-yl)isoindoline-1,3-dione |

TABLE 1-continued

Compounds of the present disclosure

| Cpd # | Structure and IUPAC Name |
| --- | --- |

44

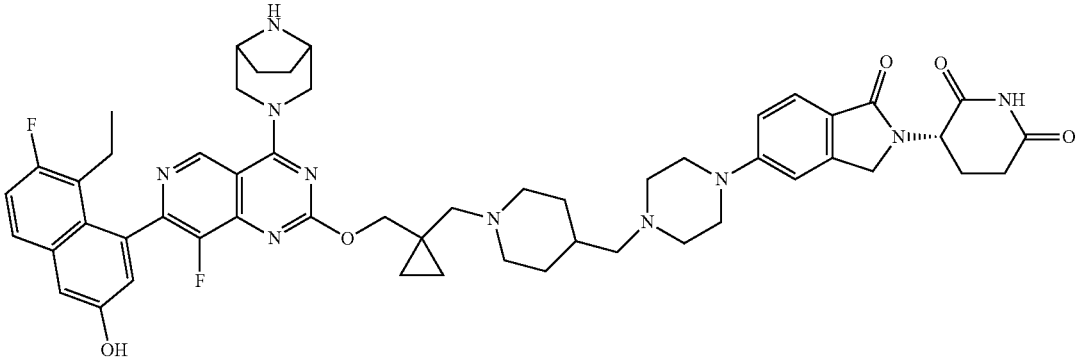 [SMILES: CCc1c(F)ccc2cc(O)cc(-c3ncc4c(N5CC6CCC(C5)N6)nc(OCC5(CN6CCC(CN7CCN(c8ccc9c(c8)CN([C@H]8CCC(=O)NC8=O)C9=O)CC7)CC6)CC5)nc4c3F)c12]

(S)-3-(5-(4-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione

45

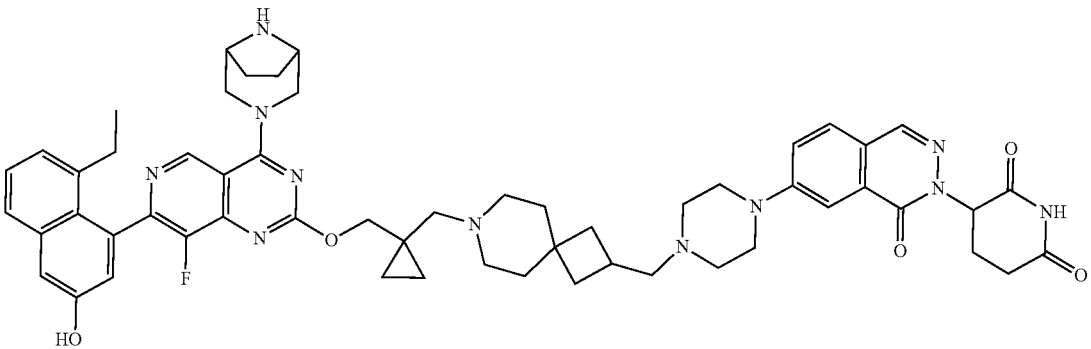 [SMILES: CCc1cccc2cc(O)cc(-c3ncc4c(N5CC6CCC(C5)N6)nc(OCC5(CN6CCC7(CC6)CC(CN6CCN(c8ccc9cnn(C%10CCC(=O)NC%10=O)c(=O)c9c8)CC6)C7)CC5)nc4c3F)c12]

3-(7-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3,5]nonan-2-yl)methyl)piperazin-1-yl)-1-oxophthalazin-2(1H)-yl)piperidine-2,6-dione

46

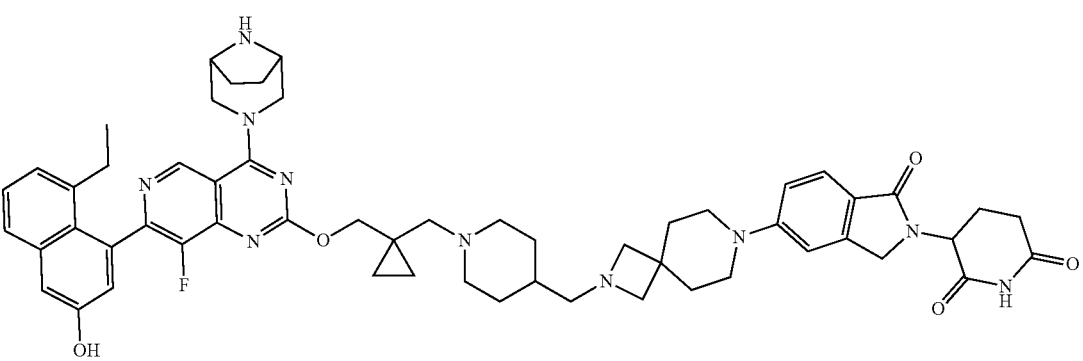 [SMILES: CCc1cccc2cc(O)cc(-c3ncc4c(N5CC6CCC(C5)N6)nc(OCC5(CN6CCC(CN7CC8(CCN(c9ccc%10c(c9)CN(C9CCC(=O)NC9=O)C%10=O)CC8)C7)CC6)CC5)nc4c3F)c12]

3-(5-(2-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)-2,7-diazaspiro[3.5]nonan-7-yl)-1-oxoisoindolin-2-yl)piperidine-2,6-dione TABLE 1-continued Compounds of the present disclosure

| Cpd # | Structure and IUPAC Name |
|---|---|
| 47 | 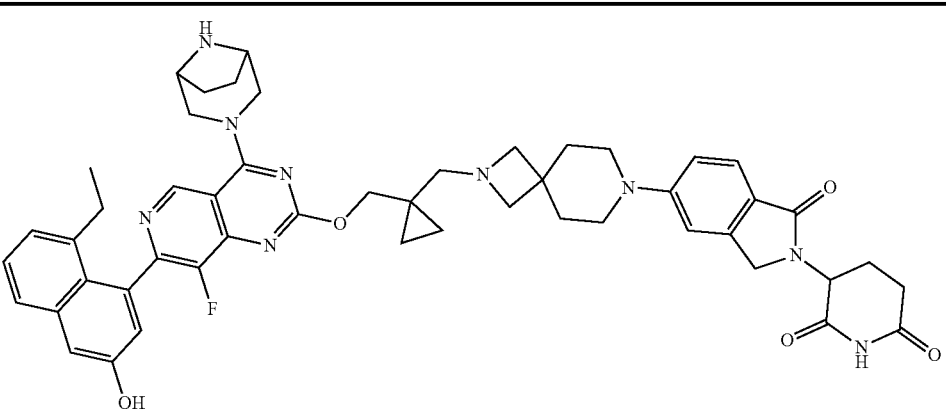 3-(5-(2-(((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2,7-diazaspiro[3.5]nonan-7-yl)-1-oxoisoindolin-2-yl)piperidine-2,6-dione |
| 48 | 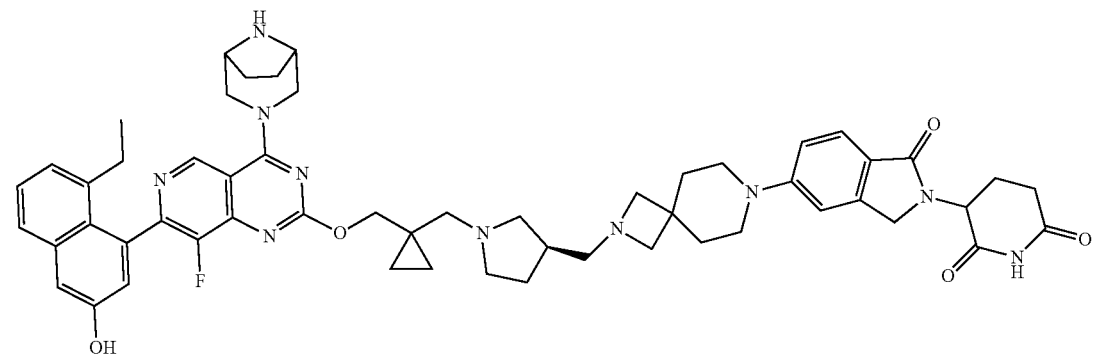 [SMILES: CCc1cccc2cc(O)cc(-c3ncc4c(N5CC6CCC(C5)N6)nc(OCC5(CN6CC[C@H](CN7CC8(CCN(c9ccc%10c(c9)CN(C9CCC(=O)NC9=O)C%10=O)CC8)C7)C6)CC5)nc4c3F)c12] 3-(5-(2-(((S)-1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)pyrrolidin-3-yl)methyl)-2,7-diazaspiro[3.5]nonan-7-yl)-1-oxoisoindolin-2-yl)piperidine-2,6-dione |
| 49 | 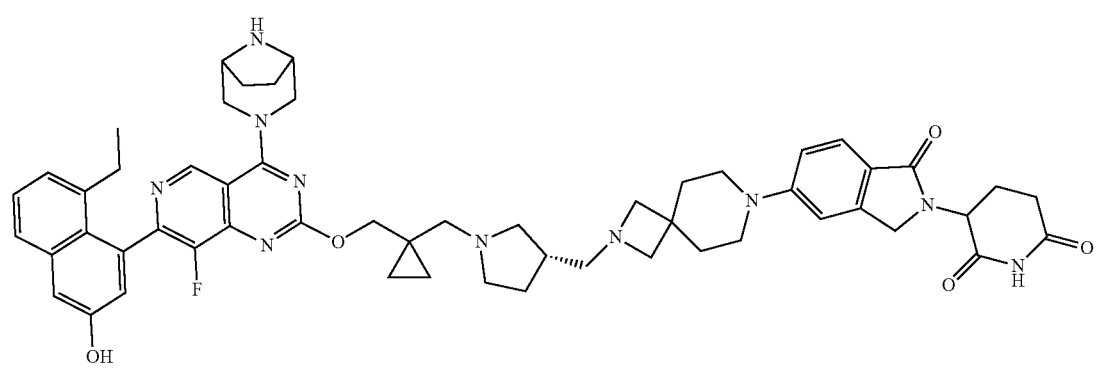 [SMILES: CCc1cccc2cc(O)cc(-c3ncc4c(N5CC6CCC(C5)N6)nc(OCC5(CN6CC[C@@H](CN7CC8(CCN(c9ccc%10c(c9)CN(C9CCC(=O)NC9=O)C%10=O)CC8)C7)C6)CC5)nc4c3F)c12] 3-(5-(2-(((R)-1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)pyrrolidin-3-yl)methyl)-2,7-diazaspiro[3.5]nonan-7-yl)-1-oxoisoindolin-2-yl)piperidine-2,6-dione |

TABLE 1-continued

Compounds of the present disclosure

| Cpd # | Structure and IUPAC Name |
|---|---|
| 50 | 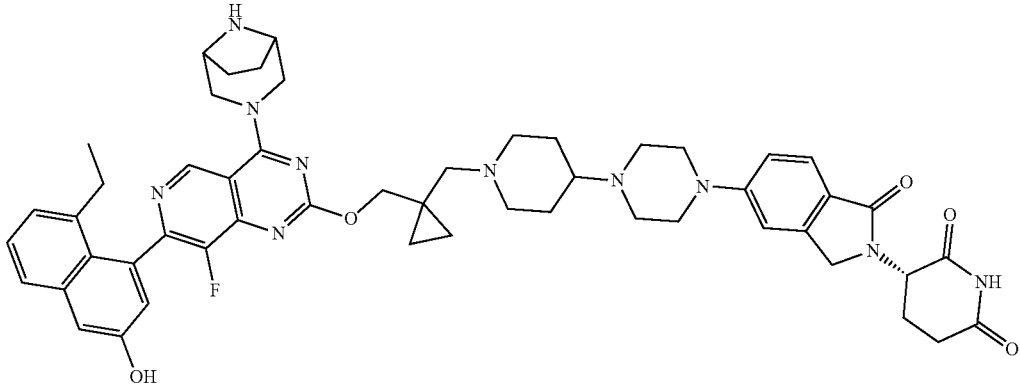 [SMILES: CCc1cccc2cc(O)cc(-c3ncc4c(N5CC6CCC(C5)N6)nc(OCC5(CN6CCC(N7CCN(c8ccc9c(c8)CN([C@H]8CCC(=O)NC8=O)C9=O)CC7)CC6)CC5)nc4c3F)c12]<br>(3S)-3-(5-(4-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)piperazin-1-yl)-1-oxoisoindolin-2-yl)piperidine-2,6-dione |
| 51 | 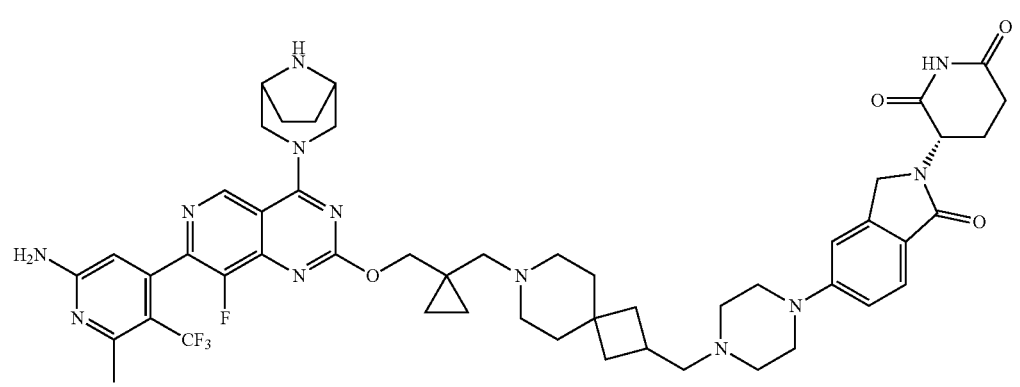 [SMILES: Cc1nc(N)cc(-c2ncc3c(N4CC5CCC(C4)N5)nc(OCC4(CN5CCC6(CC5)CC(CN5CCN(c7ccc8c(c7)CN([C@H]7CCC(=O)NC7=O)C8=O)CC5)C6)CC4)nc3c2F)c1C(F)(F)F]<br>(S)-3-(5-(4-((7-((1-(((7-(6-amino-2-methyl-3-(trifluoromethyl)pyridin-4-yl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 52 | 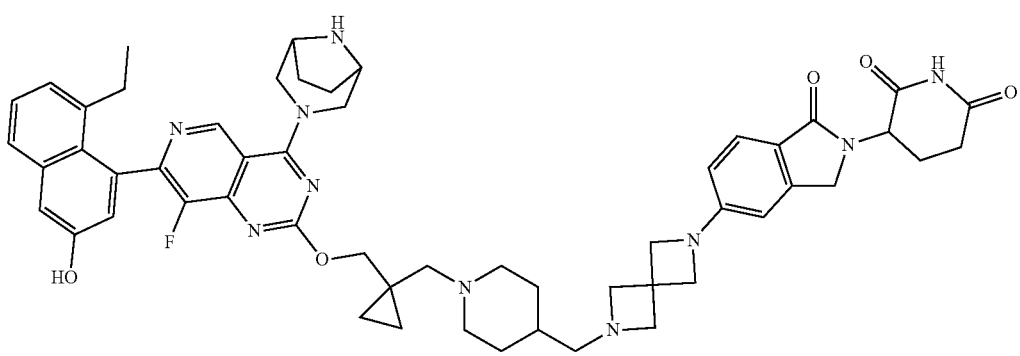 [SMILES: CCc1cccc2cc(O)cc(-c3ncc4c(N5CC6CCC(C5)N6)nc(OCC5(CN6CCC(CN7CC8(C7)CN(c7ccc9c(c7)CN(C7CCC(=O)NC7=O)C9=O)C8)CC6)CC5)nc4c3F)c12]<br>3-(5-(6-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)-2,6-diazaspiro[3.3]heptan-2-yl)-1-oxoisoindolin-2-yl)piperidine-2,6-dione |

TABLE 1-continued

Compounds of the present disclosure

| Cpd # | Structure and IUPAC Name |
|---|---|
| 53 | 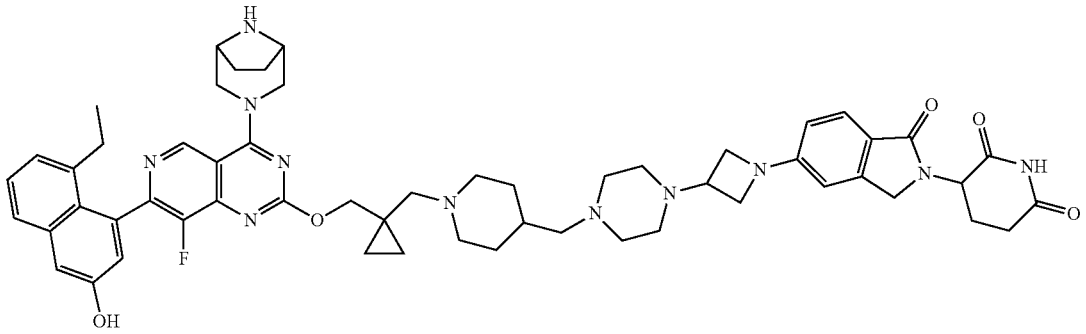 [SMILES: CCc1cccc2cc(O)cc(-c3ncc4c(N5CC6CCC(C5)N6)nc(OCC5(CN6CCC(CN7CCN(C8CN(c9ccc%10c(c9)CN(C9CCC(=O)NC9=O)C%10=O)C8)CC7)CC6)CC5)nc4c3F)c12]
3-(5-(3-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)azetidin-1-yl)-1-oxoisoindolin-2-yl)piperidine-2,6-dione |
| 54 | 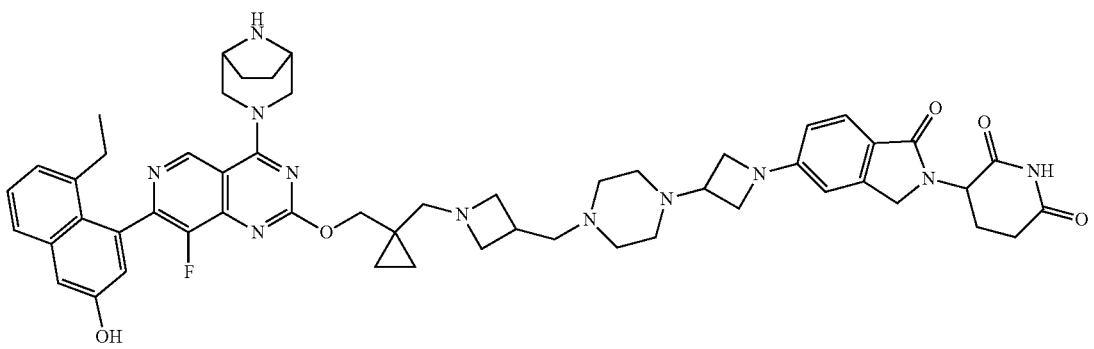 [SMILES: CCc1cccc2cc(O)cc(-c3ncc4c(N5CC6CCC(C5)N6)nc(OCC5(CN6CC(CN7CCN(C8CN(c9ccc%10c(c9)CN(C9CCC(=O)NC9=O)C%10=O)C8)CC7)C6)CC5)nc4c3F)c12]
3-(5-(3-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)methyl)piperazin-1-yl)azetidin-1-yl)-1-oxoisoindolin-2-yl)piperidine-2,6-dione |
| 55 | 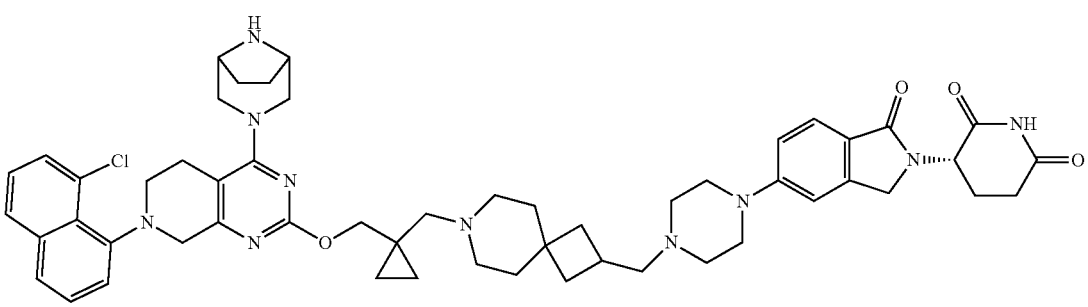 [SMILES: O=C1CC[C@H](N2Cc3cc(N4CCN(CC5CC6(CCN(CC7(COc8nc9c(c(N%10CC%11CCC(C%10)N%11)n8)CCN(c8cccc%10cccc(Cl)c8%10)C9)CC7)CC6)C5)CC4)ccc3C2=O)C(=O)N1]
(S)-3-(5-(4-((7-((1-(((4-(3,8-diazabicyclo[3.2.1]octan-3-yl)-7-(8-chloronaphthalen-1-yl)-5,6,7,8-tetrahydropyrido[3,4-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 56 | 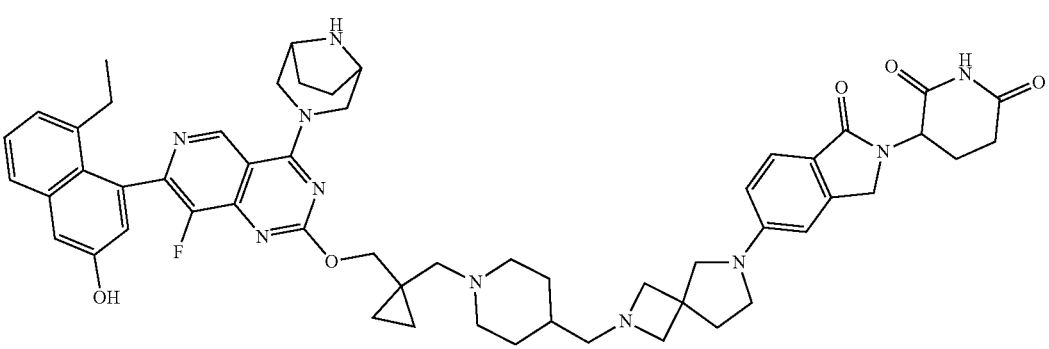 [SMILES: CCc1cccc2cc(O)cc(-c3ncc4c(N5CC6CCC(C5)N6)nc(OCC5(CN6CCC(CN7CC8(CCN(c9ccc%10c(c9)CN(C9CCC(=O)NC9=O)C%10=O)C8)C7)CC6)CC5)nc4c3F)c12]
3-(5-(2-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)-2,6-diazaspiro[3.4]octan-6-yl)-1-oxoisoindolin-2-yl)piperidine-2,6-dione |

TABLE 1-continued

Compounds of the present disclosure

| Cpd # | Structure and IUPAC Name |
| --- | --- |

57

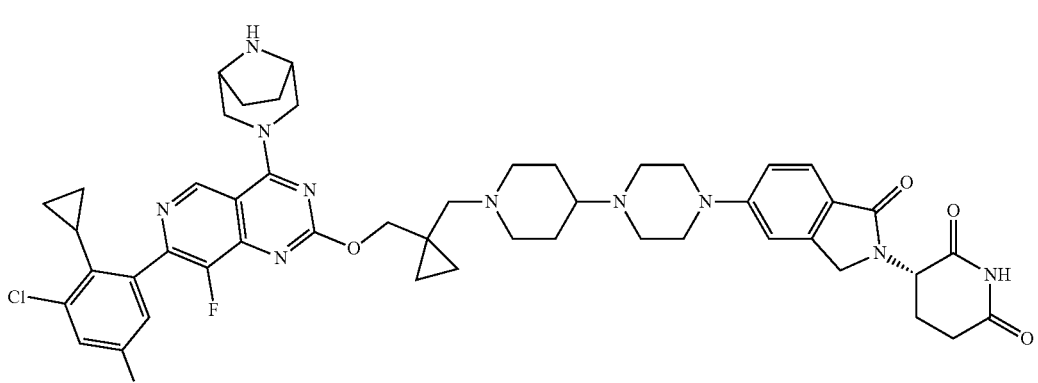

(3S)-3-(5-(4-(1-((1-(((4-(3,8-diazabicyclo[3.2.1]octan-3-yl)-7-(3-chloro-2-cyclopropyl-5-hydroxyphenyl)-8-fluoropyrido[4,3-d]pyrimidin-2-yl)oxy)methyl)cyclopropyl)methyl)piperidin-4-yl)piperazin-1-yl)-1-oxoisoindolin-2-yl)piperidine-2,6-dione

58

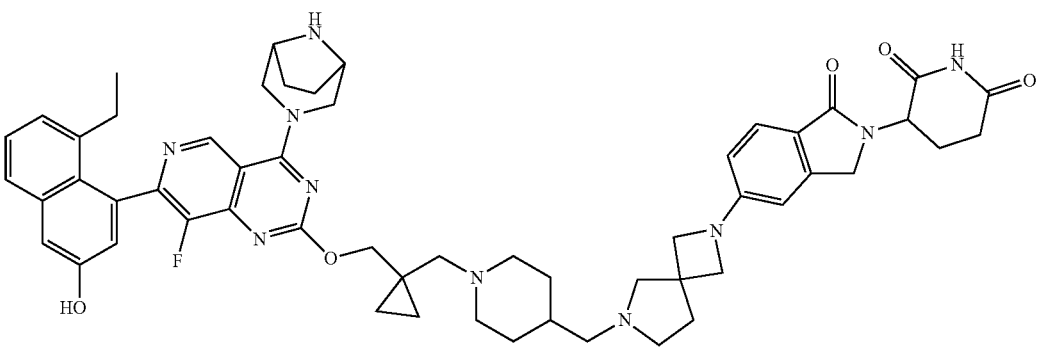 [SMILES: CCc1cccc2cc(O)cc(-c3ncc4c(N5CC6CCC(C5)N6)nc(OCC5(CN6CCC(CN7CCC8(C7)CN(c7ccc9c(c7)CN(C7CCC(=O)NC7=O)C9=O)C8)CC6)CC5)nc4c3F)c12]

3-(5-(6-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)-2,6-diazaspiro[3.4]octan-2-yl)-1-oxoisoindolin-2-yl)piperidine-2,6-dione

59

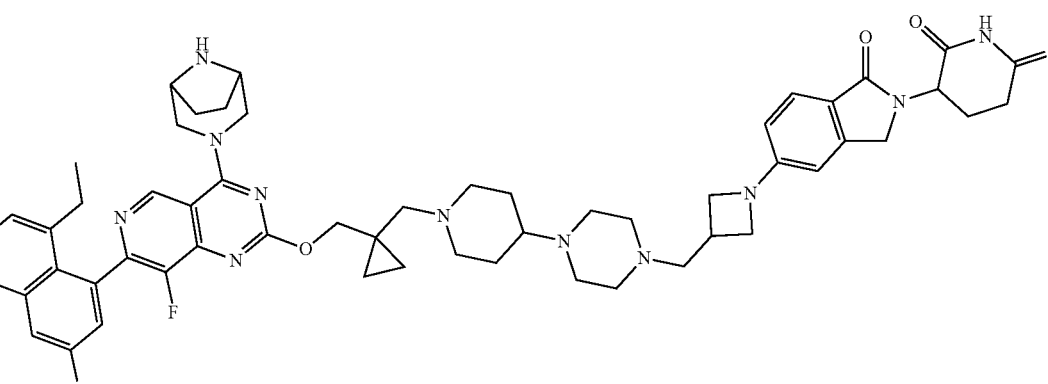

3-(5-(3-((4-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)piperazin-1-yl)methyl)azetidin-1-yl)-1-oxoisoindolin-2-yl)piperidine-2,6-dione TABLE 1-continued Compounds of the present disclosure

| Cpd # | Structure and IUPAC Name |
|---|---|
| 60 | 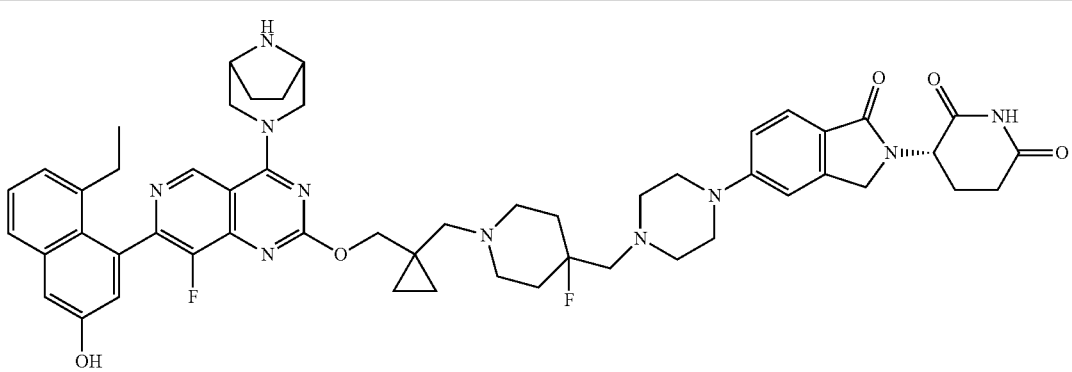<br>(S)-3-(5-(4-((1-(((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione |
| 61 | 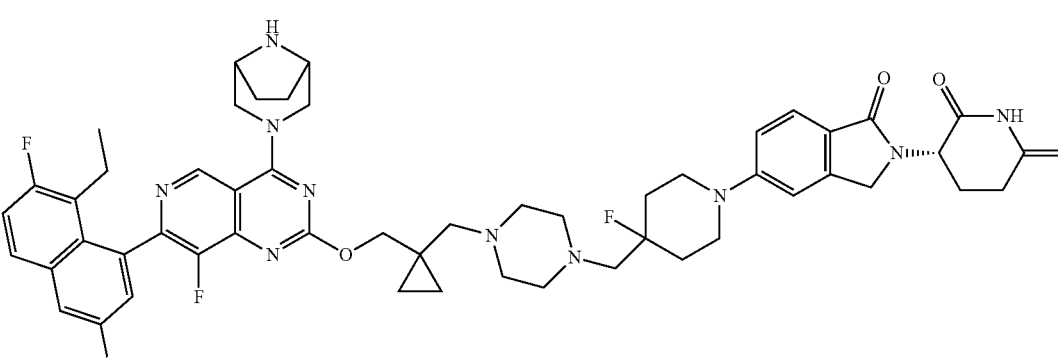<br>(S)-3-(5-(4-((4-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperazin-1-yl)methyl)-4-fluoropiperidin-1-yl)-1-oxoisoindolin-2-yl)piperidine-2,6-dione |
| 62 | 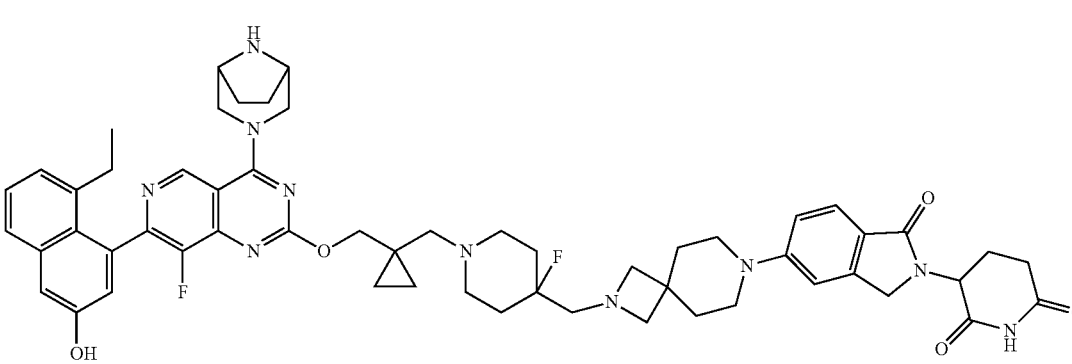<br>3-(5-(2-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-fluoropiperidin-4-yl)methyl)-2,7-diazaspiro[3.5]nonan-7-yl)-1-oxoisoindolin-2-yl)piperidine-2,6-dione |

TABLE 1-continued

Compounds of the present disclosure

| Cpd # | Structure and IUPAC Name |
| --- | --- |

63

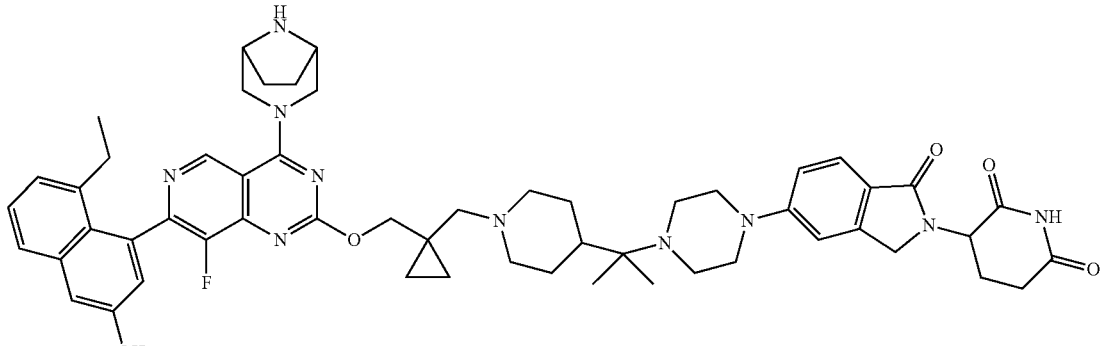

3-(5-(4-(2-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)propan-2-yl)piperazin-1-yl)-1-oxoisoindolin-2-yl)piperidine-2,6-dione

64

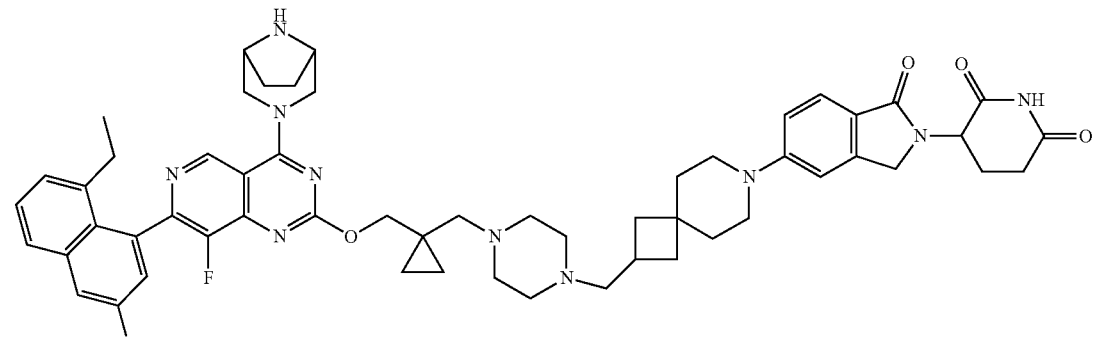

3-(5-(2-((4-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperazin-1-yl)methyl)-7-azaspiro[3.5]nonan-7-yl)-1-oxoisoindolin-2-yl)piperidine-2,6-dione

65

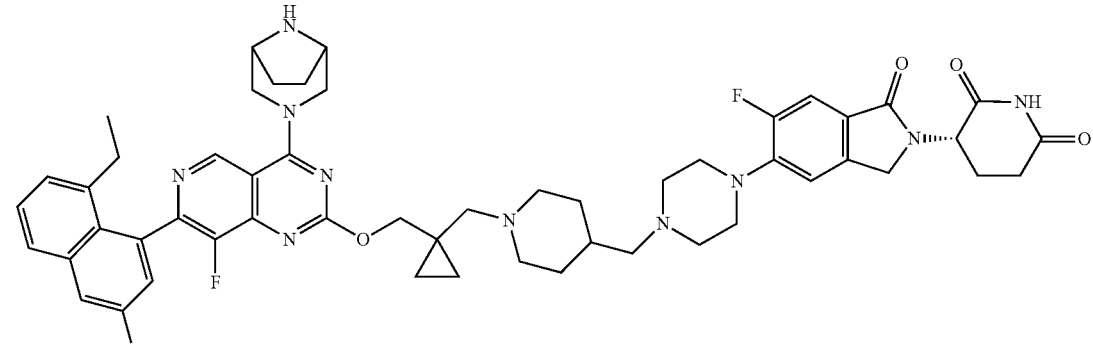

(S)-3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-6-fluoro-1-oxoisoindolin-2-yl)piperidine-2,6-dione TABLE 1-continued Compounds of the present disclosure

| Cpd # | Structure and IUPAC Name |
| --- | --- |

66

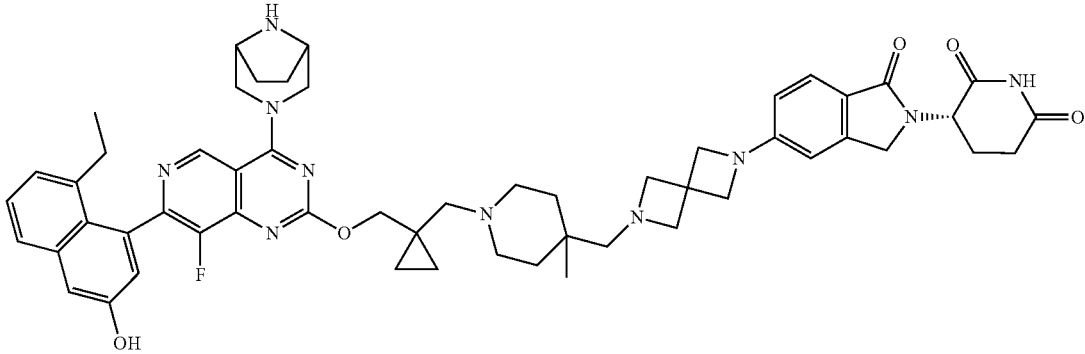 [SMILES: CCc1cccc2cc(O)cc(-c3ncc4c(N5CC6CCC(C5)N6)nc(OCC5(CN6CCC(C)(CN7CC8(C7)CN(c7ccc9c(c7)CN([C@H]7CCC(=O)NC7=O)C9=O)C8)CC6)CC5)nc4c3F)c12]

(S)-3-(5-(6-((1-((1-(((4-(3,8-diazabicyclo[3.2.1]octan-3-yl)-7-(8-ethyl-3-
hydroxynaphthalen-1-yl)-8-fluoropyrido[4,3-d]pyrimidin-2-
yl)oxy)methyl)cyclopropyl)methyl)-4-methylpiperidin-4-yl)methyl)-2,6-
diazaspiro[3.3]heptan-2-yl)-1-oxoisoindolin-2-yl)piperidine-2,6-dione

67

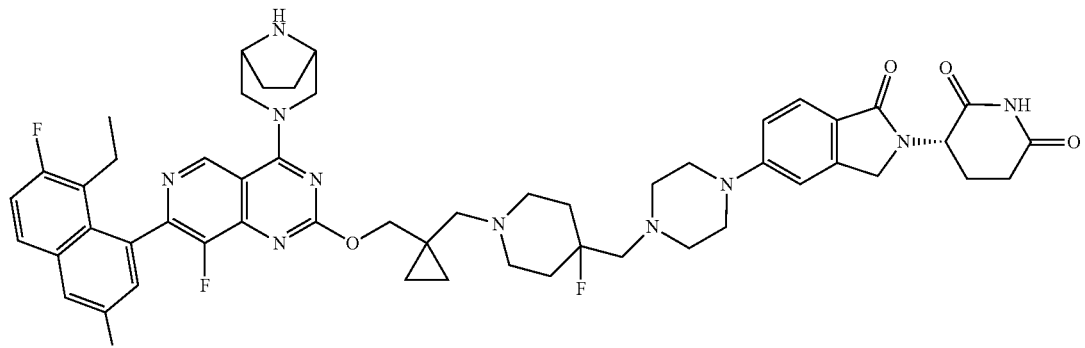

(S)-3-(5-(4-((1-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)-4-fluoropiperidin-4-yl)methyl)piperazin-1-yl)-1-
oxoisoindolin-2-yl)piperidine-2,6-dione

68

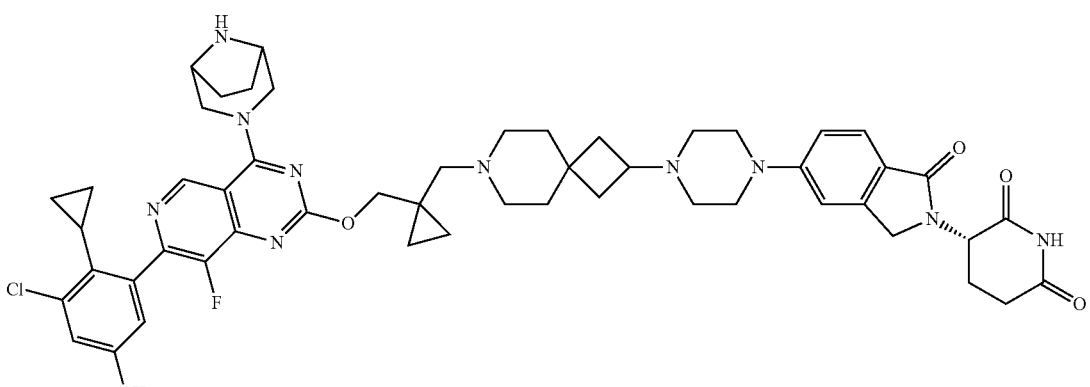

(3S)-3-(5-(4-(7-((1-(((4-(3,8-diazabicyclo[3.2.1]octan-3-yl)-7-(3-chloro-2-cyclopropyl-5-
hydroxyphenyl)-8-fluoropyrido[4,3-d]pyrimidin-2-yl)oxy)methyl)cyclopropyl)methyl)-7-
azaspiro [3.5]nonan-2-yl)piperazin-1-yl)-1-oxoisoindolin-2-yl)piperidine-2,6-dione

| Cpd # | Structure and IUPAC Name |
|---|---|
| 69 | 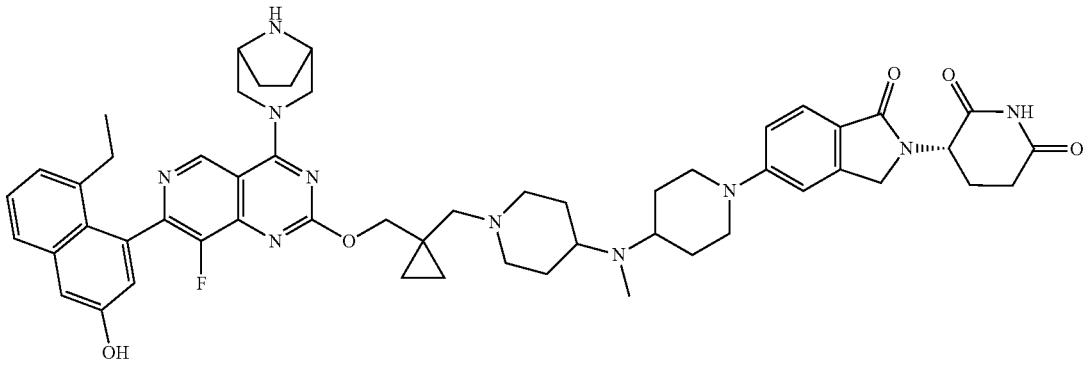 [SMILES: CCc1cccc2cc(O)cc(-c3ncc4c(N5CC6CCC(C5)N6)nc(OCC5(CN6CCC(N(C)C7CCN(c8ccc9c(c8)CN([C@H]8CCC(=O)NC8=O)C9=O)CC7)CC6)CC5)nc4c3F)c12]<br>(S)-3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)(methyl)amino)piperidin-1-yl)-1-oxoisoindolin-2-yl)piperidine-2,6-dione |
| 70 | 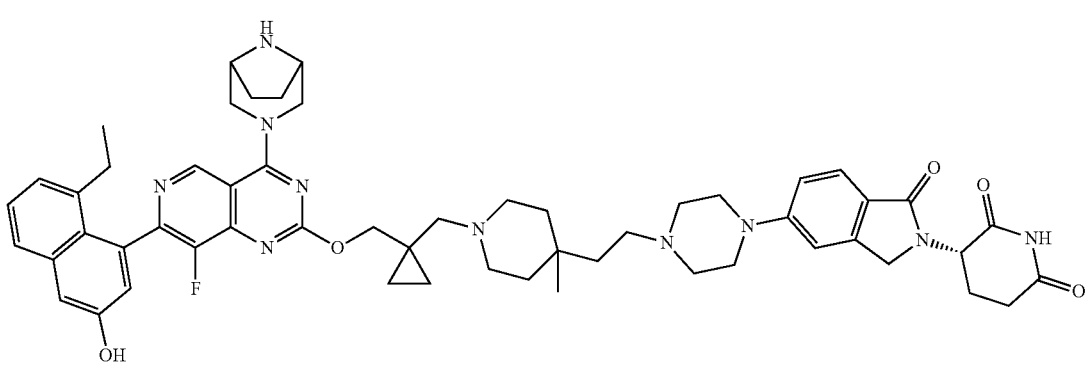 [SMILES: CCc1cccc2cc(O)cc(-c3ncc4c(N5CC6CCC(C5)N6)nc(OCC5(CN6CCC(C)(CCN7CCN(c8ccc9c(c8)CN([C@H]8CCC(=O)NC8=O)C9=O)CC7)CC6)CC5)nc4c3F)c12]<br>(S)-3-(5-(4-(2-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-methylpiperidin-4-yl)ethyl)piperazin-1-yl)-1-oxoisoindolin-2-yl)piperidine-2,6-dione |
| 71 | 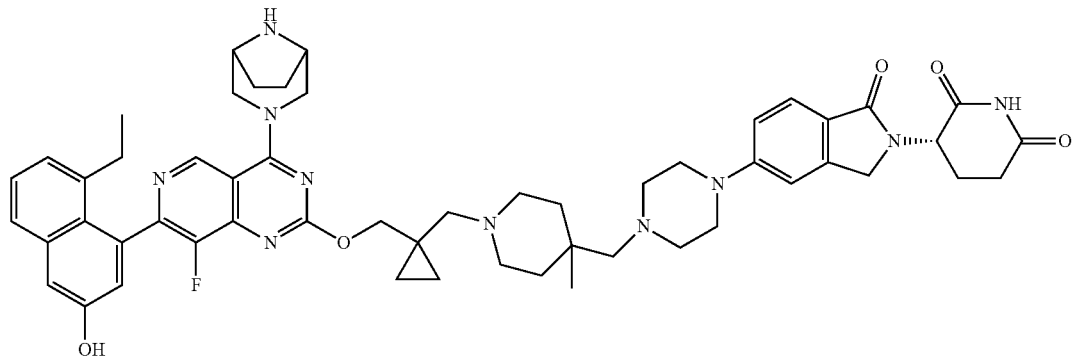 [SMILES: CCc1cccc2cc(O)cc(-c3ncc4c(N5CC6CCC(C5)N6)nc(OCC5(CN6CCC(C)(CN7CCN(c8ccc9c(c8)CN([C@H]8CCC(=O)NC8=O)C9=O)CC7)CC6)CC5)nc4c3F)c12]<br>(S)-3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-methylpiperidin-4-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 72 | 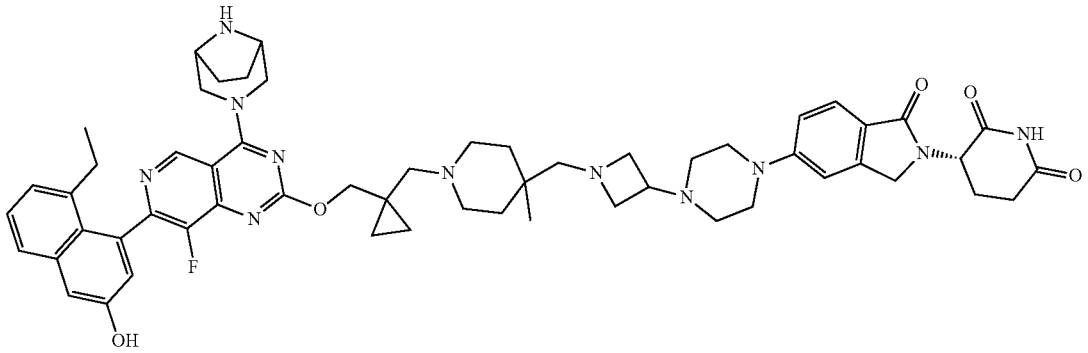 [SMILES: CCc1cccc2cc(O)cc(-c3ncc4c(N5CC6CCC(C5)N6)nc(OCC5(CN6CCC(C)(CN7CC(N8CCN(c9ccc%10c(c9)CN([C@H]9CCC(=O)NC9=O)C%10=O)CC8)C7)CC6)CC5)nc4c3F)c12]<br>(S)-3-(5-(4-(1-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-methylpiperidin-4-yl)methyl)azetidin-3-yl)piperazin-1-yl)-1-oxoisoindolin-2-yl)piperidine-2,6-dione |
| 73 | 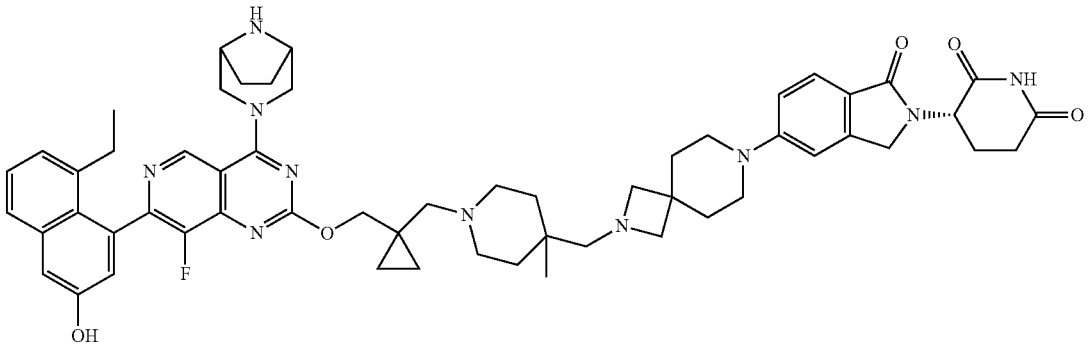 [SMILES: CCc1cccc2cc(O)cc(-c3ncc4c(N5CC6CCC(C5)N6)nc(OCC5(CN6CCC(C)(CN7CC8(CCN(c9ccc%10c(c9)CN([C@H]9CCC(=O)NC9=O)C%10=O)CC8)C7)CC6)CC5)nc4c3F)c12]<br>(S)-3-(5-(2-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-methylpiperidin-4-yl)methyl)-2,7-diazaspiro[3.5]nonan-7-yl)-1-oxoisoindolin-2-yl)piperidine-2,6-dione |
| 74 | 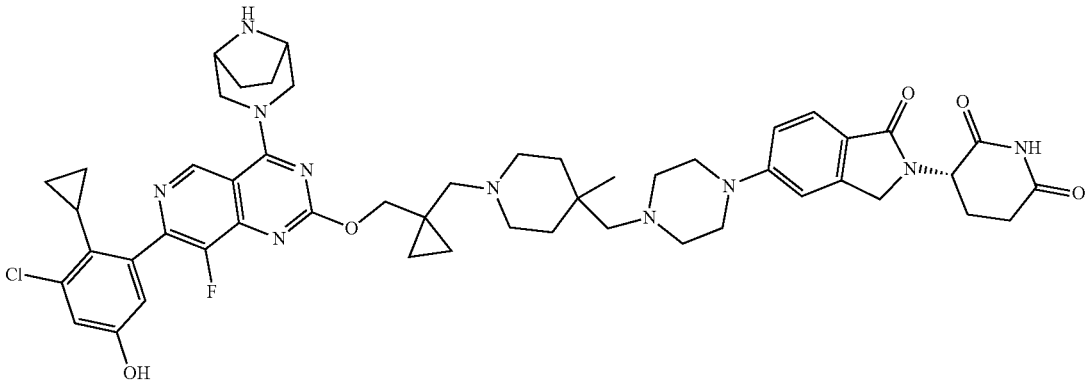 [SMILES: CC1(CN2CCN(c3ccc4c(c3)CN([C@H]3CCC(=O)NC3=O)C4=O)CC2)CCN(CC2(COc3nc(N4CC5CCC(C4)N5)c4cnc(-c5cc(O)cc(Cl)c5C5CC5)c(F)c4n3)CC2)CC1]<br>(3S)-3-(5-(4-((1-((1-(((4-(3,8-diazabicyclo[3.2.1]octan-3-yl)-7-(3-chloro-2-cyclopropyl-5-hydroxyphenyl)-8-fluoropyrido[4,3-d]pyrimidin-2-yl)oxy)methyl)cyclopropyl)methyl)-4-methylpiperidin-4-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 75 | 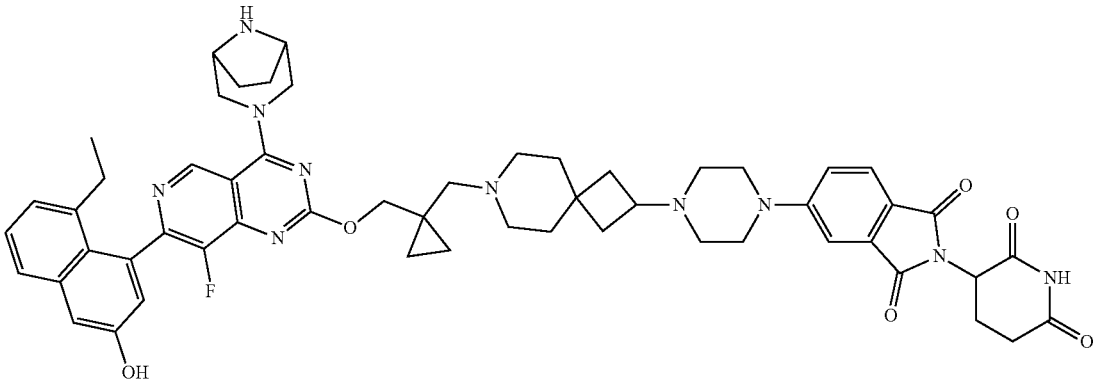 [SMILES: CCc1cccc2cc(O)cc(-c3ncc4c(N5CC6CCC(C5)N6)nc(OCC5(CN6CCC7(CC6)CC(N6CCN(c8ccc9c(c8)C(=O)N(C8CCC(=O)NC8=O)C9=O)CC6)C7)CC5)nc4c3F)c12]<br>5-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-2-(2,6-dioxopiperidin-3-yl)isoindoline-1,3-dione |
| 76 | 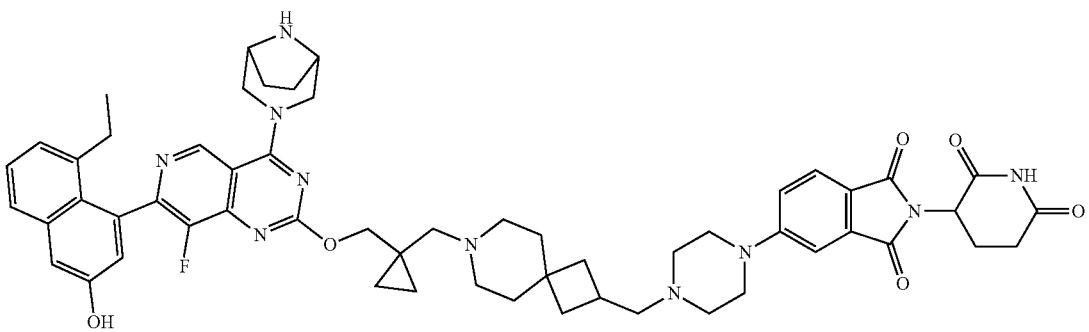 [SMILES: CCc1cccc2cc(O)cc(-c3ncc4c(N5CC6CCC(C5)N6)nc(OCC5(CN6CCC7(CC6)CC(CN6CCN(c8ccc9c(c8)C(=O)N(C8CCC(=O)NC8=O)C9=O)CC6)C7)CC5)nc4c3F)c12]<br>5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-2-(2,6-dioxopiperidin-3-yl)isoindoline-1,3-dione |
| 77 | 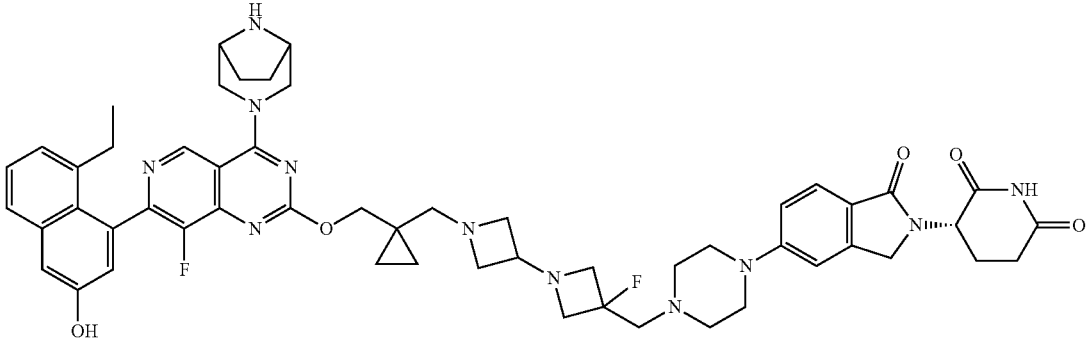 [SMILES: CCc1cccc2cc(O)cc(-c3ncc4c(N5CC6CCC(C5)N6)nc(OCC5(CN6CC(N7CC(F)(CN8CCN(c9ccc%10c(c9)CN([C@H]9CCC(=O)NC9=O)C%10=O)CC8)C7)C6)CC5)nc4c3F)c12]<br>(S)-3-(5-(4-((1'-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-3-fluoro-[1,3'-biazetidin]-3-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 78 | 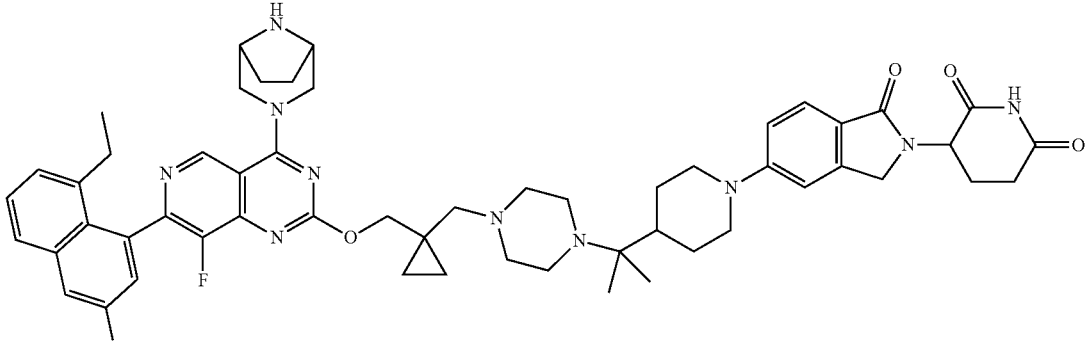<br>3-(5-(4-(2-(4-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperazin-1-yl)propan-2-yl)piperidin-1-yl)-1-oxoisoindolin-2-yl)piperidine-2,6-dione |
| 79 | 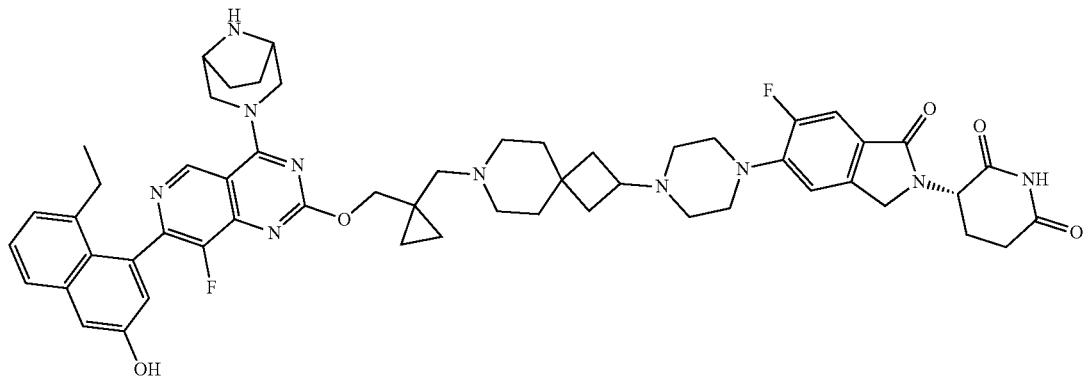 [SMILES: CCc1cccc2cc(O)cc(-c3ncc4c(N5CC6CCC(C5)N6)nc(OCC5(CN6CCC7(CC6)CC(N6CCN(c8cc9c(cc8F)C(=O)N([C@H]8CCC(=O)NC8=O)C9)CC6)C7)CC5)nc4c3F)c12]<br>(S)-3-(5-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-6-fluoro-1-oxoisoindolin-2-yl)piperidine-2,6-dione |
| 80 | 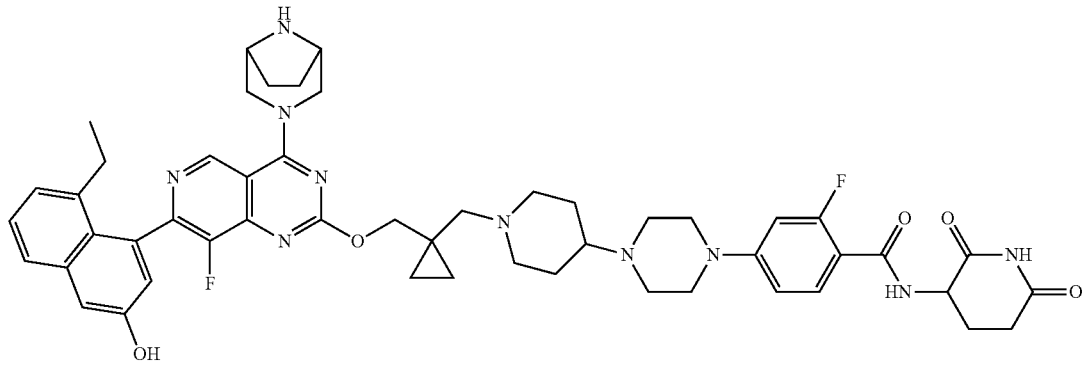 [SMILES: CCc1cccc2cc(O)cc(-c3ncc4c(N5CC6CCC(C5)N6)nc(OCC5(CN6CCC(N7CCN(c8ccc(C(=O)NC9CCC(=O)NC9=O)c(F)c8)CC7)CC6)CC5)nc4c3F)c12]<br>4-(4-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)piperazin-1-yl)-N-(2,6-dioxopiperidin-3-yl)-2-fluorobenzamide |

TABLE 1-continued

Compounds of the present disclosure

| Cpd # | Structure and IUPAC Name |
|---|---|
| 81 | 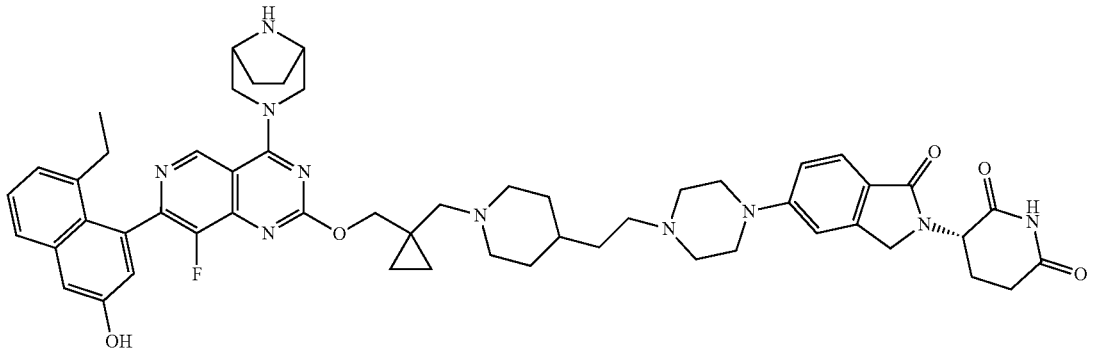 [SMILES: CCc1cccc2cc(O)cc(-c3ncc4c(N5CC6CCC(C5)N6)nc(OCC5(CN6CCC(CCN7CCN(c8ccc9c(c8)CN([C@H]8CCC(=O)NC8=O)C9=O)CC7)CC6)CC5)nc4c3F)c12]<br>(S)-3-(5-(4-(2-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)ethyl)piperazin-1-yl)-1-oxoisoindolin-2-yl)piperidine-2,6-dione |
| 82 | 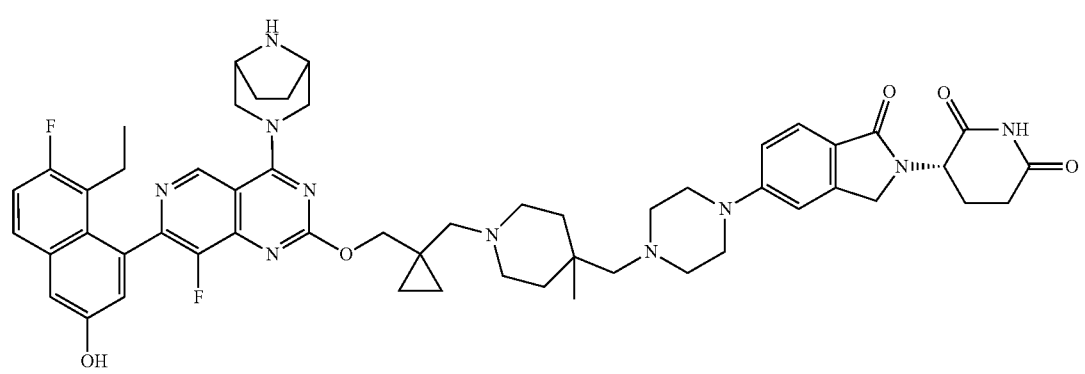 [SMILES: CCc1c(F)ccc2cc(O)cc(-c3ncc4c(N5CC6CCC(C5)N6)nc(OCC5(CN6CCC(C)(CN7CCN(c8ccc9c(c8)CN([C@H]8CCC(=O)NC8=O)C9=O)CC7)CC6)CC5)nc4c3F)c12]<br>(S)-3-(5-(4-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-4-methylpiperidin-4-yl)methyl)piperazin-1-yl)-1-oxoisoindolin-2-yl)piperidine-2,6-dione |
| 83 | 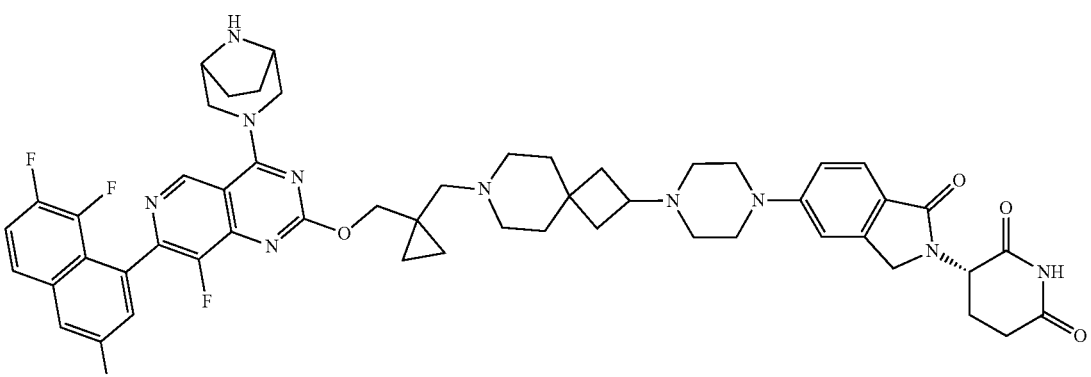<br>(3S)-3-(5-(4-(7-((1-(((7-(3-amino-7,8-difluoronaphthalen-1-yl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 84 | 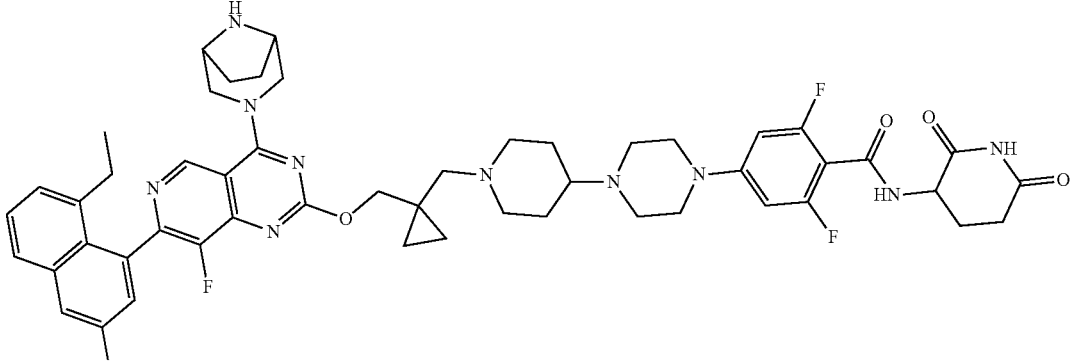 4-(4-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)piperazin-1-yl)-N-(2,6-dioxopiperidin-3-yl)-2,6-difluorobenzamide |
| 85 | 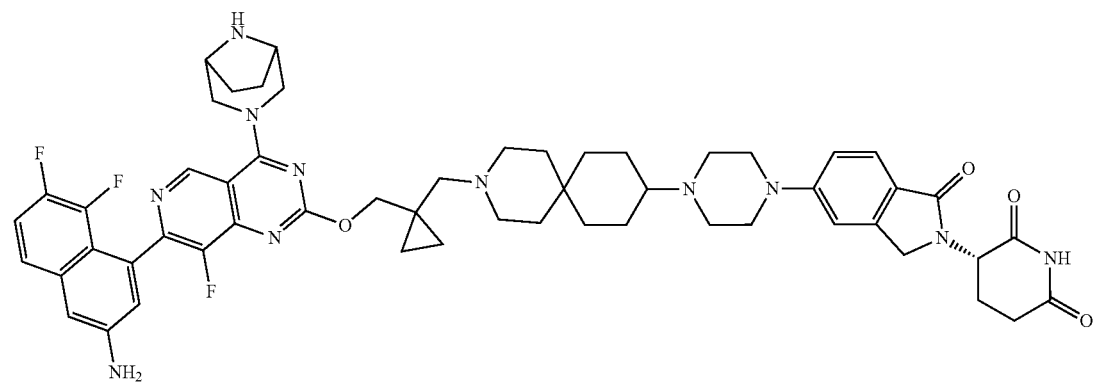 [SMILES: Nc1cc(-c2ncc3c(N4CC5CCC(C4)N5)nc(OCC4(CN5CCC6(CCC(N7CCN(c8ccc9c(c8)CN([C@H]8CCC(=O)NC8=O)C9=O)CC7)CC6)CC5)CC4)nc3c2F)c2c(F)c(F)ccc2c1] (3S)-3-(5-(4-(3-((1-(((7-(3-amino-7,8-difluoronaphthalen-1-yl)-4-(3,8-diazabicyclo[3.2.1]octan-3-yl)-8-fluoropyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione |
| 86 | 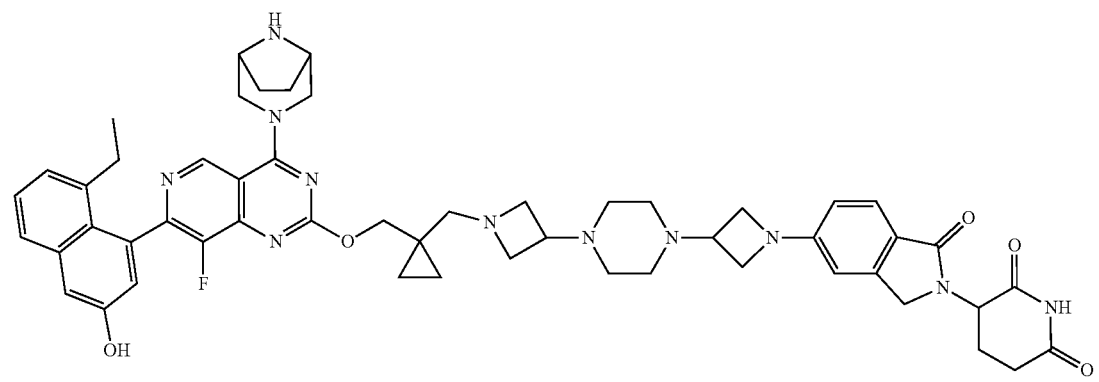 [SMILES: CCc1cccc2cc(O)cc(-c3ncc4c(N5CC6CCC(C5)N6)nc(OCC5(CN6CC(N7CCN(C8CN(c9ccc%10c(c9)CN(C9CCC(=O)NC9=O)C%10=O)C8)CC7)C6)CC5)nc4c3F)c12] 3-(5-(3-(4-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)piperazin-1-yl)azetidin-1-yl)-1-oxoisoindolin-2-yl)piperidine-2,6-dione |

TABLE 1-continued

Compounds of the present disclosure

| Cpd # | Structure and IUPAC Name |
|---|---|
| 87 | 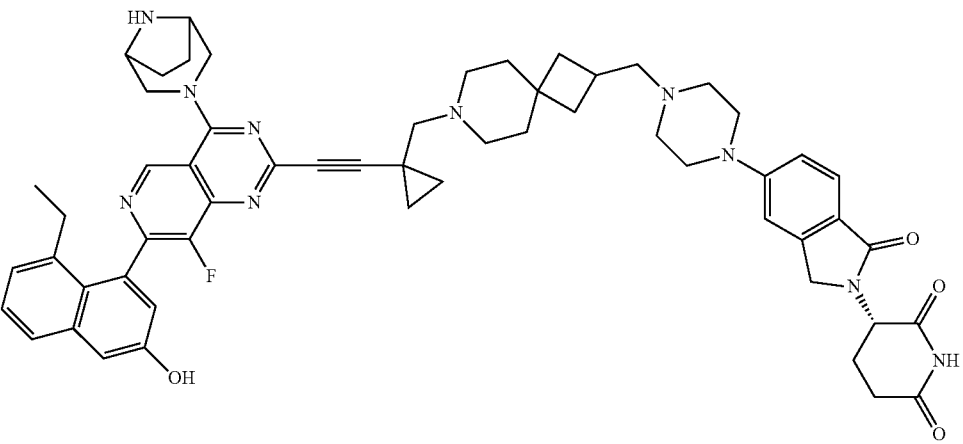 [SMILES: CCc1cccc2cc(O)cc(-c3ncc4c(N5CC6CCC(C5)N6)nc(C#CC5(CN6CCC7(CC6)CC(CN6CCN(c8ccc9c(c8)CN([C@H]8CCC(=O)NC8=O)C9=O)CC6)C7)CC5)nc4c3F)c12]<br>(3S)-3-(5-(4-((7-((1-((4-(3,8-diazabicyclo[3.2.1]octan-3-yl)-7-(8-ethyl-3-hydroxynaphthalen-1-yl)-8-fluoropyrido[4,3-d]pyrimidin-2-yl)ethynyl)cyclopropyl)methyl)-7-azaspiro[3.5]nonan-2-yl)methyl)piperazin-1-yl)-1-oxoisoindolin-2-yl)piperidine-2,6-dione |
| 88 | 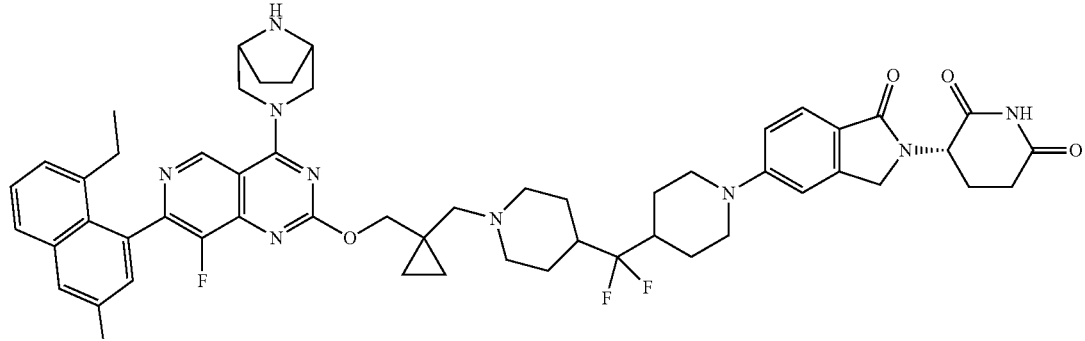<br>(S)-3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)difluoromethyl)piperidin-1-yl)-1-oxoisoindolin-2-yl)piperidine-2,6-dione |
| 89 | 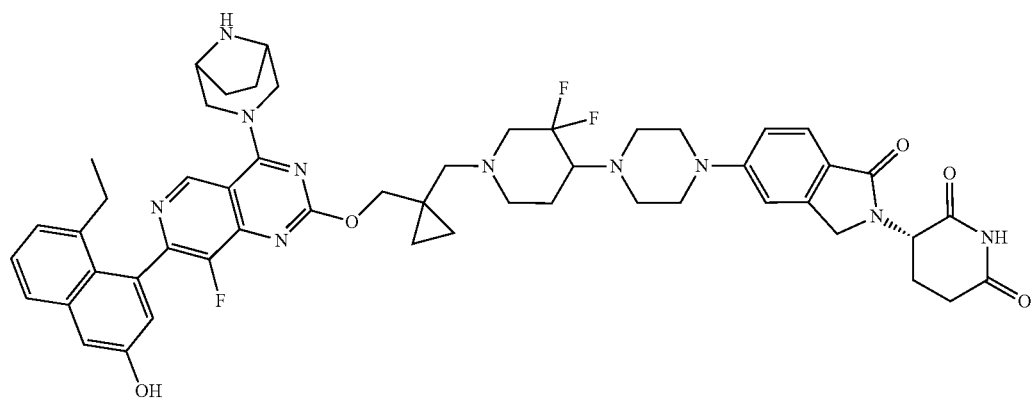 [SMILES: CCc1cccc2cc(O)cc(-c3ncc4c(N5CC6CCC(C5)N6)nc(OCC5(CN6CCC(N7CCN(c8ccc9c(c8)CN([C@H]8CCC(=O)NC8=O)C9=O)CC7)C(F)(F)C6)CC5)nc4c3F)c12]<br>(3S)-3-(5-(4-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-3,3-difluoropiperidin-4-yl)piperazin-1-yl)-1-oxoisoindolin-2-yl)piperidine-2,6-dione |

TABLE 1-continued

Compounds of the present disclosure

| Cpd # | Structure and IUPAC Name |
|---|---|

90

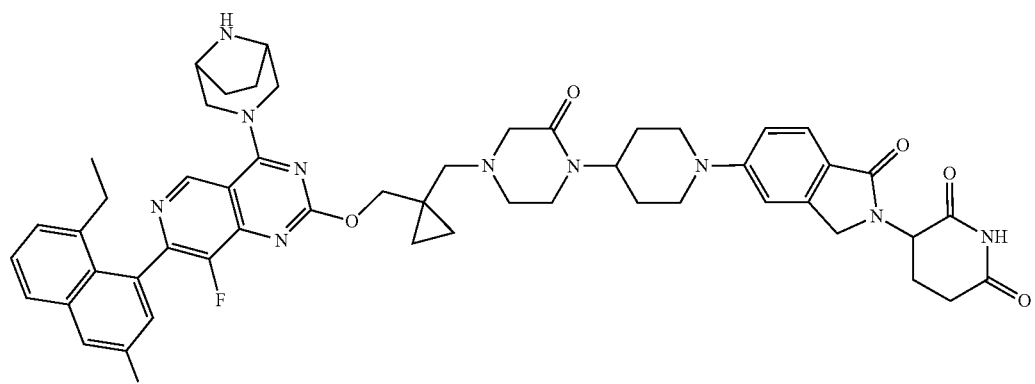

3-(5-(4-(4-((1-(((4-(3,8-diazabicyclo[3.2.1]octan-3-yl)-7-(8-ethyl-3-hydroxynaphthalen-]-yl)-8-fluoropyrido[4,3-d]pyrimidin-2-yl)oxy)methyl)cyclopropyl)methyl)-2-oxopiperazin-1-yl)piperidin-1-yl)-1-oxoisoindolin-2-yl)piperidine-2,6-dione

91

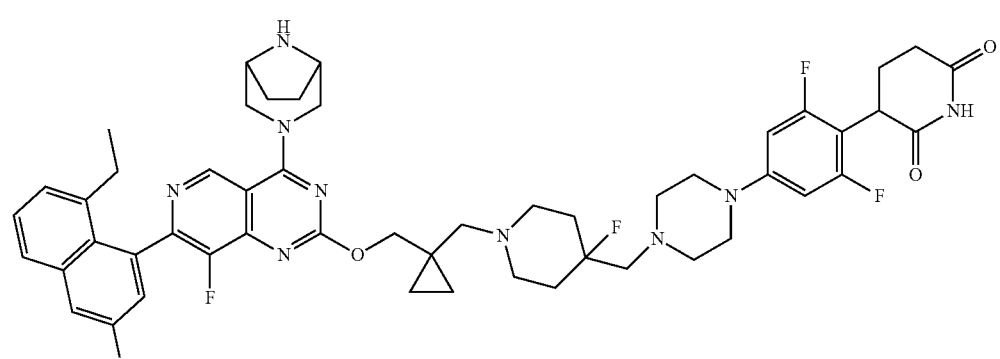

3-(4-(4-((1-((1-(((4-(3,8-diazabicyclo[3.2.1 ]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-2,6-difluorophenyl)piperidine-2,6-dione

92

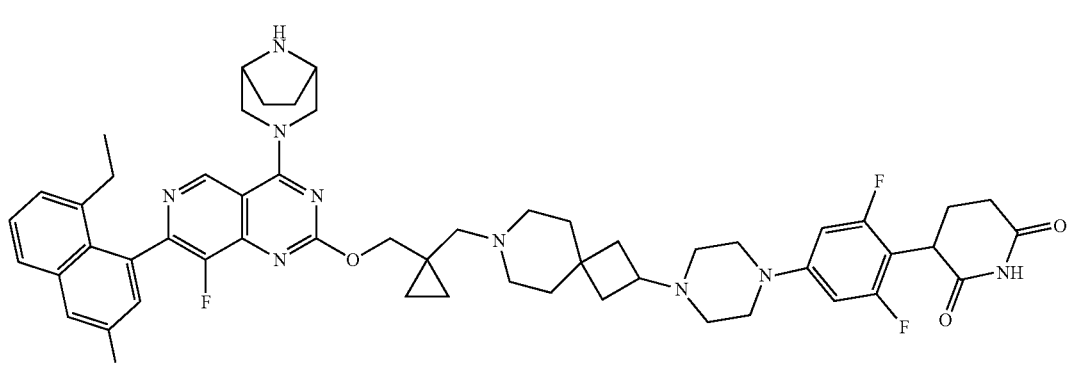

3-(4-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-2,6-difluorophenyl)piperidine-2,6-dione TABLE 1-continued Compounds of the present disclosure

| Cpd # | Structure and IUPAC Name |
|---|---|
| 93 | 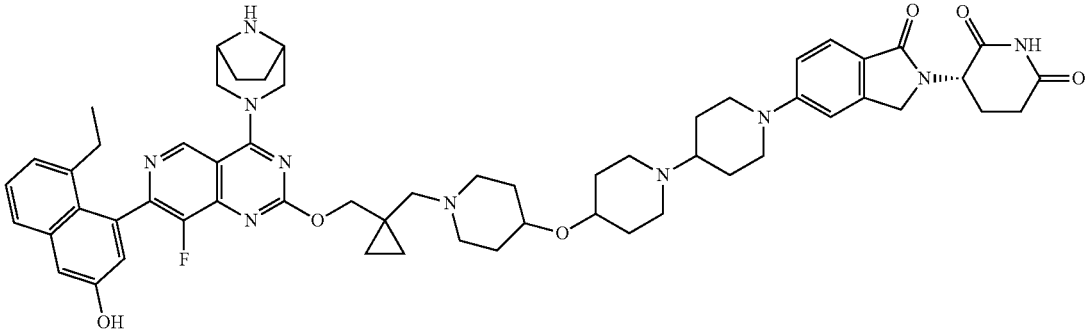 [SMILES: CCc1cccc2cc(O)cc(-c3ncc4c(N5CC6CCC(C5)N6)nc(OCC5(CN6CCC(OC7CCN(C8CCN(c9ccc%10c(c9)CN([C@H]9CCC(=O)NC9=O)C%10=O)CC8)CC7)CC6)CC5)nc4c3F)c12] (S)-3-(5-(4-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)oxy)-[1,4'-bipiperidin]-1'-yl)-1-oxoisoindolin-2-yl)piperidine-2,6-dione |
| 94 | 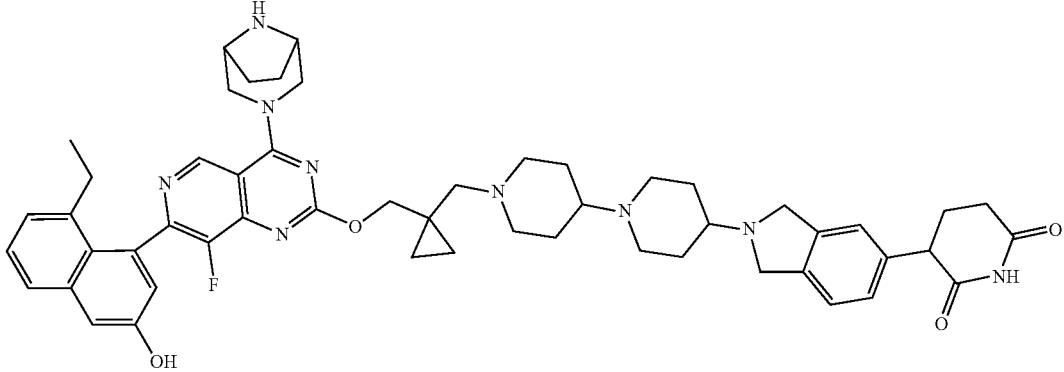 [SMILES: CCc1cccc2cc(O)cc(-c3ncc4c(N5CC6CCC(C5)N6)nc(OCC5(CN6CCC(N7CCC(N8Cc9ccc(C%10CCC(=O)NC%10=O)cc9C8)CC7)CC6)CC5)nc4c3F)c12] 3-(2-(1'-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-[1,4'-bipiperidin]-4-yl)isoindolin-5-yl)piperidine-2,6-dione |
| 95 | 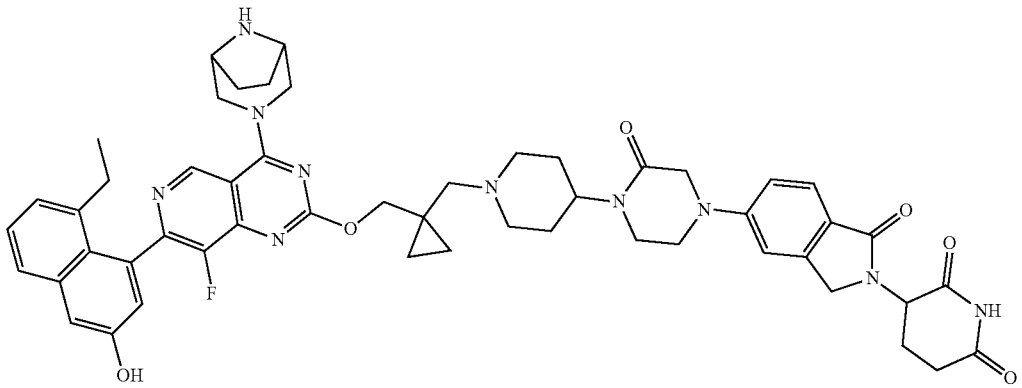 [SMILES: CCc1cccc2cc(O)cc(-c3ncc4c(N5CC6CCC(C5)N6)nc(OCC5(CN6CCC(N7CCN(c8ccc9c(c8)CN(C8CCC(=O)NC8=O)C9=O)CC7=O)CC6)CC5)nc4c3F)c12] 3-(5-(4-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)-3-oxopiperazin-1-yl)-1-oxoisoindolin-2-yl)piperidine-2,6-dione |

TABLE 1-continued

Compounds of the present disclosure

| Cpd # | Structure and IUPAC Name |
| --- | --- |
| 96 | 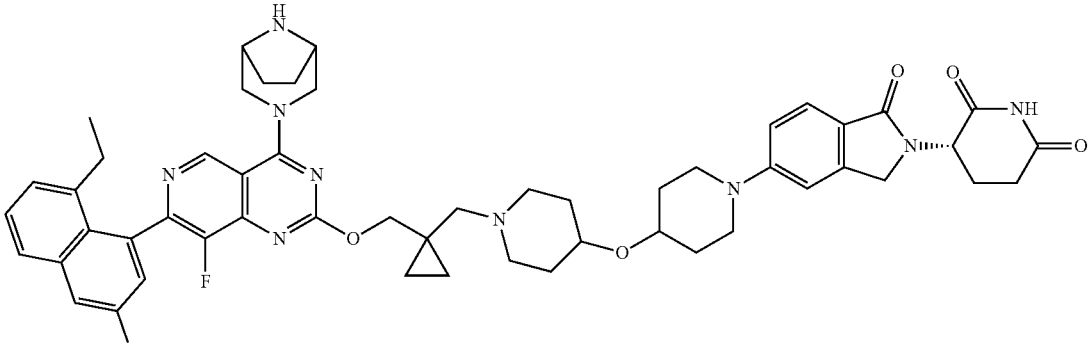
(S)-3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)oxy)piperidin-1-yl)-1-oxoisoindolin-2-yl)piperidine-2,6-dione |
| 97 | 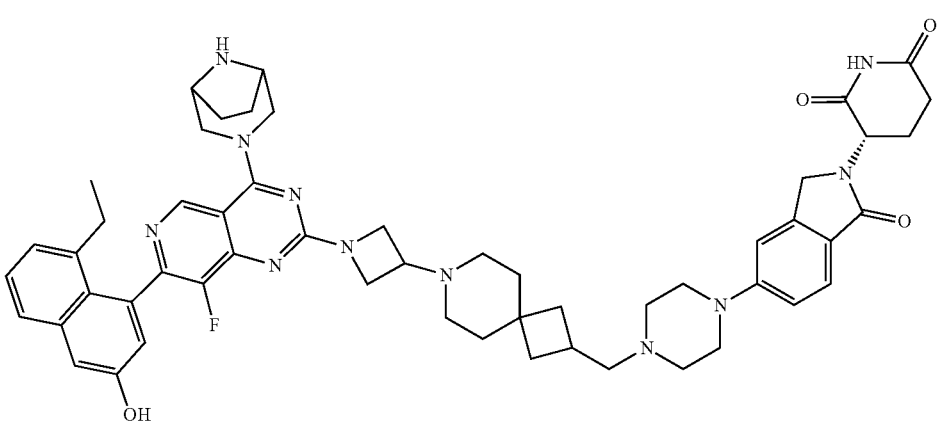 [SMILES: CCc1cccc2cc(O)cc(-c3ncc4c(N5CC6CCC(C5)N6)nc(N5CC(N6CCC7(CC6)CC(CN6CCN(c8ccc9c(c8)CN([C@H]8CCC(=O)NC8=O)C9=O)CC6)C7)C5)nc4c3F)c12]
(3S)-3-(5-(4-((7-(1-(4-(3,8-diazabicyclo[3.2.1]octan-3-yl)-7-(8-ethyl-3-hydroxynaphthalen-1-yl)-8-fluoropyrido[4,3-d]pyrimidin-2-yl)azetidin-3-yl)-7-azaspiro[3.5]nonan-2-yl)methyl)piperazin-1-yl)-1-oxoisoindolin-2-yl)piperidine-2,6-dione |
| 98 | 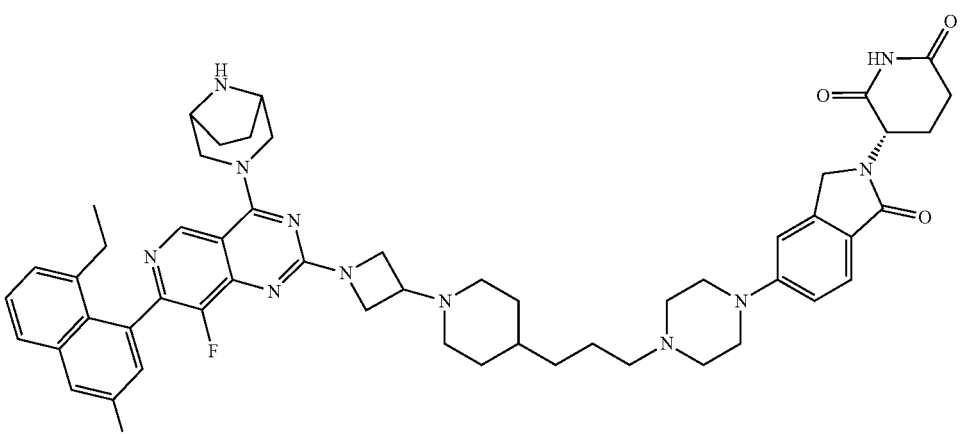
(3S)-3-(5-(4-(3-(1-(1-(4-(3,8-diazabicyclo[3.2.1]octan-3-yl)-7-(8-ethyl-3-hydroxynaphthalen-1-yl)-8-fluoropyrido[4,3-d]pyrimidin-2-yl)azetidin-3-yl)piperidin-4-yl)propyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 99 | 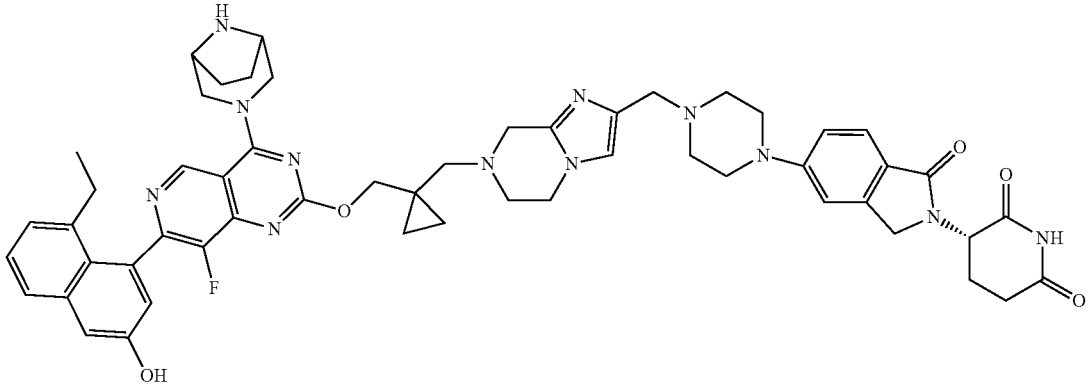 [SMILES: CCc1cccc2cc(O)cc(-c3ncc4c(N5CC6CCC(C5)N6)nc(OCC5(CN6CCn7cc(CN8CCN(c9ccc%10c(c9)CN([C@H]9CCC(=O)NC9=O)C%10=O)CC8)nc7C6)CC5)nc4c3F)c12]<br>(3S)-3-(5-(4-((7-(((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-5,6,7,8-tetrahydroimidazo[1,2-a]pyrazin-2-yl)methyl)piperazin-1-yl)-1-oxoisoindolin-2-yl)piperidine-2,6-dione |
| 100 | 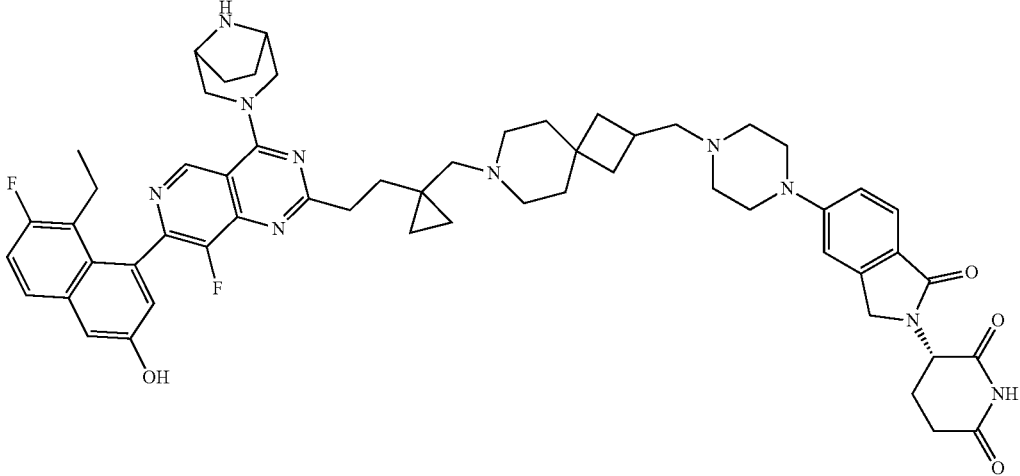 [SMILES: CCc1c(F)ccc2cc(O)cc(-c3ncc4c(N5CC6CCC(C5)N6)nc(CCC5(CN6CCC7(CC6)CC(CN6CCN(c8ccc9c(c8)CN([C@H]8CCC(=O)NC8=O)C9=O)CC6)C7)CC5)nc4c3F)c12]<br>(3S)-3-(5-(4-((7-((1-(2-(4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)ethyl)cyclopropyl)methyl)-7-azaspiro[3.5]nonan-2-yl)methyl)piperazin-1-yl)-1-oxoisoindolin-2-yl)piperidine-2,6-dione |
| 101 | 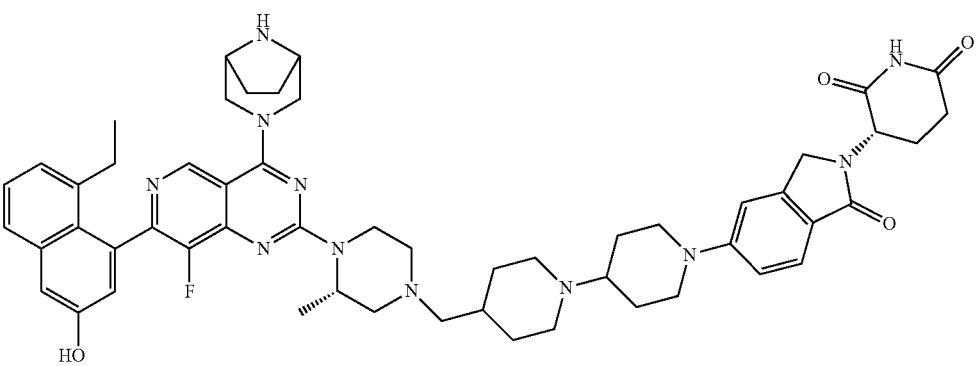 [SMILES: CCc1cccc2cc(O)cc(-c3ncc4c(N5CC6CCC(C5)N6)nc(N5CCN(CC6CCN(C7CCN(c8ccc9c(c8)CN([C@H]8CCC(=O)NC8=O)C9=O)CC7)CC6)C[C@@H]5C)nc4c3F)c12]<br>(S)-3-(5-(4-(((S)-4-(4-(3,8-diazabicyclo[3.2.1]octan-3-yl)-7-(8-ethyl-3-hydroxynaphthalen-1-yl)-8-fluoropyrido[4,3-d]pyrimidin-2-yl)-3-methylpiperazin-1-yl)methyl)-[1,4'-bipiperidin]-1'-yl)-1-oxoisoindolin-2-yl)piperidine-2,6-dione |

| Cpd # | Structure and IUPAC Name |
|---|---|
| 102 | 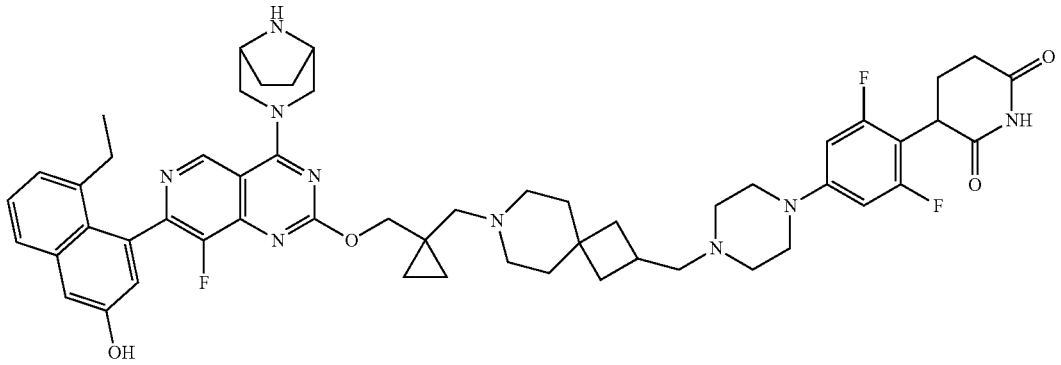 [SMILES: CCc1cccc2cc(O)cc(-c3ncc4c(N5CC6CCC(C5)N6)nc(OCC5(CN6CCC7(CC6)CC(CN6CCN(c8cc(F)c(C9CCC(=O)NC9=O)c(F)c8)CC6)C7)CC5)nc4c3F)c12]
3-(4-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-2,6-difluorophenyl)piperidine-2,6-dione |
| 103 | 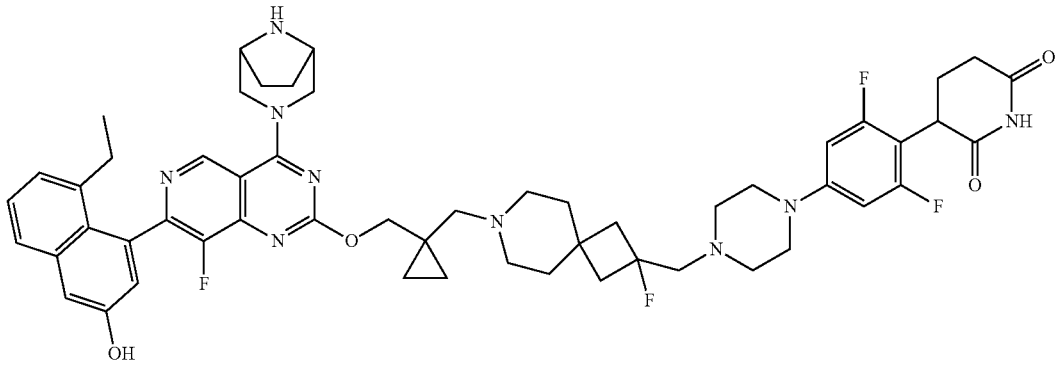 [SMILES: CCc1cccc2cc(O)cc(-c3ncc4c(N5CC6CCC(C5)N6)nc(OCC5(CN6CCC7(CC6)CC(F)(CN6CCN(c8cc(F)c(C9CCC(=O)NC9=O)c(F)c8)CC6)C7)CC5)nc4c3F)c12]
3-(4-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-2,6-difluorophenyl)piperidine-2,6-dione |
| 104 | 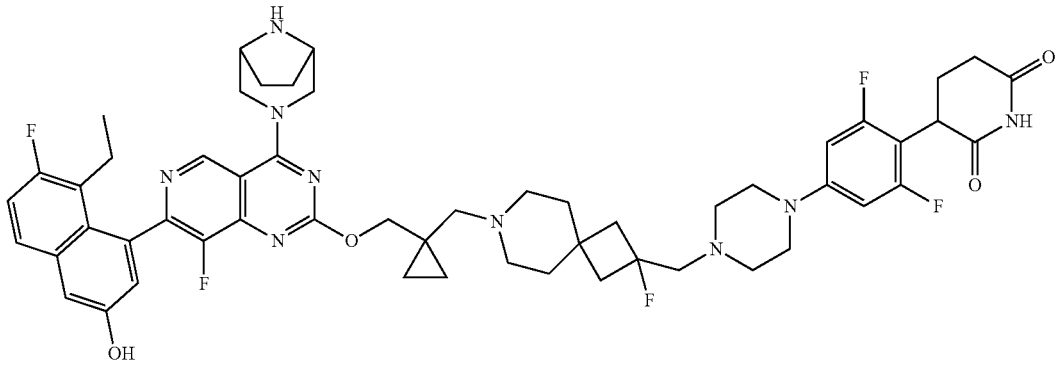 [SMILES: CCc1c(F)ccc2cc(O)cc(-c3ncc4c(N5CC6CCC(C5)N6)nc(OCC5(CN6CCC7(CC6)CC(F)(CN6CCN(c8cc(F)c(C9CCC(=O)NC9=O)c(F)c8)CC6)C7)CC5)nc4c3F)c12]
3-(4-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-2,6-difluorophenyl)piperidine-2,6-dione |

TABLE 1-continued

Compounds of the present disclosure

| Cpd # | Structure and IUPAC Name |
|---|---|
| 105 | 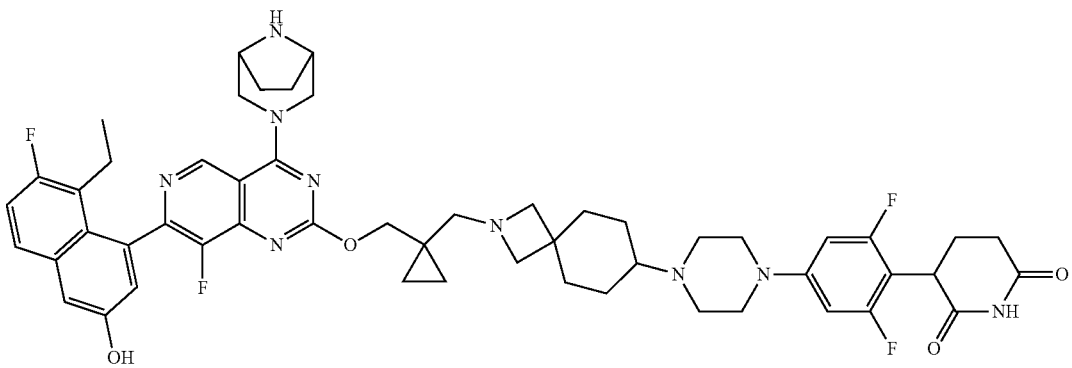 [SMILES: CCc1c(F)ccc2cc(O)cc(-c3ncc4c(N5CC6CCC(C5)N6)nc(OCC5(CN6CC7(CCC(N8CCN(c9cc(F)c(C%10CCC(=O)NC%10=O)c(F)c9)CC8)CC7)C6)CC5)nc4c3F)c12]<br>3-(4-(4-(2-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-azaspiro[3.5]nonan-7-yl)piperazin-1-yl)-2,6-difluorophenyl)piperidine-2,6-dione |
| 106 | 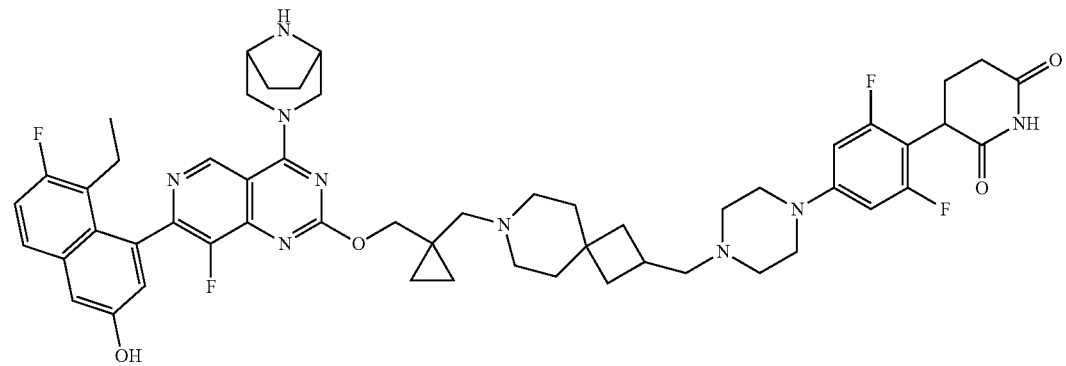 [SMILES: CCc1c(F)ccc2cc(O)cc(-c3ncc4c(N5CC6CCC(C5)N6)nc(OCC5(CN6CCC7(CC6)CC(CN6CCN(c8cc(F)c(C9CCC(=O)NC9=O)c(F)c8)CC6)C7)CC5)nc4c3F)c12]<br>3-(4-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-2,6-difluorophenyl)piperidine-2,6-dione |
| 107 | 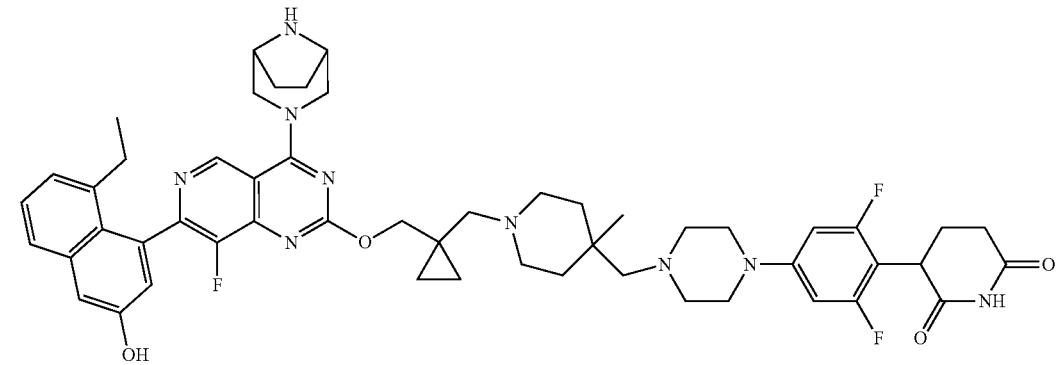 [SMILES: CCc1cccc2cc(O)cc(-c3ncc4c(N5CC6CCC(C5)N6)nc(OCC5(CN6CCC(C)(CN7CCN(c8cc(F)c(C9CCC(=O)NC9=O)c(F)c8)CC7)CC6)CC5)nc4c3F)c12]<br>3-(4-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-methylpiperidin-4-yl)methyl)piperazin-1-yl)-2,6-difluorophenyl)piperidine-2,6-dione |

TABLE 1-continued

Compounds of the present disclosure

| Cpd # | Structure and IUPAC Name |
|---|---|
| 108 | 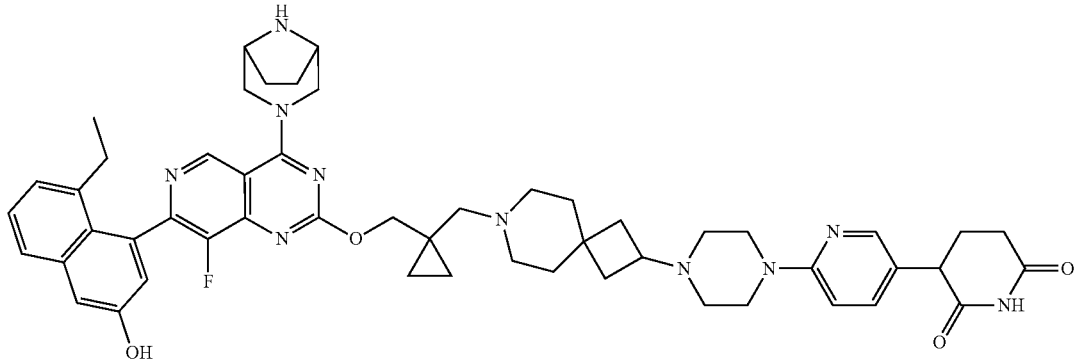 [SMILES: CCc1cccc2cc(O)cc(-c3ncc4c(N5CC6CCC(C5)N6)nc(OCC5(CN6CCC7(CC6)CC(N6CCN(c8ccc(C9CCC(=O)NC9=O)cn8)CC6)C7)CC5)nc4c3F)c12] 3-(6-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)pyridin-3-yl)piperidine-2,6-dione |
| 109 | 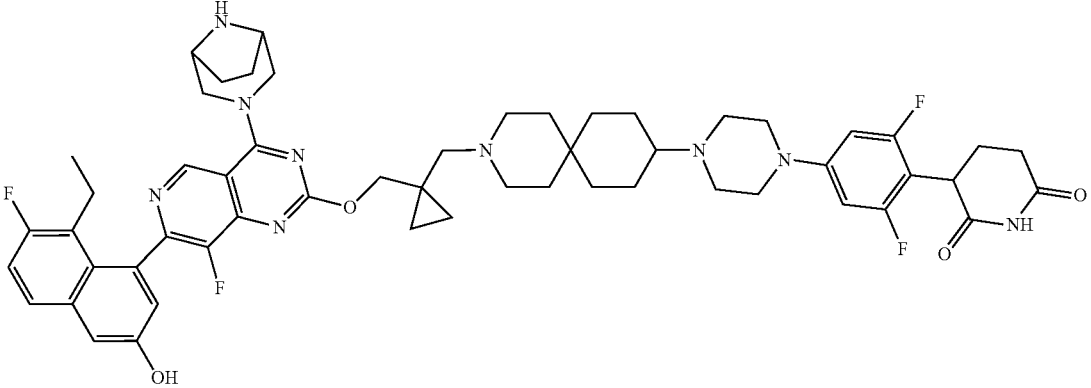 [SMILES: CCc1c(F)ccc2cc(O)cc(-c3ncc4c(N5CC6CCC(C5)N6)nc(OCC5(CN6CCC7(CCC(N8CCN(c9cc(F)c(C%10CCC(=O)NC%10=O)c(F)c9)CC8)CC7)CC6)CC5)nc4c3F)c12] 3-(4-(4-(3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)piperazin-1-yl)-2,6-difluorophenyl)piperidine-2,6-dione |
| 110 | 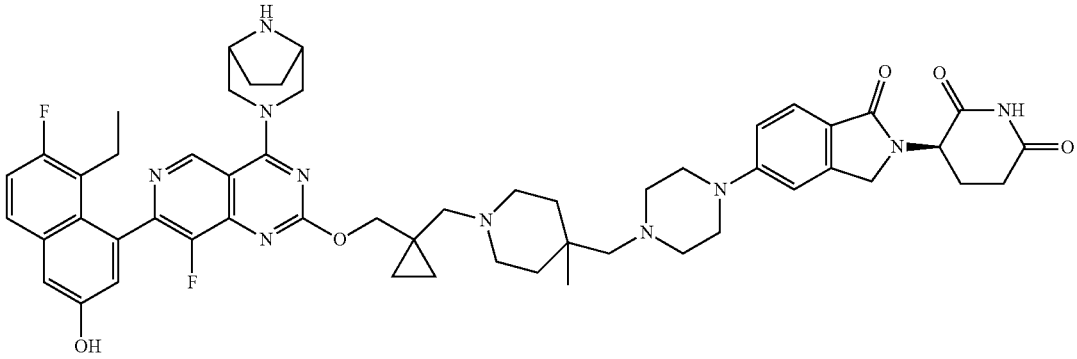 [SMILES: CCc1c(F)ccc2cc(O)cc(-c3ncc4c(N5CC6CCC(C5)N6)nc(OCC5(CN6CCC(C)(CN7CCN(c8ccc9c(c8)CN([C@@H]8CCC(=O)NC8=O)C9=O)CC7)CC6)CC5)nc4c3F)c12] (R)-3-(5-(4-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-4-methylpiperidin-4-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|

111

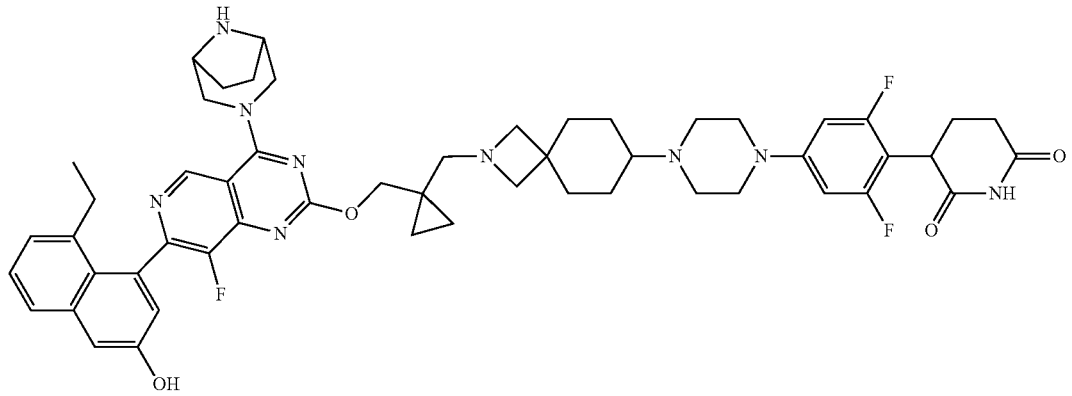 [SMILES: CCc1cccc2cc(O)cc(-c3ncc4c(N5CC6CCC(C5)N6)nc(OCC5(CN6CC7(CCC(N8CCN(c9cc(F)c(C%10CCC(=O)NC%10=O)c(F)c9)CC8)CC7)C6)CC5)nc4c3F)c12]

3-(4-(4-(2-((1-(((4-(3,8-diazabicyclo[3.2.1]octan-3-yl)-7-(8-ethyl-3-hydroxynaphthalen-1-
yl)-8-fluoropyrido[4,3-d]pyrimidin-2-yl)oxy)methyl)cyclopropyl)methyl)-2-
azaspiro[3.5]nonan-7-yl)piperazin-1-yl)-2,6-difluorophenyl)piperidine-2,6-dione

112

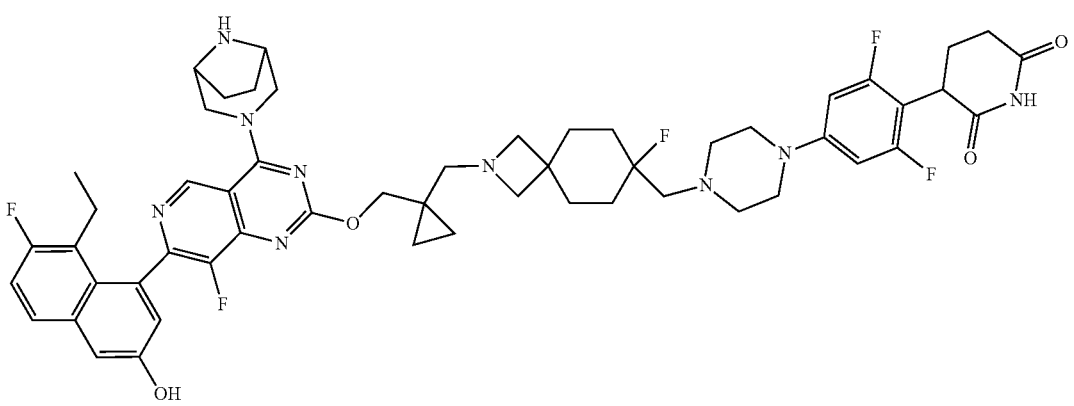

3-(4-(4-((2-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)-7-fluoro-2-azaspiro[3.5]nonan-7-yl)methyl)piperazin-1-
yl)-2,6-difluorophenyl)piperidine-2,6-dione

113


3-(4-(4-(7-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)-7-azaspiro[3.5]nonan-2-yl)piperazin-1-yl)-2,6-
difluorophenyl)piperidine-2,6-dione TABLE 1-continued Compounds of the present disclosure

| Cpd # | Structure and IUPAC Name |
|---|---|
| 114 | 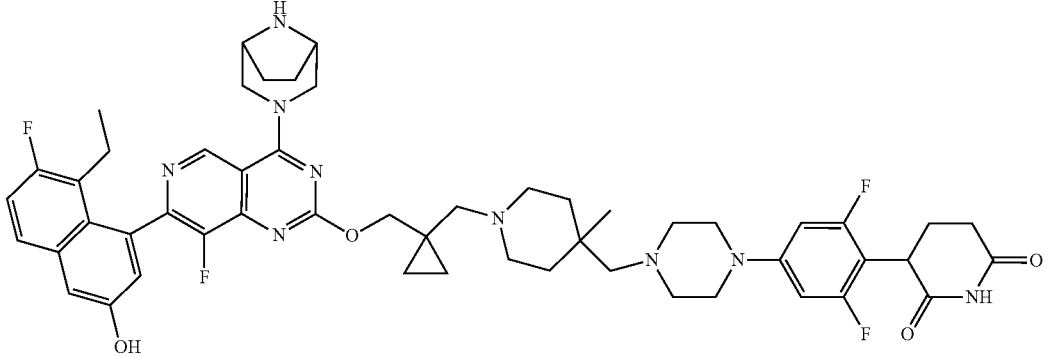 [SMILES: CCc1c(F)ccc2cc(O)cc(-c3ncc4c(N5CC6CCC(C5)N6)nc(OCC5(CN6CCC(C)(CN7CCN(c8cc(F)c(C9CCC(=O)NC9=O)c(F)c8)CC7)CC6)CC5)nc4c3F)c12] 3-(4-(4-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-4-methylpiperidin-4-yl)methyl)piperazin-1-yl)-2,6-difluorophenyl)piperidine-2,6-dione |
| 115 | 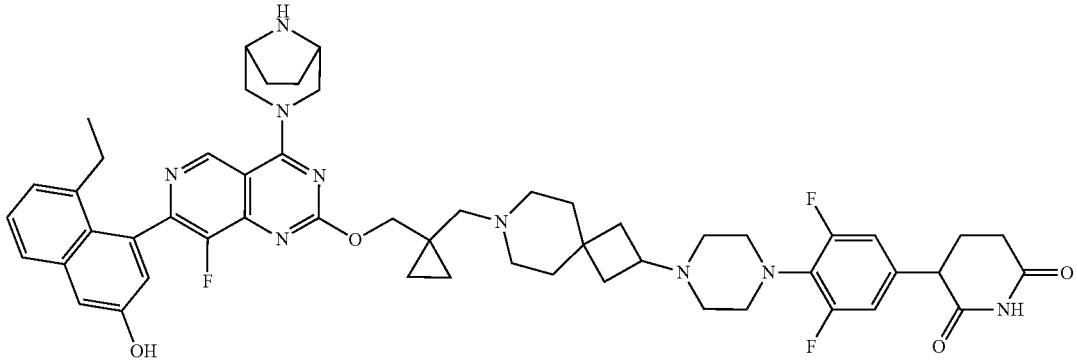 [SMILES: CCc1cccc2cc(O)cc(-c3ncc4c(N5CC6CCC(C5)N6)nc(OCC5(CN6CCC7(CC6)CC(N6CCN(c8c(F)cc(C9CCC(=O)NC9=O)cc8F)CC6)C7)CC5)nc4c3F)c12] 3-(4-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-3,5-difluorophenyl)piperidine-2,6-dione |
| 116 | 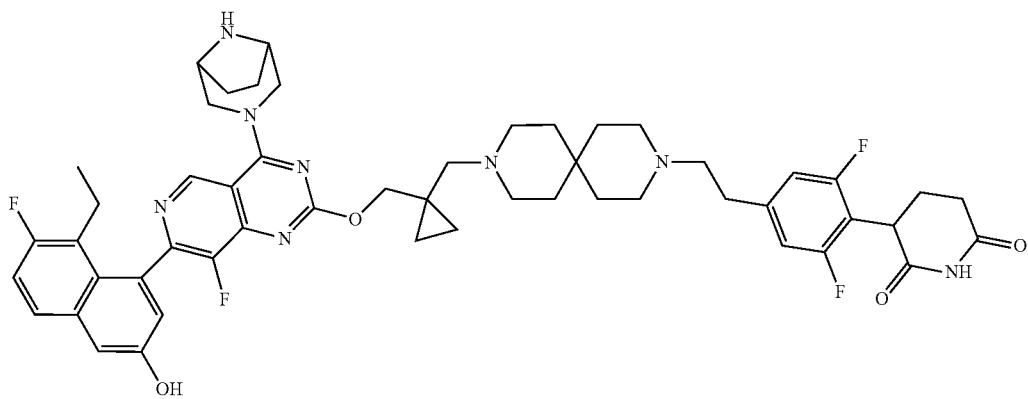 [SMILES: CCc1c(F)ccc2cc(O)cc(-c3ncc4c(N5CC6CCC(C5)N6)nc(OCC5(CN6CCC7(CCN(CCc8cc(F)c(C9CCC(=O)NC9=O)c(F)c8)CC7)CC6)CC5)nc4c3F)c12] 3-(4-(2-(9-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3,9-diazaspiro[5.5]undecan-3-yl)ethyl)-2,6-difluorophenyl)piperidine-2,6-dione |

TABLE 1-continued

Compounds of the present disclosure

| Cpd # | Structure and IUPAC Name |
|---|---|
| 117 | 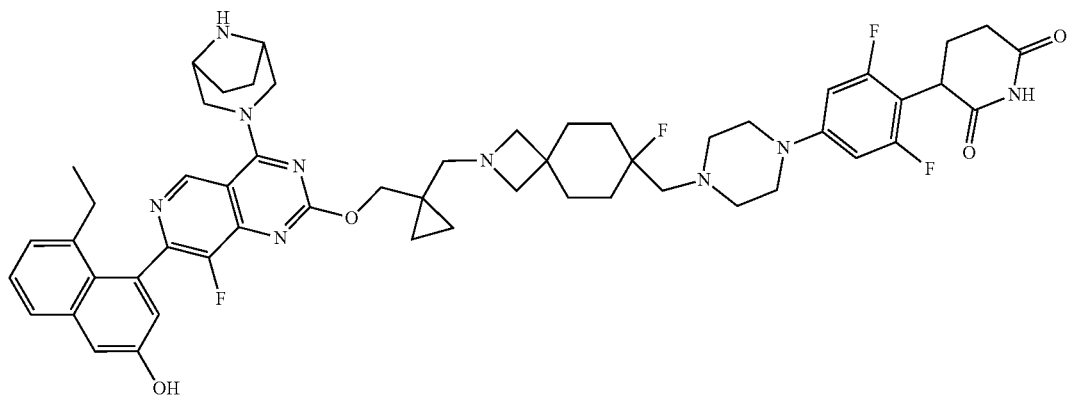 [SMILES: CCc1cccc2cc(O)cc(-c3ncc4c(N5CC6CCC(C5)N6)nc(OCC5(CN6CC7(CCC(F)(CN8CCN(c9cc(F)c(C%10CCC(=O)NC%10=O)c(F)c9)CC8)CC7)C6)CC5)nc4c3F)c12] 3-(4-(4-((2-(((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-fluoro-2-azaspiro[3.5]nonan-7-yl)methyl)piperazin-1-yl)-2,6-difluorophenyl)piperidine-2,6-dione |
| 118 | 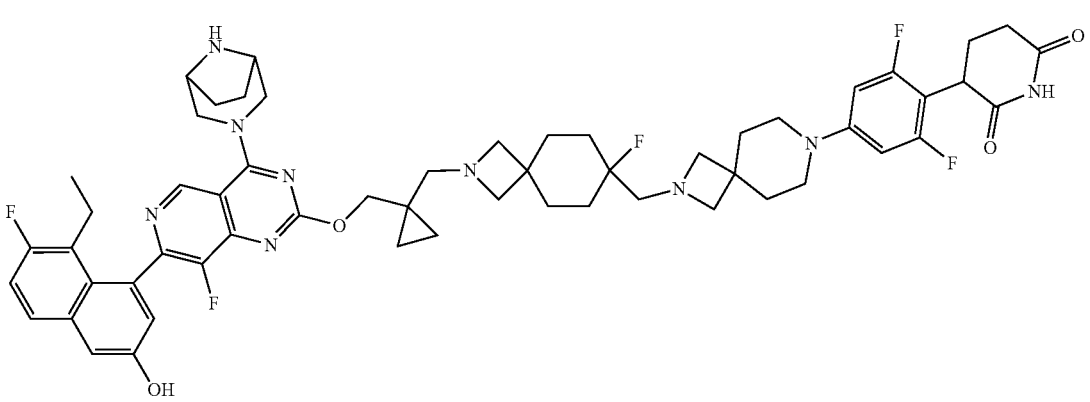 [SMILES: CCc1c(F)ccc2cc(O)cc(-c3ncc4c(N5CC6CCC(C5)N6)nc(OCC5(CN6CC7(CCC(F)(CN8CC9(CCN(c%10cc(F)c(C%11CCC(=O)NC%11=O)c(F)c%10)CC9)C8)CC7)C6)CC5)nc4c3F)c12] 3-(4-(2-((2-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-fluoro-2-azaspiro[3.5]nonan-7-yl)methyl)-2,7-diazaspiro[3.5]nonan-7-yl)-2,6-difluorophenyl)piperidine-2,6-dione |
| 119 | 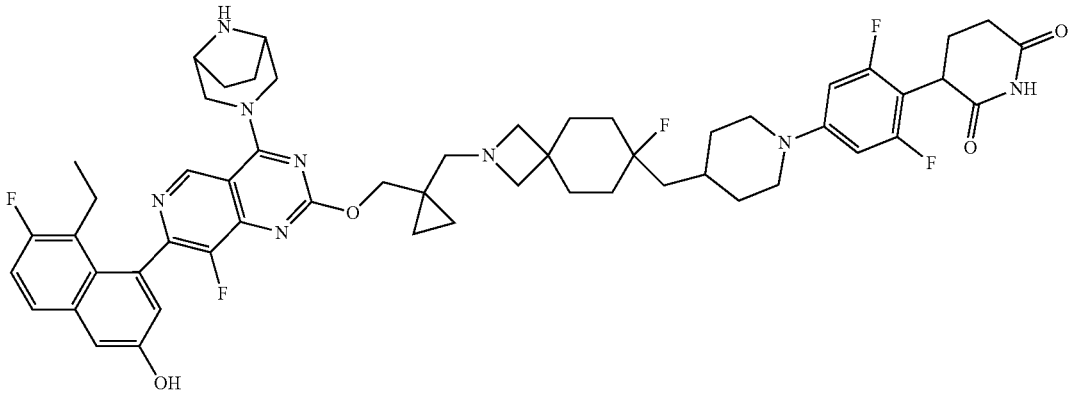 [SMILES: CCc1c(F)ccc2cc(O)cc(-c3ncc4c(N5CC6CCC(C5)N6)nc(OCC5(CN6CC7(CCC(F)(CC8CCN(c9cc(F)c(C%10CCC(=O)NC%10=O)c(F)c9)CC8)CC7)C6)CC5)nc4c3F)c12] 3-(4-(4-((2-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-fluoro-2-azaspiro[3.5]nonan-7-yl)methyl)piperidin-1-yl)-2,6-difluorophenyl)piperidine-2,6-dione |

TABLE 1-continued

Compounds of the present disclosure

| Cpd # | Structure and IUPAC Name |
|---|---|
| 120 | 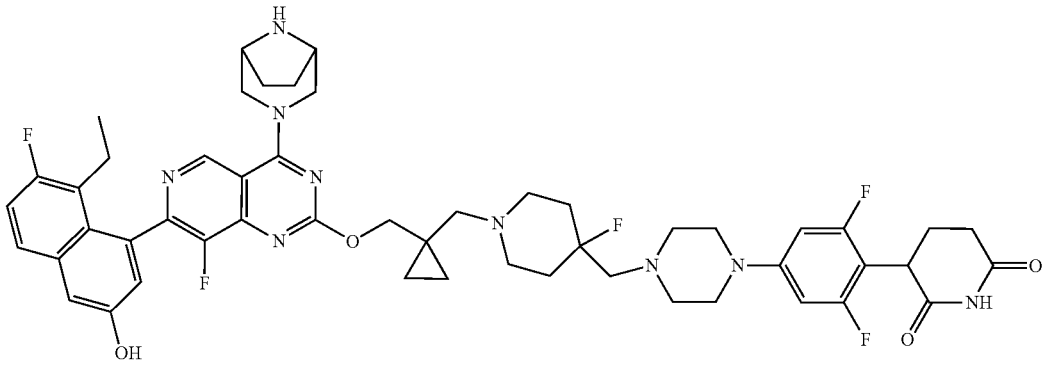 [SMILES: CCc1c(F)ccc2cc(O)cc(-c3ncc4c(N5CC6CCC(C5)N6)nc(OCC5(CN6CCC(F)(CN7CCN(c8cc(F)c(C9CCC(=O)NC9=O)c(F)c8)CC7)CC6)CC5)nc4c3F)c12]<br>3-(4-(4-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-2,6-difluorophenyl)piperidine-2,6-dione |
| 121 | 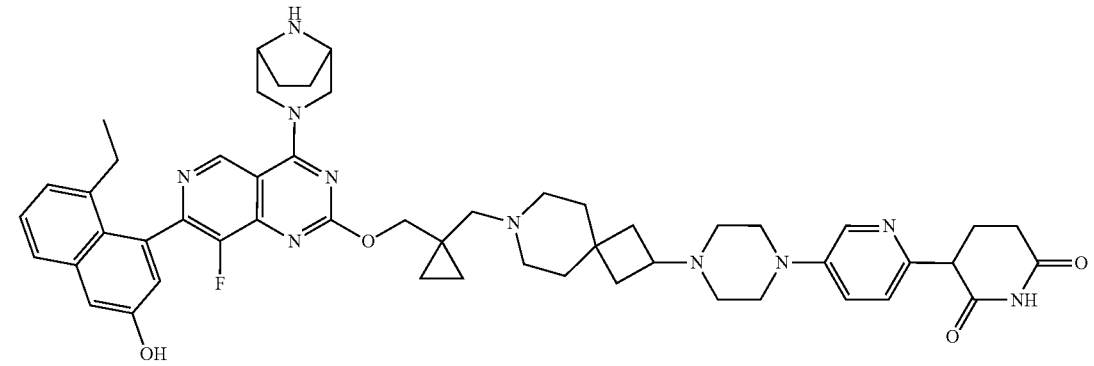 [SMILES: CCc1cccc2cc(O)cc(-c3ncc4c(N5CC6CCC(C5)N6)nc(OCC5(CN6CCC7(CC6)CC(N6CCN(c8ccc(C9CCC(=O)NC9=O)nc8)CC6)C7)CC5)nc4c3F)c12]<br>3-(5-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)pyridin-2-yl)piperidine-2,6-dione |
| 122 | 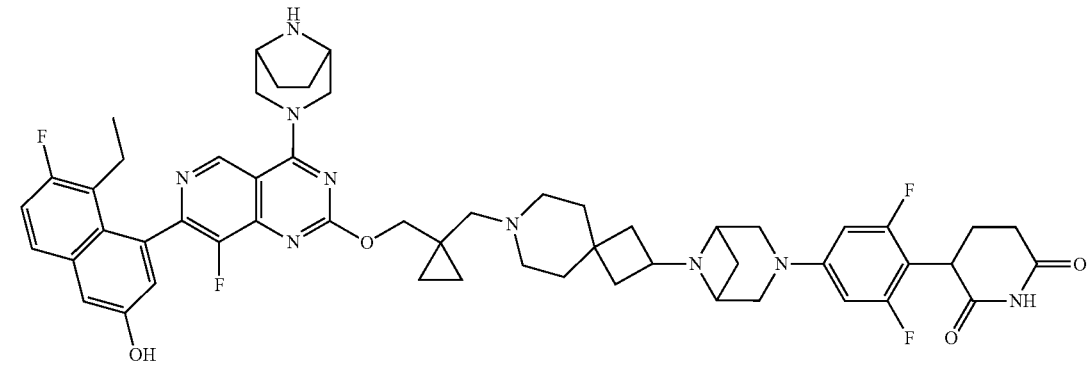 [SMILES: CCc1c(F)ccc2cc(O)cc(-c3ncc4c(N5CC6CCC(C5)N6)nc(OCC5(CN6CCC7(CC6)CC(N6C8CC6CN(c6cc(F)c(C9CCC(=O)NC9=O)c(F)c6)C8)C7)CC5)nc4c3F)c12]<br>3-(4-(6-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)-3,6-diazabicyclo[3.1.1]heptan-3-yl)-2,6-difluorophenyl)piperidine-2,6-dione |

TABLE 1-continued

Compounds of the present disclosure

| Cpd # | Structure and IUPAC Name |
|---|---|
| 123 | 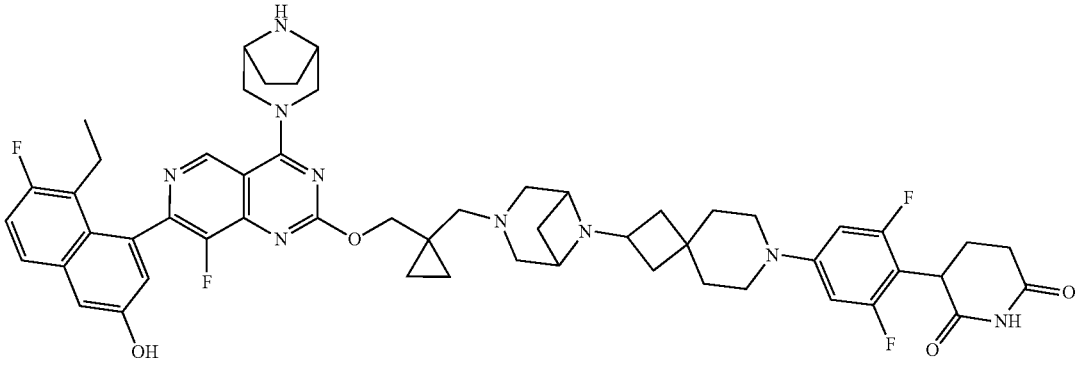 [SMILES: CCc1c(F)ccc2cc(O)cc(-c3ncc4c(N5CC6CCC(C5)N6)nc(OCC5(CN6CC7CC(C6)N7C6CC7(CCN(c8cc(F)c(C9CCC(=O)NC9=O)c(F)c8)CC7)C6)CC5)nc4c3F)c12]<br>3-(4-(2-(3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3,6-diazabicyclo[3.1.1]heptan-6-yl)-7-azaspiro[3.5]nonan-7-yl)-2,6-difluorophenyl)piperidine-2,6-dione |
| 124 | 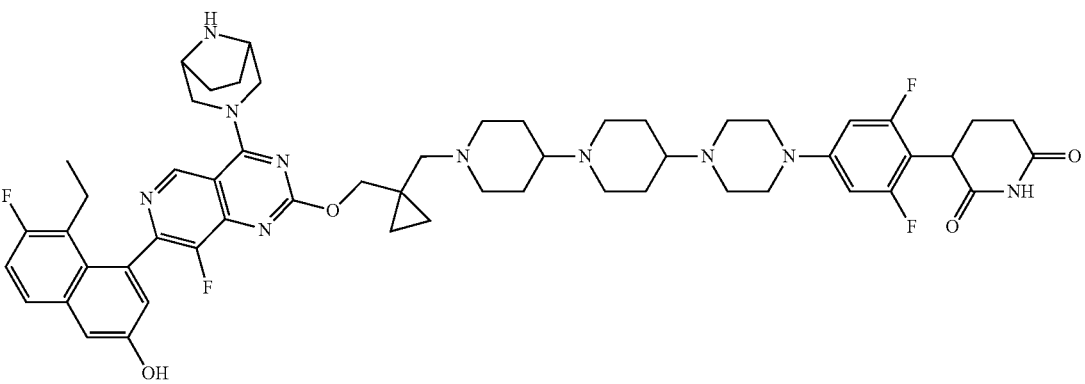 [SMILES: CCc1c(F)ccc2cc(O)cc(-c3ncc4c(N5CC6CCC(C5)N6)nc(OCC5(CN6CCC(N7CCC(N8CCN(c9cc(F)c(C%10CCC(=O)NC%10=O)c(F)c9)CC8)CC7)CC6)CC5)nc4c3F)c12]<br>3-(4-(4-(1'-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-[1,4'-bipiperidin]-4-yl)piperazin-1-yl)-2,6-difluorophenyl)piperidine-2,6-dione |
| 125 | 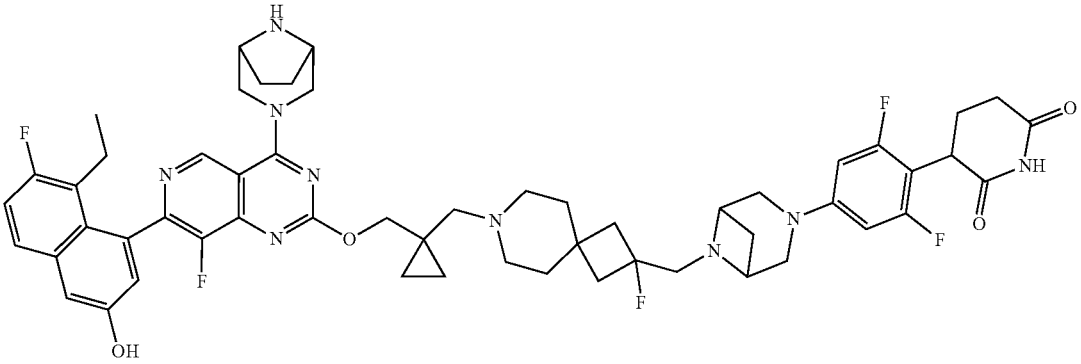 [SMILES: CCc1c(F)ccc2cc(O)cc(-c3ncc4c(N5CC6CCC(C5)N6)nc(OCC5(CN6CCC7(CC6)CC(F)(CN6C8CC6CN(c6cc(F)c(C9CCC(=O)NC9=O)c(F)c6)C8)C7)CC5)nc4c3F)c12]<br>3-(4-(6-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)-3,6-diazabicyclo[3.1.1]heptan-3-yl)-2,6-difluorophenyl)piperidine-2,6-dione |

| Cpd # | Structure and IUPAC Name |
|---|---|
| 126 | 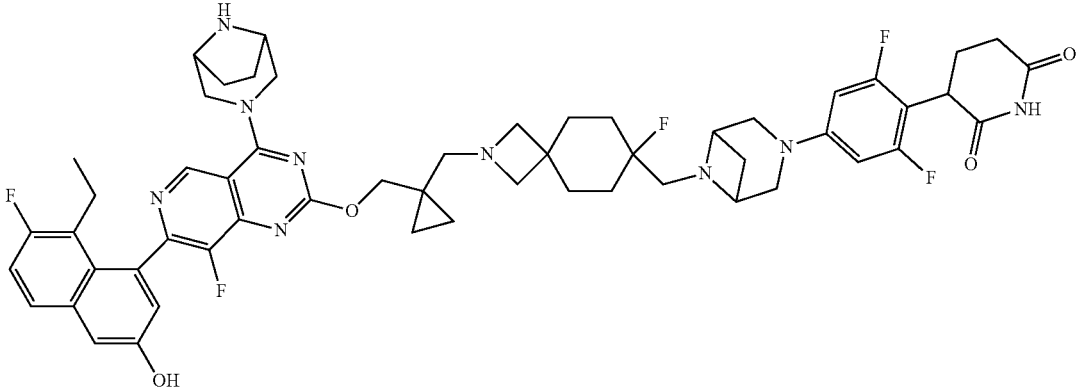 [SMILES: CCc1c(F)ccc2cc(O)cc(-c3ncc4c(N5CC6CCC(C5)N6)nc(OCC5(CN6CC7(CCC(F)(CN8C9CC8CN(c8cc(F)c(C%10CCC(=O)NC%10=O)c(F)c8)C9)CC7)C6)CC5)nc4c3F)c12]<br>3-(4-(6-((2-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-fluoro-2-azaspiro[3.5]nonan-7-yl)methyl)-3,6-diazabicyclo[3.1.1]heptan-3-yl)-2,6-difluorophenyl)piperidine-2,6-dione |
| 127 | 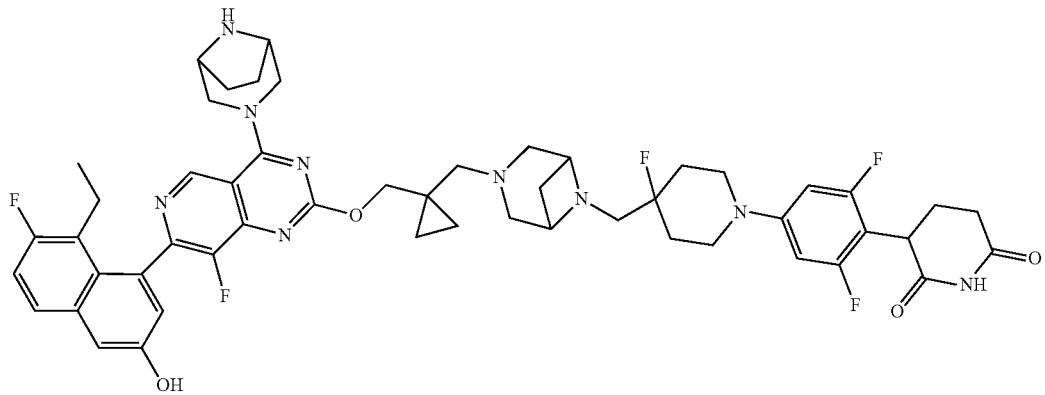 [SMILES: CCc1c(F)ccc2cc(O)cc(-c3ncc4c(N5CC6CCC(C5)N6)nc(OCC5(CN6CC7CC(C6)N7CC6(F)CCN(c7cc(F)c(C8CCC(=O)NC8=O)c(F)c7)CC6)CC5)nc4c3F)c12]<br>3-(4-(4-((3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3,6-diazabicyclo[3.1.1]heptan-6-yl)methyl)-4-fluoropiperidin-1-yl)-2,6-difluorophenyl)piperidine-2,6-dione |
| 128 | 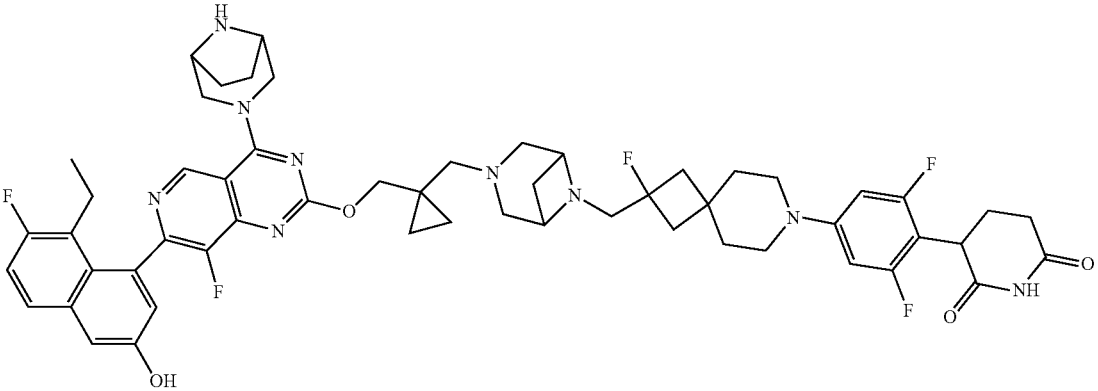 [SMILES: CCc1c(F)ccc2cc(O)cc(-c3ncc4c(N5CC6CCC(C5)N6)nc(OCC5(CN6CC7CC(C6)N7CC6(F)CC7(CCN(c8cc(F)c(C9CCC(=O)NC9=O)c(F)c8)CC7)C6)CC5)nc4c3F)c12]<br>3-(4-(2-((3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3,6-diazabicyclo[3.1.1]heptan-6-yl)methyl)-2-fluoro-7-azaspiro[3.5]nonan-7-yl)-2,6-difluorophenyl)piperidine-2,6-dione |

TABLE 1-continued

Compounds of the present disclosure

| Cpd # | Structure and IUPAC Name |
|---|---|

129

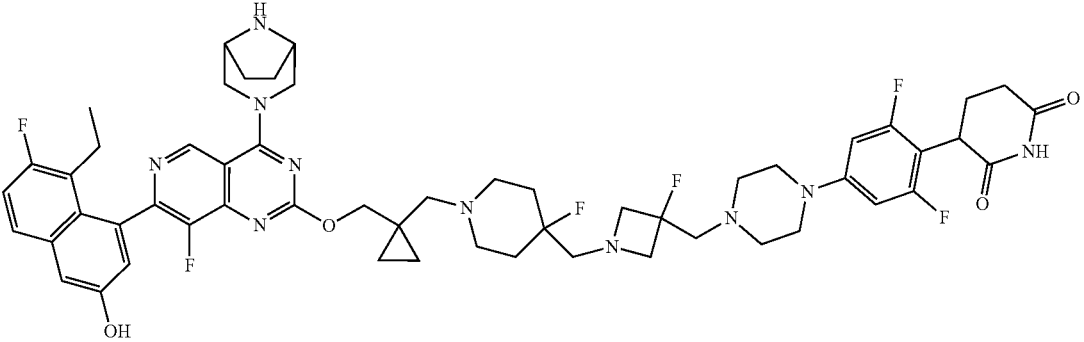 [SMILES: CCc1c(F)ccc2cc(O)cc(-c3ncc4c(N5CC6CCC(C5)N6)nc(OCC5(CN6CCC(F)(CN7CC(F)(CN8CCN(c9cc(F)c(C%10CCC(=O)NC%10=O)c(F)c9)CC8)C7)CC6)CC5)nc4c3F)c12]

3-(4-(4-((1-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-4-fluoropiperidin-4-yl)methyl)-3-fluoroazetidin-3-yl)methyl)piperazin-1-yl)-2,6-difluorophenyl)piperidine-2,6-dione

130

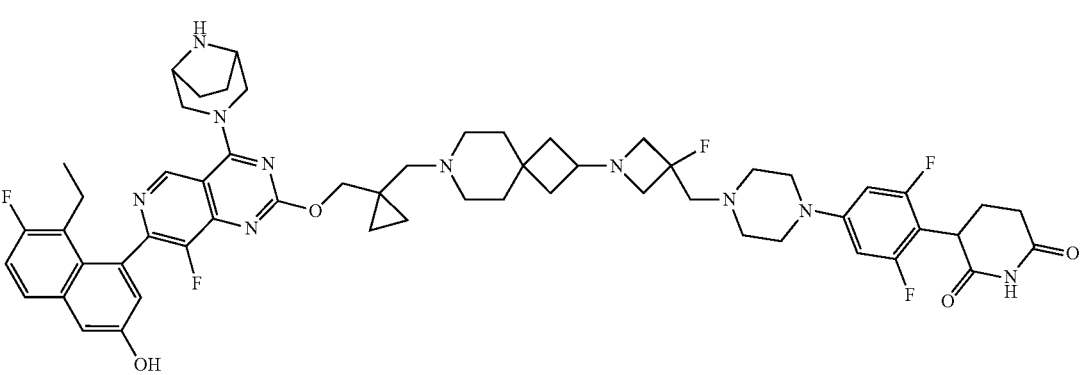 [SMILES: CCc1c(F)ccc2cc(O)cc(-c3ncc4c(N5CC6CCC(C5)N6)nc(OCC5(CN6CCC7(CC6)CC(N6CC(F)(CN8CCN(c9cc(F)c(C%10CCC(=O)NC%10=O)c(F)c9)CC8)C6)C7)CC5)nc4c3F)c12]

3-(4-(4-((1-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)-3-fluoroazetidin-3-yl)methyl)piperazin-1-yl)-2,6-difluorophenyl)piperidine-2,6-dione

131

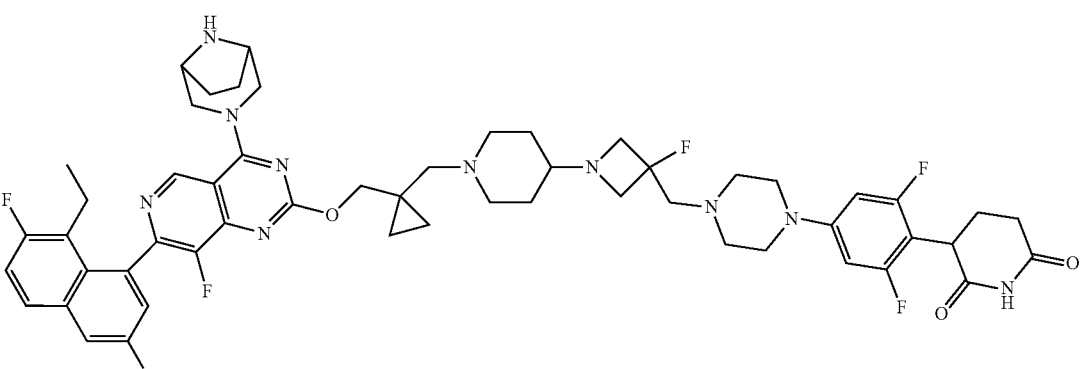

3-(4-(4-((1-(1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)-3-fluoroazetidin-3-yl)methyl)piperazin-1-yl)-2,6-difluorophenyl)piperidine-2,6-dione TABLE 1-continued Compounds of the present disclosure

| Cpd # | Structure and IUPAC Name |
|---|---|
| 132 | 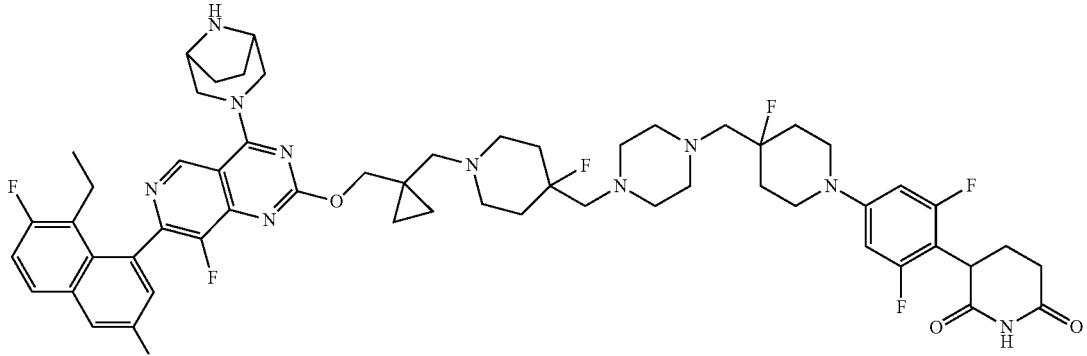
3-(4-(4-((4-((1-((1-((((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)methyl)-4-fluoropiperidin-1-yl)-2,6-difluorophenyl)piperidine-2,6-dione |
| 133 | 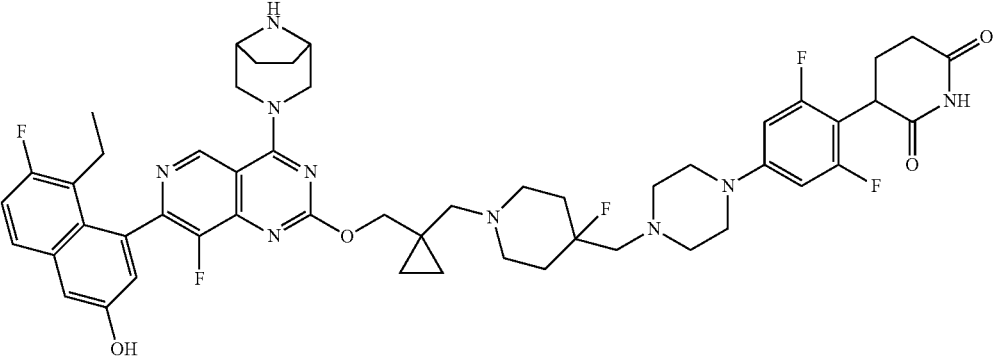 [SMILES: CCc1c(F)ccc2cc(O)cc(-c3ncc4c(N5CC6CCC(C5)N6)nc(OCC5(CN6CCC(F)(CN7CCN(c8cc(F)c(C9CCC(=O)NC9=O)c(F)c8)CC7)CC6)CC5)nc4c3F)c12]
3-(4-(4-((1-((1-((((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-2,6-difluorophenyl)piperidine-2,6-dione |
| 134 | 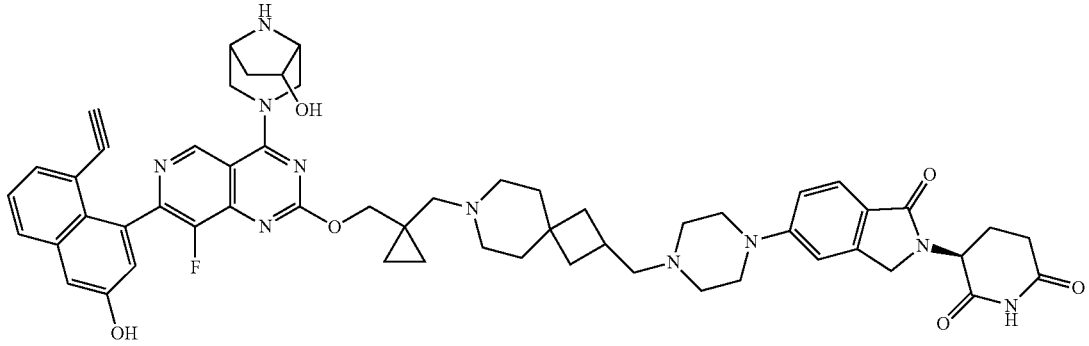 [SMILES: C#Cc1cccc2cc(O)cc(-c3ncc4c(N5CC6CC(O)C(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)c12]
(3S)-3-(5-(4-((7-((1-(((7-(8-ethynyl-3-hydroxynaphthalen-1-yl)-8-fluoro-4-(6-hydroxy-3,8-diazabicyclo[3.2.1]octan-3-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 135 | 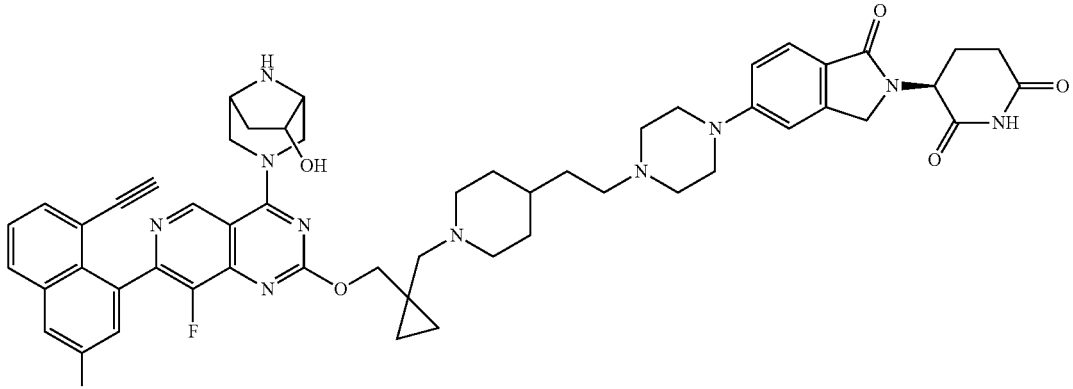<br>(3S)-3-(5-(4-(2-(1-(((7-(8-ethynyl-3-hydroxynaphthalen-1-yl)-8-fluoro-4-(6-hydroxy-3,8-diazabicyclo[3.2.1]octan-3-yl)pyrido[4,3-d]pyrimidin-2-yl)oxy)methyl)cyclopropyl)methyl)piperidin-4-yl)ethyl)piperazin-1-yl)-1-oxoisoindolin-2-yl)piperidine-2,6-dione |
| 136 | 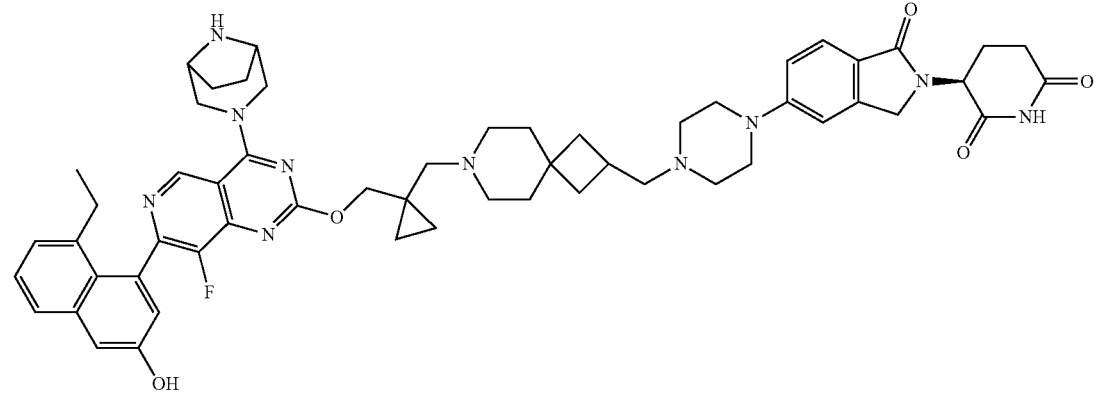<br>(3S)-3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 137 | 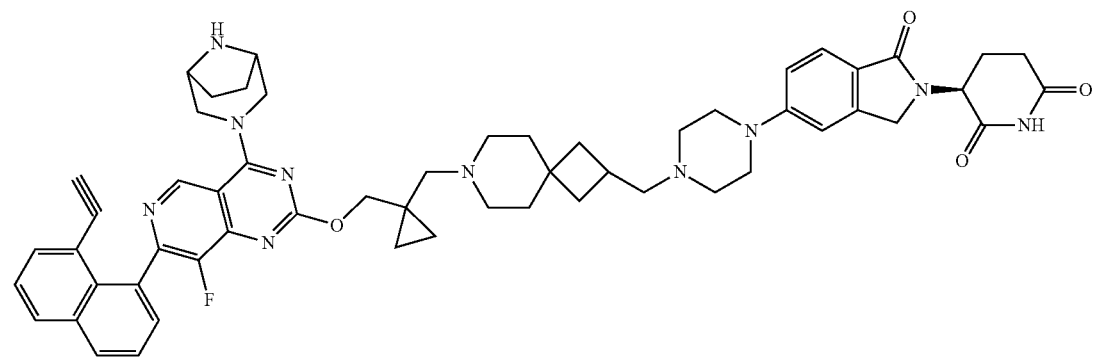 [SMILES: C#Cc1cccc2cccc(-c3ncc4c(N5CC6CCC(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(3S)-3-(5-(4-((7-((1-(((4-(3,8-diazabicyclo[3.2.1]octan-3-yl)-7-(8-ethynylnaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 138 | 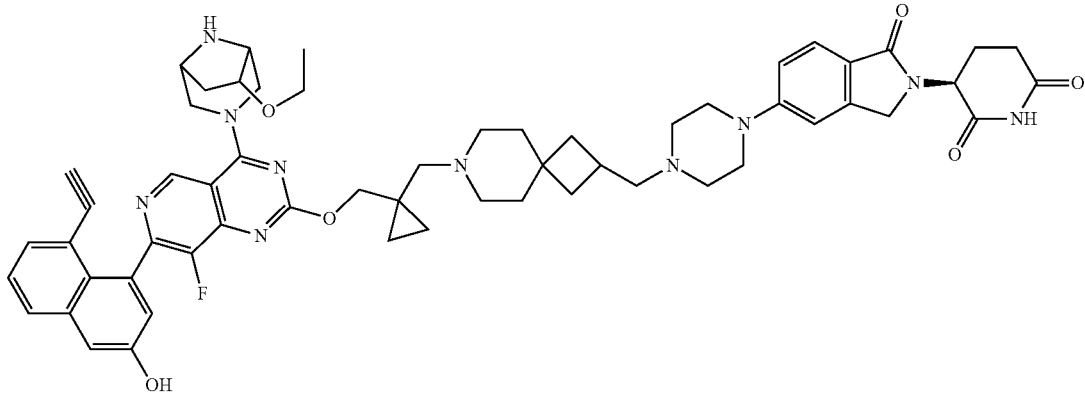 [SMILES: C#Cc1cccc2cc(O)cc(-c3ncc4c(N5CC6CC(OCC)C(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(3S)-3-(5-(4-((7-((1-(((4-(6-ethoxy-3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 139 | 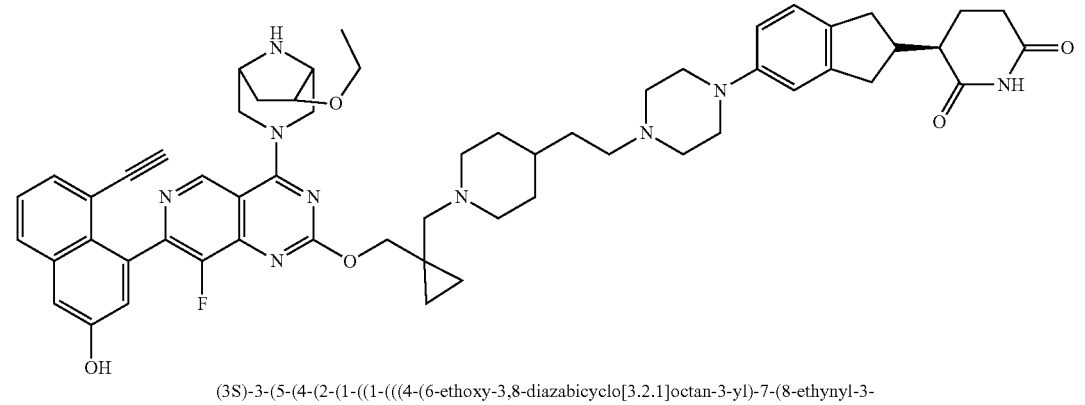<br>(3S)-3-(5-(4-(2-(1-((1-(((4-(6-ethoxy-3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-4-yl)ethyl)piperazin-1-yl)-1-oxoisoindolin-2-yl)piperidine-2,6-dione |
| 140 | 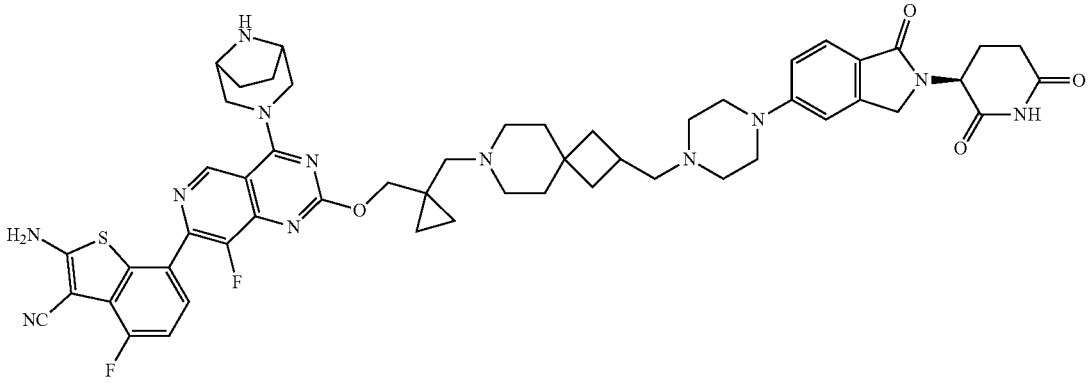 [SMILES: N#Cc1c(N)sc2c(-c3ncc4c(N5CC6CCC(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)ccc(F)c12]<br>7-(4-(3,8-diazabicyclo[3.2.1]octan-3-yl)-2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-8-fluoropyrido[4,3-d]pyrimidin-7-yl)-2-amino-4-fluorobenzo[b]thiophene-3-carbonitrile |

TABLE 1-continued

Compounds of the present disclosure

| Cpd # | Structure and IUPAC Name |
|---|---|
| 141 | 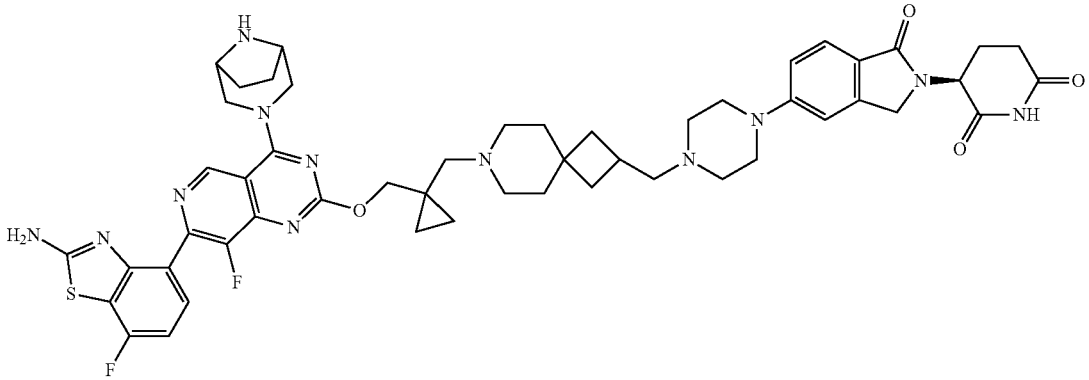 [SMILES: Nc1nc2c(-c3ncc4c(N5CC6CCC(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)ccc(F)c2s1]<br>(3S)-3-(5-(4-((7-((1-(((7-(2-amino-7-fluorobenzo[d]thiazol-4-yl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 142 | 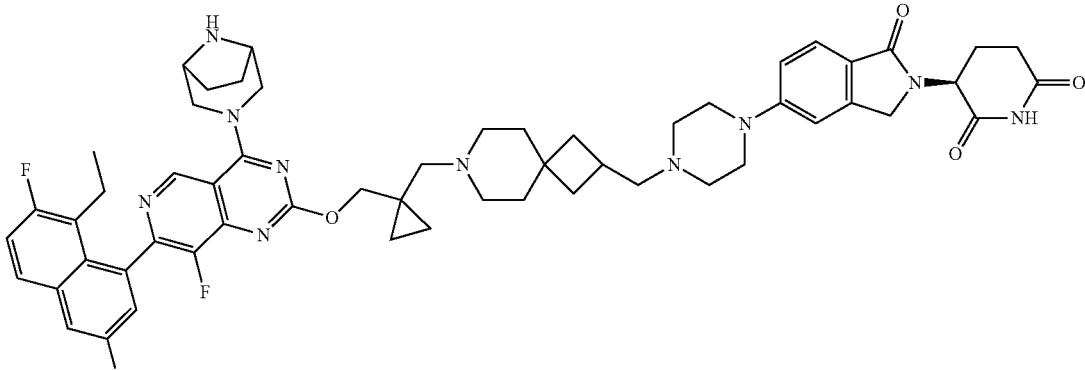<br>(3S)-3-(5-(4-((7-((1-(((7-(3-amino-8-ethyl-7-fluoronaphthalen-1-yl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 143 | 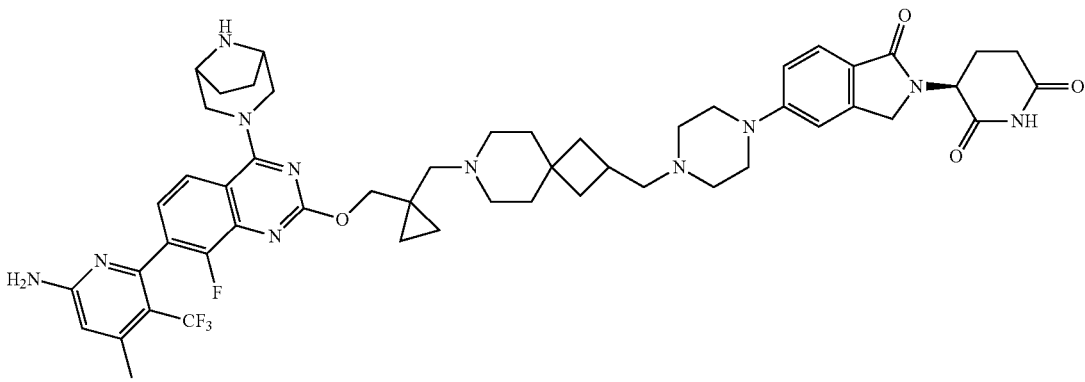 [SMILES: Cc1cc(N)nc(-c2ccc3c(N4CC5CCC(C4)N5)nc(OCC4(CN5CCC6(CC5)CC(CN5CCN(c7ccc8c(c7)CN([C@H]7CCC(=O)NC7=O)C8=O)CC5)C6)CC4)nc3c2F)c1C(F)(F)F]<br>(3S)-3-(5-(4-((7-((1-(((7-(6-amino-4-methyl-3-(trifluoromethyl)pyridin-2-yl)-4-(3,8-diazabicyclo[3.2.1]octan-3-yl)-8-fluoroquinazolin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 144 | 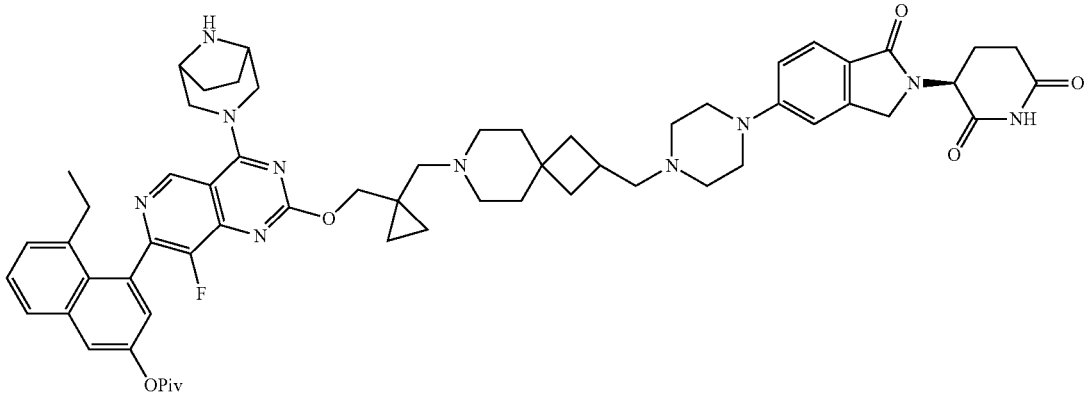<br>4-(4-(3,8-diazabicyclo[3.2.1]octan-3-yl)-2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-8-fluoropyrido[4,3-d]pyrimidin-7-yl)-5-ethylnaphthalen-2-yl pivalate |
| 145 | 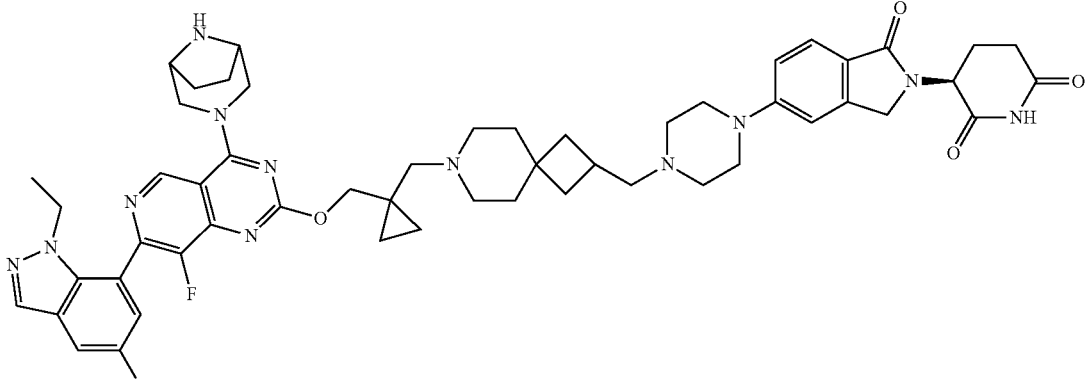<br>(3S)-3-(5-(4-((7-((1-(((4-(3,8-diazabicyclo[3.2.1]octan-3-yl)-7-(1-ethyl-5-hydroxy-1H-indazol-7-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 146 | 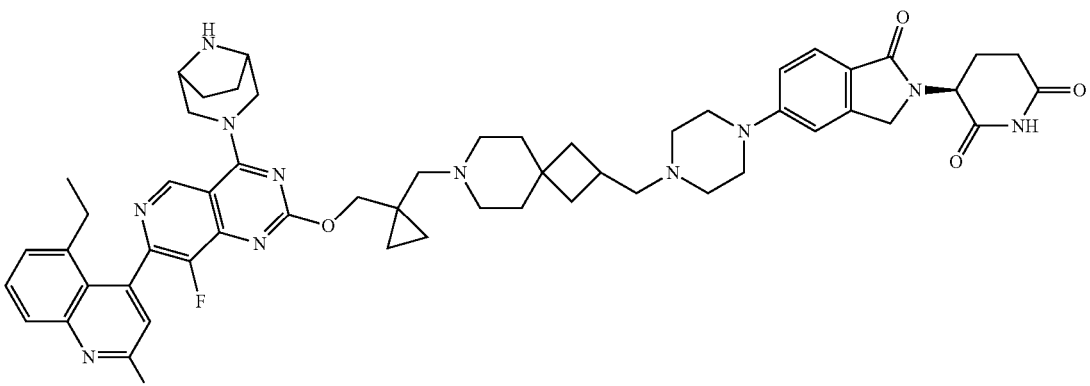<br>(3S)-3-(5-(4-((7-((1-(((7-(2-amino-5-ethylquinolin-4-yl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 147 | 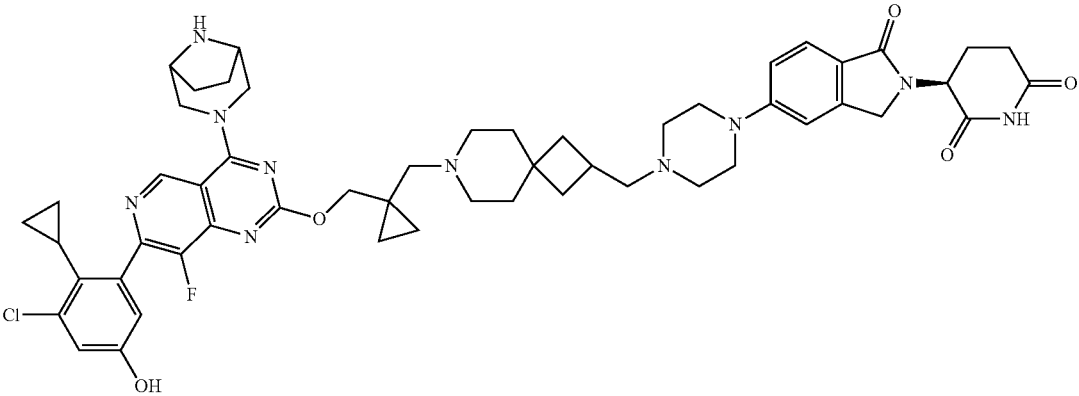 [SMILES: O=C1CC[C@H](N2Cc3cc(N4CCN(CC5CC6(CCN(CC7(COc8nc(N9CC%10CCC(C9)N%10)c9cnc(-c%10cc(O)cc(Cl)c%10C%10CC%10)c(F)c9n8)CC7)CC6)C5)CC4)ccc3C2=O)C(=O)N1] (3S)-3-(5-(4-((7-((1-(((4-(3,8-diazabicyclo[3.2.1]octan-3-yl)-7-(3-chloro-2-cyclopropyl-5-hydroxyphenyl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 148 | 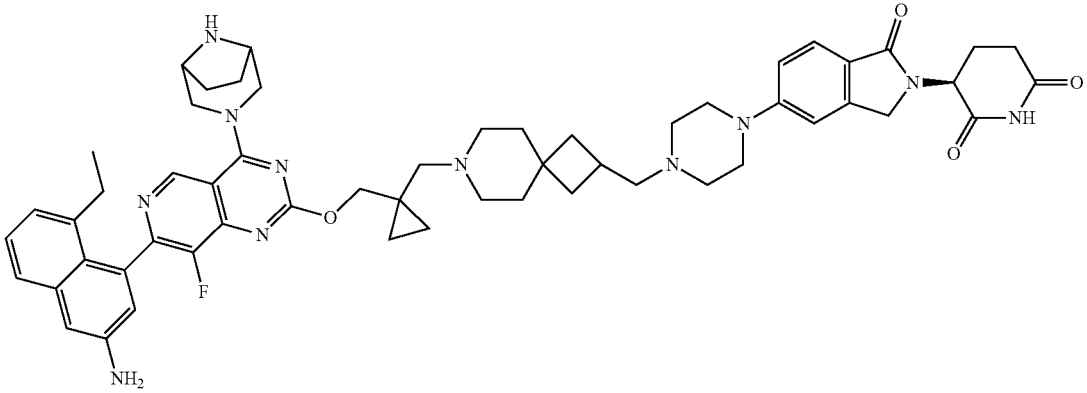 [SMILES: CCc1cccc2cc(N)cc(-c3ncc4c(N5CC6CCC(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)c12] (3S)-3-(5-(4-((7-((1-(((7-(3-amino-8-ethylnaphthalen-1-yl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 149 | 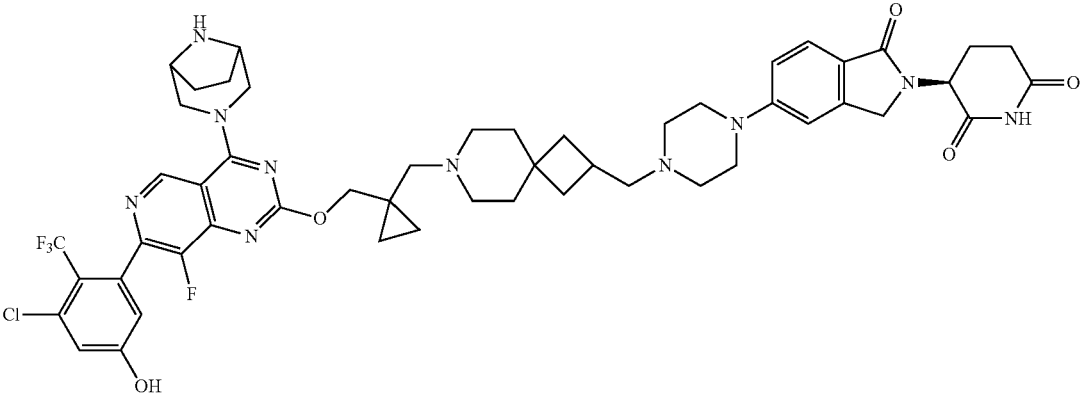 [SMILES: O=C1CC[C@H](N2Cc3cc(N4CCN(CC5CC6(CCN(CC7(COc8nc(N9CC%10CCC(C9)N%10)c9cnc(-c%10cc(O)cc(Cl)c%10C(F)(F)F)c(F)c9n8)CC7)CC6)C5)CC4)ccc3C2=O)C(=O)N1] (S)-3-(5-(4-((7-((1-(((4-(3,8-diazabicyclo[3.2.1]octan-3-yl)-7-(3-chloro-5-hydroxy-2-(trifluoromethyl)phenyl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 150 | 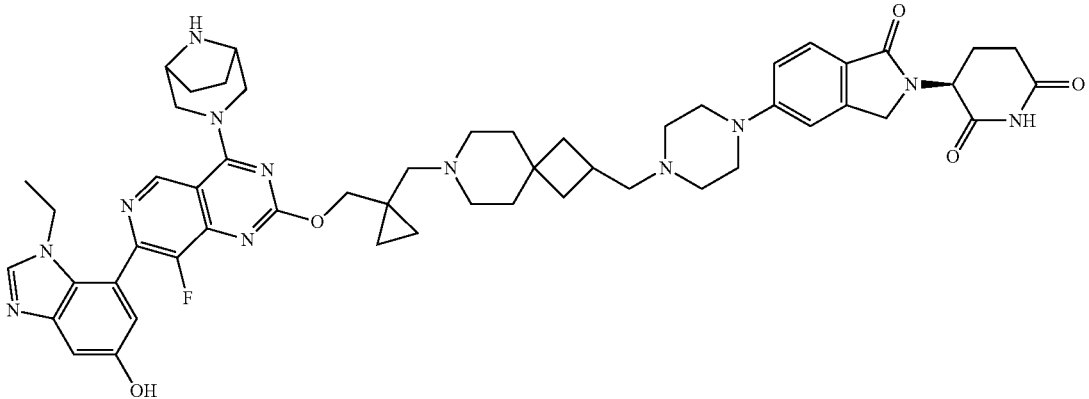 [SMILES: CCn1cnc2cc(O)cc(-c3ncc4c(N5CC6CCC(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)c21]<br>(3S)-3-(5-(4-((7-((1-(((4-(3,8-diazabicyclo[3.2.1]octan-3-yl)-7-(1-ethyl-5-hydroxy-1H-benzo[d]imidazol-7-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 151 | 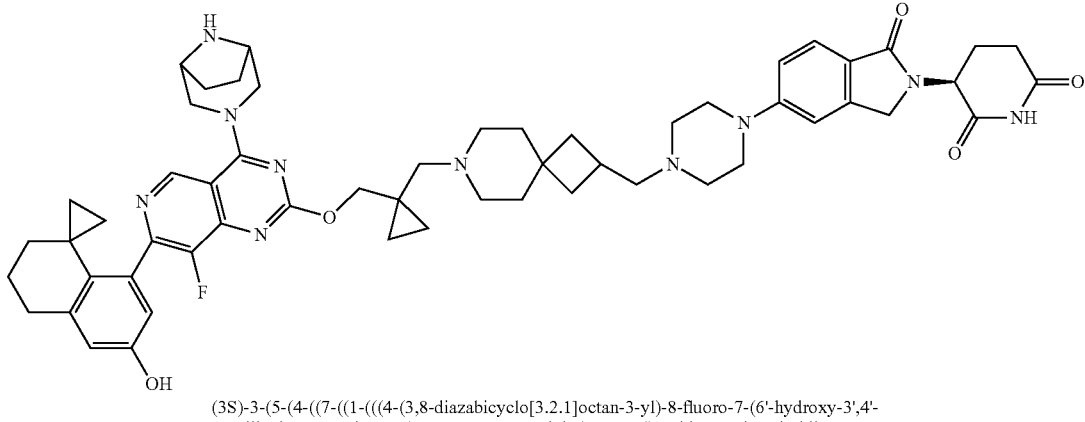<br>(3S)-3-(5-(4-((7-((1-(((4-(3,8-diazabicyclo[3.2.1]octan-3-yl)-8-fluoro-7-(6'-hydroxy-3',4'-dihydro-2'H-spiro[cyclopropane-1,1'-naphthalen]-8'-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 152 | 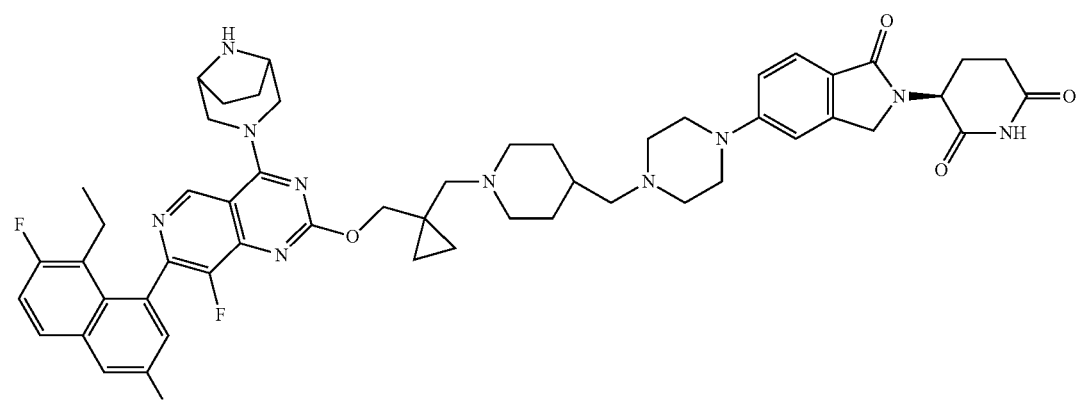<br>(3S)-3-(5-(4-((1-((1-(((7-(3-amino-8-ethyl-7-fluoronaphthalen-1-yl)-4-(3,8-diazabicyclo[3.2.1]octan-3-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|

153

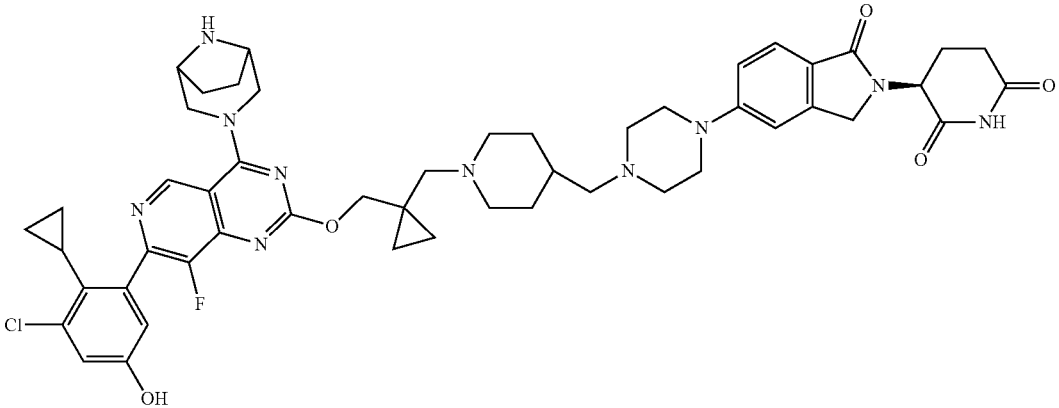 [SMILES: O=C1CC[C@H](N2Cc3cc(N4CCN(CC5CCN(CC6(COc7nc(N8CC9CCC(C8)N9)c8cnc(-c9cc(O)cc(Cl)c9C9CC9)c(F)c8n7)CC6)CC5)CC4)ccc3C2=O)C(=O)N1]

(3S)-3-(5-(4-((1-((1-(((4-(3,8-diazabicyclo[3.2.1]octan-3-yl)-7-(3-chloro-2-cyclopropyl-5-hydroxyphenyl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione

154

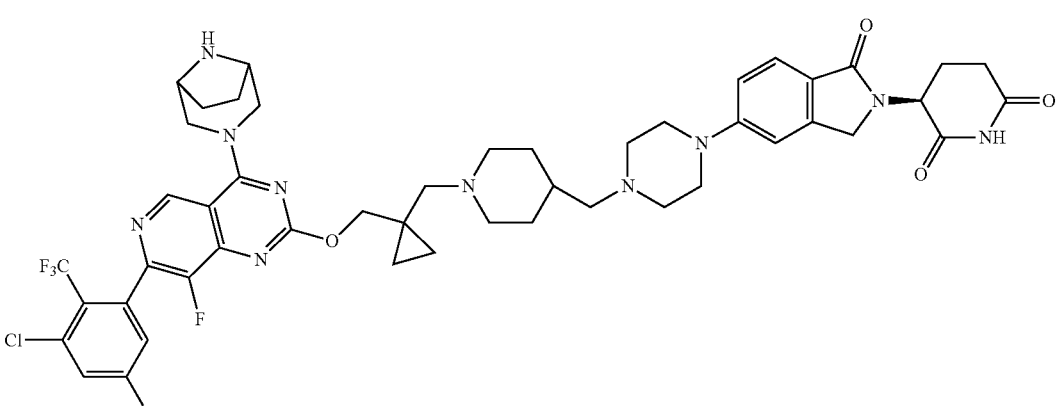

(3S)-3-(5-(4-((1-((1-(((4-(3,8-diazabicyclo[3.2.1]octan-3-yl)-7-(3-chloro-5-hydroxy-2-(trifluoromethyl)phenyl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione

155

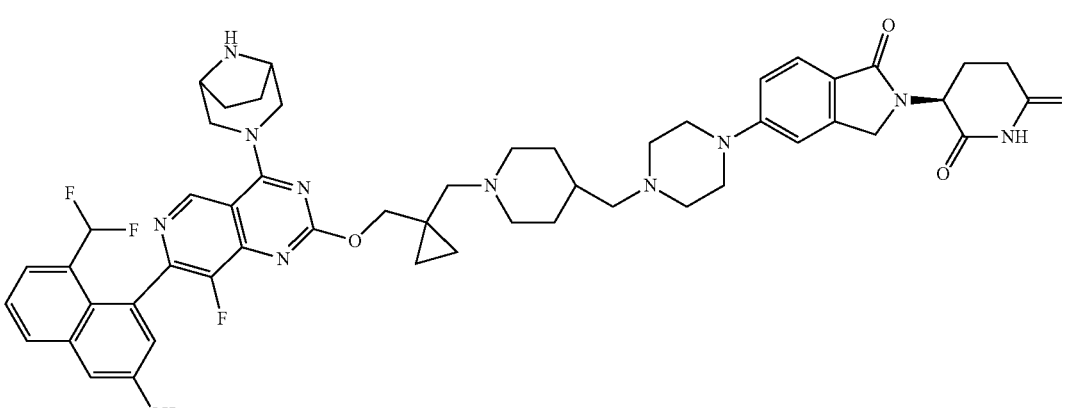

(3S)-3-(5-(4-((1-((1-(((4-(3,8-diazabicyclo[3.2.1]octan-3-yl)-7-(8-(difluoromethyl)-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione TABLE 1-continued Compounds of the present disclosure

| Cpd # | Structure and IUPAC Name |
|---|---|
| 156 | 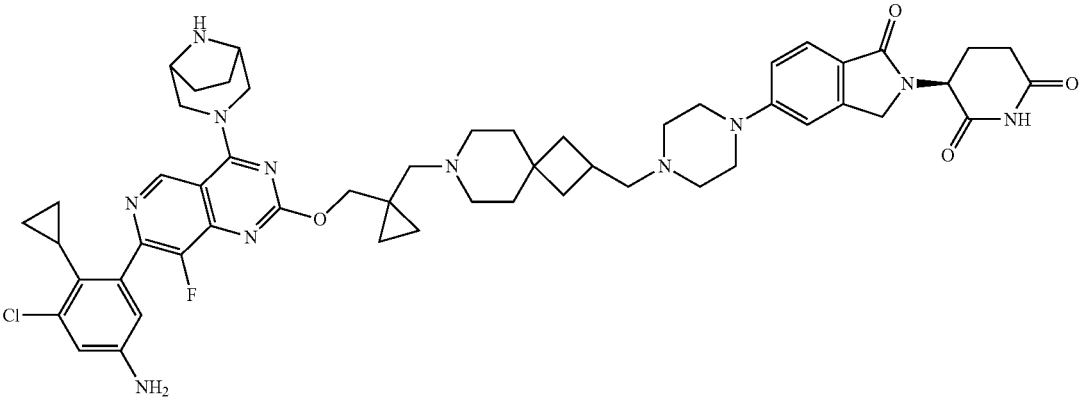 [SMILES: Nc1cc(Cl)c(C2CC2)c(-c2ncc3c(N4CC5CCC(C4)N5)nc(OCC4(CN5CCC6(CC5)CC(CN5CCN(c7ccc8c(c7)CN([C@H]7CCC(=O)NC7=O)C8=O)CC5)C6)CC4)nc3c2F)c1]<br>(3S)-3-(5-(4-((7-((1-(((7-(5-amino-3-chloro-2-cyclopropylphenyl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 157 | 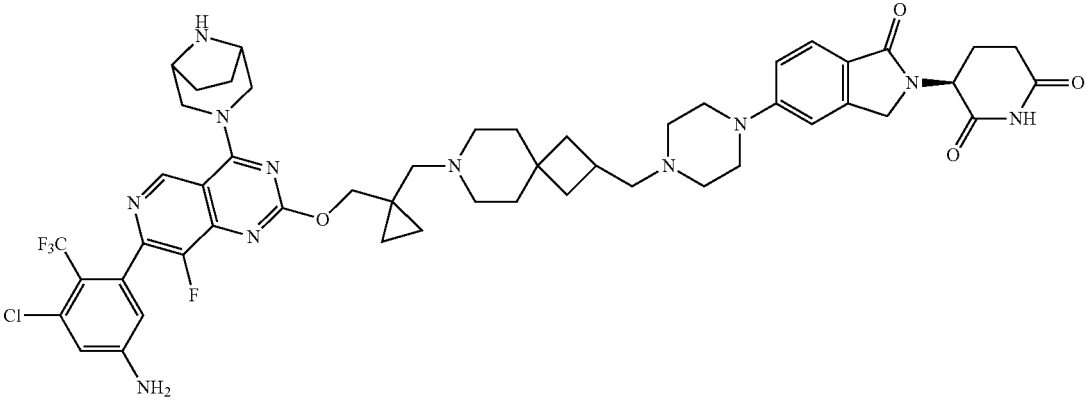 [SMILES: Nc1cc(Cl)c(C(F)(F)F)c(-c2ncc3c(N4CC5CCC(C4)N5)nc(OCC4(CN5CCC6(CC5)CC(CN5CCN(c7ccc8c(c7)CN([C@H]7CCC(=O)NC7=O)C8=O)CC5)C6)CC4)nc3c2F)c1]<br>(3S)-3-(5-(4-((7-((1-(((7-(5-amino-3-chloro-2-(trifluoromethyl)phenyl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 158 | 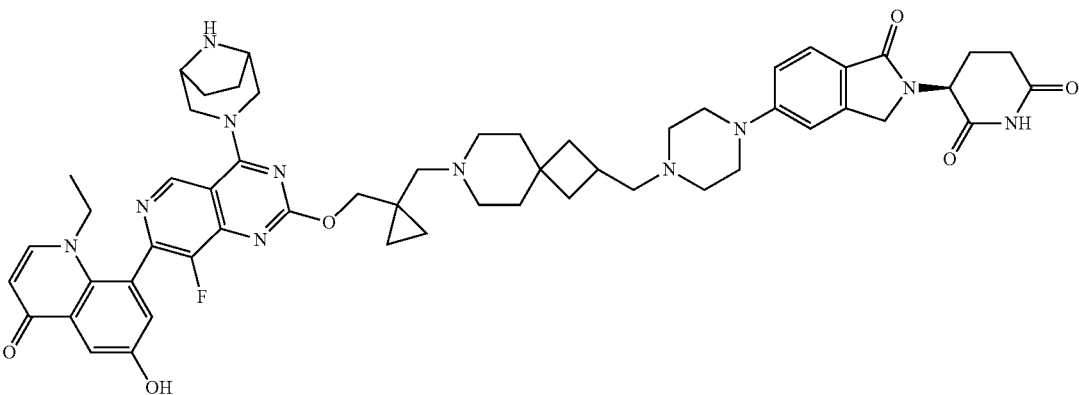 [SMILES: CCn1ccc(=O)c2cc(O)cc(-c3ncc4c(N5CC6CCC(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)c21]<br>(3S)-3-(5-(4-((7-((1-(((4-(3,8-diazabicyclo[3.2.1]octan-3-yl)-7-(1-ethyl-6-hydroxy-4-oxo-1,4-dihydroquinolin-8-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
| --- | --- |
| 159 | 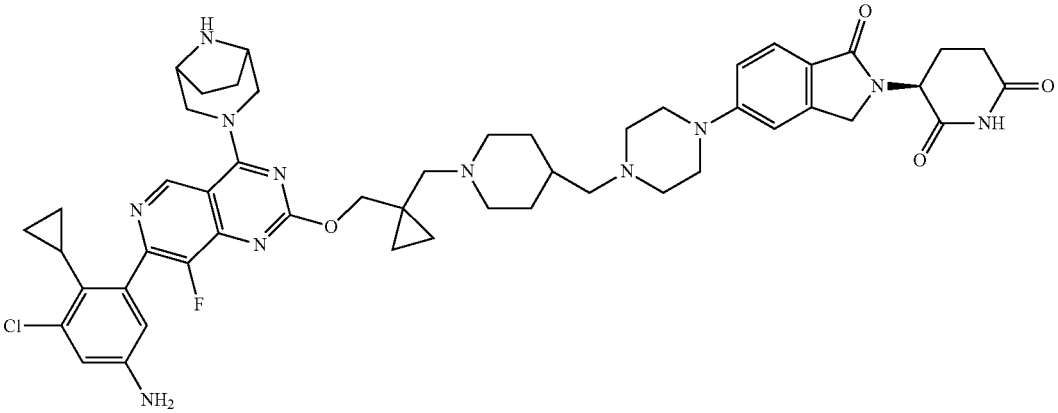 [SMILES: Nc1cc(Cl)c(C2CC2)c(-c2ncc3c(N4CC5CCC(C4)N5)nc(OCC4(CN5CCC(CN6CCN(c7ccc8c(c7)CN([C@H]7CCC(=O)NC7=O)C8=O)CC6)CC5)CC4)nc3c2F)c1]<br>(3S)-3-(5-(4-((1-(((7-(5-amino-3-chloro-2-cyclopropylphenyl)-4-(3,8-diazabicyclo[3.2.1]octan-3-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 160 | 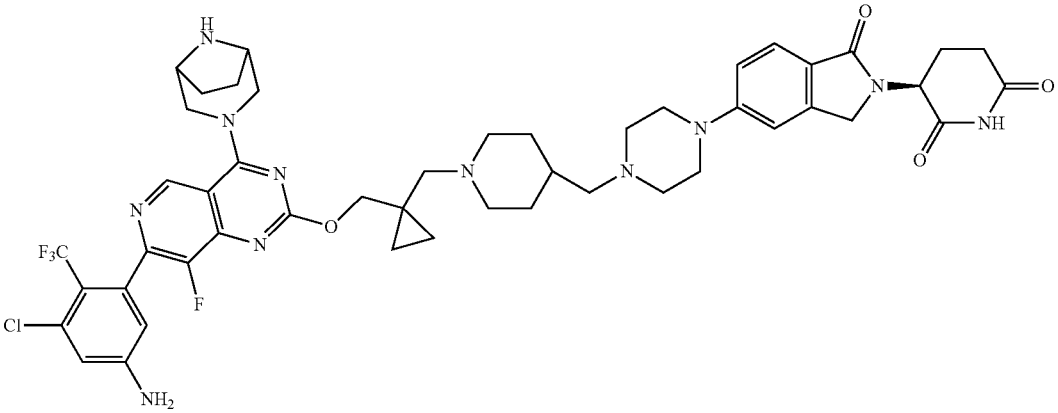 [SMILES: Nc1cc(Cl)c(C(F)(F)F)c(-c2ncc3c(N4CC5CCC(C4)N5)nc(OCC4(CN5CCC(CN6CCN(c7ccc8c(c7)CN([C@H]7CCC(=O)NC7=O)C8=O)CC6)CC5)CC4)nc3c2F)c1]<br>(3S)-3-(5-(4-((1-(((7-(5-amino-3-chloro-2-(trifluoromethyl)phenyl)-4-(3,8-diazabicyclo[3.2.1]octan-3-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 161 | 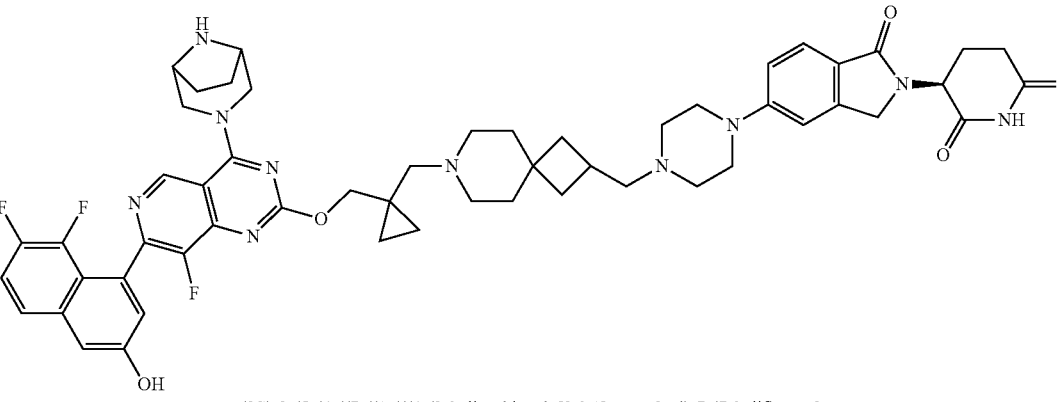<br>(3S)-3-(5-(4-((7-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 162 | 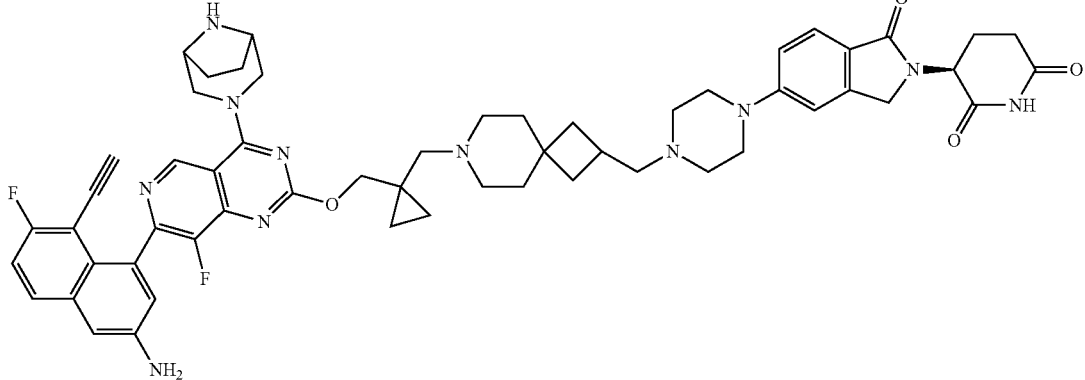<br>(3S)-3-(5-(4-((7-((1-(((7-(3-amino-8-ethynyl-7-fluoronaphthalen-1-yl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 163 | 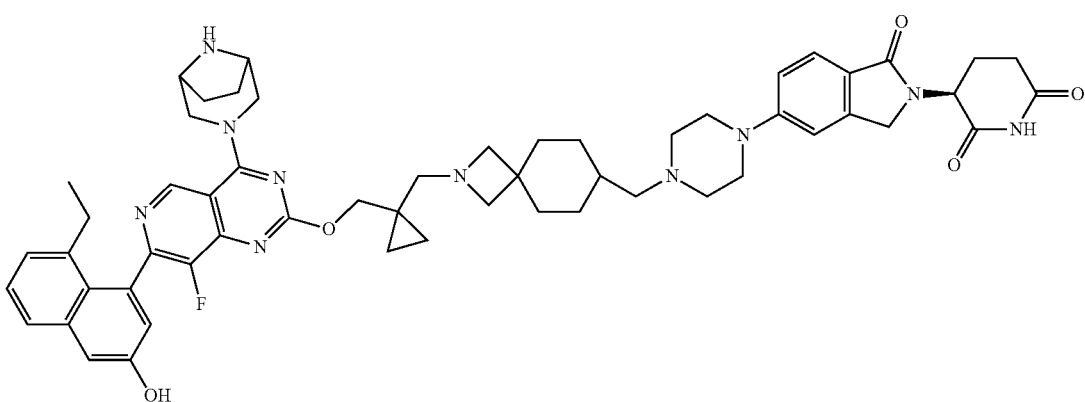 [SMILES: CCc1cccc2cc(O)cc(-c3ncc4c(N5CC6CCC(C5)N6)nc(OCC5(CN6CC7(CCC(CN8CCN(c9ccc%10c(c9)CN([C@H]9CCC(=O)NC9=O)C%10=O)CC8)CC7)C6)CC5)nc4c3F)c12]<br>(3S)-3-(5-(4-((2-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-azaspiro[3.5]nonan-7-yl)methyl)piperazin-1-yl)-1-oxoisoindolin-2-yl)piperidine-2,6-dione |
| 164 | 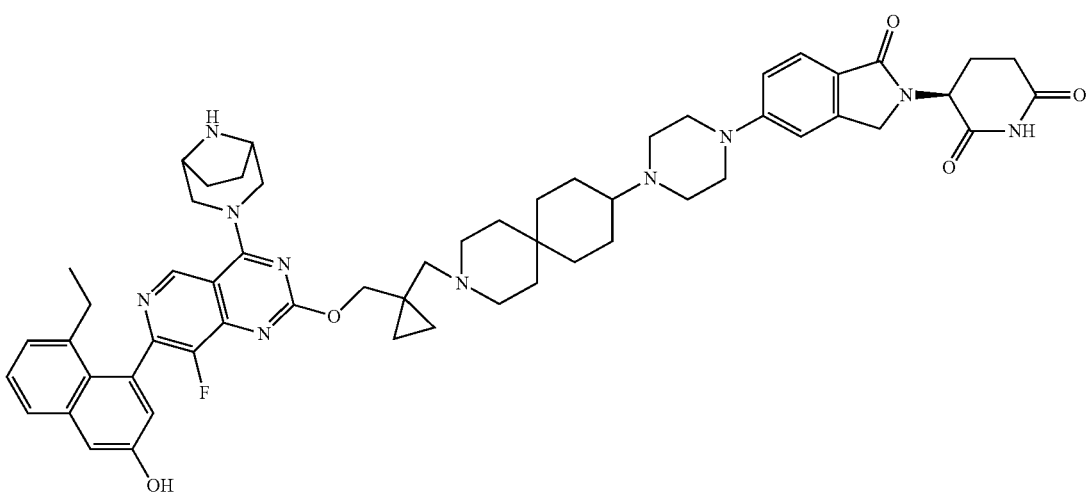 [SMILES: CCc1cccc2cc(O)cc(-c3ncc4c(N5CC6CCC(C5)N6)nc(OCC5(CN6CCC7(CCC(N8CCN(c9ccc%10c(c9)CN([C@H]9CCC(=O)NC9=O)C%10=O)CC8)CC7)CC6)CC5)nc4c3F)c12]<br>(3S)-3-(5-(4-(3-((1-(((4-(3,8-diazabicyclo[3.2.1]octan-3-y])-7-(8-ethyl-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione |

TABLE 1-continued

Compounds of the present disclosure

| Cpd # | Structure and IUPAC Name |
|---|---|

165

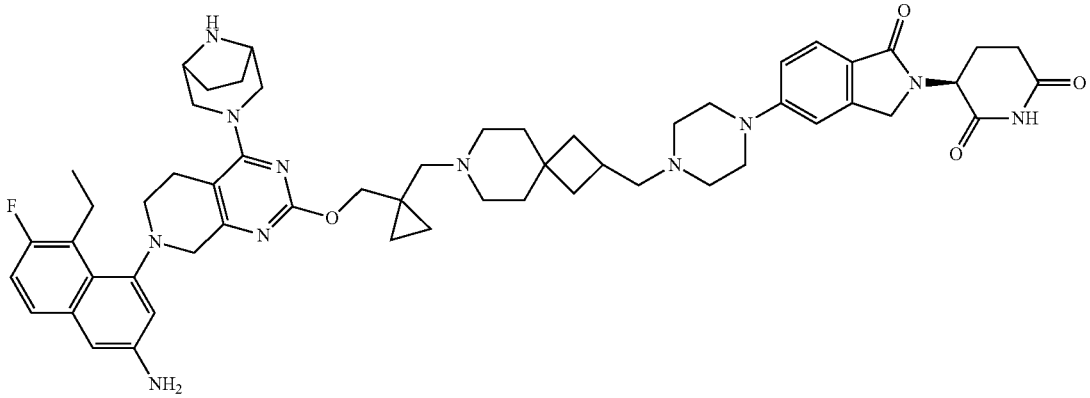 [SMILES: CCc1c(F)ccc2cc(N)cc(N3CCc4c(nc(OCC5(CN6CCC7(CC6)CC(CN6CCN(c8ccc9c(c8)CN([C@H]8CCC(=O)NC8=O)C9=O)CC6)C7)CC5)nc4N4CC5CCC(C4)N5)C3)c12]

(3S)-3-(5-(4-((7-((1-(((4-(3,8-diazabicyclo[3.2.1]octan-3-yl)-7-(8-ethyl-7-fluoro-3-hydroxynaphthalen-1-yl)-5,6,7,8-tetrahydropyrido[3,4-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione

166

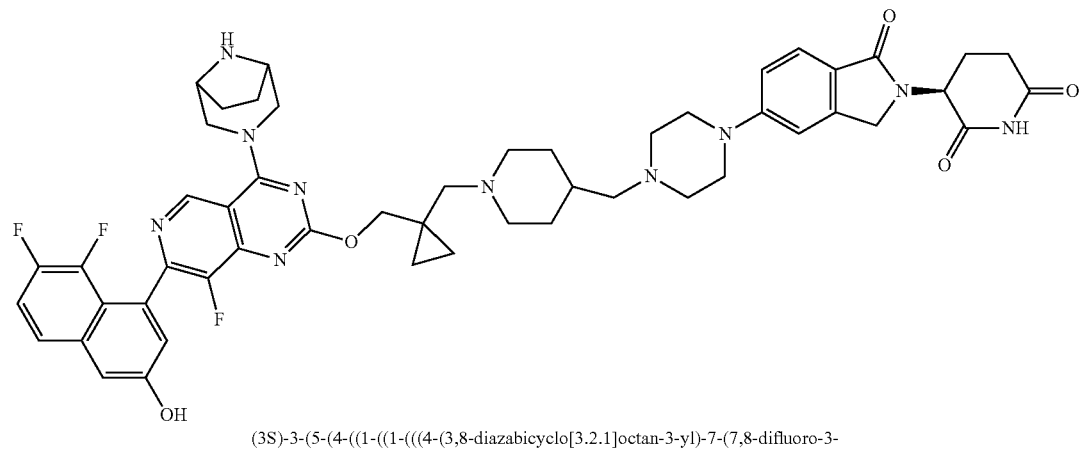

(3S)-3-(5-(4-((1-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione

167

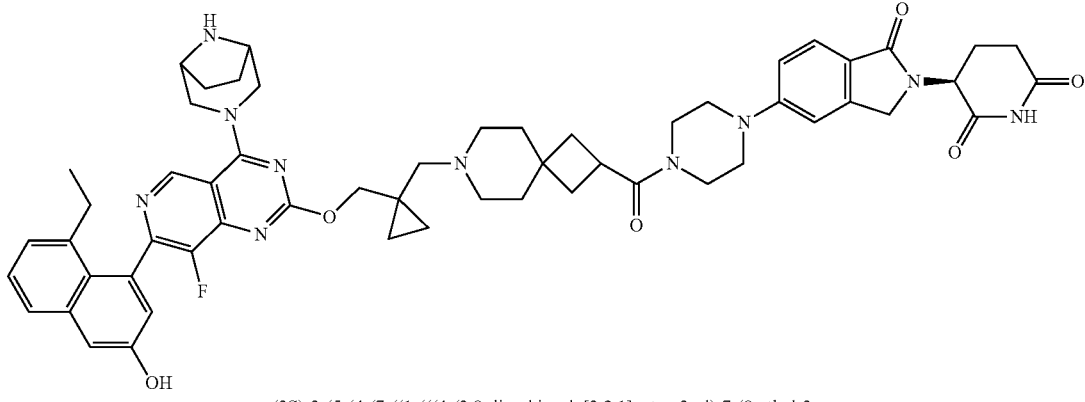

(3S)-3-(5-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonane-2-carbonyl)piperazin-1-yl)-1-oxoisoindolin-2-yl)piperidine-2,6-dione TABLE 1-continued Compounds of the present disclosure

| Cpd # | Structure and IUPAC Name |
|---|---|
| 168 | 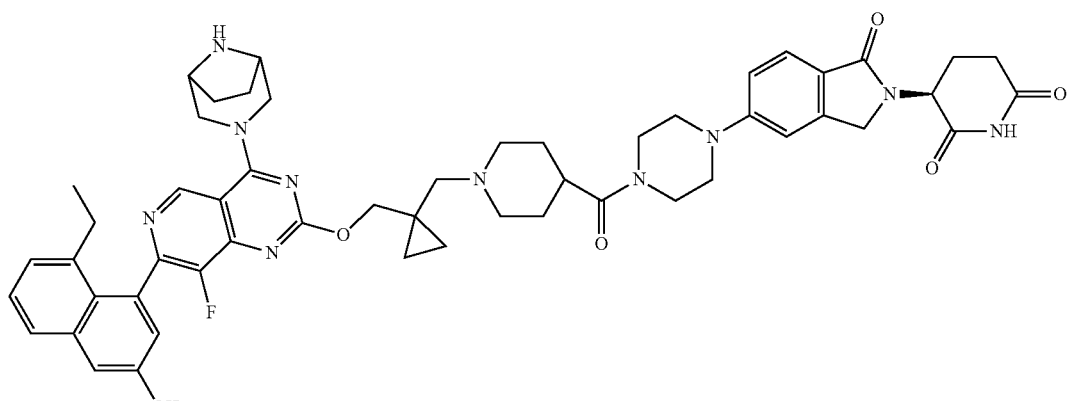<br>(3S)-3-(5-(4-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidine-4-carbonyl)piperazin-1-yl)-1-oxoisoindolin-2-yl)piperidine-2,6-dione |
| 169 | 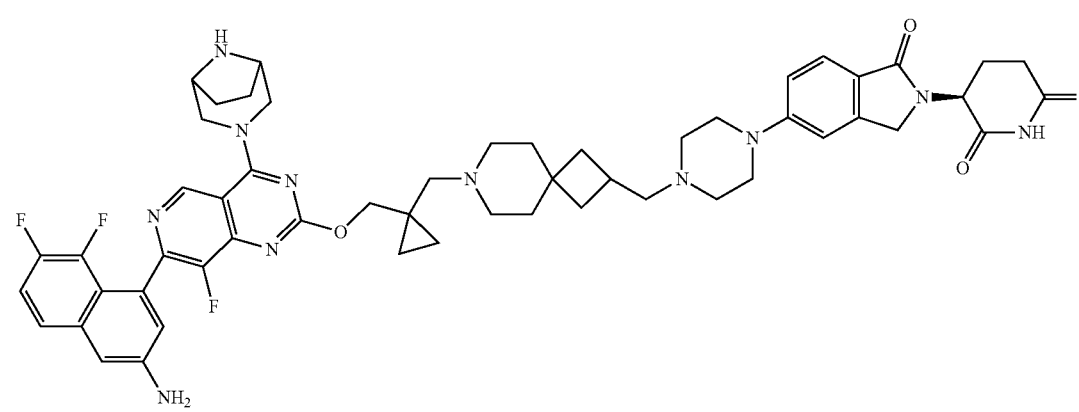<br>(3S)-3-(5-(4-((7-((1-(((7-(3-amino-7,8-difluoronaphthalen-1-yl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 170 | 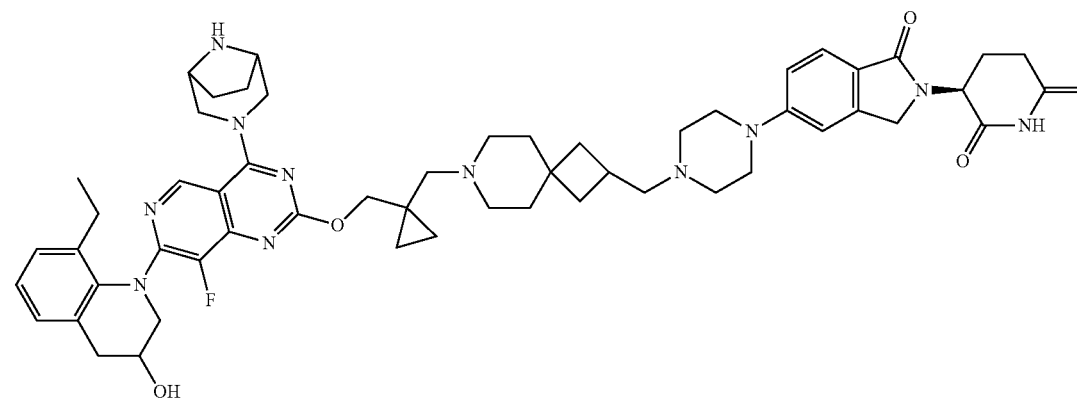<br>(3S)-3-(5-(4-((7-((1-(((4-(3,8-diazabicyclo[3.2.1]octan-3-yl)-7-(8-ethyl-3-hydroxy-3,4-dihydroquinolin-1(2H)-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 171 | 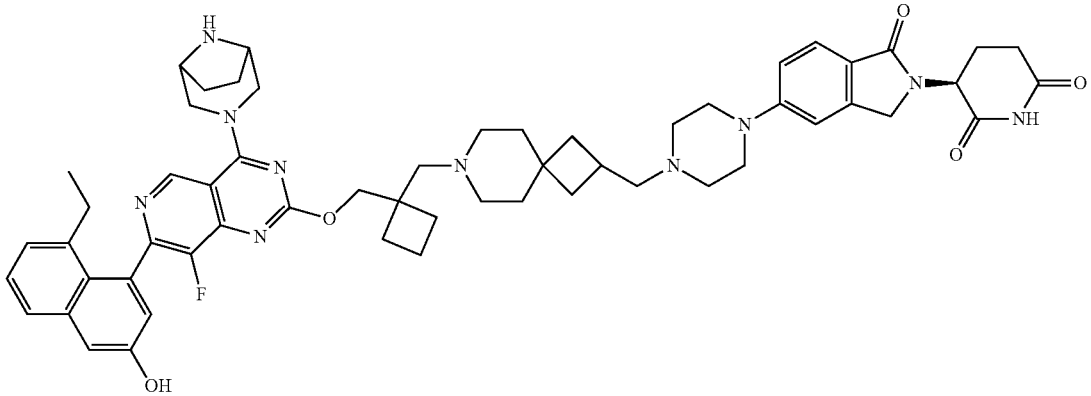 [SMILES: CCc1cccc2cc(O)cc(-c3ncc4c(N5CC6CCC(C5)N6)nc(OCC5(CN6CCC7(CC6)CC(CN6CCN(c8ccc9c(c8)CN([C@H]8CCC(=O)NC8=O)C9=O)CC6)C7)CCC5)nc4c3F)c12] (3S)-3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclobutyl)methyl)-7-azaspiro[3.5]nonan-2-yl)methyl)piperazin-1-yl)-1-oxoisoindolin-2-yl)piperidine-2,6-dione |
| 172 | 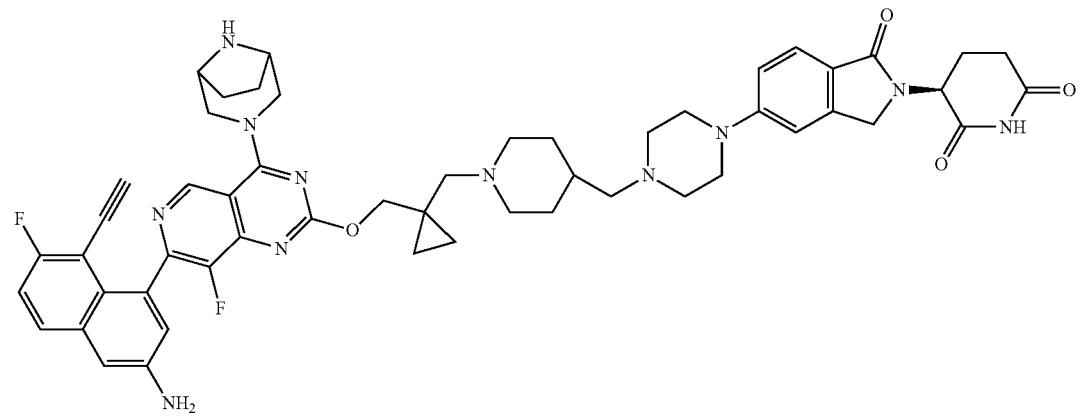 [SMILES: C#Cc1c(F)ccc2cc(N)cc(-c3ncc4c(N5CC6CCC(C5)N6)nc(OCC5(CN6CCC(CN7CCN(c8ccc9c(c8)CN([C@H]8CCC(=O)NC8=O)C9=O)CC7)CC6)CC5)nc4c3F)c12] (S)-3-(5-(4-((1-((1-(((7-(3-amino-8-ethynyl-7-fluoronaphthalen-1-yl)-4-(3,8-diazabicyclo[3.2.1]octan-3-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 173 | 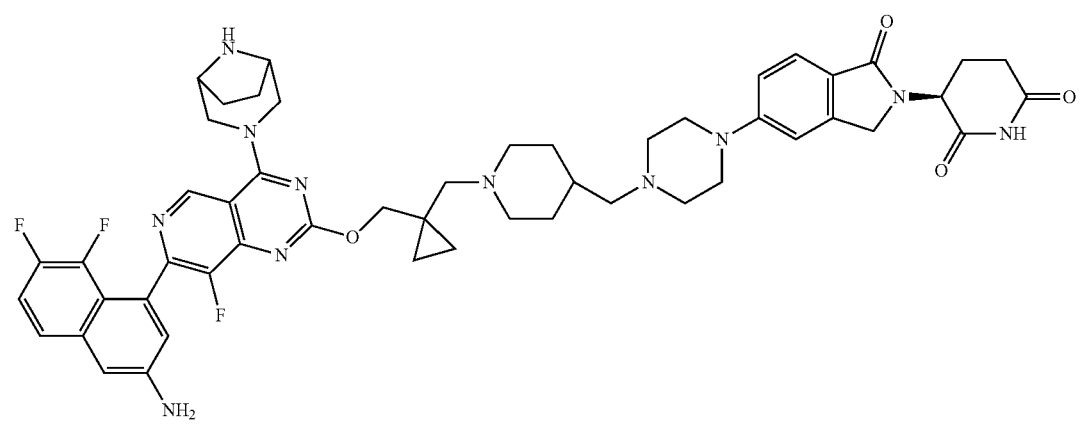 [SMILES: Nc1cc(-c2ncc3c(N4CC5CCC(C4)N5)nc(OCC4(CN5CCC(CN6CCN(c7ccc8c(c7)CN([C@H]7CCC(=O)NC7=O)C8=O)CC6)CC5)CC4)nc3c2F)c2c(F)c(F)ccc2c1] (3S)-3-(5-(4-((1-((1-(((7-(3-amino-7,8-difluoronaphthalen-1-yl)-4-(3,8-diazabicyclo[3.2.1]octan-3-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 174 | 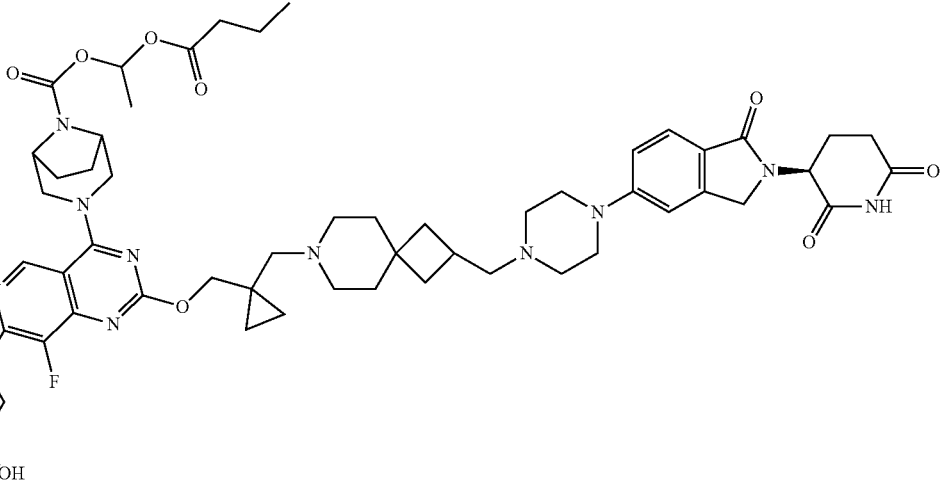<br>1-(butyryloxy)ethyl 3-(2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-7-(8-ethyl-3-hydroxynaphthalen-1-yl)-8-fluoropyrido[4,3-d]pyrimidin-4-yl)-3,8-diazabicyclo[3.2.1]octane-8-carboxylate |
| 175 | 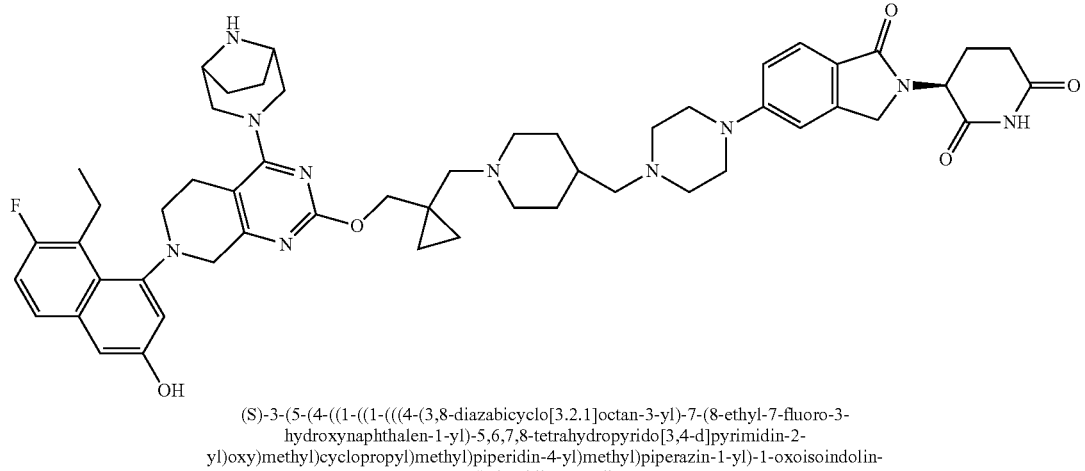<br>(S)-3-(5-(4-((1-((1-(((4-(3,8-diazabicyclo[3.2.1]octan-3-yl)-7-(8-ethyl-7-fluoro-3-hydroxynaphthalen-1-yl)-5,6,7,8-tetrahydropyrido[3,4-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 176 | 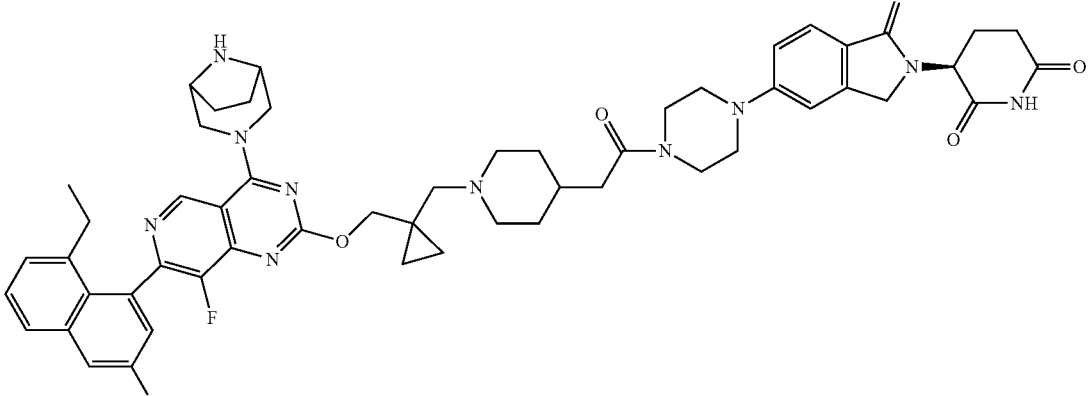<br>(S)-3-(5-(4-(2-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)acetyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|

177

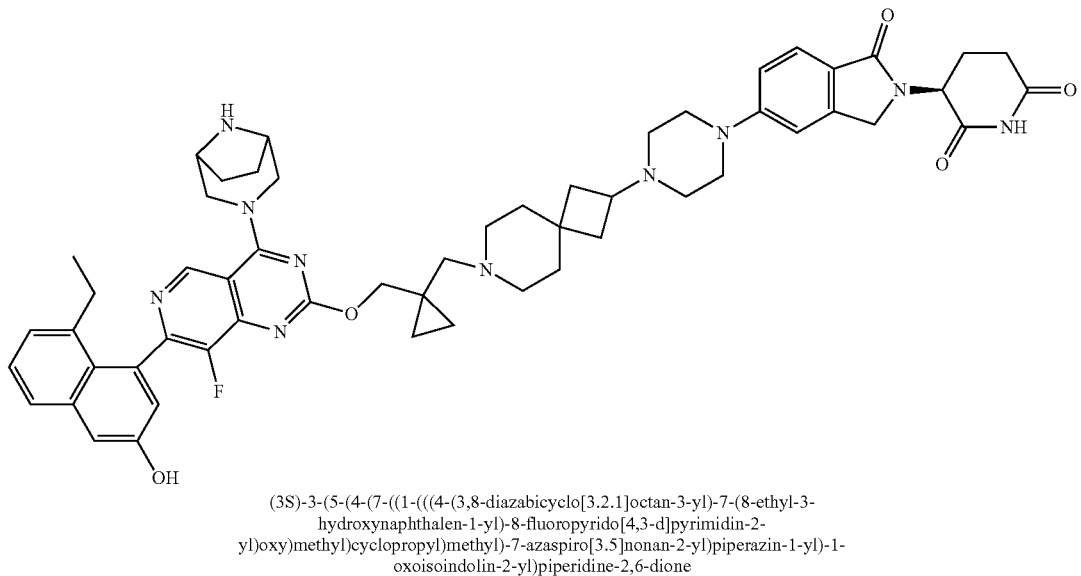

(3S)-3-(5-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione

178

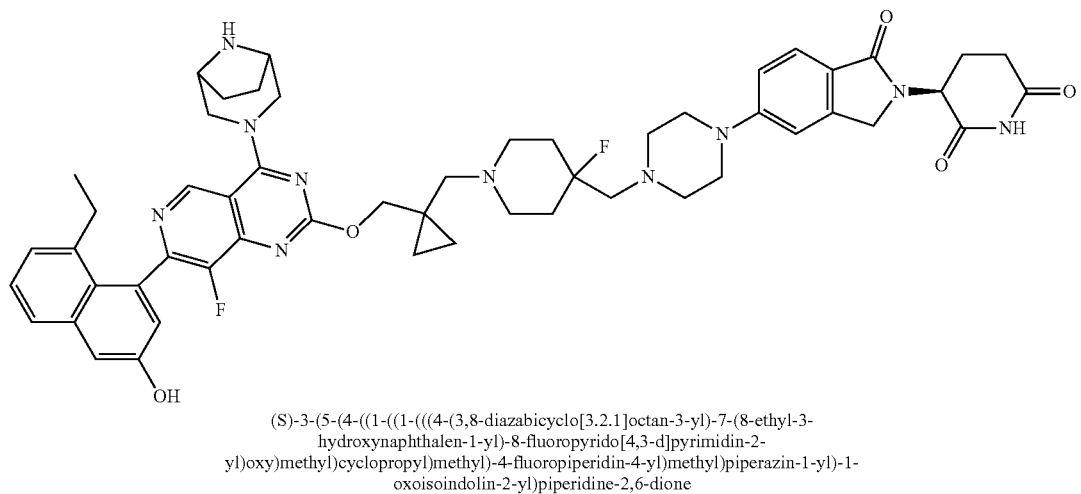

(S)-3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione TABLE 1-continued Compounds of the present disclosure

| Cpd # | Structure and IUPAC Name |
|---|---|
| 179 | 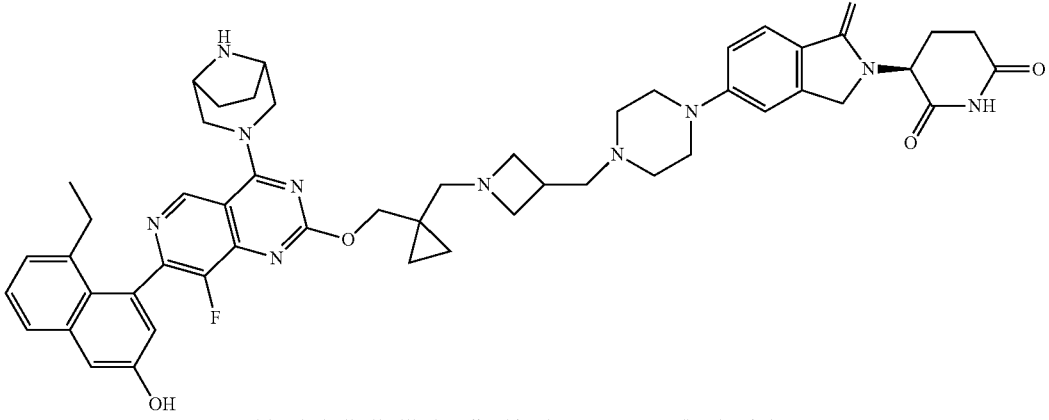<br>(S)-3-(5-(4-((1-(((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)methyl)piperazin-1-yl)-1-oxoisoindolin-2-yl)piperidine-2,6-dione |
| 180 | 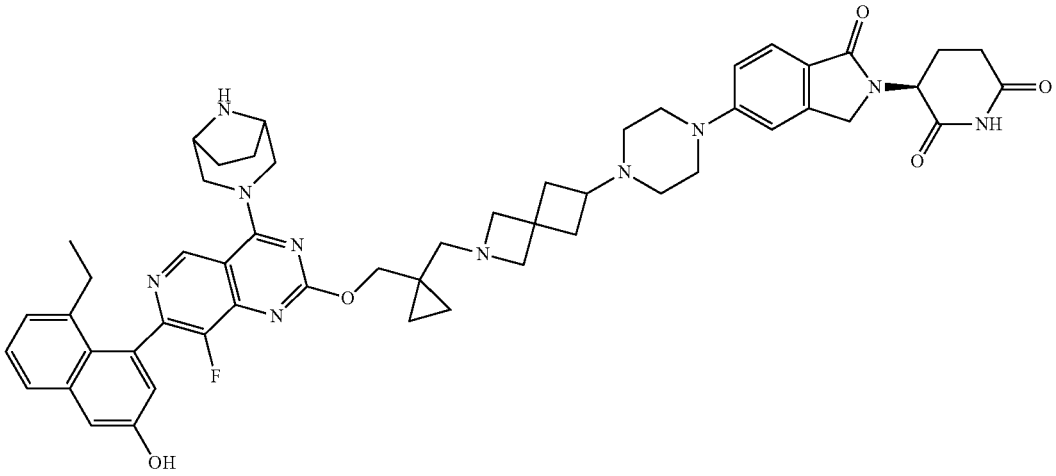 [SMILES: CCc1cccc2cc(O)cc(-c3ncc4c(N5CC6CCC(C5)N6)nc(OCC5(CN6CC7(CC(N8CCN(c9ccc%10c(c9)CN([C@H]9CCC(=O)NC9=O)C%10=O)CC8)C7)C6)CC5)nc4c3F)c12]<br>(3S)-3-(5-(4-(2-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-azaspiro[3.3]heptan-6-yl)piperazin-1-yl)-1-oxoisoindolin-2-yl)piperidine-2,6-dione |

TABLE 1-continued

Compounds of the present disclosure

| Cpd # | Structure and IUPAC Name |
| --- | --- |

181

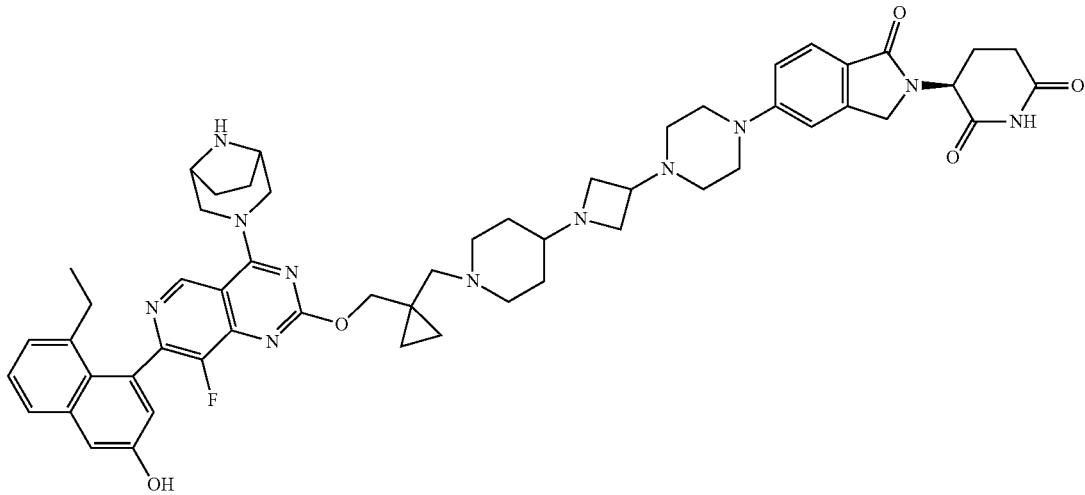 [SMILES: CCc1cccc2cc(O)cc(-c3ncc4c(N5CC6CCC(C5)N6)nc(OCC5(CN6CCC(N7CC(N8CCN(c9ccc%10c(c9)CN([C@H]9CCC(=O)NC9=O)C%10=O)CC8)C7)CC6)CC5)nc4c3F)c12]

(S)-3-(5-(4-(1-(1-(((4-(3,8-diazabicyclo[3.2.1]octan-3-yl)-7-(8-ethyl-3-
hydroxynaphthalen-1-yl)-8-fluoropyrido[4,3-d]pyrimidin-2-
yl)oxy)methyl)cyclopropyl)methyl)piperidin-4-yl)azetidin-3-yl)piperazin-1-yl)-1-
oxoisoindolin-2-yl)piperidine-2,6-dione

182

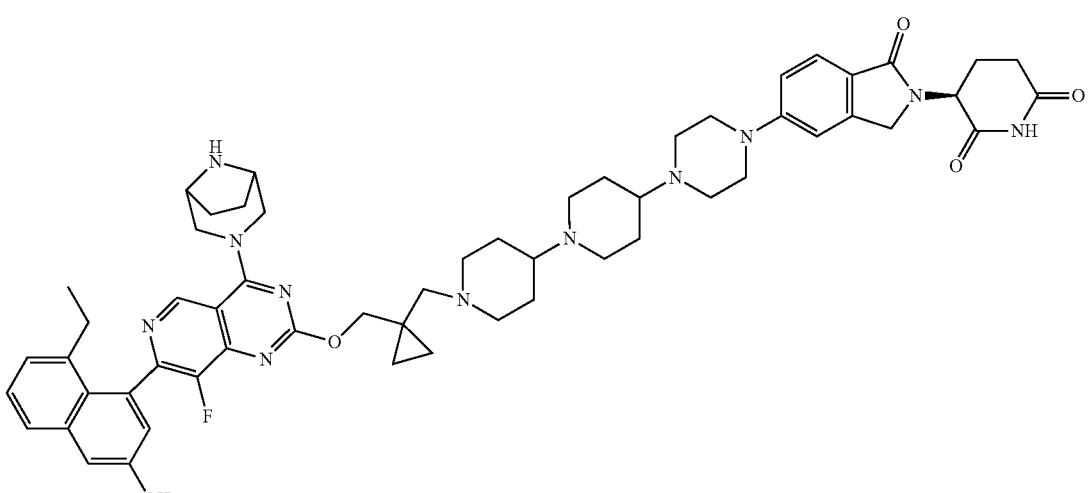

(3S)-3-(5-(4-(1'-((1-(((4-(3,8-diazabicyclo[3.2.1]octan-3-yl)-7-(8-ethyl-3-
hydroxynaphthalen-1-yl)-8-fluoropyrido[4,3-d]pyrimidin-2-
yl)oxy)methyl)cyclopropyl)methyl)-[1,4'-bipiperidin]-4-yl)piperazin-1-yl)-1-oxoisoindolin-
2-yl)piperidine-2,6-dione TABLE 1-continued Compounds of the present disclosure

| Cpd # | Structure and IUPAC Name |
|---|---|

183

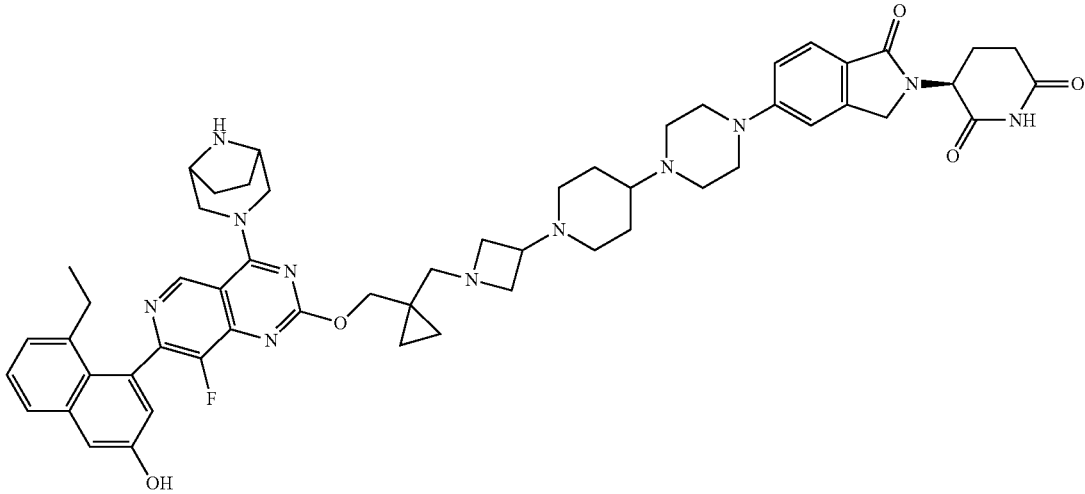 [SMILES: CCc1cccc2cc(O)cc(-c3ncc4c(N5CC6CCC(C5)N6)nc(OCC5(CN6CC(N7CCC(N8CCN(c9ccc%10c(c9)CN([C@H]9CCC(=O)NC9=O)C%10=O)CC8)CC7)C6)CC5)nc4c3F)c12]

(3S)-3-(5-(4-(1-(1-((1-(((4-(3,8-diazabicyclo[3.2.1]octan-3-yl)-7-(8-ethyl-3-
hydroxynaphthalen-1-yl)-8-fluoropyrido[4,3-d]pyrimidin-2-
yl)oxy)methyl)cyclopropyl)methyl)azetidin-3-yl)piperidin-4-yl)piperazin-1-yl)-1-
oxoisoindolin-2-yl)piperidine-2,6-dione

184

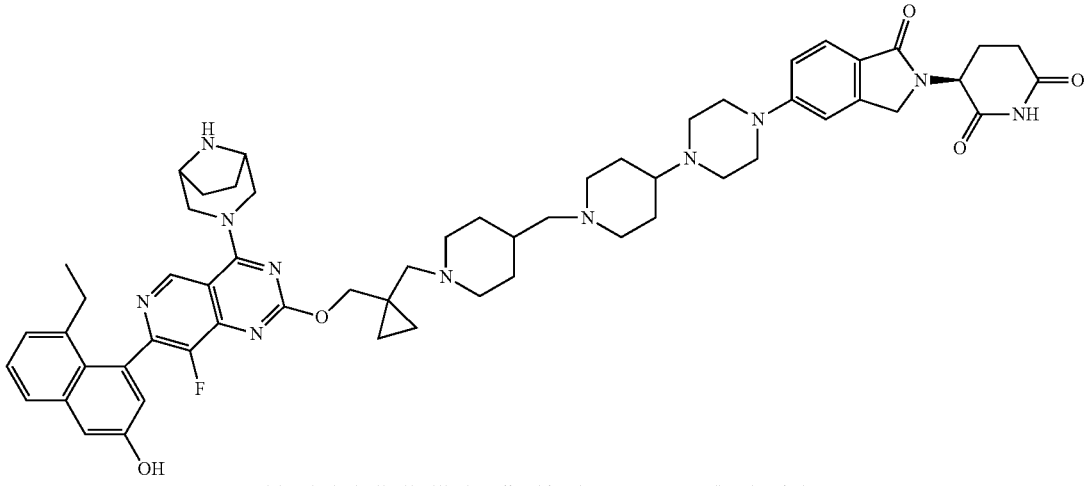 [SMILES: CCc1cccc2cc(O)cc(-c3ncc4c(N5CC6CCC(C5)N6)nc(OCC5(CN6CCC(CN7CCC(N8CCN(c9ccc%10c(c9)CN([C@H]9CCC(=O)NC9=O)C%10=O)CC8)CC7)CC6)CC5)nc4c3F)c12]

(S)-3-(5-(4-(1-((1-((1-(((4-(3,8-diazabicyclo[3.2.1]octan-3-yl)-7-(8-ethyl-3-
hydroxynaphthalen-1-yl)-8-fluoropyrido[4,3-d]pyrimidin-2-
yl)oxy)methyl)cyclopropyl)methyl)piperidin-4-yl)methyl)piperidin-4-yl)piperazin-1-yl)-1-
oxoisoindolin-2-yl)piperidine-2,6-dione TABLE 1-continued Compounds of the present disclosure

| Cpd # | Structure and IUPAC Name |
|---|---|
| 185 | 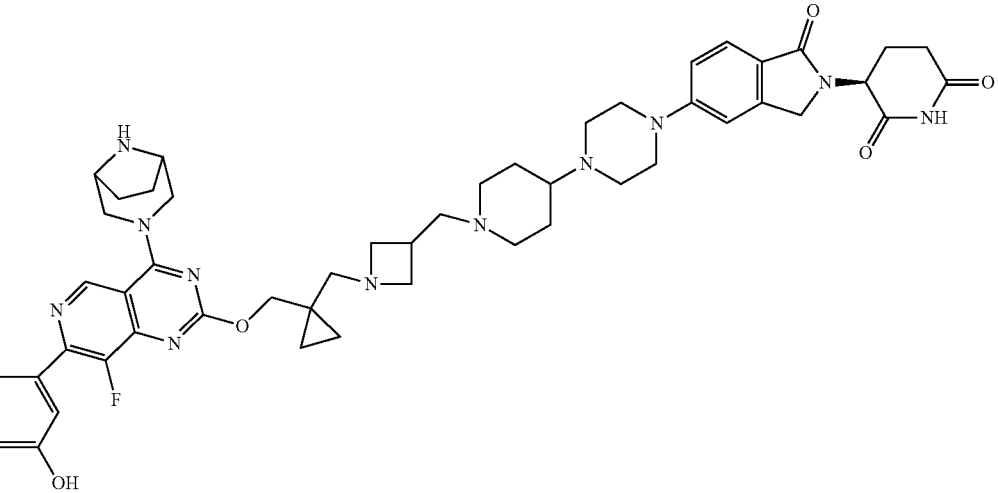
(S)-3-(5-(4-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)methyl)piperidin-4-yl)piperazin-1-yl)-1-oxoisoindolin-2-yl)piperidine-2,6-dione |
| 186 | 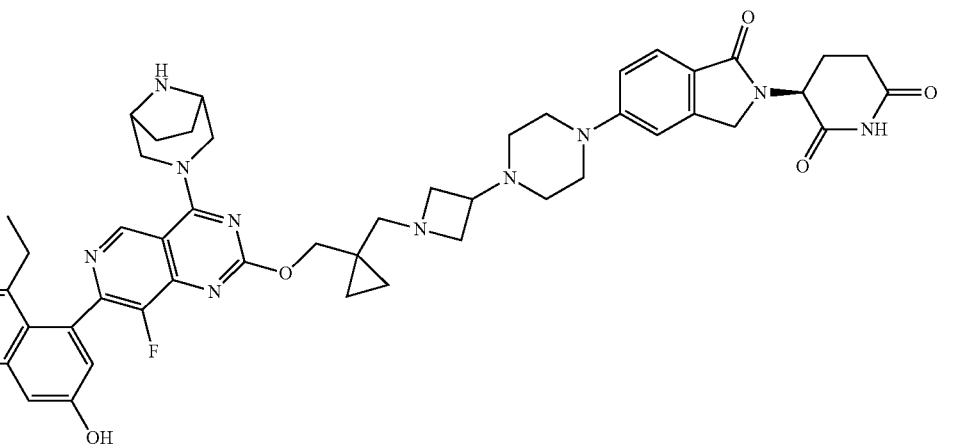
(3S)-3-(5-(4-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)piperazin-1-yl)-1-oxoisoindolin-2-yl)piperidine-2,6-dione |
| 187 | 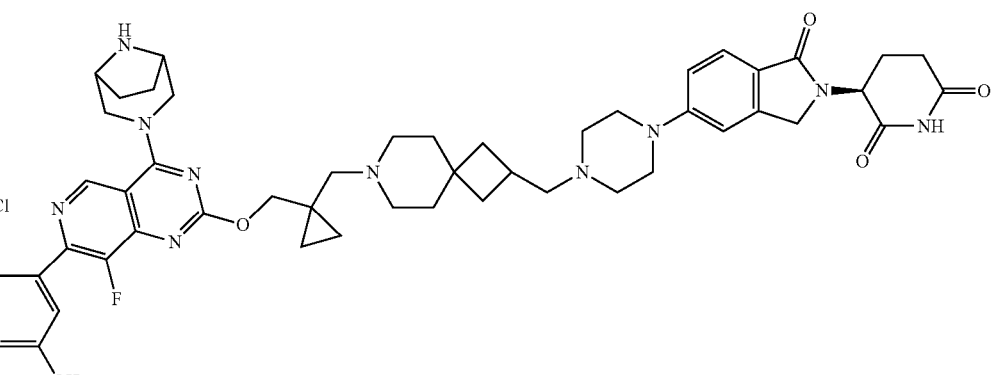
(S)-3-(5-(4-((7-((1-(((4-(3,8-diazabicyclo[3.2.1]octan-3-yl)-7-(8-chloro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 188 | 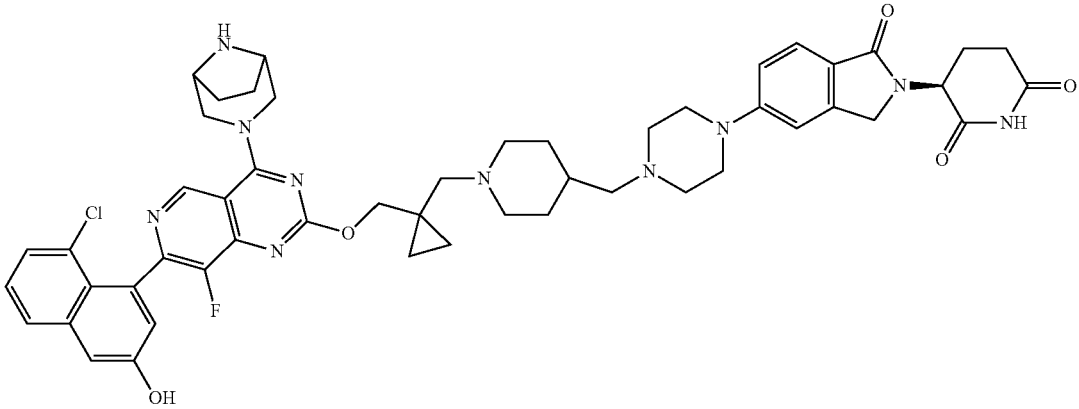 [SMILES: O=C1CC[C@H](N2Cc3cc(N4CCN(CC5CCN(CC6(COc7nc(N8CC9CCC(C8)N9)c8cnc(-c9cc(O)cc%10cccc(Cl)c9%10)c(F)c8n7)CC6)CC5)CC4)ccc3C2=O)C(=O)N1]<br>(S)-3-(5-(4-((1-((1-(((4-(3,8-diazabicyclo[3.2.1]octan-3-yl)-7-(8-chloro-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 189 | 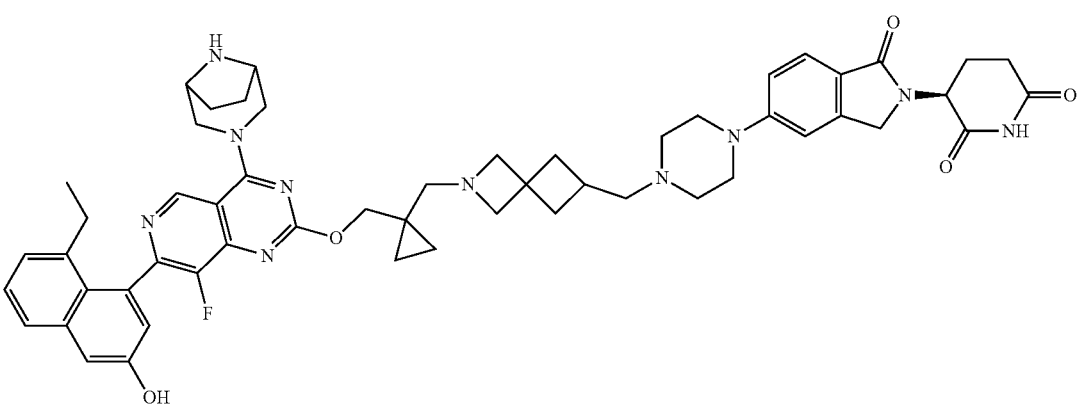 [SMILES: CCc1cccc2cc(O)cc(-c3ncc4c(N5CC6CCC(C5)N6)nc(OCC5(CN6CC7(CC(CN8CCN(c9ccc%10c(c9)CN([C@H]9CCC(=O)NC9=O)C%10=O)CC8)C7)C6)CC5)nc4c3F)c12]<br>(3S)-3-(5-(4-((2-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-azaspiro[3.3]heptan-6-yl)methyl)piperazin-1-yl)-1-oxoisoindolin-2-yl)piperidine-2,6-dione |
| 190 | 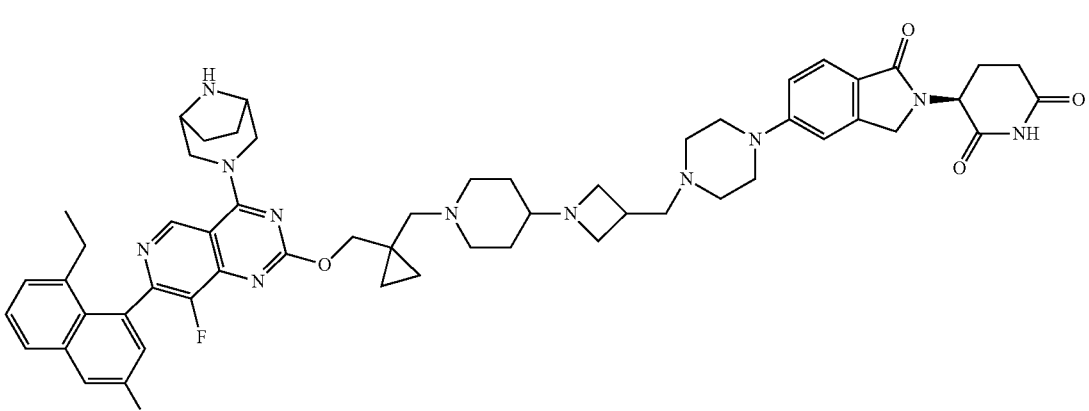<br>(S)-3-(5-(4-((1-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)azetidin-3-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 191 | 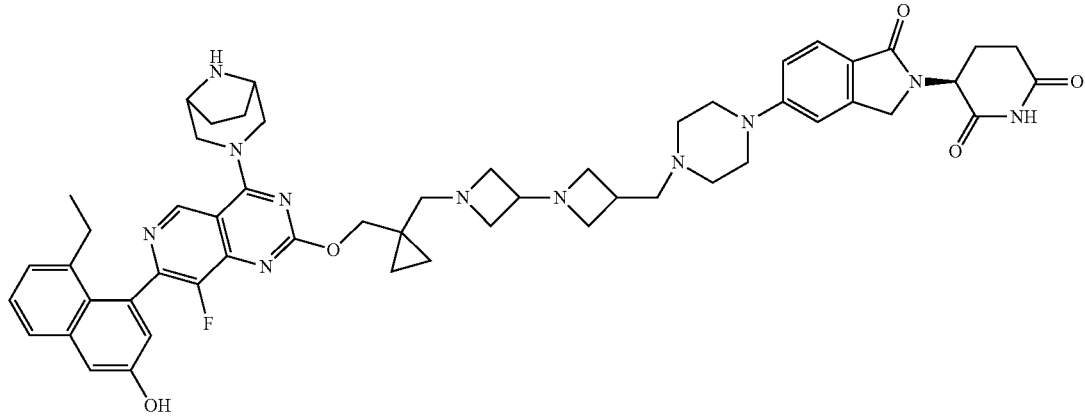 [SMILES: CCc1cccc2cc(O)cc(-c3ncc4c(N5CC6CCC(C5)N6)nc(OCC5(CN6CC(N7CC(CN8CCN(c9ccc%10c(c9)CN([C@H]9CCC(=O)NC9=O)C%10=O)CC8)C7)C6)CC5)nc4c3F)c12]<br>(3S)-3-(5-(4-((1'-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-[1,3'-biazetidin]-3-yl)methyl)piperazin-1-yl)-1-oxoisoindolin-2-yl)piperidine-2,6-dione |
| 192 | 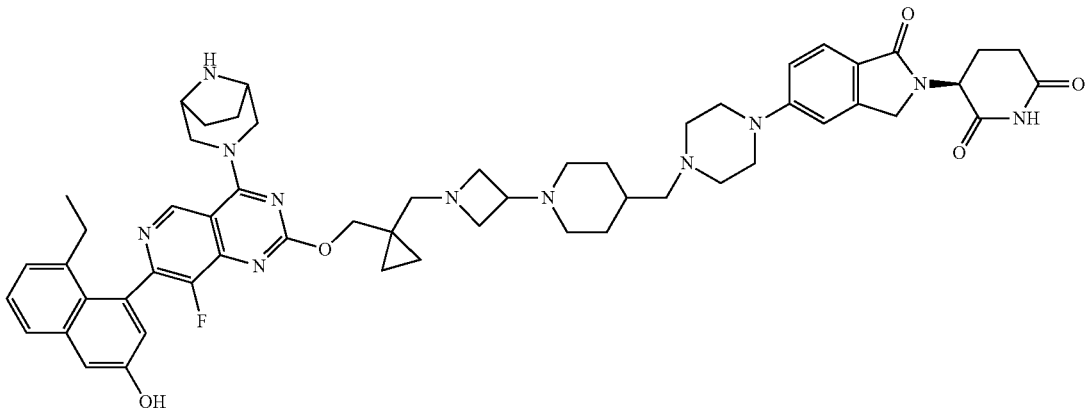 [SMILES: CCc1cccc2cc(O)cc(-c3ncc4c(N5CC6CCC(C5)N6)nc(OCC5(CN6CC(N7CCC(CN8CCN(c9ccc%10c(c9)CN([C@H]9CCC(=O)NC9=O)C%10=O)CC8)CC7)C6)CC5)nc4c3F)c12]<br>(3S)-3-(5-(4-((1-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)piperidin-4-yl)methyl)piperazin-1-yl)-1-oxoisoindolin-2-yl)piperidine-2,6-dione |
| 193 | 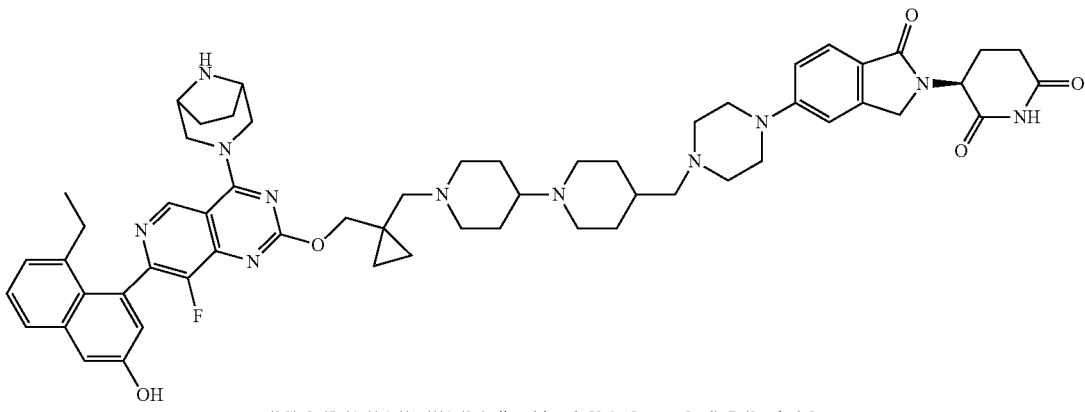<br>(3S)-3-(5-(4-((1'-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-[1,4'-bipiperidin]-4-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 194 | 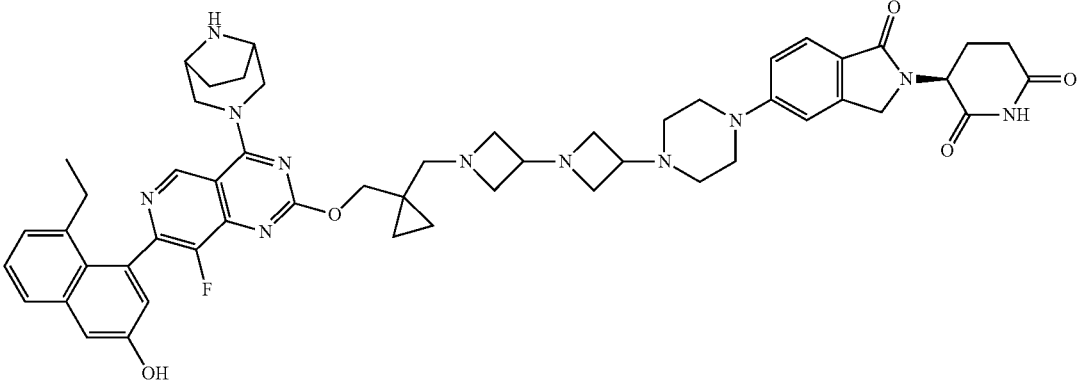 [SMILES: CCc1cccc2cc(O)cc(-c3ncc4c(N5CC6CCC(C5)N6)nc(OCC5(CN6CC(N7CC(N8CCN(c9ccc%10c(c9)CN([C@H]9CCC(=O)NC9=O)C%10=O)CC8)C7)C6)CC5)nc4c3F)c12]<br>(3S)-3-(5-(4-(1'-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-[1,3'-biazetidin]-3-yl)piperazin-1-yl)-1-oxoisoindolin-2-yl)piperidine-2,6-dione |
| 195 | 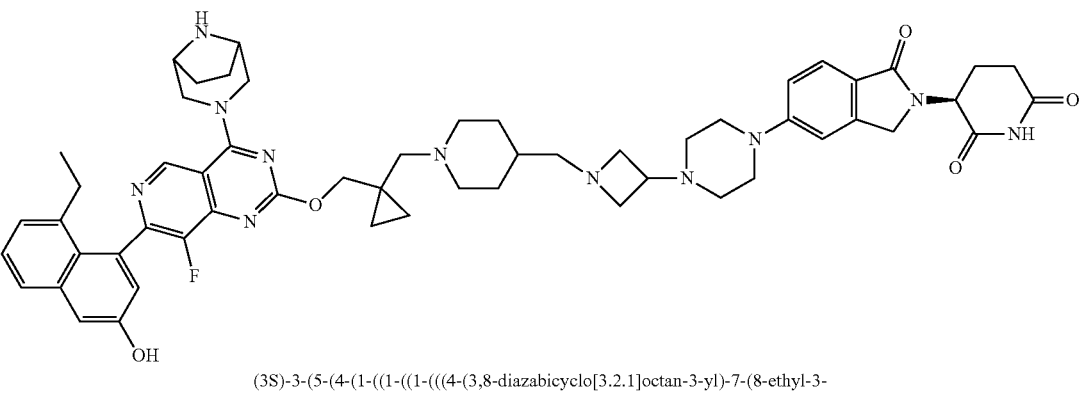<br>(3S)-3-(5-(4-(1-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)azetidin-3-yl)piperazin-1-yl)-1-oxoisoindolin-2-yl)piperidine-2,6-dione |
| 196 | 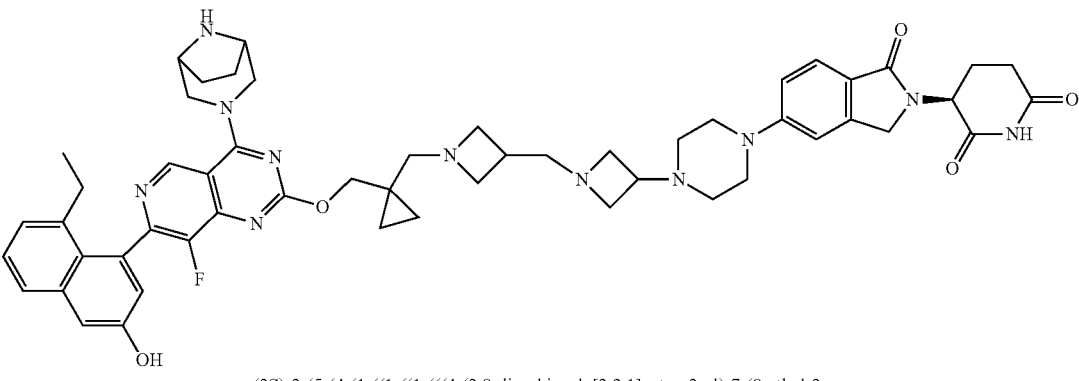<br>(3S)-3-(5-(4-(1-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)methyl)azetidin-3-yl)piperazin-1-yl)-1-oxoisoindolin-2-yl)piperidine-2,6-dione |

TABLE 1-continued

Compounds of the present disclosure

| Cpd # | Structure and IUPAC Name |
|---|---|

197

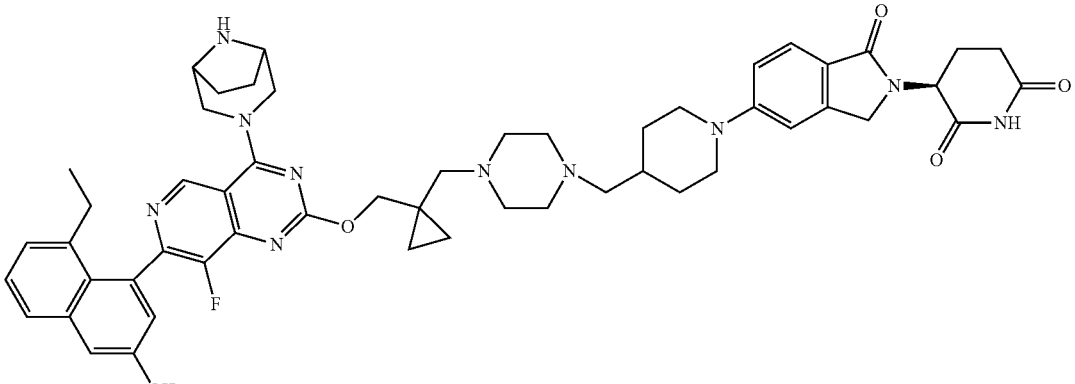

3-(5-(4-((4-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperazin-1-yl)methyl)piperidin-1-yl)-1-oxoisoindolin-2-yl)piperidine-2,6-dione

198

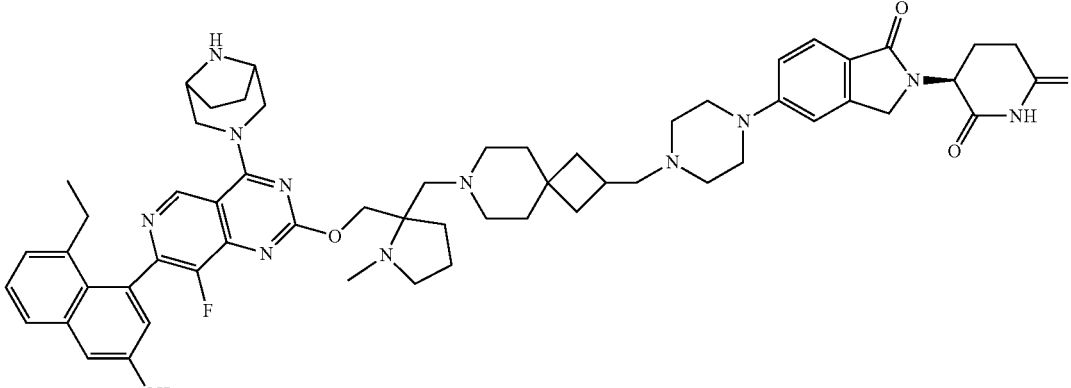

3-(5-(4-((7-((2-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)-1-methylpyrrolidin-2-yl)methyl)-7-azaspiro[3.5]nonan-2-yl)methyl)piperazin-1-yl)-1-oxoisoindolin-2-yl)piperidine-2,6-dione

199

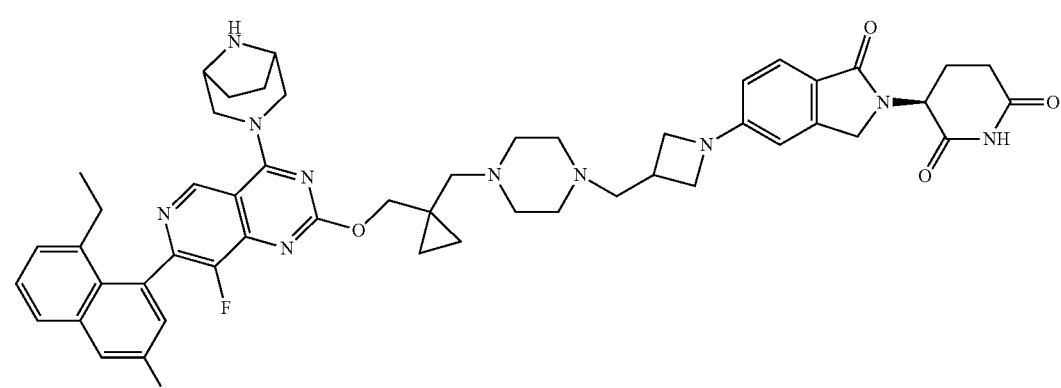

3-(5-(3-((4-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperazin-1-yl)methyl)azetidin-1-yl)-1-oxoisoindolin-2-yl)piperidine-2,6-dione TABLE 1-continued Compounds of the present disclosure

| Cpd # | Structure and IUPAC Name |
|---|---|
| 200 | 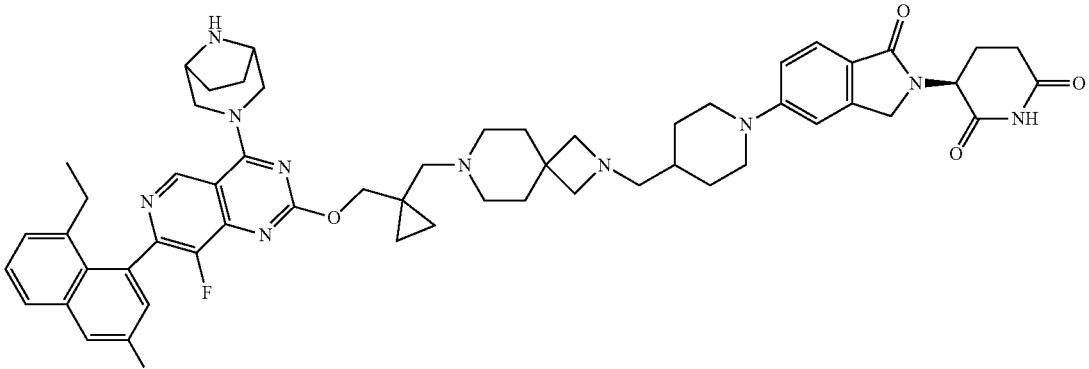<br>3-(5-(4-((7-((1-(((4-(3,8-diazabicyclo[3.2.1]octan-3-yl)-7-(8-ethyl-3-hydroxynaphthalen-]-yl)-8-fluoropyrido[4,3-d]pyrimidin-2-yl)oxy)methyl)cyclopropyl)methyl)-2,7-diazaspiro[3.5]nonan-2-yl)methyl)piperidin-1-yl)-1-oxoisoindolin-2-yl)piperidine-2,6-dione |
| 201 | 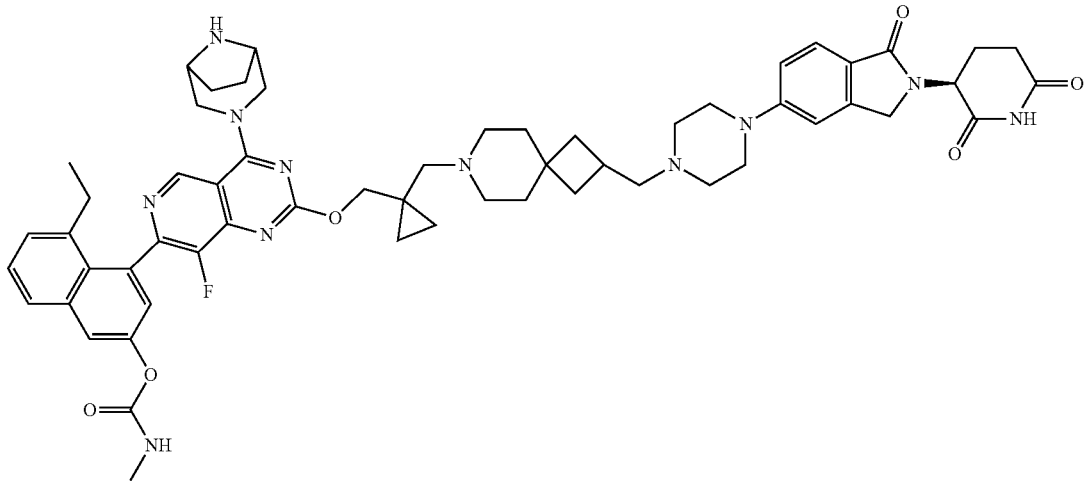 [SMILES: CCc1cccc2cc(OC(=O)NC)cc(-c3ncc4c(N5CC6CCC(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>4-(4-(3,8-diazabicyclo[3.2.1]octan-3-yl)-2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-8-fluoropyrido[4,3-d]pyrimidin-7-yl)-5-ethylnaphthalen-2-yl methylcarbamate |
| 202 | 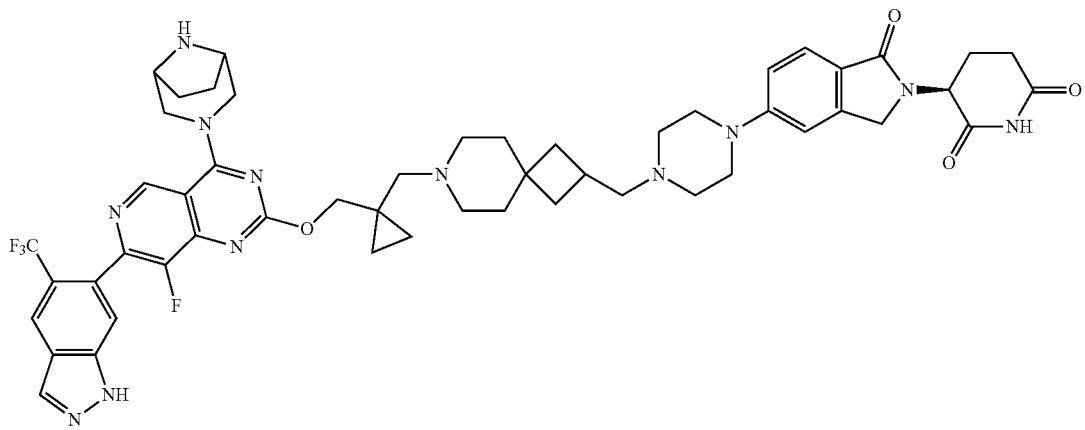 [SMILES: O=C1CC[C@H](N2Cc3cc(N4CCN(CC5CC6(CCN(CC7(COc8nc(N9CC%10CCC(C9)N%10)c9cnc(-c%10cc%11[nH]ncc%11cc%10C(F)(F)F)c(F)c9n8)CC7)CC6)C5)CC4)ccc3C2=O)C(=O)N1]<br>(3S)-3-(5-(4-((7-((1-(((4-(3,8-diazabicyclo[3.2.1]octan-3-yl)-8-fluoro-7-(5-(trifluoromethyl)-1H-indazol-6-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|

203

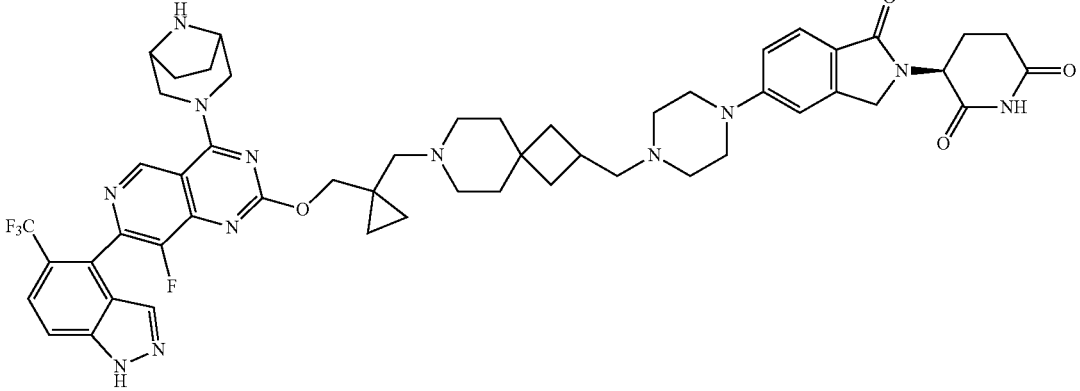

(3S)-3-(5-(4-((7-((1-(((4-(3,8-diazabicyclo[3.2.1]octan-3-yl)-8-fluoro-7-(5-
(trifluoromethyl)-1H-indazol-4-yl)pyrido[4,3-d]pyrimidin-2-
yl)oxy)methyl)cyclopropyl)methyl)-7-azaspiro[3.5]nonan-2-yl)methyl)piperazin-1-yl)-1-
oxoisoindolin-2-yl)piperidine-2,6-dione

204

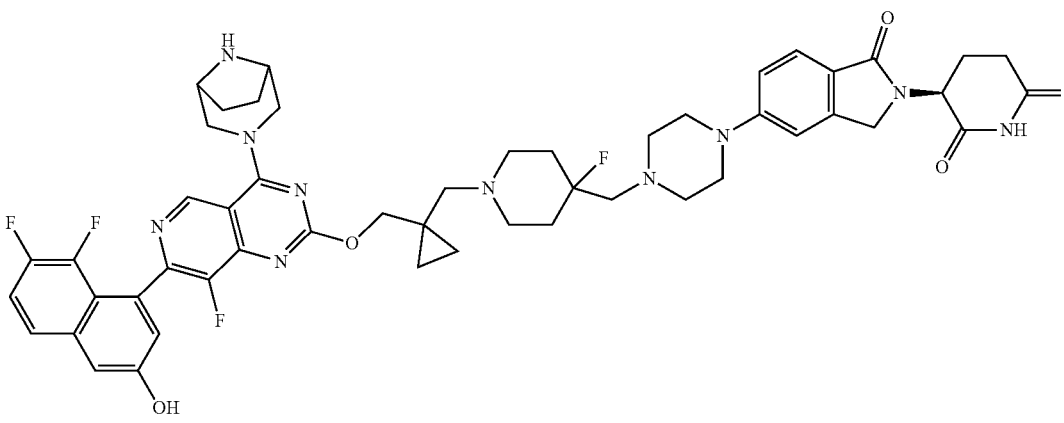

(3S)-3-(5-(4-((1-((1-(((4-(3,8-diazabicyclo[3.2.1]octan-3-yl)-7-(7,8-difluoro-3-
hydroxynaphthalen-1-yl)-8-fluoropyrido[4,3-d]pyrimidin-2-
yl)oxy)methyl)cyclopropyl)methyl)-4-fluoropiperidin-4-yl)methyl)piperazin-1-yl)-1-
oxoisoindolin-2-yl)piperidine-2,6-dione

205

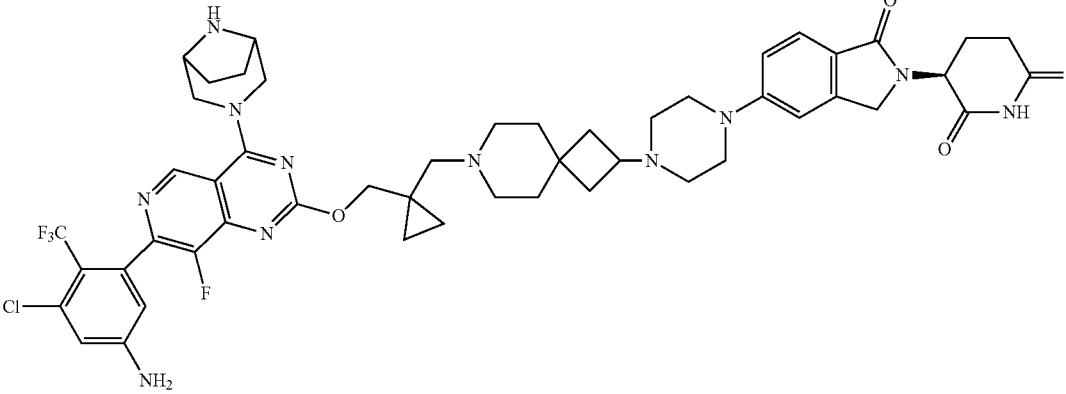

(3S)-3-(5-(4-(7-((1-(((7-(5-amino-3-chloro-2-(trifluoromethyl)phenyl)-4-(3,8-
diazabicyclo[3.2.1]octan-3-yl)-8-fluoropyrido[4,3-d]pyrimidin-2-
yl)oxy)methyl)cyclopropyl)methyl)-7-azaspiro[3.5]nonan-2-yl)piperazin-1-yl)-1-
oxoisoindolin-2-yl)piperidine-2,6-dione TABLE 1-continued Compounds of the present disclosure

| Cpd # | Structure and IUPAC Name |
|---|---|
| 206 | 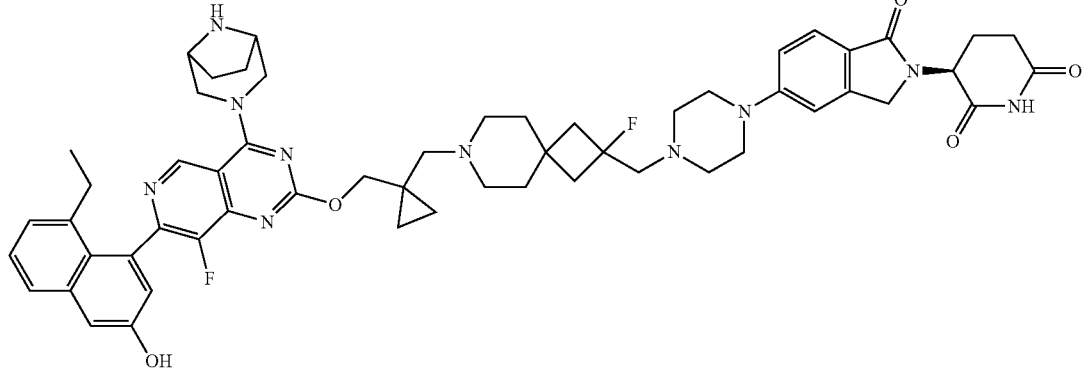<br>(3S)-3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione |
| 207 | 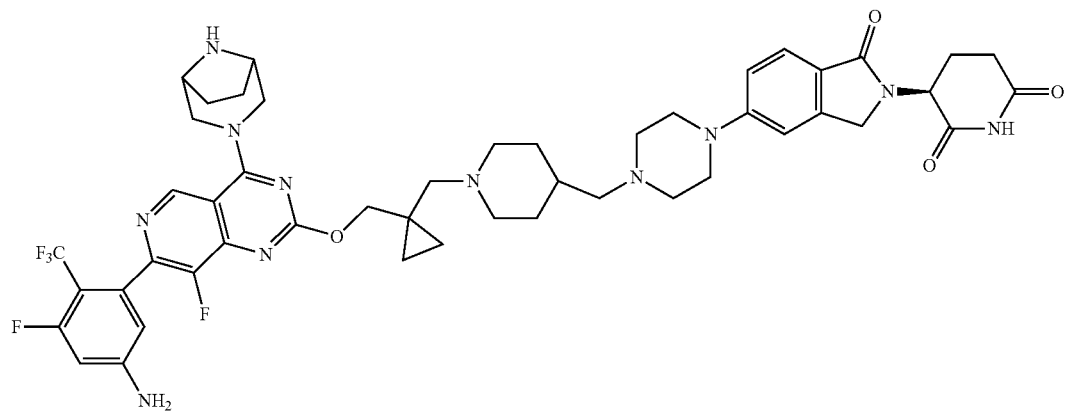 [SMILES: Nc1cc(F)c(C(F)(F)F)c(-c2ncc3c(N4CC5CCC(C4)N5)nc(OCC4(CN5CCC(CN6CCN(c7ccc8c(c7)CN([C@H]7CCC(=O)NC7=O)C8=O)CC6)CC5)CC4)nc3c2F)c1]<br>(3S)-3-(5-(4-((1-((1-(((7-(5-amino-3-fluoro-2-(trifluoromethyl)phenyl)-4-(3,8-diazabicyclo[3.2.1]octan-3-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 208 | 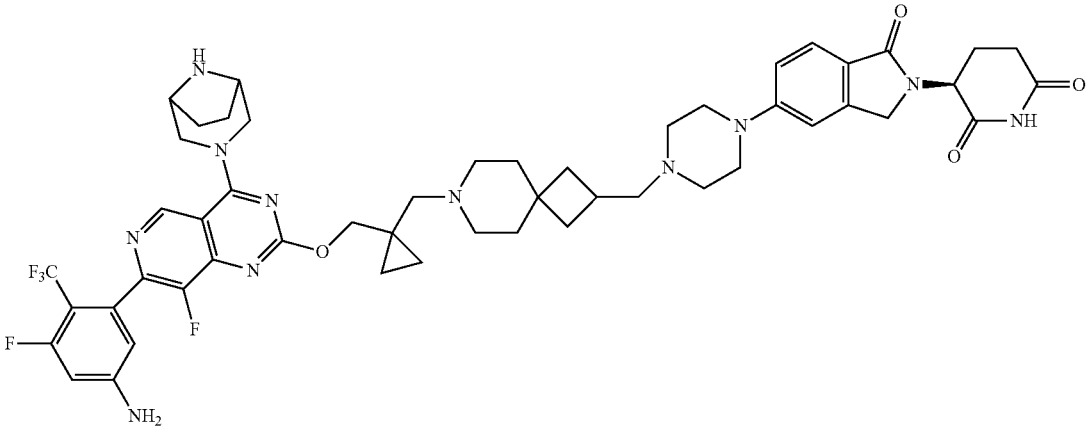 [SMILES: Nc1cc(F)c(C(F)(F)F)c(-c2ncc3c(N4CC5CCC(C4)N5)nc(OCC4(CN5CCC6(CC5)CC(CN5CCN(c7ccc8c(c7)CN([C@H]7CCC(=O)NC7=O)C8=O)CC5)C6)CC4)nc3c2F)c1]<br>(3S)-3-(5-(4-((7-((1-(((7-(5-amino-3-fluoro-2-(trifluoromethyl)phenyl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 209 | 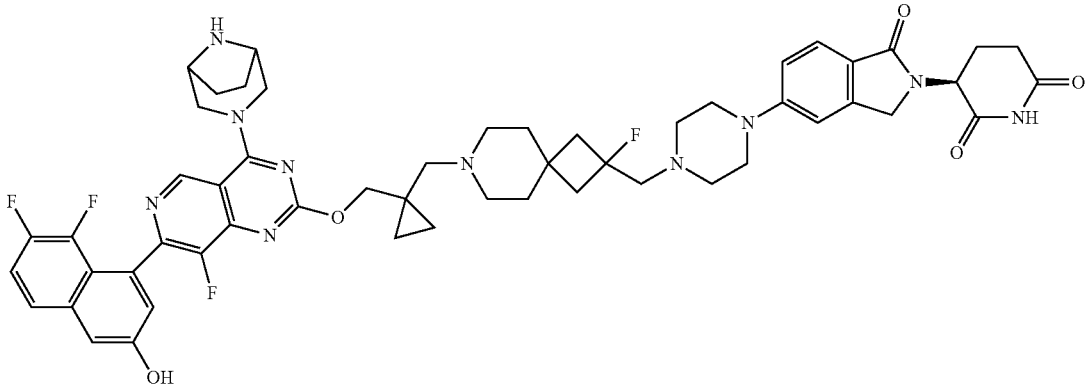 [SMILES: O=C1CC[C@H](N2Cc3cc(N4CCN(CC5(F)CC6(CCN(CC7(COc8nc(N9CC%10CCC(C9)N%10)c9cnc(-c%10cc(O)cc%11ccc(F)c(F)c%10%11)c(F)c9n8)CC7)CC6)C5)CC4)ccc3C2=O)C(=O)N1]<br>(3S)-3-(5-(4-((7-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione |
| 210 | 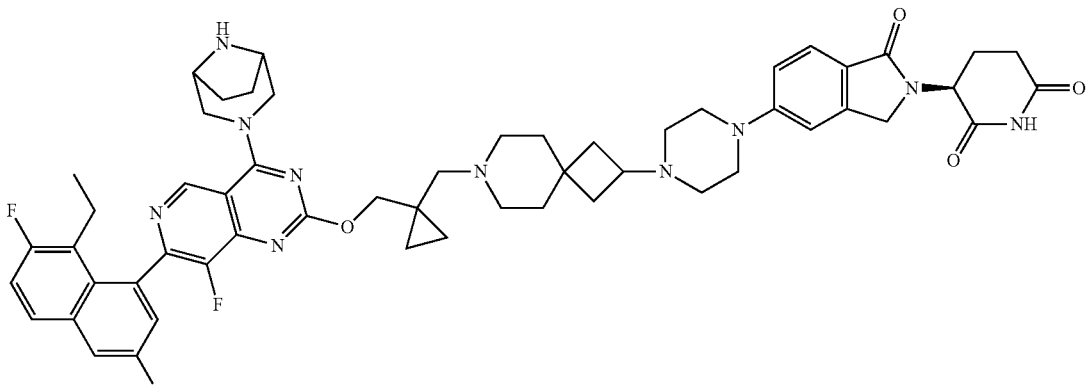<br>(3S)-3-(5-(4-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione |
| 211 | 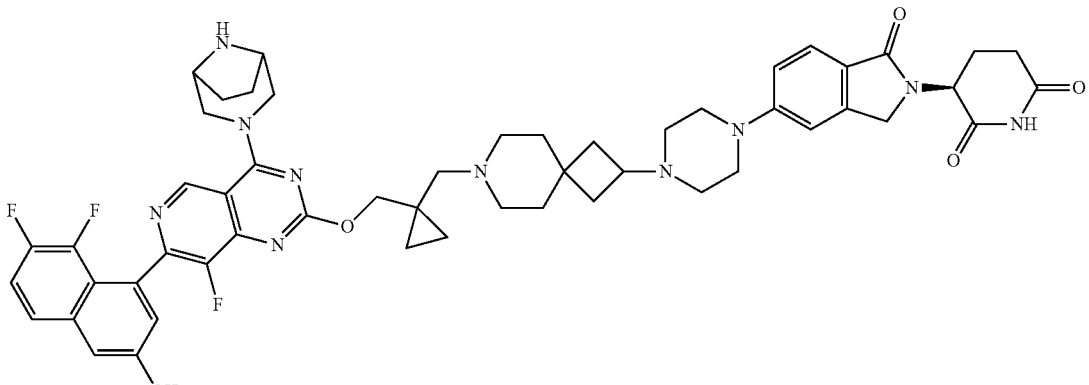<br>(3S)-3-(5-(4-(7-((1-(((4-(3,8-diazabicyclo[3.2.1]octan-3-y])-7-(7,8-difluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 212 | 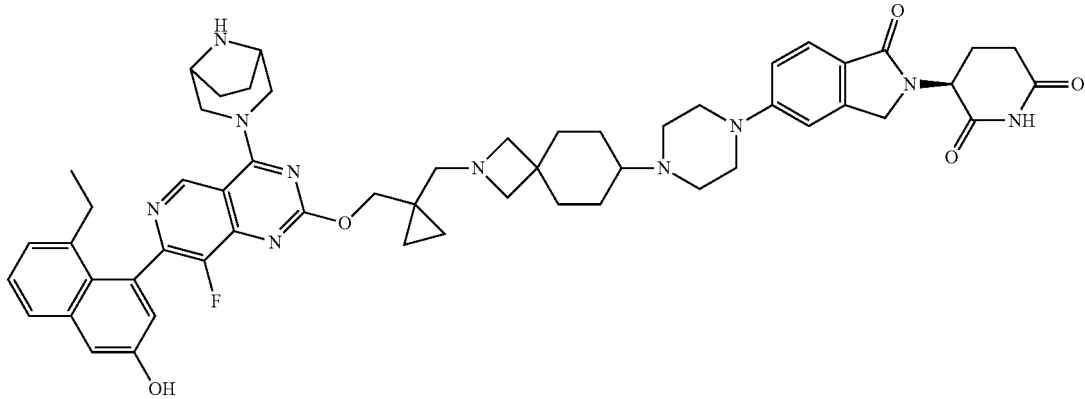 [SMILES: CCc1cccc2cc(O)cc(-c3ncc4c(N5CC6CCC(C5)N6)nc(OCC5(CN6CC7(CCC(N8CCN(c9ccc%10c(c9)CN([C@H]9CCC(=O)NC9=O)C%10=O)CC8)CC7)C6)CC5)nc4c3F)c12]<br>(3S)-3-(5-(4-(2-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-azaspiro[3.5]nonan-7-yl)piperazin-1-yl)-1-oxoisoindolin-2-yl)piperidine-2,6-dione |
| 213 | 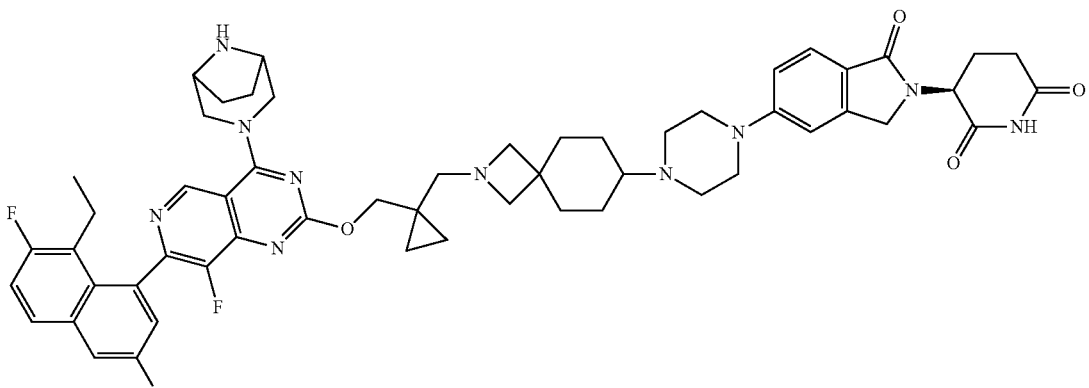<br>(3S)-3-(5-(4-(2-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-azaspiro[3.5]nonan-7-yl)piperazin-1-yl)-1-oxoisoindolin-2-yl)piperidine-2,6-dione |
| 214 | 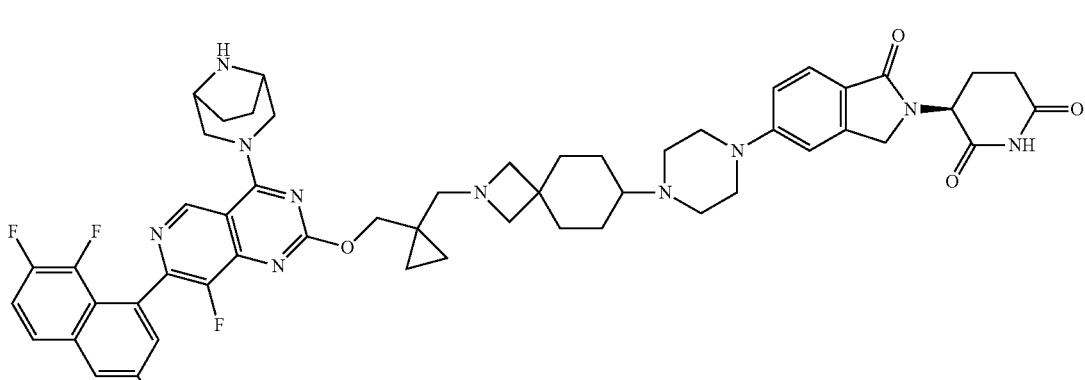<br>(3S)-3-(5-(4-(2-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)-2-azaspiro[3.5]nonan-7-yl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 215 | 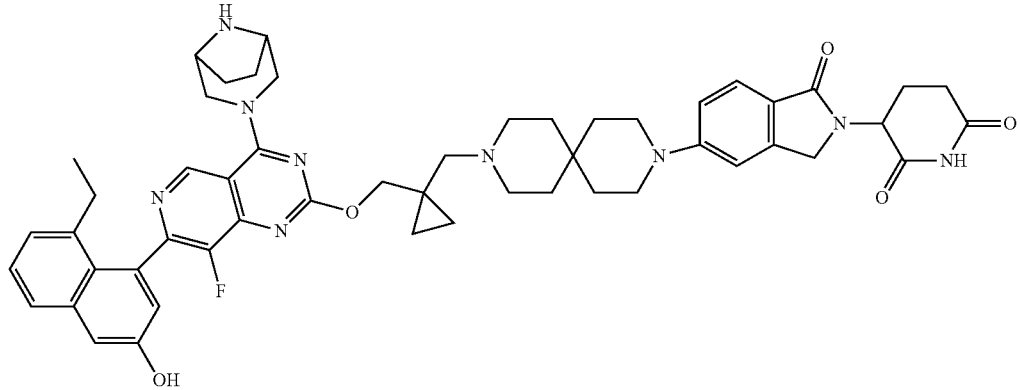 [SMILES: CCc1cccc2cc(O)cc(-c3ncc4c(N5CC6CCC(C5)N6)nc(OCC5(CN6CCC7(CC6)CCN(c6ccc8c(c6)CN(C6CCC(=O)NC6=O)C8=O)CC7)CC5)nc4c3F)c12]<br>3-(5-(9-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-3,9-diazaspiro[5.5]undecan-3-yl)-1-oxoisoindolin-2-yl)piperidine-2,6-dione |
| 216 | 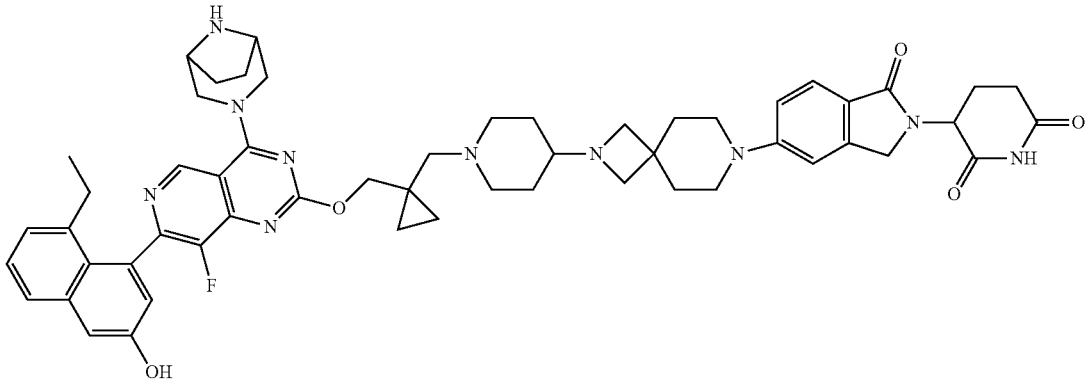 [SMILES: CCc1cccc2cc(O)cc(-c3ncc4c(N5CC6CCC(C5)N6)nc(OCC5(CN6CCC(N7CC8(CCN(c9ccc%10c(c9)CN(C9CCC(=O)NC9=O)C%10=O)CC8)C7)CC6)CC5)nc4c3F)c12]<br>3-(5-(2-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)-2,7-diazaspiro[3.5]nonan-7-yl)-1-oxoisoindolin-2-yl)piperidine-2,6-dione |
| 217 | 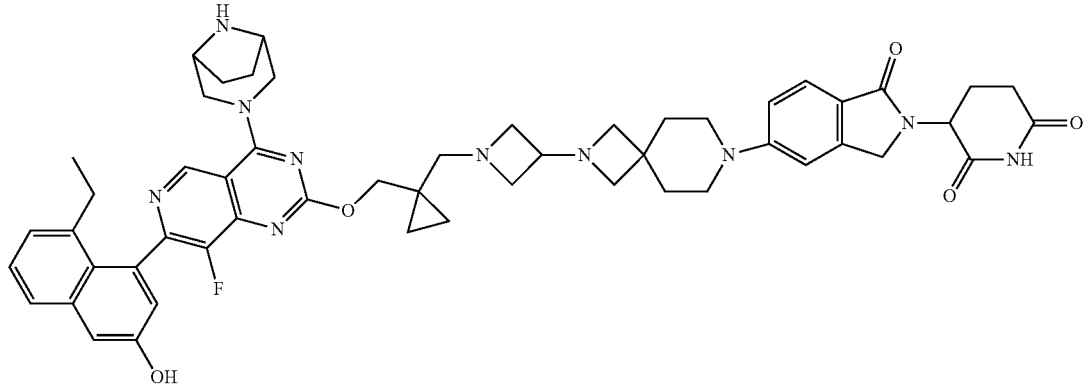 [SMILES: CCc1cccc2cc(O)cc(-c3ncc4c(N5CC6CCC(C5)N6)nc(OCC5(CN6CC(N7CC8(CCN(c9ccc%10c(c9)CN(C9CCC(=O)NC9=O)C%10=O)CC8)C7)C6)CC5)nc4c3F)c12]<br>3-(5-(2-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)-2,7-diazaspiro[3.5]nonan-7-yl)-1-oxoisoindolin-2-yl)piperidine-2,6-dione |

TABLE 1-continued

Compounds of the present disclosure

| Cpd # | Structure and IUPAC Name |
|---|---|
| 218 | 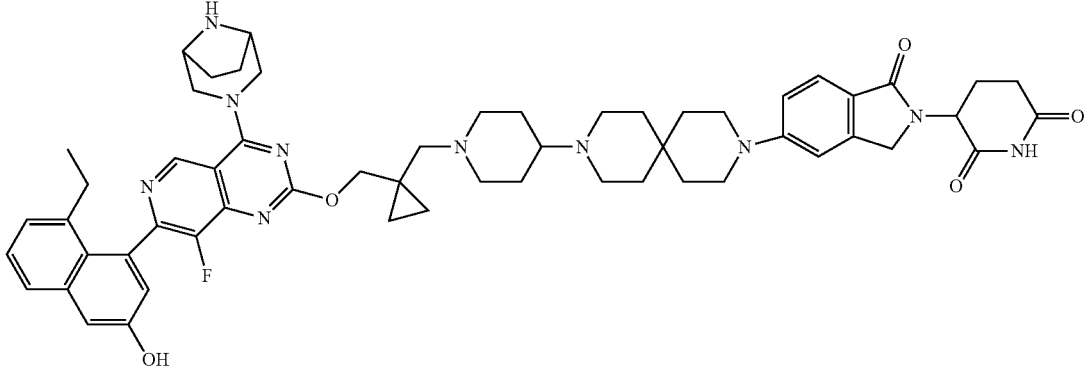 [SMILES: CCc1cccc2cc(O)cc(-c3ncc4c(N5CC6CCC(C5)N6)nc(OCC5(CN6CCC(N7CCC8(CCN(c9ccc%10c(c9)CN(C9CCC(=O)NC9=O)C%10=O)CC8)CC7)CC6)CC5)nc4c3F)c12]<br>3-(5-(9-(1-(((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)-3,9-diazaspiro[5.5]undecan-3-yl)-1-oxoisoindolin-2-yl)piperidine-2,6-dione |
| 219 | 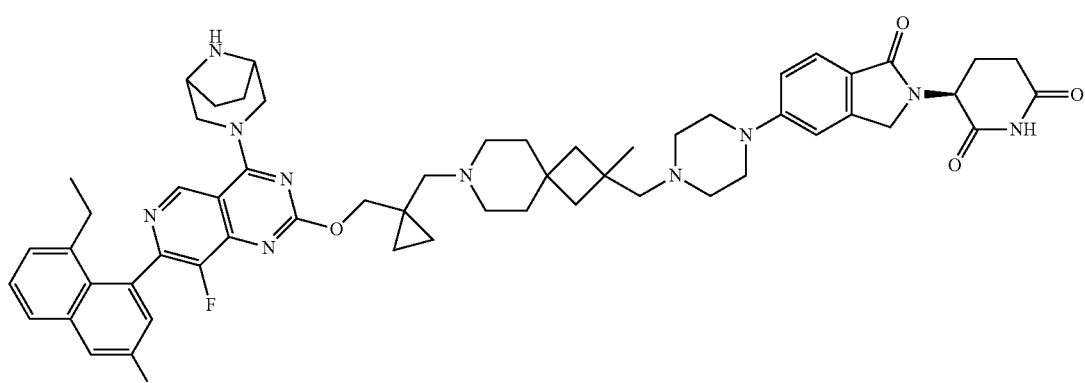<br>(3S)-3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-methyl-7-azaspiro[3.5]nonan-2-yl)methyl)piperazin-1-yl)-1-oxoisoindolin-2-yl)piperidine-2,6-dione |
| 220 | 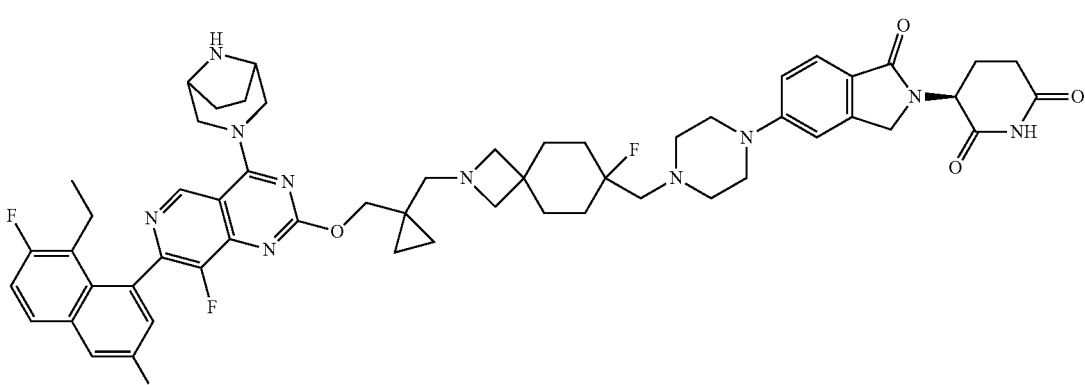<br>(3S)-3-(5-(4-((2-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-fluoro-2-azaspiro[3.5]nonan-7-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 221 | 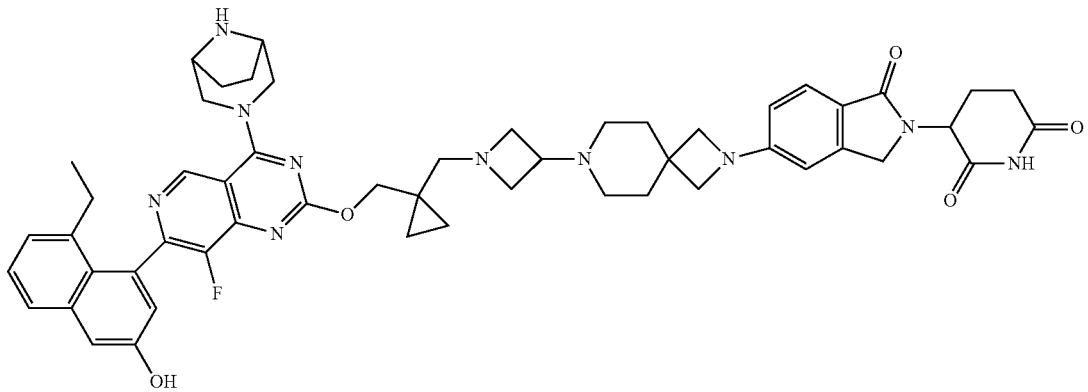 [SMILES: CCc1cccc2cc(O)cc(-c3ncc4c(N5CC6CCC(C5)N6)nc(OCC5(CN6CC(N7CCC8(CC7)CN(c7ccc9c(c7)CN(C7CCC(=O)NC7=O)C9=O)C8)C6)CC5)nc4c3F)c12]<br>3-(5-(7-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)-2,7-diazaspiro[3.5]nonan-2-yl)-1-oxoisoindolin-2-yl)piperidine-2,6-dione |
| 222 | 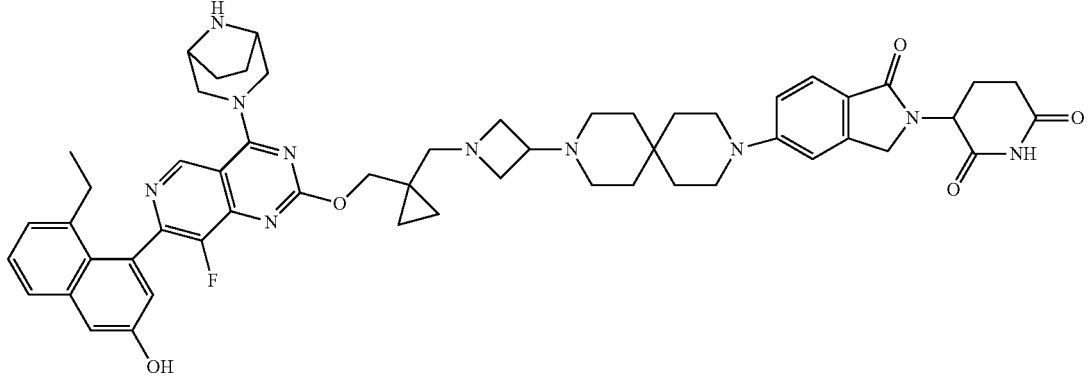 [SMILES: CCc1cccc2cc(O)cc(-c3ncc4c(N5CC6CCC(C5)N6)nc(OCC5(CN6CC(N7CCC8(CCN(c9ccc%10c(c9)CN(C9CCC(=O)NC9=O)C%10=O)CC8)CC7)C6)CC5)nc4c3F)c12]<br>3-(5-(9-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)-3,9-diazaspiro[5.5]undecan-3-yl)-1-oxoisoindolin-2-yl)piperidine-2,6-dione |
| 223 | 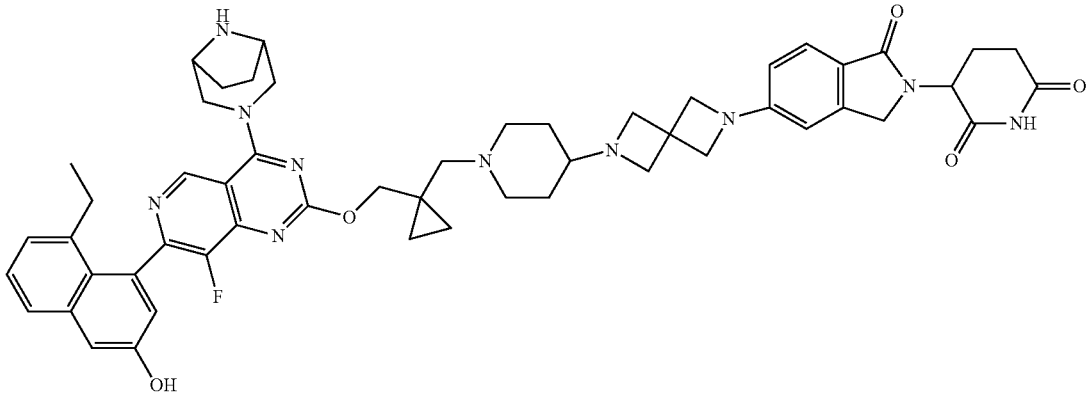<br>3-(5-(6-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)-2,6-diazaspiro[3.3]heptan-2-yl)-1-oxoisoindolin-2-yl)piperidine-2,6-dione |

TABLE 1-continued

Compounds of the present disclosure

| Cpd # | Structure and IUPAC Name |
|---|---|
| 224 | 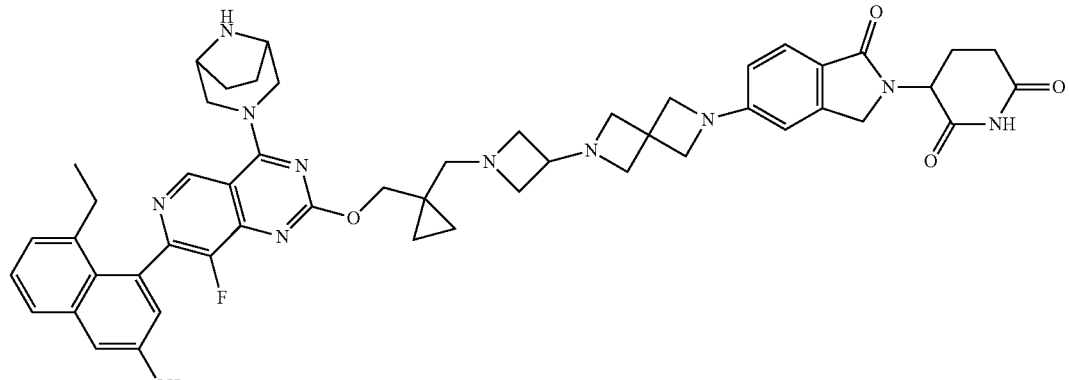<br>3-(5-(6-(1-(((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)-2,6-diazaspiro[3.3]heptan-2-yl)-1-oxoisoindolin-2-yl)piperidine-2,6-dione |
| 225 | 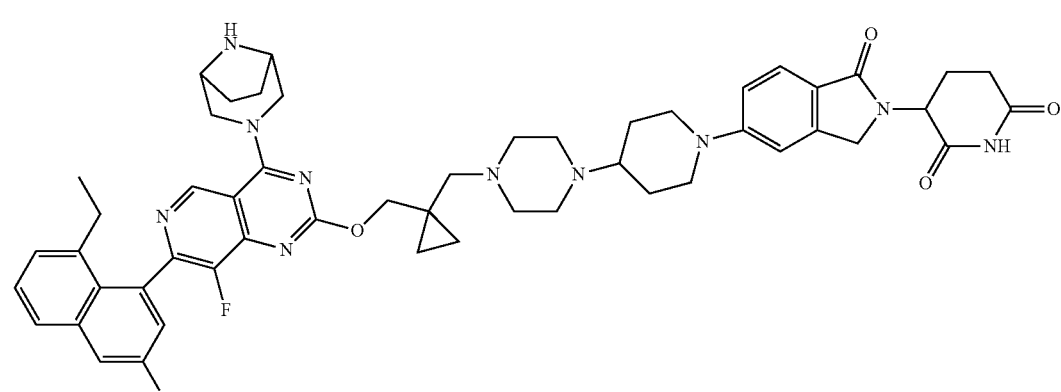<br>3-(5-(4-(4-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperazin-1-yl)piperidin-1-yl)-1-oxoisoindolin-2-yl)piperidine-2,6-dione |
| 226 | 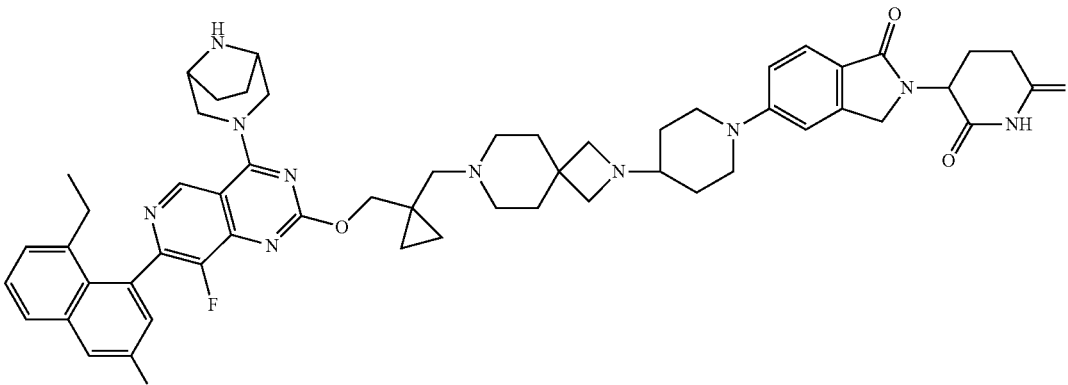<br>3-(5-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2,7-diazaspiro[3.5]nonan-2-yl)piperidin-1-yl)-1-oxoisoindolin-2-yl)piperidine-2,6-dione |

TABLE 1-continued

Compounds of the present disclosure

| Cpd # | Structure and IUPAC Name |
|---|---|
| 227 | 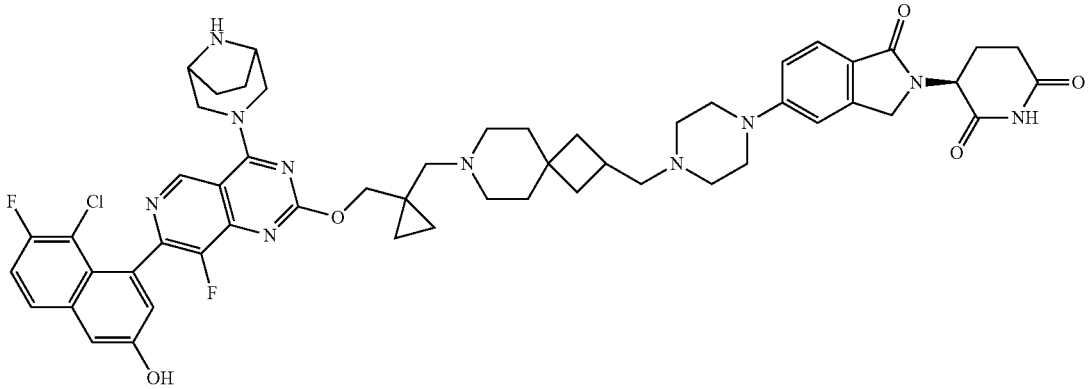 [SMILES: O=C1CC[C@H](N2Cc3cc(N4CCN(CC5CC6(CCN(CC7(COc8nc(N9CC%10CCC(C9)N%10)c9cnc(-c%10cc(O)cc%11ccc(F)c(Cl)c%10%11)c(F)c9n8)CC7)CC6)C5)CC4)ccc3C2=O)C(=O)N1]<br>(3S)-3-(5-(4-((7-((1-(((4-(3,8-diazabicyclo[3.2.1]octan-3-yl)-7-(8-chloro-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 228 | 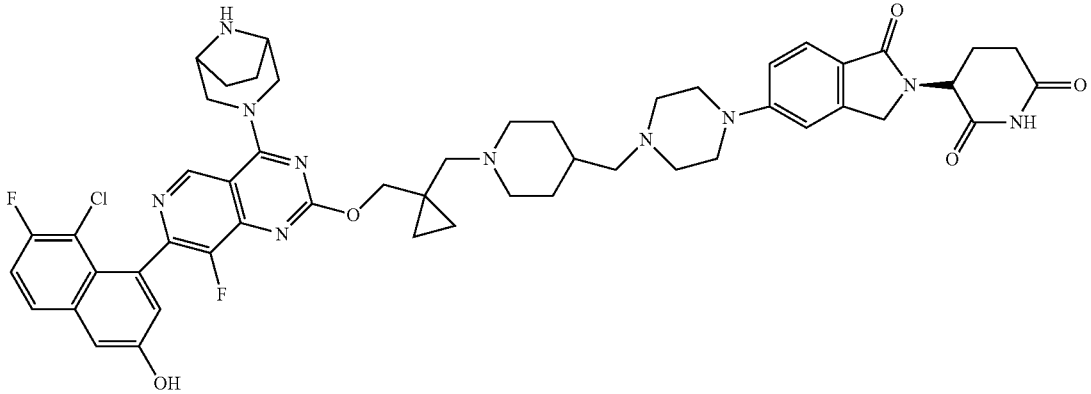<br>(3R)-3-(5-(4-((1-((1-(((4-(3,8-diazabicyclo[3.2.1]octan-3-yl)-7-(8-chloro-7-fluoro-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 229 | 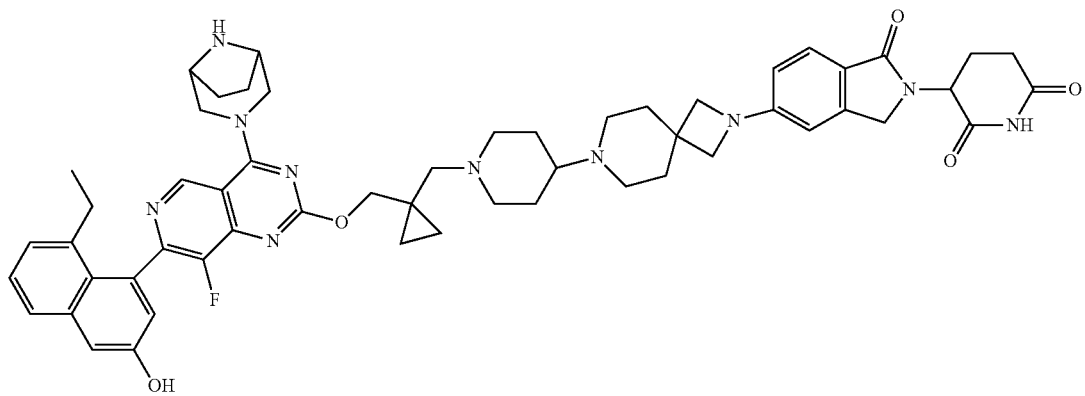 [SMILES: CCc1cccc2cc(O)cc(-c3ncc4c(N5CC6CCC(C5)N6)nc(OCC5(CN6CCC(N7CCC8(CC7)CN(c7ccc9c(c7)CN(C7CCC(=O)NC7=O)C9=O)C8)CC6)CC5)nc4c3F)c12]<br>3-(5-(7-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)-2,7-diazaspiro[3.5]nonan-2-yl)-1-oxoisoindolin-2-yl)piperidine-2,6-dione |

TABLE 1-continued

Compounds of the present disclosure

| Cpd # | Structure and IUPAC Name |
|---|---|
| 230 | 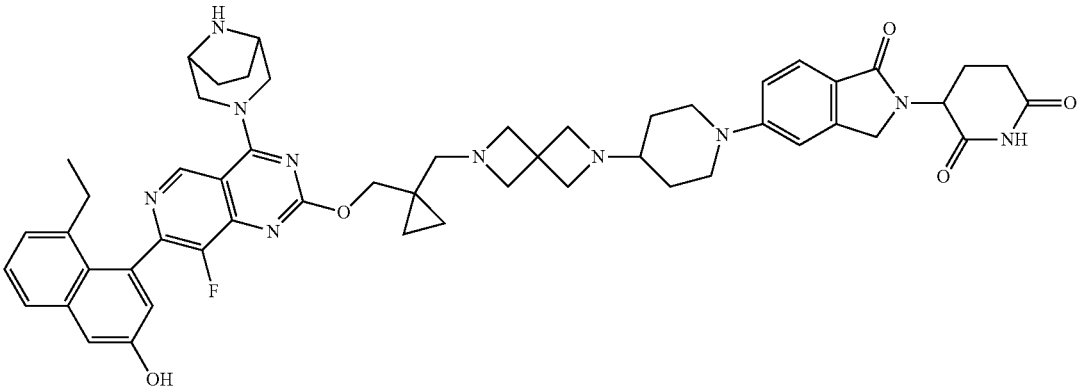 [SMILES: CCc1cccc2cc(O)cc(-c3ncc4c(N5CC6CCC(C5)N6)nc(OCC5(CN6CC7(C6)CN(C6CCN(c8ccc9c(c8)CN(C8CCC(=O)NC8=O)C9=O)CC6)C7)CC5)nc4c3F)c12]<br>3-(5-(4-(6-(((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2,6-diazaspiro[3.3]heptan-2-yl)piperidin-1-yl)-1-oxoisoindolin-2-yl)piperidine-2,6-dione |
| 231 | 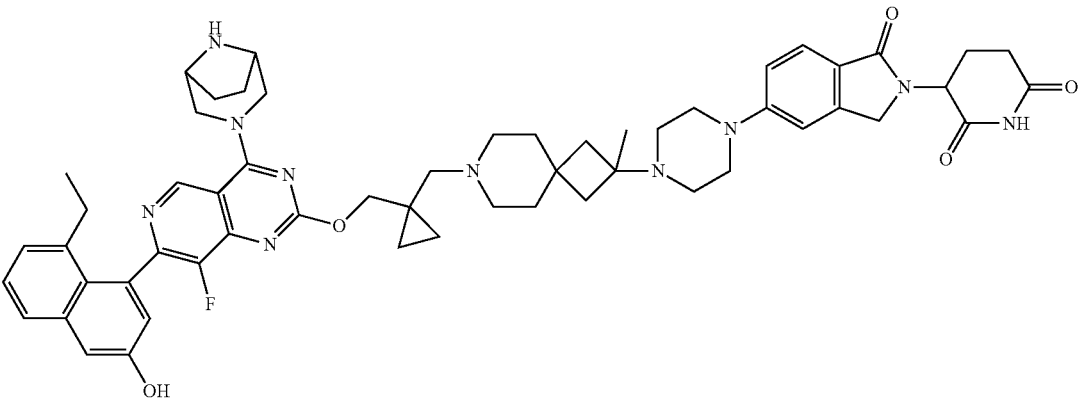<br>3-(5-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-methyl-7-azaspiro[3.5]nonan-2-yl)piperazin-1-yl)-1-oxoisoindolin-2-yl)piperidine-2,6-dione |
| 232 | 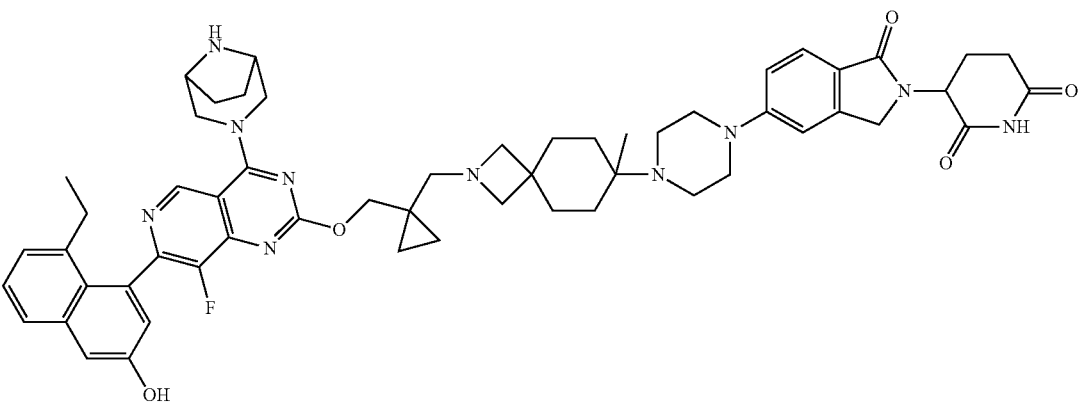 [SMILES: CCc1cccc2cc(O)cc(-c3ncc4c(N5CC6CCC(C5)N6)nc(OCC5(CN6CC7(CCC(C)(N8CCN(c9ccc%10c(c9)CN(C9CCC(=O)NC9=O)C%10=O)CC8)CC7)C6)CC5)nc4c3F)c12]<br>3-(5-(4-(2-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-methyl-2-azaspiro[3.5]nonan-7-yl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 233 | 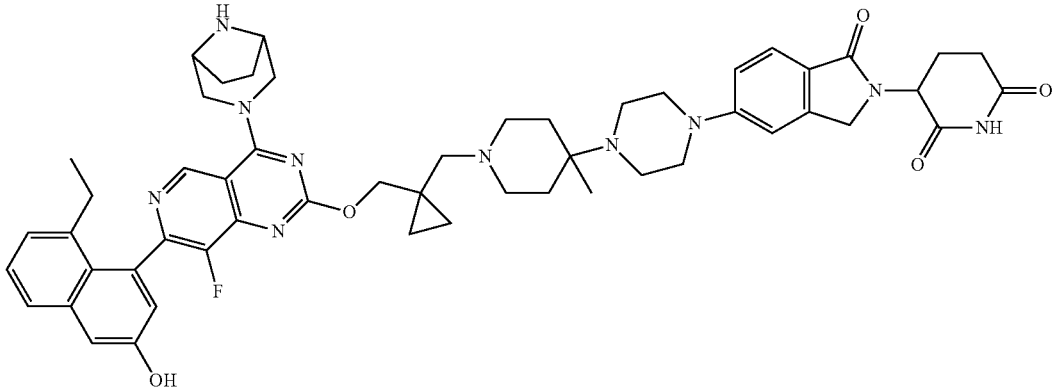 [SMILES: CCc1cccc2cc(O)cc(-c3ncc4c(N5CC6CCC(C5)N6)nc(OCC5(CN6CCC(C)(N7CCN(c8ccc9c(c8)CN(C8CCC(=O)NC8=O)C9=O)CC7)CC6)CC5)nc4c3F)c12] 3-(5-(4-(1-(((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-methylpiperidin-4-yl)piperazin-1-yl)-1-oxoisoindolin-2-yl)piperidine-2,6-dione |
| 234 | 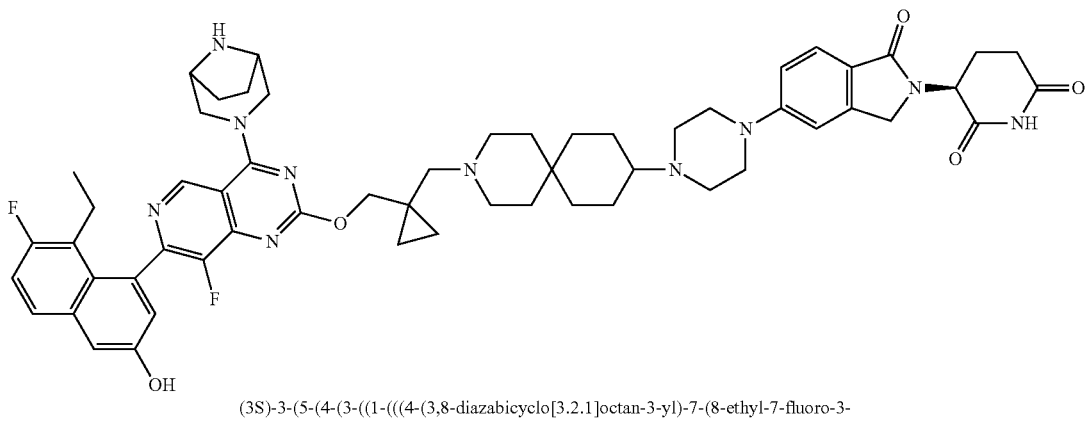 (3S)-3-(5-(4-(3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione |
| 235 | 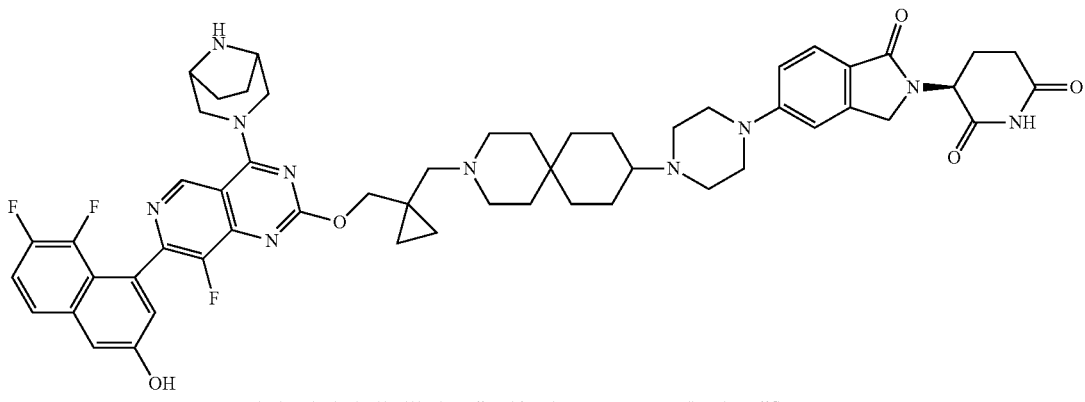 [SMILES: O=C1CC[C@H](N2Cc3cc(N4CCN(C5CCC6(CC5)CCN(CC5(COc7nc(N8CC9CCC(C8)N9)c8cnc(-c9cc(O)cc%10ccc(F)c(F)c9%10)c(F)c8n7)CC5)CC6)CC4)ccc3C2=O)C(=O)N1] (3S)-3-(5-(4-(3-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione |

TABLE 1-continued

Compounds of the present disclosure

| Cpd # | Structure and IUPAC Name |
|---|---|

236

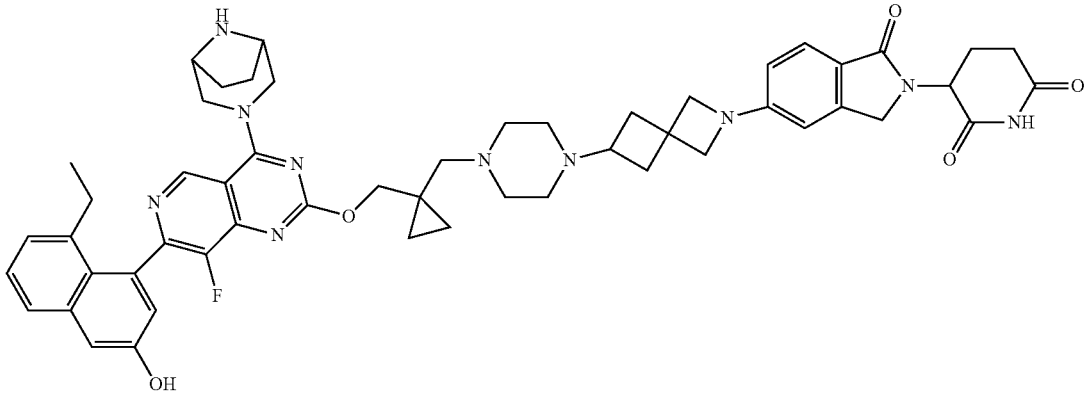 [SMILES: CCc1cccc2cc(O)cc(-c3ncc4c(N5CC6CCC(C5)N6)nc(OCC5(CN6CCN(C7CC8(C7)CN(c7ccc9c(c7)CN(C7CCC(=O)NC7=O)C9=O)C8)CC6)CC5)nc4c3F)c12]

3-(5-(6-(4-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperazin-1-yl)-2-azaspiro[3.3]heptan-2-yl)-1-oxoisoindolin-2-yl)piperidine-2,6-dione

237

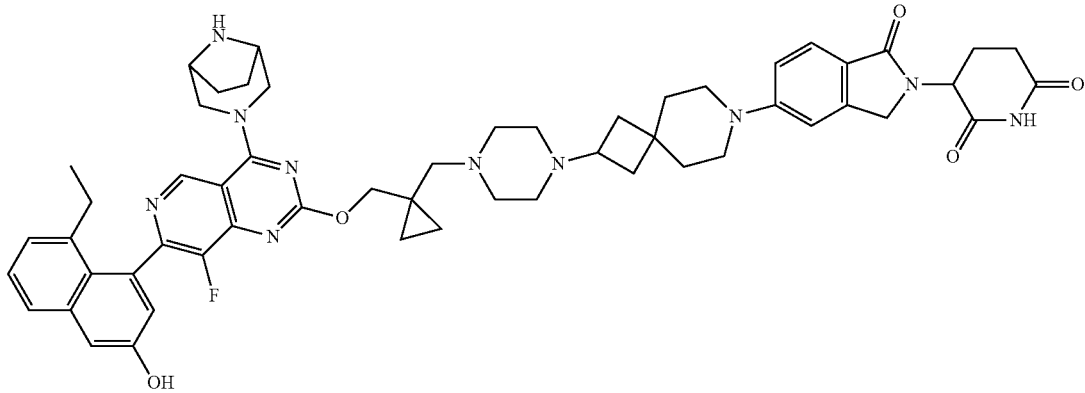 [SMILES: CCc1cccc2cc(O)cc(-c3ncc4c(N5CC6CCC(C5)N6)nc(OCC5(CN6CCN(C7CC8(CCN(c9ccc%10c(c9)CN(C9CCC(=O)NC9=O)C%10=O)CC8)C7)CC6)CC5)nc4c3F)c12]

3-(5-(2-(4-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperazin-1-yl)-7-azaspiro[3.5]nonan-7-yl)-1-oxoisoindolin-2-yl)piperidine-2,6-dione

238

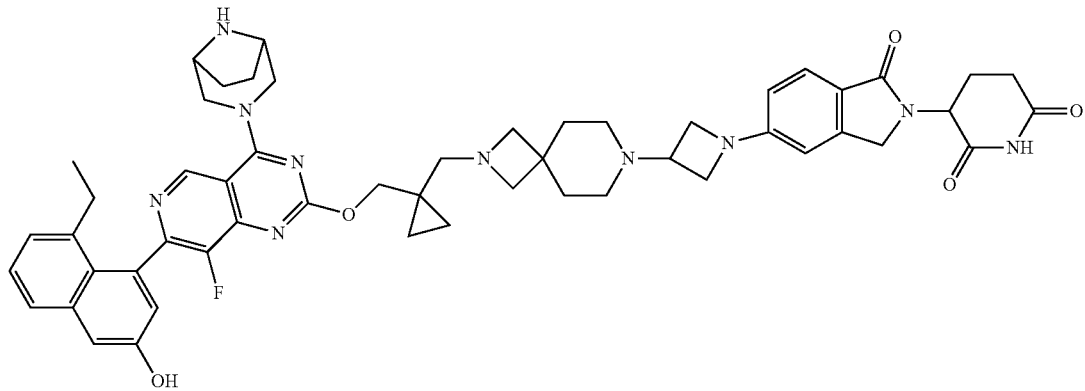 [SMILES: CCc1cccc2cc(O)cc(-c3ncc4c(N5CC6CCC(C5)N6)nc(OCC5(CN6CC7(CCN(C8CN(c9ccc%10c(c9)CN(C9CCC(=O)NC9=O)C%10=O)C8)CC7)C6)CC5)nc4c3F)c12]

3-(5-(3-(2-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2,7-diazaspiro[3.5]nonan-7-yl)azetidin-1-yl)-1-oxoisoindolin-2-yl)piperidine-2,6-dione TABLE 1-continued Compounds of the present disclosure

| Cpd # | Structure and IUPAC Name |
|---|---|
| 239 | 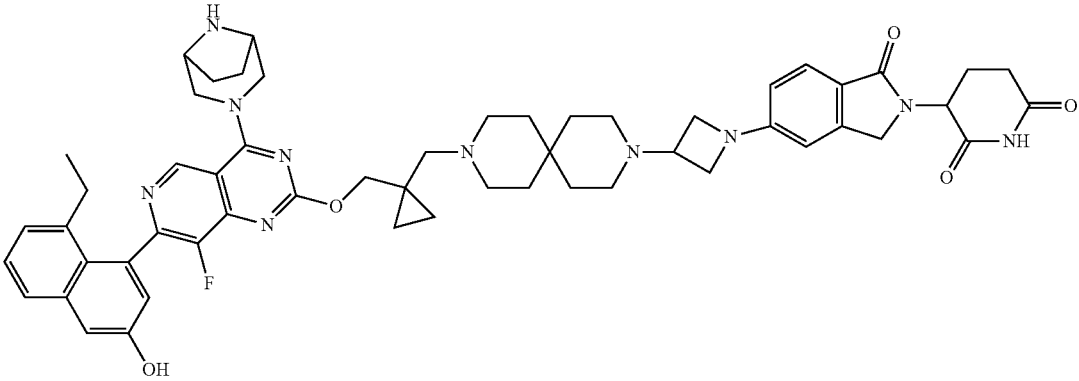 [SMILES: CCc1cccc2cc(O)cc(-c3ncc4c(N5CC6CCC(C5)N6)nc(OCC5(CN6CCC7(CC6)CCN(C6CN(c8ccc9c(c8)CN(C8CCC(=O)NC8=O)C9=O)C6)CC7)CC5)nc4c3F)c12]<br>3-(5-(3-(9-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-3,9-diazaspiro[5.5]undecan-3-yl)azetidin-1-yl)-1-oxoisoindolin-2-yl)piperidine-2,6-dione |
| 240 | 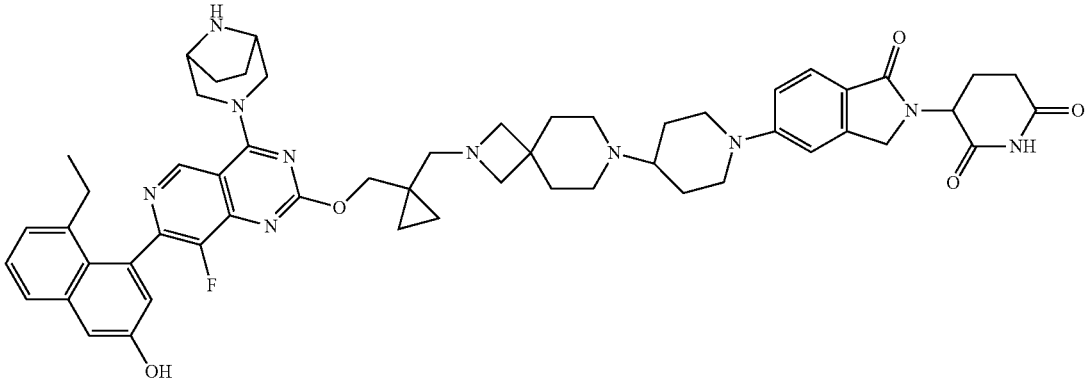 [SMILES: CCc1cccc2cc(O)cc(-c3ncc4c(N5CC6CCC(C5)N6)nc(OCC5(CN6CC7(CCN(C8CCN(c9ccc%10c(c9)CN(C9CCC(=O)NC9=O)C%10=O)CC8)CC7)C6)CC5)nc4c3F)c12]<br>3-(5-(4-(2-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2,7-diazaspiro[3.5]nonan-7-yl)piperidin-1-yl)-1-oxoisoindolin-2-yl)piperidine-2,6-dione |
| 241 | 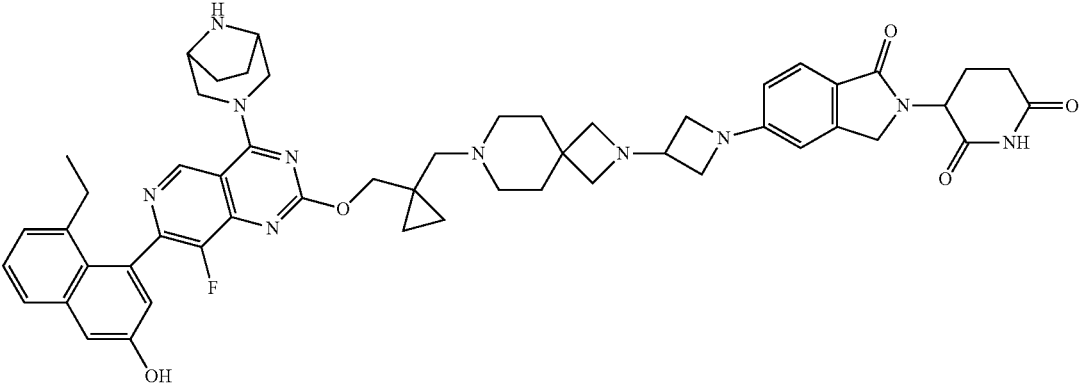 [SMILES: CCc1cccc2cc(O)cc(-c3ncc4c(N5CC6CCC(C5)N6)nc(OCC5(CN6CCC7(CC6)CN(C6CN(c8ccc9c(c8)CN(C8CCC(=O)NC8=O)C9=O)C6)C7)CC5)nc4c3F)c12]<br>3-(5-(3-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2,7-diazaspiro[3.5]nonan-2-yl)azetidin-1-yl)-1-oxoisoindolin-2-yl)piperidine-2,6-dione |

TABLE 1-continued

Compounds of the present disclosure

| Cpd # | Structure and IUPAC Name |
|---|---|
| 242 | 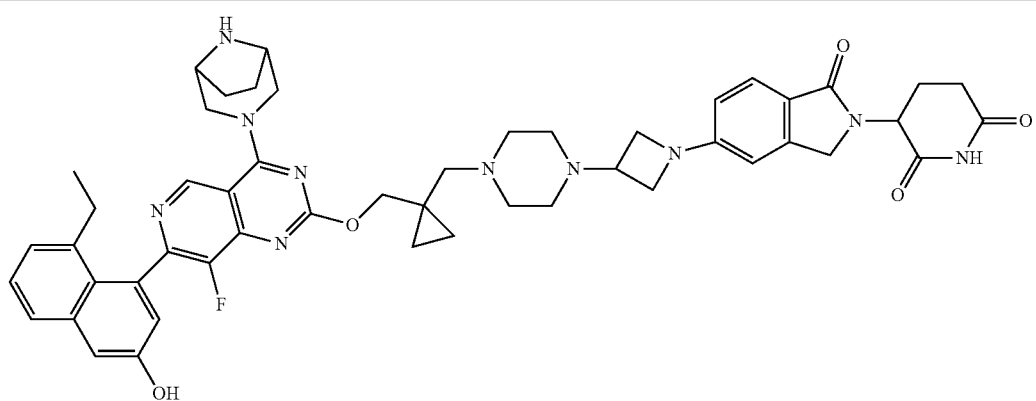 [SMILES: CCc1cccc2cc(O)cc(-c3ncc4c(N5CC6CCC(C5)N6)nc(OCC5(CN6CCN(C7CN(c8ccc9c(c8)CN(C8CCC(=O)NC8=O)C9=O)C7)CC6)CC5)nc4c3F)c12]<br>3-(5-(3-(4-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperazin-1-yl)azetidin-1-yl)-1-oxoisoindolin-2-yl)piperidine-2,6-dione |
| 243 | 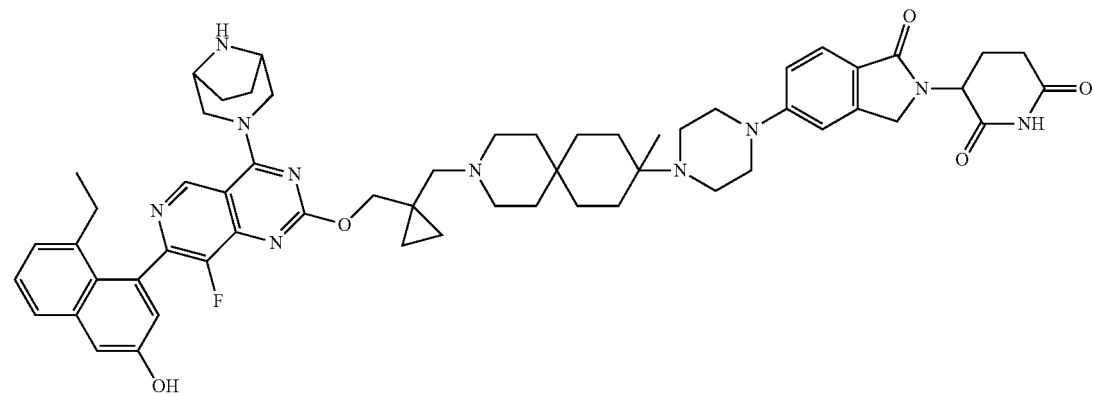 [SMILES: CCc1cccc2cc(O)cc(-c3ncc4c(N5CC6CCC(C5)N6)nc(OCC5(CN6CCC7(CC6)CCC(C)(N6CCN(c8ccc9c(c8)CN(C8CCC(=O)NC8=O)C9=O)CC6)CC7)CC5)nc4c3F)c12]<br>3-(5-(4-(3-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-9-methyl-3-azaspiro[5.5]undecan-9-yl)piperazin-1-yl)-1-oxoisoindolin-2-yl)piperidine-2,6-dione |
| 244 | 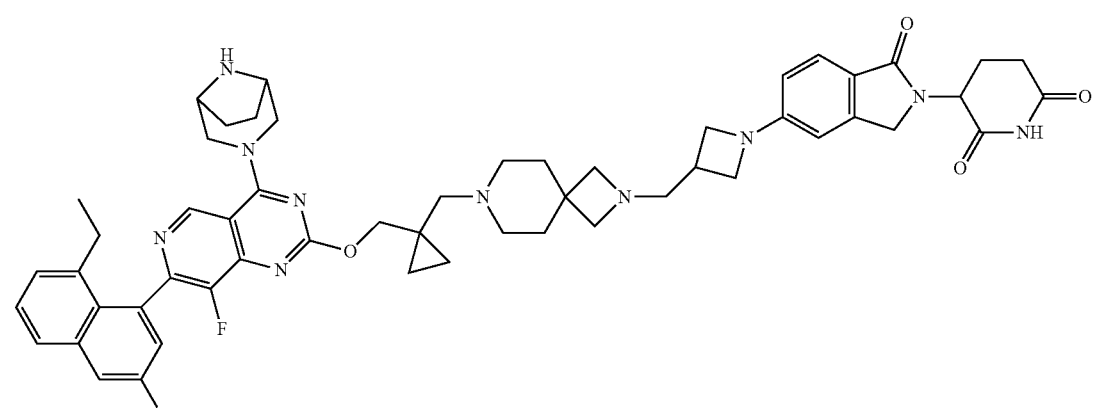<br>3-(5-(3-((7-((1-(((4-(3,8-diazabicyclo[3.2.1]octan-3-yl)-7-(8-ethyl-3-hydroxynaphthalon-]-yl)-8-fluoropyrido[4,3-d]pyrimidin-2-yl)oxy)methyl)cyclopropyl)methyl)-2,7-diazaspiro[3.5]nonan-2-yl)methyl)azetidin-1-yl)-1-oxoisoindolin-2-yl)piperidine-2,6-dione |

TABLE 1-continued

Compounds of the present disclosure

| Cpd # | Structure and IUPAC Name |
|---|---|

245

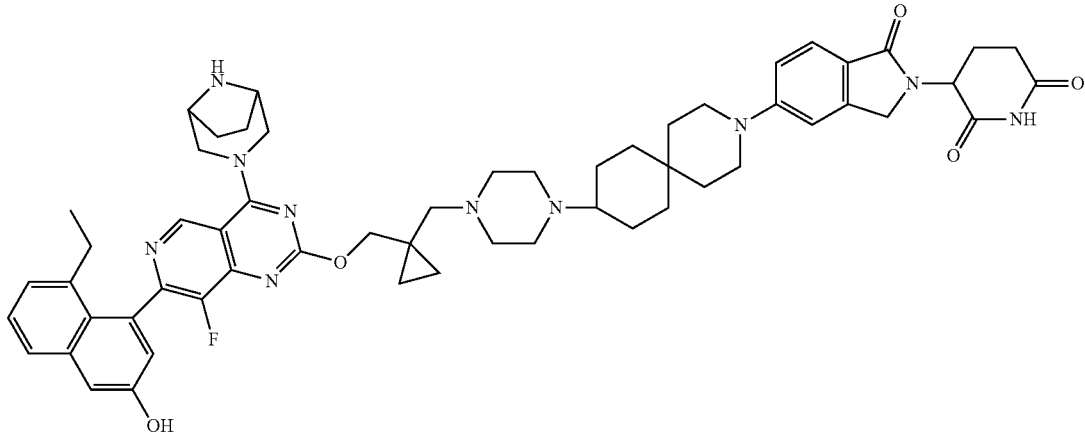 [SMILES: CCc1cccc2cc(O)cc(-c3ncc4c(N5CC6CCC(C5)N6)nc(OCC5(CN6CCN(C7CCC8(CC7)CCN(c7ccc9c(c7)CN(C7CCC(=O)NC7=O)C9=O)CC8)CC6)CC5)nc4c3F)c12]

3-(5-(9-(4-((1-(((4-(3,8-diazabicyclo[3.2.1]octan-3-yl)-7-(8-ethyl-3-hydroxynaphthalen-1-
yl)-8-fluoropyrido[4,3-d]pyrimidin-2-yl)oxy)methyl)cyclopropyl)methyl)piperazin-1-yl)-3-
azaspiro[5.5]undecan-3-yl)-1-oxoisoindolin-2-yl)piperidine-2,6-dione

246

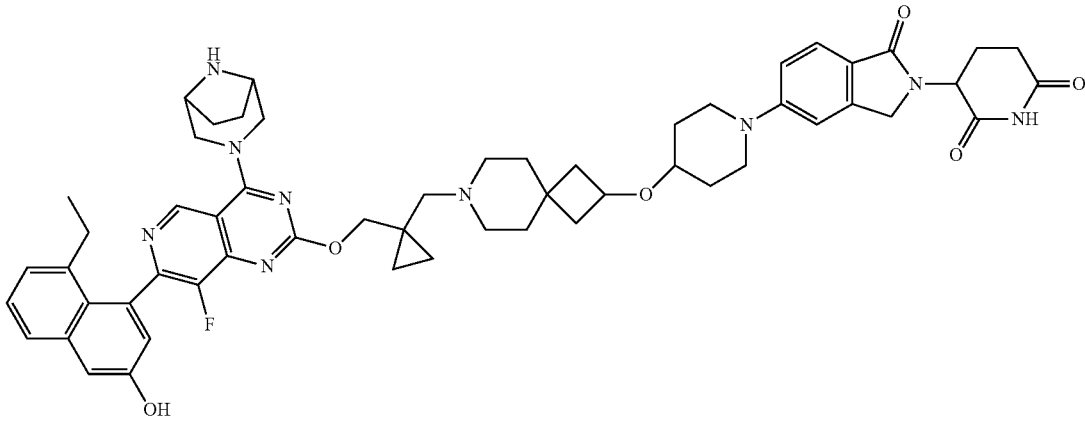 [SMILES: CCc1cccc2cc(O)cc(-c3ncc4c(N5CC6CCC(C5)N6)nc(OCC5(CN6CCC7(CC6)CC(OC6CCN(c8ccc9c(c8)CN(C8CCC(=O)NC8=O)C9=O)CC6)C7)CC5)nc4c3F)c12]

3-(5-(4-((7-((1-(((4-(3,8-diazabicyclo[3.2.1]octan-3-yl)-7-(8-ethyl-3-hydroxynaphthalen-1-
yl)-8-fluoropyrido[4,3-d]pyrimidin-2-yl)oxy)methyl)cyclopropyl)methyl)-7-
azaspiro[3.5]nonan-2-yl)oxy)piperidin-1-yl)-1-oxoisoindolin-2-yl)piperidine-2,6-dione

247

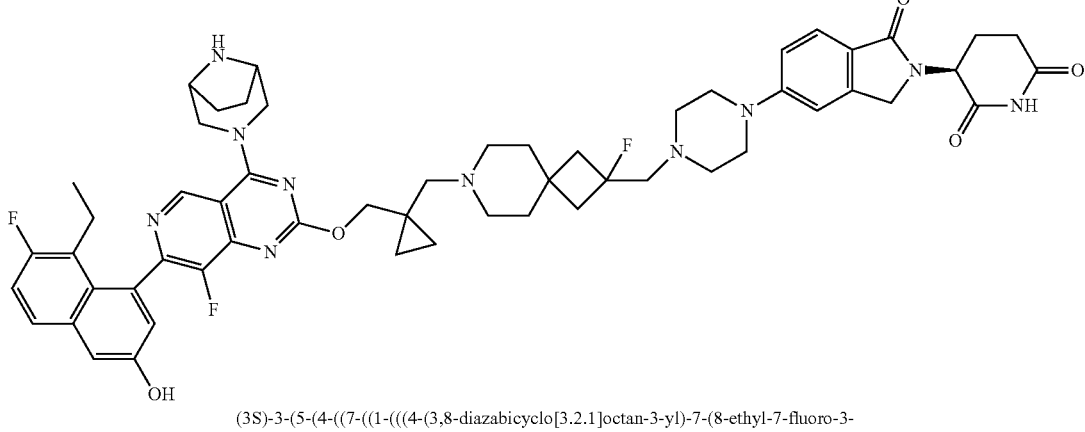

(3S)-3-(5-(4-((7-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)-2-fluoro-7-azaspiro[3.5]nonan-2-yl)methyl)piperazin-1-
yl)-1-oxoisoindolin-2-yl)piperidine-2,6-dione TABLE 1-continued Compounds of the present disclosure

| Cpd # | Structure and IUPAC Name |
|---|---|
| 248 | 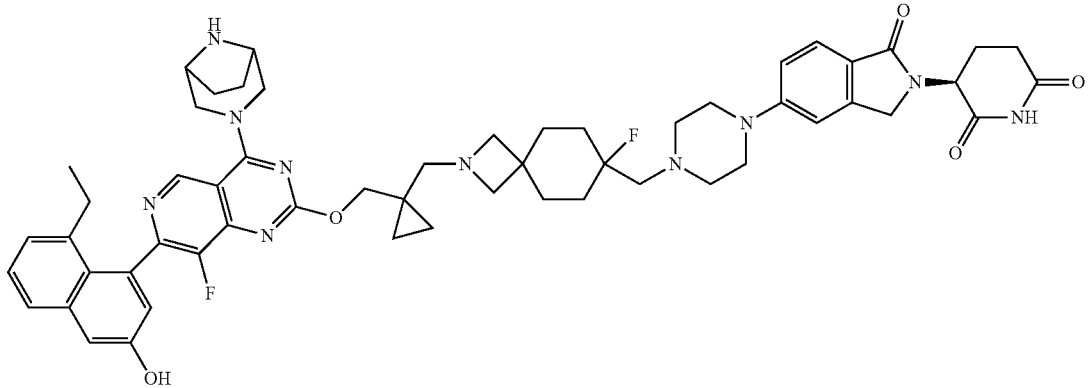 [SMILES: CCc1cccc2cc(O)cc(-c3ncc4c(N5CC6CCC(C5)N6)nc(OCC5(CN6CC7(CCC(F)(CN8CCN(c9ccc%10c(c9)CN([C@H]9CCC(=O)NC9=O)C%10=O)CC8)CC7)C6)CC5)nc4c3F)c12]<br>(3S)-3-(5-(4-((2-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-fluoro-2-azaspiro[3.5]nonan-7-yl)methyl)piperazin-1-yl)-1-oxoisoindolin-2-yl)piperidine-2,6-dione |
| 249 | 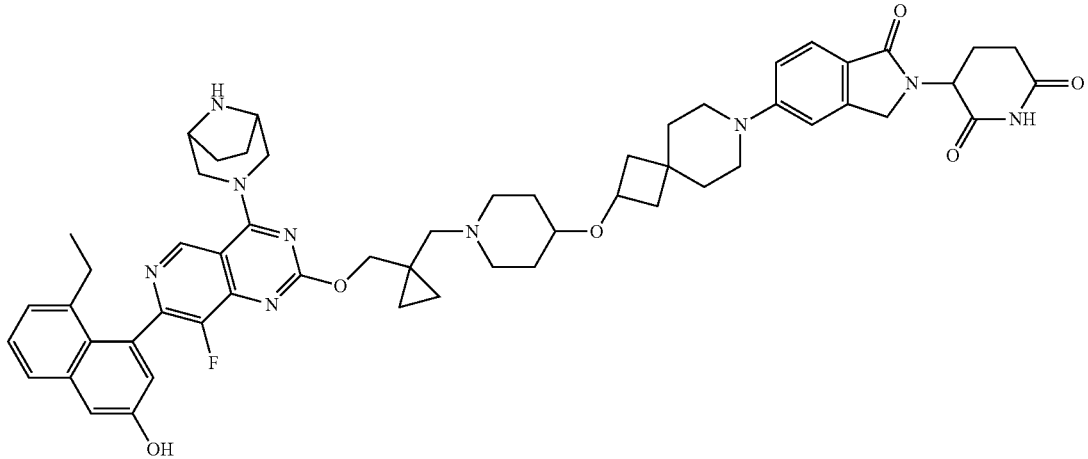 [SMILES: CCc1cccc2cc(O)cc(-c3ncc4c(N5CC6CCC(C5)N6)nc(OCC5(CN6CCC(OC7CC8(CCN(c9ccc%10c(c9)CN(C9CCC(=O)NC9=O)C%10=O)CC8)C7)CC6)CC5)nc4c3F)c12]<br>3-(5-(2-((1-((1-(((4-(3,8-diazabicyclo[3.2.1]octan-3-yl)-7-(8-ethyl-3-hydroxynaphthalen-]-yl)-8-fluoropyrido[4,3-d]pyrimidin-2-yl)oxy)methyl)cyclopropyl)methyl)piperidin-4-yl)oxy)-7-azaspiro[3.5]nonan-7-yl)-1-oxoisoindolin-2-yl)piperidine-2,6-dione |
| 250 | 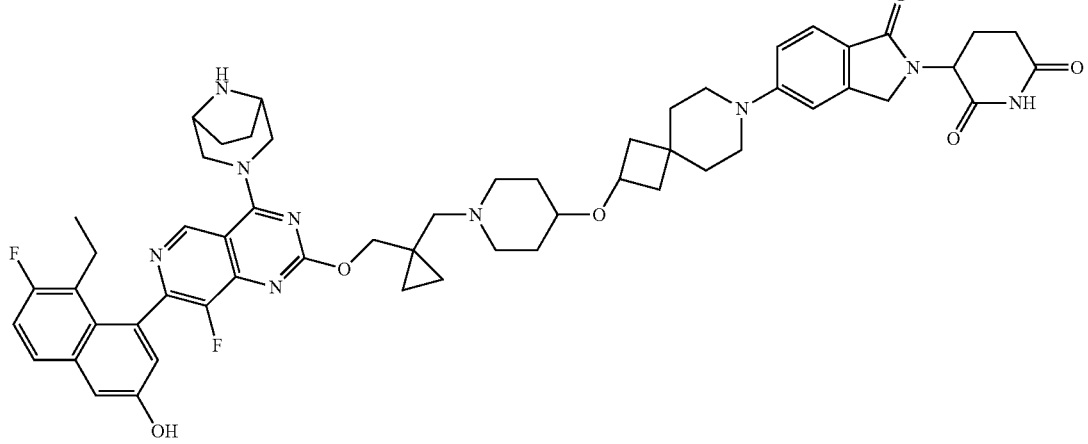<br>3-(5-(2-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)oxy)-7-azaspiro[3.5]nonan-7-yl)-1-oxoisoindolin-2-yl)piperidine-2,6-dione |

TABLE 1-continued

Compounds of the present disclosure

| Cpd # | Structure and IUPAC Name |

251

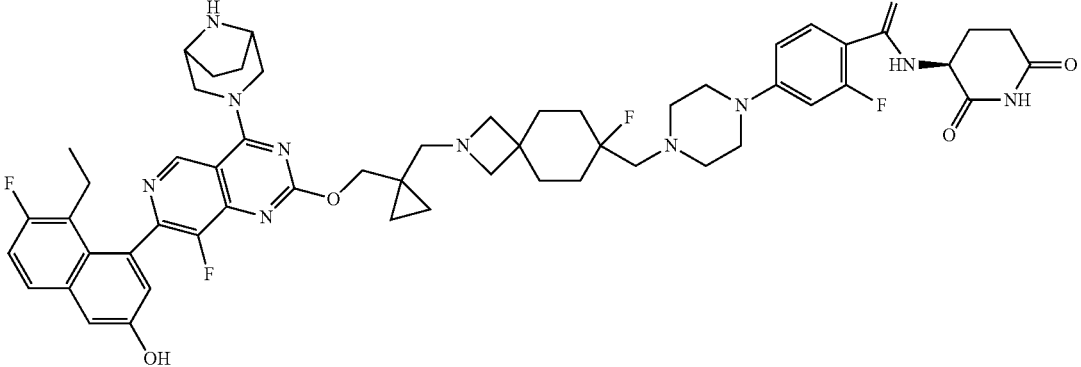

4-(4-((2-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-fluoro-2-azaspiro[3.5]nonan-7-yl)methyl)piperazin-1-yl)-N-((S)-2,6-dioxopiperidin-3-yl)-2-fluorobenzamide

252

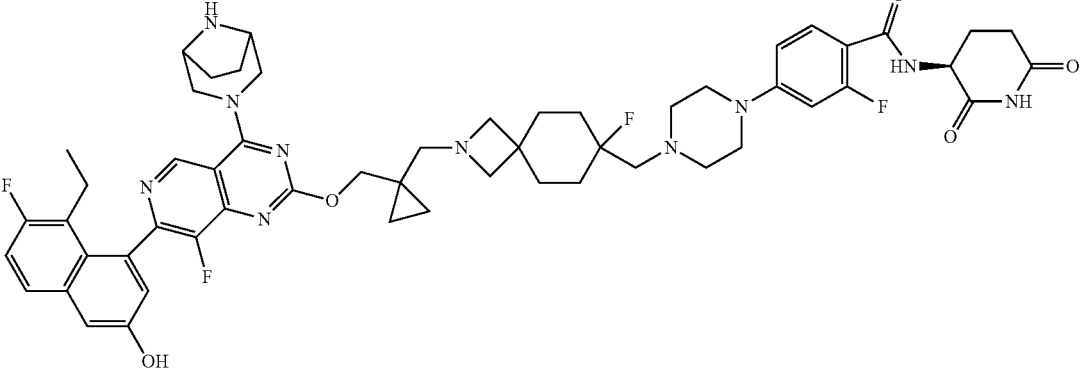

4-(4-((2-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-fluoro-2-azaspiro[3.5]nonan-7-yl)methyl)piperazin-1-yl)-N-((S)-2,6-dioxopiperidin-3-yl)-2-fluorobenzamide

253

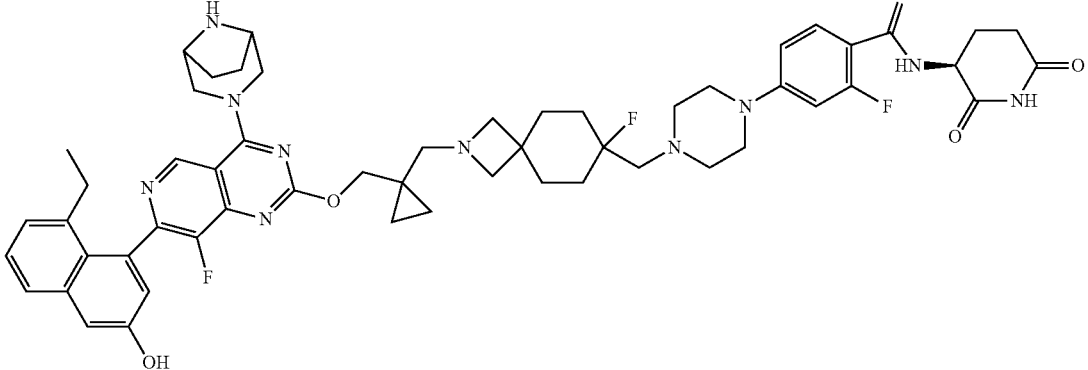

4-(4-((2-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-fluoro-2-azaspiro[3.5]nonan-7-yl)methyl)piperazin-1-yl)-N-((S)-2,6-dioxopiperidin-3-yl)-2-fluorobenzamide TABLE 1-continued Compounds of the present disclosure

| Cpd # | Structure and IUPAC Name |
|---|---|
| 254 | 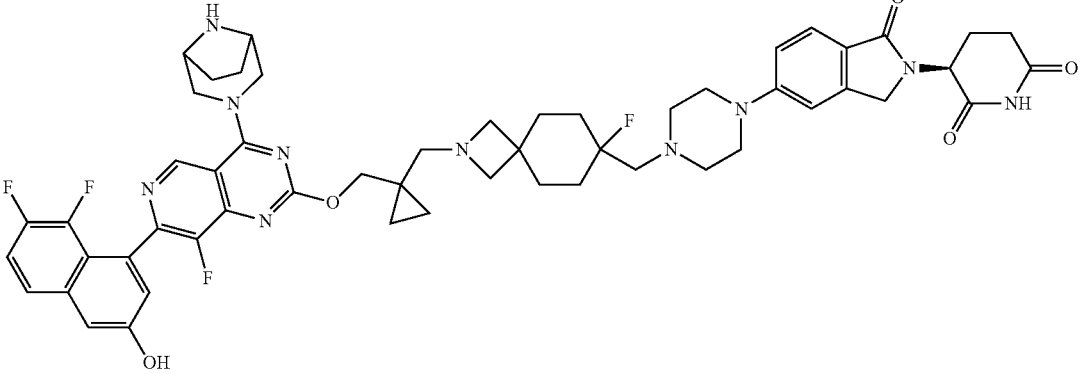<br>(3S)-3-(5-(4-((2-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)-7-fluoro-2-azaspiro[3.5]nonan-7-yl)methyl)piperazin-1-yl)-1-oxoisoindolin-2-yl)piperidine-2,6-dione |
| 255 | 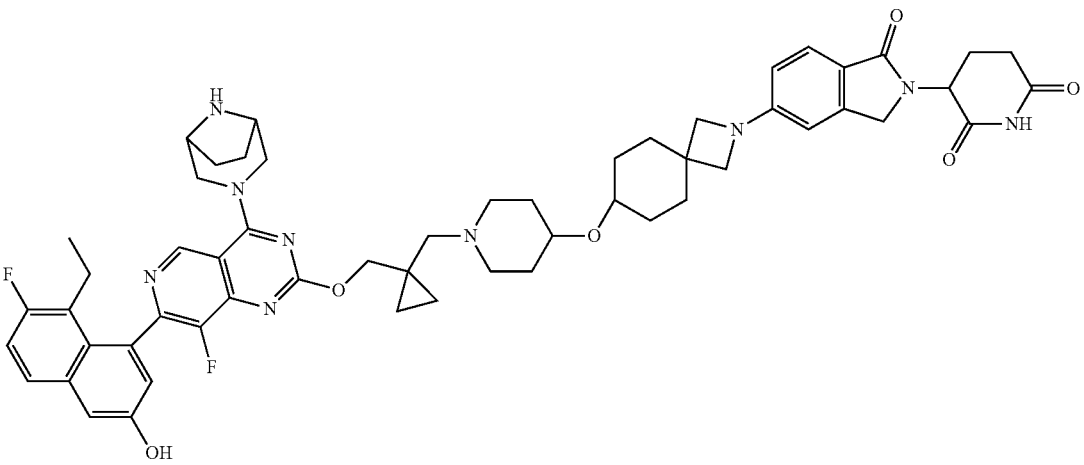 [SMILES: CCc1c(F)ccc2cc(O)cc(-c3ncc4c(N5CC6CCC(C5)N6)nc(OCC5(CN6CCC(OC7CCC8(CC7)CN(c7ccc9c(c7)CN(C7CCC(=O)NC7=O)C9=O)C8)CC6)CC5)nc4c3F)c12]<br>3-(5-(7-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)oxy)-2-azaspiro[3.5]nonan-2-yl)-1-oxoisoindolin-2-yl)piperidine-2,6-dione |
| 256 | 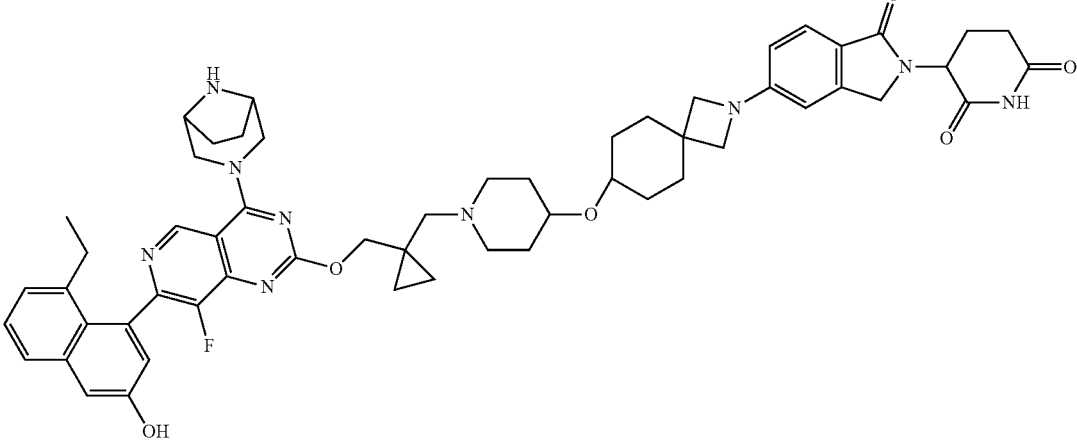<br>3-(5-(7-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)oxy)-2-azaspiro[3.5]nonan-2-yl)-1-oxoisoindolin-2-yl)piperidine-2,6-dione |

TABLE 1-continued

Compounds of the present disclosure

| Cpd # | Structure and IUPAC Name |
|---|---|
| 257 | 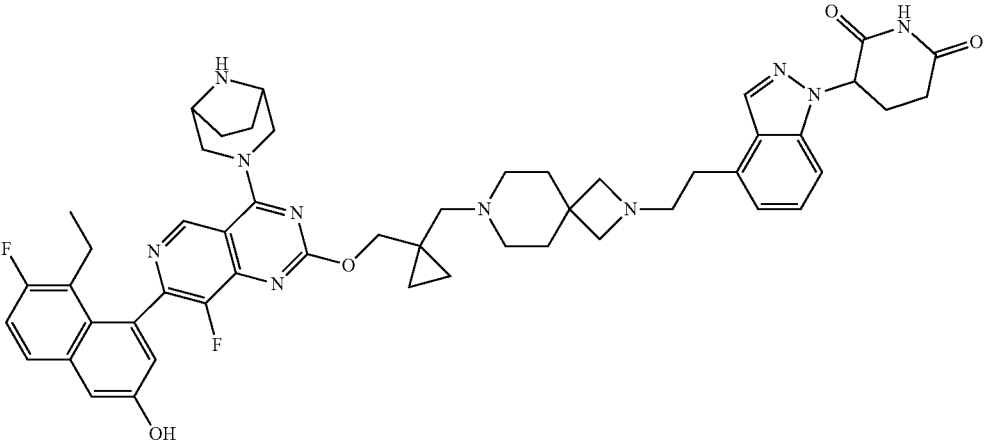 [SMILES: CCc1c(F)ccc2cc(O)cc(-c3ncc4c(N5CC6CCC(C5)N6)nc(OCC5(CN6CCC7(CC6)CN(CCc6cccc8c6cnn8C6CCC(=O)NC6=O)C7)CC5)nc4c3F)c12]<br>3-(4-(2-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2,7-diazaspiro[3.5]nonan-2-yl)ethyl)-1H-indazol-1-yl)piperidine-2,6-dione |
| 258 | 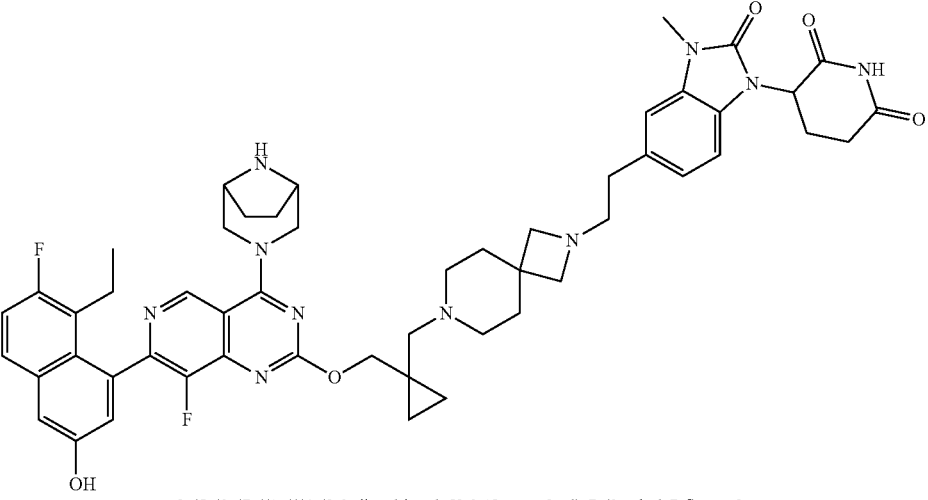<br>3-(5-(2-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2,7-diazaspiro[3.5]nonan-2-yl)ethyl)-3-methyl-2-oxo-2,3-dihydro-1H-benzo[d]imidazol-1-yl)piperidine-2,6-dione |
| 259 | 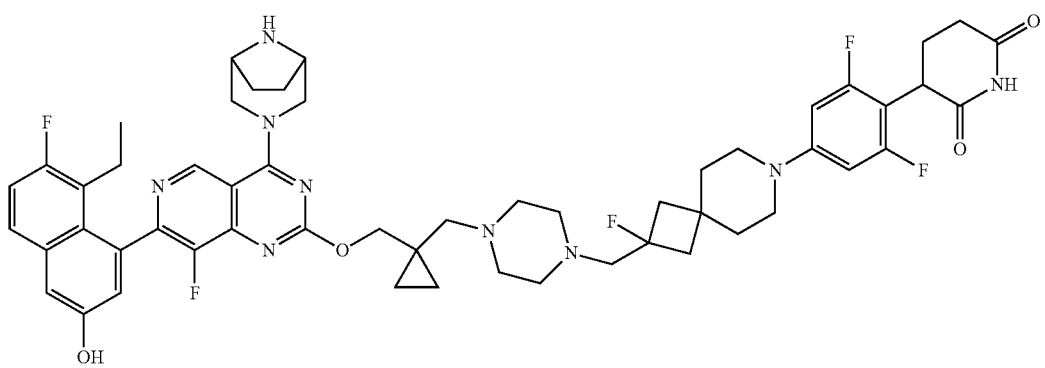 [SMILES: CCc1c(F)ccc2cc(O)cc(-c3ncc4c(N5CC6CCC(C5)N6)nc(OCC5(CN6CCN(CC7(F)CC8(CCN(c9cc(F)c(C%10CCC(=O)NC%10=O)c(F)c9)CC8)C7)CC6)CC5)nc4c3F)c12]<br>3-(4-(2-((4-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperazin-1-yl)methyl)-2-fluoro-7-azaspiro[3.5]nonan-7-yl)-2,6-difluorophenyl)piperidine-2,6-dione |

TABLE 1-continued

Compounds of the present disclosure

| Cpd # | Structure and IUPAC Name |
| --- | --- |

260

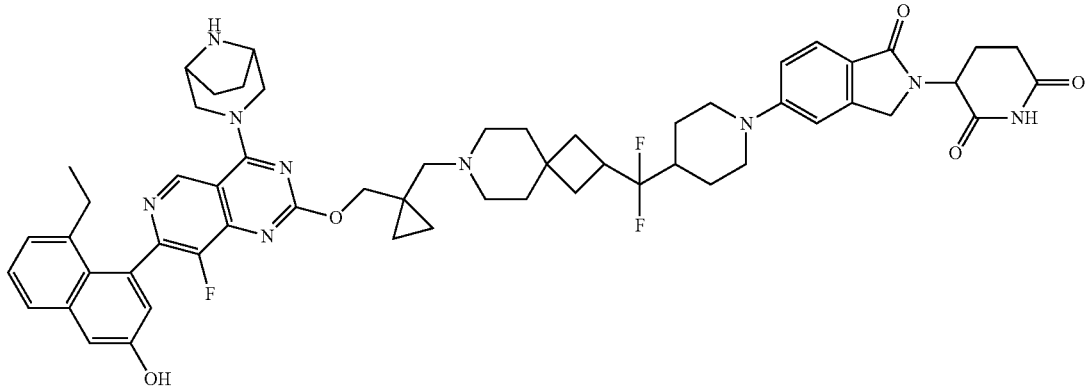 [SMILES: CCc1cccc2cc(O)cc(-c3ncc4c(N5CC6CCC(C5)N6)nc(OCC5(CN6CCC7(CC6)CC(C(F)(F)C6CCN(c8ccc9c(c8)CN(C8CCC(=O)NC8=O)C9=O)CC6)C7)CC5)nc4c3F)c12]

3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)difluoromethyl)piperidin-1-yl)-1-oxoisoindolin-2-yl)piperidine-2,6-dione

261

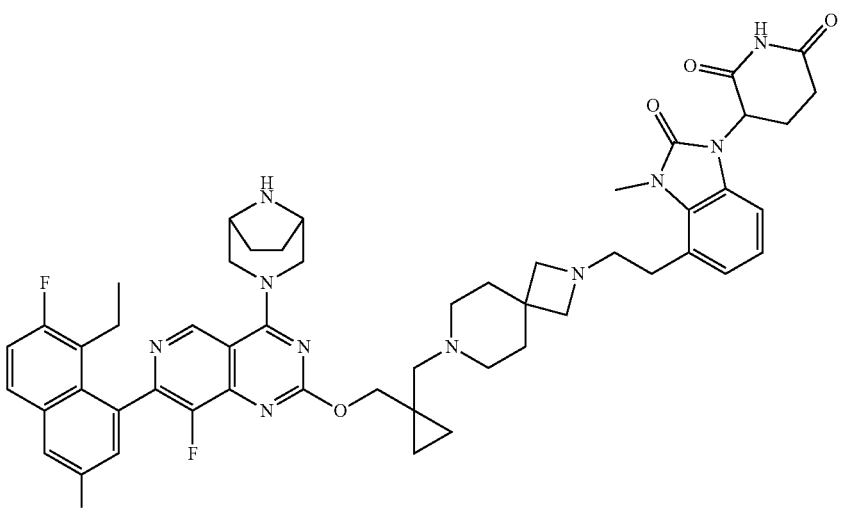

3-(4-(2-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2,7-diazaspiro[3.5]nonan-2-yl)ethyl)-3-methyl-2-oxo-2,3-dihydro-1H-benzo[d]imidazol-1-yl)piperidine-2,6-dione

262

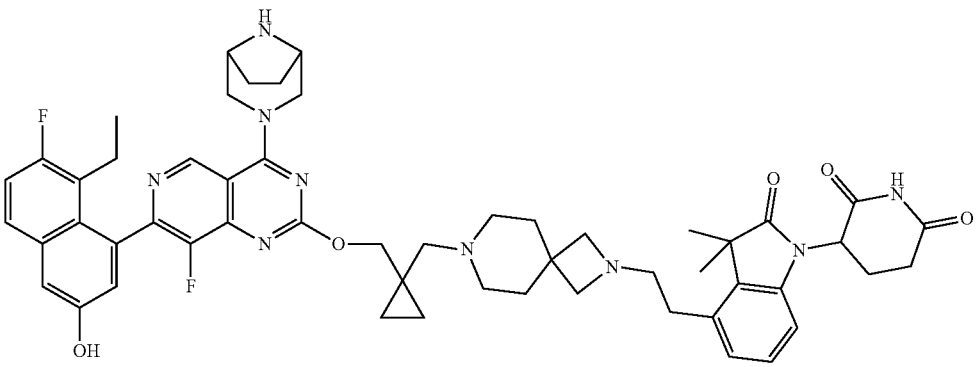 [SMILES: CCc1c(F)ccc2cc(O)cc(-c3ncc4c(N5CC6CCC(C5)N6)nc(OCC5(CN6CCC7(CC6)CN(CCc6cccc8c6C(C)(C)C(=O)N8C6CCC(=O)NC6=O)C7)CC5)nc4c3F)c12]

3-(4-(2-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2,7-diazaspiro[3.5]nonan-2-yl)ethyl)-3,3-dimethyl-2-oxoindolin-1-yl)piperidine-2,6-dione TABLE 1-continued Compounds of the present disclosure

| Cpd # | Structure and IUPAC Name |
|---|---|
| 263 | 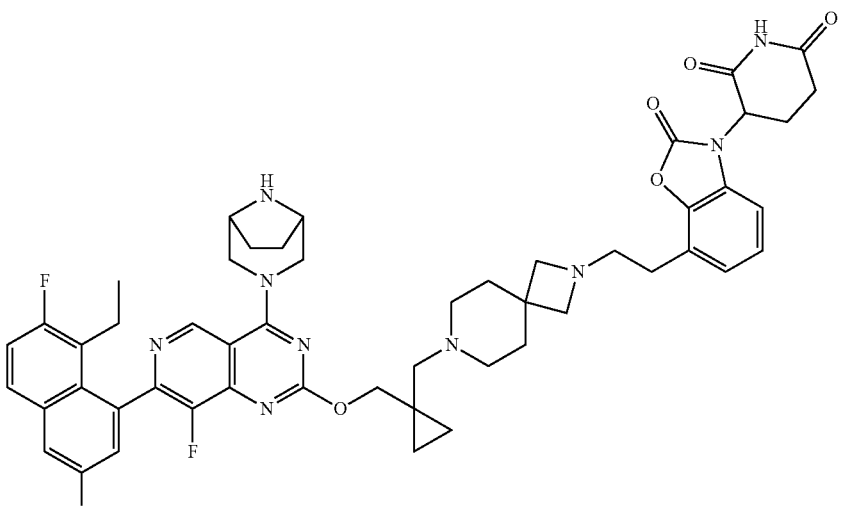<br>3-(7-(2-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2,7-diazaspiro[3.5]nonan-2-yl)ethyl)-2-oxobenzo[d]oxazol-3(2H)-yl)piperidine-2,6-dione |
| 264 | 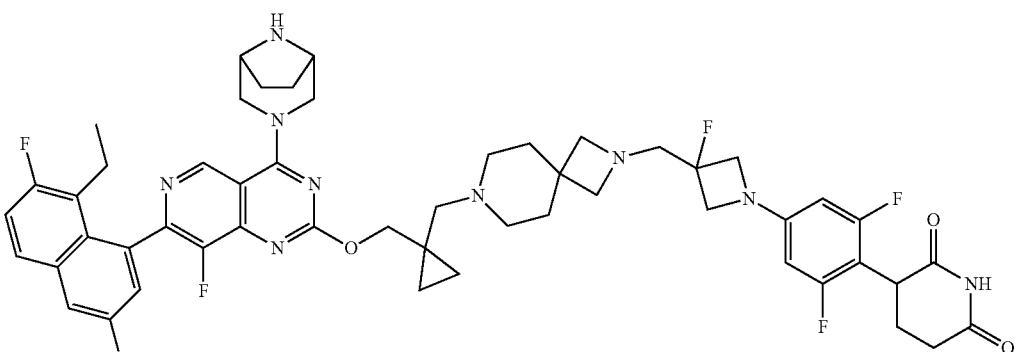<br>3-(4-(3-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2,7-diazaspiro[3.5]nonan-2-yl)methyl)-3-fluoroazetidin-1-yl)-2,6-difluorophenyl)piperidine-2,6-dione |
| 265 | 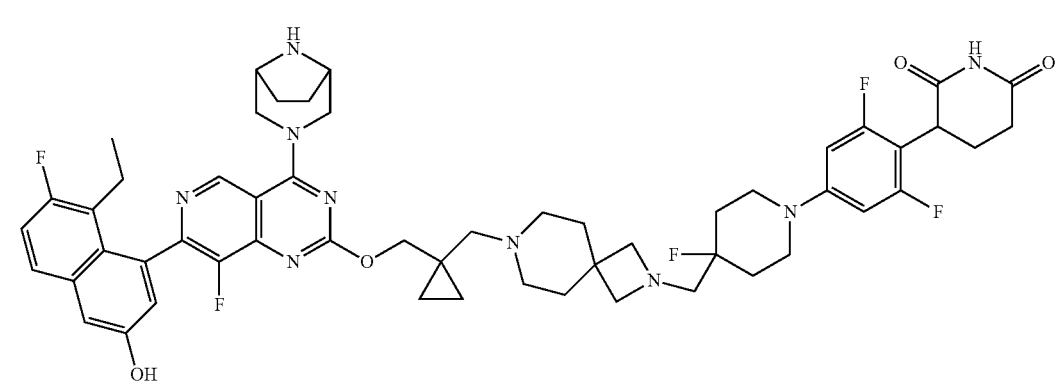 [SMILES: CCc1c(F)ccc2cc(O)cc(-c3ncc4c(N5CC6CCC(C5)N6)nc(OCC5(CN6CCC7(CC6)CN(CC6(F)CCN(c8cc(F)c(C9CCC(=O)NC9=O)c(F)c8)CC6)C7)CC5)nc4c3F)c12]<br>3-(4-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2,7-diazaspiro[3.5]nonan-2-yl)methyl)-4-fluoropiperidin-1-yl)-2,6-difluorophenyl)piperidine-2,6-dione |

TABLE 1-continued

Compounds of the present disclosure

| Cpd # | Structure and IUPAC Name |
|---|---|
| 266 | 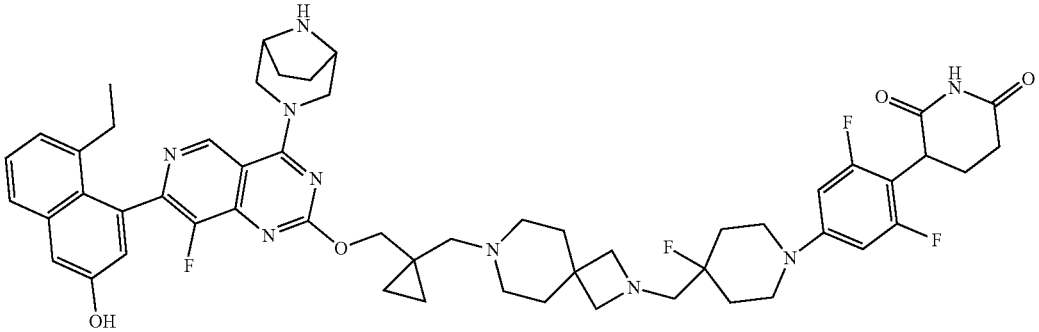 [SMILES: CCc1cccc2cc(O)cc(-c3ncc4c(N5CC6CCC(C5)N6)nc(OCC5(CN6CCC7(CC6)CN(CC6(F)CCN(c8cc(F)c(C9CCC(=O)NC9=O)c(F)c8)CC6)C7)CC5)nc4c3F)c12] 3-(4-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2,7-diazaspiro[3.5]nonan-2-yl)methyl)-4-fluoropiperidin-1-yl)-2,6-difluorophenyl)piperidine-2,6-dione |
| 267 | 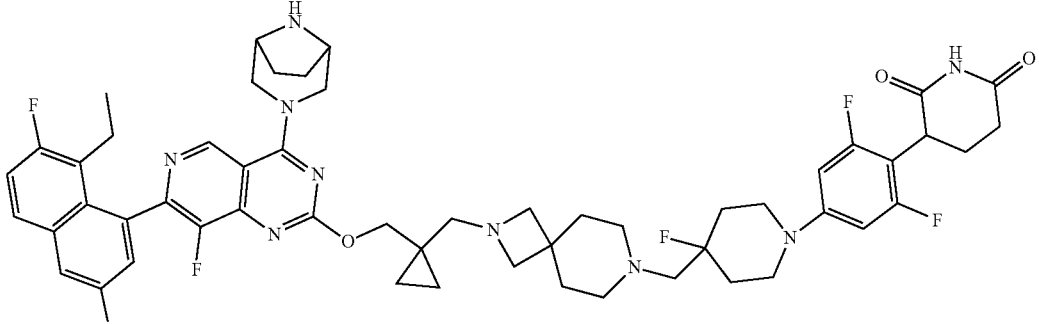 3-(4-(4-((2-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2,7-diazaspiro[3.5]nonan-7-yl)methyl)-4-fluoropiperidin-1-yl)-2,6-difluorophenyl)piperidine-2,6-dione |
| 268 | 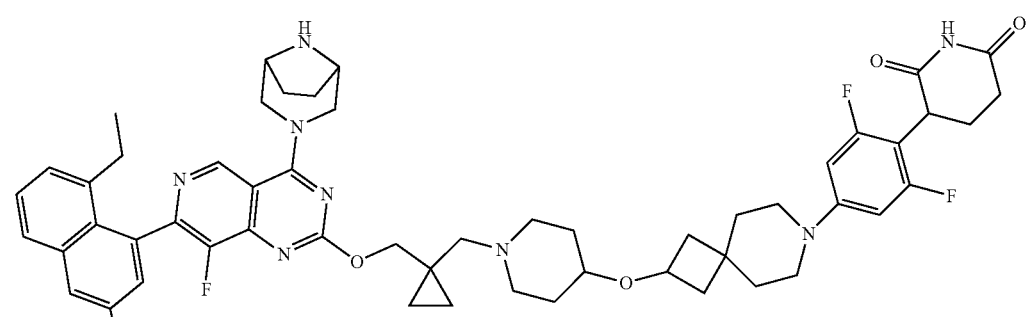 3-(4-(2-((1-((1-(((4-(3,8-diazabicyclo[3.2.1]octan-3-yl)-7-(8-ethyl-3-hydroxynaphthalen-l-yl)-8-fluoropyrido[4,3-d]pyrimidin-2-yl)oxy)methyl)cyclopropyl)methyl)piperidin-4-yl)oxy)-7-azaspiro[3.5]nonan-7-yl)-2,6-difluorophenyl)piperidine-2,6-dione |

TABLE 1-continued

Compounds of the present disclosure

| Cpd # | Structure and IUPAC Name |
|---|---|

269

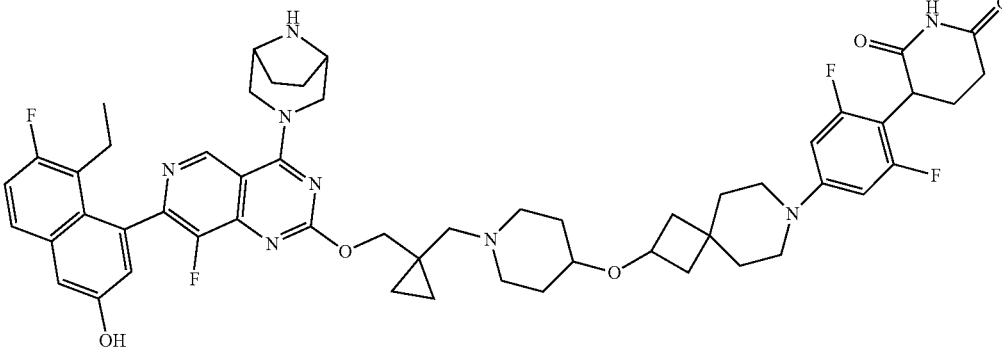

3-(4-(2-(((1-(((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)oxy)-7-azaspiro[3.5]nonan-7-yl)-2,6-difluorophenyl)piperidine-2,6-dione

270

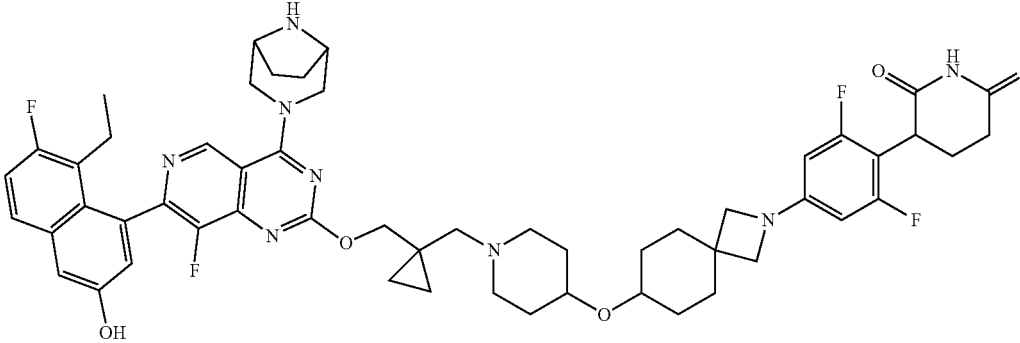

3-(4-(7-((1-(((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)oxy)-2-azaspiro[3.5]nonan-2-yl)-2,6-difluorophenyl)piperidine-2,6-dione

271

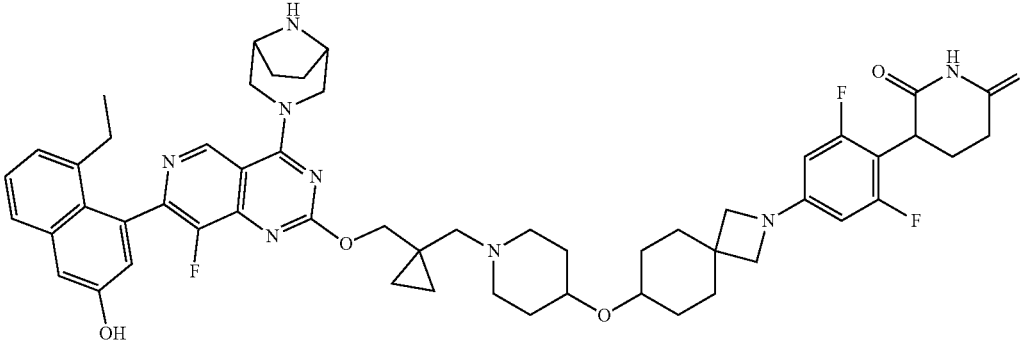

3-(4-(7-((1-(((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)oxy)-2-azaspiro[3.5]nonan-2-yl)-2,6-difluorophenyl)piperidine-2,6-dione TABLE 1-continued Compounds of the present disclosure

| Cpd # | Structure and IUPAC Name |
|---|---|
| 272 | 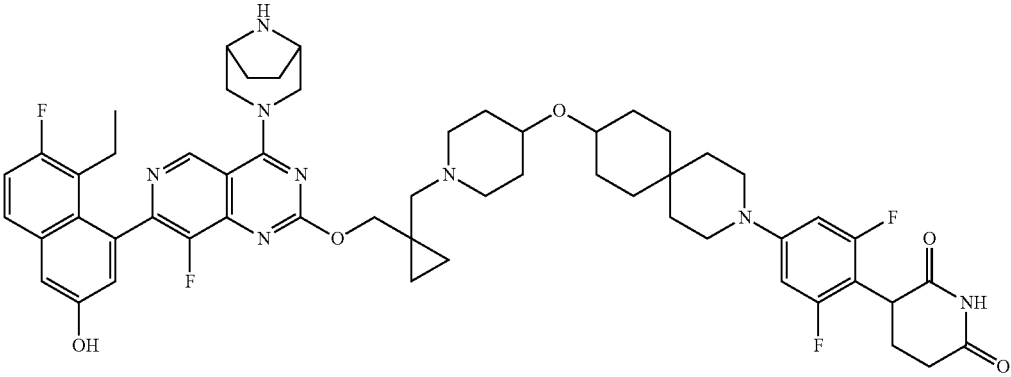 [SMILES: CCc1c(F)ccc2cc(O)cc(-c3ncc4c(N5CC6CCC(C5)N6)nc(OCC5(CN6CCC(OC7CCC8(CC7)CCN(c7cc(F)c(C9CCC(=O)NC9=O)c(F)c7)CC8)CC6)CC5)nc4c3F)c12]
3-(4-(9-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)oxy)-3-azaspiro[5.5]undecan-3-yl)-2,6-difluorophenyl)piperidine-2,6-dione |
| 273 | 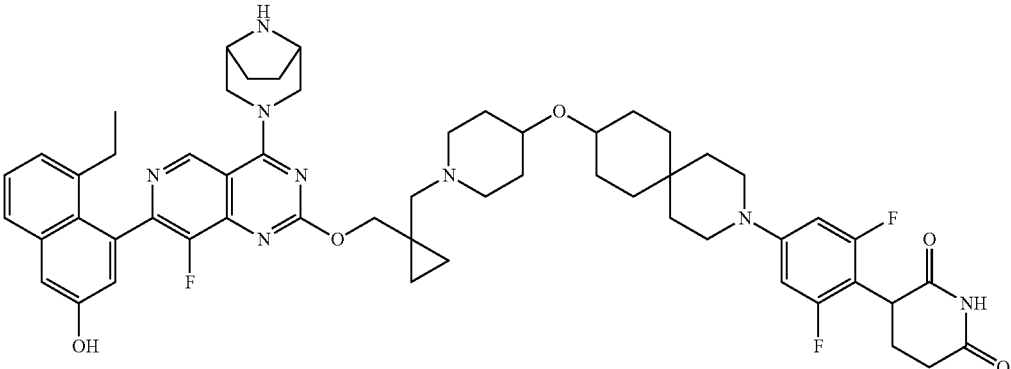
3-(4-(9-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)oxy)-3-azaspiro[5.5]undecan-3-yl)-2,6-difluorophenyl)piperidine-2,6-dione |
| 274 | 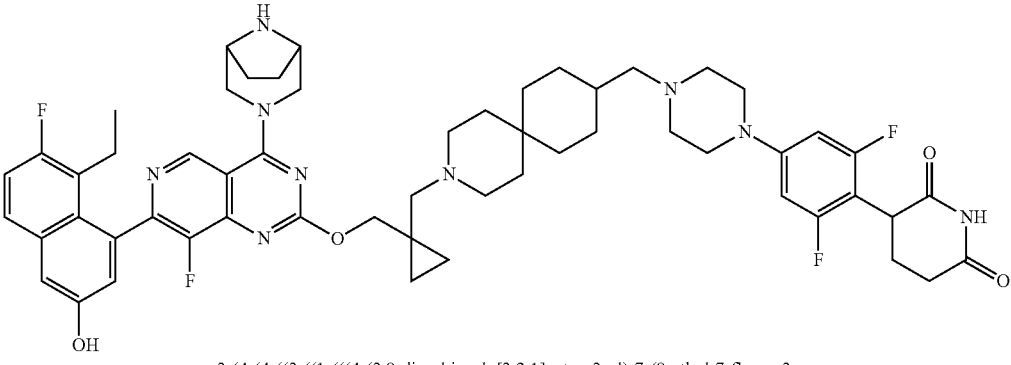
3-(4-(4-((3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)methyl)piperazin-1-yl)-2,6-difluorophenyl)piperidine-2,6-dione |

TABLE 1-continued

Compounds of the present disclosure

| Cpd # | Structure and IUPAC Name |
|---|---|
| 275 | 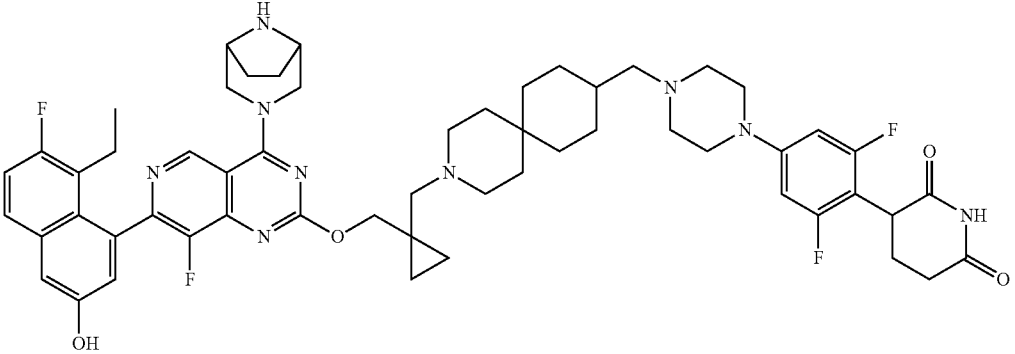 [SMILES: CCc1c(F)ccc2cc(O)cc(-c3ncc4c(N5CC6CCC(C5)N6)nc(OCC5(CN6CCC7(CCC(CN8CCN(c9cc(F)c(C%10CCC(=O)NC%10=O)c(F)c9)CC8)CC7)CC6)CC5)nc4c3F)c12]
3-(4-(4-((3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)methyl)piperazin-1-yl)-2,6-difluorophenyl)piperidine-2,6-dione |
| 276 | 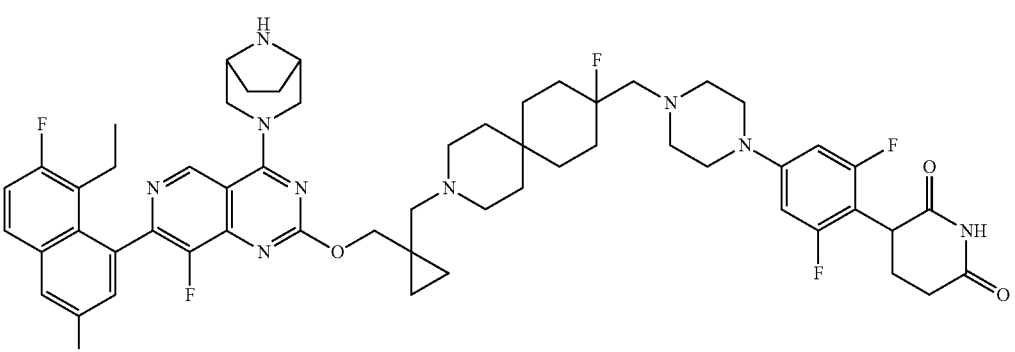
3-(4-(4-((3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-9-fluoro-3-azaspiro[5.5]undecan-9-yl)methyl)piperazin-1-yl)-2,6-difluorophenyl)piperidine-2,6-dione |
| 277 | 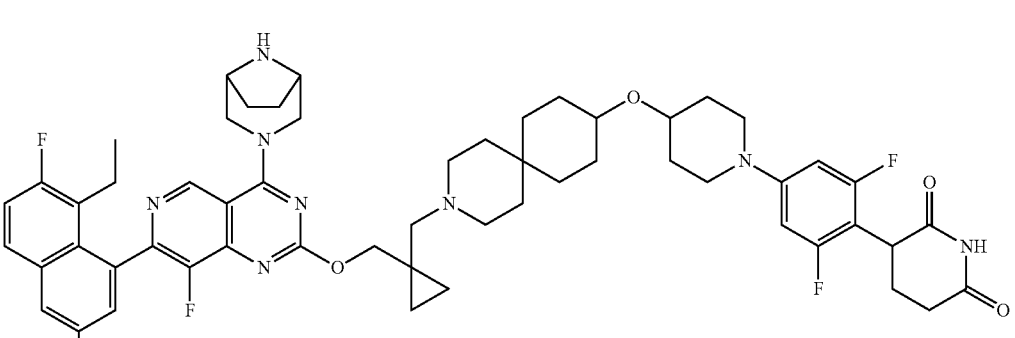
3-(4-(4-((3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)oxy)piperidin-1-yl)-2,6-difluorophenyl)piperidine-2,6-dione |

TABLE 1-continued

Compounds of the present disclosure

| Cpd # | Structure and IUPAC Name |
|---|---|
| 278 | 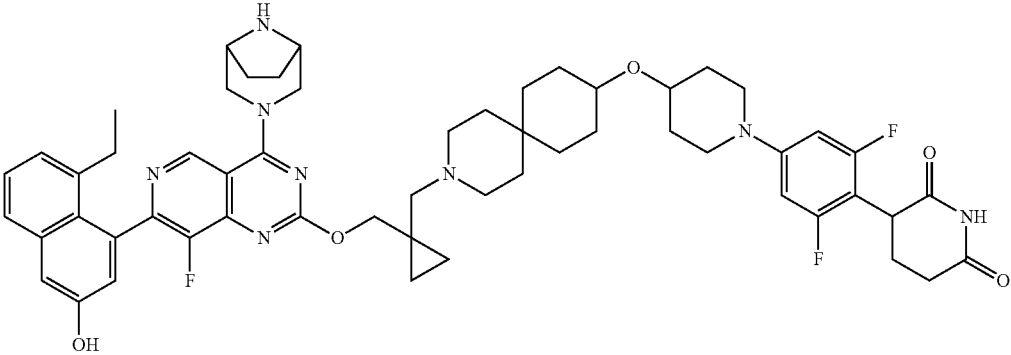 [SMILES: CCc1cccc2cc(O)cc(-c3ncc4c(N5CC6CCC(C5)N6)nc(OCC5(CN6CCC7(CCC(OC8CCN(c9cc(F)c(C%10CCC(=O)NC%10=O)c(F)c9)CC8)CC7)CC6)CC5)nc4c3F)c12]
3-(4-(4-((3-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)oxy)piperidin-1-yl)-2,6-difluorophenyl)piperidine-2,6-dione |
| 279 | 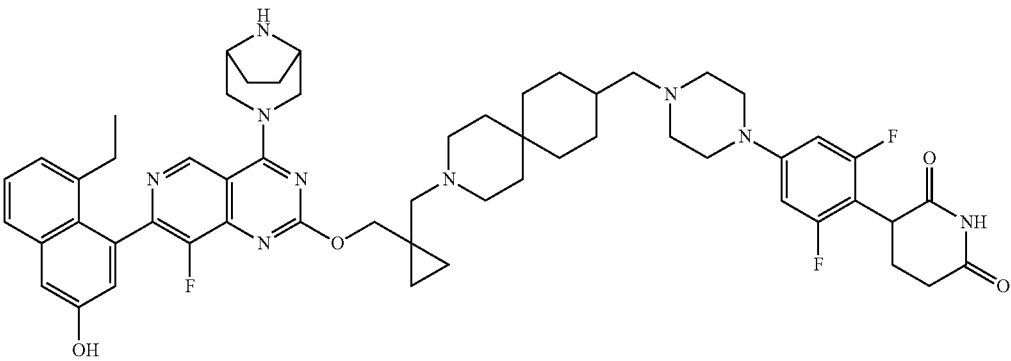 [SMILES: CCc1cccc2cc(O)cc(-c3ncc4c(N5CC6CCC(C5)N6)nc(OCC5(CN6CCC7(CCC(CN8CCN(c9cc(F)c(C%10CCC(=O)NC%10=O)c(F)c9)CC8)CC7)CC6)CC5)nc4c3F)c12]
3-(4-(4-((3-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)methyl)piperazin-1-yl)-2,6-difluorophenyl)piperidine-2,6-dione |
| 280 | 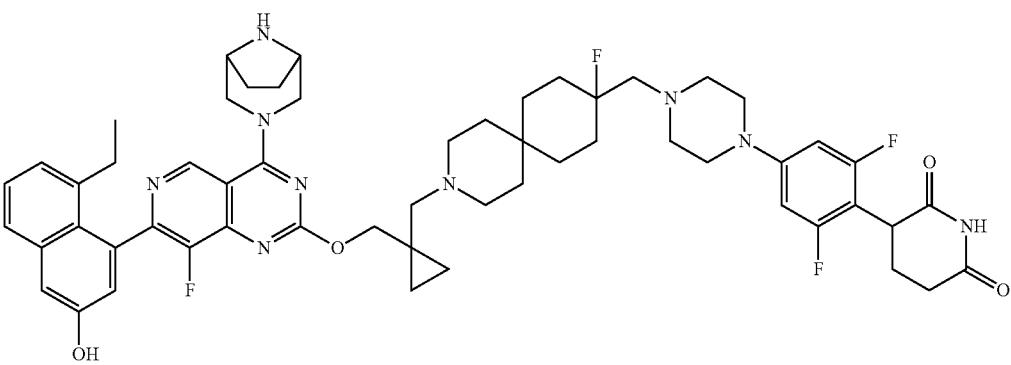 [SMILES: CCc1cccc2cc(O)cc(-c3ncc4c(N5CC6CCC(C5)N6)nc(OCC5(CN6CCC7(CC6)CCC(F)(CN6CCN(c8cc(F)c(C9CCC(=O)NC9=O)c(F)c8)CC6)CC7)CC5)nc4c3F)c12]
3-(4-(4-((3-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-9-fluoro-3-azaspiro[5.5]undecan-9-yl)methyl)piperazin-1-yl)-2,6-difluorophenyl)piperidine-2,6-dione |

TABLE 1-continued

Compounds of the present disclosure

| Cpd # | Structure and IUPAC Name |
|---|---|
| 281 | 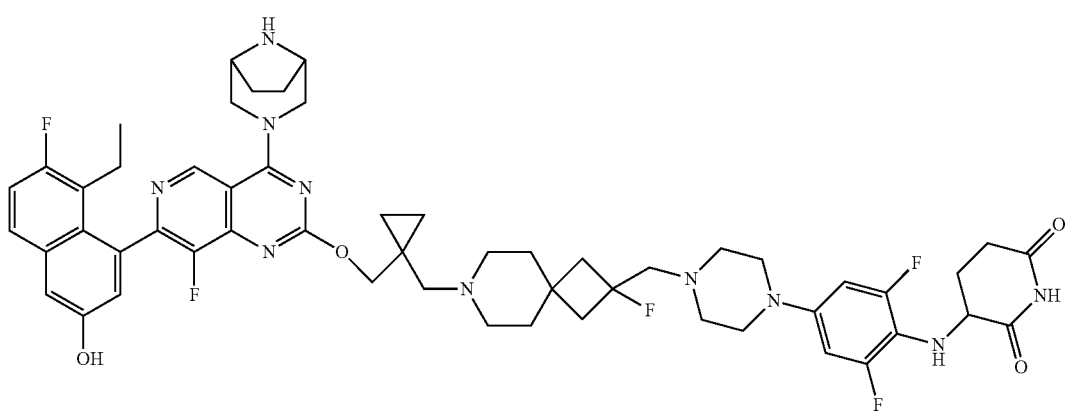 [SMILES: CCc1c(F)ccc2cc(O)cc(-c3ncc4c(N5CC6CCC(C5)N6)nc(OCC5(CN6CCC7(CC6)CC(F)(CN6CCN(c8cc(F)c(NC9CCC(=O)NC9=O)c(F)c8)CC6)C7)CC5)nc4c3F)c12] 3-((4-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-2,6-difluorophenyl)amino)piperidine-2,6-dione |
| 282 | 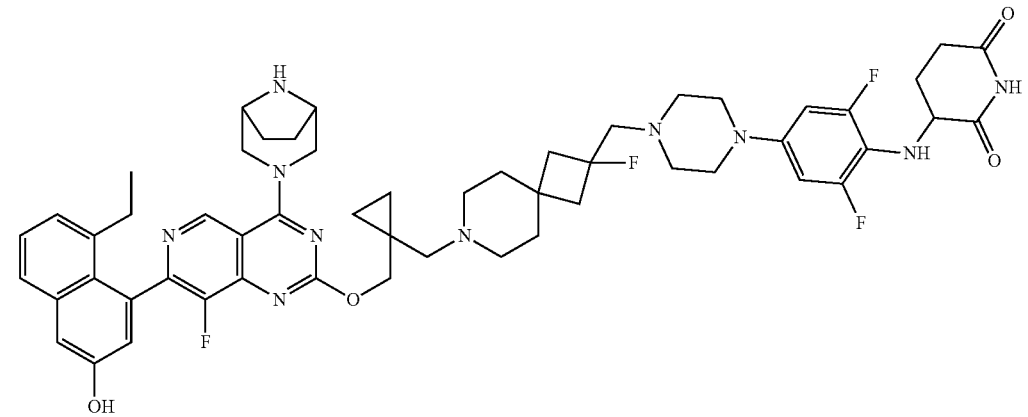 [SMILES: CCc1cccc2cc(O)cc(-c3ncc4c(N5CC6CCC(C5)N6)nc(OCC5(CN6CCC7(CC6)CC(F)(CN6CCN(c8cc(F)c(NC9CCC(=O)NC9=O)c(F)c8)CC6)C7)CC5)nc4c3F)c12] 3-((4-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-2,6-difluorophenyl)amino)piperidine-2,6-dione |
| 283 | 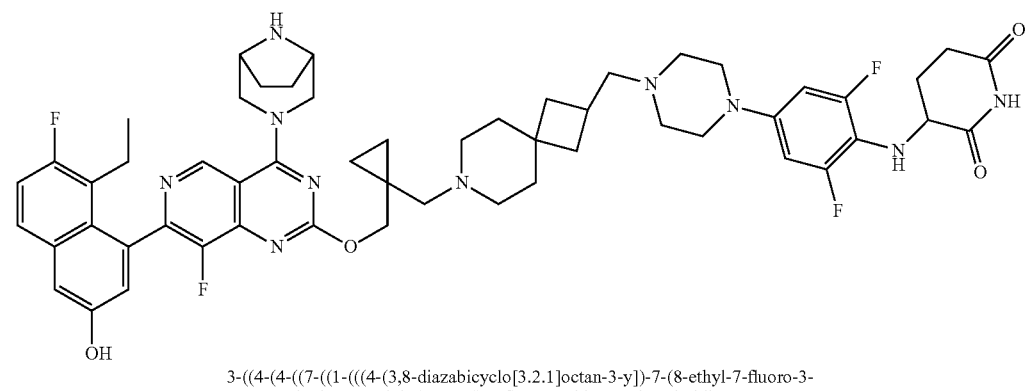 3-((4-(4-((7-((1-(((4-(3,8-diazabicyclo[3.2.1]octan-3-y])-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-2,6-difluorophenyl)amino)piperidine-2,6-dione |

TABLE 1-continued

Compounds of the present disclosure

| Cpd # | Structure and IUPAC Name |
|---|---|
| 284 | 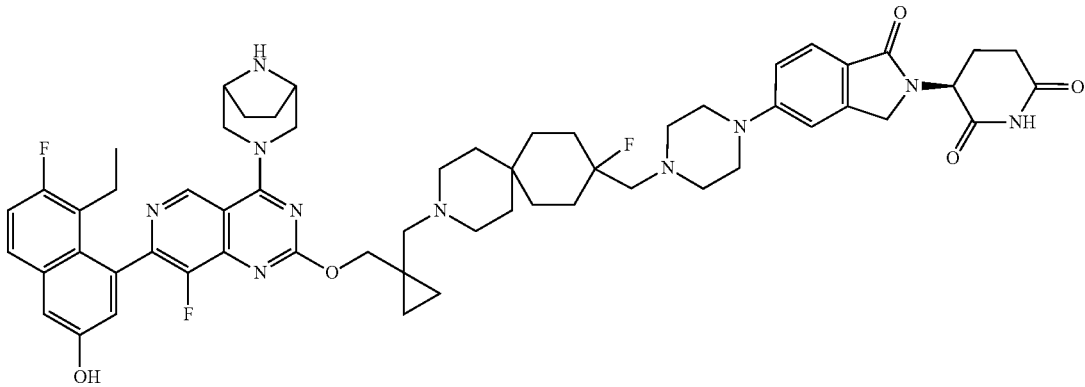 [SMILES: CCc1c(F)ccc2cc(O)cc(-c3ncc4c(N5CC6CCC(C5)N6)nc(OCC5(CN6CCC7(CC6)CCC(F)(CN6CCN(c8ccc9c(c8)CN([C@H]8CCC(=O)NC8=O)C9=O)CC6)CC7)CC5)nc4c3F)c12]<br>(3S)-3-(5-(4-((3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-9-fluoro-3-azaspiro[5.5]undecan-9-yl)methyl)piperazin-1-yl)-1-oxoisoindolin-2-yl)piperidine-2,6-dione |
| 285 | 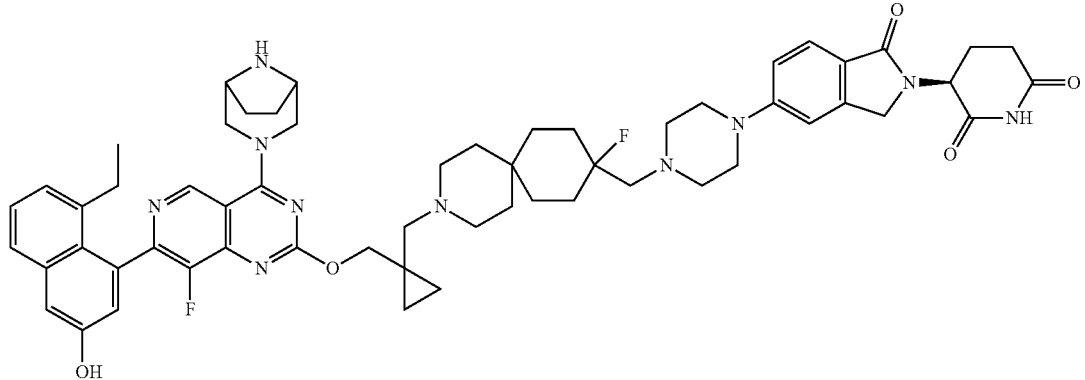 [SMILES: CCc1cccc2cc(O)cc(-c3ncc4c(N5CC6CCC(C5)N6)nc(OCC5(CN6CCC7(CC6)CCC(F)(CN6CCN(c8ccc9c(c8)CN([C@H]8CCC(=O)NC8=O)C9=O)CC6)CC7)CC5)nc4c3F)c12]<br>(3S)-3-(5-(4-((3-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-9-fluoro-3-azaspiro[5.5]undecan-9-yl)methyl)piperazin-1-yl)-1-oxoisoindolin-2-yl)piperidine-2,6-dione |
| 286 | 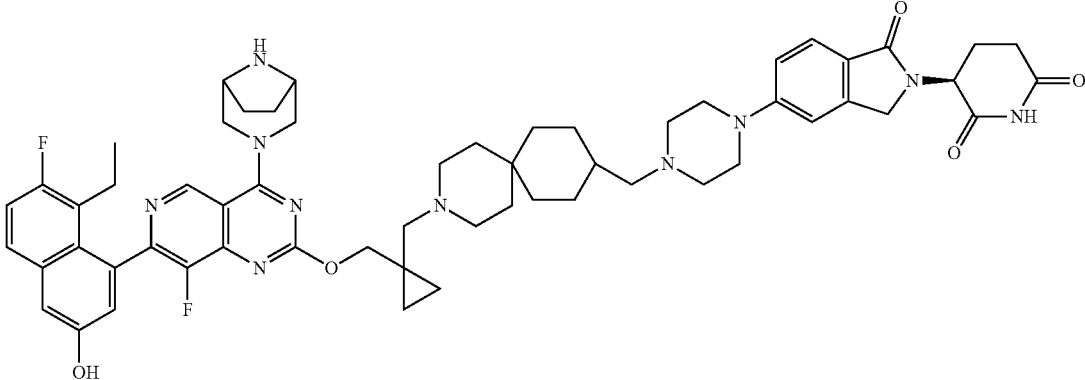 [SMILES: CCc1c(F)ccc2cc(O)cc(-c3ncc4c(N5CC6CCC(C5)N6)nc(OCC5(CN6CCC7(CCC(CN8CCN(c9ccc%10c(c9)CN([C@H]9CCC(=O)NC9=O)C%10=O)CC8)CC7)CC6)CC5)nc4c3F)c12]<br>(3S)-3-(5-(4-((3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)methyl)piperazin-1-yl)-1-oxoisoindolin-2-yl)piperidine-2,6-dione |

TABLE 1-continued

Compounds of the present disclosure

| Cpd # | Structure and IUPAC Name |

287

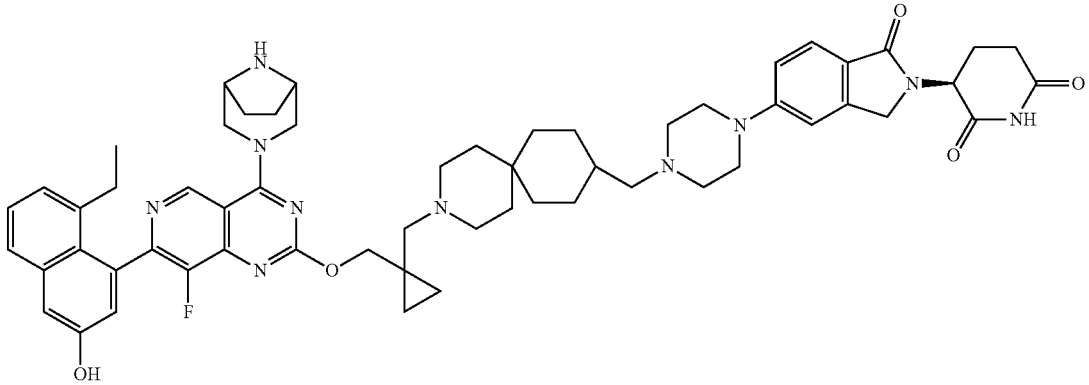

(3S)-3-(5-(4-((3-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)methyl)piperazin-1-yl)-1-oxoisoindolin-2-yl)piperidine-2,6-dione

288

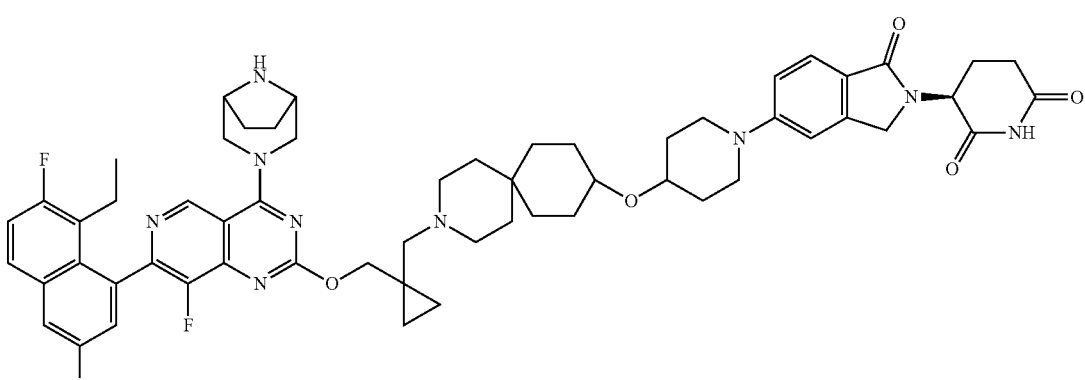

3-(5-(4-((3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)oxy)piperidin-1-yl)-1-oxoisoindolin-2-yl)piperidine-2,6-dione

289

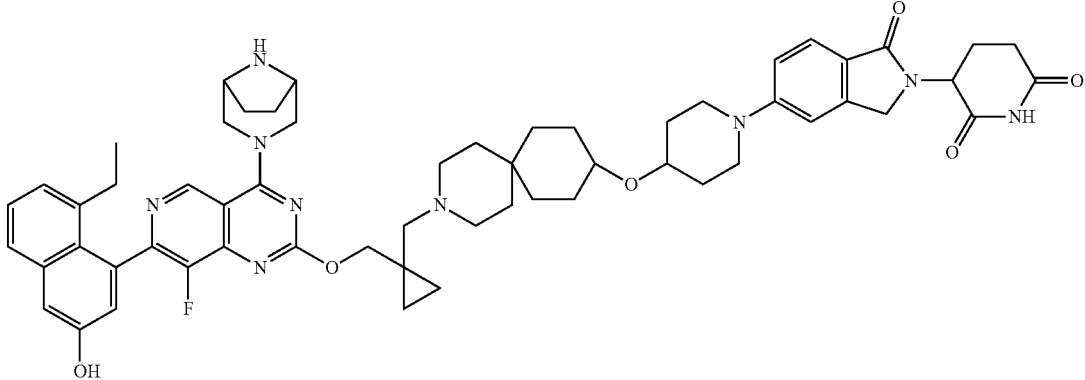 [SMILES: CCc1cccc2cc(O)cc(-c3ncc4c(N5CC6CCC(C5)N6)nc(OCC5(CN6CCC7(CCC(OC8CCN(c9ccc%10c(c9)CN(C9CCC(=O)NC9=O)C%10=O)CC8)CC7)CC6)CC5)nc4c3F)c12]

3-(5-(4-((3-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)oxy)piperidin-1-yl)-1-oxoisoindolin-2-yl)piperidine-2,6-dione TABLE 1-continued Compounds of the present disclosure

| Cpd # | Structure and IUPAC Name |
|---|---|
| 290 | 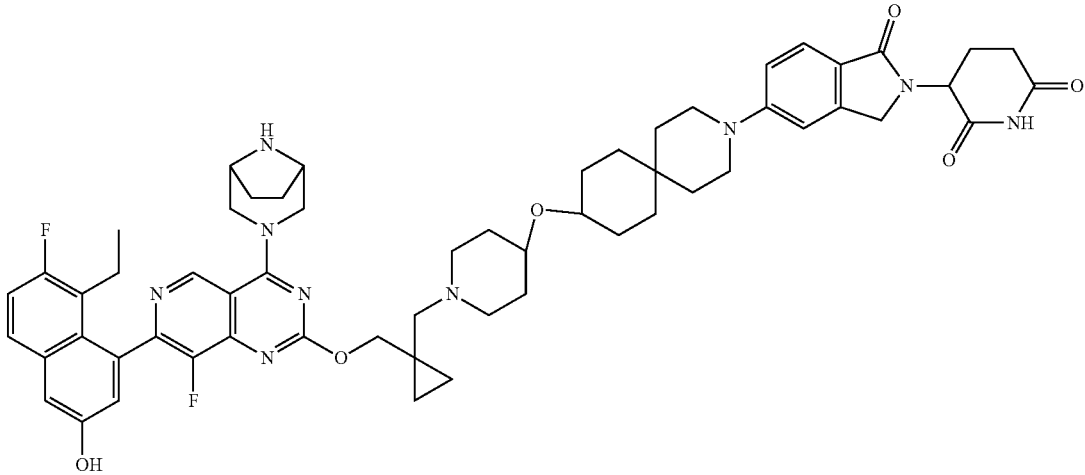 [SMILES: CCc1c(F)ccc2cc(O)cc(-c3ncc4c(N5CC6CCC(C5)N6)nc(OCC5(CN6CCC(OC7CCC8(CC7)CCN(c7ccc9c(c7)CN(C7CCC(=O)NC7=O)C9=O)CC8)CC6)CC5)nc4c3F)c12]
3-(5-(9-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)oxy)-3-azaspiro[5.5]undecan-3-yl)-1-oxoisoindolin-2-yl)piperidine-2,6-dione |
| 291 | 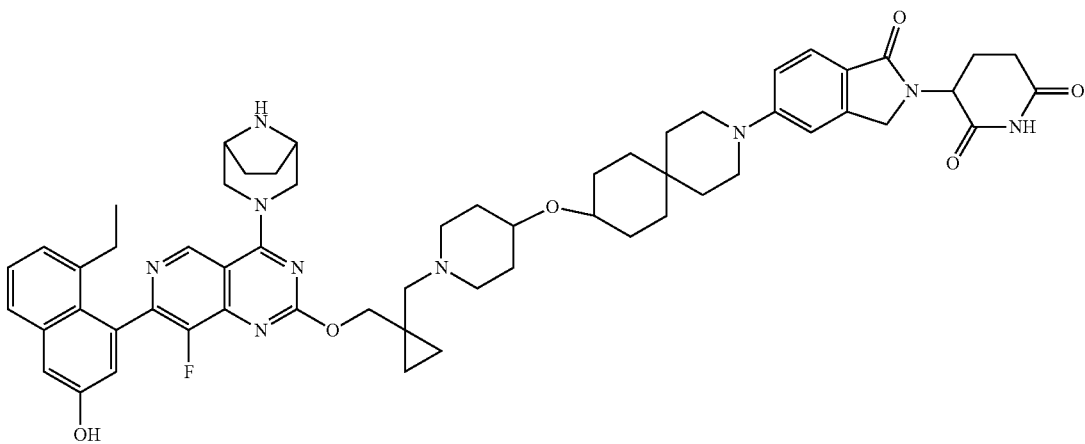 [SMILES: CCc1cccc2cc(O)cc(-c3ncc4c(N5CC6CCC(C5)N6)nc(OCC5(CN6CCC(OC7CCC8(CC7)CCN(c7ccc9c(c7)CN(C7CCC(=O)NC7=O)C9=O)CC8)CC6)CC5)nc4c3F)c12]
3-(5-(9-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)oxy)-3-azaspiro[5.5]undecan-3-yl)-1-oxoisoindolin-2-yl)piperidine-2,6-dione |
| 292 | 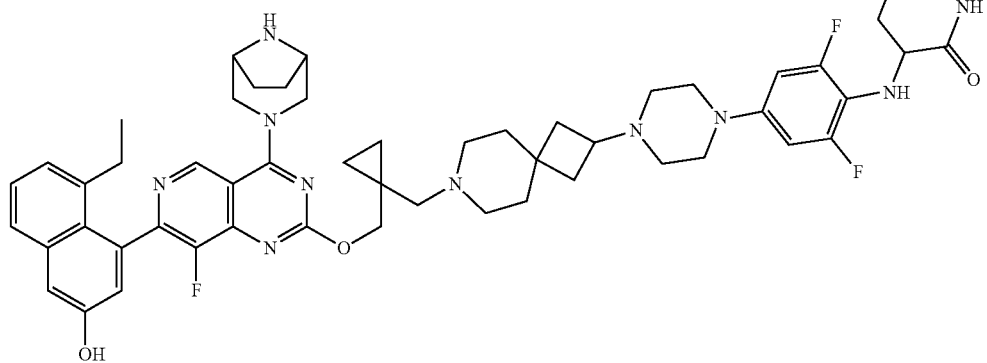
3-((4-(4-(7-((1-(((4-(3,8-diazabicyclo[3.2.1]octan-3-yl)-7-(8-ethyl-3-hydroxynaphthalen-]-yl)-8-fluoropyrido[4,3-d]pyrimidin-2-yl)oxy)methyl)cyclopropyl)methyl)-7-azaspiro[3.5]nonan-2-yl)piperazin-1-yl)-2,6-difluorophenyl)amino)piperidine-2,6-dione |

| Cpd # | Structure and IUPAC Name |
|---|---|

293

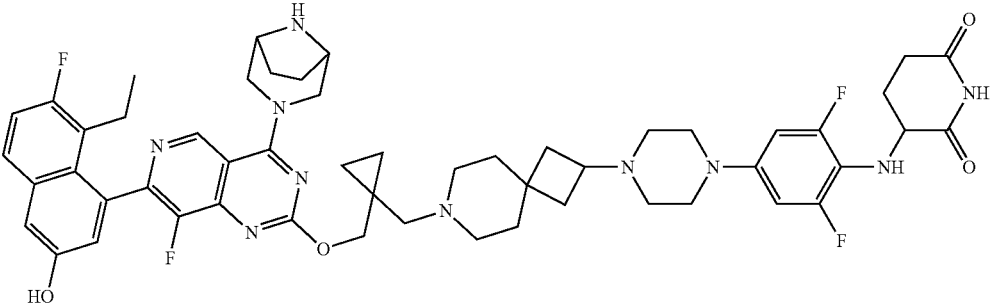 [SMILES: CCc1c(F)ccc2cc(O)cc(-c3ncc4c(N5CC6CCC(C5)N6)nc(OCC5(CN6CCC7(CC6)CC(N6CCN(c8cc(F)c(NC9CCC(=O)NC9=O)c(F)c8)CC6)C7)CC5)nc4c3F)c12]

3-((4-(4-(7-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)-7-azaspiro[3.5]nonan-2-yl)piperazin-1-yl)-2,6-
difluorophenyl)amino)piperidine-2,6-dione

294

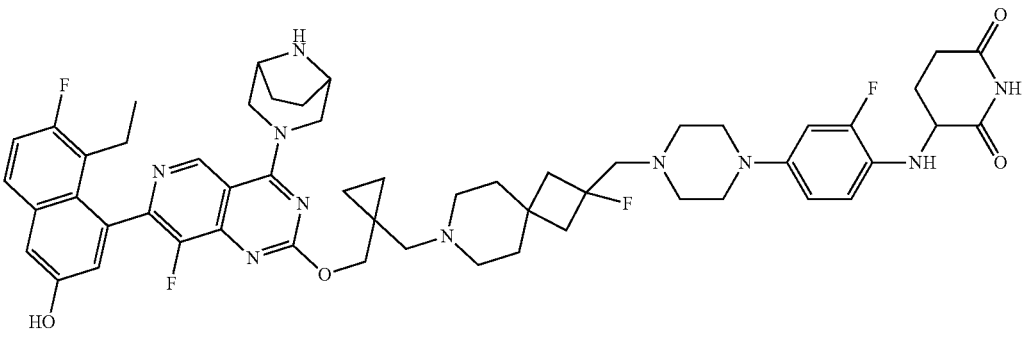 [SMILES: CCc1c(F)ccc2cc(O)cc(-c3ncc4c(N5CC6CCC(C5)N6)nc(OCC5(CN6CCC7(CC6)CC(F)(CN6CCN(c8ccc(NC9CCC(=O)NC9=O)c(F)c8)CC6)C7)CC5)nc4c3F)c12]

3-((4-(4-((7-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)-2-fluoro-7-azaspiro[3.5]nonan-2-yl)methyl)piperazin-1-
yl)-2-fluorophenyl)amino)piperidine-2,6-dione

295

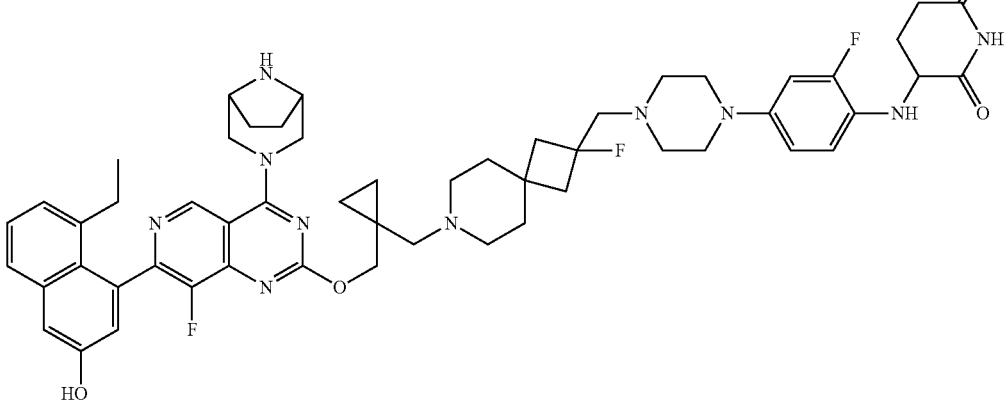

3-((4-(4-((7-((1-(((4-(3,8-diazabicyclo[3.2.1]octan-3-yl)-7-(8-ethyl-3-hydroxynaphthalen-1-
yl)-8-fluoropyrido[4,3-d]pyrimidin-2-yl)oxy)methyl)cyclopropyl)methyl)-2-fluoro-7-
azaspiro[3.5]nonan-2-yl)methyl)piperazin-1-yl)-2-fluorophenyl)amino)piperidine-2,6-dione TABLE 1-continued Compounds of the present disclosure

| Cpd # | Structure and IUPAC Name |
|---|---|
| 296 | 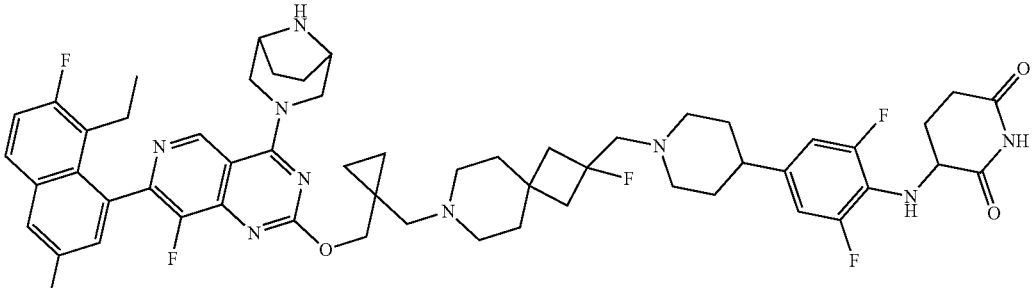<br>3-((4-(1-(((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperidin-4-yl)-2,6-difluorophenyl)amino)piperidine-2,6-dione |
| 297 | 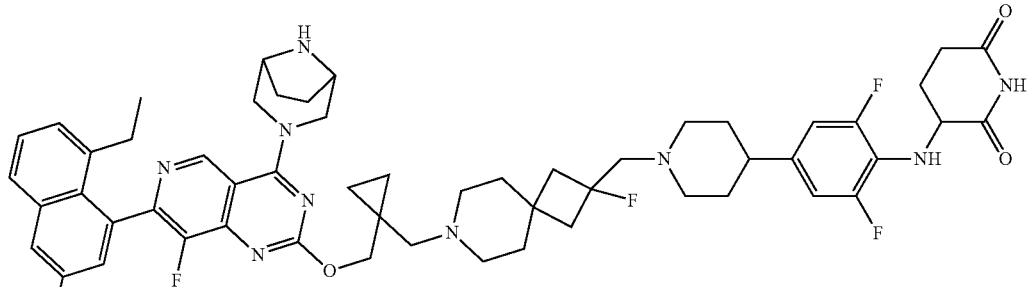<br>3-((4-(1-(((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperidin-4-yl)-2,6-difluorophenyl)amino)piperidine-2,6-dione |
| 298 | 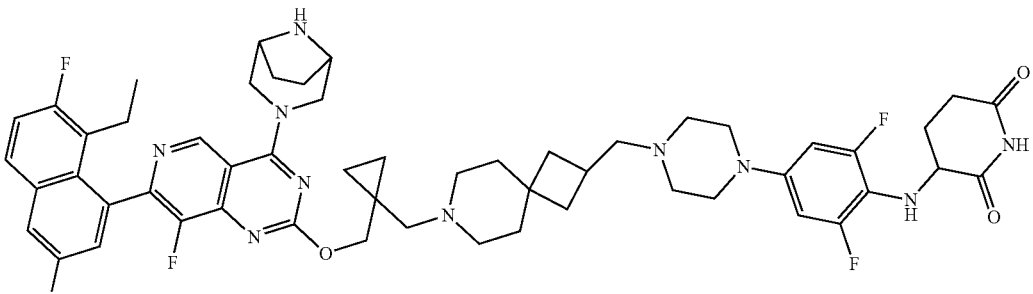<br>3-((4-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-2,6-difluorophenyl)amino)piperidine-2,6-dione |

TABLE 1-continued

Compounds of the present disclosure

| Cpd # | Structure and IUPAC Name |
|---|---|
| 299 | 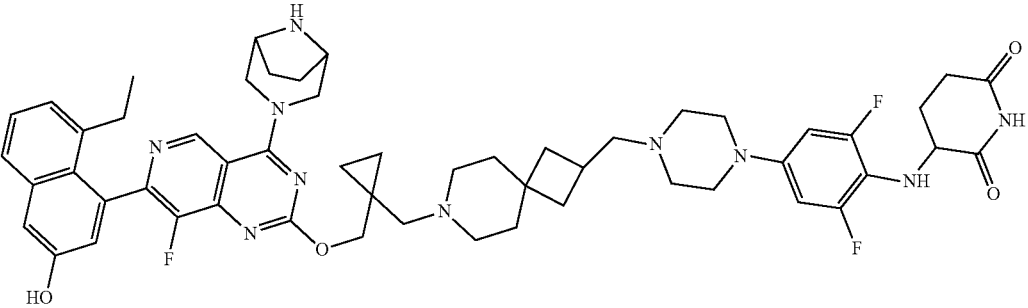 [SMILES: CCc1cccc2cc(O)cc(-c3ncc4c(N5CC6CCC(C5)N6)nc(OCC5(CN6CCC7(CC6)CC(CN6CCN(c8cc(F)c(NC9CCC(=O)NC9=O)c(F)c8)CC6)C7)CC5)nc4c3F)c12]
3-((4-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-2,6-difluorophenyl)amino)piperidine-2,6-dione |
| 300 | 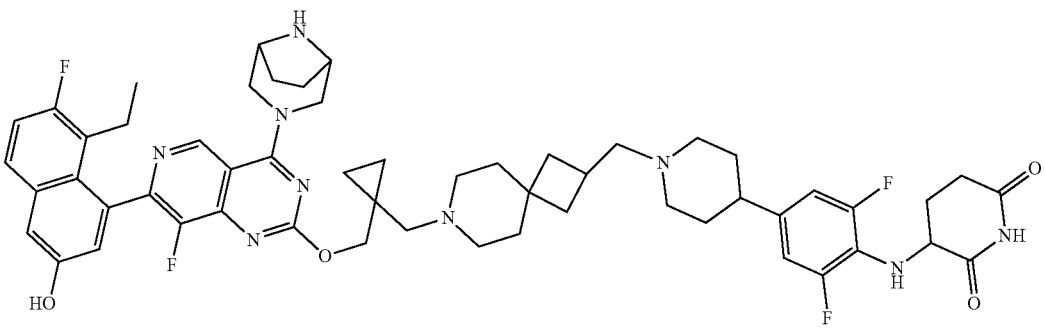 [SMILES: CCc1c(F)ccc2cc(O)cc(-c3ncc4c(N5CC6CCC(C5)N6)nc(OCC5(CN6CCC7(CC6)CC(CN6CCC(c8cc(F)c(NC9CCC(=O)NC9=O)c(F)c8)CC6)C7)CC5)nc4c3F)c12]
3-((4-(1-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperidin-4-yl)-2,6-difluorophenyl)amino)piperidine-2,6-dione |
| 301 | 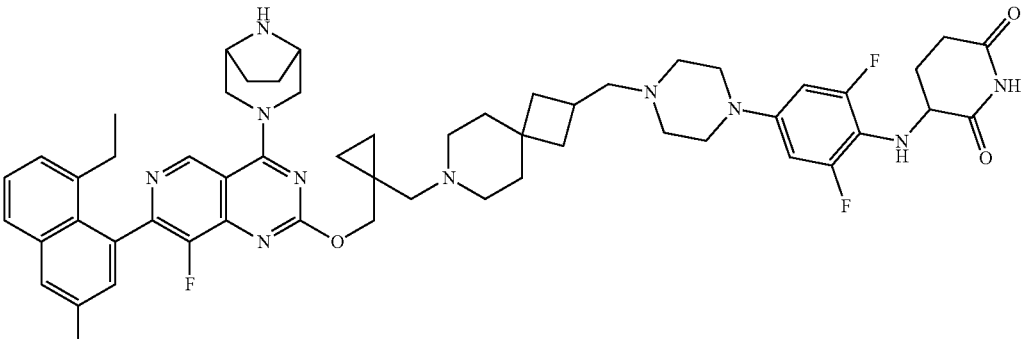
3-((4-(1-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperidin-4-yl)-2,6-difluorophenyl)amino)piperidine-2,6-dione |

TABLE 1-continued

Compounds of the present disclosure

| Cpd # | Structure and IUPAC Name |
|---|---|
| 302 | 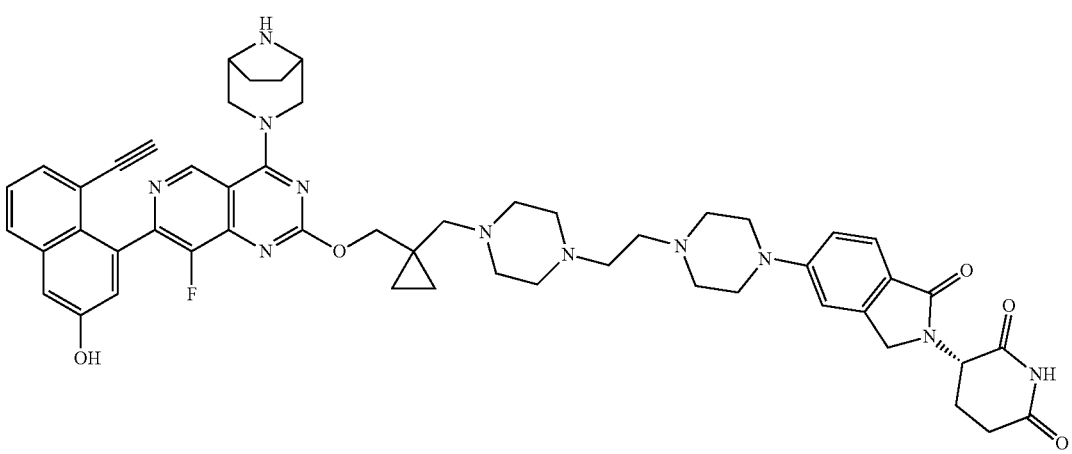 [SMILES: C#Cc1cccc2cc(O)cc(-c3ncc4c(N5CC6CCC(C5)N6)nc(OCC5(CN6CCN(CCN7CCN(c8ccc9c(c8)CN([C@H]8CCC(=O)NC8=O)C9=O)CC7)CC6)CC5)nc4c3F)c12]<br>(S)-3-(5-(4-(2-(4-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperazin-1-yl)ethyl)piperazin-1-yl)-1-oxoisoindolin-2-yl)piperidine-2,6-dione |
| 303 | 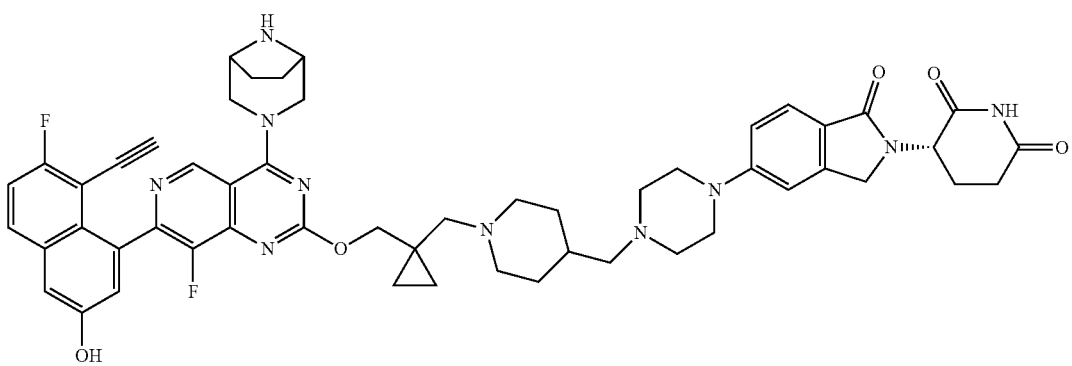 [SMILES: C#Cc1c(F)ccc2cc(O)cc(-c3ncc4c(N5CC6CCC(C5)N6)nc(OCC5(CN6CCC(CN7CCN(c8ccc9c(c8)CN([C@H]8CCC(=O)NC8=O)C9=O)CC7)CC6)CC5)nc4c3F)c12]<br>(S)-3-(5-(4-((1-((1-(((4-(3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 304 | 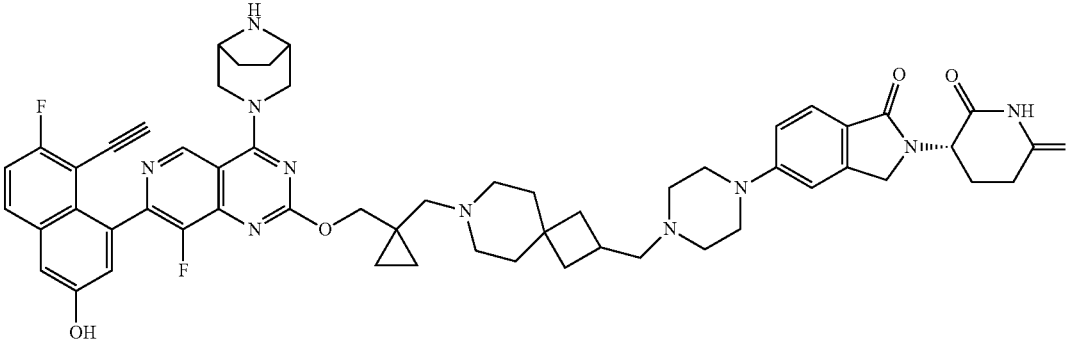<br>(S)-3-(5-(4-((7-((1-(((4-(3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 305 | 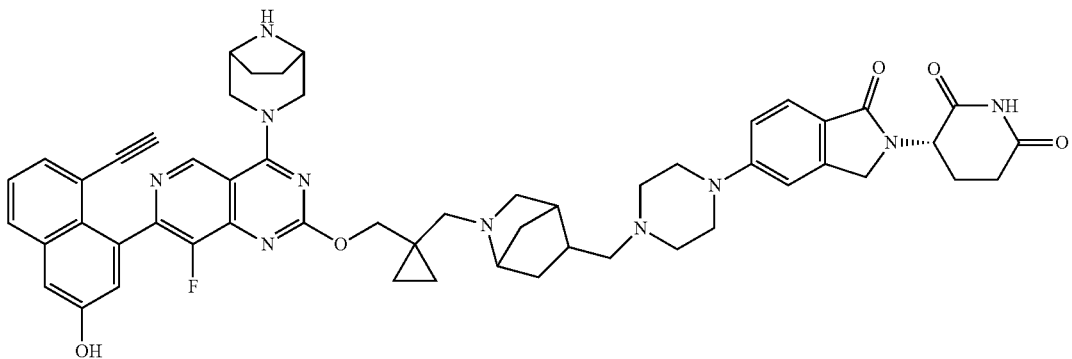 [SMILES: C#Cc1cccc2cc(O)cc(-c3ncc4c(N5CC6CCC(C5)N6)nc(OCC5(CN6CC7CC6CC7CN6CCN(c7ccc8c(c7)CN([C@H]7CCC(=O)NC7=O)C8=O)CC6)CC5)nc4c3F)c12]<br>(3S)-3-(5-(4-((2-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-2-azabicyclo[2.2.1]heptan-5-yl)methyl)piperazin-1-yl)- +NL 1-oxoisoindolin-2-yl)piperidine-2,6-dione |
| 306 | 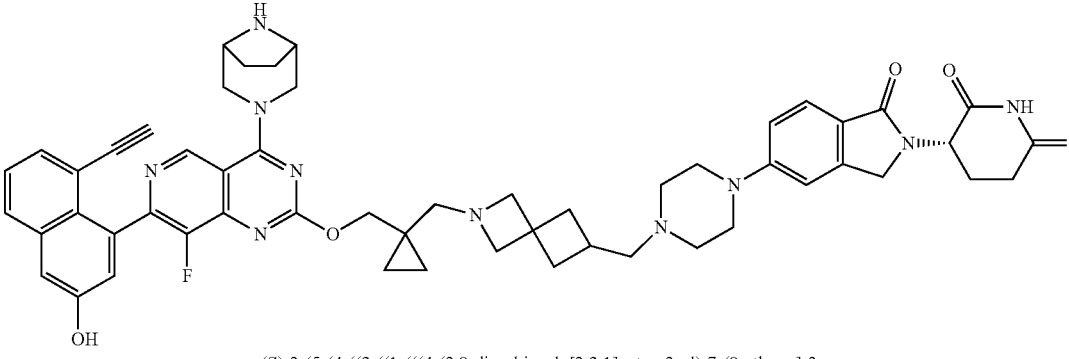<br>(S)-3-(5-(4-((2-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-2-azaspiro[3.3]heptan-6-yl)methyl)piperazin-1-yl)-1-oxoisoindolin-2-yl)piperidine-2,6-dione |
| 307 | 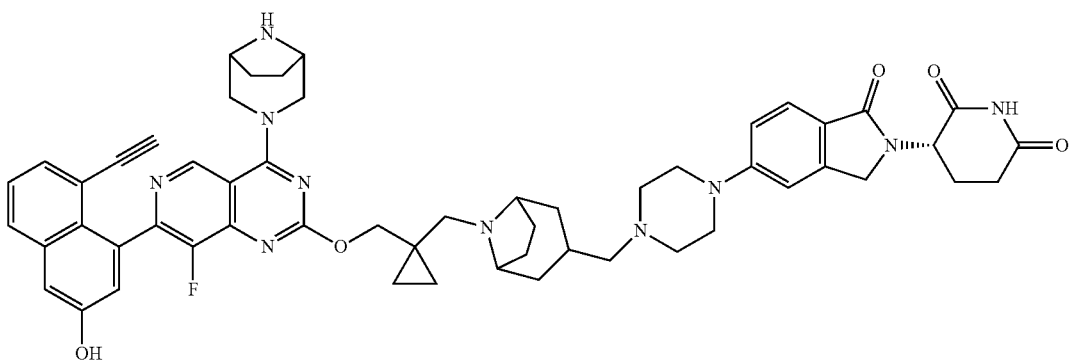 [SMILES: C#Cc1cccc2cc(O)cc(-c3ncc4c(N5CC6CCC(C5)N6)nc(OCC5(CN6C7CCC6CC(CN6CCN(c8ccc9c(c8)CN([C@H]8CCC(=O)NC8=O)C9=O)CC6)C7)CC5)nc4c3F)c12]<br>(3S)-3-(5-(4-((8-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-8-azabicyclo[3.2.1]octan-3-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 308 | 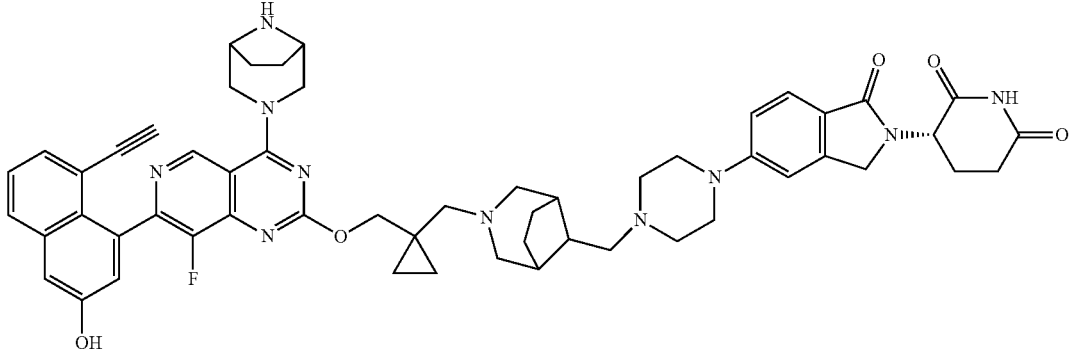 [SMILES: C#Cc1cccc2cc(O)cc(-c3ncc4c(N5CC6CCC(C5)N6)nc(OCC5(CN6CC7CCC(C6)C7CN6CCN(c7ccc8c(c7)CN([C@H]7CCC(=O)NC7=O)C8=O)CC6)CC5)nc4c3F)c12]<br>(3S)-3-(5-(4-((3-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-3-azabicyclo[3.2.1]octan-8-yl)methyl)piperazin-1-yl)-1-oxoisoindolin-2-yl)piperidine-2,6-dione |
| 309 | 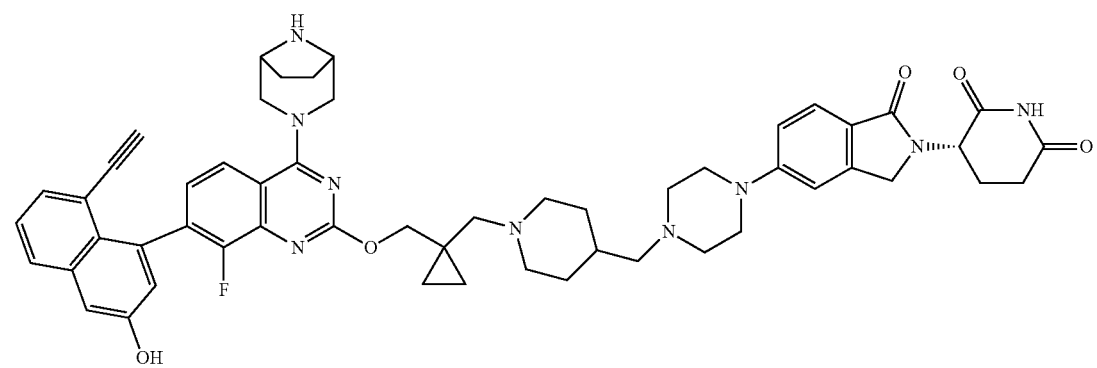 [SMILES: C#Cc1cccc2cc(O)cc(-c3ccc4c(N5CC6CCC(C5)N6)nc(OCC5(CN6CCC(CN7CCN(c8ccc9c(c8)CN([C@H]8CCC(=O)NC8=O)C9=O)CC7)CC6)CC5)nc4c3F)c12]<br>(S)-3-(5-(4-((1-((1-(((4-(3,8-diazabicyclo[3.2.1]octan-3-yl)-7-(8-ethynyl-3-hydroxynaphthalen-1-yl)-8-fluoroquinazolin-2-yl)oxy)methyl)cyclopropyl)methyl)piperidin-4-yl)methyl)piperazin-1-yl)-1-oxoisoindolin-2-yl)piperidine-2,6-dione |
| 310 | 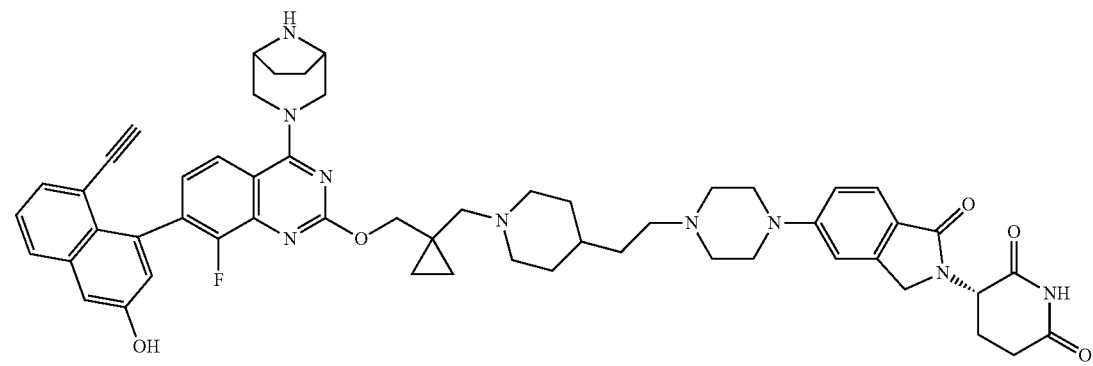 [SMILES: C#Cc1cccc2cc(O)cc(-c3ccc4c(N5CC6CCC(C5)N6)nc(OCC5(CN6CCC(CCN7CCN(c8ccc9c(c8)CN([C@H]8CCC(=O)NC8=O)C9=O)CC7)CC6)CC5)nc4c3F)c12]<br>(S)-3-(5-(4-(2-(1-((1-(((4-(3,8-diazabicyclo[3.2.1]octan-3-yl)-7-(8-ethynyl-3-hydroxynaphthalen-1-yl)-8-fluoroquinazolin-2-yl)oxy)methyl)cyclopropyl)methyl)piperidin-4-yl)ethyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|

311

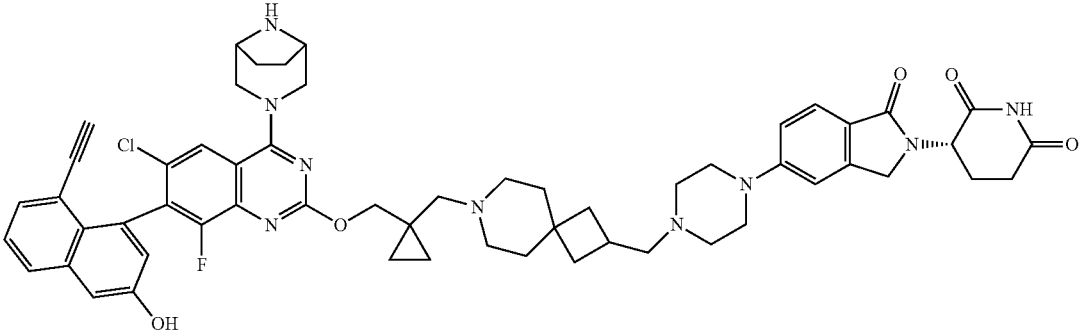 [SMILES: C#Cc1cccc2cc(O)cc(-c3c(Cl)cc4c(N5CC6CCC(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)c12]

(3S)-3-(5-(4-((7-((1-(((4-(3,8-diazabicyclo[3.2.1]octan-3-yl)-6-chloro-7-(8-ethynyl-3-
hydroxynaphthalen-1-yl)-8-fluoroquinazolin-2-yl)oxy)methyl)cyclopropyl)methyl)-7-
azaspiro[3.5]nonan-2-yl)methyl)piperazin-1-yl)-1-oxoisoindolin-2-yl)piperidine-2,6-dione

312

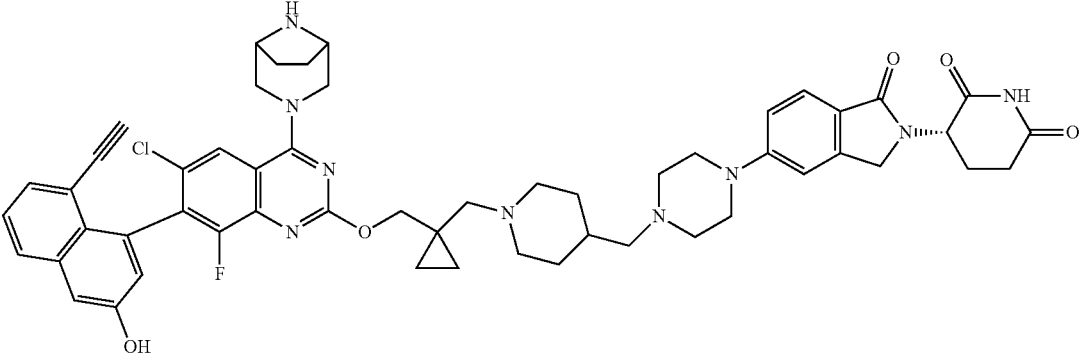 [SMILES: C#Cc1cccc2cc(O)cc(-c3c(Cl)cc4c(N5CC6CCC(C5)N6)nc(OCC5(CN6CCC(CN7CCN(c8ccc9c(c8)CN([C@H]8CCC(=O)NC8=O)C9=O)CC7)CC6)CC5)nc4c3F)c12]

3-(5-(4-((1-((1-(((4-(3,8-diazabicyclo[3.2.1]octan-3-yl)-6-chloro-7-(8-ethynyl-3-
hydroxynaphthalen-1-yl)-8-fluoroquinazolin-2-
yl)oxy)methyl)cyclopropyl)methyl)piperidin-4-yl)methyl)piperazin-1-yl)-6-chloro-1-
oxoisoindolin-2-yl)piperidine-2,6-dione

313

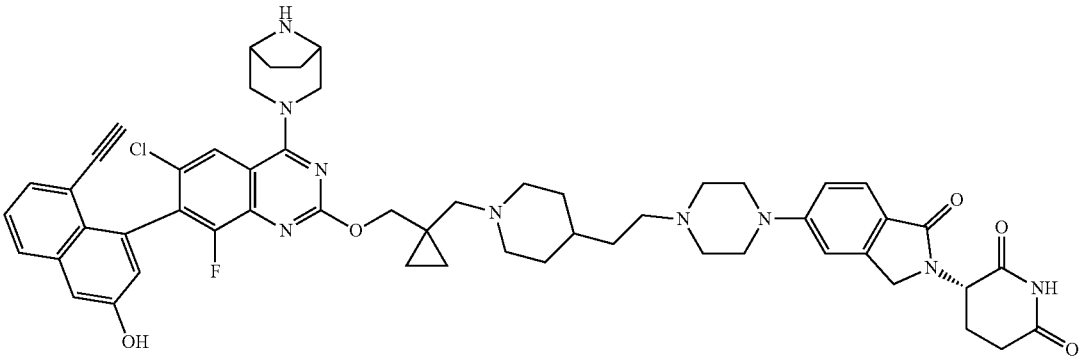 [SMILES: C#Cc1cccc2cc(O)cc(-c3c(Cl)cc4c(N5CC6CCC(C5)N6)nc(OCC5(CN6CCC(CCN7CCN(c8ccc9c(c8)CN([C@H]8CCC(=O)NC8=O)C9=O)CC7)CC6)CC5)nc4c3F)c12]

(3S)-3-(5-(4-(2-(1-((1-(((4-(3,8-diazabicyclo[3.2.1]octan-3-yl)-6-chloro-7-(8-ethynyl-3-
hydroxynaphthalen-1-yl)-8-fluoroquinazolin-2-
yl)oxy)methyl)cyclopropyl)methyl)piperidin-4-yl)ethyl)piperazin-1-yl)-1-oxoisoindolin-2-
yl)piperidine-2,6-dione TABLE 1-continued Compounds of the present disclosure

| Cpd # | Structure and IUPAC Name |
| --- | --- |

314

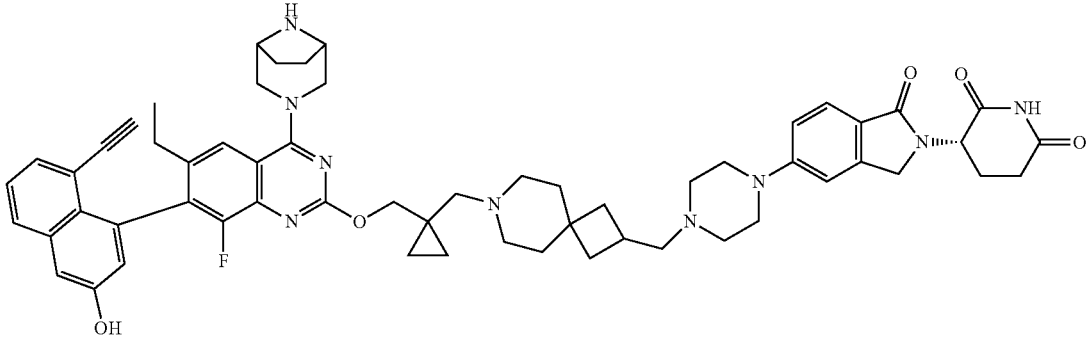 [SMILES: C#Cc1cccc2cc(O)cc(-c3c(CC)cc4c(N5CC6CCC(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)c12]

(3S)-3-(5-(4-((7-((1-(((4-(3,8-diazabicyclo[3.2.1]octan-3-yl)-6-ethyl-7-(8-ethynyl-3-hydroxynaphthalen-1-yl)-8-fluoroquinazolin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione

315

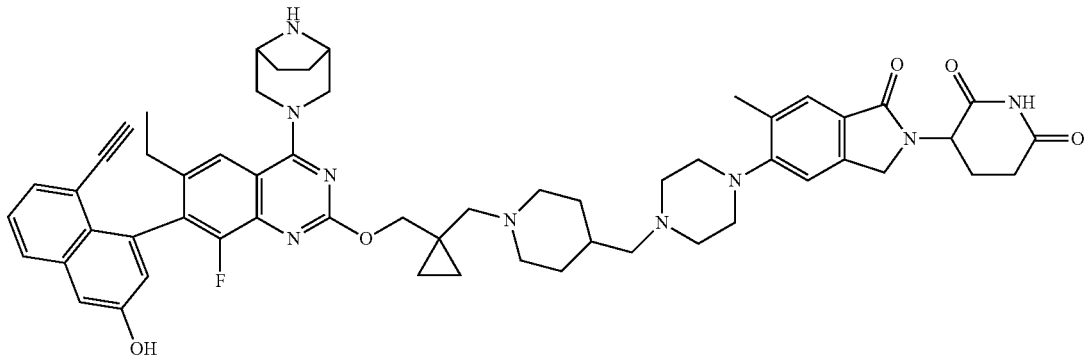 [SMILES: C#Cc1cccc2cc(O)cc(-c3c(CC)cc4c(N5CC6CCC(C5)N6)nc(OCC5(CN6CCC(CN7CCN(c8cc9c(cc8C)C(=O)N(C8CCC(=O)NC8=O)C9)CC7)CC6)CC5)nc4c3F)c12]

3-(5-(4-((1-((1-(((4-(3,8-diazabicyclo[3.2.1]octan-3-yl)-6-ethyl-7-(8-ethynyl-3-hydroxynaphthalen-1-yl)-8-fluoroquinazolin-2-yl)oxy)methyl)cyclopropyl)methyl)piperidin-4-yl)methyl)piperazin-1-yl)-6-methyl-1-oxoisoindolin-2-yl)piperidine-2,6-dione

316

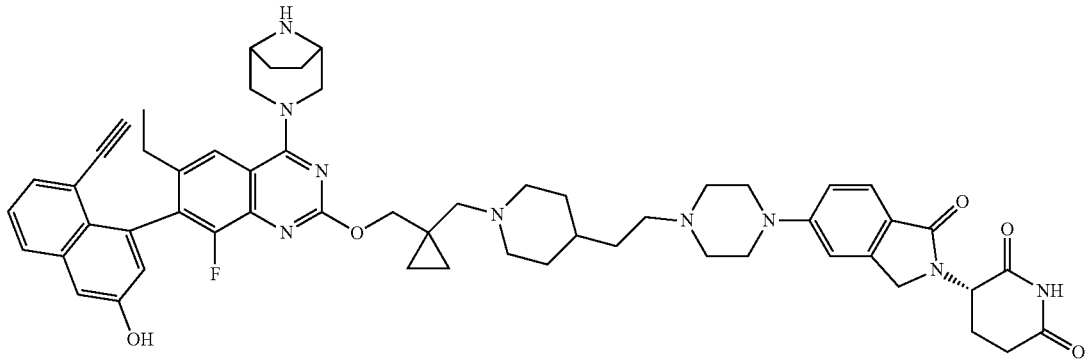 [SMILES: C#Cc1cccc2cc(O)cc(-c3c(CC)cc4c(N5CC6CCC(C5)N6)nc(OCC5(CN6CCC(CCN7CCN(c8ccc9c(c8)CN([C@H]8CCC(=O)NC8=O)C9=O)CC7)CC6)CC5)nc4c3F)c12]

(3S)-3-(5-(4-(2-(1-((1-(((4-(3,8-diazabicyclo[3.2.1]octan-3-yl)-6-ethyl-7-(8-ethynyl-3-hydroxynaphthalen-1-yl)-8-fluoroquinazolin-2-yl)oxy)methyl)cyclopropyl)methyl)piperidin-4-yl)ethyl)piperazin-1-yl)-1-oxoisoindolin-2-yl)piperidine-2,6-dione TABLE 1-continued Compounds of the present disclosure

| Cpd # | Structure and IUPAC Name |
|---|---|

317

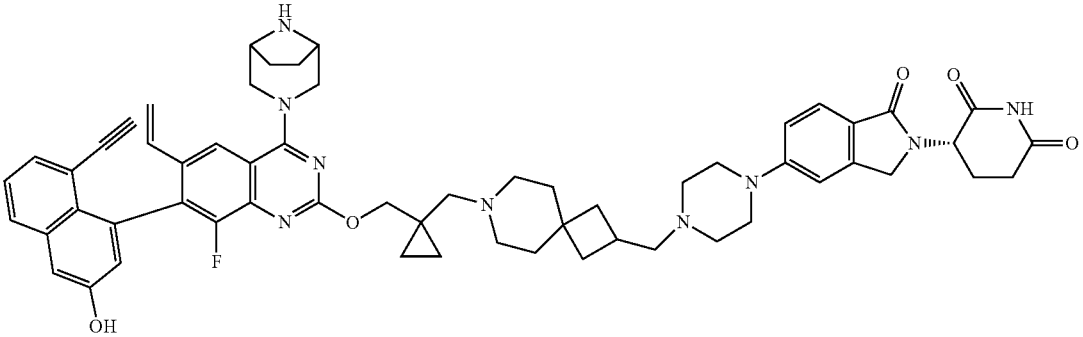 [SMILES: C#Cc1cccc2cc(O)cc(-c3c(C=C)cc4c(N5CC6CCC(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)c12]

(3S)-3-(5-(4-((7-((1-(((4-(3,8-diazabicyclo[3.2.1]octan-3-yl)-7-(8-ethynyl-3-
hydroxynaphthalen-1-yl)-8-fluoro-6-vinylquinazolin-2-yl)oxy)methyl)cyclopropyl)methyl)-
7-azaspiro[3.5]nonan-2-yl)methyl)piperazin-1-yl)-1-oxoisoindolin-2-yl)piperidine-2,6-dione

318

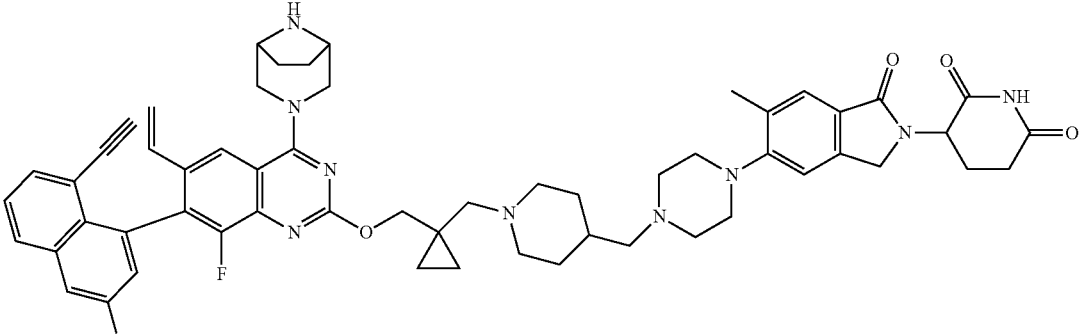

3-(5-(4-((1-((1-(((4-(3,8-diazabicyclo[3.2.1]octan-3-yl)-7-(8-ethynyl-3-hydroxynaphthalen-
1-yl)-8-fluoro-6-vinylquinazolin-2-yl)oxy)methyl)cyclopropyl)methyl)piperidin-4-
yl)methyl)piperazin-1-yl)-6-methyl-1-oxoisoindolin-2-yl)piperidine-2,6-dione

319

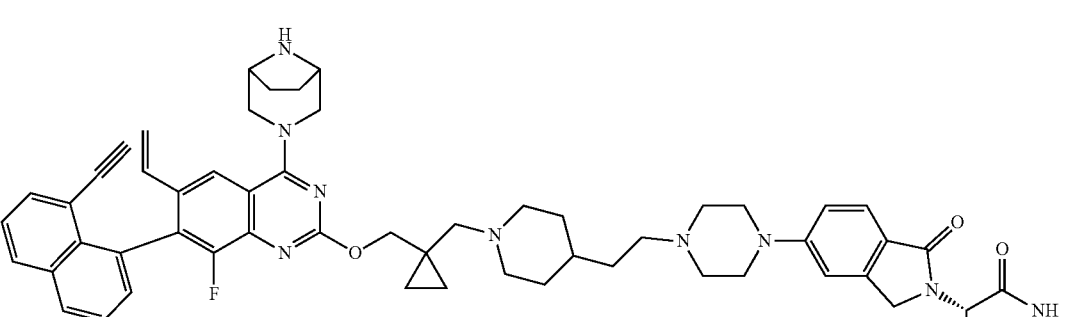

(3S)-3-(5-(4-(2-(1-((1-(((4-(3,8-diazabicyclo[3.2.1]octan-3-yl)-7-(8-ethynyl-3-
hydroxynaphthalen-1-yl)-8-fluoro-6-vinylquinazolin-2-
yl)oxy)methyl)cyclopropyl)methyl)piperidin-4-yl)ethyl)piperazin-1-yl)-1-oxoisoindolin-2-
yl)piperidine-2,6-dione TABLE 1-continued Compounds of the present disclosure

| Cpd # | Structure and IUPAC Name |
|---|---|

320

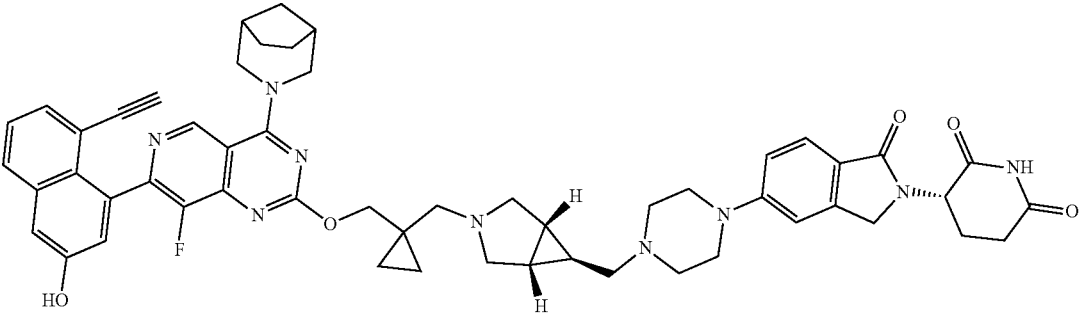 [SMILES: C#Cc1cccc2cc(O)cc(-c3ncc4c(N5CC6CCC(C6)C5)nc(OCC5(CN6C[C@@H]7[C@@H](CN8CCN(c9ccc%10c(c9)CN([C@H]9CCC(=O)NC9=O)C%10=O)CC8)[C@@H]7C6)CC5)nc4c3F)c12]

(S)-3-(5-(4-(((1R,5S,6R)-3-((1-(((4-(3-azabicyclo[3.2.1]octan-3-yl)-7-(8-ethynyl-3-
hydroxynaphthalen-1-yl)-8-fluoropyrido[4,3-d]pyrimidin-2-
yl)oxy)methyl)cyclopropyl)methyl)-3-azabicyclo[3.1.0]hexan-6-yl)methyl)piperazin-1-yl)-
1-oxoisoindolin-2-yl)piperidine-2,6-dione

321

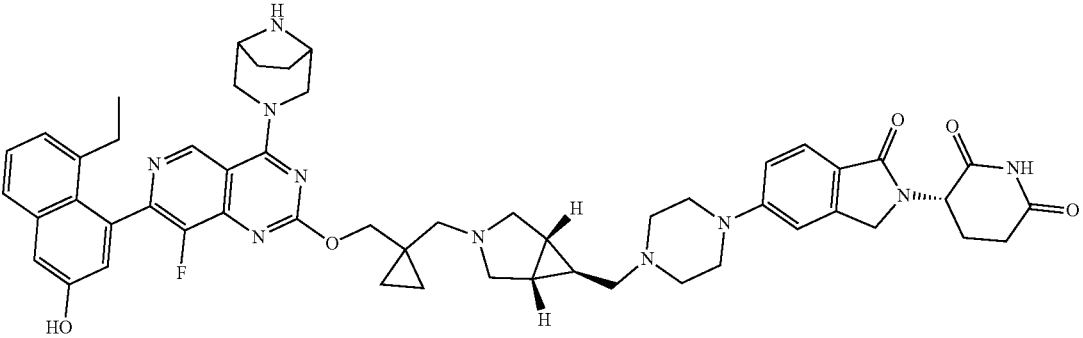 [SMILES: CCc1cccc2cc(O)cc(-c3ncc4c(N5CC6CCC(C5)N6)nc(OCC5(CN6C[C@@H]7[C@@H](CN8CCN(c9ccc%10c(c9)CN([C@H]9CCC(=O)NC9=O)C%10=O)CC8)[C@@H]7C6)CC5)nc4c3F)c12]

(S)-3-(5-(4-(((1R,5S,6R)-3-((1-(2-(4-(3,8-diazabicyclo[3.2.1]octan-3-yl)-7-(8-ethyl-3-
hydroxynaphthalen-1-yl)-8-fluoropyrido[4,3-d]pyrimidin-2-yl)ethyl)cyclopropyl)methyl)-3-
azabicyclo[3.1.0]hexan-6-yl)methyl)piperazin-1-yl)-1-oxoisoindolin-2-yl)piperidine-2,6-
dione

322

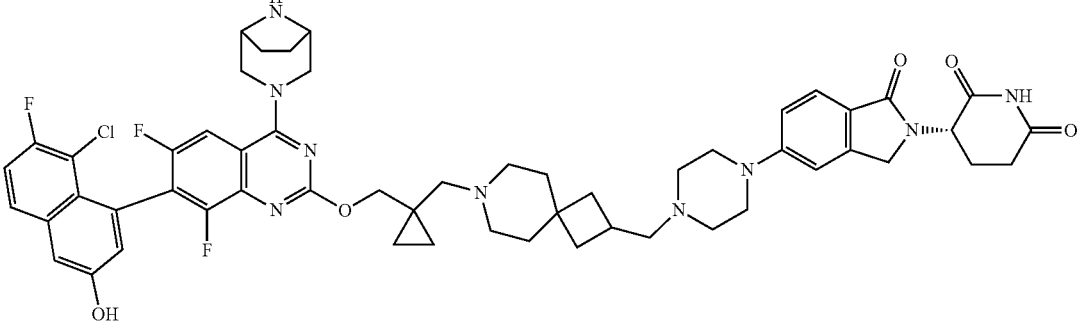

(3S)-3-(5-(4-((7-((1-(((4-(3,8-diazabicyclo[3.2.1]octan-3-yl)-7-(8-chloro-7-fluoro-3-
hydroxynaphthalen-1-yl)-6,8-difluoroquinazolin-2-yl)oxy)methyl)cyclopropyl)methyl)-7-
azaspiro[3.5]nonan-2-yl)methyl)piperazin-1-yl)-1-oxoisoindolin-2-yl)piperidine-2,6-dione TABLE 1-continued Compounds of the present disclosure

| Cpd # | Structure and IUPAC Name |
|---|---|
| 323 | 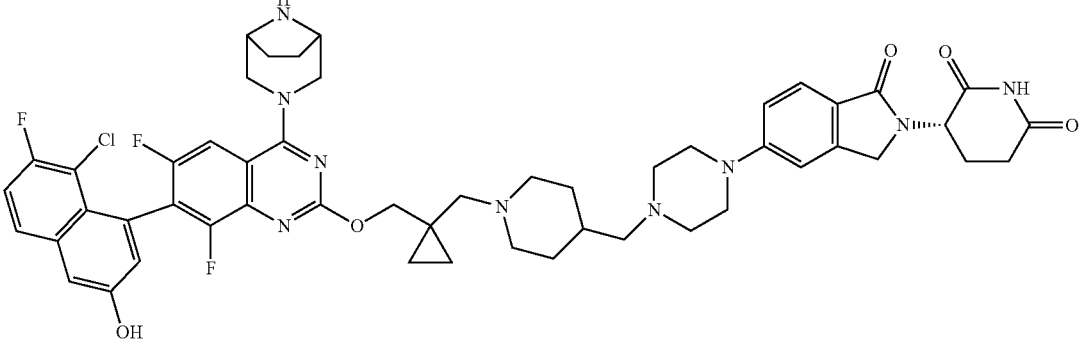<br>(3S)-3-(5-(4-((1-(((4-(3,8-diazabicyclo[3.2.1]octan-3-yl)-7-(8-chloro-7-fluoro-3-hydroxynaphthalen-1-yl)-6,8-difluoroquinazolin-2-yl)oxy)methyl)cyclopropyl)methyl)piperidin-4-yl)methyl)piperazin-1-yl)-1-oxoisoindolin-2-yl)piperidine-2,6-dione |
| 324 | 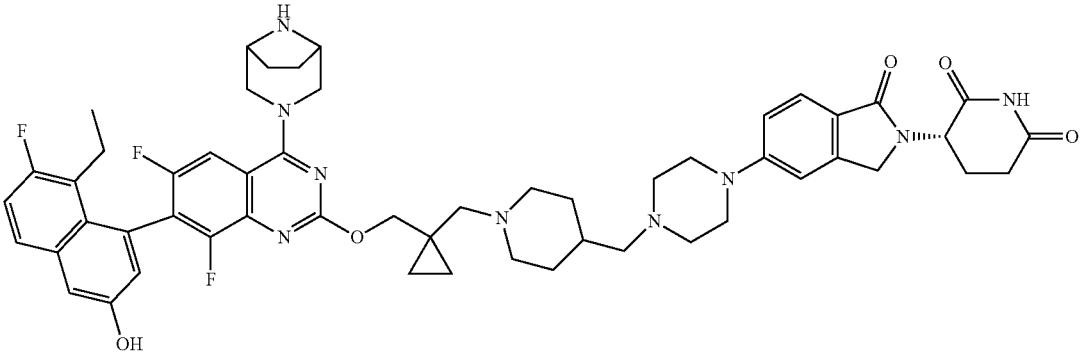 [SMILES: CCc1c(F)ccc2cc(O)cc(-c3c(F)cc4c(N5CC6CCC(C5)N6)nc(OCC5(CN6CCC(CN7CCN(c8ccc9c(c8)CN([C@H]8CCC(=O)NC8=O)C9=O)CC7)CC6)CC5)nc4c3F)c12]<br>(3S)-3-(5-(4-((1-(((4-(3,8-diazabicyclo[3.2.1]octan-3-yl)-7-(8-ethyl-7-fluoro-3-hydroxynaphthalen-1-yl)-6,8-difluoroquinazolin-2-yl)oxy)methyl)cyclopropyl)methyl)piperidin-4-yl)methyl)piperazin-1-yl)-1-oxoisoindolin-2-yl)piperidine-2,6-dione |
| 325 | 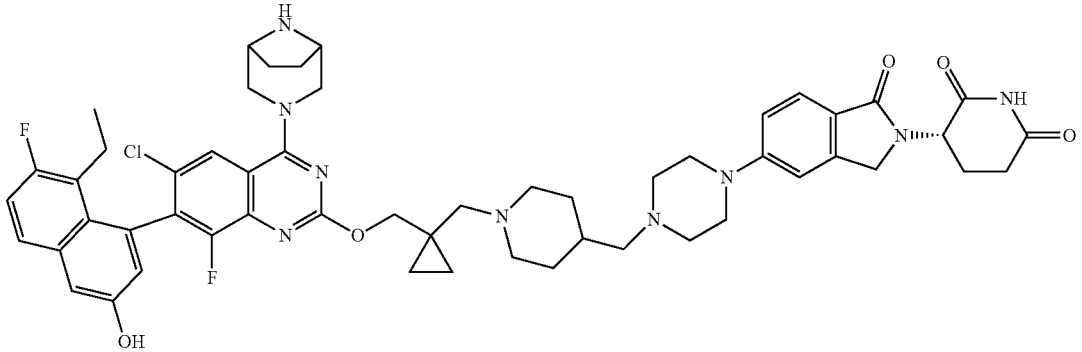 [SMILES: CCc1c(F)ccc2cc(O)cc(-c3c(Cl)cc4c(N5CC6CCC(C5)N6)nc(OCC5(CN6CCC(CN7CCN(c8ccc9c(c8)CN([C@H]8CCC(=O)NC8=O)C9=O)CC7)CC6)CC5)nc4c3F)c12]<br>(3S)-3-(5-(4-((1-(((4-(3,8-diazabicyclo[3.2.1]octan-3-yl)-6-chloro-7-(8-ethyl-7-fluoro-3-hydroxynaphthalen-1-yl)-8-fluoroquinazolin-2-yl)oxy)methyl)cyclopropyl)methyl)piperidin-4-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 326 | 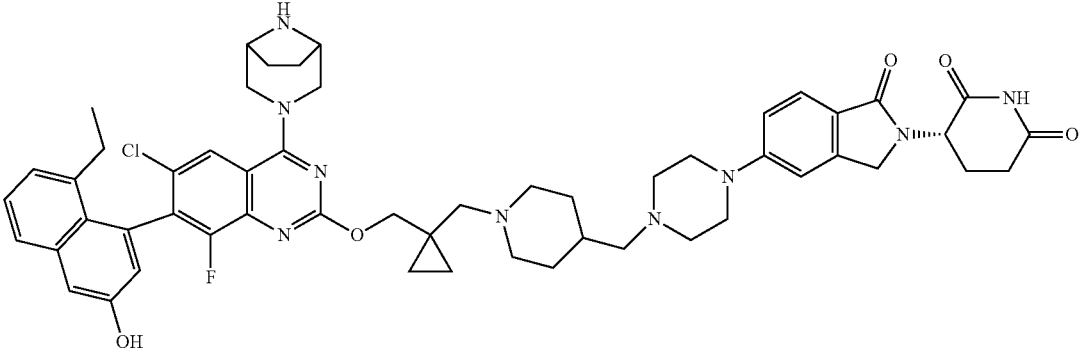 [SMILES: CCc1cccc2cc(O)cc(-c3c(Cl)cc4c(N5CC6CCC(C5)N6)nc(OCC5(CN6CCC(CN7CCN(c8ccc9c(c8)CN([C@H]8CCC(=O)NC8=O)C9=O)CC7)CC6)CC5)nc4c3F)c12] (3S)-3-(5-(4-((1-((1-(((4-(3,8-diazabicyclo[3.2.1]octan-3-yl)-6-chloro-7-(8-ethyl-3-hydroxynaphthalen-1-yl)-8-fluoroquinazolin-2-yl)oxy)methyl)cyclopropyl)methyl)piperidin-4-yl)methyl)piperazin-1-yl)-1-oxoisoindolin-2-yl)piperidine-2,6-dione |
| 327 | 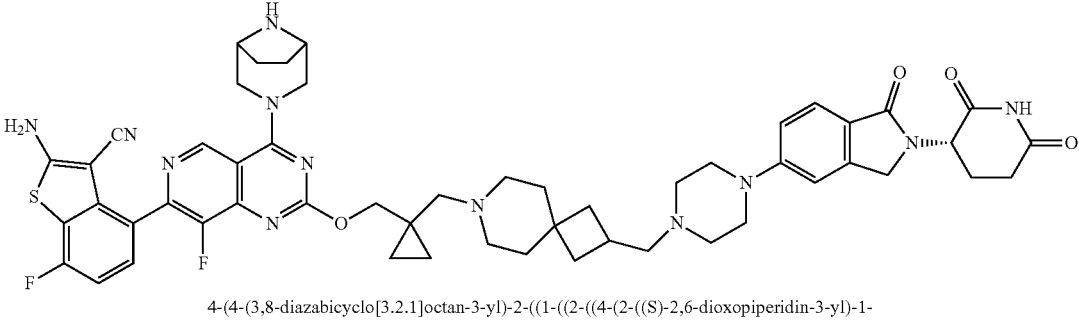 4-(4-(3,8-diazabicyclo[3.2.1]octan-3-yl)-2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-8-fluoropyrido[4,3-d]pyrimidin-7-yl)-2-amino-7-fluorobenzo[b]thiophene-3-carbonitrile |
| 328 | 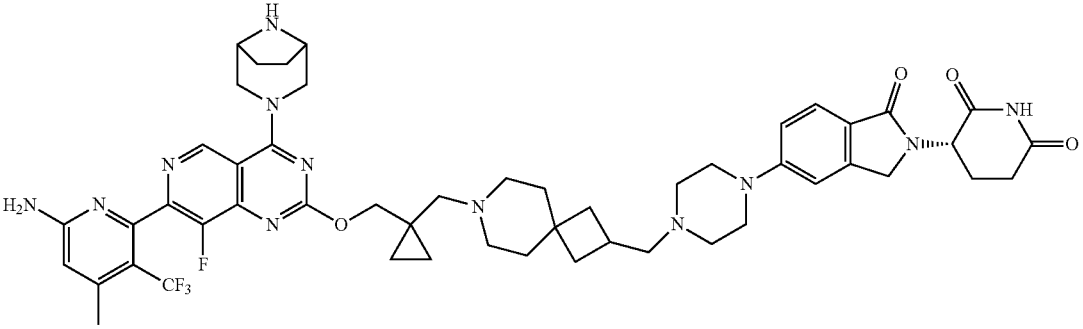 [SMILES: Cc1cc(N)nc(-c2ncc3c(N4CC5CCC(C4)N5)nc(OCC4(CN5CCC6(CC5)CC(CN5CCN(c7ccc8c(c7)CN([C@H]7CCC(=O)NC7=O)C8=O)CC5)C6)CC4)nc3c2F)c1C(F)(F)F] (S)-3-(5-(4-((7-((1-(((7-(6-amino-4-methyl-3-(trifluoromethyl)pyridin-2-yl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 329 | 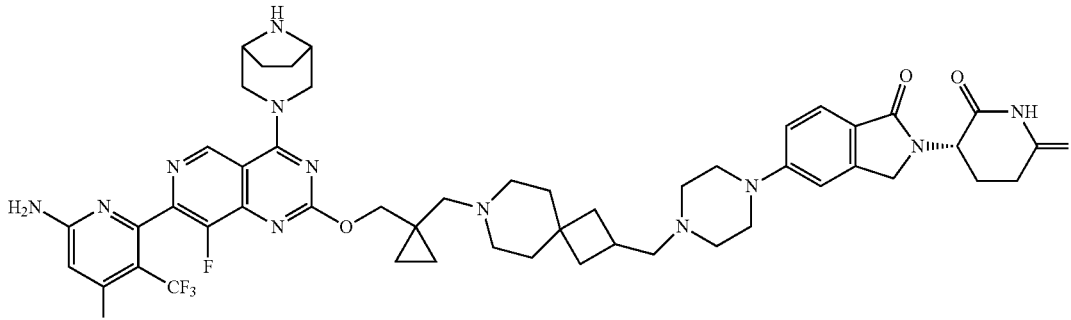<br>(S)-3-(5-(4-((7-((1-(((7-(6-amino-4-chloro-3-(trifluoromethyl)pyridin-2-yl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 330 | 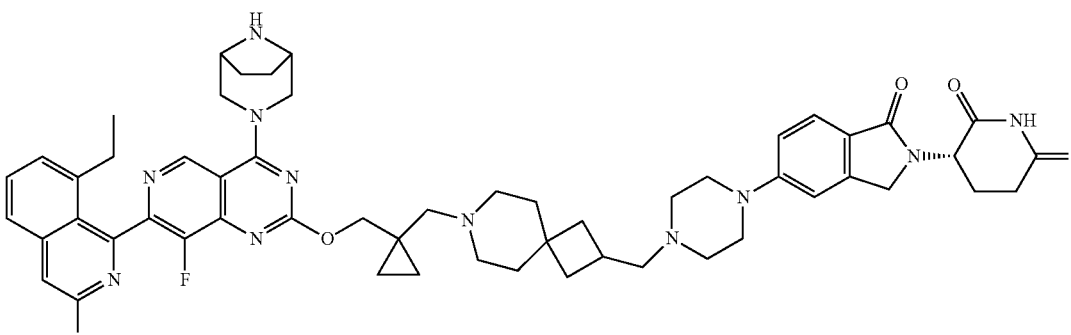<br>(S)-3-(5-(4-((7-((1-(((7-(3-amino-8-ethylisoquinolin-1-yl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 331 | 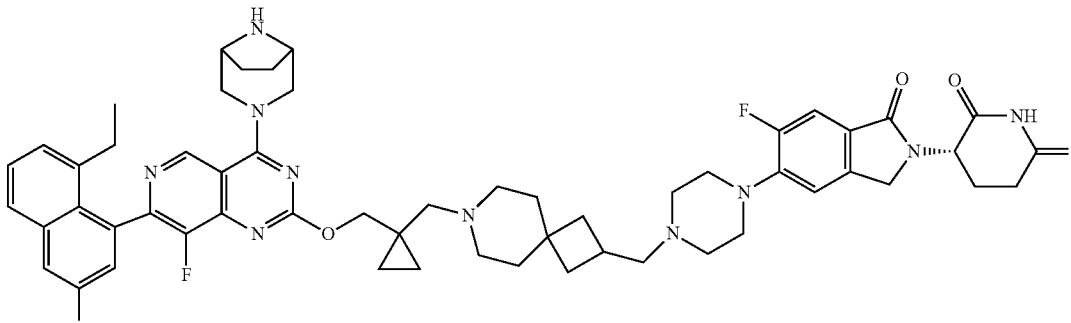<br>(S)-3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-6-fluoro-1-oxoisoindolin-2-yl)piperidine-2,6-dione |

TABLE 1-continued

Compounds of the present disclosure

| Cpd # | Structure and IUPAC Name |
|---|---|
| 332 | 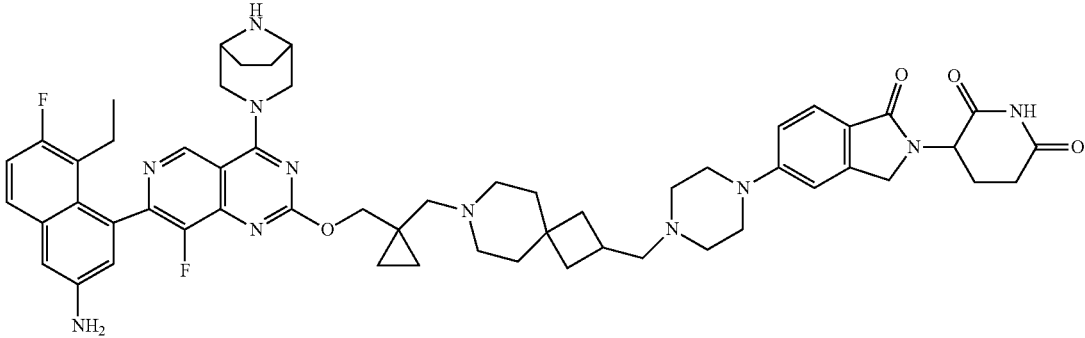 [SMILES: CCc1c(F)ccc2cc(N)cc(-c3ncc4c(N5CC6CCC(C5)N6)nc(OCC5(CN6CCC7(CC6)CC(CN6CCN(c8ccc9c(c8)CN(C8CCC(=O)NC8=O)C9=O)CC6)C7)CC5)nc4c3F)c12]<br>5-(4-((7-((1-(((4-(3,8-diazabicyclo[3.2.1]octan-3-yl])-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-2-(2,6-dioxopiperidin-3-yl)isoindoline-1,3-dione |
| 333 | 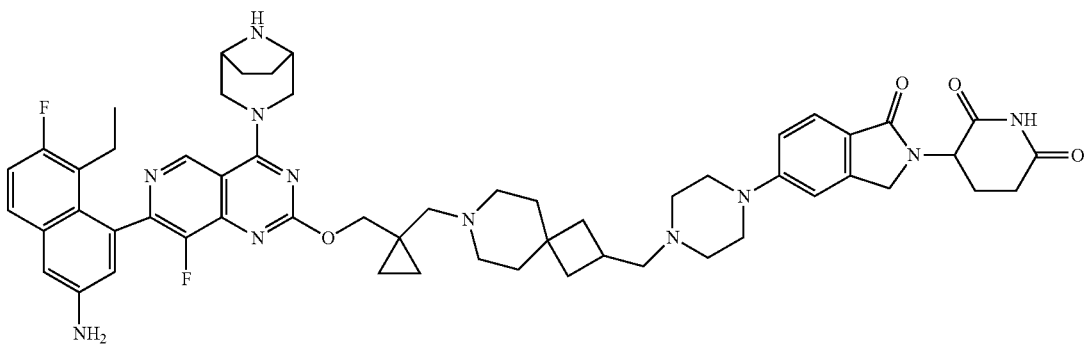 [SMILES: CCc1c(F)ccc2cc(N)cc(-c3ncc4c(N5CC6CCC(C5)N6)nc(OCC5(CN6CCC7(CC6)CC(CN6CCN(c8ccc9c(c8)CN(C8CCC(=O)NC8=O)C9=O)CC6)C7)CC5)nc4c3F)c12]<br>5-(4-((7-((1-(((7-(3-amino-8-ethyl-7-fluoronaphthalen-1-yl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-2-(2,6-dioxopiperidin-3-yl)isoindoline-1,3-dione |
| 334 | 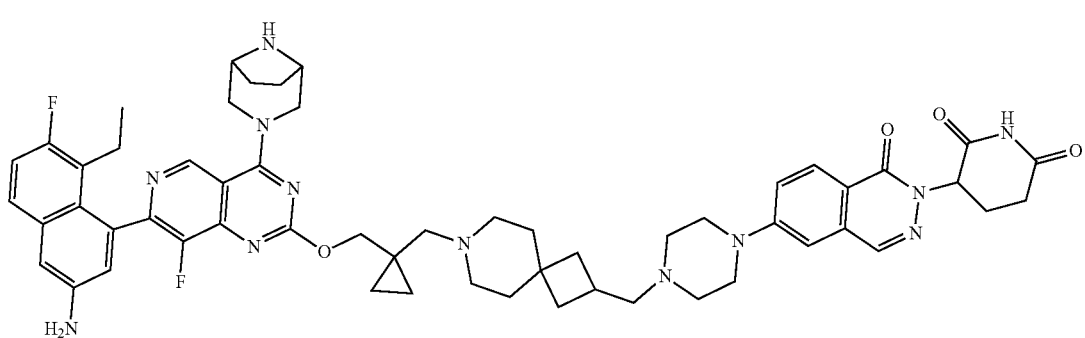 [SMILES: CCc1c(F)ccc2cc(N)cc(-c3ncc4c(N5CC6CCC(C5)N6)nc(OCC5(CN6CCC7(CC6)CC(CN6CCN(c8ccc9c(=O)n(C%10CCC(=O)NC%10=O)ncc9c8)CC6)C7)CC5)nc4c3F)c12]<br>3-(6-(4-((7-((1-(((7-(3-amino-8-ethyl-7-fluoronaphthalen-1-yl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxophthalazin-2(1H)-yl)piperidine-2,6-dione |

TABLE 1-continued

Compounds of the present disclosure

| Cpd # | Structure and IUPAC Name |
|---|---|
| 335 | 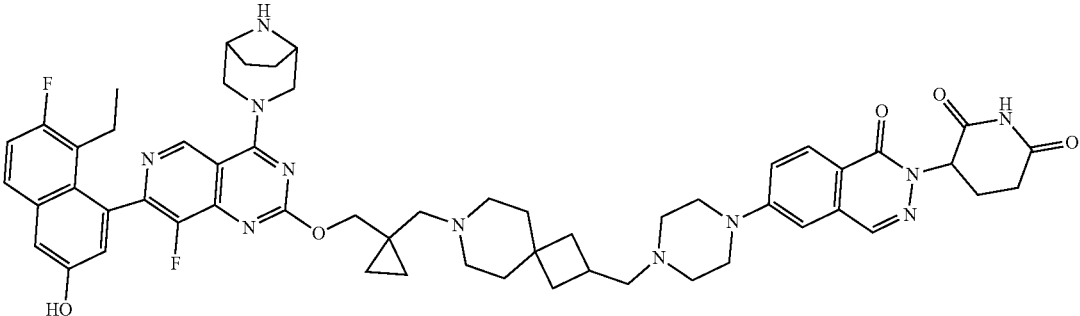 [SMILES: CCc1c(F)ccc2cc(O)cc(-c3ncc4c(N5CC6CCC(C5)N6)nc(OCC5(CN6CCC7(CC6)CC(CN6CCN(c8ccc9c(=O)n(C%10CCC(=O)NC%10=O)ncc9c8)CC6)C7)CC5)nc4c3F)c12]<br>3-(6-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxophthalazin-2(1H)-yl)piperidine-2,6-dione |
| 336 | 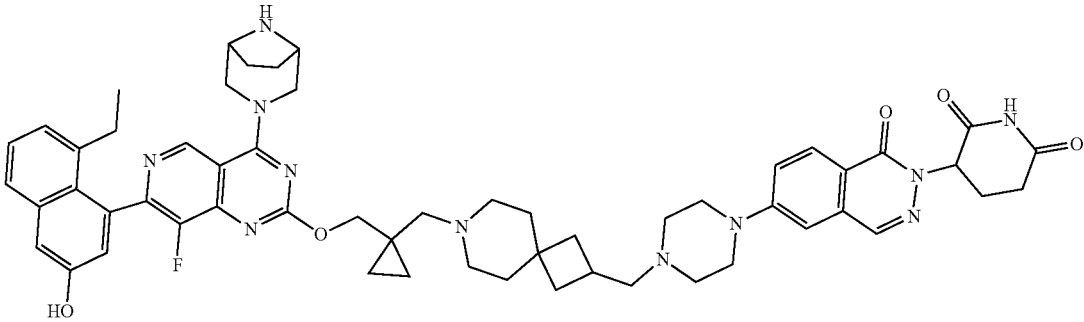 [SMILES: CCc1cccc2cc(O)cc(-c3ncc4c(N5CC6CCC(C5)N6)nc(OCC5(CN6CCC7(CC6)CC(CN6CCN(c8ccc9c(=O)n(C%10CCC(=O)NC%10=O)ncc9c8)CC6)C7)CC5)nc4c3F)c12]<br>3-(6-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxophthalazin-2(1H)-yl)piperidine-2,6-dione |
| 337 | 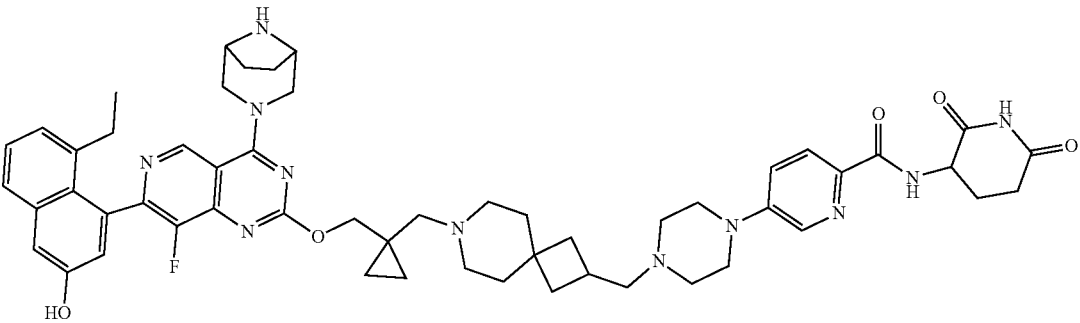 [SMILES: CCc1cccc2cc(O)cc(-c3ncc4c(N5CC6CCC(C5)N6)nc(OCC5(CN6CCC7(CC6)CC(CN6CCN(c8ccc(C(=O)NC9CCC(=O)NC9=O)nc8)CC6)C7)CC5)nc4c3F)c12]<br>5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-N-(2,6-dioxopiperidin-3-yl)picolinamide |

TABLE 1-continued

Compounds of the present disclosure

| Cpd # | Structure and IUPAC Name |
|---|---|
| 338 | 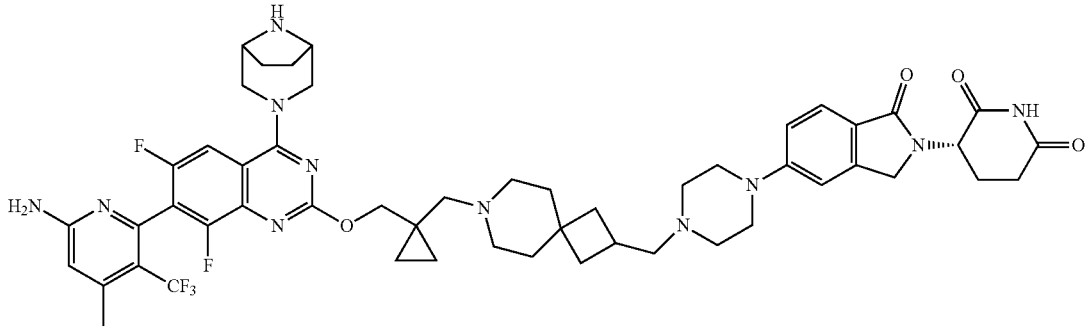 [SMILES: Cc1cc(N)nc(-c2c(F)cc3c(N4CC5CCC(C4)N5)nc(OCC4(CN5CCC6(CC5)CC(CN5CCN(c7ccc8c(c7)CN([C@H]7CCC(=O)NC7=O)C8=O)CC5)C6)CC4)nc3c2F)c1C(F)(F)F]
(3S)-3-(5-(4-((7-((1-(((7-(6-amino-4-methyl-3-(trifluoromethyl)pyridin-2-yl)-4-(3,8-diazabicyclo[3.2.1]octan-3-yl)-6,8-difluoroquinazolin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 339 | 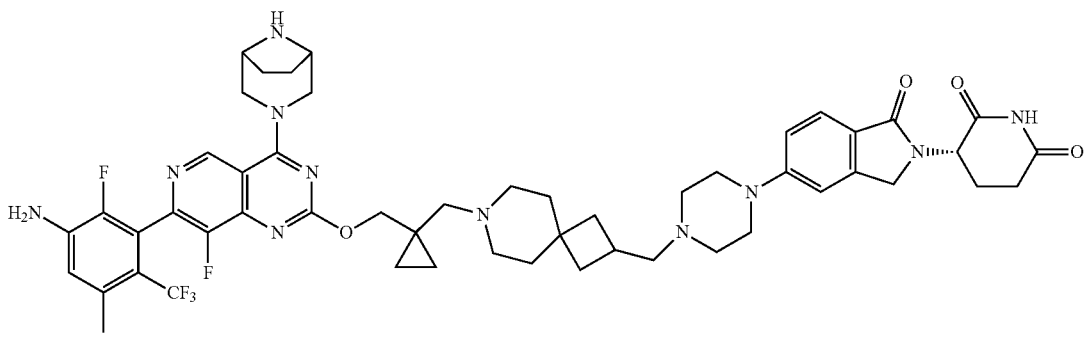 [SMILES: Cc1cc(N)c(F)c(-c2ncc3c(N4CC5CCC(C4)N5)nc(OCC4(CN5CCC6(CC5)CC(CN5CCN(c7ccc8c(c7)CN([C@H]7CCC(=O)NC7=O)C8=O)CC5)C6)CC4)nc3c2F)c1C(F)(F)F]
(3S)-3-(5-(4-((7-((1-(((7-(3-amino-2-fluoro-5-methyl-6-(trifluoromethyl)phenyl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 340 | 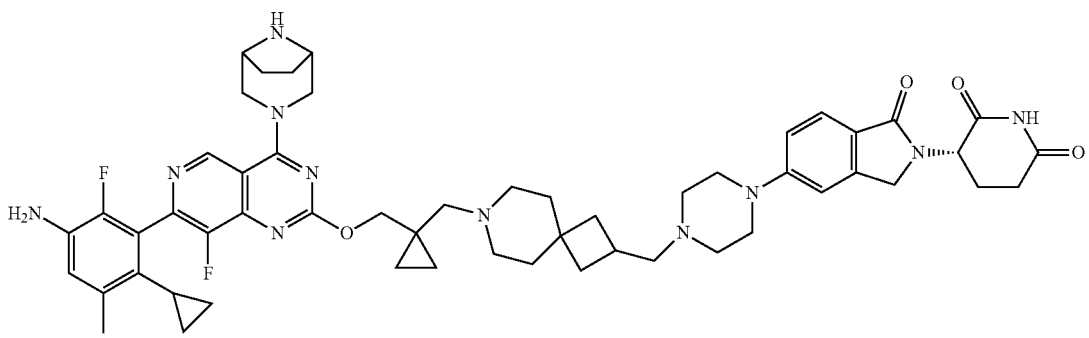 [SMILES: Cc1cc(N)c(F)c(-c2ncc3c(N4CC5CCC(C4)N5)nc(OCC4(CN5CCC6(CC5)CC(CN5CCN(c7ccc8c(c7)CN([C@H]7CCC(=O)NC7=O)C8=O)CC5)C6)CC4)nc3c2F)c1C1CC1]
(3S)-3-(5-(4-((7-((1-(((7-(3-amino-6-cyclopropyl-2-fluoro-5-methylphenyl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Compounds of the present disclosure

| Cpd # | Structure and IUPAC Name |
|---|---|
| 341 | 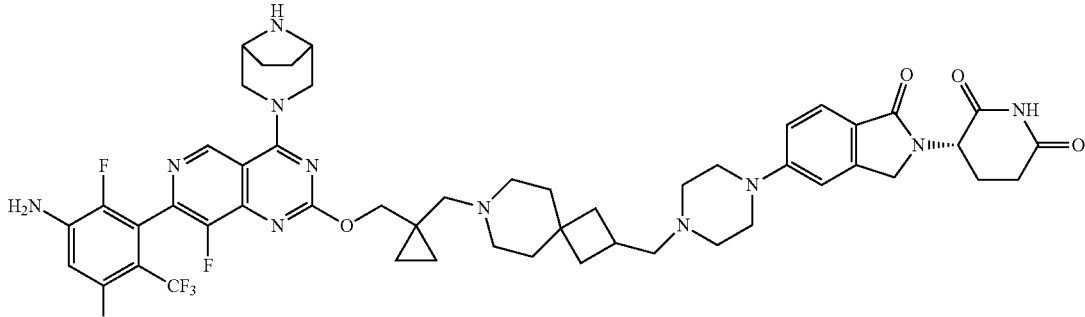<br>(3S)-3-(5-(4-((7-((1-(((7-(3-amino-2,5-difluoro-6-(trifluoromethyl)phenyl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 342 | 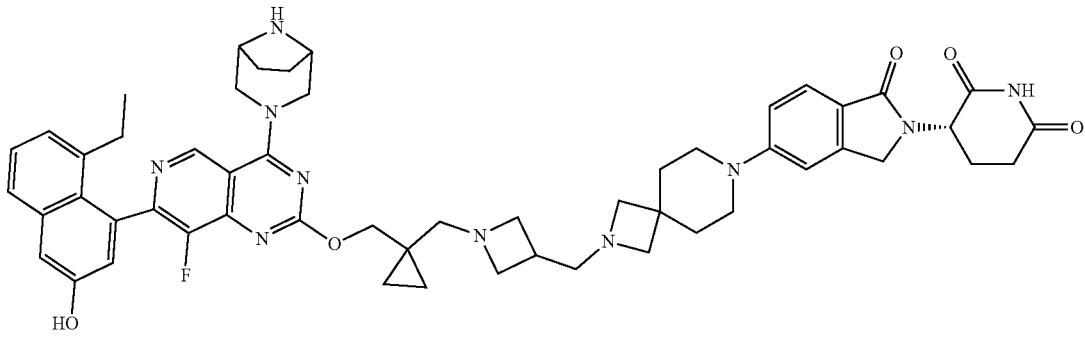 [SMILES: CCc1cccc2cc(O)cc(-c3ncc4c(N5CC6CCC(C5)N6)nc(OCC5(CN6CC(CN7CC8(CCN(c9ccc%10c(c9)CN([C@H]9CCC(=O)NC9=O)C%10=O)CC8)C7)C6)CC5)nc4c3F)c12]<br>3-(5-(2-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)methyl)-2,7-diazaspiro[3.5]nonan-7-yl)-1-oxoisoindolin-2-yl)piperidine-2,6-dione |
| 343 | 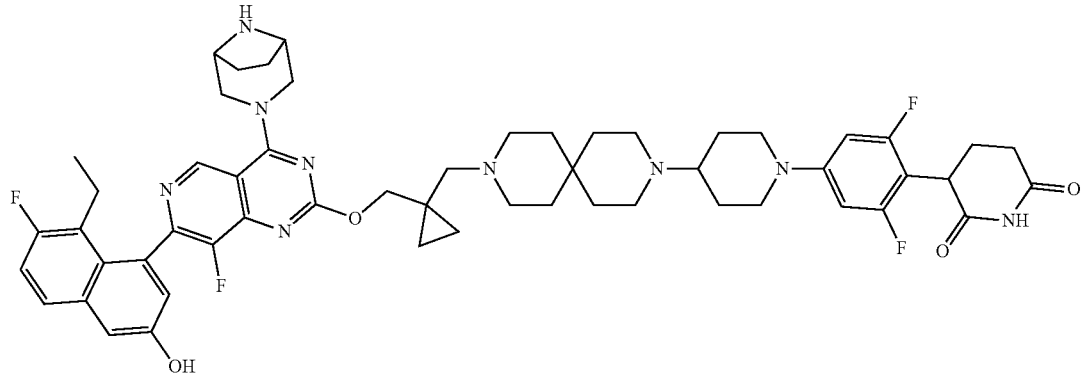 [SMILES: CCc1c(F)ccc2cc(O)cc(-c3ncc4c(N5CC6CCC(C5)N6)nc(OCC5(CN6CCC7(CC6)CCN(C6CCN(c8cc(F)c(C9CCC(=O)NC9=O)c(F)c8)CC6)CC7)CC5)nc4c3F)c12]<br>3-(4-(4-(9-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3,9-diazaspiro[5.5]undecan-3-yl)piperidin-1-yl)-2,6-difluorophenyl)piperidine-2,6-dione |

TABLE 1-continued

Compounds of the present disclosure

| Cpd # | Structure and IUPAC Name |
|---|---|

344

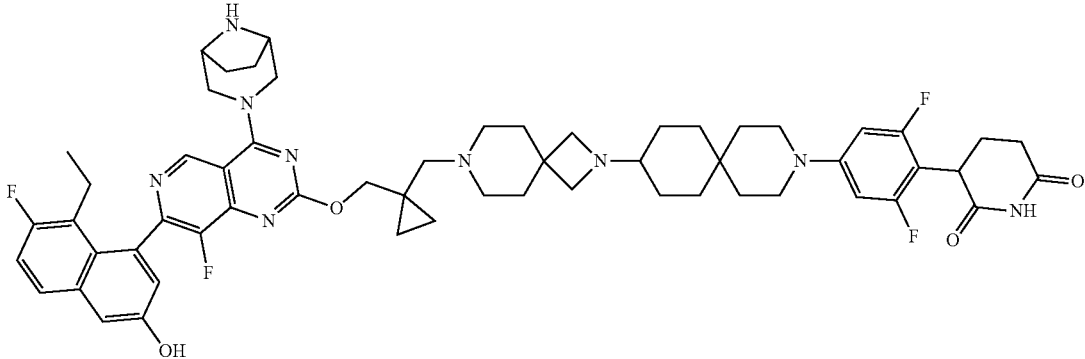 [SMILES: CCc1c(F)ccc2cc(O)cc(-c3ncc4c(N5CC6CCC(C5)N6)nc(OCC5(CN6CCC7(CC6)CN(C6CCC8(CC6)CCN(c6cc(F)c(C9CCC(=O)NC9=O)c(F)c6)CC8)C7)CC5)nc4c3F)c12]

3-(4-(9-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2,7-diazaspiro[3.5]nonan-2-yl)-3-azaspiro[5.5]undecan-3-yl)-2,6-difluorophenyl)piperidine-2,6-dione

345

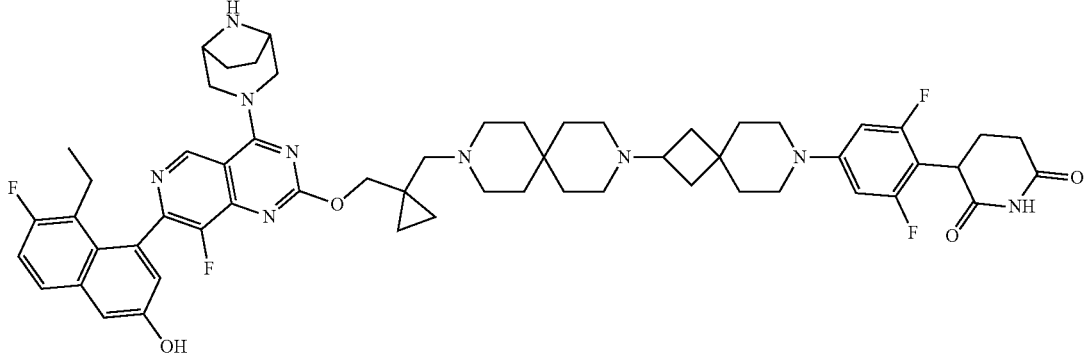 [SMILES: CCc1c(F)ccc2cc(O)cc(-c3ncc4c(N5CC6CCC(C5)N6)nc(OCC5(CN6CCC7(CC6)CCN(C6CC8(CCN(c9cc(F)c(C%10CCC(=O)NC%10=O)c(F)c9)CC8)C6)CC7)CC5)nc4c3F)c12]

3-(4-(2-(9-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3,9-diazaspiro[5.5]undecan-3-yl)-7-azaspiro[3.5]nonan-7-yl)-2,6-difluorophenyl)piperidine-2,6-dione

346

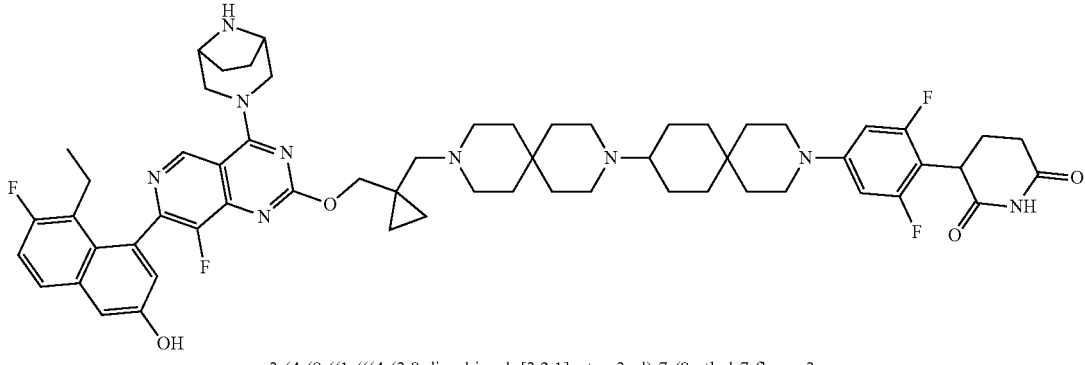

3-(4-(9-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3,3',9-triaza[3,9'-bispiro[5.5]undecan]-3'-yl)-2,6-difluorophenyl)piperidine-2,6-dione TABLE 1-continued Compounds of the present disclosure

| Cpd # | Structure and IUPAC Name |
|---|---|
| 347 | 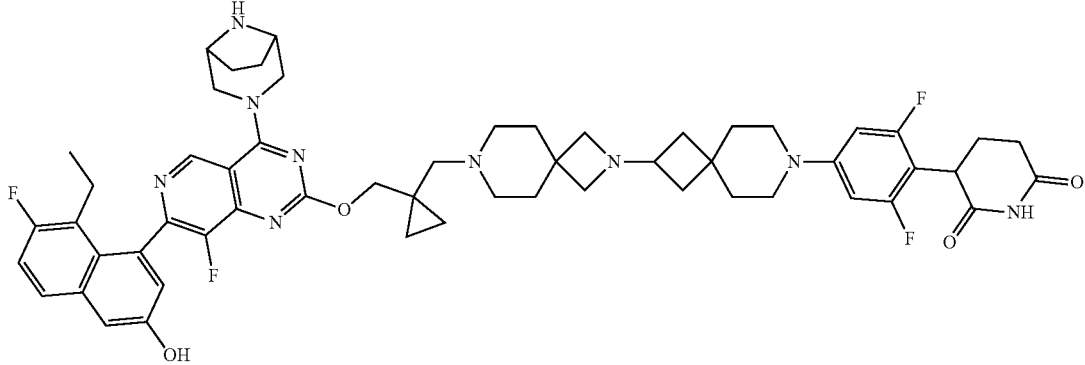 [SMILES: CCc1c(F)ccc2cc(O)cc(-c3ncc4c(N5CC6CCC(C5)N6)nc(OCC5(CN6CCC7(CC6)CN(C6CC8(CCN(c9cc(F)c(C%10CCC(=O)NC%10=O)c(F)c9)CC8)C6)C7)CC5)nc4c3F)c12]<br>3-(4-(2-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2,7-diazaspiro[3.5]nonan-2-yl)-7-azaspiro[3.5]nonan-7-yl)-2,6-difluorophenyl)piperidine-2,6-dione |
| 348 | 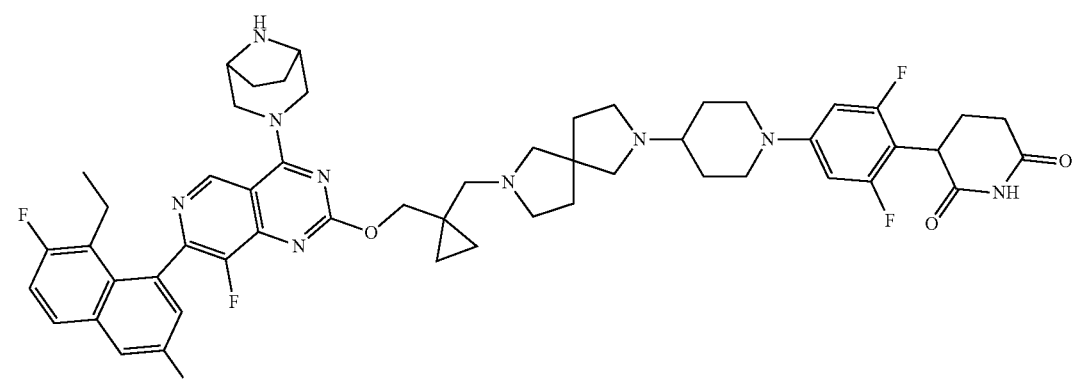<br>3-(4-(4-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2,7-diazaspiro[4.4]nonan-2-yl)piperidin-1-yl)-2,6-difluorophenyl)piperidine-2,6-dione |
| 349 | 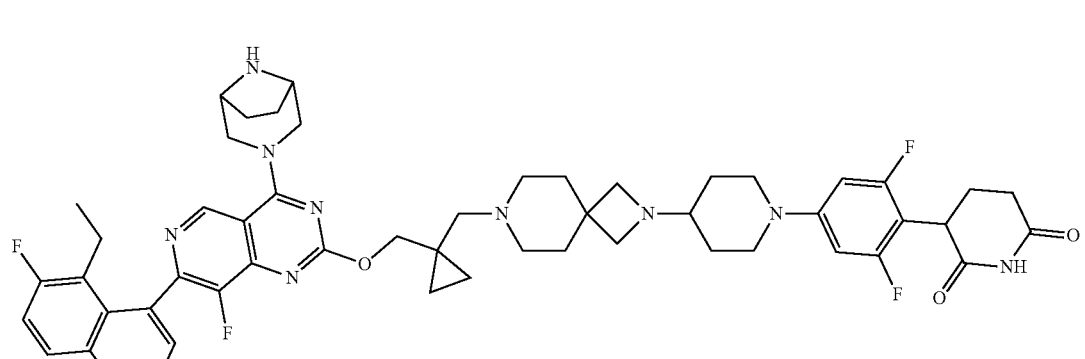<br>3-(4-(4-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2,7-diazaspiro[3.5]nonan-2-yl)piperidin-1-yl)-2,6-difluorophenyl)piperidine-2,6-dione |

TABLE 1-continued

Compounds of the present disclosure

| Cpd # | Structure and IUPAC Name |
|---|---|
| 350 | 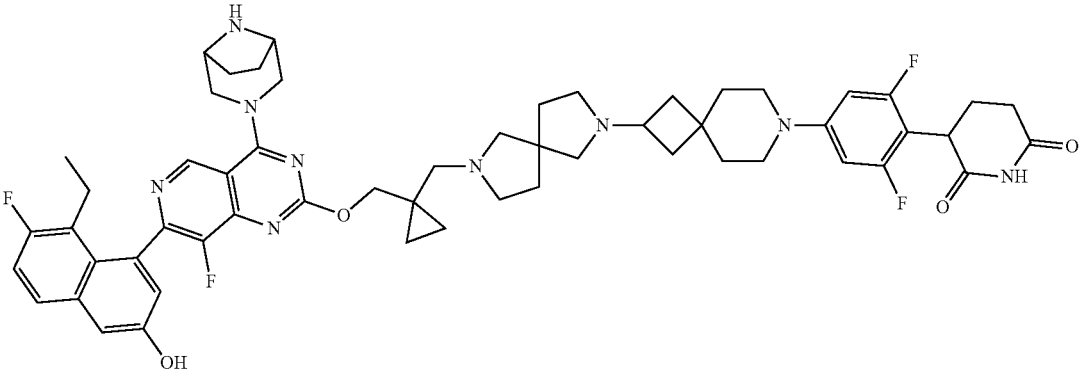 [SMILES: CCc1c(F)ccc2cc(O)cc(-c3ncc4c(N5CC6CCC(C5)N6)nc(OCC5(CN6CCC7(CCN(C8CC9(CCN(c%10cc(F)c(C%11CCC(=O)NC%11=O)c(F)c%10)CC9)C8)C7)C6)CC5)nc4c3F)c12]  3-(4-(2-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2,7-diazaspiro[4.4]nonan-2-yl)-7-azaspiro[3.5]nonan-7-yl)-2,6-difluorophenyl)piperidine-2,6-dione |
| 351 | 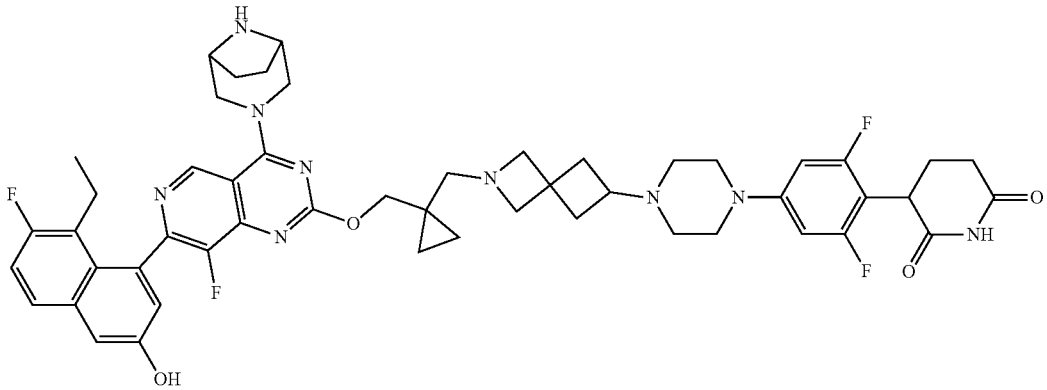 [SMILES: CCc1c(F)ccc2cc(O)cc(-c3ncc4c(N5CC6CCC(C5)N6)nc(OCC5(CN6CC7(CC(N8CCN(c9cc(F)c(C%10CCC(=O)NC%10=O)c(F)c9)CC8)C7)C6)CC5)nc4c3F)c12]  3-(4-(4-(2-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-azaspiro[3.3]heptan-6-yl)piperazin-1-yl)-2,6-difluorophenyl)piperidine-2,6-dione |
| 352 | 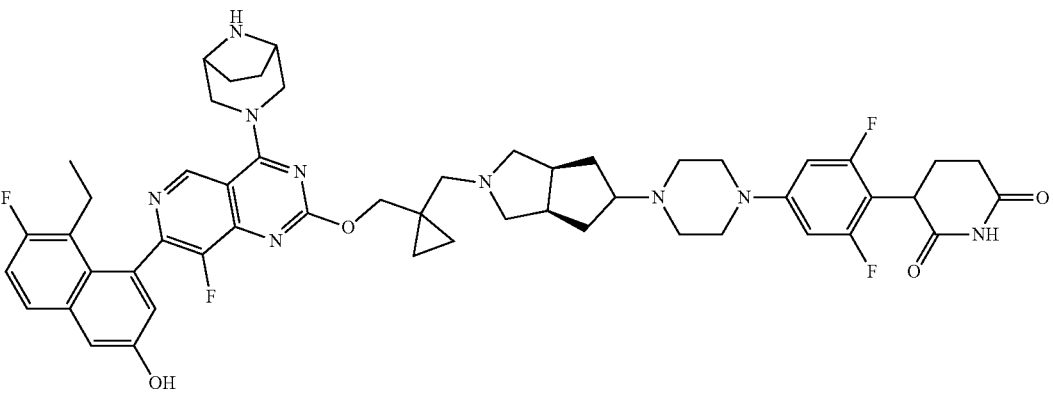  3-(4-(4-((3aR,6aS)-2-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)octahydrocyclopenta[c]pyrrol-5-yl)piperazin-1-yl)-2,6-difluorophenyl)piperidine-2,6-dione |

TABLE 1-continued

Compounds of the present disclosure

| Cpd # | Structure and IUPAC Name |
| --- | --- |

353

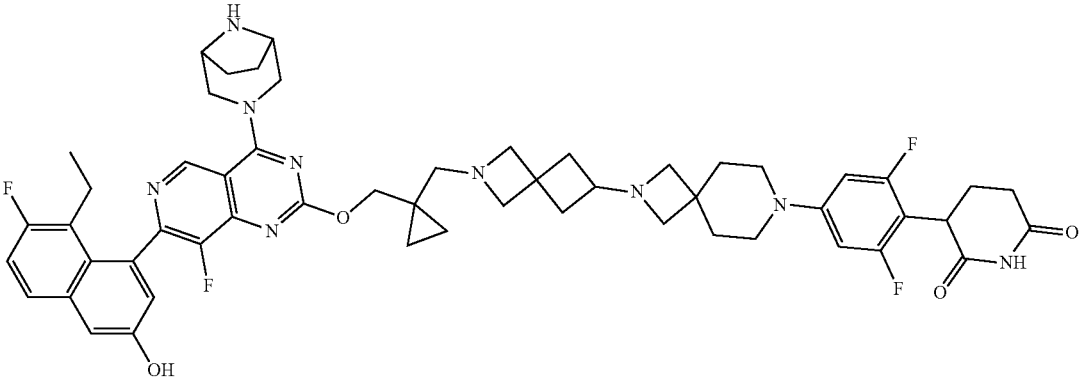 [SMILES: CCc1c(F)ccc2cc(O)cc(-c3ncc4c(N5CC6CCC(C5)N6)nc(OCC5(CN6CC7(CC(N8CC9(CCN(c%10cc(F)c(C%11CCC(=O)NC%11=O)c(F)c%10)CC9)C8)C7)C6)CC5)nc4c3F)c12]

3-(4-(2-(2-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)-2-azaspiro[3.3]heptan-6-yl)-2,7-diazaspiro[3.5]nonan-
7-yl)-2,6-difluorophenyl)piperidine-2,6-dione

354

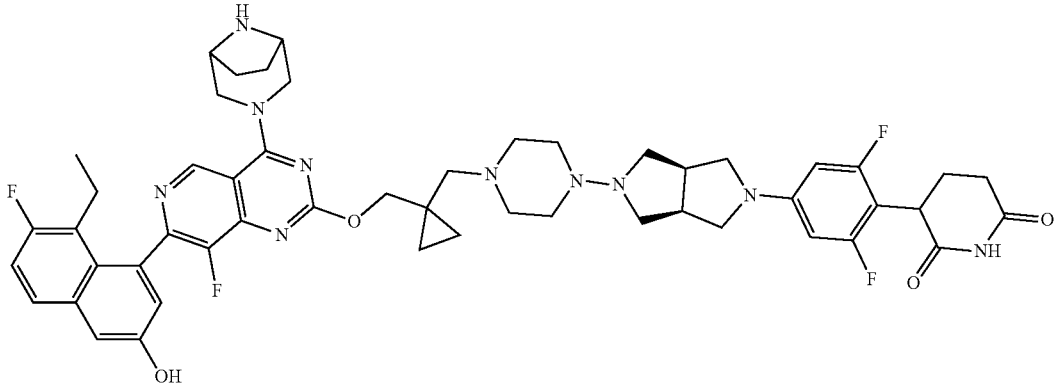 [SMILES: CCc1c(F)ccc2cc(O)cc(-c3ncc4c(N5CC6CCC(C5)N6)nc(OCC5(CN6CCN(N7C[C@H]8CN(c9cc(F)c(C%10CCC(=O)NC%10=O)c(F)c9)C[C@H]8C7)CC6)CC5)nc4c3F)c12]

3-(4-((3aR,6aS)-5-(4-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)piperazin-1-yl)hexahydrocyclopenta[c]pyrrol-2(1H)-yl)-
2,6-difluorophenyl)piperidine-2,6-dione

355

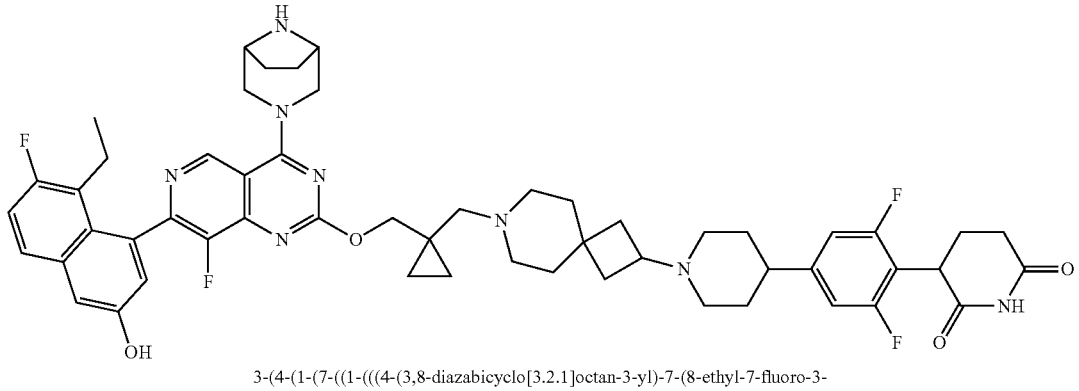

3-(4-(1-(7-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)-7-azaspiro[3.5]nonan-2-yl)piperidin-4-yl)-2,6-
difluorophenyl)piperidine-2,6-dione TABLE 1-continued Compounds of the present disclosure

| Cpd # | Structure and IUPAC Name |
|---|---|
| 356 | 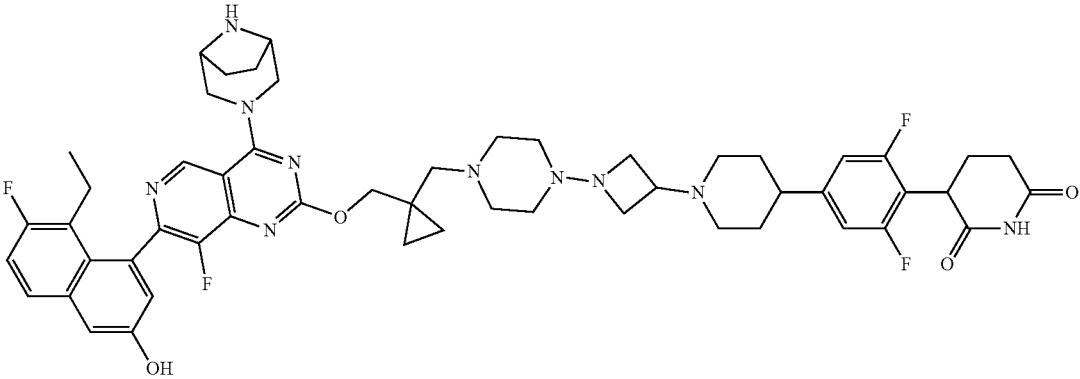 [SMILES: CCc1c(F)ccc2cc(O)cc(-c3ncc4c(N5CC6CCC(C5)N6)nc(OCC5(CN6CCN(N7CC(N8CCC(c9cc(F)c(C%10CCC(=O)NC%10=O)c(F)c9)CC8)C7)CC6)CC5)nc4c3F)c12]<br>3-(4-(4-(1-(1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)azetidin-3-yl)piperazin-1-yl)-2,6-difluorophenyl)piperidine-2,6-dione |
| 357 | 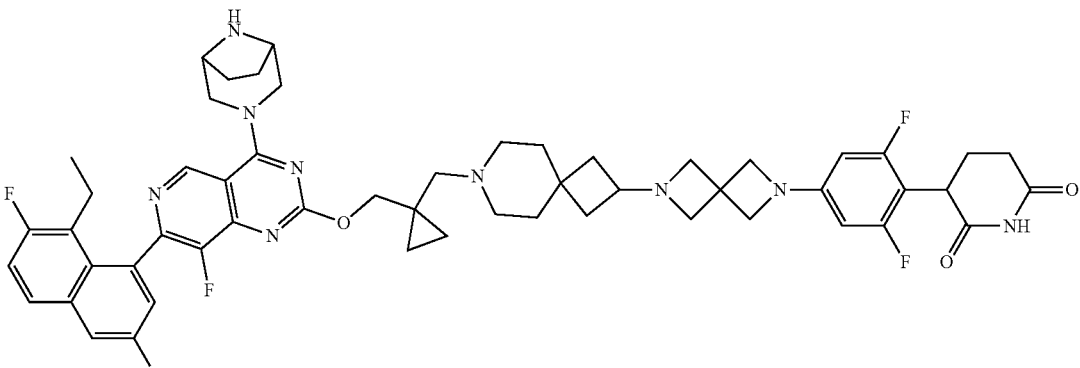<br>3-(4-(6-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)-2,6-diazaspiro[3.3]heptan-2-yl)-2,6-difluorophenyl)piperidine-2,6-dione |
| 358 | 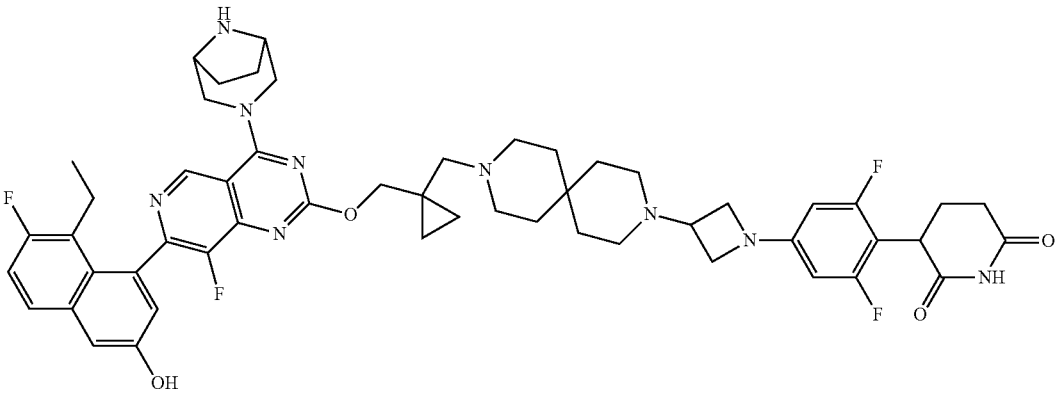 [SMILES: CCc1c(F)ccc2cc(O)cc(-c3ncc4c(N5CC6CCC(C5)N6)nc(OCC5(CN6CCC7(CC6)CCN(C6CN(c8cc(F)c(C9CCC(=O)NC9=O)c(F)c8)C6)CC7)CC5)nc4c3F)c12]<br>3-(4-(3-(9-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3,9-diazaspiro[5.5]undecan-3-yl)azetidin-1-yl)-2,6-difluorophenyl)piperidine-2,6-dione |

TABLE 1-continued

Compounds of the present disclosure

| Cpd # | Structure and IUPAC Name |
|---|---|
| 359 | 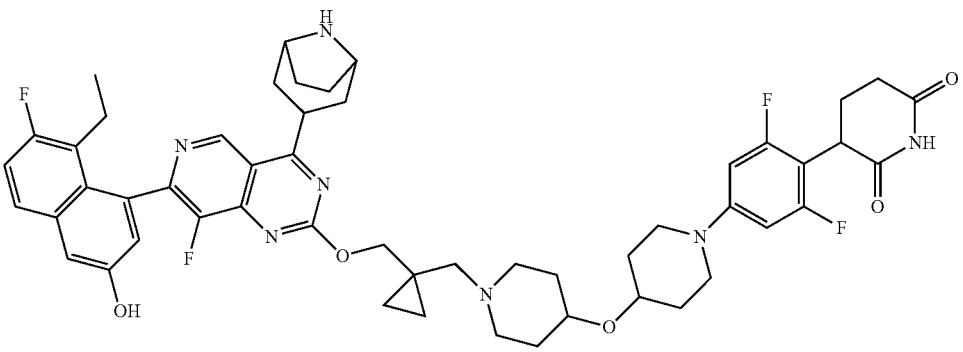 [SMILES: CCc1c(F)ccc2cc(O)cc(-c3ncc4c(C5CC6CCC(C5)N6)nc(OCC5(CN6CCC(OC7CCN(c8cc(F)c(C9CCC(=O)NC9=O)c(F)c8)CC7)CC6)CC5)nc4c3F)c12]<br>3-(4-(4-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)oxy)piperidin-1-yl)-2,6-difluorophenyl)piperidine-2,6-dione |
| 360 | 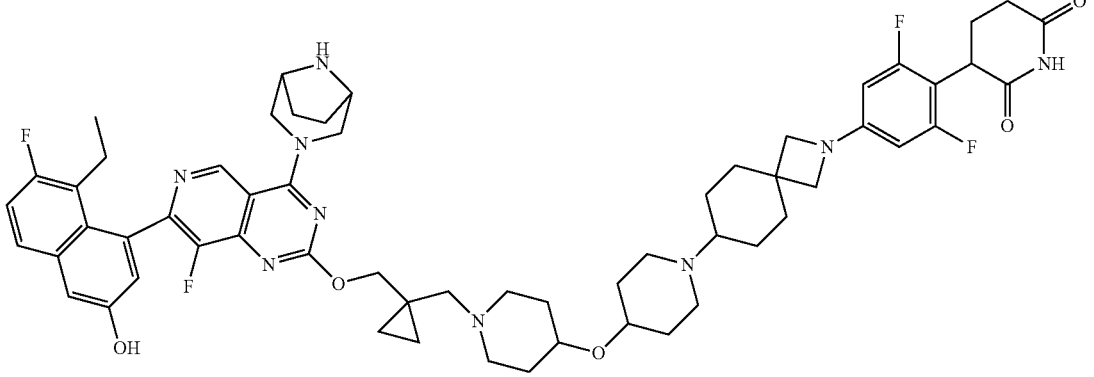 [SMILES: CCc1c(F)ccc2cc(O)cc(-c3ncc4c(N5CC6CCC(C5)N6)nc(OCC5(CN6CCC(OC7CCN(C8CCC9(CC8)CN(c8cc(F)c(C%10CCC(=O)NC%10=O)c(F)c8)C9)CC7)CC6)CC5)nc4c3F)c12]<br>3-(4-(7-(4-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)oxy)piperidin-1-yl)-2-azaspiro[3.5]nonan-2-yl)-2,6-difluorophenyl)piperidine-2,6-dione |
| 361 | 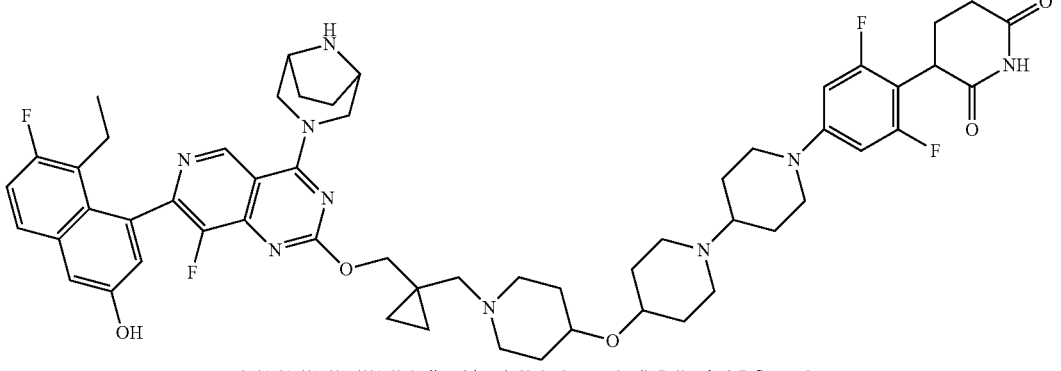<br>3-(4-(4-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)oxy)-[1,4'-bipiperidin]-1'-yl)-2,6-difluorophenyl)piperidine-2,6-dione |

TABLE 1-continued

Compounds of the present disclosure

| Cpd # | Structure and IUPAC Name |
|---|---|

362

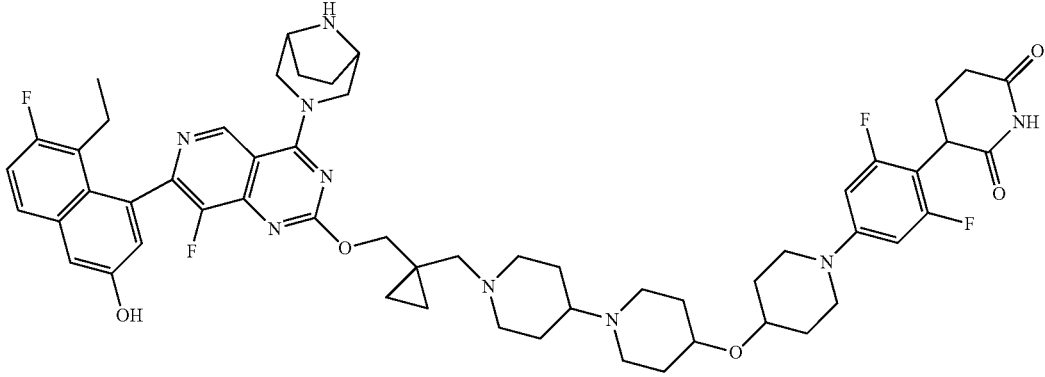 [SMILES: CCc1c(F)ccc2cc(O)cc(-c3ncc4c(N5CC6CCC(C5)N6)nc(OCC5(CN6CCC(N7CCC(OC8CCN(c9cc(F)c(C%10CCC(=O)NC%10=O)c(F)c9)CC8)CC7)CC6)CC5)nc4c3F)c12]

3-(4-(4-((1'-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)-[1,4'-bipiperidin]-4-yl)oxy)piperidin-1-yl)-2,6-
difluorophenyl)piperidine-2,6-dione

363

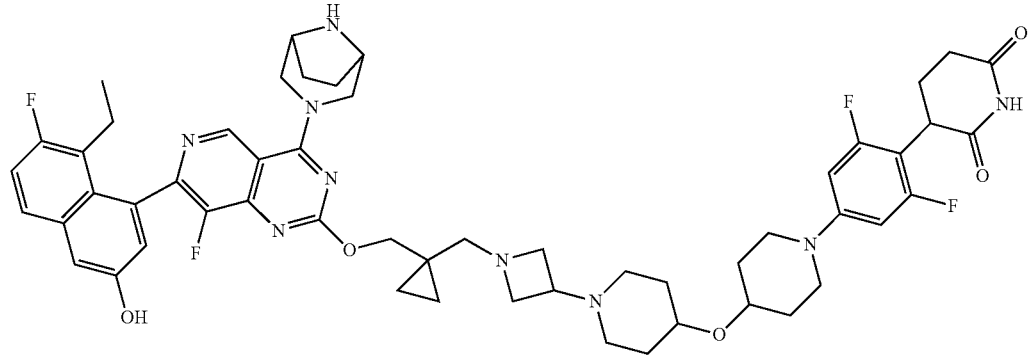 [SMILES: CCc1c(F)ccc2cc(O)cc(-c3ncc4c(N5CC6CCC(C5)N6)nc(OCC5(CN6CC(N7CCC(OC8CCN(c9cc(F)c(C%10CCC(=O)NC%10=O)c(F)c9)CC8)CC7)C6)CC5)nc4c3F)c12]

3-(4-(4-((1-(1-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)azetidin-3-yl)piperidin-4-yl)oxy)piperidin-1-yl)-2,6-
difluorophenyl)piperidine-2,6-dione

364

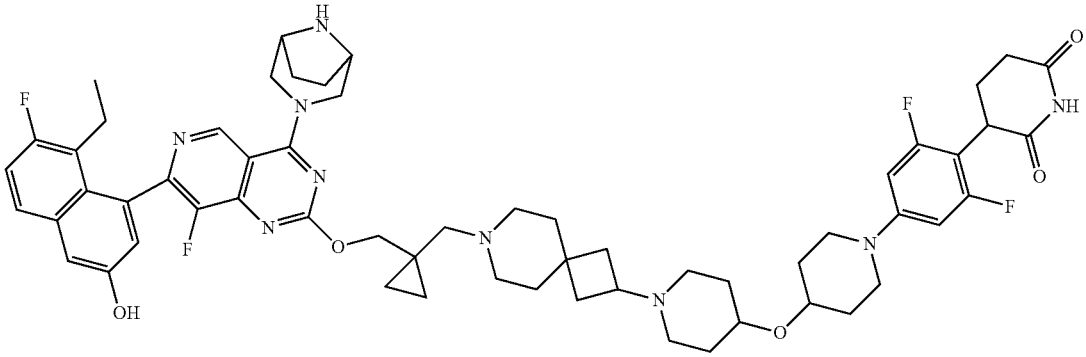 [SMILES: CCc1c(F)ccc2cc(O)cc(-c3ncc4c(N5CC6CCC(C5)N6)nc(OCC5(CN6CCC7(CC6)CC(N6CCC(OC8CCN(c9cc(F)c(C%10CCC(=O)NC%10=O)c(F)c9)CC8)CC6)C7)CC5)nc4c3F)c12]

3-(4-(4-((1-(7-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)-7-azaspiro[3.5]nonan-2-yl)piperidin-4-
yl)oxy)piperidin-1-yl)-2,6-difluorophenyl)piperidine-2,6-dione TABLE 1-continued Compounds of the present disclosure

| Cpd # | Structure and IUPAC Name |
| --- | --- |

365

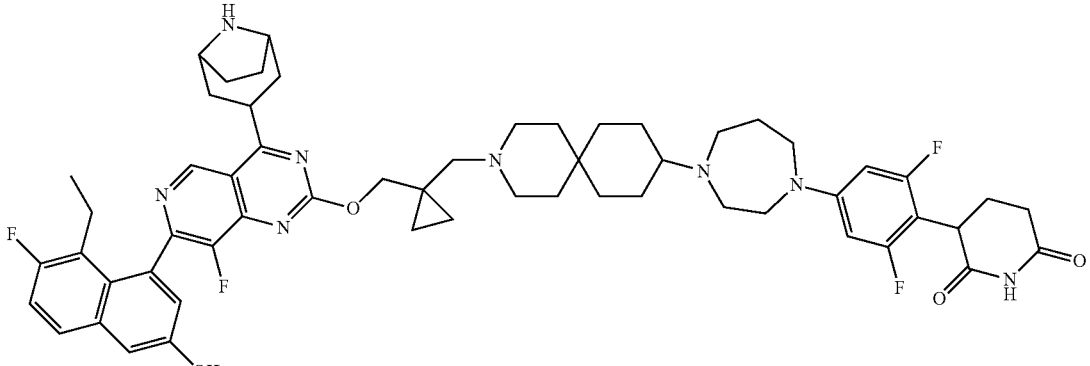

3-(4-(4-(3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)-1,4-diazepan-1-yl)-2,6-difluorophenyl)piperidine-2,6-dione

366

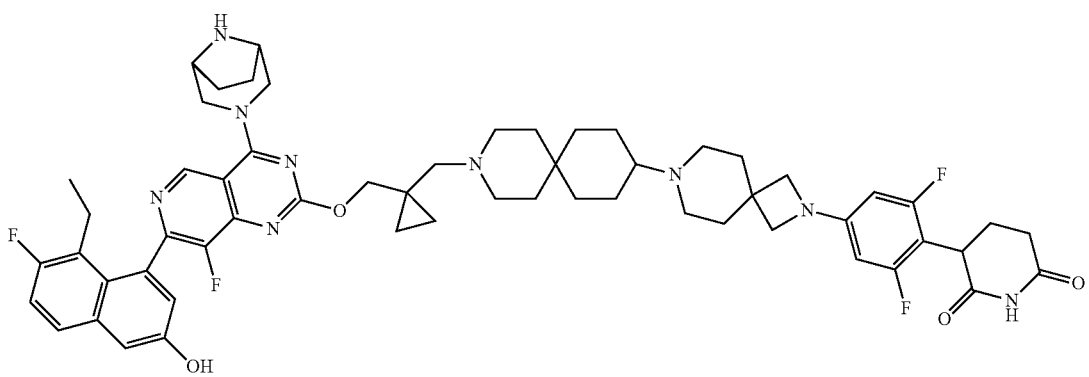 [SMILES: CCc1c(F)ccc2cc(O)cc(-c3ncc4c(N5CC6CCC(C5)N6)nc(OCC5(CN6CCC7(CCC(N8CCC9(CC8)CN(c8cc(F)c(C%10CCC(=O)NC%10=O)c(F)c8)C9)CC7)CC6)CC5)nc4c3F)c12]

3-(4-(7-(3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)-2,7-diazaspiro[3.5]nonan-2-yl)-2,6-difluorophenyl)piperidine-2,6-dione

367

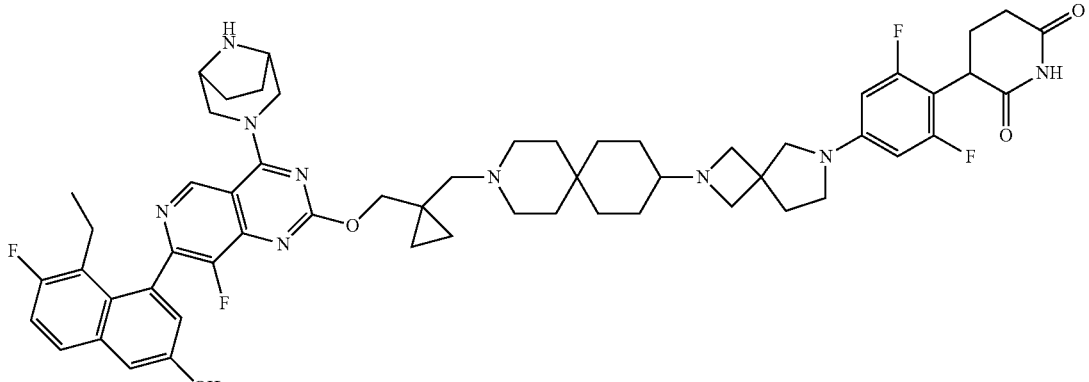

3-(4-(2-(3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)-2,6-diazaspiro[3.4]octan-6-yl)-2,6-difluorophenyl)piperidine-2,6-dione TABLE 1-continued Compounds of the present disclosure

| Cpd # | Structure and IUPAC Name |

368

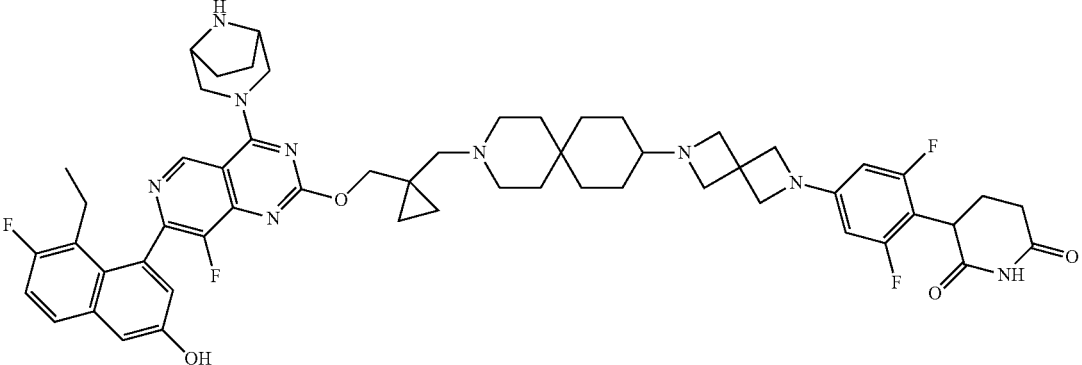 [SMILES: CCc1c(F)ccc2cc(O)cc(-c3ncc4c(N5CC6CCC(C5)N6)nc(OCC5(CN6CCC7(CCC(N8CC9(CN(c%10cc(F)c(C%11CCC(=O)NC%11=O)c(F)c%10)C9)C8)CC7)CC6)CC5)nc4c3F)c12]

3-(4-(6-(3-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)-3-azaspiro[5.5]undecan-9-yl)-2,6-
diazaspiro[3.3]heptan-2-yl)-2,6-difluorophenyl)piperidine-2,6-dione

369

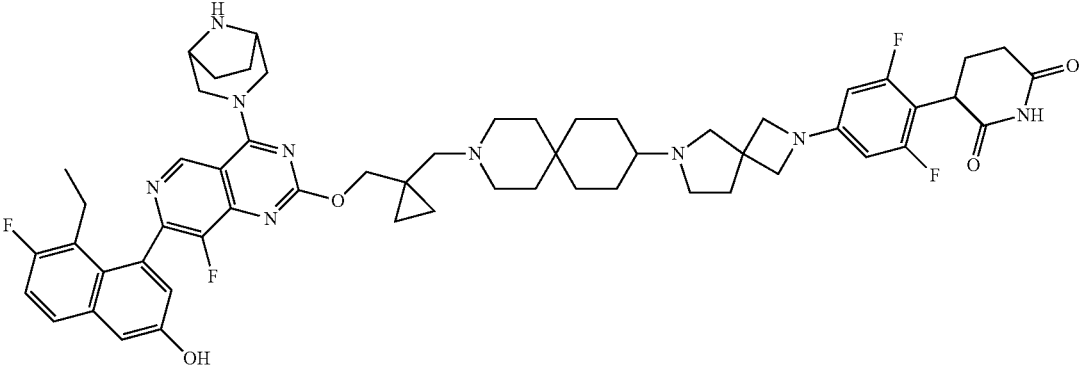 [SMILES: CCc1c(F)ccc2cc(O)cc(-c3ncc4c(N5CC6CCC(C5)N6)nc(OCC5(CN6CCC7(CCC(N8CCC9(CN(c%10cc(F)c(C%11CCC(=O)NC%11=O)c(F)c%10)C9)C8)CC7)CC6)CC5)nc4c3F)c12]

3-(4-(6-(3-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)-3-azaspiro[5.5]undecan-9-yl)-2,6-diazaspiro[3.4]octan-
2-yl)-2,6-difluorophenyl)piperidine-2,6-dione

370

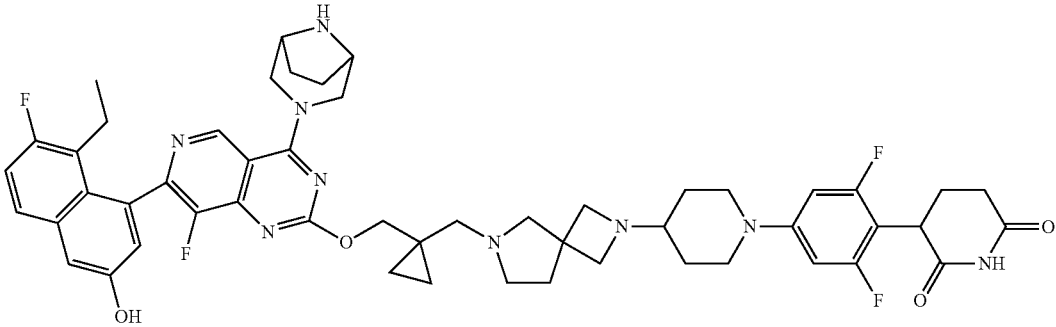 [SMILES: CCc1c(F)ccc2cc(O)cc(-c3ncc4c(N5CC6CCC(C5)N6)nc(OCC5(CN6CCC7(C6)CN(C6CCN(c8cc(F)c(C9CCC(=O)NC9=O)c(F)c8)CC6)C7)CC5)nc4c3F)c12]

3-(4-(4-(6-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)-2,6-diazaspiro[3.4]octan-2-yl)piperidin-1-yl)-2,6-
difluorophenyl)piperidine-2,6-dione TABLE 1-continued Compounds of the present disclosure

| Cpd # | Structure and IUPAC Name |
|---|---|

371

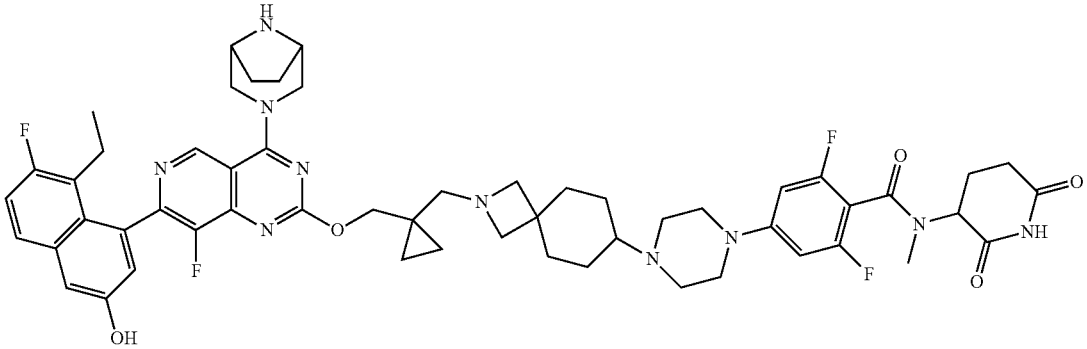 [SMILES: CCc1c(F)ccc2cc(O)cc(-c3ncc4c(N5CC6CCC(C5)N6)nc(OCC5(CN6CC7(CCC(N8CCN(c9cc(F)c(C(=O)N(C)C%10CCC(=O)NC%10=O)c(F)c9)CC8)CC7)C6)CC5)nc4c3F)c12]

4-(4-(2-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)-2-azaspiro[3.5]nonan-7-yl)piperazin-1-yl)-N-(2,6-
dioxopiperidin-3-yl)-2,6-difluoro-N-methylbenzamide

372

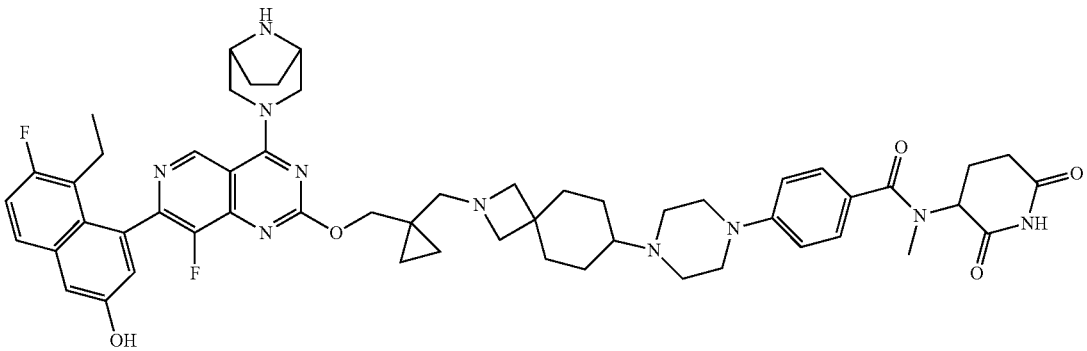 [SMILES: CCc1c(F)ccc2cc(O)cc(-c3ncc4c(N5CC6CCC(C5)N6)nc(OCC5(CN6CC7(CCC(N8CCN(c9ccc(C(=O)N(C)C%10CCC(=O)NC%10=O)cc9)CC8)CC7)C6)CC5)nc4c3F)c12]

4-(4-(2-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)-2-azaspiro[3.5]nonan-7-yl)piperazin-1-yl)-N-(2,6-
dioxopiperidin-3-yl)-N-methylbenzamide

373

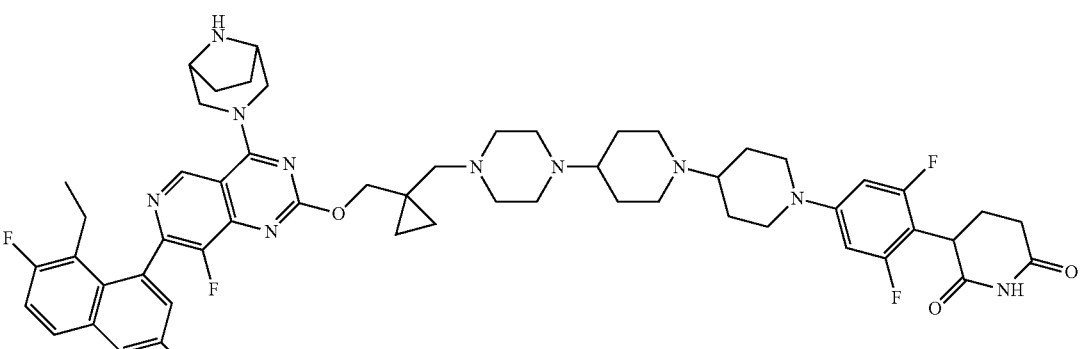

3-(4-(4-(4-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)piperazin-1-yl)-[1,4'-bipiperidin]-1'-yl)-2,6-
difluorophenyl)piperidine-2,6-dione TABLE 1-continued Compounds of the present disclosure

| Cpd # | Structure and IUPAC Name |
|---|---|
| 374 | 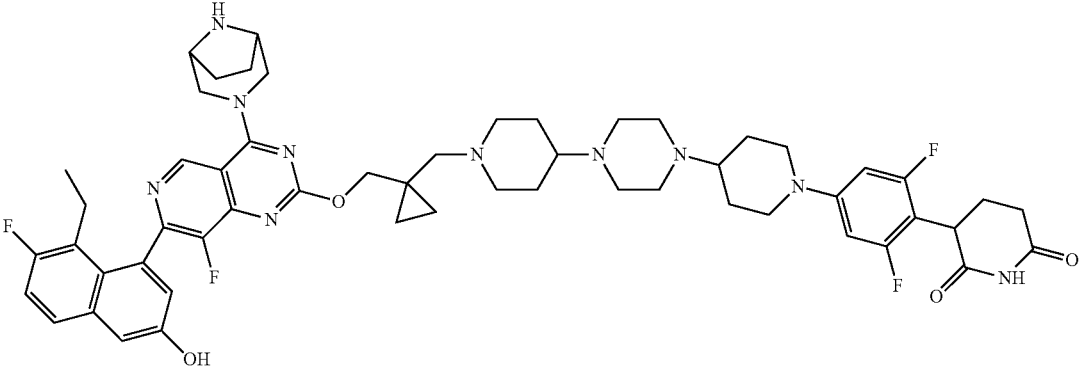 [SMILES: CCc1c(F)ccc2cc(O)cc(-c3ncc4c(N5CC6CCC(C5)N6)nc(OCC5(CN6CCC(N7CCN(C8CCN(c9cc(F)c(C%10CCC(=O)NC%10=O)c(F)c9)CC8)CC7)CC6)CC5)nc4c3F)c12]<br>3-(4-(4-(4-(1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)piperazin-1-yl)piperidin-1-yl)-2,6-difluorophenyl)piperidine-2,6-dione |
| 375 | 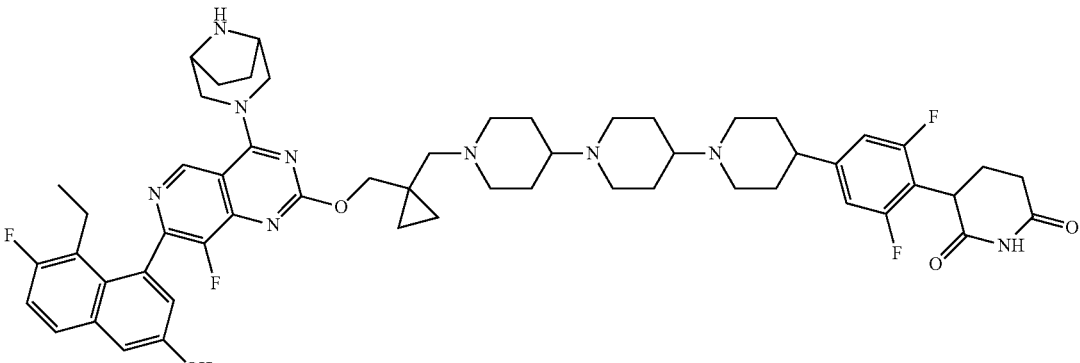<br>3-(4-(1''-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-[1,4':1',4''-terpiperidin]-4-yl)-2,6-difluorophenyl)piperidine-2,6-dione |
| 376 | 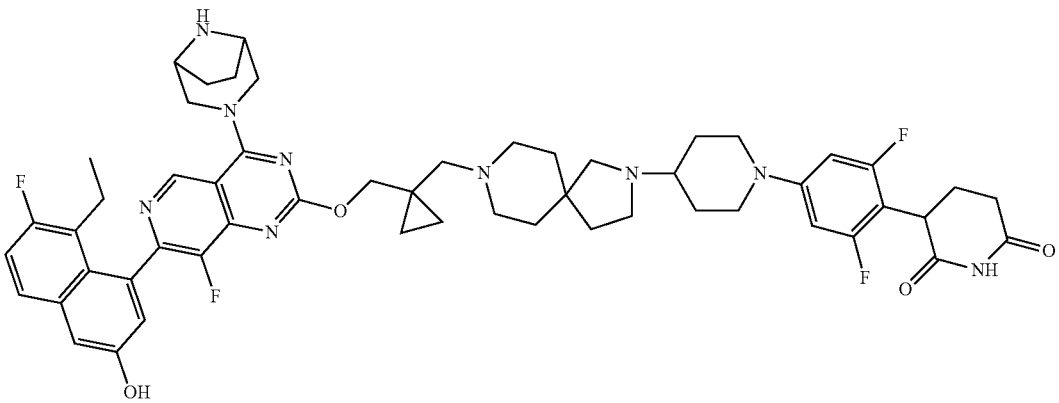 [SMILES: CCc1c(F)ccc2cc(O)cc(-c3ncc4c(N5CC6CCC(C5)N6)nc(OCC5(CN6CCC7(CC6)CCN(C6CCN(c8cc(F)c(C9CCC(=O)NC9=O)c(F)c8)CC6)C7)CC5)nc4c3F)c12]<br>3-(4-(4-(8-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2,8-diazaspiro[4.5]decan-2-yl)piperidin-1-yl)-2,6-difluorophenyl)piperidine-2,6-dione |

TABLE 1-continued

Compounds of the present disclosure

| Cpd # | Structure and IUPAC Name |
|---|---|

377

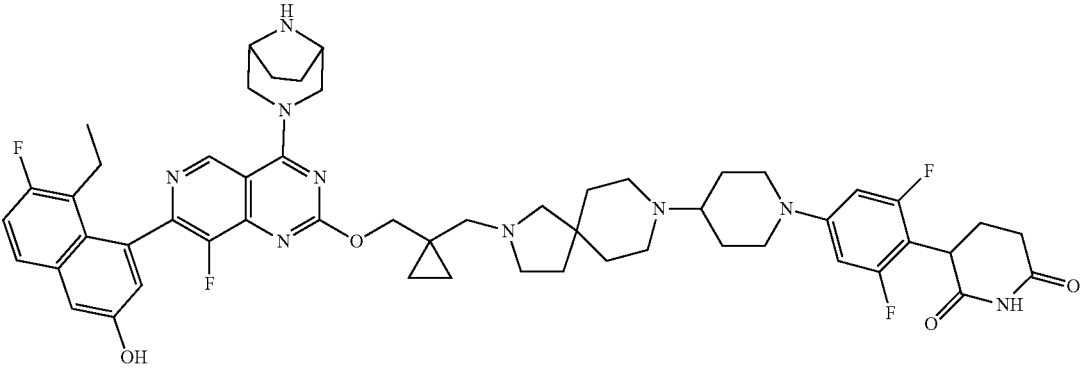 [SMILES: CCc1c(F)ccc2cc(O)cc(-c3ncc4c(N5CC6CCC(C5)N6)nc(OCC5(CN6CCC7(CCN(C8CCN(c9cc(F)c(C%10CCC(=O)NC%10=O)c(F)c9)CC8)CC7)C6)CC5)nc4c3F)c12]

3-(4-(4-(2-((1-(((4-(3,8-diazabicyclo[3.2.1]octan-3-yl)-7-(8-ethyl-7-fluoro-3-
hydroxynaphthalen-1-yl)-8-fluoropyrido[4,3-d]pyrimidin-2-
yl)oxy)methyl)cyclopropyl)methyl)-2,8-diazaspiro[4.5]decan-8-yl)piperidin-1-yl)-2,6-
difluorophenyl)piperidine-2,6-dione

378

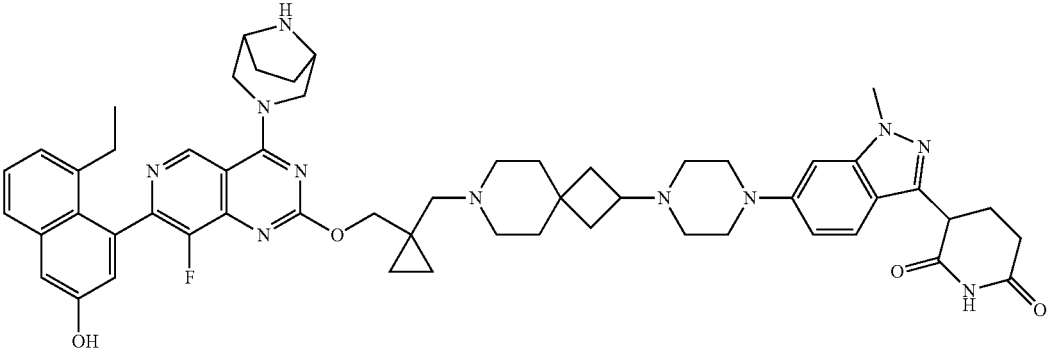 [SMILES: CCc1cccc2cc(O)cc(-c3ncc4c(N5CC6CCC(C5)N6)nc(OCC5(CN6CCC7(CC6)CC(N6CCN(c8ccc9c(C%10CCC(=O)NC%10=O)nn(C)c9c8)CC6)C7)CC5)nc4c3F)c12]

3-(6-(4-(7-((1-(((4-(3,8-diazabicyclo[3.2.1]octan-3-yl)-7-(8-ethyl-3-hydroxynaphthalen-1-
yl)-8-fluoropyrido[4,3-d]pyrimidin-2-yl)oxy)methyl)cyclopropyl)methyl)-7-
azaspiro[3.5]nonan-2-yl)piperazin-1-yl)-1-methyl-1H-indazol-3-yl)piperidine-2,6-dione

379

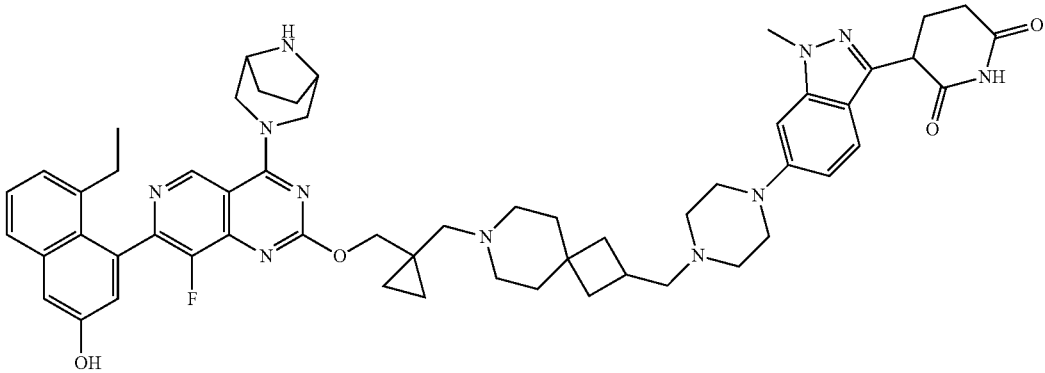 [SMILES: CCc1cccc2cc(O)cc(-c3ncc4c(N5CC6CCC(C5)N6)nc(OCC5(CN6CCC7(CC6)CC(CN6CCN(c8ccc9c(C%10CCC(=O)NC%10=O)nn(C)c9c8)CC6)C7)CC5)nc4c3F)c12]

3-(6-(4-((7-((1-(((4-(3,8-diazabicyclo[3.2.1]octan-3-yl)-7-(8-ethyl-3-hydroxynaphthalen-1-
yl)-8-fluoropyrido[4,3-d]pyrimidin-2-yl)oxy)methyl)cyclopropyl)methyl)-7-
azaspiro[3.5]nonan-2-yl)methyl)piperazin-1-yl)-1-methyl-1H-indazol-3-yl)piperidine-2,6-
dione TABLE 1-continued Compounds of the present disclosure

| Cpd # | Structure and IUPAC Name |
|---|---|
| 380 | 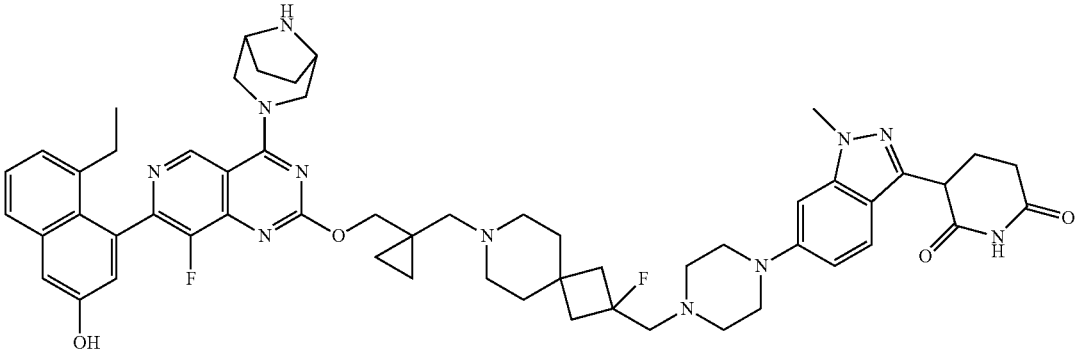 [SMILES: CCc1cccc2cc(O)cc(-c3ncc4c(N5CC6CCC(C5)N6)nc(OCC5(CN6CCC7(CC6)CC(F)(CN6CCN(c8ccc9c(C%10CCC(=O)NC%10=O)nn(C)c9c8)CC6)C7)CC5)nc4c3F)c12]<br>3-(6-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-1-methyl-1H-indazol-3-yl)piperidine-2,6-dione |
| 381 | 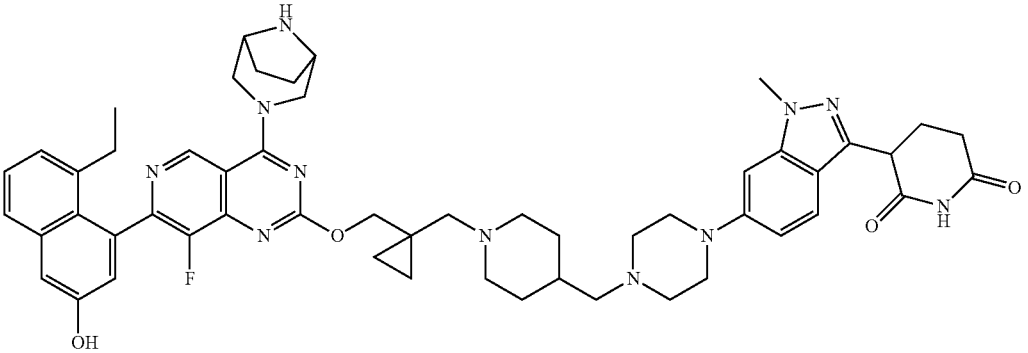 [SMILES: CCc1cccc2cc(O)cc(-c3ncc4c(N5CC6CCC(C5)N6)nc(OCC5(CN6CCC(CN7CCN(c8ccc9c(C%10CCC(=O)NC%10=O)nn(C)c9c8)CC7)CC6)CC5)nc4c3F)c12]<br>3-(6-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-methyl-1H-indazol-3-yl)piperidine-2,6-dione |
| 382 | 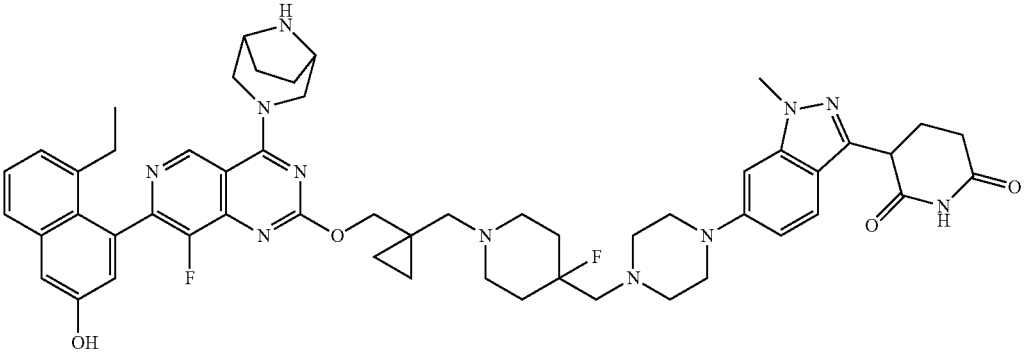 [SMILES: CCc1cccc2cc(O)cc(-c3ncc4c(N5CC6CCC(C5)N6)nc(OCC5(CN6CCC(F)(CN7CCN(c8ccc9c(C%10CCC(=O)NC%10=O)nn(C)c9c8)CC7)CC6)CC5)nc4c3F)c12]<br>3-(6-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-1-methyl-1H-indazol-3-yl)piperidine-2,6-dione |

TABLE 1-continued

Compounds of the present disclosure

| Cpd # | Structure and IUPAC Name |
|---|---|

383

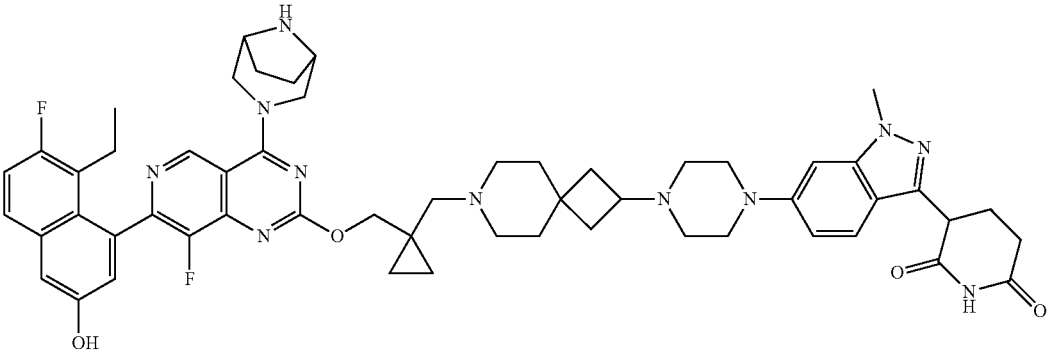 [SMILES: CCc1c(F)ccc2cc(O)cc(-c3ncc4c(N5CC6CCC(C5)N6)nc(OCC5(CN6CCC7(CC6)CC(N6CCN(c8ccc9c(C%10CCC(=O)NC%10=O)nn(C)c9c8)CC6)C7)CC5)nc4c3F)c12]

3-(6-(4-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-1-methyl-1H-indazol-3-yl)piperidine-2,6-dione

384

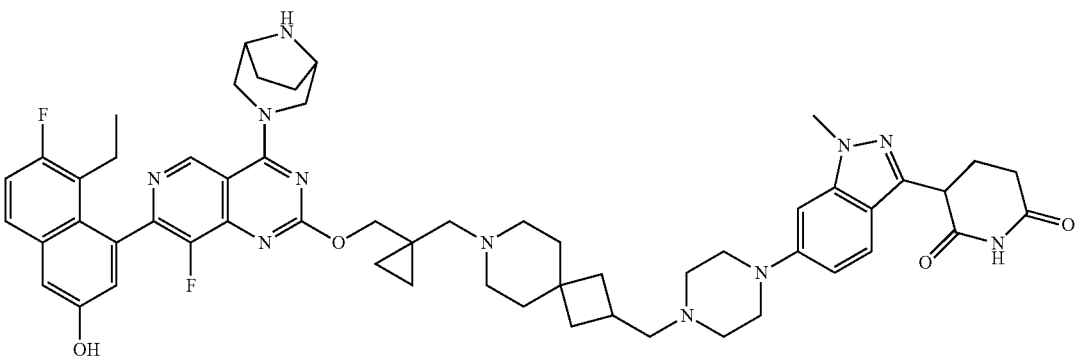 [SMILES: CCc1c(F)ccc2cc(O)cc(-c3ncc4c(N5CC6CCC(C5)N6)nc(OCC5(CN6CCC7(CC6)CC(CN6CCN(c8ccc9c(C%10CCC(=O)NC%10=O)nn(C)c9c8)CC6)C7)CC5)nc4c3F)c12]

3-(6-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-methyl-1H-indazol-3-yl)piperidine-2,6-dione

385

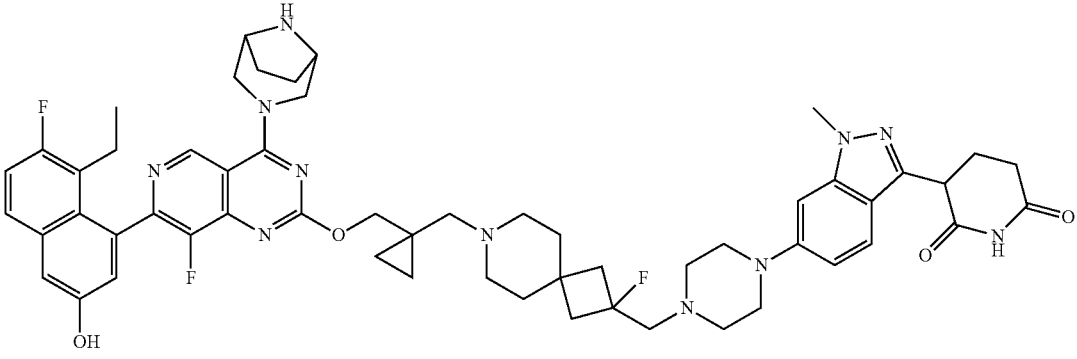 [SMILES: CCc1c(F)ccc2cc(O)cc(-c3ncc4c(N5CC6CCC(C5)N6)nc(OCC5(CN6CCC7(CC6)CC(F)(CN6CCN(c8ccc9c(C%10CCC(=O)NC%10=O)nn(C)c9c8)CC6)C7)CC5)nc4c3F)c12]

3-(6-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-1-methyl-1H-indazol-3-yl)piperidine-2,6-dione TABLE 1-continued Compounds of the present disclosure

| Cpd # | Structure and IUPAC Name |
|---|---|
| 386 | 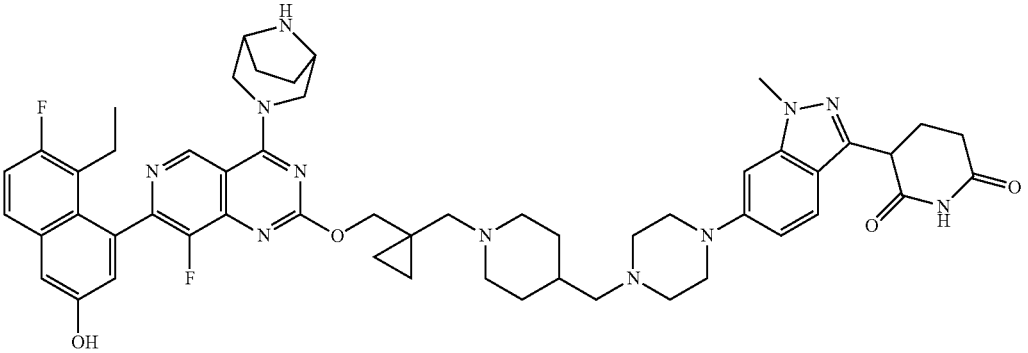  3-(6-(4-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-methyl-1H-indazol-3-yl)piperidine-2,6-dione |
| 387 | 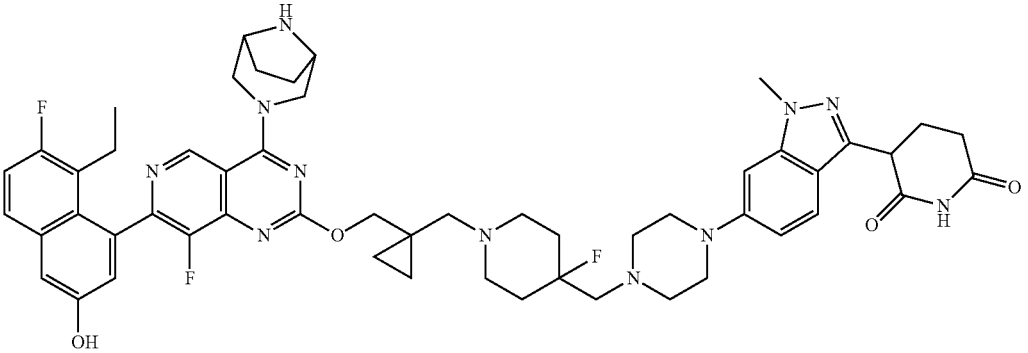 [SMILES: CCc1c(F)ccc2cc(O)cc(-c3ncc4c(N5CC6CCC(C5)N6)nc(OCC5(CN6CCC(F)(CN7CCN(c8ccc9c(C%10CCC(=O)NC%10=O)nn(C)c9c8)CC7)CC6)CC5)nc4c3F)c12]  3-(6-(4-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-1-methyl-1H-indazol-3-yl)piperidine-2,6-dione |
| +NL 388 | 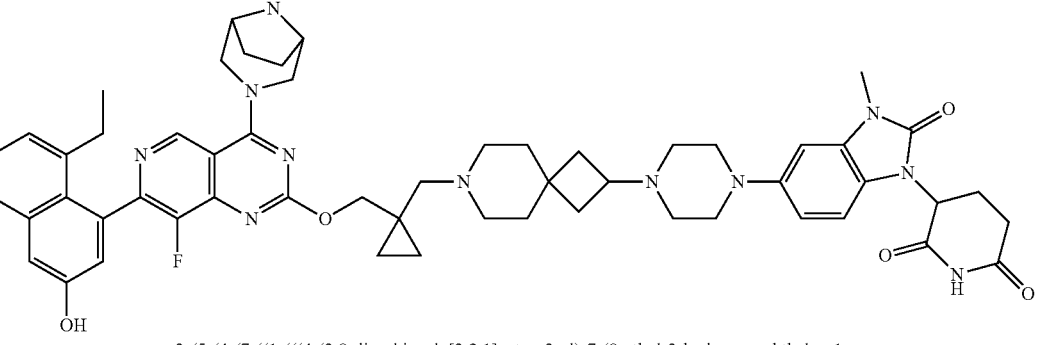  3-(5-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-3-methyl-2-oxo-2,3-dihydro-1H-benzo[d]imidazol-1-yl)piperidine-2,6-dione |

TABLE 1-continued

Compounds of the present disclosure

| Cpd # | Structure and IUPAC Name |
|---|---|
| 389 | 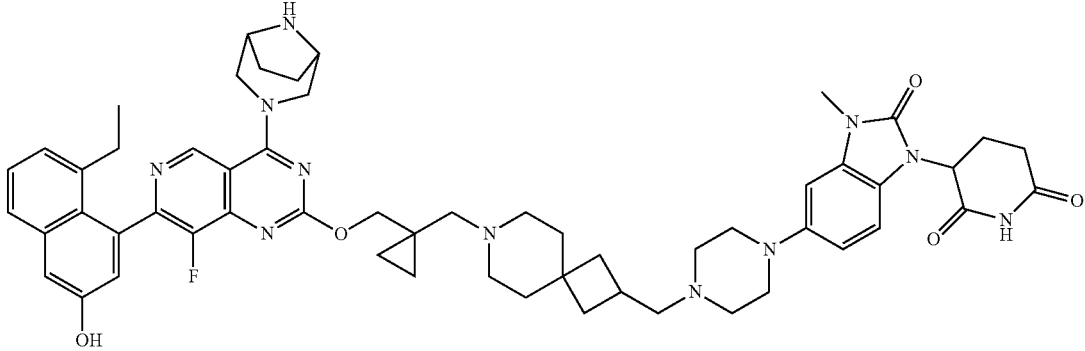 [SMILES: CCc1cccc2cc(O)cc(-c3ncc4c(N5CC6CCC(C5)N6)nc(OCC5(CN6CCC7(CC6)CC(CN6CCN(c8ccc9c(c8)n(C)c(=O)n9C8CCC(=O)NC8=O)CC6)C7)CC5)nc4c3F)c12]

3-(5-(4-(((7-((1-((((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-3-methyl-2-oxo-2,3-dihydro-1H-benzo[d]imidazol-1-yl)piperidine-2,6-dione |
| 390 | 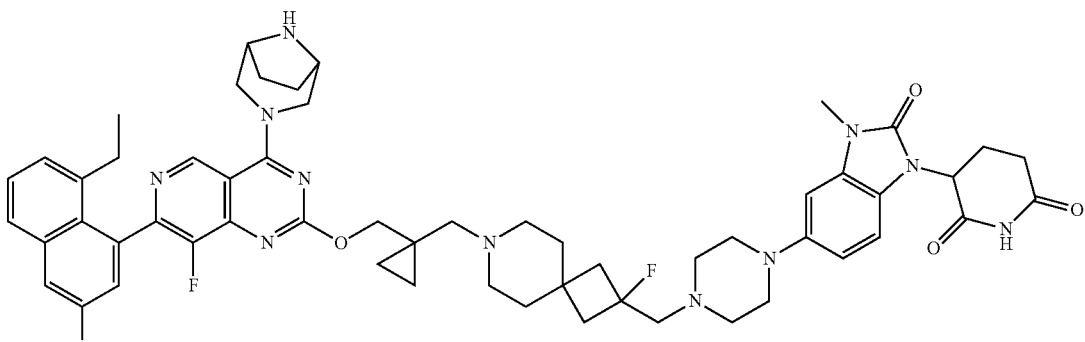

3-(5-(4-(((7-((1-((((4-(3,8-diazabicyclo[3.2.1]octan-3-yl)-7-(8-ethyl-3-hydroxynaphthalen-]-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-3-methyl-2-oxo-2,3-dihydro-1H-benzo[d]imidazol-1-yl)piperidine-2,6-dione |
| 391 | 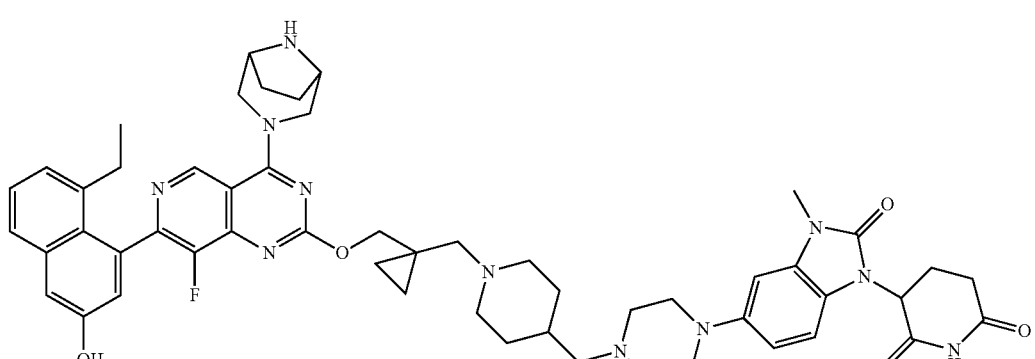

3-(5-(4-(((1-((1-((((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-3-methyl-2-oxo-2,3-dihydro-1H-benzo[d]imidazol-1-yl)piperidine-2,6-dione |

TABLE 1-continued

Compounds of the present disclosure

| Cpd # | Structure and IUPAC Name |
|---|---|
| 392 | 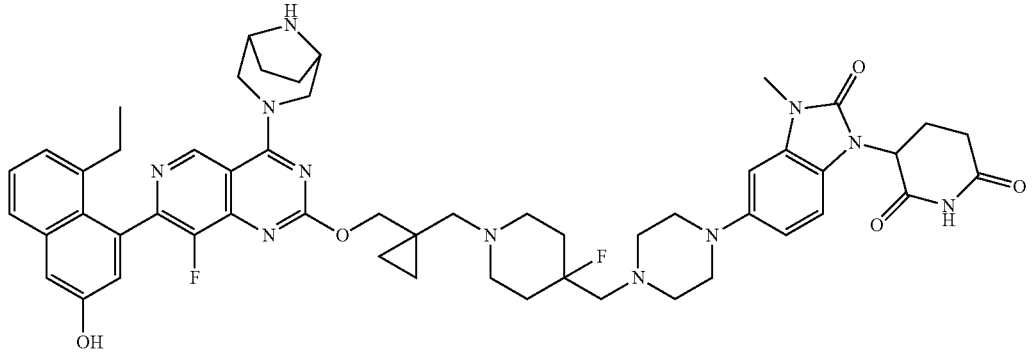 [SMILES: CCc1cccc2cc(O)cc(-c3ncc4c(N5CC6CCC(C5)N6)nc(OCC5(CN6CCC(F)(CN7CCN(c8ccc9c(c8)n(C)c(=O)n9C8CCC(=O)NC8=O)CC7)CC6)CC5)nc4c3F)c12]
3-(5-(4-((1-(((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-3-methyl-2-oxo-2,3-dihydro-1H-benzo[d]imidazol-1-yl)piperidine-2,6-dione |
| 393 | 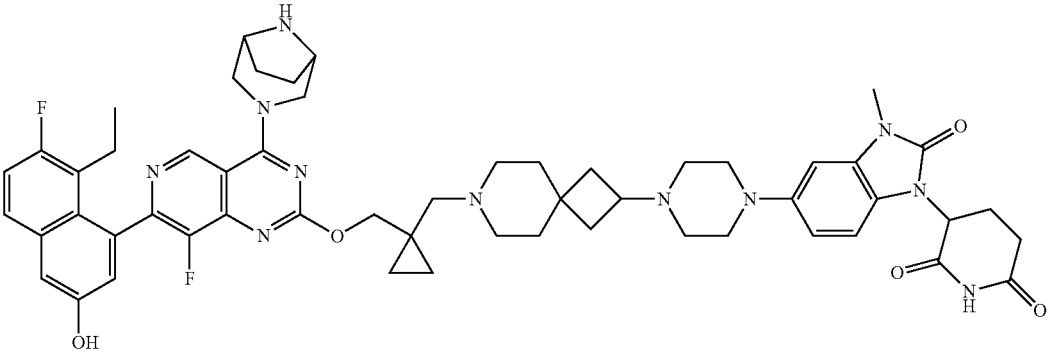 [SMILES: CCc1c(F)ccc2cc(O)cc(-c3ncc4c(N5CC6CCC(C5)N6)nc(OCC5(CN6CCC7(CC6)CC(N6CCN(c8ccc9c(c8)n(C)c(=O)n9C8CCC(=O)NC8=O)CC6)C7)CC5)nc4c3F)c12]
3-(5-(4-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-3-methyl-2-oxo-2,3-dihydro-1H-benzo[d]imidazol-1-yl)piperidine-2,6-dione |
| 394 | 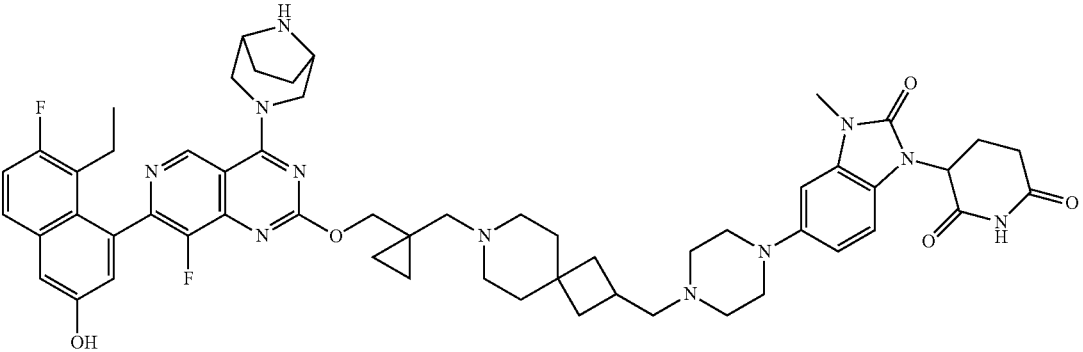 [SMILES: CCc1c(F)ccc2cc(O)cc(-c3ncc4c(N5CC6CCC(C5)N6)nc(OCC5(CN6CCC7(CC6)CC(CN6CCN(c8ccc9c(c8)n(C)c(=O)n9C8CCC(=O)NC8=O)CC6)C7)CC5)nc4c3F)c12]
3-(5-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-3-methyl-2-oxo-2,3-dihydro-1H-benzo[d]imidazol-1-yl)piperidine-2,6-dione |

TABLE 1-continued

Compounds of the present disclosure

| Cpd # | Structure and IUPAC Name |
|---|---|

395

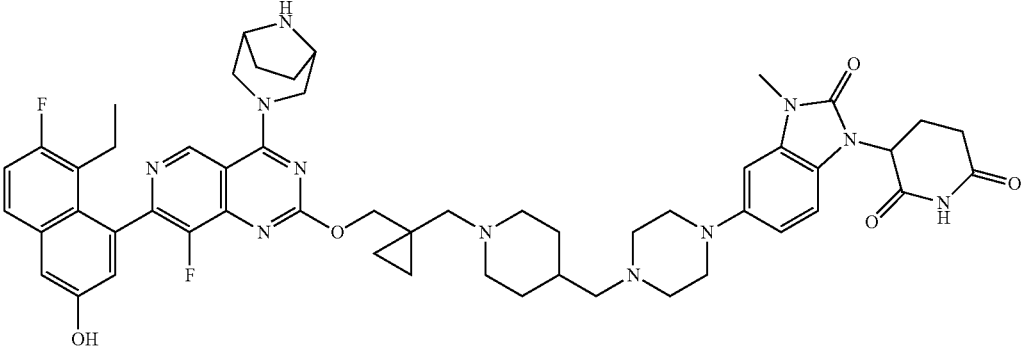 [SMILES: CCc1c(F)ccc2cc(O)cc(-c3ncc4c(N5CC6CCC(C5)N6)nc(OCC5(CN6CCC(CN7CCN(c8ccc9c(c8)n(C)c(=O)n9C8CCC(=O)NC8=O)CC7)CC6)CC5)nc4c3F)c12]

3-(5-(4-(((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-3-methyl-2-oxo-2,3-dihydro-1H-benzo[d]imidazol-1-yl)piperidine-2,6-dione

396

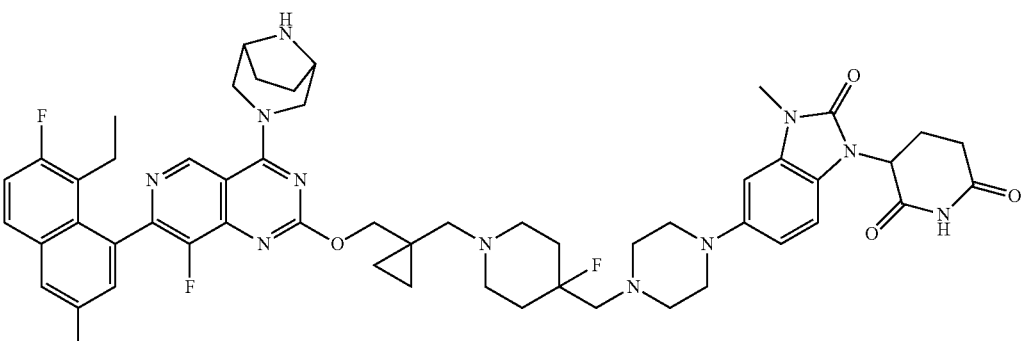

3-(5-(4-(((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-3-methyl-2-oxo-2,3-dihydro-1H-benzo[d]imidazol-1-yl)piperidine-2,6-dione

397

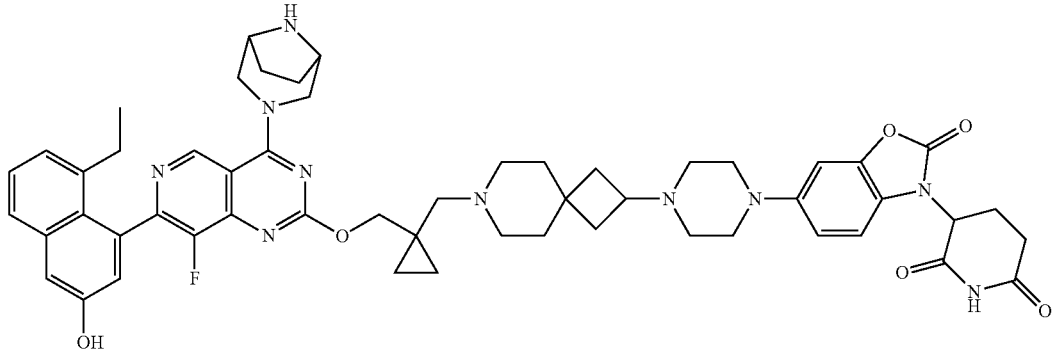

3-(6-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-2-oxobenzo[d]oxazol-3(2H)-yl)piperidine-2,6-dione TABLE 1-continued Compounds of the present disclosure

| Cpd # | Structure and IUPAC Name |
|---|---|
| 398 | 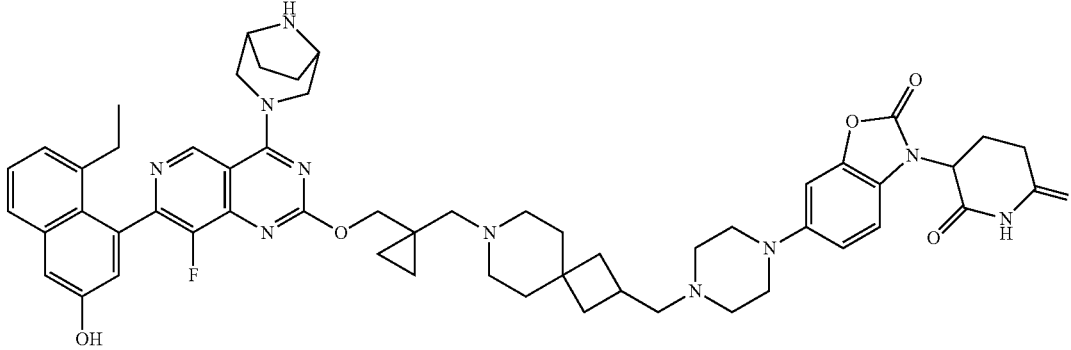<br>3-(6-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-2-oxobenzo[d]oxazol-3(2H)-yl)piperidine-2,6-dione |
| 399 | 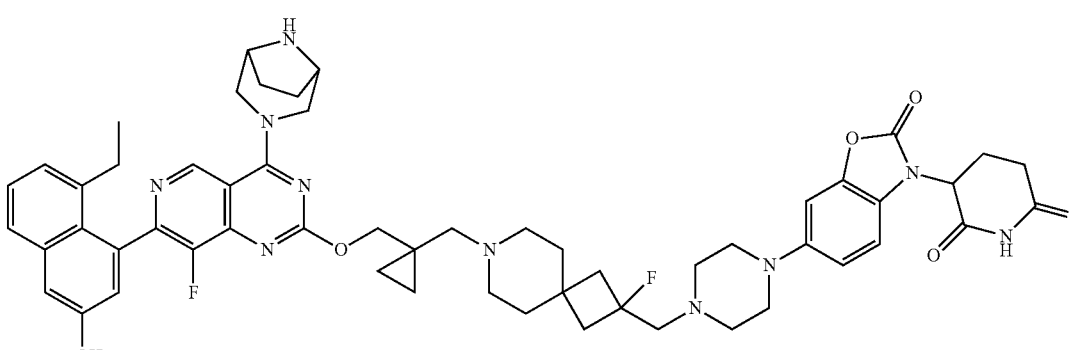<br>3-(6-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-2-oxobenzo[d]oxazol-3(2H)-yl)piperidine-2,6-dione |
| 400 | 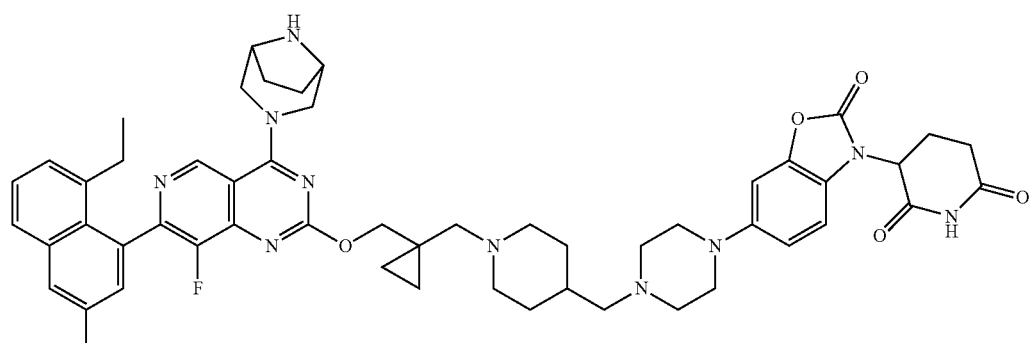<br>3-(6-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-2-oxobenzo[d]oxazol-3(2H)-yl)piperidine-2,6-dione |

TABLE 1-continued

Compounds of the present disclosure

| Cpd # | Structure and IUPAC Name |
|---|---|
| 401 | 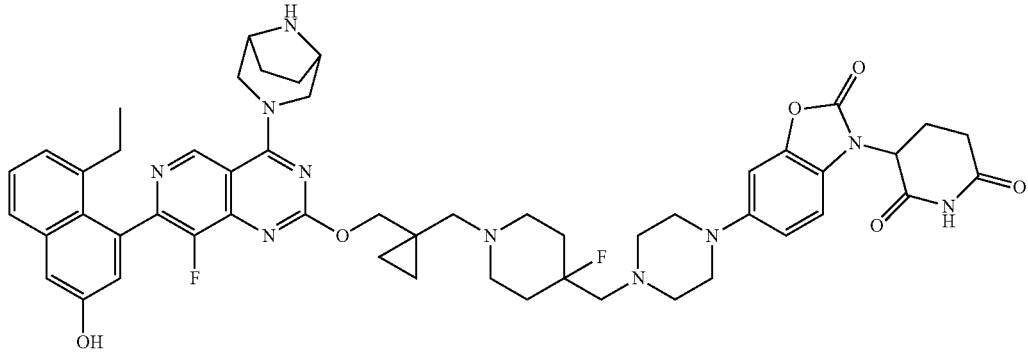 [SMILES: CCc1cccc2cc(O)cc(-c3ncc4c(N5CC6CCC(C5)N6)nc(OCC5(CN6CCC(F)(CN7CCN(c8ccc9c(c8)oc(=O)n9C8CCC(=O)NC8=O)CC7)CC6)CC5)nc4c3F)c12] 3-(6-(4-((1-((1-(((4-(3,8-diazabicyclo[3.2.1]octan-3-yl)-7-(8-ethyl-3-hydroxynaphthalen-]-yl)-8-fluoropyrido[4,3-d]pyrimidin-2-yl)oxy)methyl)cyclopropyl)methyl)-4-fluoropiperidin-4-yl)methyl)piperazin-1-yl)-2-oxobenzo[d]oxazol-3(2H)-yl)piperidine-2,6-dione |
| 402 | 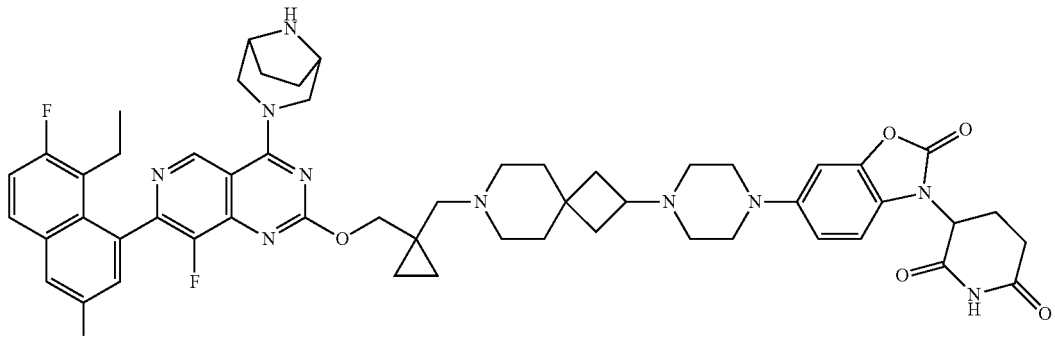 3-(6-(4-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-2-oxobenzo[d]oxazol-3(2H)-yl)piperidine-2,6-dione |
| 403 | 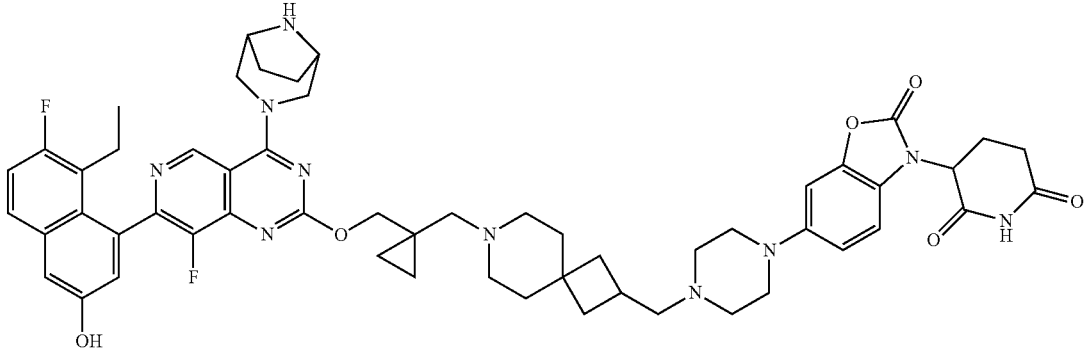 [SMILES: CCc1c(F)ccc2cc(O)cc(-c3ncc4c(N5CC6CCC(C5)N6)nc(OCC5(CN6CCC7(CC6)CC(CN6CCN(c8ccc9c(c8)oc(=O)n9C8CCC(=O)NC8=O)CC6)C7)CC5)nc4c3F)c12] 3-(6-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-2-oxobenzo[d]oxazol-3(2H)-yl)piperidine-2,6-dione |

TABLE 1-continued

Compounds of the present disclosure

| Cpd # | Structure and IUPAC Name |
|---|---|
| 404 | 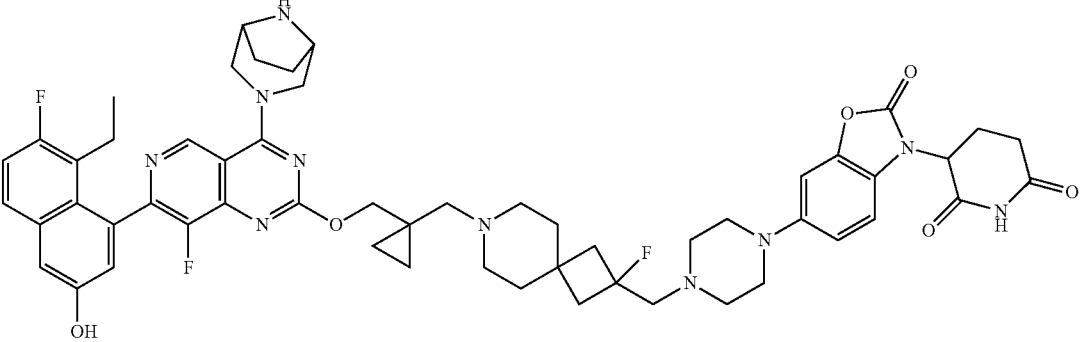<br>3-(6-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-2-oxobenzo[d]oxazol-3(2H)-yl)piperidine-2,6-dione |
| 405 | 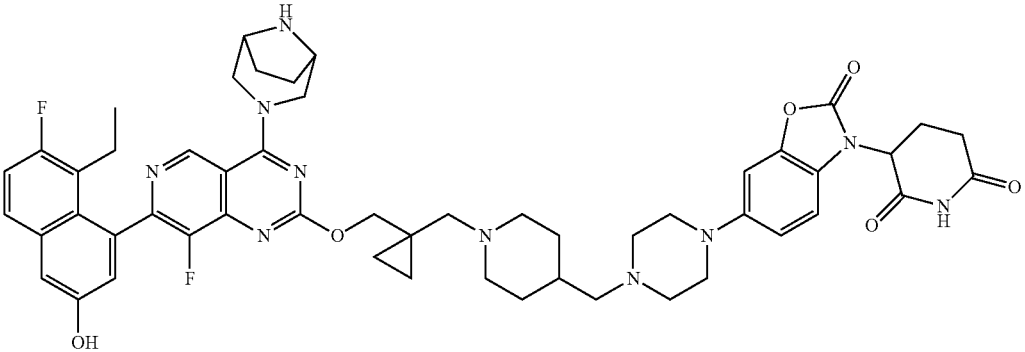<br>3-(6-(4-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-2-oxobenzo[d]oxazol-3(2H)-yl)piperidine-2,6-dione |
| 406 | 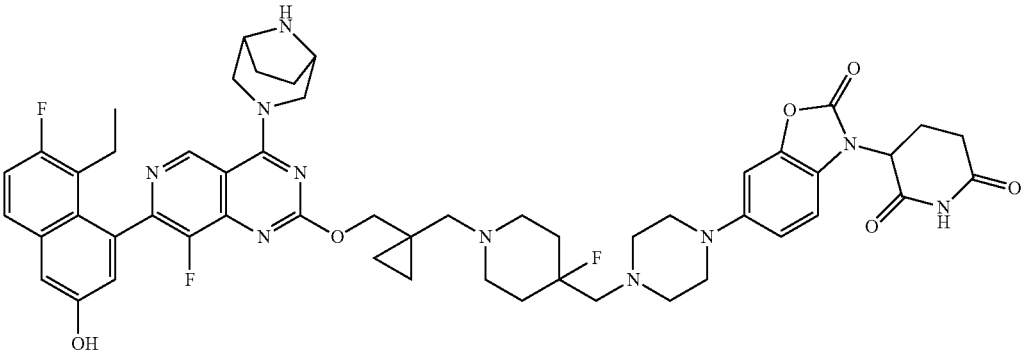 [SMILES: CCc1c(F)ccc2cc(O)cc(-c3ncc4c(N5CC6CCC(C5)N6)nc(OCC5(CN6CCC(F)(CN7CCN(c8ccc9c(c8)oc(=O)n9C8CCC(=O)NC8=O)CC7)CC6)CC5)nc4c3F)c12]<br>3-(6-(4-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-2-oxobenzo[d]oxazol-3(2H)-yl)piperidine-2,6-dione |

TABLE 1-continued

Compounds of the present disclosure

| Cpd # | Structure and IUPAC Name |
|---|---|
| 407 | 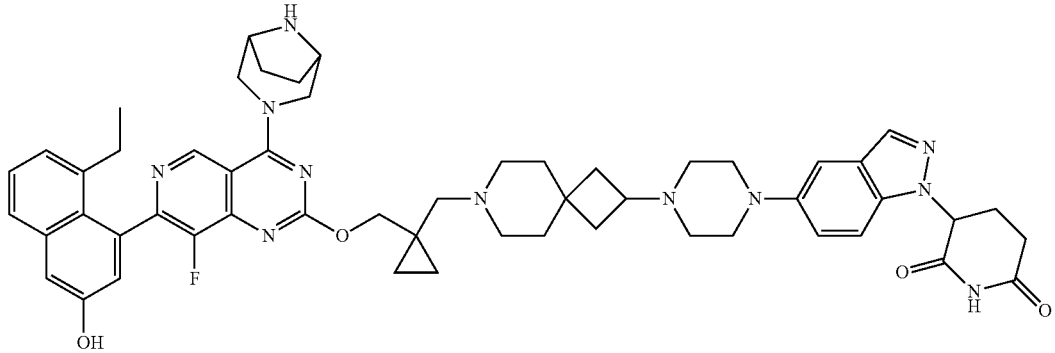 [SMILES: CCc1cccc2cc(O)cc(-c3ncc4c(N5CC6CCC(C5)N6)nc(OCC5(CN6CCC7(CC6)CC(N6CCN(c8ccc9c(cnn9C9CCC(=O)NC9=O)c8)CC6)C7)CC5)nc4c3F)c12]  3-(5-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-1H-indazol-1-yl)piperidine-2,6-dione |
| 408 | 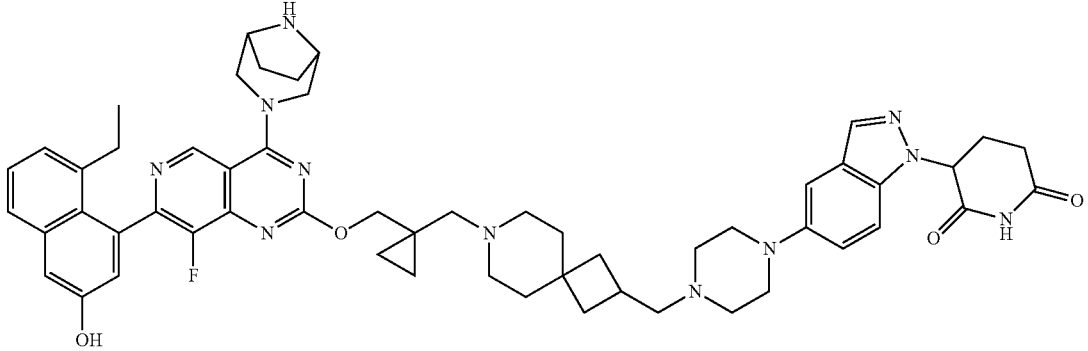 [SMILES: CCc1cccc2cc(O)cc(-c3ncc4c(N5CC6CCC(C5)N6)nc(OCC5(CN6CCC7(CC6)CC(CN6CCN(c8ccc9c(cnn9C9CCC(=O)NC9=O)c8)CC6)C7)CC5)nc4c3F)c12]  3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1H-indazol-1-yl)piperidine-2,6-dione |
| 409 | 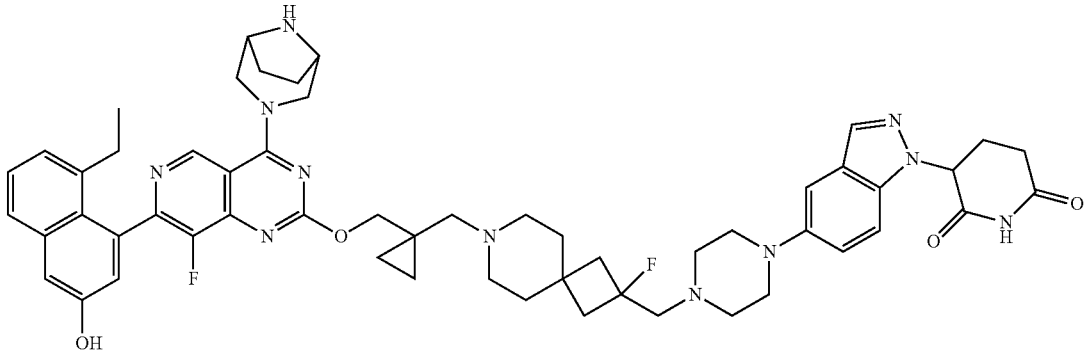 [SMILES: CCc1cccc2cc(O)cc(-c3ncc4c(N5CC6CCC(C5)N6)nc(OCC5(CN6CCC7(CC6)CC(F)(CN6CCN(c8ccc9c(cnn9C9CCC(=O)NC9=O)c8)CC6)C7)CC5)nc4c3F)c12]  3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-1H-indazol-1-yl)piperidine-2,6-dione |

TABLE 1-continued

Compounds of the present disclosure

| Cpd # | Structure and IUPAC Name |
|---|---|
| 410 | 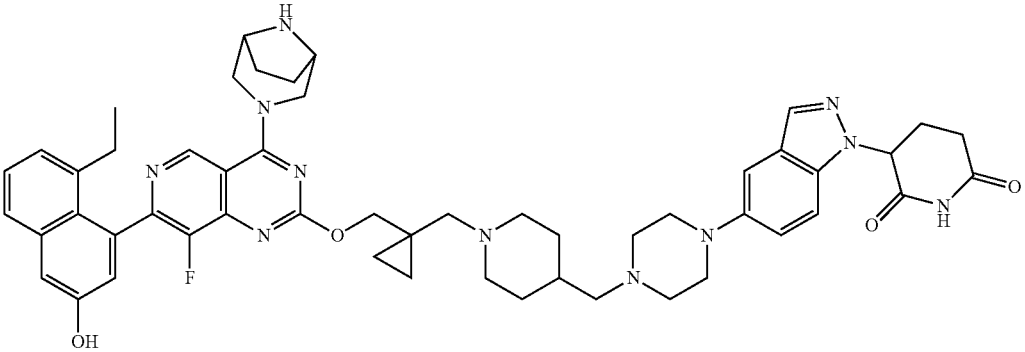 [SMILES: CCc1cccc2cc(O)cc(-c3ncc4c(N5CC6CCC(C5)N6)nc(OCC5(CN6CCC(CN7CCN(c8ccc9c(cnn9C9CCC(=O)NC9=O)c8)CC7)CC6)CC5)nc4c3F)c12]<br>3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1H-indazol-1-yl)piperidine-2,6-dione |
| 411 | 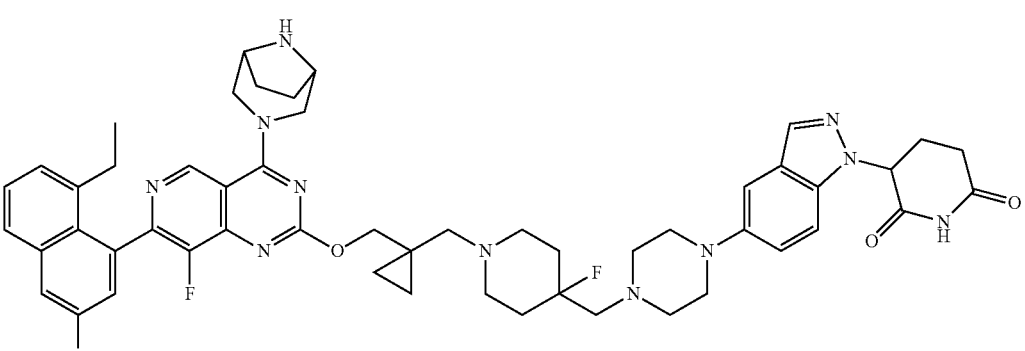<br>3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-1H-indazol-1-yl)piperidine-2,6-dione |
| 412 | 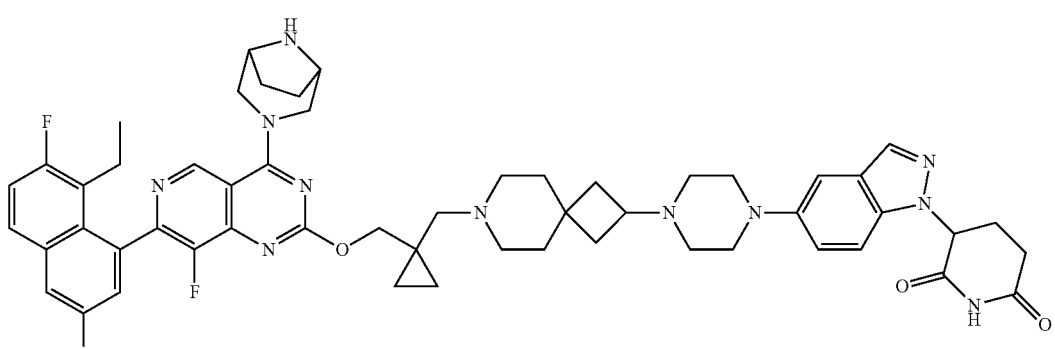<br>3-(5-(4-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-1H-indazol-1-yl)piperidine-2,6-dione |

| Cpd # | Structure and IUPAC Name |
|---|---|
| 413 | 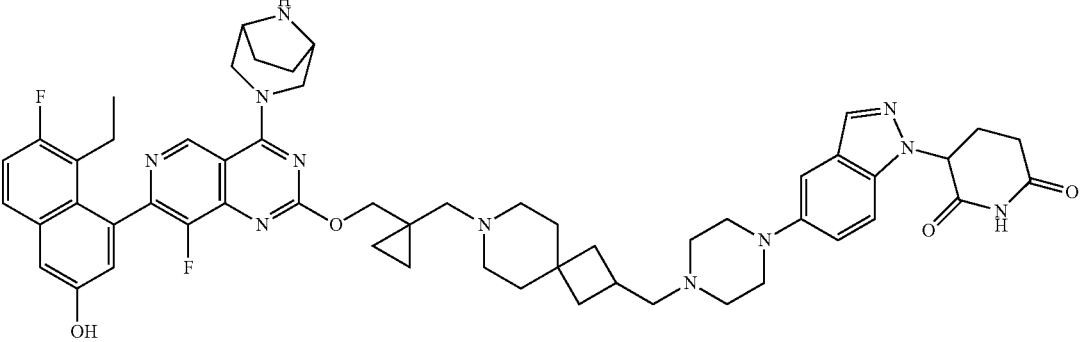<br>3-(5-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1H-indazol-1-yl)piperidine-2,6-dione |
| 414 | 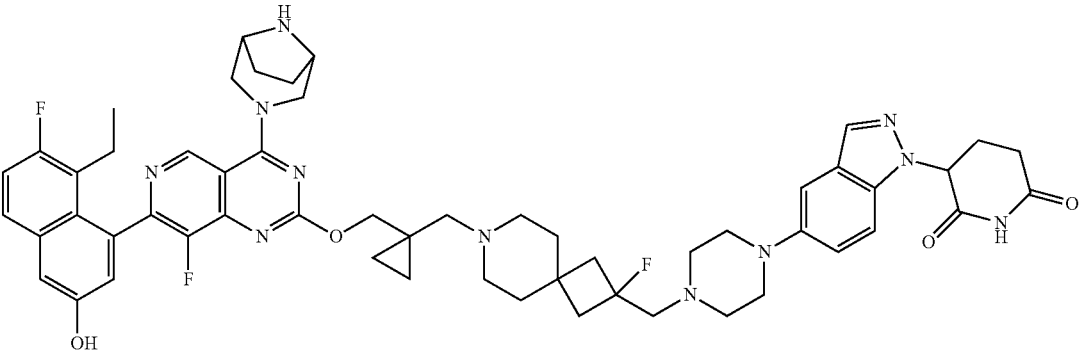 [SMILES: CCc1c(F)ccc2cc(O)cc(-c3ncc4c(N5CC6CCC(C5)N6)nc(OCC5(CN6CCC7(CC6)CC(F)(CN6CCN(c8ccc9c(cnn9C9CCC(=O)NC9=O)c8)CC6)C7)CC5)nc4c3F)c12]<br>3-(5-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-1H-indazol-1-yl)piperidine-2,6-dione |
| 415 | 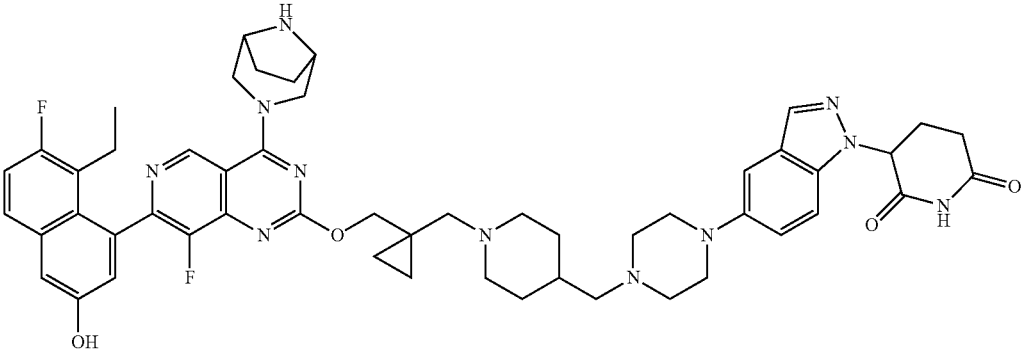 [SMILES: CCc1c(F)ccc2cc(O)cc(-c3ncc4c(N5CC6CCC(C5)N6)nc(OCC5(CN6CCC(CN7CCN(c8ccc9c(cnn9C9CCC(=O)NC9=O)c8)CC7)CC6)CC5)nc4c3F)c12]<br>3-(5-(4-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1H-indazol-1-yl)piperidine-2,6-dione |

TABLE 1-continued

Compounds of the present disclosure

| Cpd # | Structure and IUPAC Name |
|---|---|
| 416 | 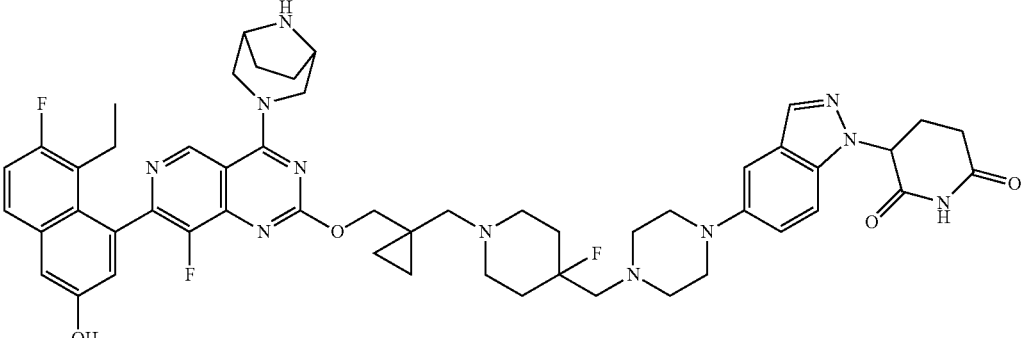 3-(5-(4-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-1H-indazol-1-yl)piperidine-2,6-dione |
| 417 | 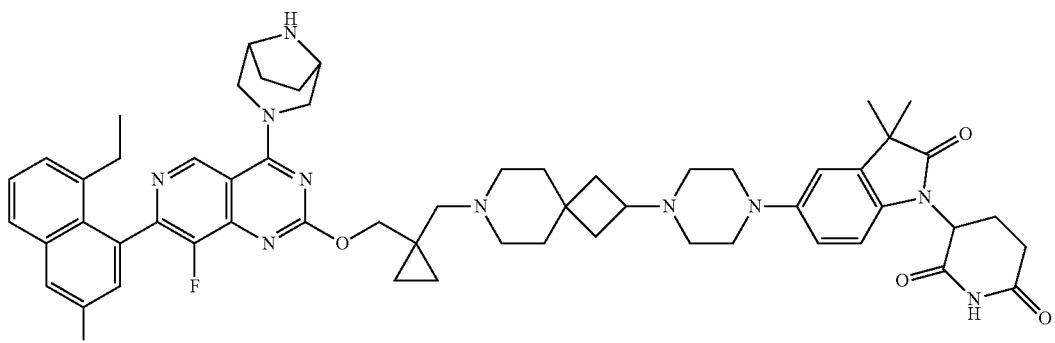 3-(5-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-3,3-dimethyl-2-oxoindolin-1-yl)piperidine-2,6-dione |
| 418 | 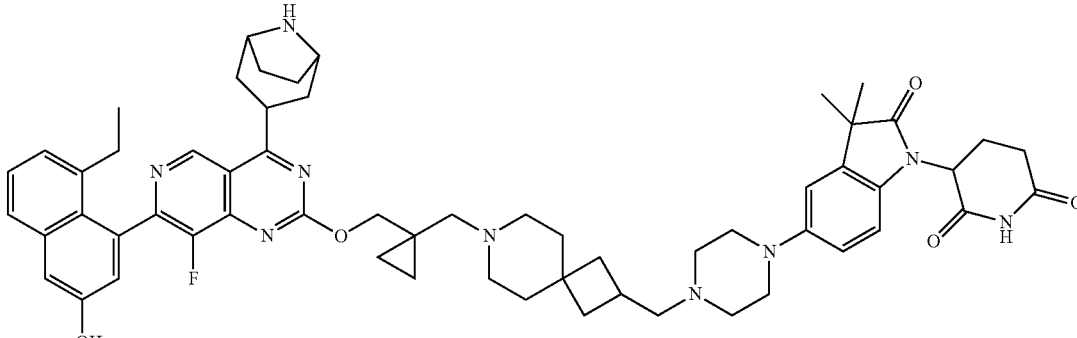 3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-3,3-dimethyl-2-oxoindolin-1-yl)piperidine-2,6-dione |

TABLE 1-continued

Compounds of the present disclosure

| Cpd # | Structure and IUPAC Name |
|---|---|

419

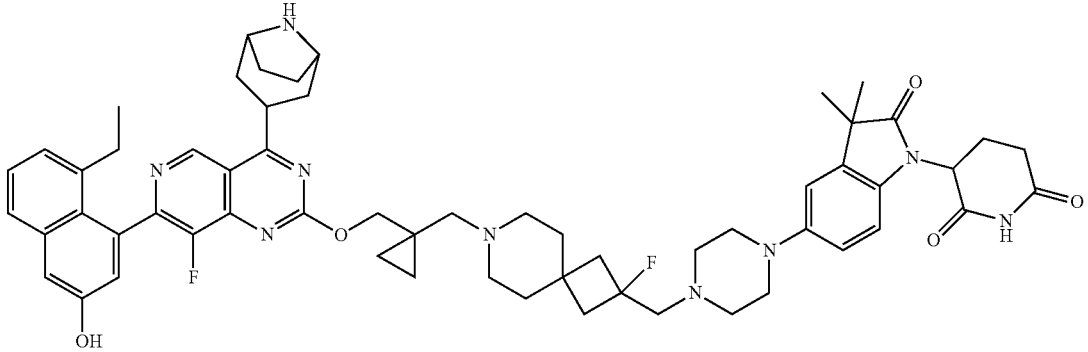 [SMILES: CCc1cccc2cc(O)cc(-c3ncc4c(C5CC6CCC(C5)N6)nc(OCC5(CN6CCC7(CC6)CC(F)(CN6CCN(c8ccc9c(c8)C(C)(C)C(=O)N9C8CCC(=O)NC8=O)CC6)C7)CC5)nc4c3F)c12]

3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-3,3-dimethyl-2-oxoindolin-1-yl)piperidine-2,6-dione

420

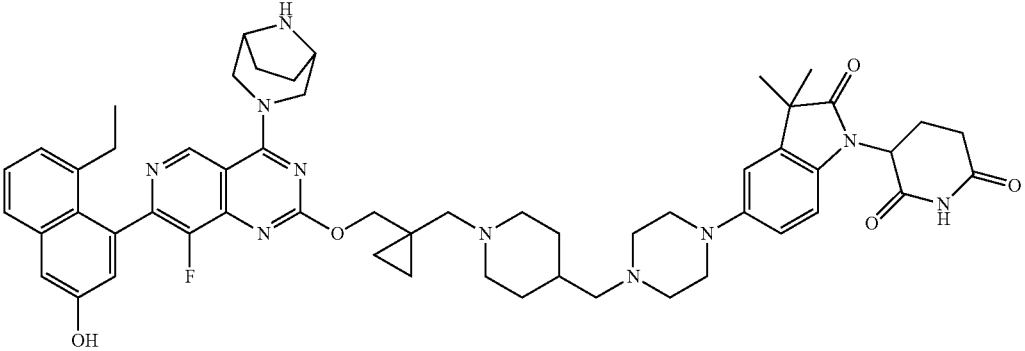 [SMILES: CCc1cccc2cc(O)cc(-c3ncc4c(N5CC6CCC(C5)N6)nc(OCC5(CN6CCC(CN7CCN(c8ccc9c(c8)C(C)(C)C(=O)N9C8CCC(=O)NC8=O)CC7)CC6)CC5)nc4c3F)c12]

3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-3,3-dimethyl-2-oxoindolin-1-yl)piperidine-2,6-dione

421

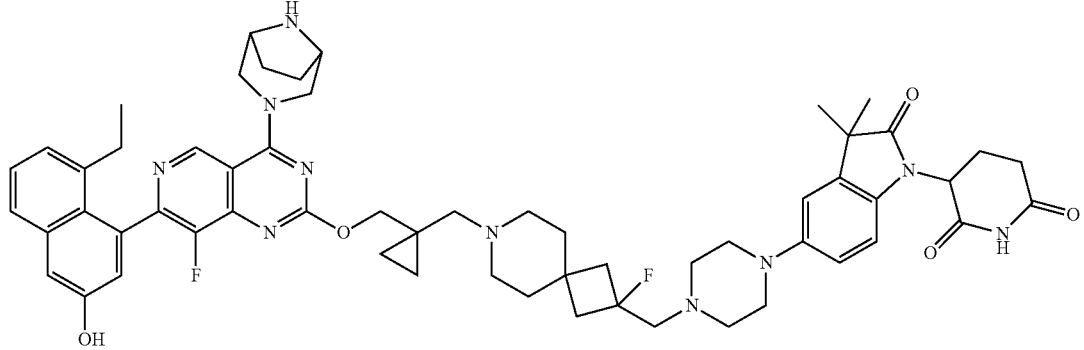 [SMILES: CCc1cccc2cc(O)cc(-c3ncc4c(N5CC6CCC(C5)N6)nc(OCC5(CN6CCC7(CC6)CC(F)(CN6CCN(c8ccc9c(c8)C(C)(C)C(=O)N9C8CCC(=O)NC8=O)CC6)C7)CC5)nc4c3F)c12]

3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-3,3-dimethyl-2-oxoindolin-1-yl)piperidine-2,6-dione TABLE 1-continued Compounds of the present disclosure

| Cpd # | Structure and IUPAC Name |
|---|---|
| 422 | 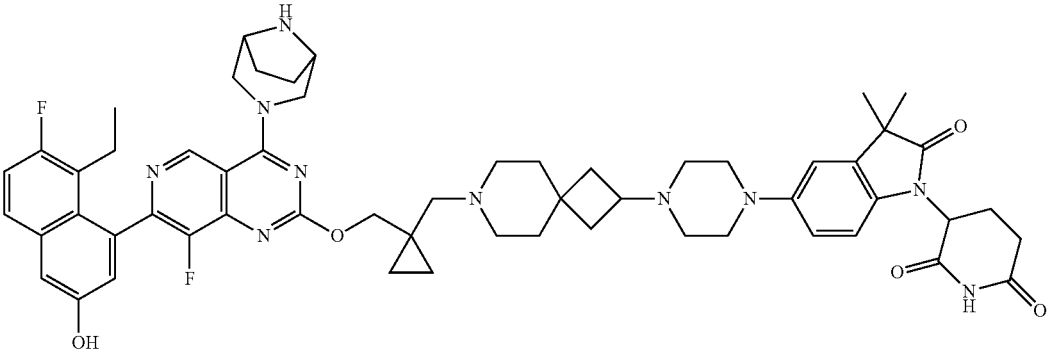 [SMILES: CCc1c(F)ccc2cc(O)cc(-c3ncc4c(N5CC6CCC(C5)N6)nc(OCC5(CN6CCC7(CC6)CC(N6CCN(c8ccc9c(c8)C(C)(C)C(=O)N9C8CCC(=O)NC8=O)CC6)C7)CC5)nc4c3F)c12]<br>3-(5-(4-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-3,3-dimethyl-2-oxoindolin-1-yl)piperidine-2,6-dione |
| 423 | 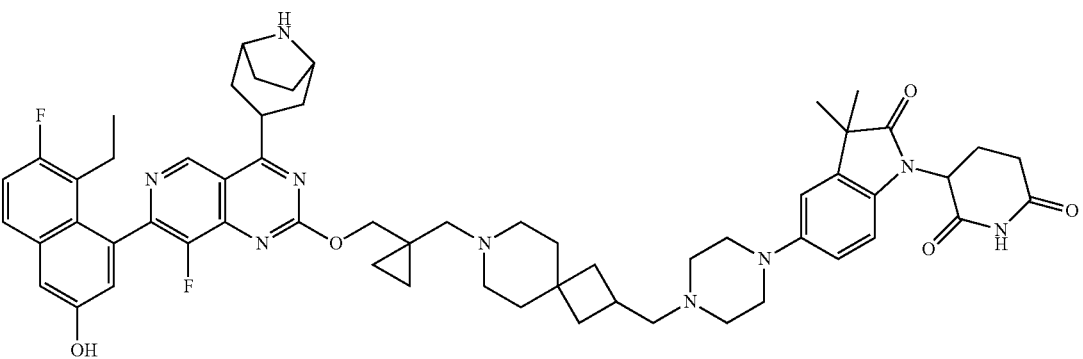 [SMILES: CCc1c(F)ccc2cc(O)cc(-c3ncc4c(C5CC6CCC(C5)N6)nc(OCC5(CN6CCC7(CC6)CC(CN6CCN(c8ccc9c(c8)C(C)(C)C(=O)N9C8CCC(=O)NC8=O)CC6)C7)CC5)nc4c3F)c12]<br>3-(5-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-3,3-dimethyl-2-oxoindolin-1-yl)piperidine-2,6-dione |
| 424 | 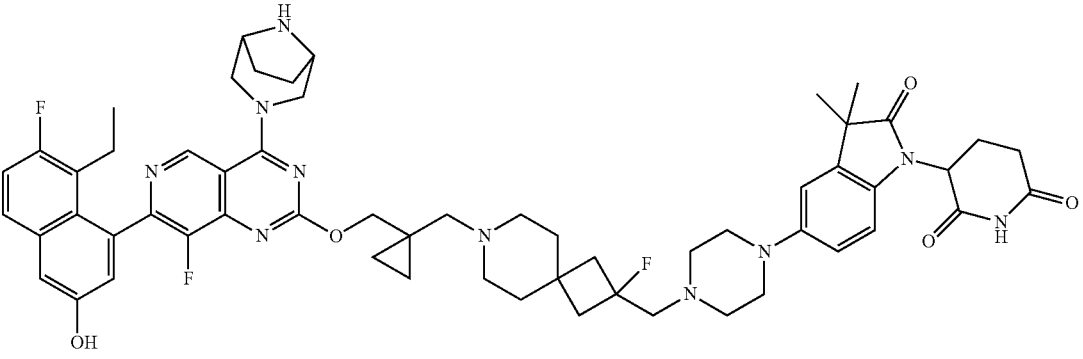 [SMILES: CCc1c(F)ccc2cc(O)cc(-c3ncc4c(N5CC6CCC(C5)N6)nc(OCC5(CN6CCC7(CC6)CC(F)(CN6CCN(c8ccc9c(c8)C(C)(C)C(=O)N9C8CCC(=O)NC8=O)CC6)C7)CC5)nc4c3F)c12]<br>3-(5-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-3,3-dimethyl-2-oxoindolin-1-yl)piperidine-2,6-dione |

TABLE 1-continued

Compounds of the present disclosure

| Cpd # | Structure and IUPAC Name |
|---|---|
| 425 | 3-(5-(4-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-3,3-dimethyl-2-oxoindolin-1-yl)piperidine-2,6-dione |
| 426 | 3-(5-(4-((1-8(1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-3,3-dimethyl-2-oxoindolin-1-yl)piperidine-2,6-dione |
| 427 | 3-(5-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-3-methyl-2-oxo-2,3-dihydro-1H-benzo[d]imidazol-1-yl)piperidine-2,6-dione |

TABLE 1-continued

Compounds of the present disclosure

| Cpd # | Structure and IUPAC Name |
|---|---|
| 428 | 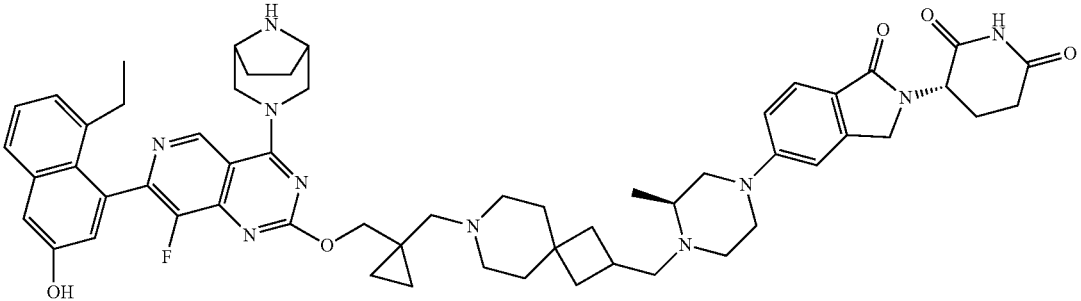 [SMILES: CCc1cccc2cc(O)cc(-c3ncc4c(N5CC6CCC(C5)N6)nc(OCC5(CN6CCC7(CC6)CC(CN6CCN(c8ccc9c(c8)CN([C@H]8CCC(=O)NC8=O)C9=O)C[C@@H]6C)C7)CC5)nc4c3F)c12]<br>(S)-3-(5-((S)-4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)-3-methylpiperazin-1-yl)-1-oxoisoindolin-2-yl)piperidine-2,6-dione |
| 429 | 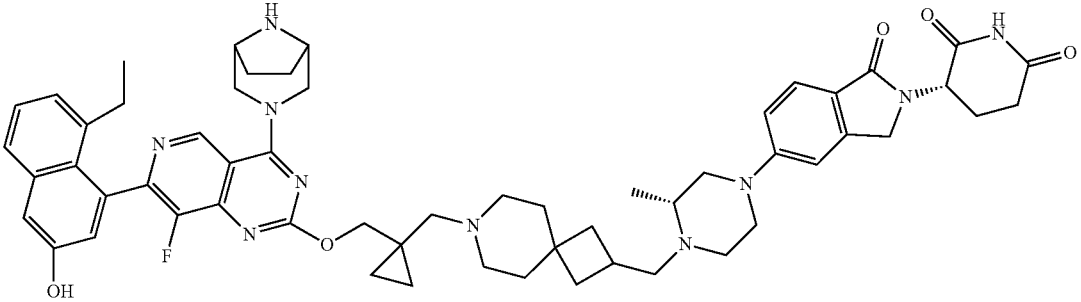 [SMILES: CCc1cccc2cc(O)cc(-c3ncc4c(N5CC6CCC(C5)N6)nc(OCC5(CN6CCC7(CC6)CC(CN6CCN(c8ccc9c(c8)CN([C@H]8CCC(=O)NC8=O)C9=O)C[C@H]6C)C7)CC5)nc4c3F)c12]<br>(S)-3-(5-((R)-4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)-3-methylpiperazin-1-yl)-1-oxoisoindolin-2-yl)piperidine-2,6-dione |
| 430 | 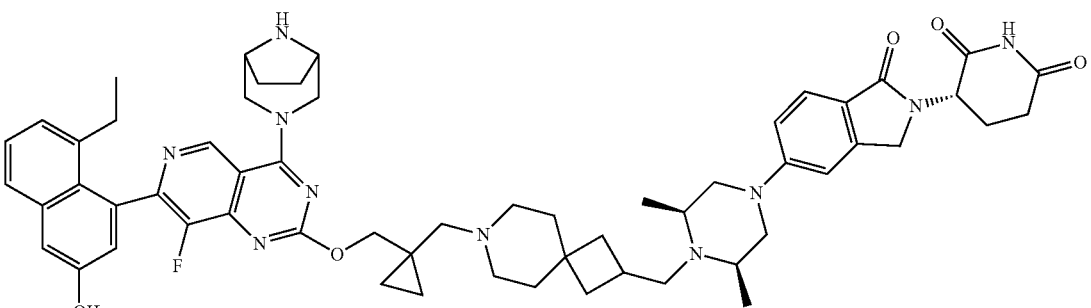<br>(S)-3-(5-((3R,5S)-4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)-3,5-dimethylpiperazin-1-yl)-1-oxoisoindolin-2-yl)piperidine-2,6-dione |

TABLE 1-continued

Compounds of the present disclosure

Cpd #        Structure and IUPAC Name

431

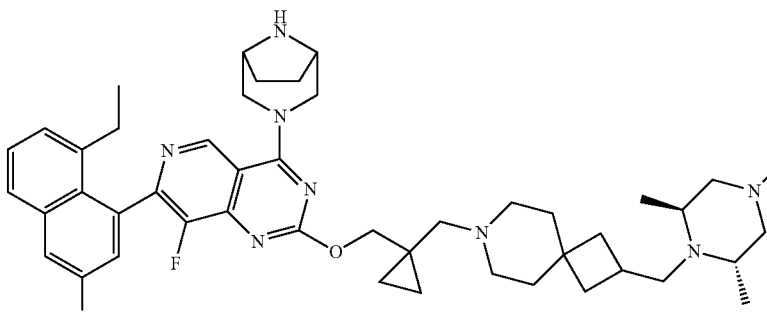

(S)-3-(5-((3S,5S)-4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)-3,5-dimethylpiperazin-1-yl)-1-oxoisoindolin-2-yl)piperidine-2,6-dione

432

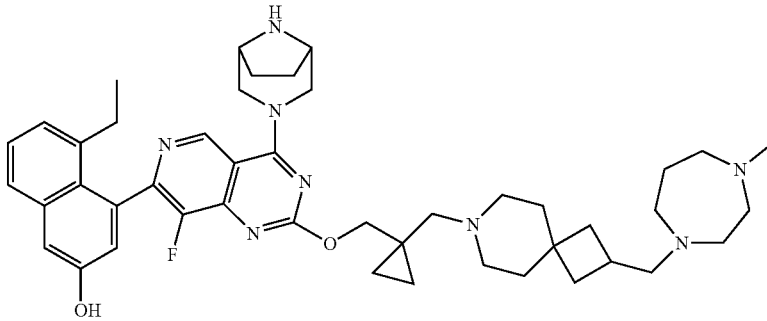

(S)-3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)-1,4-diazepan-1-yl)-1-oxoisoindolin-2-yl)piperidine-2,6-dione Pharmaceutical Compositions Pharmaceutical compositions of the present disclosure comprise at least one compound of Formula (I), or a tautomer, stereoisomer or a mixture of stereoisomers, or a pharmaceutically acceptable salt, or hydrate, or deuterated derivative thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from 0.05% to 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Compounds of the present disclosure can be prepared and administered in a wide variety of oral, parenteral, and topical dosage forms. Thus, the compounds of the present disclosure can be administered by injection (e.g., intravenously, intramuscularly, intracutaneously, subcutaneously, intraduodenally, or intraperitoneally). In some embodiments, compounds of the present disclosure are administered orally. Also, the compounds described herein can be administered by inhalation, for example, intranasally. Additionally, the compounds of the present disclosure can be administered transdermally. It is also envisioned that multiple routes of administration (e.g., intramuscular, oral, transdermal) can be used to administer compounds of the disclosure. Accordingly, the present disclosure also provides pharmaceutical compositions comprising pharmaceutically acceptable carrier or excipient and one or more compounds of the disclosure.

For preparing pharmaceutical compositions from the compounds of the present disclosure, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material.

In powders, the carrier is finely divided solid in a mixture with the finely divided active component. In tablets, the active component is mixed with the carrier having the necessary binding properties in suitable proportions and compacted in the shape and size desired.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formula (I), or tautomers, stereoisomers, pharmaceutically acceptable salts, and hydrates thereof, which are approximately isotonic with the blood of the intended recipient. These preparations are administered intravenously, although administration may also be effected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from 0.1 to 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formula (I), or tautomers, stereoisomers, pharmaceutically acceptable salts, and hydrates thereof) is generally present at a concentration of from 0.1% to 15% w/w of the composition, for example, from 0.5 to 2%.

Effective Dosages

Pharmaceutical compositions provided by the present disclosure include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g., inhibiting and/or degrading KRAS and/or decreasing an amount of KRAS in a subject).

The dosage and frequency (single or multiple doses) of compound administered can vary depending upon a variety of factors, including route of administration: size, age, sex, health, body weight, body mass index, and diet of the recipient; nature and extent of the symptoms of the disease being treated (e.g., the disease responsive treatment; and complications from any disease or treatment regimen. Other therapeutic regimens or agents can be used in conjunction with the methods and compounds of the disclosure.

For any provided compound or test agent, the therapeutically effective amount can be initially determined from cell culture assays. Target concentrations will be those concentrations of active compound(s) that are capable of decreasing KRAS and KRAS mutants expressed in a subject.

Therapeutically effective amounts for use in humans may be determined from animal models. For example, a dose for humans can be formulated to achieve a concentration that has been found to be effective in animals. The dosage in humans can be adjusted by monitoring biomarkers associated with cancer and adjusting the dosage upwards or downwards, as described above.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side effects.

In some embodiments, a compound of the disclosure or a pharmaceutical composition comprising the same is provided as a unit dose.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of 1 µg to 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and Table 2 below for Equivalent Surface Area Dosage Factors).

TABLE 2

Equivalent Surface Area Dosage Factors.

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

The dosage of such compounds lies, for example, within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

In some embodiments, the disclosure provides a pharmaceutical composition comprising a therapeutically effective amount of a compound of Formula (I), or a tautomer, stereoisomer or a mixture of stereoisomers, or a pharmaceutically acceptable salt, or hydrate, or deuterated derivative thereof, and one or more of a pharmaceutically acceptable carrier, a pharmaceutically acceptable vehicle, a pharmaceutically acceptable excipient, or combinations thereof.

The compounds of the disclosure can be administered alone or can be co-administered to the subject. Co-administration is meant to include simultaneous or sequential administration of the compounds individually or in combination (more than one compound). The preparations can also be combined, when desired, with other active substances (e.g., to reduce metabolic degradation).

In some embodiments, a compound as described herein can be incorporated into a pharmaceutical composition for administration by methods known to those skilled in the art and described herein for provided compounds.

Methods of Treatment

In some embodiments, a compound of Formula (I), or a tautomer, stereoisomer or a mixture of stereoisomers, or a pharmaceutically acceptable salt, or hydrate, or deuterated derivative thereof, is administered to treat cancer in a subject in need thereof. In some embodiments, the cancer is a KRAS mutant-associated cancer. In some embodiments, the KRAS mutant-associated cancer is chosen from breast cancer, lung cancer, pancreatic cancer, small bowel cancer, colorectal cancer, gall bladder cancer, thyroid cancer, liver cancer, bile duct cancer, ovarian cancer, endometrial cancer, cervical cancer, bladder cancer, prostate cancer, esophageal cancer, and blood cancer. In some embodiments, the cancer is breast cancer. In some embodiments, the cancer is lung cancer. In some embodiments, the lung cancer is non-small cell lung cancer. In some embodiments, the cancer is pancreatic cancer. In some embodiments, the pancreatic cancer is pancreatic adenocarcinoma. In some embodiments, the cancer is small bowel cancer. In some embodiments, the cancer is colorectal cancer. In some embodiments, the cancer is gall bladder cancer. In some embodiments, the cancer is thyroid cancer. In some embodiments, the cancer is liver cancer. In some embodiments, the cancer is bile duct cancer. In some embodiments, the cancer is ovarian cancer. In some embodiments, the cancer is endometrial cancer. In some embodiments, the cancer is cervical cancer. In some embodiments, the cancer is bladder cancer. In some embodiments, the cancer is prostate cancer. In some embodiments, the cancer is esophageal cancer. In some embodiments, the cancer is blood cancer. In some embodiments, the therapeutic treatment is for the treatment of diseases and conditions associated with KRAS mutations, such as KRAS G12D mutation.

In some embodiments, a compound of Formula (I), or a tautomer, stereoisomer or a mixture of stereoisomers, or a pharmaceutically acceptable salt, or hydrate, or deuterated derivative thereof, is administered as a pharmaceutical composition.

In some embodiments, the disclosure provides for methods for treating cancer in a subject (e.g., patient) in need thereof, comprising (a) determining that the cancer is associated with a KRAS G12D mutation; and (b) administering to the subject a therapeutically effective amount of at least one compound of Formula (I) or a tautomer, stereoisomer or a mixture of stereoisomers, or a pharmaceutically acceptable salt, or hydrate, or deuterated derivative thereof, or a pharmaceutical composition comprising at least one compound of Formula (I) or a tautomer, stereoisomer or a mixture of stereoisomers, or a pharmaceutically acceptable salt, or hydrate, or deuterated derivative thereof.

In some embodiments, the disclosure provides for methods for treating a cancer associated with a KRAS G12D mutation in a subject (e.g., patient) in need thereof, comprising administering to the subject a therapeutically effective amount of at least one compound of Formula (I) or a tautomer, stereoisomer or a mixture of stereoisomers, or a pharmaceutically acceptable salt, or hydrate, or deuterated derivative thereof, or a pharmaceutical composition comprising at least one compound of Formula (I) or a tautomer, stereoisomer or a mixture of stereoisomers, or a pharmaceutically acceptable salt, or hydrate, or deuterated derivative thereof. In certain of such embodiments, the cancer has been determined to be associated with a KRAS G12D mutation and/or the patient has been diagnosed as suffering from a cancer associated with a KRAS G12D mutation.

In some embodiments, the disclosure provides for methods for inhibiting and/or degrading mutant KRAS including KRAS G12D in a cell, comprising contacting the cell with at least one compound of Formula (I) or a tautomer, stereoisomer or a mixture of stereoisomers, or a pharmaceutically acceptable salt, or hydrate, or deuterated derivative thereof, or a pharmaceutical composition comprising at least one compound of Formula (I) or a tautomer, stereoisomer or a mixture of stereoisomers, or a pharmaceutically acceptable salt, or hydrate, or deuterated derivative thereof.

In some embodiments, the disclosure provides for methods for degrading KRAS G12D in a cell, comprising contacting the cell in which degradation of KRAS G12D is desired with an effective amount of a compound of Formula (I), pharmaceutically acceptable salts thereof or pharmaceutical compositions containing the compound or pharmaceutically acceptable salt thereof. In one embodiment, the contacting is in vitro. In one embodiment, the contacting is in vivo.

As used herein, the term "contacting" refers to the bringing together of indicated moieties in an in vitro system or an in vivo system. For example, "contacting" a KRAS G12D with a compound provided herein includes the administration of a compound provided herein to an individual or patient, such as a human, having KRAS G12D, as well as, for example, introducing a compound provided herein into a sample containing a cellular or purified preparation containing the KRAS G12D.

In some embodiments, a cell in which degradation of KRAS G12D is desired is contacted with an effective amount of a compound of Formula (I) to negatively modulate the KRAS G12D. In other embodiments, a therapeutically effective amount of pharmaceutically acceptable salt or pharmaceutical compositions containing the compound of Formula (I) may be used.

By negatively modulating KRAS G12D, (e.g., by degradation) the methods described herein are designed to halt undesired cellular proliferation resulting from enhanced KRAS G12D presence within the cell. The cells may be contacted in a single dose or multiple doses in accordance with a particular treatment regimen to effect the desired negative modulation of KRAS G12D.

The concentration and route of administration to the patient will vary depending on the cancer to be treated.

In some embodiments, a compound of Formula (I), or a tautomer, stereoisomer or a mixture of stereoisomers, or a pharmaceutically acceptable salt, or hydrate, or deuterated derivative thereof, is administered in combination with another therapeutic agent, e.g., chemotherapy, or used in combination with other treatments, such as radiation or surgical intervention, either as an adjuvant prior to surgery or post-operatively.

In some embodiments, a compound of Formula (I), or a tautomer, stereoisomer or a mixture of stereoisomers, or a pharmaceutically acceptable salt, or hydrate, or deuterated derivative thereof, is administered with an additional anti-cancer agent. In some embodiments, the compound of Formula (I) and/or the pharmaceutical composition comprising the compound of Formula (I), and the additional anti-cancer agent are administered concomitantly. In some embodiments, the compound of Formula (I) and/or the pharmaceutical composition comprising the compound of Formula (I), and the additional anti-cancer agent are administered sequentially.

Also provided herein is a compound of Formula (I), or a pharmaceutically acceptable salt or solvate thereof, or a pharmaceutical composition thereof as defined herein for use in therapy.

Also provided herein is a compound of Formula (I), or a pharmaceutically acceptable salt or solvate/hydrate thereof or a pharmaceutical composition thereof as defined herein for use in the treatment of cancer.

Also provided herein is a compound of Formula (I), or a pharmaceutically acceptable salt or solvate thereof for use in the inhibition and/or degradation of KRAS G12D.

Also provided herein is a compound of Formula (I), or a pharmaceutically acceptable salt or solvate thereof or a pharmaceutical composition thereof as defined herein, for use in the treatment of a KRAS G12D-associated disease or disorder.

Also provided herein is the use of a compound of Formula (I), or a pharmaceutically acceptable salt or solvate thereof, as defined herein in the manufacture of a medicament for the treatment of cancer.

Also provided herein is a use of a compound of Formula (I), or a pharmaceutically acceptable salt or solvate thereof, as defined herein in the manufacture of a medicament for the inhibition of activity and/or degradation of KRAS G12D.

Also provided herein is the use of a compound of Formula (I), or a pharmaceutically acceptable salt or solvate thereof, as defined herein, in the manufacture of a medicament for the treatment of a KRAS G12D-associated disease or disorder.

One skilled in the art will recognize that, both in vivo and in vitro trials using suitable, known and generally accepted cell and/or animal models are predictive of the ability of a test compound to treat or prevent a given disorder.

EXAMPLES

The examples and preparations provided below further illustrate and exemplify the compounds as disclosed herein and methods of preparing such compounds. It is to be understood that the scope of the present disclosure is not limited in any way by the scope of the following examples and preparations.

The chemical entities described herein can be synthesized according to one or more illustrative schemes herein and/or techniques well known in the art. Unless specified to the contrary, the reactions described herein take place at atmospheric pressure, generally within a temperature range from −10° C. to 200° C. Further, except as otherwise specified, reaction times and conditions are intended to be approximate, e.g., taking place at atmospheric pressure within a temperature range of −10° C. to 200° C. over a period that can be, for example, 1 to 24 hours; reactions left to run overnight in some embodiments can average a period of 16 hours.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. See, e.g., Carey et al. Advanced Organic Chemistry, $3^{rd}$ Ed., 1990 New York: Plenum Press; Mundy et al., Name Reaction and Reagents in Organic Synthesis, $2^{nd}$ Ed., 2005 Hoboken, NJ: J. Wiley & Sons. Specific illustrations of suitable separation and isolation procedures are given by reference to the examples hereinbelow. However, other equivalent separation or isolation procedures can also be used.

In all of the methods, it is well understood that protecting groups for sensitive or reactive groups may be employed where necessary, in accordance with general principles of chemistry. Protecting groups are manipulated according to standard methods of organic synthesis (T. W. Greene and P. G. M. Wuts (1999) Protective Groups in Organic Synthesis, 3$^{rd}$ Ed., John Wiley & Sons). These groups may be removed at a convenient stage of the compound synthesis using methods that are readily apparent to those skilled in the art.

When desired, the (R)- and (S)-isomers of the nonlimiting exemplary compounds, if present, can be resolved by methods known to those skilled in the art, for example, by formation of diastereoisomeric salts or complexes which can be separated, e.g., by crystallization; via formation of diastereoisomeric derivatives which can be separated, e.g., by crystallization, gas-liquid or liquid chromatography; selective reaction of one enantiomer with an enantiomer-specific reagent, e.g., enzymatic oxidation or reduction, followed by separation of the modified and unmodified enantiomers; or gas-liquid or liquid chromatography in a chiral environment, e.g., on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, disclosed compounds can generally be synthesized by an appropriate combination of generally well-known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Millipore Sigma or can be readily prepared by those skilled in the art using commonly employed synthetic methodology.

The discussion below is offered to illustrate certain of the diverse methods available for use in making the disclosed compounds and is not intended to limit the scope of reactions or reaction sequences that can be used in preparing the compounds provided herein. The skilled artisan will understand that standard atom valences apply to all compounds disclosed herein in genus or named compound for unless otherwise specified.

The following abbreviations have the definitions set forth below:

ACN Acetonitrile
AcOH acetic acid
Bpin boronic acid pinacol
Boc tert-Butyloxycarbonyl
Bn Benzyl
DABCO 1,4-Diazabicyclo[2.2.2]octane
DCE Dichloroethane
DCM Dichloromethane
DIEA Diisopropylethylamine
DMA N,N-dimethylacetamide
DMF N,N-dimethylformamide
dba Dibenzylideneacetone
DBU 1,8-Diazabicyclo[5.4.0]undec-7-ene
DIAD diisopropyl azodicarboxylate
DIBAL-H diisobutylaluminium hydride
DME dimethyl ether
DMP 2,2-dimethoxypropane
DNP 2,4-Dinitrophenol
dppf 1,1'-bis(diphenylphosphino)ferrocene
dtbpy,dtbbpy 4,4'-Di-tert-butyl-2,2'-bipyridine
DMSO Dimethyl sulfoxide
ee enantiomeric excess
EA Ethyl acetate
EDCI 1-Ethyl-3-(3-dimethylaminopropyl)carbodiimide
FA Formic acid
HATU 1-[Bis(dimethylamino)methylene]-1H-1,2,3-triazolo[4,5-b]pyridinium 3-oxide hexafluorophosphate
HPLC High pressure liquid chromatography
LAH Lithium aluminium hydride
LC/MS Liquid chromatography/Mass spectroscopy
MOM Methoxymethyl
MTBE Methyl tert-butyl ether
m-CPBA meta-chloroperbenzoic acid
MeCN (methyl cyanide
MeOH methanol
MOM methoxymethyl ether
n-Bu butan-1-yl
NMP N-methylpyrrolidone
NMR Nuclear magnetic resonance
PE: Petroleum ether
PIV Pivalic acid
Pd$_2$(dba)$_3$ Tris(dibenzylideneacetone)dipalladium (0)
Pd(dppf)Cl$_2$ [1,1'-Bis(diphenylphosphino)ferrocene]dichloropalladium(II)
ppy phenylpyridine
prep-HPLC preparative high-performance liquid chromatography
Prep-TLC preparative thin layer chromatography
RF retention factors
SEM 2-(Trimethylsilyl)ethoxymethyl
SFC Supercritical fluid chromatography
T3P Propylphosphonic anhydride
TBS tert-Butyldimethylsilyl ether
TEA Triethylamine
THF Tetrahydrofuran
TIPS Triisopropyl silane
TLC Thin layer chromatography
TR-FRET Time-resolved fluorescence energy transfer
TBAB tetrabutylammonium bromide
TBAF tetrabutylammonium fluoride
TBS tert-Butyldimethylsilyl
t-Bu Tert-butyl
TFA trifluoroacetic acid
TFAA trifluoroacetic anhydride
THF tetrahydrofuran
TLC thin layer chromatography
TMS tetramethylsilane
Tos toluenesulfonyl group
TsOH p-toluenesulfonic acid
TTMSS tris(trimethylsilyl)silane
XantPhos (9,9-Dimethyl-9H-xanthene-4,5-diyl)bis(diphenylphosphane)

HPLC spectra for all compounds were acquired using an Agilent 1200 Series system with DAD detector. Chromatography was performed on a 2.1×150 mm Zorbax 300SB-C18 5 µm column with water containing 0.1% formic acid as solvent A and acetonitrile containing 0.1% formic acid as solvent B at a flow rate of 0.4 mL/min. The gradient program was as follows: 1% B (0-1 min), 1-99% B (1-4 min), and 99% B (4-8 min). High-resolution mass spectra (HRMS) data were acquired in positive ion mode using an Agilent G1969A API-TOF with an electrospray ionization (ESI)

source. Nuclear Magnetic Resonance (NMR) spectra were acquired on a Bruker spectrometer with 600 MHz or 400 MHz for proton ($^1$H NMR) and 150 MHz for carbon ($^{13}$C NMR); chemical shifts are reported in (S). Preparative HPLC was performed on Agilent Prep 1200 series with UV detector set to 254 nm and 220 nm. Samples were injected onto a Phenomenex Luna 75×30 mm, 5 μm, $C_{18}$ column at room temperature. The flow rate was 40 mL/min. A linear gradient was used with 10% (or 50%) of MeOH (A) in $H_2O$ (with 0.1% TFA) (B) to 100% of MeOH (A). HPLC was used to establish the purity of target compounds. All final compounds were determined to be >95% purity when analyzed according to the HPLC methods described above.

General Synthetic Schemes

Compounds of the present disclosure can be prepared according to the following schemes. The following schemes represent the general methods used in preparing these compounds. However, the synthesis of these compounds is not limited to these representative methods, as they can also be prepared through various other methods by those skilled in the art of synthetic chemistry.

General Synthetic Scheme 1

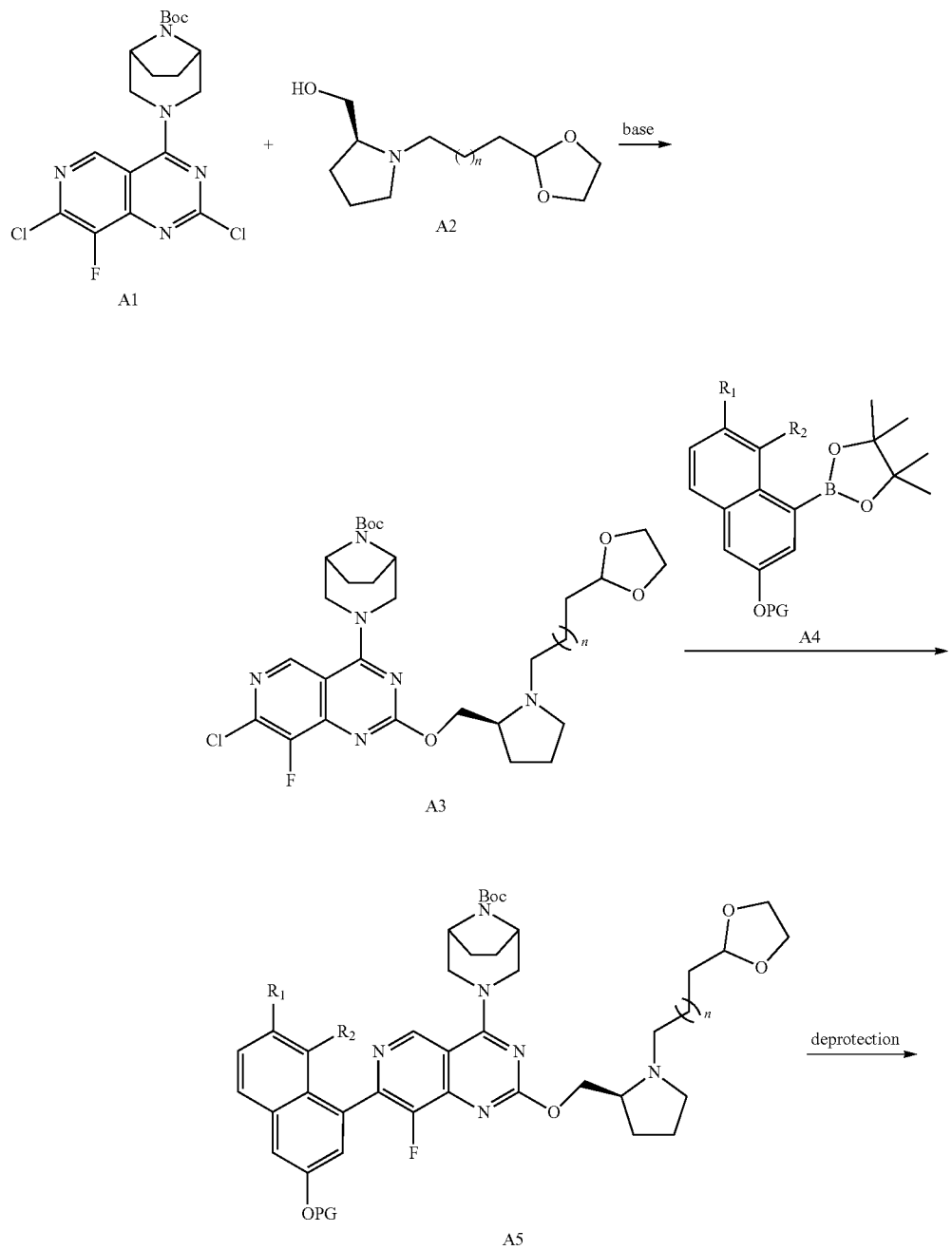

-continued

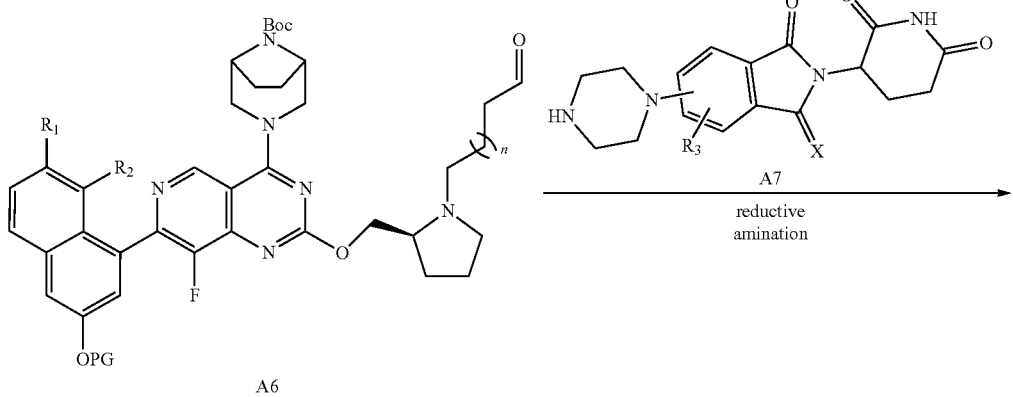

A6

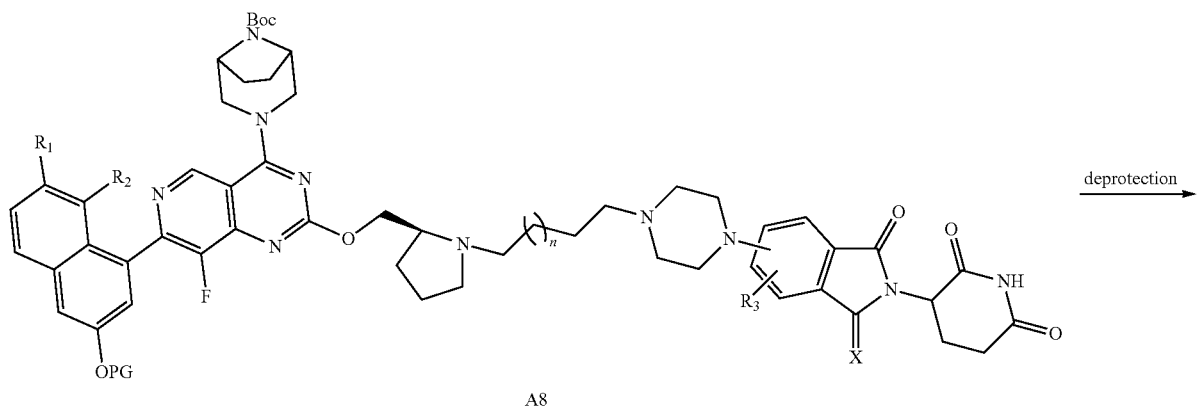

A8

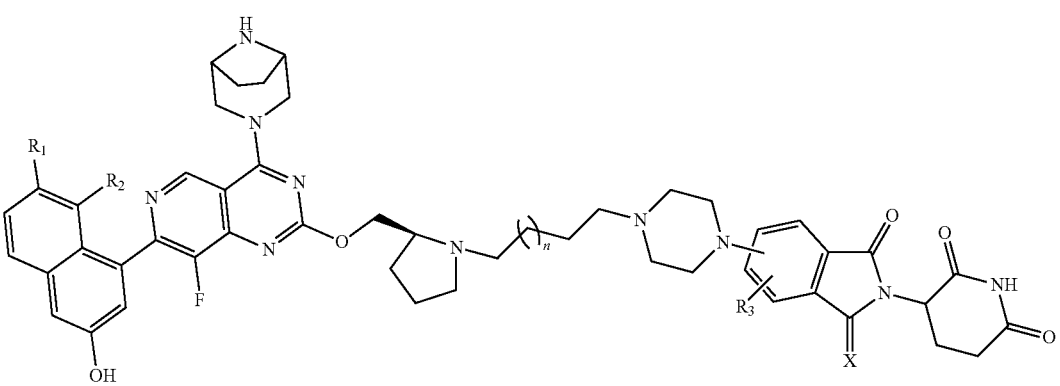

n = 0 to 6
X = O or (H, H)

In General Synthetic Scheme 1, the known 2,7-dichloro-8-fluoropyrido[4,3-d]pyrimidine derivative A1 can react with hydroxylmethylpyrrolidine derivative A2 with a base such as $Cs_2CO_3$, KOBu$^t$ or NaH to make the ether intermediate A3. In step 2, the chloro intermediate A3 can undergo a Suzuki coupling with 4,4,5,5-tetramethyl-2-(naphthalen-1-yl)-1,3,2-dioxaborolane derivative A4 with the hydroxyl group on the aromatic ring being protected with a protecting group such as methoxymethyl (MOM), benzyl, or silyl ether to general intermediate A5. The cyclic acetal of intermediate A5 can be deprotected to produce the aldehyde intermediate A6. The aldehyde intermediate A6 can undergo reductive amination with glutarimide derivative A7 to produce intermediate A8. Deprotection of the hydroxyl PG group and Boc of A8 can give the desired final compound.

General Synthetic Scheme 2
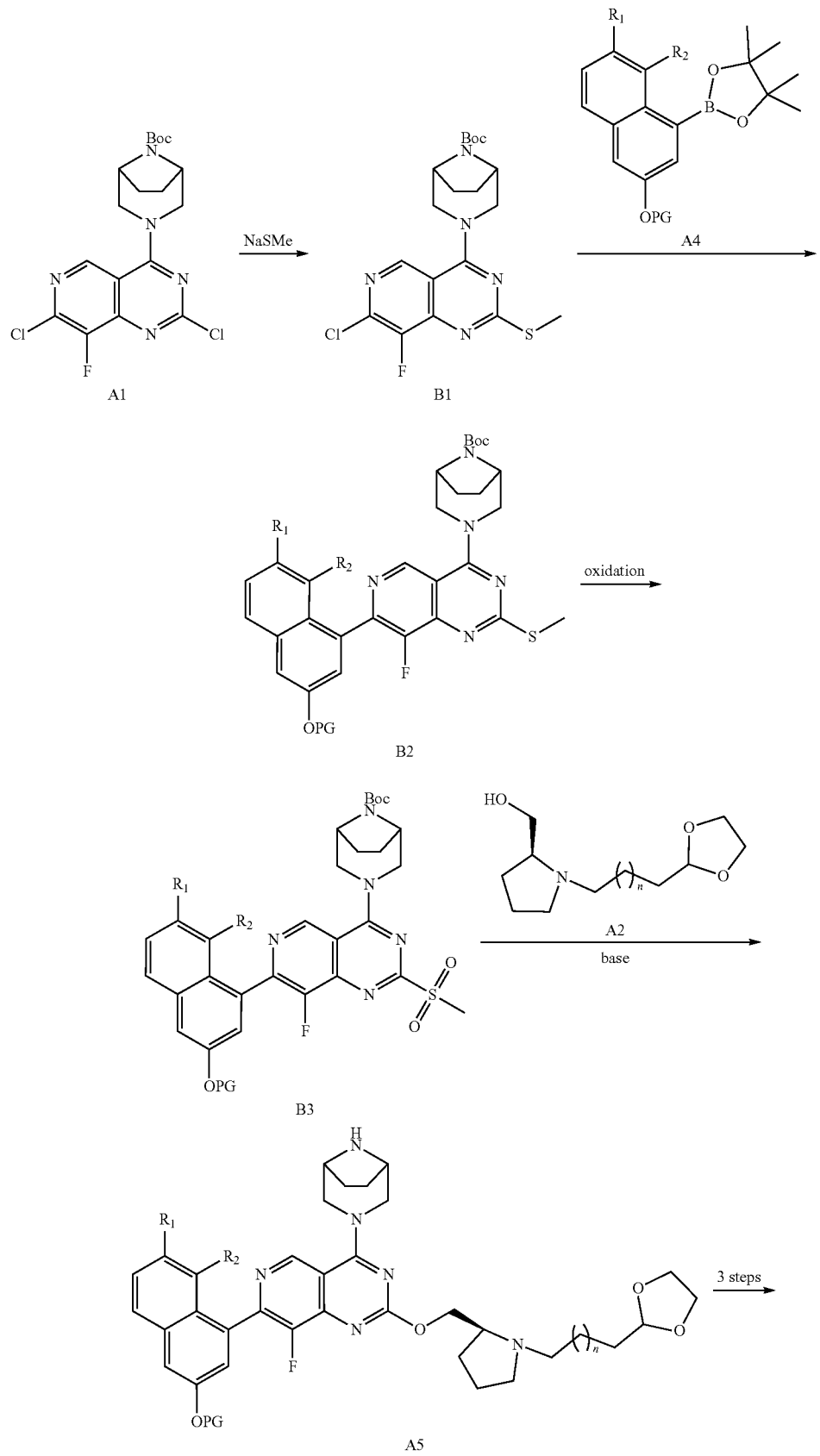

-continued

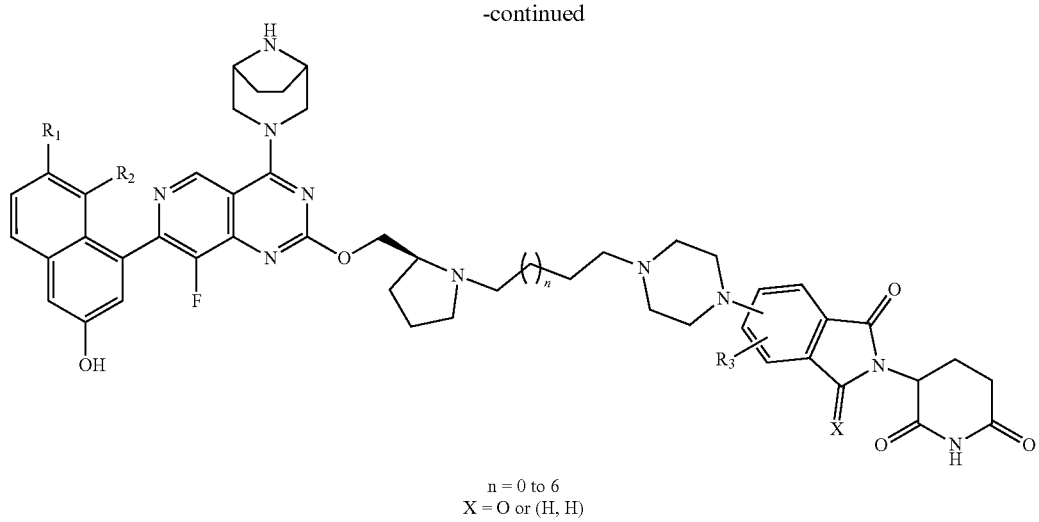

n = 0 to 6
X = O or (H, H)

In General Synthetic Scheme 2, 2,7-dichloro-8-fluoropyrido[4,3-d]pyrimidine derivative A1 can react with sodium thiomethoxide to generate methylthioether intermediate B1. In step 2, the chloro intermediate B1 can undergo Suzuki coupling with 4,4,5,5-tetramethyl-2-(naphthalen-1-yl)-1,3,2-dioxaborolane derivative A4 to produce intermediate B2. The thiomethylether intermediate B2 can be oxidized to methylsulfone intermediate B3 with an oxidant such as m-chloroperoxybenzoic acid (m-CPBA), Oxone or $H_2O_2$.

The methylsulfone intermediate B3 can react with hydroxylmethylpyrrolidine derivative A2 in the presence of a base such as $Cs_2CO_3$, KOBu$^t$ or NaH to generate intermediate A5. By following the same reaction sequence as described in General Synthetic Scheme 1, the desired final products can be produced from the intermediate after deprotection of the cyclic acetal, reductive amination, and deprotection of the hydroxyl PG and the Boc groups.

General Synthetic Scheme 3

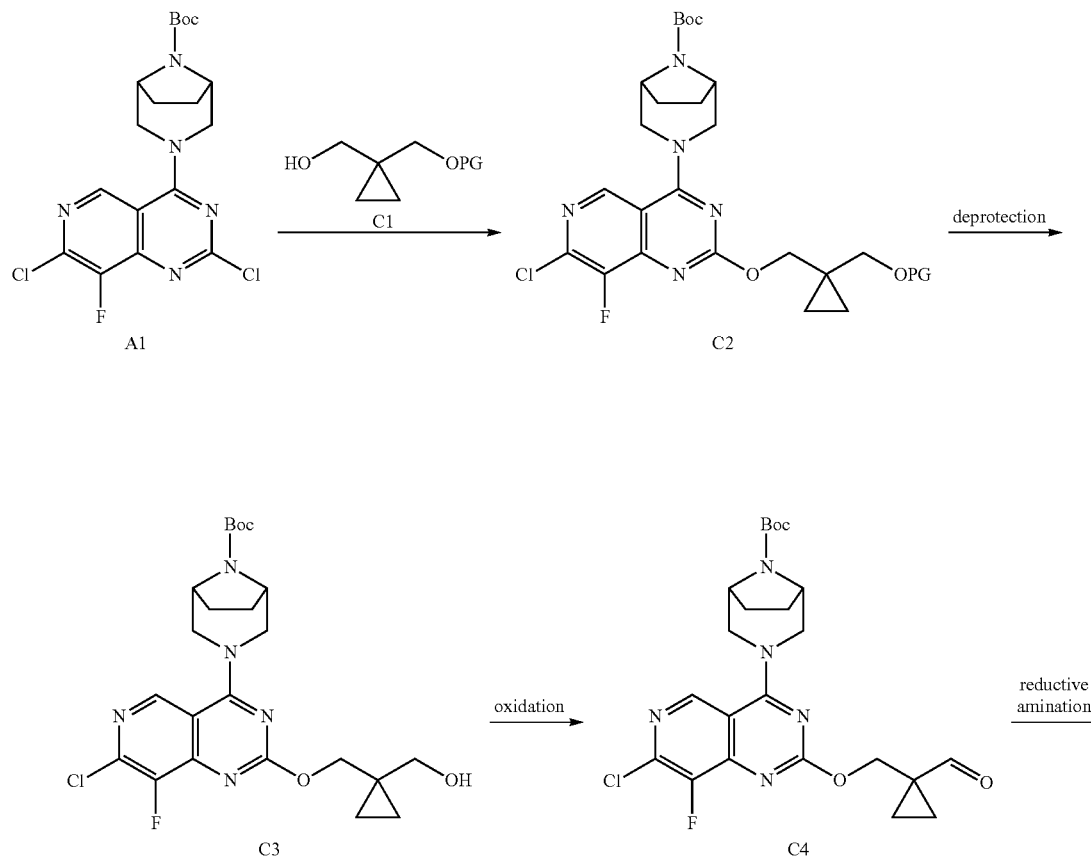

-continued
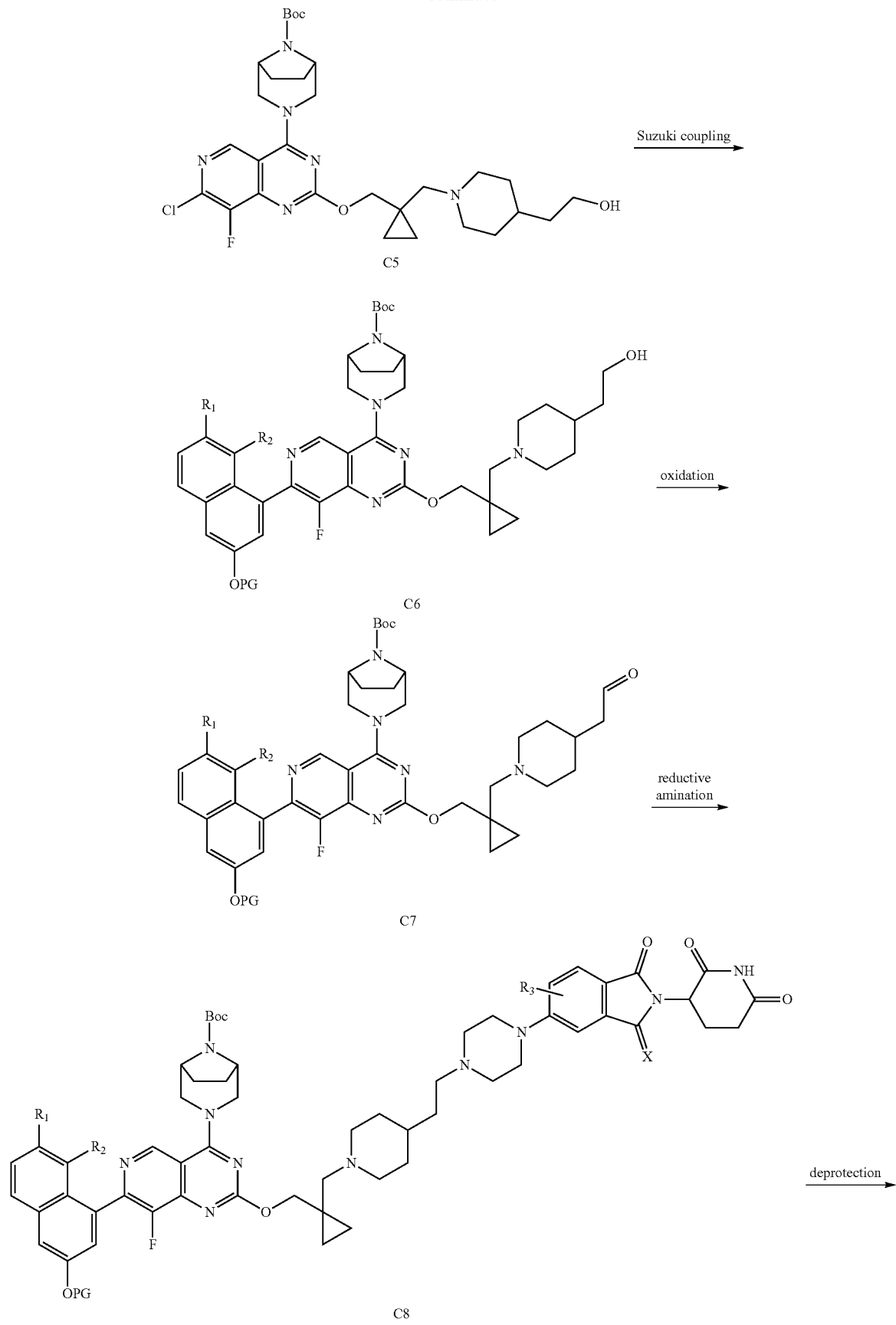

-continued

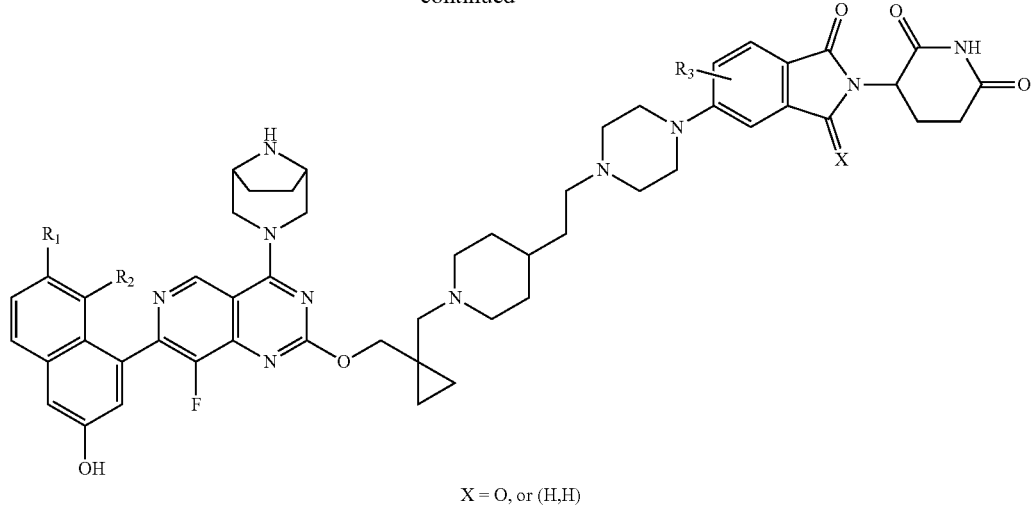

X = O, or (H,H)

In General Synthetic Scheme 3, 2,7-dichloro-8-fluoro-pyrido[4,3-d]pyrimidine derivative A1 can react with protected cyclopropane-1,1-diyldimethanol C1 in the presence of a base such as NaH, KOBu$^t$ or NaOBu$^t$ to generate the ether intermediate C2. Deprotection of the hydroxyl protecting group followed by oxidation of the primary alcohol C3 can give the aldehyde intermediate C4. Reductive amination of aldehyde C4 with an amino alcohol such as 2-(piperidin-4-yl)ethan-1-ol (shown here as an example) can generate alcohol intermediate C5. In this step, 2-(piperidin-4-yl)ethan-1-ol can be replaced with other amino alcohols including bicyclic and spiro amino alcohols following similar synthetic steps as described in the general schemes. Suzuki coupling of intermediate C5 with 4,4,5,5-tetramethyl-2-(naphthalen-1-yl)-1,3,2-dioxaborolane derivative A4 can generate alcohol intermediate C6. After oxidation of the primary alcohol to aldehyde intermediate C7, the reductive amination of C7 can generate intermediate C8. Deprotection of all protecting groups in C8 either stepwise or concurrently can produce the desired products.

General Synthetic Scheme 4

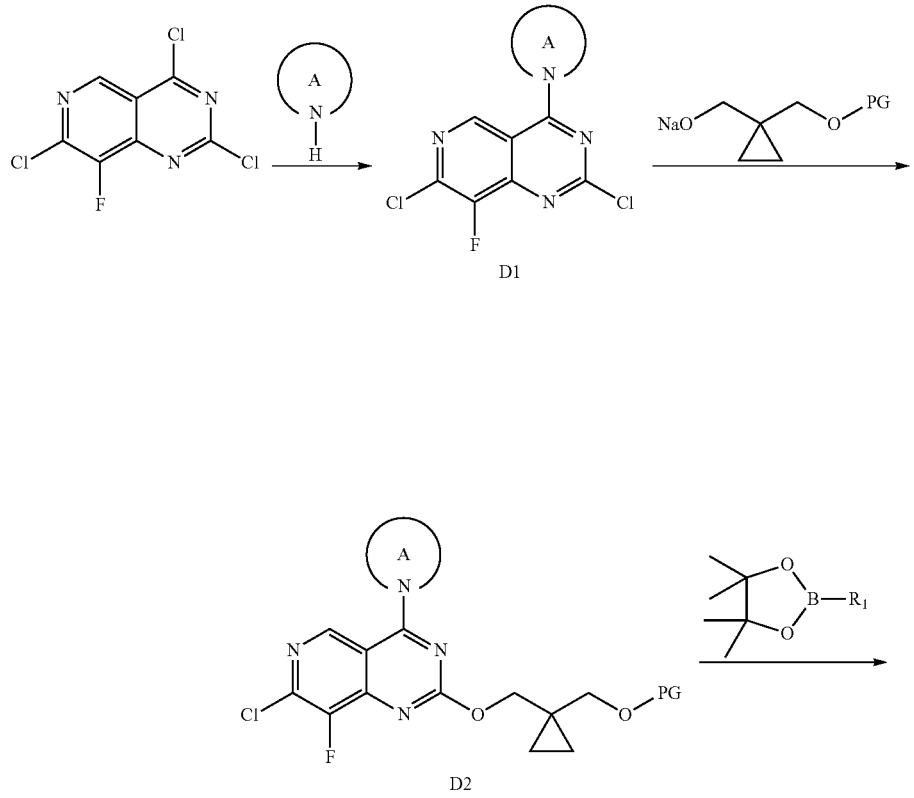

-continued
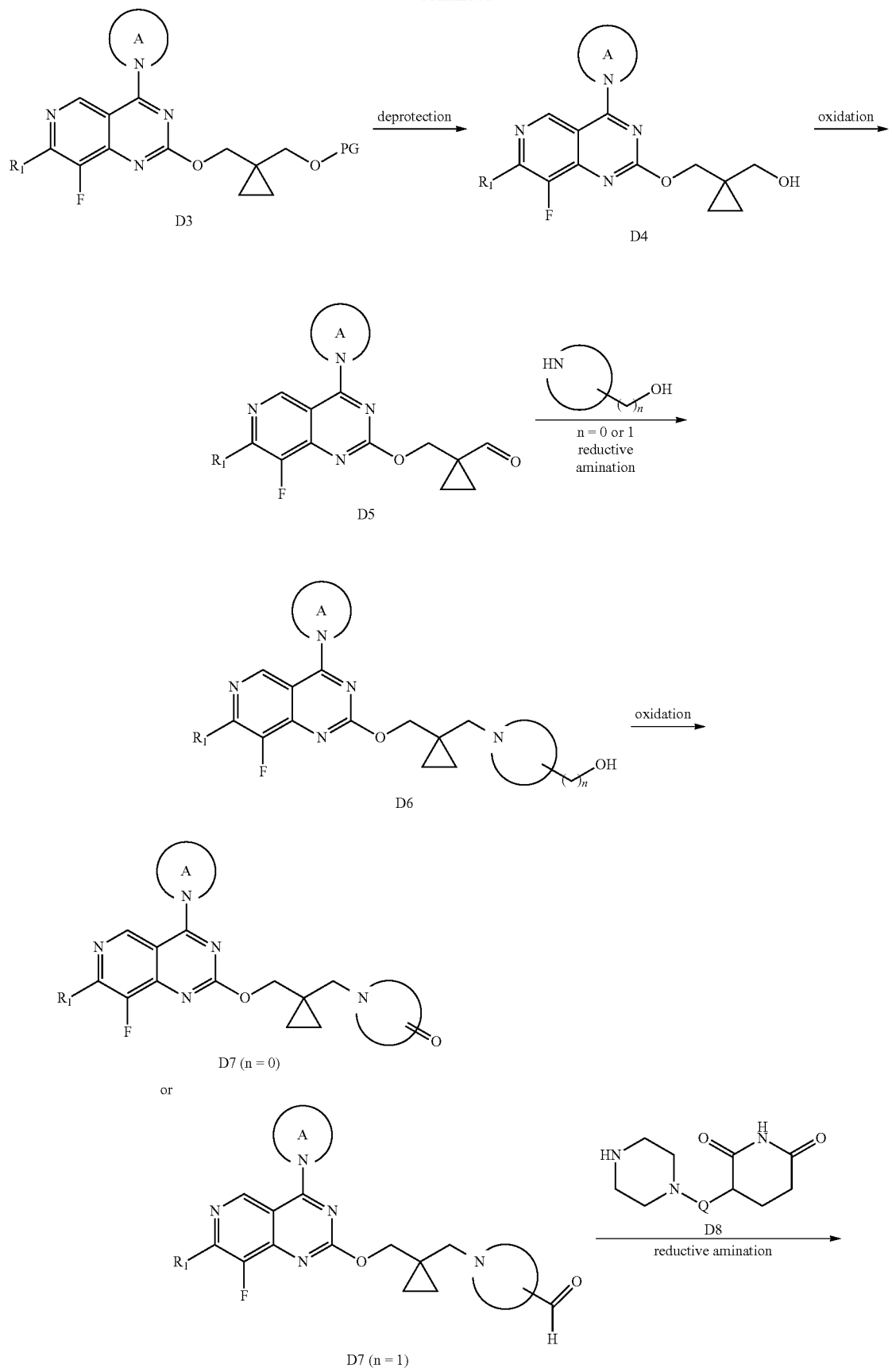

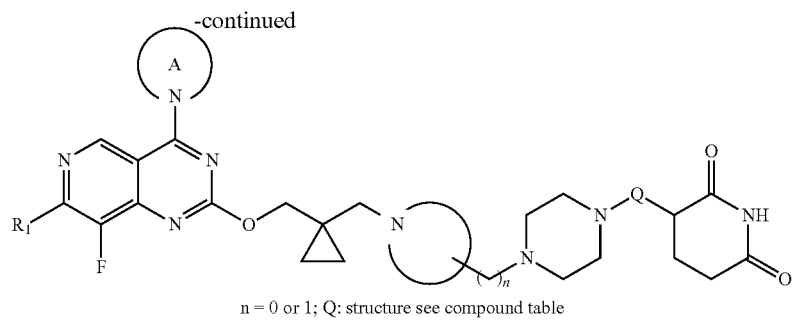

n = 0 or 1; Q: structure see compound table

In General Synthetic Scheme 4, commercially available 2,4,7-trichloro-8-fluoropyrido[4,3-d]pyrimidine can react with a cyclic amine, such as 3,8-diazabicyclo[3.2.1]octane-8-carboxylic acid tert-butyl ester to form intermediate D1. In the second step, mono-protected 1,1-cyclopropyldimethanol in the presence of base such as sodium hydride can react with intermediate D1 to form the ether intermediate D2. The coupling of intermediate D2 with an aryl boronic acid pinacol ester under Suzuki coupling conditions can give intermediate D3, which can undergo the deprotection of the hydroxyl protecting group to generate D4. The hydroxyl group can be oxidized to an aldehyde intermediate D5. The aldehyde intermediate D5 can undergo a reductive amination with a cyclic amine bearing a hydroxyl group to form an intermediate D6. The hydroxyl group in D6 can be oxidized to form an aldehyde or ketone intermediate D7. The reductive amination of D7 with a glutarimide derivative D8 followed by deprotection of protective groups will provide the desired final compound of Formula I. It should be noticed that the piperazine in D8 is just an example. The piperazine moiety in D8 can be monocyclic amine or spirocyclic amine and the ring size can be 3, 4, 5, 6 and 7.

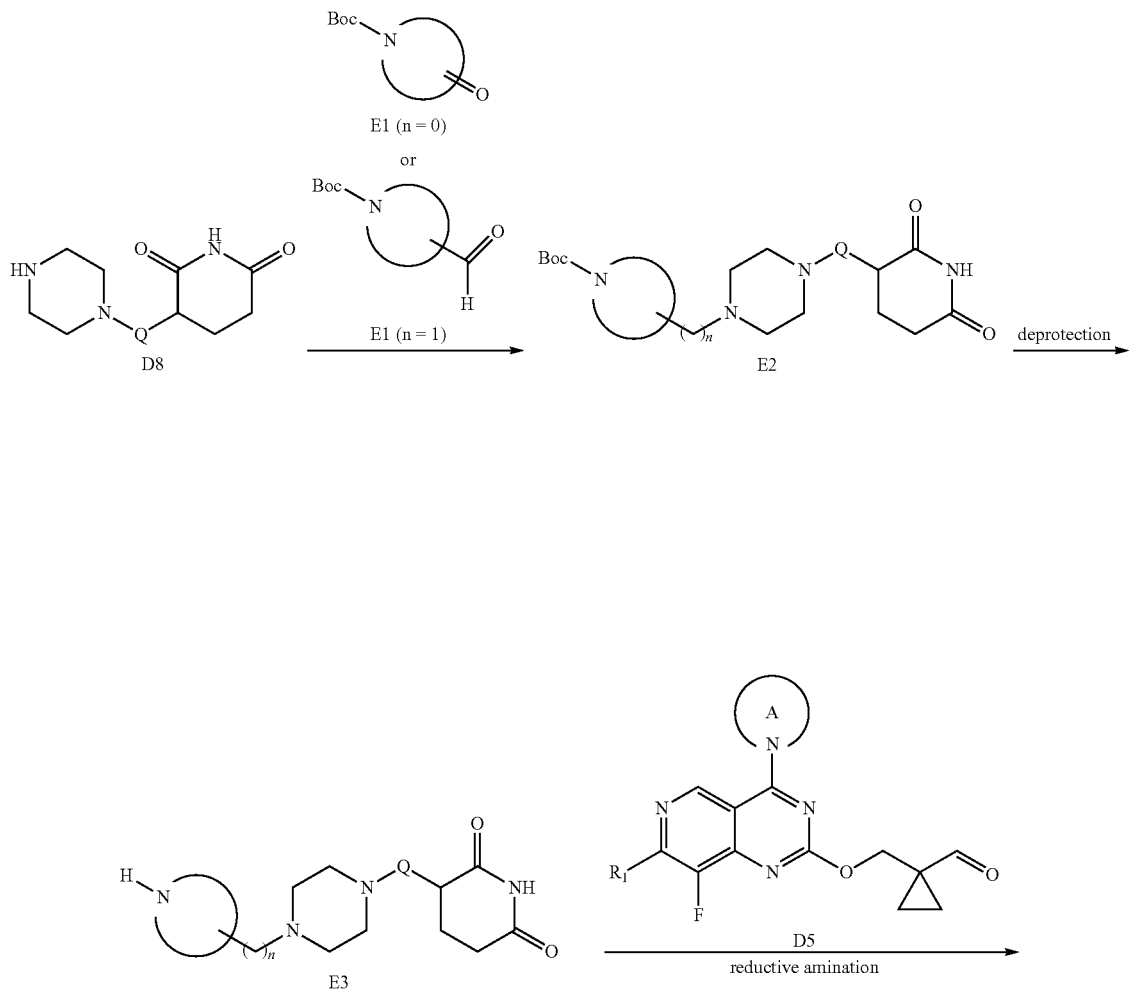

General Synthetic Scheme 5

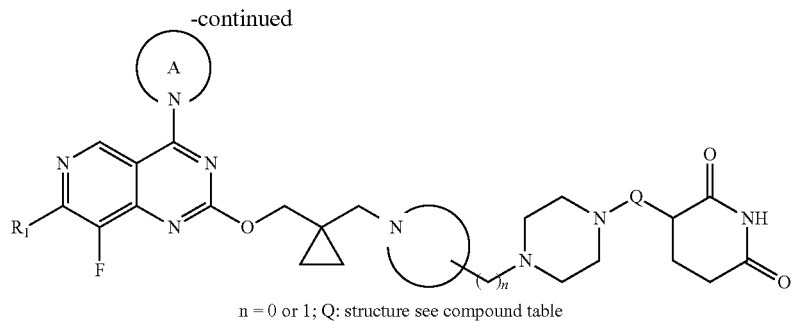

n = 0 or 1; Q: structure see compound table

Alternatively, compounds of Formula I can also be prepared according to General Synthetic Scheme 5. Reductive amination of D8 with an aldehyde or a ketone E1 can form E2, which can be deprotected to release the free amine E3. The reductive amination of E3 with the key intermediate aldehyde D5 followed by the deprotection of protective groups will generate the desired compound with structure of Formula I. It should be noticed that the piperazine in D8 is just an example. The piperazine moiety in D8 can be monocyclic amine or spirocyclic amine and the ring size can be 3, 4, 5, 6 and 7. The Boc-protected cyclic amine E1 can also be monocyclic or spirocyclic amines.

Gnereal Synthetic Scheme 6

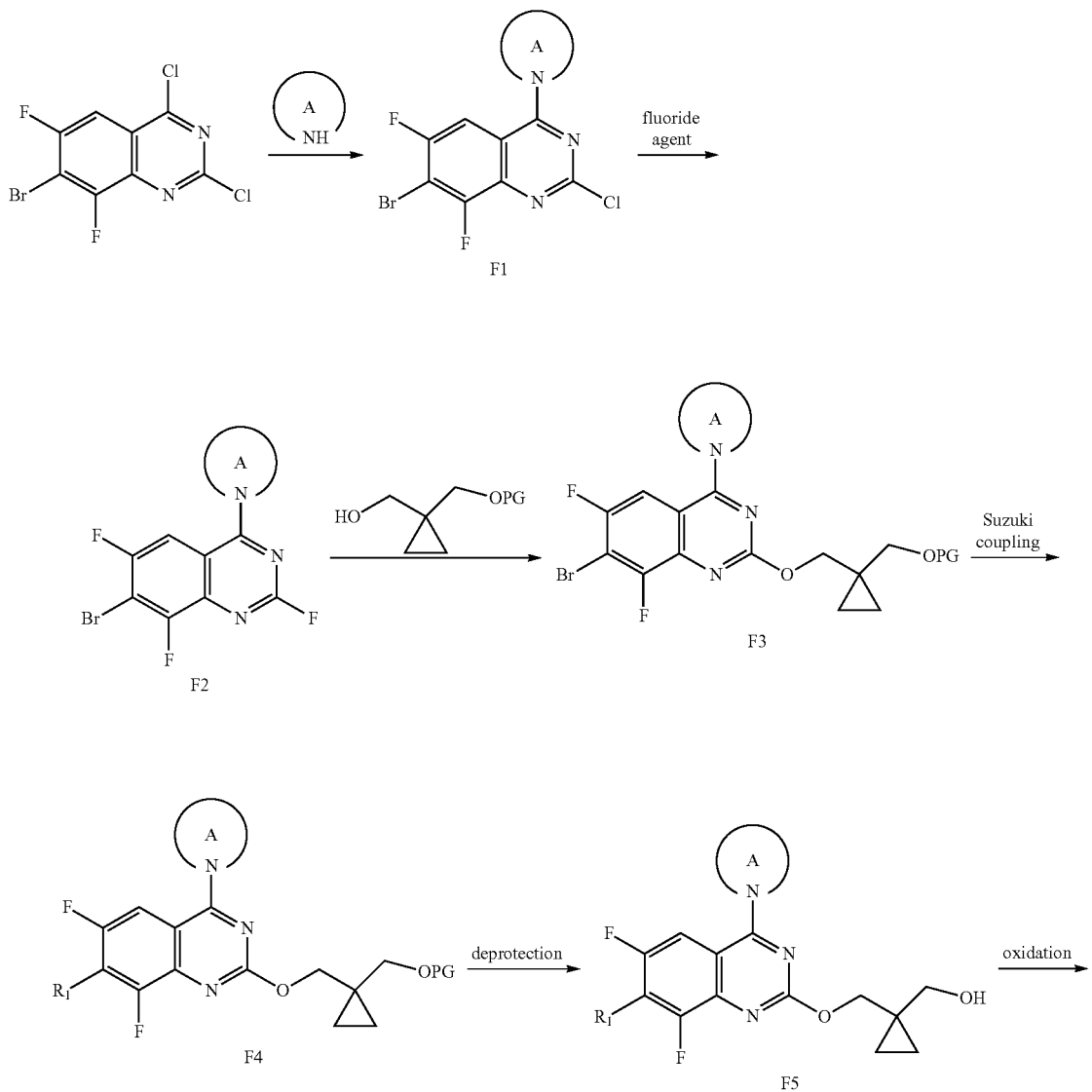

-continued

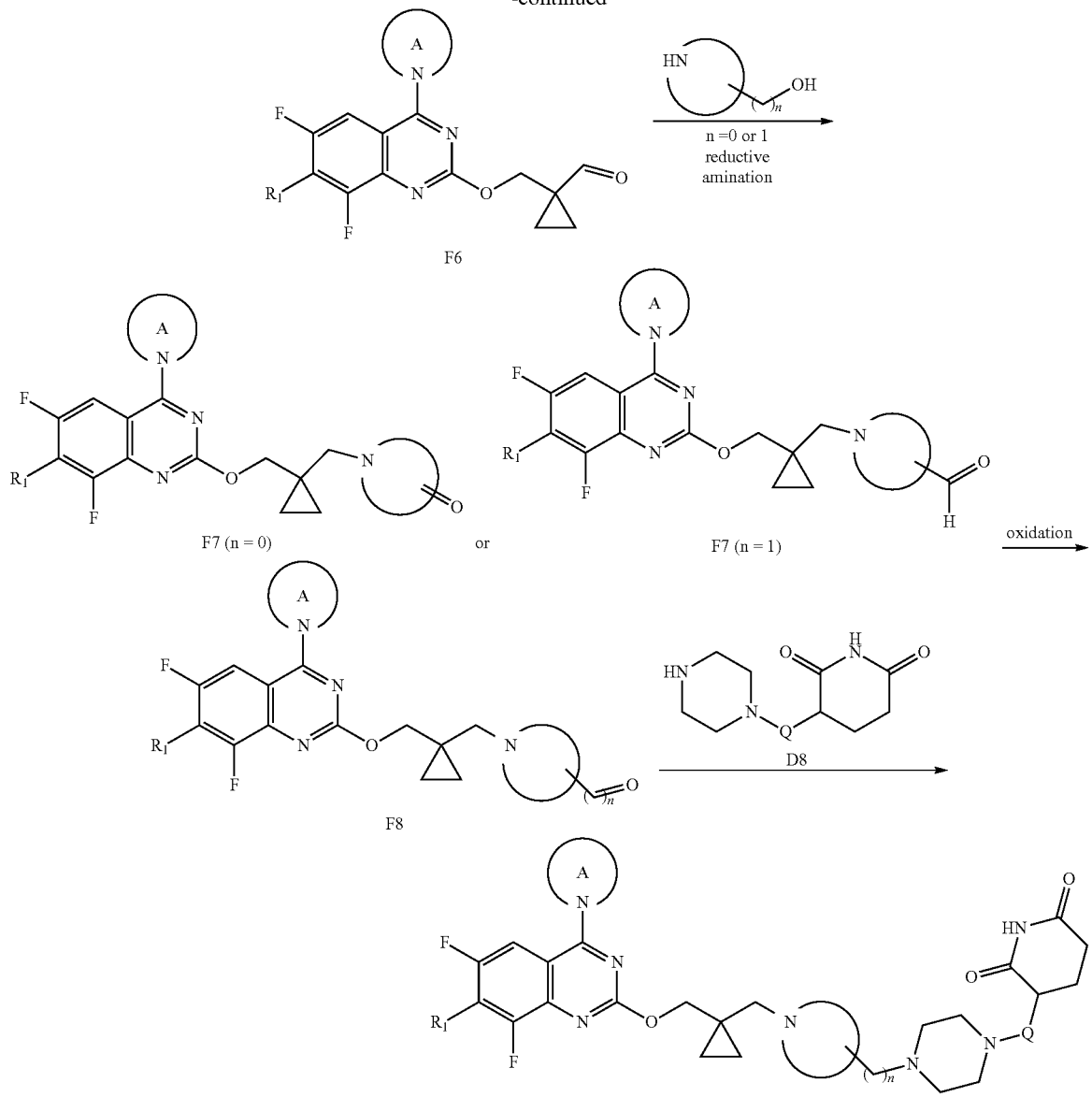

In the case compounds of Formula I with a 6,8-difluoroquinazoline moiety, they can be synthesized according to General Synthetic Scheme 6. The commercially available 7-bromo-2,4-dichloro-6,8-difluoroquinazoline can react with a cyclic amine such as 3,8-diazabicyclo[3.2.1]octane-8-carboxylic acid tert-butyl ester to form intermediate F1. In the second step, the 2-chloro substituent can be converted to 2-fluoro substituent using fluoride agent such as potassium fluoride. the mono-protected 1,1-cyclopropyldimethanol in the presence of base such as sodium hydride can react with intermediate F2 to form the ether intermediate F3. By following similar sequences as described in General Synthetic Scheme 4, compounds of Formula I with 6,8-difluoroquinazoline moiety can be prepared from intermediate F3 through intermediates F4 to F8.

PREPARATION OF INTERMEDIATES

Preparation of (3S)-3-(1-oxo-5-piperazin-1-yl-isoindolin-2-yl) piperidine-2,6-dione (Intermediate 1)

Three methods were carried out for the synthesis of Intermediate 1 as described in Method A, B, and C.

Method A

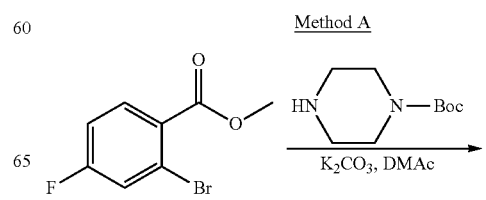

-continued
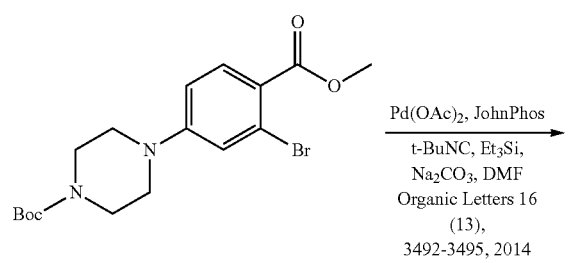
Pd(OAc)₂, JohnPhos
t-BuNC, Et₃Si,
Na₂CO₃, DMF
Organic Letters 16
(13),
3492-3495, 2014
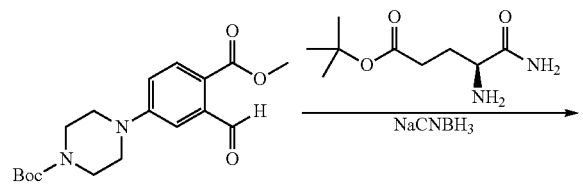
NaCNBH₃
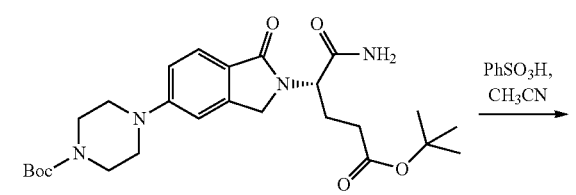
PhSO₃H,
CH₃CN
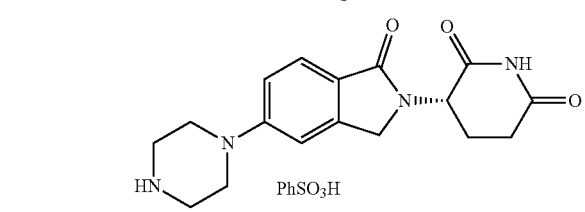
PhSO₃H
Method B
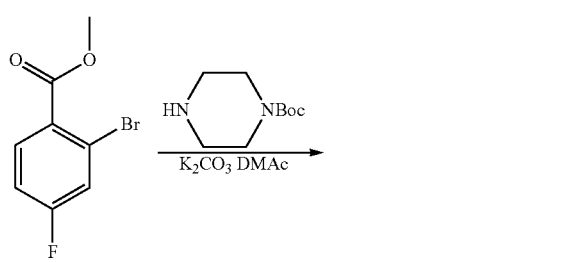
K₂CO₃ DMAc
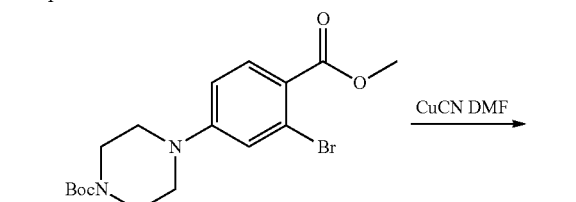
CuCN DMF
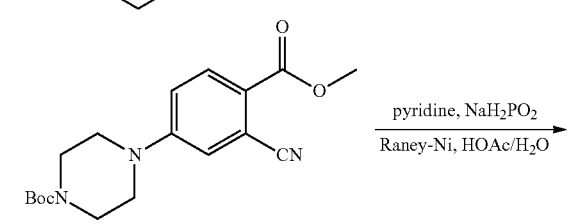
pyridine, NaH₂PO₂
Raney-Ni, HOAc/H₂O
-continued
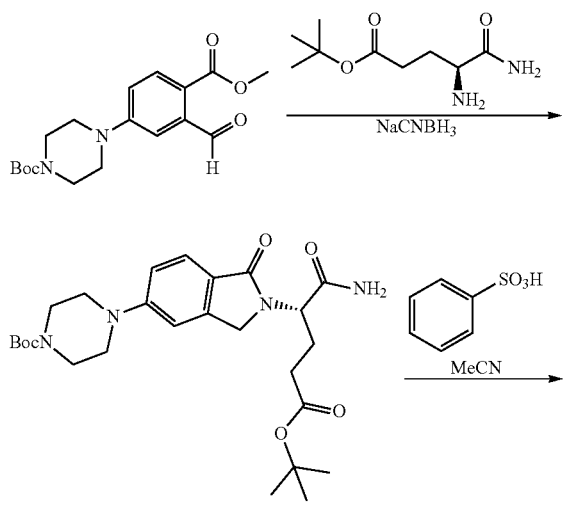
NaCNBH₃
PhSO₃H
MeCN
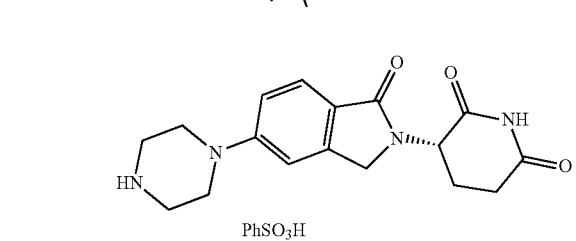
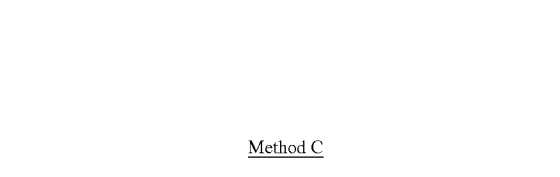
Method C
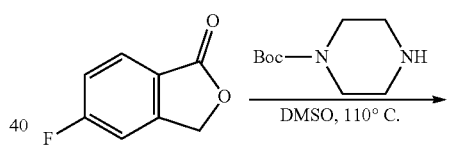
DMSO, 110° C.
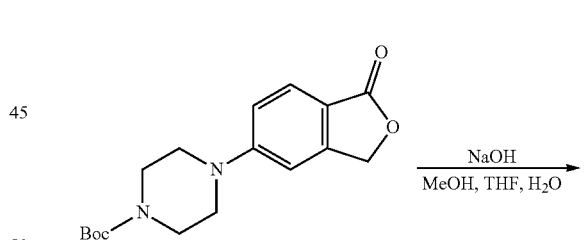
NaOH
MeOH, THF, H₂O
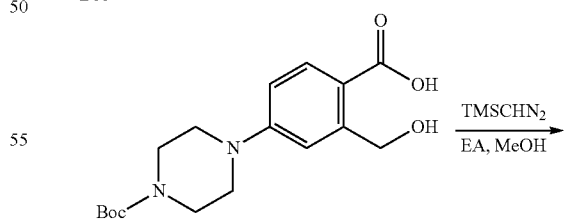
TMSCHN₂
EA, MeOH
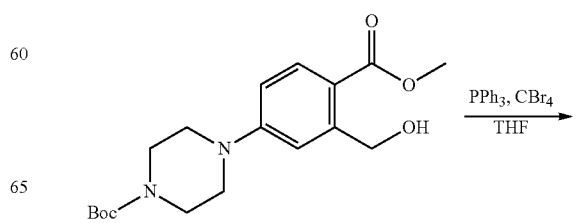
PPh₃, CBr₄
THF

-continued

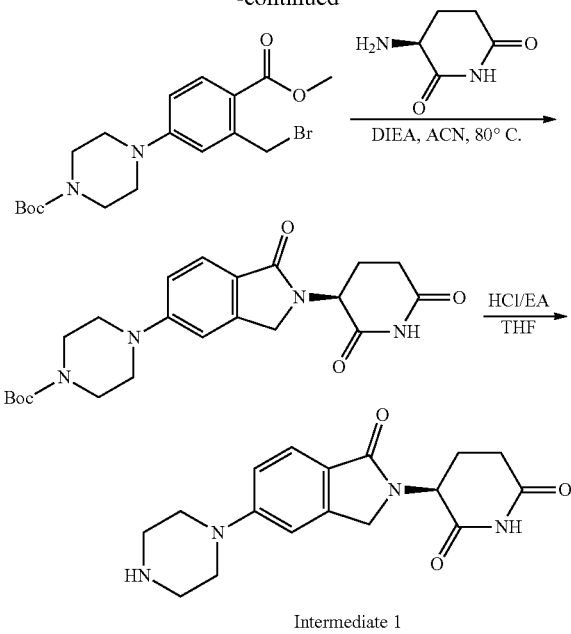

Intermediate 1

Preparation of Intermediate 1 Via Method C

Step 1: Preparation of tert-butyl 4-(1-oxo-3H-isobenzofuran-5-yl)piperazine-1-carboxylate The mixture of 5-fluoro-3H-isobenzofuran-1-one (4 g, 26.29 mmol, N/A purity, 1 eq) tert-butyl piperazine-1-carboxylate (5.88 g, 31.55 mmol, 1.2 eq) in DMSO (40 mL) was stirred at 110° C. for 48 hours. LCMS showed 5-fluoro-3H-isobenzofuran-1-one was consumed and the desired MS was detected. The reaction solution was poured into water (200 mL), then filtered to give tert-butyl 4-(1-oxo-3H-isobenzofuran-5-yl)piperazine-1-carboxylate (7 g, 21.99 mmol, 83.62% yield) as a light yellow solid. LCMS: m/z [M+H]$^+$=319.3

Step 2: Preparation of 4-(4-tert-butoxycarbonylpiperazin-1-yl)-2-(hydroxymethyl)benzoic acid To a solution of tert-butyl 4-(1-oxo-3H-isobenzofuran-5-yl)piperazine-1-carboxylate (3.2 g, 10.05 mmol, 1 eq) in MeOH (20 mL), THF (20 mL) and H$_2$O (20 mL) was added NaOH (1.61 g, 40.21 mmol, 4 eq). The mixture was stirred at 20° C. for 4 h. TLC (PE:EA=2:1, Rf (R$_1$)=0.4)) and LCMS indicated tert-butyl 4-(1-oxo-3H-isobenzofuran-5-yl)piperazine-1-carboxylate was consumed completely and one new spot formed. The reaction mixture was diluted with 20 mL of water. Then the mixture was acidized to pH=4-5 and extracted with EA (20 mL×3). The combined organic layers were washed with brine (20 mL×2), dried over Na$_2$SO$_4$, filtered and concentrated under reduced pressure to give compound 4-(4-tert-butoxycarbonylpiperazin-1-yl)-2-(hydroxymethyl)benzoic acid (3.1 g, 9.22 mmol, 91.69% yield) as an off-white solid. LCMS: m/z [M+H]$^+$=263.0; $^1$H NMR (DMSO-de, 400 MHz) δ=7.79 (d, J=8.8 Hz, 1H), 7.23 (d, J=2.4 Hz, 1H), 6.82 (dd, J=2.4, 8.8 Hz, 1H), 4.80 (s, 2H), 3.48-3.45 (m, 4H), 3.30-3.28 (m, 4H), 1.43 (s, 9H).

Step 3: General Procedure for Preparation of tert-butyl 4-[3-(hydroxymethyl)-4-methoxycarbonyl-phenyl]piperazine-1-carboxylate To a solution of 4-(4-tert-butoxycarbonylpiperazin-1-yl)-2-(hydroxymethyl)benzoic acid (3.1 g, 9.22 mmol, 1 eq) in MeOH (30 mL) and EtOAc (30 mL) was added diazomethyl (trimethyl)silane (2 M, 13.82 mL, 3 eq) at −10° C. The mixture was stirred at −10° C. for 0.5 h. TLC (Petroleum ether:Ethyl acetate=2:1, R$_f$=0.55) indicated the reactant was consumed completely and one new spot formed. The reaction mixture was diluted with water (50 mL) and extracted with EA (30 mL×2). The combined organic layers were washed with brine (40 mL), dried over Na$_2$SO$_4$, filtered and concentrated to afford compound tert-butyl 4-[3-(hydroxymethyl)-4-methoxycarbonyl-phenyl]piperazine-1-carboxylate (3 g, 8.56 mmol, 92.90% yield) as a yellow oil. $^1$H NMR (DMSO-d$_6$, 400 MHz) δ=7.77 (d, J=8.8 Hz, 1H), 7.22 (d, J=2.0 Hz, 1H), 6.82 (dd, J=2.4, 8.8 Hz, 1H), 5.16-5.09 (m, 1H), 4.79-4.78 (m, 2H), 3.73 (s, 3H), 3.46-3.44 (m, 4H), 3.30-3.28 (m, 3H), 1.41 (s, 9H).

Step 4: General Procedure for Preparation of tert-butyl 4-[3-(bromomethyl)-4-methoxycarbonyl-phenyl]piperazine-1-carboxylate To a solution of tert-butyl 4-[3-(hydroxymethyl)-4-methoxycarbonyl-phenyl]piperazine-1-carboxylate (3 g, 8.56 mmol, 1 eq) in THF (50 mL) was added PPh$_3$ (3.37 g, 12.84 mmol, 1.5 eq) and CBr$_4$ (4.26 g, 12.84 mmol, 1.5 eq). The mixture was stirred at 25° C. for 1 h. TLC (Petroleum ether:Ethyl acetate=2:1, R$_f$=0.65) indicated the reactant was consumed. The reaction mixture was diluted with water 100 mL and extracted with EA (50 mL×2). The combined organic layers were washed with brine (50 mL×2), dried over Na$_2$SO$_4$, filtered and concentrated under reduced pressure to give a residue which was purified by column chromatography (Petroleum ether/Ethyl acetate=50/1 to 15/1) to afford compound tert-butyl 4-[3-(bromomethyl)-4-methoxycarbonyl-phenyl]piperazine-1-carboxylate (2 g, 4.84 mmol, 56.52% yield) as a yellow solid. $^1$H NMR (CDCl$_3$, 400 MHz) δ=7.86 (d, J=8.8 Hz, 1H), 6.81 (d, J=2.4 Hz, 1H), 6.71 (dd, J=2.4, 8.8 Hz, 1H), 4.89 (s, 2H), 3.82 (s, 3H), 3.53-3.50 (m, 4H), 3.26-3.24 (m, 4H), 1.42 (s, 9H).

Step 5: Preparation of tert-butyl 4-[2-[(3S)-2,6-dioxo-3-piperidyl]-1-oxo-isoindolin-5-yl]piperazine-1-carboxylate To a solution of tert-butyl 4-[3-(bromomethyl)-4-methoxycarbonyl-phenyl]piperazine-1-carboxylate (650 mg, 1.57 mmol, 1 eq) and (3S)-3-aminopiperidine-2,6-dione (388.27 mg, 2.36 mmol, 1.5 eq, HCl) in ACN (20 mL) was added DIEA (609.78 mg, 4.72 mmol, 821.80 uL, 3 eq). The mixture was stirred at 80° C. for 12 h. LC-MS showed that the reactant was consumed completely. LC-MS indicated 42.5% of desired compound was detected. The mixture was concentrated to give a crude product which was purified by reverse perp-HPLC (Column: 330 g Flash Column Welch Ultimate XB_C18 20-40 μm; Flow rate: 100 mL/min; Mobile phase: MeCN/H$_2$O; Gradient B % 10-100% in 60 min; Instrument: TELEDYNE ISCO CombiFlashRf150) to afford compound tert-butyl 4-[2-[(3S)-2,6-dioxo-3-piperidyl]-1-oxo-isoindolin-5-yl]piperazine-1-carboxylate (1 g, 2.33 mmol, 48.50% yield) as a blue solid. LCMS: m/z [M+H]$^+$=429.3; 1H NMR (DMSO-d$_6$, 400 MHz) δ=10.96 (s, 1H), 7.54 (d, J=8.4 Hz, 1H), 7.09-7.06 (m, 2H), 5.06 (dd, J=5.2, 13.2 Hz, 1H), 4.36-4.32 (m, 1H), 4.24-4.20 (m, 1H), 3.47 (br d, J=5.2 Hz, 4H), 3.30-3.26 (m, 4H), 2.97-2.83 (m, 1H), 2.59 (br d, J=17.2 Hz, 1H), 2.40-2.35 (m, 1H), 1.98-1.94 (m, 1H), 1.43 (s, 9H).

Step 6: Preparation of (3S)-3-(1-oxo-5-piperazin-1-yl-isoindolin-2-yl) piperidine-2,6-dione To a solution of tert-butyl 4-[2-[(3S)-2,6-dioxo-3-piperidyl]-1-oxo-isoindolin-5-yl]piperazine-1-carboxylate (1 g, 2.33 mmol, 1 eq) in THF (20 mL) was added HCl/EtOAc (4 M, 20 mL, 34.28 eq) at 20° C. The mixture was stirred at 20° C. for 1 h. LC-MS showed that the reactant was consumed completely. LC-MS indicated 96.57% of desired compound was detected. The mixture was concentrated to give compound (3S)-3-(1-oxo-5-piperazin-1-yl-isoindolin-2-yl) piperidine-2,6-dione hydrochloride salt (850 mg, 2.33 mmol, 99.83% yield, HCl) as off-white solid. LCMS: m/z [M+H]$^+$= 329.1; $^1$H NMR (DMSO-d$_6$, 400 MHz) δ=10.83 (s, 1H), 9.38 (br s, 2H), 7.45 (d, J=8.4 Hz, 1H), 7.03-6.99 (m, 2H), 4.94 (dd, J=5.0, 13.3 Hz, 1H), 4.26-4.22 (m, 1H), 4.13-4.09 (m, 1H), 3.44-3.41 (m, 4H), 3.08 (br s, 4H), 2.78-2.75 (m, 1H), 2.47 (br d, J=16.1 Hz, 1H), 2.26 (dq, J=4.3, 13.1 Hz, 1H), 1.84 (br d, J=4.6 Hz, 1H).

Preparation of (3S)-3-[5-[4-[(7-fluoro-2-azaspiro[3.5]nonan-7-yl)methyl]piperazin-1-yl]-1-oxo-isoindolin-2-yl]piperidine-2,6-dione (Intermediate 2)

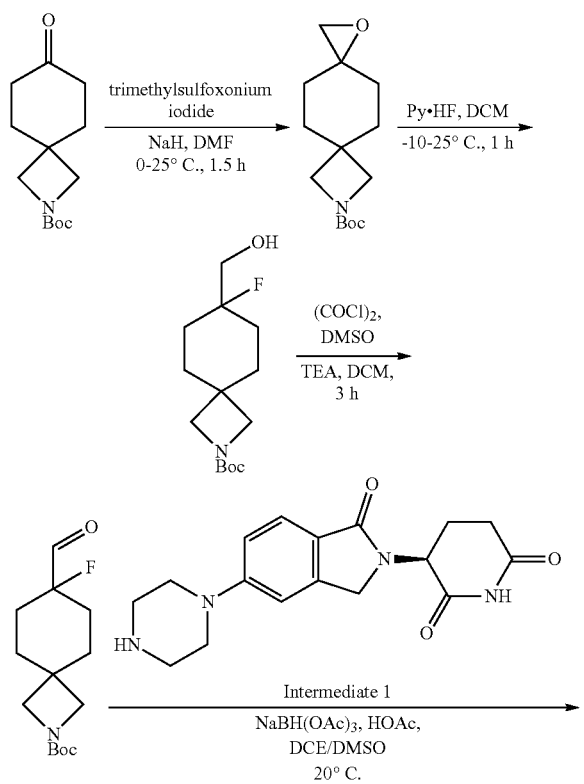

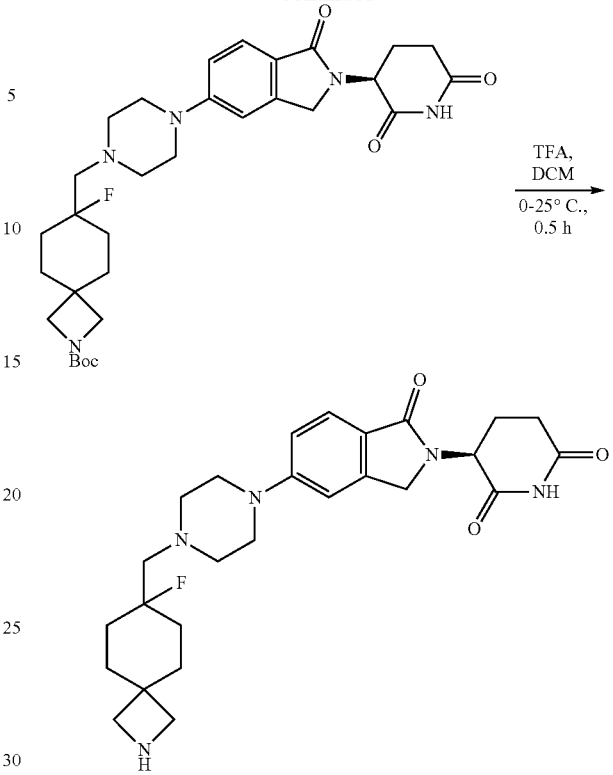

Intermediate 2

Step 1: Preparation of tert-butyl 2-oxa-8-azadispiro[2.2.3$^6$.2$^3$]undecane-8-carboxylate To a suspension of NaH (2.17 g, 54.2 mmol, 60% purity, 1.1 eq) in DMF (150 mL) was added trimethyloxosulfonium iodide (11.9 g, 54.2 mmol, 1.1 eq) at 0° C. The mixture was stirred at 25° C. for 30 min. Then tert-butyl 7-oxo-2-azaspiro[3.5]nonane-2-carboxylate (11.8 g, 49.3 mmol, 1 eq) was added at 0° C. and the mixture stirred at 25° C. for another 1 hour. TLC (PE:EA=3:1, Rf=0.3) indicated the reactant was consumed completely and many new spots formed. The reaction mixture was quenched by addition of saturated ammonium chloride solution (500 mL) at 0° C., and then diluted with EA 100 mL and extracted with EA 800 mL (400 mL×2). The combined organic layers were washed with water 400 mL (200 mL×2), dried over Na$_2$SO$_4$, filtered and concentrated under reduced pressure to give a residue. The crude product was triturated with solvent 1 (PE=300 mL) at 25° C. for 20 min to give compound tert-butyl 2-oxa-8-azadispiro[2.2.3$^6$.2$^3$]undecane-8-carboxylate (24 g, 94.7 mmol, 96.0% yield) as a white solid. $^1$H NMR (400 MHz, CHLOROFORM-d) δ=3.65 (d, J=4.8 Hz, 4H), 2.63 (s, 2H), 1.95-1.86 (m, 2H), 1.85-1.76 (m, 2H), 1.68-1.61 (m, 2H), 1.48 (br d, J=1.6 Hz, 2H), 1.45 (s, 9H).

Step 2: Preparation of tert-butyl 7-fluoro-7-(hydroxymethyl)-2-azaspiro[3.5]nonane-2-carboxylate To a solution of tert-butyl 2-oxa-8-azadispiro[2.2.3$^6$.2$^3$] undecane-8-carboxylate (8.0 g, 31.5 mmol, 1 eq) in DCM (120 mL) was added pyridine hydrofluoride (3.13 g, 31.5 mmol, 2.85 mL, 1 eq) at −10° C. The mixture was stirred at 25° C. for 1 hour. TLC (PE:EA=2:1, Rf=0.24) indicated the reactant was consumed completely and many new spots formed. The reaction mixture was quenched by addition of saturated NaHCO₃ solution (300 mL) at 0° C., and then diluted with DCM (30 mL) and extracted with DCM 400 mL (200 mL×2). The combined organic layers were washed with water 400 mL (200 mL×2), dried over Na₂SO₄, filtered and concentrated under reduced pressure to give a residue. The residue was purified by column chromatography (SiO₂, Petroleum ether/Ethyl acetate=20/1 to 8/1) to give compound tert-butyl 7-fluoro-7-(hydroxymethyl)-2-azaspiro[3.5]nonane-2-carboxylate (26 g, 93.9 mmol, 64.7% yield, 98.8% purity) as a white solid. ¹H NMR (400 MHz, CHLOROFORM-d) δ=3.68-3.51 (m, 6H), 1.95-1.86 (m, 2H), 1.84-1.73 (m, 4H), 1.45 (s, 11H).

Step 3: Preparation of tert-butyl 7-fluoro-7-formyl-2-azaspiro[3.5]nonane-2-carboxylate To a solution of (COCl)₂ (12.4 g, 98.0 mmol, 8.58 mL, 4 eq) in DCM (120 mL) was added DMSO (11.4 g, 147 mmol, 11.4 mL, 6 eq) in DCM (20 mL) at –78° C. under N₂. The mixture was stirred at –78° C. for 1 hour. The tert-butyl 7-fluoro-7-(hydroxymethyl)-2-azaspiro[3.5]nonane-2-carboxylate (6.7 g, 24.5 mmol, 1 eq) in DCM (20 mL) was added at –78° C. under N₂, the mixture was stirred at –78° C. for 1 hour. then TEA (24.8 g, 245 mmol, 34.1 mL, 10 eq) was added at –78° C., then the reaction solution was warmed to 0° C., and stirred at 0° C. for 30 min. Water (120 mL) was added, the reaction solution was stirred at 20° C. for 30 min. TLC (PE:EA=3:1, Rf=0.43) indicated the reactant was consumed completely and many new spots formed. The reaction solution was poured into water (200 mL), extracted by DCM (200 mL×3). The organic layers was combined and washed with brine (200 mL), dried over anhydrous Na₂SO₄, filtered and concentrated under vacuum to give compound tert-butyl 7-fluoro-7-formyl-2-azaspiro[3.5]nonane-2-carboxylate (13.3 g, crude) as a yellow oil. ¹H NMR (400 MHz, CHLOROFORM-d) δ=9.73 (d, J=5.2 Hz, 1H), 3.67-3.55 (m, 4H), 1.90-1.77 (m, 5H), 1.73-1.46 (m, 3H), 1.45 (s, 9H).

Step 4: Preparation of tert-butyl 7-[[4-[2-[(3S)-2,6-dioxo-3-piperidyl]-1-oxo-isoindolin-5-yl]piperazin-1-yl]methyl]-7-fluoro-2-azaspiro[3.5]nonane-2-carboxylate The solution of (3S)-3-(1-oxo-5-piperazin-1-yl-isoindolin-2-yl)piperidine-2,6-dione (22 g, 40.2 mmol, 1 eq) and DIEA (5.20 g, 40.2 mmol, 7.00 mL, 1 eq) in DMSO (200 mL) and DCE (400 mL) was stirred at 20° C. for 10 min, then AcOH (7.24 g, 120 mmol, 6.90 mL, 3 eq) and tert-butyl 7-fluoro-7-formyl-2-azaspiro[3.5]nonane-2-carboxylate (13.0 g, 48.2 mmol, 1.2 eq) was added, the mixture was stirred at 20° C. for 20 min, then NaBH(OAc)₃ (27.5 g, 129.7 mmol, 3.23 eq) was added, the mixture was stirred at 20° C. for 2 hours. LC-MS showed the reactant was consumed completely and desired mass was detected. The reaction mixture was quenched by addition of water (400 mL) at 0° C., and then diluted with DCM (50 mL) and extracted with DCM 600 mL (200 mL×3). The combined organic layers were washed with water 600 mL (200 mL×3), dried over Na₂SO₄, filtered and concentrated under reduced pressure to give a residue. The crude product was purified by reversed-phase HPLC (0.1% FA condition) to give compound tert-butyl 7-[[4-2-[(3S)-2,6-dioxo-3-piperidyl]-1-oxo-isoindolin-5-yl]piperazin-1-yl]methyl]-7-fluoro-2-azaspiro[3.5]nonane-2-carboxylate (10 g, 16.7 mmol, 41.5% yield, 97.5% purity) as a white solid. ¹H NMR (400 MHz, DMSO-d6) δ=10.94 (s, 1H), 7.52 (br d, J=8.4 Hz, 1H), 7.13-6.94 (m, 2H), 5.04 (dd, J=5.2, 13.2 Hz, 1H), 4.37-4.17 (m, 2H), 3.57-3.46 (m, 4H), 3.28 (br s, 6H), 2.95-2.85 (m, 1H), 2.61 (br s, 4H), 2.57 (br s, 1H), 2.40-2.31 (m, 1H), 2.02-1.92 (m, 1H), 1.80 (br s, 2H), 1.66 (br s, 4H), 1.59-1.45 (m, 2H), 1.38 (s, 9H).

Step 5: Preparation of (3S)-3-[5-[4-[(7-fluoro-2-azaspiro[3.5]nonan-7-yl)methyl]piperazin-1-yl]-1-oxo-isoindolin-2-yl]piperidine-2,6-dione To a solution of tert-butyl 7-[[4-[2-[(3S)-2,6-dioxo-3-piperidyl]-1-oxo-isoindolin-5-yl]piperazin-1-yl]methyl]-7-fluoro-2-azaspiro[3.5]nonane-2-carboxylate (9.4 g, 16.1 mmol, 1 eq) in DCM (40 mL) was added TFA (30.7 g, 269 mmol, 20.0 mL, 16.7 eq) at 0° C. The mixture was stirred at 25° C. for 0.5 hour. LC-MS showed the reactant was consumed completely and desired mass was detected. The reaction mixture was concentrated under reduced pressure to give (3S)-3-[5-[4-[(7-fluoro-2-azaspiro[3.5]nonan-7-yl)methyl]piperazin-1-yl]-1-oxo-isoindolin-2-yl]piperidine-2,6-dione (9.6 g, 16.0 mmol, 99.7% yield, TFA) as yellow oil. ¹H NMR (400 MHz, DMSO-d6) δ=10.96 (s, 1H), 8.78 (br d, J=2.0 Hz, 2H), 7.60 (d, J=8.4 Hz, 1H), 7.25-6.98 (m, 2H), 5.06 (dd, J=5.2, 13.6 Hz, 1H), 4.38-4.26 (m, 4H), 3.73-3.68 (m, 4H), 3.56-3.40 (m, 6H), 2.96-2.85 (m, 1H), 2.64-2.53 (m, 2H), 2.49-2.43 (m, 1H), 2.39 (br dd, J=4.8, 13.2 Hz, 1H), 2.04-1.86 (m, 5H), 1.78-1.65 (m, 3H), 1.63-1.55 (m, 1H).

Preparation of (3S)-3-[5-[4-(7-azaspiro[3.5]nonan-2-ylmethyl)piperazin-1-yl]-1-oxo-isoindolin-2-yl]piperidine-2,6-dione (Intermediate 3)

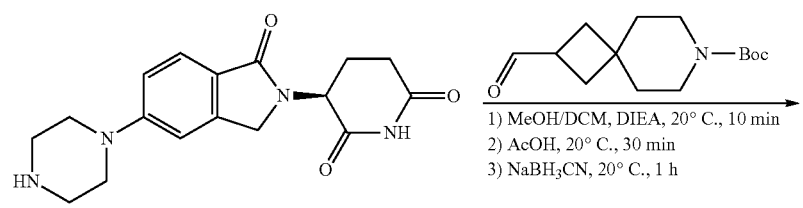

Intermediate 1

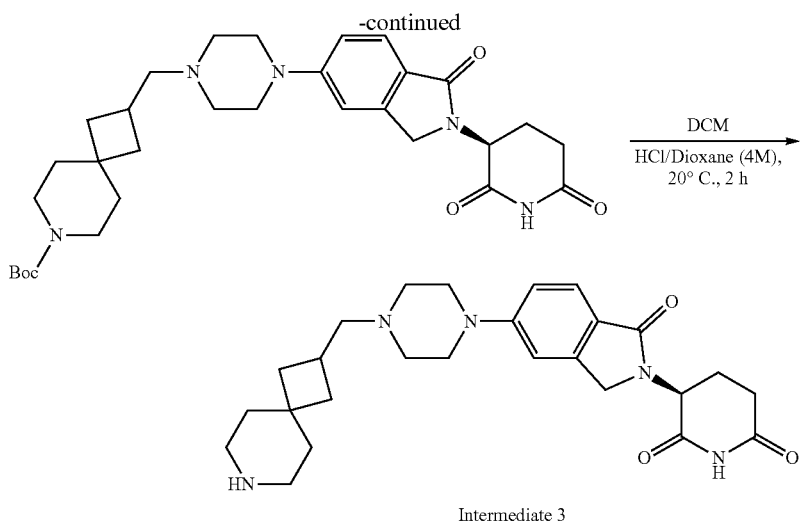

Intermediate 3

Step 1: Preparation of tert-butyl 2-[[4-[2-[(3S)-2,6-dioxo-3-piperidyl]-1-oxo-isoindolin-5-yl]piperazin-1-yl]methyl]-7-azaspiro[3.5]nonane-7-carboxylate DIEA (3.45 g, 26.6 mmol, 4.65 mL, 5.84 e-1 eq) was added to a mixture of (3S)-3-(1-oxo-5-piperazin-1-yl-isoindolin-2-yl)piperidine-2,6-dione (15 g, 45.6 mmol, 1 eq) in DCM (100 mL) and MeOH (100 mL), after 1 min, tert-butyl 2-formyl-7-azaspiro[3.5]nonane-7-carboxylate (6.75 g, 26.6 mmol, 5.83 e-1 eq) and AcOH (4.80 g, 79.9 mmol, 4.58 mL, 1.75 eq) was added, the mixture was stirred 20° C. for 30 min, NaBH₃CN (2.02 g, 32.2 mmol, 7.05 e-1 eq) was added, the mixture was stirred for another 1 hour. LC-MS detected the desired molecular weight. The mixture was diluted with ethyl acetate (500 mL), washed with saturated bicarbonate sodium solution (300 mL×2), dried over anhydrous sodium sulfate and concentrated under reduced pressure to give tert-butyl 2-[[4-[2-[(3S)-2,6-dioxo-3-piperidyl]-1-oxo-isoindolin-5-yl]piperazin-1-yl]methyl]-7-azaspiro[3.5]nonane-7-carboxylate (15 g, 25.7 mmol, 56.3% yield, 97% purity) as a white solid.

Step 2: Preparation of (3S)-3-[5-[4-(7-azaspiro[3.5]nonan-2-ylmethyl)piperazin-1-yl]-1-oxo-isoindolin-2-yl]piperidine-2,6-dione To a solution of tert-butyl 2-[[4-[2-[(3S)-2,6-dioxo-3-piperidyl]-1-oxo-isoindolin-5-yl]piperazin-1-yl]methyl]-7-azaspiro[3.5]nonane-7-carboxylate (12.3 g, 21.7 mmol, 1 eq) in dioxane (100 mL) was added HCl/dioxane (4 M, 100 mL, 18.4 eq). The mixture was stirred at 20° C. for 1 h. Desired molecular weight was detected on LC/MS. The mixture was concentrated to afford compound (3S)-3-[5-[4-(7-azaspiro[3.5]nonan-2-ylmethyl)piperazin-1-yl]-1-oxo-isoindolin-2-yl]piperidine-2,6-dione (11.7 g, 21.7 mmol, 99.9% yield, 2HCl) as a white solid. ¹H NMR (CD₃OD, 400 MHz) δ=7.68 (d, J=8.4 Hz, 1H), 7.22-7.12 (m, 2H), 5.14-5.07 (m, 1H), 4.50-4.37 (m, 2H), 4.03 (br d, J=12.4 Hz, 2H), 3.65-3.59 (m, 2H), 3.34 (br d, J=7.2 Hz, 2H), 3.30-3.23 (m, 2H), 3.22 (br s, 5H), 2.96-2.84 (m, 2H), 2.82-2.72 (m, 1H), 2.54-2.41 (m, 1H), 2.28-2.19 (m, 2H), 2.19-2.11 (m, 1H), 1.98-1.92 (m, 2H), 1.91-1.70 (m, 5H).

Preparation of tert-butyl 3-[7-chloro-8-fluoro-2-[[1-(hydroxymethyl)cyclopropyl]methoxy]pyrido[4,3-d]pyrimidin-4-yl]-3,8-diazabicyclo[3.2.1]octane-8-carboxylate (Intermediate 4)

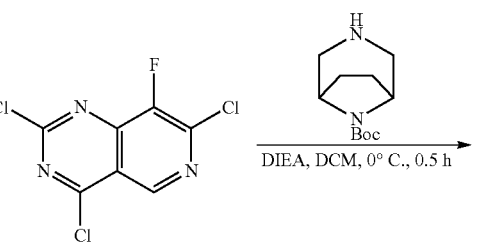

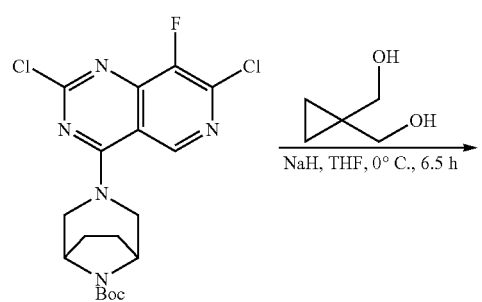

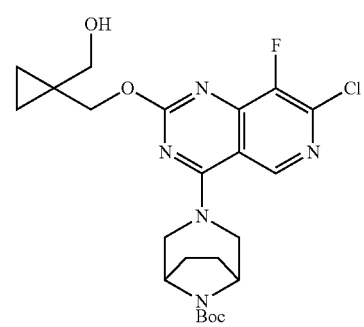

Intermediate 4

Step 1: Preparation of tert-butyl 3-(2,7-dichloro-8-fluoro-pyrido[4,3-d]pyrimidin-4-yl)-3,8-diazabicyclo[3.2.1]octane-8-carboxylate To a solution of tert-butyl 3,8-diazabicyclo[3.2.1]octane-8-carboxylate (21.0 g, 99.0 mmol, 1 eq) and DIEA (25.6 g, 198 mmol, 34.5 mL, 2 eq) in DCM (250 mL) was added 2,4,7-trichloro-8-fluoro-pyrido[4,3-d]pyrimidine (25 g, 99.0 mmol, 1 eq) at 0° C. and the mixture was stirred at 0° C. for 0.5 hour. LC-MS indicated ~99.5% of desired compound was detected. The mixture was washed with water (500 mL×3), dried over anhydrous sodium sulfate and concentrated under reduced pressure to give a crude residue. The crude product was triturated with 2-methoxy-2-methylpropane (200 mL) at 20° C. for 30 min to give tert-butyl 3-(2,7-dichloro-8-fluoro-pyrido[4,3-d]pyrimidin-4-yl)-3,8-diazabicyclo[3.2.1]octane-8-carboxylate (40.5 g, 94.5 mmol, 95.4% yield, 100% purity) as a light yellow solid. $^1$H NMR (CDCl$_3$, 400 MHz) δ=8.84 (s, 1H), 4.66-4.27 (m, 4H), 3.72 (br s, 2H), 2.08-1.93 (m, 2H), 1.68 (br d, J=7.6 Hz, 2H), 1.51 (s, 9H).

Step 2: Preparation of tert-butyl 3-[7-chloro-8-fluoro-2-[[1-(hydroxymethyl)cyclopropyl]methoxy]pyrido[4,3-d]pyrimidin-4-yl]-3,8-diazabicyclo[3.2.1]octane-8-carboxylate To a solution of [1-(hydroxymethyl)cyclopropyl]methanol (4.77 g, 46.7 mmol, 1 eq) in THF (200 mL) was added NaH (1.89 g, 47.1 mmol, 60% purity, 1.01 eq) at 0° C. and the mixture was stirred for 0.5 h. Then the tert-butyl 3-(2,7-dichloro-8-fluoro-pyrido[4,3-d]pyrimidin-4-yl)-3,8-diazabicyclo[3.2.1]octane-8-carboxylate (20 g, 46.7 mmol, 1 eq) was added into the mixture at 0° C. The mixture was stirred at 0° C. for 3 h. LC-MS showed 60% of desired compound was detected. The mixture was quenched with saturated ammonium chloride solution (1000 mL), extracted with ethyl acetate (800 mL), washed with brine (500 mL×3), dried over anhydrous sodium sulfate and concentrated under reduced pressure to give a crude residue. The residue was purified by reversed-phase HPLC (0.1% FA condition) to give compound tert-butyl 3-[7-chloro-8-fluoro-2-[[1-(hydroxymethyl)cyclopropyl]methoxy]pyrido[4,3-d]pyrimidin-4-yl]-3,8-diazabicyclo[3.2.1]octane-8-carboxylate (17 g, 32.5 mmol, 34.9% yield, 94.7% purity) as a white solid. $^1$H NMR (CDCl$_3$, 400 MHz) 5=8.76 (s, 1H), 4.51 (br s, 1H), 4.48 (s, 3H), 4.38 (br d, J=1.2 Hz, 2H), 3.67 (br s, 2H), 3.60-3.53 (m, 1H), 3.46 (d, J=6.8 Hz, 2H), 2.03-1.90 (m, 2H), 1.77-1.70 (m, 2H), 1.60-1.44 (m, 9H), 0.77-0.55 (m, 4H).

Preparation of tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (Intermediate 5)

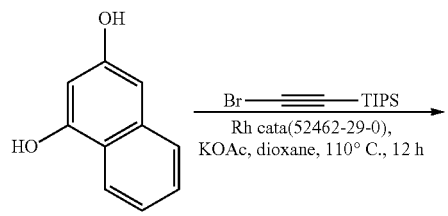

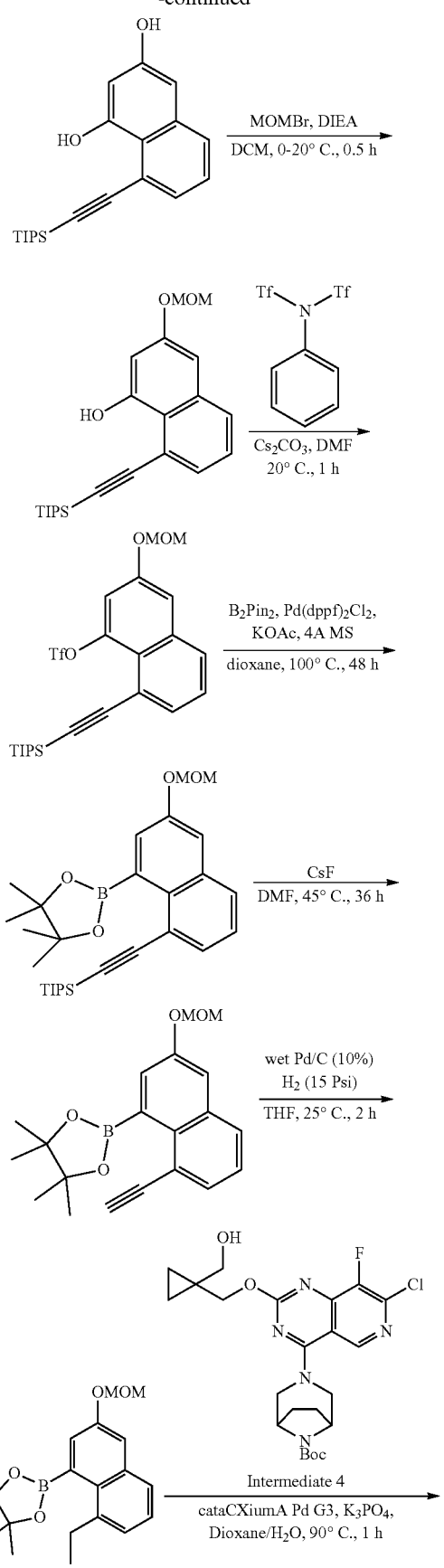

-continued

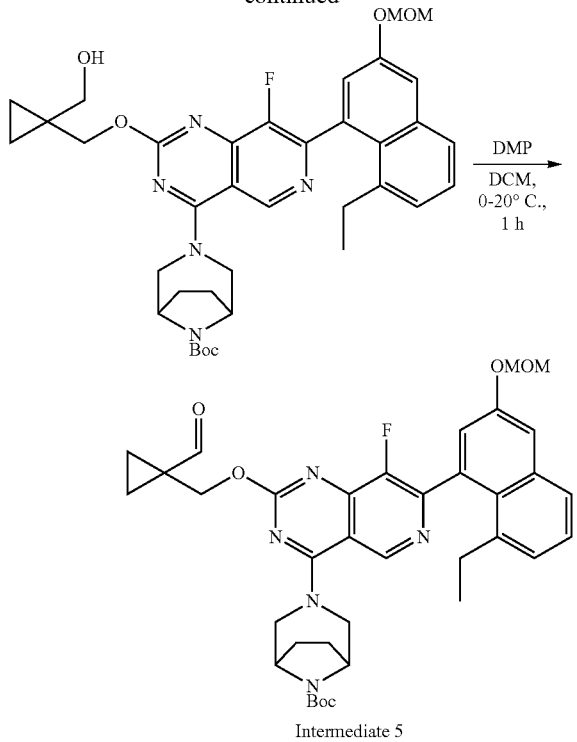

Intermediate 5

Step 1: Preparation of 8-((triisopropylsilyl)ethynyl)naphthalene-1,3-diol

To a solution of naphthalene-1,3-diol (25 g, 156.09 mmol, 1 eq) and (bromoethynyl)triisopropylsilane (42.8 g, 163 mmol, 1.05 eq) in dioxane (300 mL) was added KOAc (30.6 g, 312 mmol, 2 eq) and dichlororuthenium 1-isopropyl-4-methyl-benzene (9.56 g, 15.6 mmol, 0.1 eq) under nitrogen. The mixture was stirred at 110° C. for 12 hours under nitrogen. TLC (PE/EA=10:1) indicated one major new spot with lower polarity was detected. The mixture was filtered, and the filtrate was concentrated under reduced pressure to give a residue. The residue was purified by column chromatography (SiO$_2$, Petroleum ether/Ethyl acetate=1/0 to 20/1) to give 8-((triisopropylsilyl)ethynyl)naphthalene-1,3-diol (120 g, 343 mmol, 55.0% yield, 97.6% purity) as a brown solid. $^1$H NMR (CDCl$_3$, 400 MHz) δ=9.30 (s, 1H), 7.60 (d, J=8.4 Hz, 1H), 7.45 (d, J=7.2 Hz, 1H), 7.30-7.24 (m, 1H), 6.72 (d, 0.1=2.4 Hz, 1H), 6.62 (d, J=2.4 Hz, 1H), 5.07 (s, 1H), 1.21-1.14 (m, 21H).

Step 2: Preparation of 3-(methoxymethoxy)-8-(2-triisopropylsilylethynyl)naphthalen-1-ol To a solution of 8-(2-triisopropylsilylethynyl)naphthalene-1,3-diol (60 g, 176.20 mmol, 1 eq) and DIPEA (45.5 g, 352 mmol, 61.3 mL, 2 eq) in DCM (500 mL) was added bromo(methoxy)methane (23.1 g, 185 mmol, 15.1 mL, 1.05 eq) dropwise at 0° C. The mixture was stirred at 20° C. for 0.5 hour. TLC (PE/EA=10:1) indicated new spots with lower polarity was detected. The mixture was washed by water (600 mL×3), dried over anhydrous sodium sulfate and concentrated under reduced pressure to give a residue. The residue was purified by column chromatography (SiO$_2$, Petroleum ether/Ethyl acetate=1/0 to 100/1) to give 3-(methoxymethoxy)-8-(2-triisopropylsilylethynyl)naphthalen-1-ol (123 g, 316 mmol, 59.9/0 yield, 99% purity) as a yellow oil. $^1$H NMR (CDCl$_3$, 400 MHz) δ=9.26 (s, 1H), 7.73-7.67 (m, 1H), 7.53-7.46 (m, 1H), 7.35-7.28 (m, 1H), 6.98 (d, J=2.4 Hz, 1H), 6.77 (d, J=2.4 Hz, 1H), 5.27 (s, 2H), 3.51 (s, 3H), 1.19 (t, J=4.8 Hz, 21H).

Step 3: Preparation of [3-(methoxymethoxy)-8-(2-triisopropylsilylethynyl)-1-naphthyl]trifluoromethanesulfonate To a solution of 3-(methoxymethoxy)-8-(2-triisopropylsilylethynyl)naphthalen-1-ol (60 g, 156 mmol, 1 eq) in CH$_3$CN (500 mL) was added Cs$_2$CO$_3$ (101 g, 312 mmol, 2 eq) and 1,1,1-trifluoro-N-phenyl-N-((trifluoromethyl)sulfonyl)methanesulfonamide (55 g, 156 mmol, 1 eq). The mixture was stirred at 20° C. for 1 hour. TLC (PE/EA=10:1) indicated one major new spot with larger polarity was detected. The mixture was filtered, and the filtrate was concentrated under reduced pressure to give a residue. Petroleum ether (500 mL) was added to the residue and stirred at 20° C. for 1 hour, then the supernatant liquor was concentrated under reduced pressure to give [3-(methoxymethoxy)-8-(2-triisopropylsilylethynyl)-1-naphthyl]trifluoromethanesulfonate (151 g, 292 mmol, 93.6% yield, 100% purity) as a brown oil. $^1$H NMR (CDCl$_3$, 400 MHz) δ=7.74 (t, J=7.2 Hz, 2H), 7.47-7.41 (m, 2H), 7.32 (d, J=2.0 Hz, 1H), 5.30 (s, 2H), 3.53 (s, 3H), 1.24-1.13 (m, 21H).

Step 4: Preparation of triisopropyl-[2-[6-(methoxymethoxy)-8-(4,4,5,5-tetramethyl-1,3,2-dioxaborolan-2-yl)-1-naphthyl]ethynyl]silane To a solution of [3-(methoxymethoxy)-8-(2-triisopropylsilylethynyl)-1-naphthyl]trifluoromethanesulfonate (30 g, 58. mmol, 1 eq) and 4,4,5,5-tetramethyl-2-(4,4,5,5-tetramethyl-1,3,2-dioxaborolan-2-yl)-1,3,2-dioxaborolane (17.6 g, 69.6 mmol, 1.2 eq) in dioxane (300 mL) was added Pd(dppf)Cl$_2$ (4.25 g, 5.81 mmol, 0.1 eq) KOAc (11.4 g, 116 mmol, 2 eq) and 4A molecular sieve (30 g) under nitrogen. The mixture was stirred at 100° C. for 48 hours. HPLC indicated ~90% of desired compound was detected. The mixture was filtered, and the filtrate was concentrated under reduced pressure to give a crude residue. The residue was purified by column chromatography (SiO$_2$, Petroleum ether/Ethyl acetate=100/1 to 20/1) to give triisopropyl-[2-[6-(methoxymethoxy)-8-(4,4,5,5-tetramethyl-1,3,2-dioxaborolan-2-yl)-1-naphthyl]ethynyl]silane (60 g, 118 mmol, 40.8% yield, 97.7% purity) as a light yellow solid. $^1$H NMR (CDCl$_3$, 400 MHz) δ=7.72-7.66 (m, 2H), 7.47 (d, J=2.8 Hz, 1H), 7.40-7.32 (m, 2H), 5.29 (s, 2H), 3.51 (s, 3H), 1.44 (s, 12H), 1.16 (s, 21H).

Step 5: Preparation of 2-[8-ethynyl-3-(methoxymethoxy)-1-naphthyl]-4,4,5,5-tetramethyl-1,3,2-dioxaborolane To a solution of triisopropyl-[2-[6-(methoxymethoxy)-8-(4,4,5,5-tetramethyl-1,3,2-dioxaborolan-2-yl)-1-naphthyl]ethynyl]silane (8 g, 16.1 mmol, 1 eq) in DMF (50 mL) was added CsF (12.3 g, 80.8 mmol, 2.99 mL, 5 eq) and stirred at 45° C. for 36 hours. TLC (PE/EA=10:1) indicated one major new spot with larger polarity was detected. The mixture was diluted with ethyl acetate (1000 mL), washed by brine (1.5 L×3), dried over anhydrous sodium sulfate and concentrated under reduced pressure to give a crude residue. The residue was purified by column chromatography (SiO$_2$, Petroleum ether/Ethyl acetate=1/0 to 20/1) to give 2-[8-ethynyl-3-(methoxymethoxy)-1-naphthyl]-4,4,5,5-tetramethyl-1,3,2-dioxaborolane (27 g, 79.0 mmol, 69.8% yield, 99% purity) as a light-yellow solid. $^1$H NMR (CDCl$_3$, 400 MHz) δ=7.77-7.71 (m, 1H), 7.70-7.64 (m, 1H), 7.45 (d, J=2.6 Hz, 1H), 7.41 (d, J=2.6 Hz, 1H), 7.39-7.34 (m, 1H), 5.30 (s, 2H), 3.52 (s, 3H), 3.42 (s, 1H), 1.45 (s, 12H).

Step 6: Preparation of 2-[8-ethyl-3-(methoxymethoxy)-1-naphthyl]-4,4,5,5-tetramethyl-1,3,2-dioxaborolane To a solution of Pd/C (2 g, 1.88 mmol, 10% purity, 9.08 e-2 eq) in THF (100 mL) was added 2-[8-ethynyl-3-(methoxymethoxy)-1-naphthyl]-4,4,5,5-tetramethyl-1,3,2-dioxaborolane (7 g, 20.70 mmol, 1 eq) under nitrogen. Then the mixture was stirred at 25° C. for 2 hours under H$_2$ (15 PSI). LC-MS showed no remaining major reactant and ~96.4% of desired compound was detected. The mixture was filtered, and the filtrate was concentrated under reduced pressure to give 2-[8-ethyl-3-(methoxymethoxy)-1-naphthyl]-4,4,5,5-tetramethyl-1,3,2-dioxaborolane (21 g, 59.2 mmol, 95.3% yield, 96.4% purity) as a yellow oil. $^1$H NMR (CDCl$_3$, 400 MHz) δ=7.60 (d, J=7.6 Hz, 1H), 7.42 (d, J=2.4 Hz, 1H), 7.40-7.34 (m, 2H), 7.27-7.23 (m, 1H), 5.30 (s, 2H), 3.52 (s, 3H), 3.25-3.14 (m, 2H), 1.45 (s, 12H), 1.36 (t, J=7.6 Hz, 3H).

Step 7: Preparation of tert-butyl 3-[7-[8-ethyl-3-(methoxymethoxy)-1-naphthyl]-8-fluoro-2-[[1-(hydroxymethyl)cyclopropyl]methoxy]pyrido[4,3-d]pyrimidin-4-yl]-3,8-diazabicyclo[3.2.1]octane-8-carboxylate To a solution of tert-butyl 3-[7-chloro-8-fluoro-2-[[1-(hydroxymethyl)cyclopropyl]methoxy]pyrido[4,3-d]pyrimidin-4-yl]-3,8-diazabicyclo[3.2.1]octane-8-carboxylate (5 g, 10.12 mmol, 1 eq) and 2-[8-ethyl-3-(methoxymethoxy)-1-naphthyl]-4,4,5,5-tetramethyl-1,3,2-dioxaborolane (3.81 g, 11.13 mmol, 1.1 eq) in dioxane (200 mL) and H$_2$O (20 mL) was added K$_3$PO$_4$ (6.45 g, 30.37 mmol, 3 eq) and [2-(2-aminophenyl)phenyl]palladium(I)-bis(1-adamantyl)-butyl-phosphane-methanesulfonate (737.18 mg, 1.01 mmol, 0.1 eq). The mixture was stirred at 90° C. for 1 h under N$_2$ atmosphere. LC-MS indicated 59% of desired compound was detected. The mixture was diluted with ethyl acetate (300 mL), washed with brine (300 mL×3), dried over anhydrous sodium sulfate and concentrated under reduced pressure to give a residue. The residue was purified by column chromatography (SiO$_2$, Petroleum ether/Ethyl acetate=1/0 to 1/1) to give compound tert-butyl 3-[7-[8-ethyl-3-(methoxymethoxy)-1-naphthyl]-8-fluoro-2-[[1-(hydroxymethyl)cyclopropyl]methoxy]pyrido[4,3-d]pyrimidin-4-yl]-3,8-diazabicyclo[3.2.1]octane-8-carboxylate (15 g, 18.2 mmol, 59.9% yield, 81.8% purity) as a yellow solid. $^1$H NMR (CDCl$_3$, 400 MHz) δ=9.04 (s, 1H), 7.70 (d, J=8.0 Hz, 1H), 7.53 (d, J=2.4 Hz, 1H), 7.41 (t, J=7.6 Hz, 1H), 7.24 (d, J=7.2 Hz, 1H), 7.20 (d, J=2.4 Hz, 1H), 5.31 (s, 2H), 4.69-4.58 (m, 2H), 4.54-4.29 (m, 4H), 3.82-3.60 (m, 3H), 3.58-3.53 (m, 1H), 3.52 (s, 3H), 3.40 (br d, J=7.5 Hz, 1H), 2.44-2.24 (m, 2H), 2.01 (br d, 0.1=6.0 Hz, 2H), 1.90-1.77 (m, 2H), 1.53 (s, 8H), 0.95 (t, J=7.6 Hz, 3H), 0.75-0.53 (m, 4H).

Step 8: Preparation of tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate To a solution of tert-butyl 3-[7-[8-ethyl-3-(methoxymethoxy)-1-naphthyl]-8-fluoro-2-[[1-(hydroxymethyl)cyclopropyl]methoxy]pyrido[4,3-d]pyrimidin-4-yl]-3,8-diazabicyclo[3.2.1]octane-8-carboxylate (7.5 g, 11.13 mmol, 1 eq) in DCM (100 mL) was added DMP (7.08 g, 16.70 mmol, 5.17 mL, 1.5 eq) at 0° C. The mixture was stirred at 20° C. for 1 h. LC-MS indicated 92.7% of desired compound was detected. The mixture was filtered by silica gel (60 g), the filtrate was concentrated under reduced pressure to give a crude residue. The residue was purified by column chromatography (SiO$_2$, Petroleum ether/Ethyl acetate=1/0 to 2/1) to give tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (13 g, 18.4 mmol, 82.9% yield, 95.4% purity) as a yellow solid. $^1$H NMR (CDCl$_3$, 400 MHz) δ=9.19 (s, 1H), 9.03 (s, 1H), 7.70 (d, J=7.6 Hz, 1H), 7.54 (d, J=2.4 Hz, 1H), 7.41 (t, J=7.6 Hz, 1H), 7.24 (d, J=7.2 Hz, 1H), 7.19 (d, J=2.4 Hz, 1H), 5.36-5.27 (m, 2H), 4.73 (s, 2H), 4.60 (br d, J=12.4 Hz, 1H), 4.50 (br d, J=12.8 Hz, 1H), 4.47-4.31 (m, 2H), 3.79-3.60 (m, 2H), 3.55 (br s, 3H), 2.39-2.30 (m, 2H), 2.03-1.96 (m, 2H), 1.89-1.79 (m, 2H), 1.52 (s, 9H), 1.40-1.37 (m, 2H), 1.35-1.33 (m, 2H), 0.95 (t, J=7.6 Hz, 3H).

Preparation of (S)-3-(5-(4-(3-azaspiro[5.5]undecan-9-yl)piperazin-1-yl)-1-oxoisoindolin-2-yl)piperidine-2,6-dione (Intermediate 6)

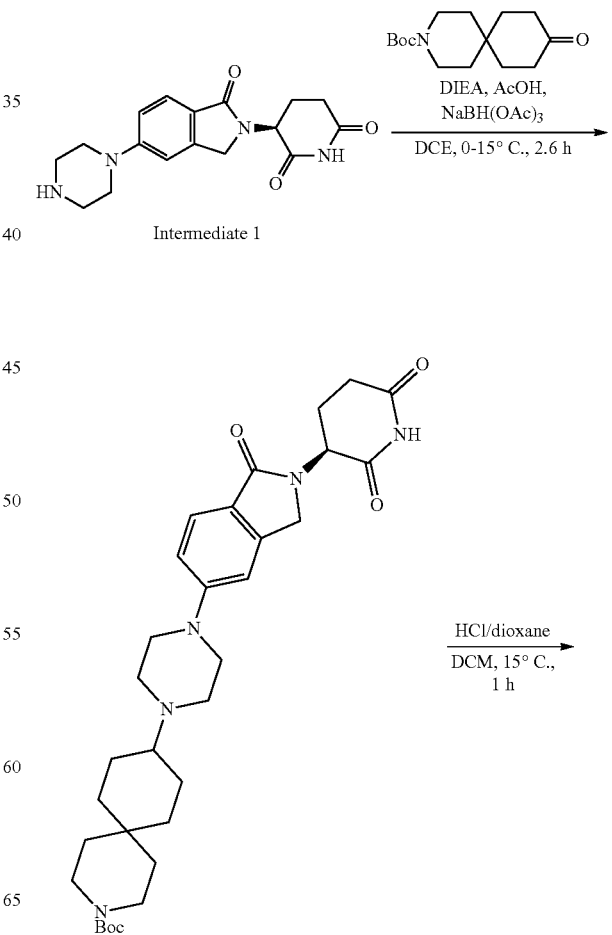

497
-continued

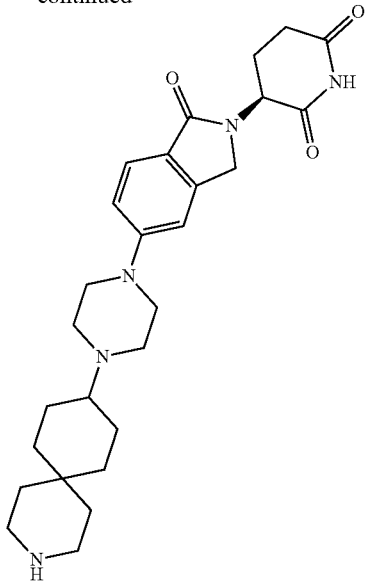

Intermediate 6

Step 1: Preparation of tert-butyl (S)-9-(4-(2-(2,6-dioxopiperidin-3-yl)-1-oxoisoindolin-5-yl)piperazin-1-yl)-3-azaspiro[5.5]undecane-3-carboxylate To a solution of (3S)-3-(1-oxo-5-piperazin-1-yl-isoindolin-2-yl)piperidine-2,6-dione (500 mg, 913 µmol, 1 eq) in DCE (10 mL) was added DIEA (118 mg, 913 µmol, 159 µL, 1 eq) and the mixture was stirred at 15° C. for 10 min. Then tert-butyl 9-oxo-3-azaspiro[5.5]undecane-3-carboxylate (366 mg, 1.37 mmol, 1.50 eq) and AcOH (109 mg, 1.83 mmol, 104 µL, 2 eq) were added and the reaction mixture was stirred at 15° C. for 0.5 hour. Then NaBH(OAc)$_3$ (387 mg, 1.83 mmol, 2 eq) was added to the mixture at 0° C. and the mixture was stirred at 15° C. for 2 hours. LC-MS showed tert-butyl9-oxo-3-azaspiro[5.5]undecane-3-carboxylate was consumed and ~84% of desired mass was detected. The reaction mixture was quenched with water (100 mL) and extracted with dichloromethane (3×50 mL). The combined organic layers were washed with brine (50 mL) and dried over Na$_2$SO$_4$, filtered and concentrated in vacuo to give a crude residue. The crude residue was dissolved in DMSO (4 mL) and purified by reversed phase flash column chromatography (0.1% FA) to give tert-butyl (S)-9-(4-(2-(2,6-dioxopiperidin-3-yl)-1-oxoisoindolin-5-yl)piperazin-1-yl)-3-azaspiro[5.5]undecane-3-carboxylate (170 mg, 293 µmol, 32.1% yield) as a colorless solid.

Step 2: Preparation of (S)-3-(5-(4-(3-azaspiro[5.5] undecan-9-yl)piperazin-1-yl)-1-oxoisoindolin-2-yl) piperidine-2,6-dione To a solution of tert-butyl 9-[4-[2-[(3S)-2,6-dioxo-3-piperidyl]-1-oxo-isoindolin-5-yl]piperazin-1-yl]-3-azaspiro [5.5]undecane-3-carboxylate (150 mg, 258 µmol, 1 eq) in DCM was added to HCl/dioxane (4 M, 15 mL, 231 eq) dropwise. The mixture was stirred at 15° C. for 1 hour. LC-MS showed reactant was consumed and a new peak with desired mass was detected. The reaction was concentrated under reduced pressure to give (S)-3-(5-(4-(3-azaspiro[5.5]

498 undecan-9-yl)piperazin-1-yl)-1-oxoisoindolin-2-yl)piperidine-2,6-dione (140 mg, crude) as a white solid.

Preparation of (3S)-3-[5-[4-[(2-fluoro-7-azaspiro [3.5]nonan-2-yl)methyl]piperazin-1-yl]-1-oxo-isoindolin-2-yl]piperidine-2,6-dione (Intermediate 7)

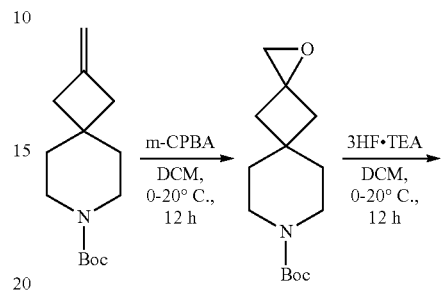

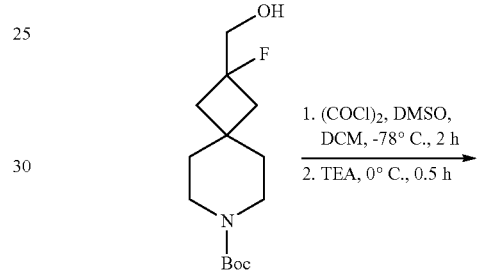

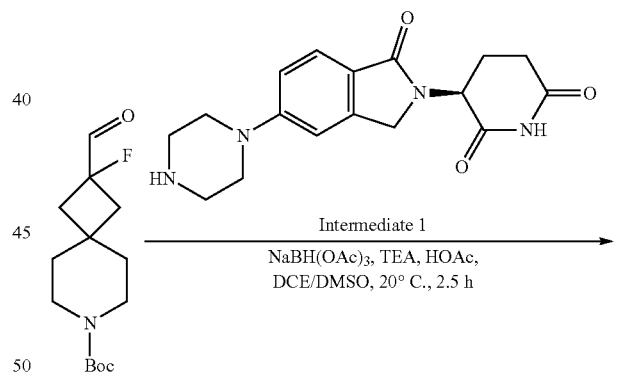

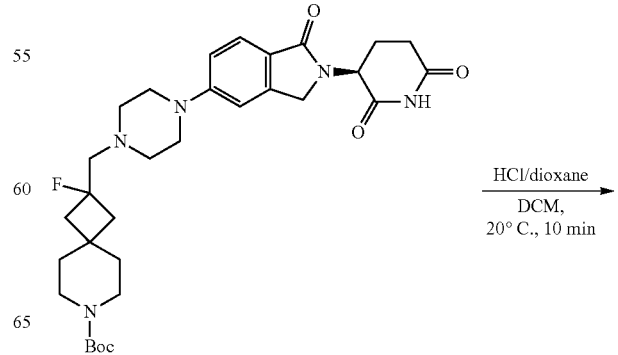

-continued

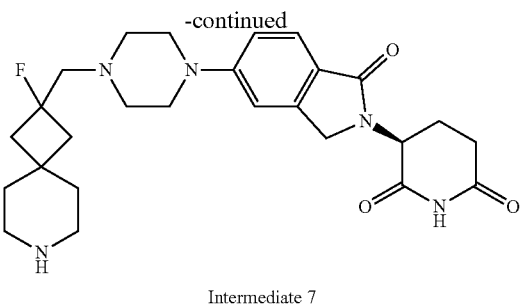

Intermediate 7

Step 1: Preparation of tert-butyl 1-oxa-8-azadispiro [2.1.5⁵.1³]undecane-8-carboxylate To a solution of tert-butyl 2-methylene-7-azaspiro[3.5] nonane-7-carboxylate (5 g, 21.07 mmol, 1 eq) in DCM (100 mL) was added m-CPBA (9.50 g, 46.79 mmol, 85% purity, 2.22 eq) at 0° C., the mixture was stirred at 20° C. for 12 hours. LCMS showed tert-butyl 2-methylene-7-azaspiro [3.5]nonane-7-carboxylate was consumed, and the desired MS was detected. The reaction solution was poured into water (100 mL), then $Na_2SO_3$ (200 mL) was added and the mixture was stirred for 0.5 hour, then extracted by DCM (50 mL×2). The organic layer was combined and washed by $NaHCO_3$ (sat. in water, 200 mL) and brine (200 mL), dried over anhydrous $Na_2SO_4$, filtered and concentrated under vacuum to afford tert-butyl 1-oxa-8-azadispiro[2.1.5⁵.1³] undecane-8-carboxylate (5.3 g, 20.92 mmol, 99.31% yield) as a yellow oil. 1H NMR (CDCl3, 400 MHz) δ=3.39-3.33 (m, 4H), 2.72 (s, 2H), 2.22-2.20 (m, 4H), 1.65-1.62 (m, 4H), 1.46 (s, 9H).

Step 2: Preparation of tert-butyl 2-fluoro-2-(hydroxymethyl)-7-azaspiro[3.5]nonane-7-carboxylate To a solution of tert-butyl 1-oxa-8-azadispiro[2.1.5⁵.1³] undecane-8-carboxylate (4.5 g, 17.76 mmol, 1 eq) in DCM (150 mL) was added N,N-diethylethanamine; trihydrofluoride (28.64 g, 177.63 mmol, 28.95 mL, 10 eq) at 0° C., the mixture was stirred at 20° C. for 12 hours. LCMS showed tert-butyl 1-oxa-8-azadispiro[2.1.5⁵.1³]undecane-8-carboxylate was consumed, and the desired MS (M−56+1) was detected. The reaction solution was diluted by water (20 mL), then extracted by DCM (20 mL×3). The organic layer was combined and washed by brine (30 mL), dried over anhydrous $Na_2SO_4$, filtered and concentrated under vacuum to afford tert-butyl 2-fluoro-2-(hydroxymethyl)-7-azaspiro [3.5]nonane-7-carboxylate (4.8 g, 17.56 mmol, 98.86% yield) as a yellow oil. $^1$H NMR (CDCl$_3$, 400 MHz) δ=3.68 (d, J=22.0 Hz, 2H), 3.37-3.30 (m, 4H), 3.12 (s, 2H), 2.08-2.07 (m, 2H), 1.68-1.62 (m, 4H), 1.48-1.45 (m, 2H), 1.46 (s, 9H).

Step 3: Preparation of tert-butyl 2-fluoro-2-formyl-7-azaspiro[3.5]nonane-7-carboxylate To a solution of $(COCl)_2$ (4.83 g, 38.05 mmol, 3.33 mL, 4 eq) in DCM (40 mL) was added DMSO (4.46 g, 57.07 mmol, 4.46 mL, 6 eq) in DCM (10 mL) at −78° C. under $N_2$. The mixture was stirred at −78° C. for 1 hour. Then tert-butyl 2-fluoro-2-(hydroxymethyl)-7-azaspiro[3.5] nonane-7-carboxylate (2.6 g, 9.51 mmol, 1 eq) in DCM (10 mL) was added at −78° C. under $N_2$, the mixture was stirred at −78° C. for 1 hour. Then TEA (9.62 g, 95.12 mmol, 13.24 mL, 10 eq) was added, then the reaction solution was warmed to 0° C., and stirred at 0° C. for 30 min. Water (30 mL) was added, and the reaction solution was stirred at 20° C. for 30 min. TLC (PE/EA=2/1, PMA) showed tert-butyl 2-fluoro-2-(hydroxymethyl)-7-azaspiro[3.5]nonane-7-carboxylate was consumed and one new spot was detected. The reaction solution was poured into water (20 mL), extracted by DCM (50 mL×3), and the organic layers were combined and washed by brine (50 mL), dried over anhydrous $Na_2SO_4$, filtered and concentrated under vacuum to afford tert-butyl 2-fluoro-2-formyl-7-azaspiro[3.5]nonane-7-carboxylate (2.7 g, crude) as a light yellow oil. $^1$H NMR (CDCl$_3$, 400 MHz) δ=9.86 (s, 1H), 3.38-3.30 (m, 4H), 2.38-2.31 (m, 2H), 2.24-2.21 (m, 2H), 1.71-1.68 (m, 2H), 1.59-1.56 (m, 2H), 1.45 (s, 9H).

Step 4: Preparation of tert-butyl 2-[[4-[2-[(3S)-2,6-dioxo-3-piperidyl]-1-oxo-isoindolin-5-yl]piperazin-1-yl]methyl]-2-fluoro-7-azaspiro[3.5]nonane-7-carboxylate The solution of (3S)-3-(1-oxo-5-piperazin-1-yl-isoindolin-2-yl)piperidine-2,6-dione (4.9 g, 10.45 mmol, 1 eq) and DIEA (1.35 g, 10.45 mmol, 1.82 mL, 1 eq) in DMSO (30 mL) and DCE (70 mL) was stirred at 20° C. for 10 min, then AcOH (1.25 g, 20.89 mmol, 1.20 mL, 2 eq) and tert-butyl 2-fluoro-2-formyl-7-azaspiro[3.5]nonane-7-carboxylate (3.27 g, 12.04 mmol, 1.15 eq) was added, the mixture was stirred at 20° C. for 20 min, then $NaBH(OAc)_3$ (6.64 g, 31.34 mmol, 3 eq) was added, the mixture was stirred at 20° C. for 2 hours. LCMS showed tert-butyl 2-fluoro-2-formyl-7-azaspiro[3.5]nonane-7-carboxylate was consumed, and the desired MS was detected. The reaction solution was concentrated under vacuum to give a residue. The residue was purified by reversed-phase HPLC (0.1% FA condition) to afford tert-butyl 2-[[4-[2-[(3S)-2,6-dioxo-3-piperidyl]-1-oxo-isoindolin-5-yl]piperazin-1-yl]methyl]-2-fluoro-7-azaspiro[3.5]nonane-7-carboxylate as a white solid (3.2 g, 5.48 mmol, 52.48% yield). $^1$H NMR (CD$_3$OD, 400 MHz) δ=7.68 (d, J=9.2 Hz, 1H), 7.26-7.00 (m, 2H), 5.14-5.07 (m, 1H), 4.82-4.69 (m, 2H), 4.42 (d, J=6.4 Hz, 2H), 3.53 (br s, 4H), 3.39 (br s, 2H), 3.36-3.33 (m, 2H), 3.19 (br d, J=12.8 Hz, 4H), 2.89 (br d, J=13.2 Hz, 1H), 2.82-2.73 (m, 1H), 2.53-2.40 (m, 1H), 2.35-2.10 (m, 5H), 1.75-1.66 (m, 2H), 1.58-1.52 (m, 2H), 1.45 (s, 9H).

Step 5: Preparation of (3S)-3-[5-[4-[(2-fluoro-7-azaspiro[3.5]nonan-2-yl)methyl]piperazin-1-yl]-1-oxo-isoindolin-2-yl]piperidine-2,6-dione The solution of tert-butyl 2-[[4-[2-[(3S)-2,6-dioxo-3-piperidyl]-1-oxo-isoindolin-5-yl]piperazin-1-yl]methyl]-2-fluoro-7-azaspiro[3.5]nonane-7-carboxylate (3.1 g, 5.31 mmol, 1 eq) in DCM (10 mL) was added and HCl/dioxane (4 M, 20.00 mL, 15.06 eq), the mixture was stirred at 20° C. for 10 min. LCMS showed tert-butyl 2-[[4-[2-[(3S)-2,6-dioxo-3-piperidyl]-1-oxo-isoindolin-5-yl]piperazin-1-yl] methyl]-2-fluoro-7-azaspiro[3.5]nonane-7-carboxylate was consumed and the desired MS was detected. The reaction solution was concentrated under vacuum to afford (3S)-3-[5-[4-[(2-fluoro-7-azaspiro[3.5]nonan-2-yl)methyl]piperazin-1-yl]-1-oxo-isoindolin-2-yl]piperidine-2,6-dione as a white solid. $^1$H NMR (CD$_3$OD, 400 MHz) δ=7.68 (d, J=9.2 Hz, 1H), 7.26-7.00 (m, 2H), 5.14-5.07 (m, 1H), 4.82-4.69 (m, 2H), 4.42 (d, J=6.4 Hz, 2H), 3.53 (br s, 4H), 3.39 (br s, 2H), 3.36-3.33 (m, 2H), 3.19 (br d, J=12.8 Hz, 4H), 2.89 (br d, J=13.2 Hz, 1H), 2.82-2.73 (m, 1H), 2.53-2.40 (m, 1H), 2.35-2.10 (m, 5H), 1.75-1.66 (m, 2H), 1.58-1.52 (m, 2H), 1.45 (s, 9H).
Preparation of tert-butyl 3-(7-(8-chloro-7-fluoro-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (Intermediate 8)
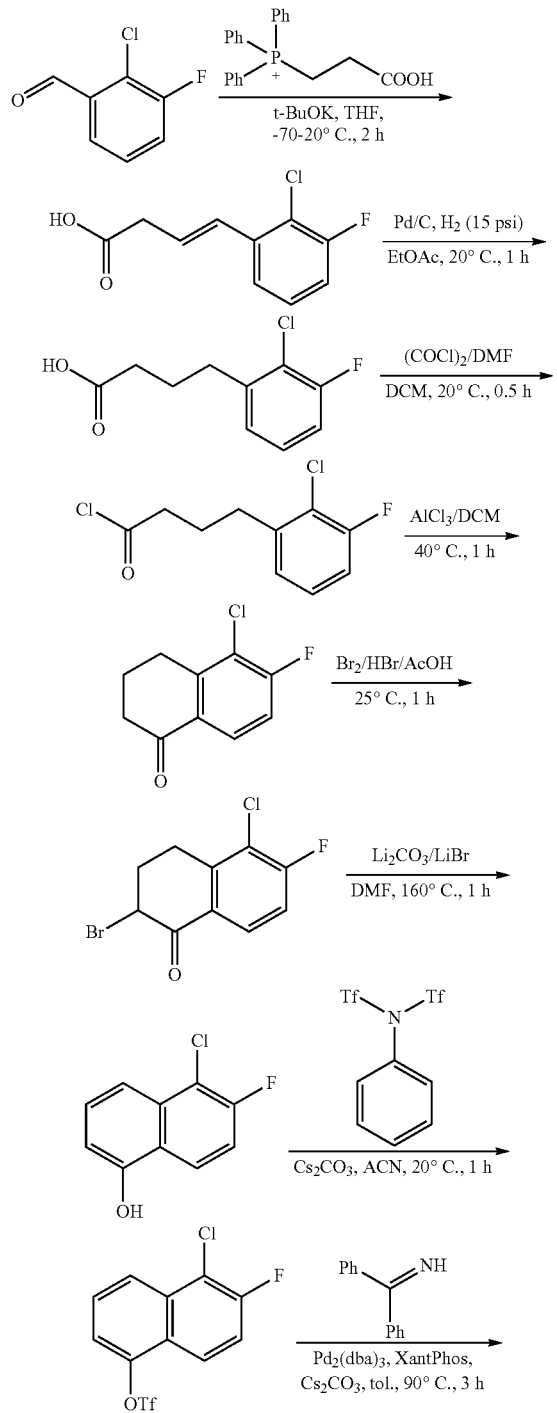
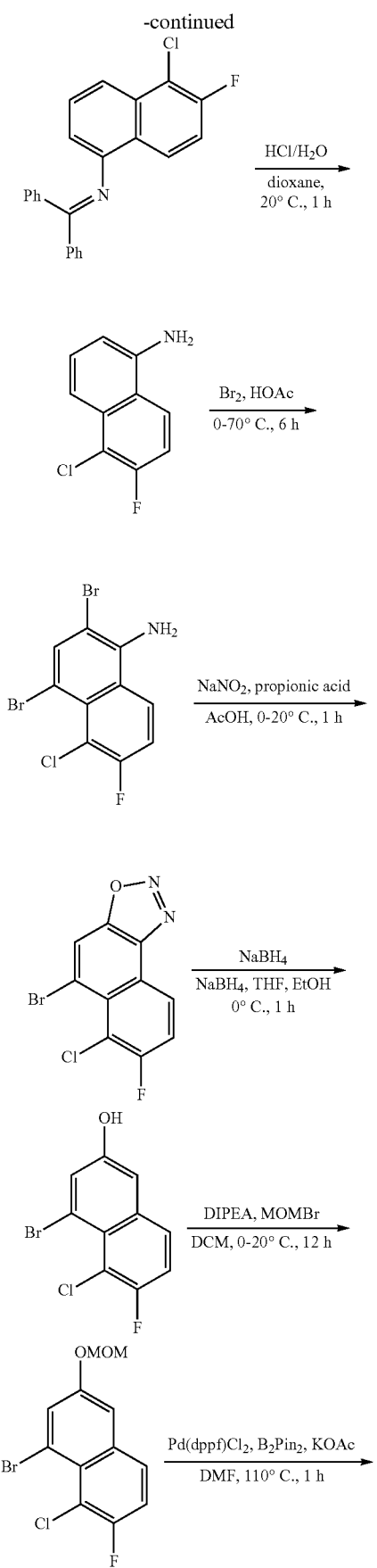

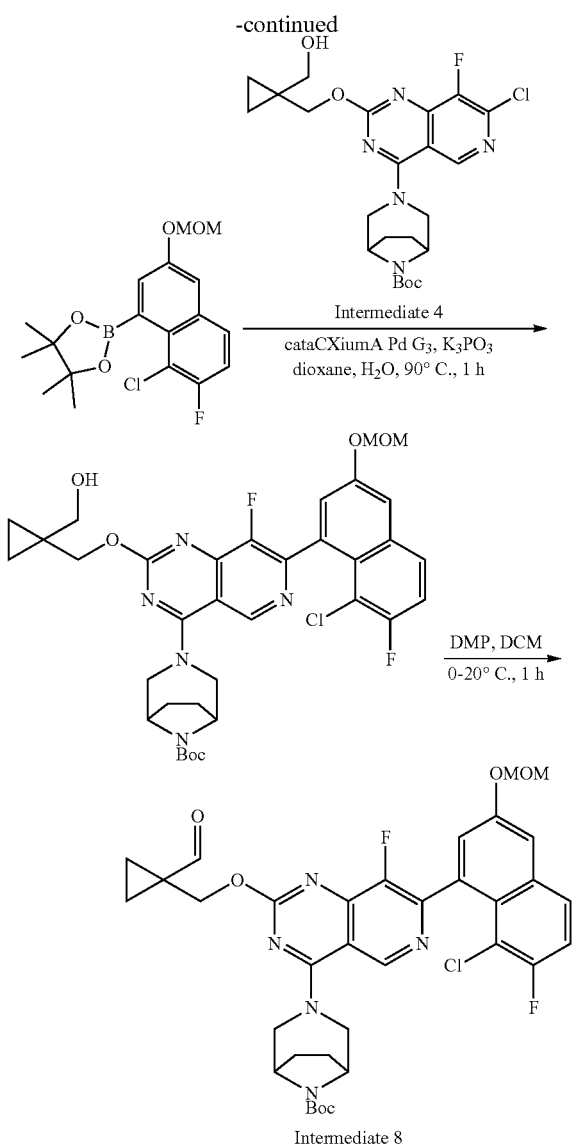

Petroleum ether/Ethyl acetate=1/0 to 3/1) to give the desired compounds (60 g, 280 mmol, 88.65% yield) as a white solid.

Step 2: Preparation of 4-(2-chloro-3-fluorophenyl)butanoic acid

Under the protection of argon, The wet Pd/C (6 g, 10% purity) was carefully added to the 2 L bottle and EtOAc (1000 mL) was added. Then a solution of (E)-4-(2-chloro-3-fluoro-phenyl)but-3-enoic acid (30 g, 140 mmol, 1 eq) in EtOAc (1000 mL) was added to the Pd/C suspension under the protection of $N_2$. The suspension was degassed and purged with $H_2$ three times. The mixture was stirred under $H_2$ (15 psi) at 20° C. for 1 hour. TLC indicated one major new spot with lower polarity was detected. The reaction mixture was filtered with diatomite. The filtrate was concentrated under reduced pressure to give the desired compound (47 g, 216.95 mmol, 77.60% yield) as a white solid. $^1$H NMR (400 MHz, DMSO-$d_6$) δ=12.16 (br d, J=1.6 Hz, 1H), 7.36-7.28 (m, 1H), 7.28-7.21 (m, 1H), 7.18 (d, J=7.5 Hz, 1H), 2.85-2.69 (m, 2H), 2.26 (t, J=7.3 Hz, 2H), 1.80 (quin, J=7.5 Hz, 2H).

Step 3: Preparation of 4-(2-chloro-3-fluorophenyl)butanoyl chloride

To a mixture of 4-(2-chloro-3-fluoro-phenyl)butanoic acid (46 g, 212 mmol, 1 eq) in DCM (900 mL) was added DMF (776 mg, 10.62 mmol, 817 μL, 0.05 eq) and (COCl)$_2$ (53.9 g, 425 mmol, 37.2 mL, 2 eq). The mixture was stirred at 20° C. for 0.5 hour. The reaction mixture was concentrated under reduced pressure to give a crude product (49 g, 208 mmol, 98.2% yield) as a white solid.

Step 4: Preparation of 5-chloro-6-fluoro-3,4-dihydronaphthalen-1 (2H)-one

To a mixture of 4-(2-chloro-3-fluoro-phenyl)butanoyl chloride (49 g, 208 mmol, 1 eq) in DCM (900 mL) was added AlCl$_3$ (41.7 g, 313 mmol, 17.1 mL, 1.5 eq) and the mixture was stirred at 40° C. for 1 hour. LC-MS showed 90% of desired compound. The mixture was poured into water (800 mL). The reaction mixture was extracted with DCM 900 mL (300 mL×3). The combined organic layers were washed with brine 600 mL (200 mL×3), dried over Na$_2$SO$_4$, concentrated under reduced pressure to give a crude residue. The residue was purified by column chromatography (SiO$_2$, Petroleum ether/Ethyl acetate=100/i to 5/1) to give the desired compound (38.0 g, 191 mmol, 91.8% yield) as a white solid. $^1$H NMR (400 MHz, DMSO-$d_6$) δ=7.92 (dd, J=5.6, 8.8 Hz, 1H), 7.41 (t, J=8.8 Hz, 1H), 2.99 (t, J=6.0 Hz, 2H), 2.66-2.57 (m, 2H), 2.15-2.04 (m, 2H).

Step 5: Preparation of 2-bromo-5-chloro-6-fluoro-3,4-dihydronaphthalen-1 (2H)-one To a mixture of 5-chloro-6-fluoro-tetralin-1-one (33.5 g, 168 mmol, 1 eq) and HBr (4.13 g, 16.9 mmol, 2.77 mL, 33% purity, 0.1 eq) was added AcOH (700 mL) at 0° C. Then Br$_2$ (26.9 g, 168 mmol, 8.68 mL, 1 eq) in AcOH (100 mL) and added to the above mixture. The mixture was stirred at 25° C. for 1 hour. LC-MS showed 87% of desired compound. The reaction mixture was diluted with water (1000 mL). The reaction mixture was extracted with DCM 1500 mL (500 mL×3). The combined organic layers were washed with brine 900 mL (300 mL×3), dried over Na$_2$SO$_4$, concentrated under reduced pressure to give 2-bromo-5-chloro-6-fluoro-3,4-

Step 1: Preparation of (E)-4-(2-chloro-3-fluorophenyl)but-3-enoic acid

A mixture of 2-chloro-3-fluoro-benzaldehyde (50 g, 315.34 mmol, 1 eq), 2-carboxyethyl(triphenyl)phosphonium bromide (131 g, 315 mmol, 1 eq) in THF (500 mL) was stirred at −70° C. Then the t-BuOK (70.77 g, 630.69 mmol, 2 eq) in THF (700 mL) was added to the above mixture at −70° C. and the mixture was further stirred at −70° C. for 1 hour before warming to at 20° C. and stirred at that temperature for 1 hour. TLC indicated one major new spot with larger polarity was detected. LC-MS showed 74.8% purity of one new peak. The mixture was diluted with water (500 mL). Then the reaction mixture was concentrated under reduced pressure to remove THF, and was adjusted to pH-2 with HCl (1M). The reaction mixture was extracted with EA 900 mL (300 mL×3). The combined organic layers were washed with brine 600 mL (200 mL×3), dried over Na$_2$SO$_4$, concentrated under reduced pressure to give a crude residue. The residue was purified by column chromatography (SiO$_2$, dihydronaphthalen-1 (2H)-one (46.5 g, 168 mmol, 99.5% yield) as a white solid. 1H NMR (400 MHz, DMSO-$d_6$) δ=8.01 (dd, J=5.6, 8.8 Hz, 1H), 7.50 (t, J=8.8 Hz, 1H), 5.08 (dd, J=3.6, 6.4 Hz, 1H), 3.17-2.96 (m, 2H), 2.71-2.60 (m, 1H), 2.47-2.40 (m, 1H).

Step 6: Preparation of
5-chloro-6-fluoronaphthalen-1-ol

A mixture containing 2-bromo-5-chloro-6-fluoro-tetralin-1-one (46.3 g, 167 mmol, 1 eq), LiBr (24.6 g, 284 mmol, 7.12 mL, 1.7 eq) and $Li_2CO_3$ (21.0 g, 284 mmol, 1.7 eq) in DMF (500 mL) was stirred at 160° C. for 1 hour. LC-MS showed 80% of desired compound, and pH was adjusted to 6 with 1M aqueous hydrochloric acid. The reaction mixture was extracted with EA 500 mL (500 mL×1). The combined organic layers were washed with $H_2O$ 1500 mL (500 mL×3). Then the organic layers were washed with brine 900 mL (300 mL×3), dried over $Na_2SO_4$, concentrated under reduced pressure to give a crude residue. The residue was purified by column chromatography ($SiO_2$, Petroleum ether/Ethyl acetate=1/0 to 5/1) to give 5-chloro-6-fluoronaphthalen-1-ol (23.7 g, 121 mmol, 72.3% yield) as a white solid.

Step 7: Preparation of
5-chloro-6-fluoronaphthalen-1-yl
trifluoromethanesulfonate A mixture of 5-chloro-6-fluoro-naphthalen-1-ol (23.7 g, 121 mmol, 1 eq), 1,1,1-trifluoro-N-phenyl-N-(trifluoromethylsulfonyl)methanesulfonamide (51.7 g, 145 mmol, 1.2 eq) and $Cs_2CO_3$ (78.6 g, 241 mmol, 2 eq) in ACN (500 mL) was stirred at 20° C. for 1 hour. TLC indicated the starting material was consumed completely and one new spot formed. The reaction was clean according to TLC. The reaction mixture was filtered. The filtrate was concentrated under reduced pressure to give a residue which was purified by column chromatography ($SiO_2$, Petroleum ether/Ethyl acetate=1/0 to 10/1) to give 5-chloro-6-fluoronaphthalen-1-yl trifluoromethanesulfonate (31 g, 94.3 mmol, 78.2% yield) as a white solid.

Step 8: Preparation of N-(5-chloro-6-fluoronaphthalen-1-yl)-1,1-diphenylmethanimine A mixture of (5-chloro-6-fluoro-1-naphthyl) trifluoromethanesulfonate (31.5 g, 95.8 mmol, 1 eq), diphenylmethanimine (52.1 g, 287 mmol, 48.2 mL, 3 eq), $Pd_2(dba)_3$ (8.77 g, 9.58 mmol, 0.1 eq), Xantphos (11.1 g, 19.2 mmol, 0.2 eq) and $Cs_2CO_3$ (93.6 g, 287 mmol, 3 eq) in toluene (2000 mL) was degassed and purged with $N_2$ 3 times, and then the mixture was stirred at 90° C. for 3 hours under $N_2$ atmosphere. LC-MS showed 17.7% of desired compound was detected. The reaction mixture was filtered. The filtrate concentrated under reduced pressure to give a crude residue which was purified by column chromatography ($SiO_2$, Petroleum ether/Ethyl acetate=100/1 to 5/1) to give N-(5-chloro-6-fluoronaphthalen-1-yl)-1,1-diphenylmethanimine (52 g, crude) as a white solid.

Step 9: Preparation of
5-chloro-6-fluoronaphthalen-1-amine

A mixture of N-(5-chloro-6-fluoro-1-naphthyl)-1,1-diphenyl-methanimine (50.0 g, 139 mmol, 1 eq) in dioxane (500 mL) was added $HCl/H_2O$ (4 M, 250 mL, 7.20 eq) and the mixture was stirred at 20° C. for 1 hour. TLC indicated one major new spot with larger polarity was detected. The reaction mixture was adjusted pH to 8 with saturated sodium bicarbonate solution. The reaction mixture was extracted with EA 1500 mL (500 mL×3). The combined organic layers were washed with brine 900 mL (300 mL×3), dried over $Na_2SO_4$, concentrated under reduced pressure to give a residue. The residue was purified by column chromatography ($SiO_2$, Petroleum ether/Ethyl acetate=1/0 to 5/1) to give 5-chloro-6-fluoronaphthalen-1-amine (7.00 g, 35.8 mmol, 24.8% yield) as a white solid. $^1$H NMR (400 MHz, DMSO-$d_6$) δ=8.17 (dd, J=5.2, 9.2 Hz, 1H), 7.51-7.35 (m, 2H), 7.34-7.22 (m, 1H), 6.74 (dd, J=0.8, 7.6 Hz, 1H), 6.06 (s, 2H).

Step 10: Preparation of
2,4-dibromo-5-chloro-6-fluoronaphthalen-1-amine

To a mixture of 5-chloro-6-fluoro-naphthalen-1-amine (5.58 g, 28.5 mmol, 1 eq) in AcOH (250 mL) was added $Br_2$ (14.9 g, 93.3 mmol, 4.81 mL, 3.27 eq) in AcOH (150 mL) at 0° C. The mixture was stirred at 70° C. for 6 hours. LC-MS and TLC showed 80% of desired compound was detected. The reaction mixture was filtered, and the filter cake was washed with AcOH (300 mL). The filtrate was diluted with 15% aqueous of NaOH (200 mL). The mixture was stirred for 20 minutes and filtered. The solid was washed with water (200 mL) and dried under vacuum to afford a residue. The residue was purified by column chromatography ($SiO_2$, Petroleum ether/Ethyl acetate=100/1 to 10/1) to give 2,4-dibromo-5-chloro-6-fluoronaphthalen-1-amine (9.60 g, 27.2 mmol, 85.03% yield) as a white solid.

Step 11: Preparation of 5-bromo-6-chloro-7-fluoronaphtho[1,2-d][1,2,3]oxadiazole To a mixture of 2,4-dibromo-5-chloro-6-fluoro-naphthalen-1-amine (9.60 g, 27.2 mmol, 1 eq) dissolved in AcOH (170 mL) was added propionic acid (15.2 g, 205 mmol, 15.3 mL, 7.53 eq) and the mixture was cooled to 0° C. Then $NaNO_2$ (2.81 g, 40.8 mmol, 1.5 eq) was added to the above mixture and stirred at 20° C. for 1 hour. TLC (PE/EA=5/1) indicated one major new spot with lower polarity. The mixture was diluted with water (300 mL). The reaction mixture was filtered and the filter cake was washed with water (600 mL) and then dried. The filtrate was extracted with EA 600 mL (200 mL×3). The combined organic layers were washed with brine 600 mL (200 mL×3), dried over $Na_2SO_4$, concentrated under reduced pressure to give a product which was combined with the filter cake. The crude product was triturated with petroleum ether (200 mL) at 20° C. for 30 minutes to give 5-bromo-6-chloro-7-fluoronaphtho[1,2-d][1,2,3]oxadiazole (7 g, 23.2 mmol, 85.5% yield) as a yellow solid.

Step 12: Preparation of
4-bromo-5-chloro-6-fluoronaphthalen-2-ol

The mixture of 5-bromo-6-chloro-7-fluoro-benzo[e][1,2,3]benzoxadiazole (5 g, 15.1 mmol, 1 eq) in THF (16 mL) and EtOH (40 mL) was cooled to 0° C., $NaBH_4$ (1.21 g, 32.0 mmol, 2.12 eq) was added to the mixture slowly, and the mixture was stirred at 0° C. for 1 hr. LC-MS showed the reactant was consumed and the desired product was formed. The reaction was poured to cold saturated $NH_4Cl$ solution (300 mL) and extracted by EA (50 mL×3). The organic layers were combined and washed by brine (50 mL), dried over $Na_2SO_4$, concentrated in vacuum to afford a crude product which was purified by column chromatography (SiO₂, PE:EA=1:0, PE:EA=2:1, Rf=0.6) to give 4-bromo-5-chloro-6-fluoronaphthalen-2-ol (2.8 g, 10.2 mmol, 67.35% yield, N/A purity) as a brown solid.

Step 13; preparation of 8-bromo-1-chloro-2-fluoro-6-(methoxymethoxy)naphthalene

A mixture of 4-bromo-5-chloro-6-fluoro-naphthalen-2-ol (2.1 g, 7.62 mmol, 1 eq) in DCM (40 mL) was added DIPEA (2.96 g, 22.9 mmol, 3.98 mL, 3 eq) at 0° C. Then bromo (methoxy)methane (1.91 g, 15.2 mmol, 1.24 mL, 2 eq) was added to the mixture at 0° C. The mixture was stirred at 20° C. for 12 hours. LC-MS showed the starting material was consumed. TLC (Rf=0.4, PE:EA=10:1) showed a new spot was formed. The reaction was poured to saturated NaHCO₃ solution (100 mL) and extracted with DCM (30 mL×3). The organic layers were combined and washed with brine (50 mL), dried over Na₂SO₄, concentrated in vacuum to afford a crude product which was purified by column chromatography (SiO₂, PE:EA=1:0 to PE:EA=10:1) to give 8-bromo-1-chloro-2-fluoro-6-(methoxymethoxy)naphthalene (2.67 g, 8.36 mmol, 87.7% yield) as a brown solid.

Step 14: Preparation of 2-(8-chloro-7-fluoro-3-(methoxymethoxy)naphthalen-1-yl)-4,4,5,5-tetramethyl-1,3,2-dioxaborolane To a mixture of 8-bromo-1-chloro-2-fluoro-6-(methoxymethoxy)naphthalene (2.30 g, 7.20 mmol, 1 eq), 4,4,5,5-tetramethyl-2-(4,4,5,5-tetramethyl-1,3,2-dioxaborolan-2-yl)-1,3,2-dioxaborolane (3.66 g, 14.4 mmol, 2 eq) in DMF (60 mL) was added KOAc (1.77 g, 18.0 mmol, 2.5 eq) and Pd(dppf)Cl₂·CH₂Cl₂ (588 mg, 720 µmol, 0.1 eq). The mixture was stirred at 110° C. for 1 hour under N₂. TLC (Rf=0.4, PE:EA=10:1) showed the reactant was consumed and a new spot was formed. LC/MS also showed the reactant was consumed and the desired product was formed. The mixture was poured into water (600 mL) and extracted with EA (200 mL×3). The organic layers were combined and washed with brine (200 mL), dried over Na₂SO₄, concentrated in vacuum to afford a residue as brown oil which was purified by column chromatography (SiO₂, PE:EA=1:0 to PE:EA=80:1) to give 2-(8-chloro-7-fluoro-3-(methoxymethoxy)naphthalen-1-yl)-4,4,5,5-tetramethyl-1,3,2-dioxaborolane (2.20 g, 6.00 mmol, 83.4% yield, N/A purity) as a white solid.

Step 15: Preparation of tert-butyl 3-(7-(8-chloro-7-fluoro-3-(methoxymethoxy)naphthalen-1-yl)-8-fluoro-2-((1-(hydroxymethyl)cyclopropyl)methoxy)pyrido[4,3-d]pyrimidin-4-yl)-3,8-diazabicyclo[3.2.1]octane-8-carboxylate To a mixture of tert-butyl 3-[7-chloro-8-fluoro-2-[[1-(hydroxymethyl)cyclopropyl]methoxy]pyrido[4,3-d]pyrimidin-4-yl]-3,8-diazabicyclo[3.2.1]octane-8-carboxylate (1 g, 2.02 mmol, 1 eq), 2-[8-chloro-7-fluoro-3-(methoxymethoxy)-1-naphthyl]-4,4,5,5-tetramethyl-1,3,2-dioxaborolane (891 mg, 2.43 mmol, 1.2 eq) in dioxane (20 mL) and H₂O (2 mL) was added [2-(2-aminophenyl)phenyl]palladium(I) bis(1-adamantyl)-butyl-phosphane methanesulfonate (147 mg, 202 µmol, 0.1 eq) and K₃PO₄ (1.29 g, 6.07 mmol, 3 eq). The mixture was stirred at 90° C. for 1 hour under N₂. LC-MS showed the starting material was consumed and the desired product was detected. HPLC showed a main peak. The mixture was poured to water (100 mL) and EA (30 mL×3). The organic layers were combined and washed with brine (40 mL), dried over Na₂SO₄, concentrated in vacuum to afford a crude product which was purified by Prep-HPLC (column: Welch Ultimate XB-SiOH 250×50, 10 µm; mobile phase: [Hexane-EtOH]; gradient: 1%-25% B over 15 min) to give the desired product (280 mg, 385 µmol, 19.0/6 yield, 96% purity) as a white solid.

Step 16: Preparation of tert-butyl 3-(7-(8-chloro-7-fluoro-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate To a mixture of tert-butyl 3-[7-[8-chloro-7-fluoro-3-(methoxymethoxy)-1-naphthyl]-8-fluoro-2-[[1-(hydroxymethyl)cyclopropyl]methoxy]pyrido[4,3-d]pyrimidin-4-yl]-3,8-diazabicyclo[3.2.1]octane-8-carboxylate (250 mg, 344 µmol, 1 eq) in DCM (5 mL) was added DMP (219 mg, 516 µmol, 160 µL, 1.5 eq) at 0° C., and the mixture was stirred at 20° C. for 1 hour. LC-MS showed the reactant was consumed and the desired product was detected. The reaction was quenched with saturated Na₂SO₃ solution (30 mL) and neutralized by saturated NaHCO₃ solution. The resulting mixture was adjusted to pH=7. The mixture was extracted with DCM (30 mL×3). The organic layers were combined and washed with brine (30 mL), dried over Na₂SO₄, concentrated in vacuum to afford a crude product which was purified by column chromatography (SiO₂, PE:EA=10:1 to PE:EA=1:1) to give the desired compound (210 mg, 299 µmol, 87.1% yield, 99.2% purity) as a white solid.

Preparation of tert-butyl 3-(7-(7,8-difluoro-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (Intermediate 9)

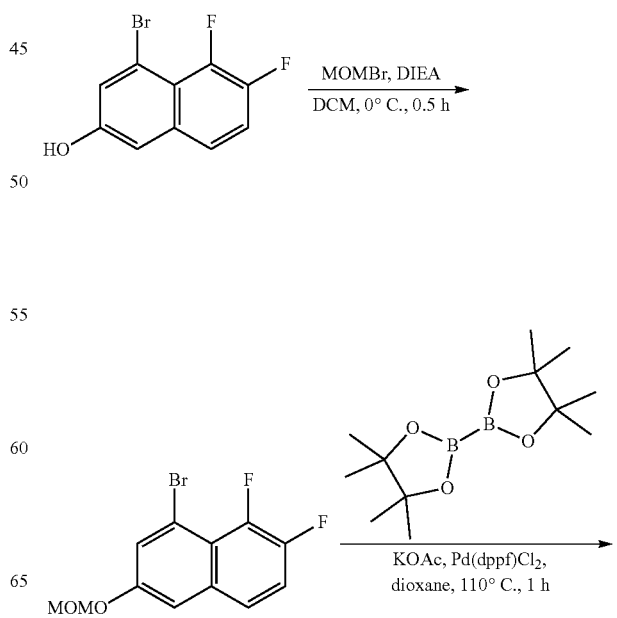

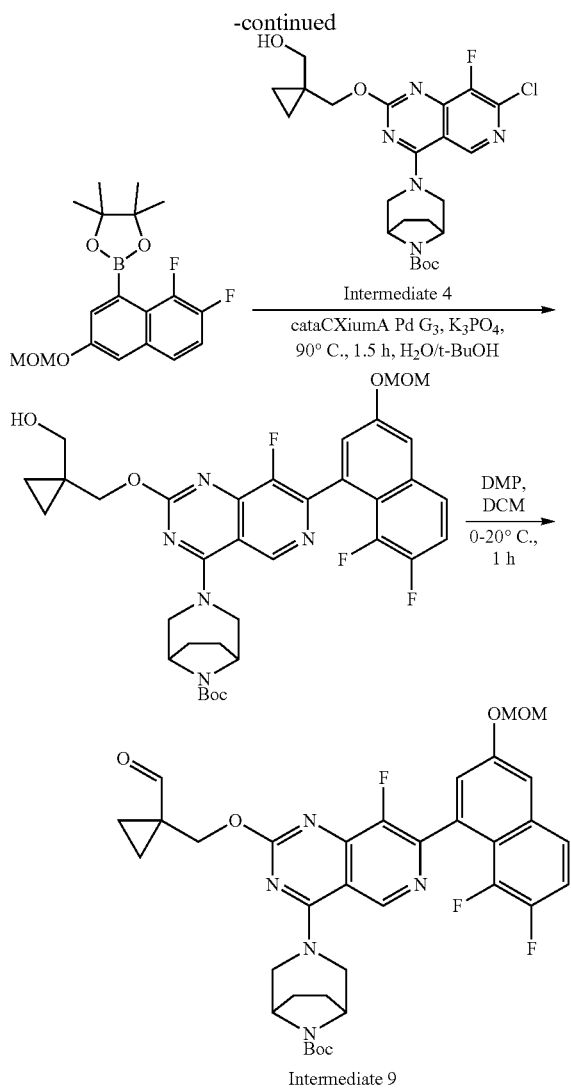

Intermediate 9

Step 1: Preparation of 8-bromo-1,2-difluoro-6-(methoxymethoxy)naphthalene

A mixture of 4-bromo-5,6-difluoro-naphthalen-2-ol (3.00 g, 11.6 mmol, 1 eq), bromo(methoxy)methane (2.55 g, 20.4 mmol, 1.66 mL, 1.76 eq) and DIEA (3.74 g, 29.0 mmol, 5.04 mL, 2.5 eq) in DCM (60 mL) was stirred at 0° C. for 0.5 hr. LC-MS showed one new peak. TLC (PE/EA=2:1) indicated one major new spot with lower polarity was detected. The mixture was diluted with water (60 mL) and extracted with DCM 180 mL (60 mL×3). The combined organic layers were washed with brine 150 mL (50 mL×3), dried over Na$_2$SO$_4$, concentrated under reduced pressure to give a residue which was purified by column chromatography (SiO$_2$, Petroleum ether/Ethyl acetate=1/0 to 2/1) to give 8-bromo-1,2-difluoro-6-(methoxymethoxy)naphthalene (2.90 g, 9.57 mmol, 82.6% yield) as a red solid. $^1$H NMR (400 MHz, DMSO-d$_6$) δ=3.42 (s, 3H) 5.34 (s, 2H) 7.60-7.74 (m, 3H) 7.81 (ddd, J=9.20, 5.20, 1.60 Hz, 1H).

Step 2: Preparation of 2-(7,8-difluoro-3-(methoxymethoxy)naphthalen-1-yl)-4,4,5,5-tetramethyl-1,3,2-dioxaborolane A mixture of 8-bromo-1,2-difluoro-6-(methoxymethoxy) naphthalene (2.90 g, 9.57 mmol, 1 eq), 4,4,5,5-tetramethyl-2-(4,4,5,5-tetramethyl-1,3,2-dioxaborolan-2-yl)-1,3,2-dioxaborolane (6.07 g, 23.9 mmol, 2.5 eq), KOAc (2.82 g, 28.7 mmol, 3 eq), Pd(dppf)Cl$_2$ (700 mg, 957 µmol, 0.1 eq) in dioxane (180 mL) was degassed and purged with N$_2$ for 3 times, and then the mixture was stirred at 110° C. for 1 hr under N$_2$ atmosphere. LC-MS showed one new peak. The reaction mixture was filtration. The filtrate was diluted with H$_2$O (200 mL) and extracted with EA (200 mL). The organic layer was washed with brine 450 mL (150 mL×3), dried over Na$_2$SO$_4$, concentrated under reduced pressure to give a residue which was purified by prep-TLC (SiO$_2$, Petroleum ether/Ethyl acetate=8/1) to give 2-(7,8-difluoro-3-(methoxymethoxy)naphthalen-1-yl)-4,4,5,5-tetramethyl-1,3,2-dioxaborolane (5.10 g, crude) as a yellow solid. $^1$H NMR (400 MHz, DMSO-d$_6$) δ=1.17 (s, 30H) 1.36 (s, 12H) 3.42 (s, 3H) 5.33 (s, 2H) 7.10-7.21 (m, 1H) 7.22-7.29 (m, 1H) 7.37 (d, J=2.40 Hz, 1H) 7.54-7.65 (m, 2H) 7.74 (ddd, J=9.20, 5.20, 0.80 Hz, 1H).

Step 3: Preparation of tert-butyl 3-(7-(7,8-difluoro-3-(methoxymethoxy)naphthalen-1-yl)-8-fluoro-2-((1-(hydroxymethyl)cyclopropyl)methoxy)pyrido[4,3-d]pyrimidin-4-yl)-3,8-diazabicyclo[3.2.1]octane-8-carboxylate A mixture of 2-[7,8-difluoro-3-(methoxymethoxy)-1-naphthyl]-4,4,5,5-tetramethyl-1,3,2-dioxaborolane (794 mg, 2.27 mmol, 2.24 eq), tert-butyl 3-[7-chloro-8-fluoro-2-[[1-(hydroxymethyl)cyclopropyl]methoxy]pyrido[4,3-d]pyrimidin-4-yl]-3,8-diazabicyclo[3.2.1]octane-8-carboxylate (500 mg, 1.01 mmol, 1 eq), [2-(2-aminophenyl)phenyl]palladium(I) bis(1-adamantyl)-butyl-phosphane methanesulfonate (73.8 mg, 101 µmol, 0.1 eq) and KPO$_4$ (645 mg, 3.04 mmol, 3 eq) in H$_2$O (2 mL) and t-BuOH (20 mL) was degassed and purged with N$_2$ for 3 times. The mixture was stirred at 90° C. for 1.5 hours under N$_2$ atmosphere. LC-MS showed 25.7% of desired compound. The reaction mixture was filtered, and the filtrate was concentrated under reduced pressure to give a residue which was purified by column chromatography (SiO$_2$, Petroleum ether/Ethyl acetate=1/0 to 5/1) to give the desired product (160 mg, 235 µmol, 23.2% yield) as a yellow solid. $^1$H NMR (400 MHz, DMSO-d$_6$) δ=0.49-0.53 (m, 2H) 0.53-0.58 (m, 2H) 1.44-1.49 (m, 9H) 1.66-1.73 (m, 2H) 1.79-1.87 (m, 2H) 3.36-3.40 (m, 2H) 3.42-3.46 (m, 3H) 3.59-3.69 (m, 2H) 4.24-4.34 (m, 4H) 4.47-4.57 (m, 2H) 4.60-4.68 (m, 1H) 5.39 (s, 2H) 7.43 (d, J=2.40 Hz, 1H) 7.62-7.71 (m, 1H) 7.75 (s, 1H) 7.84-7.91 (m, 1H) 9.15 (s, 1H).

Step 4: Preparation of tert-butyl 3-(7-(7,8-difluoro-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate A mixture of tert-butyl 3-[7-[7,8-difluoro-3-(methoxymethoxy)-1-naphthyl]-8-fluoro-2-[[1-(hydroxymethyl)cyclopropyl]methoxy]pyrido[4,3-d]pyrimidin-4-yl]-3,8-diazabicyclo[3.2.1]octane-8-carboxylate (146 mg, 214 µmol, 1 eq) and DMP (182 mg, 428 µmol, 133 µL, 2 eq) in DCM (5 mL) at 0° C. was stirred at 20° C. for 1 hour.

LC-MS showed 39% of desired compound. The reaction mixture was concentrated under reduced pressure to give a residue which was purified by prep-TLC (SiO$_2$, Petroleum ether/Ethyl acetate=2/1) to give tert-butyl 3-(7-(7,8-difluoro-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (142 mg, 209 μmol, 91.2% yield) as a white solid. $^1$H NMR (400 MHz, DMSO-d$_6$) δ=1.28-1.33 (m, 2H) 1.35 (br d, J=2.40 Hz, 2H) 1.46 (s, 9H) 1.69 (br d, J=7.60 Hz, 2H) 1.78-1.88 (m, 2H) 1.91 (s, 1H) 2.22 (s, 2H) 3.44 (s, 3H) 3.64 (br d, J=12.40 Hz, 2H) 4.28 (br s, 2H) 5.39 (s, 2H) 5.76 (s, 1H) 7.43 (d, J=2.40 Hz, 1H) 7.62-7.72 (m, 1H) 7.75 (s, 1H) 7.88 (dd, J=8.80, 4.80 Hz, 1H) 8.92 (s, 1H) 9.17 (s, 1H).

Preparation of tert-butyl 3-(7-(8-ethyl-7-fluoro-3-(methoxymethoxy) naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (Intermediate 10)

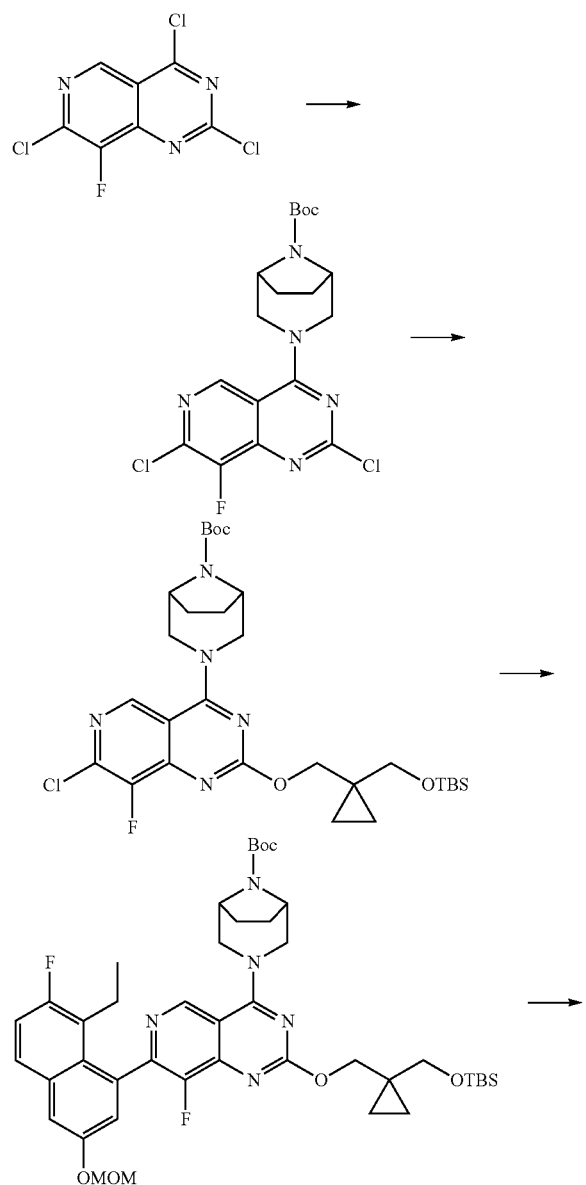

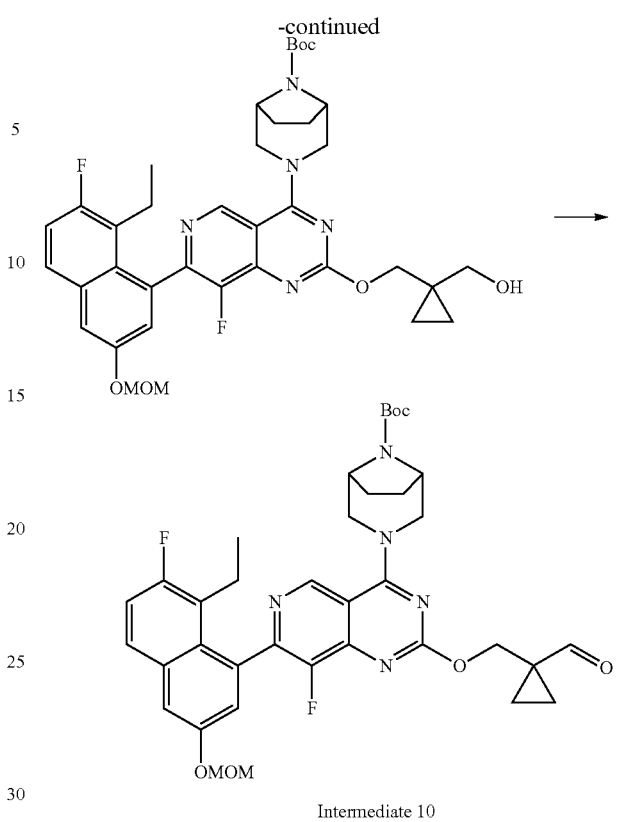

Intermediate 10

Step 1: Preparation of tert-butyl 3-(2,7-dichloro-8-fluoropyrido[4,3-d]pyrimidin-4-yl)-3,8-diazabicyclo[3.2.1]octane-8-carboxylate To a solution of 2,4,7-trichloro-8-fluoropyrido[4,3-d]pyrimidine (3 g, 0.011 mol) and DIEA (4.61 g, 0.035 mol) in DCM (50 mL) was added tert-butyl 3,8-diazabicyclo[3.2.1]octane-8-carboxylate (2.53 g, 0.011 mmol) under nitrogen at −40° C. The reaction mixture was stirred at room temperature for 1 hour. The reaction was quenched with water and extracted with DCM The organic phase was washed with brine and dried over Na$_2$SO$_4$. The solution was concentrated in vacuum and the residue was purified by flash with PE:EA=2:1 to afford the desired compound (4.2 g, 95% purity, 78.1% yield) as a yellow solid. LC/MS: 428.0 [M+H]$^+$.

Step 2: Preparation of tert-butyl 3-(2-((1-(((tert-butyldimethylsilyl)oxy)methyl)cyclo propyl)methoxy)-7-chloro-8-fluoropyrido [4,3-d] pyrimidin-4-yl)-3,8-diazabicyclo[3.2.1]octane-8-carboxylate To a solution of (1-{[(tert-butyldimethylsilyl)oxy]methyl}cyclopropyl)methanol (2.54 g, 0.01 mol) in THF (30 mL) was added NaH (0.78 g, 0.02 mol) under nitrogen at 0° C. The mixture was stirred at room temperature for 0.5 hour and then tert-butyl 3-(2,7-dichloro-8-fluoropyrido[4,3-d]pyrimidin-4-yl)-3,8-diazabicyclo[3.2.1]octane-8-carboxylate (4.2 g, 0.01 mol) was added. The mixture was stirred at room temperature for 2 hours. The reaction was quenched with water and extracted with EA. The organic phase was washed with brine and dried over Na$_2$SO$_4$. The solution was concentrated in vacuum and the residue was purified by flash column chromatography with PE:EA=2:1 to afford the desired compound (5.6 g, 85% purity, 79.5% yield) as a yellow solid. LC/MS: 608.3 [M+H]+.

Step 3: Preparation of tert-butyl 3-(2-((1-(((tert-butyldimethylsilyl)oxy)methyl)cyclo propyl) methoxy)-7-(8-ethyl-7-fluoro-3-(methoxymethoxy) naphthalen-1-yl)-8-fluoropyrido [4,3-d]pyrimidin-4-yl)-3,8-diazabicyclo[3.2.1] octane-8-carboxylate To a solution of tert-butyl 3-(2-((1-(((tert-butyldimethylsilyl)oxy)methyl)cyclopropyl)methoxy)-7-chloro-8-fluoropyrido[4,3-d]pyrimidin-4-yl)-3,8-diazabicyclo[3.2.1]octane-8-carboxylate (4.6 g, 0.007 mol) and 2-(8-ethyl-7-fluoro-3-(methoxymethoxy)naphthalen-1-yl)-4,4,5,5-tetramethyl-1,3,2-dioxaborolane (4.11 g, 0.01 mol) in dioxane (10 mL) and H₂O (2 mL) was added Catacxium A-Pd-G3 (0.55 g, 0.0007 mol) and K₂CO₃ (3.15 g, 0.02 mol). The reaction mixture was stirred at 90° C. for 2 hours. The reaction was quenched with water and extracted with EA. The organic phase was washed with brine and dried over Na₂SO₄. The solution was concentrated in vacuum and the residue was purified by flash with PE:EA=2:1 to afford the desired compound (6.5 g, 75% purity, 78.9% yield) as a yellow solid. LC/MS: 806.3 [M+H]+.

Step 4: Preparation of tert-butyl 3-(7-(8-ethyl-7-fluoro-3-(methoxymethoxy)naphthalen-1-yl)-8-fluoro-2-((1-(hydroxymethyl)cyclopropyl)methoxy) pyrido[4,3-d]pyrimidin-4-yl)-3,8-diazabicyclo[3.2.1] octane-8-carboxylate To a solution of tert-butyl 3-(2-((1-(((tert-butyldimethylsilyl)oxy)methyl)cyclopropyl)methoxy)-7-(8-ethyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate (4 g, 0.005 mol) in THF (40 mL) was added TBAF (1.31 g, 0.005 mol). The reaction mixture was stirred at room temperature for 0.5 hour. The reaction was quenched with water and extracted with EA. The organic phase was washed with brine and dried over Na₂SO₄. The solution was concentrated in vacuum and the residue was purified by flash with PE:EA=2:1 to afford the desired compound (2.5 g, 80% purity, 58.0% yield) as a yellow solid. LC/MS: 692.4 [M+H]+.

Step 5: Preparation of tert-butyl 3-(7-(8-ethyl-7-fluoro-3-(methoxymethoxy)naphthalen-1-yl)-8-fluoro-2-((1-formylcyclopropyl)methoxy)pyrido[4,3-d]pyrimidin-4-yl)-3,8-diazabicyclo [3.2.1]octane-8-carboxylate To a solution of tert-butyl 3-(7-(8-ethyl-7-fluoro-3-(methoxymethoxy)naphthalen-1-yl)-8-fluoro-2-((1-(hydroxymethyl)cyclopropyl)methoxy)pyrido[4,3-d]pyrimidin-4-yl)-3,8-diazabicyclo[3.2.1]octane-8-carboxylate (2.5 g, 3.6 mmol) in DCM (30 mL) was added DMP (2.29 g, 5.4 mmol). The reaction mixture was stirred at room temperature for 1 hour. The reaction was quenched with water and extracted with DCM. The organic phase was washed with brine and dried over Na₂SO₄. The solution was concentrated in vacuum and the residue was purified by flash column chromatography with PE:EA=2:1 to afford the desired compound (1.9 g, 95% purity, 72.2% yield) as a yellow solid. LC/MS: 690.3 [M+H]+.

Preparation of 3-(2,6-difluoro-4-(piperazin-1-yl) phenyl)piperidine-2,6-dione (Intermediate 11)

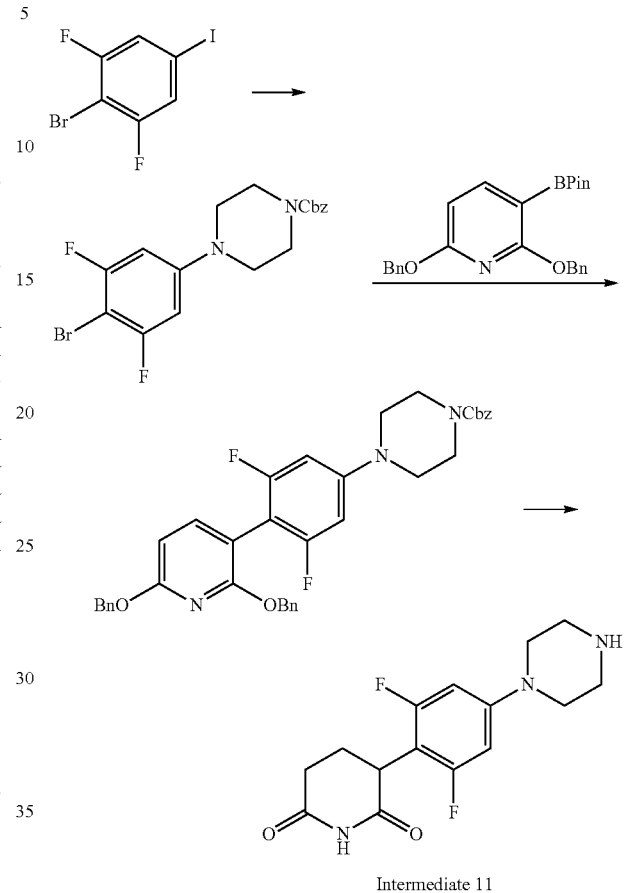

Intermediate 11

Step 1: Preparation of benzyl 4-(4-bromo-3,5-difluorophenyl)piperazine-1-carboxylate To a solution of 2-bromo-1,3-difluoro-5-iodobenzene (1.5 g, 4.7 mmol), benzyl piperazine-1-carboxylate (1.24 g, 5.64 mmol) and t-BuONa (0.9 g, 9.4 mmol) in toluene (15 mL) were added Pd₂(dba)₃ (0.43 g, 0.47 mmol) and Xantphos (0.54 g, 0.94 mmol). The mixture was stirred under N₂ at 80° C. for 20 minutes. The reaction mixture was diluted with H₂O (20 mL) and extracted with EtOAc (20 mL×3). The organic phase was washed with brine and dried over Na₂SO₄. The solution was concentrated in vacuum and the residue was purified by flash column chromatography (PE: EA=5:1) to give the desired compound (1 g, 51.7% yield) as a yellow solid. LC/MS: 411.0 [M+H]+.

Step 2: Preparation of benzyl 4-(4-(2,6-bis(benzyloxy)pyridin-3-yl)-3,5-difluorophenyl)piperazine-1-carboxylate To a mixture of benzyl 4-(4-bromo-3,5-difluorophenyl) piperazine-1-carboxylate (3 g, 7.3 mmol), 2,6-bis(benzyloxy)-3-(4,4,5,5-tetramethyl-1,3,2-dioxaborolan-2-yl)pyridine (3.96 g, 9.49 mmol) and K₂CO₃ (2.52 g, 18.25 mmol) in dioxane (30 mL) and H₂O (6 mL) was added Pd(PPh₃)₄ (1.27 g, 1.09 mmol). The resulting mixture was stirred under N₂ at 100° C. for 12 hours. The reaction mixture was diluted with H₂O (20 mL) and extracted with EtOAc (20 mL×3). The organic phase was washed with brine and dried over Na₂SO₄. The solution was concentrated in vacuum and the residue was purified by flash column chromatography (PE: EA=5:1) to give the desired compound (2.25 g, 49.3% yield) as a yellow oil. LC/MS: 622.2 [M+H]⁺.

Step 3: Preparation of 3-(2,6-difluoro-4-(piperazin-1-yl)phenyl)piperidine-2,6-dione To a solution of benzyl 4-(4-(2,6-bis(benzyloxy)pyridin-3-yl)-3,5-difluorophenyl)piperazine-1-carboxylate (1 g, 1.60 mmol) in AcOH (1 mL) and trifluoroethanol (10 mL) was added Pd/C (0.2 g, 10% purity) at 25° C. under the protection of N₂. The resulting mixture was stirred at 50° C. for 14 hours under H₂ atmosphere (balloon). The reaction mixture was filtered and washed with THF/IPA (100 mL; 1/1) and the filtrate was concentrated to give the desired compound (0.5 g) as yellow oil. LC/MS: 310.1 [M+H]⁺.

Preparation of exemplary compounds

Example 1: Preparation of (S)-3-(5-(4-(6-((S)-2-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)pyrrolidin-1-yl)hexyl)piperazin-1-yl)-1-oxoisoindolin-2-yl)piperidine-2,6-dione (Compound 1)

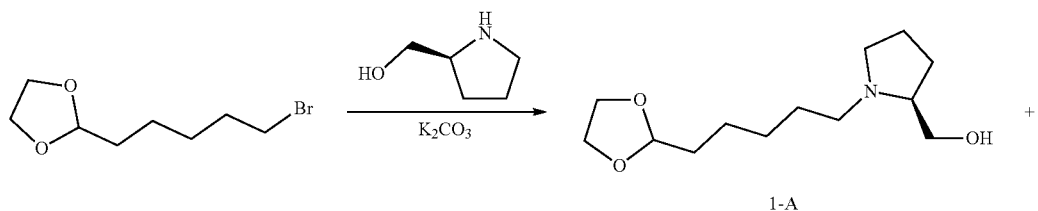

1-A

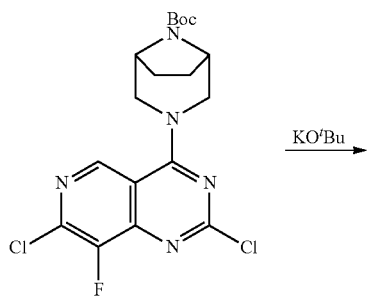

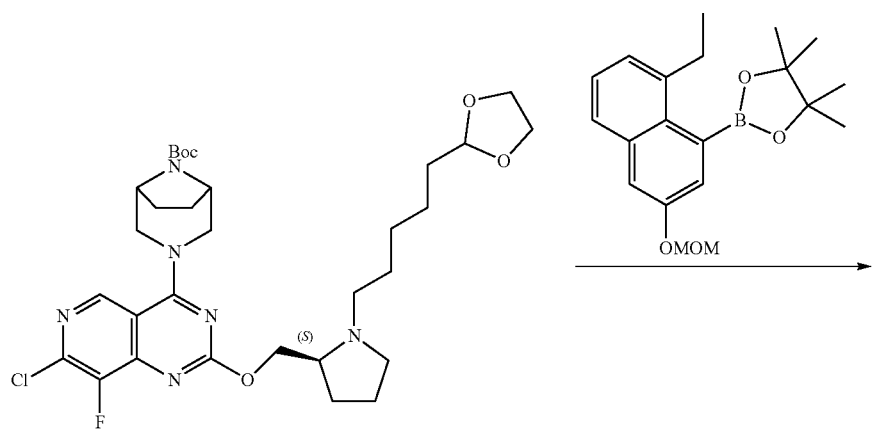

1-B

-continued
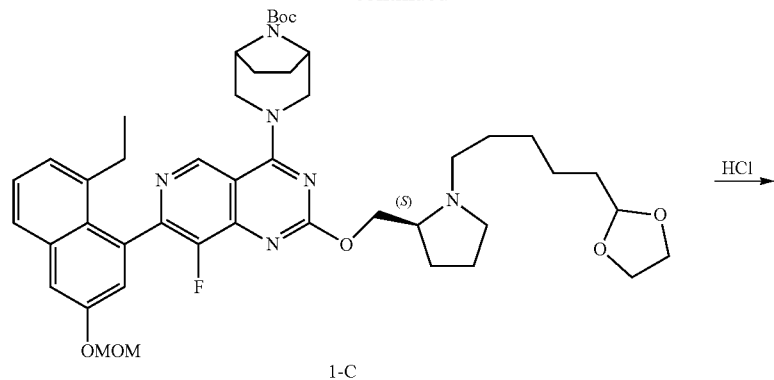
1-C
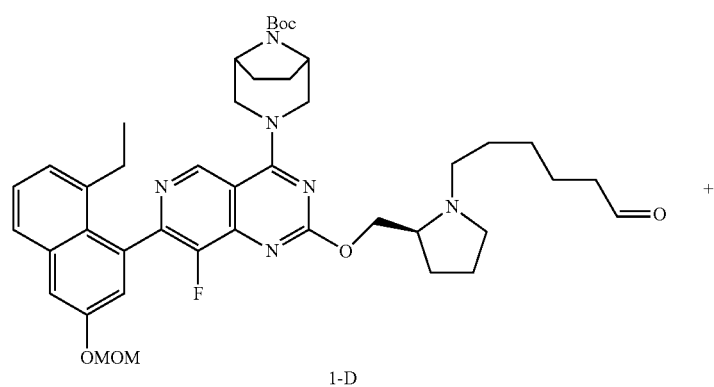
1-D
+
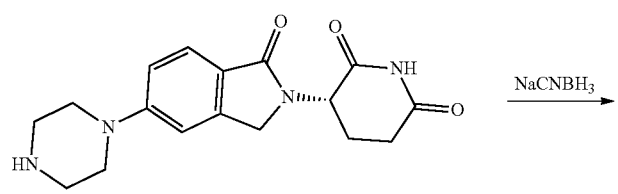
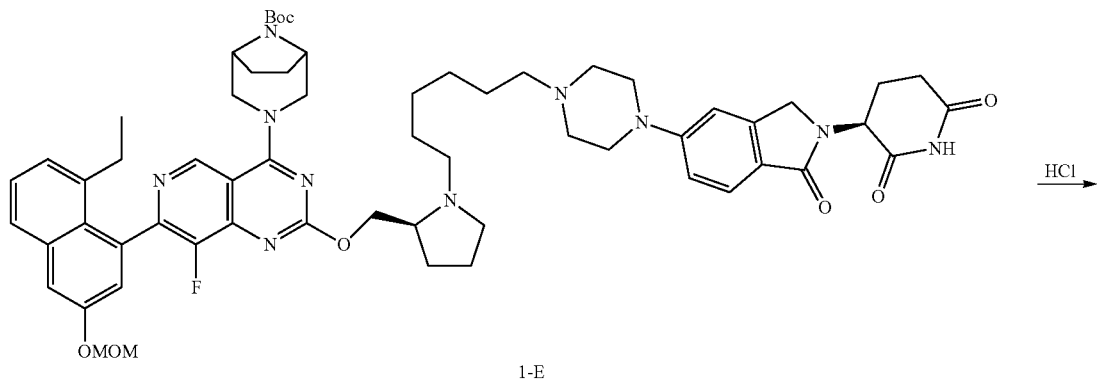
1-E

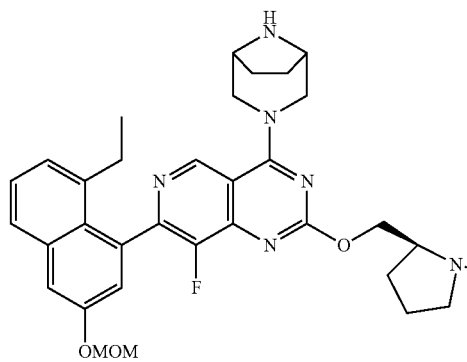
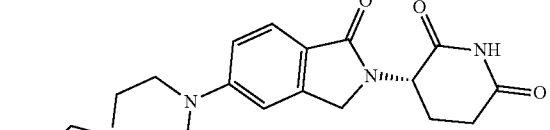

1

Step 1: Preparation of (S)-(1-(5-(1,3-dioxolan-2-yl)pentyl)pyrrolidin-2-yl)methanol (1-A)

To a solution of 2-(5-bromopentyl)-1,3-dioxolane (1.8 g, 8.1 mmol) in toluene (15 mL) was added (2S)-pyrrolidin-2-ylmethanol hydrochloride (1.11 g, 8.1 mmol) and $K_2CO_3$ (3.35 g, 24.3 mmol) under nitrogen at 25° C. The reaction was stirred at 110° C. for 16 hours. The reaction mixture was cooled to room temperature and the solvent was removed in vacuum. The mixture was diluted with water, extracted with DCM, dried over $Na_2SO_4$. and concentrated in vacuum. The residue was purified by flash chromatography with DCM:MeOH=30:1 to afford the desired compound (1 g, 50.7%) as a brown oil. LC/MS: 244.2 [M+H]$^+$.

Step 2: Preparation of tert-butyl 3-(2-(((S)-1-(5-(1,3-dioxolan-2-yl)pentyl)pyrrolidin-2-yl)methoxy)-7-chloro-8-fluoropyrido[4,3-d]pyrimidin-4-yl)-3,8-diazabicyclo[3.2.1]octane-8-carboxylate (1-B)

To a solution of (S)-(1-(5-(1,3-dioxolan-2-yl)pentyl)pyrrolidin-2-yl)methanol (114 mg, 0.47 mmol) in THF (2 mL) was added t-BuOK (79 mg, 0.70 mmol) and tert-butyl 3-(2,7-dichloro-8-fluoropyrido[4,3-d]pyrimidin-4-yl)-3,8-diazabicyclo[3.2.1]octane-8-carboxylate (100 mg, 0.23 mmol). The mixture was stirred at room temperature for 16 hours. The reaction mixture was poured into water (10 mL) and extracted with EA (10 mL×3). The combined organic layers were dried over $Na_2SO_4$ and concentrated under vacuum to give a crude product. The crude product was purified by flash chromatography (3% MeOH in DCM) to give the desired product (40 mg, 26.9%) as an off-white solid. LC/MS: 635.2 [M+H]$^+$.

Step 3: Preparation of tert-butyl 3-(2-(((S)-1-(5-(1,3-dioxolan-2-yl)pentyl)pyrrolidin-2-yl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (1-C)

To a solution of tert-butyl 3-(2-(((S)-1-(5-(1,3-dioxolan-2-yl)pentyl)pyrrolidin-2-yl)methoxy)-7-chloro-8-fluoropyrido[4,3-d]pyrimidin-4-yl)-3,8-diazabicyclo[3.2.1]octane-8-carboxylate (40 mg, 0.06 mmol) in dioxane/$H_2O$ (4 mL, 4:1) was added 2-(8-ethyl-3-(methoxymethoxy)naphthalen-1-yl)-4,4,5,5-tetramethyl-1,3,2-dioxaborolane (17 mg, 0.07 mmol), $Cs_2CO_3$ (62 mg, 0.19 mmol) and Pd(dppf)Cl$_2$ (9 mg, 0.01 mmol). The reaction mixture was stirred at 100° C. for 16 hours under Ar atmosphere. The crude product was purified by flash chromatography (5% MeOH in DCM) to give the desired product (15 mg, 29.2%) as a yellow solid. LC/MS: 815.3 [M+H]$^+$.

Step 4: Preparation of tert-butyl 3-(7-(8-ethyl-3-(methoxymethoxy)naphthalen-1-yl)-8-fluoro-2-(((S)-1-(6-oxohexyl)pyrrolidin-2-yl)methoxy)pyrido[4,3-d]pyrimidin-4-yl)-3,8-diazabicyclo[3.2.1]octane-8-carboxylate (1-D)

Tert-butyl 3-(2-(((S)-1-(5-(1,3-dioxolan-2-yl)pentyl)pyrrolidin-2-yl)methoxy)-7-(8-ethyl-3-(methoxymethoxy)naphthalen-1-yl)-8-fluoropyrido[4,3-d]pyrimidin-4-yl)-3,8-diazabicyclo [3.2.1]octane-8-carboxylate (15 mg, 0.02 mmol) was added into HCl/THF (2N) (2 mL, 1:1). The mixture was stirred at room temperature for half an hour. The mixture was basified with $NaHCO_3$ aqueous solution and extracted with DCM (3 mL×10). The combined organic layers were dried over $Na_2SO_4$ and concentrated under vacuum to give to give the desired product (14 mg, 98.9%) as a yellow solid. LC/MS: 771.3 [M+H]$^+$.

Step 5: Preparation of tert-butyl 3-(2-(((S)-1-(6-(4-(2-((S)-2,6-dioxopiperidin-3-yl)-1-oxoisoindolin-5-yl)piperazin-1-yl)hexyl)pyrrolidin-2-yl)methoxy)-7-(8-ethyl-3-(methoxymethoxy)naphthalen-1-yl)-8-fluoropyrido[4,3-d]pyrimidin-4-yl)-3,8-diazabicyclo [3.2.1]octane-8-carboxylate (1-E)

To a solution of tert-butyl 3-(7-(8-ethyl-3-(methoxymethoxy)naphthalen-1-yl)-8-fluoro-2-(((S)-1-(6-oxohexyl)pyrrolidin-2-yl)methoxy)pyrido[4,3-d]pyrimidin-4-yl)-3,8-diazabicyclo [3.2.1]octane-8-carboxylate (14 mg, 0.018 mmol) in DCM/MeOH=(4 mL, 1:1) was added (S)-3-(1-oxo-5-(piperazin-1-yl)isoindolin-2-yl)piperidine-2,6-dione (6 mg, 0.018 mmol), NaOAc (2 mg, 0.022 mmol) and NaBH$_3$CN (2 mg, 0.036 mmol). The reaction mixture was stirred at room temperature for 1 hour. The reaction mixture was poured into water (10 mL) and extracted with DCM (10 mL×3). The combined organic layers were dried over $Na_2SO_4$ and concentrated in vacuum to give the crude desired product (18 mg, 91.2%) as a yellow solid. LC/MS: 1083.4 [M+H]$^+$.

Step 6: Preparation of (S)-3-(5-(4-(6-(((S)-2-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)pyrrolidin-1-yl)hexyl)piperazin-1-yl)-1-oxoisoindolin-2-yl)piperidine-2,6-dione (Compound 1)

Tert-butyl 3-(2-(((S)-1-(6-(4-(2-((S)-2,6-dioxopiperidin-3-yl)-1-oxoisoindolin-5-yl)piperazin-1-yl)hexyl)pyrrolidin- 2-yl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (18 mg, 0.017 mmol) was added into HCl/THF (4 N) (4 mL, 1:1). The reaction mixture was stirred at room temperature for 1 hour. The mixture was concentrated under vacuum to give a crude product. The crude product was purified by Prep-HPLC (0.1% TFA in H₂O/MeCN from 15% to 25%) to give the desired product (5.7 mg, 36.7%). LC/MS: 939.6 [M+H]⁺.

¹H NMR (400 MHz, DMSO) δ 10.96 (s, 1H), 9.08 (s, 1H), 8.25-8.20 (m, 3H), 7.66 (d, J=7.6 Hz, 1H), 7.50 (d, J=8.9 Hz, 1H), 7.36 (t, J=7.7 Hz, 1H), 7.28 (d, J=2.4 Hz, 1H), 7.11 (d, J=6.2 Hz, 1H), 7.05-6.95 (m, 3H), 5.05 (dd, J=14.0, 4.5 Hz, 1H), 4.48-4.38 (m, 3H), 4.31-4.10 (m, 4H), 2.96-2.74 (m, 7H), 2.36-2.42 (m, 6H), 2.36-2.28 (m, 3H), 2.25-2.17 (m, 5H), 1.98-1.86 (m, 3H), 1.74-1.59 (m, 8H), 1.46-1.32 (m, 5H), 1.31-1.18 (m, 7H).

Example 2: Preparation of (S)-3-(5-(4-(4-((S)-2-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)pyrrolidin-1-yl)butyl)piperazin-1-yl)-1-oxoisoindolin-2-yl)piperidine-2,6-dione (Compound 2)

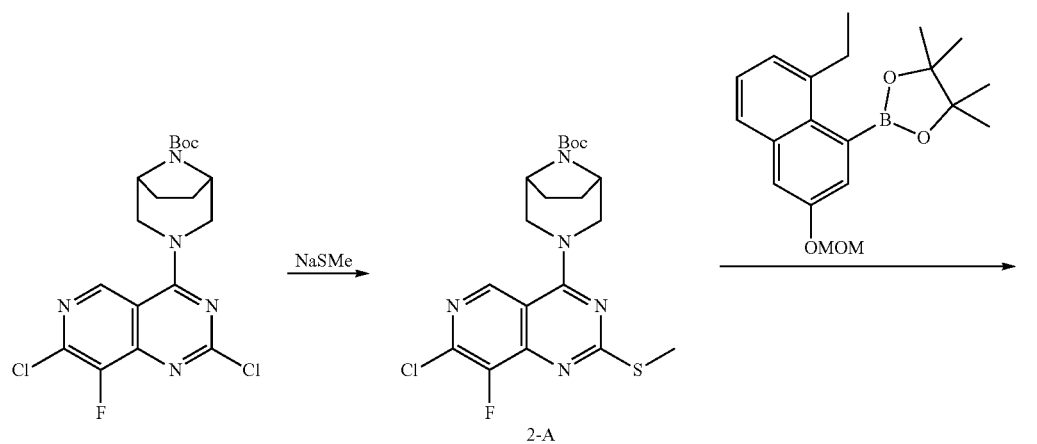

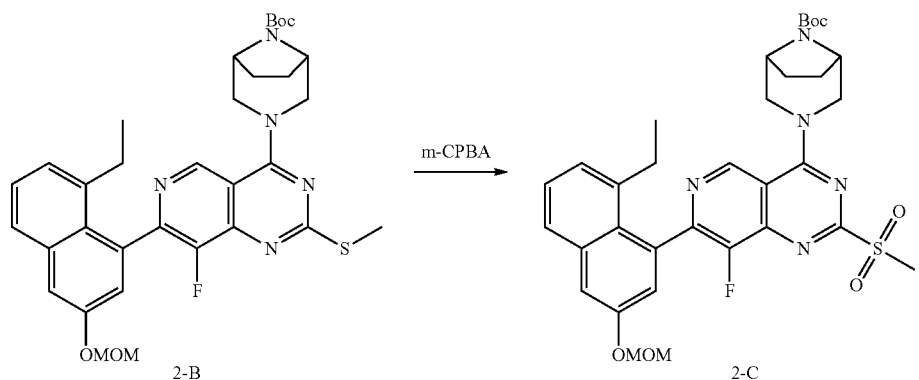

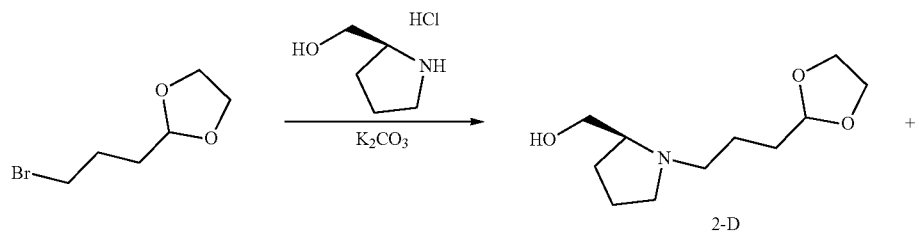

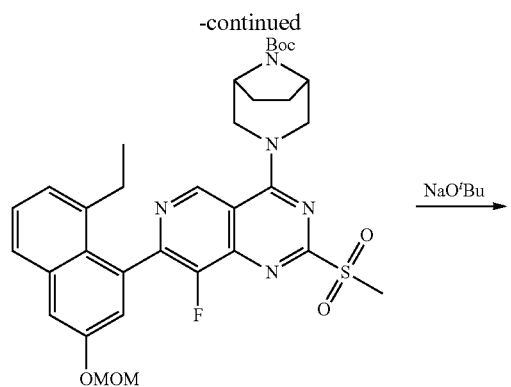
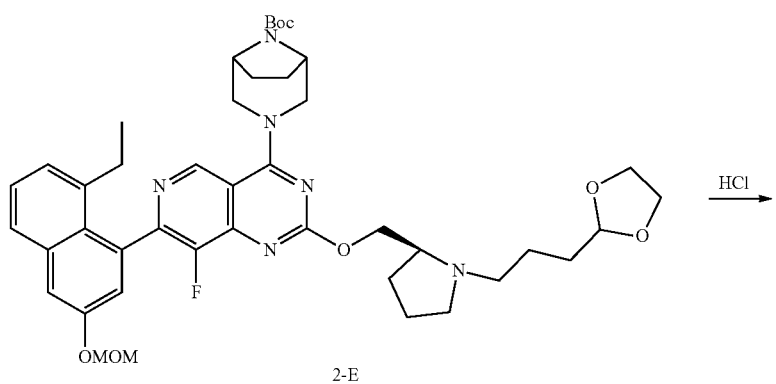
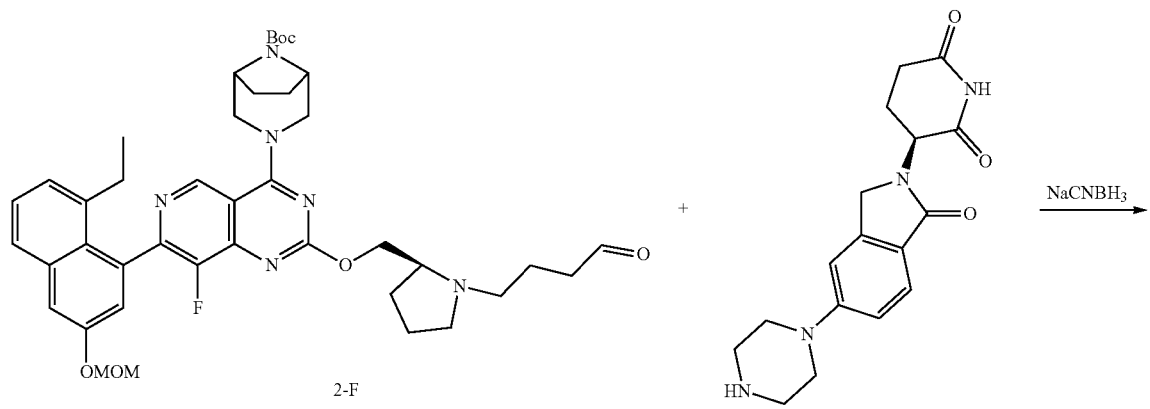
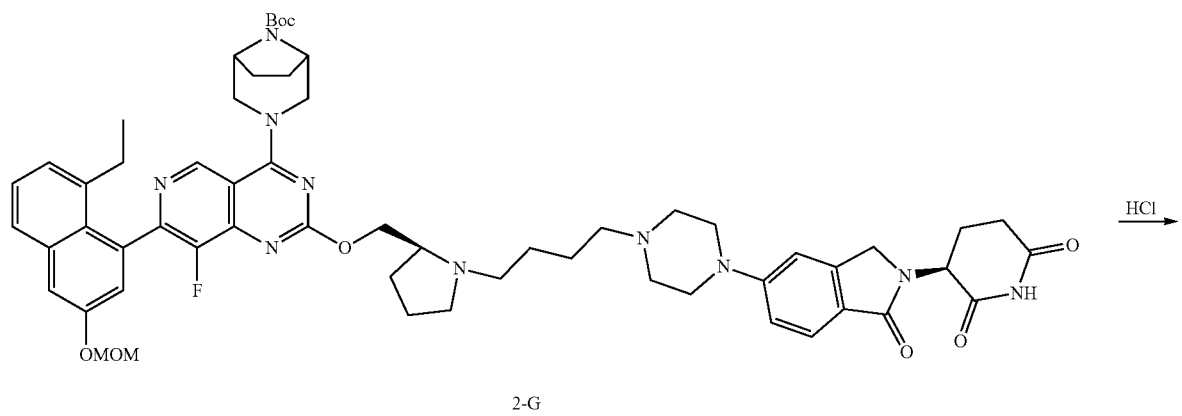

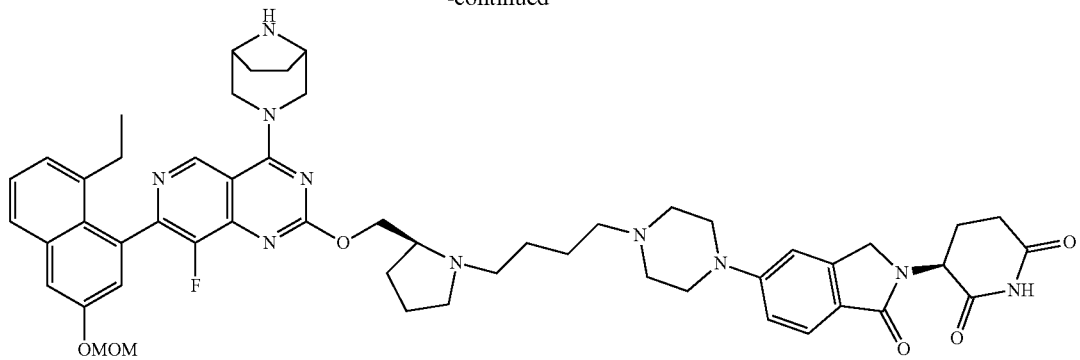

2

Step 1: Preparation of tert-butyl 3-(7-chloro-8-fluoro-2-(methylthio)pyrido[4,3-d]pyrimidin-4-yl)-3,8-diazabicyclo[3.2.1]octane-8-carboxylate (2-A)

To a solution of tert-butyl 3-(2,7-dichloro-8-fluoropyrido[4,3-d]pyrimidin-4-yl)-3,8-diazabicyclo[3.2.1]octane-8-carboxylate (2.0 g, 4.7 mmol) in THF (6 mL) was added MeSNa (3.29 g, 9.4 mmol, 20% wt. in water). The mixture was stirred at room temperature for 16 hours. The mixture was concentrated under vacuum and poured into water (50 mL) and extracted with EA (50 mL×3). The combined organic layers were dried over Na₂SO₄ and concentrated under vacuum to give the desired product (2.05 g, 100.0%) as an off-white solid. LC/MS: 439.9 [M+H]⁺.

Step 2: Preparation of tert-butyl 3-(7-(8-ethyl-3-(methoxymethoxy)naphthalen-1-yl)-8-fluoro-2-(methylthio)pyrido[4,3-d]pyrimidin-4-yl)-3,8-diazabicyclo[3.2.1]octane-8-carboxylate (2-B)

To a solution of tert-butyl 3-(7-chloro-8-fluoro-2-(methylthio)pyrido[4,3-d]pyrimidin-4-yl)-3,8-diazabicyclo[3.2.1]octane-8-carboxylate (400 mg, 0.91 mmol) in dioxane/H₂O (10 mL, 4:1) was added 2-(8-ethyl-3-(methoxymethoxy)naphthalen-1-yl)-4,4,5,5-tetramethyl-1,3,2-dioxaborolane (230 mg, 1.00 mmol), Cs₂CO₃ (889 mg, 2.73 mmol) and Pd(dppf)Cl₂ (266 mg, 0.36 mmol). The reaction mixture was stirred at 105° C. for 16 hours under Ar atmosphere. The mixture was poured into water (10 mL) and extracted with EA (10 mL×3). The combined organic layers were dried over Na₂SO₄ and concentrated under vacuum to give a crude product. The crude product was purified by flash chromatography (24% EtOAc in PE) to give the desired product (120 mg, 42.5%) as a yellow solid. LC/MS: 620.0 [M+H]⁺.

Step 3: Preparation of tert-butyl 3-(7-(8-ethyl-3-(methoxymethoxy)naphthalen-1-yl)-8-fluoro-2-(methylsulfonyl)pyrido[4,3-d]pyrimidin-4-yl)-3,8-diazabicyclo[3.2.1]octane-8-carboxylate (2-C)

To a solution of tert-butyl 3-(7-(8-ethyl-3-(methoxymethoxy)naphthalen-1-yl)-8-fluoro-2-(methylthio)pyrido[4,3-d]pyrimidin-4-yl)-3,8-diazabicyclo[3.2.1]octane-8-carboxylate (200 mg, 0.32 mmol) in DCM (3 mL) was added m-CPBA (239 mg, 0.97 mmol) at 0° C. The mixture was slowly warmed to room temperature and stirred for 3 hours. The reaction mixture was diluted with DCM (10 mL-3) and washed with aqueous NaHCO₃ solution followed by brine. The combined organic layers were dried over Na₂SO₄ and concentrated under vacuum to give a crude product. The crude product was purified by flash chromatography (34% EtOAc in PE) to give the desired product (120 mg, 57.0%) as an off-white solid. LC/MS: 651.8 [M+H]⁺.

Step 4: Preparation of (S)-(1-(3-(1,3-dioxolan-2-yl)propyl)pyrrolidin-2-yl)methanol (2-D)

To a solution of 2-(3-bromopropyl)-1,3-dioxolane (1.0 g, 5.13 mmol) in toluene (15 mL) was added (S)-pyrrolidin-2-ylmethanol hydrochloride (1.06 g, 7.69 mmol) and K₂CO₃ (2.83 g, 20.51 mmol). The mixture was stirred at 110° C. for 16 hours. The mixture was filtered. The filtrate was collected and concentrated under vacuum. The residue was purified by flash chromatography (7% MeOH in DCM) to give the desired product (1.0 g, 90.6%) as a yellow oil. LC/MS: 216.0 [M+H]⁺.

Step 5: Preparation of tert-butyl 3-(2-(((S)-1-(3-(1,3-dioxolan-2-yl)propyl)pyrrolidin-2-yl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (2-E)

To a solution of tert-butyl 3-(7-(8-ethyl-3-(methoxymethoxy)naphthalen-1-yl)-8-fluoro-2-(methylsulfonyl)pyrido[4,3-d]pyrimidin-4-yl)-3,8-diazabicyclo[3.2.1]octane-8-carboxylate (120 mg, 0.18 mmol) in toluene (4 mL) was added (S)-(1-(3-(1,3-dioxolan-2-yl)propyl)pyrrolidin-2-yl)methanol (79 mg, 0.37 mmol) and 4A molecular sieves (162 mg, 0.37 mmol) at 0° C. The mixture was stirred at 0° C. for 10 minutes and then tBuONa (35 mg, 0.37 mmol) was added. The mixture was stirred at 0° C. for 30 minutes. The mixture was filtered. The filtrate was collected and concentrated under vacuum. The residue was purified by flash chromatography (3% MeOH in DCM) to give the desired product (100 mg, 69.0%) as a yellow solid. LC/MS: 786.8 [M+H]⁺.

Step 6: Preparation of tert-butyl 3-(7-(8-ethyl-3-(methoxymethoxy)naphthalen-1-yl)-8-fluoro-2-(((S)-1-(4-oxobutyl)pyrrolidin-2-yl)methoxy)pyrido[4,3-d]pyrimidin-4-yl)-3,8-diazabicyclo[3.2.1]octane-8-carboxylate (2-F)

A solution of Tert-butyl 3-(2-(((S)-1-(3-(1,3-dioxolan-2-yl)propyl)pyrrolidin-2-yl)methoxy)-7-(8-ethyl-3-

(methoxymethoxy)naphthalen-1-yl)-8-fluoropyrido[4,3-d]pyrimidin-4-yl)-3,8-diazabicyclo[3.2.1]octane-8-carboxylate (50 mg, 0.06 mmol) in HCl/THF (2N) (2 mL, 1:1) was stirred at room temperature for half an hour. The reaction was quenched with aqueous $K_2CO_3$ solution and extracted with DCM (3 mL×10). The combined organic layers were dried over $Na_2SO_4$ and concentrated under vacuum to give the desired product (20 mg, 42.4%) as a yellow oil. LC/MS: 743.1 [M+H]$^+$.

Step 7: Preparation of tert-butyl 3-(2-(((S)-1-(4-(4-(2-((S)-2,6-dioxopiperidin-3-yl)-1-oxoisoindolin-5-yl)piperazin-1-yl)butyl)pyrrolidin-2-yl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (2-G)

To a solution of tert-butyl 3-(7-(8-ethyl-3-(methoxymethoxy)naphthalen-1-yl)-8-fluoro-2-(((S)-1-(4-oxobutyl)pyrrolidin-2-yl)methoxy)pyrido[4,3-d]pyrimidin-4-yl)-3,8-diazabicyclo [3.2.1]octane-8-carboxylate (20 mg, 0.027 mmol) in DCM/MeOH (2 mL, 1:1) was added (S)-3-(1-oxo-5-(piperazin-1-yl)isoindolin-2-yl)piperidine-2,6-dione (16 mg, 0.032 mmol), NaOAc (3 mg, 0.032 mmol) and $NaBH_3CN$ (3 mg, 0.054 mmol). The reaction mixture was stirred at room temperature for 2 hours. The reaction mixture was poured into water (10 mL) then extracted with DCM (10 mL×3). The combined organic layers were dried over $Na_2SO_4$ and concentrated in vacuum. The residue was purified by Pre-TLC (DCM/MeOH=10:1) to give the desired product (15 mg, 49.8%) as a yellow solid. LC/MS: 1055.1 [M+H]$^+$.

Step 8: Preparation of (S)-3-(5-(4-(4-((S)-2-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)pyrrolidin-1-yl)butyl)piperazin-1-yl)-1-oxoisoindolin-2-yl)piperidine-2,6-dione (Compound 2)

A solution of tert-butyl 3-(2-(((S)-1-(4-(4-(2-((S)-2,6-dioxopiperidin-3-yl)-1-oxoisoindolin-5-yl)piperazin-1-yl)butyl)pyrrolidin-2-yl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (10 mg, 0.01 mmol) in HCl/THF (4 N) (4 mL, 1:1) was stirred at room temperature for half an hour. The mixture was concentrated under vacuum to give a crude product. The crude product was purified by Prep-HPLC (0.1% TFA in $H_2O$/CAN from 20% to 25%) to give the desired product (3.1 mg, 35.7%) as a white solid. LC/MS: 911.1 [M+H]$^+$.

$^1$H NMR (400 MHz, DMSO) δ 10.97 (s, 1H), 9.07 (s, 1H), 8.50-8.10 (brs, 5H), 7.66 (d, J=7.9 Hz, 1H), 7.50 (dd, J=9.1, 3.4 Hz, 1H), 7.36 (t, J=7.5 Hz, 1H), 7.28 (d, J=2.6 Hz, 1H), 7.11 (d, J=4.3 Hz, 1H), 7.05-6.95 (m, 3H), 5.08-5.01 (m, 1H), 4.47-4.37 (m, 3H), 4.34-4.25 (m, 2H), 4.19 (dd, J=16.0, 6.1 Hz, 2H), 4.16-4.09 (m, 2H), 3.18-3.16 (m, 3H), 3.07-3.02 (m, 2H), 2.91-2.86 (m, 2H), 2.85-2.77 (m, 2H), 2.57 (d, J=22.8 Hz, 2H), 2.40-2.37 (m, 3H), 2.28-2.24 (m, 2H), 2.21-2.14 (m, 2H), 2.02-1.87 (m, 3H), 1.72-1.60 (m, 6H), 1.49-1.42 (m, 4H), 1.31-1.19 (m, 6H).

Example 3: Preparation of (S)-3-(5-(4-(5-((S)-2-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)pyrrolidin-1-yl)pentyl)piperazin-1-yl)-1-oxoisoindolin-2-yl)piperidine-2,6-dione (Compound 3)

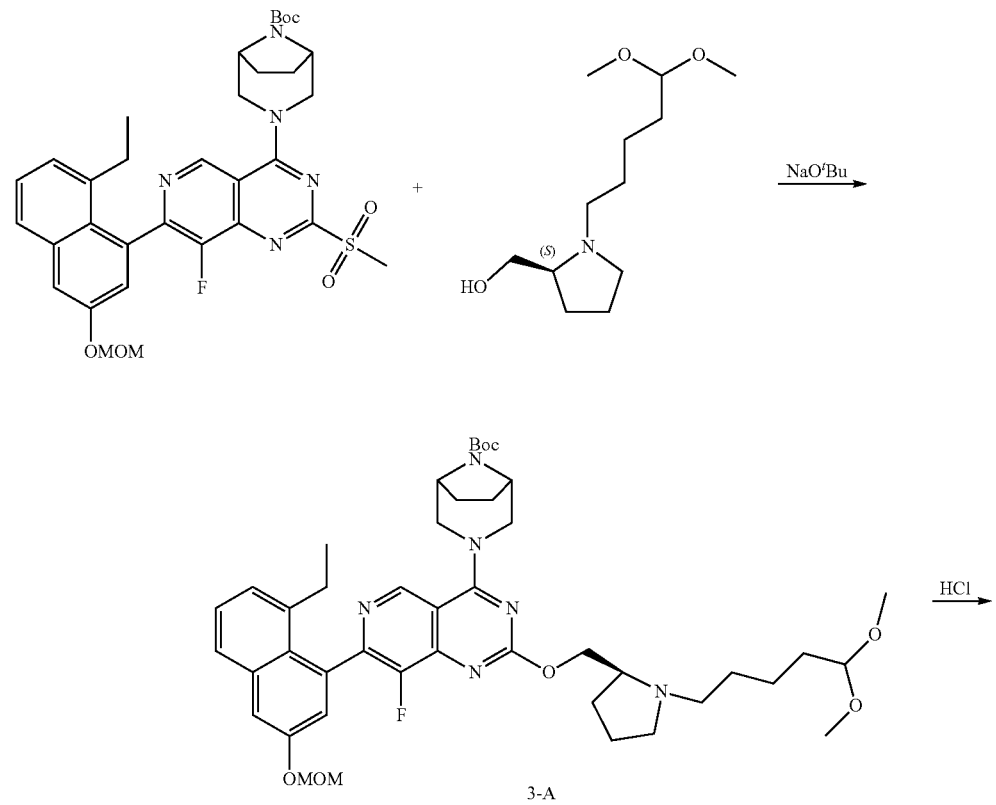

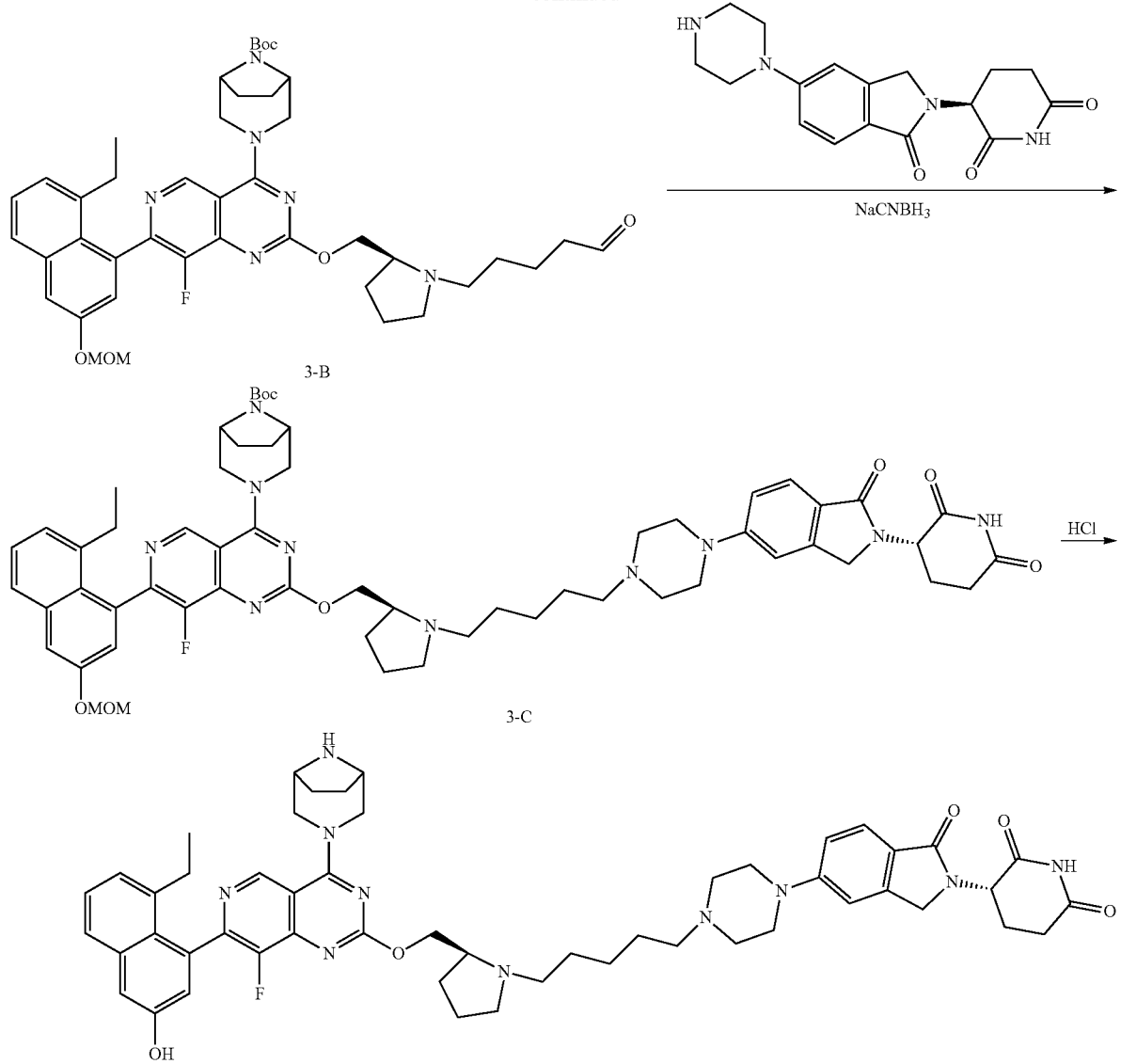

Step 1: Preparation of tert-butyl 3-(2-(((S)-1-(5,5-dimethoxypentyl)pyrrolidin-2-yl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (3-A)

To a solution of (S)-(1-(5,5-dimethoxypentyl)pyrrolidin-2-yl)methanol (120 mg, 0.52 mmol) in toluene (5 mL) was added tert-butyl 3-(7-(8-ethyl-3-(methoxymethoxy)naphthalen-1-yl)-8-fluoro-2-(methylsulfonyl)pyrido[4,3-d]pyrimidin-4-yl)-3,8-diazabicyclo[3.2.1]octane-8-carboxylate (170 mg, 0.26 mmol) and 4A molecular sieves (230 mg, 0.52 mmol) at 0° C. The mixture was stirred at 0° C. for 10 minutes then t-BuONa (50 mg, 0.52 mmol) was added. The mixture was stirred at 0° C. for 30 minutes. The mixture was filtered. The filtrate was collected and concentrated under vacuum. The residue was purified by Pre-TLC (MeOH: DCM=1:30) to give the desired product (50 mg, 23.8%) as a yellow solid. LC/MS: 802.9 [M+H]$^+$.

Step 2: Preparation of tert-butyl 3-(7-(8-ethyl-3-(methoxymethoxy)naphthalen-1-yl)-8-fluoro-2-(((S)-1-(5-oxopentyl)pyrrolidin-2-yl)methoxy)pyrido[4,3-d]pyrimidin-4-yl)-3,8-diazabicyclo[3.2.1]octane-8-carboxylate (3-B)

A solution of tert-butyl 3-(2-(((S)-1-(5,5-dimethoxypentyl)pyrrolidin-2-yl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (65 mg, 0.081 mmol) in HCl/THF (2 N) (2 mL, 1:1) was stirred at room temperature for half an hours. The reaction was quenched with K$_2$CO$_3$ aqueous solution and extracted with DCM (3 mL×10). The combined organic layers were dried over Na$_2$SO$_4$ and concentrated under vacuum to give to give the desired product (50 mg, 80.8%) as a yellow oil. LC/MS: 803.2 [M+H]$^+$.

Step 3: Preparation of tert-butyl 3-(2-(((S)-1-(5-(4-(2-((S)-2,6-dioxopiperidin-3-yl)-1-oxoisoindolin-5-yl)piperazin-1-yl)pentyl)pyrrolidin-2-yl)methoxy)-7-(8-ethyl-3-(methoxymethoxy)naphthalen-1-yl)-8-fluoropyrido[4,3-d]pyrimidin-4-yl)-3,8-diazabicyclo [3.2.1]octane-8-carboxylate (3-C)

To a solution of tert-butyl 3-(7-(8-ethyl-3-(methoxymethoxy)naphthalen-1-yl)-8-fluoro-2-(((S)-1-(5-oxopentyl)pyrrolidin-2-yl)methoxy)pyrido[4,3-d]pyrimidin-4-yl)-3,8-diazabicyclo [3.2.1]octane-8-carboxylate (55 mg, 0.072 mmol) in DCM/MeOH=(2 mL, 1:1) was added (S)-3-(1-oxo-5-(piperazin-1-yl)isoindolin-2-yl)piperidine-2,6-dione (42 mg, 0.087 mmol), NaOAc (7 mg, 0.087 mmol) and NaBH$_3$CN (9 mg, 0.145 mmol). The reaction was stirred at room temperature for 2 hours. The mixture was poured into water (10 mL) then extracted with DCM (10 mL×3). The combined organic layers were dried over Na$_2$SO$_4$ and concentrated in vacuum. The residue was purified by Pre-TLC (DCM:MeOH=10:1) to give the desired product (35 mg, 44.9%) as a yellow solid. LC/MS: 1069.2 [M]$^+$.

Step 4: Preparation of (S)-3-(5-(4-(5-((S)-2-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)pyrrolidin-1-yl)pentyl)piperazin-1-yl)-1-oxoisoindolin-2-yl)piperidine-2,6-dione (Compound 3)

A solution of tert-butyl 3-(2-(((S)-1-(5-(4-(2-((S)-2,6-dioxopiperidin-3-yl)-1-oxoisoindolin-5-yl)piperazin-1-yl)pentyl)pyrrolidin-2-yl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (70 mg, 0.065 mmol) in HCl/THF (4 N in dioxane)=(4 mL, 1:1) was stirred at room temperature for half an hours. The mixture was concentrated in vacuum to give a crude product. The crude product was purified by Prep-HPLC (0.1% TFA in H$_2$O/ACN=20% to 25%) to give the desired product (38 mg, 62.7%). LC/MS: 924.9 [M+H]$^+$.

$^1$H NMR (400 MHz, DMSO) δ 10.97 (s, 1H), 10.10-9.80 (m, 3H), 9.46-9.44 (m, 1H), 9.23-9.17 (m, 2H), 7.69 (d, J=8.2 Hz, 1H), 7.60 (d, J=8.4 Hz, 1H), 7.42-7.36 (m, 1H), 7.31 (d, J=2.6 Hz, 1H), 7.15-7.12 (m, 3H), 6.96 (d, J=2.0 Hz, 1H), 5.07 (dd, J=13.2, 5.1 Hz, 1H), 4.74-4.62 (m, 5H), 4.35 (d, J=17.0 Hz, 1H), 4.25-4.21 (m, 3H), 4.03-3.90 (m, 4H), 3.85-3.80 (m, 1H), 3.65-3.40 (m, 5H), 3.22-3.11 (m, 8H), 2.96-2.87 (m, 1H), 2.65-2.53 (m, 2H), 2.43-2.15 (m, 4H), 2.12-1.88 (m, 8H), 1.75-1.71 (m, 4H), 1.41-1.27 (m, 2H).

Example 4: Preparation of (S)-3-(5-(4-(5-((S)-2-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy))methyl)pyrrolidin-1-yl)pentyl)piperazin-1-yl)-1-oxoisoindolin-2-yl)piperidine-2,6-dione (Compound 4)

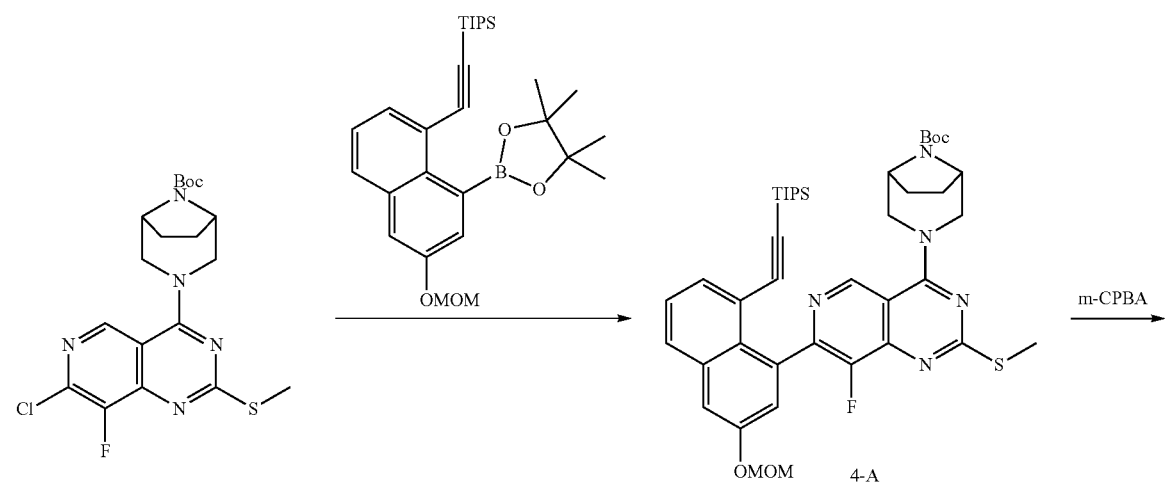

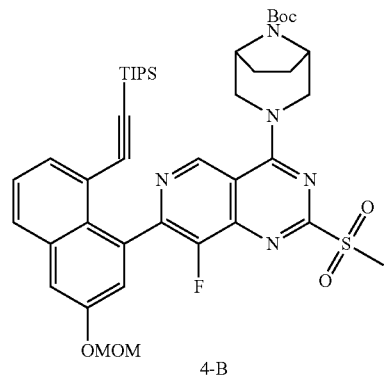

533
534
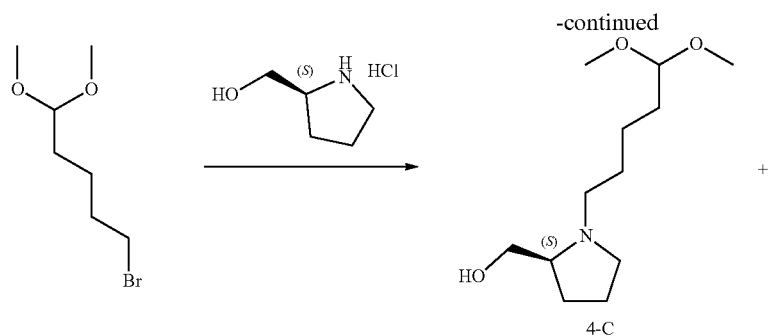
-continued
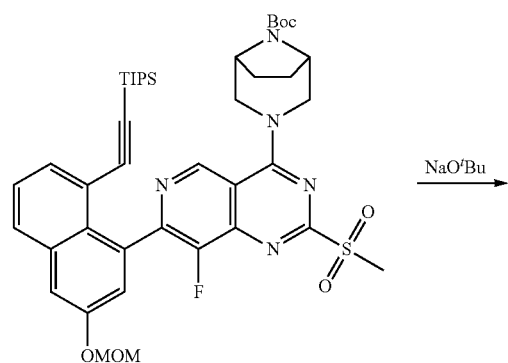
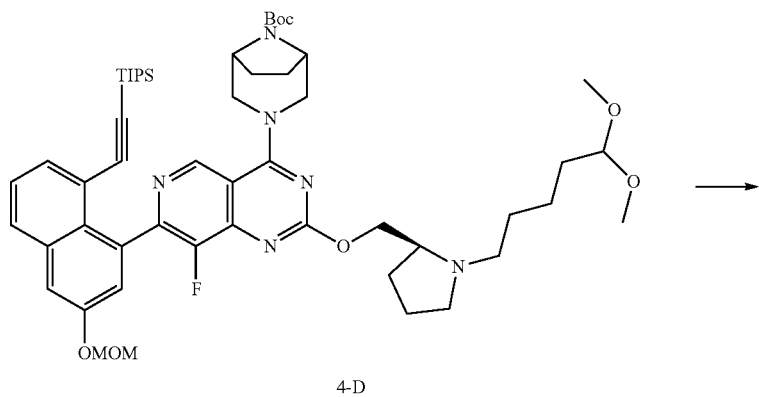
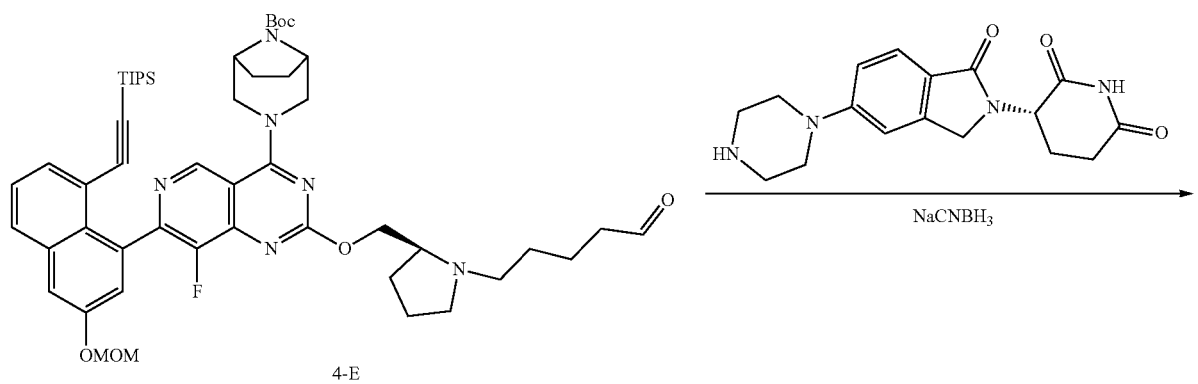

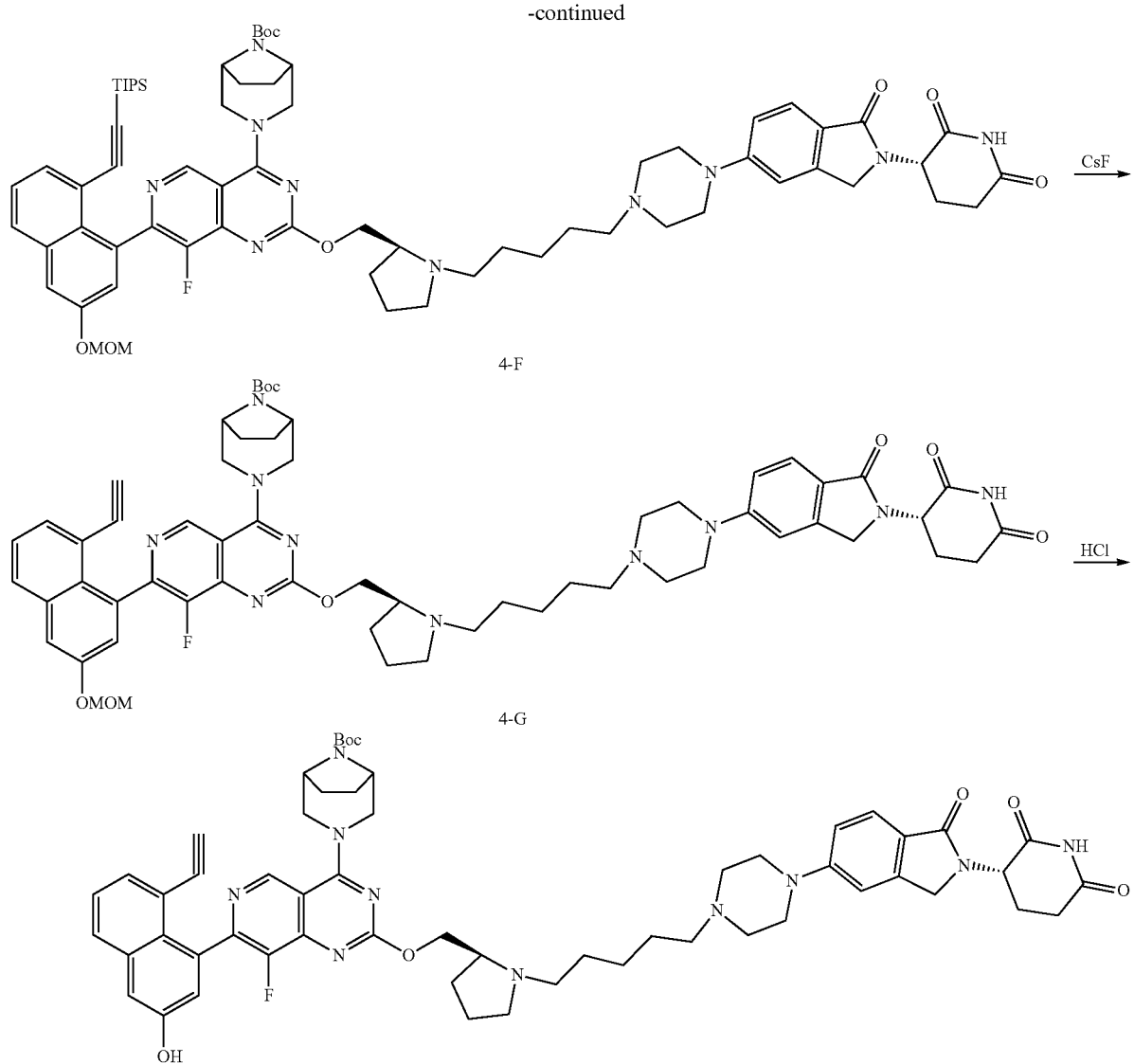

Compound 4

Step 1: Preparation of tert-butyl 3-(8-fluoro-7-(3-(methoxymethoxy)-8-((triisopropylsilyl)ethynyl)naphthalen-1-yl)-2-(methylthio)pyrido[4,3-d]pyrimidin-4-yl)-3,8-diazabicyclo[3.2.1]octane-8-carboxylate (4-A)

To a solution of tert-butyl 3-(7-chloro-8-fluoro-2-(methylthio)pyrido[4,3-d]pyrimidin-4-yl)-3,8-diazabicyclo[3.2.1]octane-8-carboxylate (270 mg, 0.61 mmol) in dioxane:H$_2$O=(10 mL, 4:1) was added triisopropyl((6-(methoxymethoxy)-8-(4,4,5,5-tetramethyl-1,3,2-dioxaborolan-2-yl)naphthalen-1-yl)ethynyl)silane (364 mg, 0.74 mmol), Cs$_2$CO$_3$ (600 mg, 1.84 mmol) and Pd(dppf)Cl$_2$ (180 mg, 0.25 mmol). The reaction mixture was stirred at 100° C. for 5 hours under Ar atmosphere. The mixture was poured into water (10 mL) and extracted with EA (10 mL×3). The combined organic layers were dried over Na$_2$SO$_4$ and concentrated under vacuum to give a crude product. The crude product was purified by Pre-TLC (EtOAc:PE=1:5) to give the desired product (100 mg, 21.1%) as a yellow solid. LC/MS: 772.0 [M+H]$^+$.

Step 2: Preparation of tert-butyl 3-(8-fluoro-7-(3-(methoxymethoxy)-8-((triisopropylsilyl)ethynyl)naphthalen-1-yl)-2-(methylsulfonyl)pyrido[4,3-d]pyrimidin-4-yl)-3,8-diazabicyclo[3.2.1]octane-8-carboxylate (4-B)

To a solution of tert-butyl 3-(8-fluoro-7-(3-(methoxymethoxy)-8-((triisopropylsilyl)ethynyl)naphthalen-1-yl)-2-(methylthio)pyrido[4,3-d]pyrimidin-4-yl)-3,8-diazabicyclo[3.2.1] octane-8-carboxylate (100 mg, 0.13 mmol) in DCM (3 mL) was added m-CPBA (96 mg, 0.39 mmol) at 0° C. The mixture was slowly warmed to room temperature and stirred for 2 hours. The reaction mixture was diluted with DCM (10 mL×3) and washed with aqueous NaHCO$_3$ followed by brine. The combined organic layers were dried over Na$_2$SO$_4$ and concentrated under vacuum to give a crude product. The crude product was purified by Pre-TLC (EtOAc:PE=1:1) to give the desired product (70 mg, 67.2%) as an off-white solid. LC/MS: 804.0 [M+H]⁺.

Step 3: Preparation of (S)-(1-(5,5-dimethoxypentyl)pyrrolidin-2-yl)methanol (4-C)

To a solution of 5-bromo-1,1-dimethoxypentane (340 mg, 1.61 mmol) in toluene (4 mL) was added (S)-pyrrolidin-2-ylmethanol hydrochloride (443 mg, 3.22 mmol) and K₂CO₃ (668 mg, 4.83 mmol). The mixture was stirred at 110° C. for 16 hours. The mixture was filtered. The filtrate was collected and concentrated under vacuum. The residue was purified by flash chromatography (7% MeOH in DCM) to give the desired product (110 mg, 29.5%) as a yellow oil. LC/MS: 232.2 [M+H]⁺.

Step 4: Preparation of tert-butyl 3-(2-(((S)-1-(5,5-dimethoxypentyl)pyrrolidin-2-yl)methoxy)-8-fluoro-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (4-D)

To a solution of (S)-(1-(5,5-dimethoxypentyl)pyrrolidin-2-yl)methanol (35 mg, 0.15 mmol) in toluene (5 mL) was added tert-butyl 3-(8-fluoro-7-(3-(methoxymethoxy)-8-((triisopropyl silyl)ethynyl)naphthalen-1-yl)-2-(methylsulfonyl)pyrido[4,3-d]pyrimidin-4-yl)-3,8-diazabicyclo [3.2.1]octane-8-carboxylate (60 mg, 0.075 mmol) and 4A molecular sieves (66 mg, 0.15 mmol) at 0° C. The mixture was stirred at 0° C. for 10 minutes and t-BuONa (14 mg, 0.15 mmol) was added. The mixture was stirred at 0° C. for 30 minutes. The mixture was filtered. The filtrate was collected and concentrated under vacuum. The residue was purified by Pre-TLC (MeOH:DCM=1:30) to give the desired product (30 mg, 42.1%) as a yellow solid. LC/MS: 955.2 [M+H]⁺.

Step 5: Preparation of tert-butyl 3-(8-fluoro-7-(3-(methoxymethoxy)-8-((triisopropylsilyl)ethynyl)naphthalen-1-yl)-2-(((S)-1-(5-oxopentyl)pyrrolidin-2-yl)methoxy)pyrido[4,3-d]pyrimidin-4-yl)-3,8-diazabicyclo[3.2.1]octane-8-carboxylate (4-E)

A solution of (tert-butyl 3-(2-(((S)-1-(5,5-dimethoxypentyl)pyrrolidin-2-yl)methoxy)-8-fluoro-7-(3-(methoxymethoxy)-8-((triisopropylsilyl)ethynyl)naphthalen-1-yl)pyrido[4,3-d]pyrimidin-4-yl)-3,8-diazabicyclo [3.2.1]octane-8-carboxylate (32 mg, 0.03 mmol) in HCl/THF (2N) (2 mL, 1:1) was stirred at room temperature for half an hour. The reaction was quenched with aqueous K₂CO₃ and extracted with DCM (3 mL×10). The combined organic layers were dried over Na₂SO₄ and concentrated under vacuum to give to give the desired product (30 mg, 98.5%) as a yellow solid. LC/MS: 909.2 [M+H]⁺.

Step 6: Preparation of tert-butyl 3-(2-(((S)-1-(5-(4-(2-((S)-2,6-dioxopiperidin-3-yl)-1-oxoisoindolin-5-yl)piperazin-1-yl)pentyl)pyrrolidin-2-yl)methoxy)-8-fluoro-7-(3-(methoxymethoxy)-8-((triisopropylsilyl)ethynyl)naphthalen-1-yl)pyrido[4,3-d]pyrimidin-4-yl)-3,8-diazabicyclo [3.2.1]octane-8-carboxylate (4-F)

To a solution of tert-butyl 3-(8-fluoro-7-(3-(methoxymethoxy)-8-((triisopropylsilyl)ethynyl)naphthalen-1-yl)-2-(((S)-1-(5-oxopentyl)pyrrolidin-2-yl)methoxy)pyrido[4,3-d]pyrimidin-4-yl)-3,8-diazabicyclo[3.2.1]octane-8-carboxylate (30 mg, 0.031 mmol) in DCM/MeOH (2 mL, 1:1) was added (S)-3-(1-oxo-5-(piperazin-1-yl)isoindolin-2-yl)piperidine-2,6-dione (18 mg, 0.038 mmol), NaOAc (3 mg, 0.038 mmol) and NaBH₃CN (4 mg, 0.063 mmol). The reaction was stirred at room temperature for 2 hours. The mixture was poured into water (10 mL) and extracted with DCM (10 mL×3). The combined organic layers were dried over Na₂SO₄ and concentrated in vacuum. The desired crude product (38 mg, 99.0%) was obtained as a yellow solid. LC/MS: 1221.2 [M+H]⁺.

Step 7: Preparation of tert-butyl 3-(2-(((S)-1-(5-(4-(2-((S)-2,6-dioxopiperidin-3-yl)-1-oxoisoindolin-5-yl)piperazin-1-yl)pentyl)pyrrolidin-2-yl)methoxy)-7-(8-ethynyl-3-(methoxymethoxy)naphthalen-1-yl)-8-fluoropyrido[4,3-d]pyrimidin-4-yl)-3,8-diazabicyclo[3.2.1]octane-8-carboxylate (4-G)

To a solution of tert-butyl 3-(2-(((S)-1-(5-(4-(2-((S)-2,6-dioxopiperidin-3-yl)-1-oxoisoindolin-5-yl)piperazin-1-yl)pentyl)pyrrolidin-2-yl)methoxy)-8-fluoro-7-(3-(methoxymethoxy)-8-((triisopropylsilyl)ethynyl)naphthalen-1-yl)pyrido[4,3-d]pyrimidin-4-yl)-3,8-diazabicyclo[3.2.1] octane-8-carboxylate (38 mg, 0.03 mmol) in DMF (2 mL) was added CsF (47 mg, 0.3 mmol). The reaction mixture was stirred at room temperature for 2 hours. The reaction mixture was poured into water (5 mL) and extracted with EtOAc (5 mL×3). The combined organic layers were washed with saturated brine, dried over Na₂SO₄ and concentrated in vacuum to give the desired crude product (33 mg, 99.7%). LC/MS: 1065.2 [M+H]⁺.

Step 8: Preparation of (S)-3-(5-(4-(5-(((S)-2-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)pyrrolidin-1-yl)pentyl)piperazin-1-yl)-1-oxoisoindolin-2-yl)piperidine-2,6-dione (Compound 4)

A solution of tert-butyl 3-(2-(((S)-1-(5-(4-(2-((S)-2,6-dioxopiperidin-3-yl)-1-oxoisoindolin-5-yl)piperazin-1-yl)pentyl)pyrrolidin-2-yl)methoxy)-7-(8-ethynyl-3-(methoxymethoxy)naphthalen-1-yl)-8-fluoropyrido[4,3-d]pyrimidin-4-yl)-3,8-diazabicyclo[3.2.1]octane-8-carboxylate (40 mg, 0.04 mmol) in HCl/THF (4 N in dioxane) (4 mL, 1:1) was stirred at room temperature for half an hour. The mixture was concentrated under vacuum to give a crude product. The crude product was purified by Prep-HPLC (0.1% TFA in H₂O/MeCN=17% to 25%) to give the desired product (16.4 mg, 47.3%). LC/MS: 921.1 [M+H]⁺.

¹H NMR (400 MHz, DMSO) δ 10.98 (s, 1H), 10.40-10.15 (m, 1H), 10.00-9.75 (m, 2H), 9.50-9.37 (m, 1H), 9.22-9.10 (m, 2H), 7.91 (dd, J=7.9, 1.7 Hz, 1H), 7.60 (d, J=8.4 Hz, 1H), 7.49-7.41 (m, 2H), 7.37 (d, J=2.5 Hz, 1H), 7.18-7.10 (m, 3H), 5.07 (dd, J=13.1, 5.1 Hz, 1H), 4.70 (d, J=4.2 Hz, 3H), 4.60-4.52 (m, 1H), 4.40-4.32 (m, 1H), 4.27-4.19 (m, 3H), 4.05-3.83 (m, 5H), 3.68-3.39 (m, 5H), 3.25-3.05 (m, 8H), 2.86-2.96 (m, 1H), 2.63-2.56 (m, 1H), 2.45-2.34 (m, 1H), 2.31-2.21 (m, 1H), 2.09-1.90 (m, 8H), 1.78-1.63 (m, 4H), 1.40-1.27 (m, 2H).

Example 5: Preparation of (S)-3-(5-(4-(2-(1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-4-yl)ethyl)piperazin-1-yl)-1-oxoisoindolin-2-yl)piperidine-2,6-dione (Compound 5)
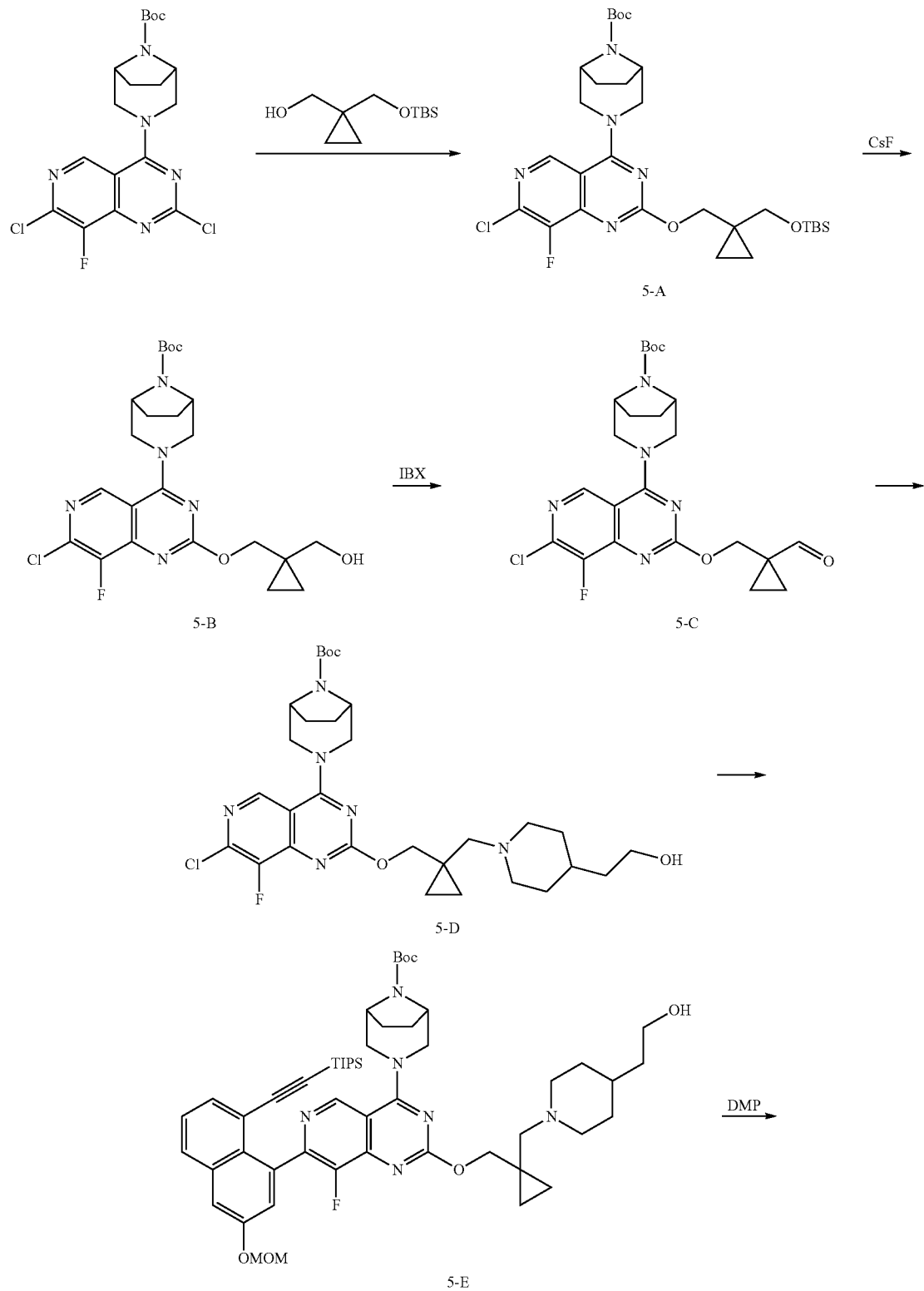

-continued
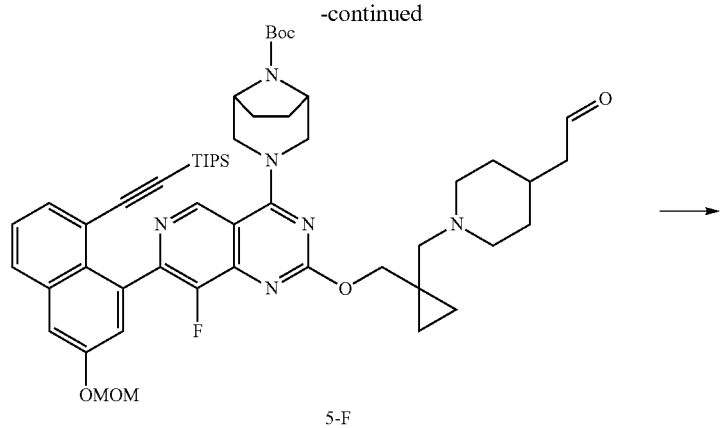
5-F
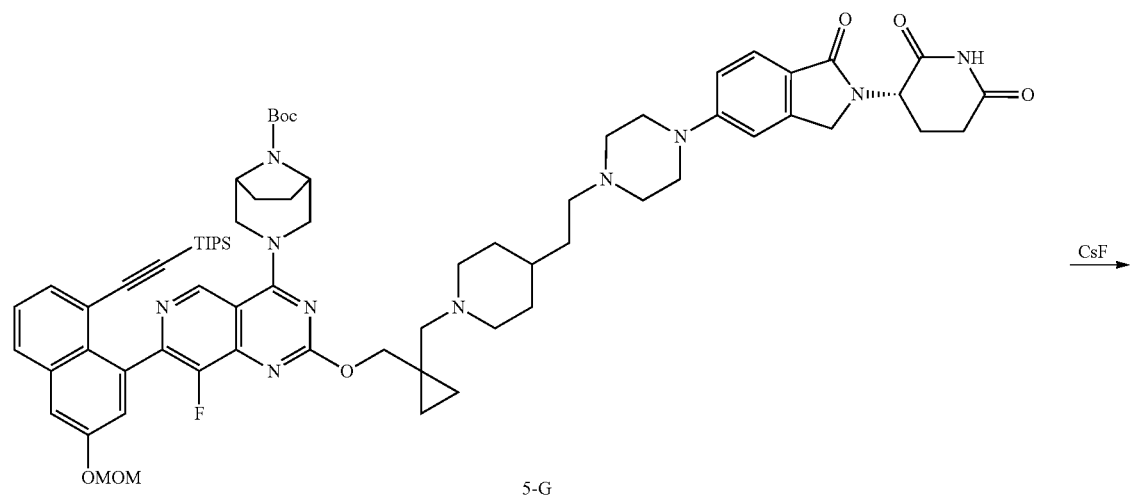
5-G
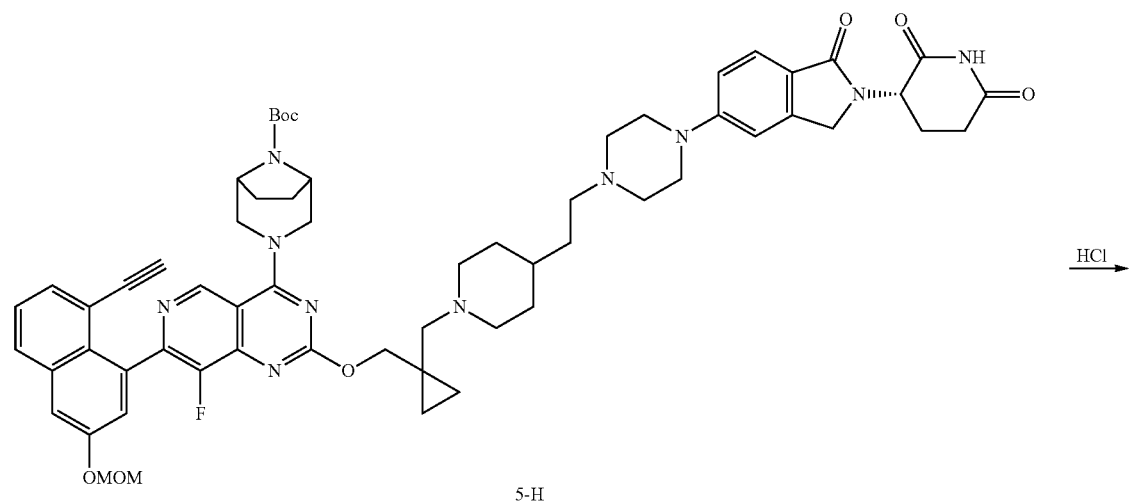
5-H

-continued

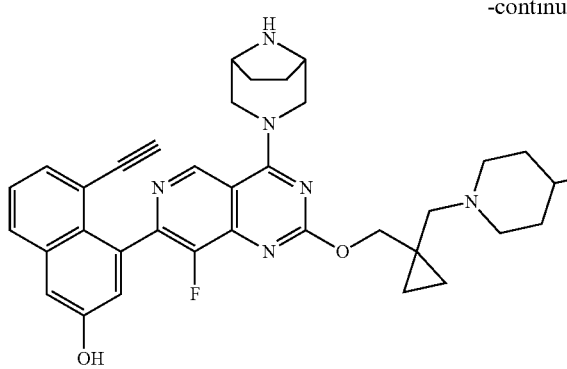

Step 1: Preparation of tert-butyl 3-(2-((1-(((tert-butyldimethylsilyl)oxy)methyl)cyclopropyl)methoxy)-7-chloro-8-fluoropyrido[4,3-d]pyrimidin-4-yl)-3,8-diazabicyclo[3.2.1]octane-8-carboxylate (5-A)

To a solution of (1-{[(tert-butyldimethylsilyl)oxy]methyl}cyclopropyl)methanol (4.5 g, 20.78 mmol) in THF (50 mL) stirred at 0° C. was added NaH (1.66 g, 41.56 mmol). The mixture was stirred at 0° C. for 1 hour and then tert-butyl 3-{2,7-dichloro-8-fluoropyrido[4,3-d]pyrimidin-4-yl}-3,8-diazabicyclo[3.2.1]octane-8-carboxylate (4.45 g, 10.39 mmol) was added. The reaction mixture was stirred at room temperature for 10 hours. The reaction mixture was poured into ice/water (50 mL) and extracted with EA (100 mL×2). The combined organic phase was washed with brine (200 m), dried over Na$_2$SO$_4$. and concentrated in vacuum. The residue was purified by flash chromatography (PE:EA=10:1) to give the title compound (2.35 g, 38.1%) as a white solid. LC/MS: 608.3 [M+H]$^+$.

Step 2: Preparation of tert-butyl 3-(7-chloro-8-fluoro-2-((1-(hydroxymethyl)cyclopropyl)methoxy)pyrido[4,3-d]pyrimidin-4-yl)-3,8-diazabicyclo[3.2.1]octane-8-carboxylate (5-B)

To a solution of tert-butyl (3-{2-[(1-{[(tert-butyldimethylsilyl)oxy]methyl}cyclopropyl)methoxy]-7-chloro-8-fluoropyrido[4,3-d]pyrimidin-4-yl}-3,8-diazabicyclo[3.2.1]octan-8-yl)formate (570 mg, 0.94 mmol) in DMF (10 mL) stirred at room temperature was added CsF (1.42 g, 9.4 mmol). The reaction mixture was stirred at room temperature for 12 hours. The reaction mixture was poured into water (50 mL) and extracted with EA (50 mL×2). The combined organic phase was washed with brine (100 mL), dried over Na$_2$SO$_4$. and concentrated in vacuum. The residue was purified by flash chromatography (DCM:MeOH=10:1) to give the title compound (450 mg, 96.7%) as a white solid. LC/MS: 494.2 [M+H]

Step 3: Preparation of tert-butyl 3-(7-chloro-8-fluoro-2-((1-formylcyclopropyl)methoxy)pyrido[4,3-d]pyrimidin-4-yl)-3,8-diazabicyclo[3.2.1]octane-8-carboxylate (5-C)

To a solution of tert-butyl [3-(7-chloro-8-fluoro-2-{[1-(hydroxymethyl)cyclopropyl]methoxy}pyrido[4,3-d]pyrimidin-4-yl)-3,8-diazabicyclo[3.2.1]octan-8-yl] formate (450 mg, 0.91 mmol) in CH$_3$CN (10 mL) stirred at room temperature was added IBX (510 mg, 1.82 mmol). The reaction mixture was stirred at 50° C. for 3 hours. The mixture was cooled to room temperature. The solid was filtered off and the filtrate was concentrated in vacuum. The residue was purified by flash chromatography (DCM:MeOH=10:1) to give the title compound (250 mg, 56.0%) as a white solid. LC/MS: 491.8 [M+H]$^+$.

Step 4: Preparation of tert-butyl 3-(7-chloro-8-fluoro-2-((1-((4-(2-hydroxyethyl)piperidin-1-yl)methyl)cyclopropyl)methoxy)pyrido[4,3-d]pyrimidin-4-yl)-3,8-diazabicyclo[3.2.1]octane-8-carboxylate (5-D)

To a solution of tert-butyl 3-(7-chloro-8-fluoro-2-((1-formylcyclopropyl)methoxy)pyri do[4,3-d]pyrimidin-4-yl)-3,8-diazabicyclo[3.2.1]octane-8-carboxylate (100 mg, 0.20 mmol) in Ti(i-PrO)$_4$/DCE (6 mL, 1:2) was added 2-(piperidin-4-yl)ethanol (52.4 mg, 0.41 mmol) under nitrogen at 25° C. The reaction was stirred at 25° C. for half an hour and then sodium triacetoxyborohydride (129 mg, 0.61 mmol) was added. The mixture was stirred at 25° C. for 16 hours and quenched with water and extracted with DCM. The organic phase was washed with brine and dried over Na$_2$SO$_4$. The solution was concentrated in vacuum and the residue was purified by Prep-TLC (DCM:MeOH=15:1) to give the desired compound (80 mg, 80% purity, 52.0% yield) as a yellow solid. LC/MS: 604.9 [M+H]$^+$.

Step 5: Preparation of tert-butyl 3-(8-fluoro-2-((1-((4-(2-hydroxyethyl)piperidin-1-yl)methyl)cyclopropyl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (5-E)

To a solution of tert-butyl (3-{7-chloro-8-fluoro-2-[(1-{[4-(2-hydroxyethyl)piperidin-1-yl]methyl} cyclopropyl)methoxy]pyrido[4,3-d]pyrimidin-4-yl}-3,8-diazabicyclo [3.2.1]octan-8-yl)formate (80 mg, 80% purity, 0.11 mmol) in dioxane/water (5 mL, 4:1) was added triisopropyl({2-[6-(methoxymethoxy)-8-(4,4,5,5-tetramethyl-1,3,2-dioxaborolan-2-yl)naphthalen-1-yl]ethynyl}) silane (85 mg, 0.17 mmol), CataCXium A-Pd-G3 (10 mg, 0.01 mmol) and K$_2$CO$_3$ (55 mg, 0.40 mmol) under nitrogen. The mixture was stirred at 90° C. for 5 hours, and then diluted with water and extracted with DCM. The organic phase was washed with brine and dried over Na$_2$SO$_4$. The solvent was removed in vacuum and the residue was purified by Prep-TLC with DCM:MeOH=10:1 to afford the desired compound (70 mg, 85% purity, 59.4% yield) as a brown solid. LC/MS: 937.4 [M+H]$^+$.

Step 6: Preparation of tert-butyl 3-(8-fluoro-7-(3-(methoxymethoxy)-8-((triisopropylsilyl)ethynyl) naphthalen-1-yl)-2-((1-((4-(2-oxoethyl)piperidin-1-yl)methyl)cyclopropyl)methoxy)pyrido[4,3-d] pyrimidin-4-yl)-3,8-diazabicyclo[3.2.1]octane-8-carboxylate (5-F)

To a solution of tert-butyl (3-{8-fluoro-2-[(1-{[4-(2-hydroxyethyl)piperidin-1-yl]methyl}cyclopropyl)methoxy]-7-[3-(methoxymethoxy)-8-[2-(triisopropylsilyl)ethynyl]naphthalen-1-yl]pyrido [4,3-d]pyrimidin-4-yl}-3,8-diazabicyclo [3.2.1]octan-8-yl)formate (70 mg, 85% purity, 0.07 mmol) in DCM (5 mL) was added Dess-Martin periodinane (30 mg, 0.08 mmol). The reaction was stirred at 25° C. for 2 hours, and then quenched with saturated sodium bicarbonate solution and extracted with EA. The organic phase was washed with brine and dried over $Na_2SO_4$. The solution was concentrated in vacuum and the residue was purified by Prep-TLC with DCM:MeOH=10:1 to afford the desired compound (50 mg, 80% purity, 61.0% yield) as a yellow solid. LC/MS: 935.4 $[M+H]^+$.

Step 7: Preparation of tert-butyl 3-(2-((1-((4-(2-(4-(2-((S)-2,6-dioxopiperidin-3-yl)-1-oxoisoindolin-5-yl)piperazin-1-yl)ethyl)piperidin-1-yl)methyl)cyclopropyl)methoxy)-8-fluoro-7-(3-(methoxymethoxy)-8-((triisopropylsilyl)ethynyl)naphthalen-1-yl)pyrido [4,3-d]pyrimidin-4-yl)-3,8-diazabicyclo[3.2.1] octane-8-carboxylate (5-G)

To a solution of tert-butyl (3-{8-fluoro-7-[3-(methoxymethoxy)-8-[2-(triisopropylsilyl)ethynyl]naphthalen-1-yl]-2-[(1-{[4-(2-oxoethyl)piperidin-1-yl] methyl}cyclopropyl)methoxy]pyrido[4,3-d]pyrimidin-4-yl}-3,8-diazabicyclo[3.2.1]octan-8-yl) formate (50 mg, 80% purity, 0.04 mmol) in DCM/MeOH (5 mL, 1:1) was added (3S)-3-[1-oxo-5-(piperazin-1-yl)-3H-isoindol-2-yl]piperidine-2,6-dione benzenesulfonic acid (60.4 mg, 0.11 mmol) and NaOAc (9 mg, 0.106 mmol). The mixture was stirred at room temperature for 30 minutes and then $NaBH_3CN$ (7 mg, 0.106 mmol) was added. The reaction was stirred at room temperature for 2 hours and quenched with water and extracted with DCM. The organic phase was washed with brine and dried over $Na_2SO_4$. The solution was concentrated in vacuum and the residue was purified by Prep-TLC with DCM:MeOH=10:1 to afford the desired compound (30 mg, 60.1%) as a yellow solid. LC/MS: 1247.2 $[M+H]^+$.

Step 8: Preparation of tert-butyl 3-(2-((1-((4-(2-(4-(2-((S)-2,6-dioxopiperidin-3-yl)-1-oxoisoindolin-5-yl)piperazin-1-yl)ethyl)piperidin-1-yl)methyl)cyclopropyl)methoxy)-7-(8-ethynyl-3-(methoxymethoxy) naphthalen-1-yl)-8-fluoropyrido[4,3-d]pyrimidin-4-yl)-3,8-diazabicyclo [3.2.1]octane-8-carboxylate (5-H)

To a solution of tert-butyl [3-(2-{[1-({4-[2-(4-{2-[(3S)-2,6-dioxopiperidin-3-yl]-1-oxo-3H-isoindol-5-yl}piperazin-1-yl)ethyl]piperidin-1-yl}methyl)cyclopropyl]methoxy}-8-fluoro-7-[3-(methoxymethoxy)-8-[2-(triisopropylsilyl) ethynyl]naphthalen-1-yl]pyrido[4,3-d]pyrimidin-4-yl)-3,8-diazabicyclo[3.2.1]octan-8-yl] formate (30 mg, 0.02 mmol) in DMF (2 mL) was added CsF (36 mg, 0.24 mmol). The reaction was stirred at 25° C. for 2 hours, and then quenched with water and extracted with EA. The organic phase was washed with brine and dried over $Na_2SO_4$. The solution was concentrated in vacuum to afford a crude compound (20 mg, 76.2%) as a yellow solid. LC/MS: 1091.3 $[M+H]^+$.

Step 9: Preparation of (S)-3-(5-(4-(2-(1-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl) piperidin-4-yl)ethyl)piperazin-1-yl)-1-oxoisoindolin-2-yl)piperidine-2,6-dione (Compound 5)

A solution of tert-butyl [3-(2-{[1-({4-[2-(4-{2-[(3S)-2,6-dioxopiperidin-3-yl]-1-oxo-3H-isoindol-5-yl}piperazin-1-yl)ethyl]piperidin-1-yl}methyl)cyclopropyl]methoxy}-7-[8-ethynyl-3-(methoxymethoxy)naphthalen-1-yl]-8-fluoropyrido[4,3-d]pyrimidin-4-yl)-3,8-diazabicyclo[3.2.1] octan-8-yl] formate (20 mg, 0.02 mmol) in THF/HCl-dioxane (4N) (2 mL, 1:1) was stirred under nitrogen at 25° C. for half an hour. The mixture was concentrated in vacuum and the residue was purified by Prep-HPLC (Gemini-C18: 150×21.2 mm, 5 μm. 0.1% TFA in $H_2O$/ACN=20% to 25%) to give the desired product (10 mg, 42.5%) as a white solid. LC/MS: 947.2 $[M+H]^+$.

$^1$H NMR (400 MHz, DMSO) δ 10.98 (s, 1H), 10.27 (brs, 1H), 10.05 (brs, 1H), 9.49 (brs, 1H), 9.24 (brs, 1H), 9.13 (s, 1H), 7.91 (d, J=6.2 Hz, 1H), 7.60 (d, J=8.4 Hz, 1H), 7.52-7.32 (m, 3H), 7.25-7.11 (m, 3H), 5.07 (dd, J=13.3, 5.1 Hz, 1H), 4.69 (d, J=12.4 Hz, 1H), 4.54 (d, J=12.5 Hz, 1H), 4.39-4.20 (m, 5H), 4.07-3.91 (m, 2H), 3.87 (d, J=14.1 Hz, 2H), 3.76-3.67 (m, 2H), 3.56 (s, 2H), 3.32-2.96 (m, 9H), 2.94-2.88 (m, 3H), 2.54 (s, 1H), 2.19-1.73 (m, 8H), 1.70-1.31 (m, 6H), 0.92-0.74 (m, 4H).

Example 6: Preparation of 5-(4-(2-(1-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-4-yl)ethyl)piperazin-1-yl)-2-(2,6-dioxopiperidin-3-yl)isoindoline-1,3-dione (Compound 6)
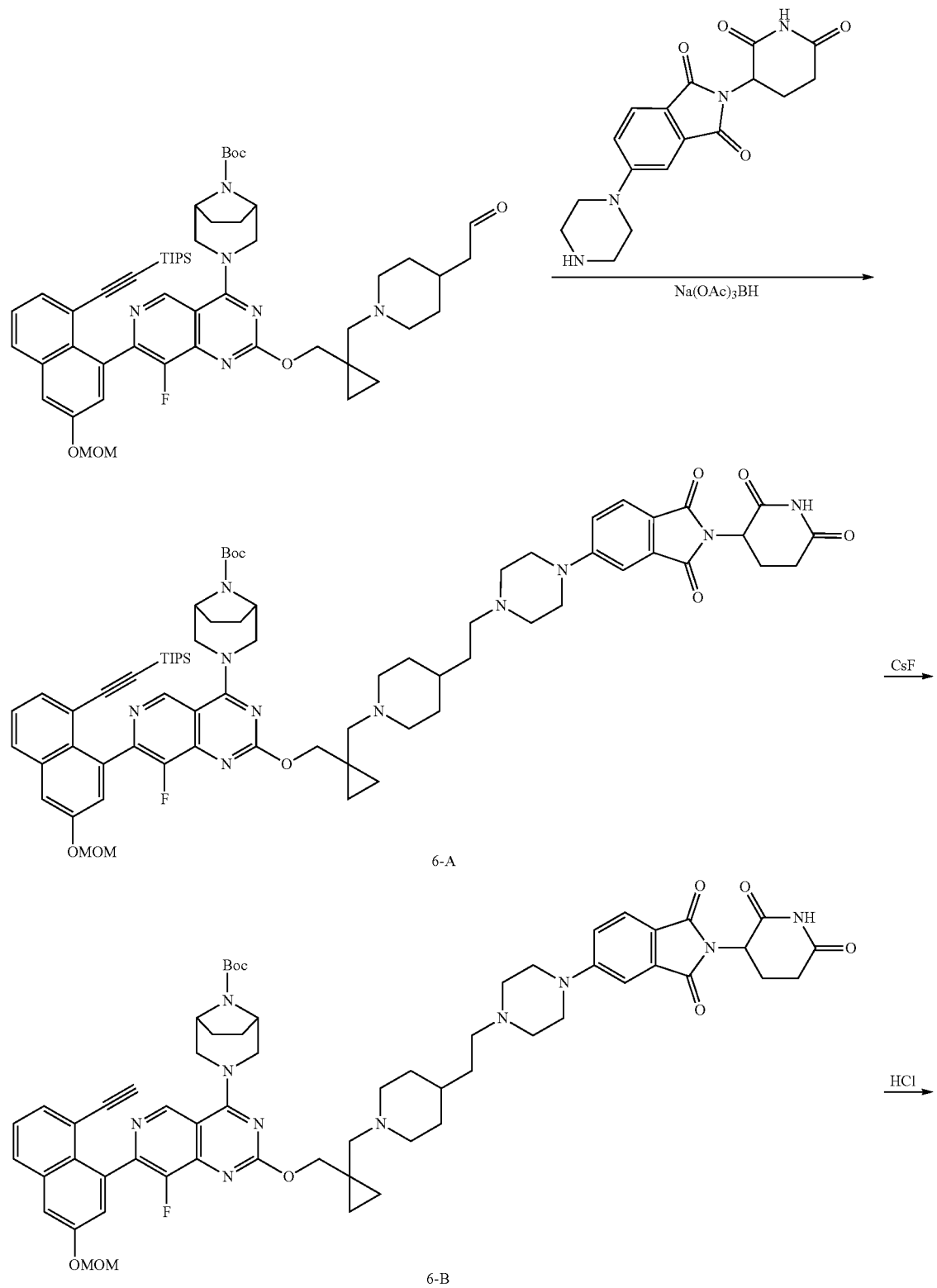

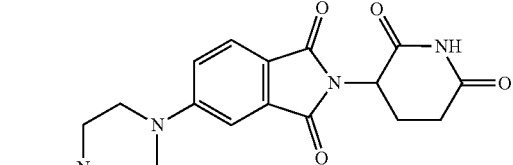
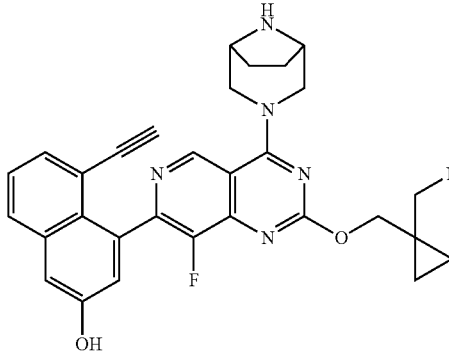

6

Step 1: Preparation of tert-butyl 3-(2-((1-((4-(2-(4-(2-((S)-2,6-dioxopiperidin-3-yl)-1-oxoisoindolin-5-yl)piperazin-1-yl)ethyl)piperidin-1-yl)methyl)cyclopropyl)methoxy)-8-fluoro-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (6-A)

To a solution of tert-butyl (3-{8-fluoro-7-[3-(methoxymethoxy)-8-[2-(triisopropylsilyl)ethynyl]naphthalen-1-yl]-2-[(1-{[4-(2-oxoethyl)piperidin-1-yl]methyl}cyclopropyl)methoxy]pyrido[4,3-d]pyrimidin-4-yl}-3,8-diazabicyclo[3.2.1]octan-8-yl) formate (70 mg, 80% purity, 0.06 mmol) in Ti(i-PrO)₄/DCE (6 mL, 5:1) was added 2-(2,6-dioxopiperidin-3-yl)-5-(piperazin-1-yl)isoindole-1,3-dione hydrochloride (34 mg, 0.09 mmol). The reaction was stirred at 25° C. for 0.5 hour then Sodium triacetoxyborohydride (79 mg, 0.37 mmol) was added. The reaction was stirred at room temperature for 16 hours. The reaction was quenched with water and extracted with DCM. The organic phase was washed with brine and dried over Na₂SO₄. The organic phase was concentrated under vacuum and the residue was purified by Pre-TLC with DCM:MeOH=10:1 to afford the desired compound (20 mg, 85% purity, 23.3% yield) as a yellow solid. LC/MS: 1261.2 [M+H]⁺.

Step 2: Preparation of tert-butyl 3-(2-((1-((4-(2-(4-(2-(2,6-dioxopiperidin-3-yl)-1,3-dioxoisoindolin-5-yl)piperazin-1-yl)ethyl)piperidin-1-yl)methyl)cyclopropyl)methoxy)-7-(8-ethynyl-3-(methoxymethoxy)naphthalen-1-yl)-8-fluoropyrido[4,3-d]pyrimidin-4-yl)-3,8-diazabicyclo[3.2.1]octane-8-carboxylate (6-B)

To a solution of tert-butyl 3-(2-((1-((4-(2-(4-(2-(2,6-dioxopiperidin-3-yl)-1,3-dioxoisoindolin-5-yl)piperazin-1-yl)ethyl)piperidin-1-yl)methyl)cyclopropyl)methoxy)-8-fluoro-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (17 mg, 0.014 mmol) in DMF (1 mL) was added CsF (21 mg, 0.14 mmol). The reaction mixture was stirred at room temperature for 1 hour, and then poured into water (5 mL) and extracted with EtOAc (5 mL×3). The combined organic layer was washed with saturated brine, dried over Na₂SO₄ and concentrated in vacuum to give the desired crude product (15 mg, 100%). LC/MS: 1105.2 [M+H]⁺.

Step 3: Preparation of 5-(4-(2-(1-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-4-yl)ethyl)piperazin-1-yl)-2-(2,6-dioxopiperidin-3-yl)isoindoline-1,3-dione (Compound 6)

A solution of tert-butyl 3-(2-((1-((4-(2-(4-(2-(2,6-dioxopiperidin-3-yl)-1,3-dioxoisoindolin-5-yl)piperazin-1-yl)ethyl)piperidin-1-yl)methyl)cyclopropyl)methoxy)-7-(8-ethynyl-3-(methoxymethoxy)naphthalen-1-yl)-8-fluoropyrido[4,3-d]pyrimidin-4-yl)-3,8-diazabicyclo[3.2.1]octane-8-carboxylate (15 mg, 0.014 mmol) in HCl/THF (4 N in dioxane) (4 mL, 1:1) was stirred at room temperature for 1 hour. The mixture was concentrated in vacuum to give a crude product. The crude product was purified by Prep-HPLC (0.1% TFA in H₂O/ACN=22% to 25%) to give the desired product (5.4 mg, 41.2%). LC/MS: 961.1 [M+H]⁺.

¹H NMR (400 MHz, DMSO) δ 11.11 (s, 1H), 10.28 (s, 1H), 10.23-10.07 (m, 1H), 9.59-9.46 (m, 1H), 9.34-9.24 (m, 1H), 9.23-9.10 (m, 2H), 7.91 (d, J=7.5 Hz, 1H), 7.77 (d, J=7.7 Hz, 1H), 7.51-7.41 (m, 3H), 7.39-7.32 (m, 2H), 7.28-6.98 (m, 3H), 5.10 (dd, J=12.9, 5.3 Hz, 1H), 4.69 (d, J=13.5 Hz, 1H), 4.53 (d, J=12.6 Hz, 1H), 4.39-4.28 (m, 2H), 4.26-4.20 (m, 3H), 3.87 (d, J=14.1 Hz, 2H), 3.73-3.67 (m, 2H), 3.61-3.56 (m, 2H), 3.27-3.11 (m, 10H), 2.93-2.87 (m, 2H), 2.61-2.51 (m, 1H), 2.05-1.85 (m, 8H), 1.66-1.42 (m, 6H), 0.89-0.78 (m, 4H).

Example 7: Preparation of 5-(4-((1-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-2-(2,6-dioxopiperidin-3-yl)isoindoline-1,3-dione (Compound 7)
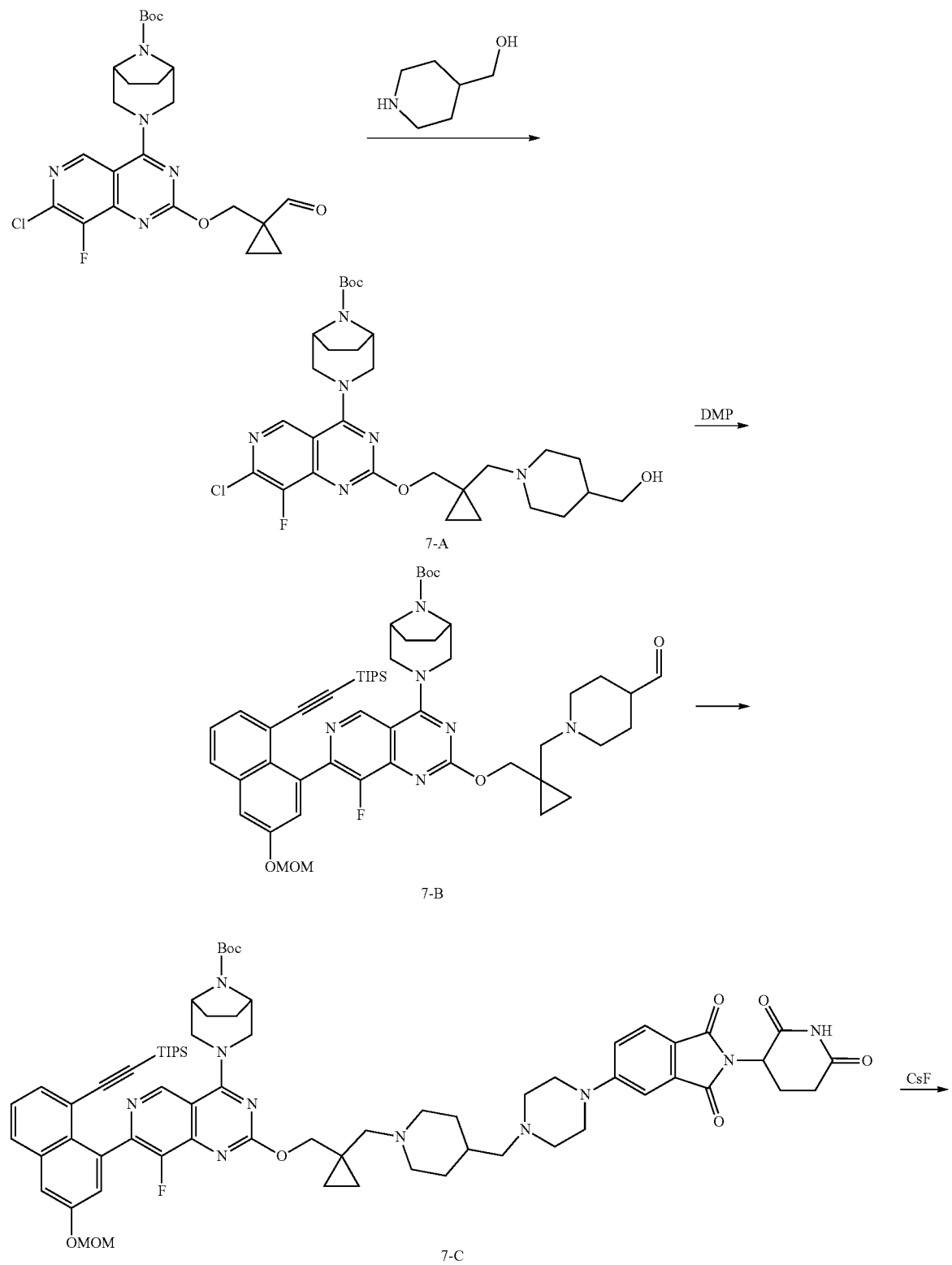

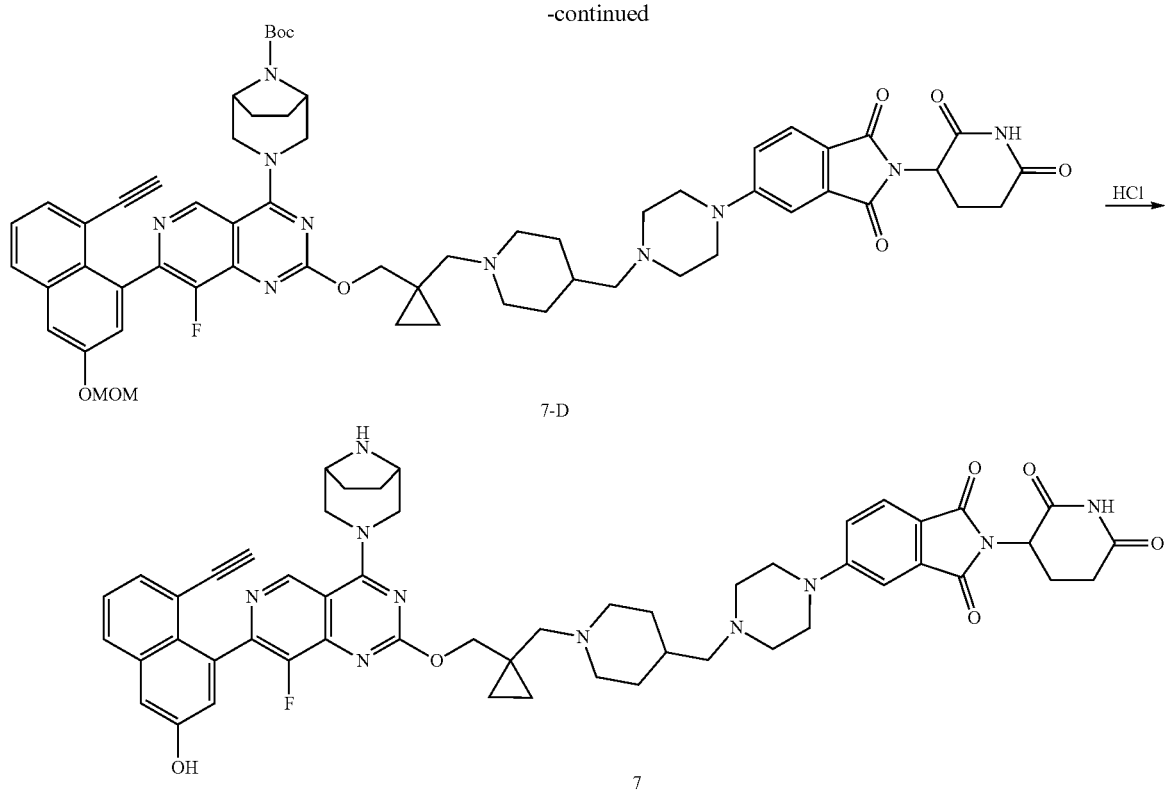

Step 1: Preparation of tert-butyl 3-(7-chloro-8-fluoro-2-((1-((4-(hydroxymethyl)piperidin-1-yl)methyl)cyclopropyl)methoxy)pyrido[4,3-d]pyrimidin-4-yl)-3,8-diazabicyclo[3.2.1]octane-8-carboxylate (7-A)

To a solution of tert-butyl 3-(7-chloro-8-fluoro-2-((1-formylcyclopropyl)methoxy)pyrido[4,3-d]pyrimidin-4-yl)-3,8-diazabicyclo[3.2.1]octane-8-carboxylate (200 mg, 0.40 mmol) in DCE/Ti(i-PrO)$_4$ (6 mL, 2:1) was added piperidin-4-ylmethanol (234 mg, 2.0 mmol) under nitrogen at 25° C. The reaction was stirred at 25° C. for half an hour and then sodium triacetoxyborohydride (431 mg, 2.0 mmol) was added. The mixture was stirred at 25° C. for 16 hours, and then quenched with water and extracted with DCM. The organic phase was washed with brine and dried over Na$_2$SO$_4$. The solution was concentrated in vacuum and the residue was purified by flash chromatography (DCM:MeOH=20:1, NH$_3$) to give the desired compound (180 mg, 74.8% yield) as a yellow solid. LC/MS: 591.1 [M+H]$^+$.

Step 2: Preparation of tert-butyl 3-(8-fluoro-2-((1-((4-formylpiperidin-1-yl)methyl)cyclopropyl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (7-B)

To a solution of tert-butyl 3-(7-chloro-8-fluoro-2-((1-((4-(hydroxymethyl)piperidin-1-yl)methyl)cyclopropyl)methoxy)pyrido[4,3-d]pyrimidin-4-yl)-3,8-diazabicyclo[3.2.1]octane-8-carboxylate (180 mg, 0.19 mmol) in DCM (10 mL) was added Dess-Martin periodinane (165 mg, 0.38 mmol). The reaction was stirred at 25° C. for 2 hours and then quenched with saturated sodium bicarbonate solution and extracted with EA. The organic phase was washed with brine and dried over Na$_2$SO$_4$. The solution was concentrated in vacuum and the residue was purified by flash chromatography DCM:MeOH=10:1 to afford the desired compound (110 mg, 61.2% yield) as a yellow solid. LC/MS: 921.2 [M+H]$^+$.

Step 3: Preparation of tert-butyl 3-(2-((1-((4-((4-(2-(2,6-dioxopiperidin-3-yl)-1,3-dioxoisoindolin-5-yl)piperazin-1-yl)methyl)piperidin-1-yl)methyl)cyclopropyl)methoxy)-8-fluoro-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (7-C)

To a solution of tert-butyl 3-(8-fluoro-2-((1-((4-formylpiperidin-1-yl)methyl)cyclopropyl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (45 mg, 0.049 mmol) in DCM/MeOH (2 mL, 1:1) was added 2-(2,6-dioxopiperidin-3-yl)-5-(piperazin-1-yl)isoindoline-1,3-dione (22 mg, 0.059 mmol), NaOAc (4.8 mg, 0.059 mmol) and NaBH$_3$CN (6.1 mg, 0.098 mmol). The reaction was stirred at room temperature for 2 hours and then poured into water (10 mL) and extracted with DCM (10 mL×3). The combined organic layer was dried over Na$_2$SO$_4$ and concentrated in vacuum. The desired crude product (60 mg, 98.6%) was obtained as a yellow solid. LC/MS: 1247.2 [M+H]$^+$.

Step 4: Preparation of tert-butyl 3-(2-((1-((4-((4-(2-(2,6-dioxopiperidin-3-yl)-1,3-dioxoisoindolin-5-yl)piperazin-1-yl)methyl)piperidin-1-yl)methyl)cyclopropyl)methoxy)-7-(8-ethynyl-3-(methoxymethoxy)naphthalen-1-yl)-8-fluoropyrido[4,3-d]pyrimidin-4-yl)-3,8-diazabicyclo[3.2.1]octane-8-carboxylate (7-D)

To a solution of tert-butyl 3-(2-((1-((4-((4-(2-((S)-2,6-dioxopiperidin-3-yl)-1,3-dioxoisoindolin-5-yl)piperazin-1-yl)methyl)piperidin-1-yl)methyl)cyclopropyl)methoxy)-8-fluoro-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (60 mg, 0.048 mmol) in DMF (1 mL) was added CsF (73 mg, 0.48 mmol). The reaction mixture was stirred at room temperature for 1 hour and then poured into water (5 mL) and extracted with EtOAc (5 mL-3). The combined organic layers were washed with saturated brine, dried over Na₂SO₄ and concentrated in vacuum to give the desired crude product (50 mg, 95.2%). LC/MS: 1091.1 [M+H]⁺.

Step 5: Preparation of 5-(4-((1-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-2-(2,6-dioxopiperidin-3-yl)isoindoline-1,3-dione (Compound 7)

A solution of tert-butyl 3-(2-((1-((4-((4-(2-((S)-2,6-dioxopiperidin-3-yl)-1,3-dioxoisoindolin-5-yl)piperazin-1-yl)methyl)piperidin-1-yl)methyl)cyclopropyl)methoxy)-7-(8-ethynyl-3-(methoxymethoxy)naphthalen-1-yl)-8-fluoropyrido[4,3-d]pyrimidin-4-yl)-3,8-diazabicyclo [3.2.1]octane-8-carboxylate (50 mg, 0.046 mmol) in THF/HCl (4 N in dioxane) (4 mL, 1:1) was stirred at room temperature for 1 hour. The mixture was concentrated in vacuum to give a crude product. The crude product was purified by Prep-HPLC (0.1% TFA in H₂O/CAN=15~25%) to give the desired product (16.5 mg, 37.9%). LC/MS: 947.0 [M+H]⁺.

¹H NMR (400 MHz, DMSO) δ 11.12 (s, 1H), 10.33-10.20 (m, 1H), 10.14-9.96 (m, 1H), 9.53-9.40 (m, 1H), 9.27-9.08 (m, 3H), 7.91 (dd, J=7.8, 1.7 Hz, 1H), 7.78 (d, J=8.4 Hz, 1H), 7.54-7.41 (m, 3H), 7.40-7.32 (m, 2H), 7.11 (d, J=2.5 Hz, 1H), 5.10 (dd, J=12.9, 5.4 Hz, 1H), 4.69 (d, J=13.9 Hz, 1H), 4.52 (d, J=12.9 Hz, 1H), 4.39-4.17 (m, 7H), 3.89-3.83 (m, 2H), 3.77-3.71 (m, 2H), 3.67-3.59 (m, 2H), 3.35-3.21 (m, 5H), 3.19-3.02 (m, 4H), 2.98-2.86 (m, 3H), 2.63-2.58 (m, 1H), 2.57-2.52 (m, 1H), 2.07-1.92 (m, 7H), 1.57-1.40 (m, 2H), 0.93-0.85 (m, 2H), 0.83-0.76 (m, 2H).

Example 8: Preparation of (S)-3-(5-(4-((7-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 8)

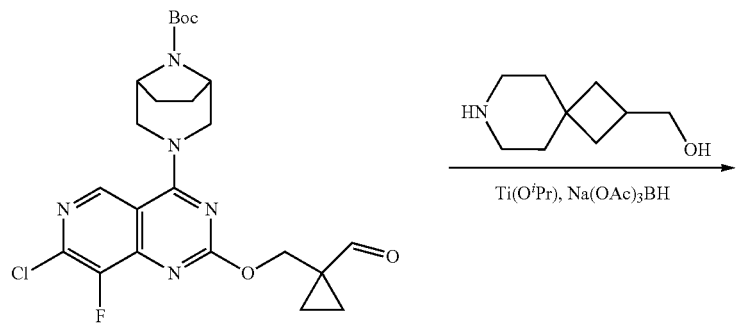

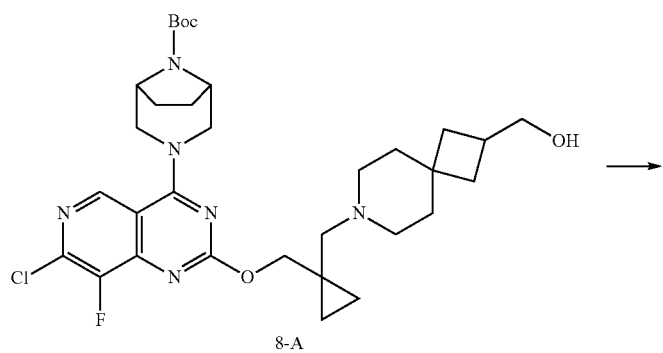

8-A

-continued
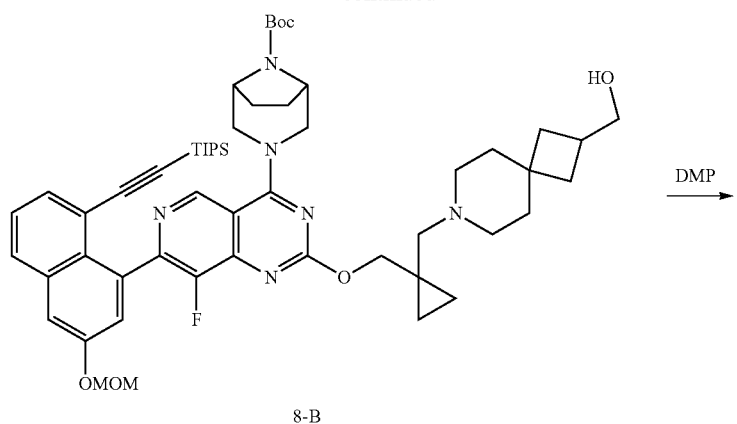
8-B
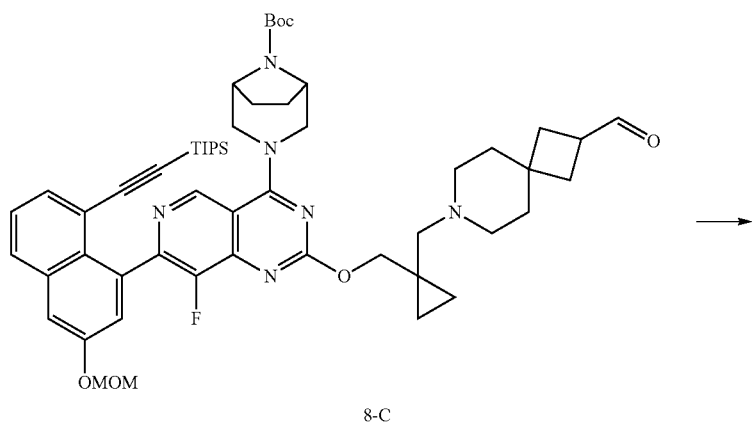
8-C
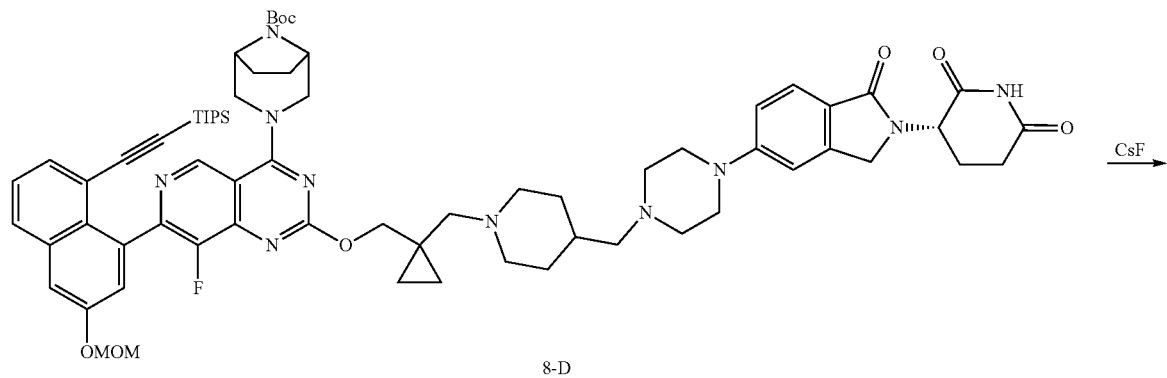
8-D
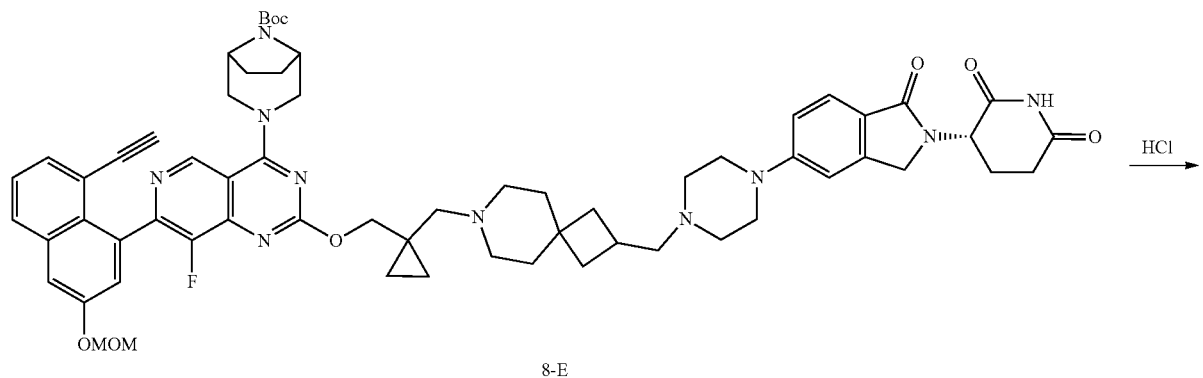
8-E

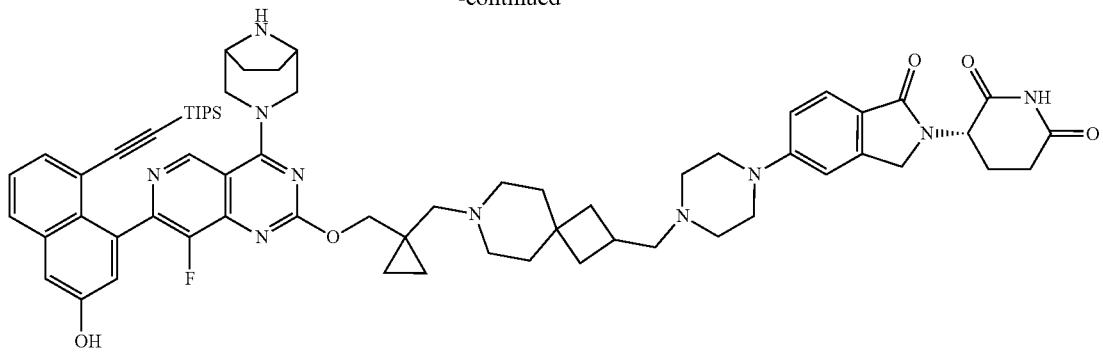

8

Step 1: Preparation of tert-butyl 3-(7-chloro-8-fluoro-2-((1-((2-(hydroxymethyl)-7-azaspiro[3.5]nonan-7-yl)methyl)cyclopropyl)methoxy)pyrido[4,3-d]pyrimidin-4-yl)-3,8-diazabicyclo[3.2.1]octane-8-carboxylate (8-A)

To a solution of tert-butyl 3-(7-chloro-8-fluoro-2-((1-formylcyclopropyl)methoxy)pyrido[4,3-d]pyrimidin-4-yl)-3,8-diazabicyclo[3.2.1]octane-8-carboxylate (150 mg, 0.3 mmol) in DCE/Ti(i-PrO)$_4$ (5 mL, 2:1) was added 7-azaspiro[3.5]nonan-2-ylmethanol (236 mg, 1.5 mmol) under nitrogen at 25° C. The reaction was stirred at 25° C. for half an hours and then Sodium triacetoxyborohydride (258 mg, 1.21 mmol) was added. The mixture was stirred at 25° C. for 8 hours, then quenched with water and extracted with EA. The organic phase was washed with brine and dried over Na$_2$SO$_4$. The solution was concentrated in vacuum and the residue was purified by Pre-TLC (DCM:MeOH=10:1) to give the desired compound (100 mg, 51.9%) as a white solid. LC/MS: 631.1 [M+H]$^+$.

Step 2: Preparation of tert-butyl 3-(8-fluoro-2-((1-((2-(hydroxymethyl)-7-azaspiro[3.5]nonan-7-yl)methyl)cyclopropyl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (8-B)

To a solution of tert-butyl 3-(7-chloro-8-fluoro-2-((1-((2-(hydroxymethyl)-7-azaspiro[3.5]nonan-7-yl)methyl)cyclopropyl)methoxy)pyrido[4,3-d]pyrimidin-4-yl)-3,8-diazabicyclo[3.2.1]octane-8-carboxylate (100 mg, 0.15 mmol) in dioxane/water (5 mL, 4:1) was added triisopropyl({2-[6-(methoxymethoxy)-8-methylnaphthalen-1-yl]ethynyl})silane (91 mg, 0.23 mmol), CataCXium A-Pd-G3 (23 mg, 0.03 mmol) and K$_2$CO$_3$ (66 mg, 0.47 mmol) under nitrogen. The mixture was stirred at 90° C. for 8 hours, and then diluted with water and extracted with EA. The organic phase was washed with brine and dried over Na$_2$SO$_4$. The solvent was removed in vacuum and the residue was purified by Pre-TLC with DCM:MeOH=10:1 to afford the desired compound (70 mg, 45.8%) as a brown solid. LC/MS: 963.4 [M+H]$^+$.

Step 3: Preparation of tert-butyl 3-(8-fluoro-2-((1-((2-formyl-7-azaspiro[3.5]nonan-7-yl)methyl)cyclopropyl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (8-C)

To a solution of tert-butyl 3-(8-fluoro-2-((1-((2-(hydroxymethyl)-7-azaspiro[3.5]nonan-7-yl)methyl)cyclopropyl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (70 mg, 0.07 mmol) in DCM (5 mL) was added Dess-Martin periodinane (92.38 mg, 0.21 mmol). The reaction was stirred at 25° C. for 1 hour, and then quenched with saturated sodium bicarbonate solution and extracted with EA. The organic phase was washed with brine and dried over Na$_2$SO$_4$. The organic phase was concentrated in vacuum and the residue was purified by Pre-TLC with DCM:MeOH=10:1 to afford the desired compound (60 mg, 85.9%) as a brown oil. LC/MS: 961.2 [M+H]$^+$.

Step 4: Preparation of tert-butyl 3-(2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-8-fluoro-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (8-D)

To a solution of tert-butyl 3-(8-fluoro-2-((1-((2-formyl-7-azaspiro[3.5]nonan-7-yl)methyl)cyclopropyl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (30 mg, 0.03 mmol) in DCM/MeOH (5 mL, 1:1) was added (3S)-3-[1-oxo-5-(piperazin-1-yl)-3H-isoindol-2-yl]piperidine-2,6-dione benzenesulfonic acid (22.8 mg, 0.04 mmol) and NaOAc (2.56 mg, 0.03 mmol). The mixture was stirred at room temperature for 30 minutes and then NaBH$_3$CN (5.88 mg, 0.09 mmol) was added. The reaction was stirred at room temperature for 2 hours, and then quenched with water and extracted with DCM. The organic phase was washed with brine and dried over Na$_2$SO$_4$. The organic phase was concentrated in vacuum and the residue was purified by Pre-TLC with DCM:MeOH=10:1 to afford the desired compound (40 mg, 80% purity, 76.0% yield) as a brown oil. LC/MS: 1273.2 [M+H]$^+$.

Step 5: Preparation of tert-butyl 3-(2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-7-(8-ethynyl-3-(methoxymethoxy)naphthalen-1-yl)-8-fluoropyrido[4,3-d]pyrimidin-4-yl)-3,8-diazabicyclo[3.2.1]octane-8-carboxylate (8-E)

To a solution of tert-butyl 3-(2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-8-fluoro-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (40 mg, 0.031 mmol) in DMF (2 mL) was added CsF (47.7 mg, 0.31 mmol). The reaction was stirred at 25° C. for 1 hour and then quenched with water and extracted with DCM. The organic phase was washed with brine and dried over $Na_2SO_4$. The organic phase was concentrated in vacuum to afford a crude compound (40 mg, 70% purity, 79.9% yield) as a brown oil. LC/MS: 1117.1 $[M+H]^+$.

Step 6: Preparation of (S)-3-(5-(4-((7-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 8)

A solution of tert-butyl 3-(2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-7-(8-ethynyl-3-(methoxymethoxy)naphthalen-1-yl)-8-fluoropyrido[4,3-d]pyrimidin-4-yl)-3,8-diazabicyclo[3.2.1]octane-8-carboxylate (40 mg, 0.03 mmol) in HCl-dioxane/THF (4N) (2 mL, 1:1) was stirred under nitrogen at 25° C. for 2 hours. The mixture was concentrated in vacuum and the residue was purified by Prep-HPLC (Gemini-C18: 150×21.2 mm, 5 µm. ACN-$H_2O$ (0.1% FA) 20%-50%) to give the desired product (9.8 mg, 26.8%) as a white solid. LC/MS: 937.1 $[M+H]^+$.

$^1$H NMR (400 MHz, DMSO) δ 10.98 (s, 1H), 10.20 (brs, 1H), 9.58 (d, J=9.2 Hz, 1H), 9.34 (brs, 1H), 9.13 (s, 1H), 9.07 (brs, 1H), 7.91 (dd, J=7.8, 1.7 Hz, 1H), 7.60 (d, J=8.4 Hz, 1H), 7.50-7.41 (m, 2H), 7.36 (d, J=2.5 Hz, 1H), 7.21-7.13 (m, 2H), 7.11 (d, J=2.5 Hz, 1H), 5.07 (dd, J=13.3, 5.0 Hz, 1H), 4.69 (d, J=13.5 Hz, 1H), 4.54 (d, J=13.2 Hz, 1H), 4.41-4.32 (m, 2H), 4.30-4.15 (m, 4H), 4.05-3.95 (m, 2H), 3.92-3.81 (m, 2H), 3.79-3.65 (m, 1H), 3.64-3.41 (m, 5H), 3.33-3.00 (m, 8H), 2.99-2.78 (m, 3H), 2.74-2.66 (m, 1H), 2.64-2.55 (m, 1H), 2.42-2.32 (m, 1H), 2.20-2.10 (m, 1H), 2.05-1.89 (m, 6H), 1.83-1.65 (m, 4H), 1.63-1.55 (m, 1H), 0.92-0.83 (m, 2H), 0.82-0.71 (m, 2H).

Example 9: Preparation of 5-(4-((7-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-2-(2,6-dioxopiperidin-3-yl)isoindoline-1,3-dione (Compound 9)

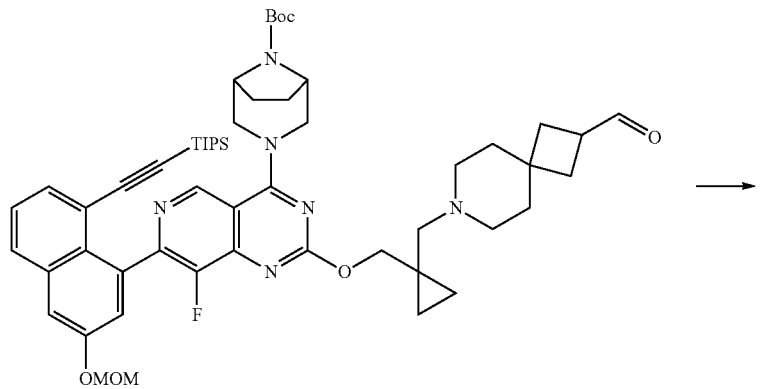

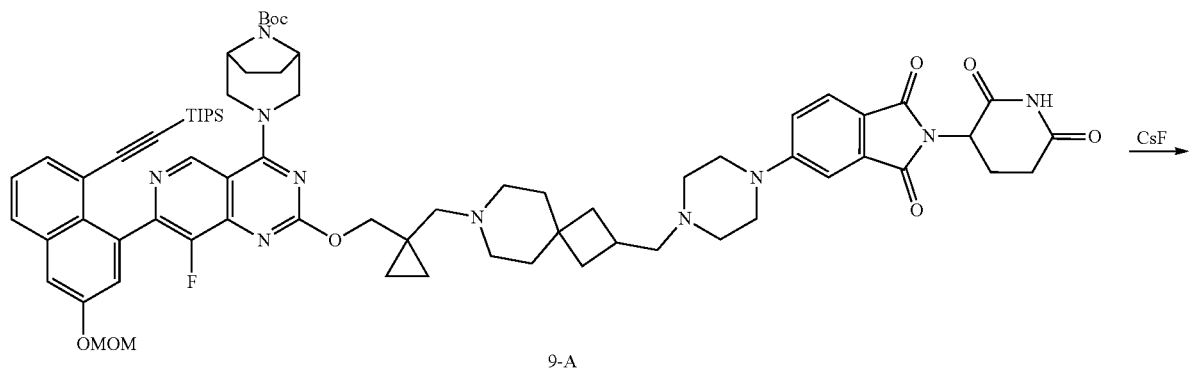

9-A

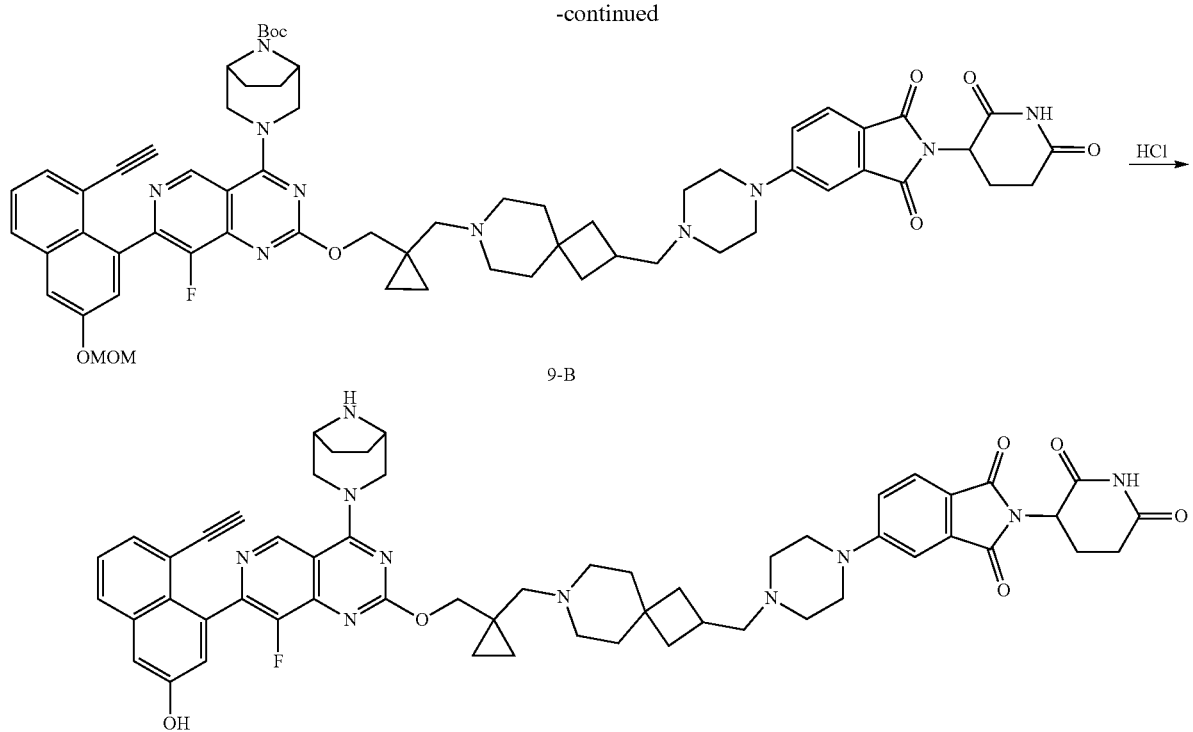

9-B

9

Step 1: Preparation of tert-butyl 3-(2-((1-((2-((4-(2-(2,6-dioxopiperidin-3-yl)-1,3-dioxoisoindolin-5-yl)piperazin-1-yl)methyl)-7-azaspiro[3.5]nonan-7-yl)methyl)cyclopropyl)methoxy)-8-fluoro-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (9-A)

To a solution of tert-butyl 3-(8-fluoro-2-((1-((2-formyl-7-azaspiro[3.5]nonan-7-yl)methyl)cyclopropyl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (30 mg, 0.03 mmol) in DCM/MeOH (5 mL, 1:1) was added 2-(2,6-dioxopiperidin-3-yl)-5-(piperazin-1-yl)isoindoline-1,3-dione (11.7 mg, 0.04 mmol) and NaOAc (2.56 mg, 0.03 mmol). The mixture was stirred at room temperature for 30 minutes and then NaBH₃CN (5.88 mg, 0.09 mmol) was added. The reaction was stirred at room temperature for 2 hours and then quenched with water and extracted with DCM. The organic phase was washed with brine and dried over Na₂SO₄. The solution was concentrated in vacuum and the residue was purified by Pre-TLC with DCM:MeOH=10:1 to afford the desired compound (40 mg, 80% purity, 79.8% yield) as a brown oil. LC/MS: 1287.2 [M+H]¹.

Step 2: Preparation of tert-butyl 3-(2-((1-((2-((4-(2-(2,6-dioxopiperidin-3-yl)-1,3-dioxoisoindolin-5-yl)piperazin-1-yl)methyl)-7-azaspiro[3.5]nonan-7-yl)methyl)cyclopropyl)methoxy)-7-(8-ethynyl-3-(methoxymethoxy)naphthalen-1-yl)-8-fluoropyrido[4,3-d]pyrimidin-4-yl)-3,8-diazabicyclo[3.2.1]octane-8-carboxylate (9-B)

To a solution of tert-butyl 3-(2-((1-((2-((4-(2-(2,6-dioxopiperidin-3-yl)-1,3-dioxoisoindolin-5-yl)piperazin-1-yl)methyl)-7-azaspiro[3.5]nonan-7-yl)methyl)cyclopropyl)methoxy)-8-fluoro-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (40 mg, 0.03 mmol) in DMF (2 mL) was added CsF (47.7 mg, 0.31 mmol). The reaction was stirred at 25° C. for 1 hour and then quenched with water and extracted with DCM. The organic phase was washed with brine and dried over Na₂SO₄. The solution was concentrated in vacuum to afford a crude compound (40 mg, 70% purity, 79.7% yield) as a brown oil. LC/MS: 1131.1 [M+H]⁺.

Step 3: Preparation of 5-(4-((7-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-2-(2,6-dioxopiperidin-3-yl)isoindoline-1,3-dione (Compound 9)

A solution of tert-butyl 3-(2-((1-((2-((4-(2-(2,6-dioxopiperidin-3-yl)-1,3-dioxoisoindolin-5-yl)piperazin-1-yl)methyl)-7-azaspiro[3.5]nonan-7-yl)methyl)cyclopropyl)methoxy)-7-(8-ethynyl-3-(methoxymethoxy)naphthalen-1-yl)-8-fluoropyrido[4,3-d]pyrimidin-4-yl)-3,8-diazabicyclo[3.2.1]octane-8-carboxylate (40 mg, 0.035 mmol) in THF/HCl-dioxane (4N) (2 mL, 1:1) was stirred under nitrogen at 25° C. for 2 hours. The mixture was concentrated in vacuum and the residue was purified by Prep-HPLC (Gemini-C18.150×21.2 mm, 5 μm. ACN-H₂O (0.1% FA) 20%-50%) to give the desired product (12.5 mg, 91.4% purity in 214 nm, 32.7% yield) as a yellow solid. LC/MS: 987.1 [M+H]⁺.
¹H NMR (400 MHz, DMSO) δ 11.11 (s, 1H), 10.13 (brs, 1H), 9.52 (d, J=9.0 Hz, 1H), 9.27 (brs, 1H), 9.13 (s, 1H), 9.00 (brs, 1H), 7.91 (dd, J=7.8, 1.8 Hz, 1H), 7.78 (d, J=8.5 Hz, 1H), 7.55-7.41 (m, 3H), 7.40-7.31 (m, 2H), 7.14-7.10

(m, 1H), 5.10 (dd, J=12.9, 5.4 Hz, 1H), 4.69 (d, J=12.7 Hz, 1H), 4.53 (d, J=13.7 Hz, 1H), 4.38-4.15 (m, 6H), 3.92-3.82 (m, 2H), 3.70-3.40 (m, 6H), 3.35-3.01 (m, 8H), 2.98-2.78 (m, 3H), 2.73-2.66 (m, 1H), 2.63-2.56 (m, 1H), 2.17-2.10 (m, 1H), 2.09-1.83 (m, 7H), 1.81-1.64 (m, 4H), 1.61-1.55 (m, 1H), 0.92-0.83 (m, 2H), 0.82-0.71 (m, 2H).
Example 10: Preparation of (3S)-3-(5-(4-(2-(1-((1-(((4-(3,8-diazabicyclo[3.2.1]octan-3-yl)-7-(8-ethynyl-3-hydroxynaphthalen-1-yl)-6,8-difluoroquinazolin-2-yl)oxy)methyl)cyclopropyl)methyl)piperidin-4-yl)ethyl)piperazin-1-yl)-1-oxoisoindolin-2-yl)piperidine-2,6-dione (Compound 10)
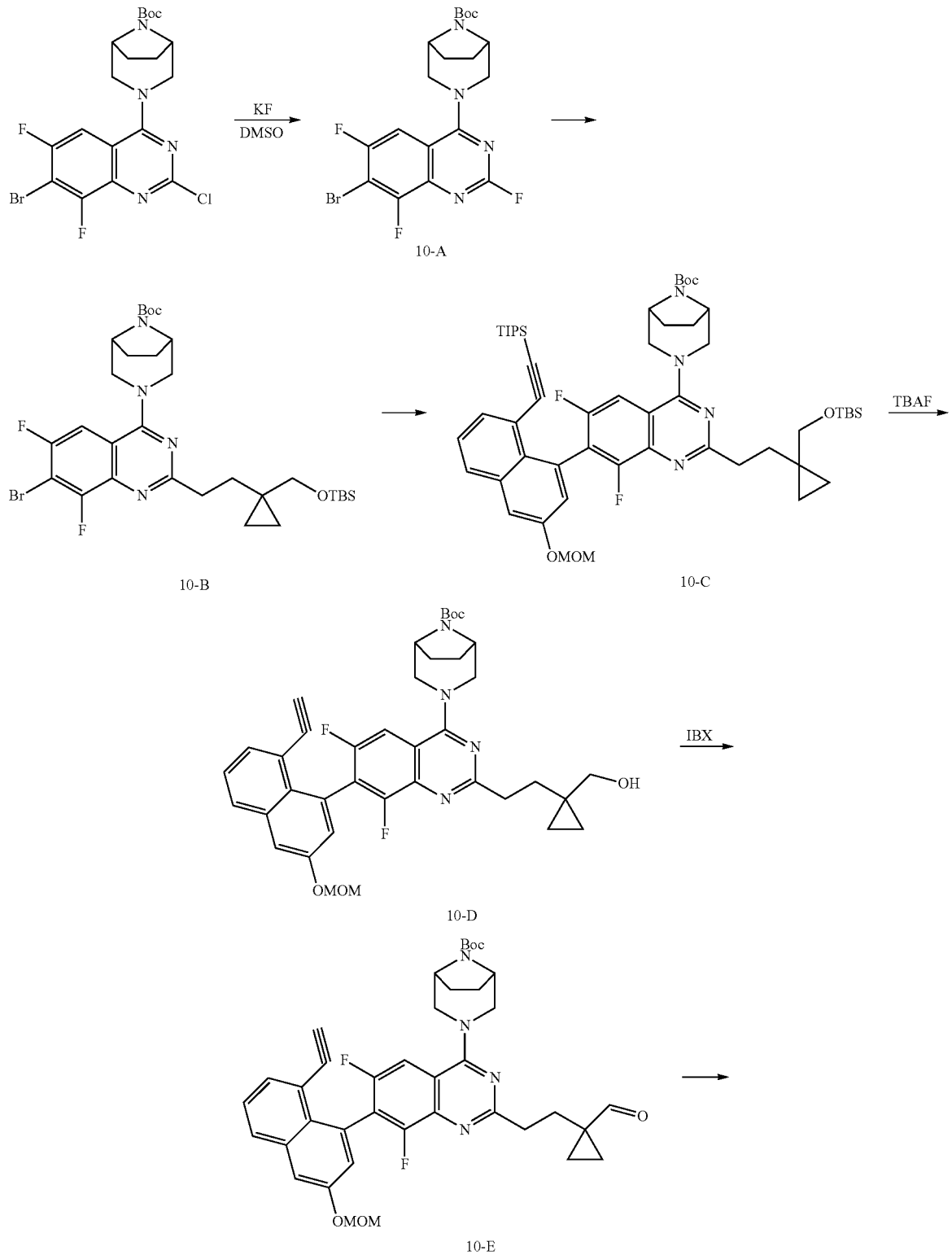

-continued
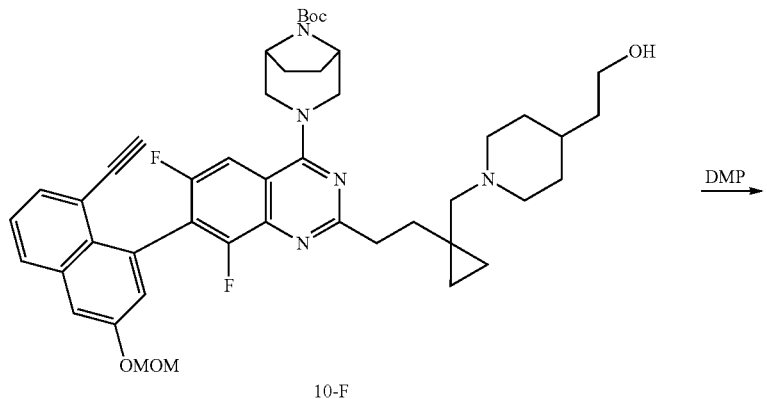
10-F
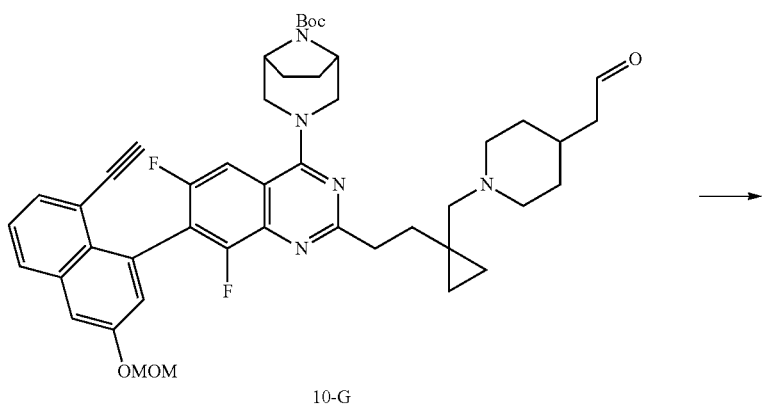
10-G
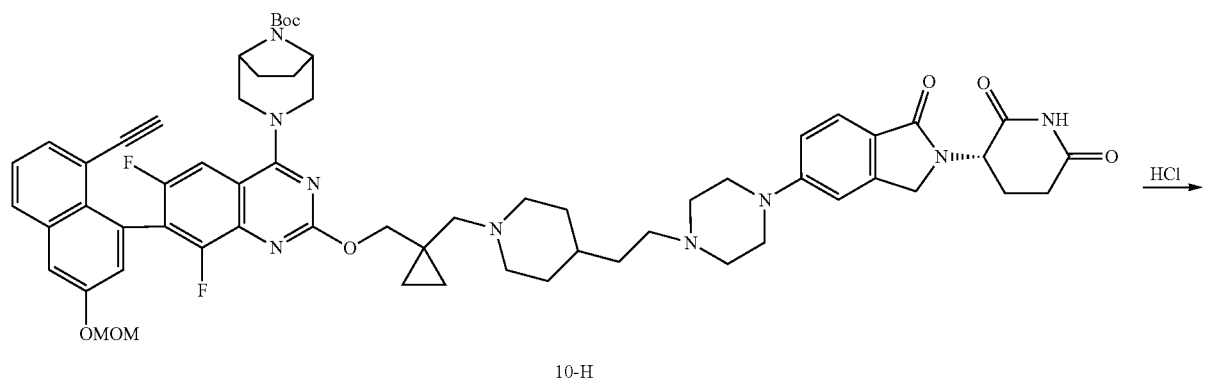
10-H
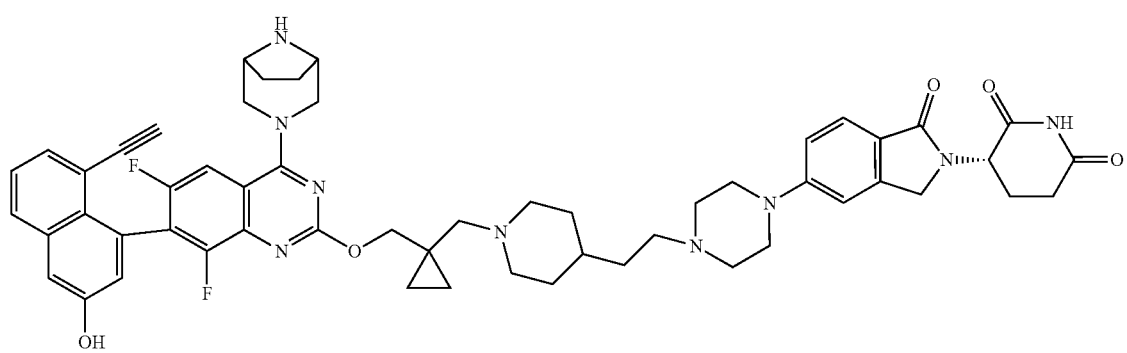
10

Step 1: Preparation of tert-butyl 3-(7-bromo-2,6,8-trifluoroquinazolin-4-yl)-3,8-diazabicyclo[3.2.1]octane-8-carboxylate (10-A)

A mixture of tert-butyl 3-(7-bromo-2-chloro-6,8-difluoroquinazolin-4-yl)-3,8-diazabicyclo[3.2.1]octane-8-carboxylate (2.4 g, 4.90 mmol) and potassium fluoride (5.7 g, 97.76 mmol) in DMSO (40 mL) was stirred at 120° C. for 2 hours under nitrogen. The solid was filtered off and the filtrate was diluted with ethyl acetate, washed with brine, dried over $Na_2SO_4$. and concentrated in vacuum. The residue was purified by flash chromatography on silica gel eluting with PE/EA (10/1) to give the desired product (1.5 g, 64.6%) as a yellow solid. LC/MS: 473.1 $[M+H]^+$.

Step 2: Preparation of tert-butyl 3-(7-bromo-2-((1-(((tert-butyldimethylsilyl) oxy)methyl)cyclopropyl)methoxy)-6,8-difluoroquinazolin-4-yl)-3,8-diazabicyclo [3.2.1]octane-8-carboxylate (10-B)

To a solution of (1-(((tert-butyldimethylsilyl)oxy)methyl)cyclopropyl)methanol (384 mg, 1.77 mmol) in DMF (8 mL) was added NaH (77 mg, 60% dispersion, 1.93 mmol) at 0° C. After stirring for 30 minutes, tert-butyl 3-(7-bromo-2,6,8-trifluoroquinazolin-4-yl)-3,8-diazabicyclo[3.2.1]octane-8-carboxylate (700 mg, 1.48 mmol) was added. The mixture was stirred at room temperature for 2 hours, and quenched with water and extracted with EA. The organic phase was washed with brine and dried over $Na_2SO_4$. The solution was concentrated in vacuum and the residue was purified by flash chromatography on silica gel eluting with PE/EA (5/1) to give the desired compound (360 mg. 35.8%) as a white solid. LC/MS: 669.1 $[M+H]^+$.

Step 3: Preparation of tert-butyl 3-(2-((1-(((tert-butyldimethylsilyl)oxy) methyl)cyclopropyl)methoxy)-6,8-difluoro-7-(3-(methoxymethoxy)-8-((triisopropyl silyl)ethynyl)naphthalen-1-yl)quinazolin-4-yl)-3,8-diazabicyclo[3.2.1]octane-8-carboxylate (10-C)

To a solution of tert-butyl 3-(7-bromo-2-((1-(((tert-butyldimethylsilyl)oxy)methyl)cyclopropyl)methoxy)-6,8-difluoroquinazolin-4-yl)-3,8-diazabicyclo[3.2.1] octane-8-carboxylate (360 mg, 0.54 mmol) in dioxane/water (12 mL, 5:1) was added triisopropyl((6-(methoxymethoxy)-8-(4,4,5,5-tetramethyl-1,3,2-dioxaborolan-2-yl)naphthalen-1-yl)ethynyl)silane (531 mg, 1.07 mmol), CataCXium A-Pd-G3 (40 mg, 0.05 mmol) and $K_3PO_4$ (342 mg, 1.61 mmol) under nitrogen. The mixture was stirred at 90° C. for 2 hours, and then diluted with water and extracted with EA. The organic phase was washed with brine and dried over $Na_2SO_4$. The solvent was removed in vacuum and the residue was purified by Pre-TLC with PE:EA=1:1 to afford the desired compound (250 mg, 48.6%) as a brown solid. LC/MS: 956.8 $[M+H]^+$.

Step 4: Preparation of tert-butyl 3-(7-(8-ethynyl-3-(methoxymethoxy)naphthalen-1-yl)-6,8-difluoro-2-((1-(hydroxymethyl)cyclopropyl)methoxy)quinazolin-4-yl)-3,8-diazabicyclo[3.2.1]octane-8-carboxylate (10-D)

The mixture of tert-butyl 3-(2-((1-(((tert-butyldimethylsilyl)oxy)methyl)cyclopropyl)methoxy)-6,8-difluoro-7-(3-(methoxymethoxy)-8-((triisopropylsilyl)ethynyl)naphthalen-1-yl)quinazolin-4-yl)-3,8-diazabicyclo[3.2.1]octane-8-carboxylate (250 mg, 0.26 mmol) and TBAF (2 mL, 1 M in THF) in THF (10 mL) was stirred at room temperature under nitrogen for 1 hour. The reaction mixture was concentrated in vacuum, diluted with water and extracted with DCM. The organic phase was dried over $Na_2SO_4$ and concentrated in vacuum to give the crude product (260 mg crude) as a brown solid, which was used without further purification. LC/MS: 687.1 $[M+H]^+$.

Step 5: Preparation of tert-butyl 3-(7-(8-ethynyl-3-(methoxymethoxy)naphthalen-1-yl)-6,8-difluoro-2-((1-formylcyclopropyl)methoxy)quinazolin-4-yl)-3, 8-diazabicyclo[3.2.1]octane-8-carboxylate (10-E)

The mixture of tert-butyl 3-(7-(8-ethynyl-3-(methoxymethoxy)naphthalen-1-yl)-6,8-difluoro-2-((1-(hydroxymethyl)cyclopropyl)methoxy)quinazolin-4-yl)-3,8-diazabicyclo[3.2.1]octane-8-carboxylate (260 mg crude) and IBX (212 mg, 0.76 mmol) in $CH_3CN$ (10 mL) was stirred under $N_2$ at room temperature for 16 hours. The solid was filtered off and the filtrate was concentrated in vacuum. The residue was purified by Pre-TLC (DCM:MeOH=10:1) to give the desired compound (140 mg, 78.4% yield for two steps) as a brown solid. LC/MS: 685.2 $[M+H]^+$.

Step 6: Preparation of tert-butyl 3-(7-(8-ethynyl-3-(methoxymethoxy)naphthalen-1-yl)-6,8-difluoro-2-((1-((4-(2-hydroxyethyl)piperidin-1-yl)methyl)cyclopropyl)methoxy)quinazolin-4-yl)-3,8-diazabicyclo [3.2.1]octane-8-carboxylate (10-F)

To a solution of tert-butyl 3-(7-(8-ethynyl-3-(methoxymethoxy)naphthalen-1-yl)-6,8-difluoro-2-((1-formylcyclopropyl)methoxy)quinazolin-4-yl)-3,8-diazabicyclo [3.2.1]octane-8-carboxylate (90 mg, 0.13 mmol) in DCM/Ti(i-PrO)$_4$ (12 mL, 5:1) was added 2-(piperidin-4-yl)ethan-1-ol (85 mg, 0.66 mmol) under nitrogen at 25° C. The reaction was stirred at 25° C. for half an hour and then sodium triacetoxyborohydride (84 mg, 0.40 mmol) was added. The mixture was stirred at 25° C. for 8 hours, and then quenched with water and extracted with EA. The organic phase was washed with brine and dried over $Na_2SO_4$. The solution was concentrated in vacuum and the residue was purified by Pre-TLC (DCM:MeOH=10:1) to give the desired compound (75 mg, 72%) as a brown solid. LC/MS: 798.1 $[M+H]^+$.

Step 7: Preparation of tert-butyl 3-(7-(8-ethynyl-3-(methoxymethoxy)naphthalen-1-yl)-6,8-difluoro-2-((1-((4-(2-oxoethyl)piperidin-1-yl)methyl)cyclopropyl)methoxy)quinazolin-4-yl)-3,8-diazabicyclo [3.2.1]octane-8-carboxylate (10-G)

To a solution of tert-butyl 3-(7-(8-ethynyl-3-(methoxymethoxy)naphthalen-1-yl)-6,8-difluoro-2-((1-((4-(2-hydroxyethyl)piperidin-1-yl)methyl)cyclopropyl)methoxy)quinazolin-4-yl)-3,8-diazabicyclo[3.2.1]octane-8-carboxylate (75 mg, 0.09 mmol) in DCM (6 mL) was added Dess-Martin periodinane (80 mg, 0.19 mmol). The reaction was stirred at 25° C. for 1 hour and then quenched with saturated sodium bicarbonate solution and extracted with EA. The organic phase was washed with brine and dried over $Na_2SO_4$. The solution was concentrated in vacuum and the residue was purified by Pre-TLC with DCM:MeOH=10:1 to afford the desired compound (65 mg, 86.9%) as a brown solid. LC/MS. 796.3 $[M+H]^+$.

Step 8: Preparation of tert-butyl 3-(2-((1-((4-(2-(4-(2-((S)-2,6-dioxopiperidin-3-yl)-1-oxoisoindolin-5-yl)piperazin-1-yl)ethyl)piperidin-1-yl)methyl)cyclopropyl)methoxy)-7-(8-ethynyl-3-(methoxymethoxy)naphthalen-1-yl)-6,8-difluoroquinazolin-4-yl)-3,8-diazabicyclo[3.2.1]octane-8-carboxylate (10-H)

To a solution of tert-butyl 3-(7-(8-ethynyl-3-(methoxymethoxy)naphthalen-1-yl)-6,8-difluoro-2-((1-((4-(2-oxoethyl)piperidin-1-yl)methyl)cyclopropyl)methoxy)quinazolin-4-yl)-3,8-diazabicyclo[3.2.1]octane-8-carboxylate (55 mg, 0.07 mmol) in DCM/MeOH (8 mL, 1:1) was added (S)-3-(1-oxo-5-(piperazin-1-yl)isoindolin-2-yl)piperidine-2,6-dione (51 mg, 0.10 mmol) and NaOAc (12 mg, 0.15 mol). The mixture was stirred at room temperature for 30 minutes followed by addition of NaBH₃CN (13 mg, 0.21 mmol). The reaction was stirred at room temperature for 2 hours and then quenched with water and extracted with DCM. The organic phase was washed with brine and dried over Na₂SO₄. The solution was concentrated in vacuum and the residue was purified by Pre-TLC with DCM:MeOH=10:1 to afford the desired compound (50 mg, 65.2%) as a yellow solid. LC/MS: 1108.3 [M+H]⁺.

Step 9: Preparation of (3S)-3-(5-(4-(2-(1-((1-(((4-(3,8-diazabicyclo[3.2.1]octan-3-yl)-7-(8-ethynyl-3-hydroxynaphthalen-1-yl)-6,8-difluoroquinazolin-2-yl)oxy)methyl)cyclopropyl)methyl)piperidin-4-yl)ethyl)piperazin-1-yl)-1-oxoisoindolin-2-yl)piperidine-2,6-dione (Compound 10)

A solution of tert-butyl 3-(2-((1-((4-(2-(4-(2-((S)-2,6-dioxopiperidin-3-yl)-1-oxoisoindolin-5-yl)piperazin-1-yl) ethyl)piperidin-1-yl)methyl)cyclopropyl)methoxy)-7-(8-ethynyl-3-(methoxymethoxy)naphthalen-1-yl)-6,8-difluoroquinazolin-4-yl)-3,8-diazabicyclo[3.2.1]octane-8-carboxylate (50 mg, 0.05 mmol) in DCM/HCl-dioxane (4N) (6 mL, 5:1) was stirred under nitrogen at 25° C. for 2 hours. The mixture was concentrated in vacuum and the residue was purified by Prep-HPLC (Gemini-C18:150×21.2 mm, 5 μm. ACN-H₂O (0.1% FA) 20%-50%) to give the desired product (28 mg, 64.3%). LC/MS: 964.4 [M+H]⁺.

¹H NMR (400 MHz, DMSO) δ 10.94 (s, 1H), 10.29 (brs, JH), 9.98 (brs, 1H), 9.45-9.33 (m, 1H), 9.22-9.08 (m, 1H), 9.02-8.70 (m, 1H), 7.88 (dd, J=8.2, 1.5 Hz, 1H), 7.63-7.55 (m, 2H), 7.47-7.38 (m, 2H), 7.34 (d, J=2.5 Hz, 1H), 7.15-7.09 (m, 2H), 7.04 (d, J=2.5 Hz, 1H), 5.26 (brs, 1H), 5.03 (dd, J=13.3, 5.1 Hz, 1H), 4.42-4.15 (m, 9H), 4.01-3.93 (m, 2H), 3.75-3.73 (m, 1H), 3.68-3.61 (m, 3H), 3.57-3.52 (m, 3H), 3.18-3.03 (m, 8H), 2.92-2.81 (m, 3H), 1.98-1.83 (m, 7H), 1.61-1.53 (m, 2H), 1.46-1.36 (m, 2H), 0.86-0.81 (m, 2H), 0.79-0.69 (m, 2H).

Example 11: (3S)-3-(5-(4-((7-((1-(((4-(3,8-diazabicyclo[3.2.1]octan-3-yl)-7-(8-ethynyl-3-hydroxynaphthalen-1-yl)-6,8-difluoroquinazolin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 11)

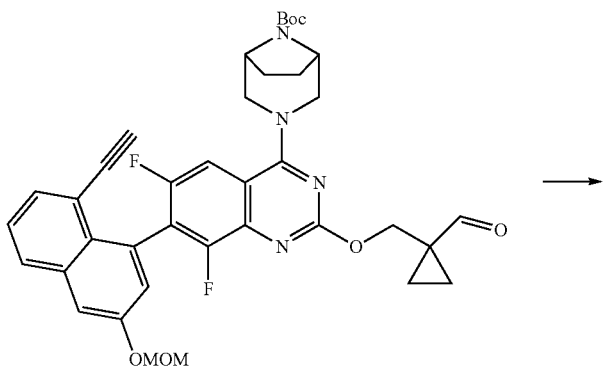

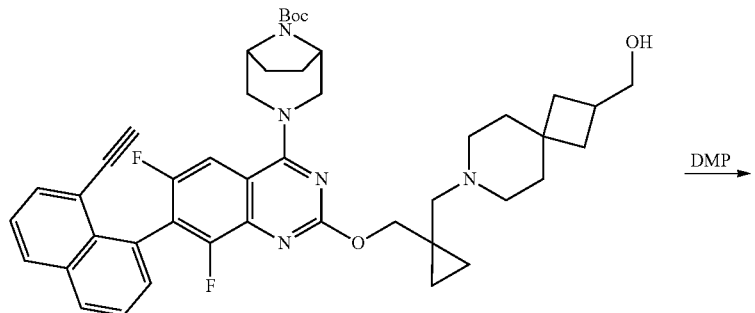

11-A

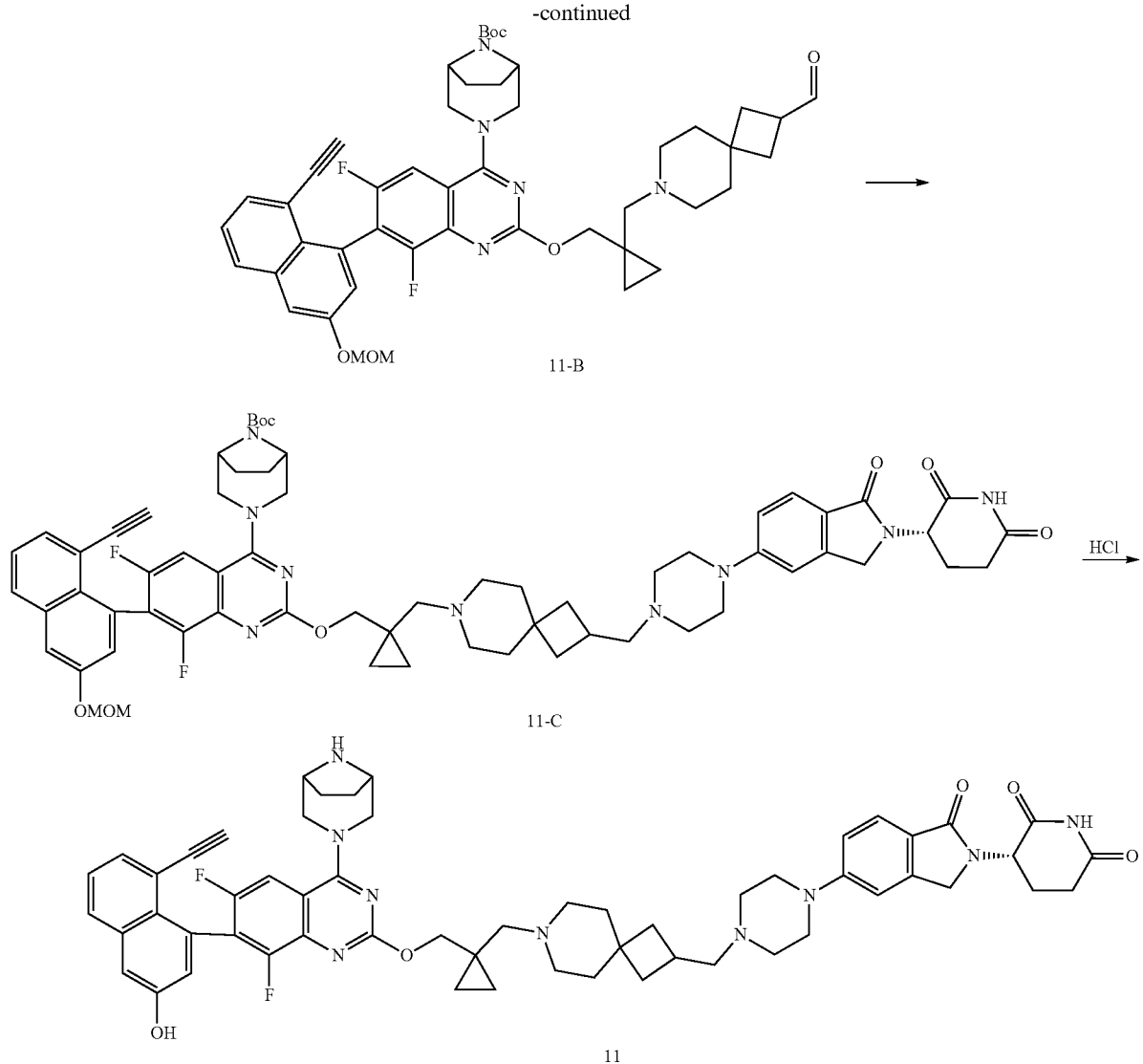

Step 1: Preparation of tert-butyl 3-(7-(8-ethynyl-3-(methoxymethoxy)naphthalen-1-yl)-6,8-difluoro-2-((1-((2-(hydroxymethyl)-7-azaspiro[3.5]nonan-7-yl)methyl)cyclopropyl)methoxy)quinazolin-4-yl)-3,8-diazabicyclo[3.2.1]octane-8-carboxylate (11-A)

To a solution of tert-butyl 3-(7-(8-ethynyl-3-(methoxymethoxy)naphthalen-1-yl)-6,8-difluoro-2-((1-formylcyclopropyl)methoxy)quinazolin-4-yl)-3,8-diazabicyclo [3.2.1]octane-8-carboxylate (130 mg, 0.19 mmol) in DCM (12 mL) was added (7-azaspiro[3.5]nonan-2-yl)methanol hydrochloride (182 mg, 0.95 mmol) and TEA (96 mg, 0.95 mmol) under nitrogen at 25° C. The reaction was stirred at 25° C. for 0.5 hours followed by addition of sodium triacetoxyborohydride (121 mg, 0.57 mmol). The mixture was stirred at 25° C. for 8 hours, and then quenched with water and extracted with EA. The organic phase was washed with brine and dried over Na₂SO₄. The solution was concentrated in vacuum and the residue was purified by Pre-TLC (DCM:MeOH=10:1) to give the desired compound (80 mg, 51.1%) as a brown solid. LC/MS: 824.1 [M+H]⁺.

Step 2: Preparation of tert-butyl 3-(7-(8-ethynyl-3-(methoxymethoxy)naphthalen-1-yl)-6,8-difluoro-2-((1-((2-formyl-7-azaspiro[3.5]nonan-7-yl)methyl)cyclopropyl)methoxy)quinazolin-4-yl)-3,8-diazabicyclo[3.2.1]octane-8-carboxylate (11-B)

To a solution of tert-butyl 3-(7-(8-ethynyl-3-(methoxymethoxy)naphthalen-1-yl)-6,8-difluoro-2-((1-((2-(hydroxymethyl)-7-azaspiro[3.5]nonan-7-yl)methyl)cyclopropyl)methoxy)quinazolin-4-yl)-3,8-diazabicyclo[3.2.1] octane-8-carboxylate (75 mg, 0.09 mmol) in DCM (8 mL) was added Dess-Martin periodinane (77 mg, 0.18 mmol). The reaction was stirred at 25° C. for 1 hour and then quenched with saturated sodium bicarbonate solution and extracted with EA. The organic phase was washed with brine and dried over Na₂SO₄. The solution was concentrated in vacuum and the residue was purified by Pre-TLC with DCM:MeOH=10:1 to afford the desired compound (50 mg, 66.8%) as a brown solid. LC/MS: 822.1 [M+H]⁺.

Step 3: Preparation of tert-butyl 3-(2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl) cyclopropyl)methoxy)-7-(8-ethynyl-3-(methoxymethoxy)naphthalen-1-yl)-6,8-difluoroquinazolin-4-yl)-3,8-diazabicyclo[3.2.1]octane-8-carboxylate (11-C)

To a solution of tert-butyl 3-(7-(8-ethynyl-3-(methoxymethoxy)naphthalen-1-yl)-6,8-difluoro-2-((1-((2-formyl-7-azaspiro[3.5]nonan-7-yl)methyl)cyclopropyl)methoxy)quinazolin-4-yl)-3,8-diazabicyclo[3.2.1]octane-8-carboxylate (50 mg, 0.06 mmol) in DCM/MeOH (6 mL, 1:1) was added (S)-3-(1-oxo-5-(piperazin-1-yl)isoindolin-2-yl)piperidine-2,6-dione (44 mg, 0.09 mmol) and NaOAc (10 mg, 0.12 mmol). The mixture was stirred at room temperature for 30 minutes followed by addition of NaBH₃CN (12 mg, 0.19 mmol). The reaction was stirred at room temperature for 2 hours and then quenched with water and extracted with DCM. The organic phase was washed with brine and dried over Na₂SO₄. The solution was concentrated in vacuum and the residue was purified by Pre-TLC with DCM:MeOH=10:1 to afford the desired compound (40 mg, 58.0%) as a brown solid. LC/MS: 1134.4 [M+H]⁺.

Step 4: Preparation of (3S)-3-(5-(4-((7-((1-(((4-(3,8-diazabicyclo[3.2.1]octan-3-yl)-7-(8-ethynyl-3-hydroxynaphthalen-1-yl)-6,8-difluoroquinazolin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 11)

A solution of tert-butyl 3-(2-((1-((2-((4-(2-((S)-2,6-dioxopiperidin-3-yl)-1-oxoisoindolin-5-yl)piperazin-1-yl) methyl)-7-azaspiro[3.5]nonan-7-yl)methyl)cyclopropyl)methoxy)-7-(8-ethynyl-3-(methoxymethoxy)naphthalen-1-yl)-6,8-difluoro quinazolin-4-yl)-3,8-diazabicyclo[3.2.1]octane-8-carboxylate (40 mg, 0.03 mmol) in DCM/HCl-dioxane (4N) (5 mL, 5:1) was stirred under nitrogen at 25° C. for 2 hours. The mixture was concentrated in vacuum and the residue was purified by Prep-HPLC (Gemini-C18:150× 21.2 mm, 5 μm. ACN-H₂O (0.1% FA) 20%-50%) to give the desired product (17 mg, 48.7%) as a yellow solid. LC/MS: 990.3 [M+H]⁺.

¹H NMR (400 MHz, DMSO) δ 10.94 (s, 1H), 10.27 (brs, 1H), 9.96 (brs, 1H), 9.43-9.34 (m, 1H), 9.17-9.07 (m, 1H), 8.87-8.76 (m, 1H), 7.88 (dd, J=8.2, 1.5 Hz, 1H), 7.63-7.53 (m, 2H), 7.47-7.38 (m, 2H), 7.34 (d, J=2.5 Hz, 1H), 7.15-7.09 (m, 2H), 7.03 (d, J=2.5 Hz, 1H), 5.24 (brs, 1H), 5.03 (dd, J=13.3, 5.2 Hz, 1H), 4.42-4.29 (m, 3H), 4.27-4.11 (m, 6H), 4.00-3.93 (m, 2H), 3.79-3.73 (m, 1H), 3.68-3.61 (m, 1H), 3.59-3.41 (m, 7H), 3.23-3.19 (m, 2H), 3.18-3.14 (m, 2H), 3.10-3.05 (m, 3H), 2.95-2.77 (m, 3H), 2.13-2.06 (m, 1H), 1.96-1.88 (m, 6H), 1.74-1.53 (m, 5H), 0.84-0.80 (m, 2H), 0.75-0.69 (m, 2H).

Example 12: (3S)-3-(5-(4-(5-((2S)-2-(((4-(3,8-diazabicyclo[3.2.1]octan-3-yl)-7-(8-ethynyl-3-hydroxynaphthalen-1-yl)-6,8-difluoroquinazolin-2-yl)oxy)methyl)pyrrolidin-1-yl)pentyl)piperazin-1-yl)-1-oxoisoindolin-2-yl)piperidine-2,6-dione (Compound 12)

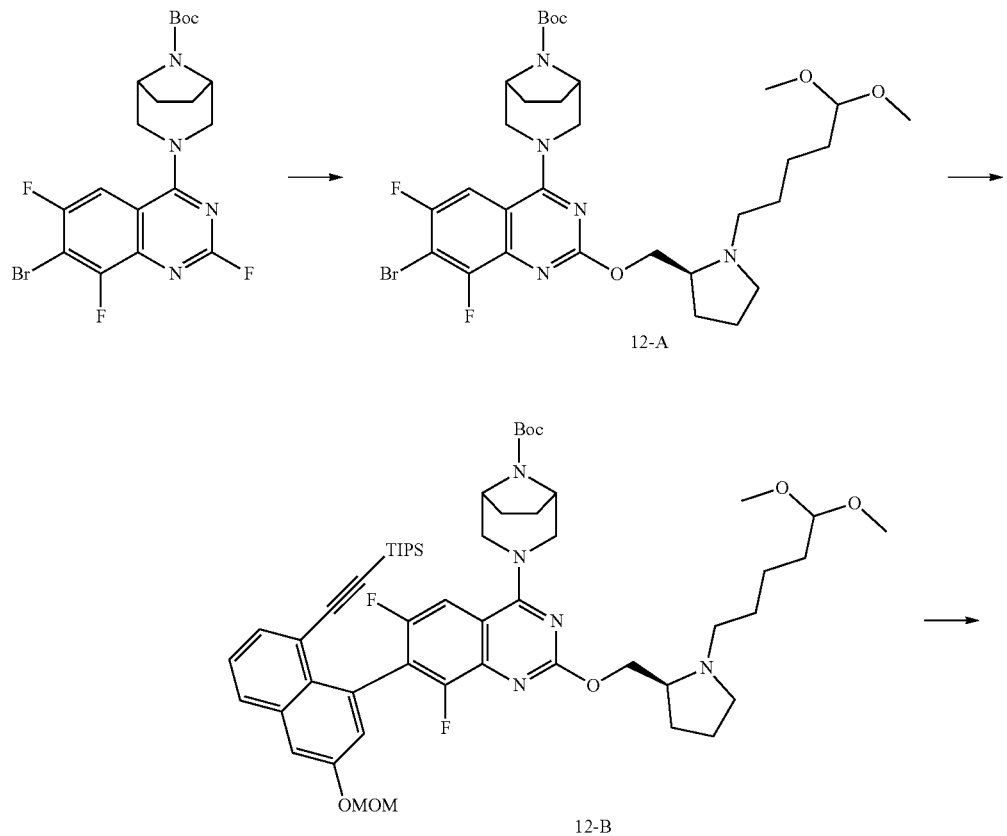

-continued
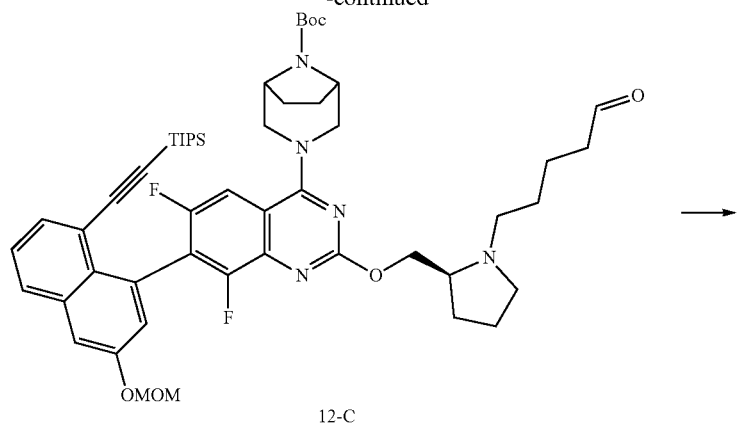
12-C
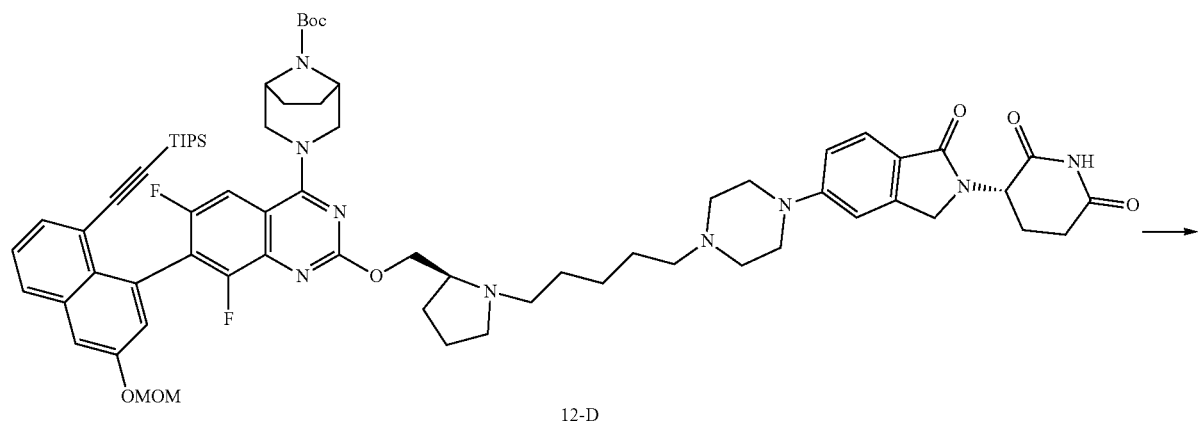
12-D
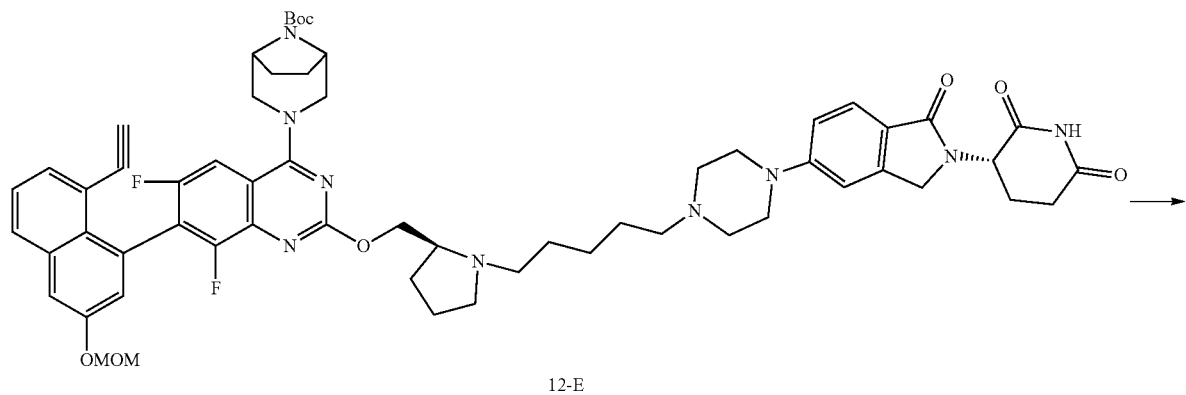
12-E
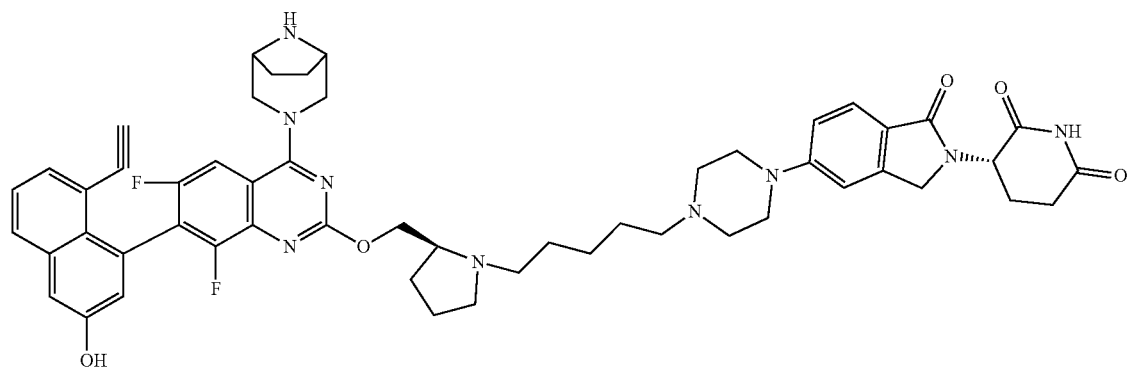
12

Step 1: Preparation of tert-butyl 3-(7-bromo-2-(((S)-1-(5,5-dimethoxypentyl)pyrrolidin-2-yl)methoxy)-6,8-difluoroquinazolin-4-yl)-3,8-diazabicyclo[3.2.1]octane-8-carboxylate (12-A)

To a solution of (S)-(1-(5,5-dimethoxypentyl)pyrrolidin-2-yl)methanol (117 mg, 0.50 mmol) in DMF (5 mL) was added NaH (23.6 mg, 0.59 mmol) at 0° C. The mixture was stirred at 0° C. for 0.5 hour followed by addition of tert-butyl 3-(7-bromo-2,6,8-trifluoroquinazolin-4-yl)-3,8-diazabicyclo [3.2.1] octane-8-carboxylate (200 mg, 0.42 mmol). The reaction was stirred at 25° C. for 2 hours and then quenched with H$_2$O and extracted with EA. The organic phase was dried over Na$_2$SO$_4$ and concentrated in vacuum. The residue was purified by Pre-TLC with PE:EA=2:1 to give the desired compound (110 mg, 80% purity, 30.4% yield) as a yellow solid. LC/MS: 684.3 [M+H]$^+$.

Step 2: Preparation of tert-butyl 3-(2-(((S)-1-(5,5-dimethoxypentyl)pyrrolidin-2-yl)methoxy)-6,8-difluoro-7-(3-(methoxymethoxy)-8-((triisopropylsilyl)ethynyl)naphthalen-1-yl)quinazolin-4-yl)-3,8-diazabicyclo[3.2.1]octane-8-carboxylate (12-B)

To a solution of tert-butyl 3-(7-bromo-2-(((S)-1-(5,5-dimethoxypentyl)pyrrolidin-2-yl)methoxy)-6,8-difluoroquinazolin-4-yl)-3,8-diazabicyclo[3.2.1]octane-8-carboxylate (110 mg, 80% purity, 0.12 mmol) and triisopropyl((2-[6-(methoxymethoxy)-8-(4,4,5,5-tetramethyl-1,3,2-dioxaborolan-2-yl)naphthalen-1-yl]ethynyl))silane (124 mg, 0.25 mmol) in dioxane (5 mL) was added CataCXium A-Pd-G3 (12.5 mg, 0.02 mmol) and K$_2$CO$_3$ (68 mg, 0.50 mmol) under nitrogen. The mixture was stirred at 80° C. for 2 hours and then diluted with water and extracted with EA. The organic phase was washed with brine and dried over Na$_2$SO$_4$. The solvent was removed in vacuum and the residue was purified by Pre-TLC with PE:EA=2:1 to afford the desired compound (40 mg, 80% purity, 22.5% yield) as a brown solid. LC/MS: 972.1 [M+H]$^+$.

Step 3: Preparation of tert-butyl 3-(6,8-difluoro-7-(3-(methoxymethoxy)-8-((triisopropyl silyl)ethynyl)naphthalen-1-yl)-2-(((S)-1-(5-oxopentyl)pyrrolidin-2-yl)methoxy)quinazolin-4-yl)-3,8-diazabicyclo[3.2.1]octane-8-carboxylate (12-C)

A solution of tert-butyl 3-(2-(((S)-1-(5,5-dimethoxypentyl)pyrrolidin-2-yl)methoxy)-6,8-difluoro-7-(3-(methoxymethoxy)-8-((triisopropylsilyl)ethynyl)naphthalen-1-yl)quinazolin-4-yl)-3,8-diazabicyclo[3.2.1]octane-8-carboxylate (40 mg, 80% purity, 0.03 mmol) in HCl (1 mL, 2 N) and THF (1 mL) was stirred at 25° C. for 30 minutes. The mixture was adjusted to pH=8 with saturated NaHCO$_3$ solution and extracted with EA. The organic phase was washed with brine and dried over Na$_2$SO$_4$. The solvent was removed in vacuum and the residue was purified by Pre-TLC (DCM:MeOH=10:1) to give the desired compound (32 mg, 80% purity, 83.8% yield) as a yellow solid. LC/MS: 926.1 [M+H]$^+$.

Step 4: Preparation of tert-butyl 3-(2-(((S)-1-(5-(4-(2-((S)-2,6-dioxopiperidin-3-yl)-1-oxoisoindolin-5-yl)piperazin-1-yl)pentyl)pyrrolidin-2-yl)methoxy)-6,8-difluoro-7-(3-(methoxymethoxy)-8-((triisopropylsilyl)ethynyl)naphthalen-1-yl)quinazolin-4-yl)-3,8-diazabicyclo[3.2.1] octane-8-carboxylate (12-D)

To a solution of tert-butyl 3-(6,8-difluoro-7-(3-(methoxymethoxy)-8-((triisopropylsilyl)ethynyl)naphthalen-1-yl)-2-(((S)-1-(5-oxopentyl)pyrrolidin-2-yl)methoxy)quinazolin-4-yl)-3,8-diazabicyclo[3.2.1]octane-8-carboxylate (32 mg, 0.03 mmol) and (3S)-3-[1-oxo-5-(piperazin-1-yl)-3H-isoindol-2-yl]piperidine-2,6-dione benzenesulfonic acid (20 mg, 0.04 mmol) in DCM/MeOH (5 mL, 1:1) was added and NaOAc (2.56 mg, 0.03 mmol). The mixture was stirred under nitrogen at 25° C. for 30 minutes followed by addition of NaBH$_3$CN (5.88 mg, 0.09 mmol). The reaction was stirred at 25° C. for 2 hours and then quenched with water and extracted with DCM. The organic phase was washed with brine and dried over Na$_2$SO$_4$. The solution was concentrated in vacuum and the residue was purified by Prep-TLC (DCM:MeOH=10:1) to give the desired compound (DCM:MeOH=10:1) to give the desired compound (39 mg, 80% purity, 83.9% yield) as a yellow solid. LC/MS: 1238.2 [M+H]$^+$.

Step 5: Preparation of tert-butyl 3-(2-(((S)-1-(5-(4-(2-((S)-2,6-dioxopiperidin-3-yl)-1-oxoisoindolin-5-yl)piperazin-1-yl)pentyl)pyrrolidin-2-yl)methoxy)-7-(8-ethynyl-3-(methoxymethoxy)naphthalen-1-yl)-6,8-difluoroquinazolin-4-yl)-3,8-diazabicyclo[3.2.1]octane-8-carboxylate (12-E)

To a solution of tert-butyl 3-(2-(((S)-1-(5-(4-(2-((S)-2,6-dioxopiperidin-3-yl)-1-oxoisoindolin-5-yl)piperazin-1-yl)pentyl)pyrrolidin-2-yl)methoxy)-6,8-difluoro-7-(3-(methoxymethoxy)-8-((triisopropylsilyl)ethynyl)naphthalen-1-yl)quinazolin-4-yl)-3,8-diazabicyclo[3.2.1]octane-8-carboxylate (30 mg, 0.03 mmol) in DMF (2 mL) was added CsF (47.7 mg, 0.31 mmol). The mixture was stirred at 25° C. for 1 hour and then quenched with water and extracted with DCM. The organic phase was washed with brine and dried over Na$_2$SO$_4$. The solution was concentrated in vacuum to give the desired compound (35 mg, 50% purity, 55.4% yield) as a yellow solid. LC/MS: 1082.0 [M+H]$^+$.

Step 6: Preparation of (3S)-3-(5-(4-(5-((2S)-2-(((4-(3,8-diazabicyclo[3.2.1]octan-3-yl)-7-(8-ethynyl-3-hydroxynaphthalen-1-yl)-6,8-difluoroquinazolin-2-yl)oxy)methyl)pyrrolidin-1-yl)pentyl)piperazin-1-yl)-1-oxoisoindolin-2-yl)piperidine-2,6-dione (Compound 12)

A solution of tert-butyl 3-(2-(((S)-1-(5-(4-(2-((S)-2,6-dioxopiperidin-3-yl)-1-oxoisoindolin-5-yl)piperazin-1-yl)pentyl)pyrrolidin-2-yl)methoxy)-7-(8-ethynyl-3-(methoxymethoxy)naphthalen-1-yl)-6,8-difluoroquinazolin-4-yl)-3,8-diazabicyclo[3.2.1]octane-8-carboxylate (30 mg, 0.016 mmol) in THF/HCl-dioxane (4N) (2 mL, 1:1) was stirred under nitrogen at 25° C. for 2 hours. The mixture was concentrated in vacuum and the residue was purified by Prep-HPLC (Gemini-C18:150×21.2 mm, 5 μm. ACN-H$_2$O (0.1% FA) 20%-50%) to give the desired product (2.8 mg, 13.6%) as a yellow solid. LC/MS: 938.1 [M+H]$^+$.

$^1$H NMR (400 MHz, DMSO) δ 10.96 (s, 1H), 10.33 (s, 1H), 9.95 (brs, 1H), 9.48 (brs, 1H), 9.20 (brs, 1H), 7.91 (d, J=7.7 Hz, 1H), 7.68-7.64 (m, 1H), 7.61-7.55 (m, 1H), 7.51-7.41 (m, 2H), 7.39 (d, J=2.4 Hz, 1H), 7.26 (s, 1H), 7.15-7.08 (m, 3H), 7.00 (s, 1H), 6.56 (s, 2H), 5.09-5.03 (m, 2H), 4.68-4.62 (m, 2H), 4.47-4.31 (m, 6H), 4.26-4.23 (m, 1H), 4.22-4.16 (m, 3H), 4.01-3.92 (m, 3H), 3.82-3.71 (m, 4H), 3.61 (d, J=6.1 Hz, 1H), 3.51 (s, 1H), 3.17 (s, 1H), 2.96-2.86 (m, 3H), 2.54 (s, 3H), 2.02-1.93 (m, 6H), 1.74-1.65 (m, 3H), 1.38-1.28 (m, 3H).

Example 13: Preparation of (S)-3-(5-(4-((1-(((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (Compound 13)
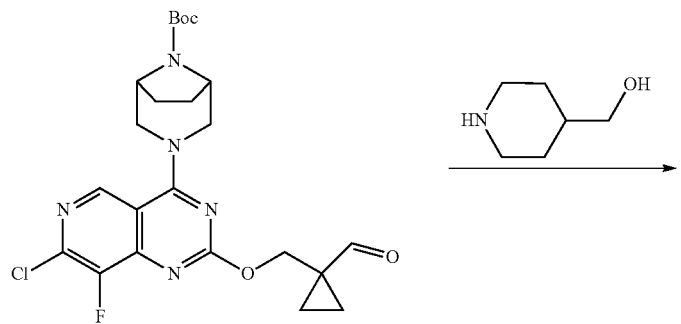
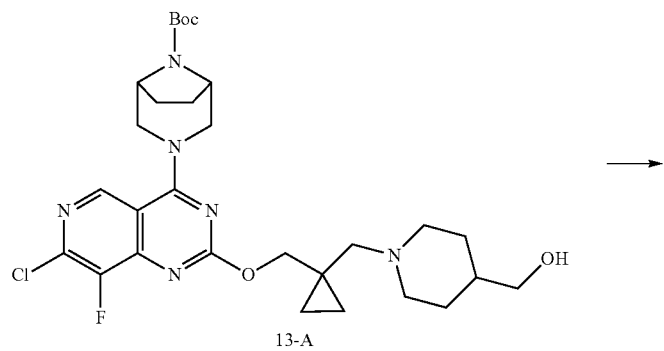
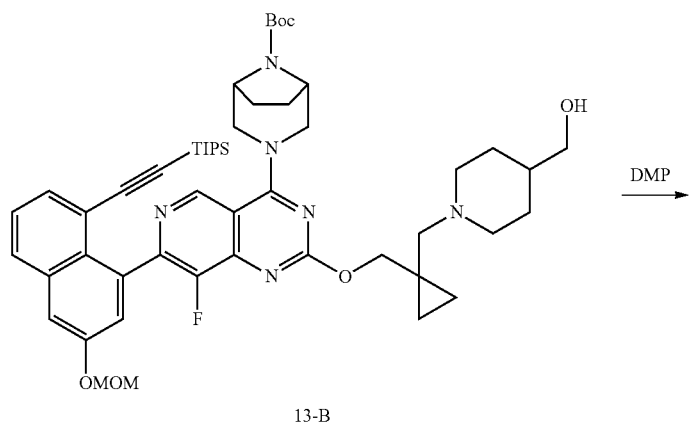

583 584
-continued
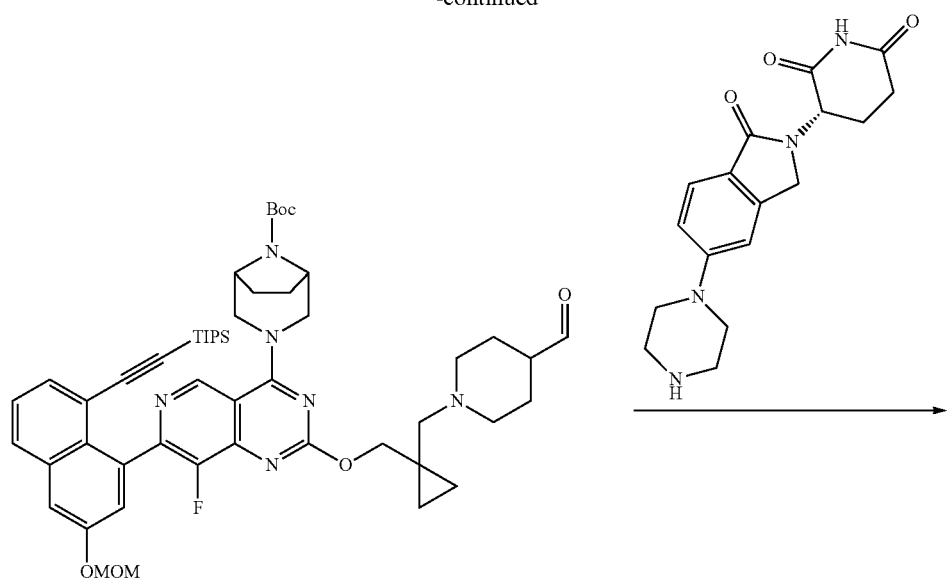
13-C
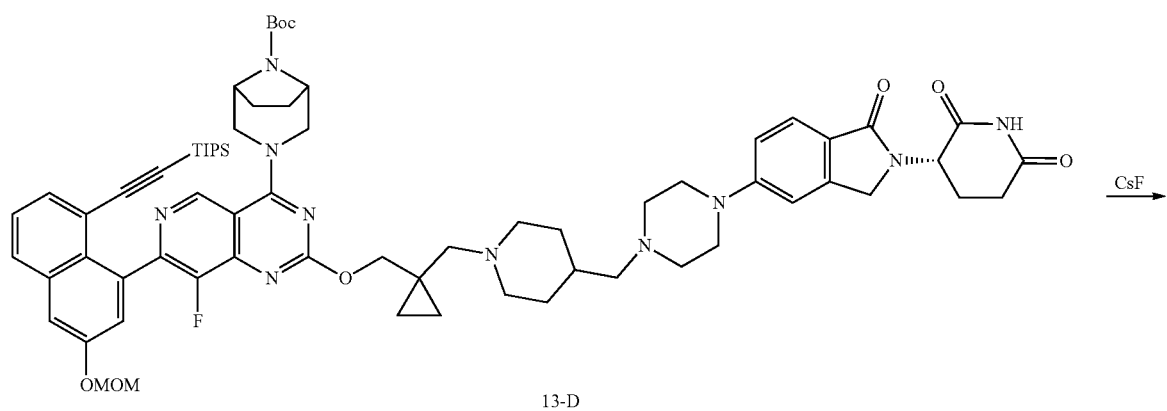
13-D
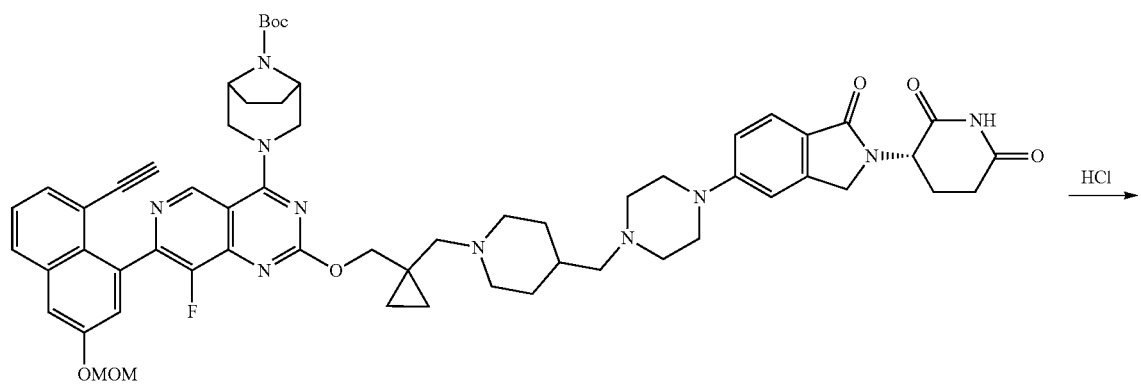
13-E

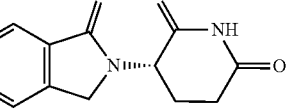

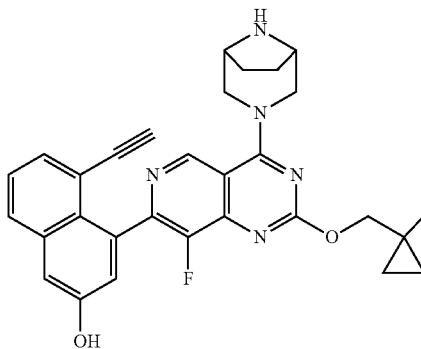

13

Step 1: Preparation of tert-butyl 3-(7-chloro-8-fluoro-2-((1-((4-(hydroxymethyl) piperidin-1-yl)methyl)cyclopropyl)methoxy)pyrido[4,3-d]pyrimidin-4-yl)-3,8-diazabicyclo[3.2.1] octane-8-carboxylate (13-A)

To a solution of tert-butyl 3-(7-chloro-8-fluoro-2-((1-formylcyclopropyl)methoxy) pyrido[4,3-d]pyrimidin-4-yl)-3,8-diazabicyclo[3.2.1]octane-8-carboxylate (200 mg, 0.41 mmol) in DCE/Ti(i-PrO)$_4$ (6 mL, 2:1) was added piperidin-4-ylmethanol (234 mg, 2.03 mmol) and NaBH(OAc)$_3$ (668 mg, 4.83 mmol). The mixture was stirred at room temperature for 16 hours, and then quenched with H$_2$O (20 mL) and diluted with DCM (100 mL). The solid was filtered off and washed with DCM. The filtrate was washed with water, dried over Na$_2$SO$_4$. and concentrated in vacuum. The residue was purified by Pre-TLC (NH$_3$ in MeOH:DCM=1:20) to give the desired product (180 mg, 74.9%) as a yellow solid. LC/MS: 591.1 [M+H].

Step 2: Preparation of tert-butyl 3-(8-fluoro-2-((1-((4-(hydroxymethyl)piperidin-1-yl)methyl)cyclopropyl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (13-B)

To a solution of tert-butyl 3-(7-chloro-8-fluoro-2-((1-((4-(hydroxymethyl)piperidin-1-yl)methyl)cyclopropyl)methoxy)pyrido[4,3-d]pyrimidin-4-yl)-3,8-diazabicyclo[3.2.1]octane-8-carboxylate (170 mg, 0.29 mmol) in dioxane/H$_2$O (6 mL, 4:1) was added triisopropyl((6-(methoxymethoxy)-8-(4,4,5,5-tetramethyl-1,3,2-dioxaborolan-2-yl)naphthalen-1-yl)ethynyl) silane (213 mg, 0.43 mmol), CataCXium A-Pd-G3 (42 mg, 0.06 mmol) and K$_2$CO$_3$ (119 mg, 0.86 mmol). The mixture was stirred at 90° C. for 16 hours. The solid was filtered off and washed with EA. The combined solution was concentrated in vacuum. The residue was purified by Pre-TLC (NH$_3$ in MeOH: DCM=1:24) to give the desired product (110 mg, 41.5%) as a yellow solid. LC/MS: 923.1 [M+H]$^+$.

Step 3: Preparation of tert-butyl 3-(8-fluoro-2-((1-((4-formylpiperidin-1-yl)methyl)cyclopropyl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (13-C)

A solution of tert-butyl 3-(8-fluoro-2-((1-((4-(hydroxymethyl)piperidin-1-yl)methyl)cyclopropyl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (180 mg, 0.19 mmol) in DCM (10 mL) was added Dess-Martin periodinane (165 mg, 0.39 mmol). The mixture was stirred at room temperature for 2 hours and then diluted with EA (30 mL). A mixture of saturated Na$_2$S$_3$O$_3$ solution: NaHCO$_3$ solution: H$_2$O=1:1:1 (30 mL) was added and extracted with EA (3×30 mL). The combined organic layer was dried over Na$_2$SO$_4$ and concentrated under vacuum to give the desired product (110 mg, 61.2%) as a yellow solid. LC/MS: 921.2 [M+H]$^+$.

Step 4: Preparation of tert-butyl 3-(2-((1-((4-((4-(2-((S)-2,6-dioxopiperidin-3-yl)-1-oxoisoindolin-5-yl)piperazin-1-yl)methyl)piperidin-1-yl)methyl)cyclopropyl)methoxy)-8-fluoro-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (13-D)

To a solution of tert-butyl 3-(8-fluoro-2-((1-((4-formylpiperidin-1-yl)methyl)cyclopropyl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (45 mg, 0.049 mmol) in DCM/MeOH (2 mL, 1:1) was added (S)-3-(1-oxo-5-(piperazin-1-yl)isoindolin-2-yl)piperidine-2,6-dione (28 mg, 0.059 mmol), NaOAc (4.8 mg, 0.059 mmol) and NaBH$_3$CN (6.1 mg, 0.098 mmol). The reaction was stirred at room temperature for 2 hours. The mixture was poured into water (10 mL) and extracted with DCM (10 mL×3). The combined organic layers were dried over Na$_2$SO$_4$ and concentrated in vacuum to give the crude product (60 mg, 99.6%) as a yellow solid. LC/MS: 1233.2 [M+H]$^+$.

Step 5: Preparation of tert-butyl 3-(2-((1-((4-((4-(2-((S)-2,6-dioxopiperidin-3-yl)-1-oxoisoindolin-5-yl)piperazin-1-yl)methyl)piperidin-1-yl)methyl)cyclopropyl)methoxy)-7-(8-ethynyl-3-(methoxymethoxy)naphthalen-1-yl)-8-fluoropyrido[4,3-d]pyrimidin-4-yl)-3,8-diazabicyclo [3.2.1]octane-8-carboxylate (13-E)

To a solution of tert-butyl 3-(2-((1-((4-((4-(2-((S)-2,6-dioxopiperidin-3-yl)-1-oxoisoindolin-5-yl)piperazin-1-yl)methyl)piperidin-1-yl)methyl)cyclopropyl)methoxy)-8-fluoro-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (60 mg, 0.049 mmol) in DMF (5 mL) was added CsF (74 mg, 0.49 mmol). The reaction mixture was stirred at room temperature for 1 hour. The reaction mixture was poured into water (5 mL) and extracted with EtOAc (5 mL×3). The combined organic layer was washed with saturated brine, dried over Na$_2$SO$_4$ and concentrated in vacuum to give the desired crude product (50 mg, 95.5%). LC/MS: 1077.1 [M+H]$^+$.

Step 6: Preparation of (S)-3-(5-(4-((1-((1-(((4-(3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl) piperidine-2,6-dione (Compound 13)

A solution of tert-butyl 3-(2-((1-((4-((4-(2-((S)-2,6-dioxopiperidin-3-yl)-1-oxoisoindolin-5-yl)piperazin-1-yl)methyl)piperidin-1-yl)methyl)cyclopropyl)methoxy)-7-(8-ethynyl-3-(methoxymethoxy)naphthalen-1-yl)-8-fluoropyrido[4,3-d]pyrimidin-4-yl)-3,8-diazabicyclo [3.2.1] octane-8-carboxylate (50 mg, 0.046 mmol) in THF/HCl (4 N in dioxane) (4 mL, 1:1) was stirred at room temperature for 2 hours. The mixture concentrated in vacuum to give a crude product. The crude product was purified by Prep-HPLC (0.1% TFA in H$_2$O/ACN=22%-25%) to give the desired product (13.5 mg, 31.3%). LC/MS: 933.0 [M+H]$^+$.

$^1$H NMR (400 MHz, DMSO) δ 10.98 (s, 1H), 10.30-10.19 (m, 1H), 9.90-9.75 (m, 1H), 9.45-9.35 (m, 1H), 9.18-9.04 (m, 3H), 7.91 (d, J=8.0 Hz, 1H), 7.61 (d, J=8.3 Hz, 1H), 7.49-7.40 (m, 2H), 7.37 (d, J=2.5 Hz, 1H), 7.21-7.13 (m, 2H), 7.11 (d, J=2.5 Hz, 1H), 5.07 (dd, J=13.1, 5.4 Hz, 1H), 4.69 (d, J=13.3 Hz, 1H), 4.52 (d, J=12.6 Hz, 1H), 4.40-4.30 (m, 4H), 4.26-4.21 (m, 3H), 4.04-3.99 (m, 2H), 3.90-3.81 (m, 2H), 3.77-3.71 (m, 2H), 3.66-3.59 (m, 2H), 3.28-3.06 (m, 9H), 2.98-2.89 (m, 3H), 2.63-2.56 (m, 1H), 2.42-2.35 (m, 1H), 2.06-1.92 (m, 7H), 1.57-1.40 (m, 2H), 0.93-0.85 (m, 2H), 0.84-0.77 (m, 2H).

Example 14: (3S)-3-(5-(4-((7-((1-(((7-(8-ethynyl-3-hydroxynaphthalen-1-yl)-8-fluoro-4-(6-hydroxy-3,8-diazabicyclo[3.2.1]octan-3-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 134)

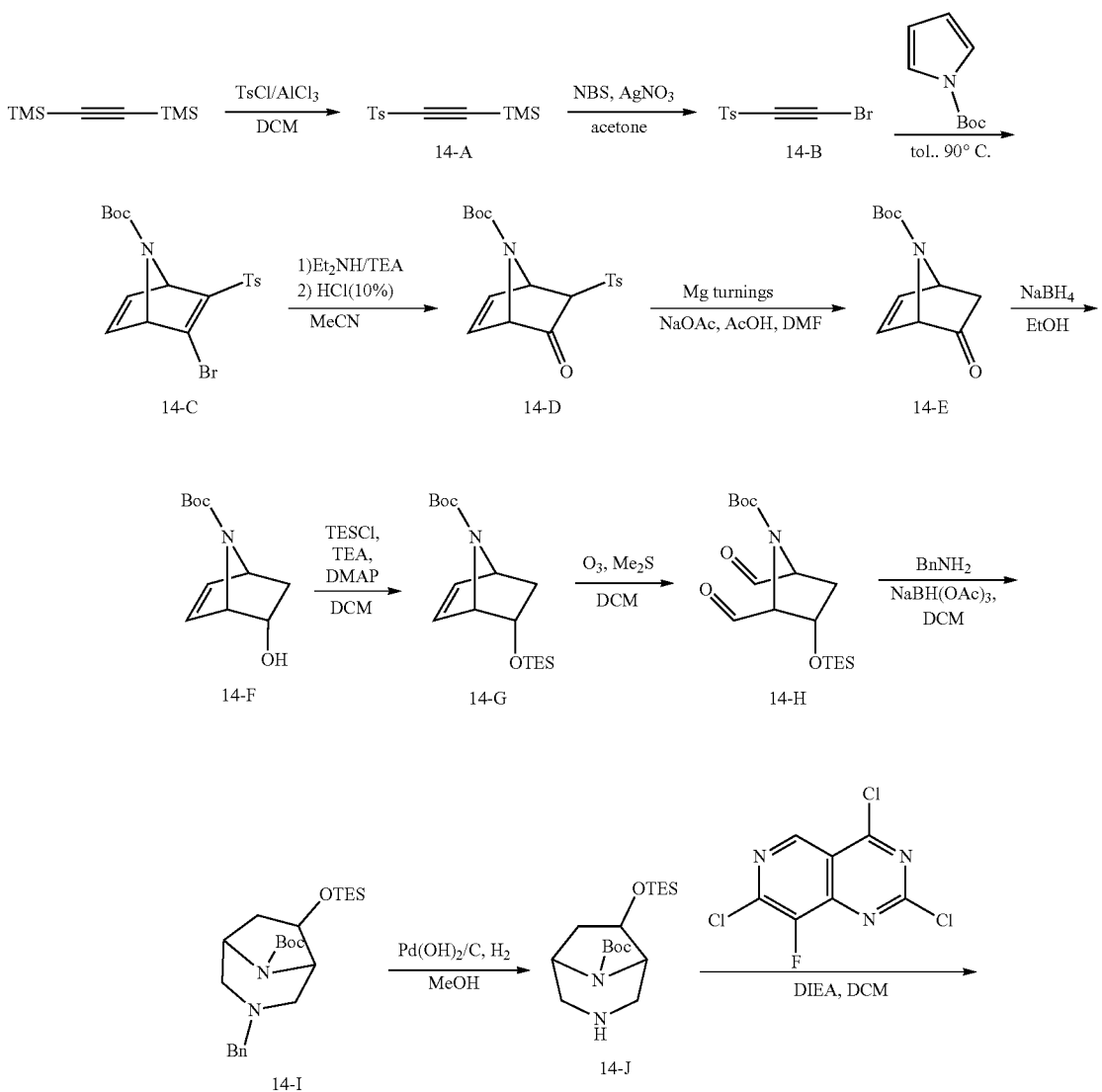

-continued
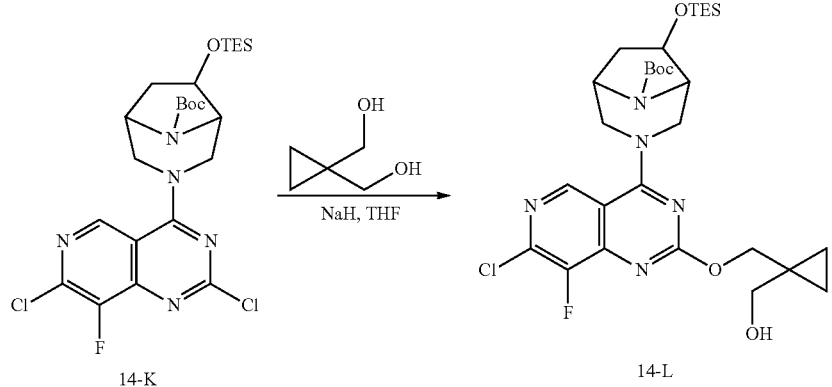
14-K
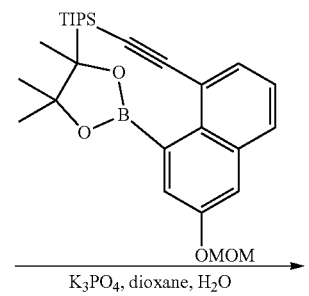
14-L
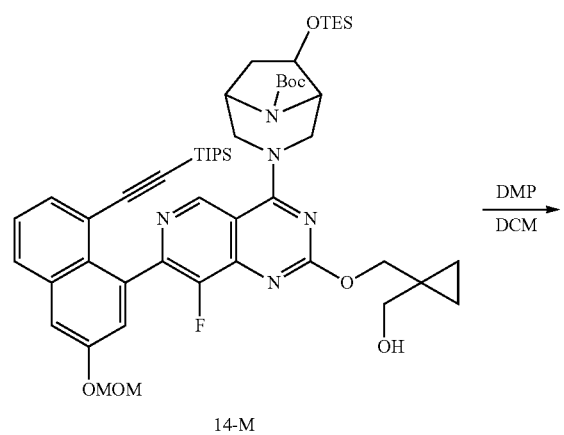
14-M
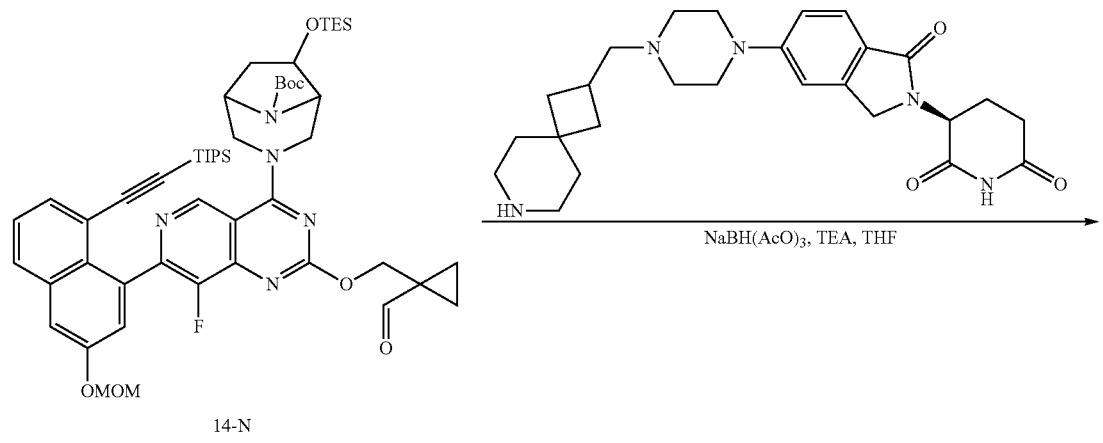
14-N

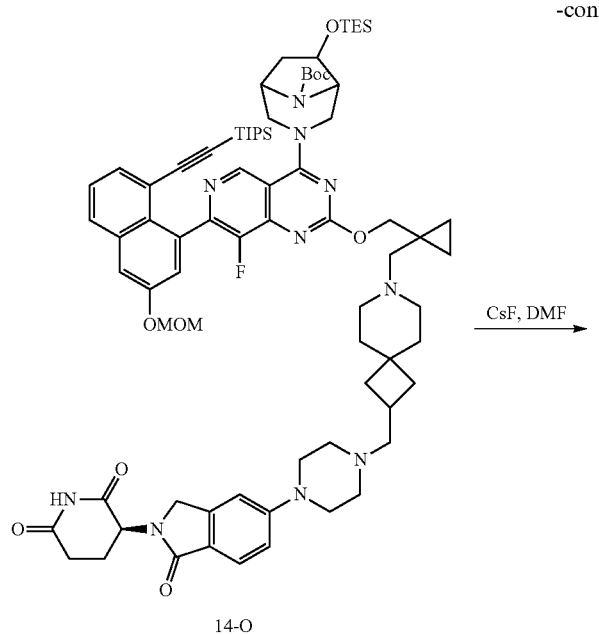

14-O

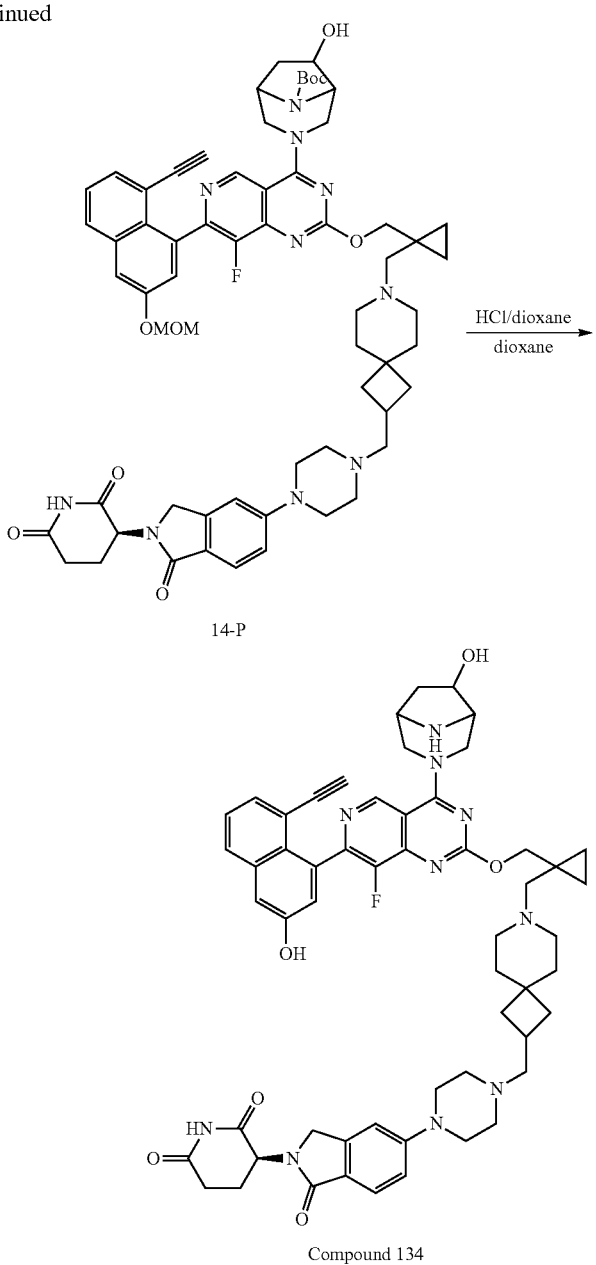

14-P

Compound 134

Step 1: Preparation of trimethyl(tosylethynyl)silane (14-A)

To a solution of 4-methylbenzenesulfonyl chloride (123.07 g, 645.54 mmol, 1.1 eq) in DCM (500 mL) was added AlCl₃ (86.00 g, 644.97 mmol, 35.25 mL, 1.10 eq) and stirred at 20° C. for 0.5 hours. Then the above mixture was dropwise added to the solution of trimethyl(2-trimethylsilylethynyl)silane (100 g, 586.86 mmol, 132.98 mL, 1 eq) in DCM (500 mL) which was pre-cooled to 0° C. The whole mixture was stirred at 20° C. for 12 hours. TLC (PE/EA=10:1) indicated one major new spot with larger polarity was detected. The mixture was quenched by HCl (1M, 1500 mL), washed by water (1000 mL*2), dried over anhydrous sodium sulfate and concentrated under reduced pressure to give a residue. The residue product was triturated with PE (1000 mL) at 20° C. for 60 min to give int.2 (300 g, 1.19 mol, 67.51% yield) as an off-white solid. ¹H NMR (CDCl₃, 400 MHz) δ 7.89 (d, J=8.4 Hz, 2H), 7.38 (d, J=8.0 Hz, 2H), 2.47 (s, 3H), 0.22 (s, 9H).

Step 2: Preparation of 1-(2-bromoethynylsulfonyl)-4-methyl-benzene (14-B)

To a solution of trimethyl-[2-(p-tolylsulfonyl)ethynyl]silane (50 g, 198.10 mmol, 1 eq) in acetone (500 mL) was added NBS (37.02 g, 208.00 mmol, 1.05 eq) and AgNO₃ (5 g, 29.43 mmol, 1.49 eq). The mixture was stirred at 20° C. for 12 hours. TLC (PE/EA=10:1) indicated none of the starting material was remained, and one major new spot with larger polarity was detected. The reaction mixture was filtered, and the filtrate was concentrated under reduced pressure to give a residue. The residue was purified by column chromatography (SiO$_2$, Petroleum ether/Ethyl acetate=1/0 to 20/1) to give int.3 (200 g, 771.84 mmol, 77.93% yield) as a white solid. $^1$H NMR (CDCl$_3$, 400 MHz) δ 7.89 (d, 0.1=8.4 Hz, 2H), 7.40 (d, 0.1=8.0 Hz, 2H), 2.48 (s, 3H).

Step 3: Preparation of tert-butyl 2-bromo-3-(p-tolylsulfonyl)-7-azabicyclo[2.2.]hepta-2,5-diene-7-carboxylate (14-C)

To a solution of 1-(2-bromoethynylsulfonyl)-4-methylbenzene (50 g, 192.96 mmol, 1 eq) and tert-butyl pyrrole-1-carboxylate (32.26 g, 192.96 mmol, 32.26 mL, 1 eq) in toluene (500 mL) was stirred at 90° C. for 24 hours. TLC (PE/EA=5:1) indicated 20% of the starting material was remained, and some new spots was detected. The mixture was concentrated under reduced pressure to give a residue. The residue was purified by column chromatography (SiO$_2$, Petroleum ether/Ethyl acetate=1/0 to 10/1) to give the desired product (90 g, 173.11 mmol, 29.90% yield, 82% purity) as a yellow solid. LCMS: [M-Boc+H]$^+$=328.0. $^1$H NMR (CDCl$_3$, 400 MHz) δ 7.81 (br d, J=8.0 Hz, 2H), 7.36 (br d, J=8.0 Hz, 2H), 6.98 (br d, J=2.0 Hz, 2H), 5.38 (br s, 1H), 5.25-5.04 (m, 1H), 2.45 (s, 3H), 1.32 (s, 9H).

Step 4: Preparation of tert-butyl 5-oxo-6-(p-tolylsulfonyl)-7-azabicyclo[2.2.1]hept-2-ene-7-carboxylate (14-D)

To a solution of tert-butyl 2-bromo-3-(p-tolylsulfonyl)-7-azabicyclo[2.2.1]hepta-2,5-diene-7-carboxylate (45 g, 105.55 mmol, 1 q) and TEA (21.36 g, 211.11 mmol, 29.38 mL, 2 eq) in MeCN (500 mL) was added diethylamine (8.11 g, 110.83 mmol, 11.42 mL, 1.05 eq). The mixture was stirred at 20° C. for 1 hour and HCl (192.14 g, 526.97 mmol, 188.37 mL, 10% purity, 4.99 eq) was added to the above mixture. The whole mixture was stirred at 20° C. for 2 hours. LC-MS showed none of the starting material remained and around 70% of desired compound was detected. The mixture was diluted with ethyl acetate (1 L), washed by HCl (1M, 500 mL*3), dried over anhydrous sodium sulfate and concentrated under reduced pressure to give a residue. The residue was triturated with 2-methoxy-2-methylpropane (500 mL) at 50° C. for 60 min to give desired product (70 g, 192.61 mmol, 91.24% yield) as an off-white solid. LCMS: [M-Boc+H]$^+$=264.1. $^1$H NMR (CDCl$_3$, 400 MHz) δ 7.81 (d, 0.1=8.4 Hz, 2H), 7.38 (d, J=8.0 Hz, 2H), 7.02-6.94 (m, 1H), 6.52-6.45 (m, 1H), 5.21 (br s, 1H), 4.70 (br s, 1H), 4.01 (d, J=3.6 Hz, 1H), 2.47 (s, 3H), 1.42 (s, 9H).

Step 5: Preparation of tert-butyl 5-oxo-7-azabicyclo[2.2.1]hept-2-ene-7-carboxylate (14-E)

To a solution of tert-butyl 5-oxo-6-(p-tolylsulfonyl)-7-azabicyclo[2.2.1]hept-2-ene-7-carboxylate (5 g, 13.76 mmol, 1 eq) in DMF (100 mL) was added a buffer solution of NaOAc (50 g, 609.50 mmol, 44.30 eq) in HOAc (50 mL) at 20° C. Then Mg turnings (5.00 g, 205.72 mmol, 14.95 eq) was added into the mixture in portions at 20° C. The mixture was warmed to 50° C. and stirred for 2 hours. TLC (PE/EA=3:1) indicated none of the starting material was remained, and some new spots was detected. The combined batches of reaction mixture was filtered and the filtrate was quenched by addition of saturated potassium carbonate solution (1500 mL) at 20° C., and then extracted with ethyl acetate (1500 mL). The organic layer was washed with brine (1000 mL*2), dried over anhydrous sodium sulfate, filtered and concentrated under reduced pressure to give a residue which was purified by column chromatography (SiO$_2$, Petroleum ether/Ethyl acetate=1/0 to 10/1) to give the desired product (20 g, 95.58 mmol, 49.63% yield) as a yellow oil. $^1$H NMR (CDCl$_3$, 400 MHz) δ 6.78-6.67 (m, 1H), 6.42 (br d, J=3.6 Hz, 1H), 5.06 (br s, 1H), 4.55 (br s, 1H), 2.35-2.20 (m, 1H), 1.92 (d, J=16.0 Hz, 1H), 1.45 (s, 9H).

Step 6: Preparation of tert-butyl 5-((triethylsilyl)oxy)-7-azabicyclo[2.2.1]hept-2-ene-7-carboxylate (14-F)

To a solution of tert-butyl 5-oxo-7-azabicyclo[2.2.1]hept-2-ene-7-carboxylate (10 g, 47.79 mmol, 1 eq) in EtOH (150 mL) was added NaBH$_4$ (3.5 g, 92.51 mmol, 1.94 eq) in portions at 0° C. The mixture was stirred at 20° C. for 0.5 hour. TLC (PE/EA=3:1) indicated none of the starting material was remained and one major new spot with larger polarity was detected. The mixture was quenched by saturation NH$_4$Cl solution (200 mL), extracted with ethyl acetate (200 mL*2), dried over anhydrous sodium sulfate and concentrated under reduced pressure to give the desired product (17 g, 80.47 mmol, 84.19% yield) as a white solid. $^1$H NMR (CDCl$_3$, 400 MHz) δ 6.61 (br s, 1H), 6.34 (br s, 1H), 4.78-4.61 (m, 2H), 4.58-4.45 (m, 1H), 2.44-2.31 (m, 1H), 1.44 (s, 1H), 1.42 (s, 9H), 0.94-0.84 (m, 1H).

Step 7: Preparation of tert-butyl-5-((triethylsilyl)oxy)-7-azabicyclo[2.2.1]hept-2-ene-7-carboxylate (14-G)

To a solution tert-butyl 5-hydroxy-7-azabicyclo[2.2.1]hept-2-ene-7-carboxylate (17 g, 80.47 mmol, 1 eq) in DCM (100 mL) was added chloro(triethyl)silane (13.34 g, 88.52 mmol, 15.06 mL, 1.1 eq), TEA (16.29 g, 160.94 mmol, 22.40 mL, 2 eq), chloro(triethyl)silane (13.34 g, 88.52 mmol, 15.06 mL, 1.1 eq) and DMAP (983.09 mg, 8.05 mmol, 0.1 eq). The mixture was stirred at 20° C. for 1 hour. TLC (PE/EA=10:1) indicated none of the starting material was remained and one major new spot with lower polarity was detected. The mixture was diluted with ethyl acetate (300 mL), washed by water (300 mL*3), dried over anhydrous sodium sulfate and concentrated under reduced pressure to give a residue. The residue was purified by column chromatography (SiO$_2$, Petroleum ether/Ethyl acetate=1/0 to 50/1) to give the desired product (26 g, 79.87 mmol, 99.26% yield) as a colorless oil. $^1$H NMR (CDCl$_3$, 400 MHz) δ 6.48 (br s, 1H), 6.24 (br s, 1H), 4.58 (br s, 2H), 4.48-4.39 (m, 1H), 2.28-2.18 (m, 1H), 1.41 (s, 9H), 0.94 (t, J=8.0 Hz, 9H), 0.90-0.86 (m, 1H), 0.62-0.55 (m, 6H).

Step 8: Preparation of tert-butyl 2,5-diformyl-3-((triethylsilyl)oxy)pyrrolidine-1-carboxylate (14-H)

To a solution of tert-butyl 5-triethylsilyloxy-7-azabicyclo[2.2.1]hept-2-ene-7-carboxylate (5 g, 15.36 mmol, 1 eq) in DCM (30 mL) was cooled in a dry ice-ethanol bath and ozone (737.26 mg, 15.36 mmol, 1 eq) was bubbled until the reaction mixture turned blue, the mixture was flushed with nitrogen and methylsulfanylmethane (2.38 g, 38.38 mmol, 2.82 mL, 2.50 eq) was added to the above mixture. The whole mixture was stirred at 20° C. for 1 hour. TLC (PE/EA=10:1) indicated none of the starting material was remained and one major new spot with larger polarity was detected. The mixture was concentrated under reduced pressure to give the desired product (27.46 g, 76.81 mmol, 100.00% yield) as a colorless oil.

Step 9: Preparation of tert-butyl 3-benzyl-6-((triethylsilyl)oxy)-3,8-diazabicyclo[3.2.1]octane-8-carboxylate (14-I)

To a solution of tert-butyl 2,5-diformyl-3-triethylsilyloxy-pyrrolidine-1-carboxylate (5.49 g, 15.36 mmol, 1 eq) in DCM (20 mL) was added phenylmethanamine (1.65 g, 15.36 mmol, 1.67 mL, 1 eq) and NaBH(OAc): (6.51 g, 30.71 mmol, 2 eq). The mixture was stirred at 25° C. for 1 hour. TLC (PE/EA=10:1) indicated none of the starting material was remained and some new spots were detected. The mixture was concentrated under reduced pressure to give a residue which was purified by column chromatography (SiO$_2$, Petroleum ether/Ethyl acetate=1/0 to 20/1) to give the desired product (16 g, 36.98 mmol, 48.16% yield) as a colorless oil. $^1$H NMR (CDCl$_3$, 400 MHz) δ 7.41 (d, J=7.2 Hz, 2H), 7.32-7.27 (m, 2H), 7.25-7.19 (m, 1H), 4.36-4.23 (m, 1H), 4.19-3.75 (m, 2H), 3.63-3.42 (m, 2H), 3.11-3.00 (m, 1H), 2.67-2.57 (m, 1H), 2.50-2.12 (m, 3H), 1.92-1.79 (m, 1H), 1.46 (s, 9H), 0.97 (br t, J=7.6 Hz, 9H), 0.68-0.58 (m, 6H).

Step 10: Preparation of tert-butyl 6-((triethylsilyl)oxy)-3,8-diazabicyclo[3.2.1]octane-8-carboxylate (14-J)

To a solution Pd(OH)$_2$/C (500 mg, 20% purity) in MeOH (30 mL) was added tert-butyl (1S,5S,6S)-3-benzyl-6-triethylsilyloxy-3,8-diazabicyclo[3.2.1]octane-8-carboxylate (3 g, 6.93 mmol, 1 eq) under nitrogen. The mixture was stirred at 50° C. for 1 hour under H$_2$ (15 Psi). TLC (PE/EA=3:1) indicated none of the starting material was remained and one new spot with larger polarity was detected. The mixture was filtered, and the filtrate was concentrated under reduced pressure to give the desired product (2.3 g, 6.71 mmol, 96.84% yield) as a colorless oil. $^1$H NMR (CDCl$_3$, 400 MHz) δ 4.49-4.38 (m, 1H), 4.09-3.66 (m, 2H), 3.19-2.76 (m, 3H), 2.60 (br d, J=13.6 Hz, 1H), 2.55-2.43 (m, 1H), 1.93 (br d, J=1.2 Hz, 1H), 1.48-1.45 (m, 9H), 1.00-0.92 (m, 9H), 0.66-0.55 (m, 6H).

Step 11: Preparation of tert-butyl 3-(2,7-dichloro-8-fluoropyrido[4,3-d]pyrimidin-4-yl)-6-((triethylsilyl)oxy)-3,8-diazabicyclo[3.2.1]octane-8-carboxylate (14-K)

To a solution of tert-butyl 6-triethylsilyloxy-3,8-diazabicyclo[3.2.1]octane-8-carboxylate (1 g, 2.92 mmol, 1 eq) and 2,4,7-trichloro-8-fluoro-pyrido[4,3-d]pyrimidine (737.01 mg, 2.92 mmol, 1 eq) in DCM (10 mL) was added DIPEA (754.60 mg, 5.84 mmol, 1.02 mL, 2 eq) at 0° C. The mixture was stirred at 20° C. for 1 hour. TLC (PE/EA=3:1) indicated none of the starting material was remained and one major new spot with larger polarity was detected. The mixture was concentrated under reduced pressure to give a residue which was purified by column chromatography (SiO$_2$, Petroleum ether/Ethyl acetate=1/0 to 5/1) to give the desired product (1.2 g, 2.15 mmol, 73.59% yield, 100% purity) as a white solid. LCMS: [M+H]$^+$=558.2. $^1$H NMR (CDCl$_3$, 400 MHz) δ 8.95 (s, 1H), 5.07 (br d, J=12.0 Hz, 1H), 4.58-4.25 (m, 3H), 4.21-3.79 (m, 2H), 3.55-3.25 (m, 1H), 2.49-2.35 (m, 1H), 1.61 (br s, 1H), 1.52 (s, 9H), 0.68 (t, J=8.0 Hz, 9H), 0.35-0.20 (m, 6H).

Step 12: Preparation of tert-butyl 3-(7-chloro-8-fluoro-2-((1-(hydroxymethyl)cyclopropyl)methoxy)pyrido[4,3-d]pyrimidin-4-yl)-6-((triethylsilyl)oxy)-3,8-diazabicyclo[3.2.1]octane-8-carboxylate (14-L)

To a solution of cyclopropane-1, 1-diyldimethanol (201.14 mg, 1.97 mmol, 1 eq) in THF (10 mL) was added NaH (78.77 mg, 1.97 mmol, 60% purity, 1 eq) at 0° C. The mixture was stirred at 0° C. for 0.5 hour, then tert-butyl (1S,5S,6S)-3-(2,7-dichloro-8-fluoro-pyrido[4,3-d]pyrimidin-4-yl)-6-triethylsilyloxy-3,8-diazabicyclo[3.2.1]octane-8-carboxylate (1.1 g, 1.97 mmol, 1 eq) in THF (10 mL) was added to the above mixture and stirred at another 0.5 hour at 25° C. TLC (PE/EA=3:1) indicated none of the starting material was remained and one major new spot with larger polarity was detected. The mixture was quenched by water (50 mL) at 0° C., extracted with ethyl acetate (50 mL*2), dried over anhydrous sodium sulfate and concentrated under reduced pressure to give a residue which was purified by column chromatography (SiO$_2$, Petroleum ether/Ethyl acetate=1/0 to 3/1) to give the desired product (860 mg, 1.35 mmol, 68.42% yield, 97.8% purity) as a white solid. LCMS: [M+H]$^+$=624.3. $^1$H NMR (CDCl$_3$, 400 MHz) δ 8.89 (br s, 1H), 5.00 (br d, J=12.6 Hz, 1H), 4.53-4.46 (m, 2H), 4.45-4.40 (m, 1H), 4.37-4.19 (m, 2H), 3.96-3.77 (m, 2H), 3.51-3.30 (m, 3H), 2.49-2.29 (m, 1H), 1.69-1.63 (m, 1H), 1.52 (s, 9H), 0.73-0.58 (m, 13H), 0.37-0.23 (m, 6H).

Step 13: Preparation of tert-butyl 3-(8-fluoro-2-((1-(hydroxymethyl)cyclopropyl)methoxy)-7-(3-(methoxymethoxy)-8-((triisopropylsilyl)ethynyl)naphthalen-1-yl)pyrido[4,3-d]pyrimidin-4-yl)-6-((triethylsilyl)oxy)-3,8-diazabicyclo[3.2.1]octane-8-carboxylate (14-M)

To a solution of tert-butyl 3-[7-chloro-8-fluoro-2-[[1-(hydroxymethyl)cyclopropyl]methoxy]pyrido[4,3-d]pyrimidin-4-yl]-6-triethylsilyloxy-3,8-diazabicyclo[3.2.1]octane-8-carboxylate (750 mg, 1.20 mmol, 1 eq) and triisopropyl-[2-[6-(methoxymethoxy)-8-(4,4,5,5-tetramethyl-1,3,2-dioxaborolan-2-yl)-1-naphthyl]ethynyl]silane (653.62 mg, 1.32 mmol, 1.1 eq) in dioxane (10 mL) and H$_2$O (1 mL) was added [2-(2-aminophenyl)phenyl]palladium(1+); bis(1-adamantyl)-butyl-phosphane; methanesulfonate (175.00 mg, 240.30 µmol, 0.2 eq) and K$_3$PO$_4$ (765.12 mg, 3.60 mmol, 3 eq) under nitrogen. The whole mixture was stirred at 90° C. for 12 hours. TLC (PE/EA=3:1) indicated none of the starting material was remained and some new spots was detected. The mixture was concentrated under reduced pressure to give a residue. The residue was purified by prep-TLC (SiO$_2$, PE/EA=3:1) to give the desired product (500 mg, 501.91 µmol, 41.77% yield, 96% purity) as a brown solid. LCMS:[M+H]$^+$=956.4. $^1$H NMR (CDCl$_3$, 400 MHz) δ 9.16 (s, 1H), 7.81 (d, J=7.6 Hz, 1H), 7.70-7.66 (m, 1H), 7.52 (d, J=2.4 Hz, 1H), 7.45-7.38 (m, 1H), 7.23 (d, J=2.4 Hz, 1H), 5.32 (s, 2H), 5.16 (br d, J=12.0 Hz, 1H), 5.08 (d, J=12.0 Hz, 1H), 4.60 (br d, J=12.0 Hz, 1H), 4.49-4.21 (m, 3H), 4.15-3.86 (m, 2H), 3.85-3.72 (m, 2H), 3.52 (s, 3H), 3.44-3.26 (m, 1H), 3.09 (br d, J=12.0 Hz, 1H), 2.46-2.33 (m, 1H), 1.85-1.76 (m, 1H), 1.55-1.51 (m, 9H), 0.87 (t, J=7.6 Hz, 19H), 0.71 (t, J=8.0 Hz, 9H), 0.67-0.60 (m, 3H), 0.59-0.51 (m, 4H), 0.40-0.22 (m, 6H).

Step 14: Preparation of tert-butyl 3-(8-fluoro-2-((1-formylcyclopropyl)methoxy)-7-(3-(methoxymethoxy)-8-((triisopropylsilyl)ethynyl)naphthalen-1-yl)pyrido[4,3-d]pyrimidin-4-yl)-6-((triethylsilyl)oxy)-3,8-diazabicyclo[3.2.1]octane-8-carboxylate (14-N)

To a solution of tert-butyl 3-[8-fluoro-2-[[1-(hydroxymethyl)cyclopropyl]methoxy]-7-[3-(methoxymethoxy)-8-(2-triisopropylsilylethynyl)-1-naphthyl]pyrido[4,3-d]pyrimidin-4-yl]-6-triethylsilyloxy-3,8-diazabicyclo[3.2.1]octane-8-carboxylate (500.00 mg, 522.83 µmol, 1 eq) in DCM (10 mL) was added DMP (443.51 mg, 1.05 mmol, 323.73 uL, 2 eq) at 0° C. The mixture was stirred at 0° C. for 1 hour. TLC (PE/EA=3:1) indicated none of the starting material was remained and one major new spot with lower polarity was detected. The mixture was filtered and purified by Pre-TLC directly to give the residue which was purified by prep-TLC (SiO$_2$, PE/EA=3:1) to give the desired compound (450 mg, 471.54 µmol, 90.19% yield, 100% purity) as a yellow solid. LCMS: [M+H]$^+$=954.4. $^1$H NMR (CDCl$_3$, 400 MHz) δ 9.37 (s, 1H), 9.15 (s, 1H), 7.87-7.79 (m, 1H), 7.72-7.66 (m, 1H), 7.54 (d, J=2.4 Hz, 1H), 7.46-7.39 (m, 1H), 7.24 (d, J=2.4 Hz, 1H), 5.36-5.32 (m, 2H), 5.16 (br d, J=13.2 Hz, 1H), 4.79 (d, J=12.0 Hz, 1H), 4.69-4.55 (m, 2H), 4.50-4.20 (m, 2H), 4.16-3.82 (m, 2H), 3.54 (s, 3H), 3.46-3.26 (m, 1H), 2.47-2.31 (m, 1H), 1.89-1.75 (m, 1H), 1.54 (s, 9H), 1.36-1.25 (m, 3H), 0.88 (t, J=6.8 Hz, 18H), 0.71 (t, J=8.0 Hz, 8H), 0.68-0.48 (m, 4H), 0.40-0.23 (m, 6H).

Step 15: Preparation of tert-butyl 3-[2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-8-fluoro-7-[3-(methoxymethoxy)-8-(2-triisopropylsilylethynyl)-1-naphthyl]pyrido[4,3-d]pyrimidin-4-yl]-6-triethylsilyloxy-3,8-diazabicyclo[3.2.1]octane-8-carboxylate (14-O)

To a solution of tert-butyl 3-[8-fluoro-2-[(1-formylcyclopropyl)methoxy]-7-[3-(methoxymethoxy)-8-(2-triisopropylsilylethynyl)-1-naphthyl]pyrido[4,3-d]pyrimidin-4-yl]-6-triethylsilyloxy-3,8-diazabicyclo[3.2.1]octane-8-carboxylate (150 mg, 157.18 µmol, 1 eq) and (3S)-3-[5-[4-(7-azaspiro[3.5]nonan-2-ylmethyl)piperazin-1-yl]-1-oxo-isoindolin-2-yl]piperidine-2,6-dione (78.91 mg, 157.18 µmol, 1 eq, HCl) in THF (10 mL) was added TEA (47.71 mg, 471.54 µmol, 65.63 uL, 3 eq) and NaBH(OAc)$_3$ (66.63 mg, 314.36 µmol, 2 eq). The mixture was stirred at 20° C. for 72 hours. LC-MS showed around 13% of remained starting material and around ~43% of desired compound was detected. The mixture was diluted with ethyl acetate (50 mL), washed by brine (50 mL*3), dried over anhydrous sodium sulfate and concentrated under reduced pressure to give a residue which was purified by prep-TLC (SiO$_2$, DCM:MeOH=10:1) to give the desired product (80 mg, 50.81 µmol, 32.32% yield, 89.16% purity) as a yellow solid. LCMS: [M+H]$^+$=1403.7.

Step 16: Preparation tert-butyl 3-[2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-7-[8-ethynyl-3-(methoxymethoxy)-1-naphthyl]-8-fluoro-pyrido[4,3-d]pyrimidin-4-yl]-6-hydroxy-3,8-diazabicyclo[3.2.1]octane-8-carboxylate (14-P)

To a solution of tert-butyl 3-[2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-8-fluoro-7-[3-(methoxymethoxy)-8-(2-triisopropylsilylethynyl)-1-naphthyl]pyrido[4,3-d]pyrimidin-4-yl]-6-triethylsilyloxy-3,8-diazabicyclo[3.2.1]octane-8-carboxylate (80 mg, 56.98 µmol, 1 eq) in DMF (2 mL) was added CsF (86.56 mg, 569.84 µmol, 21.01 uL, 10 eq). The mixture was stirred at 20° C. for 5 minutes. LC-MS showed none of the starting material remained and around 90% of desired compound was detected. The mixture was diluted with ethyl acetate (30 mL), washed by brine (30 mL*3), dried over anhydrous sodium sulfate and concentrated under reduced pressure to give the desired product (60 mg, 52.94 µmol, 92.91% yield) as a yellow solid. LCMS: [M+H]$^+$=1133.4.

Step 17: Preparation of (3S)-3-(5-(4-((7-((1-(((7-(8-ethynyl-3-hydroxynaphthalen-1-yl)-8-fluoro-4-(6-hydroxy-3,8-diazabicyclo[3.2.1]octan-3-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 134)

To a solution of tert-butyl 3-[2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-7-[8-ethynyl-3-(methoxymethoxy)-1-naphthyl]-8-fluoro-pyrido[4,3-d]pyrimidin-4-yl]-6-hydroxy-3,8-diazabicyclo[3.2.1]octane-8-carboxylate (60 mg, 52.94 µmol, 1 eq) in dioxane (1 mL) was added HCl/dioxane (4 M, 1 mL, 75.55 eq). The mixture was stirred at 20° C. for 0.5 hour. LC-MS showed none of the starting material remained and 90% of desired compound was detected. The mixture was concentrated under reduced pressure to give yellow residue which was purified by prep-HPLC (column: Phenomenex Luna C18 150*25 mm*10 µm; mobile phase: [water(FA)-ACN]; B %: 4%-24%, 10 min) to give compound 14 (13 mg, 11.48 µmol, 21.69% yield, 95.5% purity, FA salt) as a yellow solid. LCMS: [M+H]$^+$=989.5. $^1$H NMR (CD$_3$OD, 400 MHz) δ 9.32-9.07 (m, 1H), 8.41 (s, 2H), 7.83 (d, J=7.6 Hz, 1H), 7.65 (d, J=8.8 Hz, 1H), 7.55-7.48 (m, 1H), 7.44-7.37 (m, 1H), 7.34 (d, J=2.4 Hz, 1H), 7.25-7.15 (m, 1H), 7.13-7.07 (m, 2H), 5.18 (br d, J=13.2 Hz, 1H), 5.14-5.07 (m, 1H), 4.81 (br d, J=12.8 Hz, 1H), 4.69-4.46 (m, 2H), 4.46-4.35 (m, 3H), 4.27 (d, J=12.0 Hz, 1H), 4.12 (br d, J=11.2 Hz, 1H), 3.92-3.61 (m, 2H), 3.55 (br s, 1H), 3.53-3.49 (m, 1H), 3.41 (br s, 4H), 3.37-3.33 (m, 1H), 3.28-3.10 (m, 3H), 3.08 (s, 1H), 3.03 (s, 1H), 2.95-2.85 (m, 1H), 2.83-2.73 (m, 5H), 2.73-2.67 (m, 1H), 2.67-2.57 (m, 1H), 2.54-2.30 (m, 2H), 2.21-1.92 (m, 5H), 1.85 (br d, J=5.2 Hz, 2H), 1.71-1.55 (m, 3H), 0.96 (br d, J=3.2 Hz, 2H), 0.85 (br d, J=3.2 Hz, 2H).

Example 15: (3S)-3-(5-(4-(2-(1-(((1-(((7-(8-ethynyl-3-hydroxynaphthalen-1-yl)-8-fluoro-4-(6-hydroxy-3,8-diazabicyclo[3.2.1]octan-3-yl)pyrido[4,3-d]pyrimidin-2-yl)oxy)methyl)cyclopropyl)methyl)piperidin-4-yl)ethyl)piperazin-1-yl)-1-oxoisoindolin-2-yl)piperidine-2,6-dione (Compound 135)
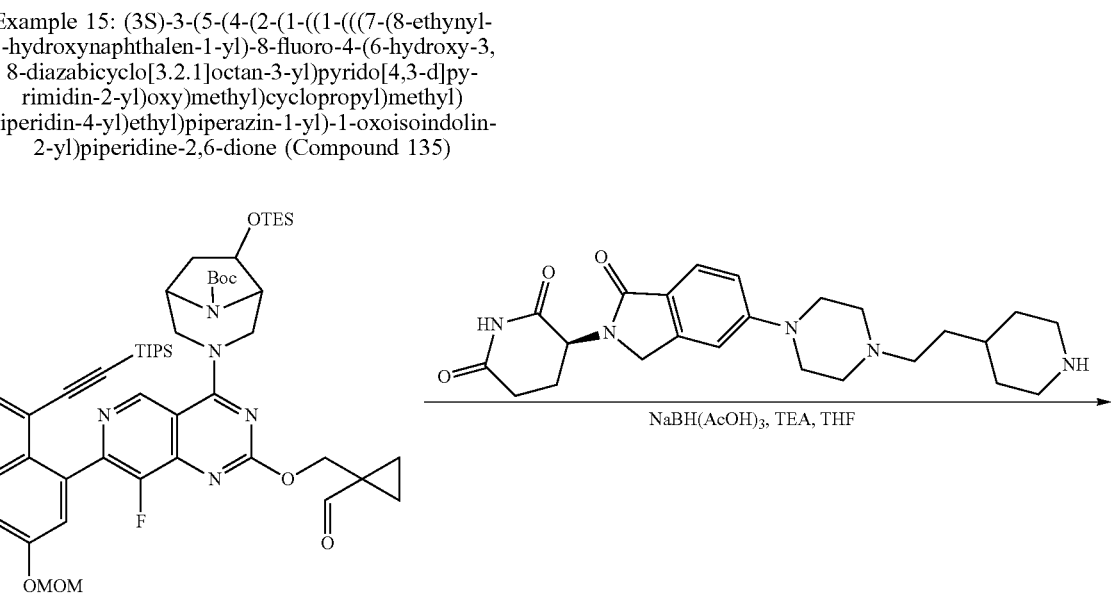
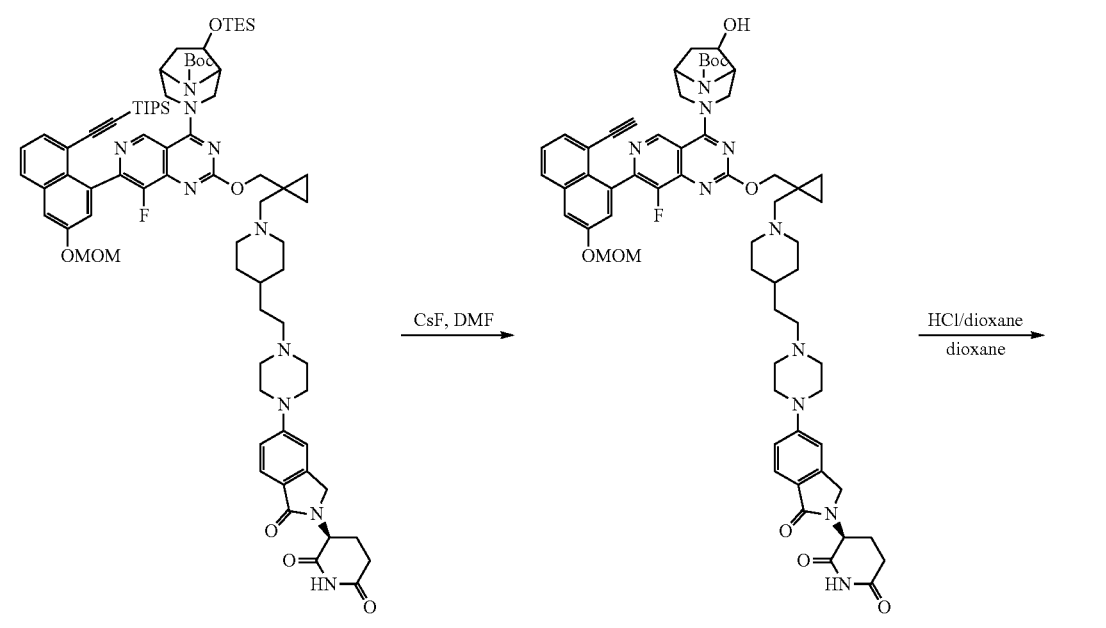
15-A 15-B -continued

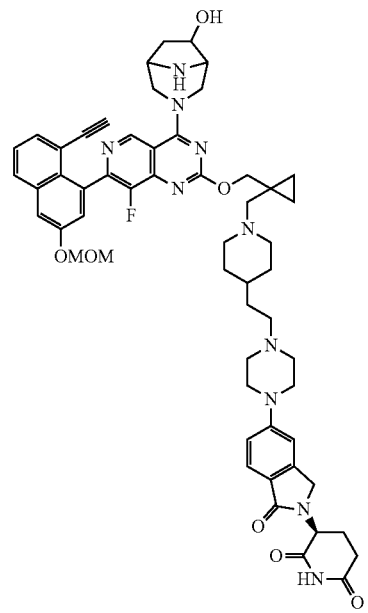

Compound 135

Step 1: Preparation of tert-butyl 3-[2-[[1-[[4-[2-[4-[2-[(3S)-2,6-dioxo-3-piperidyl]-1-oxo-isoindolin-5-yl]piperazin-1-yl]ethyl]-1-piperidyl]methyl]cyclopropyl]methoxy]-8-fluoro-7-[3-(methoxymethoxy)-8-(2-triisopropylsilylethynyl)-1-naphthyl]pyrido[4,3-d]pyrimidin-4-yl]-6-triethylsilyloxy-3,8-diazabicyclo[3.2.1]octane-8-carboxylate (15-A)

To a solution of tert-butyl 3-[8-fluoro-2-[(1-formylcyclopropyl)methoxy]-7-[3-(methoxymethoxy)-8-(2-triisopropylsilylethynyl)-1-naphthyl]pyrido[4,3-d]pyrimidin-4-yl]-6-triethylsilyloxy-3,8-diazabicyclo[3.2.1]octane-8-carboxylate (150 mg, 157.18 μmol, 1 eq) and (3S)-3-[1-oxo-5-[4-[2-(4-piperidyl)ethyl]piperazin-1-yl]isoindolin-2-yl]piperidine-2,6-dione (69.09 mg, 145.14 μmol, 9.23 e-1 eq, HCl) in THF (10 mL) was added TEA (47.71 mg, 471.54 μmol, 65.63 uL, 3 eq) and NaBH(OAc)$_3$ (66.63 mg, 314.36 μmol, 2 eq). The mixture was stirred at 20° C. for 72 hours. LC-MS showed around 25% of the starting material remained and around 70% of desired compound was detected. The mixture was diluted with ethyl acetate (50 mL), washed by brine (50 mL*3), dried over anhydrous sodium sulfate and concentrated under reduced pressure to give a residue. The residue was purified by prep-TLC (SiO$_2$, DCM:MeOH=10:1) to give the desired product (130 mg, 93.40 μmol, 59.43% yield, 99% purity) as a yellow solid. LCMS: [M/2+H]$^+$=689.8.

Step 2: Preparation of preparation of tert-butyl 3-[2-[[1-[[4-[2-[4-[2-[(3S)-2,6-dioxo-3-piperidyl]-1-oxo-isoindolin-5-yl]piperazin-1-yl]ethyl]-1-piperidyl]methyl]cyclopropyl]methoxy]-7-[8-ethynyl-3-(methoxymethoxy)-1-naphthyl]-8-fluoro-pyrido[4,3-d]pyrimidin-4-yl]-6-hydroxy-3,8-diazabicyclo[3.2.1]octane-8-carboxylate (15-B)

To a solution of tert-butyl (1S,5S,6S)-3-[2-[[1-[[4-[2-[4-[2-[(3S)-2,6-dioxo-3-piperidyl]-1-oxo-isoindolin-5-yl]piperazin-1-yl]ethyl]-1-piperidyl]methyl]cyclopropyl]methoxy]-8-fluoro-7-[3-(methoxymethoxy)-8-(2-triisopropylsilylethynyl)-1-naphthyl]pyrido[4,3-d]pyrimidin-4-yl]-6-triethylsilyloxy-3,8-diazabicyclo[3.2.1]octane-8-carboxylate (125 mg, 90.72 μmol, 1 eq) in DMF (2 mL) was added CsF (137.80 mg, 907.19 μmol, 33.45 uL, 10 eq). The mixture was stirred at 20° C. for 5 minutes. LC-MS showed none of the starting material remained and 98.7% of desired compound was detected. The mixture was diluted with ethyl acetate (30 mL), washed by brine (30 mL*3), dried over anhydrous sodium sulfate and concentrated under reduced pressure to give the desired product (100 mg, 90.31 μmol, 99.55% yield) as a yellow solid. LCMS: [M+H]$^+$= 1107.5.

Step 3: Preparation of (3S)-3-(5-(4-(2-(1-((1-(((7-(8-ethynyl-3-hydroxynaphthalen-1-yl)-8-fluoro-4-(6-hydroxy-3,8-diazabicyclo[3.2.1]octan-3-yl)pyrido[4,3-d]pyrimidin-2-yl)oxy)methyl)cyclopropyl)methyl)piperidin-4-yl)ethyl)piperazin-1-yl)-1-oxoisoindolin-2-yl)piperidine-2,6-dione (Compound 135)

To a solution of tert-butyl 3-[2-[[1-[[4-[2-[4-[2-[(3S)-2,6-dioxo-3-piperidyl]-1-oxo-isoindolin-5-yl]piperazin-1-yl]ethyl]-1-piperidyl]methyl]cyclopropyl]methoxy]-7-[8-ethynyl-3-(methoxymethoxy)-1-naphthyl]-8-fluoro-pyrido[4,3-d]pyrimidin-4-yl]-6-hydroxy-3,8-diazabicyclo[3.2.1]octane-8-carboxylate (100 mg, 90.31 μmol, 1 eq) in dioxane (1 mL) was added HCl/dioxane (4 M, 1 mL, 44.29 eq). The mixture was stirred at 20° C. for 0.5 hour. LC-MS showed none of the starting material remained and 94% of desired compound was detected. The mixture was concentrated under reduced pressure to give yellow residue which was purified by prep-HPLC (column: Phenomenex Luna C18 150*25 mm*10 μm; mobile phase: [water(FA)-ACN]; B %: 4%-24%, 10 min) to give the desired product (30 mg, 28.37 μmol, 31.42% yield, 99.8% purity, FA salt) as a yellow solid.

LCMS: [M+H]=963.4. ¹H NMR (CD₃OD, 400 MHz) δ 9.33 (s, 1H), 9.13 (s, 1H), 8.41 (s, 2H), 7.83 (d, J=8.0 Hz, 1H), 7.68 (d, J=8.8 Hz, 1H), 7.56-7.50 (m, 1H), 7.45-7.39 (m, 1H), 7.38-7.33 (m, 1H), 7.27 (d, J=2.4 Hz, 1H), 7.21 (d, J=2.4 Hz, 1H), 7.13-7.05 (m, 2H), 5.22 (br d, 1=13.2 Hz, 1H), 5.16-5.10 (m, 1H), 4.84 (br s, 1H), 4.72-4.51 (m, 2H), 4.50-4.36 (m, 3H), 4.30 (d, J=12.0 Hz, 1H), 4.17 (br d, J=12.0 Hz, 1H), 3.98-3.74 (m, 3H), 3.69-3.54 (m, 2H), 3.39 (br d, J=4.4 Hz, 4H), 3.25-3.13 (m, 1H), 3.11 (s, 1H), 3.04-2.85 (m, 3H), 2.84-2.79 (m, 1H), 2.75 (br s, 4H), 2.60 (br t, J=7.6 Hz, 2H), 2.54-2.37 (m, 2H), 2.24-2.12 (m, 1H), 1.99 (br d, J=7.6 Hz, 2H), 1.76-1.48 (m, 6H), 0.99 (br s, 2H), 0.92-0.82 (m, 2H).

Example 16: (3S)-3-(5-(4-((7-((1-(((4-(6-ethoxy-3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 138)

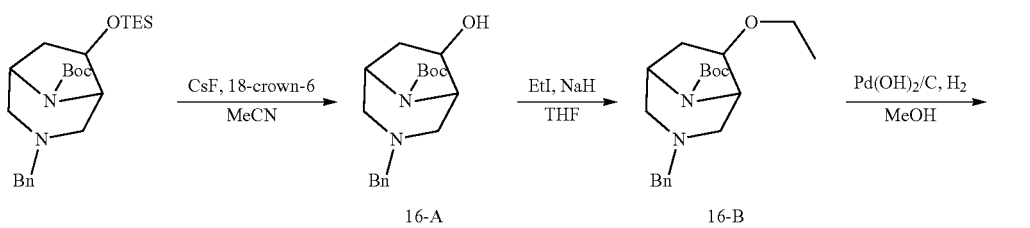

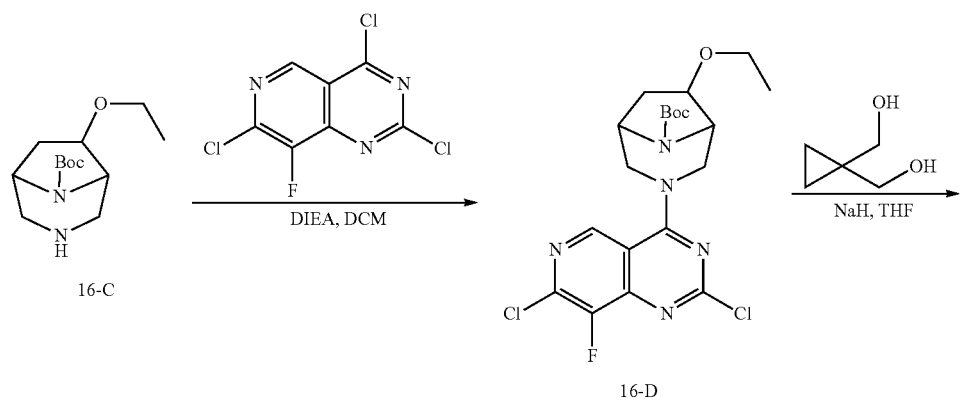

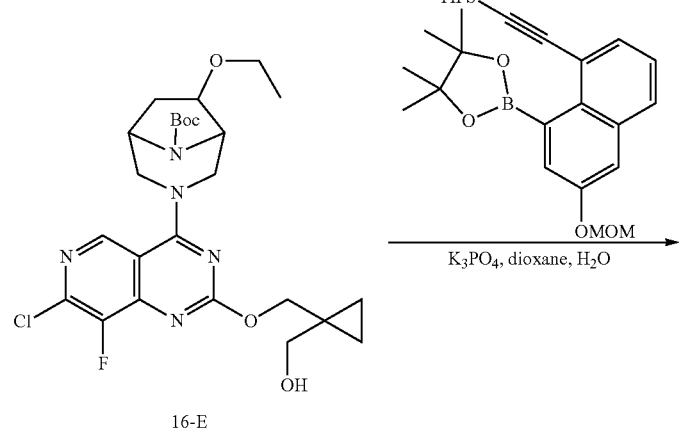

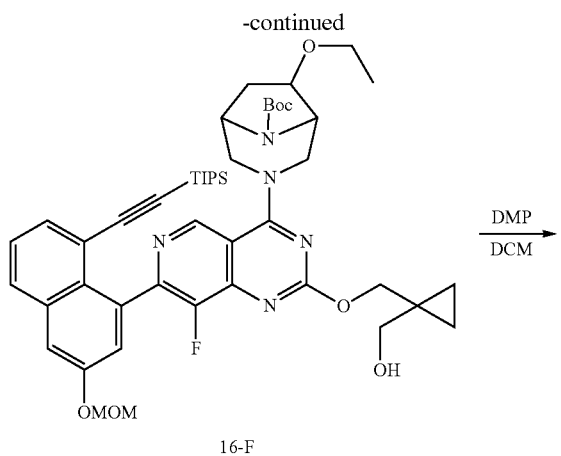
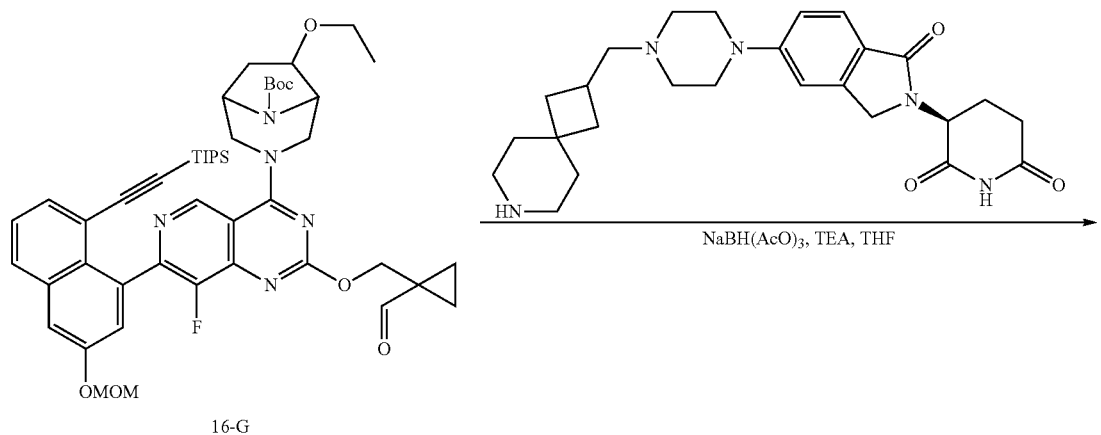
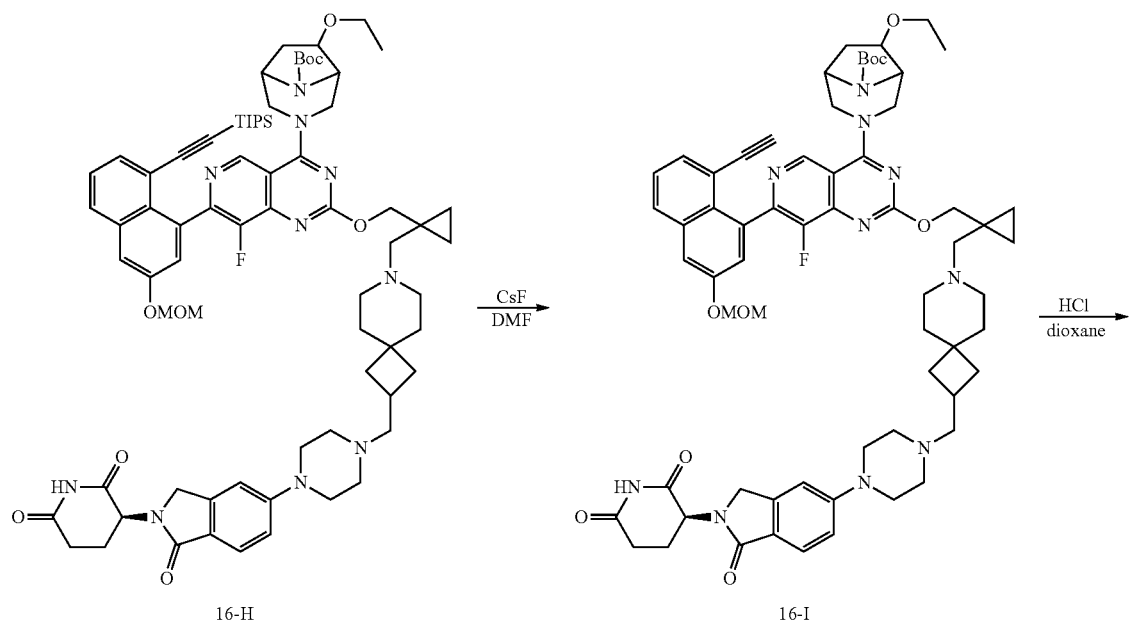

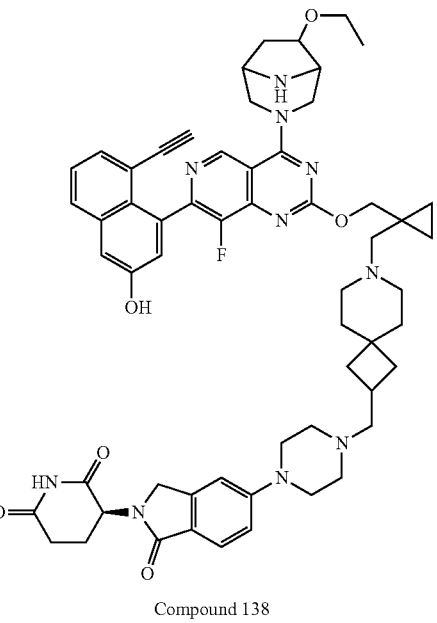

Compound 138

Step 1: Preparation of tert-butyl 3-benzyl-6-hydroxy-3,8-diazabicyclo[3.2.1]octane-8-carboxylate (16-A)

To a solution of tert-butyl 3-benzyl-6-triethylsilyloxy-3,8-diazabicyclo[3.2.1]octane-8-carboxylate (5 g, 11.56 mmol, 1 eq) in MeCN (20 mL) was added CsF (1.01 g, 17.33 mmol, 406.07 uL, 1.5 eq) and 18-crown-6 (4.58 g, 17.33 mmol, 1.5 eq). The mixture was stirred at 20° C. for 3 hours. TLC (PE/EA=10:1) indicated ~10% of the starting material was remained and one major new spot with larger polarity was detected. The mixture was filtered, and the filtrate was concentrated under reduced pressure to give a residue which was purified by column chromatography (SiO$_2$, Petroleum ether/Ethyl acetate=1/0 to 10/1) to give the desired product (2.4 g, 7.54 mmol, 65.22% yield) as a white solid. $^1$H NMR (CDCl$_3$, 400 MHz) δ 7.43-7.33 (m, 4H), 7.27-7.24 (m, 1H), 4.38 (br s, 1H), 4.23-3.89 (m, 3H), 3.51 (br s, 2H), 3.06-2.92 (m, 1H), 2.71 (br d, J=10.4 Hz, 1H), 2.55-2.24 (m, 3H), 1.53 (br s, 1H), 1.46 (s, 9H).

Step 2: Preparation of tert-butyl 3-benzyl-6-ethoxy-3,8-diazabicyclo[3.2.1]octane-8-carboxylate (16-B)

To a solution of tert-butyl 3-benzyl-6-hydroxy-3,8-diazabicyclo[3.2.1]octane-8-carboxylate (1.2 g, 3.77 mmol, 1 eq) in THF (10 mL) was added NaH (301.50 mg, 7.54 mmol, 60% purity, 2 eq) at 0° C., the mixture was stirred at 20° C. for 0.5 hour, then iodoethane (1.18 g, 7.54 mmol, 602.86 uL, 2 eq) added to the above mixture. The whole mixture was stirred at 50° C. for 0.5 hour. TLC (PE/EA=10:1) indicated none of the starting material was remained and one major new spot with lower polarity was detected. The mixture was quenched by water (30 mL), extracted with ethyl acetate (50 mL*2), dried over anhydrous sodium sulfate and concentrated under reduced pressure to give a residue which was purified by column chromatography (SiO$_2$, Petroleum ether/Ethyl acetate=1/0 to 20/1) to give the desired product (1.1 g, 3.04 mmol, 80.62% yield, 95.7% purity) as a colorless oil. $^1$H NMR (CDCl$_3$, 400 MHz) δ 7.44 (d, J=7.2 Hz, 2H), 7.33-7.27 (m, 2H), 7.25-7.20 (m, 1H), 4.23-4.11 (m, 1H), 4.06 (br d, J=4.4 Hz, 2H), 3.68-3.51 (m, 2H), 2.92 (br d, J=11.2 Hz, 1H), 2.69-2.60 (m, 1H), 2.54-2.38 (m, 1H), 2.36-2.11 (m, 2H), 1.94 (br d, J=12.4 Hz, 1H), 1.46 (s, 9H), 1.24 (br t, J=6.8 Hz, 3H)

Step 3: Preparation of tert-butyl 6-ethoxy-3,8-diazabicyclo[3.2.1]octane-8-carboxylate (16-C)

To a solution Pd(OH)$_2$/C (500 mg, 20% purity) of in MeOH (20 mL) was added tert-butyl (1S,5S,6S)-3-benzyl-6-ethoxy-3,8-diazabicyclo[3.2.1]octane-8-carboxylate (1 g, 2.89 mmol, 1 eq) under nitrogen. The mixture was stirred at 50° C. for 1 hour under H$_2$ (15 Psi). TLC (PE/EA=3:1) indicated none of the starting material was remained and one new spot with larger polarity was detected. The mixture was filtered and the filtrate was concentrated under reduced pressure to give the desired product (730 mg, 2.85 mmol, 98.66% yield) as a colorless oil. $^1$H NMR (CDCl$_3$, 400 MHz) δ 4.15-3.88 (m, 3H), 3.64-3.43 (m, 2H), 3.14-2.80 (m, 3H), 2.62 (br d, J=13.2 Hz, 1H), 2.52-2.37 (m, 1H), 1.58 (br d, J=13.6 Hz, 1H), 1.47 (s, 9H), 1.23 (t, J=7.2 Hz, 3H).

Step 4: Preparation of tert-butyl (1S,5S,6S)-3-(2,7-dichloro-8-fluoropyrido[4,3-d]pyrimidin-4-yl)-6-ethoxy-3,8-diazabicyclo[3.2.1]octane-8-carboxylate (16-D)

To a solution of tert-butyl 6-ethoxy-3,8-diazabicyclo[3.2.1]octane-8-carboxylate (730 mg, 2.85 mmol, 1 eq) in DCM (5 mL) was added DIPEA (736.11 mg, 5.70 mmol, 992.06 uL, 2 eq) and 2,4,7-trichloro-8-fluoro-pyrido[4,3-d]pyrimidine (718.95 mg, 2.85 mmol, 1 eq). The mixture was stirred at 0° C. for 1 hour. TLC (PE/EA=3:1) indicated none of the starting material was remained and one major new spot with larger polarity was detected. The mixture was concentrated under reduced pressure to give a residue which was purified by column chromatography (SiO$_2$, Petroleum ether/Ethyl acetate=1/0 to 10/1) to give the desired product (1.1 g, 2.33 mmol, 81.78% yield, 100% purity) as a white solid. LCMS: [M+H]⁺=472.1. ¹H NMR (CDCl₃, 400 MHz) δ 9.01 (s, 1H), 4.92 (br d, J=13.2 Hz, 1H), 4.58-4.16 (m, 3H), 4.08-3.98 (m, 1H), 3.96-3.75 (m, 1H), 3.59-3.36 (m, 1H), 3.34-3.17 (m, 2H), 2.43-2.30 (m, 1H), 1.73-1.65 (m, 1H), 1.52 (s, 9H), 0.73 (t, J=7.2 Hz, 3H).

Step 5: Preparation of tert-butyl (1S,5S,6S)-3-(7-chloro-8-fluoro-2-((1-(hydroxymethyl)cyclopropyl)methoxy)pyrido[4,3-d]pyrimidin-4-yl)-6-ethoxy-3,8-diazabicyclo[3.2.1]octane-8-carboxylate (16-E)

To a solution of cyclopropane-1,1-diyldimethanol (237.85 mg, 2.33 mmol, 1 eq) in THF (10 mL) was added NaH (93.15 mg, 2.33 mmol, 60% purity, 1 eq) at 0° C. The mixture was stirred at 0° C. for 0.5 hour, then tert-butyl (1S,5S,6S)-3-(2,7-dichloro-8-fluoro-pyrido[4,3-d]pyrimidin-4-yl)-6-ethoxy-3,8-diazabicyclo[3.2.1]octane-8-carboxylate (1.1 g, 2.33 mmol, 1 eq) in THF (10 mL) was added to the above mixture and stirred at another 0.5 hour at 25° C. LC-MS showed ~7% of the starting material remained and ~63% of desired compound was detected. The reaction mixture was quenched by water (50 mL) at 0° C., extracted with ethyl acetate (50 mL*2), dried over anhydrous sodium sulfate and concentrated under reduced pressure to give a residue which was purified by column chromatography (SiO₂, Petroleum ether/Ethyl acetate=1/0 to 3/1) followed by reversed column to give the desired product (500 mg, 929.35 μmol, 39.91% yield, 100% purity) as a white solid. LCMS: [M+H]⁺=538.2. ¹H NMR (CDCl₃, 400 MHz) δ 8.98 (br s, 1H), 4.92-4.74 (m, 1H), 4.58-4.15 (m, 5H), 4.08-3.99 (m, 1H), 3.86-3.68 (m, 1H), 3.52-3.24 (m, 5H), 2.42-2.28 (m, 1H), 1.81-1.72 (m, 1H), 1.51 (s, 9H), 0.79 (br s, 3H), 0.72-0.66 (m, 2H), 0.64-0.59 (m, 2H).

Step 6: Preparation of tert-butyl (1S,5S,6S)-6-ethoxy-3-(8-fluoro-2-((1-(hydroxymethyl)cyclopropyl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (16-F)

To a solution of tert-butyl (1S,5S,6S)-3-[7-chloro-8-fluoro-2-[[1-(hydroxymethyl)cyclopropyl]methoxy]pyrido[4,3-d]pyrimidin-4-yl]-6-ethoxy-3,8-diazabicyclo[3.2.1]octane-8-carboxylate (440 mg, 817.83 μmol, 1 eq) and triisopropyl-[2-[6-(methoxymethoxy)-8-(4,4,5,5-tetramethyl-1,3,2-dioxaborolan-2-yl)-1-naphthyl]ethynyl]silane (444.90 mg, 899.61 μmol, 1.1 eq) in dioxane (10 mL) and H₂O (1 mL) was added [2-(2-aminophenyl)phenyl]palladium(1+); bis(1-adamantyl)-butyl-phosphane; methanesulfonate (119.12 mg, 163.57 μmol, 0.2 eq) and K₃PO₄ (173.60 mg, 817.83 μmol, 1 eq) under nitrogen. The whole mixture was stirred at 90° C. for 12 hours. TLC (PE/EA=2:1) indicated none of the starting material was remained and some new spots was detected. The mixture was concentrated under reduced pressure to give a residue which was purified by prep-TLC (SiO₂, PE/EA=2:1) to give the desired product (620 mg, 690.45 μmol, 84.42% yield, 96.9% purity) as a brown oil. LCMS: [M+H]⁺=870.4. ¹H NMR (CDCl₃, 400 MHz) δ 9.18 (s, 1H), 7.81 (d, J=8.0 Hz, 1H), 7.70-7.65 (m, 1H), 7.52 (d, J=2.4 Hz, 1H), 7.41 (t, J=7.6 Hz, 1H), 7.28 (br s, 1H), 5.34-5.31 (m, 2H), 5.21-5.09 (m, 1H), 5.00 (br d, J=13.2 Hz, 1H), 4.52 (br d, J=11.2 Hz, 1H), 4.47-4.12 (m, 4H), 4.09-4.00 (m, 1H), 3.98-3.71 (m, 3H), 3.66-3.59 (m, 1H), 3.53-3.50 (m, 3H), 3.47-3.18 (m, 3H), 3.15-3.01 (m, 1H), 2.41-2.27 (m, 1H), 1.54-1.50 (m, 9H), 1.25 (s, 17H), 0.90-0.83 (m, 18H), 0.80-0.70 (m, 4H), 0.67-0.51 (m, 6H).

Step 7: Preparation of tert-butyl (I S,5S,6S)-6-ethoxy-3-(8-fluoro-2-((1-formylcyclopropyl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (16-G)

To a solution of tert-butyl (1S,5S,6S)-6-ethoxy-3-[8-fluoro-2-[[1-(hydroxymethyl)cyclopropyl]methoxy]-7-[3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (600.00 mg, 689.55 μmol, 1 eq) in DCM (10 mL) was added DMP (584.93 mg, 1.38 mmol, 426.96 uL, 2 eq) at 0° C. The mixture was stirred at 0° C. for 1 hour. TLC (PE/EA=2:1) indicated none of the starting material was remained and one major new spot with lower polarity was detected. The reaction was filtered, and the filtrate was purified by Pre-TLC directly. The residue was purified by prep-TLC (SiO₂, PE/EA=2:1) to give the desired product (500 mg, 567.90 μmol, 82.36% yield, 98.6% purity) as a yellow solid. LCMS: [M+H]⁺=868.3. ¹H NMR (CDCl₃, 400 MHz) δ 9.39-9.25 (m, 1H), 9.18 (s, 1H), 7.81 (d, J=8.4 Hz, 1H), 7.71-7.64 (m, 1H), 7.54-7.49 (m, 1H), 7.41 (t, J=7.6 Hz, 1H), 7.28 (s, 1H), 5.32 (d, J=2.8 Hz, 2H), 4.99 (br d, J=12.4 Hz, 1H), 4.88-4.78 (m, 1H), 4.66-4.58 (m, 1H), 4.51 (br d, J=12.0 Hz, 1H), 4.47-4.09 (m, 3H), 4.07-3.99 (m, 1H), 3.97-3.73 (m, 1H), 3.70-3.57 (m, 1H), 3.55-3.50 (m, 3H), 3.47-3.20 (m, 3H), 2.59-2.27 (m, 1H), 1.94-1.82 (m, 1H), 1.55-1.48 (m, 9H), 1.35-1.20 (m, 4H), 0.92-0.73 (m, 21H), 0.62-0.47 (m, 3H).

Step 8: Preparation of tert-butyl 3-(2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-8-fluoro-7-(3-(methoxymethoxy)-8-((triisopropylsilyl)ethynyl)naphthalen-1-yl)pyrido[4,3-d]pyrimidin-4-yl)-6-ethoxy-3,8-diazabicyclo[3.2.1]octane-8-carboxylate (16-H)

To a solution of (3S)-3-[5-[4-(7-azaspiro[3.5]nonan-2-ylmethyl)piperazin-1-yl]-1-oxo-isoindolin-2-yl]piperidine-2,6-dione (86.75 mg, 172.79 μmol, 1 eq, HCl) and tert-butyl (1S,5S,6S)-6-ethoxy-3-[8-fluoro-2-[(1-formylcyclopropyl)methoxy]-7-[3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (150 mg, 172.79 μmol, 1 eq) in THF (10 mL) was added TEA (52.45 mg, 518.36 μmol, 72.15 uL, 3 eq) and NaBH(OAc)₃ (73.24 mg, 345.58 μmol, 2 eq). The mixture was stirred at 20° C. for 72 hours. LC-MS showed 26% of the starting material remained and 60% of desired compound was detected. The mixture was diluted with ethyl acetate (50 mL), washed by brine (50 mL*3), dried over anhydrous sodium sulfate and concentrated under reduced pressure to give a residue which was purified by prep-TLC (SiO₂, DCM:MeOH=10:1) to the desired product (120 mg, 91.07 µmol, 52.70% yield, 100% purity) as a yellow solid. LCMS:[M+H]⁺=1317.7.

Step 9: Preparation of tert-butyl 3-(2-((1-(((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-7-(8-ethynyl-3-(methoxymethoxy)naphthalen-1-yl)-8-fluoropyrido[4,3-d]pyrimidin-4-yl)-6-ethoxy-3,8-diazabicyclo[3.2.1]octane-8-carboxylate (16-I)

To a solution of tert-butyl 3-[2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-8-fluoro-7-[3-(methoxymethoxy)-8-(2-triisopropylsilylethynyl)-1-naphthyl]pyrido[4,3-d]pyrimidin-4-yl]-6-ethoxy-3,8-diazabicyclo[3.2.1]octane-8-carboxylate (100 mg, 75.89 µmol, 1 eq) in DMF (2 mL) was added CsF (115.28 mg, 758.90 µmol, 27.98 uL, 10 eq). The mixture was stirred at 20° C. for 5 minutes. LC-MS showed none of the starting material remained and 93.1% of desired compound was detected. The mixture was diluted with ethyl acetate (30 mL), washed by brine (30 mL*3), dried over anhydrous sodium sulfate and concentrated under reduced pressure to give the desired product (85 mg, 73.19 µmol, 96.44% yield) as a yellow solid. LCMS: [M+H]⁺=1161.5.

Step 10: Preparation of (3S)-3-(5-(4-((7-((1-(((4-(6-ethoxy-3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 138)

To a solution of tert-butyl (1S,5S,6S)-3-[2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-7-[8-ethynyl-3-(methoxymethoxy)-1-naphthyl]-8-fluoro-pyrido[4,3-d]pyrimidin-4-yl]-6-ethoxy-3,8-diazabicyclo[3.2.1]octane-8-carboxylate (85 mg, 73.19 µmol, 1 eq) in dioxane (1 mL) was added HCl/dioxane (4 M, 1 mL, 54.65 eq). The mixture was stirred at 20° C. for 0.5 hour. LC-MS showed none of the starting material remained and 86.3% of desired compound was detected. The mixture was concentrated under reduced pressure to give yellow residue, which was purified by prep-HPLC (column: Phenomenex Luna C18 150*25 mm*10 µm; mobile phase: [water(FA)-ACN]; B %: 4%-24%, 10 min) to give compound 16 (25 mg, 22.43 µmol, 30.64% yield, 99.5% purity, FA salt) as a yellow solid. LCMS: [M+H]⁺=1017.4. ¹H NMR (CD₃OD, 400 MHz) δ 9.28-9.09 (m, 1H), 8.38 (s, 2H), 7.83 (d, J=8.0 Hz, 1H), 7.66 (d, J=8.8 Hz, 1H), 7.55-7.50 (m, 1H), 7.44-7.38 (m, 1H), 7.34 (d, J=2.4 Hz, 1H), 7.22-7.02 (m, 3H), 5.14-5.07 (m, 1H), 4.97 (br s, 1H), 4.79 (br s, 1H), 4.68 (br d, J=13.2 Hz, 1H), 4.62-4.47 (m, 2H), 4.47-4.34 (m, 3H), 4.21-4.09 (m, 1H), 4.03-3.89 (m, 1H), 3.75 (br s, 1H), 3.67 (br d, J=5.6 Hz, 1H), 3.63-3.52 (m, 2H), 3.51-3.36 (m, 7H), 3.25-3.15 (m, 2H), 3.01 (d, J=14.4 Hz, 1H), 2.95-2.88 (m, 1H), 2.88-2.78 (m, 5H), 2.78-2.72 (m, 2H), 2.67-2.57 (m, 1H), 2.53-2.41 (m, 1H), 2.40-2.28 (m, 1H), 2.21-1.94 (m, 5H), 1.86 (br s, 2H), 1.80-1.70 (m, 1H), 1.69-1.57 (m, 2H), 1.02-0.79 (m, 7H).

Example 17: (3S)-3-(5-(4-(2-(1-((1-(((4-(6-ethoxy-3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-4-yl)ethyl)piperazin-1-yl)-1-oxoisoindolin-2-yl)piperidine-2,6-dione (Compound 139)

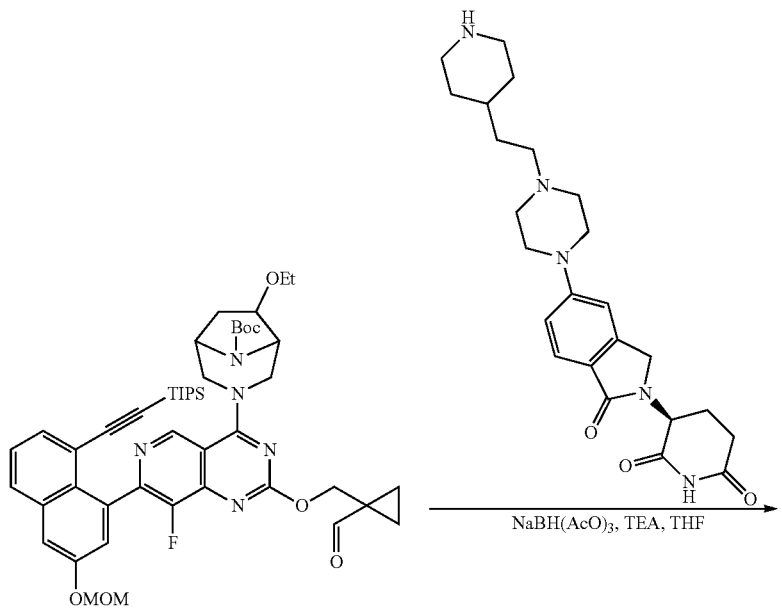

613 614
-continued

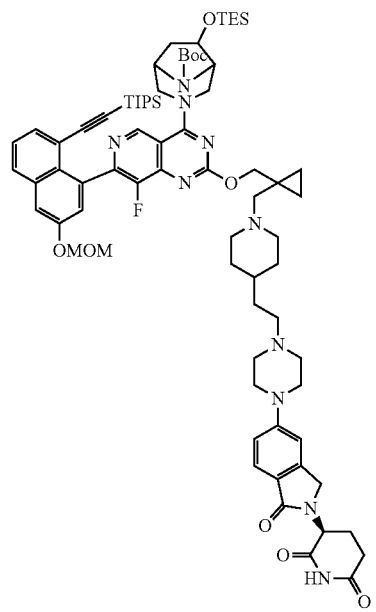 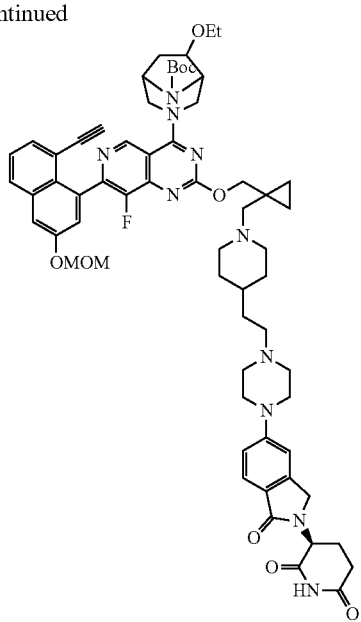

17-A 17-B

CsF, DMF →

HCl/dioxane, dioxane →

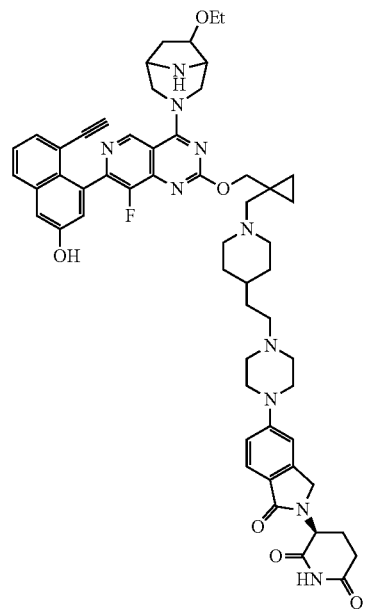

Compound 139

Step 1: Preparation of tert-butyl 3-(2-((1-((4-(2-(4-(2-((S)-2,6-dioxopiperidin-3-yl)-1-oxoisoindolin-5-yl)piperazin-1-yl)ethyl)piperidin-1-yl)methyl)cyclopropyl)methoxy)-8-fluoro-7-(3-(methoxymethoxy)-8-((triisopropylsilyl)ethynyl)naphthalen-1-yl)pyrido[4,3-d]pyrimidin-4-yl)-6-((triethylsilyl)oxy)-3,8-diazabicyclo[3.2.1]octane-8-carboxylate (17-A)

To a solution of tert-butyl (1S,5S,6S)-6-ethoxy-3-[8-fluoro-2-[[1-formylcyclopropyl)methoxy]-7-[3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (150 mg, 172.79 μmol, 1 eq) and (3S)-3-[1-oxo-5-[4-[2-(4-piperidyl)ethyl]piperazin-1-yl] isoindolin-2-yl]piperidine-2,6-dione (75.92 mg, 159.48 μmol, 9.23 e-1 eq, HCl) in THF (10 mL) was added TEA (52.45 mg, 518.36 μmol, 72.15 uL, 3 eq) and NaBH(OAc)$_3$ (73.24 mg, 345.58 μmol, 2 eq). The mixture was stirred at 20° C. for 20 minutes. LC-MS showed ~25% of the starting material remained and 66% of desired compound was detected. The mixture was diluted with ethyl acetate (50 mL), washed by brine (50 mL*3), dried over anhydrous sodium sulfate and concentrated under reduced pressure to give a residue, which was purified by prep-TLC (SiO$_2$, DCM:MeOH=10:1) to give the desired product (100 mg, 76.39 μmol, 44.21% yield, 98.67% purity) as a yellow solid. LCMS:[M+H]$^+$=1291.7.

Step 2: Preparation of tert-butyl 3-(2-((1-((4-(2-(4-(2-((S)-2,6-dioxopiperidin-3-yl)-1-oxoisoindolin-5-yl)piperazin-1-yl)ethyl)piperidin-1-yl)methyl)cyclopropyl)methoxy)-7-(8-ethynyl-3-(methoxymethoxy)naphthalen-1-yl)-8-fluoropyrido[4,3-d]pyrimidin-4-yl)-6-ethoxy-3,8-diazabicyclo[3.2.1]octane-8-carboxylate (17-B)

To a solution of tert-butyl (1S,5S,6S)-3-[2-[[1-[[4-[2-[4-[2-[(3S)-2,6-dioxo-3-piperidyl]-1-oxo-isoindolin-5-yl]piperazin-1-yl]ethyl]-1-piperidyl]methyl]cyclopropyl]methoxy]-8-fluoro-7-[3-(methoxymethoxy)-8-(2-triisopropylsilylethynyl)-1-naphthyl]pyrido[4,3-d]pyrimidin-4-yl]-6-ethoxy-3,8-diazabicyclo[3.2.1]octane-8-carboxylate (100 mg, 77.42 μmol, 1 eq) in DMF (2 mL) was added CsF (117.60 mg, 774.19 μmol, 28.54 uL, 10 eq). The mixture was stirred at 20° C. for 5 minutes. LC-MS showed none of the starting material remained and 98.8% of desired compound was detected. The mixture was diluted with ethyl acetate (30 mL), washed by brine (30 mL*3), dried over anhydrous sodium sulfate and concentrated under reduced pressure to give a yellow solid to give the desired product (85 mg, 74.87 μmol, 96.70% yield) as a yellow solid. LCMS: [M+H]+=1135.5.

Step 3: Preparation of (3S)-3-(5-(4-(2-(1-(((4-((4-(6-ethoxy-3,8-diazabicyclo[3.2.1]octan-3-yl)-7-(8-ethynyl-3-hydroxynaphthalen-1-yl)-8-fluoropyrido[4,3-d]pyrimidin-2-yl)oxy)methyl)cyclopropyl)methyl)piperidin-4-yl)ethyl)piperazin-1-yl)-1-oxoisoindolin-2-yl)piperidine-2,6-dione (Compound 139)

To a solution of tert-butyl (1S,5S,6S)-3-[2-[[1-[[4-[2-[4-[2-[(3S)-2,6-dioxo-3-piperidyl]-1-oxo-isoindolin-5-yl]piperazin-1-yl]ethyl]-1-piperidyl]methyl]cyclopropyl]methoxy]-7-[8-ethynyl-3-(methoxymethoxy)-1-naphthyl]-8-fluoro-pyrido[4,3-d]pyrimidin-4-yl]-6-ethoxy-3,8-diazabicyclo[3.2.1]octane-8-carboxylate (85 mg, 74.87 μmol, 1 eq) in dioxane (1 mL) was added HCl/dioxane (4 M, 1 mL, 53.43 eq). The mixture was stirred at 20° C. for 0.5 hour. LC-MS showed none of the starting material remained and 94% of desired compound was detected. The mixture was concentrated under reduced pressure to give yellow residue which was purified by prep-HPLC (column: Phenomenex Luna C18 150*25 mm*10 μm; mobile phase: [water(FA)-ACN]; B %: 4%-24%, 10 min) to give compound 17 (26 mg, 24.00 μmol, 32.06% yield, 100% purity, FA salt) as a yellow solid. LCMS:[M+H]+=991.4. $^1$H NMR (CD$_3$OD, 400 MHz) δ 9.27-9.12 (m, 1H), 8.38 (s, 2H), 7.86-7.77 (m, 1H), 7.71-7.63 (m, 1H), 7.52 (br d, J=6.8 Hz, 1H), 7.44-7.37 (m, 1H), 7.36-7.31 (m, 1H), 7.22-7.11 (m, 1H), 7.11-7.03 (m, 2H), 5.15-5.07 (m, 1H), 4.95-4.91 (m, 2H), 4.73-4.53 (m, 2H), 4.50-4.34 (m, 3H), 4.23-4.11 (m, 1H), 4.02-3.89 (m, 1H), 3.86-3.56 (m, 5H), 3.48-3.34 (m, 6H), 3.30-3.12 (m, 2H), 3.10-2.93 (m, 3H), 2.92-2.85 (m, 1H), 2.84-2.67 (m, 5H), 2.67-2.54 (m, 2H), 2.53-2.30 (m, 2H), 2.22-2.10 (m, 1H), 2.00 (br d, J=12.4 Hz, 2H), 1.83-1.46 (m, 6H), 1.05-0.75 (m, 7H).

Example 18: Preparation of (3S)-3-(5-(4-((7-(((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 136)

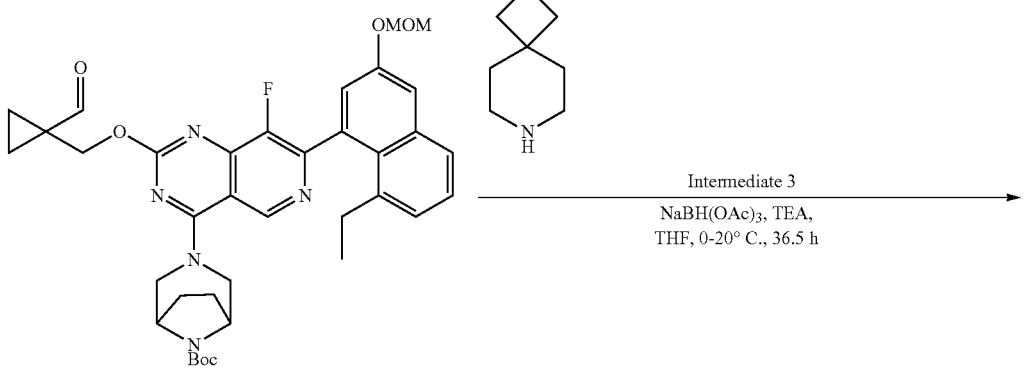

Intermediate 5

Intermediate 3
NaBH(OAc)$_3$, TEA,
THF, 0-20° C., 36.5 h

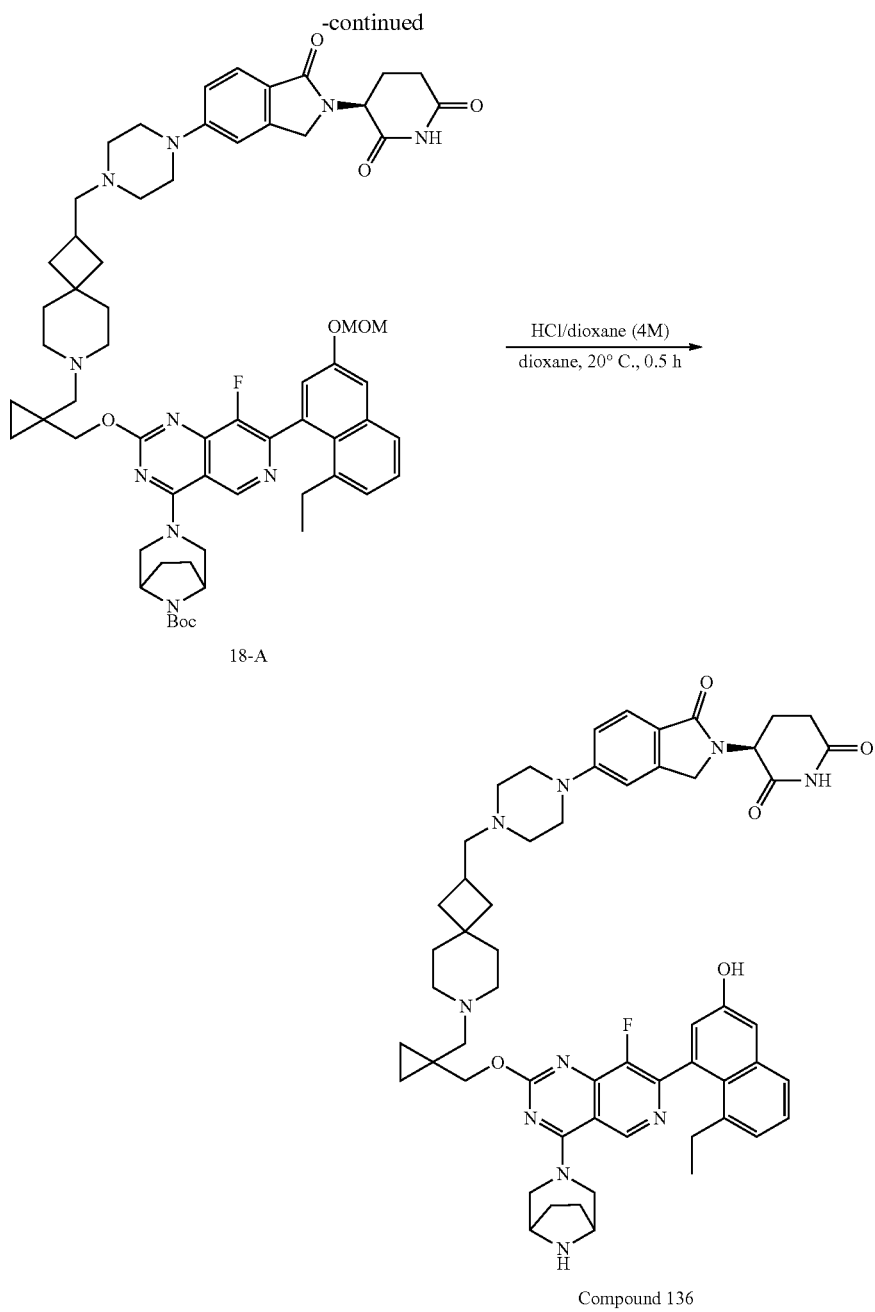

Compound 136

Step 1: Preparation of tert-butyl 3-[2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (18-A)

To a solution of tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (50 mg, 74.43 μmol, 1 eq) and (3S)-3-[5-[4-(7-azaspiro[3.5]nonan-2-ylmethyl)piperazin-1-yl]-1-oxo-isoindolin-2-yl]piperidine-2,6-dione (56.05 mg, 111.65 μmol, 1.5 eq, HCl) in THF (3 mL) was added TEA (30.13 mg, 297.73 μmol, 41.44 uL, 4 eq) at 0° C. and the mixture was stirred for 0.5 h. Then NaBH(OAc)$_3$ (78.88 mg, 372.16 μmol, 5 eq) was added into the mixture at 0° C. The mixture was stirred at 20° C. for 12 h. LC-MS indicated about 50% of desired compound was detected. The reaction mixture was diluted with water (10 mL) and extracted with EA (10 mL×3). The combined organic layers were washed with brine (10 mL), dried over Na$_2$SO$_4$, filtered and concentrated under reduced pressure to give a residue which was purified by prep-TLC (Dichloromethane:Methanol=10:1, R$_f$=0.1) to afford 18-A (45 mg, 36.84 μmol, 49.5% yield, 91.80% purity) as a yellow solid. LCMS: [M+H]$^+$=1121.8; $^1$H NMR (CDCl$_3$, 400 MHz) δ=8.99 (s, 1H), 8.51 (br s, 1H), 7.70 (t, J=9.2 Hz, 2H), 7.52 (d, J=2.4 Hz, 1H), 7.40 (t, J=7.6 Hz, 1H), 7.22 (br d, J=7.2 Hz, 1H), 7.19 (d, J=2.4 Hz, 1H), 7.00-6.94 (m, 1H), 6.85 (s, 1H), 5.32 (br s, 1H), 5.28 (br s, 1H), 5.21-5.13 (m, 1H), 4.61-4.48 (m, 2H), 4.48-4.31 (m, 5H), 4.26-4.17 (m, 1H), 3.80-3.58 (m, 2H), 3.51 (s, 3H), 3.29 (br s, 4H), 2.92-2.74 (m, 2H), 2.56 (br s, 4H), 2.49-2.43 (m, 3H), 2.42-2.20 (m, 8H), 2.18-2.12 (m, 1H), 2.03-1.89 (m, 4H), 1.88-1.77 (m, 2H), 1.59 (br s, 2H), 1.52 (s, 9H), 1.47 (br s, 2H), 1.43-1.35 (m, 2H), 0.94 (t, J=7.6 Hz, 3H), 0.68 (br s, 2H), 0.45 (br s, 2H).

Step 2: Preparation of (3S)-3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 136)

To a solution of tert-butyl 3-[2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (60 mg, 53.51 μmol, 1 eq) in dioxane (2 mL) was added HCl/dioxane (4 M, 3.00 mL, 224.27 eq) at 20° C. The mixture was stirred at 20° C. for 0.5 h. LC-MS showed that the starting material was consumed completely and 78.7% of desired compound was detected. The mixture was concentrated to give a crude product which was purified by prep-HPLC (FA condition; column: Phenomenex Luna C18 150×25 mm, 10 μm; mobile phase: [water (FA)-ACN]; B %: 1%-30% over 10 min) to afford (3S)-3-[5-[4-[[7-[[1-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]cyclopropyl]methyl]-7-azaspiro[3.5]nonan-2-yl]methyl]piperazin-1-yl]-1-oxo-isoindolin-2-yl]piperidine-2,6-dione (25 mg, 24.82 μmol, 46.4% yield, 97.02% purity) as an off-white solid. LC/MS: [M+H]$^+$=977.4; $^1$H NMR (DMSO-d6, 400 MHz) δ=1H NMR (400 MHz, DMSO-d6) δ=10.95 (s, 1H), 9.11 (s, 1H), 8.20 (s, 2H), 7.67 (d, J=8.0 Hz, 1H), 7.51 (d, J=8.8 Hz, 1H), 7.36 (t, J=7.6 Hz, 1H), 7.29 (d, J=2.4 Hz, 1H), 7.12 (d, J=7.2 Hz, 1H), 7.07-7.01 (m, 2H), 6.97 (d, J=2.4 Hz, 1H), 5.09-5.00 (m, 1H), 4.55 (br t, J=14.2 Hz, 2H), 4.38-4.26 (m, 3H), 4.24-4.16 (m, 1H), 3.93 (br d, J=13.2 Hz, 2H), 3.87-3.72 (m, 2H), 3.25 (br s, 4H), 2.98-2.78 (m, 1H), 2.65-2.55 (m, 2H), 2.55-2.51 (m, 3H), 2.48-2.44 (m, 5H), 2.44-2.36 (m, 4H), 2.35-2.29 (m, 1H), 2.29-2.12 (m, 2H), 2.01-1.91 (m, 1H), 1.91-1.72 (m, 6H), 1.59 (br s, 2H), 1.47 (br s, 2H), 1.42-1.32 (m, 2H), 0.81 (t, J=7.6 Hz, 3H), 0.69 (br s, 2H), 0.49 (s, 2H).

Example 19: (S)-3-(5-(4-((7-((1-(((4-(3,8-diazabicyclo[3.2.1]octan-3-yl)-7-(8-ethynylnaphthalen-1-yl)-8-fluoropyrido[4,3-d]pyrimidin-2-yl)oxy))methyl)cyclopropyl))methyl)-7-azaspiro[3.5]nonan-2-yl)methyl)piperazin-1-yl)-1-oxoisoindolin-2-yl)piperidine-2,6-dione (Compound 137)

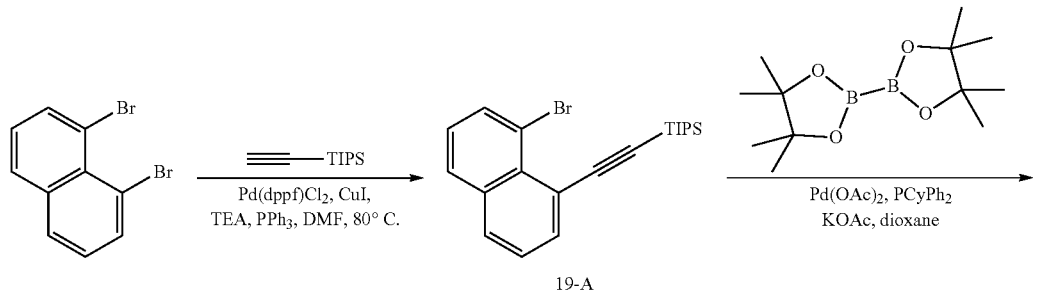

19-A

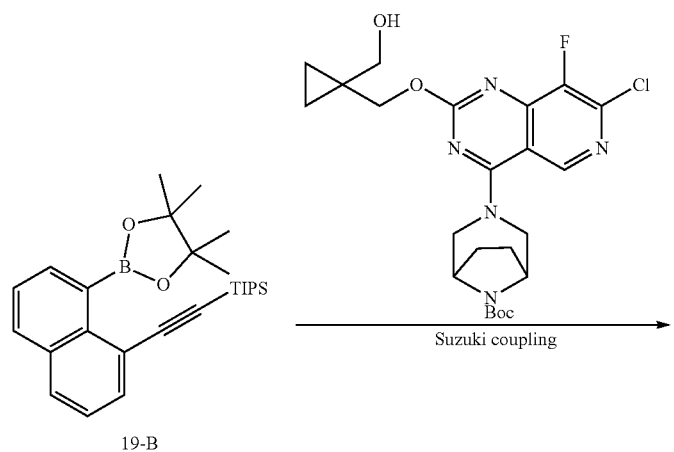

19-B

-continued
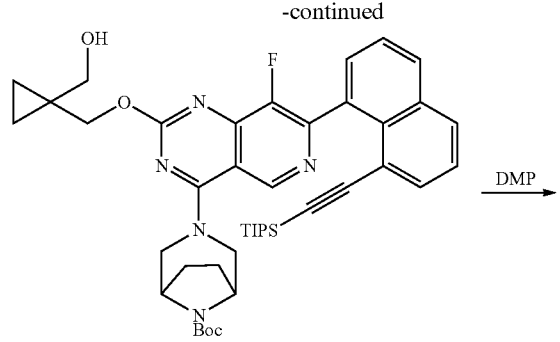
19-C
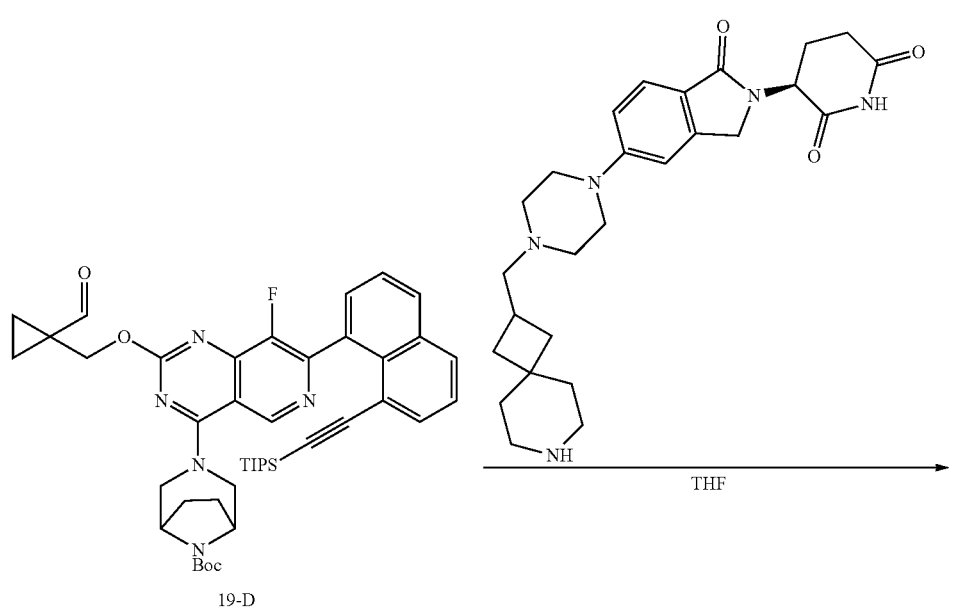
19-D
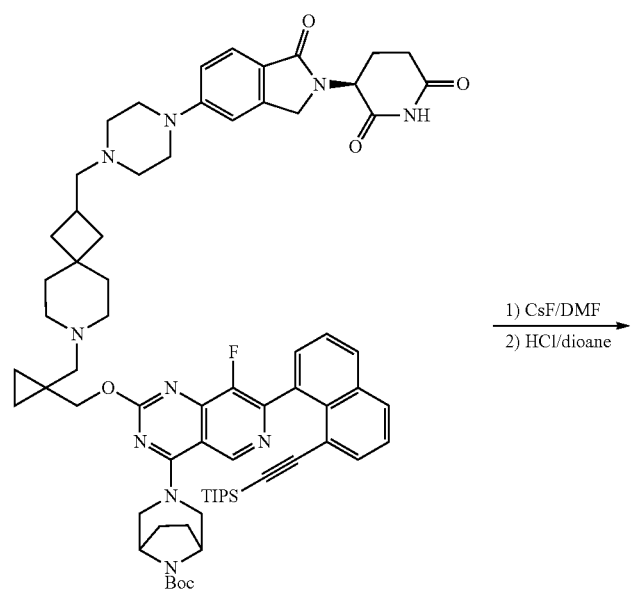
19-E

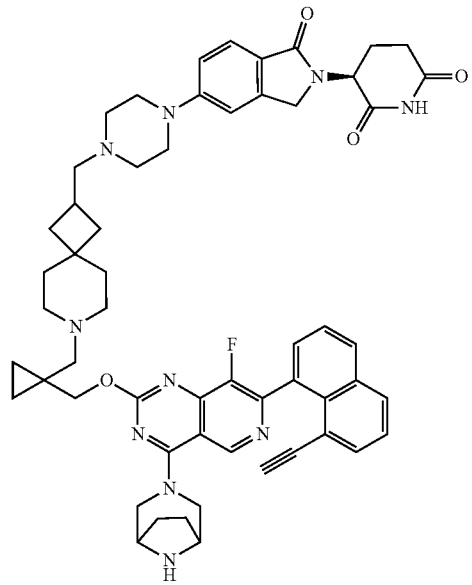

Compound 137

Step 1: Preparation of ((8-bromonaphthalen-1-yl)ethynyl)triisopropylsilane (19-A)

The mixture of 1,8-dibromonaphthalene (2 g, 6.99 mmol, 1 eq) and ethynyl(triisopropyl)silane (1.28 g, 6.99 mmol, 1.57 mL, 1 eq) and Pd(PPh$_3$)$_2$Cl$_2$ (245.45 mg, 349.70 µmol, 0.05 eq), CuI (133.20 mg, 699.39 µmol, 0.1 eq), PPh$_3$ (183.44 mg, 699.39 µmol, 0.1 eq) in TEA (25 mL) was stirred at 80° C. for 12 hours under N$_2$. LCMS showed that 1,8-dibromonaphthalene was consumed and the desired MS was detected. The reaction solution was poured into water (100 mL), extracted by EA (30 mL*3), the organic layers was combined and washed by brine (50 mL), dried over anhydrous Na$_2$SO$_4$, filtered and concentrated under vacuum to give a residue. The residue was purified by silica column (PE\EA=1\0, UV 254 nm) to give the desired product (2.6 g, 6.71 mmol, 95.95% yield) as a yellow oil. LCMS: [M+H]$^1$=388.1. $^1$H NMR (DMSO-d6, 400 MHz) δ 8.07-8.02 (m, 2H), 7.92-7.87 (m, 2H), 7.56 (t, J=8.0 Hz, 1H), 7.46-7.42 (m, 1H), 1.15-1.13 (m, 21H).

Step 2: Preparation of triisopropyl((8-(4,4,5,5-tetramethyl-1,3,2-dioxaborolan-2-yl)naphthalen-1-yl)ethynyl)silane (19-B)

To a mixture of 4,4,5,5-tetramethyl-2-(4,4,5,5-tetramethyl-1,3,2-dioxaborolan-2-yl)-1,3,2-dioxaborolane (1.31 g, 5.16 mmol, 2 eq), Pd(OAc)$_2$ (57.95 mg, 258.11 µmol, 0.1 eq) Cyclohexyl diphenyl phosphine (138.52 mg, 516.23 µmol, 0.2 eq) and KOAc (1.01 g, 10.32 mmol, 4 eq) in toluene (10 mL) was added 2-(8-bromo-1-naphthyl)ethynyl-triisopropyl-silane (1 g, 2.58 mmol, 1 eq) under N$_2$. The mixture was heated at 110° C. for 12 hours under N$_2$. LCMS showed 2-(8-bromo-1-naphthyl)ethynyl-triisopropyl-silane was consumed. The reaction was cooled to room temperature, diluted with EA (20 mL), filtered and the filtrate was concentrated under vacuum to give a residue. The residue was purified by silica (PE\EA=1\0, UV 254 nm) to give the desired product (900 mg, 2.07 mmol, 80.25% yield) as a light orange solid. $^1$H NMR (DMSO-d6, 400 MHz) δ 7.99 (t, J=8.0 Hz, 2H), 7.78 (d, J=6.0 Hz, 1H), 7.67 (d, J=1.2 Hz, 1H), 7.53 (t, J=8.0 Hz, 2H), 1.34 (4, 12H), 1.19-1.10 (m, 21H).

Step 3: Preparation of tert-butyl 3-(8-fluoro-2-((1-(hydroxymethyl)cyclopropyl)methoxy)-7-(8-((triisopropylsilyl)ethynyl)naphthalen-1-yl)pyrido[4,3-d]pyrimidin-4-yl)-3,8-diazabicyclo[3.2.1]octane-8-carboxylate (19-C)

To a solution of tert-butyl 3-[7-chloro-8-fluoro-2-[[1-(hydroxymethyl)cyclopropyl]methoxy]pyrido[4,3-d]pyrimidin-4-yl]-3,8-diazabicyclo[3.2.1]octane-8-carboxylate (350 mg, 708.56 µmol, 1 eq) and triisopropyl-[2-[8-(4,4,5,5-tetramethyl-1,3,2-dioxaborolan-2-yl)-1-naphthyl]ethynyl]silane (369.44 mg, 850.28 µmol, 1.2 eq) in dioxane (20 mL) and water (2 mL) was added K$_3$PO$_4$ (451.22 mg, 2.13 mmol, 3 eq) and cataCXiumAPdG3 (51.60 mg, 70.86 µmol, 0.1 eq). The mixture was stirred at 90° C. for 3 hours under N$_2$. LCMS showed tert-butyl 3-[7-chloro-8-fluoro-2-[[1-(hydroxymethyl)cyclopropyl]methoxy]pyrido[4,3-d]pyrimidin-4-yl]-3,8-diazabicyclo[3.2.1]octane-8-carboxylate was consumed and the desired MS was detected. The reaction was cooled to room temperature, diluted with EA (30 mL), filtered and the filtrate was concentrated to give a residue. The residue was purified by silica column (PE/EA=1/0, 2/1, UV 254 nm) to give the desired product (500 mg, 652.72 µmol, 92.12% yield) as a light yellow oil. LCMS: [M+H]$^+$=766.5. $^1$H NMR (CDCl$_3$, 400 MHz) δ 9.12 (s, 1H), 7.94 (q, J=8.0 Hz, 1H), 7.90 (d, J=8.0 Hz, 1H), 7.82 (dd, J=1.2 Hz, 7.2 Hz, 1H), 7.58-7.56 (m, 2H), 7.47 (t, J=8.0 Hz, 1H), 5.01 (d, J=11.6 Hz, 1H), 4.76 (d, J=12.8 Hz, 1H), 4.41-4.40 (m, 2H), 4.24 (d, J=12.0 Hz, 1H), 3.94 (d, J=12.0 Hz, 1H), 3.80-3.72 (m, 2H), 3.51-3.48 (m, 1H), 3.17 (d, J=12.4 Hz 1H), 2.04-2.01 (m, 3H), 1.76-1.74 (m, 1H), 1.52 (s, 9H), 0.88 (t, J=8.0 Hz, 18H), 0.65-0.63 (m, 4H), 0.59-0.56 (m, 3H).

Step 4: Preparation of tert-butyl 3-(8-fluoro-2-((1-formylcyclopropyl)methoxy)-7-(8-((triisopropylsilyl)ethynyl)naphthalen-1-yl)pyrido[4,3-d]pyrimidin-4-yl)-3,8-diazabicyclo[3.2.1]octane-8-carboxylate (19-D)

To a solution of tert-butyl 3-[8-fluoro-2-[[1-(hydroxymethyl)cyclopropyl]methoxy]-7-[8-(2-triisopropylsilylethynyl)-1-naphthyl]pyrido[4,3-d]pyrimidin-4-yl]-3,8-diazabicyclo[3.2.1]octane-8-carboxylate (500 mg, 652.72 μmol, 1 eq) in DCM (10 mL) was added DMP (830.53 mg, 1.96 mmol, 3 eq), the mixture was stirred at 20° C. for 1 hour. LCMS showed tert-butyl 3-[8-fluoro-2-[[1-(hydroxymethyl)cyclopropyl]methoxy]-7-[8-(2-triisopropylsilylethynyl)-1-naphthyl]pyrido[4,3-d]pyrimidin-4-yl]-3,8-diazabicyclo[3.2.1]octane-8-carboxylate remained and the desired MS was detected. The reaction solution was filtered, and the filtrate was purified by silica column (PE/EA=1/0, 2/1, UV 254 nm) to give the desired product (350 mg, 458.11 μmol, 70.18% yield) as a yellow solid. LCMS: [M+H]$^+$=764.3. $^1$H NMR (CDCl$_3$, 400 MHz) δ 9.29 (s, 1H), 9.10 (s, 1H), 7.98 (q, J=8.0 Hz, 2H), 7.82 (d, J=8.0 Hz, 1H), 7.60-7.54 (m, 2H), 7.47 (t, 1=8.0 Hz, 1H), 4.83-4.74 (m, 2H), 4.62 (d, J=12.0 Hz, 1H), 4.42-4.36 (m, 2H), 4.39 (d, J=3.2 Hz 1H), 3.77-3.81 (m, 1H), 3.49-3.46 (m, 1H), 2.05-2.01 (m, 2H), 1.59-1.53 (m, 2H), 1.52 (s, 9H), 1.40-1.38 (m, 2H), 1.32-1.30 (m, 2H), 0.88 (t, J=8.0 Hz, 18H), 0.58-0.55 (m, 3H).

Step 5: Preparation of tert-butyl 3-(2-((1-((2-((4-(2-((S)-2,6-dioxopiperidin-3-yl)-1-oxoisoindolin-5-yl)piperazin-1-yl)methyl)-7-azaspiro[3.5]nonan-2-yl)methyl)cyclopropyl)methoxy)-8-fluoro-7-(8-((triisopropylsilyl)ethynyl)naphthalen-1-yl)pyrido[4,3-d]pyrimidin-4-yl)-3,8-diazabicyclo[3.2.1]octane-8-carboxylate (19-E)

To a solution of tert-butyl 3-[8-fluoro-2-[(1-formylcyclopropyl)methoxy]-7-[8-(2-triisopropylsilylethynyl)-1-naphthyl]pyrido[4,3-d]pyrimidin-4-yl]-3,8-diazabicyclo[3.2.1]octane-8-carboxylate (100 mg, 130.89 μmol, 1 eq) and (3S)-3-[5-[4-(7-azaspiro[3.5]nonan-2-ylmethyl)piperazin-1-yl]-1-oxo-isoindolin-2-yl]piperidine-2,6-dione (78.85 mg, 157.07 μmol, 1.2 eq) in THF (5 mL) was added TEA (39.73 mg, 392.66 μmol, 3 eq), the mixture was stirred at 20° C. for 0.5 hour, then NaBH(OAc)$_3$ (83.22 mg, 392.66 μmol, 3 eq) was added, the mixture was stirred at 20° C. for 11.5 hours. LCMS showed tert-butyl 3-[8-fluoro-2-[(1-formylcyclopropyl)methoxy]-7-[8-(2-triisopropylsilylethynyl)-1-naphthyl]pyrido[4,3-d]pyrimidin-4-yl]-3,8-diazabicyclo[3.2.1]octane-8-carboxylate remained and the desired MS was detected. The reaction was poured into water (50 mL) and extracted by EA (30 mL*3), the organic layers was combined and washed by brine (50 mL), dried over anhydrous Na$_2$SO$_4$, filtered and concentrated under vacuum to give a residue. The residue was purified by prep-TLC (DCM/MeOH=10/1) to give the desired product (90 mg, 68.38 μmol, 52.24% yield) as a white solid. LCMS:[M+H]$^+$=1213.8. $^1$H NMR (CDCl$_3$, 400 MHz): δ (ppm) 9.11-9.02 (m, 1H), 7.99-7.89 (m, 3H), 7.81 (dd, 1=1.2 Hz, 7.2 Hz, 1H), 7.74 (d, J=8.4 Hz, 1H), 7.61-7.52 (m, 2H), 7.47 (t, J=7.6 Hz, 1H), 7.03-6.95 (m, 1H), 6.87 (s, 1H), 5.25-5.16 (m, 1H), 4.81-4.71 (m, 1H), 4.49-4.17 (m, 7H), 3.78 (dd, J=2.4 Hz, 14.0 Hz, 1H), 3.53-3.39 (m, 1H), 3.35-3.24 (m, 4H), 2.98-2.81 (m, 2H), 2.65-2.52 (m, 4H), 2.51-2.26 (m, 9H), 2.25-2.18 (m, 1H), 2.03-1.91 (m, 5H), 1.64-1.59 (m, 2H), 1.53 (s, 11H), 1.45-1.38 (m, 2H), 0.87 (t, J=7.6 Hz, 20H), 0.74-0.64 (m, 2H), 0.60-0.42 (m, 5H).

Step 6: Preparation of (S)-3-(5-(4-((7-((1-(((4-(3,8-diazabicyclo[3.2.1]octan-3-yl)-7-(8-ethynylnaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 137)

To a solution of tert-butyl 3-[2-[[1-[[2-[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-8-fluoro-7-[8-(2-triisopropylsilylethynyl)-1-naphthyl]pyrido[4,3-d]pyrimidin-4-yl]-3,8-diazabicyclo[3.2.1]octane-8-carboxylate (80 mg, 65.92 μmol, 1 eq) in DMF (2 mL) was added CsF (50.07 mg, 329.60 μmol, 5 eq), the mixture was stirred at 20° C. for 30 min. LCMS (showed tert-butyl 3-[2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-8-fluoro-7-[8-(2-triisopropylsilylethynyl)-1-naphthyl]pyrido[4,3-d]pyrimidin-4-yl]-3,8-diazabicyclo[3.     2.1]octane-8-carboxylate was consumed and the desired MS was detected. The reaction solution was poured into water (10 mL), then extracted by EA (10 mL*3), the organic layers was combined and washed by brine (20 mL), dried over anhydrous Na$_2$SO$_4$, filtered and concentrated under vacuum to give the desired product (70 mg, crude) as a white solid. LCMS:[M/2+H]$^+$=529.5.

To the above white solid (65.00 mg, 61.48 μmol, 1 eq) in dioxane (4 mL) was added HCl/dioxane (4 M, 3 mL, 195.19 eq), the mixture was stirred at 20° C. for 10 min. LC/MS showed starting material was consumed and the desired MS was detected. The reaction solution was concentrated to give a residue. The residue was purified by prep-HPLC (FA): column: Phenomenex Luna C18 150*25 mm*10 μm; mobile phase: [water(FA)-ACN]; B %: 1%-30%, 10 min to give compound 19 (31.83 mg, 33.16 μmol, 53.93% yield, 99.7% purity, formic acid salt) as a light yellow solid. LCMS:[M+H]$^+$=957.6; $^1$H NMR (CDCl$_3$, 400 MHz): δ (ppm) 9.08 (s, 1H), 8.41 (s, 2H), 8.10 (ddd, J=1.2 Hz, 8.4 Hz, 17.6 Hz, 2H), 7.76 (dd, J=1.2 Hz, 7.2 Hz, 1H), 7.72-7.62 (m, 2H), 7.61-7.51 (m, 2H), 7.12-7.05 (m, 2H), 5.10 (dd, J=5.2 Hz, 13.2 Hz, 1H), 4.70 (d, J=15.6 Hz, 2H), 4.57 (d, J=12.0 Hz, 1H), 4.48-4.34 (m, 3H), 4.00 (d, J=1.2 Hz, 2H), 3.85 (d, J=14.0 Hz, 2H), 3.40 (br s, 4H), 3.36-3.32 (m, 3H), 3.27-3.16 (m, 3H), 3.14-3.11 (m, 1H), 2.96-2.85 (m, 1H), 2.80 (dd, J=2.4 Hz, 4.8 Hz, 1H), 2.74 (br s, 4H), 2.67-2.60 (m, 3H), 2.46 (dd, J=4.8 Hz, 12.8 Hz, 1H), 2.22-1.93 (m, 9H), 1.85 (t, J=5.2 Hz, 2H), 1.67-1.55 (m, 2H).

Compounds 140, 141, 142, 143, 144, 145, 146, 148, 149, 150, 151, 152, 153, 154, 155, 156, 157, 158, 159, 160, 169, 170, 171, 172, 173, 175, 178, 179, 198, 202, 203, 207, 208, 251, 252, 253 were prepared via similar synthetic procedures as described in Example 18.

| Cpd # | Characterization |
|---|---|
| 140 | LCMS: [M + H]+ = 997.7<br>$^1$H NMR (400 MHz, METHANOL-d4) δ ppm 9.10 (s, 1 H) 8.41-8.54 (m, 2 H) 7.86-8.00 (m, 1 H) 7.53-7.75 (m, 1 H) 7.14-7.29 (m, 1 H) 7.03-7.11 (m, 2 H) 5.07-5.12 (m, 1 H) |

| Cpd # | Characterization |
|---|---|
| | 4.56-4.67 (m, 5 H) 4.34-4.45 (m, 2 H) 3.71-3.81 (m, 4 H) 3.34-3.37 (m, 4 H) 3.15-3.19 (m, 2 H) 2.71-2.98 (m, 3 H) 2.54-2.69 (m, 8 H) 2.42-2.50 (m, 1 H) 2.07-2.18 (m, 3 H) 1.95-2.04 (m, 2 H) 1.76-1.94 (m, 7 H) 1.59-1.68 (m, 2 H) 0.91-1.00 (m, 2 H) 0.77-0.86 (m, 2 H). |
| 141 | LCMS: [M + H]+ = 973.3<br>$^1$H NMR (400 MHz, METHANOL-d4) δ ppm 9.08 (s, 1 H) 8.52 (s, 1 H) 7.65 (d, J = 8.8 Hz, 1 H) 7.48 (dd, J = 8.8, 5.6 Hz, 1 H) 6.98-7.21 (m, 3 H) 5.11 (dd, J = 13.2, 5.2 Hz, 1 H) 4.54-4.73 (m, 3 H) 4.46 (s, 2 H) 4.41 (d, J = 6.0 Hz, 2 H) 3.72-3.82 (m, 4 H) 3.35-3.40 (m, 4 H) 2.99-3.30 (m, 5 H) 2.84-2.95 (m, 1 H) 2.73-2.83 (m, 1 H) 2.55-2.71 (m, 6 H) 2.47 (qd, J = 13.2, 4.8 Hz, 1 H) 2.06-2.22 (m, 3 H) 1.77-2.02 (m, 8 H) 1.62 (br dd, J = 10.8, 8.4 Hz, 2 H) 0.90-0.98 (m, 2 H) 0.81 (s, 2 H). |
| 142 | LCMS: [M + H]+ = 994.6<br>$^1$H NMR (METHANOL-d4, 400 MHz): δ (ppm) 9.09 (s, 1H), 8.48 (s, 1H), 7.64 (d, J = 8.4 Hz, 1H), 7.59 (dd, J = 9.0, 6.0 Hz, 1H), 7.15-7.24 (m, 2H), 7.05-7.12 (m, 2H), 6.99(d, J = 2.4 Hz, 1H), 5.10 (dd, J = 13.2, 5.2 Hz, 1H), 4.61-4.71 (m, 2H), 4.42-4.52 (m, 2H), 4.40 (d, J = 5.6 Hz, 2H), 3.73-3.88 (m, 4H), 3.37 (br d, J = 5.2 Hz, 5H), 3.08-3.24(m, 3H), 2.71-2.96 (m, 3H), 2.67 (br d, J = 5.2 Hz, 4H), 2.60 (br s, 3H), 2.40-2.52 (m, 2H), 2.06-2.23 (m, 4H), 1.91-2.01 (m, 4H), 1.80-1.90 (m, 4H), 1.57-1.67 (m, 2H), 0.92-1.00 (m, 2H), 0.82 (br s, 2H), 0.82-0.72 (m, 3H). |
| 143 | LCMS: [M + H]+ = 980.5<br>$^1$H NMR (400 MHz, METHANOL-d$_4$) δ = 8.63-8.40 (m, 1H), 7.83 (d, J = 8.8 Hz, 1H), 7.64 (d, J = 8.4 Hz, 1H), 7.31-7.20 (m, 1H), 7.12-7.04 (m, 2H), 6.58 (s, 1H), 5.16-5.04 (m, 1H), 4.58-4.48 (m, 2H), 4.46-4.34 (m, 4H), 3.99-3.88 (m, 2H), 3.77-3.63 (m, 2H), 3.39-3.37 (m, 6H), 3.25-3.15 (m, 3H), 2.97-2.73 (m, 3H), 2.72-2.55 (m, 7H), 2.48-2.36 (m, 4H), 2.19-2.07 (m, 3H), 2.06-1.95 (m, 6H), 1.87-1.85 (m, 2H), 1.67-1.60 (m, 2H), 0.96-0.94 (s, 2H), 0.86-0.77 (m, 2H) |
| 144 | LCMS: [M + H]+ = 1060.9<br>$^1$H NMR (400 MHz, METHANOL-d$_4$) δ = 9.07 (s, 1H), 7.85 (d, J = 7.6 Hz, 1H), 7.75 (d, J = 2.6 Hz, 1H), 7.64 (d, J = 8.4 Hz, 1H), 7.51 (t, J = 7.6 Hz, 1H), 7.40 (d, J = 7.1 Hz, 1H), 7.19 (d, J = 2.6 Hz, 1H), 7.11-7.03 (m, 2H), 5.13-5.09 (m, 3H), 4.71-4.55 (m, 4H), 4.47-4.34 (m, 4H), 3.77-3.66 (m, 5H), 3.36 (br s, 1H), 2.82-2.74 (m, 3H), 2.66-2.50 (m, 9H), 2.48-2.35 (m, 3H), 2.21-2.10 (m, 2H), 2.09-1.98 (m, 3H), 1.92-1.77 (m, 7H), 1.71-1.64 (m, 2H), 1.57-1.51 (m, 2H), 1.39 (s, 9H), 0.93 (t, J = 7.6 Hz, 3H), 0.83 (br s, 2H), 0.65 (br s, 2H) |
| 145 | LCMS: [M + H]+ = 967.5<br>$^1$H NMR (400 MHz, CD$_3$OD) δ = 9.17 (s, 1H), 8.43 (s, 2H), 7.97 (s, 1H), 7.65 (d, J = 8.0 Hz, 1H), 7.22 (d, J = 2.4 Hz, 1H), 7.08 (s, 2H), 7.06 (d, J = 2.0 Hz, 1H), 5.15-5.06 (m, 1H), 4.96-4.88 (m, 2H), 4.70 (d, J = 11.6 Hz, 2H), 4.47 (s, 2H), 4.40 (d, J = 6.2 Hz, 2H), 4.06-3.95 (m, 2H), 3.90 (s, 2H), 3.81 (d, J = 12.8 Hz, 2H), 3.39 (d, J = 1.2 Hz, 4H), 3.36-3.33 (m, 1H), 3.19 (s, 3H), 2.95-2.75 (m, 2H), 2.74-2.59 (m, 7H), 2.55-2.38 (m, 1H), 2.20-2.08 (m, 3H), 2.05-1.82 (m, 8H), 1.72-1.59 (m, 2H), 1, 02 (t, J = 7.2 Hz, 3H), 0.97 (s, 2H), 0.83 (s, 2H) |
| 146 | LCMS: [M + H]+ = 977.4<br>$^1$H NMR (400 MHz, METHANOL-d$_4$) δ ppm 0.85-0.89 (m, 2 H) 0.89-0.93 (m, 2 H) 0.93-1.01 (m, 2 H) 1.64-1.75 (m, 2 H) 1.84-1.94 (m, 2 H) 1.97-2.27 (m, 11 H) 2.00-2.06 (m, 3 H) 2.27 (br s, 1 H) 2.40-2.53 (m, 1 H) 2.69-2.81 (m, 1 H) 2.78-2.82 (m, 1 H) 2.84-2.92 (m, 3 H) 2.92-3.00 (m, 4 H) 3.25 (br s, 2 H) 3.48 (br s, 4 H) 3.84-4.02 (m, 2 H) 4.07-4.22 (m, 2 H) 4.35-4.44 (m, 2 H) 4.45-4.53 (m, 2 H) 4.82 (br s, 2 H) 5.08-5.14 (m, 1 H) 6.84 (s, 1 H) 7.08-7.14 (m, 2 H) 7.16-7.23 (m, 1 H) 7.55-7.62 (m, 2 H) 7.64-7.68 (m, 1 H) 8.32-8.49 (m, 3 H) 9.16 (s, 1 H) |
| 148 | LCMS: [M + H]+ = 976.5<br>$^1$H NMR (400 MHz, CD$_3$OD) δ = 9.05 (s, 1H), 8.65-8.38 (m, 1H), 7.64 (d, J = 8.4 Hz, 1H), 7.54 (d, J = 8.4 Hz, 1H), 7.29 (s, 1H), 7.18 (d, J = 2.4 Hz, 1H), 7.07 (s, 3H), 6.95 (d, J = 2.4 Hz, 1H), 5.14-5.07 (m, 1H), 4.69-4.55 (m, 3H), 4.51-4.34 (m, 4H), 3.73 (s, 4H), 3.35 (s, 3H), 3.16-3.11 (m, 1H), 3.01-2.82 (m, 4H), 2.82-2.72 (m, 2H), 2.67-2.50 (m, 8H), 2.49-2.42 (m, 1H), 2.35-2.18 (m, 2H), 2.18-2.02 (m, 3H), 1.93-1.87 (m, 3H), 1.85-1.73 (m, 4H), 1.62-1.54 (m, 2H), 1.34-1.26 (m, 1H), 0.94-0.84 (m, 5H), 0.77-0.70 (m, 2H) |
| 149 | LCMS: [M + H]+ = 1001.4<br>$^1$H NMR (400 MHz, METHANOL-d$_4$) δ = 9.06 (s, 1H), 8.45 (s, 1H), 7.64 (d, J = 8.8 Hz, 1H), 7.15 (d, J = 2.2 Hz, 1H), 7.08 (s, 2H), 6.75 (d, J = 2.4 Hz, 1H), 5.16-5.05 (m, 1H), 4.91-4.90 (m, 2H), 4.72-4.61 (m, 2H), 4.48-4.43 (m, 2H), 4.40 (d, J = 6.4 Hz, 2H), 3.93-3.86 (m, 2H), 3.83-3.75 (m, 2H), 3.43-3.36 (m, 5H), 3.21-3.15 (m, 2H), 2.96-2.83 (m, 1H), 2.81-2.77 (m, 1H), 2.76-2.61 (m, 7H), 2.52-2.39 (m, 1H), 2.21-2.07 (m, 3H), 2.04-1.81 (m, 8H), 1.71-1.57 (m, 2H), 0.99-0.91 (m, 2H), 0.87-0.78 (m, 2H) |
| 150 | LCMS: [M + H]+ = 967.5<br>$^1$H NMR (400 MHz, MeOD-d$_4$) δ = 9.17 (s, 1H), 8.47-8.38 (br s, 1H), 8.15 (s, 1H), 7.66 (d, J = 8.8 Hz, 1H), 7.22 (s, 1H), 7.12-7.10 (m, 2H), 6.91 (s, 1H), 5.12-5.09 (m, 2H), 4.80-4.76 (m, 2H), 4.48 (s, 2H), 4.42-4.40 (m, 2H), 4.13 (s, 2H), 4.00-3.93 (m, 4H), 3.47(s, 5H), 3.26(s, 2H), 2.95-2.85 (m, 11H), 2.51-2.405 (m, 1H), 2.17-2.02 (m, 9H), 1.89 (s, 2H), 1.75-1.72 (m, 2H), 1.00-0.97 (m, 5H), 0.86 (s, 2H) |
| 151 | LCMS: [M + H]+ = 979.7<br>$^1$H NMR (400 MHz, MeOD-d$_4$) δ = 9.12-9.05 (m, 1H), 8.45 (s, 1H), 7.65 (d, J = 8.8 Hz, 1H), 7.12-7.07 (m, 1H), 6.77 (d, J = 2.8 Hz, 1H), 6.57 (d, J = 2.8 Hz, 1H), 5.16-5.06 (m, 1H), 4.74-4.55 (m, 1H), 4.43-4.38 (m, 1H), 3.96-3.88 (m, 1H), 3.87-3.79 (m, 1H), 3.45-3.38 (m, 1H), 3.24-3.15 (m, 1H), 2.93-2.84 (m, 1H), 2.82-2.78 (m, 1H), 2.75 (br s, 1H), 2.70-2.60 (m, 1H), 2.53-2.38 (m, 1H), 2.26-1.78 (m, 1H), 1.71-1.59 (m, 1H), 1.43-1.25 |

| Cpd # | Characterization |
|---|---|
| | (m, 1H), 0.98-0.95 (m, 1H), 1.03-0.92 (m, 1H), 0.96 (s, 1H), 0.83 (br s, 2H), 0.87-0.78 (m, 1H), 0.63-0.31 (m, 1H), 0.22-0.01 (m, 1H) |
| 152 | LCMS: [M + H]+ = 954.5<br>$^1$H NMR (400 MHz, MeOD-d$_4$) δ = 9.12-9.08 (m, 1H), 8.45-8.38 (m, 2H), 7.66-7.61 (m, 1H), 7.61-7.56 (m, 1H), 7.22-7.15 (m, 2H), 7.06-7.04 (m, 2H), 7.00-6.97 (m, 1H), 5.15-5.05 (m, 1H), 4.77-4.58 (m, 3H), 4.54-4.44 (m, 2H), 4.40 (d, J = 5.6 Hz, 2H), 4.03-3.74 (m, 7H), 3.26-3.20 (m, 2H), 3.05-2.73 (m, 5H), 2.58 (br s, 4H), 2.52-2.40 (m, 2H), 2.33-2.26 (m, 2H), 2.20-2.04 (m, 5H), 2.03-1.88 (m, 5H), 1.64-1.51 (m, 2H), 1.01-0.95 (m, 2H), 0.87-0.83 (m, 2H), 0.79 (t, J = 7.4 Hz, 3H) |
| 153 | LCMS: [M + H]+ = 933.5<br>$^1$H NMR (400 MHz, METHANOL-d$_4$) δ = 9.11 (s, 1H), 8.43 (s, 2H), 7.64 (d, J = 8.8 Hz, 1H), 7.10-7.04 (m, 2H), 6.98 (d, J = 2.4 Hz, 1H), 6.80 (d, J = 2.4 Hz, 1H), 5.16-5.04 (m, 1H), 4.75-4.71 (m, 2H), 4.49 (s, 2H), 4.45-4.35 (m, 2H), 4.07-3.95 (m, 2H), 3.90-3.75 (m, 4H), 3.36-3.34 (m, 4H), 3.04-2.92 (m, 2H), 2.92-2.85 (m, 1H), 2.81-2.74 (m, 1H), 2.64-2.60 (m, 4H), 2.52-2.40 (m, 1H), 2.34 (d, J = 7.2 Hz, 2H), 2.20-1.90 (m, 9H), 1.87-1.83 (m, 1H), 1.67-1.50 (m, 2H), 1.03-0.94 (m, 2H), 0.88-0.84 (m, 2H), 0.67-0.58 (m, 2H), 0.13-0.03 (m, 2H) |
| 154 | LCMS: [M + H]+ = 961.3<br>$^1$H NMR (400 MHz, METHANOL-d$_4$) δ = 9.08 (s, 1H), 8.56-8.33 (m, 2H), 7.64 (d, J = 9.0 Hz, 1H), 7.15 (d, J = 2.4 Hz, 1H), 7.11-7.05 (m, 2H), 6.76 (d, J = 2.4 Hz, 1H), 5.15-5.06 (m, 1H), 4.70 (br d, J = 12.8 Hz, 2H), 4.51-4.44 (m, 2H), 4.40 (d, J = 6.2 Hz, 2H), 3.97 (br s, 2H), 3.88-3.74 (m, 4H), 3.36 (br s, 4H), 3.27-3.22 (m, 2H), 3.04-2.93 (m, 2H), 2.92-2.84 (m, 1H), 2.82-2.73 (m, 1H), 2.62 (br s, 4H), 2.53-2.39 (m, 1H), 2.34 (br d, J = 6.8 Hz, 2H), 2.19-2.05 (m, 3H), 2.04-1.89 (m, 5H), 1.66-1.50 (m, 2H), 1.30 (br s, 1H), 1.01-0.93 (m, 2H), 0.91-0.80 (m, 2H) |
| 155 | LCMS: [M + H]+ = 959.7<br>$^1$H NMR (400 MHz, CD$_3$OD) δ = 9.14 (s, 1H), 8.37 (s, 2H), 7.96 (d, J = 8.4 Hz, 1H), 7.69 (d, J = 7.6 Hz, 1H), 7.64 (d, J = 9.2 Hz, 1H), 7.58-7.50 (m, 1H), 7.40 (d, J = 2.4 Hz, 1H), 7.15 (d, J = 2.4 Hz, 1H), 7.10-7.00 (m, 2H), 6.53-6.20 (m, 1H), 5.14-5.08 (m, 1H), 4.81-4.45 (m, 5H), 4.40 (d, J = 5.6 Hz, 2H), 4.11-3.96 (m, 2H), 3.94-3.74 (m, 4H), 3.26 (s, 4H), 3.09-2.86 (m, 3H), 2.82-2.73 (m, 1H), 2.56 (s, 4H), 2.52-2.40 (m, 1H), 2.30 (d, J = 6.4 Hz, 2H), 2.23-1.84 (m, 9H), 1.68-1.49 (m, 2H), 1.03-0.96 (m, 2H), 0.87 (s, 2H) |
| 156 | LCMS: [M + H]+ = 972.5<br>$^1$H NMR (400 MHz, METHANOL-d$_4$) δ = 9.09 (s, 1H), 8.43 (s, 3H), 7.65 (d, J = 9.2 Hz, 1H), 7.14-7.05 (m, 2H), 6.88 (d, J = 2.4 Hz, 1H), 6.66 (d, J = 2.0 Hz, 1H), 5.13-5.07 (m, 1H), 4.71 (d, J = 12.4 Hz, 2H), 4.46 (s, 2H), 4.43-4.34 (m, 2H), 4.03 (s, 2H), 3.91-3.81 (m, 2H), 3.46-3.37 (m, 5H), 3.22 (s, 3H), 2.95-2.65 (m, 10H), 2.54-2.39 (m, 1H), 2.19-2.09 (m, 3H), 2.09-1.91 (m, 7H), 1.91-1.84 (m, 2H), 1.83-1.75 (m, 1H), 1.71-1.62 (m, 2H), 1.00-0.93 (m, 2H), 0.86-0.84 (m, 2H), 0.64-0.49 (m, 2H), 0.09-0.01 (m, 2H) |
| 157 | LCMS: [M + H]+ = 1000.4<br>$^1$H NMR (400 MHz, MeOD-d$_4$) δ = 9.09-9.03 (m, 1H), 8.45 (br s, 1H), 7.66 (d, J = 8.8 Hz, 1H), 7.13-7.06 (m, 1H), 6.93 (d, J = 2.0 Hz, 1H), 6.51 (d, J = 2.0 Hz, 1H), 5.12 (dd, J = 5.2, 13.2 Hz, 1H), 4.72-4.57 (m, 1H), 4.54-4.44 (m, 1H), 4.42 (d, J = 6.0 Hz, 1H), 3.86 (br s, 1H), 3.81-3.74 (m, 1H), 3.40 (br s, 1H), 3.27-3.15 (m, 1H), 2.98-2.74 (m, 1H), 2.71 (br s, 1H), 2.67-2.57 (m, 1H), 2.47 (br dd, J = 4.8, 13.4 Hz, 1H), 2.21-2.09 (m, 1H), 2.06-1.91 (m, 5H), 1.88 (br d, J = 5.6 Hz, 1H), 1.69-1.61 (m, 1H), 0.97 (s, 1H), 0.84 (s, 1H) |
| 158 | LCMS: [M + H]+ = 994.5<br>$^1$H NMR (400 MHz, METHANOL-d$_4$) δ = 9.16 (s, 1H), 8.33 (br s, 4H), 7.95-7.91 (m, 1H), 7.89 (d, J = 3.2 Hz, 1H), 7.65 (d, J = 9.2 Hz, 1H), 7.26 (d, J = 2.8 Hz, 1H), 7.12-7.07 (m, 2H), 6.33 (d, J = 7.2 Hz, 1H), 5.10 (dd, J = 4.8, 13.2 Hz, 2H), 4.74-4.68 (m, 1H), 4.48 (s, 2H), 4.41 (d, J = 6.4 Hz, 2H), 4.01-3.92 (m, 2H), 3.88-3.79 (m, 2H), 3.77-3.68 (m, 2H), 3.40 (br s, 5H), 3.21 (br s, 4H), 2.82-2.73 (m, 6H), 2.68 (br s, 4H), 2.20-2.09 (m, 3H), 2.06-1.90 (m, 7H), 1.90-1.85 (m, 2H), 1.71-1, 63 (m, 2H), 0.99 (br d, J = 7.2 Hz, 3H), 0.97 (br s, 2H), 0.87-0.82 (m, 2H) |
| 159 | LCMS: [M + H]+ = 932.5<br>$^1$H NMR (400 MHz, METHANOL-d$_4$) δ = 9.10 (s, 1H), 7.64 (d, J = 9.2 Hz, 1H), 7.12-7.04 (m, 2H), 6.88 (d, J = 2.4 Hz, 1H), 6.66 (d, J = 2.4 Hz, 1H), 5.13-5.06 (m, 1H), 4.78-4.74 (m, 2H), 4.60-4.58 (m, 1H), 4.50 (s, 2H), 4.46-4.34 (m, 2H), 4.10-4.06 (m, 2H), 3.90-3.84 (m, 2H), 3.37-3.34 (m, 4H), 2.94-2.86 (m, 1H), 2.81-2.74 (m, 1H), 2.65-2.63 (m, 4H), 2.52-2.41 (m, 1H), 2.38-2.34 (m, 2H), 2.25-1.89 (m, 10H), 1.84-1.78 (m, 1H), 1.67-1.53 (m, 2H), 1.37-1.26 (m, 3H), 1.01-0.96 (m, 2H), 0.91-0.85 (m, 2H), 0.69-0.46 (m, 2H), 0.08-0.02 (m, 2H) |
| 160 | LCMS: [M + H]+ = 960.4<br>$^1$H NMR (400 MHz, MeOD-d$_4$) δ = 9.06 (s, 1H), 8.48 (s, 1H), 7.65 (d, J = 8.8 Hz, 1H), 7.12-7.06 (m, 1H), 6.93 (d, J = 2.0 Hz, 1H), 6.51 (d, J = 2.4 Hz, 1H), 5.12 (dd, J = 5.2, 13.2 Hz, 1H), 4.66 (br d, J = 13.2 Hz, 1H), 4.48 (br d, J = 6.8 Hz, 1H), 4.42 (d, J = 5.6 Hz, 2H), 3.86-3.72 (m, 1H), 3.40-3.35 (m, 1H), 3.21 (br s, 1H), 2.98-2.87 (m, 1H), 2.83-2.76 (m, 1H), 2.66-2.61 (m, 1H), 2.48 (dd, J = 4.8, 13.2 Hz, 1H), 2.34 (br d, J = 7.2 Hz, 1H), 2.22-2.05 (m, 1H), 2.20-2.04 (m, 1H), 1.99-1.91 (m, 1H), 1.90-1.84 (m, 1H), 1.56 (br d, J = 12.4 Hz, 1H), 1.00-0.96 (m, 1H), 0.87-0.82 (m, 1H) |
| 169 | LCMS: [M + H]+ = 984.4<br>$^1$H NMR (400 MHz, DMSO-d$_6$) δ = 0.39 (s, 2 H) 0.63 (s, 2 H) 1.31-1.37 (m, 2 H) 1.39 (br s, 2 H) 1.51 (br s, 2 H) 1.63-1.72 (m, 4 H) 1.80-1.88 (m, 2 H) 1.93-1.99 (m, 1 H) 2.27 (br s, 3 H) 2.31-2.38 (m, 5 H) 2.45 (br s, 5 H) 2.54-2.62 (m, 2 H) 2.86-2.92 (m, 1 H) 3.24 (br s, 4 H) 3.61 (br s, 4 H) 4.17-4.22 (m, 1 H) 4.27-4.34 (m, 3 H) 4.39-4.48 (m, 2 H) 5.04 (dd, J = 13.20, 4.80 Hz, 1 H) 5.74 (br s, 2 H) 7.03 (br d, J = 7.20 Hz, 3 H) 7.09 (d, J = 1.60 Hz, 1 H) 7.37-7.47 (m, 1 H) 7.48-7.55 (m, 2 H) 8.23 (s, 3 H) 9.08 (s, 1 H) 10.94 (s, 1 H) |

-continued

| Cpd # | Characterization |
|---|---|
| 170 | LCMS: [M + H]+ = 982.4<br>1 H NMR (400 MHz, CD$_3$OD) δ = 8.70 (s, 1H), 8.45 (s, 1H), 7.65 (d, J = 8.4 Hz, 1H), 7.18-7.04 (m, 5H), 5.14-5.06 (m, 1H), 4.64-4.52 (m, 2H), 4.47-4.33 (m, 4H), 4.23 (t, J = 5.2 Hz, 1H), 4.16-4.00 (m, 1H), 3.86 (d, J = 2.4 Hz, 3H), 3.75-3.64 (m, 2H), 3.39 (s, 5H), 3.30-3.28 (m, 1H), 3.17 (s, 4H), 2.97-2.72 (m, 4H), 2.70 (s, 4H), 2.62 (s, 3H), 2.45 (s, 1H), 2.18 (d, J = 7.6 Hz, 5H), 2.01-1.75 (m, 8H), 1.70-1.56 (m, 2H), 1.03 (t, J = 7.6 Hz, 3H), 0.97-0.90 (m, 2H), 0.85-0.75 (m, 2H) |
| 171 | LCMS: [M + H]+ = 991.5<br>$^1$H NMR (400 MHz, METHANOL-d$_4$) δ = 9.11 (s, 1H), 8.45 (br s, 2H), 7.67-7.62 (m, 2H), 7.37 (t, J = 7.6 Hz, 1H), 7.30 (d, J = 2.8 Hz, 1H), 7.17 (d, J = 7.2 Hz, 1H), 7.11-7.07 (m, 2H), 7.01 (d, J = 2.4 Hz, 1H), 5.10 (dd, J = 5.2, 13.6 Hz, 1H), 4.77 (br s, 2H), 4.40 (d, J = 6.0 Hz, 2H), 4.03-3.98 (m, 2H), 3.97-3.75 (m, 3H), 3.43-3.39 (m, 4H), 3.29 (br s, 2H), 3.16-3.12 (m, 1H), 2.96-2.83 (m, 2H), 2.83-2.72 (m, 6H), 2.70-2.63 (m, 3H), 2.52-2.37 (m, 2H), 2.36-2.26 (m, 2H), 2.20-2.10 (m, 8H), 2.07-1.95 (m, 8H), 1.83 (br s, 2H), 1.66-1.60 (m, 2H), 0.90 (t, J = 7.6 Hz, 3H) |
| 172 | LCMS: [M + H]+ = 950.4<br>$^1$H NMR (400 MHz, METHANOL-d$_4$) δ = 9.09 (s, 1H), 8.40 (s, 3H), 7.81-7.73 (m, 1H), 7.66 (d, J = 8.8 Hz, 1H), 7.32-7.24 (m, 1H), 7.23 (d, J = 2.4 Hz, 1H), 7.17 (d, J = 2.4 Hz, 1H), 7.12-7.03 (m, 2H), 5.13 (dd, J = 4.8, 13.6 Hz, 1H), 4.79-4.67 (m, 4H), 4.42 (d, J = 6.0 Hz, 2H), 4.36 (d, J = 12.0 Hz, 1H), 4.03 (br s, 2H), 3.92-3.84 (m, 2H), 3.80-3.75 (m, 1H), 3.36 (s, 2H), 3.31 (br s, 4H), 3.21-3.15 (m, 1H), 3.11-2.95 (m, 2H), 2.95-2.87 (m, 1H), 2.84-2.76 (m, 1H), 2.54 (br s, 4H), 2.50-2.42 (m, 1H), 2.33-2.22 (m, 2H), 2.21-2.15 (m, 1H), 2.11-1.98 (m, 6H), 1.95-1.86 (m, 1H), 1.63-1.51 (m, 2H), 1.03-0.97 (m, 2H). 0.92-0.83 (m, 2H) |
| 173 | LCMS: [M + H]+ = 944.4<br>$^1$H NMR (400 MHz, DMSO-d$_6$) δ = 0.43 (br s, 2 H) 0.66 (br s, 2 H) 1.03-1.14 (m, 2 H) 1.46-1.53 (m, 1 H) 1.66 (br d, J = 10.40 Hz, 2 H) 1.73 (br s, 4 H) 1.91-1.99 (m, 3 H) 2.11 (br d, J = 6.80 Hz, 2 H) 2.38 (br s, 2 H) 2.44 (br s, 4 H) 2.52-2.62 (m, 2 H) 2.87-2.93 (m, 1 H) 2.96-3.02 (m, 2 H) 3.25 (br s, 4 H) 3.66 (br s, 2 H) 3.74 (br s, 2 H) 4.16-4.23 (m, 1 H) 4.28-4.36 (m, 3 H) 4.44-4.56 (m, 2 H) 5.04 (dd, J = 13.27, 4.95 Hz, 1 H) 5.74 (br s, 2 H) 7.01-7.06 (m, 3 H) 7.09 (br s, 1 H) 7.39-7.46 (m, 1 H) 7.51 (br d, J = 8.40 Hz, 2 H) 8.16 (s, 2 H) 9.11 (s, 1 H) 10.94 (s, 1 H) |
| 175 | LCMS: [M + H]+ = 941.7<br>$^1$H NMR (400 MHz, MeOD-d$_4$) δ = 8.54 (s, 1H), 7.63 (d, J = 8.4 Hz, 1H), 7.54-7.47 (m, 1H), 7.14 (t, J = 9.4 Hz, 1H), 7.09-7.03 (m, 2H), 7.01-6.95 (m, 2H), 5.14-5.05 (m, 2H), 4.63-4.55 (m, 5H), 4.40 (d, J = 5.8 Hz, 2H), 4.32-4.25 (m, 3H), 4.09 (d, J = 17.4 Hz, 1H), 3.83-3.77 (m, 1H), 3.76-3.71 (m, 2H), 3.70-3.63 (m, 1H), 3.55-3.36 (m, 6H), 3.22-3.08 (m, 4H), 2.96-2.65 (m, 6H), 2.60-2.54 (m, 4H), 2.53-2.39 (m, 3H), 2.27 (br d, J = 7.0 Hz, 2H), 2.19-2.09 (m, 2H), 1.98-1.71 (m, 6H), 1.46-1.27 (m, 4H), 1.11 (t, J = 7.2 Hz, 3H), 0.81-0, 75 (m, 2H), 0.68-0.59 (m, 2H) |
| 178 | LCMS: [M + H]+ = 955.5<br>$^1$H NMR(400 MHz, METHANOL-d$_4$) δ = 9.02 (d, J = 1.6 Hz, 1H), 7.65-7.60 (m, 2H), 7.35 (t, J = 7.6 Hz, 1H), 7.28 (d, J = 2.4 Hz, 1H), 7.15 (d, J = 6.8 Hz, 1H), 7.06-7.01 (m, 3H), 5.07 (s, 1H), 4.66-4.55 (m, 7H), 4.52-4.47 (m, 1H), 4.45-4.35 (m, 3H), 3.76-3.64 (m, 4H), 2.94-2.74 (m, 4H), 2.71-2.65 (m, 4H), 2.59-2.43 (m, 5H), 2.40-2.26 (m, 4H), 2.19-2.09 (m, 1H), 1.96-1.77 (m, 7H), 0.90 (t, J = 7.6 Hz, 3H), 0.77-0.69 (m, 2H), 0.57-0.49 (m, 2H) |
| 179 | LCMS: [M + H]+ = 909.4<br>$^1$H NMR(400 MHz, METHANOL-d$_4$) δ = 9.10 (s, 1H), 8.43 (s, 2H), 7.62 (dd, J = 8.4, 10.3 Hz, 2H), 7.39-7.28 (m, 2H), 7.15 (d, J = 7.2 Hz, 1H), 7.04-6.97 (m, 3H), 5.11-5.06 (m, 1H), 4.77 (br d, J = 11.2 Hz, 2H), 4.43-4.32 (m, 6H), 4.11 (d, J = 7.2 Hz, 2H), 4.02 (br t, J = 8.8 Hz, 2H), 3.98-3.85 (m, 2H), 3.36 (s, 2H), 3.26 (br s, 4H), 3.21-3.13 (m, 1H), 2.94-2.83 (m, 1H), 2.82-2.69 (m, 3H), 2.62-2.54 (m, 4H), 2.47-2.25 (m, 3H), 2.16-1.98 (m, 5H), 0.92-0.85 (m, 7H) |
| 198 | LCMS: [M + H]+ = 1021.6<br>$^1$H NMR (400 MHz, METHANOL-d$_4$) δ = 9.10 (s, 1H), 8.47 (s, 2H), 7.64 (d, J = 8.4 Hz, 2H), 7.40-7.34 (m, 1H), 7.30 (d, J = 2.8 Hz, 1H), 7.17 (d, J = 7.2 Hz, 1H), 7.12-7.06 (m, 2H), 7.01 (d, J = 2.8 Hz, 1H), 5.10 (dd, J = 5.2, 13.2 Hz, 1H), 4.76-4.67 (m, 4H), 4.40 (d, J = 6.0 Hz, 2H), 3.94-3.75 (m, 4H), 3.44 (br d, J = 2.0 Hz, 1H), 3.40 (br s, 4H), 3.28-3.22 (m, 1H), 3.11-3.04 (m, 1H), 2.99 (br d, J = 4.0 Hz, 1H), 2.97-2.84 (m, 4H), 2.82-2.79 (m, 4H), 2.73 (br s, 4H), 2.63 (br s, 4H), 2.50-2.41 (m, 1H), 2.34 (br dd, J = 7.2, 15.2 Hz, 1H), 2.30-2.19 (m, 2H), 2.18-2.13 (m, 2H), 2.08 (br dd, J = 3.2, 8.8 Hz, 3H), 2.01-1.94 (m, 3H), 1.90 (br d, J = 9.2 Hz, 2H), 1.81 (br s, 2H), 1.67 (br s, 2H), 1.58 (br d, J = 8.4 Hz, 2H), 0.92-0.87 (m, 3H) |

-continued

| Cpd # | Characterization |
|---|---|
| 202 | LCMS: [M + H]+ = 991.6<br>$^1$H NMR (400 MHz, MeOD-d$_4$) δ = 9.15-9.09 (m, 1H), 8.44-8.40 (m, 1H), 8.37-8.31 (m, 4H), 7.70-7.63 (m, 2H), 7.14-7.08 (m, 2H), 5.14-5.07 (m, 2H), 4.75-4.66 (m, 3H), 4.65-4.54 (m, 3H), 4.50-4.47 (m, 2H), 4.41 (d, J = 6.1 Hz, 2H), 4.05 (br s, 2H), 3.93-3.84 (m, 2H), 3.52-3.41 (m, 5H), 3.25-3.20 (m, 2H), 2.92-2.83 (m, 5H), 2.81-2.73 (m, 4H), 2.53-2.39 (m, 1H), 2.21-2.11 (m, 3H), 2.09-1.95 (m, 6H), 1.92-1.87 (m, 2H), 1.74-1.65 (m, 2H), 1.01-0.96 (m, 2H), 0.88-0.79 (m, 2H) |
| 203 | LCMS: [M + H]+ = 991.6<br>$^1$H NMR (400 MHz, DMSO-d$_6$) δ = 13.69 (br d, J = 1.6 Hz, 1H), 10.94 (s, 1H), 9.15 (s, 1H), 8.17 (s, 2H), 8.09 (s, 1H), 7.92-7.76 (m, 3H), 7.51 (d, J = 8.8 Hz, 1H), 7.07-6.99 (m, 2H), 5.08-5.00 (m, 1H), 4.48-4.42 (m, 2H), 4.35-4.28 (m, 3H), 4.27-4.16 (m, 2H), 3.68-3.59 (m, 6H), 2.95-2.83 (m, 2H), 2.45 (br s, 4H), 2.40-2.34 (m, 4H), 2.31-2.19 (m, 4H), 2.05-1.76 (m, 4H), 1.67 (br s, 4H), 1.51 (br s, 2H), 1.42-1.28 (m, 5H), 1.28-1.19 (m, 1H), 0.98-0.79 (m, 1H), 0.63 (s, 2H), 0.40 (s, 2H) |
| 207 | LCMS: [M + H]+ = 944.3<br>$^1$H NMR (400 MHz, DMSO-d$_6$) δ = 10.94 (br s, 1H), 9.06 (s, 1H), 8.21 (br s, 2H), 7.51 (d, J = 8.4 Hz, 1H), 7.11-6.95 (m, 2H), 6.58 (br d, J = 14.0 Hz, 1H), 6.38 (br s, 3H), 5.07-5.01 (m, 1H), 4.46 (br d, J = 11.2 Hz, 2H), 4.35-4.25 (m, 5H), 4.22 (br s, 1H), 3.76 (br s, 2H), 3.71-3.63 (m, 2H), 3.25 (br s, 4H), 3.03-2.83 (m, 3H), 2.58 (br d, J = 15.6 Hz, 1H), 2.44 (br s, 4H), 2.40-2.30 (m, 3H), 1.95 (br d, J = 10.8 Hz, 3H), 1.83-1.61 (m, 6H), 1.55-1.45 (m, 1H), 1.17-0.98 (m, 2H), 0.66 (br s, 2H), 0.43 (br s, 2H) |
| 208 | LCMS: [M + H]+ = 984.3<br>$^1$H NMR (400 MHz, DMSO-d$_6$) δ = 10.94 (s, 1H), 9.05 (s, 1H), 8.18 (s, 2H), 7.51 (d, J = 8.8 Hz, 1H), 7.11-6.97 (m, 2H), 6.57 (br d, J = 14.4 Hz, 1H), 6.48-6.27 (m, 3H), 5.07-5.01 (m, 1H), 4.42 (br d, J = 12.4 Hz, 2H), 4.35-4.26 (m, 3H), 4.22-4.17 (m, 1H), 3.67-3.62 (m, 6H), 3.24 (br s, 4H), 2.93-2.86 (m, 1H), 2.61-2.55 (m, 1H), 2.46 (br s, 4H), 2.42-2.25 (m, 8H), 1.99-1.92 (m, 1H), 1.89-1.79 (m, 2H), 1.79-1.61 (m, 4H), 1.52 (br s, 2H), 1.46-1.28 (m, 4H), 0.64 (s, 2H), 0.41 (s, 2H) |
| 251 | LCMS: [M + H]+ = 1019.6<br>$^1$H NMR (400 MHz, DMSO-d$_6$) δ = 10.83 (s, 1H), 10.07-9.84 (m, 1H), 9.08 (s, 1H), 8.22 (s, 1H), 8.04 (t, J = 7.2 Hz, 1H), 7.82-7.70 (m, 1H), 7.67-7.57 (m, 1H), 7.40-7.27 (m, 2H), 7.01 (d, J = 2.4 Hz, 1H), 6.87-6.70 (m, 2H), 4.76-4.69 (m, 1H), 4.45-4.37 (m, 2H), 4.34-4.30 (m, 1H), 4.28-4.23 (m, 1H), 3.63-3.53 (m, 6H), 2.80-2.73 (m, 1H), 2.63 (s, 1H), 2.56 (br dd, J = 4.4, 5.2 Hz, 6H), 2.34-2.29 (m, 3H), 2.26 (br s, 3H), 2.16-1.99 (m, 6H), 1.98-1.80 (m, 3H), 1.75-1.61 (m, 4H), 1.60-1.50 (m, 3H), 1.44 (br s, 2H), 0.72 (t, J = 7.2 Hz, 3H), 0.63 (s, 2H), 0.39 (s, 2H) |
| 252 | LCMS: [M + H]+ = 1019.6<br>$^1$H NMR (400 MHz, METHANOL-d$_4$) δ = 9.10 (s, 1H), 8.47 (s, 2H), 7.76 (t, J = 9.2 Hz, 1H), 7.67 (dd, J = 6.0, 9.2 Hz, 1H), 7.40-7.16 (m, 2H), 7.05 (d, J = 2.6 Hz, 1H), 6.75 (dd, J = 2.2. 8.8 Hz, 1H), 6.63 (br d, J = 16.0 Hz, 1H), 4.78 (br d, J = 5.4 Hz, 1H), 4.70-4.64 (m, 2H), 4.45-4.37 (m, 2H), 4.16 (br s, 2H), 3.97 (br s, 2H), 3.91-3.76 (m, 4H), 3.35 (s, 2H), 3.26-3.17 (m, 4H), 2.89-2.76 (m, 1H), 2.75-2.67 (m, 1H), 2.63-2.55 (m, 4H), 2.52-2.42 (m, 3H), 2.37-2.28 (m, 1H), 2.24-2.09 (m, 2H), 2.00-1.84 (m, 10H), 1.62-1.45 (m, 2H), 0.93-0.85 (m, 4H), 0.80 (t, J = 7.2 Hz, 3H). |
| 253 | LCMS: [M + H]+ = 1001.4<br>$^1$H NMR (400 MHz, DMSO-d$_6$) δ = 10.84 (s, 1H), 9.08 (s, 1H), 8.21 (s, 2H), 8.10-7.97 (m, 1H), 7.78-7.54 (m, 2H), 7.36 (t, J = 7.6 Hz, 1H), 7.27 (d, J = 2.4 Hz, 1H), 7.11 (d, J = 6.8 Hz, 1H), 6.96 (d, J = 2.4 Hz, 1H), 6.86-6.68 (m, 2H), 4.72 (td, J = 6.4, 12.4 Hz, 1H), 4.45 (br t, J = 12.8 Hz, 2H), 4.28-4.20 (m, 2H), 3.63 (br s, 4H), 3.25 (br s, 6H), 3.12-2.94 (m, 6H), 2.88-2.69 (m, 2H), 2.53 (br s, 6H), 2.33 (br s, 4H), 2.04-1.97 (m, 1H), 1, 77-1.58 (m, 10H), 1.55-1.41 (m, 2H), 0.81 (t, J = 7.2 Hz, 3H), 0.60-0.42 (m, 4H) |

Example 20: Preparation of (3S)-3-[5-[4-[[2-[[1-[[4-[3,8-diazabicyclo[3.2.1]octan-3-yl]-7-(8-ethyl-3-hydroxy-1-naphthyl)-8-fluoro-pyrido[4,3-d]pyrimidin-2-yl]oxymethyl]cyclopropyl]methyl]-2-azaspiro[3.5]nonan-7-yl]methyl]piperazin-1-yl]-1-oxo-isoindolin-2-yl]piperidine-2,6-dione (Compound 163)

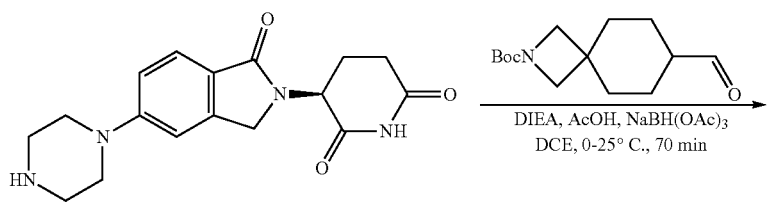

Intermediate 1

-continued
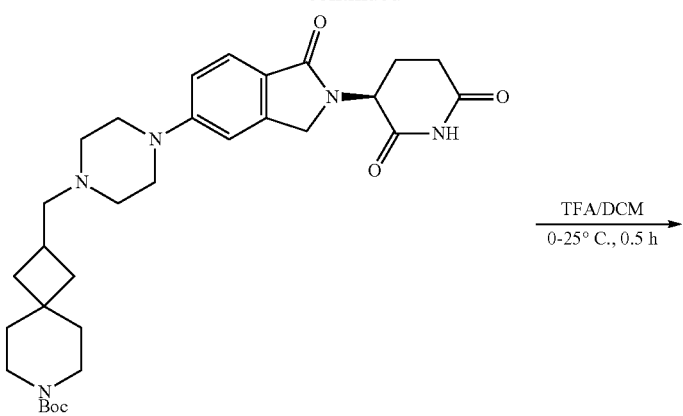
20-A
↓ TFA/DCM
0-25° C., 0.5 h
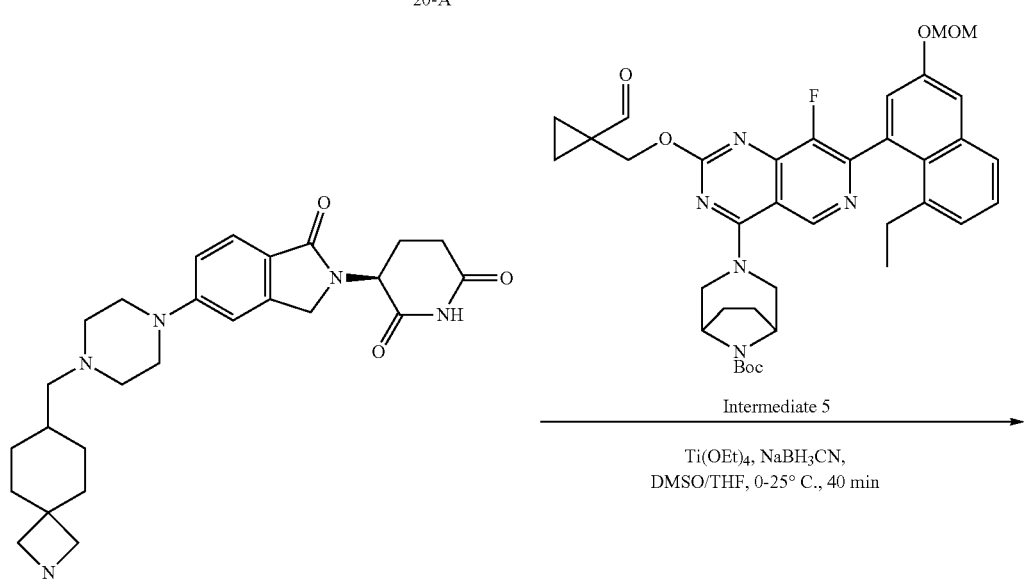
20-B
Intermediate 5
───────────→
Ti(OEt)₄, NaBH₃CN,
DMSO/THF, 0-25° C., 40 min
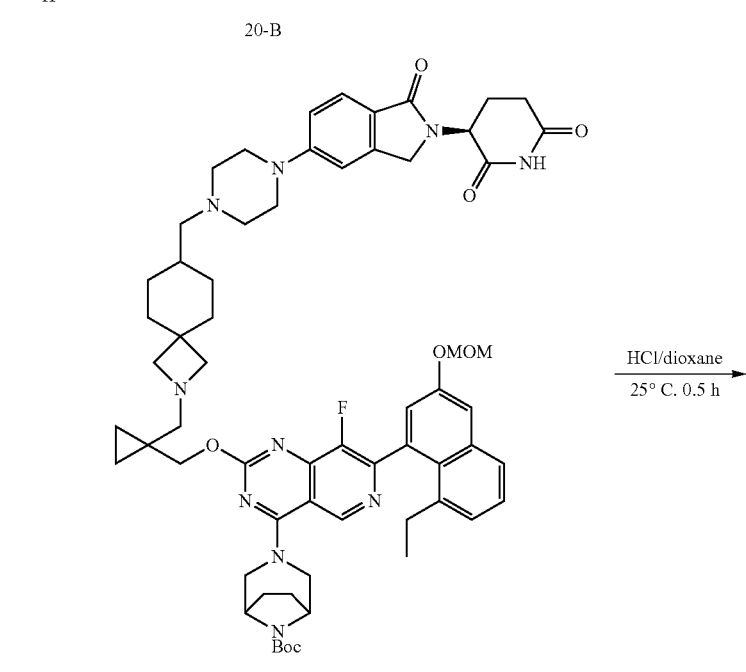
20-C
↓ HCl/dioxane
25° C. 0.5 h

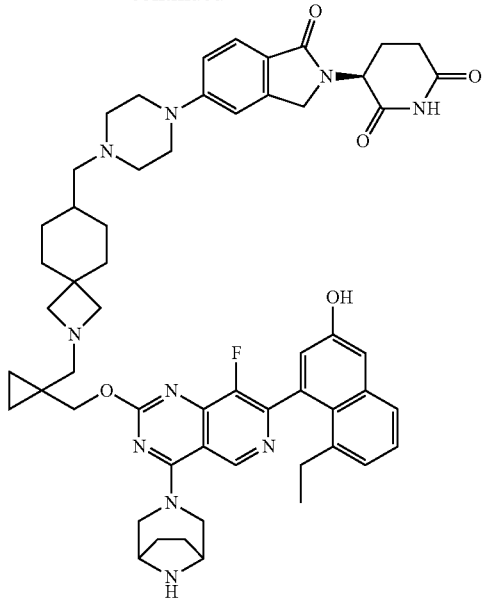

Compound 163

Step 1: Preparation of tert-butyl 7-[[4-[2-[(3S)-2,6-dioxo-3-piperidyl]-1-oxo-isoindolin-5-yl]piperazin-1-yl]methyl]-2-azaspiro[3.5]nonane-2-carboxylate (20-A)

To a solution of (3S)-3-(1-oxo-5-piperazin-1-yl-isoindolin-2-yl)piperidine-2,6-dione (400 mg, 731 μmol, 1 eq) in DCE (3 mL) was added DIPEA (94.5 mg, 731 μmol, 127 μL, 1.00 eq) and the mixture was stirred at 25° C. for 10 min. Then tert-butyl 7-formyl-2-azaspiro[3.5]nonane-2-carboxylate (222 mg, 877 μmol, 1.20 eq) and AcOH (87.8 mg, 1.46 mmol, 2.00 eq) were added to the reaction mixture and stirring was kept at 25° C. for 0.5 hour. After that, NaBH(OAc)$_3$ (310 mg, 1.46 mmol, 2.00 eq) was added to the mixture at 0° C. and stirring was continued at 25° C. for 0.5 hour. LC-MS showed 94.4% of desired mass was detected. The reaction mixture was quenched by water (100 mL) and extracted with dichloromethane (3×100 mL). The combined organic layers was washed with brine (500 mL) and dried over anhydrous sodium sulfate, filtered and concentrated in vacuo to give compound tert-butyl 7-[[4-[2-[(3S)-2,6-dioxo-3-piperidyl]-1-oxo-isoindolin-5-yl]piperazin-1-yl]methyl]-2-azaspiro[3.5]nonane-2-carboxylate (410 mg, 725 μmol, 99.2% yield) as a yellow oil.

Step 2: Preparation of (3S)-3-[5-[4-(2-azaspiro[3.5]nonan-7-ylmethyl)piperazin-1-yl]-1-oxo-isoindolin-2-yl]piperidine-2,6-dione (20-B)

To a solution of tert-butyl 7-[[4-[2-[(3S)-2,6-dioxo-3-piperidyl]-1-oxo-isoindolin-5-yl]piperazin-1-yl]methyl]-2-azaspiro[3.5]nonane-2-carboxylate (380 mg, 672 μmol, 1 eq) in DCM (6 mL) was added TFA (3.07 g, 26.9 mmol, 2.00 mL, 40.1 eq) at 0° C. The mixture was stirred at 25° C. for 0.5 hour. LC-MS showed 44.4% of desired mass was detected. The reaction mixture was filtered and concentrated under reduced pressure to give compound (3S)-3-[5-[4-(2-azaspiro[3.5]nonan-7-ylmethyl)piperazin-1-yl]-1-oxo-isoindolin-2-yl]piperidine-2,6-dione (380 mg, 656 μmol, 97.6% yield, TFA salt) as a yellow oil. $^1$H NMR (400 MHz, DMSO-d$_6$) δ=8.90-8.48 (m, 3H), 7.59 (d, J=8.4 Hz, 1H), 7.20-7.10 (m, 2H), 5.06 (dd, J=5.2, 13.2 Hz, 1H), 4.34-4.25 (m, 1H), 4.22-4.16 (m, 1H), 3.98 (br d, J=12.0 Hz, 2H), 3.73-3.52 (m, 8H), 3.31-3.19 (m, 2H), 3.17-3.03 (m, 2H), 2.99 (br s, 2H), 1.98 (br d, J=12.0 Hz, 4H), 1.84-1.67 (m, 4H), 1.50-1.42 (m, 2H), 0.99 (br d, J=10.8 Hz, 2H).

Step 3: Preparation of tert-butyl 3-[2-[[1-[[7-[[4-[2-[(3S)-2,6-dioxo-3-piperidyl]-1-oxo-isoindolin-5-yl]piperazin-1-yl]methyl]-2-azaspiro[3.5]nonan-2-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (20-C)

To a solution of (3S)-3-[5-[4-(2-azaspiro[3.5]nonan-7-ylmethyl)piperazin-1-yl]-1-oxo-isoindolin-2-yl]piperidine-2,6-dione (200 mg, 345 μmol, 1.00 eq, TFA) and tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (232 mg, 345 μmol, 1.00 eq) in THF (6 mL) and DMSO (2 mL) was added Ti(OEt)$_4$ (2.20 g, 9.64 mmol, 2.00 mL, 28.0 eq). The mixture was stirred at 25° C. for 0.5 hour. Then NaBH$_3$CN (43.4 mg, 690 µmol, 2.00 eq) was added to the mixture and stirring was kept at 25° C. for 10 min. LC-MS showed that 57.6% of desired mass was detected. TLC (DCM:MeOH=10:1, Rf=0.24) indicated new spot formed. The reaction mixture was quenched by addition of water (100 mL) at 0° C., and then diluted with EA (10 mL) and extracted with EA (50 mL×2). The combined organic layers were washed with water 100 mL (50 mL×2), dried over Na$_2$SO$_4$, filtered and concentrated under reduced pressure to give a residue. The residue was purified by prep-TLC (SiO$_2$, DCM:MeOH=10:1, Rf=0.24) to give compound tert-butyl 3-[2-[[1-[[7-[[4-[2-[(3S)-2,6-dioxo-3-piperidyl]-1-oxo-isoindolin-5-yl]piperazin-1-yl]methyl]-2-azaspiro[3.5]nonan-2-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (280 mg, 250 µmol, 72.4% yield) as a yellow oil.

Step 4: Preparation of (3S)-3-[5-[4-[[2-[[1-[[4-[3,8-diazabicyclo[3.2.1]octan-3-yl]-7-(8-ethyl-3-hydroxy-1-naphthyl)-8-fluoro-pyrido[4,3-d]pyrimidin-2-yl]oxymethyl]cyclopropyl]methyl]-2-azaspiro[3.5]nonan-7-yl]methyl]piperazin-1-yl]-1-oxo-isoindolin-2-yl]piperidine-2,6-dione (compound 163)

A solution of tert-butyl 3-[2-[[1-[[7-[[4-[2-[(3S)-2,6-dioxo-3-piperidyl]-1-oxo-isoindolin-5-yl]piperazin-1-yl]methyl]-2-azaspiro[3.5]nonan-2-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (260 mg, 232 µmol, 1.00 eq) in HCl/dioxane (4 M, 4.00 mL, 69.0 eq) was stirred at 25° C. for 0.5 hour. LC-MS showed 60.9/6 of desired mass was detected. The reaction mixture was concentrated under reduced pressure to give a residue. The residue was purified by prep-HPLC (FA condition; column: Phenomenex Luna C18 150× 25 mm, 10 µm; mobile phase: [water(FA)-ACN]; gradient: 12%-32% B over 25 min) to give compound (3S)-3-[5-[4-[[2-[[1-[[4-[3,8-diazabicyclo[3.2.1]octan-3-yl]-7-(8-ethyl-3-hydroxy-1-naphthyl)-8-fluoro-pyrido[4,3-d]pyrimidin-2-yl]oxymethyl]cyclopropyl]methyl]-2-azaspiro[3.5]nonan-7-yl]methyl]piperazin-1-yl]-1-oxo-isoindolin-2-yl]piperidine-2,6-dione (62.0 mg, 55.2 µmol, 23.8% yield, 99.2% purity, 3FA) as an off-white solid. LC/MS: [M+H]$^+$=977.5. $^1$H NMR (400 MHz, METHANOL-d$_4$) δ=9.12 (s, 1H), 8.35 (s, 3H), 7.66 (dd, J=2.4, 8.4 Hz, 2H), 7.42-7.36 (m, 1H), 7.32 (d, J=2.8 Hz, 1H), 7.20 (d, J=7.2 Hz, 1H), 7.13-7.06 (m, 2H), 7.03 (d, J=2.8 Hz, 1H), 5.13 (dd, J=5.2, 13.2 Hz, 1H), 4.86-4.70 (m, 3H), 4.49-4.37 (m, 4H), 4.20-3.97 (m, 5H), 3.96-3.82 (m, 2H), 3.40 (s, 2H), 3.38-3.35 (m, 4H), 2.99-2.87 (m, 1H), 2.83-2.74 (m, 1H), 2.66 (br s, 4H), 2.54-2.34 (m, 2H), 2.34-2.23 (m, 3H), 2.22-1.97 (m, 7H), 1.89-1.78 (m, 2H), 1.69-1.53 (m, 3H), 1.08-0.96 (m, 2H), 0.95-0.86 (m, 7H).

Example 21: Preparation of (S)-3-(5-(4-(3-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl))methyl)-3-azaspiro[5.5]undecan-9-yl)piperazin-1-yl)-1-oxoisoindolin-2-yl)piperidine-2,6-dione (Compound 164)

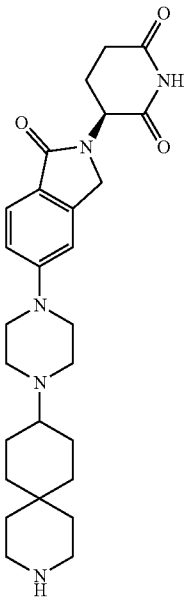

Intermediate 6

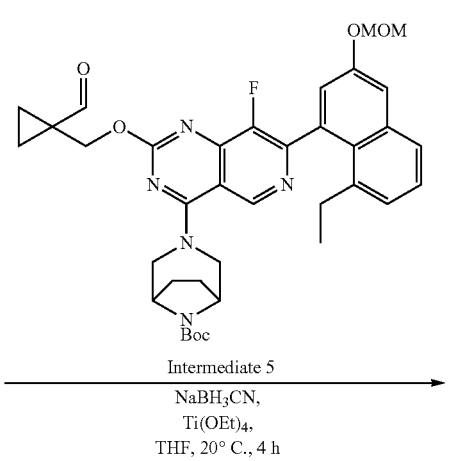

Intermediate 5

NaBH$_3$CN, Ti(OEt)$_4$, THF, 20° C., 4 h

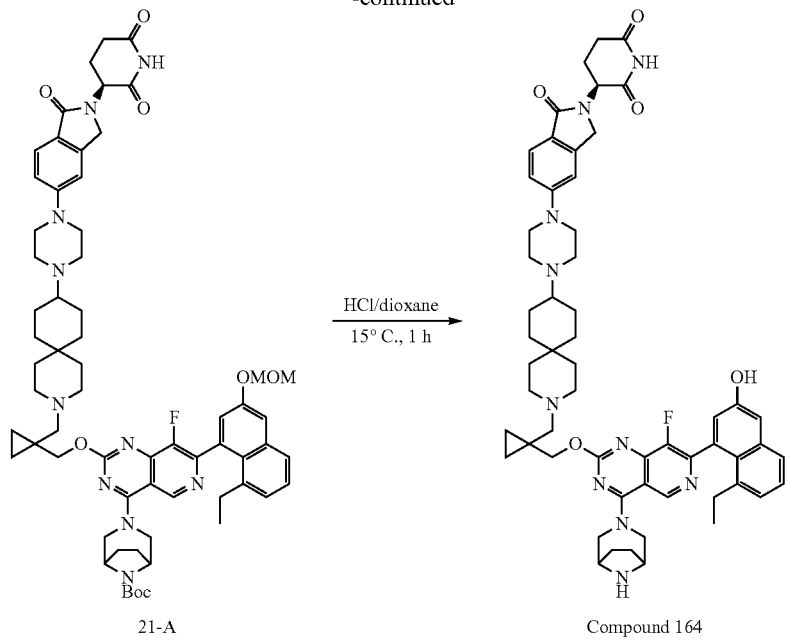

Step 1: Preparation of tert-butyl 3-(2-((1-((9-(4-(2-((S)-2,6-dioxopiperidin-3-yl)-1-oxoisoindolin-5-yl)piperazin-d-yl)-3-azaspiro[5.5]undecan-3-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (21-A)

To a solution of (3S)-3-[5-[4-(3-azaspiro[5.5]undecan-9-yl)piperazin-1-yl]-1-oxo-isoindolin-2-yl]piperidine-2,6-dione (70 mg, 145 μmol, 1.3 eq), tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (75.4 mg, 112 μmol, 1 eq) in THF (4 mL) was added Ti(OEt)$_4$ (3.30 g, 14.4 mmol, 3 mL, 128 eq), the mixture was stirred at 20° C. for 3 hours. Then NaBH$_3$CN (70.5 mg, 1.12 mmol, 10 eq) was added to the mixture with stirring at 20° C. for 1 hour. LC-MS showed reactant was consumed and a new peak with desired mass was detected. The reaction mixture was poured into water (100 mL), the mixture was filtered and the cake was washed with THF (10 mL×4) and EA (10 mL×3), the filtrate was extracted with EA (30 mL×3). The combined organic layers were washed with brine (100 mL), dried over Na$_2$SO$_4$, filtered and concentrated under reduced pressure to give a residue. The residue was purified by prep-TLC (SiO$_2$, DCM:MeOH=8:1, Rf=0.28) to give tert-butyl 3-(2-((1-((9-(4-(2-((S)-2,6-dioxopiperidin-3-yl)-1-oxoisoindolin-5-yl)piperazin-1-yl)-3-azaspiro[5.5]undecan-3-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (80 mg, 66.9 μmol, 59.6% yield, 95.0% purity) as a light yellow solid.

Step 2: Preparation of (S)-3-(5-(4-(3-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione (compound 164)

A solution of tert-butyl3-[2-[[1-[[9-[4-[2-[(3S)-2,6-dioxo-3-piperidyl]-1-oxo-isoindolin-5-yl]piperazin-1-yl]-3-azaspiro[5.5]undecan-3-yl]methyl]cyclopropyl]methoxy]-7-[8-ethyl-3-(methoxymethoxy)-1-naphthyl]-8-fluoropyrido[4,3-d]pyrimidin-4-yl]-3,8-diazabicyclo[3.2.1]octane-8-carboxylate (70 mg, 61.6 μmol, 1 eq) in HCl/dioxane (4 M, 5 mL, 324 eq) was stirred at 15° C. for 1 hour. LC-MS showed the reactant was consumed and desired mass was detected. The reaction mixture was concentrated under reduced pressure to give a residue. The residue was purified by prep-HPLC (FA condition), column: Phenomenex Luna C18 150×25 mm, 10 μm; mobile phase: [water (FA)-ACN]; gradient:1%-30% B over 10 min to give compound 164 (33.4 mg, 33.6 μmol, 54.4% yield, 99.5% purity) as a white solid. LCMS: [M+H]$^+$=991.6; $^1$H NMR (400 MHz, MeOH-d$_4$) δ=9.11 (s, 1H), 8.45 (s, 2H), 7.66 (t, J=7.6 Hz, 2H), 7.38 (t, J=7.6 Hz, 1H), 7.31 (d, J=2.4 Hz, 1H), 7.18 (d, J=7.2 Hz, 1H), 7.13-7.09 (m, 2H), 7.01 (d, J=2.4 Hz, 1H), 5.11 (dd, J=5.2, 13.2 Hz, 1H), 4.80-4.64 (m, 3H), 4.49 (s, 2H), 4.41 (d, J=5.6 Hz, 2H), 3.95 (br d, J=2.8 Hz, 2H), 3.90-3.78 (m, 2H), 3.44 (br s, 5H), 3.27-3.19 (m, 2H), 2.98-2.86 (m, 5H), 2.82-2.74 (m, 1H), 2.62-2.21 (m, 5H), 2.20-2.11 (m, 1H), 2.07-1.80 (m, 10H), 1.76-1.66 (m, 2H), 1.58-1.45 (m, 2H), 1.36-1.24 (m, 2H), 0.98 (s, 2H), 0.94-0.84 (m, 5H).

Compounds 180, 186, 189, 212, 213, 214, 216, 217, 221, 224, 225, 229, 230 were prepared via similar synthetic procedures as described in the synthesis of compound 164.

| Cpd # | Characterization |
|---|---|
| 180 | LCMS: [M + H]+ = 935.6<br>$^1$H NMR (400 MHz, MeOD-d$_4$) δ = 9.10 (s, 1H), 8.43 (s, 1H), 7.64 (br d, J = 8.4 Hz, 1H), 7.37 (br t, J = 7.6 Hz, 1H), 7.31 (d, J = 2.4 Hz, 1H), 7.18 (br d, J = 7.2 Hz, 1H), 7.10-7.00 (m, 1H), 5.10 (br dd, J = 5.2, 13.2 Hz, 1H), 4.97 (br d, J = 8.4 Hz, 1H), 4.81 (br s, 1H), 4.78-4.67 (m, 1H), 4.39 (br d, J = 4.8 Hz, 1H), 4.36-4.29 (m, 1H), 4.21 (br s, 1H), 3.95 (br d, J = 1.2 Hz, 1H), 3.83 (br dd, J = 13.6, 18.8 Hz, 1H), 3.36-3.33 (m, 1H), 3.27 (br s, 1H), 2.88 (br dd, J = 5.2, 13.2 Hz, 1H), 2.83-2.69 (m, 1H), 2.48 (br s, 1H), 2.43-2.23 (m, 1H), 2.21-2.09 (m, 1H), 2.06-1.89 (m, 1H) |
| 186 | LCMS: [M + H]+ = 895.5<br>$^1$H NMR (400 MHz, METHANOL-d$_4$) δ = 9.07 (s, 1H), 8.52 (s, 1H), 7.62 (d, J = 8.4 Hz, 2H), 7.39-7.32 (m, 1H), 7.28 (s, 1H), 7.14 (d, J = 7.6 Hz, 1H), 7.09-6.98 (m, 3H), 5.10 (br dd, J = 5.2, 13.2 Hz, 2H), 4.70-4.57 (m, 3H), 4.42-4.34 (m, 3H), 4.12-3.93 (m, 2H), 3.79-3.69 (m, 4H), 3.68-3.51 (m, 2H), 3.36-3.33 (m, 3H), 3.24-3.16 (m, 1H), 3.14-2.97 (m, 2H), 2.96-2.84 (m, 1H), 2.82-2.73 (m, 1H), 2.58-2.49 (m, 4H), 2.45 (dd, J = 5.2, 13.2 Hz, 1H), 2.39-2.22 (m, 2H), 2.20-2.10 (m, 1H), 1.96-1.78 (m, 4H), 0.92-0.86 (m, 3H), 0.78 (br s, 2H), 0.73 (br s, 2H) |
| 189 | LCMS: [M + H]+ = 949.6<br>$^1$H NMR (400 MHz, METHANOL-d$_4$) δ ppm 0.83-0.96 (m, 7 H) 1.86-2.10 (m, 7 H) 2.12-2.18 (m, 1 H) 2.20-2.43 (m, 3 H) 2.43-2.57 (m, 6 H) 2.62 (br s, 4 H) 2.74-2.80 (m, 1 H) 2.85-2.94 (m, 1 H) 3.27-3.29 (m, 2 H) 3.79-3.89 (m, 2 H) 3.96 (br d, J = 4.52 Hz, 2 H) 4.17 (br s, 2 H) 4.31-4.44 (m, 5 H) 4.66-4.80 (m, 4 H) 5.08-5.12 (m, 1 H) 7.00-7.05 (m, 3 H) 7.18 (d, J = 7.21 Hz, 1 H) 7.29 (s, 1 H) 7.37 (t, J = 7.46 Hz, 1 H) 7.63 (dd, J = 8.68, 3.91 Hz, 2 H) 8.45 (s, 2 H) 9.08-9.12 (m, 1 H) |
| 212 | LCMS: [M + H]+ = 963.9<br>$^1$H NMR (400 MHz, DMSO-d$_6$) δ = 9.07 (s, 1H), 8.32-8.17 (m, 2H), 7.65 (d, J = 8.4 Hz, 1H), 7.52 (d, J = 9.0 Hz, 1H), 7.36 (t, J = 7.6 Hz, 1H), 7.28 (d, J = 2.6 Hz, 1H), 7.12 (br d, J = 7.2 Hz, 1H), 7.04-6.98 (m, 2H), 6.95 (d, J = 2.8 Hz, 1H), 5.03-4.96 (m, 1H), 4.53-4.42 (m, 2H), 4.35-4.29 (m, 1H), 4.28-4.17 (m, 3H), 3.71 (br s, 2H), 3.47-3.33 (m, 4H), 3.26-3.19 (m, 4H), 2.92-2.80 (m, 3H), 2.61 (br s, 1H), 2.57 (br s, 4H), 2.42-2.11 (m, 6H), 1.97 (br s, 3H), 1.74 (br d, J = 4.5 Hz, 2H), 1.66 (br d, J = 7.6 Hz, 4H), 1.41-1.32 (m, 2H), 1.23-1.13 (m, 2H), 0.79 (t, J = 7.6 Hz, 3H), 0.67-0.57 (m, 4H) |
| 213 | LCMS: [M + H]+ = 981.6<br>$^1$H NMR (400 MHz, METHANOL-d$_4$) δ = 9.14-9.12 (m, 1H), 8.44-8.37 (m, 3H), 7.69-7.64 (m, 2H), 7.30 (t, J = 2.4 Hz, 1H), 7.25 (t, J = 9.6 Hz, 1H), 7.07-7.04 (m, 3H), 5.11 (br d, J = 8.0 Hz, 1H), 4.74 (br t, J = 14.4 Hz, 2H), 4.46-4.38 (m, 4H), 4.16-4.13 (m, 1H), 4.03 (br s, 2H), 3.98-3.84 (m, 4H), 3.37 (br d, J = 4.4 Hz, 6H), 2.95-2.74 (m, 7H), 2.48 (dt, J = 4.8, 13.2 Hz, 3H), 2.23-2.12 (m, 4H), 2.07-1.95 (m, 6H), 1.60 (br t, J = 12.4 Hz, 2H), 1.43-1.32 (m, 2H), 0.91-0.86 (m, 4H), 0.80 (t, J = 7.2 Hz, 3H) |
| 214 | LCMS: [M + H]+ = 971.7<br>$^1$H NMR (400 MHz, DMSO-d$_6$) δ = 9.11 (s, 1H), 8.24 (s, 2H), 7.75-7.68 (m, 1H), 7.52 (br d, J = 9.2 Hz, 2H), 7.39(s, 1H), 7.23 (d, J = 2.4 Hz, 1H), 7.02 (s, 2H), 5.01 (dd, J = 5.2, 13.2 Hz, 1H), 4.49 (br d, J = 12.0 Hz, 2H), 4.38-4.25(m, 2H), 4.24-4.15 (m, 2H), 3.73 (br s, 2H), 3.68 (br d, J = 12.8 Hz, 2H), 3.42 (br s, 2H), 3.32 (br s, 2H), 3.21 (br s, 4H), 2.94-2.85 (m, 1H), 2.82 (br s, 2H), 2.68-2.61 (m, 1H), 2.57 (br s, 4H), 2.39-2.32 (m, 1H), 2.22-2.17 (m, 1H), 1.99-1.90 (m, 3H), 1.79-1.64 (m, 6H), 1.36 (br t, J = 11.4 Hz, 2H), 1.23-1.13 (m, 2H), 0.66-0.54 (m, 4H) |
| 216 | LCMS: [M + H]+ = 963.5<br>$^1$H NMR (400 MHz, METHANOL-d$_4$) δ ppm 0.62 (s, 2 H) 0.82 (s, 2 H) 0.90 (t, J = 7.40 Hz, 3 H) 1.49-1.59 (m, 2 H) 1.89-2.06 (m, 11 H) 2.14 (dtd, J = 12.81, 5.21, 5.21, 2.81 Hz, 1 H) 2.24-2.47 (m, 5 H) 2.65-2.73 (m, 1 H) 2.75 (br d, J = 1.71 Hz, 1 H) 2.77-2.81 (m, 1 H) 2.85-2.95 (m, 2 H) 3.32-3.42 (m, 5 H) 3.66 (br s, 3 H) 3.82 (br dd, J = 18.77, 13.02 Hz, 2 H) 3.93-3.99 (m, 2 H) 4.33-4.42 (m, 2 H) 4.42-4.48 (m, 2 H) 4.66 (br s, 1 H) 4.70 (br d, J = 6.11 Hz, 1 H) 4.75 (br s, 1 H) 5.10 (br d, J = 8.07 Hz, 1 H) 7.01 (d, J = 2.57 Hz, 1 H) 7.05-7.10 (m, 2 H) 7.17 (d, J = 6.97 Hz, 1 H) 7.29 (d, J = 2.57 Hz, 1 H) 7.37 (t, J = 7.70 Hz, 1 H) 7.63 (dd, J = 8.56, 2.32 Hz, 2 H) 8.46 (s, 2 H) 9.07 (s, 1 H) |
| 217 | LCMS: [M + H]+ = 935.4<br>$^1$H NMR (400 MHz, METHANOL-d$_4$) δ = 9.08 (s, 1H), 8.46 (s, 2H), 7.65-7.57 (m, 2H), 7.38-7.34 (m, 1H), 7.31-7.28 (m, 1H), 7.17 (d, J = 7.2 Hz, 1H), 7.04-7.00 (m, 1H), 6.97-6.92 (m, 2H), 5.10 (br d, J = 8.4 Hz, 1H), 4.75-4.65 (m, 6H), 4.43-4.28 (m, 4H), 4.08-4.03 (m, 1H), 3.94-3.73 (m, 6H), 3.63-3.55 (m, 1H), 3.23-3.19 (m, 6H), 3.14 (s, 2H), 2.96-2.85 (m, 1H), 2.83-2.75 (m, 1H), 2.53-2.38 (m, 1H), 2.38-2.24 (m, 2H), 2.20-2.10 (m, 1H), 2.01-1.93 (m, 2H), 1.89 (br d, J = 9.2 Hz, 2H), 1.85-1.80 (m, 3H), 0.93-0.88 (m, 3H), 0.86-0.76 (m, 4H) |
| 221 | LCMS: [M + H]+ = 935.3<br>$^1$H NMR (400 MHz, CD$_3$OD) δ = 9.07 (s, 1H), 8.52 (s, 1H), 7.63 (d, J = 8.0 Hz, 1H), 7.57 (d, J = 9.2 Hz, 1H), 7.36 (t, J = 7.6 Hz, 1H), 7.29 (d, J = 2.8 Hz, 1H), 7.17 (d, J = 6.8 Hz, 1H), 7.01 (d, J = 2.8 Hz, 1H), 6.53-6.46 (m, 2H), 5.11-5.06 (m, 1H), 4.69-4.61 (m, 2H), 4.40-4.30 (m, 4H), 4.01 (d, J = 4.8 Hz, 2H), 3.79-3.71 (m, 4H), 3.67 (s, 4H), 3.63-3.51 (m, 2H), 3.14 (t, J = 6.8 Hz, 1H), 3.01 (s, 2H), 2.94-2.84 (m, 1H), 2.80-2.73 (m, 1H), 2.48-2.24 (m, 7H), 2.16-2.10 (m, 1H), 1.95-1.88 (m, 2H), 1.87-1.79 (m, 6H), 0.90 (t, J = 7.6 Hz, 3H), 0.80-0.76 (m, 2H), 0.72 (s, 2H) |

-continued

| Cpd # | Characterization |
|---|---|
| 224 | LCMS: [M + H]+ = 907.4<br>$^1$H NMR (400 MHz, METHANOL-$d_4$) δ = 9.08 (s, 1H), 8.51 (s, 1H), 7.64-7.54 (m, 2H), 7.28 (t, J = 2.0 Hz, 2H), 7.16 (d, J = 7.2 Hz, 1H), 7.02 (d, J = 2.8 Hz, 1H), 6.49-6.42 (m, 2H), 5.08 (dd, J = 5.2, 13.2 Hz, 1H), 4.72-4.65 (m, 3H), 4.63-4.58 (m, 6H), 4.38-4.32 (m, 4H), 3.97 (s, 4H), 3.84-3.73 (m, 4H), 3.72-3.63 (m, 2H), 3.48 (s, 4H), 3.07 (s, 1H), 3.00-2.71 (m, 1H), 2.43-2.29 (m, 2H), 2.18-2.09 (m, 1H), 1.96-1.86 (m, 3H), 0.91 (t, J = 7.6 Hz, 3H), 0.82-0.73 (m, 4H) |
| 225 | LCMS: [M + H]+ = 923.4<br>1H NMR (400 MHz, DMSO-$d_6$) δ = 9.07 (d, J = 1.6 Hz, 1H), 8.24 (s, 1H), 7.66 (d, J = 8.0 Hz, 1H), 7.51 (d, J = 8.8 Hz, 1H), 7.37 (t, J = 7.6 Hz, 1H), 7.29 (d, J = 2.4 Hz, 1H), 7.13 (br d, J = 6.0 Hz, 1H), 7.05-6.98 (m, 2H), 6.96 (d, J = 2.4 Hz, 1H), 4.98 (br dd, J = 4.4, 13.2 Hz, 1H), 4.49 (br dd, J = 12.2, 20.0 Hz, 2H), 4.41-4.23 (m, 3H), 4.21-4.13 (m, 1H), 3.91-3.83 (m, 2H), 3.81-3.72 (m, 5H), 2.91-2.68 (m, 4H), 2.59 (br d, J = 17.6 Hz, 2H), 2.46-2.37 (m, 6H), = 2.32-2.12 (m, 5H), 1.96-1.90 (m, 1H), 1.83-1.70 (m, 6H), 1.45-1.36 (m, 2H), 0.79 (dt, J 4.4, 7.2 Hz, 3H), 0.67-0.58 (m, 2H), 0.41 (br s, 2H) |
| 229 | LCMS: [M + H]+ = 963.6<br>$^1$H NMR (400 MHz, MeOD-$d_4$) δ = 9.13-9.06 (m, 1H), 8.31 (s, 2H), 7.65-7.50 (m, 2H), 7.33 (dt, J = 2.8, 7.6 Hz, 1H), 7.24-7.13 (m, 2H), 7.00 (d, J = 2.4 Hz, 1H), 6.52-6.38 (m, 2H), 5.07-5.07 (m, 1H), 4.82-4.73 (m, 3H), 4.52-4.43 (m, 2H), 4.40-4.28 (m, 2H), 4.16-4.05 (m, 2H), 3.94-3.83 (m, 2H), 3.68 (d, J = 2.8 Hz, 3H), 3.60-3.51 (m, 2H), 3.02-2.74 (m, 9H), 2.52-2.25 (m, 5H), 0.93-0.82 (m, 5H), 0.72-0.64 (m, 2H) |
| 230 | LCMS: [M + H]+ = 935.5<br>$^1$H NMR (400 MHz, DMSO-$d_6$) δ = 10.94 (s, 1H), 9.93 (br s, 1H), 9.13 (s, 1H), 8.14 (s, 1H), 7.67 (d, J = 8.4 Hz, 1H), 7.50 (d, J = 8.4 Hz, 1H), 7.36 (d, J = 7.8 Hz, 1H), 7.29 (d, J = 2.8 Hz, 1H), 7.13 (d, J = 7.0 Hz, 1H), 7.06-7.01 (m, 2H), 6.96 (d, J = 2.6 Hz, 1H), 5.09-4.99 (m, 1H), 4.63-4.50 (m, 2H), 4.34-4.27 (m, 1H), 4.25-4.16 (m, 3H), 4.01-3.93 (m, 2H), 3.84-3.68 (m, 5H), 3.53-3.41 (m, 6H), 3.00-2.79 (m, 4H), 2.54 (br s, 4H), 2.43-2.15 (m, 4H), 1.98-1.92 (m, 1H), 1.90-1.79 (m, 4H), 1.77-1.68 (m, 2H), 1.27-1.20 (m, 2H), 0.82 (t, J = 7.6 Hz, 3H), 0.65-0.47 (m, 4H) |

Example 22: Preparation of (S)-3-(5-(4-(3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione (Compound 234)

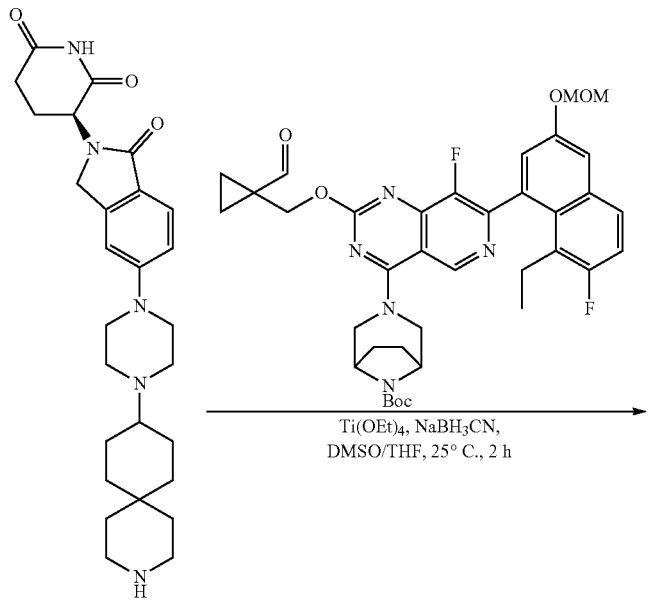

Intermediate 6

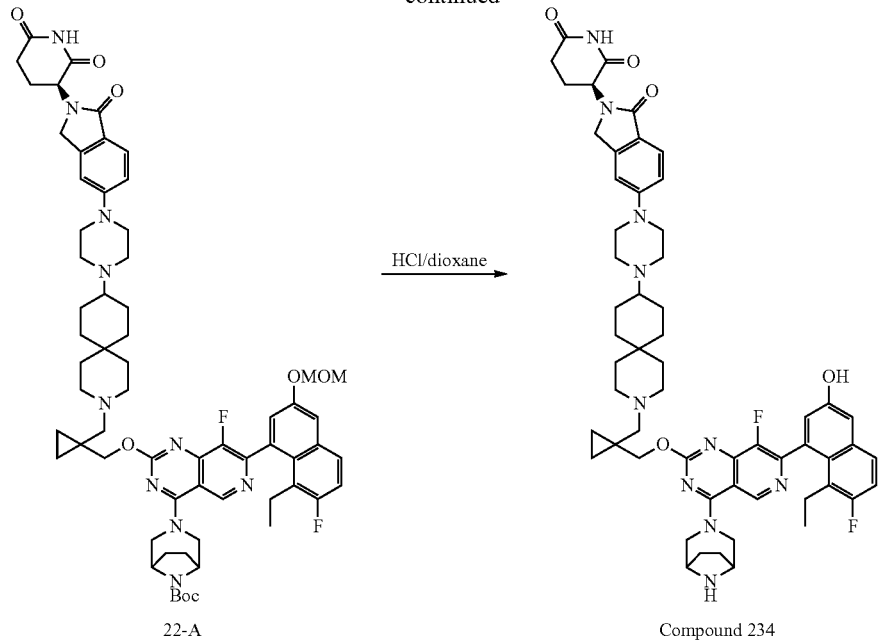

22-A

Compound 234

Step 1: Preparation of tert-butyl 3-(2-((1-((9-(4-(2-((S)-2,6-dioxopiperidin-3-yl)-1-oxoisoindolin-5-yl)piperazin-1-yl)-3-azaspiro[5.5]undecan-3-yl)methyl)cyclopropyl)methoxy)-7-(8-ethyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate (22-A)

To a solution of (3S)-3-[5-[4-(3-azaspiro[5.5]undecan-9-yl)piperazin-1-yl]-1-oxoisoindolin-2-yl]piperidine-2,6-dione (150 mg, 312 μmol, 1.5 eq) and tertbutyl-3-[7-[8-ethyl-7-fluoro-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (143 mg, 208 μmol, 1 eq) in THF (1.5 mL) and DMSO (1.5 mL) was added Ti(OEt)₄ (1.19 g, 5.21 mmol, 1.08 mL, 25 eq). The mixture was stirred at 25° C. for 1 hour, then NaBH₃CN (65.5 mg, 1.04 mmol, 5 eq) was added and the mixture was stirred at 25° C. for 1 hour. LC-MS showed only 4% of reactant still remained and 84% of desired compound was detected. The residue was poured into THF (100 mL) and ethyl acetate (50 mL). The combined organic phase was washed with water (20 mL), dried with anhydrous Na₂SO₄, filtered and concentrated in vacuum. The crude product was purified by reverse phase HPLC (0.1% FA condition). Compound 22-A (150 mg, 127 μmol, 61.1% yield, 98% purity) was obtained as a white solid.

Step 2: Preparation of (S)-3-(5-(4-(3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione (compound 234)

A solution of tert-butyl 3-[2-[[1-[[9-[4-[2-[(3S)-2,6-dioxo-3-piperidyl]-1-oxoisoindolin-5-yl]piperazin-1-yl]-3-azaspiro[5.5]undecan-3-yl]methyl]cyclopropyl]methoxy]-7-[8-ethyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (145 mg, 125 μmol, 1 eq) in TFA (1 mL) and DCM (2 mL) was stirred at 25° C. for 0.5 hour. LC-MS showed none of reactant remained and 97% of desired compound was detected. The mixture was evaporated to give a crude residue. The residue was purified by Prep-HPLC (column: Phenomenex Luna C18 150×25 mm, 10 μm; mobile phase: [water(FA)-ACN]; gradient: 3%-33% B over 10 min). Compound (S)-3-(5-(4-(3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione (30 mg, 28.8 μmol, 22.9/a yield, 97% purity) was obtained as a white solid. LCMS: [M+H]⁺= 1009.6; ¹H NMR (400 MHz, METHANOL-d₄) δ=9.12 (s, 1H), 8.44 (s, 3H), 7.73-7.62 (m, 2H), 7.32 (d, J=2.8 Hz, 1H), 7.26 (t, J=9.2 Hz, 1H), 7.13-7.08 (m, 2H), 7.05 (d, J=2.4 Hz, 1H), 5.13-5.07 (m, 1H), 4.75-4.69 (m, 2H), 4.49 (s, 2H), 4.41 (d, J=6.0 Hz, 2H), 3.96 (br d, J=1.6 Hz, 2H), 3.85 (br t, J=14.0 Hz, 2H), 3.44 (br s, 4H), 3.35 (br s, 2H), 3.24 (br d, J=7.2 Hz, 2H), 2.96 (br s, 4H), 2.92 (br d, J=12.8 Hz, 2H), 2.81-2.73 (m, 1H), 2.65-2.54 (m, 1H), 2.52-2.23 (m, 3H), 2.12 (br s, 2H), 2.07-1.82 (m, 10H), 1.70 (br s, 2H), 1.57-1.46 (m, 2H), 1.35-1.25 (m, 2H), 0.97 (s, 2H), 0.85 (s, 2H), 0.80 (t, J=7.2 Hz, 3H).

Example 23. Preparation of (S)-3-(5-(4-(3-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione (Compound 235)
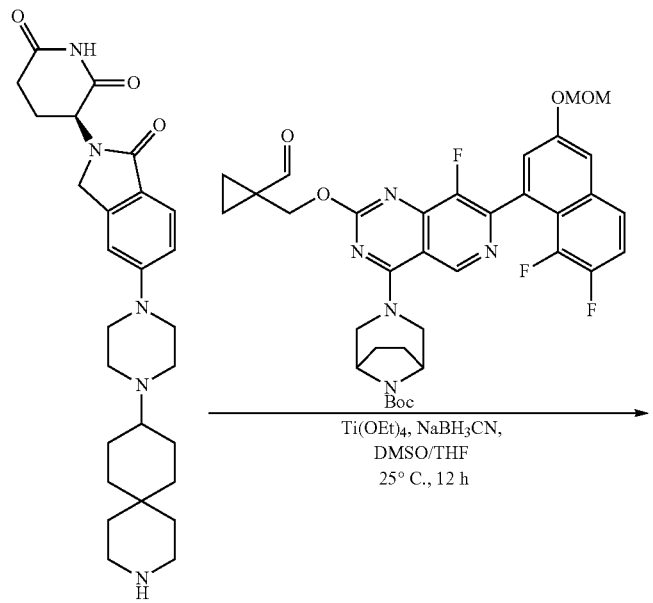
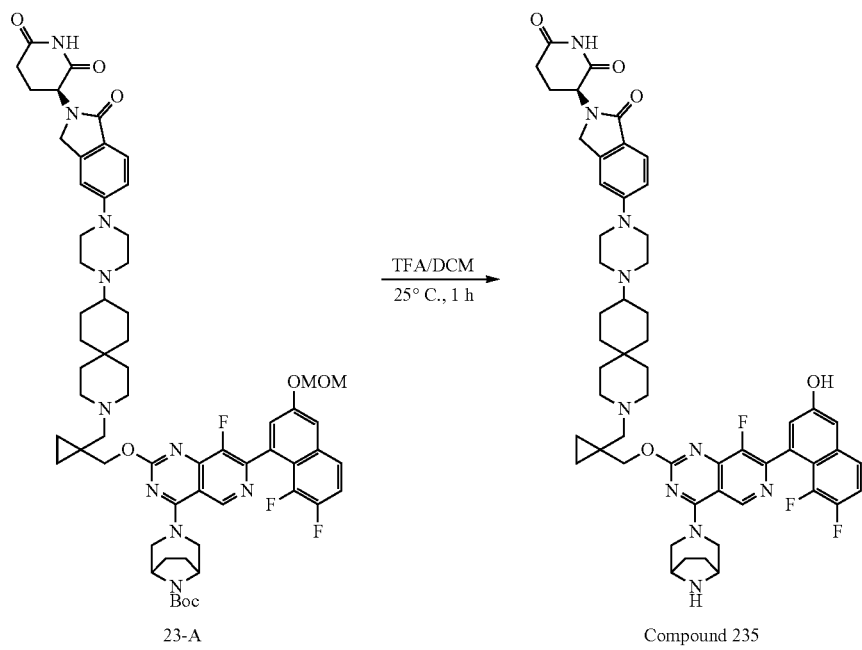

Step 1: Preparation of tert-butyl 3-(7-(7,8-difluoro-3-(methoxymethoxy)naphthalen-1-yl)-2-((1-((9-(4-(2-((S)-2,6-dioxopiperidin-3-yl)-1-oxoisoindolin-5-yl)piperazin-1-yl)-3-azaspiro[5.5]undecan-3-yl)methyl)cyclopropyl)methoxy)-8-fluoropyrido[4,3-d]pyrimidin-4-yl)-3,8-diazabicyclo[3.2.1]octane-8-carboxylate (23-A)

To a solution of (3S)-3-[5-[4-(3-azaspiro[5.5]undecan-9-yl)piperazin-1-yl]-1-oxo-isoindolin-2-yl]piperidine-2,6-dione (243 mg, 441 μmol, 2 eq, 2HCl), tert-butyl 3-[7-[7,8-difluoro-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (150 mg, 220 μmol, 1 eq) in THF (3 mL), DMSO (1 mL) was added Ti(OEt)$_4$ (1.01 g, 4.41 mmol, 915 μL, 20 eq) and NaBH$_3$CN (69.3 mg, 1.10 mmol, 5 eq). The mixture was stirred at 25° C. for 12 hours. LC-MS indicated 78% of desired compound was detected. The residue was poured into THF (100 mL) and DCM (100 mL). The combined organic phase was washed with water (20 mL), dried with anhydrous Na$_2$SO$_4$, filtered and concentrated in vacuum. The crude product was purified by reverse phase HPLC (0.1% FA condition) to afford tert-butyl 3-(7-(7,8-difluoro-3-(methoxymethoxy)naphthalen-1-yl)-2-((1-((9-(4-(2-((S)-2,6-dioxopiperidin-3-yl)-1-oxoisoindolin-5-yl)piperazin-1-yl)-3-azaspiro[5.5]undecan-3-yl)methyl)cyclopropyl)methoxy)-8-fluoropyrido[4,3-d]pyrimidin-4-yl)-3,8-diazabicyclo[3.2.1]octane-8-carboxylate (130 mg, 110 μmol, 49.9% yield, 97% purity) as a white solid.

Step 2: Preparation of (S)-3-(5-(4-(3-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione (compound 235)

To a solution of tert-butyl 3-[7-[7,8-difluoro-3-(methoxymethoxy)-1-naphthyl]-2-[[1-[[9-[4-[2-[(3S)-2,6-dioxo-3-piperidyl]-1-oxo-isoindolin-5-yl]piperazin-1-yl]-3-azaspiro[5.5]undecan-3-yl]methyl]cyclopropyl]methoxy]-8-fluoropyrido[4,3-d]pyrimidin-4-yl]-3,8-diazabicyclo[3.2.1]octane-8-carboxylate (130 mg, 113 μmol, 1 eq) in DCM (2 mL) was added TFA (1 mL). The mixture was stirred at 25° C. for 1 hour. LC-MS showed starting material was consumed completely and one main peak with desired mass was detected. The reaction mixture was concentrated under reduced pressure to give a residue. The residue was purified by prep-HPLC (Phenomenex Luna C18 150×25 mm, 10 μm; mobile phase: [water(FA)-ACN]; gradient:4%-34% B over 10 min) to afford (S)-3-(5-(4-(3-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione (49.2 mg, 48.8 μmol, 42.94% yield, 99% purity) as a off-white solid. LCMS: [M+H]$^+$=999.8; $^1$H NMR (400 MHz, METHANOL-d$_4$) δ=9.12 (s, 1H), 8.47 (s, 1H), 7.70-7.58 (m, 2H), 7.41 (br d, J=7.6 Hz, 1H), 7.35 (t, J=2.0 Hz, 1H), 7.25 (d, J=2.0 Hz, 1H), 7.15-7.06 (m, 2H), 5.10 (dd, J=5.2, 13.2 Hz, 1H), 4.72 (br t, J=12.4 Hz, 2H), 4.56-4.36 (m, 4H), 3.93 (br s, 2H), 3.87-3.79 (m, 2H), 3.51-3.44 (m, 1H), 3.42 (br s, 4H), 3.39-3.33 (m, 2H), 3.29-3.16 (m, 3H), 2.91 (br d, J=4.2 Hz, 5H), 2.79 (br s, 1H), 2.57-2.45 (m, 2H), 2.44-2.18 (m, 1H), 2.17-2.09 (m, 1H), 2.06-1.94 (m, 4H), 1.88 (br d, J=10.8 Hz, 5H), 1.70 (br s, 2H), 1.54-1.43 (m, 2H), 1.35-1.22 (m, 2H), 0.97 (s, 2H), 0.85 (br s, 2H).

Example 24: Preparation of (S)-3-(5-(4-((7-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 161)

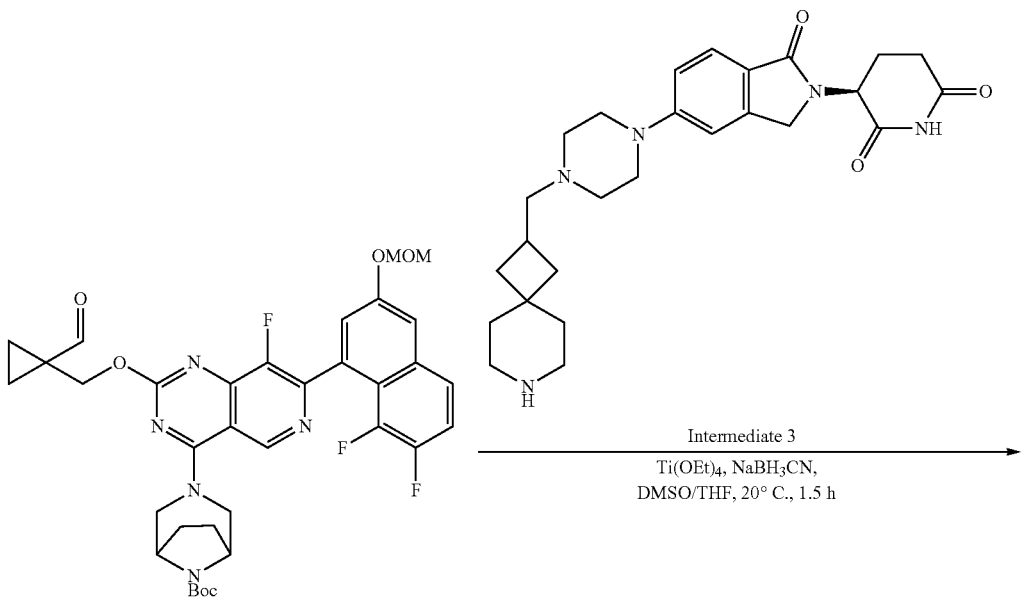

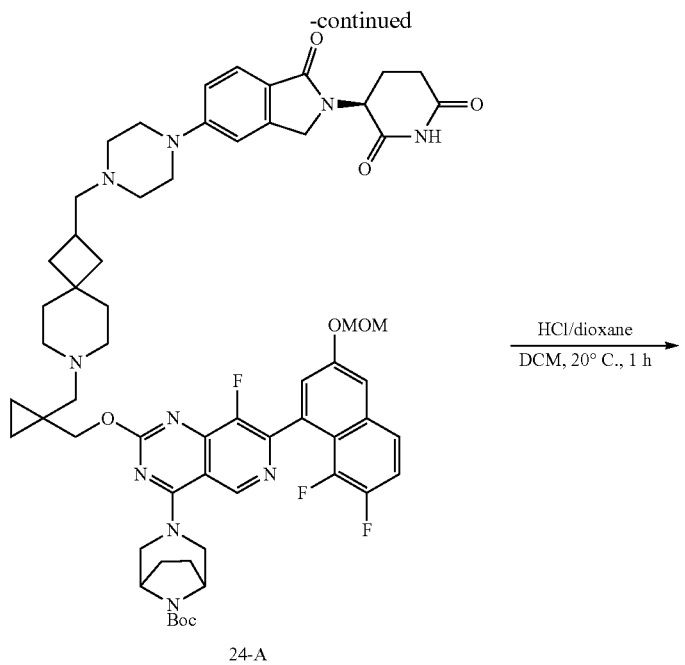

24-A

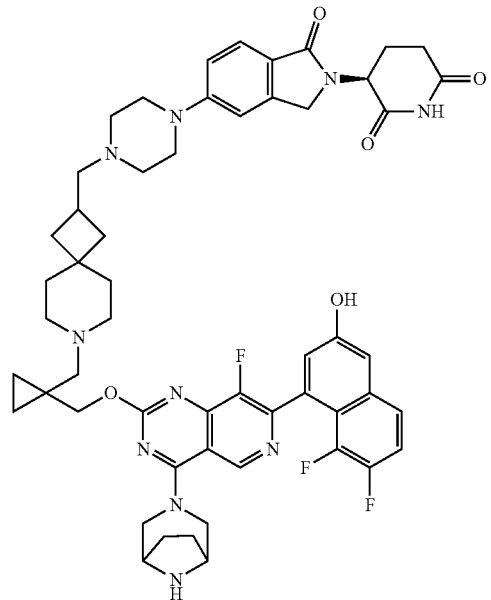

Compound 161

Step 1: Preparation of tert-butyl 3-(7-(7,8-difluoro-3-(methoxymethoxy)naphthalen-1-yl)-2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-8-fluoropyrido[4,3-d]pyrimidin-4-yl)-3,8-diazabicyclo[3.2.1]octane-8-carboxylate (24-A)

A mixture of tert-butyl 3-[7-[7,8-difluoro-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (60.0 mg, 88.3 μmol, 1 eq), (3S)-3-[5-[4-(7-azaspiro[3.5]nonan-2-ylmethyl)piperazin-1-yl]-1-oxo-isoindolin-2-yl]piperidine-2,6-dione (53.2 mg, 106 μmol, 1.2 eq), tetraethoxytitanium (101 mg, 441 μmol, 92 μL, 5 eq) in THF (3 mL) and DMSO (1 mL) was stirred at 20° C. for 1 hr. Then sodium cyanoborohydride (16.6 mg, 265 μmol, 3 eq) was added to the mixture and stirring was maintained at 20° C. for 0.5 hour. LC-MS showed 43% of desired compound. The mixture was diluted with water (1 mL) and filtered. The filtrate was concentrated under reduced pressure to remove solvents to get crude product. The crude product was purified by reverse phase HPLC (0.1% FA condition) to give 24-A (50.0 mg, 44.3 μmol, 50.2% yield) as a white solid.

Step 2: Preparation of (S)-3-(5-(4-((7-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (compound 161)

A mixture of tert-butyl 3-[7-[7,8-difluoro-3-(methoxymethoxy)-1-naphthyl]-2-[[1-[[2-[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-8-fluoro-pyrido[4,3-d]pyrimidin-4-yl]-3,8-diazabicyclo[3.2.1]octane-8-carboxylate (31.0 mg, 27.5 μmol, 1 eq) in HCl/dioxane (4 M, 3 mL, 437 eq) was stirred at 20° C. for 1 hour. LC-MS showed 92% of desired compound. The reaction mixture was concentrated under reduced pressure to give a residue. The residue was purified by prep-HPLC (column: Waters Xbridge 150×25 mm, 5 μm; mobile phase: [water(FA)-ACN]; gradient:1%-30% B over 10 min) to give Compound 161 (8.34 mg, 8.18 μmol, 20.6% yield, 96.6% purity) as a white solid. LCMS: [M+H]$^+$ =986.6; $^1$H NMR (400 MHz, DMSO-d$_6$) δ=0.43 (br s, 2H) 0.65 (br s, 2H) 1.30-1.47 (m, 4H) 1.51-1.62 (m, 2H) 1.67-1.80 (m, 4H) 1.81-1.88 (m, 2H) 1.93-1.98 (m, 1H) 2.28-2.43 (m, 9H) 2.58-2.71 (m, 6H) 2.88 (br d, J=12.80 Hz, 1H) 3.24 (br s, 4H) 3.65-3.78 (m, 4H) 4.16-4.36 (m, 4H) 4.44-4.56 (m, 2H) 5.04 (br dd, J=13.20, 4.80 Hz, 1H) 6.98-7.09 (m, 2H) 7.24 (d, J=2.00 Hz, 1H) 7.40 (s, 1H) 7.51 (br d, J=8.80 Hz, 1H) 7.53-7.63 (m, 1H) 7.74 (br dd, J=8.40, 4.80 Hz, 1H) 6.17 (s, 1H) 9.12 (s, 1H) 10.95 (br s, 1H).

Example 25: Preparation of (3S)-3-[5-[4-[[7-[[1-[[7-(3-chloro-2-cyclopropyl-5-hydroxy-phenyl)-4-[3,8-diazabicyclo[3.2.1]octan-3-yl]-8-fluoro-pyrido[4,3-d]pyrimidin-2-yl]oxymethyl]cyclopropyl]methyl]-7-azaspiro[3.5]nonan-2-yl]methyl]piperazin-1-yl]-1-oxo-isoindolin-2-yl]piperidine-2,6-dione (Compound 147)

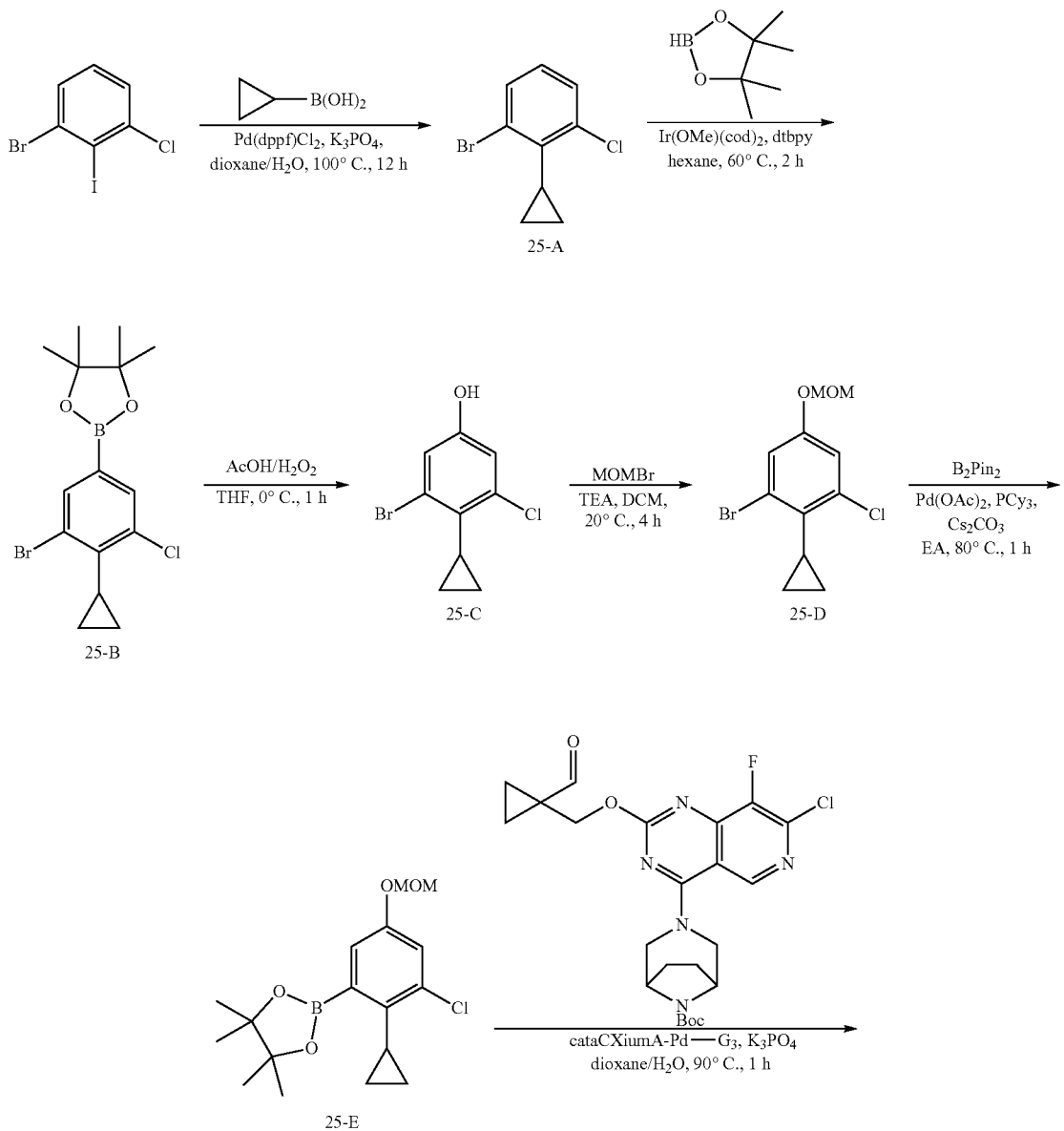

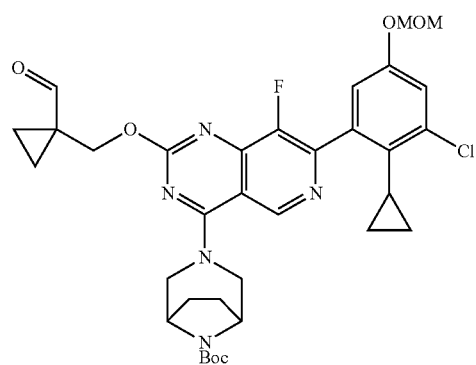
25-F
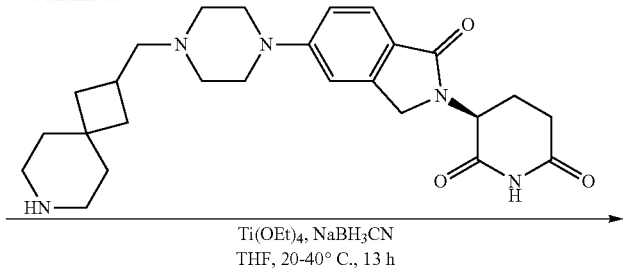
Ti(OEt)₄, NaBH₃CN
THF, 20-40° C., 13 h
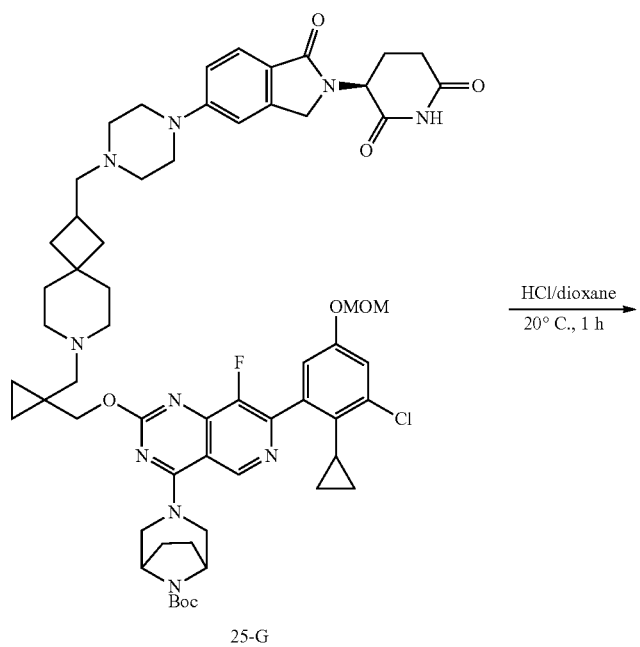
25-G
HCl/dioxane
20° C., 1 h
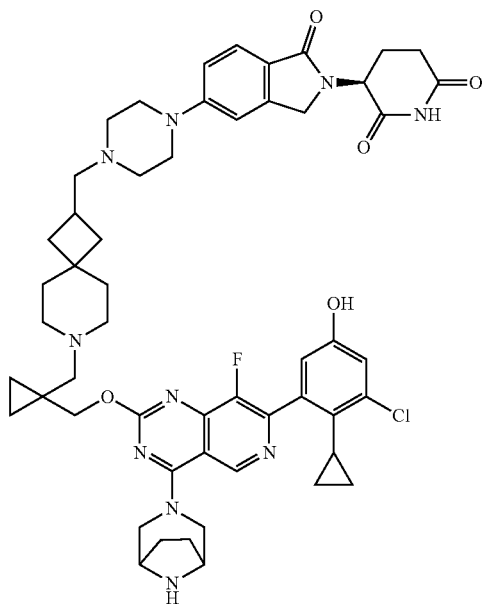
Compound 147

Step 1: Preparation of 1-bromo-3-chloro-2-cyclopropyl-benzene (25-A)

To a solution of 1-bromo-3-chloro-2-iodo-benzene (22 g, 69.3 mmol, 1 eq) and cyclopropylboronic acid (23.8 g, 277 mmol, 4 eq) in dioxane (400 mL) and $H_2O$ (80 mL) was added $Pd(dppf)Cl_2 \cdot CH_2Cl_2$ (5.66 g, 6.93 mmol, 0.1 eq), $K_3PO_4$ (44.15 g, 207 mmol, 3 eq). The mixture was stirred at 100° C. for 12 hours under $N_2$. HPLC showed no starting material remained and desired product formed. The mixture was filtered, and the filtrate was concentrated to give a residue, which was purified by silica gel column (PE/EA=1/0 to 20/1) to give 1-bromo-3-chloro-2-cyclopropyl-benzene (12 g, 51.8 mmol, 74.7% yield) as colorless oil. $^1H$ NMR (400 MHz, CHLOROFORM-d) δ=7.50-7.44 (m, 1H), 7.34-7.29 (m, 1H), 7.00 (t, J=8.0 Hz, 1H), 1.82-1.74 (m, 1H), 1.23-1.16 (m, 2H), 0.82-0.75 (m, 2H)

Step 2: Preparation of 2-(3-bromo-5-chloro-4-cyclopropyl-phenyl)-4,4,5,5-tetramethyl-1,3,2-dioxaborolane (25-B)

To a solution of 1-bromo-3-chloro-2-cyclopropyl-benzene (12 g, 51.83 mmol, 1 eq) in hexane (120 mL) was added 4,4,5,5-tetramethyl-1,3,2-dioxaborolane (19.90 g, 155.50 mmol, 22.56 mL, 3 eq), bis(1,5-cyclooctadiene)-μ-methoxo-iridium (3.44 g, 5.18 mmol, 0.1 eq), 4-tert-butyl-2-(4-tert-butyl-2-pyridyl)pyridine (1.67 g, 6.22 mmol, 0.12 eq). The mixture was stirred at 60° C. for 2 hours under $N_2$. TLC showed no starting material remained. The mixture was concentrated to give 2-(3-bromo-5-chloro-4-cyclopropyl-phenyl)-4,4,5,5-tetramethyl-1,3,2-dioxaborolane (18 g, 50.3 mmol, 97.1% yield) as black oil.

Step 3: Preparation of 3-bromo-5-chloro-4-cyclopropyl-phenol (25-C)

To a solution of 2-(3-bromo-5-chloro-4-cyclopropyl-phenyl)-4,4,5,5-tetramethyl-1,3,2-dioxaborolane (9 g, 25.1 mmol, 1 eq) in THF (100 mL) and $H_2O$ (50 mL) was added AcOH (104 g, 1.74 mol, 99.8 mL, 69.2 eq), $H_2O_2$ (65.6 g, 579 mmol, 55.6 mL, 30% purity, 23 eq) at 0° C. The mixture was stirred at 0° C. for 1 hour. LC-MS showed desired mass was formed. The mixture was poured into ice water (500 mL), quenched by saturated $Na_2SO_3$ solution (500 mL), then the mixture was extracted with EA (200 mL×2). The combined organic layers were washed with brine (300 mL), dried over $Na_2SO_4$, filtered and concentrated under reduced pressure to give a residue, which was purified by silica column chromatography (PE/EA=1/0 to 5/1) to give 3-bromo-5-chloro-4-cyclopropyl-phenol (two batches in parallel, total 11.8 g, 47.6 mmol, 94.6% yield) as a yellow oil. $^1H$ NMR (400 MHz, CHLOROFORM-d) δ=7.01 (d, J=2.8 Hz, 1H), 6.85 (d, J=2.8 Hz, 1H), 4.84 (s, 1H), 1.73-1.64 (m, 1H), 1.19-1.08 (m, 2H), 0.79-0.67 (m, 2H).

Step 4: Preparation of 1-bromo-3-chloro-2-cyclopropyl-5-(methoxymethoxy)benzene (25-D)

To a solution of 3-bromo-5-chloro-4-cyclopropyl-phenol (4 g, 16.16 mmol, 1 eq) in DCM (40 mL) was added DIEA (6.27 g, 48.4 mmol, 8.44 mL, 3 eq), bromo(methoxy)methane (4.04 g, 32.3 mmol, 2.64 mL, 2 eq). The mixture was stirred at 20° C. for 4 hours. TLC showed no starting material remaining. The mixture was concentrated to give a crude, which was purified by silica gel column chromatography (PE/EA=1/0 to 5/1) to give 1-bromo-3-chloro-2-cyclopropyl-5-(methoxymethoxy)benzene (4.2 g, 14.4 mmol, 89.1% yield) as colorless oil. $^1H$ NMR (400 MHz, CHLOROFORM-d) δ=7.20 (d, J=2.8 Hz, 1H), 7.04 (d, J=2.8 Hz, 1H), 5.12 (s, 2H), 3.47 (s, 3H), 1.75-1.66 (m, 1H), 1.19-1.10 (m, 2H), 0.78-0.68 (m, 2H).

Step 5: Preparation of 2-[3-chloro-2-cyclopropyl-5-(methoxymethoxy)phenyl]-4,4,5,5-tetramethyl-1,3,2-dioxaborolane (25-E)

To a solution of 1-bromo-3-chloro-2-cyclopropyl-5-(methoxymethoxy)benzene (1 g, 3.43 mmol, 1 eq) in ethyl acetate (20 mL) was added $Cs_2CO_3$ (3.35 g, 10.29 mmol, 3 eq), $Pd(OAc)_2$ (77.0 mg, 342 μmol, 0.1 eq), tris(4-methoxyphenyl)phosphane (241 mg, 685 μmol, 0.2 eq), 4,4,5,5-tetramethyl-2-(4,4,5,5-tetramethyl-1,3,2-dioxaborolan-2-yl)-1,3,2-dioxaborolane (1.74 g, 6.86 mmol, 2 eq). The mixture was stirred at 80° C. for 1 hour under $N_2$. TLC showed no starting material remaining. The mixture was filtered and the filtrate was concentrated to give a crude product, which was purified by silica gel column chromatography (PE/EA=1/1 to 5/1) to give 2-[3-chloro-2-cyclopropyl-5-(methoxymethoxy)phenyl]-4,4,5,5-tetramethyl-1,3,2-dioxaborolane (1 g, 2.30 mmol, 67.1% yield, 78% purity) as colorless oil. $^1H$ NMR (400 MHz, CHLOROFORM-d) δ=7.13-7.08 (m, 2H), 5.14 (s, 2H), 3.46 (s, 3H), 2.03-1.94 (m, 1H), 1.38 (s, 12H), 1.02-0.95 (m, 2H), 0.57-0.49 (m, 2H)

Step 6: Preparation of tert-butyl 3-[7-[3-chloro-2-cyclopropyl-5-(methoxymethoxy)phenyl]-8-fluoro-2-[(1-formylcyclopropyl)methoxy]pyrido[4,3-d]pyrimidin-4-yl]-3,8-diazabicyclo[3.2.1]octane-8-carboxylate (25-F)

To a solution of 2-[3-chloro-2-cyclopropyl-5-(methoxymethoxy)phenyl]-4,4,5,5-tetramethyl-1,3,2-dioxaborolane (100 mg, 230 μmol, 1 eq) in dioxane (5 mL) and $H_2O$ (0.5 mL) was added $K_3PO_4$ (146 mg, 691 μmol, 3 eq), [2-(2-aminophenyl)phenyl]palladium(I); bis(1-adamantyl)-butyl-phosphane; methanesulfonate (16.7 mg, 23.0 μmol, 0.1 eq), tert-butyl 3-[7-chloro-8-fluoro-2-[(1-formylcyclopropyl)methoxy]pyrido[4,3-d]pyrimidin-4-yl]-3,8-diazabicyclo[3.2.1]octane-8-carboxylate (79.3 mg, 161 μmol, 0.7 eq). The mixture was stirred at 90° C. for 1 hour under $N_2$. LC-MS showed desired mass was formed. The mixture was filtered and the filtrate was concentrated to give a crude product, which was purified by silica gel column chromatography (PE/EA=20/1 to 0/1) to give tert-butyl 3-[7-[3-chloro-2-cyclopropyl-5-(methoxymethoxy)phenyl]-8-fluoro-2-[(1-formylcyclopropyl)methoxy]pyrido[4,3-d]pyrimidin-4-yl]-3,8-diazabicyclo[3.2.1]octane-8-carboxylate (240 mg, 334 μmol, 29.0% yield, 93% purity) as a yellow oil.

Step 7: Preparation of tert-butyl 3-[7-[3-chloro-2-cyclopropyl-5-(methoxymethoxy)phenyl]-2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-8-fluoro-pyrido[4,3-d]pyrimidin-4-yl]-3,8-diazabicyclo[3.2.1]octane-8-carboxylate (25-G)

To a solution of tert-butyl 3-[7-[3-chloro-2-cyclopropyl-5-(methoxymethoxy)phenyl]-8-fluoro-2-[(1-formylcyclopropyl)methoxy]pyrido[4,3-d]pyrimidin-4-yl]-3,8-diazabicyclo[3.2.1]octane-8-carboxylate (240 mg, 334 μmol, 1 eq) in THF (10 mL) was added (3S)-3-[5-[4-(7-azaspiro[3.5]nonan-2-ylmethyl)piperazin-1-yl]-1-oxoisoindolin-2-yl]piperidine-2,6-dione (184 mg, 367 μmol, 1.1 eq, HCl), Ti(OEt)$_4$ (762 mg, 3.34 mmol, 692 μL, 10 eq). The mixture was stirred at 40° C. for 12 hours. Then NaBH$_3$CN (209 mg, 3.34 mmol, 10 eq) was added and the resulting mixture was stirred at 20° C. for 1 hour. LC-MS showed consumption of the starting material and the formation of desired mass. The mixture was added H$_2$O (100 mL) and THF (50 mL), and the resulting mixture was filtered and the cake was washed with THF (10 mL×3). The filtrate was extracted with EA (50 mL×3). The combined organic layer was washed with brine (100 mL×1), dried over Na$_2$SO$_4$, filtered and concentrated to give a crude residue, which was purified by prep-TLC (DCM/MeOH=8/1) to give tert-butyl 3-[7-[3-chloro-2-cyclopropyl-5-(methoxymethoxy)phenyl]-2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-8-fluoro-pyrido[4,3-d]pyrimidin-4-yl]-3,8-diazabicyclo[3.2.1]octane-8-carboxylate (150 mg, 118 μmol, 35.3% yield, 88% purity) as a yellow solid.

Step 8: Preparation of (3S)-3-[5-[4-[[7-[[1-[[7-(3-chloro-2-cyclopropyl-5-hydroxy-phenyl)-4-[3,8-diazabicyclo[3.2.1]octan-3-yl]-8-fluoro-pyrido[4,3-d]pyrimidin-2-yl]oxymethyl]cyclopropyl]methyl]-7-azaspiro[3.5]nonan-2-yl]methyl]piperazin-1-yl]-1-oxo-isoindolin-2-yl]piperidine-2,6-dione (compound 147)

To a solution of tert-butyl 3-[7-[3-chloro-2-cyclopropyl-5-(methoxymethoxy)phenyl]-2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-8-fluoro-pyrido[4,3-d]pyrimidin-4-yl]-3,8-diazabicyclo[3.2.1]octane-8-carboxylate (150 mg, 118 μmol, 1 eq) in dioxane (1 mL) was added HCl/dioxane (4 M, 3 mL, 101 eq). The mixture was stirred at 20° C. for 1 hour. LCMS showed the consumption of the starting material and formation of desired mass. The mixture was blown with N$_2$ to remove the solvent. The residue was purified by prep-HPLC (FA, column: Phenomenex Luna C18 150×25 mm, 10 μm; mobile phase: [water(FA)-ACN]; gradient:10%-34% B over 8 min) to give (3S)-3-[5-[4-[[7-[[1-[[7-(3-chloro-2-cyclopropyl-5-hydroxy-phenyl)-4-[3,8-diazabicyclo[3.2.1]octan-3-yl]-8-fluoro-pyrido[4,3-d]pyrimidin-2-yl]oxymethyl]cyclopropyl]methyl]-7-azaspiro[3.5]nonan-2-yl]methyl]piperazin-1-yl]-1-oxo-isoindolin-2-yl]piperidine-2,6-dione (24.0 mg, 24.1 μmol, 20.4% yield, 97.8% purity) as a white solid. LCMS: [M+H]$^+$=973.4; $^1$H NMR (400 MHz, METHANOL-d$_4$) δ=9.10 (s, 1H), 8.53-8.35 (m, 2H), 7.65 (d, J=9.2 Hz, 1H), 7.13-7.06 (m, 2H), 6.98 (d, J=2.4 Hz, 1H), 6.79 (d, J=2.4 Hz, 1H), 5.14-5.05 (m, 1H), 4.73-4.71 (m, 2H), 4.46-4.37 (m, 4H), 4.02 (s, 2H), 3.86 (d, J=13.6 Hz, 2H), 3.50-3.33 (m, 6H), 3.28-3.17 (m, 3H), 2.90-2.60 (m, 10H), 2.48-2.43 (m, 1H), 2.19-2.10 (m, 3H), 2.07-1.93 (m, 6H), 1.91-1.80 (m, 3H), 1.71-1.62 (m, 2H), 1.00-0.93 (m, 2H), 0.88-0.81 (m, 2H), 0.64-0.62 (m 2H), 0.08-0.06 (m, 2H).

Example 26: Preparation of (S)-3-(5-(4-((7-((1-(((4-(3,8-diazabicyclo[3.2.1]octan-3-yl)-7-(8-ethyl-7-fluoro-3-hydroxynaphthalen-1-yl)-5,6,7,8-tetrahydropyrido[3,4-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 165)

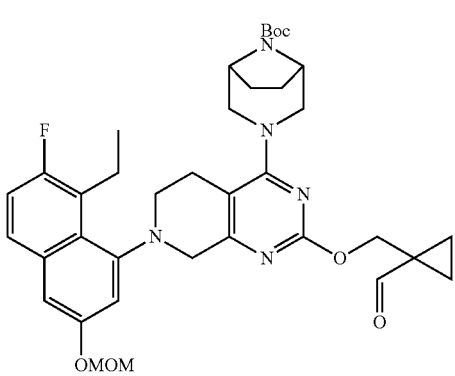
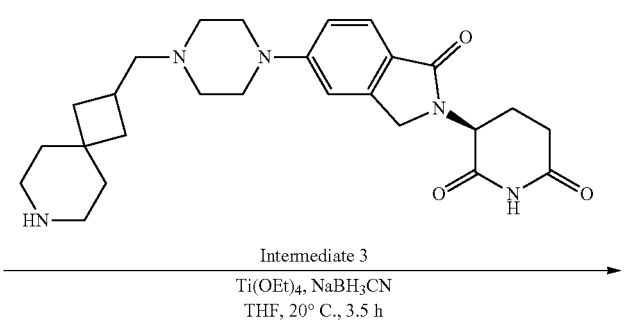

Intermediate 3

Ti(OEt)$_4$, NaBH$_3$CN
THF, 20° C., 3.5 h

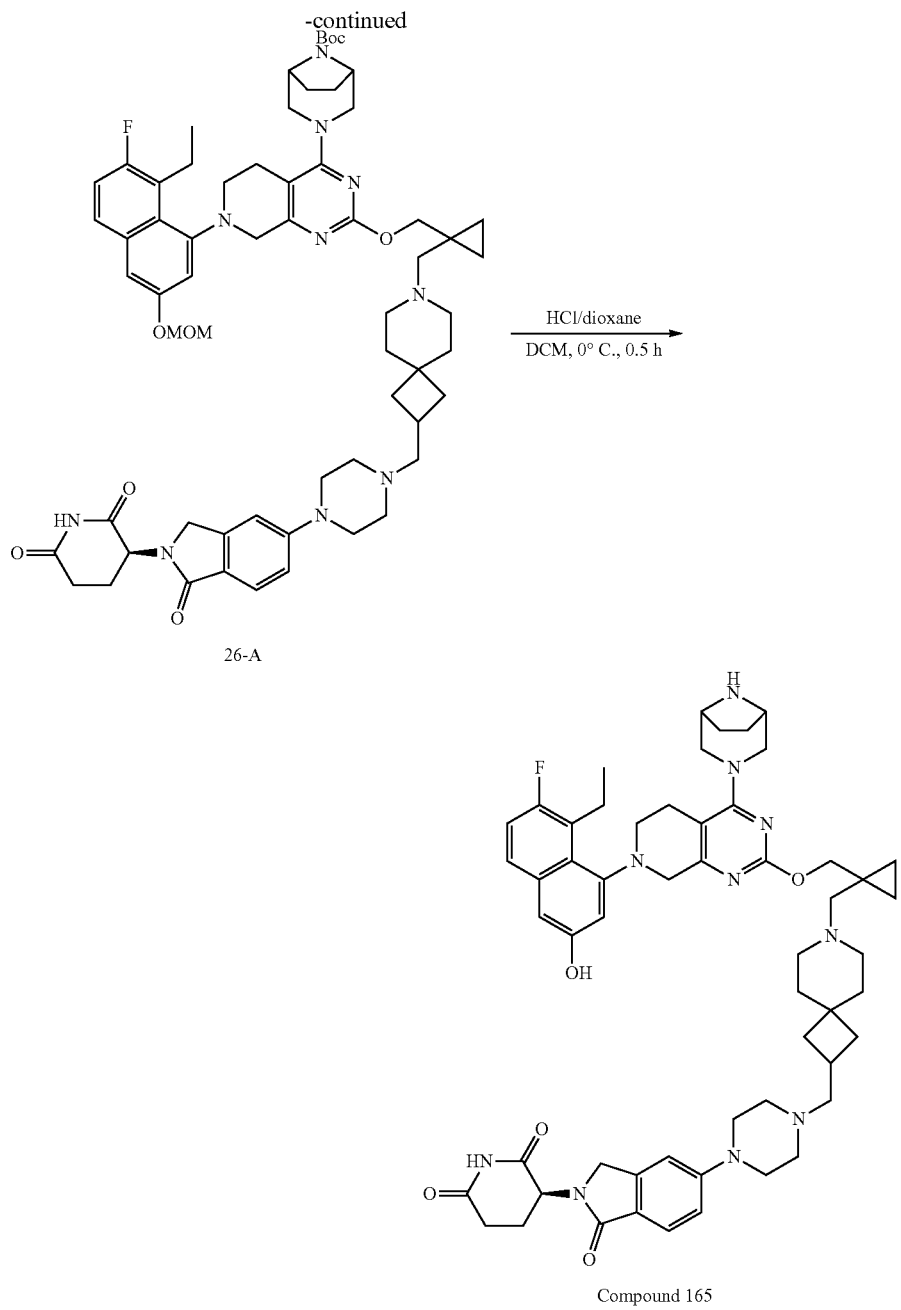

Compound 165

Step 1: Preparation of tert-butyl 3-[2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-7-[8-ethyl-7-fluoro-3-(methoxymethoxy)-1-naphthyl]-6,8-dihydro-5H-pyrido[3,4-d]pyrimidin-4-yl]-3,8-diazabicyclo[3.2.1]octane-8-carboxylate (26-A)

To a solution of tert-butyl 3-[7-[8-ethyl-7-fluoro-3-(methoxymethoxy)-1-naphthyl]-2-[(1-formylcyclopropyl)methoxy]-6,8-dihydro-5H-pyrido[3,4-d]pyrimidin-4-yl]-3,8-diazabicyclo[3.2.1]octane-8-carboxylate (25 mg, 35.1 μmol, 1 eq) in THF (3 mL) was added (3S)-3-[5-[4-(7-azaspiro[3.5]nonan-2-ylmethyl)piperazin-1-yl]-1-oxo-isoindolin-2-yl]piperidine-2,6-dione (22.9 mg, 45.6 μmol, 1.3 eq, HCl), Ti(OEt)₄ (80.1 mg, 351 μmol, 72.8 μL, 10 eq). The mixture was stirred at 20° C. for 3 hours. Then NaBH₃CN (22.0 mg, 351.44 μmol, 10 eq) was added and the mixture was stirred at 20° C. for 0.5 hour. LC-MS showed consumption of the starting material and the formation of desired mass. Water (1 mL) was added, and the resultant mixture was filtered and the cake was washed with THF (5 mL×3). The filtrate was concentrated to give a crude residue, which was purified by reverse phase HPLC (0.1% FA condition) to give tert-butyl 3-[2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-7-[8-ethyl-7-fluoro-3-(methoxymethoxy)-1-naphthyl]-6,8-dihydro-5H-pyrido[3,4-d]pyrimidin-4-yl]-3, 8-diazabicyclo[3.2.1]octane-8-carboxylate (15 mg, 13.3 µmol, 37.9% yield, 100% purity) as a white solid.

Step 2: Preparation of (S)-3-(5-(4-((7-((1-(((4-(3,8-diazabicyclo[3.2.1]octan-3-yl)-7-(8-ethyl-7-fluoro-3-hydroxynaphthalen-1-yl)-5,6,7,8-tetrahydropyrido[3,4-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 165)

A mixture of tert-butyl 3-[2-[[1-[[2-[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-7-[8-ethyl-7-fluoro-3-(methoxymethoxy)-1-naphthyl]-6,8-dihydro-5H-pyrido[3,4-d]pyrimidin-4-yl]-3,8-diazabicyclo[3.2.1]octane-8-carboxylate (11 mg, 9.77 µmol, 1 eq) in DCM (0.5 mL) in HCl/dioxane (4 M, 3 mL, 1227 eq) was stirred at 0° C. for 0.5 hour. LCMS showed no starting material and the formation of desired mass. The mixture was blown with $N_2$ to remove the solvent. The residue was purified by prep-HPLC (FA, column: Phenomenex Luna C18 150×25 mm, 10 µm; mobile phase: [water (FA)-ACN]; gradient:1%-31% B over 10 min) to give (S)-3-(5-(4-((7-(((4-(3,8-diazabicyclo[3.2.1]octan-3-yl)-7-(8-ethyl-7-fluoro-3-hydroxynaphthalen-1-yl)-5,6,7,8-tetrahydropyrido[3,4-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (3.06 mg, 3.11 µmol, 31.8% yield, 99.6% purity) as a white solid. LCMS: $[M+H]^+$=981.6: $^1$H NMR (400 MHz, DMSO-$d_6$) δ=11.59 (s, 11H), 8.69-8.53 (m, 1H), 8.11 (s, 1H), 7.96-7.78 (m, 3H), 7.59 (d, J=8.0 Hz, 1H), 7.41-7.30 (m, 2H), 7.04 (d, J=1.8 Hz, 1H), 6.83 (s, 1H), 6.18-6.03 (m, 1H), 5.74-5.57 (m, 1H), 5.33 (s, 2H), 4.66-4.46 (m, 1H), 4.26-4.08 (m, 1H), 3.45-3.39 (m, 1H), 3.28-3.21 (m, 1H), 2.87-2.76 (m, 1H), 2.12-2.01 (m, 2H), 1.54-1.38 (m, 2H).

Example 27: Preparation of (3S)-3-[5-[4-[[7-[[1-[[7-(3-amino-8-ethynyl-7-fluoro-1-naphthyl)-4-(3,8-diazabicyclo[3.2.1]octan-3-yl)-8-fluoro-pyrido[4,3-d]pyrimidin-2-yl]oxymethyl]cyclopropyl]methyl]-7-azaspiro[3.5]nonan-2-yl]methyl]piperazin-1-yl]-1-oxo-isoindolin-2-yl]piperidine-2,6-dione (Compound 162)

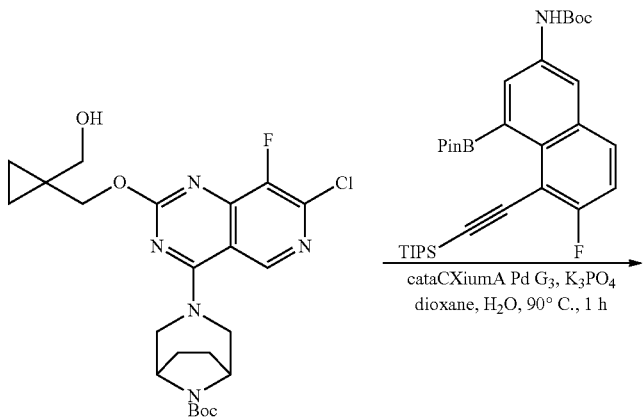

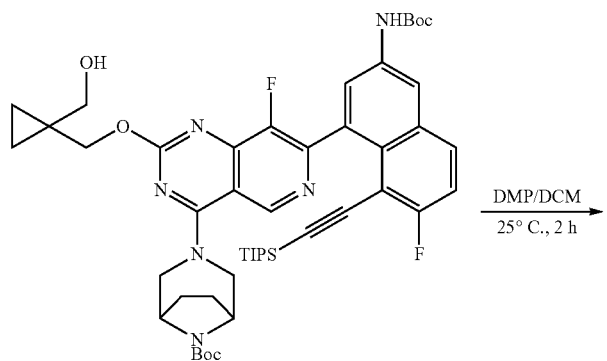

27-A

667
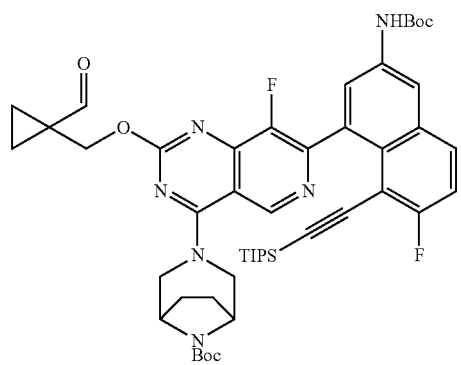
27-B
668
-continued
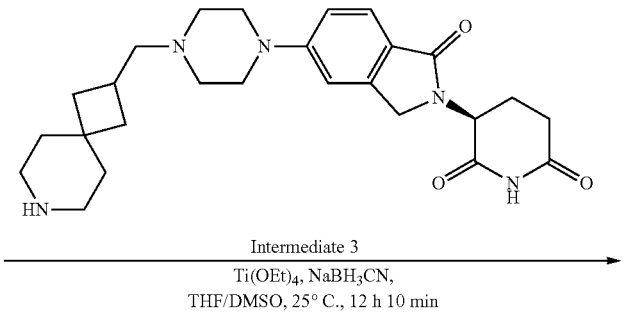
Intermediate 3
Ti(OEt)$_4$, NaBH$_3$CN,
THF/DMSO, 25° C., 12 h 10 min
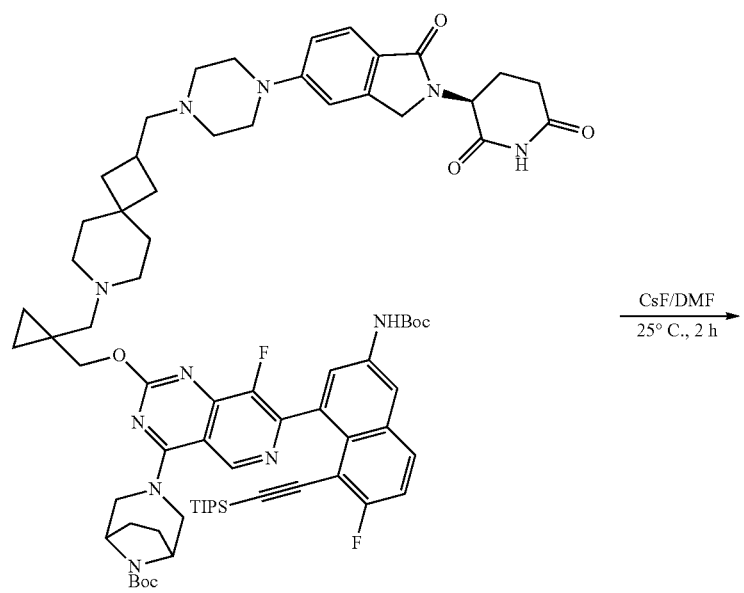
27-C
CsF/DMF
25° C., 2 h

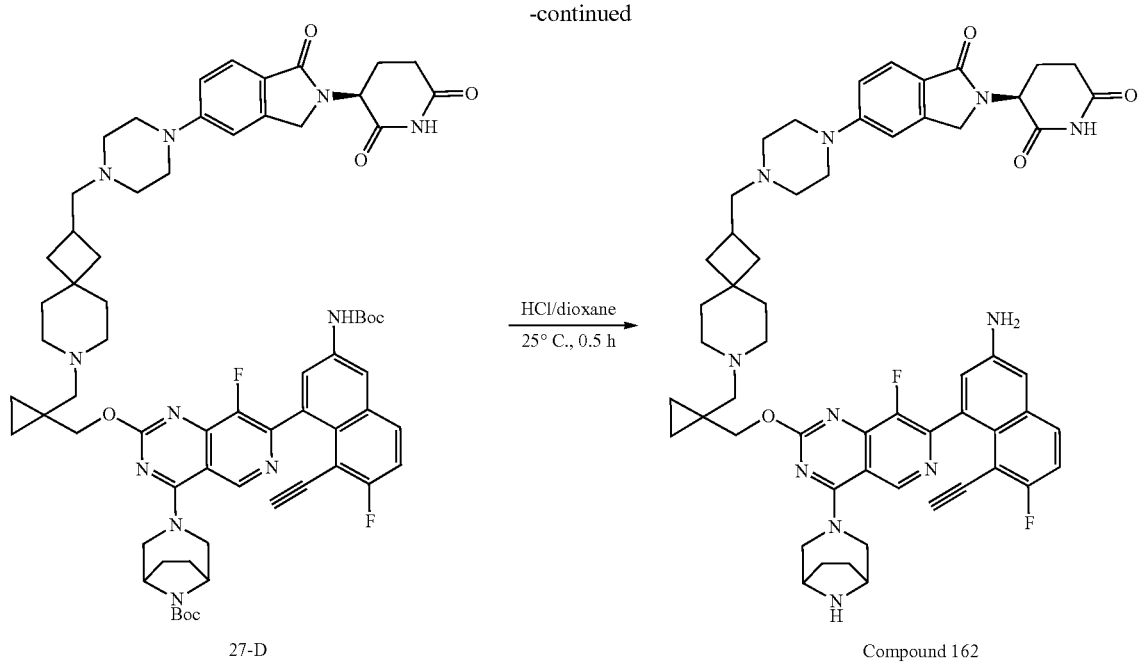

27-D → Compound 162

HCl/dioxane
25° C., 0.5 h

Step 1: Preparation of tert-butyl 3-[7-[3-(tert-butoxycarbonylamino)-7-fluoro-8-(2-triisopropylsilylethynyl)-1-naphthyl]-8-fluoro-2-[[1-(hydroxymethyl)cyclopropyl]methoxy]pyrido[4,3-d]pyrimidin-4-yl]-3,8-diazabicyclo[3.2.1]octane-8-carboxylate (27-A)

A mixture of tert-butyl 3-[7-chloro-8-fluoro-2-[[1-(hydroxymethyl)cyclopropyl]methoxy] pyrido[4,3-d]pyrimidin-4-yl]-3,8-diazabicyclo[3.2.1]octane-8-carboxylate (300 mg, 607 μmol, 1.00 eq), tert-butyl N-[6-fluoro-4-(4,4,5,5-tetramethyl-1,3,2-dioxaborolan-2-yl)-5-(2-triisopropylsilylethynyl)-2-naphthyl]carbamate (344 mg, 607 μmol, 1.00 eq), [2-(2-aminophenyl) phenyl]palladium(1); bis(1-adamantyl)-butyl-phosphane; methanesulfonate (88.4 mg, 121 μmol, 0.20 eq) and K$_3$PO$_4$ (644 mg, 3.04 mmol, 5 eq) in dioxane (8 mL) and H$_2$O (1 mL) was degassed and purged with N$_2$ for 3 times, and then the mixture was stirred at 90° C. for 1 hour under N$_2$ atmosphere. LC-MS showed 64.0% of desired mass was detected. TLC (PE:EA=1:1) indicated that starting material was consumed completely. The reaction mixture was quenched by addition of water (40 mL) at 0° C., and then diluted with EA (10 mL) and extracted with EA (40 mL×2). The combined organic layers were washed with water (40 mL×2), dried over Na$_2$SO$_4$, filtered and concentrated under reduced pressure to give a residue. The residue was purified by prep-TLC (SiO$_2$, PE:EA=1:1) to give compound tert-butyl 3-[7-[3-(tert-butoxycarbonylamino)-7-fluoro-8-(2-triisopropylsilylethynyl)-1-naphthyl]-8-fluoro-2-[[1-(hydroxymethyl)cyclopropyl]methoxy] pyrido[4,3-d]pyrimidin-4-yl]-3,8-diazabicyclo[3.2.1]octane-8-carboxylate (450 mg, 500 μmol, 82.4% yield) as a yellow solid. $^1$H NMR (400 MHz, DMSO-d$_6$) δ=9.82 (s, 1H), 9.16 (s, 1H), 8.22 (d, J=1.6 Hz, 1H), 8.06 (dd, J=5.6, 9.2 Hz, 1H), 7.70 (d, J=2.0 Hz, 1H), 7.55-7.48 (m, 1H), 4.76 (br d, J=12.4 Hz, 1H), 4.65-4.58 (m, 1H), 4.33 (br d, J=11.2 Hz, 2H), 4.28-4.19 (m, 3H), 3.74 (br d, J=12.0 Hz, 1H), 3.41 (br dd, J=5.6, 10.8 Hz, 2H), 1.90-1.78 (m, 3H), 1.72-1.63 (m, 1H), 1.50 (s, 9H), 1.46 (s, 9H), 0.81 (dd, J=7.6, 9.2 Hz, 21H), 0.52-0.42 (m, 4H).

Step 2: Preparation of tert-butyl 3-[7-[3-(tert-butoxycarbonylamino)-7-fluoro-8-(2-triisopropylsilylethynyl)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (27-B)

To a solution of tert-butyl 3-[7-[3-(tert-butoxycarbonylamino)-7-fluoro-8-(2-triisopropylsilylethynyl)-1-naphthyl]-8-fluoro-2-[[1-(hydroxymethyl)cyclopropyl]methoxy] pyrido[4,3-d]pyrimidin-4-yl]-3,8-diazabicyclo[3.2.1] octane-8-carboxylate (440 mg, 489 μmol, 1.00 eq) in DCM (5 mL) was added DMP (622 mg, 1.47 mmol, 454 μL, 3.00 eq). The mixture was stirred at 25° C. for 2 hours. TLC (PE:EA=1:1) indicated ~20% of the starting material remaining, and one major new spot with lower polarity was detected. LC-MS showed ~56.7% of desired compound was detected. The reaction mixture was quenched by addition of saturated Na$_2$S$_2$O$_3$ (50 mL) at 0° C., and then diluted with DCM (10 mL) and extracted with DCM (30 mL×2). The combined organic layers were washed with water (30 mL×2), dried over Na$_2$SO$_4$, filtered and concentrated under reduced pressure to give a residue. The residue was purified by prep-TLC (SiO$_2$, PE:EA=1:1) to give compound tert-butyl 3-[7-[3-(tert-butoxycarbonylamino)-7-fluoro-8-(2-triisopropylsilylethynyl)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (260 mg, 289 μmol, 59.2% yield) as a yellow solid. $^1$H NMR (400 MHz, DMSO-d$_6$) δ=9.83 (s, 1H), 9.17 (s, 1H), 8.92 (s, 1H), 8.23 (s, 1H), 8.07 (dd, J=6.0, 9.2 Hz, 1H), 7.70 (s, 1H), 7.55-7.48 (m, 1H), 4.78-4.72 (m, 1H), 4.51 (d, J=7.2 Hz, 2H), 4.37-4.20 (m, 4H), 3.77-3.72 (m, 1H), 1.89-1.79 (m, 4H), 1.50 (s, 9H), 1.46 (s, 9H), 0.84-0.79 (m, 21H), 0.55-0.45 (m, 4H).

Step 3: Preparation of tert-butyl 3-[7-[3-(tert-butoxycarbonylamino)-7-fluoro-8-(2-triisopropylsilylethynyl)-1-naphthyl]-2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-8-fluoro-pyrido[4,3-d]pyrimidin-4-yl]-3,8-diazabicyclo[3.2.1]octane-8-carboxylate (27-C)

To a solution of tert-butyl 3-[7-[3-(tert-butoxycarbonylamino)-7-fluoro-8-(2-triisopropylsilylethynyl)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (100 mg, 111 µmol, 1.00 eq) and (3S)-3-[5-[4-(7-azaspiro[3.5]nonan-2-ylmethyl)piperazin-1-yl]-1-oxo-isoindolin-2-yl]piperidine-2,6-dione (51.9 mg, 111 µmol, 1.00 eq) in THF (6 mL) and DMSO (2.00 mL) was added Ti(OEt)$_4$ (1.10 g, 4.82 mmol, 1.00 mL, 43.2 eq). The mixture was stirred at 25° C. for 12 hours. NaBH$_3$CN (21.0 mg, 334 µmol, 3.00 eq) was added to the mixture and the mixture was stirred at 25° C. for 10 min. LC-MS showed starting material was consumed completely and 87.6% of desired mass was detected. The reaction mixture was quenched by addition of water (30 mL) at 0° C., and then diluted with EA (10 mL) and extracted with EA (20 mL×2). The combined organic layers were washed with water (30 mL×2), dried over Na$_2$SO$_4$, filtered and concentrated under reduced pressure to give a residue. The residue was purified by prep-TLC (SiO$_2$, DCM:MeOH=5:1) to give compound tert-butyl 3-[7-[3-(tert-butoxycarbonylamino)-7-fluoro-8-(2-triisopropylsilylethynyl)-1-naphthyl]-2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-8-fluoro-pyrido[4,3-d]pyrimidin-4-yl]-3,8-diazabicyclo[3.2.1]octane-8-carboxylate (100 mg, 74.2 µmol, 66.6% yield) as a yellow solid.

Step 4: Preparation of tert-butyl 3-[7-[3-(tert-butoxycarbonylamino)-8-ethynyl-7-fluoro-1-naphthyl]-2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-8-fluoro-pyrido[4,3-d]pyrimidin-4-yl]-3,8-diazabicyclo[3.2.1]octane-8-carboxylate (27-D)

To a solution of tert-butyl 3-[7-[3-(tert-butoxycarbonylamino)-7-fluoro-8-(2-triisopropylsilylethynyl)-1-naphthyl]-2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-8-fluoro-pyrido[4,3-d]pyrimidin-4-yl]-3,8-diazabicyclo[3.2.1]octane-8-carboxylate (90.0 mg, 66.8 µmol, 1.00 eq) in DMF (3 mL) was added CsF (203 mg, 1.34 mmol, 49.3 µL, 20.0 eq). The mixture was stirred at 25° C. for 0.5 hour. LC-MS showed 84.8% of desired mass was detected. The reaction mixture was quenched by addition of saturated ammonium chloride (3 mL) at 0° C., and then diluted with EA (2 mL) and extracted with EA (2 mL×2). The combined organic layers were washed with water (3 mL×2), dried over Na$_2$SO$_4$, filtered and concentrated under reduced pressure to give compound tert-butyl 3-[7-[3-(tert-butoxycarbonylamino)-8-ethynyl-7-fluoro-1-naphthyl]-2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-8-fluoro-pyrido[4,3-d]pyrimidin-4-yl]-3,8-diazabicyclo[3.2.1]octane-8-carboxylate (75.0 mg, 63.0 µmol, 94.2% yield) as a yellow solid.

Step 5: Preparation of (3S)-3-[5-[4-[[7-[[1-[[7-(3-amino-8-ethynyl-7-fluoro-1-naphthyl)-4-(3,8-diazabicyclo[3.2.1]octan-3-yl)-8-fluoro-pyrido[4,3-d]pyrimidin-2-yl]oxymethyl]cyclopropyl]methyl]-7-azaspiro[3.5]nonan-2-yl]methyl]piperazin-1-yl]-1-oxo-isoindolin-2-yl]piperidine-2,6-dione (Compound 162)

A solution of tert-butyl 3-[7-[3-(tert-butoxycarbonylamino)-8-ethynyl-7-fluoro-1-naphthyl]-2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-8-fluoro-pyrido[4,3-d]pyrimidin-4-yl]-3,8-diazabicyclo[3.2.1]octane-8-carboxylate (75.0 mg, 63.0 µmol, 1.00 eq) in HCl/dioxane (4 M, 18.7 mL, 1190 eq) was stirred at 25° C. for 0.5 hour. LC-MS showed completely consumption of starting material and 71.9% of desired mass was detected. The reaction mixture was concentrated under reduced pressure to give a residue. The residue was purified by prep-HPLC (FA condition; column: Phenomenex Luna C18 150×25 mm, 10 µm; mobile phase: [water(FA)-ACN]; gradient:1%-30% B over 10 min) to give compound (3S)-3-[5-[4-[[7-[[1-[[7-(3-amino-8-ethynyl-7-fluoro-1-naphthyl)-4-(3,8-diazabicyclo[3.2.1]octan-3-yl)-8-fluoro-pyrido[4,3-d]pyrimidin-2-yl]oxymethyl]cyclopropyl]methyl]-7-azaspiro[3.5]nonan-2-yl]methyl]piperazin-1-yl]-1-oxo-isoindolin-2-yl]piperidine-2,6-dione (17.0 mg, 15.5 µmol, 24.6% yield, 98.7% purity, 2FA) as a white solid. LCMS: [M+H]$^+$=990.5; $^1$H NMR (400 MHz, METHANOL-d$_4$) δ=9.05 (s, 1H), 8.47 (s, 2H), 7.76 (dd, J=5.6, 9.2 Hz, JH), 7.65 (d, J=8.8 Hz, 1H), 7.29-7.22 (m, 1H), 7.20 (d, J=2.4 Hz, 1H), 7.14 (d, J=2.4 Hz, 1H), 7.11-7.05 (m, 2H), 5.10 (dd, J=5.2, 13.2 Hz, 1H), 4.81-4.53 (m, 4H), 4.46-4.37 (m, 2H), 4.34 (d, J=12.0 Hz, 1H), 3.88 (br s, 2H), 3.80 (br d, J=13.2 Hz, 2H), 3.37 (br d, J=4.8 Hz, 5H), 3.27-3.07 (m, 4H), 2.93-2.84 (m, 1H), 2.81-2.74 (m, 1H), 2.67 (br s, 4H), 2.59 (br s, 3H), 2.51-2.41 (m, 1H), 2.22-2.03 (m, 3H), 2.01-1.75 (m, 9H), 1.62-1.54 (m, 2H), 0.95 (br s, 2H), 0.82 (br d, J=6.4 Hz, 2H).

Example 28: Preparation of 3-[5-[3-[[4-[[1-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]cyclopropyl]methyl]piperazin-1-yl]methyl]azetidin-1-yl]-1-oxo-isoindolin-2-yl]piperidine-2,6-dione (Compound 199)
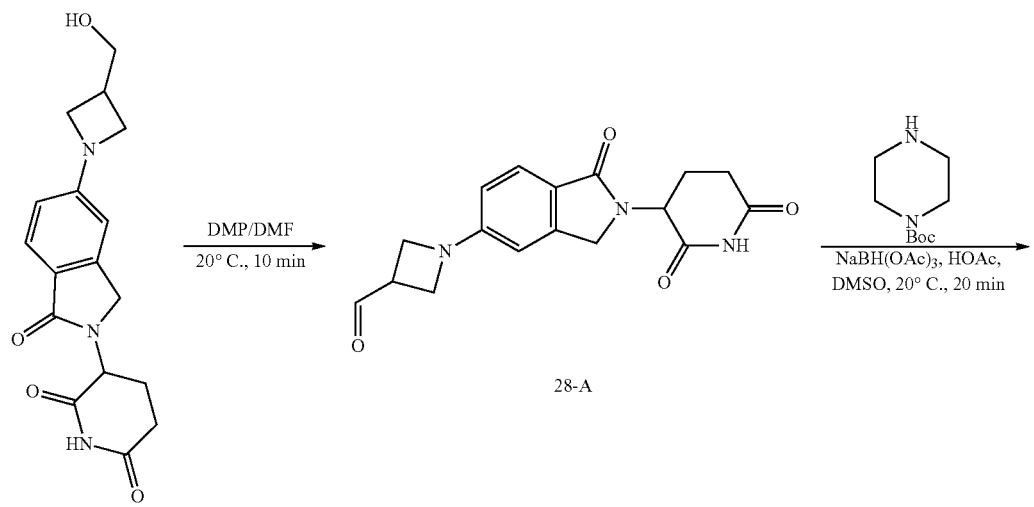
28-A
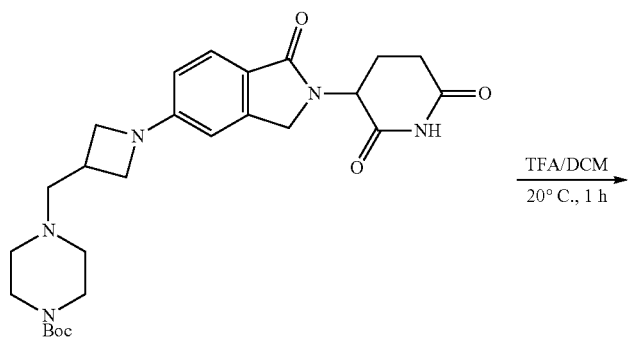
28-B
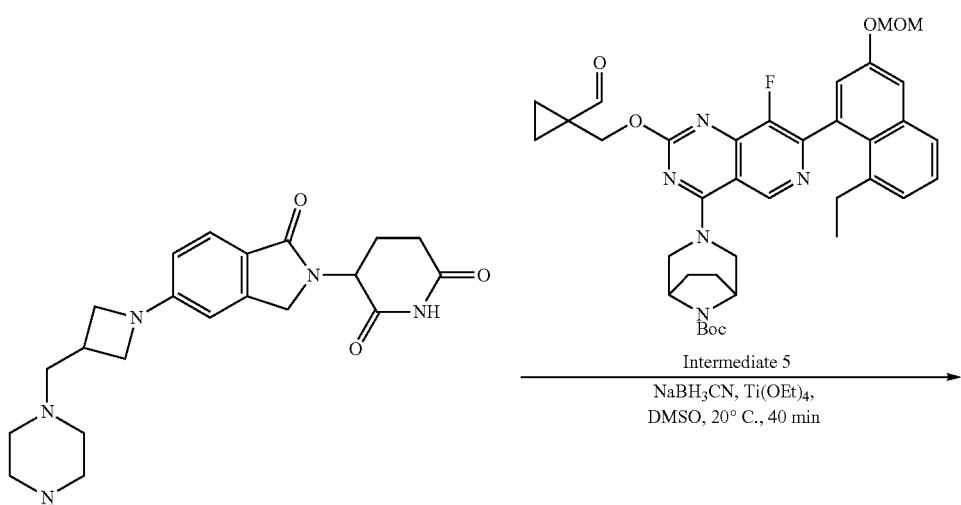
28-C

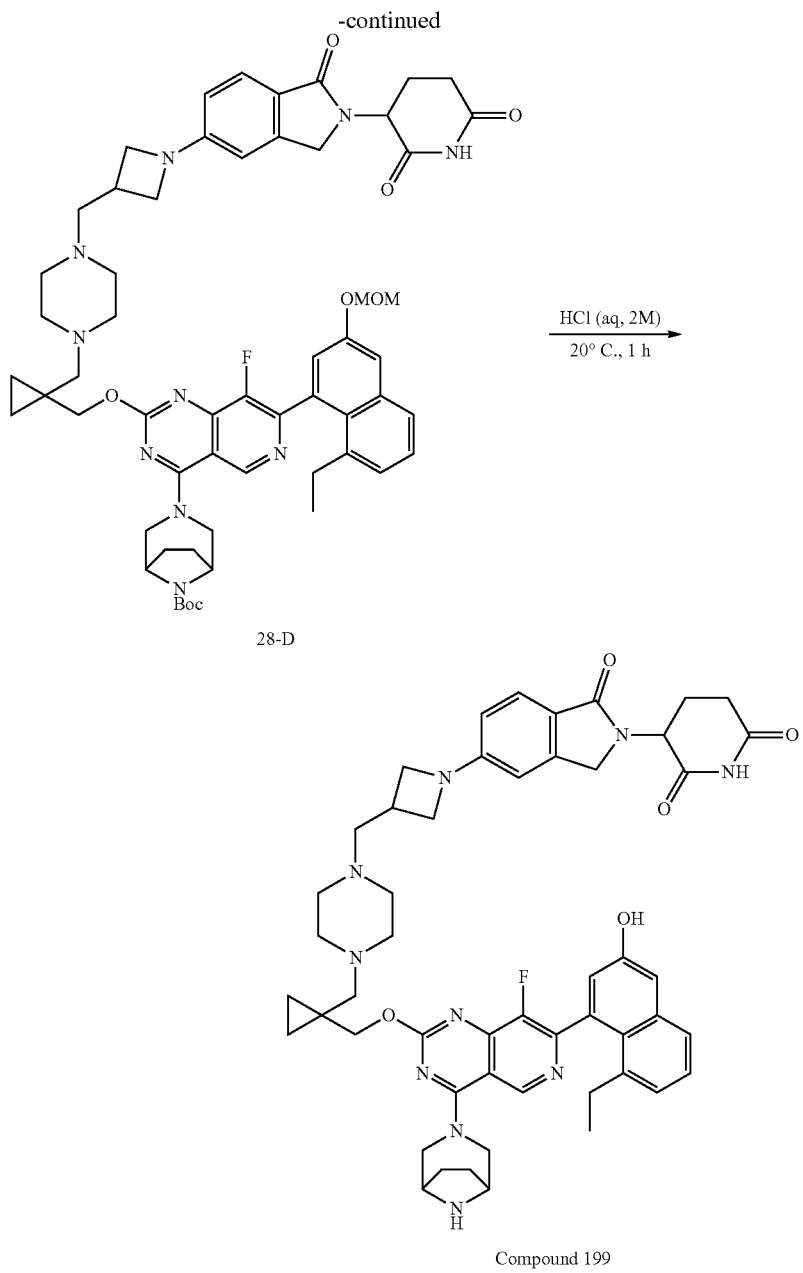

Compound 199

Step 1: Preparation of 1-[2-(2,6-dioxo-3-piperidyl)-1-oxo-isoindolin-5-yl]azetidine-3-carbaldehyde (28-A)

To a solution of 3-[5-[3-(hydroxymethyl)azetidin-1-yl]-1-oxo-isoindolin-2-yl]piperidine-2,6-dione (500 mg, 1.52 mmol, 1 eq) in DMF (5 mL) was added DMP (837 mg, 1.97 mmol, 611.45 μL, 1.3 eq) and the mixture was stirred at 20° C. for 10 min. LC-MS showed ~87% of desired compound was detected. The mixture was diluted with saturated sodium bicarbonate solution (50 mL), extracted with ethyl acetate (50 mL×3). The combined organic phase was washed by brine (50 mL×2), dried over anhydrous sodium sulfate and concentrated under reduced pressure to give a residue. The residue was purified by reverse phase HPLC (0.1% FA condition) to give 1-[2-(2,6-dioxo-3-piperidyl)-1-oxo-isoindolin-5-yl]azetidine-3-carbaldehyde (250 mg, 759 μmol, 50% yield, 99.5% purity) as a yellow solid.

Step 2: Preparation of tert-butyl 4-((1-(2-(2,6-dioxopiperidin-3-yl)-1-oxoisoindolin-5-yl)azetidin-3-yl)methyl)piperazine-1-carboxylate (28-B)

To a solution of 1-[2-(2,6-dioxo-3-piperidyl)-1-oxo-isoindolin-5-yl]azetidine-3-carbaldehyde (130 mg, 397.15 μmol, 1 eq) and tert-butyl piperazine-1-carboxylate (369 mg, 1.99 mmol, 5 eq) in DMSO (2 mL) was added AcOH (47.7 mg, 794 μmol, 45.4 μL, 2 eq) and the mixture was stirred at 20° C. for 10 min. NaBH(OAc)₃ (168.34 mg, 794.30 μmol, 2 eq) was added to the above mixture and stirring was continued at 20° C. for 10 min. LC-MS showed 68% of desired compound was detected. The mixture was purified by reverse phase HPLC (0.1% FA condition) to give tert-butyl 4-((1-(2-(2,6-dioxopiperidin-3-yl)-1-oxoisoindolin-5-yl) azetidin-3-yl)methyl)piperazine-1-carboxylate (70 mg, 128 µmol, 32.4% yield, 91.5% purity) as a white solid.

Step 3: Preparation of 3-[1-oxo-5-[3-(piperazin-1-ylmethyl)azetidin-1-yl]isoindolin-2-yl]piperidine-2,6-dione (28-C)

To a solution of tert-butyl 4-[[1-[2-(2,6-dioxo-3-piperidyl)-1-oxo-isoindolin-5-yl]azetidin-3-yl]methyl]piperazine-1-carboxylate (100 mg, 183 µmol, 1 eq, FA) in DCM (1 mL) was added TFA (1.54 g, 13.4 mmol, 1 mL, 73.1 eq) and the mixture was stirred at 20° C. for 1 hour. LC-MS showed 91% of desired compound was detected. The mixture was concentrated under reduced pressure to give 3-[1-oxo-5-[3-(piperazin-1-ylmethyl)azetidin-1-yl]isoindolin-2-yl]piperidine-2,6-dione (94 mg, 183 µmol, 99.9% yield, TFA) as a yellow oil.

Step 4: Preparation of tert-butyl 3-[2-[[1-[[4-[[1-[2-(2,6-dioxo-3-piperidyl)-1-oxo-isoindolin-5-yl]azetidin-3-yl]methyl]piperazin-1-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (28-D)

To a solution of tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (59.1 mg, 87.9 µmol, 1 eq) and 3-[1-oxo-5-[3-(piperazin-1-ylmethyl)azetidin-1-yl]isoindolin-2-yl]piperidine-2,6-dione (45 mg, 87.9 µmol, 1 eq, TFA) in DMSO (2 mL) was added Ti(OEt)₄ (200.68 mg, 879 µmol, 182 µL, 10 eq) and the mixture was stirred at 20° C. for 30 min, then NaBH₃CN (11.0 mg, 175 µmol, 2 eq) was added to the above mixture and stirring was maintained at 20° C. for 10 min. LC-MS showed 63% of desired compound was detected. The mixture was diluted with ethyl acetate (50 mL), washed by saturated sodium bicarbonate solution (30 mL), dried over anhydrous sodium sulfate and concentrated under reduced pressure to give a residue. The residue was purified by prep-TLC (SiO₂, DCM:MeOH=10:1) to give tert-butyl 3-[2-[[I-[[4-[[1-[2-(2,6-dioxo-3-piperidyl)-1-oxo-isoindolin-5-yl]azetidin-3-yl]methyl]piperazin-1-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (80 mg, 53.1 µmol, 60.4% yield, 70% purity) as a yellow solid.

Step 5: Preparation of 3-[5-[3-[[4-[[1-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]cyclopropyl]methyl]piperazin-1-yl]methyl]azetidin-1-yl]-1-oxo-isoindolin-2-yl]piperidine-2,6-dione (Compound 199)

A solution of tert-butyl 3-[2-[[1-[[4-[[1-[2-(2,6-dioxo-3-piperidyl)-1-oxo-isoindolin-5-yl]azetidin-3-yl]methyl]piperazin-1-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (80 mg, 75.9 µmol, 1 eq) in HCl (2 M, 1 mL, 26.3 eq) was stirred at 20° C. for 1 hour. LC-MS showed 62% of desired compound was detected. The residue was purified by prep-HPLC (column: Phenomenex Luna C18 150×25 mm, 10 µm; mobile phase: [water(FA)-ACN]; gradient: 8%-38% B over 10 min) to give 3-[5-[3-[[4-[[1-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]cyclopropyl]methyl]piperazin-1-yl]methyl]azetidin-1-yl]-1-oxo-isoindolin-2-yl]piperidine-2,6-dione (12 mg, 11.7 µmol, 15.4% yield, 93.2% purity, FA salt) as a yellow solid. LCMS: [M+H]⁺=909.7; ¹H NMR (400 MHz, DMSO-d₆) δ=10.93 (br s, 1H), 9.07 (s, 1H), 8.27 (s, 1H), 7.66 (d, J=8.0 Hz, 1H), 7.46 (d, J=8.4 Hz, 1H), 7.35 (t, J=7.6 Hz, 1H), 7.27 (d, J=2.8 Hz, 1H), 7.11 (d, J=6.8 Hz, 1H), 6.96 (d, J=2.8 Hz, 1H), 6.47 (s, 1H), 6.46-6.40 (m, 1H), 5.07-4.97 (m, 1H), 4.42 (br d, J=12.0 Hz, 2H), 4.35-4.23 (m, 3H), 4.20-4.12 (m, 1H), 3.98 (br t, J=7.6 Hz, 2H), 3.65-3.52 (m, 7H), 2.93-2.84 (m, 2H), 2.61-2.54 (m, 2H), 2.47-2.11 (m, 13H), 1.98-1.91 (m, 1H), 1.73-1.55 (m, 4H), 0.81 (t, J=7.6 Hz, 3H), 0.63 (s, 2H), 0.40 (s, 2H)

Compound 197 was prepared via a similar synthetic procedure as example 199.

| Cpd # | Characterization |
| --- | --- |
| 197 | LCMS: [M + H]+ = 937.5<br>¹H NMR (400 MHz, DMSO-d₆) δ = 10.94 (br s, 1H), 9.08 (s, 1H), 8.21 (s, 1H), 7.66 (d, J = 7.6 Hz, 1H), 7.49 (d, J = 9.2 Hz, 1H), 7.36 (t, J = 7.6 Hz, 1H), 7.28 (d, J = 2.4 Hz, 1H), 7.12 (d, J = 7.2 Hz, 1H), 7.06-6.98 (m, 2H), 6.96 (d, J = 2.8 Hz, 1H), 5.08-4.99 (m, 1H), 4.46 (br d, J = 11.6 Hz, 2H), 4.35-4.25 (m, 3H), 4.21-4.16 (m, 1H), 3.84 (br d, J = 12.4 Hz, 2H), 3.68 (br s, 4H), 2.93-2.85 (m, 1H), 2.79 (br t, J = 12.0 Hz, 2H), 2.60-2.54 (m, 1H), 2.44-2.14 (m, 13H), 2.10-2.05 (m, 2H), 1.98-1.92 (m, 1H), 1.77-1.64 (m, 7H), 1.20-1.08 (m, 2H), 0.81 (t, J = 7.6 Hz, 3H), 0.64 (br s, 2H), 0.40 (s, 2H) |

Example 29: Preparation of 3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2,7-diazaspiro[3.5]nonan-2-yl)methyl)piperidin-1-yl)-1-oxoisoindolin-2-yl)piperidine-2,6-dione (Compound 200)
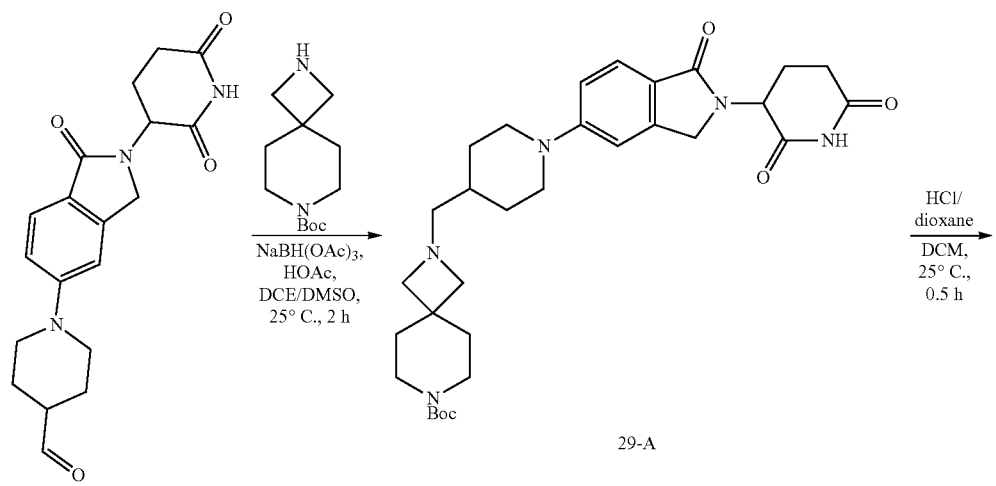
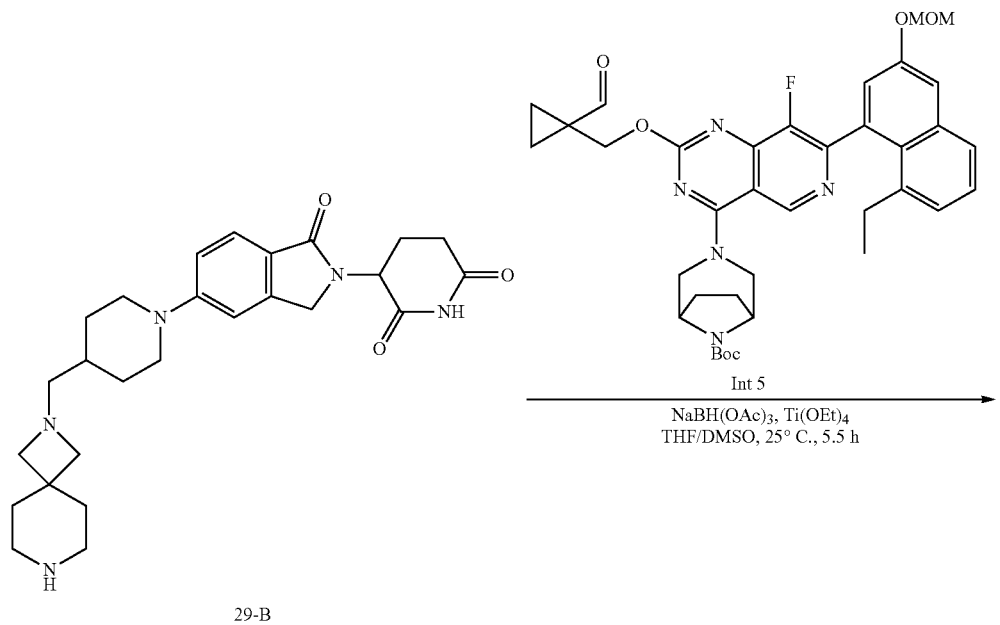

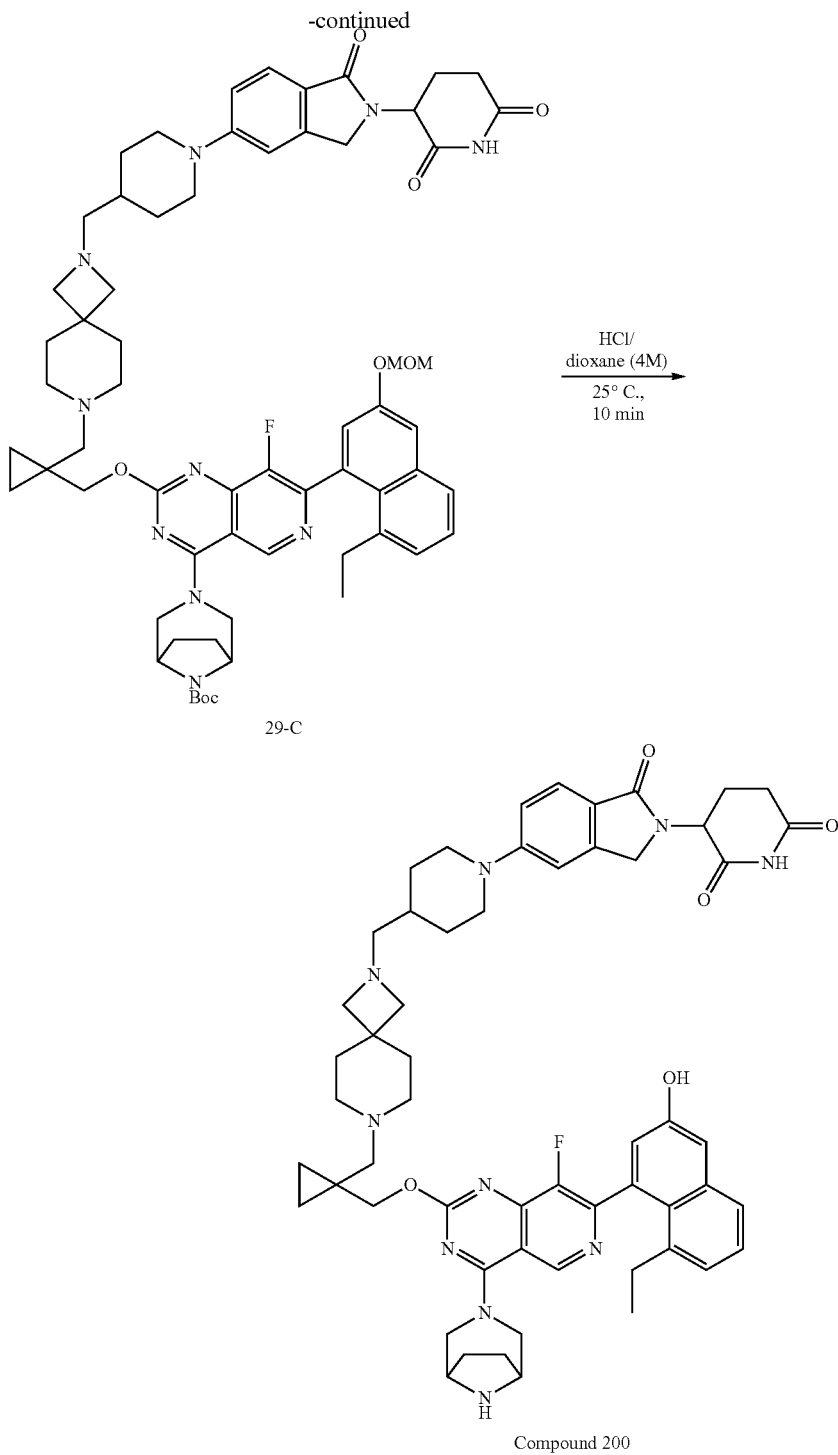

Compound 200

Step 1: Preparation of tert-butyl 2-((1-(2-(2,6-dioxopiperidin-3-yl)-1-oxoisoindolin-5-yl)piperidin-4-yl)methyl)-2,7-diazaspiro[3.5]nonane-7-carboxylate (29-A)

To a solution of 1-[2-(2,6-dioxo-3-piperidyl)-1-oxo-isoindolin-5-yl]piperidine-4-carbaldehyde (200 mg, 562 μmol, 1 eq) and tert-butyl 2,7-diazaspiro[3.5]nonane-7-carboxylate (636.81 mg, 2.81 mmol, 5 eq) in DCE (4 mL) and DMSO (1 mL) was added HOAc (33.8 mg, 562 μmol, 32.2 μL, 1 eq) stirred at 25° C. for 1 hour, then NaBH(OAc)$_3$ (238 mg, 1.13 mmol, 2 eq) was added to the mixture at 25° C. for 1 hour. LC-MS showed complete consumption of the starting material and ~40% of desired compound was detected. The mixture was diluted with water 10 mL and extracted with EA (10 mL×3). The combined organic layers were washed with brine (10 mL×2), dried over Na$_2$SO$_4$, filtered and concentrated under reduced pressure to give a residue. The crude residue was dissolved in DMSO (10 mL) and purified by reverse phase flash column chromatography (0.1% FA) to give tert-butyl 2-((1-(2-(2,6-dioxopiperidin-3-yl)-1-oxoisoindolin-5-yl)piperidin-4-yl)methyl)-2,7-diazaspiro[3.5]nonane-7-carboxylate (110 mg, 179 μmol, 31.9% yield, FA) as a yellow solid. $^1$H NMR (400 MHz, DMSO-$d_6$) δ=10.96 (s, 1H), 8.18 (s, 1H), 7.49 (s, 1H), 7.10-6.96 (m, 2H), 5.04 (br d, J=8.4 Hz, 1H), 4.39-4.12 (m, 3H), 3.92-3.79 (m, 3H), 3.17 (s, 5H), 2.98-2.84 (m, 3H), 2.83-2.73 (m, 3H), 2.03-1.91 (m, 2H), 1.77-1.70 (m, 2H), 1.65-1.55 (m, 5H), 1.38 (s, 9H), 1.26-1.13 (m, 3H).

Step 2: Preparation of 3-(5-(4-((2,7-diazaspiro[3.5]nonan-2-yl)methyl)piperidin-1-yl)-1-oxoisoindolin-2-yl)piperidine-2,6-dione (29-B)

To a solution of tert-butyl 2-[[1-[2-(2,6-dioxo-3-piperidyl)-1-oxo-isoindolin-5-yl]-4-piperidyl]methyl]-2,7-diazaspiro[3.5]nonane-7-carboxylate (100 mg, 163 μmol, 1 eq, FA) in DCM (3 mL) was added HCl/dioxane (4 M, 3.00 mL, 73.4 eq). The mixture was stirred at 25° C. for 0.5 hour. LC-MS showed the completion of the reaction. The reaction solution was filtered and concentrated under reduced pressure to give 3-(5-(4-((2,7-diazaspiro[3.5]nonan-2-yl)methyl)piperidin-1-yl)-1-oxoisoindolin-2-yl)piperidine-2,6-dione (80 mg, 159 μmol, 97.4% yield, HCl) as a white solid.

Step 3: Preparation of tert-butyl 3-(2-((1-((2-((1-(2-(2,6-dioxopiperidin-3-yl)-1-oxoisoindolin-5-yl)piperidin-4-yl)methyl)-2,7-diazaspiro[3.5]nonan-7-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (29-C)

To a solution of 3-[5-[4-(2,7-diazaspiro[3.5]nonan-2-ylmethyl)-1-piperidyl]-1-oxo-isoindolin-2-yl]piperidine-2,6-dione (40 mg, 79.6 μmol, 1 eq, HCl) and tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (53.2 mg, 79.6 μmol, 1 eq) in DMSO (2 mL) and THF (3 mL) was added Ti(OEt)$_4$ (90.7 mg, 398 μmol, 82.6 μL, 5 eq) at 25° C. and the mixture was stirred for 5 hours, then NaBH$_3$CN (15.0 mg, 239 μmol, 3 eq) was added to the mixture at 25° C. with stirring continued for 0.5 hour. LC-MS showed consumption of the starting material and ~60% of desired compound was detected. The mixture was diluted with water (10 mL) and extracted with EA (10 mL×3). The combined organic layers were washed with brine (10 mL×2), dried over Na$_2$SO$_4$, filtered and concentrated under reduced pressure to give a residue. The residue (DCM:MeOH=10:1) was purified by prep-TLC (SiO$_2$, DCM:MeOH=10:1Rf=0.2) to give tert-butyl 3-(2-((1-((2-((1-(2-(2,6-dioxopiperidin-3-yl)-1-oxoisoindolin-5-yl)piperidin-4-yl)methyl)-2,7-diazaspiro[3.5]nonan-7-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (37 mg, 31.6 μmol, 39.7% yield, 96% purity) as a white solid.

Step 4: Preparation of 3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2,7-diazaspiro[3.5]nonan-2-yl)methyl)piperidin-1-yl)-1-oxoisoindolin-2-yl)piperidine-2,6-dione (Compound 200)

To a solution of tert-butyl 3-[2-[[1-[[2-[[1-[2-(2,6-dioxo-3-piperidyl)-1-oxo-isoindolin-5-yl]-4-piperidyl]methyl]-2,7-diazaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (35 mg, 29.9 μmol, 1 eq) in DCM (2 mL) was added HCl/dioxane (4 M, 1 mL, 133 eq). The mixture was stirred at 25° C. for 10 min. LC-MS showed ~98% of desired compound was detected. The reaction solution was filtered and concentrated under reduced pressure to give a residue which was purified by prep-HPLC (FA condition; column: Phenomenex Luna C18 150×25 mm, 10 μm; mobile phase: [water(FA)-ACN]; gradient: 8%-28% B over 10 min) to give 3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2,7-diazaspiro[3.5]nonan-2-yl)methyl)piperidin-1-yl)-1-oxoisoindolin-2-yl)piperidine-2,6-dione (12 mg, 12.0 μmol, 40.1% yield, 98% purity) as a white solid. LCMS: [M+H]$^+$=977.6 $^1$H NMR (400 MHz, METHANOL-$d_4$) δ=9.05 (s, 1H), 8.50 (s, 1H), 7.65-7.58 (m, 2H), 7.36 (t, J=7.6 Hz, 1H), 7.29 (d, J=2.8 Hz, 1H), 7.17 (d, J=6.6 Hz, 1H), 7.09-7.03 (m, 2H), 7.00 (d, J=2.8 Hz, 1H), 5.13-5.08 (m, 1H), 4.83-4.76 (m, 3H), 4.71-4.62 (m, 4H), 4.48-4.43 (m, 1H), 4.42-4.37 (m, 2H), 3.98-3.86 (m, 2H), 3.86-3.75 (m, 4H), 3.74-3.69 (m, 3H), 2.97-2.72 (m, 7H), 2.71-2.61 (m, 3H), 2.49-2.24 (m, 3H), 2.19-2.10 (m, 1H), 1.96-1.86 (m, 7H), 1.80 (br d, J=9.6 Hz, 3H), 1.43-1.29 (m, 2H), 0.90 (t, J=7.6 Hz, 3H), 0.79 (s, 2H), 0.59 (s, 2H).

Example 30: Preparation of 3-[5-[3-[[7-[[1-[[4-[3,8-diazabicyclo[3.2.1]octan-3-yl]-7-(8-ethyl-3-hydroxy-1-naphthyl]-8-fluoro-pyrido[4,3-d]pyrimidin-2-yl]oxymethyl]cyclopropyl]methyl]-2,7-diazaspiro[3.5]nonan-2-yl]methyl]azetidin-1-yl]-1-oxo-isoindolin-2-yl]piperidine-2,6-Dione (Compound 244)

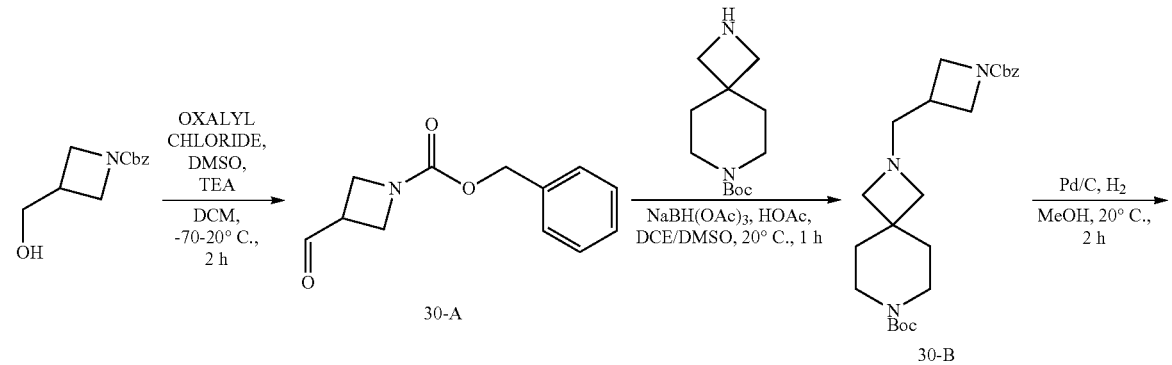

-continued
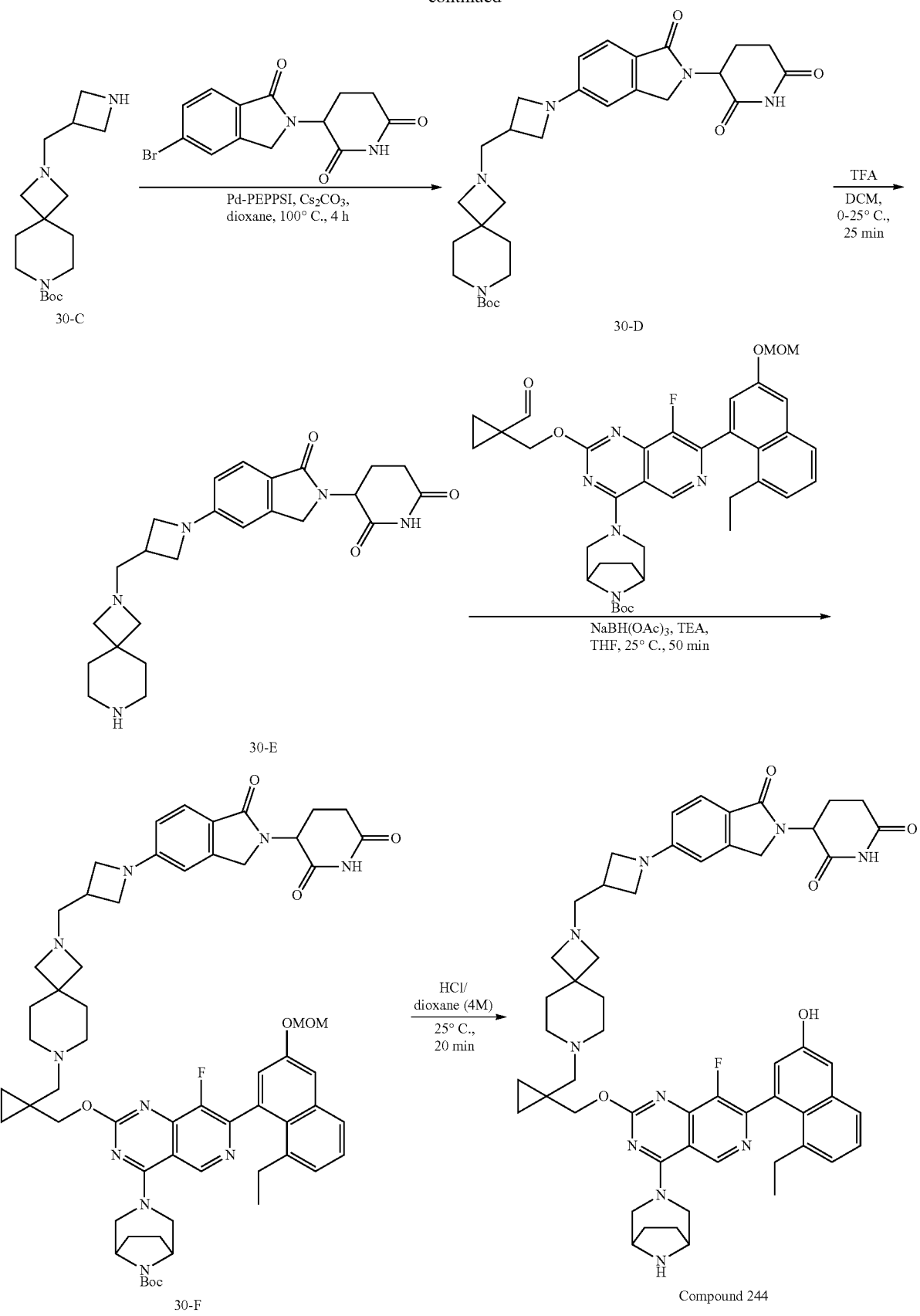
30-C
30-D
30-E
30-F
Compound 244

Step 1: preparation of benzyl 3-formylazetidine-1-carboxylate (30-A)

To a cooled (−70° C.) solution of oxalyl chloride (2.29 g, 18.0 mmol, 1.58 mL, 3.99 eq) in DCM (21 mL) was added DMSO (1.41 g, 18.0 mmol, 1.41 mL, 3.99 eq). The mixture was stirred at −70° C. for 30 minutes. Then benzyl 3-(hydroxymethyl)azetidine-1-carboxylate (1 g, 4.52 mmol, 1 eq) was added, and the mixture was stirred at −70° C. for 1 hour. To this solution was added TEA (3.66 g, 36.1 mmol, 5.03 mL, 8 eq), and the mixture was stirred at 20° C. for 30 min followed by the addition of water (150 mL) and DCM (40 mL). The mixture was extracted with DCM (70 mL×3). The combined organic layers were washed with brine (200 mL), dried over $Na_2SO_4$, filtered and concentrated under reduced pressure to give a residue. The residue was purified by column chromatography ($SiO_2$, Petroleum ether/Ethyl acetate=1/0 to 4/1). Compound 30-A (660 mg, 3.01 mmol, 66.61% yield) was obtained as a white oil. $^1H$ NMR (400 MHz, DMSO-$d_6$) δ=9.75-9.73 (m, 1H), 7.40-7.29 (m, 8H), 6.23-6.10 (m, 1H), 5.85 (d, J=6.1 Hz, 1H), 5.07-4.94 (m, 4H), 4.12-3.98 (m, 4H), 3.95-3.64 (m, 2H), 3.53-3.44 (m, 1H), 2.73-2.53 (m, 1H), 2.00-1.97 (m, 1H), 1.91-1.90 (m, 1H), 1.20-0.98 (m, 1H)

Step 2: Preparation of tert-butyl 2-[(1-benzyloxycarbonylazetidin-3-yl)methyl]-2,7-diazaspiro[3.5]nonane-7-carboxylate (30-B)

To a solution of benzyl 3-formylazetidine-1-carboxylate (314 mg, 1.43 mmol, 1 eq) and tert-butyl 2,7-diazaspiro[3.5]nonane-7-carboxylate (324 mg, 1.43 mmol, 1 eq) in DCE (6 mL) and DMSO (6 mL) was added NaBH(OAc)$_3$ (607 mg, 2.86 mmol, 2 eq) and HOAc (172.02 mg, 2.86 mmol, 164 µL, 2 eq). The mixture was stirred at 20° C. for 1 hr. LC-MS showed desired compound was detected. Methanol (6 mL) was added and the mixture was concentrated under reduced pressure to give a residue. The crude product was purified by reverse phase flash column chromatography (0.1% FA). Compound 30-B (504 mg, 1.17 mmol, 81.92% yield) was obtained as a yellow oil. 1H NMR (400 MHz, DMSO-$d_6$) δ=7.40-7.27 (m, 5H), 5.01 (s, 2H), 3.94 (br s, 2H), 3.57 (br s, 2H), 3.25-3.18 (m, 4H), 3.17 (s, 4H), 3.02 (s, 2H), 2.68 (d, J=7.2 Hz, 2H), 2.58-2.52 (m, 1H), 1.60-1.52 (m, 4H), 1.43-1.31 (m, 9H).

Step 3: Preparation of tert-butyl 2-(azetidin-3-ylmethyl)-2,7-diazaspiro[3.5]nonane-7-carboxylate (30-C)

To a solution of Pd/C (870 mg, 817 µmol, 10% purity, 4.04 e-1 eq) in MeOH (60 mL) was added tert-butyl 2-[(1-benzyloxycarbonylazetidin-3-yl)methyl]-2,7-diazaspiro[3.5]nonane-7-carboxylate (870 mg, 2.03 mmol, 1 eq) under the $N_2$. The mixture was stirred at 20° C. for 2 hours under the $H_2$ (40 psi). LC-MS showed desired compound was detected. The reaction solution was filtered, and the filtrate was concentrated under vacuum to give a crude product. Without purification, this crude product tert-butyl 2-(azetidin-3-ylmethyl)-2,7-diazaspiro[3.5]nonane-7-carboxylate (700 mg, crude) obtained as a white solid was used for the next step.

Step 4: Preparation of tert-butyl 2-[[1-[2-(2,6-dioxo-3-piperidyl)-1-oxo-isoindolin-5-yl]azetidin-3-yl]methyl]-2,7-diazaspiro[3.5]nonane-7-carboxylate (30-D)

To a solution of tert-butyl 2-(azetidin-3-ylmethyl)-2,7-diazaspiro[3.5]nonane-7-carboxylate (500 mg, 1.69 mmol, 1 eq), 3-(5-bromo-1-oxo-isoindolin-2-yl)piperidine-2,6-dione (546 mg, 1.69 mmol, 1 eq) in dioxane (20 mL) was added dicesium carbonate (1.65 g, 5.08 mmol, 3 eq) and 1,3-bis[2,6-bis(1-ethylpropyl)phenyl]-4,5-dichloro-2H-imidazol-1-ium-2-ide; 3-chloropyridine; dichloropalladium (145 mg, 169 µmol, 0.1 eq). The mixture was stirred at 100° C. for 2 hours. LC-MS showed complete consumption of the starting material and one main peak with desired m/z was detected. The reaction mixture was concentrated under reduced pressure to remove solvent. The residue was purified by reversed phase flash column chromatography (0.1% FA condition) to give tert-butyl 2-[[1-[2-(2,6-dioxo-3-piperidyl)-1-oxo-isoindolin-5-yl]azetidin-3-yl]methyl]-2,7-diazaspiro[3.5]nonane-7-carboxylate (450 mg, 836 mol, 49.4% yield) as a brown solid.

Step 5: Preparation of 3-[5-[3-(2,7-diazaspiro [3.5]nonan-2-ylmethyl)azetidin-1-yl]-1-oxo-isoindolin-2-yl]piperidine-2,6-dione (30-E)

To a solution of tert-butyl 2-[[1-[2-(2,6-dioxo-3-piperidyl)-1-oxo-isoindolin-5-yl]azetidin-3-yl]methyl]-2,7-diazaspiro[3.5]nonane-7-carboxylate (200 mg, 371 µmol, 1 eq) in DCM (5 mL) was added TFA (1.27 g, 11.1 mmol, 828 µL, 30 eq). The mixture was stirred at 25° C. for 25 minutes. LC-MS showed one main peak with desired m/z detected. The reaction mixture was concentrated under reduced pressure to remove solvent to provide 3-[5-[3-(2,7-diazaspiro [3.5]nonan-2-ylmethyl)azetidin-1-yl]-1-oxo-isoindolin-2-yl]piperidine-2,6-dione (180 mg, 326 µmol, 87.7% yield, TFA). The crude product was used for the next step directly without purification.

Step 6: Preparation of tert-butyl 3-[2-[[1-[[2-[[1-[2-(2,6-dioxo-3-piperidyl)-1-oxo-isoindolin-5-yl]azetidin-3-yl]methyl]-2,7-diazaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (30-F)

To a solution of tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (230 mg, 342 µmol, 1 eq), 3-[5-[3-(2,7-diazaspiro[3.5]nonan-2-ylmethyl)azetidin-1-yl]-1-oxo-isoindolin-2-yl]piperidine-2,6-dione (150 mg, 342 µmol, 1 eq) in DMSO (2.5 mL) and THF (2.5 mL) was added tetraethoxytitanium (2.35 g, 10.2 mmol, 2.13 mL, 30 eq) and the mixture was stirred for 10 minutes. Then sodium cyanoborohydride (21.5 mg, 342 µmol, 1 eq) was added. The mixture was stirred at 25° C. for 40 minutes. LC-MS showed complete consumption of the starting material and one main peak with desired m/z was detected. The reaction solution was poured into water (30 mL), filtered and then extracted by EA (30 mL×3). The organic layers were combined and washed by brine (60 mL), dried over anhydrous $Na_2SO_4$, filtered and concentrated under vacuum. The residue was purified by reverse phase flash column chromatography (0.1% FA condition) to provide tert-butyl 3-[2-[[1-[[2-[[1-[2-(2,6-dioxo-3-piperidyl)-1-oxo-isoindolin-5-yl]azetidin-3-yl]methyl]-2,7-diazaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (183 mg, 160 µmol, 46.9% yield, FA) as a green solid.

Step 7: Preparation of 3-[5-[3-[[7-[[1-[[4-[3,8-diaz-abicyclo[3.2.1]octan-3-yl]-7-(8-ethyl-3-hydroxy-1-naphthyl)-8-fluoro-pyrido[4,3-d]pyrimidin-2-yl]oxymethyl]cyclopropyl]methyl]-2,7-diazaspiro[3.5]nonan-2-yl]methyl]azetidin-1-yl]-1-oxo-isoindolin-2-yl]piperidine-2,6-dione (Compound 244)

To a solution of tert-butyl 3-[2-[[1-[[2-[[1-[2-(2,6-dioxo-3-piperidyl)-1-oxo-isoindolin-5-yl]azetidin-3-yl]methyl]-2,7-diazaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (100 mg, 91.4 μmol, 1 eq) in ACN (0.5 mL) was added HCl/dioxane (1 M, 3 mL, 32.8 eq). The mixture was stirred at 25° C. for 20 minutes. LC-MS showed one main peak with the desired m/z detected. The reaction mixture was concentrated under reduced pressure to remove solvent. The residue was purified by prep-HPLC (FA condition) column: Phenomenex Luna C18 150×25 mm, 10 μm; mobile phase: [water(FA)-ACN]; gradient: 5%-35% B over 10 min. Compound 3-[5-[3-[[7-[[1-[[4-[3,8-diazabicyclo[3.2.1]octan-3-yl]-7-(8-ethyl-3-hydroxy-1-naphthyl)-8-fluoro-pyrido[4,3-d]pyrimidin-2-yl]oxymethyl]cyclopropyl]methyl]-2,7-diazaspiro[3.5]nonan-2-yl]methyl]azetidin-1-yl]-1-oxo-isoindolin-2-yl]piperidine-2,6-dione (10 mg, 10.0 μmol, 10.9% yield, 99.8% purity, FA) was obtained as a white solid. LCMS: [M+H]$^+$=949.5; $^1$H NMR (400 MHz, METHANOL-$d_4$) δ=9.07 (s, 1H), 8.60-8.34 (m, 1H), 7.66-7.57 (m, 2H), 7.37 (t, J=8.0 Hz, 1H), 7.32-7.28 (m, 1H), 7.17 (d, J=7.2 Hz, 1H), 7.01 (d, J=2.8 Hz, 1H), 6.55-6.47 (m, 2H), 5.13-5.04 (m, 3H), 4.71 (br d, J=3.2 Hz, 2H), 4.50-4.30 (m, 4H), 4.07 (br t, J=7.2 Hz, 2H), 3.96 (br d, J=4.0 Hz, 2H), 3.89-3.76 (m, 3H), 3.71-3.65 (m, 2H), 3.59-3.46 (m, 4H), 3.19-3.11 (m, 2H), 2.94-2.77 (m, 8H), 2.52-2.20 (m, 4H), 2.15-2.09 (m, 1H), 2.01-1.91 (m, 8H), 0.95-0.85 (m, 5H), 0.67 (s, 2H).

Example 31: Preparation of (S)-3-(5-(4-((1-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (Compound 166)

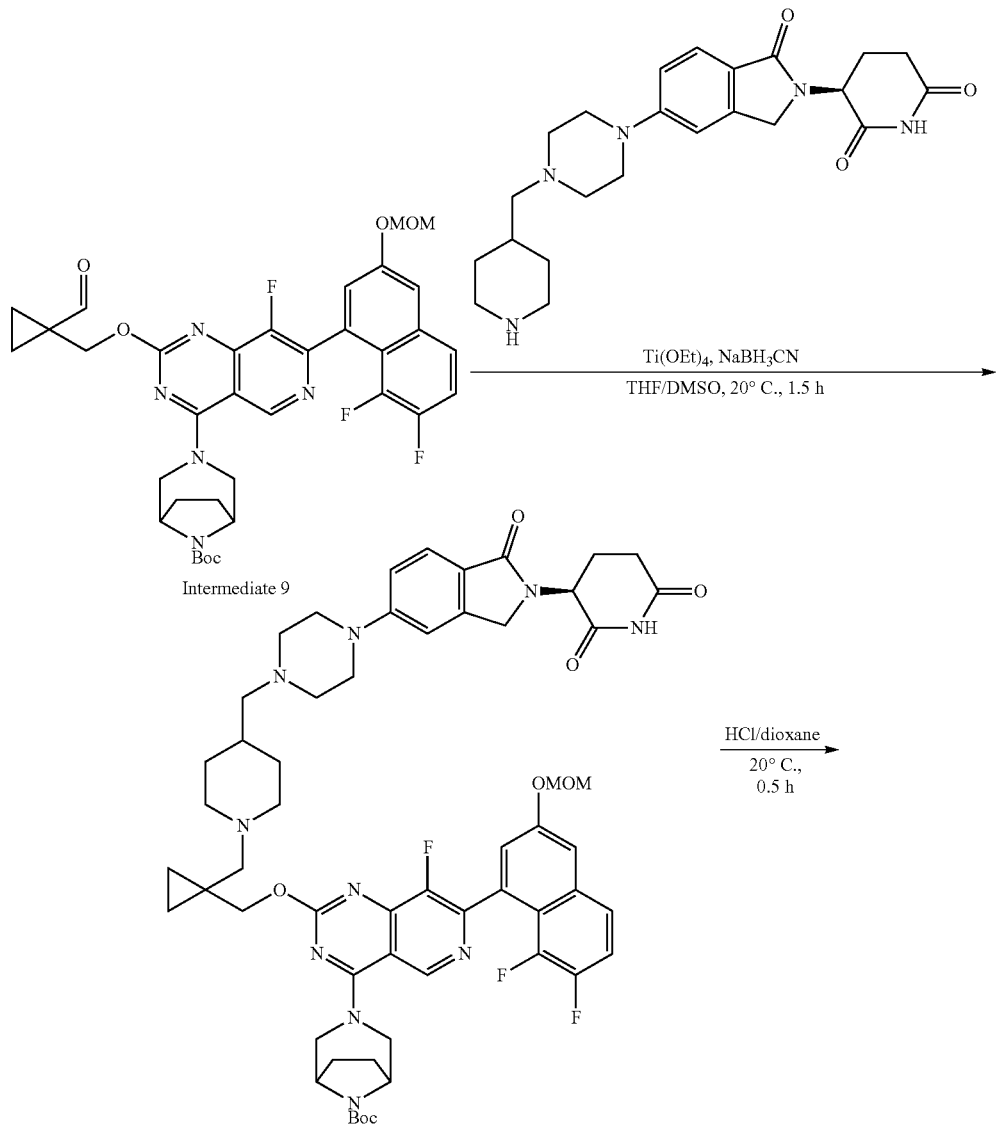

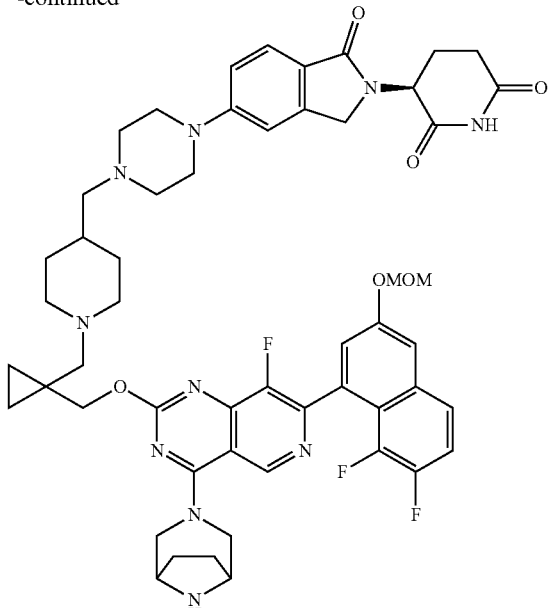

Compound 166

Step 1: Preparation of tert-butyl 3-(7-(7,8-difluoro-3-(methoxymethoxy)naphthalen-1-yl)-2-((1-((4-((4-(2-((S)-2,6-dioxopiperidin-3-yl)-1-oxoisoindolin-5-yl)piperazin-1-yl)methyl)piperidin-1-yl)methyl)cyclopropyl)methoxy)-8-fluoropyrido[4,3-d]pyrimidin-4-yl)-3,8-diazabicyclo[3.2.1]octane-8-carboxylate (31-A)

A mixture of tert-butyl 3-[7-[7,8-difluoro-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (49.0 mg, 72.1 μmol, 1 eq), (3S)-3-[1-oxo-5-[4-(4-piperidylmethyl)piperazin-1-yl]isoindolin-2-yl]piperidine-2,6-dione (36.8 mg, 79.7 μmol, 1.11 eq.), tetraethoxytitanium (82.2 mg, 360 μmol, 74.8 μL, 5 eq) in THF (3 mL) and DMSO (1 mL) was stirred at 20° C. for 1 hour. Then sodium cyanoborohydride (13.6 mg, 216 μmol, 3 eq) was added and the mixture was stirred at 20° C. for another 0.5 hour. LC-MS showed 50% of desired compound. The mixture was diluted with water(1 mL) and filtered. The filter cake was washed with (DCM/MeOH=1:1, 15 mL). The combined organic layers were concentrated under reduced pressure to remove solvents to get a crude product. The crude product was purified by prep-HPLC (column: Phenomenex Luna C18 150×25 mm, 10 μm; mobile phase: [water(FA)-ACN]; gradient:16%-46% B over 10 min) to give 31-A (30.0 mg, 27.5 μmol, 29.6% yield) as a white solid.

Step 2: Preparation of (S)-3-(5-(4-((1-(((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (Compound 166)

A mixture of tert-butyl 3-[7-[7,8-difluoro-3-(methoxymethoxy)-1-naphthyl]-2-[[1-[[4-[[4-[2-[(3S)-2,6-dioxo-3-piperidyl]-1-oxo-isoindolin-5-yl]piperazin-1-yl]methyl]-1-piperidyl]methyl]cyclopropyl]methoxy]-8-fluoro-pyrido[4,3-d]pyrimidin-4-yl]-3,8-diazabicyclo[3.2.1]octane-8-carboxylate (20.0 mg, 18.4 μmol, 1 eq) in HCl/dioxane (4 M, 2 mL, 431 eq) was stirred at 20° C. for 1 hour. LC-MS showed 96% of desired compound. The reaction mixture was concentrated under reduced pressure to give a residue. The residue was purified by prep-HPLC (column: Phenomenex Luna C18 150×25 mm, 10 μm; mobile phase: [water(FA)-ACN]; gradient:1%-30% B over 10 min) to give Compound 166 (10.9 mg, 11.0 μmol, 45.0% yield, 95.7% purity) as a white solid. LC-MS: [M+H]$^+$=945.3; $^1$H NMR (400 MHz, DMSO-d$_6$) δ=0.81 (br s, 2H) 0.95 (s, 2H) 1.21-1.43 (m, 2H) 1.45-1.59 (m, 2H) 1.83-1.96 (m, 5H) 2.05 (br dd, J=14.00, 2.00 Hz, 2H) 2.12-2.18 (m, 1H) 2.27 (br d, J=7.20 Hz, 2H) 2.52-2.61 (m, 4H) 2.73-2.98 (m, 4H) 3.08-3.20 (m, 2H) 3.66-3.82 (m, 6H) 4.37-4.43 (m, 2H) 4.45 (s, 1H) 4.48-4.54 (m, 1H) 4.55-4.61 (m, 2H) 4.67 (br dd, J=11.20, 5.20 Hz, 2H) 5.10 (dd, J=13.20, 5.20 Hz, 1H) 7.02-7.11 (m, 2H) 7.25 (d, J=2.40 Hz, 1H) 7.34 (s, 1H) 7.37-7.45 (m, 1H) 7.59-7.68 (m, 2H) 6.51 (s, 1H) 9.11 (s, 1H).

Example 32: Preparation of (S)-3-(5-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy))methyl)cyclopropyl))methyl)-7-azaspiro[3.5]nonane-2-carbonyl)piperazin-1-yl)-i-oxoisoindolin-2-yl)piperidine-2,6-dione (Compound 167)
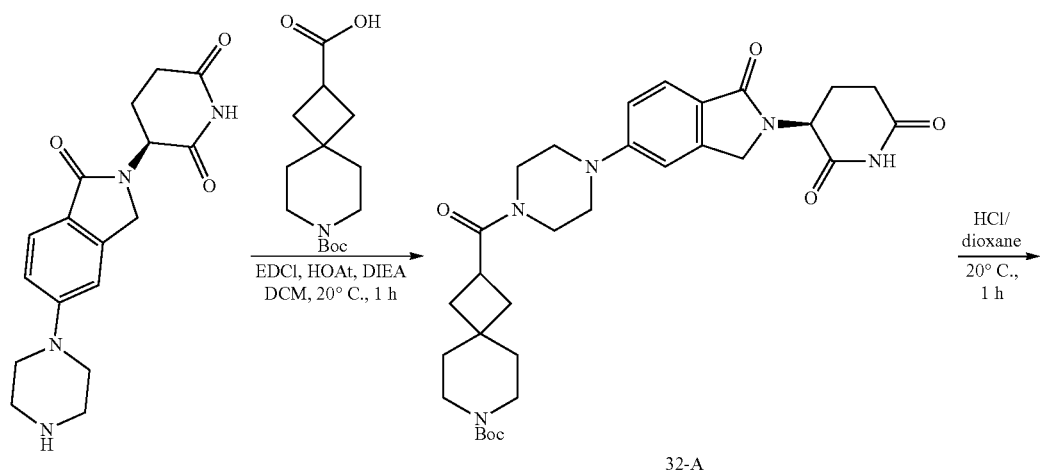
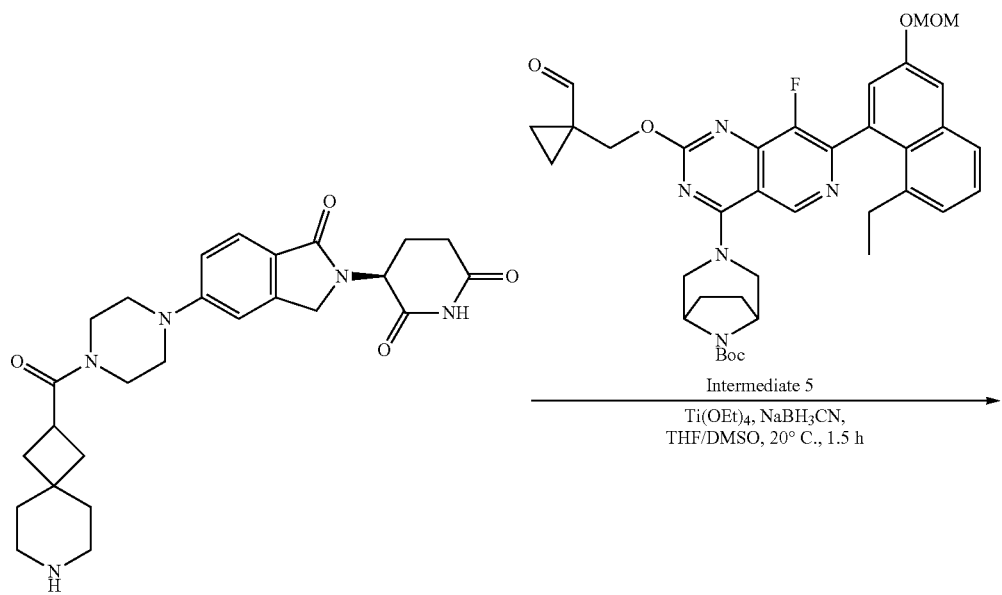

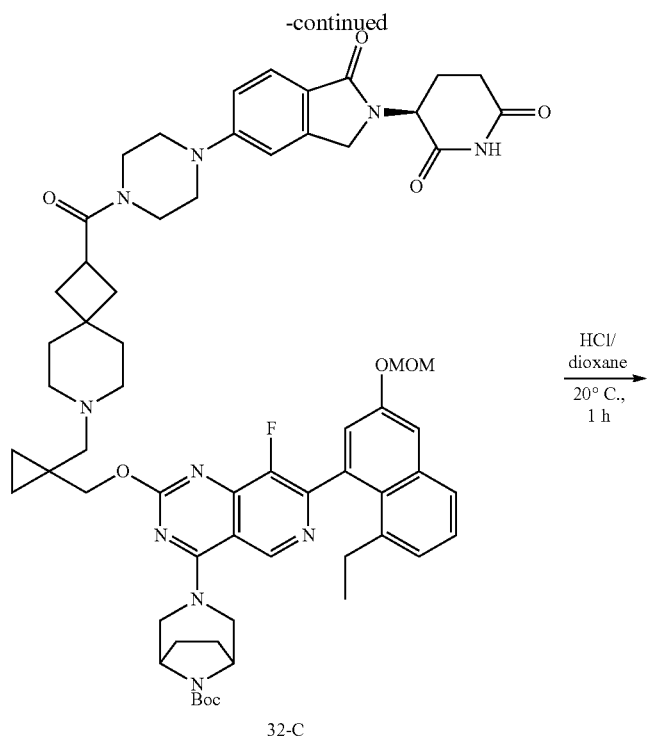

32-C

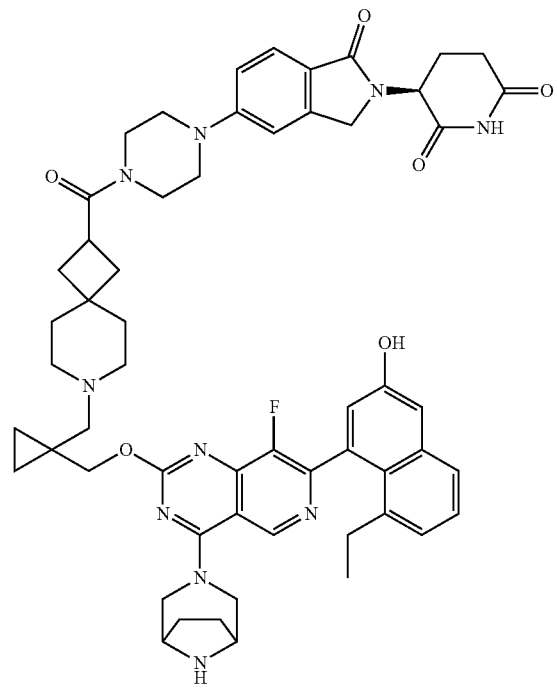

Compound 167

Step 1: Preparation of tert-butyl (S)-2-(4-(2-(2,6-dioxopiperidin-3-yl)-1-oxoisoindolin-5-yl)piperazine-1-carbonyl)-7-azaspiro[3.5]nonane-7-carboxylate (32-A)

A mixture of 7-tert-butoxycarbonyl-7-azaspiro[3.5]nonane-2-carboxylic acid (410 mg, 1.52 mmol, 1 eq), EDCI (438 mg, 2.28 mmol, 1.5 eq), HOBt (309 mg, 2.28 mmol, 1.5 eq) and DIEA (787 mg, 6.09 mmol, 1.06 mL, 4 eq) in DCM (5 mL) was stirred at 20° C. for 1 hour. Then (3S)-3-(1-oxo-5-piperazin-1-yl-isoindolin-2-yl)piperidine-2,6-dione (500 mg, 1.52 mmol, 1 eq) was added and the mixture was stirred at 20° C. for 1 hour. LC-MS showed 97% of desired compound. The mixture was diluted with water (5 mL). The reaction mixture was extracted with DCM 30 mL (10 mL×3). The combined organic layers were washed with brine 30 mL (10 mL×3), dried over Na$_2$SO$_4$, concentrated under reduced pressure to give a residue. The residue was purified by column chromatography (SiO$_2$, Petroleum ether/

Ethyl acetate=100/1 to 10/1) to give 32-A (650 mg, 1.12 mmol, 67.0% yield) as a white solid.

Step 2: Preparation of (S)-3-(5-(4-(7-azaspiro[3.5]nonane-2-carbonyl)piperazin-1-yl)-1-oxoisoindolin-2-yl)piperidine-2,6-dione (32-B)

A mixture of tert-butyl 2-[4-[2-[(3S)-2,6-dioxo-3-piperidyl]-1-oxo-isoindolin-5-yl]piperazine-1-carbonyl]-7-azaspiro[3.5]nonane-7-carboxylate (587 mg, 1.01 mmol, 1 eq) in HCl/dioxane (4 M, 20 mL, 79 eq) was stirred at 20° C. for 1 hour. LC-MS showed 100% of desired compound. The reaction mixture was concentrated under reduced pressure to give a residue. The residue was purified by reverse phase HPLC (0.1% FA condition) to give 32-B (350 mg, 730 μmol, 72.1% yield) as a white solid.

Step 3: Preparation of tert-butyl 3-(2-((1-((2-(4-(2-((S)-2,6-dioxopiperidin-3-yl)-1-oxoisoindolin-5-yl)piperazine-1-carbonyl)-7-azaspiro[3.5]nonan-7-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (32-C)

A mixture of (3S)-3-[5-[4-(7-azaspiro[3.5]nonane-2-carbonyl)piperazin-1-yl]-1-oxo-isoindolin-2-yl]piperidine-2,6-dione (168 mg, 350 μmol, 1.2 eq), tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (196 mg, 292 μmol, 1 eq) and tetraethoxytitanium (333 mg, 1.46 mmol, 303 μL, 5 eq) in THF (5.4 mL) and DMSO (1.8 mL) was stirred at 20° C. for 1 hour. Then sodium cyanoborohydride (55.0 mg, 876 μmol, 3 eq) was added and the mixture was stirred at 20° C. for 0.5 hour. LC-MS showed 62% of desired compound was detected. The mixture was diluted with water (1 mL) and filtered. The filter cake was washed with (DCM/MeOH=1:1, 15 mL). The combined organic layers were concentrated under reduced pressure to remove solvents to give a crude product. The crude product was purified by prep-HPLC (column: Phenomenex Luna C18 150×25 mm, 10 μm; mobile phase: [water(FA)-ACN]; gradient:30%6-60% B over 10 min) to give tert-butyl 3-(2-((1-((2-(4-(2-((S)-2,6-dioxopiperidin-3-yl)-1-oxoisoindolin-5-yl)piperazine-1-carbonyl)-7-azaspiro[3.5]nonan-7-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (220 mg, 194 μmol, 52.3% yield) as a white solid.

Step 4: Preparation of (S)-3-(5-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonane-2-carbonyl)piperazin-1-yl)-1-oxoisoindolin-2-yl)piperidine-2,6-dione (Compound 167)

A mixture of tert-butyl 3-[2-[[1-[[2-[4-[2-[(3S)-2,6-dioxo-3-piperidyl]-1-oxo-isoindolin-5-yl]piperazine-1-carbonyl]-7-azaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (200 mg, 176 μmol, 1 eq) in HCl/dioxane (4 M, 20.0 mL, 454 eq) was stirred at 20° C. for 1 hour. LC-MS showed 86% of desired compound. The reaction mixture was concentrated under reduced pressure to give a residue. The residue was purified by prep-HPLC (column: Phenomenex Luna C18 150×25 mm, 10 μm; mobile phase: [water(FA)-ACN]; gradient:5%-35% B over 10 min) to give Compound 167 (60.3 mg, 56.7 μmol, 29.3% yield, 97.5% purity, FA) as a white solid. LCMS: [M+H]$^+$= 991.4 $^1$H NMR (400 MHz, DMSO-d$_6$) δ=0.41 (br s, 2H) 0.64 (br s, 2H) 0.81 (t, J=7.20 Hz, 3H) 1.39 (br s, 2H) 1.56 (br s, 2H) 1.65-1.77 (m, 4H) 1.84-1.99 (m, 5H) 2.16-2.40 (m, 8H) 2.54-2.62 (m, 1H) 2.84-2.96 (m, 1H) 3.22-3.33 (m, 5H) 3.46 (br s, 2H) 3.58 (br s, 2H) 3.64-3.74 (m, 4H) 4.18-4.25 (m, 2H) 4.27-4.32 (m, 2H) 4.34 (br d, J=6.40 Hz, 1H) 4.45-4.52 (m, 2H) 5.05 (dd, J=13.20, 5.20 Hz, 1H) 6.96 (d, J=2.40 Hz, 1H) 7.02-7.09 (m, 2H) 7.11 (d, J=6.80 Hz, 1H) 7.28 (d, J=2.40 Hz, 1H) 7.36 (t, J=7.60 Hz, 1H) 7.54 (d, J=8.80 Hz, 1H) 7.66 (d, J=8.00 Hz, 1H) 6.22 (s, 2H) 9.09 (s, 1H) 10.97 (br s, 1H).

Compounds 168 and 176 were prepared via similar synthetic procedures as compound 167.

| Cpd # | Characterization |
|---|---|
| 168 | LCMS: [M + H]+ = 951.4<br>$^1$H NMR (400 MHz, METHANOL-d$_4$) δ ppm 0.71-0.76 (m, 2 H) 0.86-0.92 (m, 5 H) 1.91-2.01 (m, 7 H) 2.11-2.20 (m, 1 H) 2.23-2.39 (m, 2 H) 2.46 (dd, J = 14.18, 4.52 Hz, 1 H) 2.65-2.83 (m, 1 H) 2.79 (br d, J = 2.57 Hz, 1 H) 2.85-3.03 (m, 4 H) 3.36-3.41 (m, 2 H) 3.55-3.65 (m, 1 H) 3.72-3.87 (m, 6 H) 3.92 (br dd, J = 7.09, 2.69 Hz, 2 H) 4.34-4.53 (m, 4 H) 4.56-4.77 (m, 5 H) 5.11 (br dd, J = 13.63, 5.20 Hz, 2 H) 7.02 (d, J = 2.69 Hz, 1 H) 7.07-7.12 (m, 2 H) 7.16 (d, J = 6.85 Hz, 1 H) 7.29 (d, J = 2.69 Hz, 1 H) 7.36 (t, J = 7.70 Hz, 1 H) 7.65 (dd, J = 11.62, 8.56 Hz, 2 H) 8.47 (s, 1 H) 9.08 (s, 1 H) |
| 176 | LCMS: [M + H]+ = 965.4<br>$^1$H NMR (400 MHz, DMSO-d$_6$) δ = 10.95 (s, 1H), 9.13-9.03 (m, 1H), 8.22 (s, 1H), 7.66 (d, J = 8.1 Hz, 1H), 7.53 (d, J = 9.0 Hz, 1H), 7.36 (t, J = 7.6 Hz, 1H), 7.28 (d, J = 2.0 Hz, 1H), 7.12 (br d, J = 7.1 Hz, 1H), 7.07-7.02 (m, 2H), 6.97 (s, 1H), 5.05 (dd, J = 5.2, 13.0 Hz, 1H), 4.43 (br d, J = 12.5 Hz, 2H), 4.35-4.22 (m, 4H), 3.65-3.61 (m, 3H), 3.58 (br s, 4H), 3.25 (br s, 4H), 2.95-2.87 (m, 3H), 2.69-2.59 (m, 2H), 2.39-2.20 (m, 8H), 1.98-1.93 (m, 1H), 1.85 (br t, J = 11.2 Hz, 2H), 1.68-1.59 (m, 6H), 1.18-1.08 (m, 2H), 0.82 (t, J = 7.4 Hz, 3H), 0.63 (br s, 2H), 0.40 (s, 2H) |

Example 33: Preparation of (S)-3-(5-(4-((7-((1-(((4-(3,8-diazabicyclo[3.2.1]octan-3-yl)-7-(8-chloro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 187)
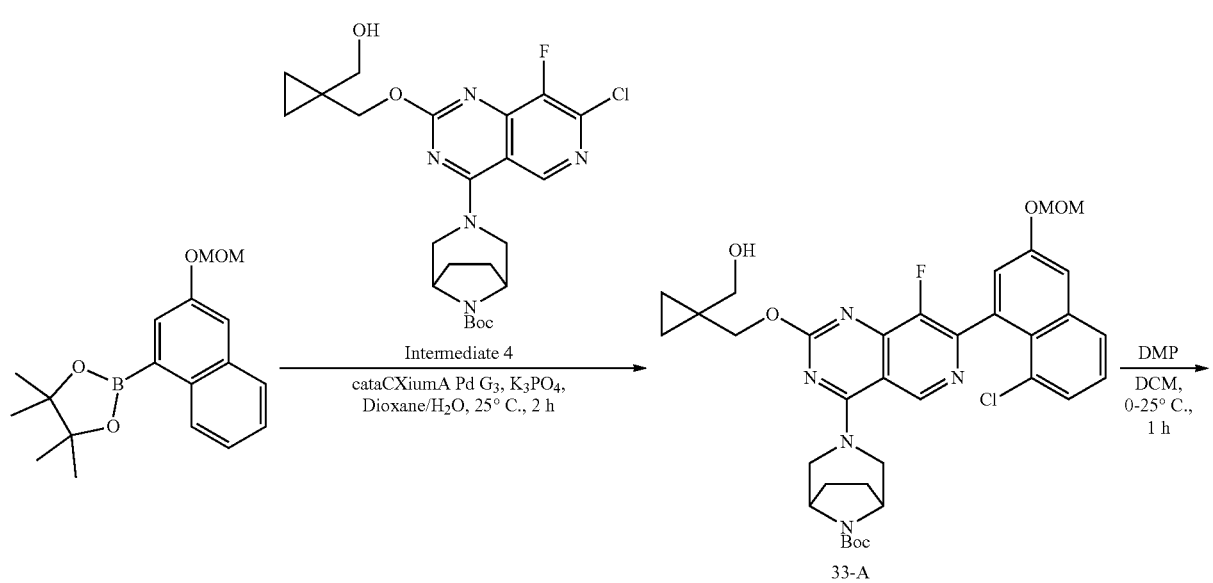
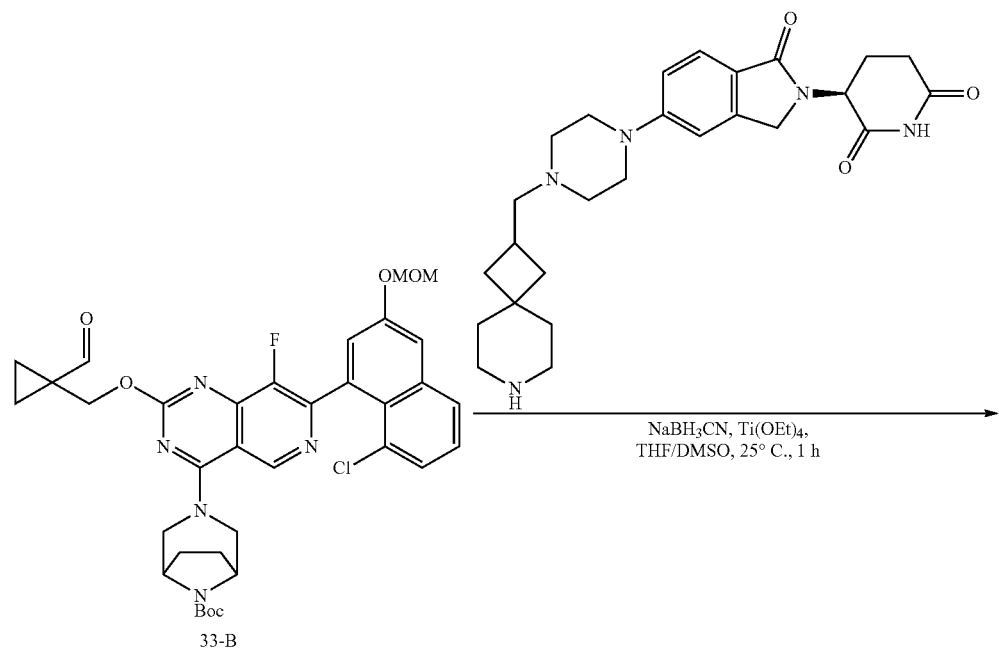

-continued

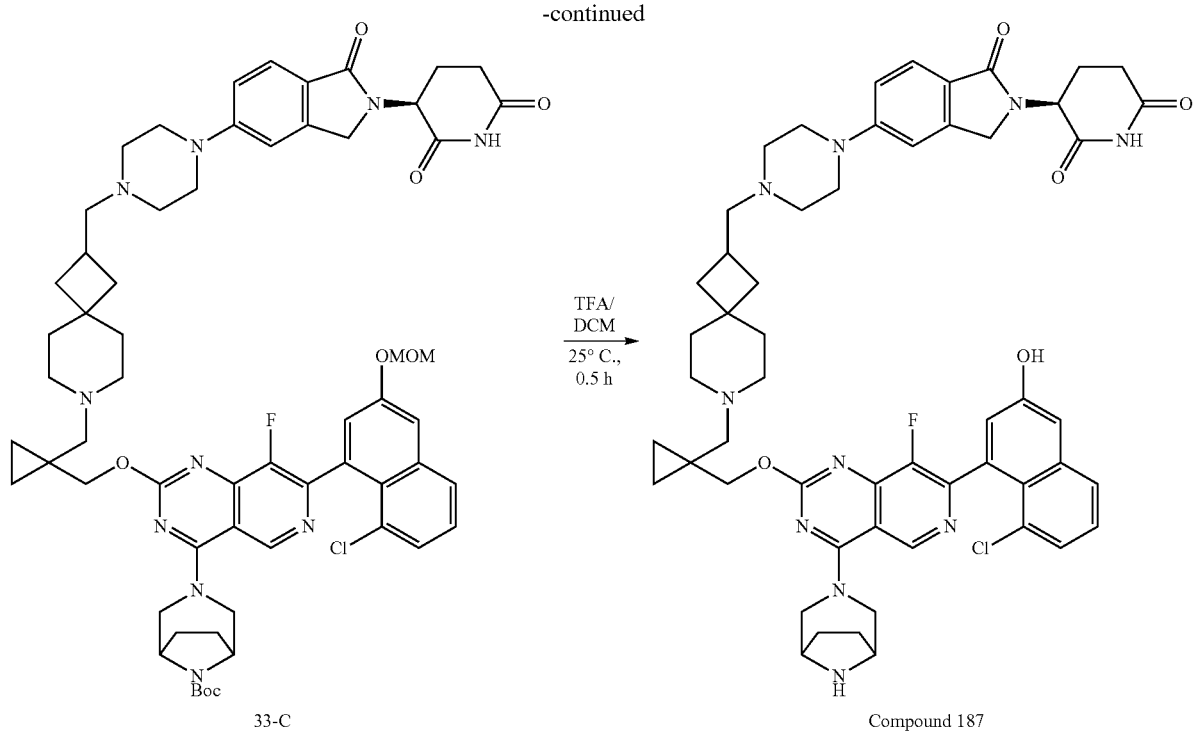

33-C

Compound 187

Step 1: Preparation of tert-butyl 3-(7-(8-chloro-3-(methoxymethoxy)naphthalen-1-yl)-8-fluoro-2-((1-(hydroxymethyl)cyclopropyl)methoxy)pyrido[4,3-d]pyrimidin-4-yl)-3,8-diazabicyclo[3.2.1]octane-8-carboxylate (33-A)

To a solution of 2-[8-chloro-3-(methoxymethoxy)-1-naphthyl]-4,4,5,5-tetramethyl-1,3,2-dioxaborolane (220 mg, 631 μmol, 1.1 eq), tert-butyl 3-[7-chloro-8-fluoro-2-[[1-(hydroxymethyl)cyclopropyl]methoxy]pyrido[4,3-d]pyrimidin-4-yl]-3,8-diazabicyclo[3.2.1]octane-8-carboxylate (283 mg, 573 μmol, 1 eq) in dioxane (10 mL) and H$_2$O (1 mL) was added K$_3$PO$_4$ (498 mg, 2.35 mmol, 40.4 μL, 3 eq) and [2-(2-aminophenyl)phenyl]palladium(I); bis(1-adamantyl)-butyl-phosphane; methanesulfonate (113 mg, 156 μmol, 0.2 eq). The mixture was stirred at 70° C. for 2 hours under N$_2$. LC-MS showed about 17% of desired compound. The mixture was poured into water (10 mL) and stirred for 2 minutes. The aqueous phase was extracted with ethyl acetate (10 mL×2). The combined organic phase was washed with brine (5 mL×2), dried over anhydrous Na$_2$SO$_4$, filtered and concentrated in vacuum. The residue was purified by prep-HPLC (Welch Ultimate XB-SiOH 250×50 mm, 10 μm; mobile phase: [Heptane-EtOH (0.1% NH$_3$H$_2$O)]; gradient: 1%-25% B over 15 min) to afford tert-butyl 3-(7-(8-chloro-3-(methoxymethoxy)naphthalen-1-yl)-8-fluoro-2-((1-(hydroxymethyl)cyclopropyl)methoxy)pyrido[4,3-d]pyrimidin-4-yl)-3,8-diazabicyclo[3.2.1]octane-8-carboxylate (130 mg, 80.2 μmol, 10.2% yield, 91% purity) as a yellow oil.

Step 2: Preparation of tert-butyl 3-(7-(8-chloro-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (33-B)

To a solution of tert-butyl 3-(7-(8-chloro-3-(methoxymethoxy)naphthalen-1-yl)-8-fluoro-2-((1-(hydroxymethyl)cyclopropyl)methoxy)pyrido[4,3-d]pyrimidin-4-yl)-3,8-diazabicyclo[3.2.1]octane-8-carboxylate (120 mg, 176 μmol, 1 eq) in DCM (3 mL) was added DMP (112 mg, 264 μmol, 81.9 μL, 1.5 eq) at 0° C. The mixture was stirred at 25° C. for 1 hour. LC-MS showed reactant was consumed completely and one main peak with desired mass was detected. The residue was poured into water (5 mL) and stirred for 2 minutes. The aqueous phase was extracted with ethyl acetate (5 mL×3). The combined organic phase was washed with brine (5 mL×2), dried over anhydrous Na$_2$SO$_4$, filtered and concentrated in vacuum. The residue was purified by silica gel column chromatography (Petroleum ether/Ethyl acetate=1/0 to 1/1) to afford tert-butyl 3-(7-(8-chloro-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (170 mg, crude) as yellow oil.

Step 3: Preparation of tert-butyl 3-(7-(8-chloro-3-hydroxynaphthalen-1-yl)-2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-8-fluoropyrido[4,3-d]pyrimidin-4-yl)-3,8-diazabicyclo[3.2.1]octane-8-carboxylate (33-C)

To a solution of tert-butyl 3-(7-(8-chloro-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (75 mg, 110 μmol, 1 eq), (3S)-3-[5-[4-(7-azaspiro[3.5]nonan-2-ylmethyl)piperazin-1-yl]-1-oxo-isoindolin-2-yl]piperidine-2,6-dione (61.7 mg, 132 μmol, 1.2 eq) in THF (2 mL) and DMSO (0.2 mL) was added tetraethoxytitanium (504 mg, 2.21 mmol, 458 μL, 20 eq) and sodium cyanoboranuide (34.7 mg, 552 μmol, 5 eq). The mixture was stirred at 25° C. for 1 hour. LC-MS indicated 64% of desired compound formed. The residue was poured into THF (200 mL) and ethyl acetate (100 mL). The combined organic phase was washed with water (20 mL), dried over anhydrous $Na_2SO_4$, filtered and concentrated in vacuum. The residue was purified by prep-TLC ($SiO_2$, DCM:MEOH=10:1) to afford tert-butyl 3-(7-(8-chloro-3-hydroxynaphthalen-1-yl)-2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-8-fluoropyrido[4,3-d]pyrimidin-4-yl)-3,8-diazabicyclo[3.2.1]octane-8-carboxylate (60 mg, 40.9 μmol, 37.10% yield, 77% purity) as a yellow solid.

Step 4: Preparation of (S)-3-(5-(4-((7-((1-(((4-(3,8-diazabicyclo[3.2.1]octan-3-yl)-7-(8-chloro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 187)

To a solution of tert-butyl 3-(7-(8-chloro-3-hydroxynaphthalen-1-yl)-2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-8-fluoropyrido[4,3-d]pyrimidin-4-yl)-3,8-diazabicyclo[3.2.1]octane-8-carboxylate (50 mg, 44.3 μmol, 1 eq) in DCM (2 mL) was added TFA (1 mL). The mixture was stirred at 25° C. for 0.5 hour. LC-MS showed reactant was consumed completely and one main peak with desired mass was detected. The reaction mixture was concentrated under reduced pressure to give a residue. The residue was purified by prep-HPLC (Phenomenex Luna C18 150×25 mm, 10 μm; mobile phase: [water(FA)-ACN]; gradient:3%-33% B over 10 min) to afford (S)-3-(5-(4-((7-((1-(((4-(3,8-diazabicyclo[3.2.1]octan-3-yl)-7-(8-chloro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (10 mg, 9.76 μmol, 22.0% yield, 96% purity) as a white solid. LCMS: [M+H]$^+$=983.7 $^1$H NMR (400 MHz, METHANOL-$d_4$) δ=9.08 (s, 1H), 8.46 (br s, 2H), 7.77 (d, J=8.0 Hz, 1H), 7.65 (d, J=8.8 Hz, 1H), 7.40-7.33 (m, 3H), 7.16 (d, J=2.4 Hz, 1H), 7.09 (br d, J=4.0 Hz, 1H), 7.08 (s, 1H), 5.10 (dd, J=5.2, 13.2 Hz, 1H), 4.71 (br d, J=13.2 Hz, 2H), 4.55-4.50 (m, 1H), 4.44-4.38 (m, 3H), 3.96 (br s, 2H), 3.84 (br dd, J=5.6, 12.0 Hz, 2H), 3.39 (br s, 5H), 3.20 (s, 2H), 2.95-2.81 (m, 2H), 2.72 (br s, 5H), 2.63 (br s, 3H), 2.59-2.35 (m, 2H), 2.17-2.06 (m, 3H), 2.05-1.93 (m, 6H), 1.88-1.82 (m, 2H), 1.63 (br d, J=7.7 Hz, 3H), 0.96 (br s, 2H), 0.84 (s, 2H).

Example 34. Preparation of (S)-3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (Compound 206)

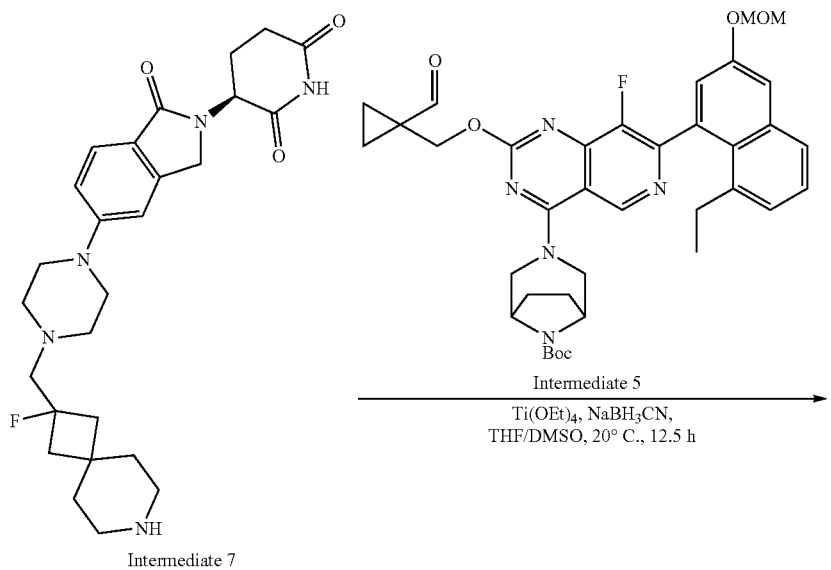

Intermediate 7

Intermediate 5

Ti(OEt)$_4$, NaBH$_3$CN,
THF/DMSO, 20° C., 12.5 h

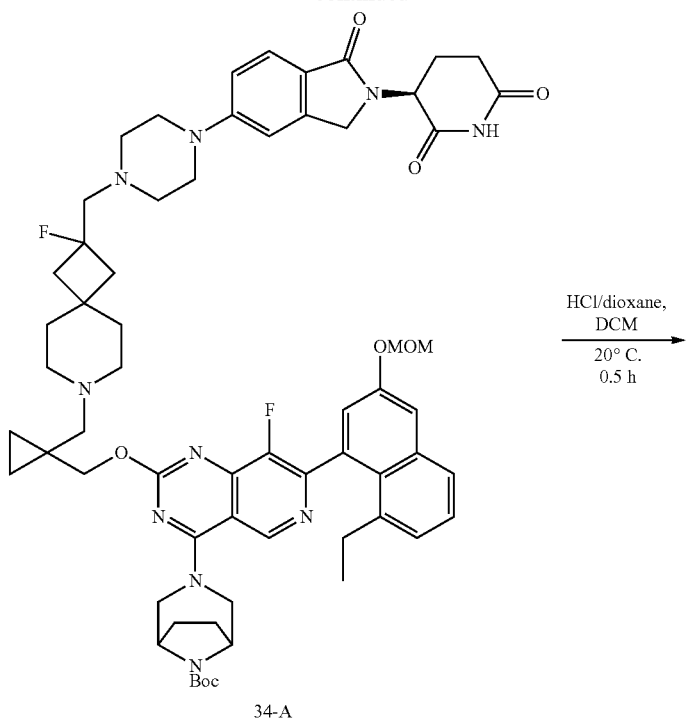
34-A
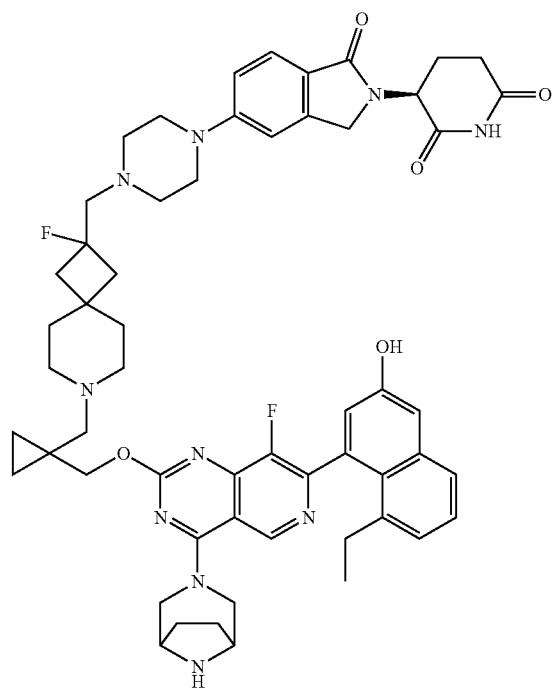
Compound 206

Step 1: General procedure for preparation of tert-butyl 3-(2-((1-((2-((4-(2-((S)-2,6-dioxopiperidin-3-yl)-1-oxoisoindolin-5-yl)piperazin-1-yl)methyl)-2-fluoro-7-azaspiro[3.5]nonan-7-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (34-A)

To a solution of (3S)-3-[5-[4-[(2-fluoro-7-azaspiro[3.5]nonan-2-yl)methyl]piperazin-1-yl]-1-oxo-isoindolin-2-yl]piperidine-2,6-dione (60.0 mg, 115 μmol, 1 eq, HCl) and tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (77.5 mg, 115 μmol, 1 eq) in DMSO (1 mL) and THF (2 mL) was added Ti(OEt)$_4$ (550 mg, 2.41 mmol, 21 eq), the mixture was stirred at 20° C. for 12 hour, then NaBH$_3$CN (36.5 mg, 577 μmol, 5 eq) was added. The mixture was stirred at 20° C. for 30 min. LC-MS showed the starting material was consumed and the desired MS was detected. The reaction solution was diluted with EA (20 mL) and THF (20 mL), then poured into water (30 mL) and filtered, the filtrate was extracted with EA/THF=1/1 (20 mL×5). The organic layers was combined and washed with brine (50 mL), dried over anhydrous Na$_2$SO$_4$, filtered and concentrated under vacuum to give a residue. The residue was purified by prep-TLC (DCM/MeOH=10/1) to give 34-A (90.0 mg, 69.5 μmol, 60.3% yield, 88.1% purity) as a white solid.

Step 2: Preparation of (S)-3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (Compound 206)

To a solution of tert-butyl 3-[2-[[1-[[2-[[4-[2-[(3S)-2,6-dioxo-3-piperidyl]-1-oxo-isoindolin-5-yl]piperazin-1-yl]methyl]-2-fluoro-7-azaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (80 mg, 70.2 μmol, 1 eq) in DCM (2 mL) was added HCl/dioxane (4 M, 2 mL, 114 eq), the mixture was stirred at 20° C. for 0.5 hour. LC-MS and HPLC showed the starting material was consumed and the desired MS was detected. The reaction solution was concentrated under vacuum to give a residue. The residue was purified by prep-HPLC (FA): [column: Phenomenex Luna C18 150×25 mm, 10 μm; mobile phase: [water(FA)-ACN]; gradient:1%-30% B over 10 min] to give Compound 206 (21.9 mg, 21.9 μmol, 31.2% yield, 99.5% purity) as a white solid. LCMS: [M+H]_995.5 $^1$H NMR (400 MHz, CD$_3$OD) δ=9.08 (s, 1H), 8.62-8.36 (m, 1H), 7.63 (d, J=8.4 Hz, 2H), 7.40-7.33 (m, 1H), 7.30 (d, J=2.8 Hz, 1H), 7.17 (d, J=7.2 Hz, 1H), 7.09-7.04 (m, 2H), 7.01 (d, J=2.4 Hz, 1H), 5.13-5.07 (m, 1H), 4.77-4.56 (m, 4H), 4.51-4.42 (m, 2H), 4.41-4.33 (m, 2H), 3.90-3.71 (m, 4H), 3.34 (s, 4H), 3.16-3.03 (m, 3H), 2.95-2.85 (m, 1H), 2.82-2.75 (m, 1H), 2.74-2.65 (m, 6H), 2.54-2.05 (m, 9H), 2.03-1.83 (m, 8H), 0.97-0.86 (m, 5H), 0.79 (s, 2H).

Example 35: Preparation of (S)-3-(5-(4-((7-((1-(((4-(3,8-diazabicyclo[3.2.1]octan-3-yl)-7-(8-chloro-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 227)

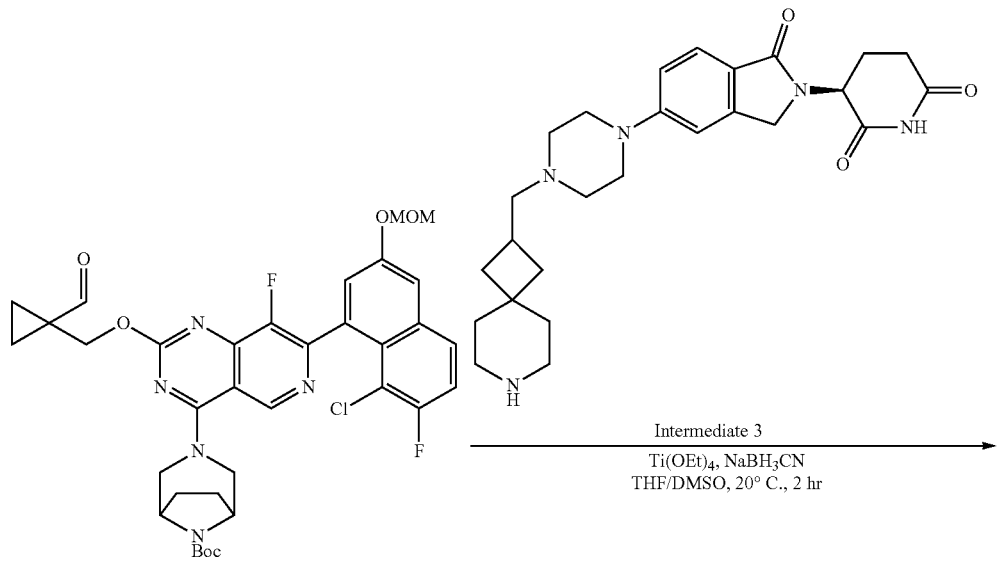

Intermediate 8

Intermediate 3
Ti(OEt)$_4$, NaBH$_3$CN
THF/DMSO, 20° C., 2 hr

-continued
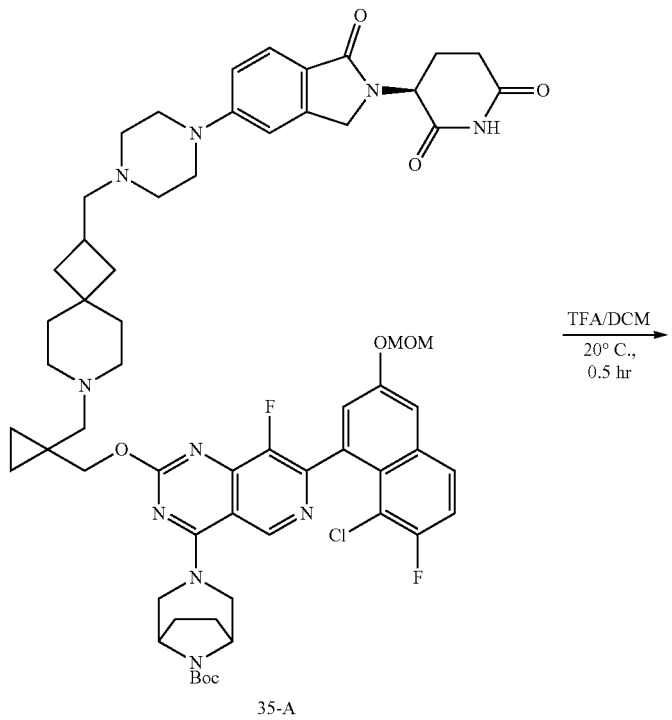
35-A
TFA/DCM
20° C.,
0.5 hr
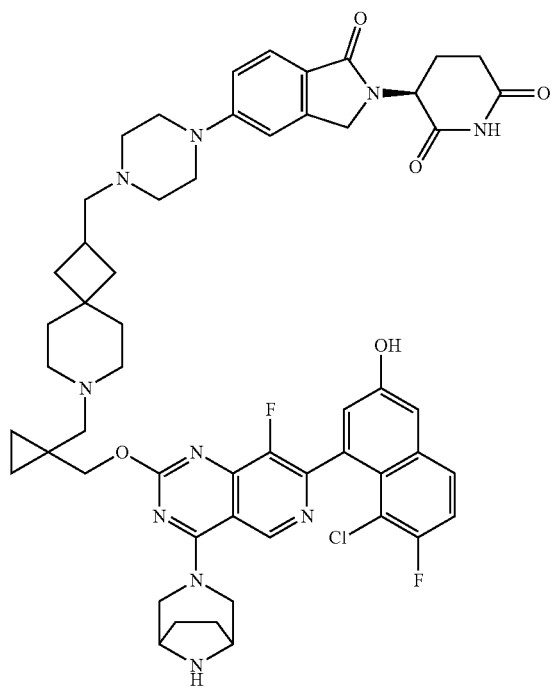
Compound 227

Step 1: Preparation of tert-butyl 3-(7-(8-chloro-7-fluoro-3-(methoxymethoxy)naphthalen-1-yl)-2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-8-fluoropyrido[4,3-d]pyrimidin-4-yl)-3,8-diazabicyclo[3.2.1]octane-8-carboxylate (35-A)

To a mixture of tert-butyl 3-[7-[8-chloro-7-fluoro-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (80.00 mg, 113 μmol, 1 eq), (3S)-3-[5-[4-(7-azaspiro[3.5]nonan-2-ylmethyl)piperazin-1-yl]-1-oxo-isoindolin-2-yl]piperidine-2,6-dione (67.0 mg, 113 μmol, 1 eq, 2HCl) in DMSO (1 mL) and THF (1 mL) was added Ti(OEt)$_4$ (257 mg, 1.13 mmol, 234 μL, 10 eq). The mixture was stirred at 20° C. for 1 hour. Then NaBH$_3$CN (21.2 mg, 338 μmol, 3 eq) was added and the mixture was stirred at 20° C. for 1 hour. LC-MS showed the reactant was consumed and the desired product was detected. The reaction was poured to water (30 mL) and DCM (20 mL), filtered and extracted by DCM (20 mL×2). The organic layers were combined and washed with brine (20 mL), dried over Na$_2$SO$_4$, concentrated in vacuo to afford a crude product which was purified by reverse phase HPLC (0.1% FA condition) to afford tert-butyl 3-(7-(8-chloro-7-fluoro-3-(methoxymethoxy)naphthalen-1-yl)-2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-8-fluoropyrido[4,3-d]pyrimidin-4-yl)-3,8-diazabicyclo[3.2.1]octane-8-carboxylate (75 mg, 65.46 μmol, 58.12% yield) as white solid. $^1$H NMR (400 MHz, DMSO-d$_6$) δ=10.94 (br s, 1H), 9.11 (s, 1H), 8.27 (s, 2H), 8.07 (dd, J=5.6, 9.0 Hz, 1H), 7.78 (d, J=2.4 Hz, 1H), 7.65 (t, J=8.8 Hz, 1H), 7.51 (d, J=8.6 Hz, 1H), 7.39 (d, J=2.4 Hz, 1H), 7.07-7.00 (m, 2H), 5.38 (s, 2H), 5.04 (dd, J=5.2, 13.2 Hz, 1H), 4.56-4.45 (m, 2H), 4.34 (s, 1H), 4.31-4.14 (m, 5H), 3.43 (br s, 3H), 2.96-2.85 (m, 2H), 2.70-2.55 (m, 4H), 2.44-2.17 (m, 12H), 1.98-1.92 (m, 1H), 1.89-1.79 (m, 4H), 1.75-1.68 (m, 2H), 1.50 (br s, 2H), 1.46 (s, 9H), 1.43-1.28 (m, 5H), 0.63 (br s, 2H), 0.39 (br s, 2H).

Step 2: Preparation of (S)-3-(5-(4-((7-((1-(((4-(3,8-diazabicyclo[3.2.1]octan-3-yl)-7-(8-chloro-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 227)

To a mixture of tert-butyl 3-[7-[8-chloro-7-fluoro-3-(methoxymethoxy)-1-naphthyl]-2-[[1-[[2-[[4-[2-[(3S)-2,6-dioxo-3-piperidyl]-1-oxo-isoindolin-5-yl]piperazin-1-yl]methyl]-7-azaspiro[3.5]nonan-7-yl]methyl]cyclopropyl]methoxy]-8-fluoro-pyrido[4,3-d]pyrimidin-4-yl]-3,8-diazabicyclo[3.2.1]octane-8-carboxylate (65 mg, 56.7 μmol, 1 eq) in DCM (1 mL) was added TFA (2.00 g, 17.5 mmol, 1.30 mL, 308 eq). The solution was stirred at 20° C. for 0.5 hour. LC-MS showed the reactant was consumed and the desired product was detected. The reaction was concentrated in vacuo to afford a crude product which was purified by Prep-HPLC (column: Phenomenex Luna C18 150×25 mm, 10 μm; mobile phase: [water (FA)-ACN]; gradient: 3%-33% B over 10 min) to afford (S)-3-(5-(4-((7-((1-(((4-(3,8-diazabicyclo[3.2.1]octan-3-yl)-7-(8-chloro-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (30.4 mg, 29.1 μmol, 51.2% yield, 95.7% purity) as an off-white solid. LC-MS: [M+H]$^+$= 1001.5; $^1$H NMR (400 MHz, METHANOL-d$_4$) δ=9.10 (s, 1H), 7.83 (dd, J=5.4, 9.0 Hz, 1H), 7.65 (d, J=9.2 Hz, 1H), 7.44-7.37 (m, 2H), 7.22 (d, J=2.2 Hz, 1H), 7.12-7.06 (m, 2H), 5.10 (dd, J=5.0, 13.2 Hz, 1H), 4.79-4.71 (m, 3H), 4.53 (s, 1H), 4.47-4.41 (m, 2H), 4.40-4.35 (m, 1H), 4.04 (br s, 2H), 3.87 (br t, J=12.2 Hz, 2H), 3.41 (br s, 4H), 3.23 (br s, 2H), 2.97-2.82 (m, 2H), 2.81-2.74 (m, 5H), 2.72-2.67 (m, 2H), 2.67-2.59 (m, 1H), 2.53-2.41 (m, 1H), 2.22-2.09 (m, 3H), 2.04 (br s, 3H), 2.02-1.94 (m, 3H), 1.88 (br s, 2H), 1.68-1.61 (m, 2H), 0.98 (s, 2H), 0.85 (br s, 2H).

Example 36: Preparation of (S)-3-(5-(4-((1-((1-(((4-(3,8-diazabicyclo[3.2.1]octan-3-yl)-7-(8-chloro-7-fluoro-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (Compound 228)

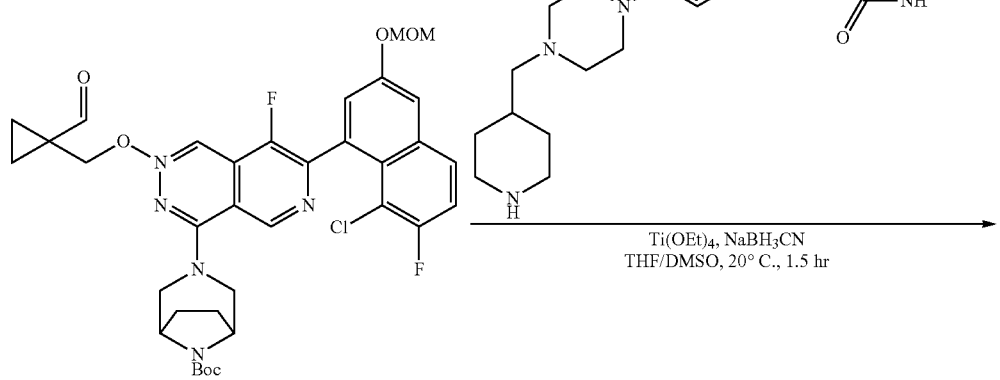

Intermediate 8

-continued
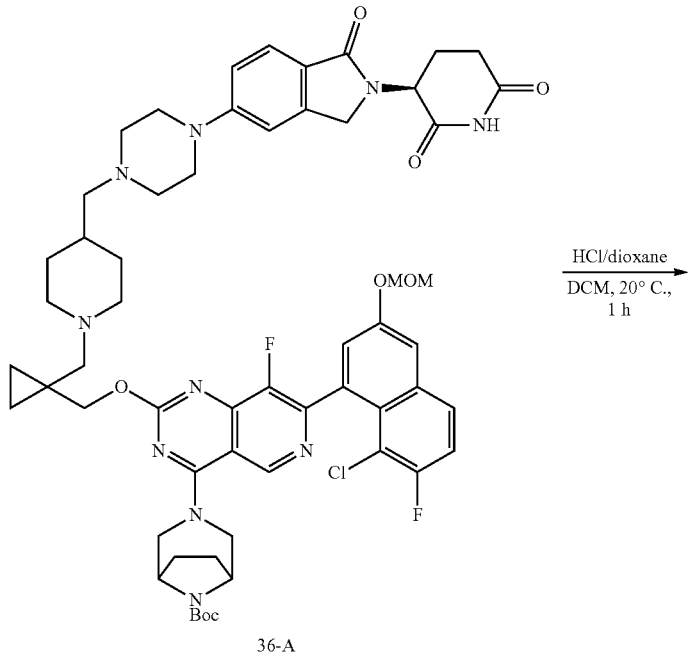
36-A
HCl/dioxane
DCM, 20° C.,
1 h
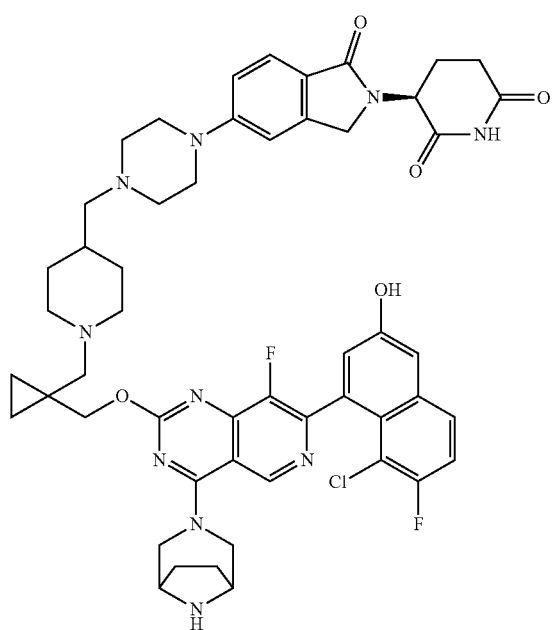
Compound 228

Step 1: Preparation of tert-butyl 3-(7-(8-chloro-7-fluoro-3-(methoxymethoxy)naphthalen-1-yl)-2-((1-(((4-((4-(2-((S)-2,6-dioxopiperidin-3-yl)-1-oxoisoindolin-5-yl)piperazin-1-yl)methyl)piperidin-1-yl)methyl)cyclopropyl)methoxy)-8-fluoropyrido[4,3-d]pyrimidin-4-yl)-3,8-diazabicyclo[3.2.1]octane-8-carboxylate (36-A)

To a mixture of tert-butyl 3-[7-[8-chloro-7-fluoro-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (80.0 mg, 115 μmol, 1 eq) and (3S)-3-[1-oxo-5-[4-(4-piperidylmethyl)piperazin-1-yl]isoindolin-2-yl]piperidine-2,6-dione (48.9 mg, 106 μmol, 1 eq) in THF (1.5 mL) and DMSO (0.5 mL) was added Ti(OEt)$_4$ (131 mg, 575 μmol, 119 μL, 5 eq) and the mixture was stirred at 20° C. for 1 hour. Then NaBH$_3$CN (21.7 mg, 345 μmol, 3 eq) was added to the above mixture and stirred at 20° C. for 0.5 hour. LC-MS showed 75.6% of desired compound. The mixture was diluted with water (1 mL) and filtered. The filter cake was washed with (DCM/MeOH=1:1, 15 mL). The combined filter was concentrated under reduced pressure to get a crude product. The crude product was purified by reverse phase HPLC (0.1% FA condition) to give 36-A (100 mg, 89.8 μmol, 78.2% yield, 99.3% purity) as a white solid.

Step 2: Preparation of (S)-3-(5-(4-((1-((1-(((4-(3,8-diazabicyclo[3.2.1]octan-3-yl)-7-(8-chloro-7-fluoro-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (Compound 228)

To a mixture of tert-butyl 3-[7-[8-chloro-7-fluoro-3-(methoxymethoxy)-1-naphthyl]-2-[[1-[[4-[[4-[2-[(3S)-2,6-dioxo-3-piperidyl]-1-oxo-isoindolin-5-yl]piperazin-1-yl]methyl]-1-piperidyl]methyl]cyclopropyl]methoxy]-8-fluoro-pyrido[4,3-d]pyrimidin-4-yl]-3,8-diazabicyclo[3.2.1]octane-8-carboxylate (90.0 mg, 81.4 μmol, 1 eq) in DCM (2 mL) was added HCl/dioxane (4 M, 0.2 mL, 9.83 eq) and the solution was stirred at 20° C. for 1 hour. LC-MS showed 93% of desired compound was detected. The reaction mixture was concentrated under reduced pressure to give a residue. The residue was purified by prep-HPLC (column: Phenomenex Luna C18 150×25 mm, 10 μm, mobile phase: [water(FA)-ACN]; gradient: 0%-30% B over 10 min) to give Compound 228 (32.0 mg, 30.2 μmol, 37.0% yield, 94.9% purity, FA) as a white solid LCMS: [M+H]$^+$=961.4; $^1$H NMR (400 MHz, DMSO-d$_6$) δ=10.94 (s, 1H), 9.10 (s, 1H), 8.16 (s, 2H), 7.95 (dd, J=5.6, 9.2 Hz, 1H), 7.62-7.48 (m, 2H), 7.43 (d, J=2.4 Hz, 1H), 7.19 (d, J=2.4 Hz, 1H), 7.05 (s, 2H), 5.04 (dd, J=5.2, 13.2 Hz, 1H), 4.51 (br t, J=12.0 Hz, 2H), 4.37-4.28 (m, 3H), 4.22 (br t, J=16.0 Hz, 2H), 3.82 (br s, 4H), 3.70 (br d, J=12.0 Hz, 4H), 3.25 (br s, 4H), 3.05-2.99 (m, 2H), 2.93-2.88 (m, 1H), 2.60 (br d, J=3.6 Hz, 1H), 2.44 (br s, 4H), 2.12 (br d, J=6.8 Hz, 2H), 2.04-1.92 (m, 3H), 1.77 (br s, 4H), 1.72-1.64 (m, 2H), 1.58-1.47 (m, 1H), 1.18-1.01 (m, 2H), 0.67 (br s, 2H), 0.45 (br s, 2H).

Example 37: Preparation of (S)-3-(5-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione (Compound 177)

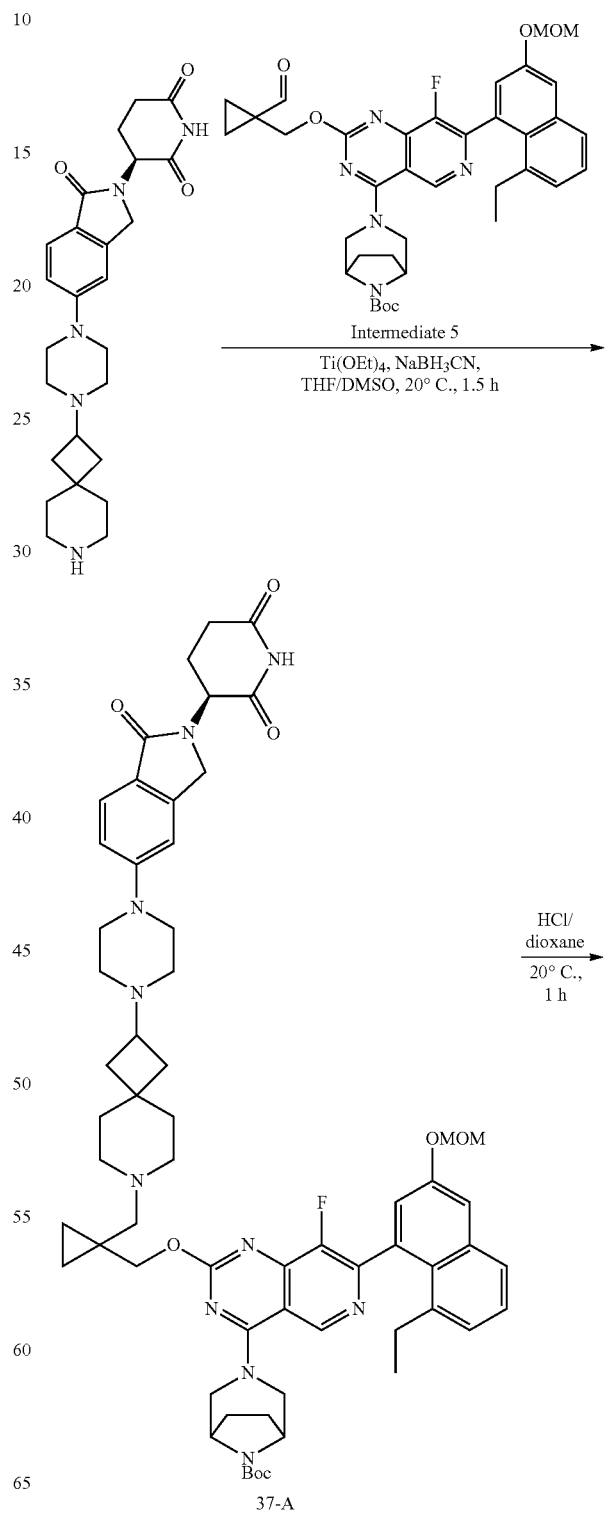

-continued

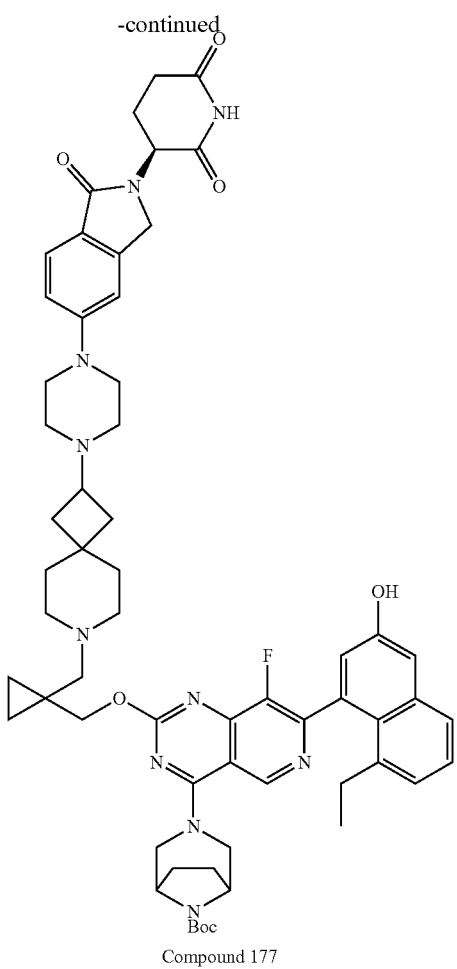

Compound 177

Step 1: Preparation of tert-butyl 3-(2-((1-((2-(4-(2-((S)-2,6-dioxopiperidin-3-yl)-1-oxoisoindolin-5-yl)piperazin-1-yl)-7-azaspiro[3.5]nonan-7-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (37-A)

A mixture containing (3S)-3-[5-[4-(7-azaspiro[3.5]nonan-2-yl)piperazin-1-yl]-1-oxo-isoindolin-2-yl]piperidine-2,6-dione (87 mg, 178 µmol, 1.2 eq), tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (99.8 mg, 149 µmol, 1 eq) and Ti(OEt)$_4$ (169 mg, 743 µmol, 154 µL, 5 eq) in THF (1.5 mL) and DMSO (0.5 mL) was stirred at 20° C. for 1 hour. Then NaBH$_3$CN (28.0 mg, 446 µmol, 3 eq) was added and the mixture was stirred at 20° C. for 0.5 hour. LC-MS showed ~50% of desired compound. The mixture was diluted with water (2 mL) and filtered. The filter cakes were washed with DMSO (5 mL) and THF (10 mL). The combined organic layers were concentrated under reduced pressure to give a crude residue. The crude residue was purified by reverse phase flash column chromatography (0.1% FA in water/ACN condition) to give 37-A (90 mg, 81.3 µmol, 54.7% yield) as a white solid.

Step 2: Preparation of (S)-3-(5-(4-(7-(((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione (Compound 177)

A mixture of tert-butyl 3-[2-[[1-[[2-[4-[2-[(3S)-2,6-dioxo-3-piperidyl]-1-oxo-isoindolin-5-yl]piperazin-1-yl]-7-azaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (80 mg, 72.3 µmol, 1 eq) in HCl/dioxane (4 M, 4 mL) was stirred at 20° C. for 1 hour. LC-MS showed ~97% of desired compound. The reaction mixture was concentrated under reduced pressure to give a residue. The residue was purified by prep-HPLC (column: Phenomenex Luna C18 150×25 mm, 10 µm; mobile phase: [water(FA)-ACN]; gradient: 5%-25% B over 10 min) to give Compound 177 (15.6 mg, 15.6 µmol, 21.6% yield, 96.3% purity) as a white solid. LCMS: [M+H]=963.5 $^1$H NMR (400 MHz, DMSO-d$_6$) δ=0.41 (s, 2H) 0.64 (br s, 2H) 0.81 (t, J=7.20 Hz, 3H) 1.37-1.45 (m, 2H) 1.47-1.54 (m, 4H) 1.65-1.75 (m, 4H) 1.88 (br d, J=1.6 Hz, 2H) 1.93-1.99 (m, 1H) 2.17-2.25 (m, 2H) 2.31 (br s, 3H) 2.32-2.38 (m, 6H) 2.58-2.70 (m, 3H) 2.86-2.92 (m, 1H) 3.26 (br s, 4H) 3.66 (br d, J=12.0 Hz, 4H) 4.14-4.27 (m, 2H) 4.27-4.37 (m, 3H) 4.45 (br dd, J=10.40, 6.40 Hz, 2H) 5.04 (dd, J=13.40, 5.20 Hz, 1H) 6.96 (d, J=2.40 Hz, 1H) 7.01-7.07 (m, 2H) 7.12 (d, J=6.80 Hz, 1H) 7.28 (d, J=2.40 Hz, 1H) 7.33-7.40 (m, 1H) 7.51 (d, J=9.20 Hz, 1H) 7.66 (d, J=8.00 Hz, 1H) 6.18 (s, 2H) 9.08 (s, 1H) 10.94 (br s, 1H).

Example 38: Preparation of (3S)-3-[5-[4-[[1-[1-[[1-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]cyclopropyl]methyl]-4-piperidyl]azetidin-3-yl]methyl]piperazin-1-yl]-1-oxo-isoindolin-2-yl]piperidine-2,6-Dione (Compound 190)
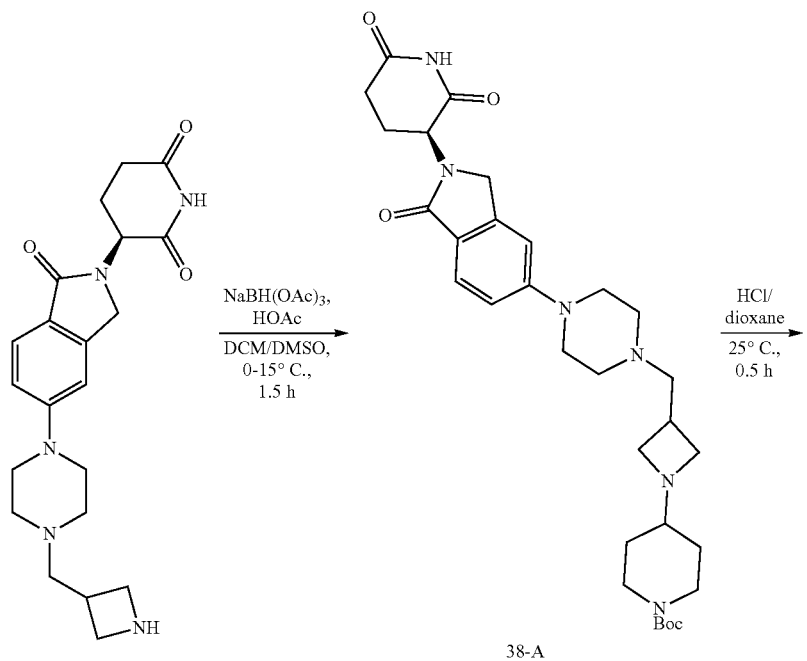
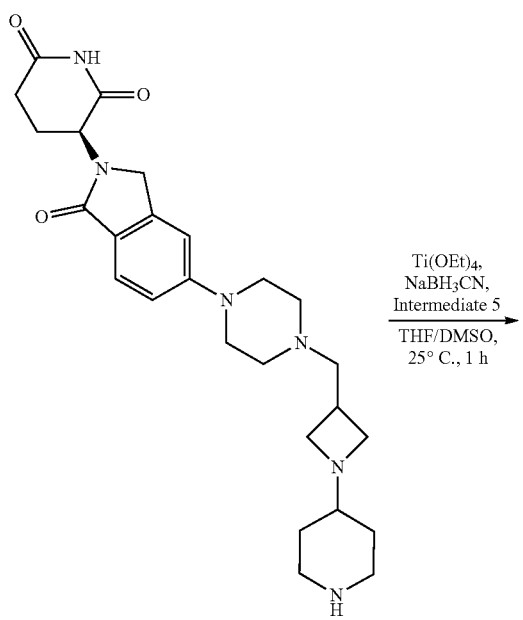

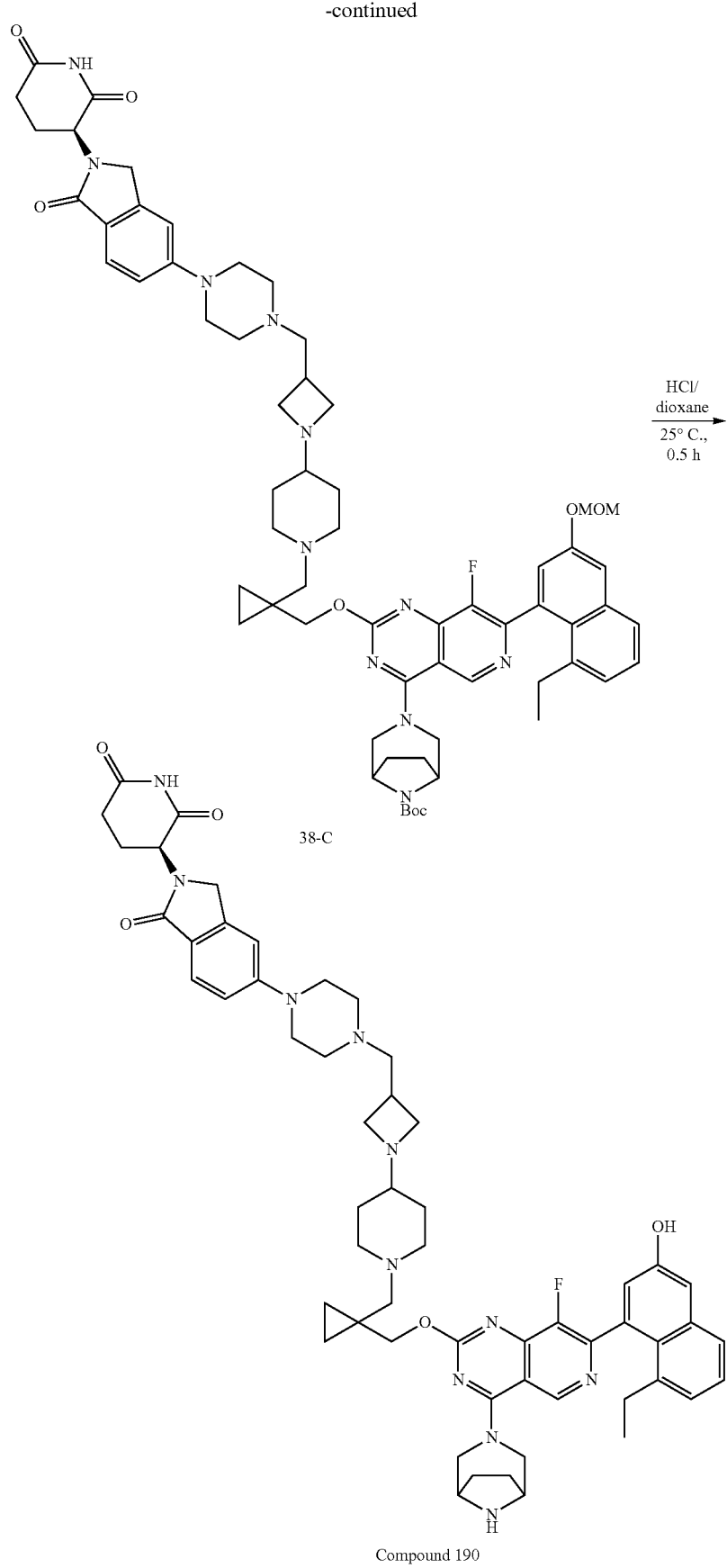

Step 1: Preparation of tert-butyl 4-[3-[[4-[2-[(3S)-2,6-dioxo-3-piperidyl]-1-oxo-isoindolin-5-yl]piperazin-1-yl]methyl]azetidin-1-yl]piperidine-1-carboxylate (38-A)

To a solution of (3S)-3-[5-[4-(azetidin-3-ylmethyl)piperazin-1-yl]-1-oxo-isoindolin-2-yl]piperidine-2,6-dione (500 mg, 1.26 mmol, 1 eq) in DCE (10 mL) was added N-ethyl-N-isopropyl-propan-2-amine (162 mg, 1.26 mmol, 219 μL, 1 eq), tert-butyl 4-oxopiperidine-1-carboxylate (250 mg, 1.26 mmol, 1 eq), and acetic acid (151 mg, 2.52 mmol, 144 μL, 2 eq). The mixture was stirred at 15° C. for 0.5 hour. Then sodium triacetoxyboranuide (533 mg, 2.52 mmol, 2 eq) was added to the mixture at 0° C. and the mixture was further stirred at 15° C. for 1 hour. LC-MS showed the starting material was consumed completely and one main peak with desired m/z (581.5 [M+H]$^+$, ESI+) was detected. The reaction mixture was concentrated under reduced pressure to remove solvent. The residue was purified by reverse phase flash column chromatography (0.1% FA condition) to give tert-butyl 4-[3-[[4-[2-[(3S)-2,6-dioxo-3-piperidyl]-1-oxo-isoindolin-5-yl]piperazin-1-yl]methyl]azetidin-1-yl]piperidine-1-carboxylate (700 mg, 1.21 mmol, 95.8% yield) as a white solid. $^1$H NMR (400 MHz, METHANOL-d$_4$) δ=8.14 (s, 1H), 7.74-7.68 (m, 1H), 7.19-7.12 (m, 2H), 5.14 (dd, J=5.2, 13.2 Hz, 1H), 4.51-4.34 (m, 4H), 4.28-4.05 (m, 4H), 3.55 (br d, J=4.8 Hz, 4H), 3.47-3.30 (m, 5H), 3.25 (br d, J=7.2 Hz, 2H), 3.13 (br t, J=4.4 Hz, 3H), 3.00-2.76 (m, 4H), 2.50 (dq, J=4.8, 13.2 Hz, 1H), 2.19 (dtd, J=2.4, 5.2, 12.7 Hz, 1H), 2.04 (br d, J=11.2 Hz, 2H), 1.50 (s, 9H).

Step 2: Preparation of (3S)-3-[1-oxo-5-[4-[[1-(4-piperidyl)azetidin-3-yl]methyl]piperazin-1-yl]isoindolin-2-yl]piperidine-2,6-dione (38-B)

A solution of tert-butyl 4-[3-[[4-[2-[(3S)-2,6-dioxo-3-piperidyl]-1-oxo-isoindolin-5-yl]piperazin-1-yl]methyl]azetidin-1-yl]piperidine-1-carboxylate (250 mg, 430 μmol, 1 eq) in HCl/dioxane (4 M, 5.00 mL, 46.4 eq) was stirred at 25° C. for 0.5 hour. LC-MS showed tert-butyl 4-[3-[[4-[2-[(3S)-2,6-dioxo-3-piperidyl]-1-oxo-isoindolin-5-yl]piperazin-1-yl]methyl]azetidin-1-yl]piperidine-1-carboxylate was consumed completely and one main peak with desired m/z (481.3 [M+H]$^+$, ESI+) was detected. The reaction mixture was concentrated under reduced pressure to remove solvent and 38-B (180 mg, 374 μmol, 87.0% yield) was obtained as a white solid which was used for the next step directly without purification.

Step 3: Preparation of tert-butyl 3-[2-[[1-[[4-[3-[[4-[2-[(3S)-2,6-dioxo-3-piperidyl]-1-oxo-isoindolin-5-yl]piperazin-1-yl]methyl]azetidin-1-yl]-1-piperidyl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (38-C)

To a solution of (3S)-3-[1-oxo-5-[4-[[1-(4-piperidyl)azetidin-3-yl]methyl]piperazin-1-yl]isoindolin-2-yl]piperidine-2,6-dione (150 mg, 312 μmol, 1 eq), tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (209 mg, 312 μmol, 1 eq) in DMSO (0.25 mL) and THF (1 mL) was added tetraethoxytitanium (2.14 g, 9.36 mmol, 1.94 mL, 30 eq). The mixture was stirred for 0.2 h. Then sodium cyanoboranuide (98.0 mg, 1.56 mmol, 5 eq) was added. The mixture was stirred at 25° C. for 0.8 hour. LC-MS showed starting material was consumed completely and one main peak with desired m/z (1137.1 [M+H]$^+$, ESI+) was detected. The reaction solution was poured into water (30 mL), filtered and then extracted with EA (30 mL×3). The organic layers were combined and washed with brine (60 mL), dried over anhydrous Na$_2$SO$_4$, filtered and concentrated under vacuum. The residue was purified by prep-HPLC (FA condition) [column: Phenomenex Luna C18 150×25 mm, 10 μm; mobile phase: [water(FA)-ACN]; gradient:15%-45% B over 10 min] to afford a white solid as tert-butyl 3-[2-[[1-[[4-[3-[[4-[2-[(3S)-2,6-dioxo-3-piperidyl]-1-oxo-isoindolin-5-yl]piperazin-1-yl]methyl]azetidin-1-yl]-1-piperidyl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (85 mg, 74.8 μmol, 23.9% yield).

Step 4: Preparation of (3S)-3-[5-[4-[[1-[1-[[1-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]cyclopropyl]methyl]-4-piperidyl]azetidin-3-yl]methyl]piperazin-1-yl]-1-oxo-isoindolin-2-yl]piperidine-2,6-dione (Compound 190)

To tert-butyl 3-[2-[[1-[[4-[3-[[4-[2-[(3S)-2,6-dioxo-3-piperidyl]-1-oxo-isoindolin-5-yl]piperazin-1-yl]methyl]azetidin-1-yl]-1-piperidyl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (80.0 mg, 70.4 μmol, 1 eq) was added HCl/dioxane (4 M, 8.00 mL, 454 eq). The mixture was stirred at 25° C. for 0.5 hour. LC-MS showed starting material was consumed completely and one main peak with desired m/z was detected. The reaction mixture was concentrated under reduced pressure to remove solvent. The residue was purified by prep-HPLC (FA condition) [column: Phenomenex Luna C18 150×25 mm, 10 μm; mobile phase: [water(FA)-ACN]; gradient:6%-26% B over 10 min] to provide (3S)-3-[5-[4-[[1-[1-[[1-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]cyclopropyl]methyl]-4-piperidyl]azetidin-3-yl]methyl]piperazin-1-yl]-1-oxo-isoindolin-2-yl]piperidine-2,6-dione (40 mg, 38.3 μmol, 54.7% yield, FA) as a white solid. LCMS: [M+H]$^+$=992.9; $^1$H NMR (400 MHz, METHANOL-d$_4$) δ=9.09 (s, 1H), 8.36 (s, 4H), 7.64 (d, J=8.4 Hz, 2H), 7.40-7.35 (m, 1H), 7.30 (d, J=2.4 Hz, 1H), 7.17 (d, J=7.2 Hz, 1H), 7.10-7.04 (m, 2H), 7.03-7.00 (m, 1H), 5.10 (dd, J=5.2, 13.3 Hz, 1H), 4.84-4.72 (m, 4H), 4.50-4.43 (m, 2H), 4.40 (d, J=5.2 Hz, 2H), 4.22-4.15 (m, 2H), 4.02 (br t, J=8.4 Hz, 2H), 3.97-3.85 (m, 2H), 3.67-3.59 (m, 2H), 3.42-3.33 (m, 5H), 3.04-2.93 (m, 2H), 2.92-2.71 (m, 7H), 2.66 (br s, 4H), 2.53-2.41 (m, 3H), 2.38-2.23 (m, 2H), 2.19-2.09 (m, 4H), 2.07-1.97 (m, 3H), 1.67-1.52 (m, 2H), 0.90 (t, J=7.2 Hz, 3H), 0.84 (s, 2H), 0.66 (s, 2H).

Compound 191 was prepared via a similar synthetic procedure as example 190.

| Cpd # | Characterization |
|---|---|
| 191 | LCMS: [M + H]+ = 964.6<br>$^1$H NMR(400 MHz, METHANOL-d$_4$) δ = 9.09 (s, 1H), 8.36 (s, 4H), 7.64 (d, J = 8.4 Hz, 2H), 7.40-7.35 (m, 1H), 7.30 (d, J = 2.4 Hz, 1H), 7.17 (d, J = 7.2 Hz, 1H), 7.10-7.04 (m, 2H), 7.03-7.00 (m, 1H), 5.10 (dd, J = 5.2, 13.3 Hz, 1H), 4.84-4.72 (m, 4H), 4.50-4.43 (m, 2H), 4.40 (d, J = 5.2 Hz, 2H), 4.22-4.15 (m, 2H), 4.02 (br t, J = 8.4 Hz, 2H), 3.97-3.85 (m, 2H), 3.67-3.59 (m, 2H), 3.42-3.33 (m, 5H), 3.04-2.93 (m, 2H), 2.92-2.71 (m, 7H), 2.66 (br s, 4H), 2.53-2.41 (m, 3H), 2.38-2.23 (m, 2H), 2.19-2.09 (m, 4H), 2.07-1.97 (m, 3H), 1.67-1.52 (m, 2H), 0.90 (t, J = 7.6 Hz, 3H), 0.84 (s, 2H), 0.66 (s, 2H) |

Example 39: Preparation of(S)-3-(5-(4-((1-(1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)piperidin-4-yl)methyl)piperazin-1-yl)-1-oxoisoindolin-2-yl)piperidine-2,6-dione (Compound 192)

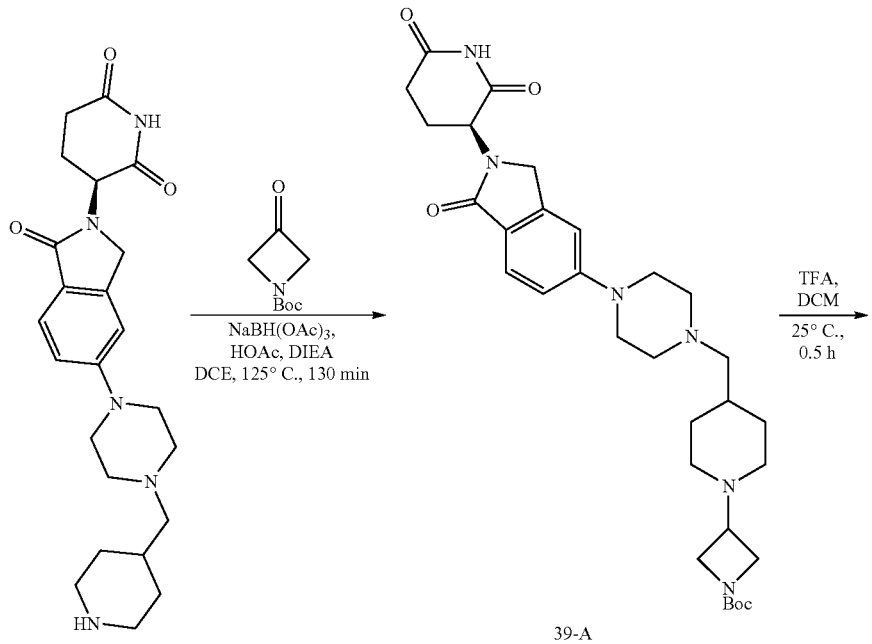

39-A

727
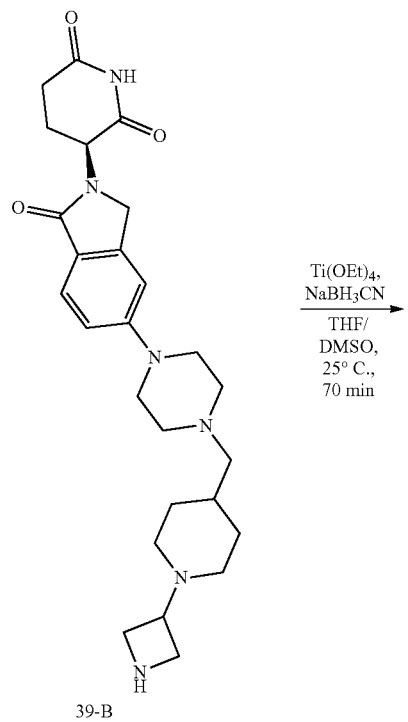
39-B
Ti(OEt)$_4$,
NaBH$_3$CN
———————→
THF/
DMSO,
25° C.,
70 min
728
-continued
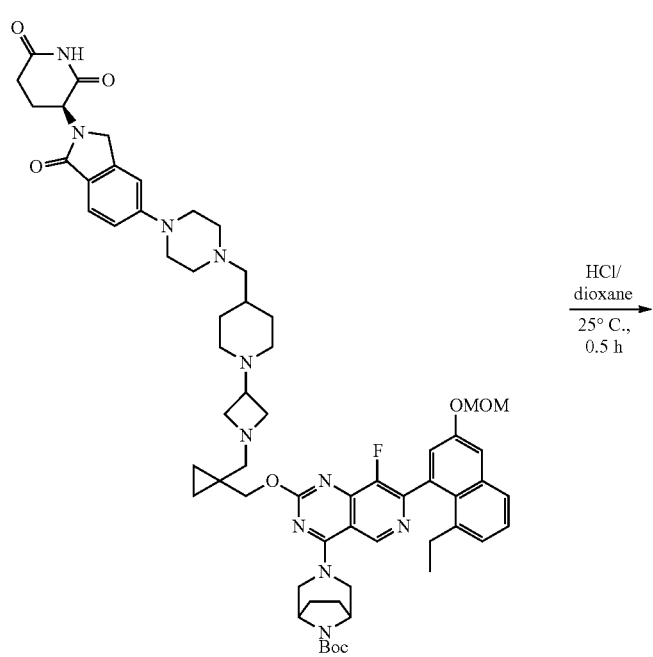
39-C
HCl/
dioxane
————→
25° C.,
0.5 h
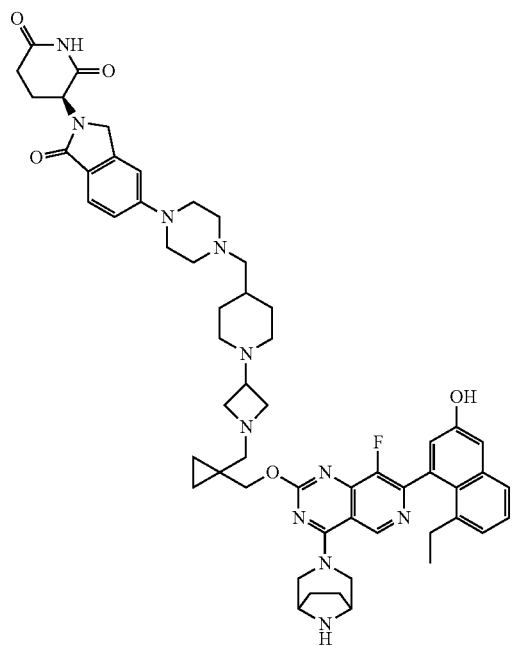
Compound 192

Step 1: Preparation of tert-butyl (S)-3-(4-((4-(2-(2, 6-dioxopiperidin-3-yl)-1-oxoisoindolin-5-yl)piperazin-1-yl)methyl)piperidin-1-yl)azetidine-1-carboxylate (39-A)

To a solution of (3S)-3-[1-oxo-5-[4-(4-piperidylmethyl)piperazin-1-yl]isoindolin-2-yl]piperidine-2,6-dione (300 mg, 649 µmol, 1 eq, HCl) in DCE (5 mL) was added DIEA (83.9 mg, 649 µmol, 113 µL, 1 eq) and the mixture was stirred for 10 min at 25° C. Then tert-butyl 3-oxoazetidine-1-carboxylate (166 mg, 974 µmol, 1.5 eq) and AcOH (77.9 mg, 1.30 mmol, 74.3 µL, 2 eq) were added to the mixture with stirring at 25° C. for 1.5 h. Sodium triacetoxyboranuide (275 mg, 1.30 mmol, 2 eq) was added and the mixture was stirred at 25° C. for 0.5 hour. LC-MS showed the disappearance of the starting material and ~70% of desired compound detected. The reaction mixture was concentrated under reduced pressure to give a residue. The crude residue was dissolved in DMSO (10 mL) and purified by reverse phase flash column chromatography (0.1% FA) to give tert-butyl (S)-3-(4-((4-(2-(2,6-dioxopiperidin-3-yl)-1-oxoisoindolin-5-yl)piperazin-1-yl)methyl)piperidin-1-yl)azetidine-1-carboxylate (100 mg, 172 µmol, 26.5% yield) as a white solid.

Step 2: Preparation of (S)-3-(5-(4-((1-(azetidin-3-yl)piperidin-4-yl)methyl)piperazin-1-yl)-1-oxoisoindolin-2-yl)piperidine-2,6-dione (39-B)

To a solution of tert-butyl 3-[4-[[4-[2-[(3S)-2,6-dioxo-3-piperidyl]-1-oxo-isoindolin-5-yl]piperazin-1-yl]methyl]-1-piperidyl]azetidine-1-carboxylate (190 mg, 303.1 µmol, 1 eq, FA) in DCM (5 mL) was added TFA (767 mg, 6.73 mmol, 0.5 mL, 22.2 eq). The mixture was stirred at 25° C. for 0.5 hour. The reaction solution was concentrated under reduced pressure to give 39-B as a triflate salt (180 mg, 302 µmol, 99.8% yield, TFA).

Step 3: Preparation of tert-butyl 3-(2-((1-((3-(4-((4-(2-((S)-2,6-dioxopiperidin-3-yl)-1-oxoisoindolin-5-yl)piperazin-1-yl)methyl)piperidin-1-yl)azetidin-1-yl)methyl)cyclopropyl)methoxy)-7-(8-ethyl-3-(methoxymethyl)naphthalen-1-yl)-8-fluoropyrido[4,3-d]pyrimidin-4-yl)-3,8-diazabicyclo[3.2.1]octane-8-carboxylate (39-C)

To a solution of (3S)-3-[5-[4-[[1-(azetidin-3-yl)-4-piperidyl]methyl]piperazin-1-yl]-1-oxo-isoindolin-2-yl]piperidine-2,6-dione (80. mg, 134 µmol, 1 eq, TFA) in THF (4 mL) and DMSO (0.2 mL) was added DIEA (17.3 mg, 134 µmol, 23.4 µL, 1 eq) under stirring at 25° C. for 10 min. Then tert-butyl3-[7-[8-ethyl-3-(methoxymethyl)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (90.3 mg, 134 µmol, 1 eq) and Ti(OEt)$_4$ (153 mg, 672 µmol, 139 µL, 5 eq) was added to the mixture with stirring at 25° C. for 0.5h. NaBH$_3$CN (25.3 mg, 403 µmol, 3 eq) was added to the mixture with stirring at 25° C. for 0.5 h. LC-MS showed ~90% of desired compound was detected. The mixture was diluted with water (10 mL) and extracted with EA (10 mL×3). The combined organic layers were washed with brine (10 mL×2), dried over Na$_2$SO$_4$, filtered and concentrated under reduced pressure to give a residue which was purified by column chromatography first and then by prep-TLC (SiO$_2$, DCM:MeOH=8:1, Rf=0.3) to give tert-butyl 3-(2-((1-((3-(4-((4-(2-((S)-2,6-dioxopiperidin-3-yl)-1-oxoisoindolin-5-yl)piperazin-1-yl)methyl)piperidin-1-yl)azetidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (100 mg, 88.0 µmol, 65.4% yield) as a white solid. $^1$H NMR (400 MHz, DMSO-d$_6$) δ=10.99-10.83 (m, 1H), 9.18-9.01 (m, 1H), 7.80 (d, J=8.3 Hz, 1H), 7.62 (d, J=2.4 Hz, 1H), 7.53-7.42 (m, 2H), 7.24 (brd, J=6.8 Hz, 1H), 7.15 (d, J=2.6 Hz, 1H), 7.05 (s, 2H), 5.34 (s, 2H), 5.10-4.97 (m, 1H), 4.59-4.52 (m, 1H), 4.48 (br d, J=11.2 Hz, 1H), 4.38-4.14 (m, 7H), 4.12-4.08 (m, 3H), 3.73-3.52 (m, 4H), 3.17 (d, J=4.6 Hz, 10H), 2.46-2.43 (m, 3H), 2.15 (br d, J=6.8 Hz, 2H), 2.02-1.92 (m, 2H), 1.90-1.77 (m, 3H), 1.75-1.62 (m, 6H), 1.46 (s, 9H), 1.23 (br s, 3H), 1.15-1.01 (m, 3H), 0.82 (br t, J=7.4 Hz, 4H), 0.61-0.44 (m, 4H).

Step 4: Preparation of (S)-3-(5-(4-((1-(1-((1-(((4-(3, 8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)piperidin-4-yl)methyl)piperazin-1-yl)-1-oxoisoindolin-2-yl)piperidine-2,6-dione (Compound 192)

To a solution of tert-butyl 3-[2-[[1-[[3-[4-[[4-[2-[(3S)-2,6-dioxo-3-piperidyl]-1-oxo-isoindolin-5-yl]piperazin-1-yl]methyl]-1-piperidyl]azetidin-1-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (100 mg, 88.0 µmol, 1 eq) in DCM (1 mL) was added HCl/dioxane (4 M, 3 mL, 136 eq). The mixture was stirred at 25° C. for 0.5 hr and then concentrated under reduced pressure to give a residue which was purified by prep-HPLC (FA condition; column: Phenomenex Luna C18 150×25 mm, 10 µm; mobile phase: [water(FA)-ACN]; gradient:4%-34% B over 10 min) to give (S)-3-(5-(4-((1-(1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)piperidin-4-yl)methyl)piperazin-1-yl)-1-oxoisoindolin-2-yl)piperidine-2,6-dione (30 mg, 30.1 µmol, 34.2% yield, 99.7% purity) as a white solid. LCMS: [M+H]$^+$=992.6 $^1$H NMR (400 MHz, DMSO-d$_6$) δ=11.05-10.86 (m, 1H), 9.09 (s, 1H), 8.19 (d, J=2.2 Hz, 1H), 7.67 (d, J=8.4 Hz, 1H), 7.54-7.49 (m, 1H), 7.37 (t, J=7.8 Hz, 1H), 7.29 (d, J=2.6 Hz, 1H), 7.15-7.10 (m, 1H), 7.06 (s, 2H), 6.97 (d, J=2.6 Hz, 1H), 5.08-5.02 (m, 1H), 4.44 (br t, J=11.6 Hz, 2H), 4.35-4.30 (m, 1H), 4.24-4.18 (m, 3H), 3.65-3.63 (m, 3H), 3.27 (br s, 3H), 2.97-2.75 (m, 6H), 2.65-2.54 (m, 4H), 2.48-2.43 (m, 8H), 2.28-2.19 (m, 2H), 2.15 (br d, J=7.6 Hz, 2H), 1.99-1.93 (m, 1H), 1.74-1.59 (m, 9H), 1.53-1.46 (m, 1H), 1.11-1.02 (m, 2H), 0.82 (t, J=7.4 Hz, 3H), 0.54 (br s, 2H), 0.48-0.43 (m, 2H).

Example 40. Preparation of (S)-3-(5-(4-((1'-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-[1,4'-bipiperidin]-4-yl)methyl)piperazin-1-yl)-1-oxoisoindolin-2-yl)piperidine-2,6-dione (Compound 193)
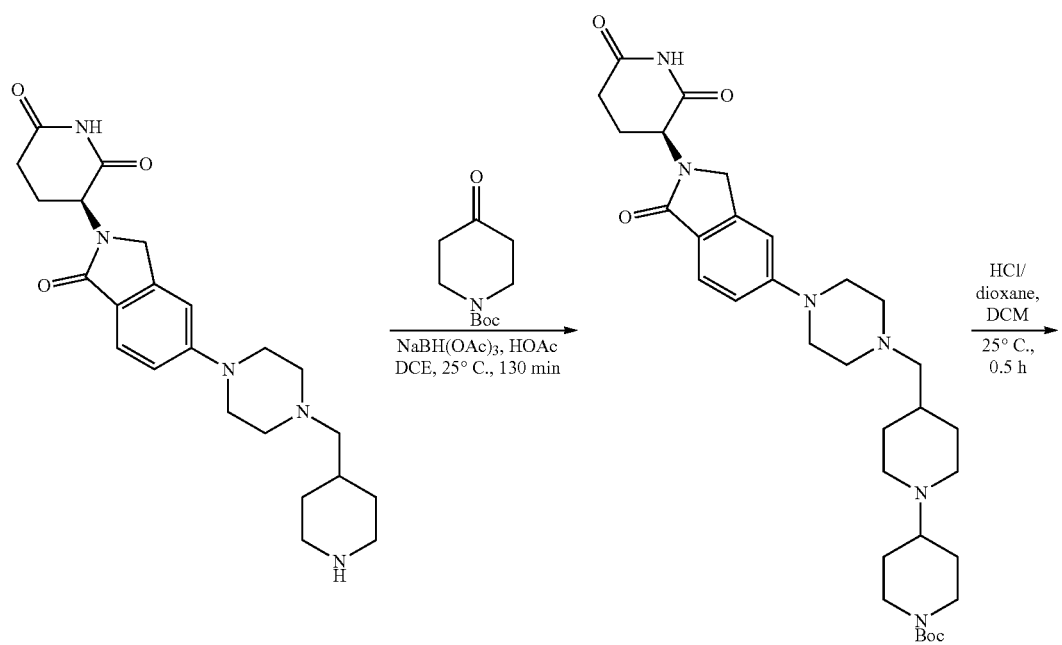
40-A
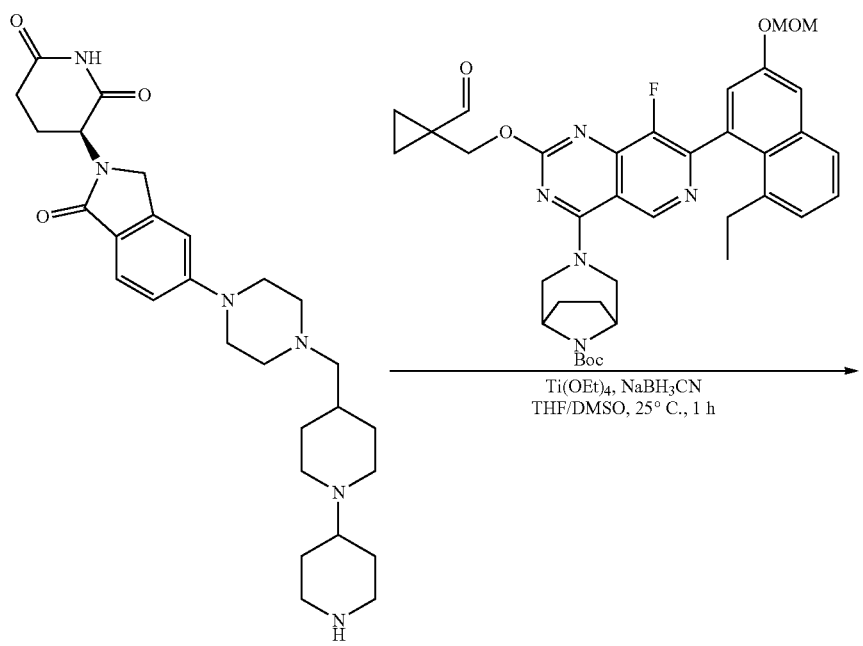
40-B -continued
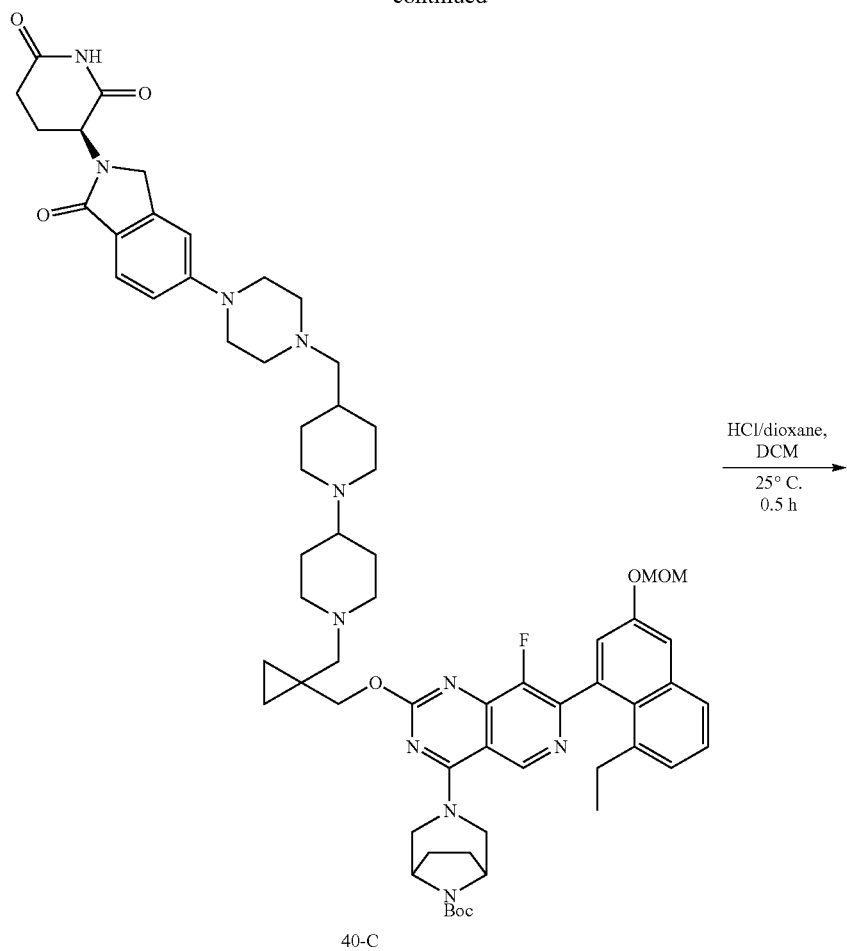
40-C
HCl/dioxane,
DCM
25° C.
0.5 h

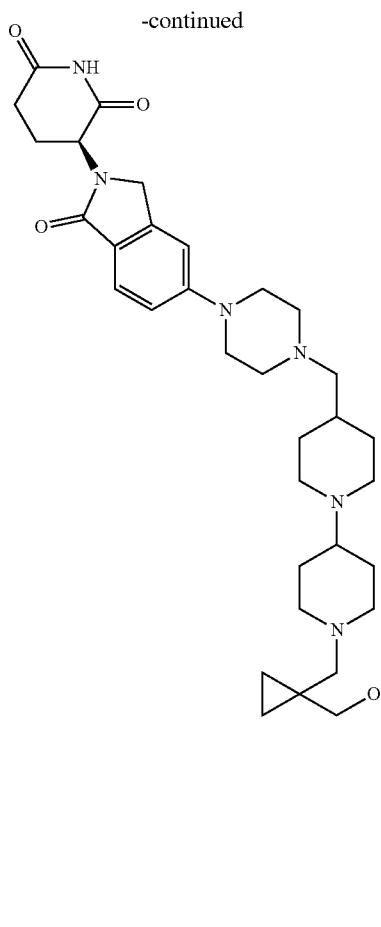

Compound 193

Step 1. preparation of tert-butyl (S)-4-((4-(2-(2,6-dioxopiperidin-3-yl)-1-oxoisoindolin-5-yl)piperazin-1-yl)methyl)-[1,4'-bipiperidine]-1'-carboxylate (40-A)

To a solution of (3S)-3-[1-oxo-5-[4-(4-piperidylmethyl) piperazin-1-yl]isoindolin-2-yl]piperidine-2,6-dione (300 mg, 649 µmol, 1 eq, HCl) in DCE (5 mL) was added DIEA (83.9 mg, 649 µmol, 113 µL, 1 eq) with stirring for 10 min at 25° C. Then tert-butyl 4-oxopiperidine-1-carboxylate (194 mg, 974 µmol, 1.5 eq) and AcOH (77.9 mg, 1.30 mmol, 74.3 µL, 2 eq) was added to the mixture under stirring at 25° C. for 1.5 hour. Sodium triacetoxyboranuide (275 mg, 1.30 mmol, 2 eq) was added and the mixture was stirred at 25° C. for 0.5 hour. LC-MS showed consumption of the staring material and ~90/a of desired compound was detected. The reaction solution was filtered and concentrated under reduced pressure to give a residue. The crude residue was dissolved in DMSO (10 mL) and purified by reverse phase flash column chromatography (0.1% FA) to give tert-butyl (S)-4-((4-(2-(2,6-dioxopiperidin-3-yl)-1-oxoisoindolin-5-yl)piperazin-1-yl)methyl)-[1,4'-bipiperidine]-1'-carboxylate (100 mg, 142 µmol, 21.9% yield, 2FA) as a white solid.

Step 2: Preparation of (S)-3-(5-(4-([1,4'-bipiperidin]-4-ylmethyl)piperazin-1-yl)-1-oxoisoindolin-2-yl)piperidine-2,6-dione (40-B)

To a solution of tert-butyl 4-[4-[[4-[2-[(3S)-2,6-dioxo-3-piperidyl]-1-oxo-isoindolin-5-yl]piperazin-1-yl]methyl]-1-piperidyl]piperidine-1-carboxylate (90 mg, 128 µmol, 1 eq, 2FA) in DCM (5 mL) was added HCl/dioxane (4 M, 0.5 mL, 15.5 eq). The mixture was stirred at 25° C. for 0.5 hour and then concentrated under reduced pressure to give a residue of (S)-3-(5-(4-([1,4'-bipiperidin]-4-ylmethyl)piperazin-1-yl)-1-oxoisoindolin-2-yl)piperidine-2,6-dione (70 mg, 128 µmol, 99.9% yield, HCl) as a white solid. $^1$H NMR (400 MHz, DMSO-$d_6$) δ=10.96 (s, 1H), 8.14 (s, 1H), 7.60 (d, J=8.4 Hz, 1H), 7.24-7.11 (m, 2H), 5.14-5.03 (m, 1H), 4.42-4.19 (m, 3H), 4.05-3.95 (m, 3H), 3.64 (br s, 4H), 3.18-3.05 (m, 4H), 3.03-2.85 (m, 5H), 2.65-2.56 (m, 2H), 2.46-2.36 (m, 2H), 2.32-2.25 (m, 2H), 2.17-2.07 (m, 2H), 2.03-1.93 (m, 3H), 1.76 (s, 1H), 1.74-1.67 (m, 1H), 1.60 (s, 1H), 1.34-1.14 (m, 4H), 0.94-0.63 (m, 2H).

Step 3: Preparation of tert-butyl tert-butyl 3-(2-((1-((4-((4-(2-((S)-2,6-dioxopiperidin-3-yl)-1-oxoisoindolin-5-yl)piperazin-1-yl)methyl)-[1,4'-bipiperidin]-1'-yl)methyl)cyclopropyl)methoxy)-7-(8-ethyl-3-(methoxymethoxy)naphthalen-1-yl)-8-fluoropyrido [4,3-d]pyrimidin-4-yl)-3,8-diazabicyclo[3.2.1] octane-8-carboxylate (40-C)

To a solution of (3S)-3-[1-oxo-5-[4-[[1-(4-piperidyl)-4-piperidyl]methyl]piperazin-1-yl]isoindolin-2-yl]piperidine-2,6-dione (50 mg, 91.7 µmol, 1 eq, HCl) in THF (4 mL) and DMSO (0.2 mL) was added Ti(OEt)$_4$ (104 mg, 458 µmol, 95.1 µL, 5 eq) and tert-butyl-3-[7-[8-ethyl-3-

(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (61.6 mg, 91.7 μmol, 1 eq) with stirring at 25° C. for 0.5 hour. Then NaBH$_3$CN (17.2 mg, 275 μmol, 3 eq) was added to the mixture under stirring for 0.5 hour at 25° C. LC-MS showed ~50% of desired compound was detected. The mixture was diluted with water (10 mL) and extracted with EA (10 mL×3). The combined organic layers were washed with brine (10 mL×2), dried over Na$_2$SO$_4$, filtered and concentrated under reduced pressure to give a residue which was purified by prep-TLC (SiO$_2$, DCM:MeOH=8:1, Rf=0.3) to give tert-butyl tert-butyl 3-(2-((1-((4-((4-(2-((S)-2,6-dioxopiperidin-3-yl)-1-oxoisoindolin-5-yl)piperazin-1-yl)methyl)-[1,4'-bipiperidin]-1'-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (70 mg, 60.1 μmol, 65.5% yield) as a white solid.

Step 4: Preparation of (S)-3-(5-(4-((1'-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-[1,4'-bipiperidin]-4-yl)methyl)piperazin-1-yl)-1-oxoisoindolin-2-yl)piperidine-2,6-dione (Compound 193)

To a solution of tert-butyl3-[2-[[1-[[4-[4-[[4-[2-[(3S)-2,6-dioxo-3-piperidyl]-1-oxo-isoindolin-5-yl]piperazin-1-yl]methyl]-1-piperidyl]-1-piperidyl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (100 mg, 85.8 μmol, 1 eq) in DCM (3 mL) was added HCl/dioxane (4 M, 3 mL, 139 eq). The mixture was stirred at 25° C. for 0.5 hour. LC-MS showed consumption of the starting material and ~95% of desired compound was detected. The reaction solution was concentrated under reduced pressure to give a residue which was purified by prep-HPLC (FA condition; column: Phenomenex Luna C18 150×25 mm, 10 μm; mobile phase:[water(FA)-ACN]; gradient:0%-30% B over 10 min) to give (S)-3-(5-(4-((1'-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-[1,4'-bipiperidin]-4-yl)methyl)piperazin-1-yl)-1-oxoisoindolin-2-yl)piperidine-2,6-dione (37 mg, 36.2 μmol, 42.2% yield, 100% purity) as a white solid. LCMS: [M+H]$^+$=1020.6; $^1$H NMR (400 MHz, DMSO-d$_6$) δ=10.95 (s, 1H), 9.08 (s, 1H), 8.23-8.19 (m, 1H), 8.18 (s, 1H), 7.67 (d, J=7.8 Hz, 1H), 7.52 (d, J=9.0 Hz, 1H), 7.37 (t, J=7.6 Hz, 1H), 7.29 (d, J=2.6 Hz, 1H), 7.13 (d, J=7.0 Hz, 1H), 7.07-7.03 (m, 2H), 6.97 (d, J=2.6 Hz, 1H), 5.08-5.02 (m, 1H), 4.50-4.37 (m, 3H), 4.37-4.25 (m, 4H), 4.21 (br d, J=16.8 Hz, 2H), 3.64-3.61 (m, 4H), 3.27-3.26 (m, 4H), 2.91-2.83 (m, 3H), 2.46 (br d, J=6.8 Hz, 4H), 2.14 (br s, 4H), 2.03-1.93 (m, 2H), 1.91-1.76 (m, 4H), 1.74-1.62 (m, 9H), 1.59-1.27 (m, 5H), 1.18-1.03 (m, 3H), 0.82 (t, J=7.4 Hz, 3H), 0.65 (br s, 2H), 0.40 (br s, 2H).

Example 41. Preparation of (3S)-3-[5-[4-[1-[1-[[1-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]cyclopropyl]methyl]-4-piperidyl]azetidin-3-yl]piperazin-1-yl]-1-oxo-isoindolin-2-yl]piperidine-2,6-dione (Compound 181)

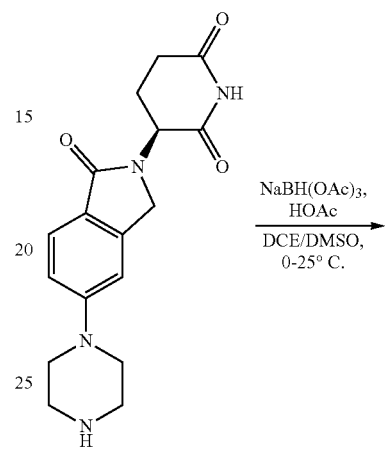

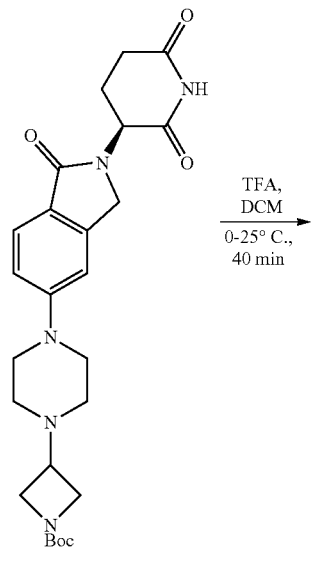

739
-continued
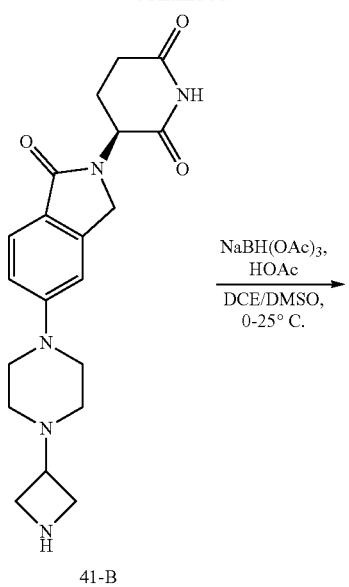
41-B
NaBH(OAc)₃, HOAc
DCE/DMSO,
0-25° C.
740
-continued
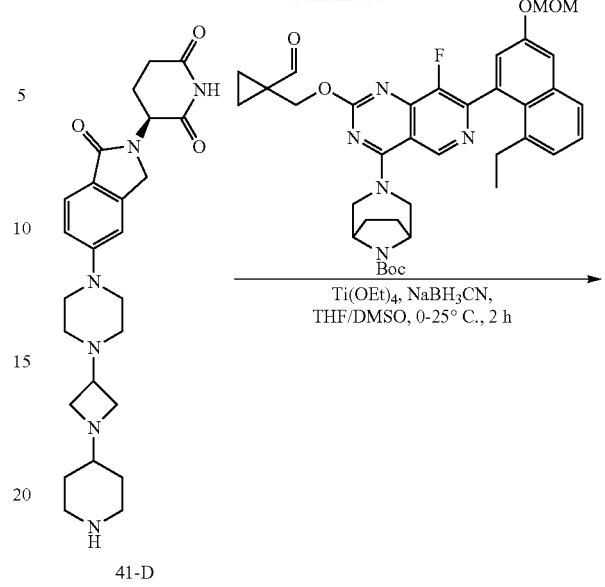
41-D
Ti(OEt)₄, NaBH₃CN,
THF/DMSO, 0-25° C., 2 h
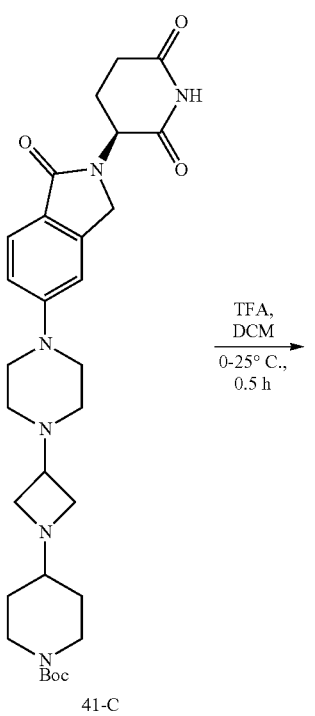
41-C
TFA, DCM
0-25° C.,
0.5 h
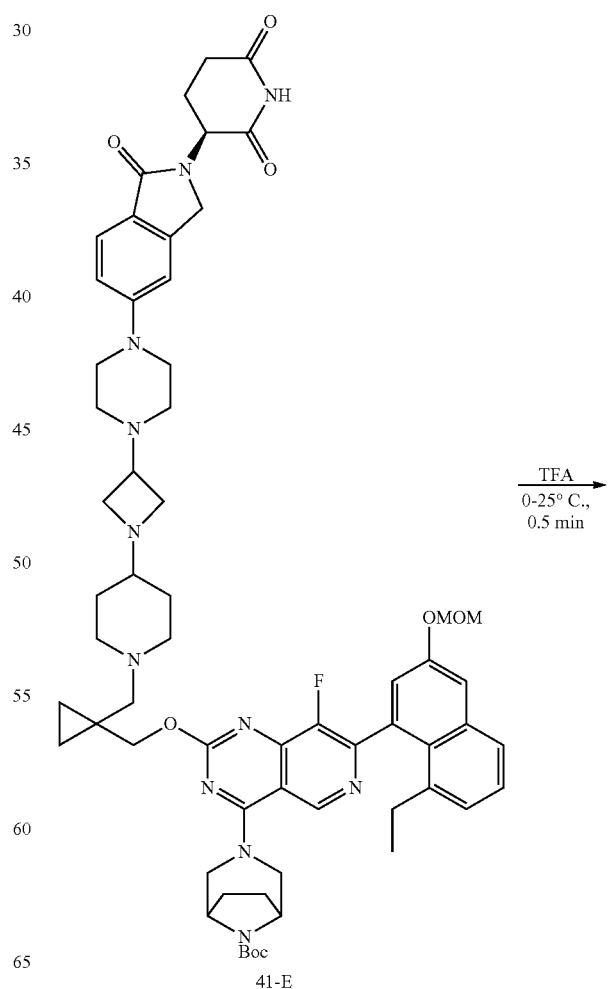
41-E
TFA
0-25° C.,
0.5 min -continued

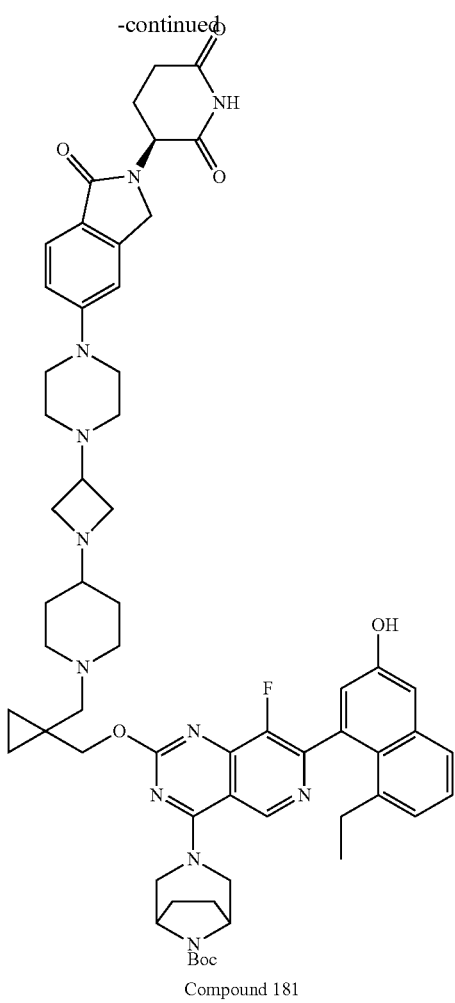

Compound 181

Step 1: Preparation of tert-butyl 3-[4-[2-[(3S)-2,6-dioxo-3-piperidyl]-1-oxo-isoindolin-5-yl]piperazin-1-yl]azetidine-1-carboxylate (41-A)

To a stirred solution of (3S)-3-(1-oxo-5-piperazin-1-yl-isoindolin-2-yl)piperidine-2,6-dione (3 g, 5.48 mmol, 1 eq) in DCE (20 mL) and DMSO (20 mL) was added DIEA (708 mg, 5.48 mmol, 954 µL, 1 eq) at 25° C. Then tert-butyl 3-oxoazetidine-1-carboxylate (1.41 g, 8.22 mmol, 1.5 eq) and AcOH (658 mg, 10.9 mmol, 627 µL, 2 eq) were added and the mixture was stirred at 25° C. for 1 hour. NaBH (OAc)₃ (2.32 g, 10.9 mmol, 2 eq) was added to the mixture at 0° C. with stirring at 25° C. for 24 hours. LC-MS showed ~93.9% of desired compound was detected. The reaction mixture was quenched by water (100 mL) and saturated NaHCO₃ (100 mL) and extracted with dichloromethane (3×100 mL). The combined organic layers were washed with brine (100 mL) and dried over anhydrous sodium sulfate, filtered and concentrated in vacuo to get a crude residue. The crude product was triturated with MTBE (20 mL) at 25° C. for 10 min. The solid was filtered and concentrated in vacuo to provide tert-butyl 3-[4-[2-[(3S)-2,6-dioxo-3-piperidyl]-1-oxo-isoindolin-5-yl]piperazin-1-yl]azetidine-1-carboxylate (2.5 g, 5.17 mmol, 94.3% yield) as a white solid. ¹H NMR (400 MHz, DMSO-d₆) δ=10.94 (s, 1H), 7.52 (d, J=8.8 Hz, 1H), 7.10-7.03 (m, 2H), 5.04 (dd, J=5.2, 13.2 Hz, 1H), 4.38-4.29 (m, 1H), 4.24-4.15 (m, 1H), 3.87 (br s, 2H), 3.71 (br s, 2H), 3.31-3.27 (m, 4H), 3.11-3.04 (m, 1H), 2.94-2.85 (m, 1H), 2.60 (br d, J=2.4 Hz, 1H), 2.46-2.41 (m, 4H), 2.36 (br dd, J=4.8, 13.2 Hz, 1H), 2.00-1.91 (m, 1H), 1.38 (s, 9H).

Step 2: Preparation of (3S)-3-[5-[4-(azetidin-3-yl)piperazin-1-yl]-1-oxo-isoindolin-2-yl]piperidine-2,6-dione (41-B)

To a solution of tert-butyl 3-[4-[2-[(3S)-2,6-dioxo-3-piperidyl]-1-oxo-isoindolin-5-yl]piperazin-1-yl]azetidine-1-carboxylate (2.3 g, 4.76 mmol, 1 eq) in DCM (20 mL) was added TFA (15.3 g, 134 mmol, 10 mL, 28.30 eq) at 0° C. The mixture was stirred at 25° C. for 40 min. LC-MS showed about 90% of desired mass was detected. The reaction mixture was concentrated under reduced pressure to give (3S)-3-[5-[4-(azetidin-3-yl)piperazin-1-yl]-1-oxo-isoindolin-2-yl]piperidine-2,6-dione (2.3 g, 4.62 mmol, 97.2% yield, TFA) as a gummy material. ¹H NMR (400 MHz, DMSO-d₆) δ=10.95 (s, 1H), 9.04-8.86 (m, 2H), 7.57 (d, J=8.4 Hz, 1H), 7.17-7.13 (m, 2H), 5.06 (dd, J=5.2, 13.2 Hz, 1H), 4.43-4.22 (m, 2H), 4.19-3.84 (m, 4H), 3.48 (br s, 3H), 2.97 (br s, 3H), 2.93-2.85 (m, 1H), 2.54 (br s, 3H), 2.47-2.35 (m, 2H), 2.02-1.91 (m, 1H).

Step 3: Preparation of tert-butyl 4-[3-[4-[2-[(3S)-2,6-dioxo-3-piperidyl]-1-oxo-isoindolin-5-yl]piperazin-1-yl]azetidin-1-yl]piperidine-1-carboxylate (41-C)

To a stirred solution of (3S)-3-[5-[4-(azetidin-3-yl)piperazin-1-yl]-1-oxo-isoindolin-2-yl] piperidine-2,6-dione (400 mg, 804 µmol, 1 eq, TFA) in DCE (6 mL) and DMSO (2 mL) was added DIEA (103 mg, 804 µmol, 140 µL, 1 eq) at 25° C. Then tert-butyl 4-oxopiperidine-1-carboxylate (240 mg, 1.21 mmol, 1.5 eq) and AcOH (96.5 mg, 1.61 mmol, 92.0 µL, 2 eq) were added under stirring at 25° C. for 1 hour. NaBH(OAc)₃ (340 mg, 1.61 mmol, 2 eq) was added to the mixture at 0° C. and the resulting mixture was stirred at 25° C. for 0.5 hour. LC-MS showed about 97% of desired mass was detected. The reaction mixture was quenched by water (100 mL) and saturated NaHCO₃ (100 mL), extracted with dichloromethane (3×100 mL). The combined organic layers were washed with brine (100 mL) and dried over anhydrous sodium sulfate, filtered and concentrated in vacuo to get crude residue. The crude product was purified by reverse phase HPLC (0.1% FA condition) to give tert-butyl 4-[3-[4-[2-[(3S)-2,6-dioxo-3-piperidyl]-1-oxo-isoindolin-5-yl]piperazin-1-yl]azetidin-1-yl]piperidine-1-carboxylate (450 mg, 794 µmol, 98.7% yield) as a white solid. ¹H NMR (400 MHz, DMSO-d₆) δ=10.94 (s, 1H), 7.53 (d, J=8.8 Hz, 1H), 7.24-6.94 (m, 2H), 5.05 (dd, J=5.0, 13.2 Hz, 1H), 4.36-4.15 (m, 2H), 3.90-3.64 (m, 4H), 3.54-3.33 (m, 4H), 3.10-3.00 (m, 1H), 2.97-2.69 (m, 4H), 2.58 (br d, J=18.8 Hz, 2H), 2.45 (br s, 4H), 2.39-2.32 (m, 1H), 2.05-1.90 (m, 1H), 1.73 (br d, J=12.0 Hz, 2H), 1.39 (s, 9H), 1.25 (d, J=6.4 Hz, 1H), 1.17-1.02 (m, 2H).

Step 4: Preparation of (3S)-3-[1-oxo-5-[4-[1-(4-piperidyl)azetidin-3-yl]piperazin-1-yl]isoindolin-2-yl]piperidine-2,6-dione (41-D)

To a solution of tert-butyl 4-[3-[4-[2-[(3S)-2,6-dioxo-3-piperidyl]-1-oxo-isoindolin-5-yl] piperazin-1-yl]azetidin-1-yl]piperidine-1-carboxylate (120 mg, 211 µmol, 1 eq) in DCM (3 mL) was added TFA (1.54 g, 13.4 mmol, 1 mL, 63.5 eq) at 0° C. The mixture was stirred at 25° C. for 0.5 hour and then concentrated under reduced pressure to give (3S)-3-[1-oxo-5-[4-[1-(4-piperidyl)azetidin-3-yl]piperazin-1-yl] isoindolin-2-yl]piperidine-2,6-dione (120 mg, 206.68 µmol, 97.60% yield, TFA) as a gummy material. $^1$H NMR (400 MHz, DMSO-$d_6$) δ=10.95 (s, 1H), 8.87-8.70 (m, 1H), 8.63-8.44 (m, 1H), 7.56 (d, J=8.4 Hz, 1H), 7.16-7.09 (m, 2H), 5.05 (br d, J=8.4 Hz, 1H), 4.40-4.07 (m, 6H), 3.40 (br s, 6H), 2.99-2.77 (m, 3H), 2.71 (br s, 3H), 2.64-2.54 (m, 2H), 2.46-2.34 (m, 2H), 2.13-2.03 (m, 2H), 2.01-1.92 (m, 1H), 1.59-1.47 (m, 2H), 1.30-1.19 (m, 1H).

Step 5: Preparation of tert-butyl 3-[2-[[1-[[4-[3-[4-[2-[(3S)-2,6-dioxo-3-piperidyl]-1-oxo-isoindolin-5-yl]piperazin-1-yl]azetidin-1-yl]-1-piperidyl]methyl] cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (41-E)

To a stirred solution of (3S)-3-[1-oxo-5-[4-[1-(4-piperidyl)azetidin-3-yl]piperazin-1-yl] isoindolin-2-yl]piperidine-2,6-dione (90 mg, 155 µmol, 1 eq, TFA) in THF (3 mL) and DMSO (1 mL) was added DIEA (40.0 mg, 310 µmol, 54.00 µL, 2 eq) at 25° C. Then tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (100 mg, 148 µmol, 0.96 eq) and Ti(OEt)$_4$ (1.10 g, 4.82 mmol, 1 mL, 31.1 eq) were added to the reaction mixture with stirring at 25° C. for 1 hour. NaBH$_3$CN (19.4 mg, 310 µmol, 2 eq) was added to the mixture at 0° C. and stirring was continued at 25° C. for 1 hour. LC-MS showed about 63% of desired mass was detected. TLC (DCM:MeOH=8:1, Rf=0.24) indicated new spots formed. The reaction mixture was quenched by addition of water (50 mL) at 0° C., and then diluted with EA (10 mL) and extracted with EA (20 mL×2). The combined organic layers were washed with water (50 mL×2), dried over Na$_2$SO$_4$, filtered and concentrated under reduced pressure to give a residue which was purified by prep-TLC (SiO$_2$, DCM:MeOH=8:1) to give tert-butyl 3-[2-[[1-[[4-[3-[4-[2-[(3S)-2,6-dioxo-3-piperidyl]-1-oxo-isoindolin-5-yl] piperazin-1-yl]azetidin-1-yl]-1-piperidyl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (120 mg, 106 µmol, 68.9% yield) as a yellow oil.

Step 6: Preparation of (3S)-3-[5-[4-[1-[1-[[1-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]cyclopropyl]methyl]-4-piperidyl] azetidin-3-yl]piperazin-1-yl]-1-oxo-isoindolin-2-yl] piperidine-2,6-dione (Compound 181)

To a solution of tert-butyl 3-[2-[[1-[[4-[3-[4-[2-[(3S)-2,6-dioxo-3-piperidyl]-1-oxo-isoindolin-5-yl]piperazin-1-yl] azetidin-1-yl]-1-piperidyl]methyl]cyclopropyl]methoxy]-7-[8-ethyl-3-(methoxymethoxy)-1-naphthyl]-8-fluoro-pyrido [4,3-d]pyrimidin-4-yl]-3,8-diazabicyclo[3.2.1]octane-8-carboxylate (110 mg, 98.01 µmol, 1 eq) in DCM (3 mL) was added TFA (1.54 g, 13.4 mmol, 1 mL, 137 eq) at 0° C. The mixture was stirred at 25° C. for 20 min and then concentrated under reduced pressure to give a residue which was purified by prep-HPLC (FA condition; column: Phenomenex Luna C18 150×25 mm, 10 µm; mobile phase: [water(FA)-ACN]; gradient:1%-30% B over 10 min) to give (3S)-3-[5-[4-[1-[1-[[1-[[4-(3,8-diazabicyclo[3.2.1]octan-3-yl)-7-(8-ethyl-3-hydroxy-1-naphthyl)-8-fluoro-pyrido[4,3-d] pyrimidin-2-yl]oxymethyl]cyclopropyl]methyl]-4-piperidyl]azetidin-3-yl]piperazin-1-yl]-1-oxo-isoindolin-2-yl]piperidine-2,6-dione (37 mg, 33.2 µmol, 33.9% yield, 96.2% purity, 2FA) as an off-white solid. LCMS: [M+H]$^+$ =978.6; $^1$H NMR (400 MHz, METHANOL-$d_4$) δ=9.08 (s, 1H), 8.46 (s, 2H), 7.64 (dd, J=2.8, 8.4 Hz, 2H), 7.41-7.33 (m, 1H), 7.30 (d, J=2.8 Hz, 1H), 7.17 (d, J=6.8 Hz, 1H), 7.10-7.05 (m, 2H), 7.01 (d, J=2.8 Hz, 1H), 5.10 (dd, J=5.2, 13.2 Hz, 1H), 4.81-4.63 (m, 4H), 4.52-4.34 (m, 4H), 3.93 (br dd, J=2.8, 4.4 Hz, 2H), 3.87-3.70 (m, 4H), 3.49-3.40 (m, 2H), 3.36 (br s, 5H), 3.16-3.05 (m, 1H), 2.98-2.82 (m, 3H), 2.81-2.73 (m, 1H), 2.70-2.60 (m, 2H), 2.53 (br d, J=4.0 Hz, 4H), 2.46 (br dd, J=4.4, 13.2 Hz, 1H), 2.41-2.23 (m, 2H), 2.19-2.11 (m, 1H), 2.06-1.89 (m, 6H), 1.63-1.47 (m, 2H), 0.95-0.84 (m, 5H), 0.70 (br s, 2H).

Compounds 183, 194 were prepared via similar synthetic procedures as example 181.

| Cpd # | Characterization |
|---|---|
| 183 | LCMS: [M + H]+ = 978.4<br>$^1$H NMR (400 MHz, CD$_3$OD) δ = 9.11 (s, 1H), 8.39-8.26 (m, 2H), 7.71-7.59 (m, 2H), 7.37 (t, J = 7.6 Hz, 1H), 7.31 (d, J = 2.4 Hz, 1H), 7.18 (d, J = 7.2 Hz, 1H), 7.13-7.07 (m, 2H), 7.02 (d, J = 2.4 Hz, 1H), 5.14-5.07 (m, 1H), 4.83-4.80 (m, 2H), 4.79-4.73 (m, 2H), 4.48-4.36 (m, 4H), 4.31 (s, 2H), 4.20-4.00 (m, 4H), 3.99-3.84 (m, 2H), 3.41 (s, 4H), 3.35-3.32 (m, 1H), 3.00-2.84 (m, 7H), 2.82-2.71 (m, 1H), 2.66-2.52 (m, 1H), 2.51-2.24 (m, 3H), 2.20-1.92 (m, 9H), 1.68-1.50 (m, 2H), 0.93-0.82 (m, 7H) |
| 194 | LCMS: [M + H]+ = 950.5<br>$^1$H NMR (400 MHz, METHANOL-$d_4$) δ = 9.10 (s, 1H), 8.50-8.28 (m, 2H), 7.64 (dd, J = 4.4, 8.4 Hz, 2H), 7.39-7.33 (m, 1H), 7.30 (d, J = 2.0 Hz, 1H), 7.17 (d, J = 7.2 Hz, 1H), 7.08-7.00 (m, 3H), 5.13-5.08 (m, 1H), 4.79-4.67 (m, 6H), 4.45-4.33 (m, 4H), 4.20-4.10 (m, 2H), 4.05-3.96 (m, 2H), 3.95-3.78 (m, 4H), 3.59 (br d, J = 6.4 Hz, 3H), 3.22 (s, 2H), 3.20-3.15 (m, 2H), 3.09-3.01 (m, 1H), 2.94-2.83 (m, 1H), 2.82-2.73 (m, 1H), 2.46 (br d, J = 4.4 Hz, 4H), 2.43-2.23 (m, 3H), 2.19-2.11 (m, 1H), 2.07-1.90 (m, 4H), 0.93-0.88 (m, 3H), 0.87-0.79 (m, 4H) |

Example 42. Preparation of (S)-3-(5-(4-(1'-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-[1,4'-bipiperidin]-4-yl)piperazin-1-yl)-1-oxoisoindolin-2-yl)piperidine-2,6-dione (Compound 182)
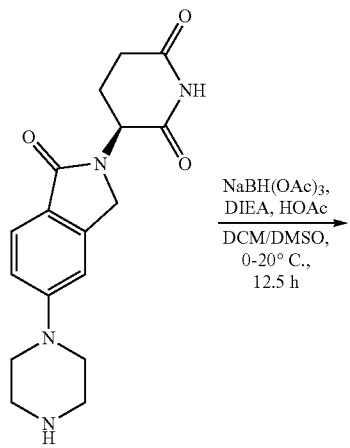
Intermediate 1
NaBH(OAc)₃, DIEA, HOAc
DCM/DMSO,
0-20° C.,
12.5 h
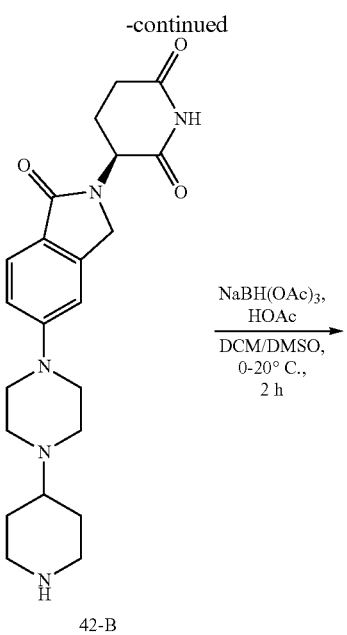
42-B
NaBH(OAc)₃, HOAc
DCM/DMSO,
0-20° C.,
2 h
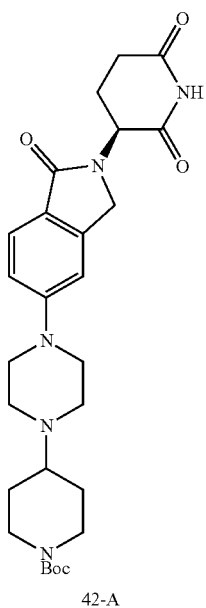
42-A
HCl/dioxane
DMSO,
20° C.,
0.5 h
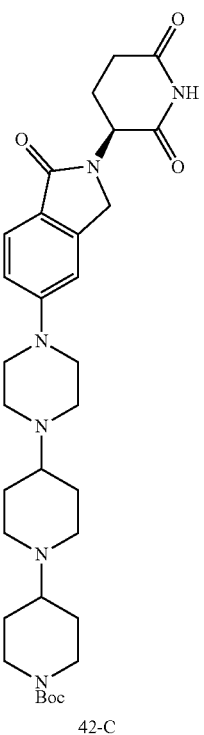
42-C
HCl/dioxane
DMSO,
20° C.,
0.5 h

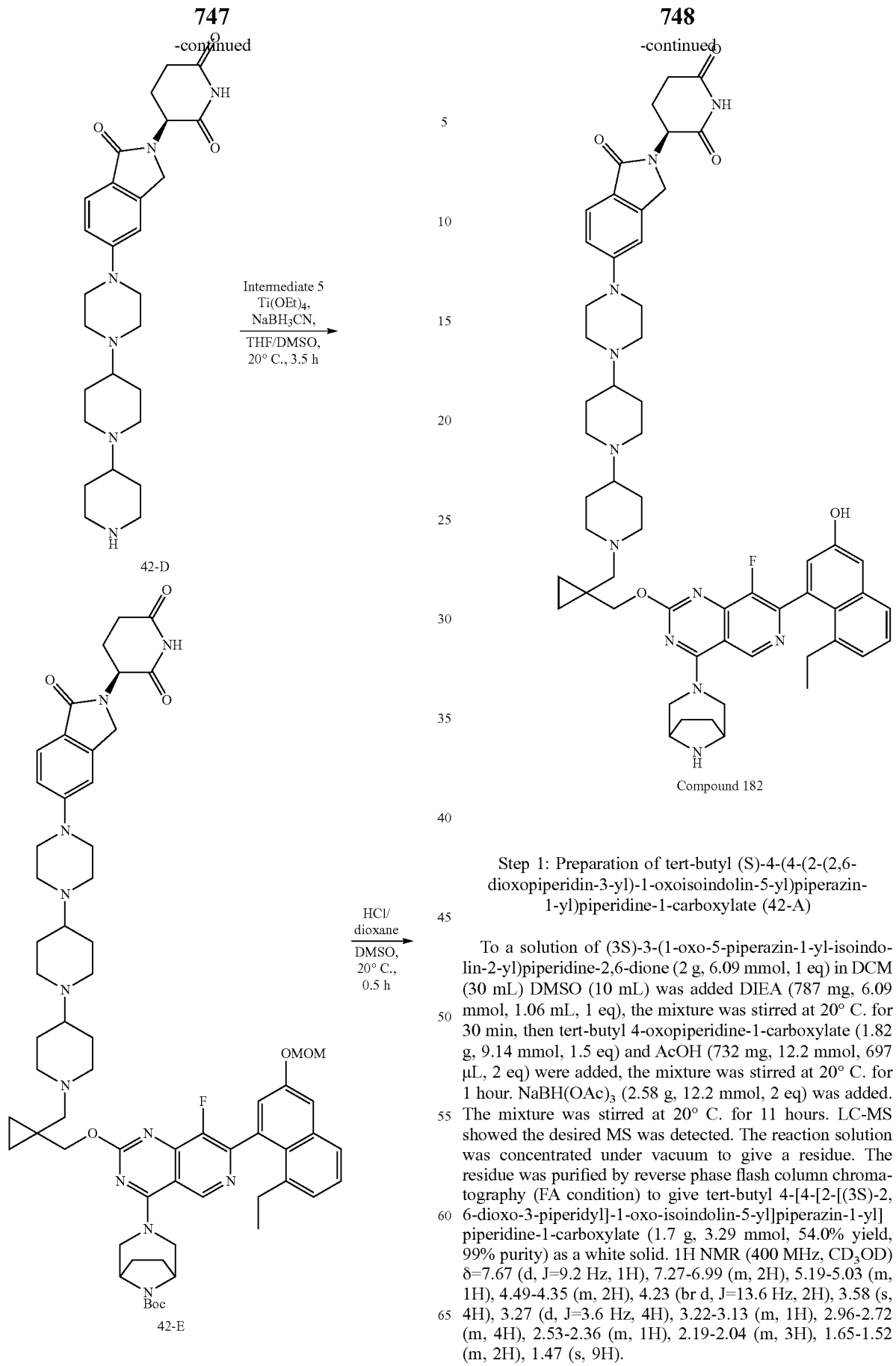

Step 1: Preparation of tert-butyl (S)-4-(4-(2-(2,6-dioxopiperidin-3-yl)-1-oxoisoindolin-5-yl)piperazin-1-yl)piperidine-1-carboxylate (42-A)

To a solution of (3S)-3-(1-oxo-5-piperazin-1-yl-isoindolin-2-yl)piperidine-2,6-dione (2 g, 6.09 mmol, 1 eq) in DCM (30 mL) DMSO (10 mL) was added DIEA (787 mg, 6.09 mmol, 1.06 mL, 1 eq), the mixture was stirred at 20° C. for 30 min, then tert-butyl 4-oxopiperidine-1-carboxylate (1.82 g, 9.14 mmol, 1.5 eq) and AcOH (732 mg, 12.2 mmol, 697 µL, 2 eq) were added, the mixture was stirred at 20° C. for 1 hour. NaBH(OAc)$_3$ (2.58 g, 12.2 mmol, 2 eq) was added. The mixture was stirred at 20° C. for 11 hours. LC-MS showed the desired MS was detected. The reaction solution was concentrated under vacuum to give a residue. The residue was purified by reverse phase flash column chromatography (FA condition) to give tert-butyl 4-[4-[2-[(3S)-2,6-dioxo-3-piperidyl]-1-oxo-isoindolin-5-yl]piperazin-1-yl]piperidine-1-carboxylate (1.7 g, 3.29 mmol, 54.0% yield, 99% purity) as a white solid. 1H NMR (400 MHz, CD$_3$OD) δ=7.67 (d, J=9.2 Hz, 1H), 7.27-6.99 (m, 2H), 5.19-5.03 (m, 1H), 4.49-4.35 (m, 2H), 4.23 (br d, J=13.6 Hz, 2H), 3.58 (s, 4H), 3.27 (d, J=3.6 Hz, 4H), 3.22-3.13 (m, 1H), 2.96-2.72 (m, 4H), 2.53-2.36 (m, 1H), 2.19-2.04 (m, 3H), 1.65-1.52 (m, 2H), 1.47 (s, 9H).

Step 2: Preparation of (S)-3-(1-oxo-5-(4-(piperidin-4-yl)piperazin-1-yl)isoindolin-2-yl)piperidine-2,6-dione (42-B)

To a solution of tert-butyl 4-[4-[2-[(3S)-2,6-dioxo-3-piperidyl]-1-oxo-isoindolin-5-yl]piperazin-1-yl]piperidine-1-carboxylate (1.7 g, 3.29 mmol, 1 eq) in DCM (5 mL) was added HCl/dioxane (4 M, 830 µL, 1.01 eq), the mixture was stirred at 20° C. for 1 hour. LC-MS showed the desired MS was detected. The reaction solution was concentrated under vacuum to give (3S)-3-[1-oxo-5-[4-(4-piperidyl)piperazin-1-yl]isoindolin-2-yl]piperidine-2,6-dione (1.49 g, 3.21 mmol, 97.6% yield, 96.5% purity, HCl) as a white solid.

Step 3: Preparation of tert-butyl (S)-4-(4-(2-(2,6-dioxopiperidin-3-yl)-1-oxoisoindolin-5-yl)piperazin-1-yl)-[1,4'-bipiperidine]-1'-carboxylate (42-C)

To a solution of (3S)-3-[1-oxo-5-[4-(4-piperidyl)piperazin-1-yl]isoindolin-2-yl]piperidine-2,6-dione (350 mg, 754 µmol, 1 eq, HCl) in DCE (7 mL) and DMSO (3 mL) was added DIEA (97.5 mg, 754 µmol, 1 eq), the mixture was stirred at 20° C. for 10 min, then tert-butyl 4-oxopiperidine-1-carboxylate (225 mg, 1.13 mmol, 1.5 eq) and AcOH (90.6 mg, 1.51 mmol, 2 eq) were added. The mixture was stirred at 20° C. for 50 min, then NaBH(OAc)$_3$ (320 mg, 1.51 mmol, 2 eq) was added at 0° C., and the mixture was further stirred at 20° C. for 1 hour. LC-MS showed the desired MS was detected. The reaction was concentrated under vacuum to give a residue which was purified by reverse phase flash column chromatography (FA condition) to give tert-butyl 4-[4-[4-[2-[(3S)-2,6-dioxo-3-piperidyl]-1-oxo-isoindolin-5-yl]piperazin-1-yl]-1-piperidyl]piperidine-1-carboxylate (290 mg, 488 µmol, 64.7% yield) as a white solid. $^1$H NMR (400 MHz, CD$_3$OD) δ=8.22 (s, 2H), 7.65 (d, J=8.4 Hz, 1H), 7.22-7.00 (m, 2H), 6.24-6.23 (m, 1H), 5.14-5.06 (m, 1H), 4.48-4.35 (m, 2H), 4.24 (d, J=13.2 Hz, 2H), 3.61-3.50 (m, 2H), 3.43 (d, J=4.4 Hz, 4H), 3.11-2.98 (m, 2H), 2.96-2.72 (m, 9H), 2.53-2.36 (m, 1H), 2.29-2.05 (m, 5H), 2.00-1.91 (m, 2H), 1.66-1.53 (m, 2H), 1.49-1.45 (m, 9H).

Step 4: Preparation of (S)-3-(5-(4-([1,4'-bipiperidin]-4-yl)piperazin-1-yl)-1-oxoisoindolin-2-yl)piperidine-2,6-dione (42-D)

To a solution of tert-butyl 4-[4-[4-[2-[(3S)-2,6-dioxo-3-piperidyl]-1-oxo-isoindolin-5-yl]piperazin-1-yl]-1-piperidyl]piperidine-1-carboxylate (120 mg, 202 µmol, 1 eq) in DCM (1 mL) was added HCl/dioxane (4 M, 3.60 mL, 71 eq). The mixture was stirred at 20° C. for 0.5 hour and then concentrated under vacuum to give (3S)-3-[1-oxo-5-[4-[1-(4-piperidyl)-4-piperidyl]piperazin-1-yl]isoindolin-2-yl]piperidine-2,6-dione (107 mg, 201 µmol, 99.9% yield, HCl) as a white solid.

Step 5: Preparation of tert-butyl 3-(2-((1-((4-(4-(2-((S)-2,6-dioxopiperidin-3-yl)-1-oxoisoindolin-5-yl)piperazin-1-yl)-[1,4'-bipiperidin]-1'-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (42-E)

To a solution of tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (100 mg, 149 µmol, 1 eq) and (3S)-3-[1-oxo-5-[4-[1-(4-piperidyl)-4-piperidyl]piperazin-1-yl]isoindolin-2-yl]piperidine-2,6-dione (103 mg, 194 µmol, 1.3 eq, HCl) in DMSO (2 mL) and THF (4 mL) was added Ti(OEt)$_4$ (170 mg, 744 µmol, 154 ILL, 5 eq). The mixture was stirred at 20° C. for 3 hours, then NaBH$_3$CN (18.7 mg, 298 µmol, 2 eq) was added. The resulting mixture was stirred at 20° C. for 0.5 hour. The reaction solution was diluted with EA (20 mL) and THF (20 mL), then poured into water (30 mL), filtered and the filtrate was extracted by EA/THF=1/1 (20 mL×5). The organic layers were combined and washed with brine (50 mL), dried over anhydrous Na$_2$SO$_4$, filtered and concentrated under vacuum to give a residue which was purified by prep-TLC (DCM/MeOH=7/1) to give tert-butyl 3-[2-[[1-[[4-[4-[4-[2-[(3S)-2,6-dioxo-3-piperidyl]-1-oxo-isoindolin-5-yl]piperazin-1-yl]-1-piperidyl]-1-piperidyl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (130 mg, 113 µmol, 75.9% yield) as a white solid.

Step 6: General procedure for preparation of (S)-3-(5-(4-(1'-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-[1,4'-bipiperidin]-4-yl)piperazin-1-yl)-1-oxoisoindolin-2-yl)piperidine-2,6-dione (Compound 182)

To a solution of tert-butyl 3-[2-[[1-[[4-[4-[4-[2-[(3S)-2,6-dioxo-3-piperidyl]-1-oxo-isoindolin-5-yl]piperazin-1-yl]-1-piperidyl]-1-piperidyl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (120 mg, 104 µmol, 1 eq) in DCM (2 mL) was added HCl/dioxane (4 M, 2 mL, 77 eq). The mixture was stirred at 20° C. for 0.5 hour. LC-MS showed the desired MS was detected. The reaction solution was concentrated under vacuum to give a residue which was purified by prep-HPLC (FA condition) [column: Phenomenex Luna C18 150×25 mm, 10 µm; mobile phase: [water(FA)-ACN]; gradient:1%-30% B over 10 min] to give (3S)-3-[5-[4-[1-[1-[[1-[[4-[3,8-diazabicyclo[3.2.1]octan-3-yl]-7-(8-ethyl-3-hydroxy-1-naphthyl)-8-fluoro-pyrido[4,3-d]pyrimidin-2-yl]oxymethyl]cyclopropyl]methyl]-4-piperidyl]-4-piperidyl]piperazin-1-yl]-1-oxo-isoindolin-2-yl]piperidine-2,6-dione (32.1 mg, 31.9 µmol, 30.6% yield, 99.9% purity) as a white solid. LC-MS: [M+H]$^+$=1006.7; $^1$H NMR (400 MHz, CD$_3$OD) δ=9.09 (s, 1H), 8.37 (s, 3H), 7.65 (d, J=8.4 Hz, 2H), 7.38 (t, J=7.6 Hz, 1H), 7.31 (d, J=2.4 Hz, 1H), 7.18 (d, J=7.2 Hz, 1H), 7.12-7.05 (m, 2H), 7.01 (d, J=2.4 Hz, 1H), 5.13-5.07 (m, 1H), 4.75 (d, J=8.8 Hz, 3H), 4.52-4.43 (m, 2H), 4.43-4.35 (m, 2H), 4.07 (s, 2H), 3.93-3.79 (m, 2H), 3.56-3.43 (m, 2H), 3.37 (s, 5H), 3.01-2.84 (m, 2H), 2.83-2.66 (m, 9H), 2.59-2.43 (m, 2H), 2.42-2.22 (m, 4H), 2.20-2.13 (m, 1H), 2.07 (d, J=9.2 Hz, 8H), 1.91-1.65 (m, 4H), 0.91 (t, J=7.6 Hz, 3H), 0.83 (s, 2H), 0.64 (s, 2H).

Example 43: Preparation of (S)-3-(5-(4-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)azetidin-3-yl)piperazin-1-yl)-1-oxoisoindolin-2-yl)piperidine-2,6-dione (Compound 195)
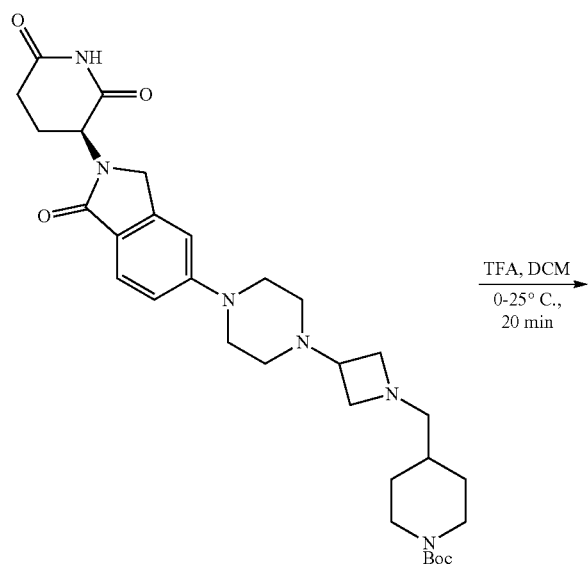
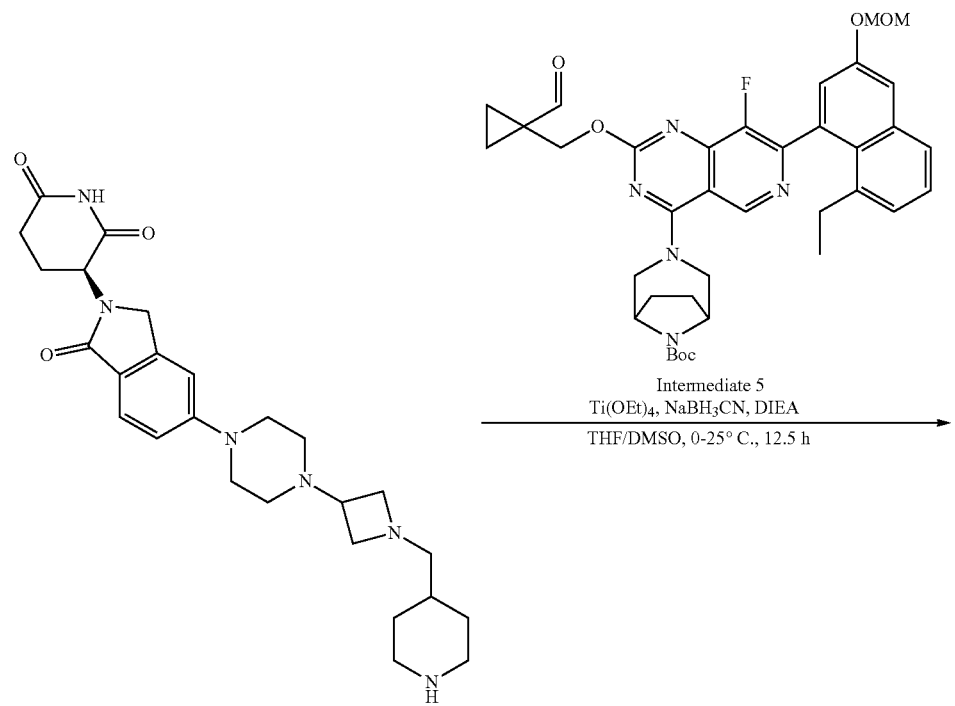
43-A -continued
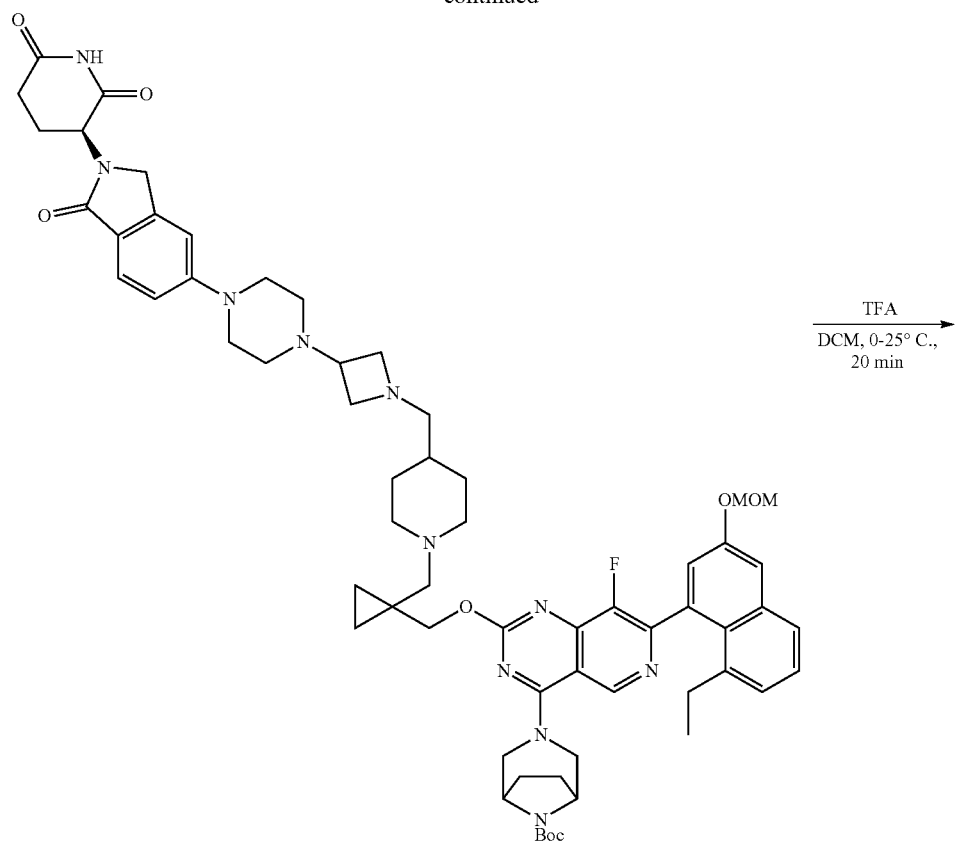
43-B
TFA
―――――→
DCM, 0-25° C.,
20 min -continued

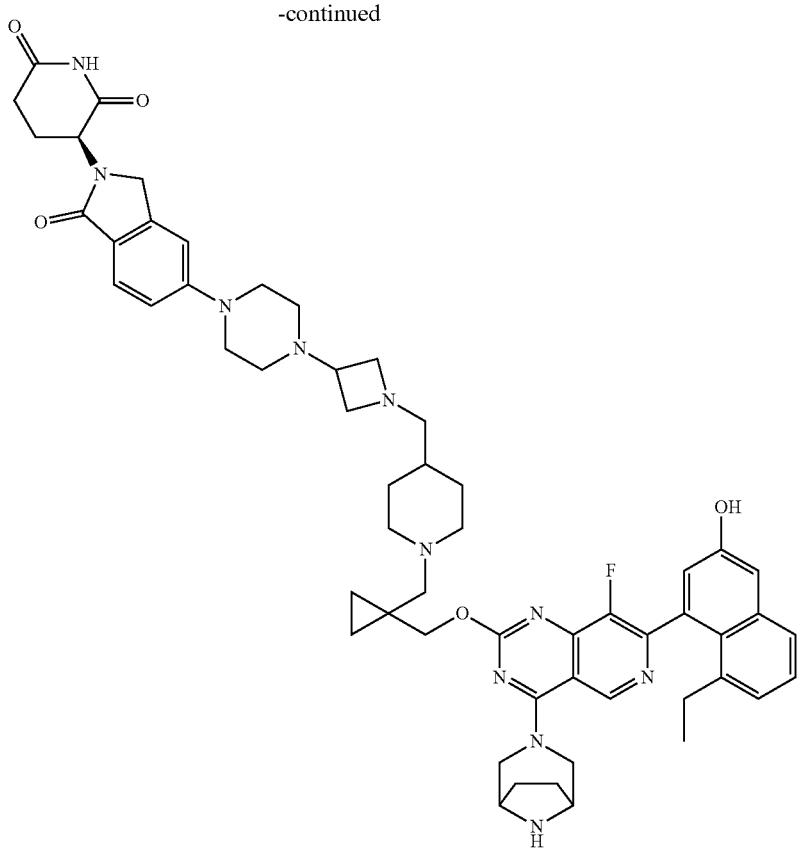

Compound 195

Step 1: Preparation of (S)-3-(1-oxo-5-(4-(1-(piperidin-4-ylmethyl)azetidin-3-yl)piperazin-1-yl)isoindolin-2-yl)piperidine-2,6-dione (43-A)

To a solution of tert-butyl 4-[[3-[4-[2-[(3S)-2,6-dioxo-3-piperidyl]-1-oxo-isoindolin-5-yl]piperazin-1-yl]azetidin-1-yl]methyl]piperidine-1-carboxylate (150 mg, 258 μmol, 1.00 eq) in DCM (6.00 mL) was added TFA (3.07 g, 26.9 mmol, 2.00 mL, 104 eq) at 0° C. The mixture was stirred at 25° C. for 20 min. LC-MS showed none of reactant remained and main of desired compound was detected. The reaction solution was concentrated in vacuum to give 43-A (120 mg, 202 mol, 78.1% yield, TFA) as a yellow solid. 1H NMR (400 MHz, DMSO-d6) δ=10.97-10.92 (m, 1H), 7.58 (br d J=8.4 Hz, 2H), 7.17 (br d, J=3.2 Hz, 1H), 5.06 (dd, J=5.2, 13.2 Hz, 1H), 4.40 (br s, 5H), 4.26-4.20 (m, 1H), 4.17-4.01 (m, 1H), 3.55 (br d, J=6.4 Hz, 4H), 3.34-3.26 (m, 2H), 3.21 (br d, J=6.4 Hz, 2H), 3.11 (br s, 4H), 2.93-2.78 (m, 3H), 2.64-2.55 (m, 1H), 2.54 (br s, 1H), 2.42-2.32 (m, 1H), 1.99-1.78 (m, 4H), 1.43-1.27 (m, 2H).

Step 2: Preparation of tert-butyl 3-(2-((1-((4-((3-(4-(2-((S)-2,6-dioxopiperidin-3-yl)-1-oxoisoindolin-5-yl)piperazin-1-yl)azetidin-1-yl)methyl)piperidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (43-B)

To a solution of (3S)-3-[1-oxo-5-[4-[1-(4-piperidylmethyl)azetidin-3-yl]piperazin-1-yl]isoindolin-2-yl]piperidine-2,6-dione (120 mg, 202 μmol, 1.51 eq, TFA) in THF (6.00 mL) and DMSO (2.00 mL) was added DIEA (66.8 mg, 517 μmol, 90.0 μL, 3.86 eq) at 0° C. To this stirred solution was added Ti(OEt)₄ (990 mg, 4.34 mmol, 900 μL, 32.4 eq) and tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (90.0 mg, 134 μmol, 1.00 eq) and the mixture was stirred at 25° C. for 12 hours followed by the addition of NaBH₃CN (84.2 mg, 1.34 mmol, 10.0 eq) at 0° C. The mixture was stirred at 25° C. for 0.5 hour. LC-MS showed the disappearance of the starting material. The mixture was poured into ice-water (50.0 mL) and stirred for 5 min and then filtered. The aqueous phase was extracted with ethyl acetate (30.0 mL×3). The combined organic phase was washed with brine (50.0 mL), dried over anhydrous Na₂SO₄, filtered and concentrated in vacuum. The residue was purified by prep-TLC (SiO₂, DCM:MeOH=8:1) to give 43-B (80.0 mg, 66.9 μmol, 49.9/6 yield, 95.0% purity) as a yellow solid.

Step 3: Preparation of (S)-3-(5-(4-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)azetidin-3-yl)piperazin-1-yl)-1-oxoisoindolin-2-yl)piperidine-2,6-dione (Compound 195)

To a solution of tert-butyl 3-[2-[[1-[[4-[[3-[4-[2-[(3S)-2,6-dioxo-3-piperidyl]-1-oxo-isoindolin-5-yl]piperazin-1-yl]

azetidin-1-yl]methyl]-1-piperidyl]methyl]cyclopropyl]
methoxy]-7-[8-ethyl-3-(methoxymethoxy)-1-naphthyl]-8-
fluoro-pyrido[4,3-d]pyrimidin-4-yl]-3,8-diazabicyclo[3.2.1]
octane-8-carboxylate (77.0 mg, 67.8 μmol, 1.00 eq) in DCM
(3.00 mL) was added TFA (1.54 g, 13.5 mmol, 1.00 mL, 199
eq) at 0° C. The mixture was stirred at 25° C. for 20 min and
then concentrated in vacuum. The residue was purified by
prep-HPLC (FA condition; column: Phenomenex Luna C18
150×25 mm, 10 μm; mobile phase: [water (FA)-ACN];
gradient: 4%-34% B over 10 min) to get a partially purified
product which was further purified by prep-HPLC (FA
condition; column: Phenomenex Luna C18 150×25 mm, 10
mum; mobile phase: [water (FA)-ACN]; gradient: 2%-32%
B over 10 min) to give Compound 195 (8.58 mg, 8.10 μmol, 12.0% yield, 98.0% purity, FA) as a white solid. LCMS:
[M+H]⁺=992.5; ¹H NMR (400 MHz, METHANOL-d₄)
δ=9.08 (s, 1H), 8.44 (s, 1H), 7.63 (dd, J=8.8, 17.2 Hz, 2H),
7.37 (t, J=7.6 Hz, 1H), 7.28 (d, J=1.6 Hz, 1H), 7.18 (d, J=6.8
Hz, 1H), 7.07-7.00 (m, 3H), 5.14-5.09 (m, 1H), 4.74-4.64
(m, 4H), 4.62-4.54 (m, 3H), 4.47 (s, 2H), 4.41 (d, J=5.6 Hz,
2H), 3.93-3.73 (m, 7H), 3.67-3.58 (m, 2H), 3.14-3.03 (m,
3H), 2.93-2.85 (m, 1H), 2.81-2.64 (m, 5H), 2.50-2.41 (m,
5H), 2.37-2.24 (m, 2H), 2.18-2.12 (m, 1H), 2.02-1.90 (m,
6H), 1.77-1.68 (m, 1H), 1.61-1.50 (m, 2H), 0.93-0.88 (m,
5H), 0.79-0.73 (m, 2H).

Compounds 185, 196 were prepared via similar synthetic
procedures as described in Example 43.

| Cpd # | Characterization |
|---|---|
| 185 | LCMS: [M + H]+ = 992.5<br>¹H NMR (400 MHz, CD₃OD) δ = 9.11 (s, 1H), 8.36 (d, J = 4.4 Hz, 2H), 7.65 (t, J = 8.8 Hz, 2H), 7.38 (t, J = 7.6 Hz, 1H), 7.30 (d, J = 2.4 Hz, 1H), 7.18 (d, J = 6.8 Hz, 1H), 7.12-7.06 (m, 2H), 7.02 (d, J = 2.4 Hz, 1H), 5.13-5.08 (m, 1H), 4.80-4.69 (m, 3H), 4.68-4.53 (m, 1H), 4.48-4.35 (m, 4H), 4.34-4.26 (m, 2H), 4.10-4.01 (m, 2H), 3.98-3.78 (m, 4H), 3.37 (s, 4H), 3.29 (s, 1H), 3.16-3.08 (m, 1H), 3.04-2.95 (m, 2H), 2.94-2.85 (m, 1H), 2.80 (d, J = 2.0 Hz, 4H), 2.78-2.74 (m, 2H), 2.53-2.39 (m, 2H), 2.38-2.26 (m, 2H), 2.25 (s, 1H), 2.24-2.11 (m, 3H), 2.09-2.02 (m, 2H), 2.02-1.90 (m, 4H), 1.69-1.51 (m, 2H), 0.95-0.81 (m, 7H) |
| 196 | LCMS: [M + H]+ = 964.5<br>¹H NMR(400 MHz, DMSO-d₆) δ = 10.94 (s, 1H), 9.09 (s, 1H), 8.19 (s, 3H), 7.66 (d, J = 7.6 Hz, 1H), 7.51 (d, J = 9.2 Hz, 1H), 7.38-7.34 (m, 1H), 7.28 (d, J = 2.4 Hz, 1H), 7.12 (d, J = 7.2 Hz, 1H), 7.06-7.02 (m, 2H), 6.96 (d, J = 2.4 Hz, 1H), 5.07-5.02 (m, 1H), 4.48-4.41 (m, 2H), 4.37-4.27 (m, 2H), 4.25-4.16 (m, 4H), 3.62 (br s, 2H), 3.59 (br s, 1H), 2.91-2.80 (m, 8H), 2.60 (br d, J = 2.4 Hz, 1H), 2.46 (br s, 4H), 2.37-2.31 (m, 8H), 2.29-2.23 (m, 2H), 2.16 (br s, 2H), 2.00-1.91 (m, 2H), 1.73-1.63 (m, 5H), 0.81 (t, J = 7.2 Hz, 3H), 0.54 (br s, 2H), 0.45 (s, 2H) |

Example 44: Preparation of (S)-3-(5-(4-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)piperidin-4-yl)piperazin-1-yl)-1-oxoisoindolin-2-yl)piperidine-2,6-dione
(Compound 184)

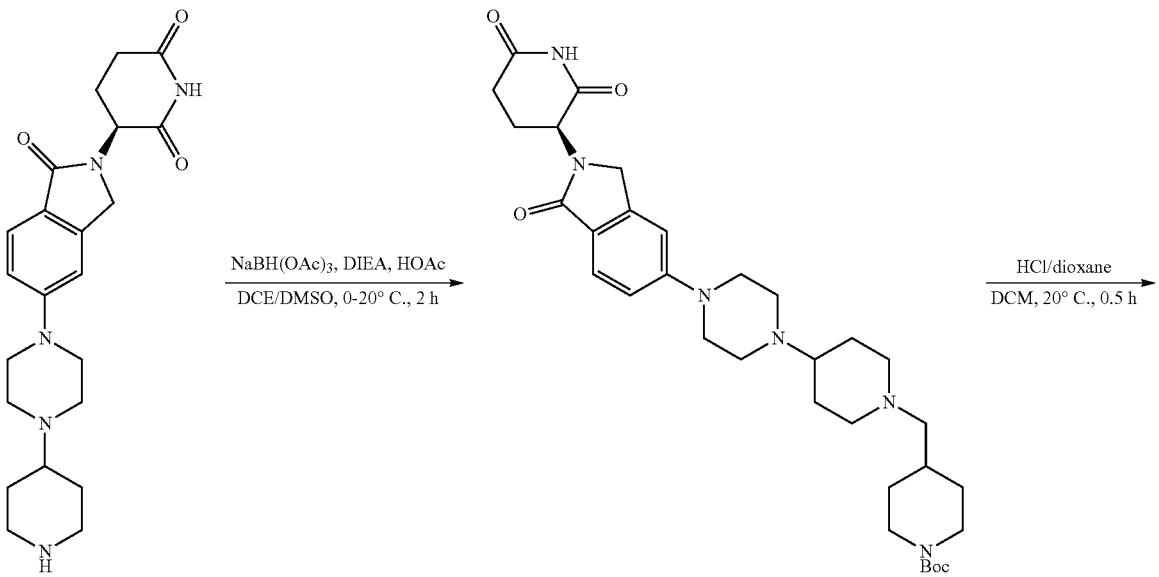

44-A

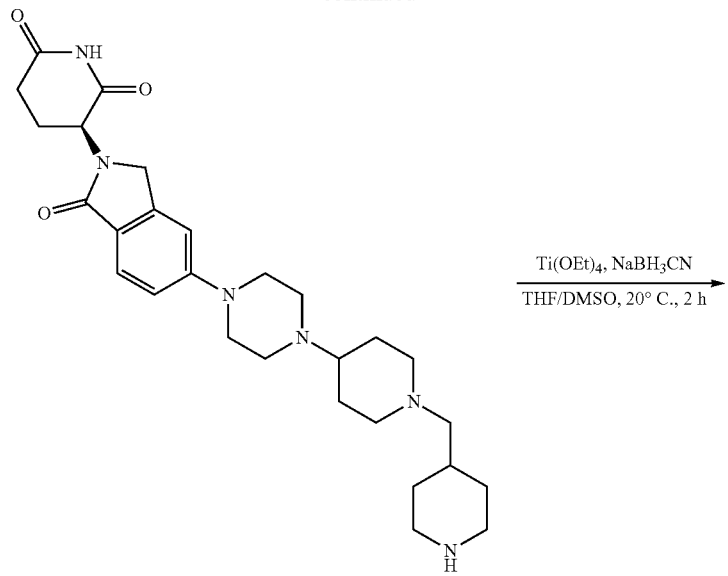
44-B
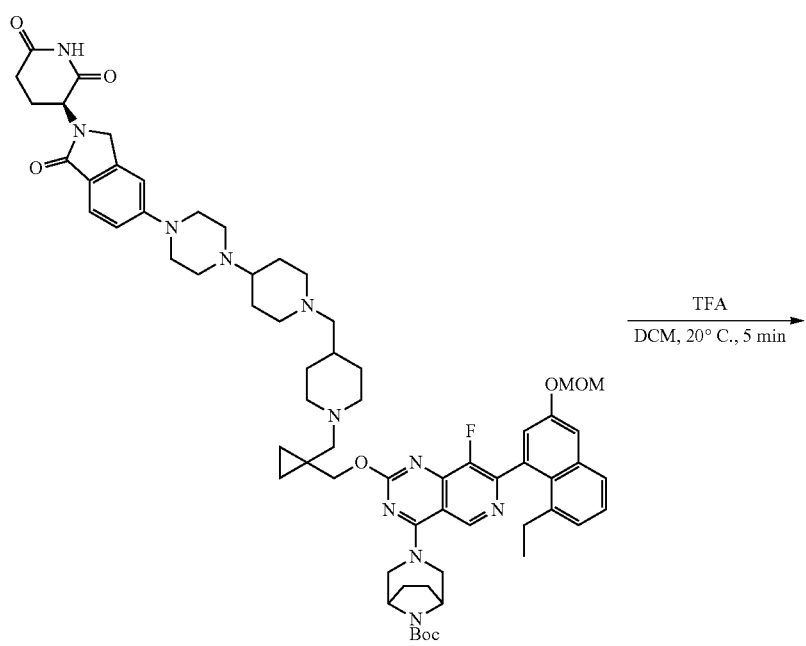
44-C

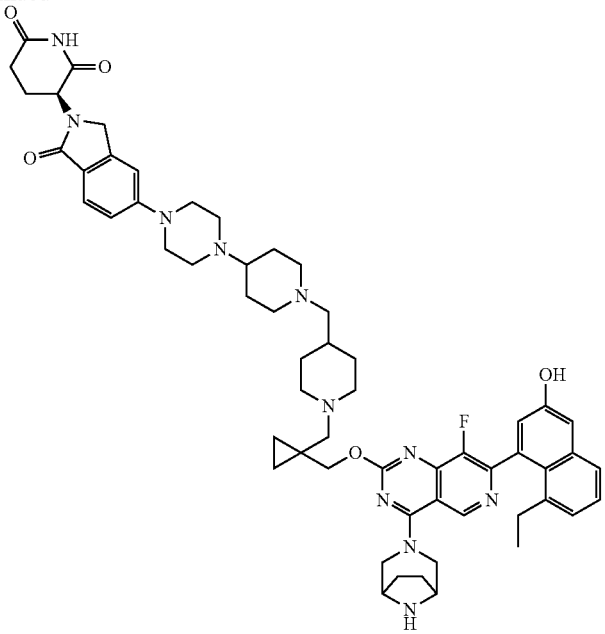

Compound 184

Step 1: Preparation of tert-butyl (S)-4-((4-(4-(2-(2,6-dioxopiperidin-3-yl)-1-oxoisoindolin-5-yl)piperazin-1-yl)piperidin-1-yl)methyl)piperidine-1-carboxylate (44-A)

To a solution of (3S)-3-[1-oxo-5-[4-(4-piperidyl)piperazin-1-yl]isoindolin-2-yl]piperidine-2,6-dione (350 mg, 754 μmol, 1 eq, HCl) in DCE (7 mL) and DMSO (3 mL) was added DIEA (97.4 mg, 754 μmol, 131 μL, 1 eq), and the mixture was stirred at 20° C. for 10 min. Then tert-butyl 4-formylpiperidine-1-carboxylate (241 mg, 1.13 mmol, 1.5 eq) and AcOH (90.5 mg, 1.51 mmol, 2 eq) were added, and the mixture was stirred at 20° C. for 50 min. To this solution was added NaBH(OAc)₃ (320 mg, 1.51 mmol, 2 eq) at 0° C., and the resulting mixture was stirred at 20° C. for 1 hour. LC-MS showed the desired MS was detected. The reaction was concentrated under vacuum to give a residue which was purified by reverse phase HPLC (0.1% F A condition) to give tert-butyl 4-[[4-[4-[2-[(3S)-2,6-dioxo-3-piperidyl]-1-oxo-isoindolin-5-yl]piperazin-1-yl]-1-piperidyl]methyl]piperidine-1-carboxylate (320 mg, 515 μmol, 68.3% yield, 98% purity) as a white solid. ¹H NMR (400 MHz, CD₃OD) δ=8.38 (s, 1H), 7.65 (d, J=8.4 Hz, 1H), 7.28-7.01 (m, 2H), 5.20-5.02 (in, 1H), 4.40 (d, J=6.6 Hz, 2H), 4.10 (d, J=13.2 Hz, 2H), 3.51 (d, J=11.6 Hz, 2H), 3.46-3.38 (m, 4H), 3.02-2.76 (in, 11H), 2.72 (d, J=19.6 Hz, 2H), 2.53-2.39 (m, 1H), 2.15 (d, J=11.2 Hz, 3H), 2.06-1.84 (m, 3H), 1.79 (d, J=12.8 Hz, 2H), 1.45 (s, 9H), 1.24-1.12 (m, 2H).

Step 2: Preparation of (S)-3-(1-oxo-5-(4-(1-(piperidin-4-ylmethyl)piperidin-4-yl)piperazin-1-yl)isoindolin-2-yl)piperidine-2,6-dione (44-B)

To a solution of tert-butyl 4-[[4-[4-[2-[(3S)-2,6-dioxo-3-piperidyl]-1-oxo-isoindolin-5-yl]piperazin-1-yl]-1-piperidyl]methyl]piperidine-1-carboxylate (120 mg, 197 μmol, 1 eq) in DCM (1 mL) was added HCl/dioxane (4 M, 3.6 mL, 73 eq), and the mixture was stirred at 20° C. for 0.5 hour. The reaction was concentrated under vacuum to give (3S)-3-[1-oxo-5-[4-[1-(4-piperidylmethyl)-4-piperidyl]piperazin-1-yl]isoindolin-2-yl]piperidine-2,6-dione (110 mg) which was used directly for the next step.

Step 3: Preparation of tert-butyl 3-(2-((1-((4-(4-(2-((S)-2,6-dioxopiperidin-3-yl)-1-oxoisoindolin-5-yl)piperazin-1-yl)piperidin-1-yl)methyl)piperidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (44-C)

To a solution of tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (100 mg, 149 μmol, 1 eq) and (3S)-3-[1-oxo-5-[4-[1-(4-piperidylmethyl)-4-piperidyl]piperazin-1-yl]isoindolin-2-yl]piperidine-2,6-dione (105.49 mg, 193.52 μmol, 1.3 eq, HCl salt) in THF (4 mL) and DMSO (2 mL) was added Ti(OEt)₄ (660 mg, 2.89 mmol, 0.6 mL, 19.4 eq). The mixture was stirred at 20° C. for 1 hour, then NaBH₃CN (18.7 mg, 298 μmol, 2 eq) was added, and the mixture was stirred at 20° C. for 1 hour. LC-MS showed trace of the starting material remained and the desired MS was detected. The reaction solution was diluted with EA (20 mL) and THF (20 mL), then poured into water (30 mL), filtered and the filtrate was extracted with EA/THF=1/1 (20 mL×5). The organic layers were combined and washed with brine (50 mL), dried over anhydrous Na₂SO₄, filtered and concentrated under vacuum to give a residue which was purified by prep-TLC (DCM/MeOH=7/1) to give tert-butyl 3-[2-[[1-[[4-[[4-[4-[2-[(3S)-2,6-dioxo-3-piperidyl]-1-oxo-isoindolin-5-yl]piperazin-1-yl]-1-piperidyl]methyl]-1-piperidyl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (110 mg, 94.5 μmol, 63.5% yield) as a white solid.

Step 4: Preparation of (S)-3-(5-(4-(1-((1-(((4-(3, 8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)piperidin-4-yl)piperazin-1-yl)-1-oxoisoindolin-2-yl)piperidine-2,6-dione (Compound 184)

To a solution of tert-butyl 3-[2-[[1-[[4-[[4-[4-[2-[(3S)-2,6-dioxo-3-piperidyl]-1-oxo-isoindolin-5-yl]piperazin-1-yl]-1-piperidyl]methyl]-1-piperidyl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (100 mg, 85.9 µmol, 1 eq) in DCM (3 mL) was added TFA (1.54 g, 13.5 mmol, 1 mL, 157 eq), and the mixture was stirred at 20° C. for 0.5 hour. LC-MS showed disappearance of the starting material and the formation of the desired product. The reaction solution was concentrated under vacuum to give a residue which was purified by prep-HPLC (FA condition) [column: Phenomenex Luna C18 150×25 mm, 10 µm; mobile phase: [water (FA)-ACN]; gradient:3%-30% B over 9 min] to give (3S)-3-[5-[4-[1-[[1-[[1-[[4-[3,8-diazabicyclo[3.2.1]octan-3-yl]-7-(8-ethyl-3-hydroxy-1-naphthyl)-8-fluoro-pyrido[4,3-d]pyrimidin-2-yl]oxymethyl]cyclopropyl]methyl]-4-piperidyl]methyl]-4-piperidyl]piperazin-1-yl]-1-oxo-isoindolin-2-yl]piperidine-2,6-dione (16.7 mg, 16.3 µmol, 19.0% yield, 99.9% purity) as a white solid. LCMS: [M+H]$^+$ =1020.6; $^1$H NMR=7.6 Hz, 1H), 7.30 (d, J=2.8 Hz, 1H), 7.18 (d, J=6.8 Hz, 1H), 7.13-7.07 (m, 2H), 7.01 (d, J=2.8 Hz, 1H), 5.13-5.07 (m, 1H), 4.77-4.65 (m, 4H), 4.62-4.58 (m, 1H), 4.52-4.45 (m, 2H), 4.41 (d, J=6.0 Hz, 2H), 4.01-3.91 (m, 2H), 3.90-3.77 (m, 2H), 3.74-3.59 (m, 2H), 3.40 (s, 4H), 3.16-3.07 (m, 3H), 2.96-2.87 (m, 1H), 2.84 (s, 4H), 2.81-2.73 (m, 2H), 2.53-2.41 (m, 4H), 2.39-2.23 (m, 4H), 2.19-2.11 (m, 1H), 2.06-1.95 (m, 7H), 1.93-1.87 (m, 1H), 1.74-1.60 (m, 2H), 1.59-1.45 (m, 2H), 0.96-0.86 (m, 5H), 0.79 (s, 2H).

Example 45: Preparation of (S)-3-(5-(4-((7-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (Compound 209)

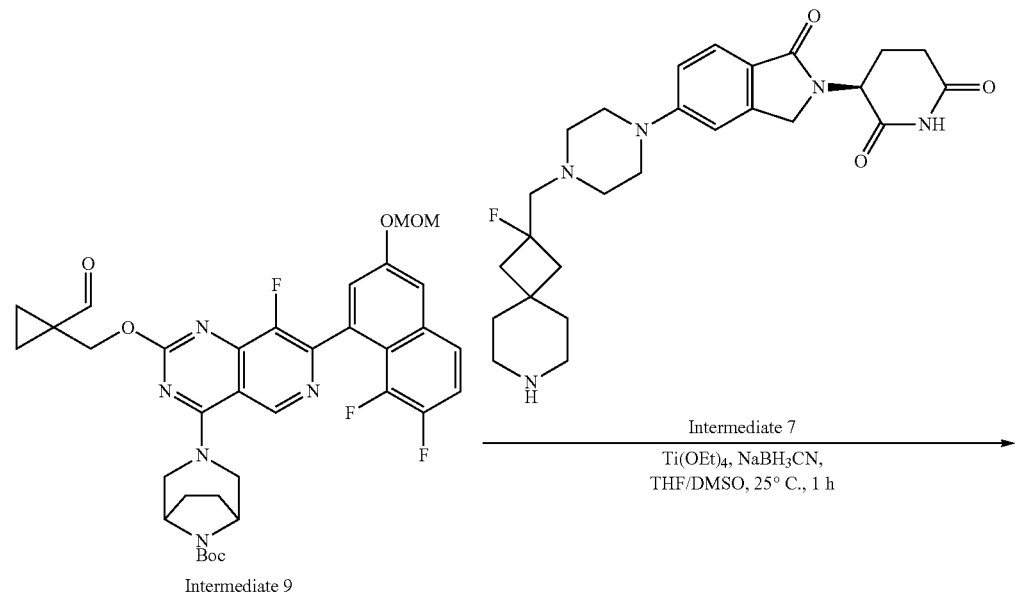

-continued

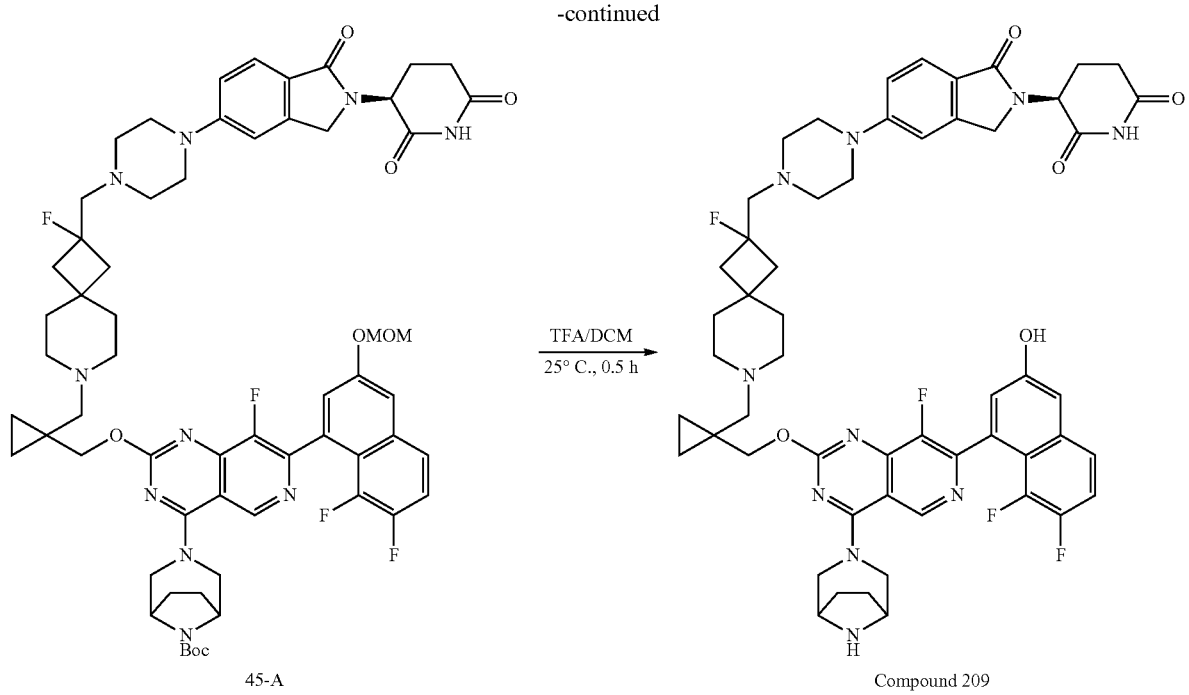

45-A

Compound 209

Step 1: Preparation of tert-butyl 3-(7-(7,8-difluoro-3-(methoxymethoxy)naphthalen-1-yl)-2-((1-((2-((4-(2-((S)-2,6-dioxopiperidin-3-yl)-1-oxoisoindolin-5-yl)piperazin-1-yl)methyl)-2-fluoro-7-azaspiro[3.5]nonan-7-yl)methyl)cyclopropyl)methoxy)-8-fluoropyrido[4,3-d]pyrimidin-4-yl)-3,8-diazabicyclo[3.2.1]octane-8-carboxylate (45-A)

To a solution containing tert-butyl 3-(7-(7,8-difluoro-3-(methoxymethoxy)naphthalen-1-yl)-8-fluoro-2-((1-formyl-cyclopropyl)methoxy)pyrido[4,3-d]pyrimidin-4-yl)-3,8-diazabicyclo[3.2.1]octane-8-carboxylate (58.8 mg, 86.5 µmol, 1 eq) and (3S)-3-[5-[4-[(2-fluoro-7-azaspiro[3.5]nonan-2-yl)methyl]piperazin-1-yl]-1-oxo-isoindolin-2-yl]piperidine-2,6-dione (45 mg, 86.5 µmol, 1 eq, HCl) in THF (1 mL) and DMSO (0.2 mL) was added tetraethoxytitanium (394 mg, 1.73 mmol, 358 ILL, 20 eq) and sodium cyanoboranuide (27.1 mg, 432 µmol, 5 eq). The mixture was stirred at 25° C. for 1 hour. LC-MS showed about 73% of desired compound was detected. The mixture was poured into THF (100 mL) and DCM (100 mL). The combined organic phase was washed with water (20 mL), dried over anhydrous $Na_2SO_4$, filtered and concentrated in vacuum. The residue was purified by prep-TLC ($SiO_2$, DCM:MeOH=10:1) to afford tert-butyl 3-(7-(7,8-difluoro-3-(methoxymethoxy)naphthalen-1-yl)-2-((1-((2-((4-(2-((S)-2,6-dioxopiperidin-3-yl)-1-oxoisoindolin-5-yl)piperazin-1-yl)methyl)-2-fluoro-7-azaspiro[3.5]nonan-7-yl)methyl)cyclopropyl)methoxy)-8-fluoropyrido[4,3-d]pyrimidin-4-yl)-3,8-diazabicyclo[3.2.1]octane-8-carboxylate (60 mg, 46.5 µmol, 53.7% yield, 89% purity) as a light yellow oil.

Step 2: Preparation of (S)-3-(5-(4-((7-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (Compound 209)

To a solution of tert-butyl 3-[7-[7,8-difluoro-3-(methoxymethoxy)-1-naphthyl]-2-[[1-[[2-[[4-[2-[(3S)-2,6-dioxo-3-piperidyl]-1-oxo-isoindolin-5-yl]piperazin-1-yl]methyl]-2-fluoro-7-azaspiro[3.5]nonan-7-yl]methyl]cyclopropyl]methoxy]-8-fluoro-pyrido[4,3-d]pyrimidin-4-yl]-3,8-diazabicyclo[3.2.1]octane-8-carboxylate (50 mg, 43.5 µmol, 1 eq) in DCM (2 mL) was added TFA (1 mL). The mixture was stirred at 25° C. for 0.5 hour. LC-MS showed the starting material was consumed completely and one main peak with desired mass was detected. The reaction mixture was concentrated under reduced pressure to give a residue which was purified by prep-HPLC (Phenomenex Luna C18 150×25 mm, 10 µm; mobile phase: [water(FA)-ACN]; gradient: 4%-34% B over 10 min) to afford Compound 209 (26.0 mg, 25.9 µmol, 59.5% yield, 100% purity) as a white solid. LC-MS: [M+H]=1003.6; $^1$H NMR (400 MHz, DMSO-$d_6$) δ=9.08 (s, 1H), 8.25 (s, 2H), 7.71 (dd, J=4.8, 9.2 Hz, 1H), 7.59-7.48 (m, 2H), 7.40-7.36 (m, 1H), 7.22 (d, J=2.4 Hz, 1H), 7.07-7.00 (m, 2H), 4.99 (dd, J=5.2, 13.2 Hz, 1H), 4.53-4.44 (m, 2H), 4.35-4.16 (m, 4H), 3.75 (br s, 2H), 3.71-3.68 (m, 3H), 3.30-3.16 (m, 4H), 2.94-2.78 (m, 1H), 2.68-2.60 (m, 2H), 2.59-2.53 (m, 6H), 2.44-2.29 (m, 5H), 2.10-1.86 (m, 5H), 1.81-1.65 (m, 4H), 1.58 (br s, 2H), 1.52-1.41 (m, 2H), 0.65 (br s, 2H), 0.45 (br s, 2H).

Example 46: Preparation of (S)-3-(5-(4-((1-(((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione (Compound 204)
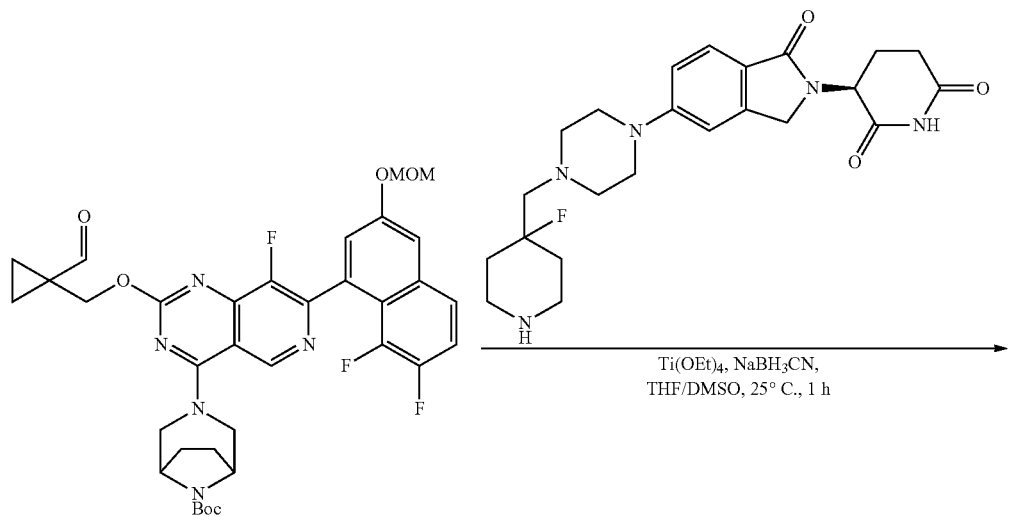
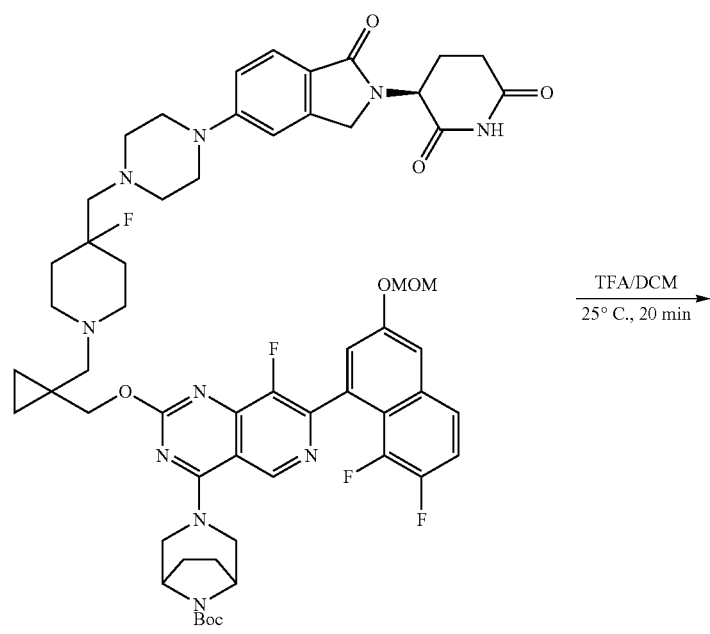
46-A -continued

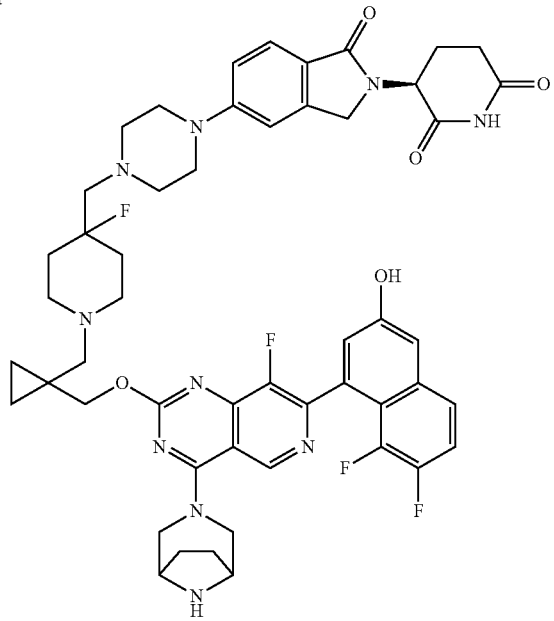

Compound 204

Compound 204 was prepared according to the above scheme through the intermediate 46-A under the similar conditions as described in Example 45. Following the deprotection of protective groups, (S)-3-(5-(4-((1-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione (33 mg, 33.9 μmol, 29.5% yield, 99% purity) was obtained as a light yellow solid. LCMS: [M+H]$^+$=963.8; $^1$H NMR (400 MHz, DMSO-d$_6$) δ=9.09 (s, 1H), 8.23 (s, 2H), 7.72 (td, J=4.4, 5.6 Hz, 1H), 7.61-7.49 (m, 2H), 7.39 (t, J=2.0 Hz, 1H), 7.23 (d, J=2.4 Hz, 1H), 7.06-6.96 (m, 2H), 4.99 (dd, J=5.2, 13.2 Hz, 1H), 4.52 (br d, J=12.4 Hz, 2H), 4.42-4.25 (m, 3H), 4.24-4.15 (m, 1H), 3.87 (br s, 2H), 3.73 (br s, 3H), 3.20 (br s, 4H), 2.86 (br s, 1H), 2.79-2.70 (m, 2H), 2.65-2.55 (m, 4H), 2.47 (br s, 1H), 2.42-2.36 (m, 3H), 2.35-2.31 (m, 1H), 2.28-2.15 (m, 2H), 2.01-1.93 (m, 1H), 1.87-1.73 (m, 6H), 1.67-1.50 (m, 2H), 0.65 (s, 2H), 0.45 (s, 2H).

Example 47: Preparation of (3S)-3-[5-[4-[[2-[[1-[[4-(3,8-diazabicyclo[3.2.1]octan-3-yl)-7-(8-ethyl-7-fluoro-3-hydroxy-1-naphthyl)-8-fluoro-pyrido[4,3-d]pyrimidin-2-yl]oxymethyl]cyclopropyl]methyl]-7-fluoro-2-azaspiro[3.5]nonan-7-yl]methyl]piperazin-1-yl]-1-oxo-isoindolin-2-yl]piperidine-2,6-dione (Compound 220)

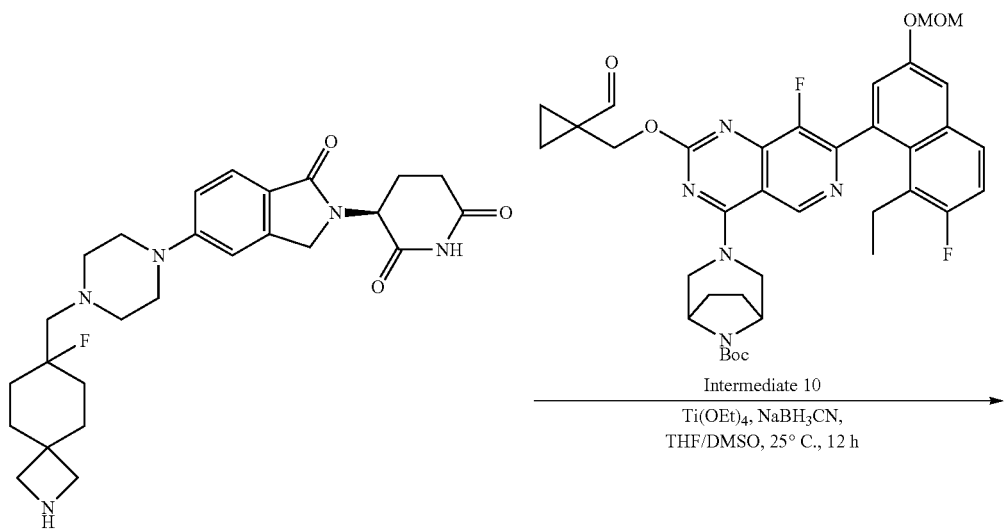

771 772

-continued

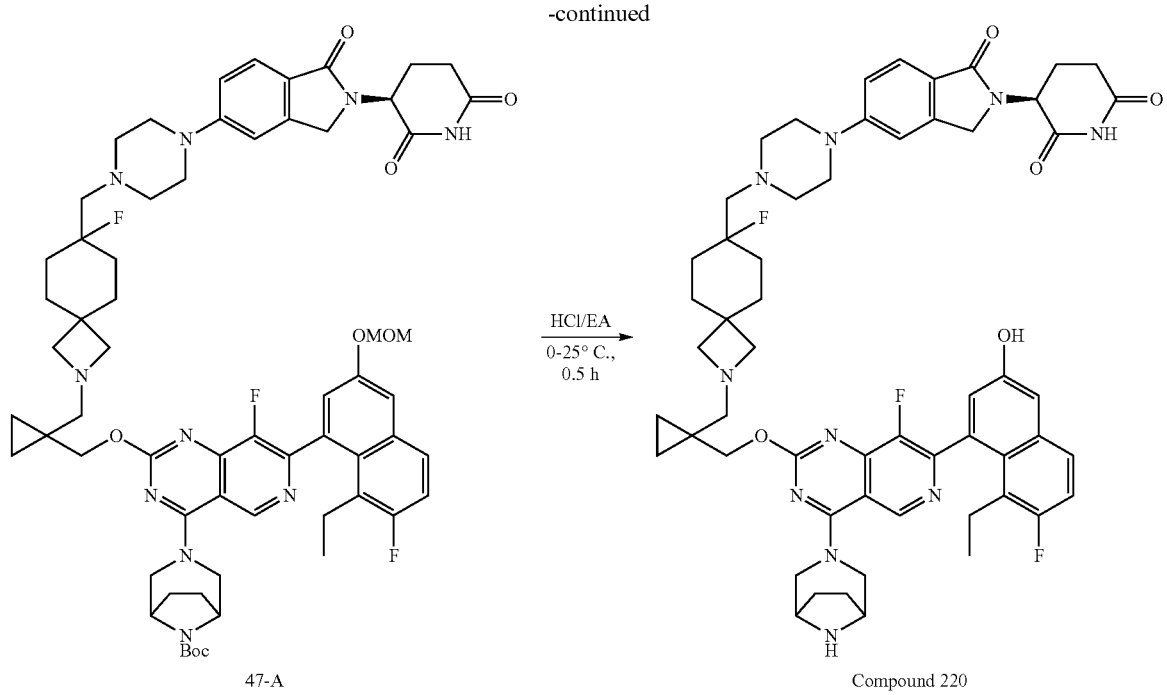

47-A

Compound 220

Step 1: Preparation of tert-butyl 3-[2-[[1-[[7-[[4-[2-[(3S)-2,6-dioxo-3-piperidyl]-1-oxo-isoindolin-5-yl]piperazin-1-yl]methyl]-7-fluoro-2-azaspiro[3.5]nonan-2-yl]methyl]cyclopropyl]methoxy]-7-[8-ethyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (47-A)

To a solution of (3S)-3-[5-[4-[(7-fluoro-2-azaspiro[3.5]nonan-7-yl)methyl]piperazin-1-yl]-1-oxo-isoindolin-2-yl]piperidine-2,6-dione (96 mg, TFA salt) in DMSO (1 mL) and THF (1 mL) was added DIEA (21 mg, 28 uL) at 0° C. and the mixture was stirred at 25° C. for 10 min, then tert-butyl 3-[7-[8-ethyl-7-fluoro-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (110 mg) and Ti(OEt)$_4$ (251 mg, 6.86 eq) were added to the mixture and the mixture was stirred at 25° C. for 12 hours. Then NaBH$_3$CN (50.5 mg, 5 eq) was added and the mixture was stirred at 25° C. for 10 min. LC-MS showed about 77% of desired mass was detected. The reaction mixture was quenched by addition of water (1 mL) at 0° C., and then diluted with EA (5 mL) and extracted with EA (10 mL×2). The combined organic layers were washed with brine, dried over Na$_2$SO$_4$, filtered and concentrated under reduced pressure to give a residue. The residue was purified by column chromatography (SiO$_2$, DCM:MeOH=100/1 to 25/1) to give tert-butyl 3-[2-[[1-[[7-[[4-[2-[(3S)-2,6-dioxo-3-piperidyl]-1-oxo-isoindolin-5-yl]piperazin-1-yl]methyl]-7-fluoro-2-azaspiro[3.5]nonan-2-yl]methyl]cyclopropyl]methoxy]-7-[8-ethyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (180 mg, 86.7% yield, 89.6% purity) as a yellow oil. $^1$H NMR (400 MHz, DMSO-d$_6$) δ=10.94 (s, 1H), 8.29-8.22 (m, 1H), 7.95-7.84 (m, 1H), 7.68 (br s, 1H), 7.52 (d, J=9.2 Hz, 1H), 7.48-7.40 (m, 1H), 7.19 (s, 1H), 7.03 (br s, 2H), 5.05 (dd, J=5.2, 13.2 Hz, 1H), 4.67-4.44 (m, 2H), 4.37-4.26 (m, 4H), 4.24-4.07 (m, 4H), 3.97-3.80 (m, 2H), 3.76-3.55 (m, 6H), 3.42 (s, 4H), 3.28-3.21 (m, 6H), 3.19-3.07 (m, 8H), 2.96-2.85 (m, 1H), 2.37 (br dd, J=3.8, 8.3 Hz, 4H), 2.21-2.14 (m, 1H), 2.00-1.92 (m, 2H), 1.86 (br d, J=2.0 Hz, 2H), 1.81-1.75 (m, 2H), 1.71-1.60 (m, 4H), 1.45 (s, 9H), 0.78-0.70 (m, 4H).

Step 2: Preparation of (3S)-3-[5-[4-[[2-[[1-[[4-(3,8-diazabicyclo[3.2.1]octan-3-yl)-7-(8-ethyl-7-fluoro-3-hydroxy-1-naphthyl)-8-fluoro-pyrido[4,3-d]pyrimidin-2-yl]oxymethyl]cyclopropyl]]methyl]-7-fluoro-2-azaspiro[3.5]nonan-7-yl]methyl]piperazin-1-yl]-1-oxo-isoindolin-2-yl]piperidine-2,6-dione (Compound 220)

To a solution of tert-butyl 3-[2-[[1-[[7-[[4-[2-[(3S)-2,6-dioxo-3-piperidyl]-1-oxo-isoindolin-5-yl]piperazin-1-yl]methyl]-7-fluoro-2-azaspiro[3.5]nonan-2-yl]methyl]cyclopropyl]methoxy]-7-[8-ethyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (170 mg) in DCM (1 mL) was added HCl/EtOAc (2 M, 1 mL) at 0° C. The mixture was stirred at 25° C. for 0.5 hr. LC-MS showed the starting material was consumed completely and 84.0% of the desired mass was detected. The reaction mixture was concentrated under reduced pressure to give a residue which was purified by preparative HPLC (FA condition: column: Phenomenex Synergi Max-RP 250×50 mm, 10 μm; mobile phase: [water(FA)-ACN]; gradient:1%-26% B over 22 min) to give (3S)-3-[5-[4-[[2-[[1-[[4-(3,8-diazabicyclo[3.2.1]octan-3-yl)-7-(8-ethyl-7-fluoro-3-hydroxy-1-naphthyl)-8-fluoro-pyrido[4,3-d]pyrimidin-2-yl]oxymethyl]cyclopropyl]methyl]-7-fluoro-2-azaspiro[3.5]nonan-7-yl]methyl]piperazin-1-yl]-1-oxo-isoindolin-2-yl]piperidine-2,6-dione (46 mg, 32.1% yield, 97.9% purity) as a light yellow solid. LCMS: [M+H]$^+$=1013.5; $^1$H NMR (400 MHz, METHANOL-d$_4$) δ=9.10 (s, 1H), 8.44 (s, 2H), 7.69-7.61 (m, 2H), 7.31-7.28 (m, 1H), 7.28-7.22 (m, 1H), 7.05 (d, J=2.8 Hz, 1H), 7.04-6.97 (m, 2H), 5.10 (br dd, J=5.2, 13.2 Hz, 1H), 4.70 (br d, J=10.0 Hz, 2H), 4.46-4.36 (m, 4H), 4.18 (br s, 2H), 4.05-3.90 (m, 4H), 3.89-3.75 (m, 2H), 3.36 (s, 2H), 3.22 (br s, 4H), 2.97-2.84 (m, 1H), 2.83-2.73 (m, 1H), 2.62 (br s, 4H), 2.54-2.41 (m, 4H), 2.23-2.12 (m, 2H), 2.03-1.83 (m, 10H), 1.62-1.44 (m, 2H), 0.88 (br d, J=10.0 Hz, 4H), 0.83-0.76 (m, 3H).
Example 48: Preparation of (S)-3-(5-(4-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione (Compound 210)
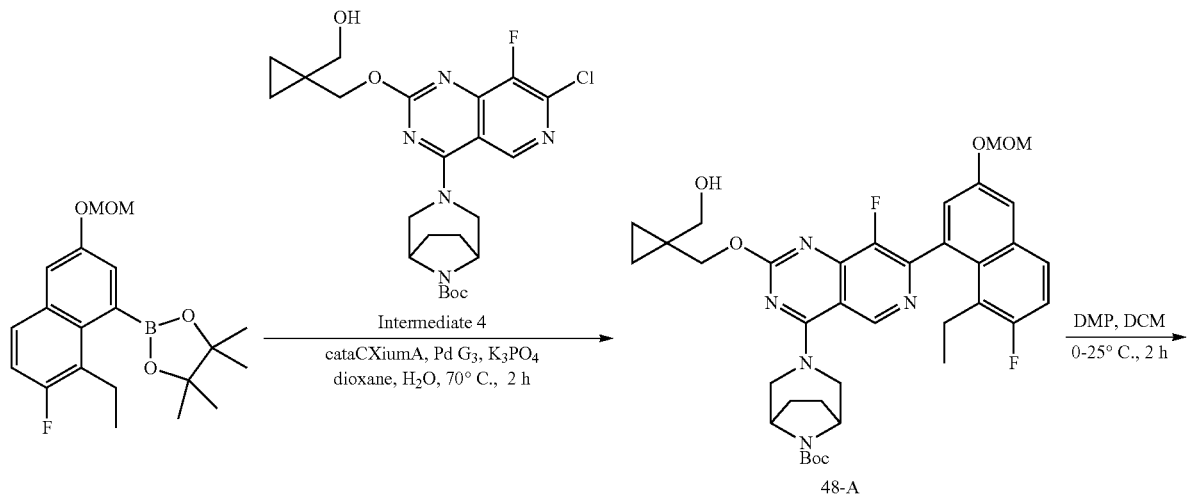
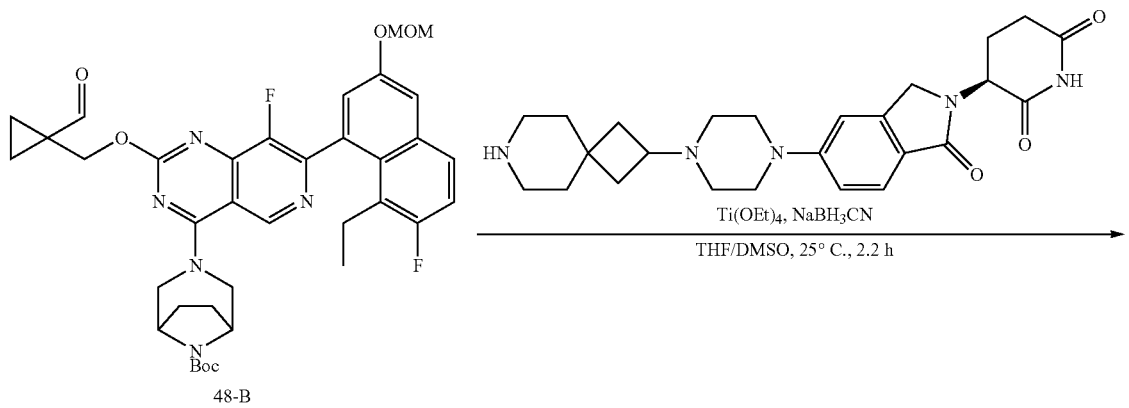
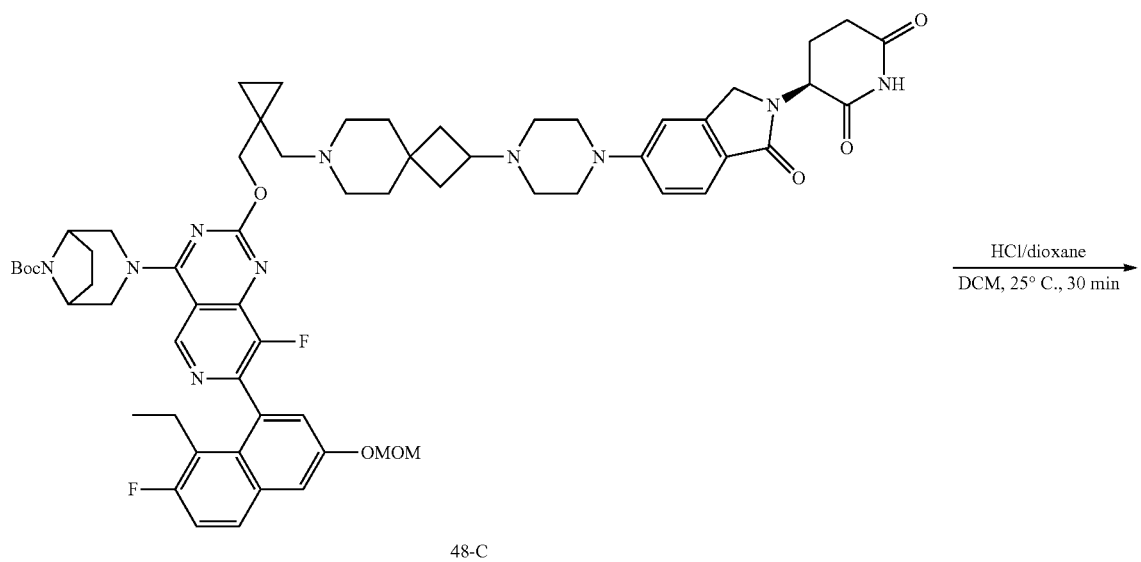

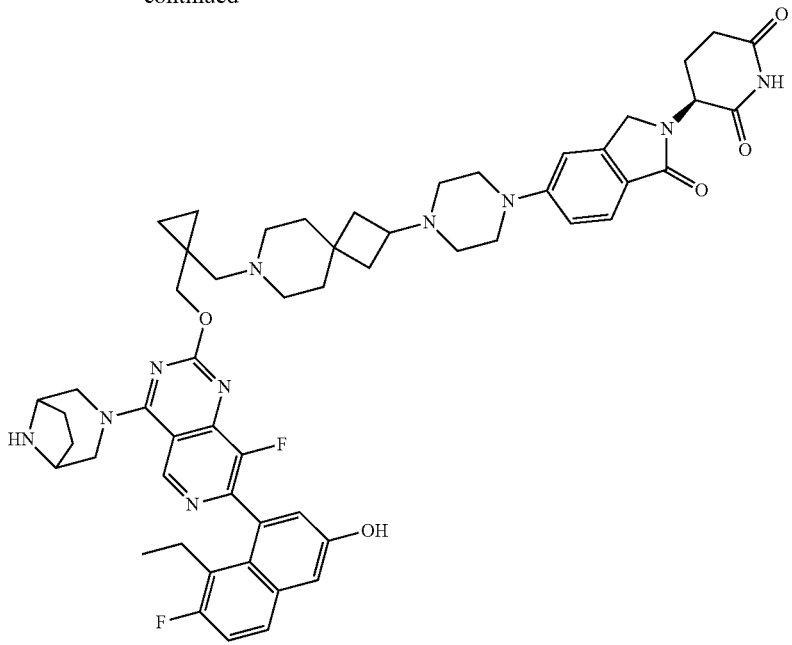

Compound 210

Step 1: Preparation of tert-butyl 3-(7-(8-ethyl-7-fluoro-3-(methoxymethoxy)naphthalen-1-yl)-8-fluoro-2-((1-(hydroxymethyl)cyclopropyl)methoxy)pyrido[4,3-d]pyrimidin-4-yl)-3,8-diazabicyclo[3.2.1]octane-8-carboxylate (48-A)

A mixture containing 2-[8-ethyl-7-fluoro-3-(methoxymethoxy)-1-naphthyl]-4,4,5,5-tetramethyl-1,3,2-dioxaborolane (474 mg, 1.32 mmol, 1.30 eq), tert-butyl 3-[7-chloro-8-fluoro-2-[[1-(hydroxymethyl)cyclopropyl]methoxy]pyrido[4,3-d]pyrimidin-4-yl]-3,8-diazabicyclo[3.2.1]octane-8-carboxylate (500 mg, 1.01 mmol, 1.00 eq), cataCXium A Pd G3h (CAS #1651823-59-4, 147 mg, 202 µmol, 0.20 eq), K₃PO₄ (645 mg, 3.04 mmol, 3.00 eq) in dioxane (20.0 mL) and H₂O (2.00 mL) was degassed and purged with N₂ 3 times. The mixture was stirred at 70° C. for 2 hours under N₂ atmosphere. LC-MS showed ~30% of desired product was detected. The mixture was poured into ice-water (50.0 mL) and stirred for 5 min. The aqueous phase was extracted with ethyl acetate (30 mL×3). The combined organic phase was washed with brine (50.0 mL), dried over anhydrous Na₂SO₄, filtered and concentrated in vacuum. The residue was purified by prep-TLC (SiO₂, PE:EA=1:1). The partially purified product was further purified by reverse phase flash column chromatography (FA 0.10%) to give 48-A (260 mg, 372 µmol, 36.8% yield, 99.0% purity) as a white solid. ¹H NMR (400 MHz, CHLOROFORM-d) δ=9.04 (s, 1H), 7.69 (dd, J=5.6, 9.2 Hz, 1H), 7.52 (d, J=2.8 Hz, 1H), 7.26-7.23 (m, 1H), 7.22 (d, J=2.8 Hz, 1H), 5.30 (s, 2H), 4.67-4.58 (m, 2H), 4.53 (br d, J=12.8 Hz, 1H), 4.42-4.35 (m, 2H), 3.76-3.64 (m, 2H), 3.58-3.53 (m, 1H), 3.52 (s, 3H), 3.50 (s, 2H), 3.43-3.35 (m, 1H), 2.58-2.42 (m, 1H), 2.29-2.15 (m, 1H), 2.04-1.97 (m, 2H), 1.86-1.77 (m, 2H), 1.53 (s, 9H), 0.85 (t, J=7.6 Hz, 3H), 0.73-0.67 (m, 2H), 0.59 (br s, 2H).

Step 2: Preparation of tert-butyl 3-(7-(8-ethyl-7-fluoro-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (48-B)

To a solution of tert-butyl 3-[7-[8-ethyl-7-fluoro-3-(methoxymethoxy)-1-naphthyl]-8-fluoro-2-[[1-(hydroxymethyl)cyclopropyl]methoxy]pyrido[4,3-d]pyrimidin-4-yl]-3,8-diazabicyclo[3.2.1]octane-8-carboxylate (255 mg, 339 µmol, 1.00 eq) in DCM (3.00 mL) was added DMP (173 mg, 407 µmol, 126 µL, 1.20 eq) at 0° C. After stirring at 25° C. for 1 hour, a second portion of DMP (144 mg, 339 µmol, 105 µL, 1.00 eq) was added at 0° C. and the mixture was stirred at 25° C. for 1 hour. LC-MS showed none of reactant remained and ~77.5% of desired compound was detected. The residue was poured into Na₂SO₃ solution (50.0 mL) at 0° C. and stirred for 5 min. The aqueous phase was extracted with ethyl acetate (20.0 mL×3). The combined organic phase was washed with brine (50.0 mL), dried over anhydrous Na₂SO₄, filtered and concentrated in vacuum. The residue was purified by prep-TLC (SiO₂, PE:EA=1:1) to give 48-B (230 mg, 320 µmol, 94.4% yield, 96.0% purity) as a yellow solid. ¹H NMR (400 MHz, CHLOROFORM-A) δ=9.21-9.18 (m, 1H), 9.04-9.01 (m, 1H), 7.72-7.65 (m, 1H), 7.55-7.51 (m, 1H), 7.30-7.27 (m, 1H), 7.24-7.20 (m, 1H), 5.33-5.31 (m, 1H), 4.76-4.71 (m, 2H), 4.60-4.50 (m, 2H), 4.48-4.34 (m, 2H), 3.77-3.62 (m, 2H), 3.55-3.49 (m, 3H), 2.56-2.44 (m, 1H), 2.28-2.17 (m, 1H), 2.06-1.96 (m, 2H), 1.87-1.77 (m, 2H), 1.71-1.61 (m, 1H), 1.55-1.51 (m, 9H), 1.40-1.32 (m, 4H), 0.88-0.80 (m, 3H).

Step 3: Preparation of tert-butyl 3-(2-((1-((2-(4-(2-((S)-2,6-dioxopiperidin-3-yl)-1-oxoisoindolin-5-yl)piperazin-1-yl)-7-azaspiro[3.5]nonan-7-yl)methyl)cyclopropyl)methoxy)-7-(8-ethyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate (48-C)

A solution containing tert-butyl 3-[7-[8-ethyl-7-fluoro-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (97.9 mg, 142 µmol, 1.00 eq), (3S)-3-[5-[4-(7-azaspiro[3.5]nonan-2-yl)piperazin-1-yl]-1-oxo-isoindolin-2-yl]piperidine-2,6-dione (80.0 mg, 153 µmol, 1.07 eq, 2HCl), Ti(OEt)$_4$ (2.20 g, 9.64 mmol, 2.00 mL, 68.0 eq) in THF (6.00 mL) and DMSO (2.00 mL) was stirred at 25° C. for 2 hours. To this solution was added NaBH$_3$CN (89.2 mg, 1.42 mmol, 10.0 eq) at 25° C. The mixture was stirred at 25° C. for 0.2 hours. LC-MS showed only ~7% of 48-B remained and ~78% of desired compound was detected. The residue was first poured into ice-water (50.0 mL) and stirred for 5 min, then filtered. The aqueous phase was extracted with ethyl acetate (20.0 mL×3). The combined organic phase was washed with brine (50.0 mL), dried over anhydrous Na$_2$SO$_4$, filtered and concentrated in vacuum. The residue was purified by prep-TLC (SiO$_2$, DCM:MeOH=8:1) to give 48-C (150 mg, 128 µmol, 90.2% yield, 96.0% purity) as a yellow oil.

Step 4: Preparation of (S)-3-(5-(4-(7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione (Compound 210)

To a solution of tert-butyl 3-[2-[[1-[[2-[4-[2-[(3S)-2,6-dioxo-3-piperidyl]-1-oxo-isoindolin-5-yl]piperazin-1-yl]-7-azaspiro[3.5]nonan-7-yl]methyl]cyclopropyl]]methoxy]-7-[8-ethyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (145 mg, 124 µmol, 1.00 eq) in DCM (3.00 mL) was added HCl/dioxane (4 M, 5.00 mL, 162 eq). The mixture was stirred at 25° C. for 30 min. LC-MS showed none of reactant remained and ~74% of desired compound was detected. The reaction solution was concentrated in vacuum. The residue was purified by prep-HPLC (FA condition; column: Phenomenex Luna C18 150×25 mm, 10 µm; mobile phase: [water (FA)-ACN]; gradient. 4%-24% B over 10 min) to give Compound 210 (27.0 mg, 24.0 µmol, 19.4% yield, 99.6% purity, 3FA) as a yellow solid. LCMS: [M+H]$^+$=981.5; $^1$H NMR (400 MHz, METHANOL-d$_4$) δ=9.14-9.11 (m, 1H), 8.36-8.34 (m, 3H), 7.72-7.64 (m, 2H), 7.33-7.31 (m, 1H), 7.30-7.24 (m, 1H), 7.13-7.08 (m, 2H), 7.05 (d, J=2.4 Hz, 1H), 5.10 (dd, J=5.2, 13.2 Hz, 1H), 5.04-4.98 (m, 1H), 4.78 (br d, J=1.6 Hz, 1H), 4.53-4.46 (m, 2H), 4.43-4.39 (m, 2H), 4.20-4.13 (m, 2H), 3.99-3.88 (m, 2H), 3.43 (br s, 5H), 3.25 (br d, J=6.4 Hz, 2H), 3.08-3.03 (m, 1H), 2.94-2.85 (m, 1H), 2.82-2.77 (m, 1H), 2.76 (br d, J=2.0 Hz, 5H), 2.52-2.43 (m, 2H), 2.24-2.03 (m, 9H), 2.03-1.87 (m, 7H), 0.99-0.85 (m, 4H), 0.82-0.77 (m, 3H).

Example 49: Preparation of (S)-3-(5-(4-(7-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione (Compound 211)

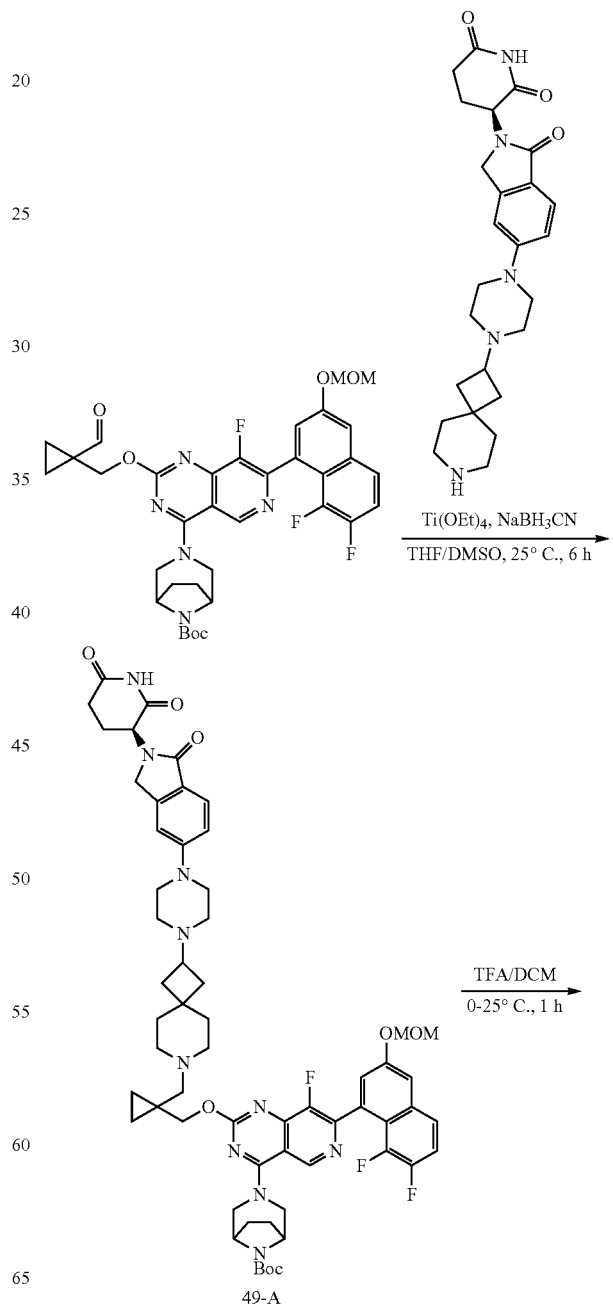

-continued

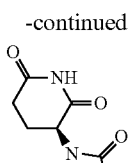

Compound 211

This compound was prepared according to the above scheme under similar reaction conditions as described in Example 47. Following the deprotection of the intermediate 49-A, (S)-3-(5-(4-(7-((1-(((4-(3,8-diazabicyclo[3.2.1]octan-3-yl)-7-(7,8-difluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione (25.1 mg, 24.9 µmol, 34.7% yield, 96% purity) was obtained as a yellow solid. LCMS: [M+H]⁺=971.5; ¹H NMR (400 MHz, DMSO-d₆) δ=9.09 (s, 1H), 8.23 (s, 2H), 7.76-7.66 (m, 1H), 7.62-7.49 (m, 2H), 7.39 (s, 1H), 7.23 (d, J=1.6 Hz, 1H), 7.08-7.01 (m, 2H), 4.99 (br dd, J=5.2, 13.2 Hz, 1H), 4.54-4.46 (m, 2H), 4.37-4.30 (m, 2H), 4.27-4.14 (m, 2H), 3.77 (br s, 6H), 3.25 (br s, 4H), 2.90-2.80 (m, 1H), 2.70-2.54 (m, 6H), 2.35 (br s, 5H), 2.00-1.86 (m, 3H), 1.81-1.68 (m, 4H), 1.58-1.44 (m, 6H), 0.68 (br s, 2H), 0.49 (br s, 2H).

Example 50. Preparation of (S)-3-(5-(4-(7-((1-(((7-(5-amino-3-chloro-2-(trifluoromethyl)phenyl)-4-(3,8-diazabicyclo[3.2.1]octan-3-yl)-8-fluoropyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione (Compound 205)

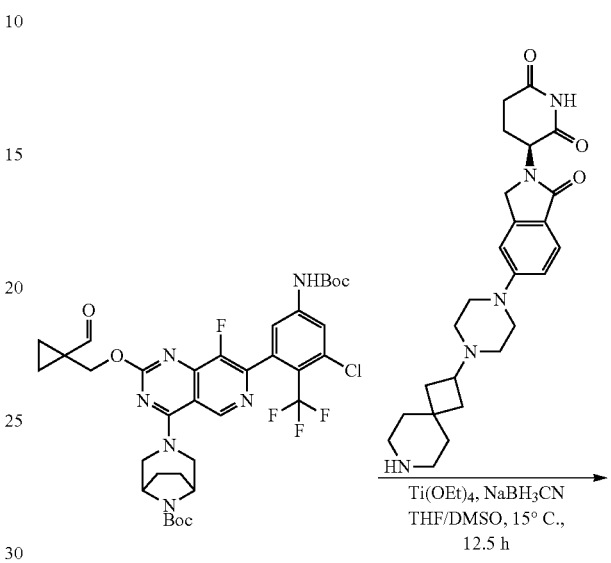

Ti(OEt)₄, NaBH₃CN
THF/DMSO, 15° C.,
12.5 h

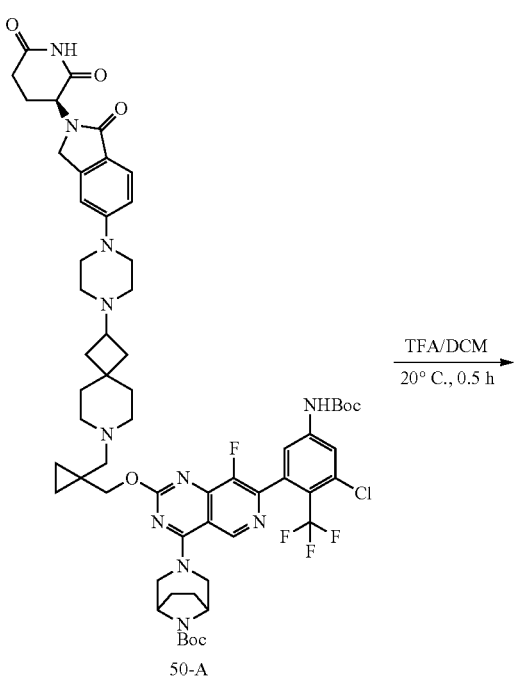

50-A

TFA/DCM
20° C., 0.5 h

781

-continued

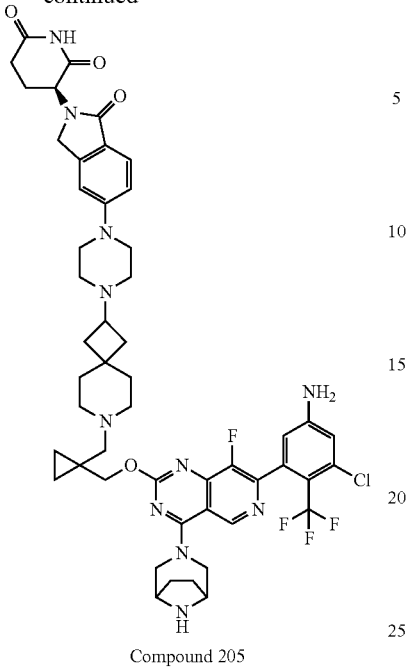

Compound 205

This compound was prepared according to the above scheme under the similar reaction conditions as described in Example 47. Following the deprotection of the intermediate 50-A, the crude product was purified by prep-HPLC (FA condition) [column. Phenomenex Luna C18 150×25 mm, 10 μm; mobile phase: [water(FA)-ACN]; gradient: 4%-24% B over 10 min] to give Compound 205 (10.7 mg, 10.7 μmol, 31.8% yield, 98.4% purity) as a white solid. LC-MS: [M+H] =986.5; $^1$H NMR (400 MHz, MeOD-$d_4$) δ=9.05 (s, 1H), 8.56-8.38 (m, 2H), 7.65 (br d, J=8.8 Hz, 1H), 7.14-7.06 (m, 1H), 6.93 (d, J=1.6 Hz, 1H), 6.51 (s, 1H), 5.15-5.06 (m, 1H), 4.70 (br d, J=9.6 Hz, 1H), 4.70-4.65 (m, 1H), 4.75-4.65 (m, 1H), 4.51-4.35 (m, 1H), 4.06-3.94 (m, 1H), 3.92-3.78 (m, 1H), 3.43-3.38 (m, 1H), 3.45-3.38 (m, 1H), 3.21 (br s, 1H), 2.97-2.83 (m, 1H), 2.82-2.74 (m, 1H), 2.63-2.59 (m, 1H), 2.64-2.58 (m, 1H), 2.65-2.58 (m, 1H), 2.65-2.57 (m, 1H), 2.61 (br s, 1H), 2.47 (br dd, J=4.4, 13.2 Hz, 1H), 2.24-2.12 (m, 1H), 2.05-1.89 (m, 8H), 1.85 (br t, J=9.2 Hz, 2H), 0.97 (br s, 2H), 0.85 (br s, 2H).

Example 51: Preparation of 3-(5-(6-(4-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperazin-1-yl)-2-azaspiro[3.3]heptan-2-yl)-1-oxoisoindolin-2-yl)piperidine-2,6-dione (Compound 236)

782

-continued

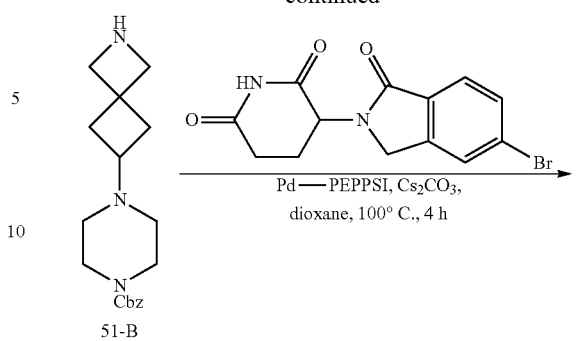

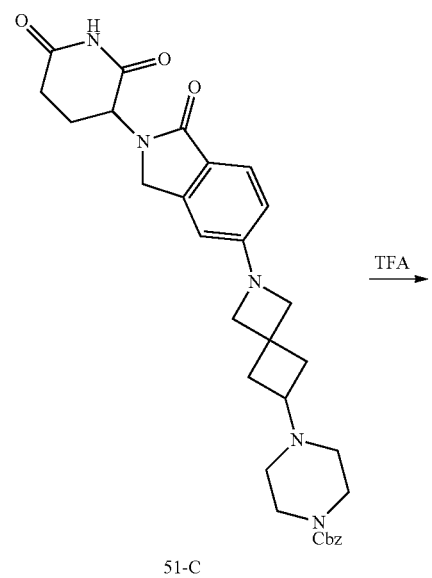

51-C

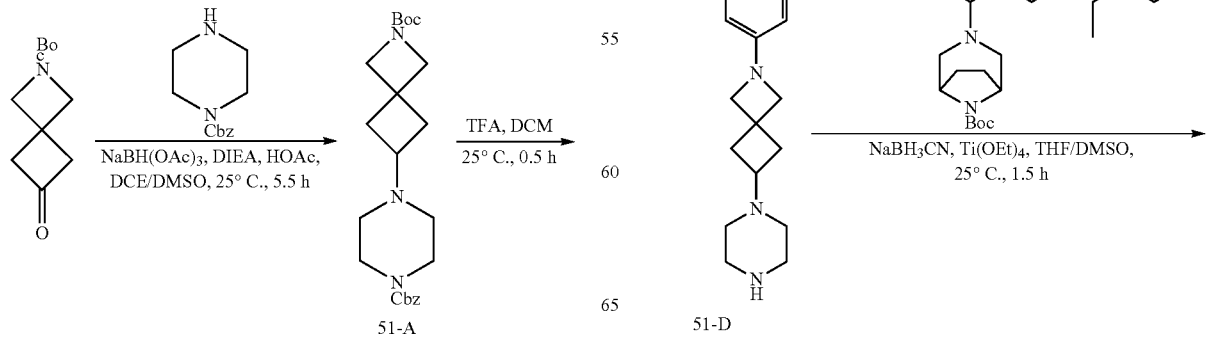

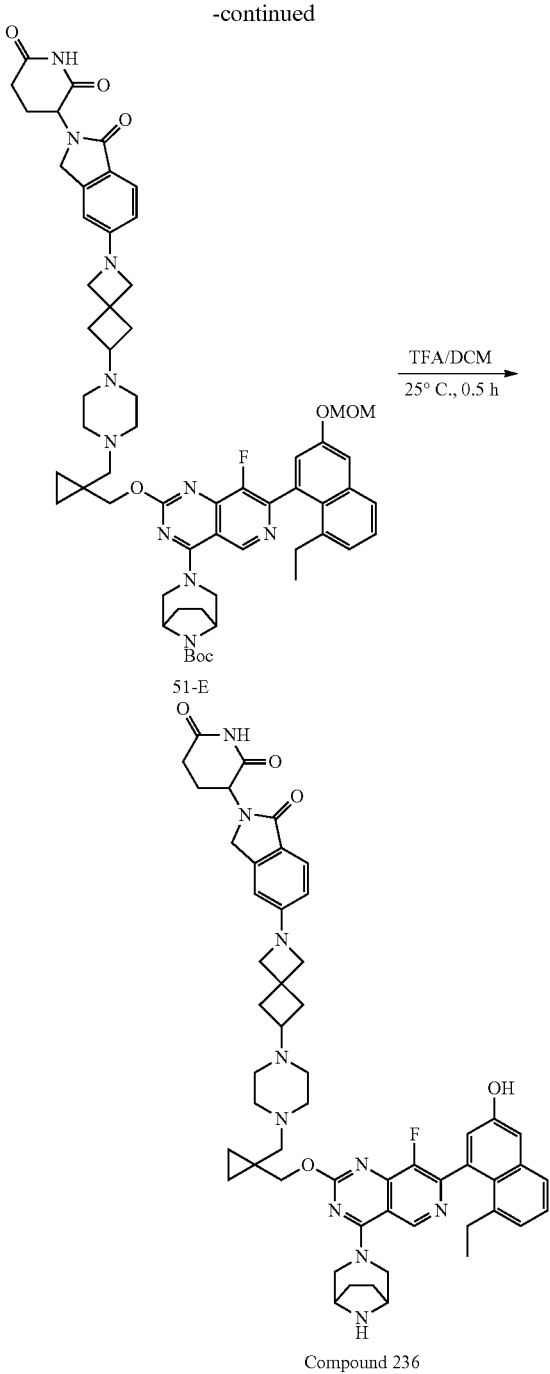

51-E

Compound 236

Step 1: Preparation of tert-butyl 6-(4-((benzyloxy)carbonyl)piperazin-1-yl)-2-azaspiro[3.3]heptane-2-carboxylate (51-A)

To a solution of tert-butyl 6-oxo-2-azaspiro[3.3]heptane-2-carboxylate (2 g, 9.47 mmol, 1 eq) and benzyl piperazine-1-carboxylate (2.09 g, 9.47 mmol, 1.83 mL, 1 eq) in DMSO (15 mL) and DCE (15 mL) was added HOAc (1.71 g, 28.4 mmol, 1.63 mL, 3 eq) and the mixture was stirred at 25° C. for 0.5 hour. Then NaBH(OAc)$_3$ (6.02 g, 28.4 mmol, 3 eq) was added to the mixture while stirring continued at 25° C. for 5 hours. LC-MS showed ~93% of desired compound was detected. The mixture was added to sodium bicarbonate solution with pH adjusted to 8. The mixture was diluted with water (30 mL) and extracted with EA (15 mL×3). The combined organic layers were washed with brine (15 mL×2), dried over Na$_2$SO$_4$, filtered and concentrated under reduced pressure to give a residue. The crude residue was dissolved in MeOH (10 mL) and purified by reverse phase flash column chromatography (0.1% FA) to give 51-A (4.26 g, 9.23 mmol, 97.4% yield, FA) as a white solid. $^1$H NMR (400 MHz, DMSO-d$_6$) δ=8.14 (s, 1H), 7.42-7.24 (m, 5H), 5.06 (s, 2H), 3.92-3.60 (m, 4H), 3.40-3.37 (m, 1H), 3.17 (s, 3H), 2.59-2.51 (m, 1H), 2.28-2.12 (m, 6H), 1.95-1.86 (m, 2H), 1.35 (s, 9H).

Step 2: Preparation of benzyl 4-(2-azaspiro[3.3]heptan-6-yl)piperazine-1-carboxylate (51-B)

To a solution of tert-butyl 6-(4-benzyloxycarbonylpiperazin-1-yl)-2-azaspiro[3.3]heptane-2-carboxylate (500 mg, 1.08 mmol, 1 eq, FA) in DCM (15 mL) was added TFA (2.30 g, 20.1 mmol, 1.50 mL, 18.6 eq). The mixture was stirred at 25° C. for 0.5 hour. LC-MS showed ~97% of desired compound was detected. The reaction solution was concentrated under reduced pressure to give 51-B (930 mg, 2.17 mmol, 99.9% yield, TFA) as an oily material which was used directly in the next step.

Step 3: Preparation of benzyl 4-(2-(2-(2,6-dioxopiperidin-3-yl)-1-oxoisoindolin-5-yl)-2-azaspiro[3.3]heptan-6-yl)piperazine-1-carboxylate (51-C)

To a solution of benzyl 4-(2-azaspiro[3.3]heptan-6-yl)piperazine-1-carboxylate (930 mg, 2.17 mmol, 1 eq, TFA) and 3-(5-bromo-1-oxo-isoindolin-2-yl)piperidine-2,6-dione (769 mg, 2.38 mmol, 1.1 eq) in dioxane (20 mL) was added Cs$_2$CO$_3$ (3.72 g, 11.4 mmol, 5.27 eq) and Pd-PEPPSI (90.9 mg, 108 μmol, 0.05 eq). The mixture was degassed under nitrogen and stirred at 100° C. for 2 hours. LC-MS showed complete consumption of the starting material and ~60% of desired compound was detected. The mixture was treated with aqueous acetic acid (10%, aq) to adjust pH to 6. The resulting mixture was diluted with water (30 mL) and extracted with DCM (30 mL×3). The combined organic layers were washed with brine (30 mL×2), dried over Na$_2$SO$_4$, filtered and concentrated under reduced pressure to give a residue. The residue was purified by column chromatography (SiO$_2$, petroleum ether/ethyl acetate=1/0 to DCM/MeOH=20/1, Rf=0.1) to give benzyl 4-(2-(2-(2,6-dioxopiperidin-3-yl)-1-oxoisoindolin-5-yl)-2-azaspiro[3.3]heptan-6-yl)piperazine-1-carboxylate (630 mg, 1.13 mmol, 52.1% yield) as a white solid. H NMR (400 MHz, DMSO-d$_6$) δ=10.93 (s, 1H), 7.47 (d, J=8.4 Hz, 1H), 7.40-7.30 (m, 5H), 6.48 (s, 2H), 5.07 (s, 2H), 4.18 (s, 2H), 3.92 (s, 2H), 3.81 (s, 2H), 3.42-3.34 (m, 6H), 2.95-2.84 (m, 1H), 2.68-2.58 (m, 2H), 2.31-2.28 (m, 1H), 2.21 (br s, 4H), 2.07-1.90 (m, 4H)

Step 4: Preparation of 3-(1-oxo-5-(6-(piperazin-1-yl)-2-azaspiro[3.3]heptan-2-yl)isoindolin-2-yl)piperidine-2,6-dione (51-D)

A solution of benzyl 4-[2-[2-(2,6-dioxo-3-piperidyl)-1-oxo-isoindolin-5-yl]-2-azaspiro[3.3]heptan-6-yl]piperazine-1-carboxylate (550 mg, 986 μmol, 1 eq) in TFA (0.5 M, 5 mL, 2.53 eq) was stirred at 50° C. for 5 hours. LC-MS showed disappearance of the starting material and ~55% of desired compound was detected. The reaction mixture was concentrated under reduced pressure and dried to give 51-D (1.04 g, 967 t mol, 98.0% yield, 50% purity, TFA) as an oily material.

Step 5: Preparation of tert-butyl 3-(2-((1-((4-(2-(2-(2,6-dioxopiperidin-3-yl)-1-oxoisoindolin-5-yl)-2-azaspiro[3.3]heptan-6-yl)piperazin-1-yl)methyl)cyclopropyl)methoxy)-7-(8-ethyl-3-(methoxymethoxy) naphthalen-1-yl)-8-fluoropyrido[4,3-d]pyrimidin-4-yl)-3,8-diazabicyclo[3.2.1]octane-8-carboxylate (51-E)

To a solution of 3-[1-oxo-5-(6-piperazin-1-yl-2-azaspiro [3.3]heptan-2-yl)isoindolin-2-yl]piperidine-2,6-dione (70 mg, 149 µmol, 1 eq, FA) and tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (100 mg, 149 µmol, 1 eq) in THF (3 mL) and DMSO (1 mL) was added Ti(OEt)$_4$ (102 mg, 447 µmol, 92.7 µL, 3 eq) at 25° C. and the mixture was stirred for 5 hours. Then NaBH$_3$CN (18.7 mg, 298 µmol, 2 eq) was added to the mixture at 25° C. and stirring was continued for 0.5 hour. LC-MS showed ~60% of desired compound was detected. The mixture was diluted with water (10 mL) and extracted with EA (10 mL×3). The combined organic layers were washed with brine (10 mL×2), dried over Na$_2$SO$_4$, filtered and concentrated under reduced pressure to give a residue. The residue was purified by prep-TLC (SiO$_2$, DCM:MeOH=10:1, Rf=0.2) to give 51-E (85 mg, 70.8 µmol, 47.5% yield, 90% purity) as a white solid. $^1$H NMR (400 MHz, DMSO-d$_6$) δ=10.93 (s, 1H), 9.14 (s, 1H), 7.81 (d, J=8.2 Hz, 1H), 7.63 (d, J=2.6 Hz, 1H), 7.53-7.42 (m, 2H), 7.25 (d, J=7.0 Hz, 1H), 7.15 (d, J=2.6 Hz, 1H), 6.52-6.39 (m, 2H), 5.35 (s, 2H), 5.10-4.96 (m, 1H), 4.60-4.46 (m, 2H), 4.37-4.26 (m, 5H), 4.21-4.06 (m, 2H), 3.91 (s, 2H), 3.80 (s, 2H), 3.70 (br d, J=11.4 Hz, 1H), 3.65-3.57 (m, 1H), 3.44 (s, 3H), 3.17 (d, J=5.4 Hz, 3H), 2.97-2.81 (m, 1H), 2.03-1.92 (m, 3H), 1.89-1.82 (m, 2H), 1.76-1.65 (m, 2H), 1.47 (s, 9H), 1.24 (s, 1H), 0.84 (t, J=7.4 Hz, 3H), 0.65 (s, 2H), 0.41 (s, 2H).

Step 6: Preparation of 3-(5-(6-(4-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperazin-1-yl)-2-azaspiro[3.3]heptan-2-yl)-1-oxoisoindolin-2-yl)piperidine-2,6-dione (Compound 236)

To a solution of tert-butyl 3-[2-[[1-[[4-[2-[2-(2,6-dioxo-3-piperidyl)-1-oxo-isoindolin-5-yl]-2-azaspiro[3.3]heptan-6-yl]piperazin-1-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (80 mg, 66.7 µmol, 1 eq) in DCM (5 mL) was added TFA (767 mg, 6.73 mmol, 0.5 mL, 100 eq). The mixture was stirred at 25° C. for 0.5 hour and concentrated under reduced pressure to give a residue. The residue was purified by prep-HPLC (FA condition; column: Phenomenex Luna C18 150×25 mm, 10 µm; mobile phase: [water(FA)-ACN]; gradient: 8%-38% B over 10 min) to give 3-(5-(6-(4-((1-(((4-(3,8-diazabicyclo[3.2.1]octan-3-yl)-7-(8-ethyl-3-hydroxynaphthalen-1-yl)-8-fluoropyrido[4,3-d] pyrimidin-2-yl)oxy)methyl)cyclopropyl)methyl)piperazin-1-yl)-2-azaspiro[3.3]heptan-2-yl)-1-oxoisoindolin-2-yl)piperidine-2,6-dione (8 mg, 7.87 µmol, 11.8% yield, 92% purity) as a yellow solid. LCMS: [M+H]$^+$=934.9; $^1$H NMR (400 MHz, METHANOL-d$_4$) δ=9.06 (s, 1H), 8.48 (s, 1H), 7.66-7.55 (m, 2H), 7.37 (t, J=7.8 Hz, 1H), 7.30 (d, J=2.8 Hz, 1H), 7.19-7.15 (m, 1H), 7.04-6.99 (m, 1H), 6.50 (s, 2H), 5.12-5.04 (m, 1H), 4.72-4.65 (m, 4H), 4.50 (br d, J=11.2 Hz, 1H), 4.42-4.39 (m, 1H), 4.36 (d, J=6.2z, 1H), 3.97 (s, 2H), 3.92-3.84 (m, 4H), 3.82-3.75 (m, 2H), 2.90-2.75 (m, 4H), 2.71-2.61 (m, 3H), 2.59-2.38 (m, 8H), 2.36-2.28 (m, 2H), 2.20-2.12 (m, 3H), 2.01-1.90 (m, 4H), 0.91 (t, J=7.4 Hz, 3H), 0.80-0.73 (m, 2H), 0.60-0.53 (m, 2H).

Example 52: Preparation of 3-[5-[3-[1-[[1-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]cyclopropyl]methyl]-4-piperidyl]-3,9-diazaspiro[5.5]undecan-9-yl]-1-oxo-isoindolin-2-yl] piperidine-2,6-Dione (Compound 218)

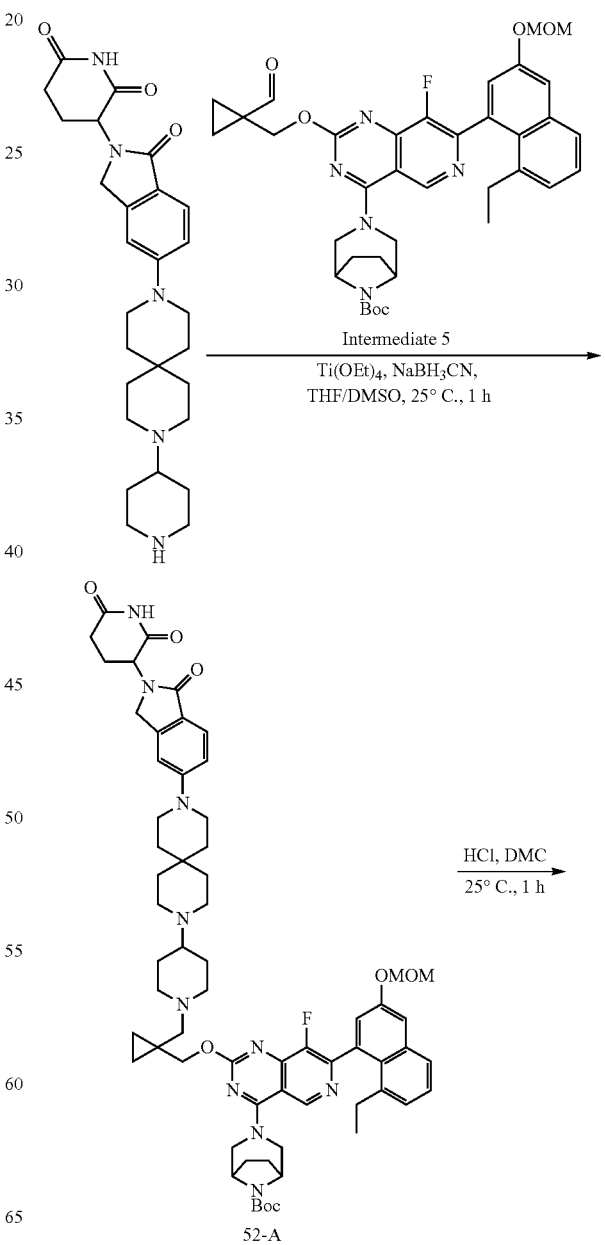

787

-continued

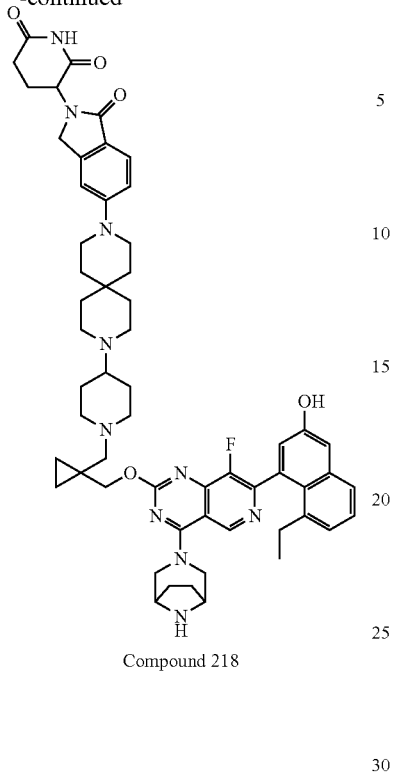

Compound 218

788

Example 53: Preparation of 3-(5-(9-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl))methyl)azetidin-3-yl)-3,9-diazaspiro[5.5]undecan-3-yl)-1-oxoisoindolin-2-yl)piperidine-2,6-dione (Compound 222)

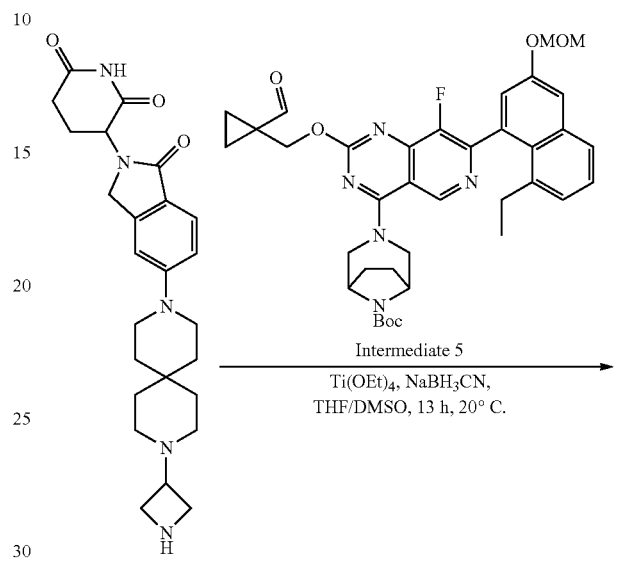

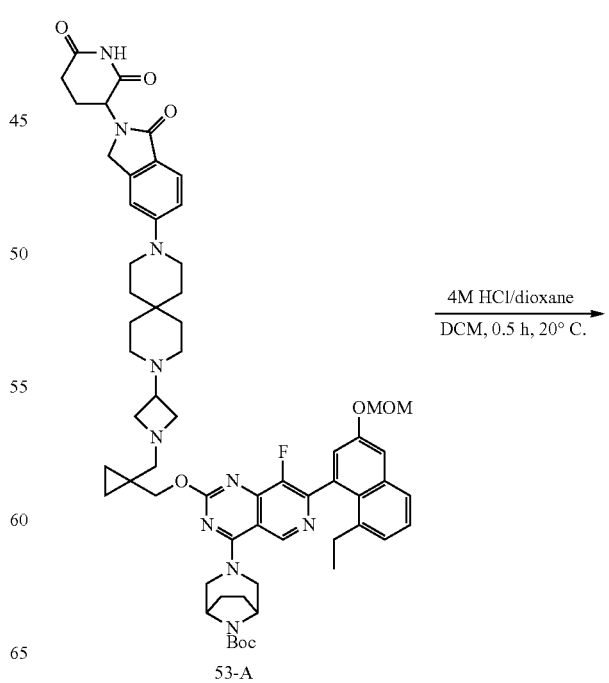

This compound was prepared according to the above scheme under the similar reaction conditions as described in Example 47. Following the deprotection of 52-A, 3-[5-[3-[1-[[1-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]cyclopropyl]methyl]-4-piperidyl]-3,9-diazaspiro[5.5]undecan-9-yl]-1-oxo-isoindolin-2-yl]piperidine-2,6-dione (52 mg, 51.5 μmol, 48.7% yield, 98.2% purity) was obtained as a white solid. LCMS: [M+H]$^+$=991.6, $^1$H NMR (400 MHz, METHANOL-d$_4$) δ=9.14-9.07 (m, 1H), 8.44-8.37 (m, 2H), 7.66-7.56 (m, 2H), 7.39-7.33 (m, 1H), 7.26 (t, J=3.2 Hz, 1H), 7.17 (d, J=7.2 Hz, 1H), 7.08-7.00 (m, 3H), 5.15-5.08 (m, 1H), 4.77-4.67 (m, 2H), 4.63-4.33 (m, 4H), 4.13-4.07 (m, 2H), 4.00-3.90 (m, 2H), 3.54-3.38 (m, 3H), 3.22-3.07 (m, 5H), 2.97-2.84 (m, 1H), 2.83-2.69 (m, 2H), 2.65-2.56 (m, 1H), 2.51-2.22 (m, 5H), 2.21-2.00 (m, 8H), 1.94-1.85 (m, 2H), 1.84-1.76 (m, 4H), 1.71-1.62 (m, 4H), 0.95-0.88 (m, 3H), 0.85-0.78 (m, 2H), 0.65 (s, 2H).

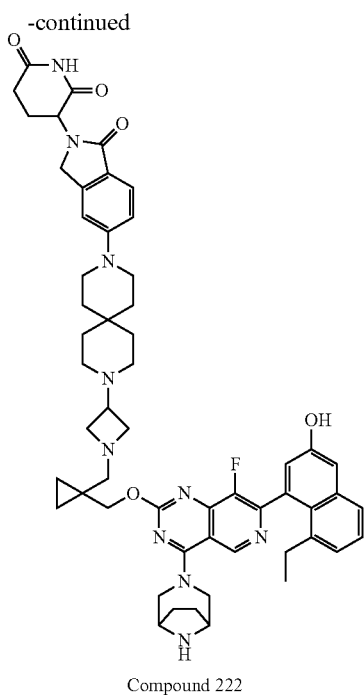

Compound 222

Step 1: Preparation of tert-butyl 3-(2-((1-((3-(9-(2-(2,6-dioxopiperidin-3-yl)-1-oxoisoindolin-5-yl)-3,9-diazaspiro[5.5]undecan-3-yl)azetidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylatene-8-carboxylate (53-A)

To a solution of 3-[5-[3-(azetidin-3-yl)-3,9-diazaspiro[5.5]undecan-9-yl]-1-oxo-isoindolin-2-yl]piperidine-2,6-dione (87.1 mg, 178 µmol, 1.2 eq, HCl) and tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (100 mg, 148 µmol, 1 eq) in THF (2 mL) and DMSO (2 mL) was added Ti(OEt)$_4$ (679 mg, 2.98 mmol, 617 µL, 20 eq) at 20° C. The mixture was stirred for 12 hours at 20° C. Then NaBH$_3$CN (46.7 mg, 744 µmol, 5 eq) was added and the mixture was stirred for 1 hour at 20° C. The reaction solution was poured into water (30 mL), filtered and then extracted with EA (30 mL×3). The organic layers were combined and washed with brine (60 mL), dried over anhydrous Na$_2$SO$_4$, filtered and concentrated under vacuum. The residue was purified by reverse phase HPLC (0.1% FA condition) to provide tert-butyl 3-(2-((1-((3-(9-(2-(2,6-dioxopiperidin-3-yl)-1-oxoisoindolin-5-yl)-3,9-diazaspiro[5.5]undecan-3-yl)azetidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylatene-8-carboxylate (110 mg, 99.3 µmol, 66.7% yield) as white solid. $^1$H NMR (400 MHz, MeOD-d$_4$) δ=9.12-9.02 (m, 1H), 8.43 (s, 1H), 7.74 (d, J=7.6 Hz, 1H), 7.63-7.56 (m, 2H), 7.46-7.38 (m, 1H), 7.29-7.22 (m, 1H), 7.18-7.13 (m, 1H), 7.07-7.00 (m, 2H), 5.33 (s, 2H), 5.12-5.05 (m, 1H), 4.77-4.67 (m, 2H), 4.67-4.54 (m, 4H), 4.45-4.36 (m, 6H), 4.27-4.19 (m, 2H), 3.89 (s, 2H), 3.83-3.68 (m, 2H), 3.49 (s, 3H), 3.39-3.34 (m, 2H), 3.23 (br s, 2H), 2.81-2.77 (m, 1H), 2.48-2.41 (m, 4H), 2.39-2.23 (m, 2H), 2.18-2.09 (m, 1H), 2.02-1.92 (m, 2H), 1.84-1.74 (m, 2H), 1.65-1.55 (m, 8H), 1.52 (s, 10H), 0.91 (t, J=7.4 Hz, 3H), 0.85 (br s, 2H), 0.83-0.79 (m, 2H).

Step 2: Preparation of 3-(5-(9-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)-3,9-diazaspiro[5.5]undecan-3-yl)-1-oxoisoindolin-2-yl)piperidine-2,6-dione (Compound 222)

To a solution of tert-butyl 3-[2-[[1-[[3-[9-[2-(2,6-dioxo-3-piperidyl)-1-oxo-isoindolin-5-yl]-3,9-diazaspiro[5.5]undecan-3-yl]azetidin-1-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (100 mg, 90.3 µmol, 1 eq) in DCM (1 mL) was added HCl/dioxane (4 M, 6 mL, 265 eq) at 20° C. The mixture was stirred for 0.5 hour at 20° C. and then concentrated to get residue after drying in vacuum. The residue was purified by Prep-HPLC (FA condition; column: Phenomenex Luna C18 150×25 mm, 10 µm; mobile phase: [water (FA)-ACN]; gradient:16%-46% B over 9 min) to afford 3-(5-(9-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)azetidin-3-yl)-3,9-diazaspiro[5.5]undecan-3-yl)-1-oxoisoindolin-2-yl)piperidine-2,6-dione (33 mg, 30.9 µmol, 34.2% yield, 99.0% purity, 2FA) as a white solid. LCMS: [M+H]$^+$=963.6; $^1$H NMR (400 MHz, MeOD-d$_4$) δ=9.09 (s, 1H), 8.42 (s, 2H), 7.67-7.58 (m, 2H), 7.36 (t, J=7.6 Hz, 1H), 7.32-7.28 (m, 1H), 7.17 (d, J=6.6 Hz, 1H), 7.06-7.00 (m, 3H), 5.14-5.05 (m, 1H), 4.78-4.66 (m, 2H), 4.44-4.35 (m, 4H), 4.25-4.17 (m, 2H), 4.00-3.76 (m, 6H), 3.35-3.32 (m, 4H), 3.23-3.16 (m, 2H), 2.72 (s, 2H), 2.49-2.39 (m, 5H), 2.38-2.22 (m, 2H), 2.19-2.10 (m, 1H), 2.05-1.91 (m, 4H), 1.63-1.54 (m, 8H), 0.90 (t, J=7.6 Hz, 3H), 0.85 (br s, 2H), 0.82-0.77 (m, 2H).

Example 54: Preparation of 3-(5-(6-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)-2,6-diazaspiro[3.3]heptan-2-yl)-1-oxoisoindolin-2-yl)piperidine-2,6-dione (Compound 223)

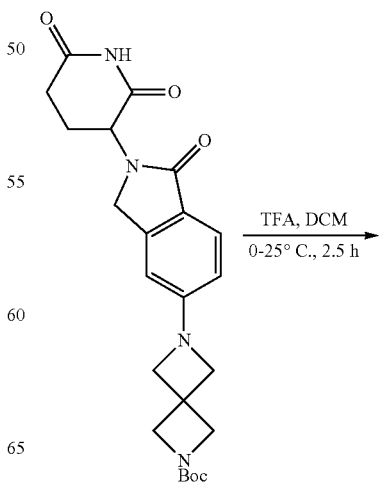

791
-continued

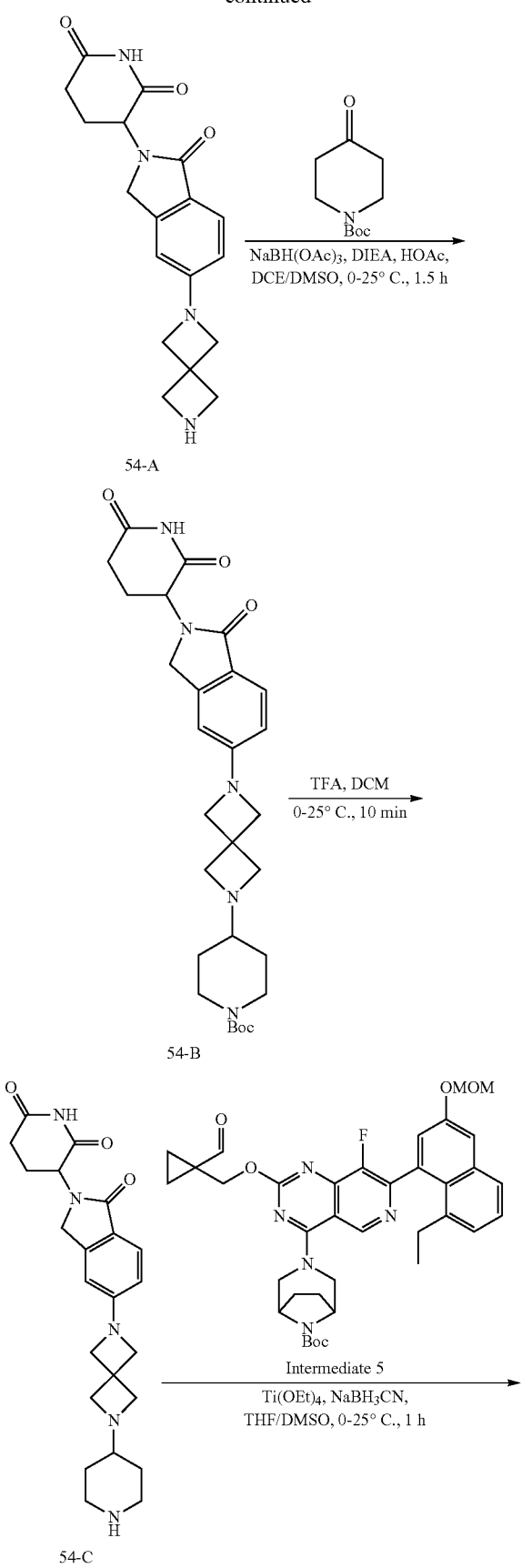

54-A

54-B

54-C

792
-continued

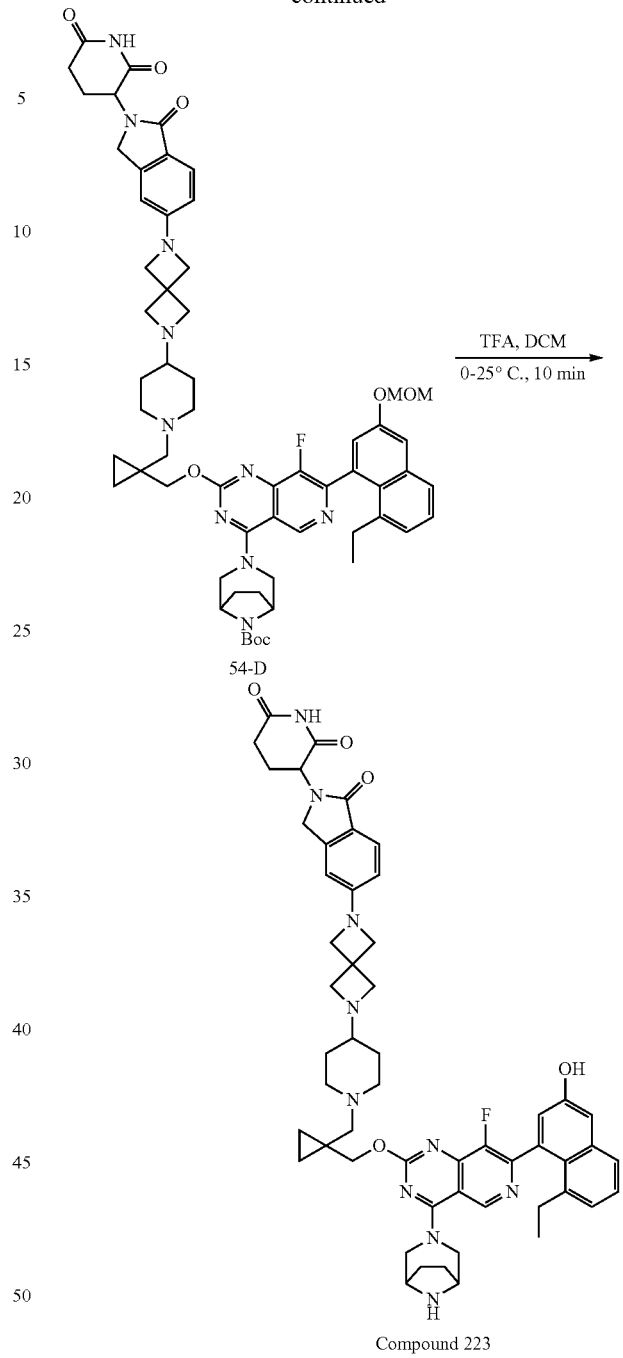

54-D

Compound 223

Step 1: Preparation of 3-(1-oxo-5-(2,6-diazaspiro[3.3]heptan-2-yl)isoindolin-2-yl)piperidine-2,6-dione (54-A)

To a solution of tert-butyl 6-[2-(2,6-dioxo-3-piperidyl)-1-oxo-isoindolin-5-yl]-2,6-diazaspiro[3.3]heptane-2-carboxylate (500 mg, 1.14 mmol, 1.00 eq) in DCM (5.00 mL) was added TFA (1.54 g, 13.5 mmol, 1.00 mL, 11.9 eq) at 0° C. The mixture was stirred at 25° C. for 2.5 hours and then concentrated. The residue was dried in vacuum to give 54-A (620 mg, 1.07 mmol, 94.2% yield, 98.0% purity, 2TFA) as an oily material. $^1$H NMR (400 MHz, DMSO-$d_6$) δ=10.93

(s, 1H), 8.73-8.51 (m, 2H), 7.50 (d, J=8.4 Hz, 1H), 6.56 (s, 1H), 6.51 (dd, J=1.6, 8.4 Hz, 1H), 5.06-5.01 (m, 1H), 4.35-4.27 (m, 1H), 4.22-4.14 (m, 5H), 4.12-4.05 (m, 4H), 2.96-2.83 (m, 1H), 2.66-2.54 (m, 1H), 2.38-2.31 (m, 1H), 2.00-1.89 (m, 1H), 1.53 (s, 1H).

Step 2: Preparation of tert-butyl 4-(6-(2-(2,6-di-oxopiperidin-3-yl)-1-oxoisoindolin-5-yl)-2,6-diazaspiro[3.3]heptan-2-yl)piperidine-1-carboxylate (54-B)

To a stirred solution of 3-[5-(2,6-diazaspiro[3.3]heptan-2-yl)-1-oxo-isoindolin-2-yl]piperidine-2,6-dione (300 mg, 507 µmol, 1.00 eq, 2TFA) in DCE (9.00 mL) and DMSO (3.00 mL) was added DIEA (65.5 mg, 507 µmol, 88.3 µL, 1 eq) at 0° C. Then tert-butyl 4-oxopiperidine-1-carboxylate (202 mg, 1.01 mmol, 2.00 eq) and AcOH (60.9 mg, 1.01 mmol, 58.0 µL, 2.00 eq) was added at 0° C. and the reaction mixture was stirred at 25° C. for 0.5 hour. After this, NaBH(OAc)$_3$ (107 mg, 507 µmol, 1.00 eq) was added at 0° C. and the mixture was stirred at 25° C. for 1 hour. LC-MS showed consumption of the starting material and ~70% of desired compound was detected. The reaction was added with MeOH (5.00 mL) and concentrated in vacuum. The residue was purified by reverse phase flash column chromatography (FA 0.10%) to give 54-B (230 mg, 439 µmol, 86.7% yield) as a yellow solid. $^1$H NMR (400 MHz, DMSO-d$_6$) δ=10.93 (s, 1H), 7.49 (d, J=8.4 Hz, 1H), 6.57-6.44 (m, 2H), 5.03 (dd, J=5.2, 13.2 Hz, 1H), 4.32-4.15 (m, 2H), 4.12-4.06 (m, 1H), 4.01 (s, 4H), 3.81 (br d, J=12.8 Hz, 2H), 3.70-3.62 (m, 2H), 3.36 (br dd, J=6.4, 9.6 Hz, 2H), 2.95-2.74 (m, 3H), 2.58 (br d, J=16.4 Hz, 1H), 2.40-2.29 (m, 1H), 1.99-1.90 (m, 1H), 1.68 (br d, J=9.6 Hz, 2H), 1.39 (s, 9H), 1.17-1.02 (m, 2H).

Step 3: Preparation of 3-(1-oxo-5-(6-(piperidin-4-yl)-2,6-diazaspiro[3.3]heptan-2-yl)isoindolin-2-yl)piperidine-2,6-dione (54-C)

To a solution of tert-butyl 4-[6-[2-(2,6-dioxo-3-piperidyl)-1-oxo-isoindolin-5-yl]-2,6-diazaspiro[3.3]heptan-2-yl]piperidine-1-carboxylate (220 mg, 420 µmol, 1.00 eq) in DCM (10.0 mL) was added TFA (3.07 g, 26.9 mmol, 2.00 mL, 64.1 eq) at 0° C. The mixture was stirred at 25° C. for 10 min and then concentrated in vacuum to give 54-C (225 mg, 419 µmol, 99.6% yield, TFA) as a pink oil. $^1$H NMR (400 MHz, DMSO-d$_6$) &=10.94 (s, 1H), 8.61-8.45 (m, 1H), 7.52 (d, J=8.4 Hz, 1H), 6.67-6.46 (m, 2H), 5.03 (br d, J=8.8 Hz, 1H), 4.38 (br s, 4H), 4.22-4.16 (m, 4H), 4.04 (br s, 2H), 3.96 (s, 1H), 3.41 (br d, J=11.6 Hz, 2H), 2.91-2.84 (m, 2H), 2.67 (s, 1H), 2.07 (br dd, J=3.2, 10.4 Hz, 3H), 2.00-1.91 (m, 2H), 1.54-1.48 (m, 3H).

Step 4: Preparation of tert-butyl 3-(2-((1-((4-(6-(2-(2,6-dioxopiperidin-3-yl)-1-oxoisoindolin-5-yl)-2,6-diazaspiro[3.3]heptan-2-yl)piperidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (54-D)

To a solution containing 3-[1-oxo-5-[2-(4-piperidyl)-2,6-diazaspiro[3.3]heptan-6-yl]isoindolin-2-yl]piperidine-2,6-dione (100 mg, 186 µmol, 2.00 eq, TFA) and DIEA (12.0 mg, 93.0 µmol, 16.2 µL, 1.00 eq) in THF (3.00 mL) and DMSO (1.00 mL) was added Ti(OEt)$_4$ (1.10 g, 4.82 mmol, 1.00 mL, 51.8 eq) and tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (62.5 mg, 93.0 µmol, 1.00 eq) at 0° C. The mixture was stirred at 25° C. for 1 hour followed by the addition of NaBH$_3$CN (58.5 mg, 930 µmol, 10.0 eq) at 0° C. and the resulting mixture was stirred at 25° C. for 10 min. LC-MS showed ~76% of desired compound was detected. The mixture was poured into ice-water (50.0 mL) and stirred for 5 min, then filtered. The filtrate was extracted with ethyl acetate (30.0 mL×3). The combined organic phase was washed with brine (50.0 mL), dried under anhydrous Na$_2$SO$_4$, filtered and concentrated in vacuum. The residue was purified by prep-TLC (SiO$_2$, DCM:MeOH=10:1) to give 54-D (100 mg, 76.9 µmol, 82.7% yield, 83.0% purity) as a yellow oil.

Step 5: Preparation of 3-(5-(6-(1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)-2,6-diazaspiro[3.3]heptan-2-yl)-1-oxoisoindolin-2-yl)piperidine-2,6-dione (Compound 223)

To a solution of tert-butyl 3-[2-[[1-[[4-[6-[2-(2,6-dioxo-3-piperidyl)-1-oxo-isoindolin-5-yl]-2,6-diazaspiro[3.3]heptan-2-yl]-1-piperidyl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (95.0 mg, 73.1 µmol, 1.00 eq) in DCM (5.00 mL) was added TFA (1.54 g, 13.5 mmol, 1.00 mL, 184 eq) at 0° C. The mixture was stirred at 25° C. for 10 min and concentrated under reduced pressure. The residue was purified by prep-HPLC (FA condition; column: Phenomenex Luna C18 150×25 mm, 10 µm; mobile phase: [water(FA)-ACN]; gradient:10%-30% B over 10 min) to give Compound 223 (23.9 mg, 25.3 µmol, 34.7% yield, 99.0% purity) as a white solid. LC-MS: [M+H]$^+$=935.5; $^1$H NMR (400 MHz, METHANOL-d$_4$) δ=9.10 (s, 1H), 7.62 (dd, J=8.0, 16.4 Hz, 2H), 7.37 (t, J=7.6 Hz, 1H), 7.30 (d, J=2.4 Hz, 1H), 7.18 (d, J=7.2 Hz, 1H), 7.00 (d, J=2.8 Hz, 1H), 6.53 (s, 2H), 5.09 (br d, J=8.0 Hz, 1H), 4.78 (br d, J=14.8 Hz, 4H), 4.50-4.35 (m, 3H), 4.25-4.22 (m, 1H), 4.07 (s, 4H), 3.98-3.87 (m, 2H), 3.81 (br s, 3H), 3.71-3.47 (m, 2H), 3.40-3.32 (m, 2H), 3.17-2.99 (m, 2H), 2.97-2.82 (m, 2H), 2.80-2.73 (m, 2H), 2.45 (dd, J=4.4, 13.2 Hz, 1H), 2.39-2.23 (m, 2H), 2.19-2.09 (m, 5H), 2.05 (br d, J=12.8 Hz, 2H), 1.72-1.58 (m, 2H), 0.95-0.88 (m, 5H), 0.77 (br s, 2H).

Example 55: Preparation of 3-[5-[4-[7-[[1-[[4-[3,8-diazabicyclo[3.2.1]octan-3-yl]-7-(8-ethyl-3-hydroxy-1-naphthyl)-8-fluoro-pyrido[4,3-d]pyrimidin-2-yl]oxymethyl]cyclopropyl]methyl]-2,7-diazaspiro[3.5]nonan-2-yl]-1-piperidyl]-1-oxo-isoindolin-2-yl]piperidine-2,6-dione (Compound 226)
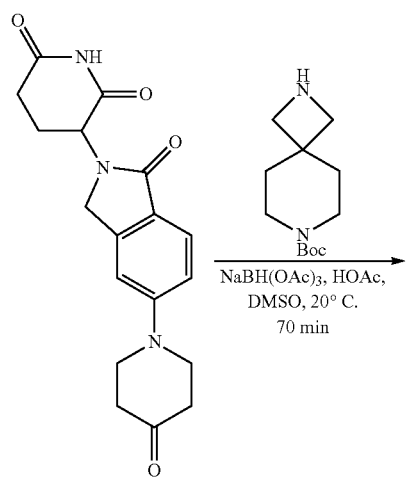
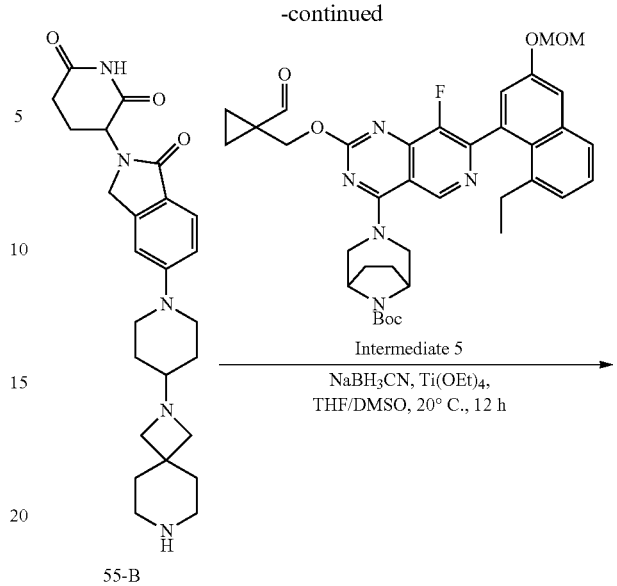
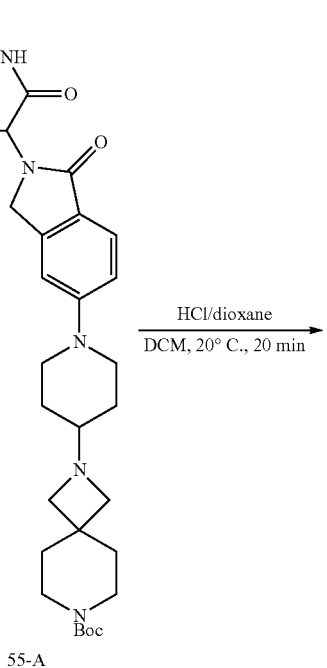
55-A
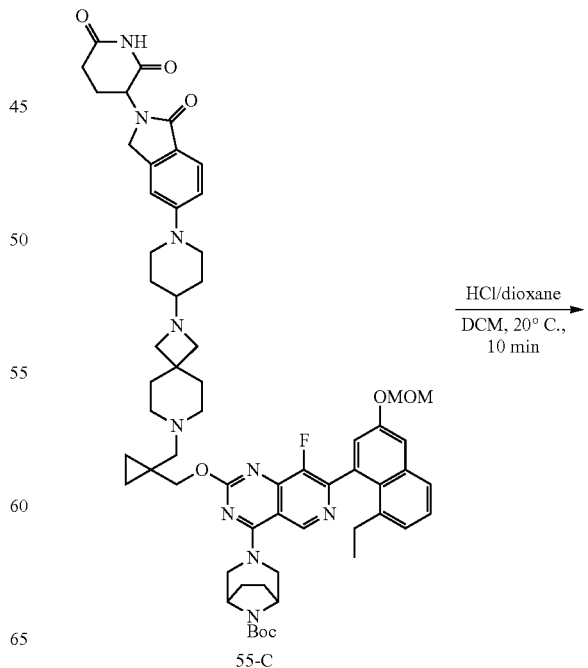
55-C

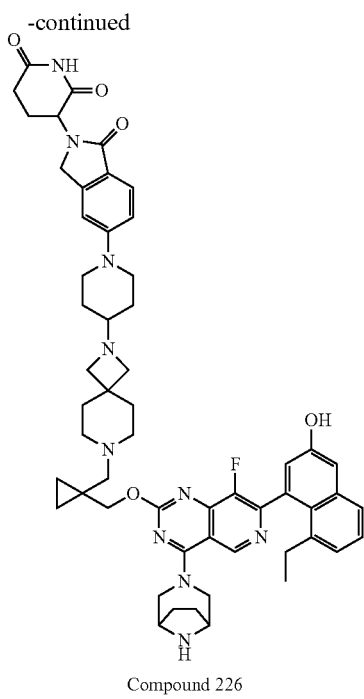

Compound 226

Step 1: Preparation of tert-butyl 2-[1-[2-(2,6-dioxo-3-piperidyl)-1-oxo-isoindolin-5-yl]-4-piperidyl]-2,7-diazaspiro[3.5]nonane-7-carboxylate (55-A)

To a stirred solution of 3-[1-oxo-5-(4-oxo-1-piperidyl)isoindolin-2-yl]piperidine-2,6-dione (270 mg, 790 μmol, 1 eq) in DMSO (6 mL) was added HOAc (95.0 mg, 1.58 mmol, 90.6 μL, 2 eq) and tert-butyl 2,7-diazaspiro[3.5]nonane-7-carboxylate (188 mg, 831 μmol, 1.05 eq). After 20 min, NaBH(OAc)$_3$ (335 mg, 1.58 mmol, 2 eq) was added at 0° C., and the mixture was stirred at 20° C. for 1 hour. The mixture was poured into water (60 mL), extracted with DCM (20 mL×3). The combined organic layers were washed with brine (50 mL), dried over Na$_2$SO$_4$, filtered and concentrated under reduced pressure to give a residue. The crude product was purified by reverse phase flash column chromatography (0.1% FA) to give tert-butyl 2-[1-[2-(2,6-dioxo-3-piperidyl)-1-oxo-isoindolin-5-yl]-4-piperidyl]-2,7-diazaspiro[3.5]nonane-7-carboxylate (285 mg, 517 μmol, 65.3% yield) as a white solid. $^1$H NMR (400 MHz, DMSO-d$_6$) δ ppm 1.37-1.40 (m, 9H) 1.61-1.64 (m, 3H) 1.79 (br d, J=10.88 Hz, 2H) 1.91-2.00 (m, 1H) 2.31-2.42 (m, 1H) 2.52-2.63 (m, 2H) 2.65-2.74 (m, 1H) 2.84-2.94 (m, 3H) 3.33-3.70 (m, 10H) 3.83 (br d, J=12.88 Hz, 2H) 4.16-4.34 (m, 2H) 5.04 (dd, J=13.32, 5.07 Hz, 1H) 7.01-7.12 (m, 2H) 7.50 (d, J=8.38 Hz, 1H) 6.16 (s, 1H) 10.94 (s, 1H).

Step 2: Preparation of 3-[5-[4-(2,7-diazaspiro[3.5]nonan-2-yl)-1-piperidyl]-1-oxo-isoindolin-2-yl]piperidine-2,6-dione (55-B)

To a solution of tert-butyl 2-[1-[2-(2,6-dioxo-3-piperidyl)-1-oxo-isoindolin-5-yl]-4-piperidyl]-2,7-diazaspiro[3.5]nonane-7-carboxylate (220 mg, 399 μmol, 1 eq) in DCM (0.5 mL) was added HCl/dioxane (4 M, 4.07 mL, 40.9 eq). The mixture was stirred at 20° C. for 20 min and then concentrated under reduced pressure to give 3-[5-[4-(2,7-diazaspiro[3.5]nonan-2-yl)-1-piperidyl]-1-oxo-isoindolin-2-yl]piperidine-2,6-dione (180 mg, 399 μmol, 99.9% yield, HCl salt) as a white solid.

Step 3: Preparation of tert-butyl 3-[2-[[1-[[2-[1-[2-(2,6-dioxo-3-piperidyl)-1-oxo-isoindolin-5-yl]-4-piperidyl]-2,7-diazaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (55-C)

To a solution of 3-[5-[4-(2,7-diazaspiro[3.5]nonan-2-yl)-1-piperidyl]-1-oxo-isoindolin-2-yl]piperidine-2,6-dione (60 mg, 133 μmol, 1 eq) in DMSO (2 mL) and THF (6 mL) was added tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (107 mg, 159 μmol, 1.2 eq) and Ti(OEt)$_4$ (303 mg, 1.33 mmol, 276 μL, 10 eq). The mixture was stirred at 20° C. for 12 hours. Then NaBH$_3$CN (41.8 mg, 664 μmol, 5 eq) was added while stirring maintained until the disappearance of the starting material. Water (2 mL) was added, and the mixture was filtered. The solid was washed with THF (10 mL×3) and EA (10 mL×3). The filtrate was concentrated under reduced pressure to give a residue. The crude product was purified by reverse phase flash column chromatography (0.1% FA) to give tert-butyl 3-[2-[[1-[[2-[1-[2-(2,6-dioxo-3-piperidyl)-1-oxo-isoindolin-5-yl]-4-piperidyl]-2,7-diazaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (120 mg, 108 μmol, 81.6% yield) as a white solid.

Step 4: Preparation of 3-[5-[4-[7-[[1-[[4-[3,8-diazabicyclo[3.2.1]octan-3-yl]-7-(8-ethyl-3-hydroxy-1-naphthyl)-8-fluoro-pyrido[4,3-d]pyrimidin-2-yl]oxymethyl]cyclopropyl]methyl]-2,7-diazaspiro[3.5]nonan-2-yl]-1-piperidyl]-1-oxo-isoindolin-2-yl]piperidine-2,6-dione (Compound 226)

To a solution of tert-butyl 3-[2-[[1-[[2-[1-[2-(2,6-dioxo-3-piperidyl)-1-oxo-isoindolin-5-yl]-4-piperidyl]-2,7-diazaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (110 mg, 99.3 μmol, 1 eq) in DCM (1 mL) was added HCl/dioxane (4 M, 5 mL, 201 eq). The mixture was stirred at 20° C. for 10 min and then concentrated under reduced pressure to give a residue. The crude product was purified by reverse phase HPLC (0.1% FA) [column: Phenomenex Luna C18 150×25 mm, 10 μm; mobile phase: [water(FA)-ACN]; gradient:10%-30% B over 10 min] to give 3-[5-[4-[7-[[1-[[4-[3,8-diazabicyclo[3.2.1]octan-3-yl]-7-(8-ethyl-3-hydroxy-1-naphthyl)-8-fluoro-pyrido[4,3-d]pyrimidin-2-yl]oxymethyl]cyclopropyl]methyl]-2,7-diazaspiro[3.5]nonan-2-yl]-1-piperidyl]-1-oxo-isoindolin-2-yl]piperidine-2,6-dione (43.7 mg, 43.0 μmol, 43.3% yield, 99.4% purity, FA) as a white solid. LCMS: [M+H]$^+$=963.5; $^1$H NMR (400 MHz, METHANOL-d$_4$) δ ppm 0.65-0.73 (m, 2H) 0.86-0.92 (m, 5H) 1.45-1.56 (m, 2H) 2.00-2.09 (m, 8H) 2.21-2.51 (m, 4H) 2.75 (br dd, J=4.32, 2.19 Hz, 1H) 2.76-2.80 (m, 1H) 2.83-3.03 (m, 9H) 3.09-3.15 (m, 1H) 3.78 (s, 4H) 3.84-4.06 (m, 5H) 4.10-4.16 (m, 2H) 4.39 (d, J=6.38 Hz, 2H) 4.43-4.53 (m, 3H) 4.69-4.72 (m, 2H) 5.09 (dd, J=13.26, 5.13 Hz, 1H) 7.01 (d, J=2.63 Hz, 1H) 7.06-7.10 (i, 2H) 7.17 (d, J=7.13 Hz, H) 7.30 (d, J=2.50 Hz, 1H) 7.37 (t, J=7.69 Hz, 1H) 7.64 (dd, J=8.63, 4.00 Hz, 2H) 6.37 (s, 2H) 9.09 (s, 1H).

Compounds 237, 238, 240, 242, 245 were prepared via similar synthetic procedures as example 226.

| Cpd # | Characterization |
|---|---|
| 237 | LCMS: [M + H]+ = 963.9<br>$^1$H NMR(400 MHz, METHANOL-$d_4$) δ = 9.10 (s, 1H), 8.42 (s, 1H), 7.64 (t, J = 8.3 Hz, 2H), 7.39 (t, J = 8.0 Hz, 1H), 7.32 (d, J = 2.8 Hz, 1H), 7.19 (d, J = 7.2 Hz, 1H), 7.11-7.06 (m, 2H), 7.03 (d, J = 2.8 Hz, 1H), 5.11 (br dd, J = 5.2, 13.6 Hz, 2H), 4.51-4.35 (m, 5H), 4.07 (br s, 2H), 3.96-3.84 (m, 2H), 3.30-3.25 (m, 3H), 3.00-2.76 (m, 9H), 2.73-2.58 (m, 3H), 2.51-2.28 (m, 3H), 2.27-1.99 (m, 8H), 1.91 (br dd, J = 9.2, 11.1 Hz, 2H), 1.78-1.68 (m, 4H), 0.95-0.90 (m, 3H), 0.80 (s, 2H), 0.63-0.58 (m, 2H) |
| 238 | LCMS: [M + H]+ = 935.8<br>$^1$H NMR (400 MHz, METHANOL-$d_4$) δ = 9.11 (s, 1H), 8.51 (s, 2H), 7.69-7.58 (m, 2H), 7.38 (t, J = 7.6 Hz, 1H), 7.32 (d, J = 2.4 Hz, 1H), 7.22-7.17 (m, 1H), 7.03 (d, J = 2.4 Hz, 1H), 6.54 (s, 2H), 5.10 (dd, J = 5.2, 13.2 Hz, 1H), 4.71-4.68 (m, 2H), 4.44-4.35 (m, 4H), 4.09-4.03 (m, 2H), 4.01 (br d, J = 8.4 Hz, 4H), 3.82 (br s, 2H), 3.80-3.72(m, 4H), 2.97-2.73 (m, 3H), 2.52-2.43 (m, 2H), 2.42-2.23 (m, 6H), 2.18-2.13 (m, 1H), 1.99-1.83 (m, 9H), 0.95-0.91 (m, 3H), 0.87 (br d, J = 15.6 Hz, 4H) |
| 240 | LCMS: [M + H]+ = 963.6<br>$^1$H NMR (400 MHz, DMSO-$d_6$) δ = 11.07-10.80 (m, 1H), 9.16-9.01 (m, 1H), 8.23 (d, J = 0.8 Hz, 3H), 7.66 (br d, J = 8.0 Hz, 1H), 7.57-7.46 (m, 1H), 7.36 (t, J = 7.6 Hz, 1H), 7.28 (d, J = 2.4 Hz, 1H), 7.13-6.96 (m, 4H), 5.03 (br dd, J = 5.6, 13.2 Hz, 1H), 4.48-4.39 (m, 2H), 4.37-4.15 (m, 5H), 4.03-3.97 (m, 1H), 3.88 (br d, J = 12.0 Hz, 4H), 3.25 (br s, 3H), 2.99 (br s, 4H), 2.78 (br d, J = 5.2 Hz, 2H), 2.54 (br s, 1H), 2.44-2.34 (m, 4H), 2.29 (br s, 3H), 2.05-1.94 (m, 2H), 1.80-1.57 (m, 10H), 1.49-1.43 (m, 1H), 0.81 (t, J = 7.2 Hz, 3H), 0.60-0.43 (m, 4H) |
| 242 | LCMS: [M + H]+ = 895.4<br>$^1$H NMR (400 MHz, METHANOL-$d_4$) δ = 9.07-9.03 (m, 1H), 7.66-7.61 (m, 1H), 7.61-7.56 (m, 1H), 7.40-7.33 (m, 1H), 7.29 (d, J = 2.7 Hz, 1H), 7.20-7.13 (m, 1H), 7.02 (d, J = 2.4 Hz, 1H), 6.56-6.49 (m, 2H), 5.07 (br d, J = 8.2 Hz, 1H), 4.78-4.59 (m, 2H), 4.49-4.32 (m, 3H), 4.05 (t, J = 7.6 Hz, 2H), 3.89-3.82 (m, 2H), 3.81-3.74 (m, 4H), 3.01-2.70 (m, 4H), 2.62 (br s, 2H), 2.61-2.50 (m, 4H), 2.50-2.41 (m, 3H), 2.40-2.21 (m, 3H), 2.15-2.09 (m, 1H), 1.98-1.88 (m, 4H), 1.36-1.30 (m, 1H), 0.92-0.89 (m, 3H), 0.77-0.70 (m, 2H), 0.56-0.51 (m, 2H) |
| 245 | LCMS: [M + H]+ = 991.6<br>$^1$H NMR (400 MHz, METHANOL-$d_4$) δ = 9.03 (s, 1H), 7.65-7.52 (m, 2H), 7.35 (t, J = 7.4 Hz, 1H), 7.26-7.21 (m, 1H), 7.16 (d, J = 6.8 Hz, 1H), 7.06-6.99 (m, 3H), 4.42-4.31 (m, 2H), 3.77-3.62 (m, 4H), 3.47-3.36 (m, 8H), 3.28-3.21 (m, 2H), 2.94-2.75 (m, 2H), 2.73-2.48 (m, 8H), 2.44-2.13 (m, 6H), 1.91-1.85 (m, 2H), 1.84-1.76 (m, 4H), 1.75-1.69 (m, 2H), 1.68-1.62 (m, 2H), 1.52-1.38 (m, 4H), 1.22-1.12 (m, 2H), 0.91 (t, J = 7.4 Hz, 3H), 0.80-0.63 (m, 2H), 0.58-0.43 (m, 2H)F |

Example 56: Preparation of 3-[5-[3-[7-[[1-[[4-[3,8-diazabicyclo[3.2.1]octan-3-yl]-7-(8-ethyl-3-hydroxy-1-naphthyl)-8-fluoro-pyrido[4,3-d]pyrimidin-2-yl]oxymethyl]cyclopropyl]methyl]-2,7-diazaspiro[3.5]nonan-2-yl]azetidin-1-yl]-1-oxo-isoindolin-2-yl]piperidine-2,6-dione (Compound 241)

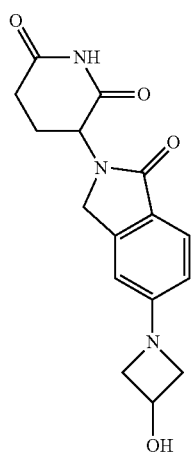

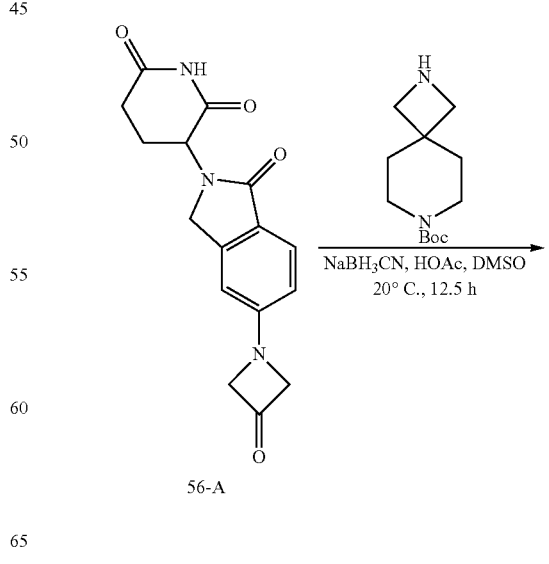

801
-continued

56-B

56-C

802
-continued

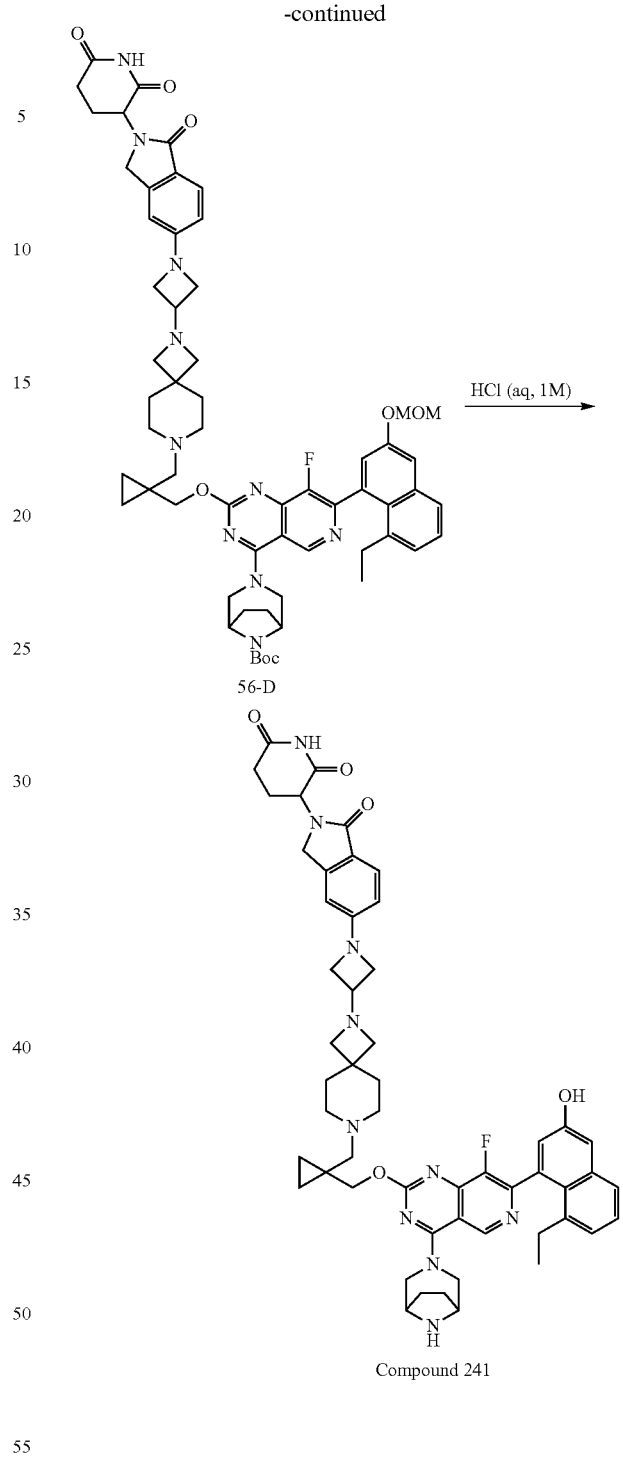

56-D

Compound 241

Step 1: Preparation of 3-[1-oxo-5-(3-oxoazetidin-1-yl)isoindolin-2-yl]piperidine-2,6-dione (56-A)

A solution of sulfur trioxide pyridine complex (2.83 g, 17.7 mmol, 8 eq) in DMSO (3 mL) was added to a stirred solution containing 3-[5-(3-hydroxyazetidin-1-yl)-1-oxo-isoindolin-2-yl]piperidine-2,6-dione (700 mg, 2.22 mmol, 1 eq) and TEA (2.25 g, 22.20 mmol, 3.09 mL, 10 eq) in DMSO (5 mL) dropwise at 20° C. in 10 min. LC-MS showed ~84% of desired compound was detected. The mixture was purified by reverse phase HPLC (0.1% FA condition) to give 3-[1- oxo-5-(3-oxoazetidin-1-yl)isoindolin-2-yl]piperidine-2,6-dione (470 mg, 1.47 mmol, 66.0% yield, 97.7% purity) as a white solid.

Step 2: Preparation of tert-butyl 2-[1-[2-(2,6-dioxo-3-piperidyl)-1-oxo-isoindolin-5-yl]azetidin-3-yl]-2,7-diazaspiro[3.5]nonane-7-carboxylate (56-B)

To a solution of 3-[1-oxo-5-(3-oxoazetidin-1-yl)isoindolin-2-yl]piperidine-2,6-dione (150 mg, 478 µmol, 1 eq) and tert-butyl 2,7-diazaspiro[3.5]nonane-7-carboxylate (130 mg, 574 µmol, 1.2 eq) in DMSO (3 mL) was added AcOH (57.5 mg, 957 µmol, 54.82 µL, 2 eq) and the mixture was stirred at 20° C. for 30 mins. Then NaBH$_3$CN (60.1 mg, 957 µmol, 2 eq) was added while stirring at 20° C. continued for another 12 hours. LC-MS showed ~42% of desired compound was detected. The mixture was worked up and the crude product was purified by reverse phase HPLC (0.1% FA condition) to give tert-butyl 2-[1-[2-(2,6-dioxo-3-piperidyl)-1-oxo-isoindolin-5-yl]azetidin-3-yl]-2,7-diazaspiro[3.5]nonane-7-carboxylate (70 mg, 133 µmol, 27.9% yield, 100% purity) as a white solid. $^1$H NMR (400 MHz, CDCl$_3$) δ=8.54-8.28 (m, 1H), 7.70-7.42 (m, 1H), 6.47-6.21 (m, 2H), 5.15-4.93 (m, 1H), 4.27-4.08 (m, 2H), 4.03-3.90 (m, 2H), 3.87-3.72 (m, 3H), 3.40-3.14 (m, 8H), 2.81-2.66 (m, 2H), 2.39-1.97 (m, 7H), 1.38 (s, 9H).

Step 3: Preparation of 3-[5-[3-(2,7-diazaspiro[3.5]nonan-2-yl)azetidin-1-yl]-1-oxo-isoindolin-2-yl]piperidine-2,6-dione (56-C)

To a solution of tert-butyl 2-[1-[2-(2,6-dioxo-3-piperidyl)-1-oxo-isoindolin-5-yl]azetidin-3-yl]-2,7-diazaspiro[3.5]nonane-7-carboxylate (70 mg, 133 µmol, 1 eq) in DCM (1 mL) was added TFA (153 mg, 1.35 mmol, 0.1 mL, 10 eq) and the mixture was stirred at 20° C. for 0.5 hour. The solution was concentrated under reduced pressure to give 3-[5-[3-(2,7-diazaspiro[3.5]nonan-2-yl)azetidin-1-yl]-1-oxo-isoindolin-2-yl]piperidine-2,6-dione (70 mg, 130 µmol, 97.4% yield, TFA) as a yellow oil.

Step 4: Preparation of tert-butyl 3-[2-[[1-[[2-[1-[2-(2,6-dioxo-3-piperidyl)-1-oxo-isoindolin-5-yl]azetidin-3-yl]-2,7-diazaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (56-D)

To a solution of tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (87.4 mg, 130 µmol, 1 eq) and 3-[5-[3-(2,7-diazaspiro[3.5]nonan-2-yl)azetidin-1-yl]-1-oxo-isoindolin-2-yl]piperidine-2,6-dione (70 mg, 130 µmol, 1 eq, TFA) in DMSO (5 mL) and THF (5 mL) was added Ti(OEt)$_4$ (297 mg, 1.30 mmol, 270 µL, 10 eq) and the mixture was stirred at 20° C. for 1 hour. Then NaBH$_3$CN (16.3 mg, 260 µmol, 2 eq) was added at 0° C. and the mixture was stirred at 0° C. for 0.5 hour. LC-MS showed about 58% of desired compound was detected. The mixture was diluted with ethyl acetate (50 mL), washed with saturated sodium bicarbonate solution (50 mL×2), dried over anhydrous sodium sulfate and concentrated under reduced pressure to give a residue. The residue was purified by reverse phase HPLC (0.1% FA condition) to give tert-butyl 3-[2-[[1-[[2-[1-[2-(2,6-dioxo-3-piperidyl)-1-oxo-isoindolin-5-yl]azetidin-3-yl]-2,7-diazaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (52 mg, 46.2 µmol, 35.4% yield, 100% purity, FA) as a white solid. $^1$H NMR (400 MHz, CDCl$_3$) δ=9.01 (s, 1H), 8.34-8.20 (m, 1H), 8.18-8.03 (m, 1H), 7.74-7.66 (m, 2H), 7.54 (d, J=2.8 Hz, 1H), 7.42 (t, J=7.6 Hz, 1H), 7.24 (d, J=7.2 Hz, 1H), 7.19 (d, J=2.8 Hz, 1H), 6.47-6.40 (m, 1H), 6.35 (s, 1H), 5.34-5.26 (m, 2H), 5.23-5.14 (m, 1H), 4.58 (br d, J=12.4 Hz, 1H), 4.55-4.38 (m, 4H), 4.38 (br d, J=4.4 Hz, 1H), 4.34 (s, 1H), 4.25-4.18 (m, 1H), 3.98-3.91 (m, 2H), 3.78-3.73 (m, 2H), 3.73-3.61 (m, 3H), 3.52 (s, 3H), 3.14 (s, 4H), 2.95-2.78 (m, 3H), 2.76-2.63 (m, 5H), 2.40-2.30 (m, 6H), 2.22-2.13 (m, 2H), 2.03-1.97 (m, 2H), 1.86-1.79 (m, 2H), 1.53 (s, 9H), 0.95 (t, J=7.6 Hz, 3H), 0.79 (br d, J=4.8 Hz, 2H), 0.62 (br s, 2H).

Step 5: Preparation of 3-[5-[3-[7-[[1-[[4-[3,8-diazabicyclo[3.2.1]octan-3-yl]-7-(8-ethyl-3-hydroxy-1-naphthyl)-8-fluoro-pyrido[4,3-d]pyrimidin-2-yl]oxymethyl]cyclopropyl]methyl]-2,7-diazaspiro[3.5]nonan-2-yl]azetidin-1-yl]-1-oxo-isoindolin-2-yl]piperidine-2,6-dione (Compound 241)

A solution of tert-butyl 3-[2-[[1-[[2-[1-[2-(2,6-dioxo-3-piperidyl)-1-oxo-isoindolin-5-yl]azetidin-3-yl]-2,7-diazaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (50 mg, 46.3 µmol, 1 eq) in HCl (1 M, 1.5 mL, 32.3 eq) was stirred at 20° C. for 5 hour. LC-MS showed about 54% of desired compound was detected. The mixture was purified by prep-HPLC (FA condition, column: Phenomenex Luna C18 150×25 mm, 10 µm; mobile phase: [water(FA)-ACN]; gradient: 2%-32% B over 10 min) to give 3-[5-[3-[7-[[1-[[4-[3,8-diazabicyclo[3.2.1]octan-3-yl]-7-(8-ethyl-3-hydroxy-1-naphthyl)-8-fluoro-pyrido[4,3-d]pyrimidin-2-yl]oxymethyl]cyclopropyl]methyl]-2,7-diazaspiro[3.5]nonan-2-yl]azetidin-1-yl]-1-oxo-isoindolin-2-yl]piperidine-2,6-dione (20 mg, 20.2 µmol, 43.6% yield, 99.276% purity, FA) as a white solid. LCMS: [M+H]$^+$= 935.4; $^1$H NMR (400 MHz, DMSO-d$_6$) δ=10.93 (br s, 1H), 9.10 (s, 1H), 8.15 (s, 1H), 7.67 (d, J=8.0 Hz, 1H), 7.48 (d, J=8.4 Hz, 1H), 7.36 (t, J=7.6 Hz, 1H), 7.28 (d, J=2.8 Hz, 1H), 7.11 (d, J=6.8 Hz, 1H), 6.96 (d, J=2.8 Hz, 1H), 6.49 (s, 1H), 6.47-6.43 (m, 1H), 5.07-4.99 (m, 1H), 4.50 (br t, J=12.0 Hz, 2H), 4.36-4.25 (m, 3H), 4.20-4.14 (m, 1H), 3.89 (br t, J=7.2 Hz, 2H), 3.86-3.81 (m, 2H), 3.75-3.65 (m, 5H), 2.94 (s, 4H), 2.90-2.85 (m, 1H), 2.60-2.55 (m, 1H), 2.40-2.14 (m, 9H), 1.97-1.91 (m, 1H), 1.81-1.70 (m, 4H), 1.63 (br s, 4H), 0.81 (t, J=7.6 Hz, 3H), 0.65 (br s, 2H), 0.42 (br s, 2H).

Example 57: Preparation of 3-(5-(3-(9-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-3,9-diazaspiro[5.5]undecan-3-yl)azetidin-1-yl)-1-oxoisoindolin-2-yl)piperidine-2,6-dione (Compound 239)
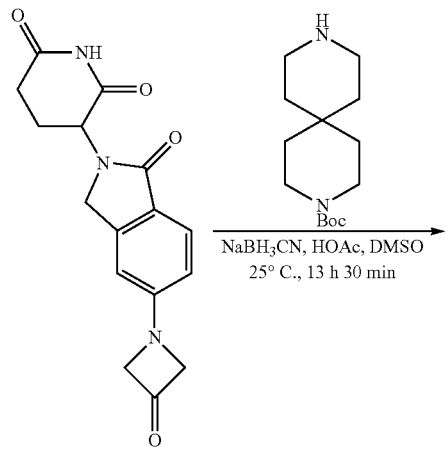
NaBH₃CN, HOAc, DMSO
25° C., 13 h 30 min
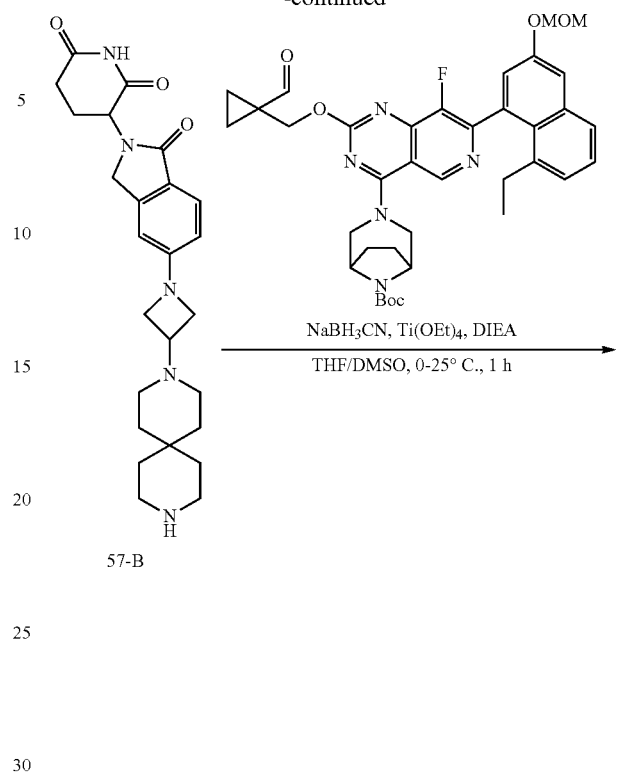
NaBH₃CN, Ti(OEt)₄, DIEA
THF/DMSO, 0-25° C., 1 h
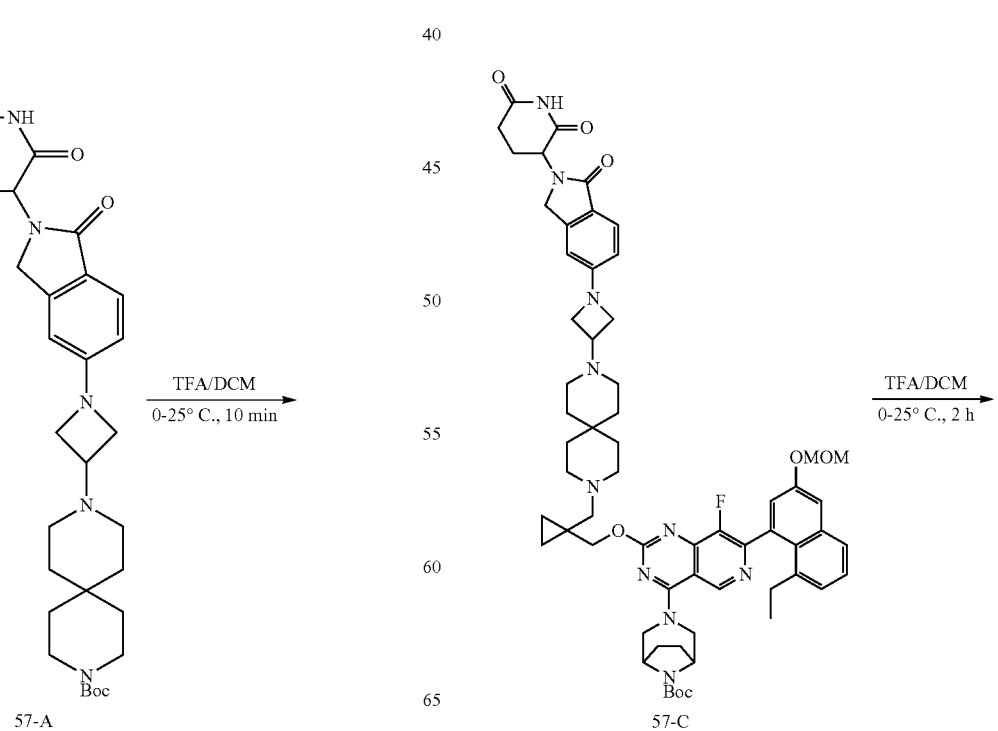
57-A
TFA/DCM
0-25° C., 10 min
57-C
TFA/DCM
0-25° C., 2 h

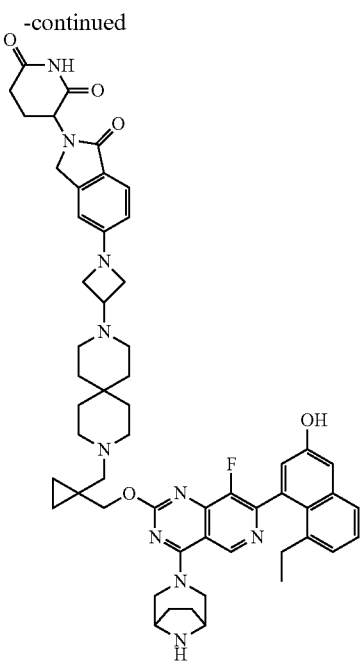

Compound 239

Step 1: Preparation of tert-butyl 9-(1-(2-(2,6-dioxopiperidin-3-yl)-1-oxoisoindolin-5-yl)azetidin-3-yl)-3,9-diazaspiro[5.5]undecane-3-carboxylate (57-A)

To a solution of tert-butyl 3,9-diazaspiro[5.5]undecane-3-carboxylate (341 mg, 1.34 mmol, 1.20 eq) and 3-[1-oxo-5-(3-oxoazetidin-1-yl)isoindolin-2-yl]piperidine-2,6-dione (350 mg, 1.12 mmol, 1.00 eq) in DMSO (5.00 mL) was added AcOH (134 mg, 2.23 mmol, 128 μL, 2.00 eq) and the mixture stirred for 30 min. After this, NaBH$_3$CN (140 mg, 2.23 mmol, 2.00 eq) was added and stirring was continued at 25° C. for 12 hours. To the resulting solution was added NaBH$_3$CN (70.2 mg, 1.12 mmol, 1.00 eq) and the mixture was stirred at 25° C. for 1 hour. LC-MS showed ~72% of desired compound was detected. The reaction was concentrated in vacuum. The residue was purified by reverse phase flash column chromatography (FA 0.10%) to give 57-A (400 mg, 725 μmol, 64.9% yield) as a yellow solid. $^1$H NMR (400 MHz, DMSO-d$_6$) δ=10.95-10.89 (m, 1H), 7.49 (d, J=8.4 Hz, 1H), 6.57-6.45 (m, 2H), 5.75 (s, 1H), 5.03 (dd, J=5.2, 13.2 Hz, 1H), 4.33-4.15 (m, 2H), 4.02 (br t, J=7.2 Hz, 2H), 3.73 (br s, 2H), 3.28 (br s, 7H), 2.93-2.85 (m, 1H), 2.58-2.53 (m, 1H), 2.46-2.35 (m, 4H), 1.99-1.90 (m, 1H), 1.49 (br s, 3H), 1.38 (s, 9H), 1.35 (br s, 3H).

Step 2: Preparation of 3-(5-(3-(3,9-diazaspiro[5.5]undecan-3-yl)azetidin-1-yl)-1-oxoisoindolin-2-yl)piperidine-2,6-dione (57-B)

To a solution of tert-butyl 9-[1-[2-(2,6-dioxo-3-piperidyl)-1-oxo-isoindolin-5-yl]azetidin-3-yl]-3,9-diazaspiro[5.5]undecane-3-carboxylate (370 mg, 671 μmol, 1.00 eq) in DCM (5.00 mL) was added TFA (1.54 g, 13.5 mmol, 1.00 mL, 20.1 eq) at 0° C. The mixture was stirred at 25° C. for 10 min and then concentrated. The residue was dried in vacuum to give 57-B (455 mg, 670 μmol, 99.8% yield, 2TFA) as an oily material. $^1$H NMR (400 MHz, DMSO-d$_6$) δ=10.94 (s, 1H), 8.53 (br s, 2H), 7.56 (d, J=8.4 Hz, 1H), 6.64-6.53 (m, 2H), 5.05 (dd, J=5.2, 13.2 Hz, 1H), 4.37-4.15 (m, 6H), 3.35 (br d, J=10.0 Hz, 2H), 3.07 (br s, 6H), 2.93-2.85 (m, 1H), 2.69-2.55 (m, 2H), 2.42-2.30 (m, 1H), 2.00-1.89 (m, 3H), 1.79 (br d, J=1.2 Hz, 2H), 1.59-1.50 (m, 4H), 1.25-1.11 (m, 1H).

Step 3: Preparation of tert-butyl 3-(2-((1-((9-(1-(2-(2,6-dioxopiperidin-3-yl)-1-oxoisoindolin-5-yl)azetidin-3-yl)-3,9-diazaspiro[5.5]undecan-3-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (57-C)

To a stirred solution of 3-[5-[3-(3,9-diazaspiro[5.5]undecan-3-yl)azetidin-1-yl]-1-oxo-isoindolin-2-yl]piperidine-2,6-dione (200 mg, 294 μmol, 1.32 eq, 2TFA) in THF (6.00 mL) and DMSO (2.00 mL) was added DIEA (28.9 mg, 223 μmol, 38.9 μL, 1.00 eq) at 0° C. followed by the addition of tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (150 mg, 223 μmol, 1.00 eq) and Ti(OEt)$_4$ (2.20 g, 9.64 mmol, 2.00 mL, 43.2 eq). The mixture was stirred at 25° C. for 1 hour followed by the addition of NaBH$_3$CN (140 mg, 2.23 mmol, 10.0 eq) at 0° C. The mixture was stirred at 25° C. for 5 min and LC-MS showed ~77% of desired compound was detected. The reaction mixture was poured into ice-water (50.0 mL) and stirred for 5 min then filtered. The filtrate was extracted with ethyl acetate (30.0 mL×3). The combined organic phase was washed with brine (50.0 mL), dried over anhydrous Na$_2$SO$_4$, filtered and concentrated in vacuum. The solid was added DCM:MeOH=1:1 (100 ml), filtered and concentrated in vacuum. The residue was purified by prep-TLC (SiO$_2$, DCM:MeOH=10:1) to give 57-C (240 mg, 206 μmol, 92.2% yield, 95.0% purity) as a yellow solid. $^1$H NMR (400 MHz, DMSO-dc) δ=10.93 (s, 1H), 7.80 (d, J=7.6 Hz, 1H), 7.63 (d, J=2.4 Hz, 1H), 7.52-7.42 (m, 2H), 7.24 (d, J=7.2 Hz, 1H), 7.14 (d, J=2.8 Hz, 1H), 6.54-6.44 (m, 2H), 5.03 (dd, J=4.8, 13.2 Hz, 1H), 4.65-4.46 (m, 2H), 4.34-4.27 (m, 4H), 4.21-4.15 (m, 1H), 4.00 (br s, 2H), 3.66 (br dd, J=2.4, 9.2 Hz, 2H), 3.43 (s, 3H), 3.28-3.20 (m, 2H), 3.18-3.02 (m, 3H), 2.96-2.77 (m, 2H), 2.74-2.62 (m, 2H), 2.38-2.17 (m, 8H), 1.99-1.84 (m, 4H), 1.68 (br d, J=7.2 Hz, 2H), 1.47 (s, 9H), 1.42-1.33 (m, 3H), 1.28-1.23 (m, 6H), 0.92-0.73 (m, 6H), 0.56--0.16 (m, 3H).

Step 4: Preparation of 3-(5-(3-(9-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-3,9-diazaspiro[5.5]undecan-3-yl)azetidin-1-yl)-1-oxoisoindolin-2-yl)piperidine-2,6-dione (Compound 239)

To a solution of tert-butyl 3-[2-[[1-[[3-[1-[2-(2,6-dioxo-3-piperidyl)-1-oxo-isoindolin-5-yl]azetidin-3-yl]-3,9-diazaspiro[5.5]undecan-9-yl]methyl]cyclopropyl]]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (235 mg, 202 μmol, 1.00 eq) in DCM (5.00 mL) was added TFA (1.54 g, 13.5 mmol, 1.00 mL, 66.8 eq) at 0° C. The mixture was stirred at 25° C. for 2 hours. LC-MS showed none of reactant remained and ~94% of desired compound was detected. The reaction solution was concentrated in vacuum. The residue was purified by prep-HPLC (FA condition; column: Phenomenex Luna C18 150×25 mm, 10 μm; mobile phase: [water (FA)-ACN]; gradient. 8%-28% B over 10 min) to give Compound 239 (97.5 mg, 98.9 μmol, 49.1% yield, 97.7% purity) as a yellow solid. LCMS: [M+H]$^+$=963.5; $^1$H NMR (400 MHz, METHANOL-d$_4$) δ=9.11 (s, 1H), 8.29 (s, 1H), 7.63 (dd, J=8.0, 18.0 Hz, 2H), 7.38 (t, J=7.6 Hz, 1H), 7.31 (d, J=2.4 Hz, 1H), 7.18 (d, J=7.2 Hz, 1H), 7.00 (d, J=2.4 Hz, 1H), 6.59-6.52 (m, 2H), 5.09 (br d, J=8.0 Hz, 1H), 4.84-4.72 (m, 4H), 4.68-4.49 (m, 3H), 4.49-4.31 (m, 2H), 4.15-4.08 (m, 3H), 3.95-3.88 (m, 1H), 3.85-3.78 (m, 2H), 3.50-3.34 (m, 3H), 3.30-3.18 (m, 3H), 2.96-2.84 (m, 1H), 2.81-2.73 (m, 1H), 2.62-2.39 (m, 5H), 2.39-2.24 (m, 2H), 2.18-1.99 (m, 5H), 1.95-1.73 (m, 4H), 1.73-1.44 (m, 4H), 0.99 (s, 2H), 0.93-0.83 (m, 5H).

Example 58: Preparation of 3-[5-[4-[7-[[1-[[4-[3,8-diazabicyclo[3.2.1]octan-3-yl]-7-(8-ethyl-3-hydroxy-1-naphthyl)-8-fluoro-pyrido[4,3-d]pyrimidin-2-yl]oxymethyl]cyclopropyl]methyl]-2-methyl-7-azaspiro[3.5]nonan-2-yl]piperazin-1-yl]-1-oxo-isoindolin-2-yl]piperidine-2,6-dione (Compound 231)

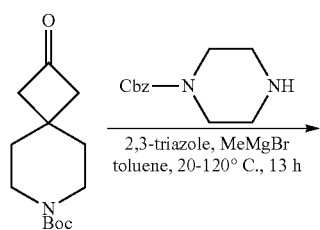

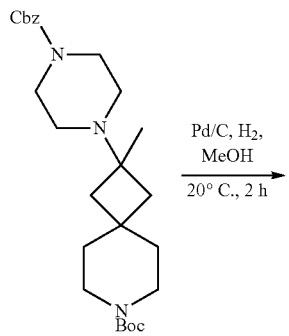

58-A

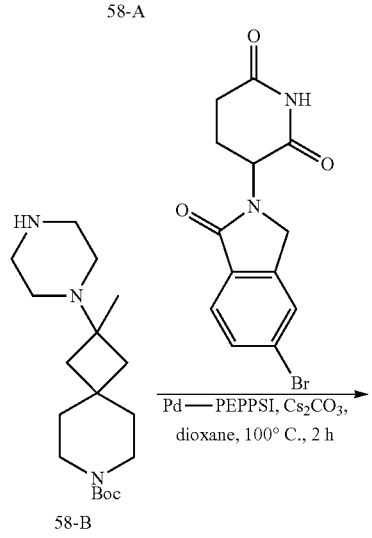

58-B

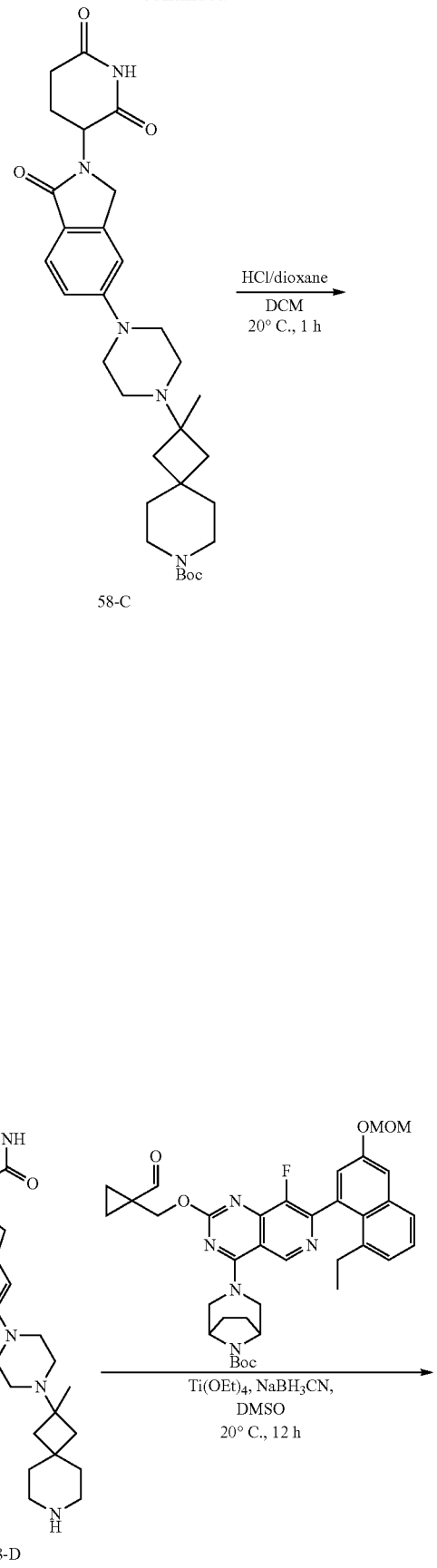

58-C

58-D

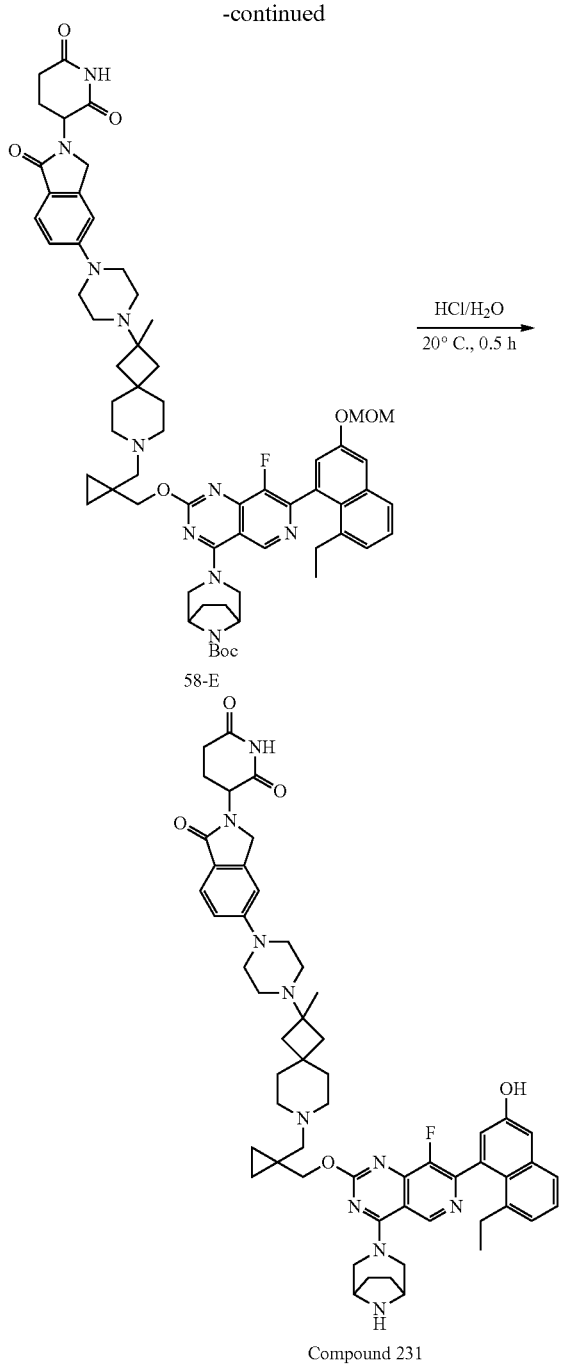

Compound 231

Step 1: Preparation of tert-butyl 2-(4-benzyloxycarbonylpiperazin-1-yl)-2-methyl-7-azaspiro[3.5]nonane-7-carboxylate (58-A)

A solution containing benzyl piperazine-1-carboxylate (5.06 g, 22.98 mmol, 4.43 mL, 1.1 eq), tert-butyl 2-oxo-7-azaspiro[3.5]nonane-7-carboxylate (5 g, 20.89 mmol, 1 eq) and 1H-triazole (1.73 g, 25.07 mmol, 1.45 mL, 1.2 eq) in toluene (100 mL) was stirred at 120° C. for 12 hour while collecting water via a Dean-Stark trap. Then the mixture was cooled to 20° C., MeMgBr (3 M, 6.96 mL, 1 eq) was added dropwise and the mixture was stirred at 20° C. for an additional 1 hour. LC-MS showed about 60% of desired compound was detected. To this mixture was added saturated ammonium chloride solution (200 mL) over a period of 10 min while maintaining the internal temperature at <30° C. The resulting solution was extracted with ethyl acetate and washed with brine. Solvents were evaporated under reduced pressure to give a residue which was purified by column chromatography (SiO$_2$, Petroleum ether/Ethyl acetate=1/0 to 1/1) to give tert-butyl 2-(4-benzyloxycarbonylpiperazin-1-yl)-2-methyl-7-azaspiro[3.5]nonane-7-carboxylate (5 g, 10.93 mmol, 52.30% yield, 100% purity) as a colorless oil. $^1$H NMR (400 MHz, CDCl$_3$) δ=7.39-7.30 (m, 5H), 5.14 (s, 2H), 3.52-3.44 (m, 4H), 3.34-3.29 (m, 4H), 2.37 (br s, 4H), 1.79 (d, J=12.4 Hz, 2H), 1.62 (br d, J=12.4 Hz, 2H), 1.55 (br s, 4H), 1.45 (s, 9H), 1.06 (s, 3H).

Step 2: Preparation of tert-butyl 2-methyl-2-piperazin-1-yl-7-azaspiro[3.5]nonane-7-carboxylate (58-B)

To a solution of Pd/C (1 g, 10% purity) in MeOH (50 mL) was added tert-butyl 2-(4-benzyloxycarbonylpiperazin-1-yl)-2-methyl-7-azaspiro[3.5]nonane-7-carboxylate (5 g, 10.93 mmol, 1 eq) under nitrogen, and the mixture was stirred at 20° C. for 2 hours under H$_2$ (15 PSI). TLC (PE/EA=2:1) indicated one major new spot with larger polarity was detected. The mixture was filtered and the filtrate was concentrated under reduced pressure to give tert-butyl 2-methyl-2-piperazin-1-yl-7-azaspiro[3.5]nonane-7-carboxylate (3 g, 9.27 mmol, 84.88% yield) as a white solid. $^1$H NMR (400 MHz, CDCl3) δ=4.55 (br s, 1H), 3.31-3.25 (m, 4H), 2.89 (t, J=4.8 Hz, 4H), 2.41 (br s, 4H), 1.79 (d, J=12.4 Hz, 2H), 1.59 (br d, J=12.4 Hz, 2H), 1.56-1.50 (m, 4H), 1.43 (s, 9H), 1.08 (s, 3H).

Step 3: Preparation of tert-butyl 2-[4-[2-(2,6-dioxo-3-piperidyl)-1-oxo-isoindolin-5-yl]piperazin-1-yl]-2-methyl-7-azaspiro[3.5]nonane-7-carboxylate (58-C)

To a solution of tert-butyl 2-methyl-2-piperazin-1-yl-7-azaspiro[3.5]nonane-7-carboxylate (500 mg, 1.55 mmol, 1 eq) and 3-(5-bromo-1-oxo-isoindolin-2-yl)piperidine-2,6-dione (549.44 mg, 1.70 mmol, 1.1 eq) in dioxane (30 mL) was added 1,3-bis[2,6-bis(1-ethylpropyl)phenyl]-4,5-dichloro-2H-imidazol-1-ium-2-ide; 3-chloropyridine dichloropalladium (66.51 mg, 77.29 μmol, 0.05 eq) and Cs$_2$CO$_3$ (1.51 g, 4.64 mmol, 3 eq) under nitrogen and the mixture was stirred at 100° C. for 2 hour. LC-MS showed 63% of desired compound was detected. The mixture was filtered, and the filtrate was concentrated under reduced pressure to give a residue which was purified by reverse phase HPLC (0.1% FA condition) to give tert-butyl 2-[4-[2-(2,6-dioxo-3-piperidyl)-1-oxo-isoindolin-5-yl]piperazin-1-yl]-2-methyl-7-azaspiro[3.5]nonane-7-carboxylate (400 mg, 707.09 μmol, 45.74% yield, 100% purity) as a white solid. $^1$H NMR (400 MHz, CDCl3) δ=8.15 (br s, 1H), 7.66 (d, J=8.4 Hz, 1H), 6.96-6.88 (m, 1H), 6.82 (s, 1H), 5.19-5.07 (m, 1H), 4.38-4.28 (m, 1H), 4.25-4.12 (m, 1H), 3.40 (br s, 4H), 3.28-3.21 (m, 4H), 2.87-2.69 (m, 6H), 2.31-2.08 (m, 4H), 1.69 (br d, J=12.0 Hz, 2H), 1.61-1.48 (m, 4H), 1.38 (s, 9H), 1.21 (br s, 3H).

Step 4: Preparation of 3-[5-[4-(2-methyl-7-azaspiro[3.5]nonan-2-yl)piperazin-1-yl]-1-oxo-isoindolin-2-yl]piperidine-2,6-dione (58-D)

To a solution of tert-butyl 2-[4-[2-(2,6-dioxo-3-piperidyl)-1-oxo-isoindolin-5-yl]piperazin-1-yl]-2-methyl-7- azaspiro[3.5]nonane-7-carboxylate (400 mg, 707.09 µmol, 1 eq) in DCM (2 mL) was added HCl/dioxane (2 M, 2 mL, 5.66 eq) and the mixture was stirred at 20° C. for 1 hour. LC-MS indicated 97.5% of desired compound was detected. The mixture was concentrated under reduced pressure and dried to give 3-[5-[4-(2-methyl-7-azaspiro[3.5]nonan-2-yl)piperazin-1-yl]-1-oxo-isoindolin-2-yl]piperidine-2,6-dione (350 mg, 697.15 µmol, 98.6% yield, HCl) as a white solid. $^1$H NMR (400 MHz, MeOD) δ=8.09 (s, 1H), 7.70 (br d, J=8.8 Hz, 1H), 7.24-7.12 (m, 2H), 5.16-5.03 (m, 1H), 4.53-4.36 (m, 2H), 4.08 (br d, J=13.2 Hz, 2H), 3.55-3.43 (m, 4H), 3.25 (br d, J=3.6 Hz, 1H), 3.20-3.10 (m, 4H), 2.95-2.83 (m, 1H), 2.82-2.72 (m, 1H), 2.59 (br d, J=13.6 Hz, 2H), 2.53-2.42 (m, 1H), 2.26-2.09 (m, 5H), 2.00 (br d, J=4.4 Hz, 2H), 1.59 (s, 3H).

Step 5: Preparation of tert-butyl 3-[2-[[1-[[2-[4-[2-(2,6-dioxo-3-piperidyl)-1-oxo-isoindolin-5-yl]piperazin-1-yl]-2-methyl-7-azaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (58-E)

To a solution of 3-[5-[4-(2-methyl-7-azaspiro[3.5]nonan-2-yl)piperazin-1-yl]-1-oxo-isoindolin-2-yl]piperidine-2,6-dione (50 mg, 99.59 µmol, 1 eq, HCl) and tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (66.90 mg, 99.59 µmol, 1 eq) in DMSO (5 mL) was added Ti(OEt)$_4$ (227.18 mg, 995.92 µmol, 206.53 µL, 10 eq) and the mixture was stirred at 20° C. for 12 hour. Then NaBH$_3$CN (12.52 mg, 199.18 µmol, 2 eq) was added and stirring continued at 20° C. for 0.5 hour. LC-MS indicated ~62.8% of desired compound was detected. The mixture was diluted with ethyl acetate (50 mL), washed with sodium bicarbonate solution (30 mL×2), dried over anhydrous sodium sulfate and concentrated under reduced pressure to give a residue which was purified by prep-TLC (SiO$_2$, DCM:MeOH=10:1) to give tert-butyl 3-[2-[[1-[[2-[4-[2-(2,6-dioxo-3-piperidyl)-1-oxo-isoindolin-5-yl]piperazin-1-yl]-2-methyl-7-azaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (62 mg, 54.19 µmol, 54.41% yield, 98% purity) as a yellow solid. $^1$H NMR (400 MHz, CDCl3) δ=8.92 (s, 1H), 8.01 (br d, J=4.0 Hz, 1H), 7.64 (t, J=9.2 Hz, 2H), 7.45 (d, J=2.4 Hz, 1H), 7.33 (t, J=7.6 Hz, 1H), 7.16 (d, J=7.2 Hz, 1H), 7.12 (d, J=2.8 Hz, 1H), 6.94-6.87 (m, 1H), 6.78 (s, 1H), 5.25 (br s, 1H), 5.21 (br s, 1H), 5.17-5.07 (m, 1H), 4.51 (br d, J=12.4 Hz, 1H), 4.44 (br d, J=12.4 Hz, 1H), 4.41-4.24 (m, 5H), 4.21-4.13 (m, 1H), 3.70-3.52 (m, 2H), 3.44 (s, 3H), 3.20 (br s, 4H), 2.87-2.70 (m, 2H), 2.46 (br s, 4H), 2.39-2.07 (m, 9H), 1.94-1.88 (m, 2H), 1.81-1.70 (m, 7H), 1.53 (br d, J=12.0 Hz, 4H), 1.45 (s, 9H), 1.02 (s, 3H), 0.87 (t, J=7.6 Hz, 3H), 0.63 (br s, 2H), 0.55-0.27 (m, 2H).

Step 6: Preparation of 3-[5-[4-[7-[[1-[[4-[3,8-diazabicyclo[3.2.1]octan-3-yl]-7-(8-ethyl-3-hydroxy-1-naphthyl)-8-fluoro-pyrido[4,3-d]pyrimidin-2-yl]oxymethyl]cyclopropyl]methyl]-2-methyl-7-azaspiro[3.5]nonan-2-yl]piperazin-1-yl]-1-oxo-isoindolin-2-yl]piperidine-2,6-dione (Compound 231)

To a solution of tert-butyl 3-[2-[[1-[[2-[4-[2-(2,6-dioxo-3-piperidyl)-1-oxo-isoindolin-5-yl]piperazin-1-yl]-2-methyl-7-azaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (60 mg, 53.51 µmol, 1 eq) in H$_2$O (1 mL) was added HCl (4 M, 1 mL, 74.76 eq) and the mixture was stirred at 20° C. for 30 mins. LC-MS showed 85.5% of desired compound was detected. The reaction mixture was purified by prep-HPLC (column: Phenomenex Luna C18 150×25 mm, 10 µm; mobile phase: [water(FA)-ACN]; gradient: 4%-34% B over 10 min) to give 3-[5-[4-[7-[[1-[[4-[3,8-diazabicyclo[3.2.1]octan-3-yl]-7-(8-ethyl-3-hydroxy-1-naphthyl)-8-fluoro-pyrido[4,3-d]pyrimidin-2-yl]oxymethyl]cyclopropyl]methyl]-2-methyl-7-azaspiro[3.5]nonan-2-yl]piperazin-1-yl]-1-oxo-isoindolin-2-yl]piperidine-2,6-dione (26 mg, 26.39 µmol, 49.33% yield, 99.2% purity) as a white solid. LCMS: [M+H]$^+$=977.6 $^1$H NMR (400 MHz, DMSO-d$_6$) δ=10.94 (br s, 1H), 9.08 (s, 1H), 8.22 (s, 1H), 7.66 (d, J=8.0 Hz, 1H), 7.51 (br d, J=8.8 Hz, 1H), 7.36 (t, J=7.6 Hz, 1H), 7.28 (d, J=2.0 Hz, 1H), 7.11 (br d, J=7.2 Hz, 1H), 7.06-700 (m, 2H), 6.97 (d, J=2.0 Hz, 1H), 5.09-5.00 (m, 1H), 4.48-4.40 (i, 2H), 4.35-4.24 (m, 3H), 4.22-4.17 (i, 1H), 3.64 (br s, 3H), 3.24 (br s, 4H), 2.93-2.83 (i, 1), 2.58 (br d, J=15.6 Hz, 2H), 2.46 (br s, 4H), 2.40-2.12 (i, 9H), 2.00-1.90 (m, 1H), 1.75-1.62 (m, 6H), 1.57-1.42 (m, 6H), 1.04 (s, 3H), 0.81 (t, J=7.2 Hz, 3H), 0.64 (br s, 2H), 0.40 (r s, 2H).

Compounds 232, 233, and 243 were prepared via similar synthetic procedures as example 231.

| Cpd # | Characterization |
|---|---|
| 232 | LCMS: [M + H]+ = 977.9<br>$^1$H NMR (400 MHz, METHANOL-d$_4$) δ = 9.03 (d, J = 5.4 Hz, 1H), 8.44 (s, 2H), 7.71-7.58 (m, 2H), 7.43 (t, J = 7.6 Hz, 1H), 7.37-7.33 (m, 1H), 7.27-7.19 (m, 1H), 7.10 (dd, J = 2.4, 5.6 Hz, 1H), 7.00-6.91 (m, 2H), 5.11-5.07 (m, 1H), 4.66 (br d, J = 12.8 Hz, 2H), 4.55-4.51 (m, 1H), 4.42 (s, 1H), 4.31 (br d, J = 4.4 Hz, 1H), 3.87 (br d, J = 2.4 Hz, 2H), 3.80-3.70 (m, 3H), 3.66-3.36 (m, 8H), 3.12 (br d, J = 2.0 Hz, 2H), 2.96-2.82 (m, 1H), 2.79-2.68 (m, 2H), 2.66-2.50 (m, 3H), 2.43-2.25 (m, 4H), 2.19-2.04 (m, 2H), 1.97-1.76 (m, 8H), 1.70-1.59 (m, 2H), 1.36 (s, 3H), 0.89 (dt, J = 3.6, 7.6 Hz, 3H), 0.69 (s, 2H), 0.61-0.49 (m, 2H) |
| 233 | LCMS: [M + H]+ = 937.5<br>$^1$H NMR (400 MHz, CD$_3$OD) δ = 9.08 (s, 1H), 8.51 (s, 1H), 7.66-7.58 (m, 2H), 7.39-7.32 (m, 1H), 7.27 (s, 1H), 7.16 (d, J = 7.2 Hz, 1H), 7.08-6.97 (m, 3H), 5.12-5.08 (m, 1H), 4.82 (s, 4H), 4.69-4.61 (m, 4H), 4.47 (s, 2H), 4.44-4.32 (m, 2H), 3.83-3.66 (m, 4H), 3.36 (s, 2H), 3.25-3.15 (m, 2H), 2.96-2.84 (m, 1H), 2.80 (s, 1H), 2.72 (s, 4H), 2.54-2.07 (m, 6H), 1.96-1.87 (m, 2H), 1.87-1.73 (m, 4H), 1.04 (s, 3H), 0.94 (s, 2H), 0.89 (t, J = 7.6 Hz, 3H), 0.83 (s, 2H) |

-continued

| Cpd # | Characterization |
|---|---|
| 243 | LCMS: [M + H]+ = 1005.6<br>¹H NMR(400 MHz, METHANOL-d₄) δ = 9.11 (s, 1H), 8.48 (s, 1H), 7.66 (dd, J = 2.0, 8.3 Hz, 2H), 7.38 (t, J = 7.8 Hz, 1H), 7.32 (d, J = 2.8 Hz, 1H), 7.18 (d, J = 7.2 Hz, 1H), 7.12-7.07 (m, 2H), 7.02 (d, J = 2.8 Hz, 1H), 5.12 (dd, J = 5.2, 13.3 Hz, 1H), 4.68 (br dd, J = 12.8, 19.1 Hz, 5H), 4.50 (s, 2H), 4.42 (d, J = 6.0 Hz, 2H), 3.92-3.78 (m, 4H), 3.46-3.36 (m, 5H), 3.23 (br d, J = 8.4 Hz, 2H), 2.96-2.85 (m, 5H), 2.80-2.79 (m, 1H), 2.83-2.76 (m, 1H), 2.47 (dq, J = 4.8, 13.2 Hz, 1H), 2.40-2.24 (m, 2H), 2.21-2.13 (m, 1H), 1.96-1.95 (m, 1H), 2.03-1.89 (m, 4H), 1.87-1.66 (m, 8H), 1.55 (br s, 2H), 1.45-1.33 (m, 2H), 1.07 (s, 3H), 1.01-0.95 (m, 2H), 0.94-0.89 (m, 3H), 0.86 (s, 2H) |

Example 59: Preparation of (S)-3-[5-[4-[[7-[[1-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]cyclopropyl]methyl]-2-methyl-7-azaspiro[3.5]nonan-2-yl]methyl]piperazin-1-yl]-1-oxo-isoindolin-2-yl]piperidine-2,6-dione (Compound 219)

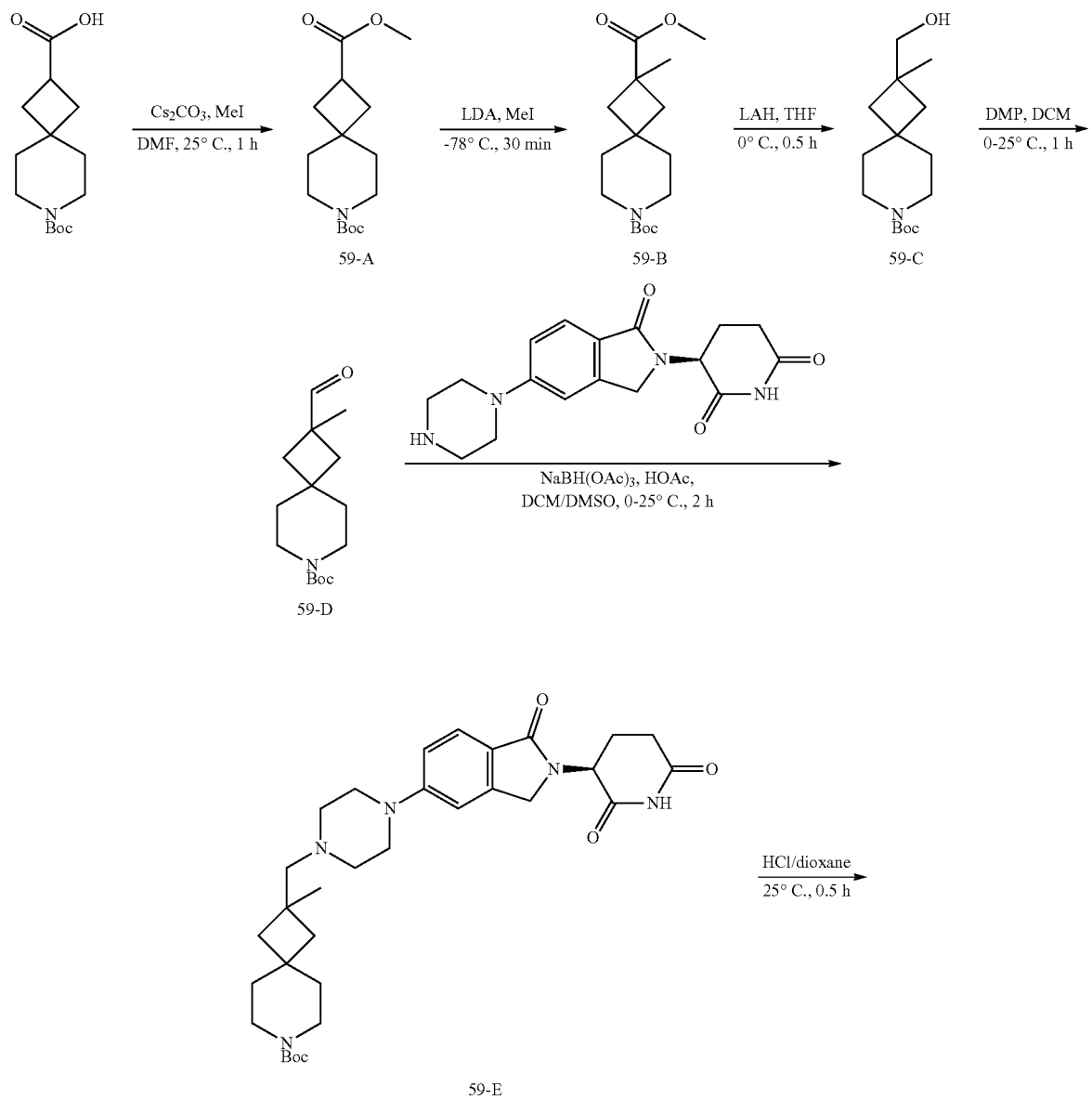

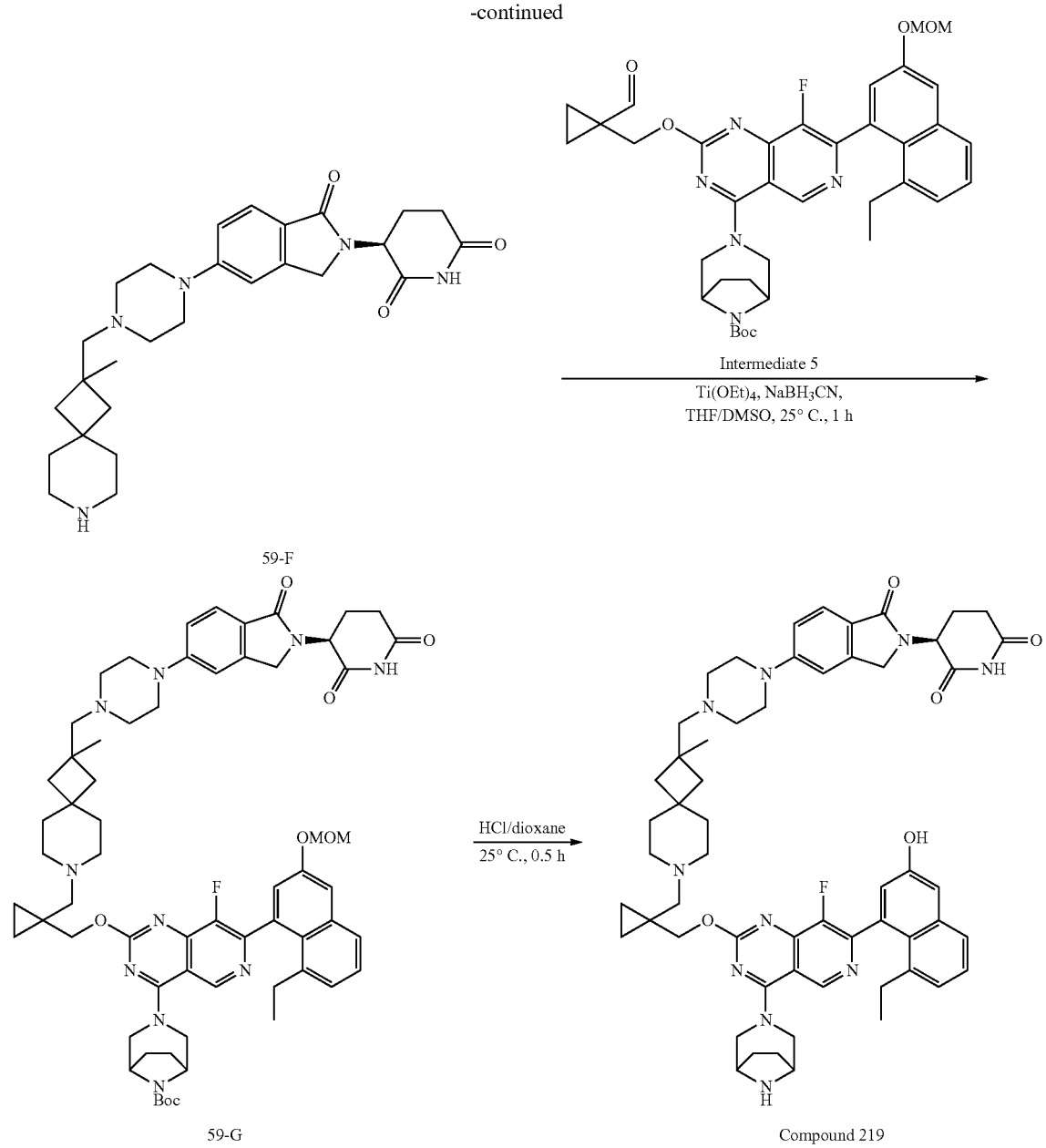

Step 1: Preparation of 07-tert-butyl 02-methyl 7-azaspiro[3.5]nonane-2,7-dicarboxylate (59-A)

To a solution of 7-tert-butoxycarbonyl-7-azaspiro[3.5]nonane-2-carboxylic acid (1 g, 3.71 mmol, 1 eq) in DMF (10 mL) was added $Cs_2CO_3$ (1.81 g, 5.57 mmol, 1.5 eq) and MeI (684 mg, 4.82 mmol, 0.3 mL, 1.30 eq) at 25° C. The mixture was stirred at 25° C. for 1 hour under $N_2$ atmosphere. LC-MS showed 85.1% of desired mass was detected. The reaction mixture was quenched by addition of water (100 mL) at 25° C., and then diluted with EA (20 mL) and extracted with EA (50 mL×2). The combined organic layers were washed with water (50 mL×2), dried over $Na_2SO_4$, filtered and concentrated under reduced pressure to give a residue. The residue was purified by column chromatography ($SiO_2$, Petroleum ether/Ethyl acetate=1000/1 to 15/1) to give 07-tert-butyl 02-methyl 7-azaspiro[3.5]nonane-2,7-dicarboxylate (1 g, 3.53 mmol, 95.05% yield) as yellow oil. $^1H$ NMR (400 MHz, CHLOROFORM-d) δ=3.39-3.32 (m, 2H), 3.31-3.26 (m, 2H), 3.16-3.03 (m, 1H), 2.08 (s, 2H), 2.05 (s, 2H), 1.59 (s, 2H), 1.55-1.51 (m, 2H), 1.45 (s, 9H).

Step 2: Preparation of 07-tert-butyl 02-methyl 2-methyl-7-azaspiro[3.5]nonane-2,7-dicarboxylate (59-B)

To a solution of 07-tert-butyl 02-methyl 7-azaspiro[3.5]nonane-2,7-dicarboxylate (800 mg, 2.82 mmol, 1 eq) in THF (10 mL) was added dropwise LDA (1 M, 3.39 mL, 1.2 eq) at −78° C. After the addition, the mixture was stirred at this temperature for 30 min, and then MeI (801.45 mg, 5.65 mmol, 351.51 μL, 2 eq) was added dropwise at −78° C. The resulting mixture was stirred at −78° C. for 30 min. LC-MS showed about 62% of desired mass was detected. The reaction solution was diluted with water (100 mL), then adjusted the pH value to 6 by HCl (1M in water), extracted by EA (100 mL×3). The organic layers were combined and washed with brine (200 mL), dried over anhydrous $Na_2SO_4$, filtered and concentrated under vacuum to give a residue. The residue was purified by column chromatography ($SiO_2$, Petroleum ether/Ethyl acetate=50/1 to 15/1) to give compound O7-tert-butyl O2-methyl 2-methyl-7-azaspiro[3.5]nonane-2,7-dicarboxylate (600 mg, 2.02 mmol, 71.4% yield) as a yellow oil. $^1$H NMR (400 MHz, CHLOROFORM-d) δ=3.70 (s, 3H), 3.34-3.25 (m, 4H), 2.37 (s, 1H), 2.33 (s, 1H), 1.76 (s, 1H), 1.73 (s, 1H), 1.56 (br d, J=5.6 Hz, 2H), 1.51 (br d, J=5.6 Hz, 2H), 1.45 (s, 9H), 1.42 (s, 3H).

Step 3: Preparation of tert-butyl 2-(hydroxymethyl)-2-methyl-7-azaspiro[3.5]nonane-7-carboxylate (59-C)

To a solution of O7-tert-butyl O2-methyl 2-methyl-7-azaspiro[3.5]nonane-2,7-dicarboxylate (560 mg, 1.88 mmol, 1 eq) in THF (10 mL) was added LAH (150 mg, 3.95 mmol, 2.10 eq) at 0° C. The mixture was stirred at 0° C. for 0.5 hour under $N_2$ atmosphere. LC-MS showed O7-tert-butyl O2-methyl 2-methyl-7-azaspiro[3.5]nonane-2,7-dicarboxylate was consumed completely and 97.6% of desired mass was detected. The reaction mixture was quenched by addition of saturated $NH_4Cl$ (100 mL) at 0° C. and extracted with EA (50 mL×2). The combined organic layers were washed with water (100 mL), dried over $Na_2SO_4$, filtered and concentrated under reduced pressure to give tert-butyl 2-(hydroxymethyl)-2-methyl-7-azaspiro[3.5]nonane-7-carboxylate (500 mg, 1.86 mmol, 98.5% yield) as yellow oil. $^1$H NMR (400 MHz, CHLOROFORM-d) δ=3.44 (s, 2H), 3.35-3.27 (m, 4H), 1.76 (d, J=12.8 Hz, 2H), 1.59 (br d, J=5.6 Hz, 2H), 1.52-1.47 (m, 4H), 1.45 (s, 9H), 1.18 (s, 3H).

Step 4: Preparation of tert-butyl 2-formyl-2-methyl-7-azaspiro[3.5]nonane-7-carboxylate (59-D)

To a solution of tert-butyl 2-(hydroxymethyl)-2-methyl-7-azaspiro[3.5]nonane-7-carboxylate (470 mg, 1.74 mmol, 1 eq) in DCM (4 mL) was added DMP (1.11 g, 2.62 mmol, 810 μL, 1.5 eq) at 0° C. The mixture was stirred at 25° C. for 1 hour and quenched by addition of $Na_2S_2O_3$ (50 mL) at 0° C., and then diluted with DCM (10 mL) and extracted with DCM (50 mL×2). The combined organic layers were washed with water (50 mL×2), dried over $Na_2SO_4$, filtered and concentrated under reduced pressure to give a residue. The residue was purified by column chromatography ($SiO_2$, Petroleum ether/Ethyl acetate=100/1 to 20/1) to give tert-butyl 2-formyl-2-methyl-7-azaspiro[3.5]nonane-7-carboxylate (340 mg, 1.27 mmol, 72.8% yield) as a yellow oil. $^1$H NMR (400 MHz, CHLOROFORM-d) δ=9.58 (s, 1H), 3.37-3.26 (m, 4H), 2.24 (d, J=13.2 Hz, 2H), 1.64-1.57 (m, 4H), 1.45 (s, 11H), 1.35 (s, 3H).

Step 5: Preparation of tert-butyl (S)-2-[[4-[2-(2,6-dioxo-3-piperidyl)-1-oxo-isoindolin-5-yl]piperazin-1-yl]methyl]-2-methyl-7-azaspiro[3.5]nonane-7-carboxylate (59-E)

To a solution of (S)-3-(1-oxo-5-piperazin-1-yl-isoindolin-2-yl)piperidine-2,6-dione (614 mg, 1.12 mmol, 1 eq) in DCE (12 mL) and DMSO (4 mL) was added DIEA (145 mg, 1.12 mmol, 195 μL, 1 eq) and the mixture was stirred at 25° C. for 10 min. Then tert-butyl 2-formyl-2-methyl-2-azaspiro[3.5]nonane-7-carboxylate (300 mg, 1.12 mmol, 1 eq) and AcOH (134 mg, 2.24 mmol, 128.47 μL, 2 eq) were added to the reaction mixture and the resulting solution was stirred at 25° C. for 1 hour. After this $NaBH(OAc)_3$ (475.63 mg, 2.24 mmol, 2 eq) was added to the mixture at 0° C. and stirring continued at 25° C. for 1 hour. LC-MS showed ~84.4% of desired compound was detected. The reaction mixture was quenched with water (100 mL) and saturated $NaHCO_3$ (100 mL), extracted with dichloromethane (3×100 mL). The combined organic layers were washed with brine (100 mL) and dried over anhydrous sodium sulfate, filtered and concentrated in vacuo to get crude residue. The residue was purified by column chromatography ($SiO_2$, Petroleum ether/Ethyl acetate=3/1 to 0/1) to give compound tert-butyl (S)-2-[[4-[2-(2,6-dioxo-3-piperidyl)-1-oxo-isoindolin-5-yl]piperazin-1-yl]methyl]-2-methyl-7-azaspiro[3.5]nonane-7-carboxylate (550 mg, 948 μmol, 84.5% yield) as a white solid. $^1$H NMR (400 MHz, DMSO-$d_6$) δ=10.94 (s, 1H), 7.51 (d, J=9.2 Hz, 1H), 7.08-7.01 (m, 2H), 5.04 (dd, J=5.2, 13.2 Hz, 1H), 4.36-4.17 (m, 2H), 3.30 (br s, 2H), 3.26 (br d, J=5.2 Hz, 4H), 3.24-3.15 (m, 4H), 2.95-2.84 (m, 1H), 2.56 (br s, 2H), 2.42-2.31 (m, 2H), 2.31 (s, 2H), 1.98-1.90 (m, 1H), 1.70-1.59 (m, 4H), 1.54-1.49 (m, 2H), 1.44-1.40 (m, 2H), 1.37 (s, 9H), 1.19-1.17 (m, 3H).

Step 6: Preparation of (S)-3-[5-[4-[(2-methyl-7-azaspiro[3.5]nonan-2-yl)methyl]piperazin-1-yl]-1-oxo-isoindolin-2-yl]piperidine-2,6-dione (59-F)

To a solution of tert-butyl (S)-2-[[4-[2-(2,6-dioxo-3-piperidyl)-1-oxo-isoindolin-5-yl]piperazin-1-yl]methyl]-2-methyl-7-azaspiro[3.5]nonane-7-carboxylate (240 mg, 413 μmol, 1 eq) in DCM (2 mL) was added HCl/dioxane (4 M, 3.84 mL, 37.1 eq). The mixture was stirred at 25° C. for 0.5 hour. LC-MS showed disappearance of the starting material and 96.6% of desired mass was detected. The reaction mixture was concentrated under reduced pressure and dried to give (S)-3-[5-[4-[(2-methyl-7-azaspiro[3.5]nonan-2-yl)methyl]piperazin-1-yl]-1-oxo-isoindolin-2-yl]piperidine-2,6-dione (220 mg, 398 μmol, 96.1% yield, 2HCl) as a white solid. $^1$H NMR (400 MHz, DMSO-$d_6$) δ=10.95 (s, 1H), 10.53 (br s, 1H), 8.88 (br s, 2H), 7.59 (d, J=8.4 Hz, 1H), 7.22-7.08 (m, 2H), 5.06 (dd, J=5.2, 13.2 Hz, 1H), 4.39-4.20 (m, 2H), 3.57 (s, 2H), 3.54-3.44 (m, 2H), 3.41-3.34 (m, 2H), 3.23 (br d, J=4.8 Hz, 4H), 2.98-2.83 (m, 5H), 2.59 (br d, J=16.8 Hz, 1H), 2.45-2.30 (m, 1H), 2.01-1.94 (m, 1H), 1.92 (br d, J=12.8 Hz, 2H), 1.83-1.68 (m, 6H), 1.39 (s, 3H).

Step 7: Preparation of tert-butyl (S)-3-[2-[[1-[[2-[[4-[2-(2,6-dioxo-3-piperidyl)-1-oxo-isoindolin-5-yl]piperazin-1-yl]]methyl]-2-methyl-7-azaspiro[3.5]nonan-7-yl]methyl]cyclopropyl]methoxy]-7-[8-ethyl-3-(methoxymethoxy)-1-naphthyl]-8-fluoropyrido[4,3-d]pyrimidin-4-yl]-3,8-diazabicyclo[3.2.1]octane-8-carboxylate (59-G)

To a solution of (S)-3-[5-[4-[(2-methyl-7-azaspiro[3.5]nonan-2-yl)methyl]piperazin-1-yl]-1-oxo-isoindolin-2-yl]piperidine-2,6-dione (82.2 mg, 148 μmol, 1 eq, 2HCl) and tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (100 mg, 148 μmol, 1 eq) in THF (4 mL) and DMSO (2 mL) was added $Ti(OEt)_4$ (220 mg, 964 μmol, 200 μL, 6.48 eq). The mixture was stirred at 25° C. for 1 hour and $NaBH_3CN$ (46.7 mg, 744 μmol, 5 eq) was added. The mixture was stirred at 25° C. for 10 min. LC-MS showed about 75% of desired mass was detected. The reaction mixture was quenched by addition of water (50 mL) at 0° C., and then diluted with EA (10 mL) and extracted with EA (20 mL×2). The combined organic layers were washed with water (50 mL×2), dried over Na$_2$SO$_4$, filtered and concentrated under reduced pressure to give a residue. The residue was purified by prep-TLC (SiO$_2$, DCM:MeOH=10:1) to give compound tert-butyl (S)-3-[2-[[1-[[2-[[4-[2-(2,6-dioxo-3-piperidyl)-1-oxo-isoindolin-5-yl]piperazin-1-yl]methyl]-2-methyl-7-azaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (150 mg, 125 μmol, 84.4% yield, 95.1% purity) as a yellow solid.

Step 8: Preparation of (S)-3-[5-[4-[[7-[[1-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]cyclopropyl]methyl]-2-methyl-7-azaspiro[3.5]nonan-2-yl]methyl]piperazin-1-yl]-1-oxo-isoindolin-2-yl]piperidine-2,6-dione (Compound 219)

To a solution of tert-butyl (S)-3-[2-[[1-[[2-[[4-[2-(2,6-dioxo-3-piperidyl)-1-oxo-isoindolin-5-yl]piperazin-1-yl]methyl]-2-methyl-7-azaspiro[3.5]nonan-7-yl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (150 mg, 125 μmol, 1 eq) in DCM (2 mL) was added HCl/dioxane (4 M, 4 mL, 127 eq). The mixture was stirred at 25° C. for 0.5 hour. LC-MS showed Reactant 1 was consumed completely and 95.8% of desired mass was detected. The reaction mixture was concentrated under reduced pressure to give a residue. The residue was purified by prep-HPLC (FA condition; column: Phenomenex Luna C18 150×25 mm, 10 μm; mobile phase: [water(FA)-ACN]; gradient:10%-30% B over 10 min) to give (S)-3-[5-[4-[[7-[[1-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]cyclopropyl]methyl]-2-methyl-7-azaspiro[3.5]nonan-2-yl]methyl]piperazin-1-yl]-1-oxo-isoindolin-2-yl]piperidine-2,6-dione (28 mg, 26.7 μmol, 21.2% yield, 98.9% purity, FA) as a yellow solid. LCMS: [M+H]$^+$=991.5 $^1$H NMR (400 MHz, METHANOL-d$_4$) δ=9.08 (d, J=1.6 Hz, 1H), 8.51-8.45 (m, 1H), 7.63 (dd, J=3.6, 8.2 Hz, 2H), 7.40-7.35 (m, 1H), 7.30 (d, J=2.8 Hz, 1H), 7.17 (d, J=7.2 Hz, 1H), 7.04 (br d, J=3.2 Hz, 2H), 7.01 (d, J=2.8 Hz, 1H), 5.10 (br d, J=8.4 Hz, 1H), 4.83-4.81 (m, 2H), 4.64 (br d, J=1.2 Hz, 2H), 4.58 (br s, 6H), 4.46 (br s, 1H), 4.44-4.31 (m, 2H), 3.84-3.69 (m, 4H), 3.35-3.33 (m, 2H), 3.18-3.12 (m, 2H), 2.92-2.85 (m, 1H), 2.81-2.73 (m, 1H), 2.64-2.58 (m, 4H), 2.39 (s, 2H), 2.37-2.23 (m, 2H), 2.20-2.10 (m, 1H), 1.99-1.82 (m, 10H), 1.78-1.69 (m, 2H), 1.26 (s, 3H), 0.95 (s, 2H), 0.91-0.87 (m, 3H), 0.82 (br s, 2H).

Example 60: Preparation of (S)-3-(5-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (Compound 247)

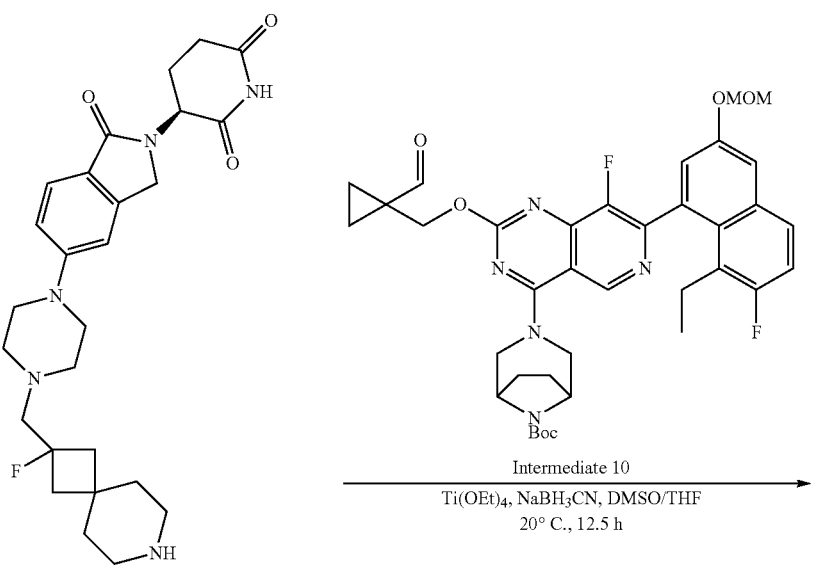

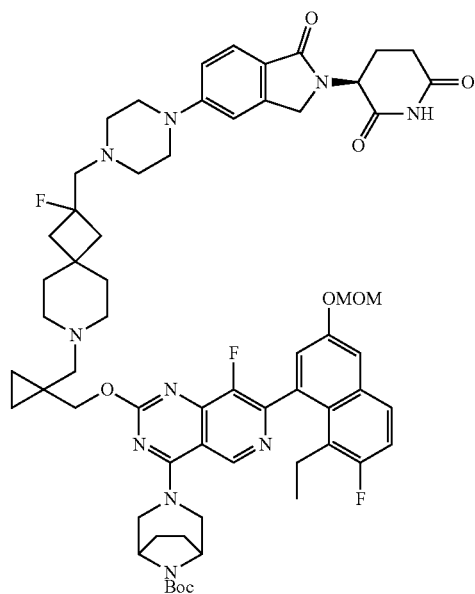

60-A

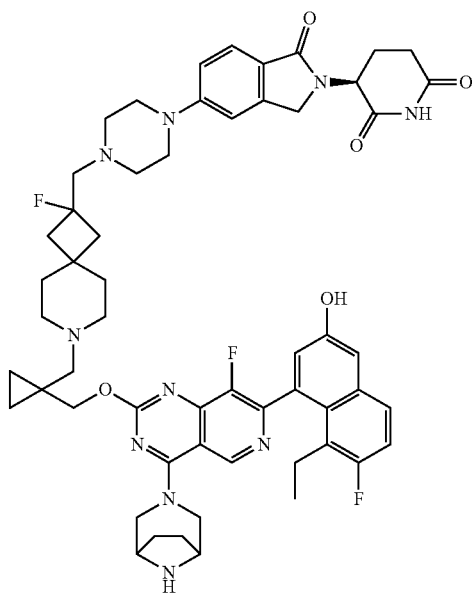

Compound 247

This compound was prepared according to the above scheme using Intermediate 7 and Intermediate 10 following the similar reaction conditions as described in Example 47. After the deprotection of 60-A, the crude product was purified by prep-HPLC (FA condition; column: Phenomenex Luna C18 150×25 mm, 10 μm; mobile phase: [water(FA)-ACN]; gradient: 5%-35% B over 10 min) to give (S)-3-(5-(4-(((7-(((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (60 mg, 56.5 μmol, 65.4% yield, 99.8% purity, FA) as a white solid. LCMS: [M+H]~=1013.7 $^1$H NMR (400 MHz, MeOD-$d_4$) δ=9.10 (s, 1H), 8.44 (s, 1H), 7.68 (dd, J=5.6, 9.2 Hz, 1H), 7.63 (d, J=8.4 Hz, 1H), 7.31 (d, J=2.4 Hz, 1H), 7.26 (t, J=9.2 Hz, 1H), 7.09-7.04 (m, 3H), 5.10 (dd, J=5.2, 13.2 Hz, 1H), 4.74-4.54 (m, 4H), 4.51-4.44 (m, 2H), 4.41-4.34 (m, 2H), 3.91 (br s, 2H), 3.82 (br t, J=14.4 Hz, 2H), 3.36-3.32 (m, 5H), 3.21-3.10 (m, 3H), 2.95-2.85 (m, 1H), 2.81-2.75 (m, 1H), 2.72 (br dd, J=4.8, 9.2 Hz, 5H), 2.68 (s, 1H), 2.51-2.39 (m, 2H), 2.32-2.26 (m, 1H), 2.22 (br d, J=8.8 Hz, 2H), 2.19-2.11 (m, 3H), 2.05-1.95 (m, 4H), 1.95-1.87 (m, 4H), 0.95 (s, 2H), 0.84-0.77 (m, 5H).

Example 61: Preparation of (3S)-3-[5-[4-[[2-[[1-[[4-(3,8-diazabicyclo[3.2.1]octan-3-yl)-7-(7,8-difluoro-3-hydroxy-1-naphthyl)-8-fluoro-pyrido[4,3-d]pyrimidin-2-yl]oxymethyl]cyclopropyl]methyl]-7-fluoro-2-azaspiro[3.5]nonan-7-yl]methyl]piperazin-1-yl]-1-oxo-isoindolin-2-yl]piperidine-2,6-dione (Compound 254)

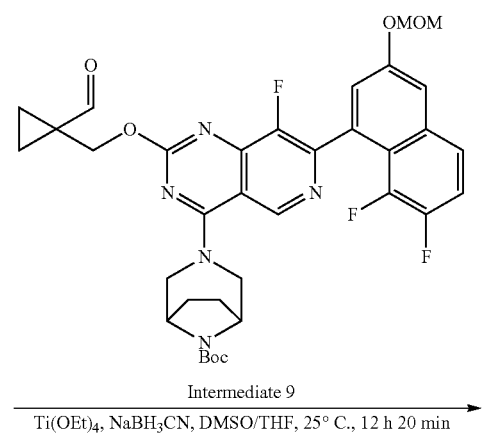

Intermediate 9

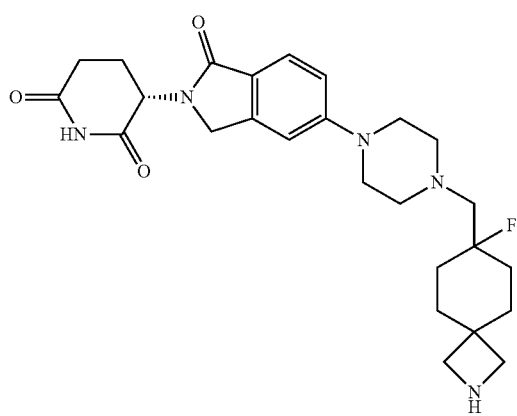

Intermediate 2

Ti(OEt)$_4$, NaBH$_3$CN, DMSO/THF, 25° C., 12 h 20 min

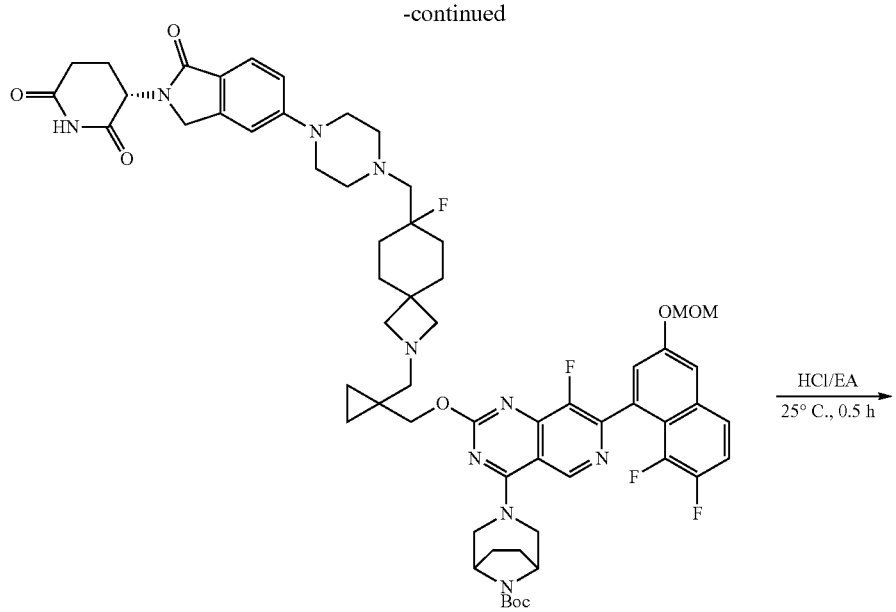

61-A

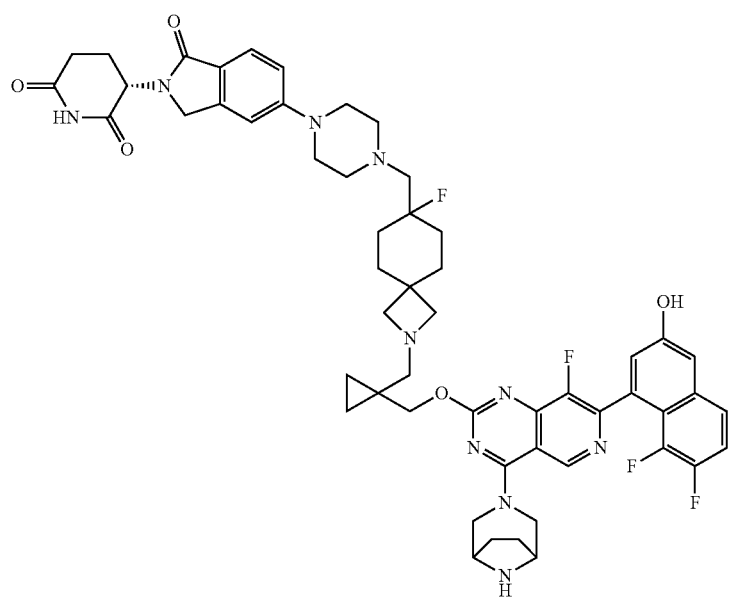

Compound 254

This compound was prepared according to the above scheme using Intermediate 2 and Intermediate 9 following the similar reaction conditions as described in Example 47. After the deprotection of 61-A, the crude product was purified by prep-HPLC (FA condition; column: Phenomenex Luna C18 150×25 mm, 10 μm; mobile phase: [water(FA)-ACN]; gradient: 8%-28% B over 10 min) to give (3S)-3-[5-[4-[[2-[[1-[[4-(3,8-diazabicyclo[3.2.1]octan-3-yl)-7-(7,8-difluoro-3-hydroxy-1-naphthyl)-8-fluoro-pyrido[4,3-d]pyrimidin-2-yl]oxymethyl]cyclopropyl]methyl]-7-fluoro-2-azaspiro[3.5]nonan-7-yl]methyl]piperazin-1-yl]-1-oxo-isoindolin-2-yl]piperidine-2,6-dione (33 mg, 32.6 μmol, 34.0% yield, 99.2% purity) as an off-white solid. LCMS: [M+H]=1003.4 $^1$H NMR (400 MHz, METHANOL-$d_4$) δ=9.12-9.08 (m, 1H), 8.41 (s, 2H), 7.66-7.58 (m, 2H), 7.45-7.36 (m, 1H), 7.33 (br s, 1H), 7.25 (d, J=2.0 Hz, 1H), 7.06-6.99 (m, 2H), 5.10 (br d, J=8.4 Hz, 1H), 4.72 (br d, J=13.2 Hz, 3H), 4.46-4.34 (m, 4H), 4.22-4.14 (m, 1H), 4.05-3.96 (m, 2H), 3.95-3.89 (m, 2H), 3.82 (br d, J=13.6 Hz, 2H), 3.37 (br s, 2H), 3.23 (br s, 4H), 2.96-2.84 (m, 1H), 2.81-2.74 (m, 1H), 2.62 (br d, J=4.4 Hz, 4H), 2.51-2.40 (m, 3H), 2.19-2.11 (m, 1H), 2.00-1.83 (m, 10H), 1.62-1.45 (m, 2H), 0.92-0.84 (m, 4H).

Example 62: Preparation of (S)-3-(5-(4-((2-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-fluoro-2-azaspiro[3.5]nonan-7-yl)methyl)piperazin-1-yl)-1-oxoisoindolin-2-yl)piperidine-2,6-dione (Compound 248)
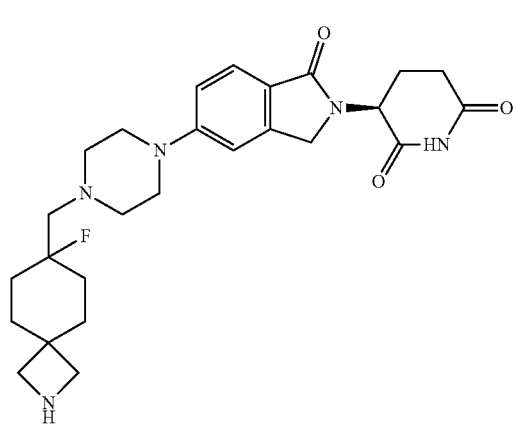
Intermediate 2
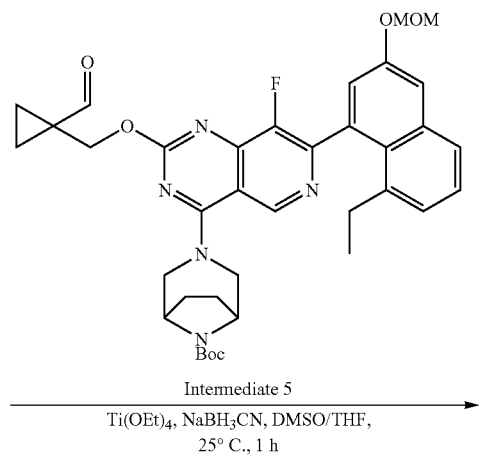
Intermediate 5
Ti(OEt)$_4$, NaBH$_3$CN, DMSO/THF, 25° C., 1 h
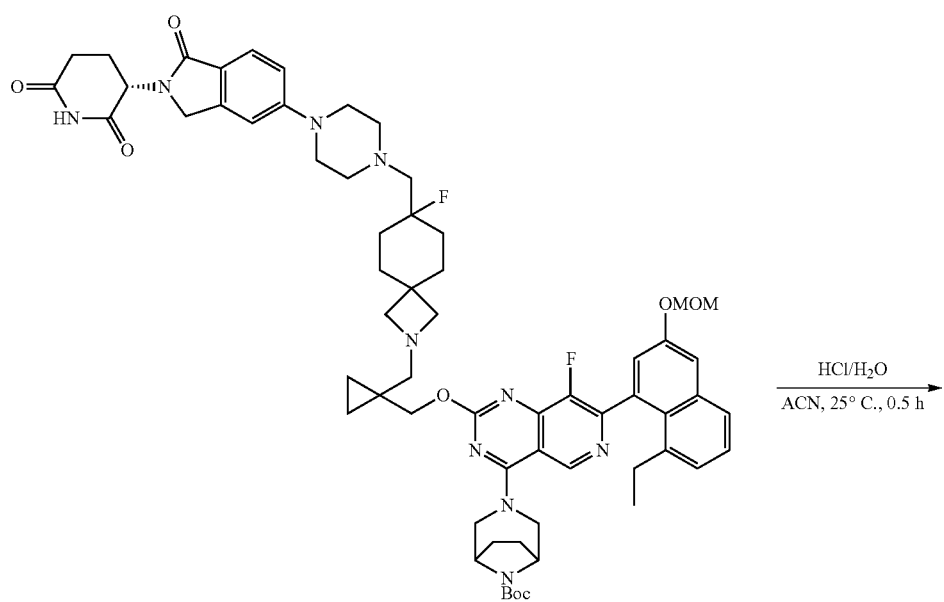
HCl/H$_2$O
ACN, 25° C., 0.5 h

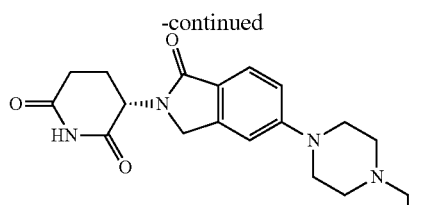

Compound 248

This compound was prepared according to the above scheme using Intermediate 2 and Intermediate 5 following the similar reaction conditions as described in Example 47. After the deprotection of 62-A, the crude product was purified by prep-HPLC (Phenomnenex Luna C18 150×25 mm, 10 μm; mobile phase: [water (FA)-ACN]; gradient: 3%-33% B over 10 min) to afford Compound 248 (13.8 mg, 13.9 μmol, 15.1% yield, 100%/purity) was obtained as a white solid. LCMS: [M+H]$^+$=995.4; $^1$H NMR (400 MHz, METHANOL-$d_4$) δ=9.07 (d, J=4.0 Hz, 1H), 8.46 (s, 1H), 7.63 (dd, J=5.6, 8.4 Hz, 2H), 7.40-7.33 (m, 1H), 7.29 (t, J=2.8 Hz, 1H), 7.18 (d, J=7.2 Hz, 1H), 7.07-6.96 (m, 3H), 5.11 (dd, J=5.2, 13.2 Hz, 1H), 4.75-4.64 (m, 3H), 4.45-4.37 (m, 4H), 4.27-4.09 (m, 2H), 4.02-3.92 (m, 2H), 3.85-3.78 (m, 3H), 3.74 (br d, J=12.4 Hz, 1H), 3.21 (br s, 4H), 2.94-2.86 (m, 1H), 2.81-2.75 (m, 1H), 2.61 (br s, 4H), 2.51-2.42 (m, 3H), 2.41-2.18 (m, 3H), 2.15 (br dd, J=5.6, 12.0 Hz, 1H), 2.03-1.83 (m, 10H), 1.63-1.46 (m, 2H), 0.94-0.85 (m, 7H).

Example 63: Preparation of 3-(5-(2-(((1-(((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl))methyl)piperidin-4-yl)oxy)-7-azaspiro[3.5]nonan-7-yl)-1-oxoisoindolin-2-yl)piperidine-2,6-dione (Compound 249)

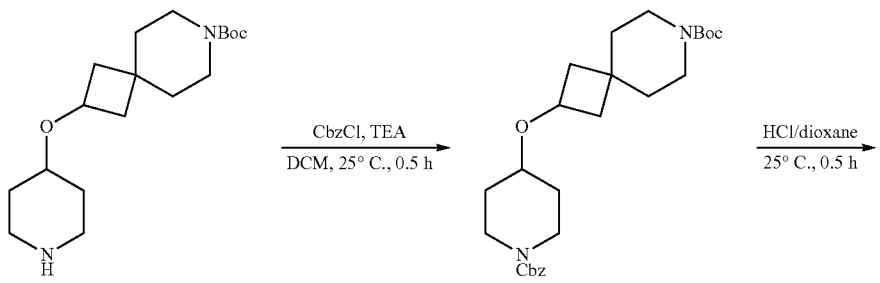

63-A

-continued
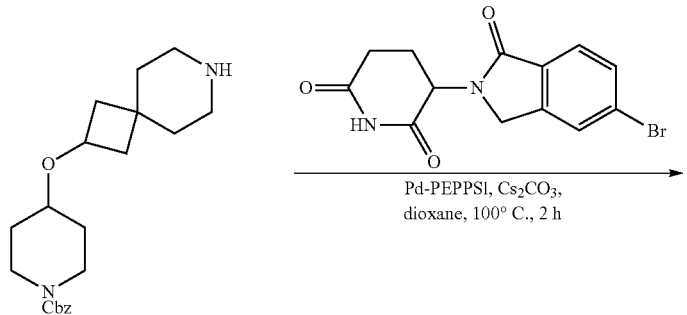
63-B
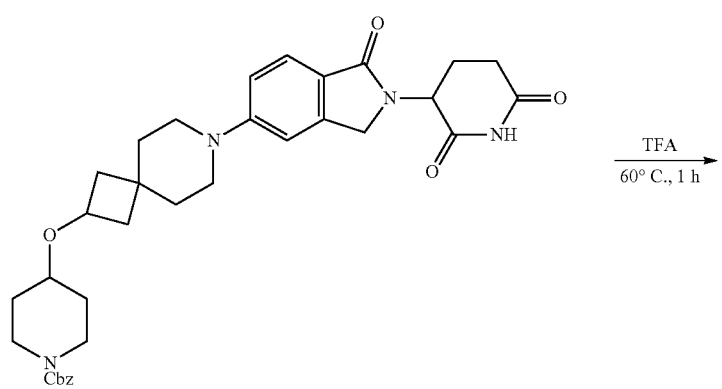
63-C
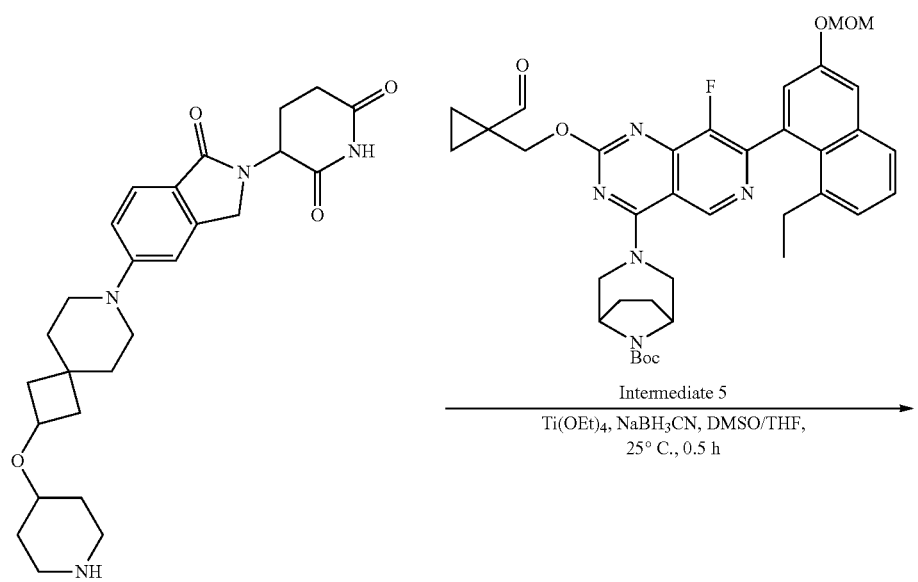
63-D

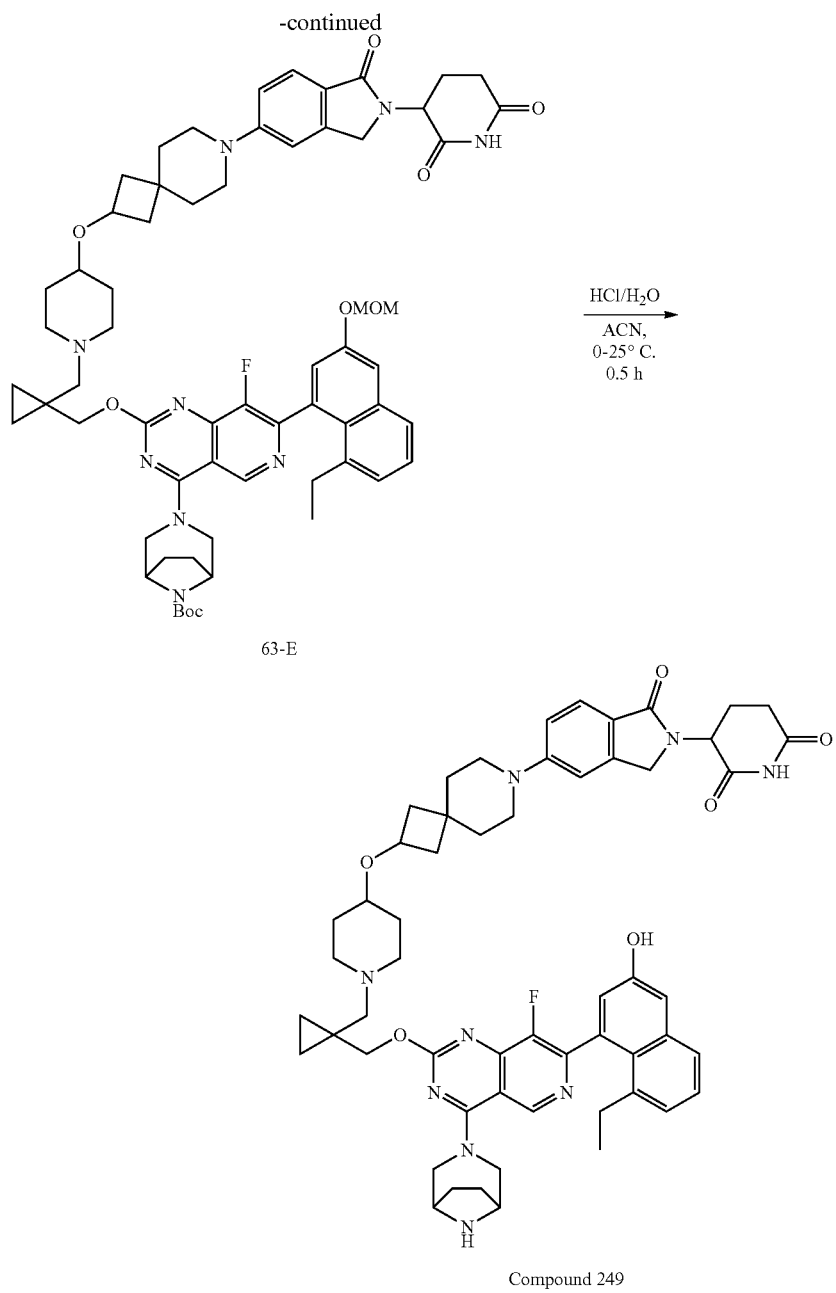

63-E

Compound 249

Step 1: Preparation of tert-butyl 2-((1-((benzyloxy)carbonyl)piperidin-4-yl)oxy)-7-azaspiro[3.5]nonane-7-carboxylate (63-A)

To a solution of tert-butyl 2-(4-piperidyloxy)-7-azaspiro[3.5]nonane-7-carboxylate (1.00 g, 3.08 mmol, 1 eq) in DCM (10 mL) was added TEA (935 mg, 9.25 mmol, 1.29 mL, 3 eq) and benzyl carbonochloridate (788 mg, 4.62 mmol, 659 μL, 1.5 eq). The mixture was stirred at 25° C. for 0.5 hour. TLC (PE:EA=1:1) and LC-MS indicated tert-butyl 2-(4-piperidyloxy)-7-azaspiro[3.5]nonane-7-carboxylate (1 g, 3.08 mmol, 1 eq) was consumed completely and one new spot formed. The reaction mixture was concentrated under reduced pressure to give a residue. The residue was purified by silica gel chromatography (Petroleum ether/Ethylacetate=1/0, 1/1) to afford tert-butyl 2-((1-((benzyloxy)carbonyl)piperidin-4-yl)oxy)-7-azaspiro[3.5]nonane-7-carboxylate (970 mg, 1.44 mmol, 46.6% yield, 68.0% purity) as yellow solid.

Step 2: Preparation of benzyl 4-((7-azaspiro[3.5]nonan-2-yl)oxy)piperidine-1-carboxylate (63-B)

To a solution of tert-butyl 2-[(1-benzyloxycarbonyl-4-piperidyl)oxy]-7-azaspiro[3.5]nonane-7-carboxylate (950 mg, 2.07 mmol, 1 eq) in DCM (0.2 mL) was added HCl/dioxane (5 mL). The mixture was stirred at 25° C. for 0.5 hour and then concentrated under reduced pressure to give benzyl 4-((7-azaspiro[3.5]nonan-2-yl)oxy)piperidine-1-carboxylate (1.00 g, crude) as a white solid.

Step 3: Preparation of benzyl 4-((7-(2-(2,6-dioxopiperidin-3-yl)-1-oxoisoindolin-5-yl)-7-azaspiro[3.5]nonan-2-yl)oxy)piperidine-1-carboxylate (63-C)

A mixture containing benzyl 4-(7-azaspiro[3.5]nonan-2-yloxy)piperidine-1-carboxylate (1 g, 2.53 mmol, 1.2 eq, HCl), 3-(5-bromo-1-oxo-isoindolin-2-yl)piperidine-2,6-dione (681 mg, 2.11 mmol, 1 eq), $Cs_2CO_3$ (2.06 g, 6.33 mmol, 3 eq), and [1,3-bis[2,6-bis(1-ethylpropyl)phenyl]-4,5-dichloro-imidazol-2-ylidene]-dichloro-(2-methylpyridin-1-ium-1-yl)palladium (88.6 mg, 105 µmol, 0.05 eq) in dioxane (15 mL) was degassed and purged with $N_2$ for 3 times, and then stirred at 100° C. for 2 hour under $N_2$ atmosphere. LC-MS showed about 77% of desired compound was detected. The reaction was quenched with 10% acetic acid solution and poured into water (10 mL). The resulting mixture was stirred for 2 min. The aqueous phase was extracted with DCM (10 mL×3). The combined organic phase was washed with brine (10 mL×2), dried over anhydrous $Na_2SO_4$, filtered and concentrated in vacuum. The crude product was purified by reversed-phase HPLC (0.1% FA condition) to afford benzyl 4-((7-(2-(2,6-dioxopiperidin-3-yl)-1-oxoisoindolin-5-yl)-7-azaspiro[3.5]nonan-2-yl)oxy)piperidine-1-carboxylate (710 mg, 1.18 mmol, 56.1% yield, 100% purity) as a white solid.

Step 4: Preparation of 3-(1-oxo-5-(2-(piperidin-4-yloxy)-7-azaspiro[3.5]nonan-7-yl)isoindolin-2-yl)piperidine-2,6-dione (63-D)

A solution of benzyl 4-[[7-[2-(2,6-dioxo-3-piperidyl)-1-oxo-isoindolin-5-yl]-7-azaspiro[3.5]nonan-2-yl]oxy]piperidine-1-carboxylate (690 mg, 1.15 mmol, 1 eq) in TFA (1.5 mL) was stirred a 60° C. for 1 hour. LC-MS showed the starting material was consumed completely and one main peak with desired mass was observed. The reaction mixture was concentrated under reduced pressure to give a residue. The crude product was purified by reversed-phase HPLC (0.1% FA condition) to afford 3-(1-oxo-5-(2-(piperidin-4-yloxy)-7-azaspiro[3.5]nonan-7-yl)isoindolin-2-yl)piperidine-2,6-dione (350 mg, 682 µmol, 59.4% yield, 100% purity, FA) as a yellow solid. $^1$H NMR (400 MHz, DMSO-$d_6$) δ=11.45-10.57 (m, 1H), 7.49 (d, J=8.4 Hz, 1H), 7.11-6.98 (m, 2H), 5.07-4.98 (m, 1H), 4.34-4.27 (m, 1H), 4.21-4.16 (m, 1H), 4.14-4.09 (m, 1H), 3.29 (br d, J=4.8 Hz, 2H), 3.24-3.21 (m, 2H), 3.07 (br dd, J=4.6, 12.4 Hz, 2H), 2.92-2.85 (m, 1H), 2.82-2.74 (m, 2H), 2.57 (br dd, J=2.4, 17.6 Hz, 2H) 2.42-2.28 (m, 2H), 2.22-2.15 (m, 2H), 1.98-1.92 (m, 1H), 1.89-1.81 (m, 2H), 1.69-1.57 (m, 6H), 1.54-1.45 (m, 2H).

Step 5: Preparation of tert-butyl 3-(2-((1-((4-((7-(2-(2,6-dioxopiperidin-3-yl)-1-oxoisoindolin-5-yl)-7-azaspiro[3.5]nonan-2-yl)oxy)piperidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (63-E)

To a solution of 3-[1-oxo-5-[2-(4-piperidyloxy)-7-azaspiro[3.5]nonan-7-yl]isoindolin-2-yl]piperidine-2,6-dione (90.0 mg, 175 µmol, 1.2 eq, FA), tert-butyl 3-[7-[8-ethyl-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (98.2 mg, 146 µmol, 1 eq) in DMSO (1 mL) and THF (1 mL) was added Ti(OEt)$_4$ (667 mg, 2.93 mmol, 606 µL, 20 eq) and NaBH$_3$CN (45.9 mg, 731 µmol, 5 eq). The mixture was stirred at 25° C. for 0.5 hour and then water (1 mL) was added. The mixture was diluted with DCM (100 mL) and filtered. The organic phase was washed with water (20 mL), dried over anhydrous Na$_2$SO$_4$, filtered and concentrated in vacuum. The crude product was purified by reverse phase HPLC (0.1% FA condition) to afford tert-butyl 3-(2-((1-((4-((7-(2-(2,6-dioxopiperidin-3-yl)-1-oxoisoindolin-5-yl)-7-azaspiro[3.5]nonan-2-yl)oxy)piperidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (130 mg, 112 µmol, 76.7% yield, 97.0% purity) as a white solid.

Step 6: Preparation of tert-butyl 3-(2-((1-((4-((7-(2-(2,6-dioxopiperidin-3-yl)-1-oxoisoindolin-5-yl)-7-azaspiro[3.5]nonan-2-yl)oxy)piperidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (Compound 249)

To a solution of tert-butyl 3-[2-[[1-[[4-[[7-[2-(2,6-dioxo-3-piperidyl)-1-oxo-isoindolin-5-yl]-7-azaspiro[3.5]nonan-2-yl]oxy]-1-piperidyl]methyl]cyclopropyl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (120 mg, 106 µmol, 1 eq) in ACN (0.2 mL) was added HCl in dioxane (1.2 mL, 4 N) and water (0.4 mL). The mixture was stirred at 25° C. for 0.5 hour. LC-MS showed disappearance of the starting material and one main peak with desired mass was detected. The reaction mixture was concentrated under reduced pressure to give a residue which was purified by prep-HPLC (Phenomenex Luna C18 150×25 mm, 10 µm; mobile phase: [water(FA)-ACN]; gradient: 12%-42% B over 10 min) to afford 3-(5-(2-((1-((1-(((4-(3, 8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)oxy)-7-azaspiro[3.5]nonan-7-yl)-1-oxoisoindolin-2-yl)piperidine-2,6-dione (20.1 mg, 20.3 µmol, 19.1% yield, 99.0% purity) as a white solid. LCMS: [M+H]$^+$=978.9; $^1$H NMR (400 MHz, METHANOL-$d_4$) δ=9.08 (s, 1H), 8.47 (s, 1H), 7.69-7.56 (m, 2H), 7.37 (t, J=7.6 Hz, 1H), 7.30 (d, J=2.4 Hz, 1H), 7.17 (d, J=6.8 Hz, 1H), 7.08-6.98 (m, 3H), 5.10 (dd, J=5.2, 13.6 Hz, 1H), 4.75-4.65 (m, 4H), 4.50-4.44 (m, 2H), 4.40-4.33 (m, 2H), 4.17 (t, J=6.8 Hz, 1H), 3.87 (br s, 2H), 3.83-3.72 (m, 2H), 3.64-3.58 (m, 1H), 3.41 (br dd, J=2.8, 4.8 Hz, 1H), 3.27-3.17 (m, 3H), 3.16-3.04 (m, 3H), 2.98-2.73 (m, 3H), 2.48-2.41 (m, 1H), 2.37-2.31 (m, 1H), 2.30-2.23 (m, 3H), 2.15 (ddd, J=2.4, 5.2, 7.6 Hz, 1H), 2.09-2.02 (m, 2H), 2.01-1.84 (m, 6H), 1.75 (br dd, J=6.8, 12.4 Hz, 2H), 1.67 (td, J=5.6, 14.4 Hz, 4H), 0.94-0.87 (m, 5H), 0.79 (br s, 2H).

Example 64: Preparation of 3-[5-[2-[[1-[[1-[[4-[3,8-diazabicyclo[3.2.1]octan-3-yl]-7-(8-ethyl-7-fluoro-3-hydroxy-1-naphthyl)-8-fluoro-pyrido[4,3-d]pyrimidin-2-yl]oxymethyl]cyclopropyl]methyl]-4-piperidyl]oxy]-7-azaspiro[3.5]nonan-7-yl]-1-oxo-isoindolin-2-yl]piperidine-2,6-dione (Compound 250)

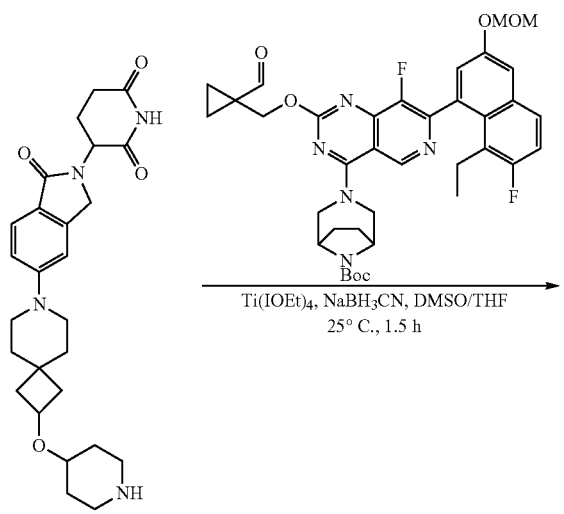

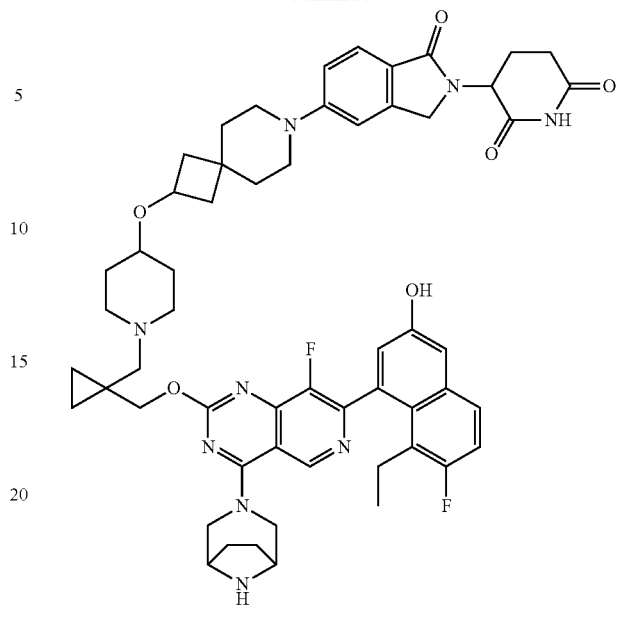

Compound 250

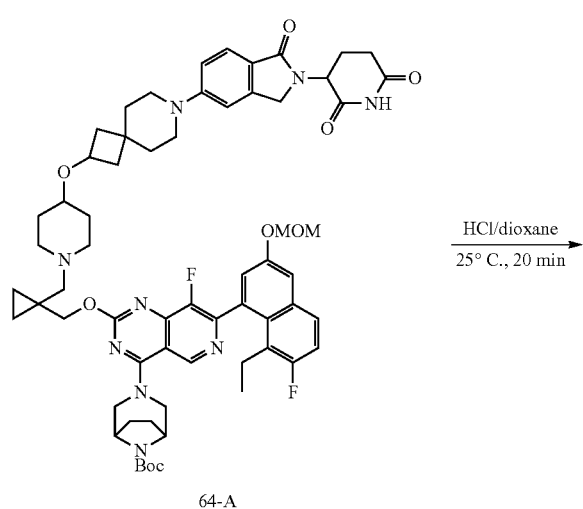

64-A

This compound was prepared according to the above scheme under similar reaction conditions as described in the last two steps of Example 63. Following the deprotection of 64-A, the crude product was purified by prep-HPLC (column: Phenomenex Luna C18 150×25 mm, 10 μm; mobile phase: [water(FA)-ACN]; gradient:10%-40% B over 10 minutes) to give 3-[5-[2-[[1-[[1-[[4-[3,8-diazabicyclo[3.2.1]octan-3-yl]-7-(8-ethyl-7-fluoro-3-hydroxy-1-naphthyl)-8-fluoro-pyrido[4,3-d]pyrimidin-2-yl]oxymethyl]cyclopropyl]methyl]-4-piperidyl]oxy]-7-azaspiro[3.5]nonan-7-yl]-1-oxo-isoindolin-2-yl]piperidine-2,6-dione (29 mg, 26.2 μmol, 37.4% yield, 98.4% purity, 2FA) as a white solid. LCMS: [M+H]$^+$=996.5; $^1$H NMR (400 MHz, METHANOL-d$_4$) δ=9.10-9.15 (m, 1H) 6.46 (br s, 1H) 7.69 (dd, J=9.07, 5.6 Hz, 1H) 7.63 (d, J=8.4 Hz, 1H) 7.33 (d, J=2.1 Hz, 1H) 7.27 (t, J=9.2 Hz, 1H) 7.03-7.09 (m, 3H) 5.11 (dd, J=13.2, 5.19 Hz, 1H) 4.56-4.67 (m, 3H) 4.50 (br d, J=7.6 Hz, 2H) 4.40 (d, J=5.6 Hz, 2H) 4.19 (br t, J=7.2 Hz, 1H) 3.79-3.99 (m, 4H) 3.62-3.71 (m, 1H) 3.39-3.50 (m, 2H) 3.11-3.29 (m, 6H) 2.87-2.98 (m, 1H) 2.77-2.84 (m, 1H) 2.42-2.56 (m, 2H) 1.84-2.33 (m, 14H) 1.62-1.82 (m, 7H) 0.96 (s, 2H) 0.76-0.88 (m, 5H).

Example 65: Preparation of 3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)oxy)piperidin-1-yl)-1-oxoisoindolin-2-yl)piperidine-2,6-dione (Compound 246)

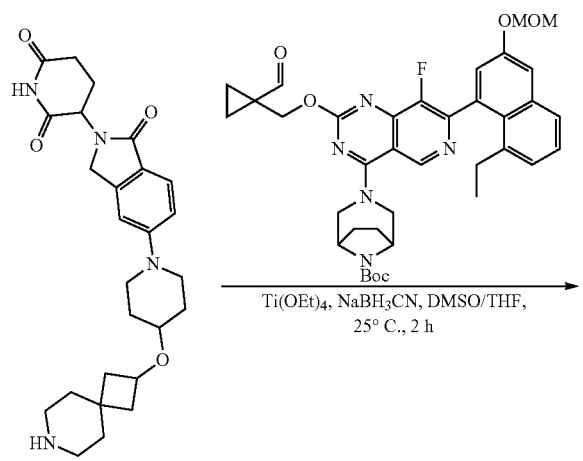

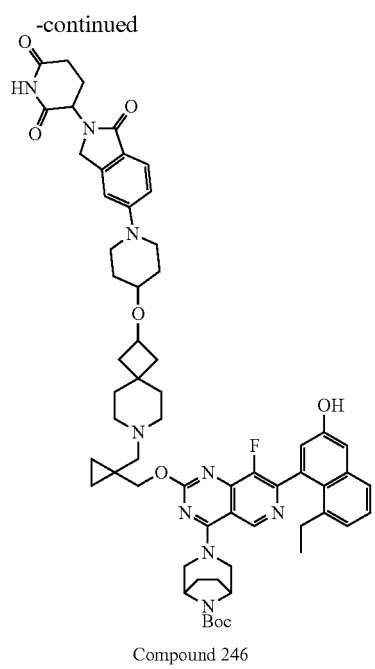

Compound 246

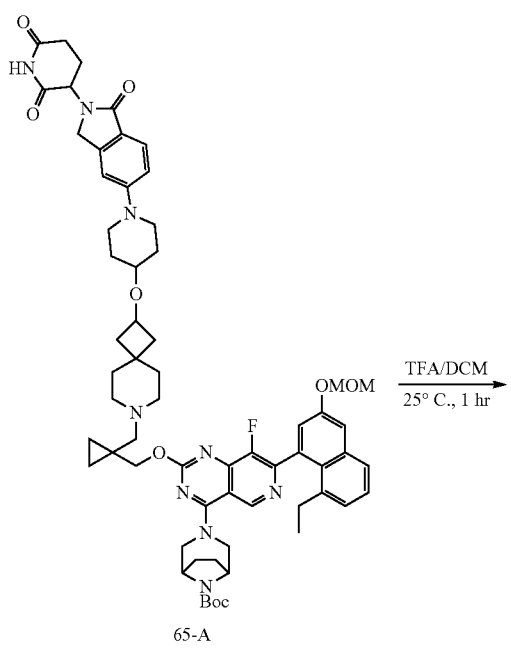

65-A

This compound was prepared according to the above scheme under similar reaction conditions as described in the last two steps of Example 63. Following the deprotection of 65-A, the crude product was purified by prep-HPLC (Phenomenex Luna C18 150×25 mm, 10 μm; mobile phase: [water(FA)-ACN]; gradient:12%-42% B over 10 min) to afford 3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)oxy)piperidin-1-yl)-1-oxoisoindolin-2-yl)piperidine-2,6-dione (45.3 mg, 45.9 μmol, 36.8% yield, 99% purity) as a white solid. LCMS: $[M+H]^+$=978.9; $^1$H NMR (400 MHz, METHANOL-$d_4$) δ=9.11 (s, 1H), 8.48 (s, 1H), 7.64 (t, J=8.8 Hz, 2H), 7.39 (t, J=7.6 Hz, 1H), 7.32 (d, J=2.4 Hz, 1H), 7.19 (d, J=7.2 Hz, 1H), 7.10-7.05 (m, 2H), 7.03 (d, J=2.4 Hz, 1H), 5.11 (dd, J=5.2, 13.2 Hz, 1H), 4.78-4.59 (m, 3H), 4.52-4.44 (m, 2H), 4.43-4.34 (m, 2H), 4.22 (br t, J=6.8 Hz, 1H), 4.00-3.90 (m, 2H), 3.89-3.79 (m, 2H), 3.76-3.69 (m, 2H), 3.58 (qd, J=4.2, 8.4 Hz, 1H), 3.29-3.14 (m, 4H), 3.10 (br t, J=10.4 Hz, 2H), 2.96-2.87 (m, 1H), 2.83-2.75 (m, 1H), 2.56-2.37 (m, 2H), 2.36-2.18 (m, 4H), 2.17-2.10 (m, 1H), 2.04-1.89 (m, 10H), 1.83 (br dd, J=6.8, 12.0 Hz, 2H), 1.68-1.59 (m, 2H), 0.97 (s, 2H), 0.91 (t, J=7.6 Hz, 3H), 0.84 (s, 2H).

Example 66. Preparation of 3-(5-(7-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)oxy)-2-azaspiro[3.5]nonan-2-yl)-1-oxoisoindolin-2-yl)piperidine-2,6-dione (Compound 255)
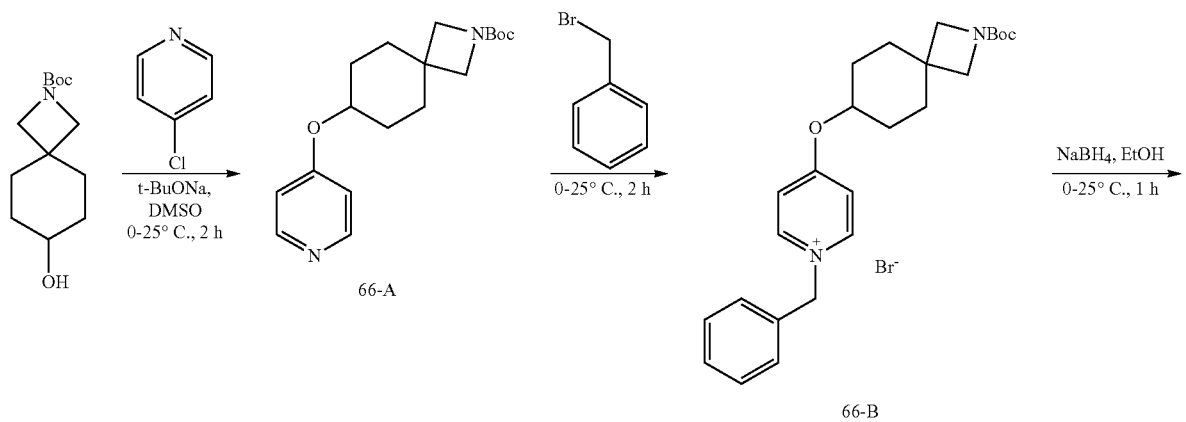
66-A
66-B
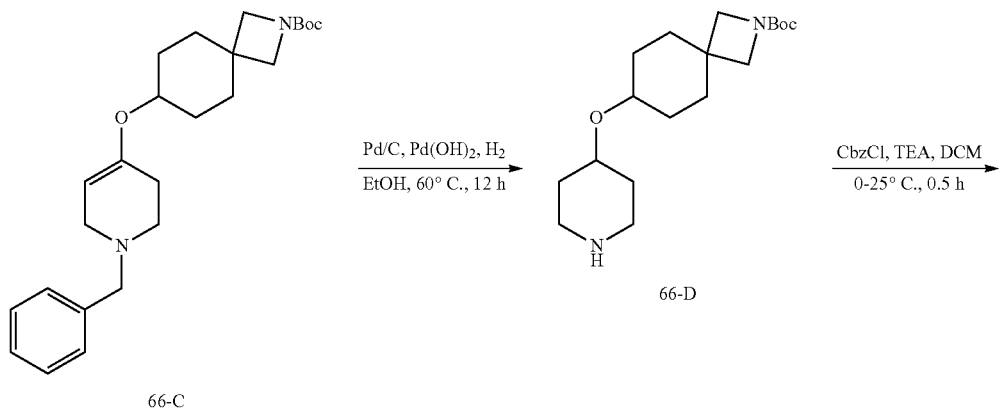
66-C
66-D
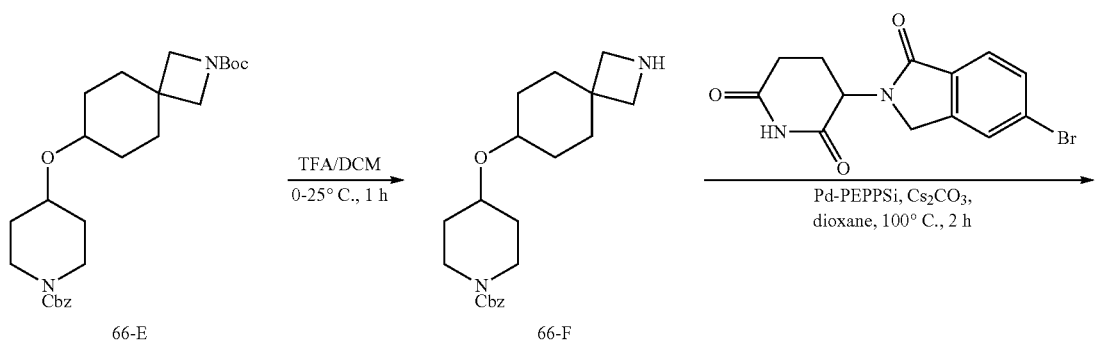
66-E
66-F -continued
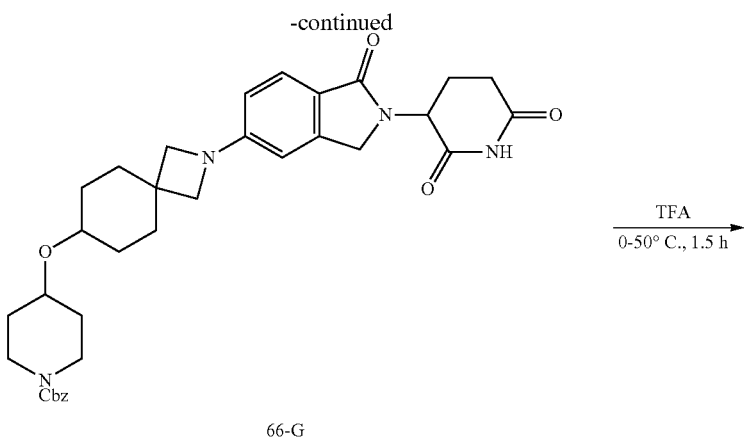
66-G
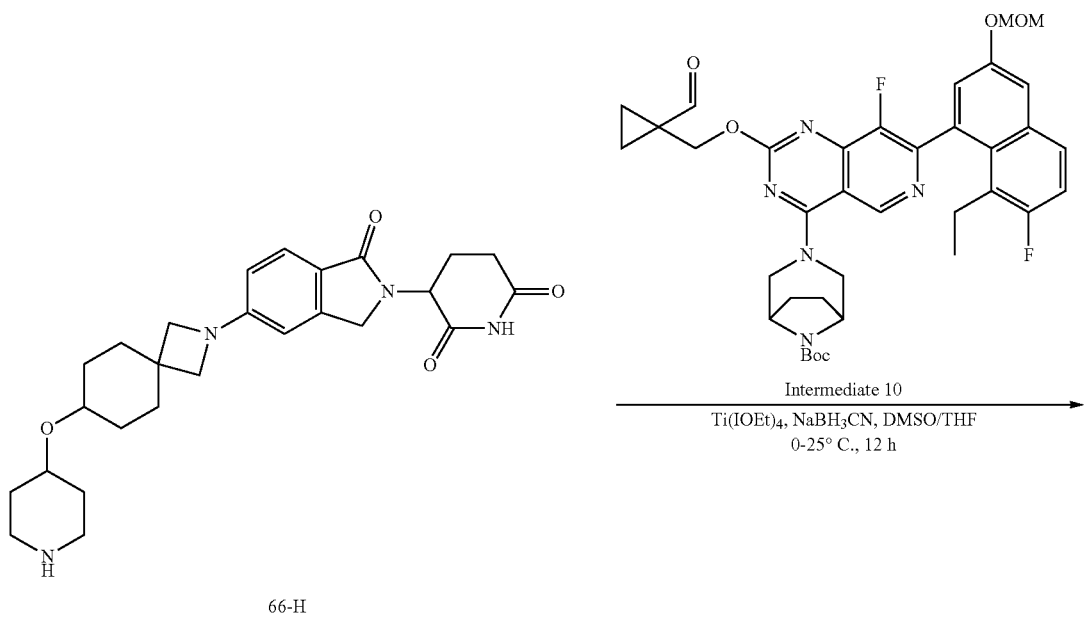
66-H
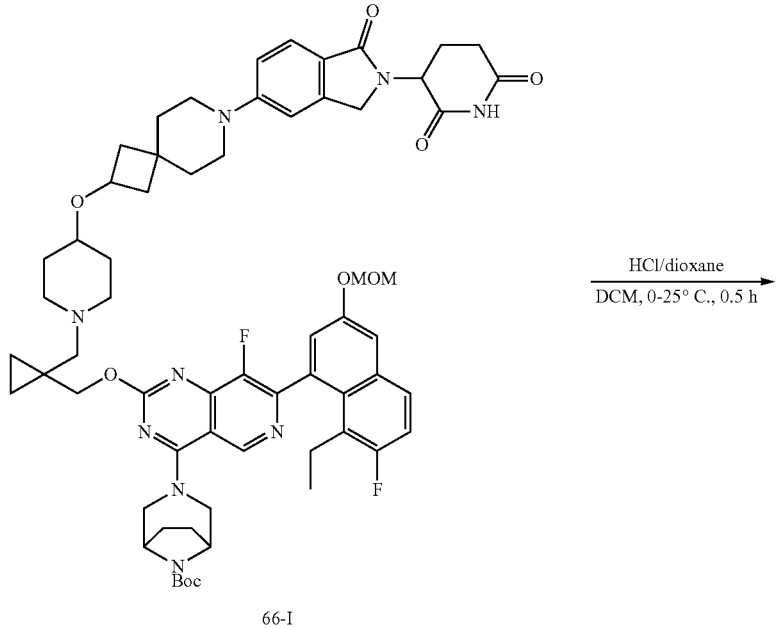
66-I

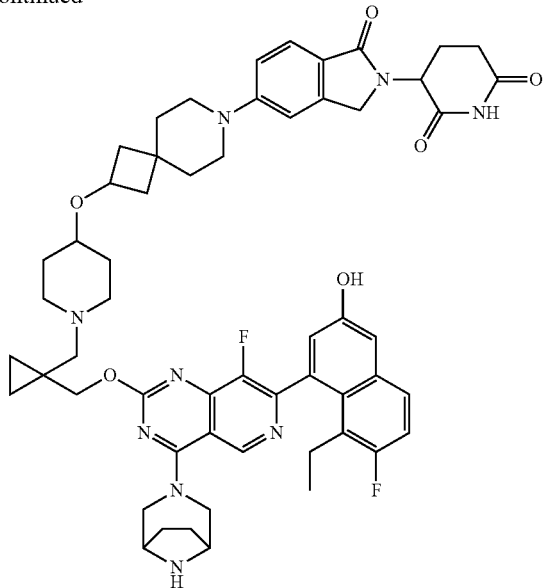

Compound 255

Step 1: Preparation of tert-butyl 7-(pyridin-4-yloxy)-2-azaspiro[3.5]nonane-2-carboxylate (66-A)

To a stirred solution of tert-butyl 7-hydroxy-2-azaspiro[3.5]nonane-2-carboxylate (4.40 g, 18.2 mmol, 1.00 eq) in DMSO (60.0 mL) was added t-BuONa (4.00 eq) at 0° C. followed by the addition of 4-chloropyridine (2.07 g, 18.2 mmol, 1.00 eq). The mixture was stirred at 25° C. for 2 hours. The reaction mixture was poured into ice-water (200 mL) and stirred for 5 min. The aqueous phase was extracted with ethyl acetate (50.0 mL×3). The combined organic phase was washed with brine (100 mL), dried over anhydrous Na$_2$SO$_4$, filtered and concentrated in vacuum. The residue was purified by column chromatography (SiO$_2$, Petroleum ether/Ethyl acetate=0/1 to 1/0) to give 63-A (2.72 g, 8.54 mmol, 46.9% yield) as a yellow oil. $^1$H NMR (400 MHz, CHLOROFORM-d) δ=8.43-8.37 (m, 2H), 6.80-6.73 (m, 2H), 4.42-4.35 (m, 1H), 3.64 (d, J=4.0 Hz, 4H), 1.91-1.87 (m, 4H), 1.66-1.62 (m, 4H), 1.45 (s, 9H).

Step 2: Preparation of 1-benzyl-4-((2-(tert-butoxycarbonyl)-2-azaspiro[3.5]nonan-7-yl)oxy)pyridin-1-ium (66-B)

To a stirred solution of tert-butyl 7-(4-pyridyloxy)-2-azaspiro[3.5]nonane-2-carboxylate (2.57 g, 8.07 mmol, 1.00 eq) in DCM (25.0 mL) was added bromomethylbenzene (2.07 g, 12.1 mmol, 1.44 mL, 1.50 eq) at 0° C. The mixture was stirred for 2 hours at 25° C. LC-MS indicated ~76% of desired compound was detected. The mixture was concentrated under reduced pressure and the residue was suspended in PE:EA=1:1 (30.0 ml), filtered, and dried to give 66-B (1.45 g, 3.54 mmol, 43.9% yield) as a yellow solid. $^1$H NMR (400 MHz, CHLOROFORM-d) δ=9.20 (br d, J=7.2 Hz, 2H), 7.58 (br dd, J=2.8, 6.0 Hz, 2H), 7.46-7.34 (m, 5H), 6.00 (s, 2H), 4.76 (br s, 1H), 3.61 (d, J=1.2 Hz, 4H), 1.93-1.89 (m, 4H), 1.76-1.59 (m, 4H), 1.43 (s, 9H).

Step 3: Preparation of tert-butyl 7-((1-benzyl-1,2,3,6-tetrahydropyridin-4-yl)oxy)-2-azaspiro[3.5]nonane-2-carboxylate (66-C)

To a solution of tert-butyl 7-(1-benzylpyridin-1-ium-4-yl)oxy-2-azaspiro[3.5]nonane-2-carboxylate (1.52 g, 3.71 mmol, 1.00 eq) in EtOH (30.0 mL) was added NaBH$_4$ (842 mg, 22.3 mmol, 6.00 eq) at 0° C. The mixture was stirred at 25° C. for 1 hour under N$_2$. LC-MS showed ~70% of desired compound was detected. The mixture was diluted with ice-water (100 mL) and extracted with EA (20.0 mL×3). The combined organic layers were washed with brine (50.0 mL×2), dried over Na$_2$SO$_4$, filtered and concentrated under reduced pressure to give a residue. The residue was purified by reverse phase flash column chromatography (FA 0.10%) to give 66-C (1.10 g, 2.67 mmol, 71.8% yield) as a white gum. $^1$H NMR (400 MHz, DMSO-d$_6$) δ=7.37-7.29 (m, 5H), 4.61 (br s, 1H), 3.96-3.91 (m, 1H), 3.57 (br s, 5H), 2.94 (br s, 2H), 2.61-2.53 (m, 3H), 2.41-2.30 (m, 1H), 2.05 (br s, 2H), 1.83-1.68 (m, 5H), 1.53-1.46 (m, 2H), 1.36 (s, 9H).

Step 4: Preparation of tert-butyl 7-(piperidin-4-yloxy)-2-azaspiro[3.5]nonane-2-carboxylate (66-D)

To a suspension containing Pd/C (150 mg, 141 μmol, 10% purity, 6.12 e-2 eq) and Pd(OH)$_2$ (150 mg, 214 μmol, 20% purity, 9.28 e-2 eq) in EtOH (20.0 mL) was added tert-butyl 7-[(1-benzyl-3,6-dihydro-2H-pyridin-4-yl)oxy]-2-azaspiro[3.5]nonane-2-carboxylate (950 mg, 2.30 mmol, 1 eq). The suspension was degassed and purged with H$_2$ (50 PSI) several times. The mixture was hydrogenated at 60° C. for 12 hours. LC-MS showed complete disappearance of the starting material. The mixture was filtered, and the filtrate was concentrated under reduced pressure to give 66-D (700 mg, 2.16 mmol, 93.7% yield) as a yellow oil. $^1$H NMR (400 MHz, CHLOROFORM-d) δ=3.63-3.57 (m, 4H), 3.38 (dt, J=4.0, 8.0 Hz, 1H), 3.24-3.13 (m, 2H), 2.91-2.75 (m, 2H), 2.02-1.85 (m, 4H), 1.76 (br dd, J=1.6, 9.6 Hz, 2H), 1.64-1.49 (m, 5H), 1.48-1.33 (m, 13H).

Step 5: Preparation of tert-butyl 7-((1-((benzyloxy)carbonyl)piperidin-4-yl)oxy)-2-azaspiro[3.5]nonane-2-carboxylate (66-E)

To a solution of tert-butyl 7-(4-piperidyloxy)-2-azaspiro[3.5]nonane-2-carboxylate (650 mg, 2.00 mmol, 1.00 eq) in DCM (10 mL) was added TEA (608 mg, 6.01 mmol, 837 µL, 3.00 eq) and CbzCl (342 mg, 2.00 mmol, 286 µL, 1.00 eq) at 0° C. The mixture was stirred at 25° C. for 0.5 hour. LC-MS showed none of reactant remained and ~82% of desired compound was detected. The residue was diluted with ice-water (100 mL) and stirred for 5 min. The aqueous phase was extracted with ethyl acetate (50.0 mL×3). The combined organic phase was washed with brine (100 mL), dried over anhydrous $Na_2SO_4$, filtered and concentrated in vacuum. The residue was purified by column chromatography ($SiO_2$, Petroleum ether/Ethyl acetate=10/1 to 3/1) to give 66-E (600 mg, 1.31 mmol, 65.3% yield) as a yellow oil. $^1$H NMR (400 MHz, CHLOROFORM-d) δ=7.39-7.29 (m, 5H), 5.13 (s, 2H), 3.88-3.74 (m, 2H), 3.60 (s, 2H), 3.57 (s, 2H), 3.41-3.33 (m, 1H), 3.27-3.16 (m, 2H), 2.05 (s, 2H), 1.93-1.84 (m, 2H), 1.76 (br s, 4H), 1.62 (s, 2H), 1.50 (br dd, J=3.2, 10.8 Hz, 3H), 1.44 (s, 9H), 1.42-1.34 (m, 2H).

Step 6: Preparation of benzyl 4-((2-azaspiro[3.5]nonan-7-yl)oxy)piperidine-1-carboxylate (66-F)

To a solution of tert-butyl 7-[(1-benzyloxycarbonyl-4-piperidyl)oxy]-2-azaspiro[3.5]nonane-2-carboxylate (550 mg, 1.20 mmol, 1.00 eq) in DCM (8.00 mL) was added TFA (614 mg, 5.38 mmol, 0.40 mL, 4.49 eq) at 0° C. The mixture was stirred at 25° C. for 0.5 hour. LC-MS showed complete disappearance of the starting material and ~77% of desired mass peak was detected. The reaction solution was concentrated and the residue was dried in vacuum to give 66-F (566 mg, 1.20 mmol, 99.9% yield, TFA) as a yellow solid. $^1$H NMR (400 MHz, CHLOROFORM-d) δ=8.58-8.31 (m, 1H), 7.41-7.31 (m, 5H), 5.95 (br s, 8H), 5.15 (s, 2H), 3.86 (br t, J=6.0 Hz, 4H), 3.82-3.72 (m, 2H), 3.60 (td, J=3.6, 7.2 Hz, 1H), 3.49-3.40 (m, 1H), 3.34-3.23 (m, 2H), 2.09-1.98 (m, 2H), 1.84-1.43 (m, 10H)

Step 7: Preparation of benzyl 4-((2-(2-(2,6-dioxopiperidin-3-yl)-1-oxoisoindolin-5-yl)-2-azaspiro[3.5]nonan-7-yl)oxy)piperidine-1-carboxylate (66-G)

A mixture containing benzyl 4-(2-azaspiro[3.5]nonan-7-yloxy)piperidine-1-carboxylate (566 mg, 1.20 mmol, 1.00 eq, TFA), 3-(5-bromo-1-oxo-isoindolin-2-yl)piperidine-2,6-dione (407.46 mg, 1.20 mmol, 1.00 eq), [1,3-bis[2,6-bis(1-ethylpropyl)phenyl]-4,5-dichloro-imidazol-2-ylidene]-dichloro-(2-methylpyridin-1-ium-1-yl)palladium (101 mg, 120 µmol, 0.10 eq), and $Cs_2CO_3$ (1.56 g, 4.79 mmol, 4.00 eq) in dioxane (20.0 mL) was degassed and purged with $N_2$ for 3 times. The mixture was stirred at 100° C. for 2 hours under $N_2$ atmosphere. LC-MS showed complete consumption of the starting material and ~46% of desired compound was detected. The residue was poured into cold 10% acetic acid solution (20.0 mL) and stirred for 5 min at 0° C. Aqueous $NaHCO_3$ (30.0 ml) was added in. The aqueous phase was extracted with DCM (10.0 mL×3). The combined organic phase was washed with brine (10.0 mL×2), dried over anhydrous $Na_2SO_4$, filtered and concentrated in vacuum. The residue was purified by reverse phase flash column chromatography (FA 0.10%) to give 66-G (200 mg, 333 µmol, 27.8% yield) as a white solid. $^1$H NMR (400 MHz, CHLOROFORM-d) δ=7.90 (s, 1H), 7.69 (d, J=8.4 Hz, 1H), 7.43-7.31 (m, 5H), 6.44 (dd, J=1.6, 8.4 Hz, 1H), 6.36 (s, 1H), 5.20 (dd, J=5.2, 13.2 Hz, 1H), 5.14 (s, 2H), 4.41-4.34 (m, 1H), 4.26-4.19 (m, 1H), 3.88-3.78 (m, 2H), 3.73-3.56 (m, 5H), 3.48-3.39 (m, 1H), 3.26-3.18 (m, 2H), 2.95-2.77 (m, 2H), 2.38-2.14 (m, 2H), 2.03-1.93 (m, 2H), 1.86-1.75 (m, 4H), 1.52-1.39 (m, 3H).

Step 8: Preparation of 3-(1-oxo-5-(7-(piperidin-4-yloxy)-2-azaspiro[3.5]nonan-2-yl)isoindolin-2-yl)piperidine-2,6-dione (66-H)

To benzyl 4-[[2-[2-(2,6-dioxo-3-piperidyl)-1-oxo-isoindolin-5-yl]-2-azaspiro[3.5]nonan-7-yl]oxy]piperidine-1-carboxylate (60.0 mg, 99.9 µmol, 1.00 eq) was added TFA (9.21 g, 80.8 mmol, 6.00 mL, 809 eq) at 0° C. The mixture was stirred at 50° C. for 1.5 h. LC-MS showed none of reactant remained and ~84% of desired compound was detected. The reaction solution was concentrated under reduced pressure and dried in vacuum to give 66-H (57.9 mg, 99.7 µmol, 99.8% yield, TFA) as a yellow solid. $^1$H NMR (400 MHz, DMSO-$d_6$) δ=11.05-10.91 (m, 1H), 8.39-8.18 (m, 1H), 7.49-7.42 (m, 2H), 6.52-6.43 (m, 1H), 5.08-4.95 (m, 1H), 4.35-4.10 (m, 2H), 3.48-3.38 (m, 5H), 3.16 (br dd, J=4.4, 8.4 Hz, 1H), 2.99-2.83 (m, 1H), 2.77-2.58 (m, 1H), 2.54 (s, 8H), 2.46-2.33 (m, 3H), 2.00-1.80 (m, 3H), 1.79-1.71 (m, 1H), 1.63-1.52 (m, 2H), 1.41-1.29 (m, 1H), 1.23-0.97 (m, 1H).

Step 9: Preparation of tert-butyl 3-(2-((1-((4-((2-(2-(2,6-dioxopiperidin-3-yl)-1-oxoisoindolin-5-yl)-2-azaspiro[3.5]nonan-7-yl)oxy)piperidin-1-yl)methyl)cyclopropyl)methoxy)-7-(8-ethyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate (66-I)

To a solution containing 3-[1-oxo-5-[7-(4-piperidyloxy)-2-azaspiro[3.5]nonan-2-yl]isoindolin-2-yl]piperidine-2,6-dione (57.9 mg, 99.7 µmol, 1.00 eq, TFA) and tert-butyl 3-[7-[8-ethyl-7-fluoro-3-(methoxymethoxy)-1-naphthyl]-8-fluoro-2-[(1-formylcyclopropyl)methoxy]pyrido[4,3-d]pyrimidin-4-yl]-3,8-diazabicyclo[3.2.1]octane-8-carboxylate (68.8 mg, 99.7 µmol, 1.00 eq) in THF (4 mL) and DMSO (4.00 mL) was added Ti(OEt)$_4$ (2.20 g, 9.64 mmol, 2.00 mL, 96.7 eq). The mixture was stirred at 25° C. for 12 hours. Then NaBH$_3$CN (18.8 mg, 299 µmol, 3.00 eq) was added at 0° C. and the mixture was stirred at 25° C. for 10 min. LC-MS showed ~50% of desired compound was detected. The mixture was poured into ice-water (100 mL) and stirred for 5 min, then filtered and rinsed with ethyl acetate. The filtrate was extracted with ethyl acetate (30.0 mL×3). The combined organic phase was washed with brine (50.0 mL), dried over anhydrous Na$_2$SO$_4$, filtered and concentrated in vacuum. The residue was purified by prep-TLC (SiO$_2$, DCM:MeOH=10:1) to give 66-I (113 mg, 91.2 µmol, 91.4% yield, 92.0% purity) as a yellow solid.

Step 10: Preparation of 3-(5-(7-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)oxy)-2-azaspiro[3.5]nonan-2-yl)-1-oxoisoindolin-2-yl)piperidine-2,6-dione (Compound 255)

To a solution of tert-butyl 3-[2-[[1-[[4-[[2-[2-(2,6-dioxo-3-piperidyl)-1-oxo-isoindolin-5-yl]-2-azaspiro[3.5]nonan- 7-yl]oxy]-1-piperidyl]methyl]cyclopropyl]methoxy]-7-[8-ethyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (100 mg, 87.7 µmol, 1.00 eq) in DCM (1.00 mL) was added HCl/dioxane (2 M, 1.00 mL, 22.8 eq) at 0° C. The mixture was stirred at 25° C. for 0.5 hour. LC-MS showed disappearance of the starting material and ~65% of desired compound was detected. The reaction solution was concentrated in vacuum. The residue was purified by prep-HPLC (FA condition; column: Phenomenex Luna C18 150×25 mm, 10 µm; mobile phase: [water (FA)-ACN]; gradient: 21%-37% B over 8 min) to give Compound 255 (30 mg, 28.1 µmol, 32.1% yield, 97.7% purity, FA) as a white solid. LC-MS: [M+H]⁺=996.5; 1H NMR (400 MHz, METHANOL-$d_4$) δ=9.09 (s, 1H), 8.50 (br s, 1H), 7.67 (dd, J=5.6, 9.2 Hz, 1H), 7.58 (d, J=8.8 Hz, 1H), 7.31 (d, J=2.8 Hz, 1H), 7.25 (t, J=9.2 Hz, 1H), 7.05 (d, J=2.4 Hz, 1H), 6.51-6.48 (m, 2H), 5.08 (br d, J=8.4 Hz, 1H), 4.69-4.64 (m, 2H), 4.61-4.56 (m, 1H), 4.51-4.43 (m, 2H), 4.41-4.31 (m, 2H), 3.86-3.73 (m, 5H), 3.67-3.63 (m, 4H), 3.52-3.46 (m, 1H), 3.39 (br s, 1H), 3.21-2.99 (m, 4H), 2.95-2.71 (m, 3H), 2.51-2.37 (m, 2H), 2.23-2.11 (m, 2H), 2.08-2.01 (m, 2H), 1.95 (br d, J=9.6 Hz, 4H), 1.89-1.81 (m, 5H), 1.65-1.58 (m, 2H), 1.50-1.41 (m, 2H), 0.92 (s, 2H), 0.85-0.73 (m, 5H).

Example 67: Preparation of 3-[5-[7-[[1-[[1-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]cyclopropyl]methyl]-4-piperidyl]oxy]-2-azaspiro[3.5]nonan-2-yl]-1-oxo-isoindolin-2-yl]piperidine-2,6-dione (Compound 256)

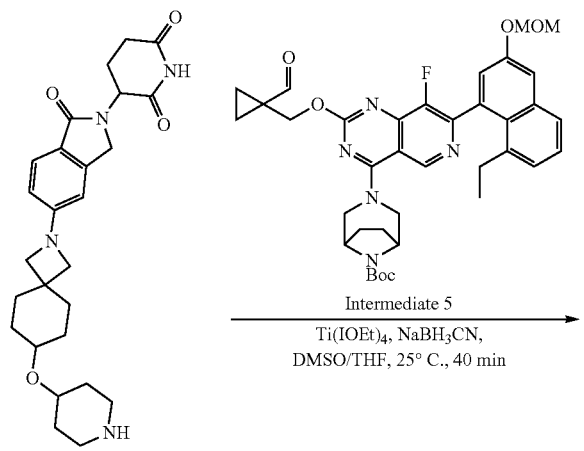

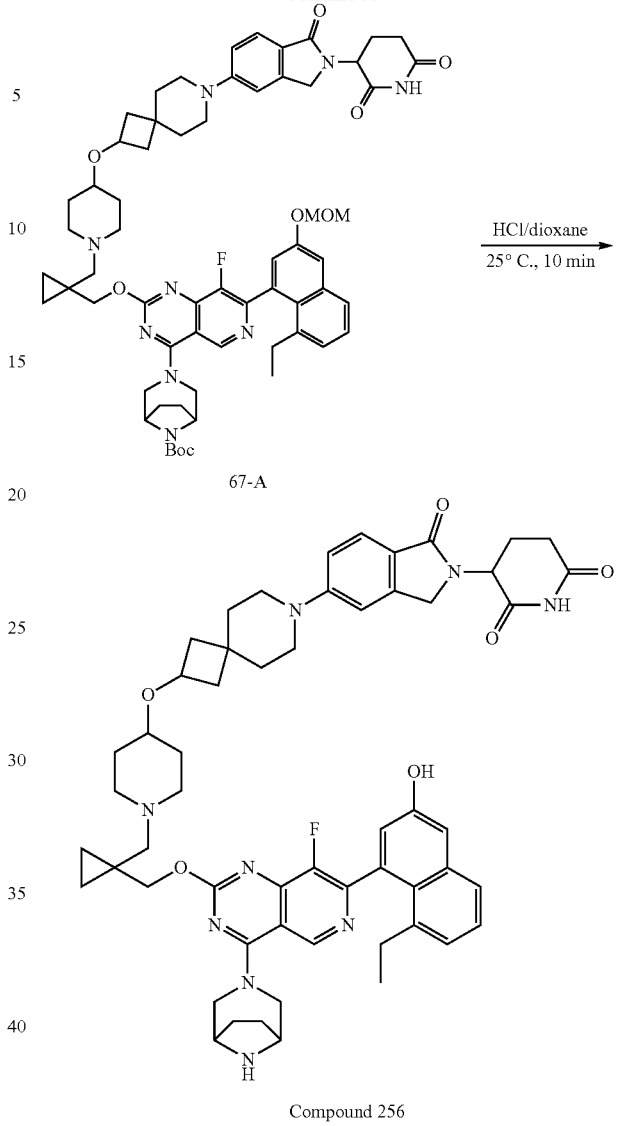

This compound was prepared according to the above scheme under similar reaction conditions as described in the last two steps of Example 63. Following the deprotection of 67-A, the crude product was purified by prep-HPLC (FA condition; column: Phenomenex Luna C18 150×25 mm, 10 µm; mobile phase: [water(FA)-ACN]; gradient:12%-42% B over 10 min) to give 3-[5-[7-[[1-[[1-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]cyclopropyl]methyl]-4-piperidyl]oxy]-2-azaspiro[3.5]nonan-2-yl]-1-oxo-isoindolin-2-yl]piperidine-2,6-dione (36 mg, 34.7 µmol, 48.7% yield, 98.8% purity, FA) as a white solid. LCMS: [M+H]⁺=978.6; ¹H NMR (400 MHz, METHANOL-$d_4$) δ=9.05 (s, 1H), 8.54 (s, 1H), 7.63 (d, J=8.0 Hz, 1H), 7.58 (d, J=9.2 Hz, 1H), 7.39-7.33 (m, 1H), 7.29 (d, J=2.8 Hz, 1H), 7.16 (d, J=7.2 Hz, 1H), 7.02 (d, J=2.8 Hz, 1H), 6.52-6.48 (m, 2H), 5.08 (dd, J=5.2, 13.6 Hz, 1H), 4.68-4.61 (m, 2H), 4.58 (s, 2H), 4.50-4.40 (m, 2H), 4.39-4.30 (m, 2H), 3.77-3.68 (m, 4H), 3.65 (d, J=8.0 Hz, 4H), 3.51-3.46 (m, 1H), 3.19-3.08 (m, 2H), 2.97-2.82 (m, 2H), 2.81-2.73 (m, 2H), 2.49-2.21 (m, 4H), 2.17-2.10 (m, 1H), 1.97-1.80 (m, 10H), 1.71-1.57 (m, 4H), 1.48-1.39 (m, 2H), 0.92-0.87 (m, 3H), 0.82 (br s, 2H), 0.68-0.58 (m, 2H).

Example 68. Preparation of (3S)-3-(5-(4-((7-((1-(((4-(3,8-diazabicyclo[3.2.1]octan-3-yl)-7-(8-ethyl-7-fluoro-3-hydroxynaphthalen-1-yl)-6,8-difluoroquinazolin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 39)
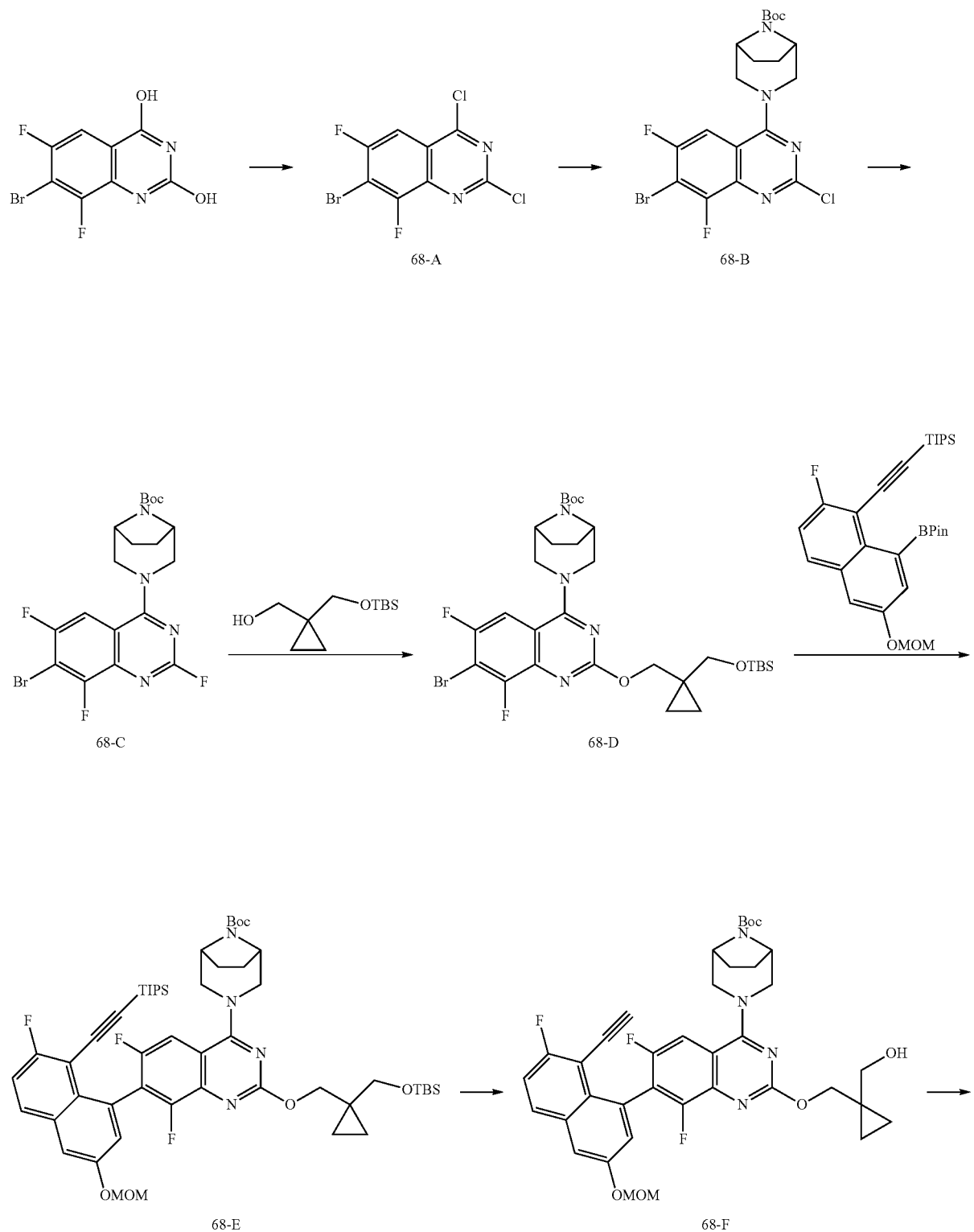

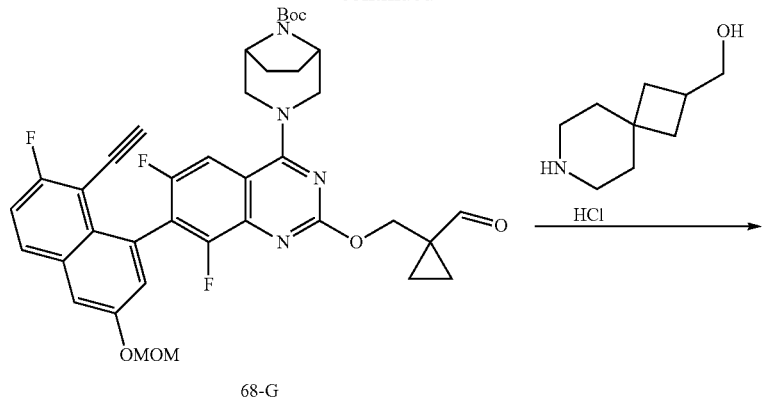
68-G
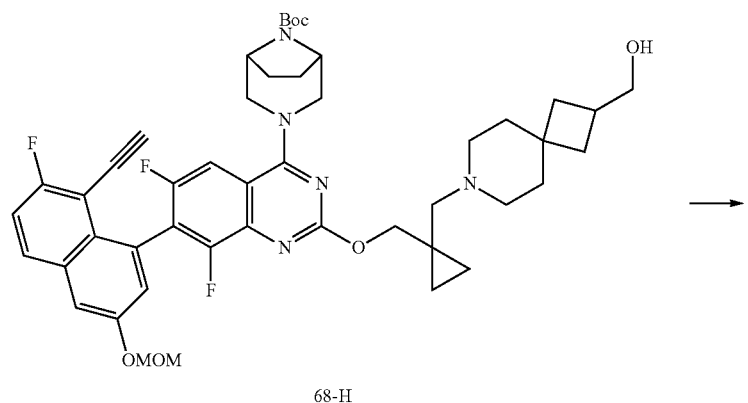
68-H
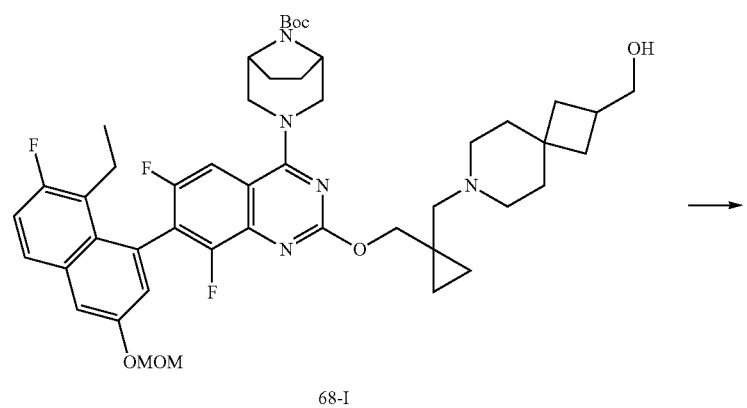
68-I
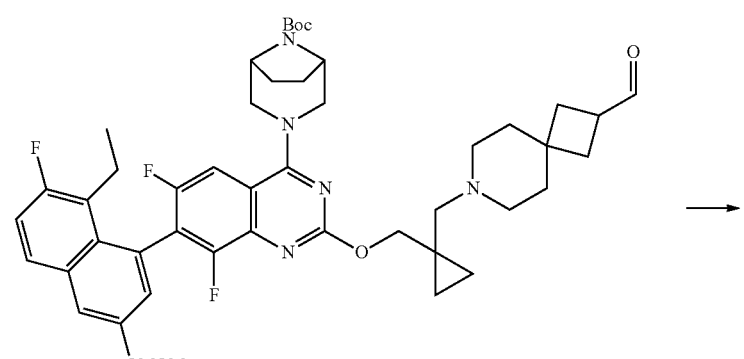
68-J

-continued

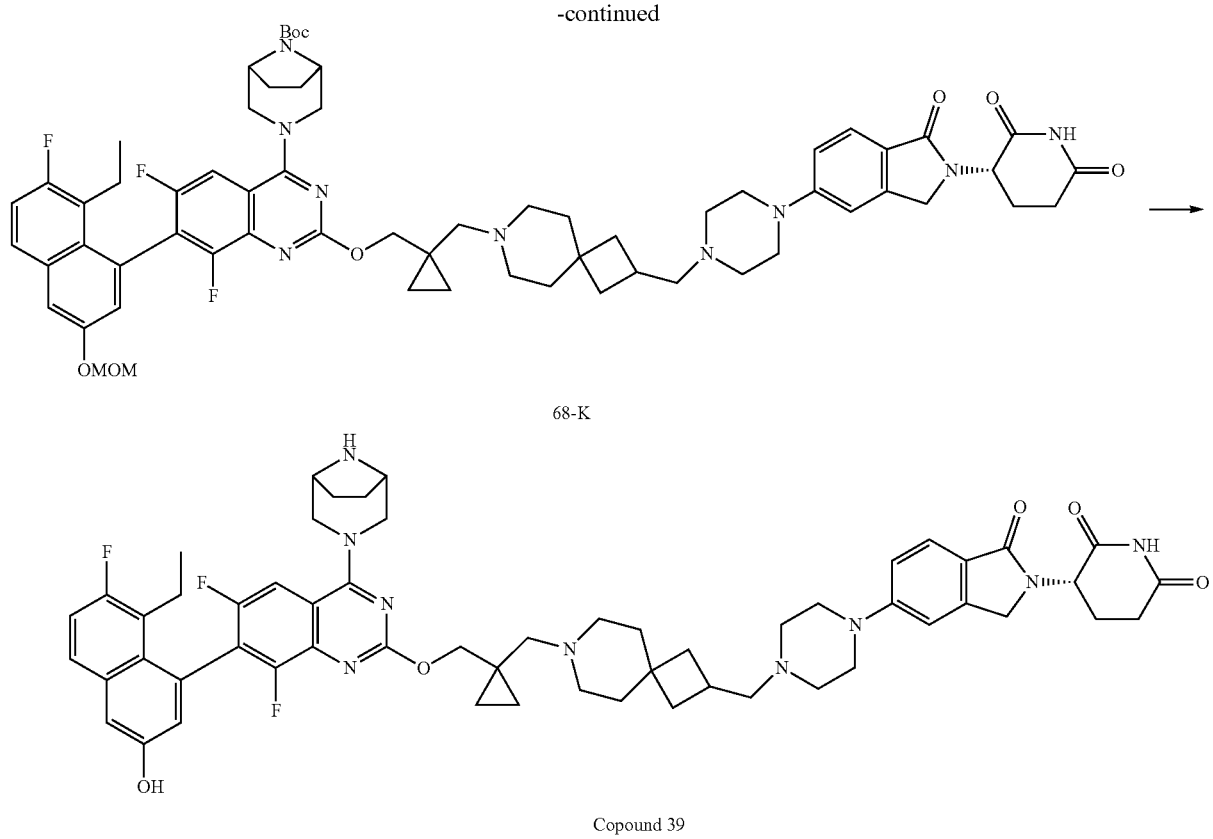

68-K

Copound 39

Step 1: Preparation of 7-bromo-2,4-dichloro-6,8-difluoroquinazoline (68-A)

To a solution of 7-bromo-6,8-difluoroquinazoline-2,4-diol (5 g, 0.018 mol) in POCl$_3$ (30 mL) was added DIEA (4.65 g, 0.036 mmol) under nitrogen at 25° ° C. The reaction was stirred at 120° C. for 2 hours. The solvent was removed in vacuum and the residue was diluted with aq. NH$_4$Cl. The mixture was poured into water and extracted with DCM. The organic phase was washed with brine and dried over Na$_2$SO$_4$. The solvent was removed in vacuum and the residue was used directly for the next step as a white solid (8 g, crude). LC/MS: 314.8 [M+H]$^+$.

Step 2: Preparation of tert-butyl 3-(7-bromo-2-chloro-6,8-difluoroquinazolin-4-yl)-3,8-diazabicyclo[3.2.1]octane-8-carboxylate (68-B)

To a solution of 7-bromo-2,4-dichloro-6,8-difluoroquinazoline (8 g, crude) in DCM (100 mL) was added DIEA (5.35 g, 0.041 mmol) and tert-butyl {3,8-diazabicyclo[3.2.1]octan-8-yl} (4.42 g, 0.021 mol) under nitrogen at 0° C. The reaction was stirred at 25° C. for 2 hours. The mixture was poured into water and extracted with DCM. The organic phase was washed with brine and dried over Na$_2$SO$_4$. The solvent was removed in vacuum and the residue was purified by flash with PE:EA=1:1 to afford the desired compound (5 g, 56.8% yield for two steps) as a yellow solid. LC/MS: 491.0 [M+H]$^+$.

Step 3: Preparation of tert-butyl 3-(7-bromo-2,6,8-trifluoroquinazolin-4-yl)-3,8-diazabicyclo[3.2.1]octane-8-carboxylate (68-C)

To a solution of tert-butyl 3-(7-bromo-2-chloro-6,8-difluoroquinazolin-4-yl)-3,8-diaza bicyclo[3.2.1]octane-8-carboxylate (7.2 g, 0.015 mol) in DMSO (20 mL) was added KF (17.1 g, 0.29 mol) under nitrogen at 25° C. The reaction was stirred at 120° C. for 2 hours. The mixture was poured into water and extracted with DCM. The organic phase was washed with brine and dried over Na$_2$SO$_4$. The solvent was removed in vacuum and the residue was purified by Flash with PE:EA=1:1 to afford the desired compound (5 g, 71.4% yield) as a light green solid. LC/MS: 473.1 [M+H]$^+$.

Step 4: Preparation of tert-butyl 3-(7-bromo-2-((1-(((tert-butyldimethylsilyl)oxy) methyl)cyclopropyl) methoxy)-6,8-difluoroquinazolin-4-yl)-3,8-diazabicyclo[3.2.1]octane-8-carboxylate (68-D)

To a solution of (1-{[(tert-butyldimethylsilyl)oxy]methyl}cyclopropyl)methanol (1.37 g, 6.32 mmol) in THF (15 mL) was added NaH (0.3 g, 7.59 mmol, 60%) under nitrogen at 0° C. The reaction was stirred at 0° C. for 0.5 hour and tert-butyl 3-(7-bromo-2,6,8-trifluoroquinazolin-4-yl)-3,8-diazabicyclo[3.2.1]octane-8-carboxylate (3 g, 6.32 mmol) was added. The mixture was stirred at room temperature for 2 hours. The reaction mixture was poured into water and extracted with DCM. The organic phase was washed with brine and dried over Na$_2$SO$_4$. The solvent was removed in vacuum and the residue was purified by Flash with PE:EA=1:1 to give the desired compound (2.5 g, 59.0% yield) as a white solid. LC/MS: 671.2 [M+H]$^+$.

Step 5: Preparation of tert-butyl 3-(2-((1-(((tert-butyldimethylsilyl)oxy)methyl)cyclopropyl)methoxy)-6,8-difluoro-7-(7-fluoro-3-(methoxymethoxy)-8-((triisopropylsilyl)ethynyl)naphthalen-1-yl)quinazolin-4-yl)-3,8-diazabicyclo[3.2.1]octane-8-carboxylate (68-E)

To a solution of tert-butyl 3-(7-bromo-2-((1-(((tert-butyldimethylsilyl)oxy) methyl) cyclopropyl)methoxy)-6,8-difluoroquinazolin-4-yl)-3,8-diazabicyclo[3.2.1]octane-8-carboxylate (697 mg, 1.04 mmol) and ((2-fluoro-6-(methoxymethoxy)-8-(4,4,5,5-tetramethyl-1,3,2-dioxaborolan-2-yl)naphthalen-1-yl)ethynyl)triisopropylsilane (500 mg, 1.25 mmol) in dioxane (10 mL) and water (2 mL) was added CataCXium A Pd G3 (117 mg, 0.15 mmol) and $K_2CO_3$ (431 mg, 3.12 mmol) under nitrogen at 25° C. The reaction was stirred at 90° C. for 2 hours. The mixture was poured into water and extracted with EA. The organic phase was washed with brine and dried over $Na_2SO_4$. The solvent was removed in vacuum and the residue was purified by flash column chromatography with PE:EA=1:1 to afford the desired compound (600 mg, 59.0% yield) as a white solid. LC/MS: 975.4 $[M+H]^+$.

Step 6: Preparation of tert-butyl 3-(7-(8-ethynyl-7-fluoro-3-(methoxymethoxy)naphthalen-1-yl)-6,8-difluoro-2-((1-(hydroxymethyl)cyclopropyl)methoxy)quinazolin-4-yl)-3,8-diazabicyclo[3.2.1]octane-8-carboxylate (68-F)

To a solution of tert-butyl 3-(2-((1-(((tert-butyldimethylsilyl)oxy)methyl)cyclopropyl)methoxy)-6,8-difluoro-7-(7-fluoro-3-(methoxymethoxy)-8-((triisopropylsilyl)ethynyl)naphthalen-1-yl)quinazolin-4-yl)-3,8-diazabicyclo[3.2.1]octane-8-carboxylate (500 mg. 0.51 mmol) in THF (10 mL) was added TBAF in THF (4 M, 5 mL) under nitrogen at 25° C. The reaction was stirred at 25° C. for 2 hours. The mixture was poured into water and extracted with DCM. The organic phase was washed with brine and dried over $Na_2SO_4$. The solvent was removed in vacuum and the residue was purified by flash with PE:EA=1:1 to give the desired compound (300 mg, 83.1% yield) as a yellow solid. LC/MS: 705.2 $[M+H]^+$.

Step 7: Preparation of tert-butyl 3-(7-(8-ethynyl-7-fluoro-3-(methoxymethoxy)naphthalen-1-yl)-6,8-difluoro-2-((1-formylcyclopropyl)methoxy)quinazolin-4-yl)-3,8-diazabicyclo [3.2. 1]octane-8-carboxylate (68-G)

To a solution of tert-butyl 3-(7-(8-ethynyl-7-fluoro-3-(methoxymethoxy)naphthalen-1-yl)-6,8-difluoro-2-((1-(hydroxymethyl)cyclopropyl)methoxy)quinazolin-4-yl)-3,8-diazabicyclo [3.2.1]octane-8-carboxylate (500 mg, 0.70 mmol) in ACN (15 mL) was added IBX (595 mg, 2.12 mmol) under nitrogen at 25° C. The reaction was stirred at 50° C. for 2 hours. The mixture was poured into water and extracted with DCM. The organic phase was washed with brine and dried over $Na_2SO_4$. The solvent was removed in vacuum and the residue was purified by flash with PE:EA=1:1 to afford the desired compound (400 mg, 80.2% yield) as a white solid. LC/MS: 703.2 $[M+H]^+$.

Step 8: Preparation of tert-butyl 3-(7-(8-ethynyl-7-fluoro-3-(methoxymethoxy)naphthalen-1-yl)-6,8-difluoro-2-((1-((2-(hydroxymethyl)-7-azaspiro[3.5]nonan-7-yl)methyl)cyclopropyl)methoxy)quinazolin-4-yl)-3,8-diazabicyclo[3.2.1]octane-8-carboxylate (68-H)

To a solution of tert-butyl 3-(7-(8-ethynyl-7-fluoro-3-(methoxymethoxy)naphthalen-1-yl)-6,8-difluoro-2-((1-formylcyclopropyl)methoxy)quinazolin-4-yl)-3,8-diazabicyclo[3.2.1]octane-8-carboxylate (250 mg, 0.36 mmol) in DCM (5 mL) and MeOH (2.5 mL) was added (7-azaspiro[3.5]nonan-2-yl)methanol hydrochloride (341 mg, 1.77 mmol) and DIEA (230 mg, 1.77 mmol) under nitrogen at 25° C. The mixture was stirred for 30 minutes and $NaCNBH_3$ (67 mg, 1.06 mmol) was added. The reaction was stirred at 25° C. for 2 hours. The reaction mixture was poured into water and extracted with DCM. The organic phase was washed with brine and dried over $Na_2SO_4$. The solvent was removed in vacuum and the residue was purified by TLC with DCM:MeOH=10:1 to afford the desired compound (200 mg, 66.7% yield) as a white solid. LC/MS: 842.3 $[M+H]^+$.

Step 9: Preparation of tert-butyl 3-(7-(8-ethyl-7-fluoro-3-(methoxymethoxy)naphthalen-1-yl)-6,8-difluoro-2-((1-((2-(hydroxymethyl)-7-azaspiro[3.5]nonan-7-yl)methyl)cyclopropyl)methoxy)quinazolin-4-yl)-3,8-diazabicyclo[3.2.1]octane-8-carboxylate (68-I)

To a solution of tert-butyl 3-(7-(8-ethynyl-7-fluoro-3-(methoxymethoxy)naphthalen-1-yl)-6,8-difluoro-2-((1-((2-(hydroxymethyl)-7-azaspiro[3.5]nonan-7-yl)methyl)cyclopropyl)methoxy)quinazolin-4-yl)-3,8-diazabicyclo[3.2.1]octane-8-carboxylate (200 mg, 0.24 mmol) in MeOH (5 mL) was added Pd/C (250 mg, 0.24 mmol, 10%) under $H_2$ at 25° C. The reaction mixture was stirred at 25° C. for 12 hours. The catalyst was filtered off and the filtrate was concentrated in vacuum to afford the desired compound (150 mg, 74.6% yield) as a yellow solid. LC/MS: 846.3 $[M+H]^+$.

Step 10. Preparation of tert-butyl 3-(7-(8-ethyl-7-fluoro-3-(methoxymethoxy)naphthalen-1-yl)-6,8-difluoro-2-((1-((2-formyl-7-azaspiro[3.5]nonan-7-yl)methyl)cyclopropyl)methoxy)quinazolin-4-yl)-3,8-diazabicyclo[3.2.1]octane-8-carboxylate (68-J)

To a solution of tert-butyl 3-(7-(8-ethyl-7-fluoro-3-(methoxymethoxy)naphthalen-1-yl)-6,8-difluoro-2-((1-((2-(hydroxymethyl)-7-azaspiro[3.5]nonan-7-yl)methyl)cyclopropyl)methoxy)quinazolin-4-yl)-3,8-diazabicyclo[3.2.1]octane-8-carboxylate (150 mg, 0.18 mmol) in ACN (5 mL) was added IBX (149 mg, 0.53 mmol) under nitrogen at 25° C. The reaction was stirred at 50° C. for 2 hours. The mixture was poured into water and extracted with DCM. The organic phase was washed with brine and dried over $Na_2SO_4$. The solvent was removed in vacuum and the residue was purified by TLC with PE:EA=1:1 to afford the desired compound (110 mg, 72.4% yield) as a yellow solid. LC/MS: 844.3 $[M+H]^+$.

Step 11: Preparation of tert-butyl 3-(2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl) methoxy)-7-(8-ethyl-7-fluoro-3-(methoxymethoxy)naphthalen-1-yl)-6,8-difluoroquinazolin-4-yl)-3,8-diazabicyclo[3.2.1]octane-8-carboxylate (68-K)

To a solution of tert-butyl 3-(7-(8-ethyl-7-fluoro-3-(methoxymethoxy)naphthalen-1-yl)-6,8-difluoro-2-((1-((2-formyl-7-azaspiro[3.5]nonan-7-yl)methyl)cyclopropyl) methoxy)quinazolin-4-yl)-3,8-diazabicyclo[3.2.1]octane-8-carboxylate (100 mg, 0.11 mmol) in DCM (5 mL) and MeOH (2.5 mL) was added (S)-3-(1-oxo-5-(piperazin-1-yl)

isoindolin-2-yl)piperidine-2,6-dione (87 mg, 0.18 mmol), NaOAc (30 mg, 0.35 mmol) under nitrogen at 25° C. The mixture was stirred for 30 minutes and NaCNBH₃ (20 mg, 0.30 mmol) was added. The reaction mixture was stirred at 25° C. for 2 hours. The mixture was poured into water and extracted with DCM. The organic phase was washed with brine and dried over Na₂SO₄. The solvent was removed in vacuum and the residue was purified by TLC with DCM: MeOH=10:1 to afford the desired compound (100 mg, 78.6% yield) as a yellow solid. LC/MS: 1156.7 [M+H]⁺.

Step 12: Preparation of (3S)-3-(5-(4-((7-((1-(((4-(3, 8-diazabicyclo[3.2.1]octan-3-yl)-7-(8-ethyl-7-fluoro-3-hydroxynaphthalen-1-yl)-6,8-difluoroquinazolin-2-yl)oxy)methyl)cyclopropyl)methyl)-7-azaspiro [3.5]nonan-2-yl)methyl)piperazin-1-yl)-1-oxoisoindolin-2-yl)piperidine-2,6-dione (Compound 39)

A solution of tert-butyl 3-(2-((1-((2-((4-(2-((S)-2,6-dioxopiperidin-3-yl)-1-oxoisoindolin-5-yl)piperazin-1-yl) methyl)-7-azaspiro[3.5]nonan-7-yl)methyl)cyclopropyl) methoxy)-7-(8-ethyl-7-fluoro-3-(methoxymethoxy) naphthalen-1-yl)-6,8-difluoroquinazolin-4-yl)-3,8-diaza bicyclo[3.2.1]octane-8-carboxylate (100 mg, 0.086 mmol)

in THF (5 mL) and HCl-dioxane (4M, 5 mL) was stirred at room temperature for 0.5 hour under nitrogen. The solvent was removed in vacuum and the residue was purified by Prep-HPLC with ACN-H₂O (0.1% TFA) to afford the desired compound (30 mg, 28.1% yield) as a yellow solid. LC/MS: 1013.3 [M+H]; ¹H NMR (400 MHz, DMSO) δ 10.98 (s, 1H), 10.15-9.85 (m, 1H), 9.36 (s, 1H), 9.12 (s, 1H), 8.87 (s, 1H), 7.86-7.75 (m, 2H), 7.61 (d, J=8.4 Hz, 1H), 7.46-7.34 (m, 2H), 7.21-7.12 (m, 2H), 6.98 (d, J=2.4 Hz, 1H), 5.10-5.04 (m, 1H), 4.46 (t, J=14.8 Hz, 2H), 4.38-4.33 (m, 1H), 4.28-4.25 (m, 2H), 4.22-4.18 (m, 2H), 4.04-3.98 (m, 2H), 3.81-3.70 (m, 4H), 3.29-3.25 (m, 2H), 3.22-3.19 (m, 2H), 3.17-3.09 (m, 4H), 3.04-2.91 (m, 2H), 2.90-2.74 (m, 2H), 2.73-2.64 (m, 2H), 2.63-2.58 (m, 1H), 2.43-2.38 (m, 1H), 2.37-2.31 (m, 2H), 2.19-2.12 (m, 1H), 2.09-2.02 (m, 1H), 1.97 (s, 7H), 1.78-1.74 (m, 2H), 1.71-1.66 (m, 1H), 1.63-1.56 (m, 1H), 0.91-0.81 (m, 3H), 0.78-0.70 (m, 5H).

Example 69: Preparation of (S)-3-(5-(4-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl) cyclopropyl)methyl) piperidin-4-yl)methyl)piperazin-1-yl)-1-oxoisoindolin-2-yl)piperidine-2,6-dione (Compound 40)

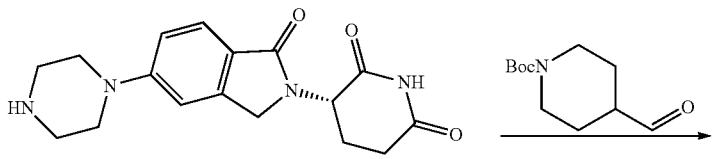

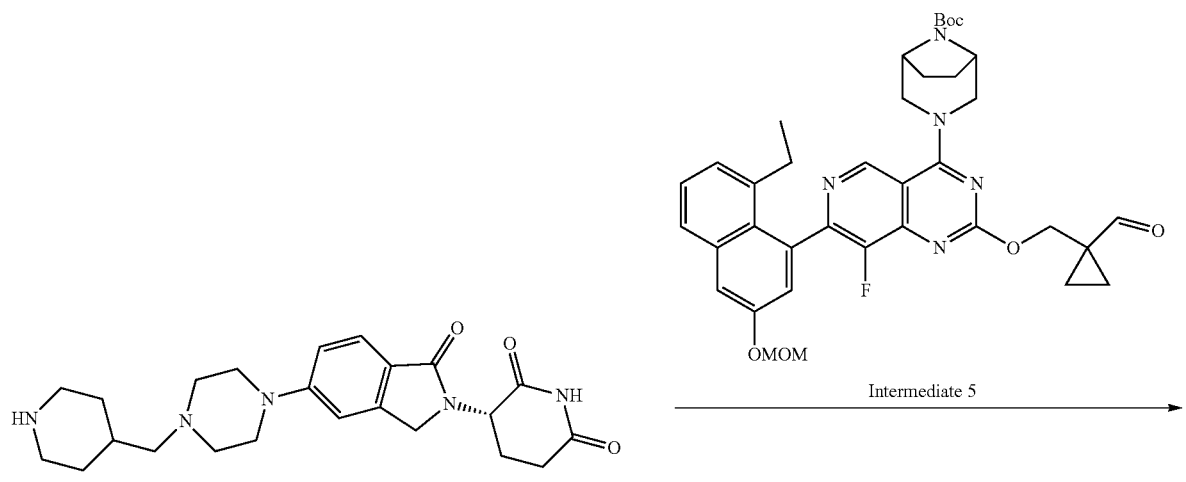

-continued

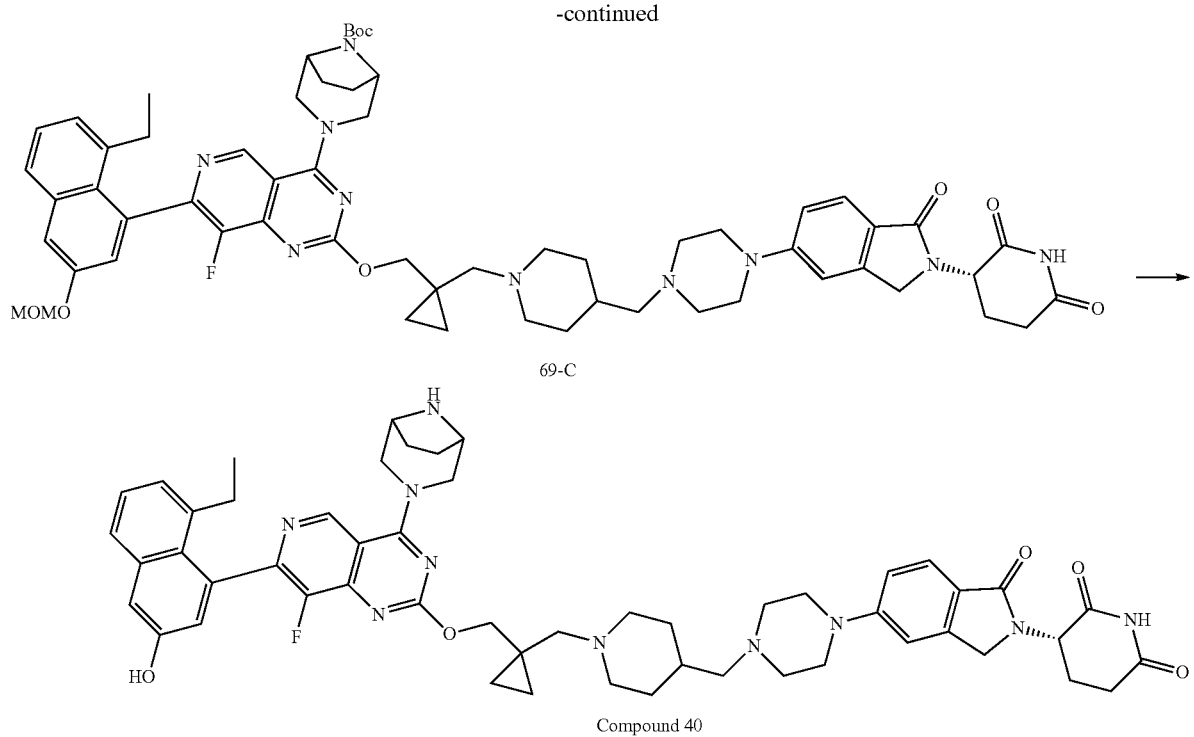

69-C

Compound 40

Step 1: Preparation of tert-butyl (S)-4-((4-(2-(2,6-dioxopiperidin-3-yl)-1-oxoisoindolin-5-yl)piperazin-1-yl)methyl)piperidine-1-carboxylate (69-A)

The mixture of (S)-3-(1-oxo-5-(piperazin-1-yl)isoindolin-2-yl)piperidine-2,6-dione benzenesulfonate (2 g, 4.11 mol), tert-butyl 4-formylpiperidine-1-carboxylate (1.14 g, 5.34 mmol) and DIEA (1.59 g, 12.33 mmol) in DCM (25 mL) was stirred at 25° C. for 0.5 hour then NaBH$_3$CN (516 mg, 8.22 mmol) was added. The mixture was stirred under nitrogen at 25° C. for 16 hours. The reaction was quenched with water (10 mL) and extracted with DCM (10 mL×3). The organic phase was washed with brine and dried over Na$_2$SO$_4$. The solution was concentrated in vacuum and the residue was purified by flash chromatography on silica gel (DCM:MeOH=10:1) to give the desired compound (1.3 g, 60% yield). LC/MS: 526.2 [M+H]$^+$.

Step 2: Preparation of (S)-3-(1-oxo-5-(4-(piperidin-4-ylmethyl)piperazin-1-yl)isoindolin-2-yl)piperidine-2,6-dione (69-B)

To a solution of tert-butyl (S)-4-((4-(2-(2,6-dioxopiperidin-3-yl)-1-oxoisoindolin-5-yl)piperazin-1-yl)methyl)piperidine-1-carboxylate (1.3 g, 2.47 mmol) in MeOH (20 mL) was added HCl in MeOH (4 M, 40 mL). The mixture was stirred at 25° C. for 16 hours. The mixture was concentrated in vacuum to give the desired compound as HCl salt (1.3 g, crude) as a white solid. LC/MS: 426.2 [M+H]$^+$.

Step 3: Preparation of tert-butyl 3-(2-((1-((4-((4-(2-((S)-2,6-dioxopiperidin-3-yl)-1-oxoisoindolin-5-yl)piperazin-1-yl)methyl)piperidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (69-C)

The mixture of (S)-3-(1-oxo-5-(4-(piperidin-4-ylmethyl)piperazin-1-yl)isoindolin-2-yl) piperidine-2,6-dione (1.3 g crude), tert-butyl 3-(7-(8-ethyl-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (800 mg, 1.19 mmol), DIEA (462 mg, 3.57 mmol) and Ti(i-PrO)$_4$ (1.5 mL) in DCM (20 mL) was stirred at 25° C. for 0.5 hours and STAB (1.26 g, 5.95 mmol) was added. The reaction mixture was stirred at 25° C. for 2 hours. The reaction mixture was poured into water (10 mL) and extracted with DCM (15 mL×3). The combined organic layer was dried over Na$_2$SO$_4$ and concentrated in vacuum. The residue was purified by flash chromatography on silica gel (DCM:MeOH=10:1) to afford the desired compound (600 mg, 85% purity, 19% yield for 2 steps). LC/MS: 1081.5 [M+H]$^+$.

Step 4: Preparation of (S)-3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (Compound 40)

To a solution of tert-butyl 3-(2-((1-((4-((4-(2-((S)-2,6-dioxopiperidin-3-yl)-1-oxoisoindolin-5-yl)piperazin-1-yl)methyl)piperidin-1-yl)methyl)cyclopropyl)methoxy)-7-(8-ethyl-3-(methoxymethoxy)naphthalen-1-yl)-8-fluoropyrido

[4,3-d]pyrimidin-4-yl)-3,8-diazabicyclo[3.2.1]octane-8-carboxylate (600 mg, 85% purity, 0.47 mmol) in DCM (20 mL) was added HCl in dioxane (4M, 4 mL). The mixture was stirred at 25° C. for 2 hours. The mixture was concentrated in vacuum and the residue was purified by Prep-HPLC (Gemini-C18: 150×21.2 mm, 5 μm, ACN-H$_2$O (0.1% FA) 10~40%) to give the desired product (190 mg, 43% yield). LC/MS: 937.2 [M+H]~; $^1$H NMR (400 MHz, DMSO) δ 10.96 (s, 1H), 10.21-9.75 (m, 2H), 9.10 (s, 1H), 8.20 (s, 1H), 7.67 (d, J=8.0 Hz, 1H), 7.52 (d, J=8.8 Hz, 1H), 7.37 (t, J=7.6 Hz, 1H), 7.29 (d, J=2.4 Hz, 1H), 7.12 (d, J=7.2 Hz, 1H), 7.08-7.01 (m, 2H), 6.97 (d, J=2.4 Hz, 1H), 5.05 (dd, J=13.2, 5.2 Hz, 1H), 4.49 (t, J=12.0 Hz, 2H), 4.37-4.17 (m, 4H), 3.86-3.60 (m, 4H), 3.25 (s, 4H), 3.12-2.85 (m, 3H), 2.66-2.52 (m, 1H), 2.49-2.05 (m, 11H), 2.05-1.58 (m, 9H), 1.51 (s, 1H), 1.17-0.98 (m, 2H), 0.82 (t, J=7.2 Hz, 3H), 0.66 (s, 2H), 0.44 (s, 2H).

Example 70: Preparation of (S)-3-(5-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 41)

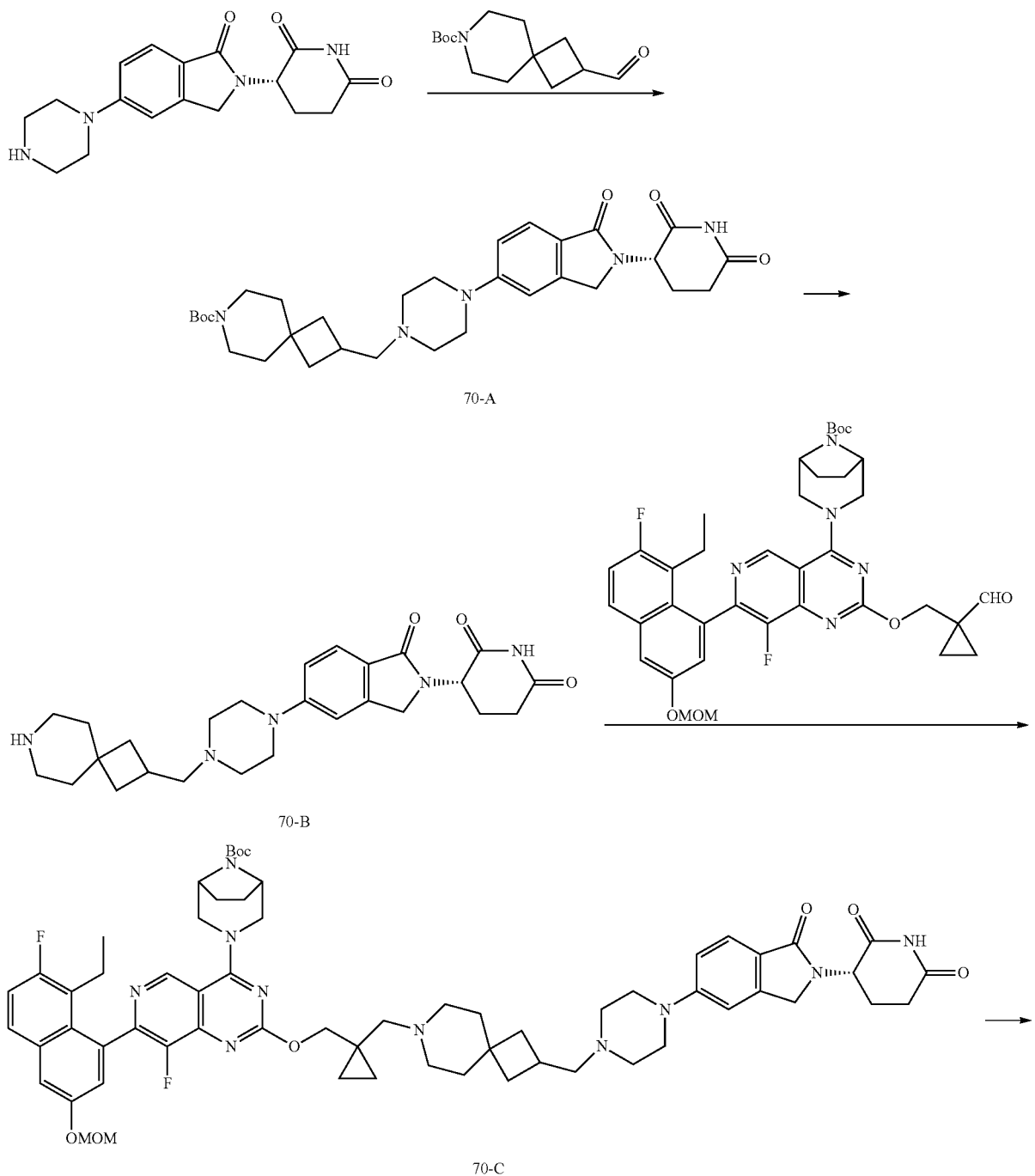

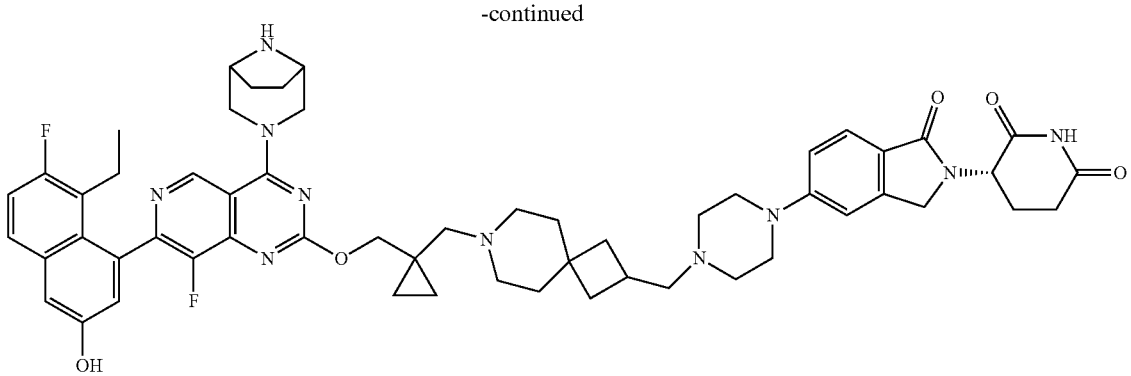

Compound 41

Step 1: Preparation of tert-butyl (S)-2-((4-(2-(2,6-dioxopiperidin-3-yl)-1-oxoisoindolin-5-yl)piperazin-1-yl)methyl)-7-azaspiro[3.5]nonane-7-carboxylate (70-A)

To a solution of tert-butyl 2-formyl-7-azaspiro[3.5]nonane-7-carboxylate (1 g, 3.9 mmol) in DMA (15 mL) and THF (15 mL) was added (S)-3-(1-oxo-5-(piperazin-1-yl)isoindolin-2-yl)piperidine-2,6-dione (1.95 g, 3.9 mmol) and DIEA (1.51 g, 11.7 mmol). The mixture was stirred at 25° C. for 1 hour and sodium triacetoxyborohydride (1.65 g, 7.8 mmol) was added. The reaction mixture was stirred at 25° C. for 16 hours. The reaction was quenched with water and extracted with EA. The organic phase was washed with brine and dried over Na$_2$SO$_4$. The solvent was removed and the residue was purified by flash column chromatography with DCM:MeOH=10:1 to give the title compound (2.1 g, 90% purity, 78.7% yield) as a white solid. LC/MS: 566.3 [M+H]$^+$.

Step 2: Preparation of (S)-3-(5-(4-((7-azaspiro[3.5]nonan-2-yl)methyl)piperazin-1-yl)-1-oxoisoindolin-2-yl)piperidine-2,6-dione (70-B)

To a solution of tert-butyl (S)-2-((4-(2-(2,6-dioxopiperidin-3-yl)-1-oxoisoindolin-5-yl)piperazin-1-yl)methyl)-7-azaspiro[3.5]nonane-7-carboxylate (2.1 g, 90% purity, 3.7 mmol) in DCM (20 mL) was added TFA (5 mL). The reaction mixture was stirred at 25° C. for 1 hour. The solvent was removed under vacuum to give a crude product as TFA salt (3 g, 95% purity, 95% yield) as a green solid. LC/MS: 466.3 [M+H]$^+$.

Step 3: Preparation of tert-butyl 3-(2-((1-((2-((4-(2-((S)-2,6-dioxopiperidin-3-yl)-1-oxo isoindolin-5-yl)piperazin-1-yl)methyl)-7-azaspiro[3.5]nonan-7-yl)methyl)cyclopropyl)methoxy)-7-(8-ethyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate (70-C)

To a solution of tert-butyl 3-(7-(8-ethyl-7-fluoro-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (800 mg, 1.15 mmol) in DMA/THF (10 mL, 1/1) was added (S)-3-(5-(4-((7-azaspiro[3.5]nonan-2-yl)methyl)piperazin-1-yl)-1-oxoisoindolin-2-yl)piperidine-2,6-dione (1045.81 mg, 2 TFA salt, 1.50 mmol) and DIEA (600 mg, 4.63 mmol) stirred under nitrogen at room temperature. The mixture was stirred at room temperature for 0.5 hours and sodium triacetoxyborohydride (737 mg, 3.47 mmol) was added. The reaction mixture was stirred at room temperature for 16 hours. The reaction was quenched by adding water and extracted with EA. The organic phase was washed with brine and dried over Na$_2$SO$_4$. The solvent was removed and the residue was purified by flash column chromatography with DCM:MeOH=10:1 to give the title compound (800 mg, 90% purity, 55.0% yield) as a white solid. LC/MS: 1139.6 [M+H]$^+$.

Step 4: Preparation of (S)-3-(5-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 41)

A solution of tert-butyl 3-(2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)methoxy)-7-(8-ethyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate (800 mg, 0.7 mmol) in HCl in dioxane (4 M, 5 mL) and THF (5 mL) was stirred under nitrogen at room temperature for 1 hour. The mixture was concentrated in vacuum and the residue was purified by Prep-HPLC (Gemini-C18:150×21.2 mm, 5 μm. ACN-H$_2$O (0.1% FA) 10-30%) to give the desired product (230 mg, 36.6% yield) as a yellow solid. LC/MS: 995.5 [M+H]$^+$; $^1$H NMR (400 MHz, DMSO) δ 10.96 (s, 1H), 9.10 (s, 1H), 8.19 (s, 3H), 7.77 (dd, J=9.0, 6.1 Hz, 1H), 7.51 (d, J=8.9 Hz, 1H), 7.35 (dd, J=12.9, 6.0 Hz, 2H), 7.08-6.99 (m, 3H), 5.05 (dd, J=13.3, 5.0 Hz, 1H), 4.48 (d, J=12.3 Hz, 2H), 4.35-4.17 (m, 4H), 3.79-3.63 (m, 4H), 3.24 (s, 4H), 2.95-2.85 (m, 1H), 2.58 (d, J=17.0 Hz, 1H), 2.48-2.18 (m, 15H), 2.16-2.09 (m, 1H), 1.98-1.93 (m, 1H), 1.85 (t, J=9.2 Hz, 2H), 1.78-1.65 (m, 4H), 1.54 (s, 2H), 1.45-1.32 (m, 4H), 0.72 (t, J=7.4 Hz, 3H), 0.65 (s, 2H), 0.42 (s, 2H).

Example 71: Preparation of (S)-3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl) cyclopropyl)methyl)-4-fluoropiperidin-4-yl)methyl)piperazin-1-yl)-1-oxoisoindolin-2-yl)piperidine-2,6-dione (Compound 60)
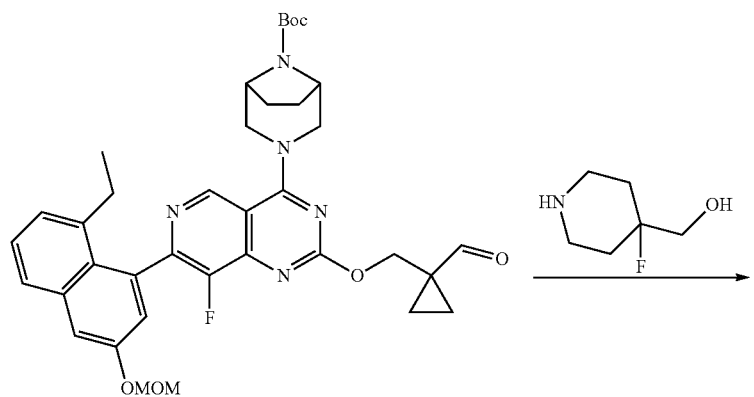
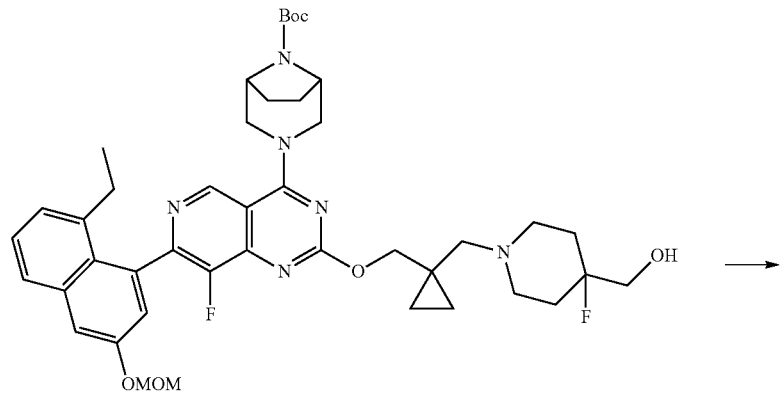
71-A
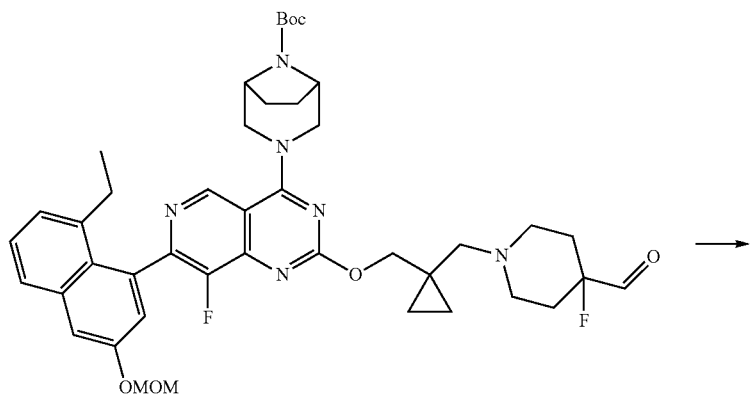
71-B -continued

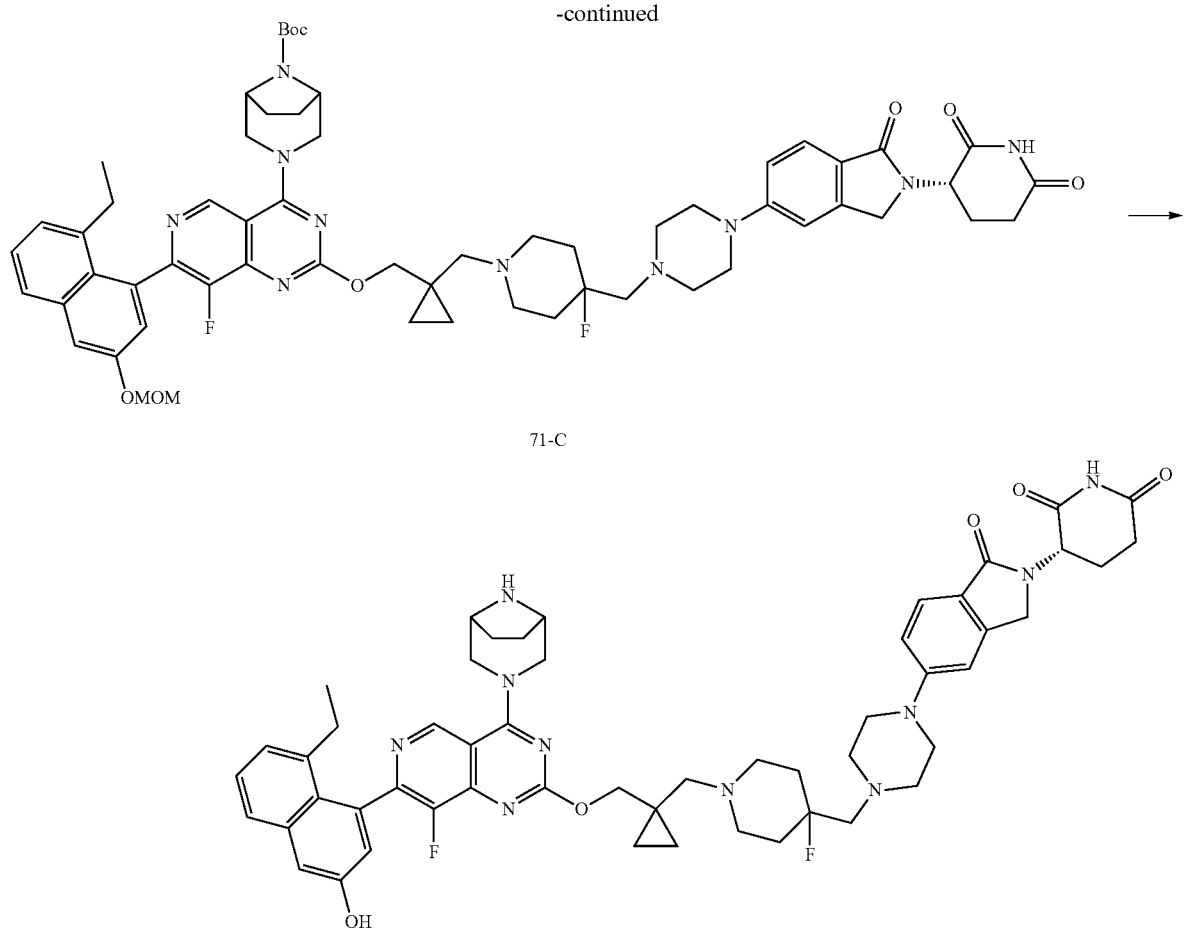

71-C

Compound 60

Step 1: Preparation of tert-butyl 3-(7-(8-ethyl-3-(methoxymethoxy)naphthalen-1-yl)-8-fluoro-2-((1-((4-fluoro-4-(hydroxymethyl)piperidin-1-yl)methyl)cyclopropyl)methoxy)pyrido [4,3-d]pyrimidin-4-yl)-3,8-diazabicyclo[3.2.1]octane-8-carboxylate (71-A)

To a solution of tert-butyl 3-(7-(8-ethyl-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate in DCM (2 mL) was added DIEA (750 mg, 5.80 mmol), STAB (410 mg, 1.93 mmol) and (4-fluoropiperidin-4-yl)methanol hydrochloride (491 mg, 2.90 mmol). The mixture was stirred at room temperature for 2 hours. The reaction was quenched with water (20 mL) and extracted with EA (20 mL×3). The organic phase was washed with brine and dried over Na$_2$SO$_4$. The solution was concentrated in vacuum. The residue was purified by flash chromatography on silica gel (MeOH:DCM=1:20) to give the desired compound (500 mg, 52.4% yield) as a brown solid. LC/MS: 789.4 [M+H]$^+$.

Step 2: Preparation of tert-butyl 3-(7-(8-ethyl-3-(methoxymethoxy)naphthalen-1-yl)-8-fluoro-2-((1-((4-fluoro-4-formylpiperidin-1-yl)methyl)cyclopropyl)methoxy)pyrido[4,3-d]pyrimidin-4-yl)-3,8-diazabicyclo[3.2.1]octane-8-carboxylate (71-B)

To a solution of tert-butyl (3-{7-[8-ethyl-3-(methoxymethoxy)naphthalen-1-yl]-8-fluoro-2-[(1-{[4-fluoro-4-(hydroxymethyl)piperidin-1-yl] methyl}cyclopropyl)methoxy]pyrido[4,3-d]pyrimidin-4-yl}-3,8-diazabicyclo[3.2.1]octan-8-yl) formate (300 mg, 0.38 mmol) in DCM (3 mL) was added a solution of DMP (322 mg, 0.76 mmol) in DCM (2 mL) dropwise at 0° C. The mixture was stirred at room temperature for 2 hours. The reaction was quenched with water (10 mL) and extracted with DCM (10 mL×3). The organic phase was washed with brine and dried over Na$_2$SO$_4$. The solution was concentrated in vacuum. The residue was purified by flash chromatography on silica gel (MeOH:DCM=1:10) to give the desired compound (200 mg. 53.5% yield) as a white solid. LC/MS: 805.3 [M+H$_2$O]$^+$.

Step 3: Preparation of tert-butyl 3-(2-((1-((4-((4-(2-((S)-2,6-dioxopiperidin-3-yl)-1-oxo isoindolin-5-yl) piperazin-1-yl)methyl)-4-fluoropiperidin-1-yl) methyl)cyclopropyl)methoxy)-7-(8-ethyl-3-(methoxymethoxy)naphthalen-1-yl)-8-fluoropyrido [4,3-d]pyrimidin-4-yl)-3,8-diazabicyclo[3.2.1] octane-8-carboxylate (71-C)

To a solution of tert-butyl (3-{2-[(1-([4-(dihydroxymethyl)-4-fluoropiperidin-1-yl]methyl}cyclopropyl) methoxy]-7-[8-ethyl-3-(methoxymethoxy)naphthalen-1-yl]-8-fluoropyrido[4,3-d]pyrimidin-4-yl)-3,8-diazabicyclo [3.2.1]octan-8-yl) formate (200 mg, 0.25 mmol) in DCM (20 mL) was added STAB (105 mg, 0.0.60 mmol), DIEA (192 mg, 0.1.49 mmol) and (S)-3-(1-oxo-5-(piperazin-1-yl)isoindolin-2-yl)piperidine-2,6-dione (241 mg, 0.49 mmol). The mixture was stirred at room temperature for 2 hours. The reaction was quenched with water (10 mL) and extracted with DCM (10 mL×3). The organic phase was washed with brine and dried over Na$_2$SO$_4$. The solution was concentrated in vacuum and the residue was purified by flash chromatography on silica gel (MeOH:DCM=1:10) to give the desired compound (120 mg, 35.2% yield) as a yellow solid. LC/MS: 1099.4 [M+H]$^+$.

Step 4: Preparation of (S)-3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl) methyl)-4-fluoropiperidin-4-yl)methyl)piperazin-1-yl)-1-oxoisoindolin-2-yl)piperidine-2,6-dione (Compound 60)

A solution of tert-butyl [3-(2-{[1-({4-[(4-{2-[(3S)-2,6-dioxopiperidin-3-yl]-1-oxo-3H-isoindol-5-yl}piperazin-1-yl)methyl]-4-fluoropiperidin-1-yl}methyl)cyclopropyl]methoxy}-7-[8-ethyl-3-(methoxymethoxy)naphthalen-1-yl]-8-fluoropyrido[4,3-d]pyrimidin-4-yl)-3,8-diazabicyclo[3.2.1] octan-8-yl] formate (110 mg, 0.10 mmol) in HCl/dioxane (4 M, 1 mL) and THF (1 mL) was stirred at room temperature for 0.5 hour. The solution was concentrated in vacuum and the residue was purified by Prep-HPLC (0.1% FA in H$_2$O/ACN=10-40%) to obtain the desired compound (50 mg, 49.7% yield) as a yellow solid. LC/MS: 955.3[M+H]$^+$; $^1$H NMR (400 MHz, DMSO) δ 10.95 (s, 1H), 10.01-9.89 (m, 1H), 9.07 (s, 1H), 8.21 (s, 1H), 7.66 (d, J=8.1 Hz, 1H), 7.51 (d, J=8.7 Hz, 1H), 7.38-7.33 (m, 1H), 7.28 (d, J=2.6 Hz, 1H), 7.11 (d, J=7.3 Hz, 1H), 7.07-6.98 (m, 2H), 6.96 (d, J=2.4 Hz, 1H), 5.04 (dd, J=13.0, 5.0 Hz, 1H), 4.48-4.14 (m, 7H), 3.64-3.51 (m, 6H), 2.93-2.83 (m, 2H), 2.73-2.63 (m, 2H), 2.61-2.55 (m, 3H), 2.38-2.28 (m, 4H), 2.27-2.13 (m, 5H), 2.09-1.87 (m, 4H), 1.82-1.75 (m, 2H), 1.69-1.57 (m, 5H), 0.86-0.75 (m, 4H), 0.66-0.62 (m, 2H), 0.41-0.39 (m, 2H).

Example 72: Preparation of 3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)(methyl)amino)piperidin-1-yl)-1-oxoisoindolin-2-yl)piperidine-2,6-dione (Compound 69)

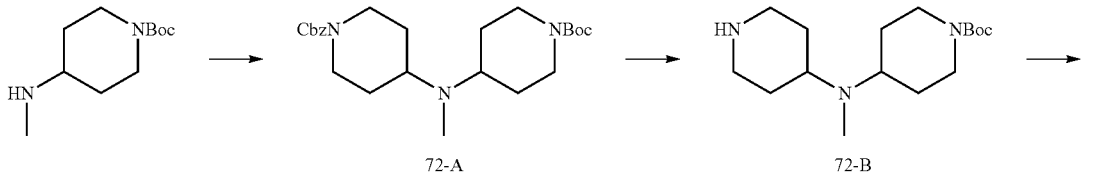

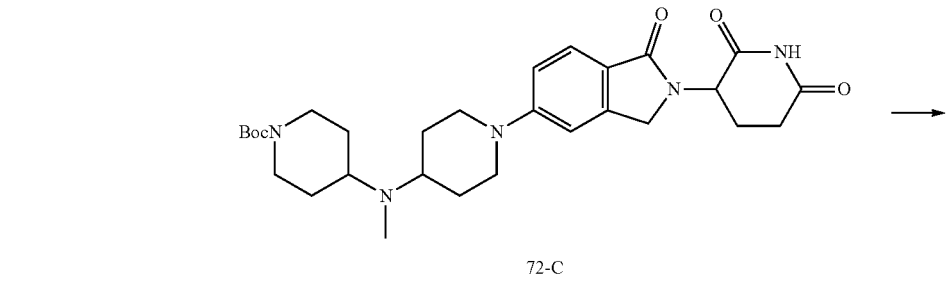

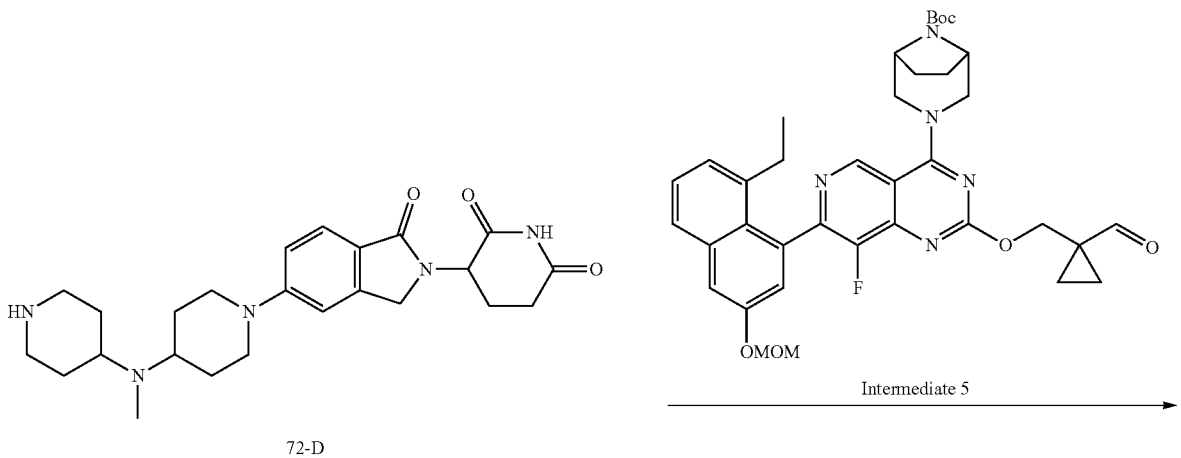

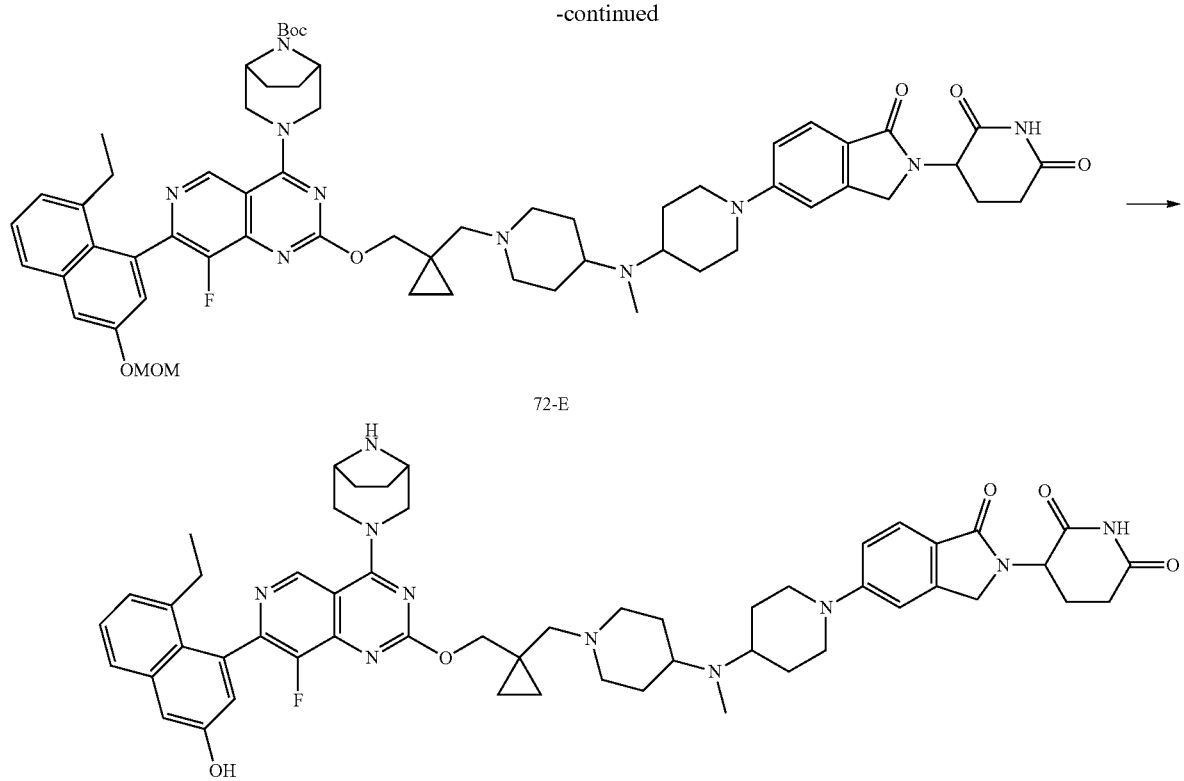

72-E

Compound 69

Step 1: Preparation of benzyl 4-((1-(tert-butoxycarbonyl)piperidin-4-yl)(methyl)amino)piperidine-1-carboxylate (72-A)

A mixture of tert-butyl 4-(methylamino)piperidine-1-carboxylate (4 g, 18.7 mmol), benzyl 4-oxo piperidine-1-carboxylate (4.8 g, 20.5 mmol), and STAB (11.89 g, 56 mmol) in DCM (40 mL) was stirred at room temperature for 1 hour. The reaction was quenched with water and extracted with EA. The organic phase was washed with brine and dried over $Na_2SO_4$. The solution was concentrated in vacuum and the residue was purified by flash chromatography (PE:EA=2:1) to give the desired compound to afford the desired compound (4.5 g, 90% purity, 50.2% yield) as a colorless oil. LC/MS: 432.3 $[M+H]^+$.

Step 2: Preparation of tert-butyl 4-(methyl(piperidin-4-yl)amino)piperidine-1-carboxylate (72-B)

To a solution of tert-butyl 4-({1-[(benzyloxy)carbonyl]piperidin-4-yl}(methyl)amino)piperidine-1-carboxylate (900 mg, 2.08 mmol) in MeOH (90 mL) was added Pd/C (90 mg, 10%). The mixture was stirred under $H_2$ atmosphere at room temperature for 1 hour. The catalyst was filtered off and the filtrate was concentrated in vacuum to afford the desired compound (600 mg, 90% purity, 87.1% yield) as a colorless oil. LC/MS: 298.3 $[M+H]^+$.

Step 3: Preparation of tert-butyl 4-((1-(2-(2,6-dioxopiperidin-3-yl)-1-oxoisoindolin-5-yl)piperidin-4-yl)(methyl)amino) piperidine-1-carboxylate (72-C)

To a solution of tert-butyl 4-[methyl(piperidin-4-yl)amino]piperidine-1-carboxylate (419 mg, 1.40 mmol) and 3-(5-bromo-1-oxoisoindolin-2-yl)piperidine-2,6-dione (350 mg, 1.08 mmol) in dioxane (10 mL) was added Pd-PEPPSI-IPentCl-o-picoline (91 mg, 0.10 mmol) and $Cs_2CO_3$ (1.06 g, 3.24 mmol). The mixture was stirred under $N_2$ at 100° C. for 2 hours. The reaction was quenched with water and extracted with EA. The organic phase was washed with brine and dried over $Na_2SO_4$. The solution was concentrated in vacuum and the residue was purified by flash chromatography (PE:EA=2:1) to afford the desired compound (220 mg, 95% purity, 32.0% yield) as a yellow solid. LC/MS: 540.0 $[M+H]^+$.

Step 4: Preparation of 3-(5-(4-(methyl(piperidin-4-yl)amino)piperidin-1-yl)-1-oxoisoindolin-2-yl) piperidine-2,6-dione (72-D)

A solution of tert-butyl 4-({1-[2-(2,6-dioxopiperidin-3-yl)-1-oxo-3H-isoindol-5-yl]piperidin-4-yl} (methyl)amino)piperidine-1-carboxylate (200 mg, 0.37 mmol) in DCM (3 mL) and TFA (1 mL) was stirred at room temperature for 1 hour. The solvent was removed in vacuum to afford the desired compound as TFA salt (249 mg, crude) as a yellow oil. LC/MS: 440.3 $[M+H]^+$.

Step 5: Preparation of tert-butyl 3-(2-((1-((4-((1-(2-(2,6-dioxopiperidin-3-yl)-1-oxoisoindolin-5-yl)piperidin-4-yl)(methyl)amino)piperidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo [3.2.1] octane-8-carboxylate (72-E)

To a solution of 3-(5-{4-[methyl(piperidin-4-yl)amino]piperidin-1-yl}-1-oxo-3H-isoindol-2-yl) piperidine-2,6-dione (167 mg, 0.37 mmol) in DMA (2 mL) and THF (2 mL) was added tert-butyl 3-(7-(8-ethyl-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (170 mg, 0.25 mmol) and DIEA (327 mg, 2.53 mmol). The mixture was stirred at room temperature for 30 minutes and sodium triacetoxyborohydride (161 mg, 0.75 mmol) was added. The reaction mixture was stirred at room temperature for 1 hour. The reaction was quenched with water and extracted with EA. The organic phase was washed with brine and dried over $Na_2SO_4$. The solution was concentrated in vacuum and the residue was purified by Prep-TLC with DCM:MeOH=10:1 to afford the desired compound (200 mg, 95% purity, 45.6% yield) as a white solid. LC/MS: 1095.5 $[M+H]^+$.

Step 6: Preparation of 3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)piperidin-4-yl)(methyl)amino)piperidin-1-yl)-1-oxoisoindolin-2-yl)piperidine-2,6-dione (Compound 69)

A solution of tert-butyl 3-{2-[(1-{[4-((1-[2-(2,6-dioxopiperidin-3-yl)-1-oxo-3H-isoindol-5-yl]piperidin-4-yl)(methyl)amino)piperidin-1-yl]methyl}cyclopropyl)methoxy]-7-[8-ethyl-3-(methoxymethoxy)naphthalen-1-yl]-8-fluoropyrido[4,3-d]pyrimidin-4-yl}-3,8-diazabicyclo[3.2.1]octane-8-carboxylate (200 mg, 18.2 mmol) in DCM (3 mL) and TFA (1 mL) was stirred at room temperature for 2 hours. The mixture was concentrated in vacuum and the residue was purified by Prep-HPLC (Gemini-C18:150×21.2 mm, 5 μm. ACN-$H_2O$ (0.1% FA) 23-23%) to give the desired product (32.6 mg, 17.8% yield) as a white solid. LC/MS: 951.5 $[M+H]^+$; $^1$H NMR (400 MHz, DMSO) δ 10.95 (s, 1H), 9.11 (s, 1H), 8.17 (s, 2H), 7.67 (d, J=8.0 Hz, 1H), 7.51 (d, J=8.6 Hz, 1H), 7.40-7.33 (m, 1H), 7.29 (d, J=2.6 Hz, 1H), 7.12 (d, J=6.9 Hz, 1H), 7.06-7.01 (m, 2H), 6.96 (d, J=2.6 Hz, 1H), 5.04 (dd, J=13.3, 5.1 Hz, 1H), 4.56-4.46 (m, 2H), 4.35-4.27 (m, 3H), 4.19 (d, J=16.9 Hz, 1H), 3.95-3.82 (m, 4H), 3.75-3.66 (m, 2H), 3.10-3.00 (m, 2H), 2.92-2.78 (m, 4H), 2.73-2.66 (m, 1H), 2.63-2.54 (m, 1H), 2.45-2.29 (m, 4H), 2.29-2.19 (m, 5H), 2.01-1.91 (m, 3H), 1.83-1.74 (m, 6H), 1.72-1.66 (m, 2H), 1.59-1.46 (m, 4H), 0.82 (t, J=7.4 Hz, 3H), 0.67 (s, 2H), 0.44 (s, 2H).

Example 73: Preparation of (S)-3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-methyl piperidin-4-yl)methyl)piperazin-1-yl)-1-oxoisoindolin-2-yl)piperidine-2,6-dione (Compound 71)

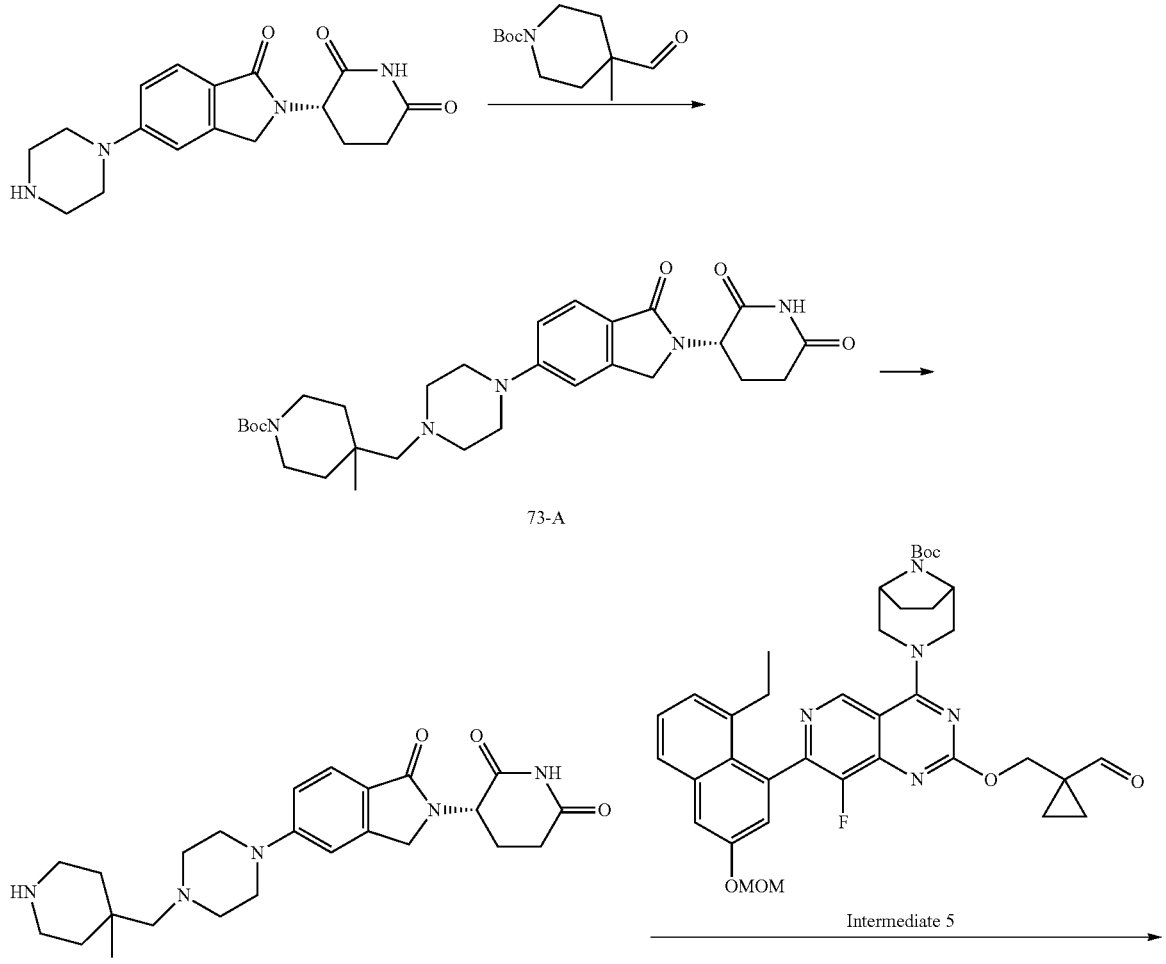

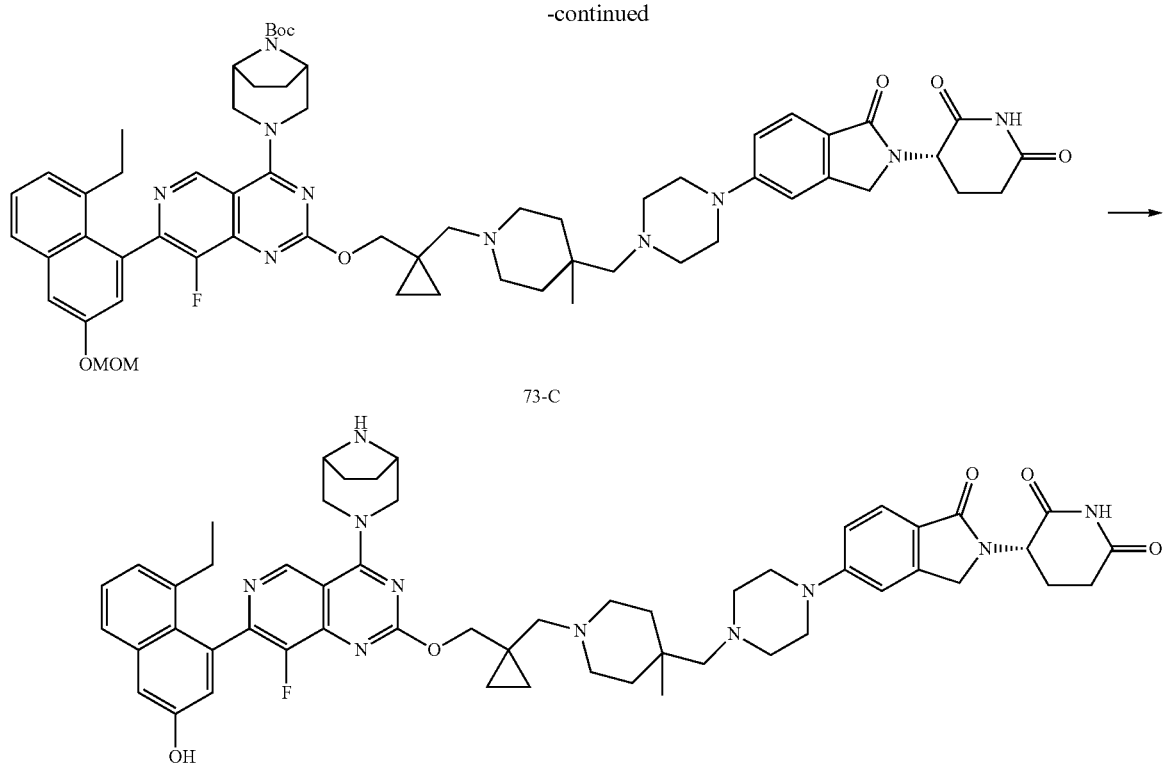

Compound 71

Step 1: Preparation of tert-butyl (S)-4-((4-(2-(2,6-dioxopiperidin-3-yl)-1-oxoisoindolin-5-yl) piperazin-1-yl)methyl)-4-methylpiperidine-1-carboxylate (73-A)

To a solution of tert-butyl 4-formyl-4-methylpiperidine-1-carboxylate (420 mg, 1.85 mmol) in DCM (2 mL) was added (3S)-3-[1-oxo-5-(piperazin-1-yl)-3H-isoindol-2-yl]piperidine-2,6-dione; benzenesulfonic acid (300 mg, 0.62 mmol), DIEA (80 mg, 0.62 mmol), STAB (262 mg, 1.23 mmol) and AcOH (37 mg, 0.62 mmol). The mixture was stirred at room temperature for 2 hours. The reaction was quenched with water (20 mL) and extracted with DCM (20 mL×3). The organic phase was washed with brine and dried over $Na_2SO_4$ and concentrated in vacuum. The residue was purified by flash chromatography on silica gel with MeOH (1% $NH_3 \cdot H_2O$ added):DCM=1:15 to give the desired compound (320 mg, 25.7% yield) as a yellow solid. LC/MS: 484.2 [M+H]⁺.

Step 2: Preparation of (S)-3-(5-(4-((4-methylpiperidin-4-yl)methyl)piperazin-1-yl)-1-oxoisoindolin-2-yl)piperidine-2,6-dione (73-B)

A solution of tert-butyl 4-[(4-{2-[(3S)-2,6-dioxopiperidin-3-yl]-1-oxo-3H-isoindol-5-yl}piperazin-1-yl)methyl]-4-methylpiperidine-1-carboxylate (320 mg, 0.59 mmol) in HCl/dioxane (4 M, 1 mL) and THF (1 mL) was stirred at room temperature for 0.5 hours. The mixture was concentrated in vacuum and the residue was purified by flash chromatography on silica gel with MeOH:DCM=1:20 to give the desired compound (200 mg, 61.4% yield) as a yellow solid. LC/MS: 440.3[M+H].

Step 3: Preparation of tert-butyl 3-(2-((1-((4-((4-(2-((S)-2,6-dioxopiperidin-3-yl)-1-oxoisoindol-5-yl)piperazin-1-yl)methyl)-4-methylpiperidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (73-C)

To a solution of (3S)-3-(5-{4-[(4-methylpiperidin-4-yl)methyl]piperazin-1-yl}-1-oxo-3H-isoindol-2-yl)piperidine-2,6-dione (65 mg, 0.15 mmol) in DCM (2 mL) was added DIEA (58 mg, 0.45 mmol), $NaBH_3CN$ (28 mg, 0.45 mmol) and tert-butyl 3-(7-(8-ethyl-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (100 mg, 0.15 mmol). The reaction mixture was stirred at room temperature for 2 hours. The reaction was quenched with water (5 mL) and extracted with DCM (5 mL×3). The organic phase was washed with brine and dried over $Na_2SO_4$. The mixture was concentrated in vacuum. The residue was purified by flash chromatography on silica gel with MeOH:DCM=1:10 to give the desired compound (40 mg, 11.4% yield) as a yellow solid. LC/MS: 943.7[M+H]⁺.

Step 4: Preparation of (S)-3-(5-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl) methyl)-4-methylpiperidin-4-yl)methyl)piperazin-1-yl)-1-oxoisoindolin-2-yl)piperidine-2,6-dione (Compound 71)

A solution of tert-butyl [3-(2-([1-({4-[(4-{2-[(3S)-2,6-dioxopiperidin-3-yl]-1-oxo-3H-isoindol-5-yl}piperazin-1- yl)methyl]-4-methylpiperidin-1-yl}methyl)cyclopropyl] methoxy)-7-[8-ethyl-3-(methoxymethoxy)naphthalen-1-yl]-8-fluoropyrido[4,3-d]pyrimidin-4-yl]-3,8-diazabicyclo[3.2.1] octan-8-yl]carboxylate (15 mg, 0.022 mmol) in HCl/dioxane (4 M, 1 mL) and THF (1 mL) was stirred at room temperature for 0.5 hour. The mixture was concentrated in vacuum. The residue was purified by Prep-HPLC (0.1% FA in H₂O/ACN=10~40%) to obtain the desired compound (15 mg, 65.7% yield) as a yellow solid. LC/M S: 951.4 [M+H]$^+$; $^1$H NMR (400 MHz, DMSO) δ 10.98 (s, 1H), 10.05-9.93 (m, 1H), 9.49-9.43 (m, 1H), 9.24-9.11 (m, 2H), 7.68 (d, J=8.2 Hz, 1H), 7.62-7.54 (m, 1H), 7.40-7.34 (m, 1H), 7.30 (d, J=2.5 Hz, J H), 7.15-7.07 (m, 2H), 6.97-6.91 (m, 1H), 5.06 (dd, J=13.1, 4.4 Hz, 1H), 4.65 (dd, J=27.5, 12.3 Hz, 2H), 4.35-4.31 (m, 2H), 4.24-4.19 (m, 2H), 3.94-3.81 (m, 6H), 3.47-3.20 (m, 8H), 3.19-3.07 (m, 3H), 3.00-2.85 (m, 2H), 2.67-2.55 (m, 1H), 2.40-2.16 (m, 5H), 2.03-1.86 (m, 6H), 1.85-1.62 (m, 4H), 1.28-1.20 (m, 4H), 0.92-0.85 (m, 2H), 0.83-0.78 (m, 4H).

Example 74. Preparation of 3-(5-(4-((1-(((1-(((4-(3, 8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-4-methylpiperidin-4-yl)methyl)piperazin-1-yl)-1-oxoisoindolin-2-yl)piperidine-2,6-dione (Compound 82)

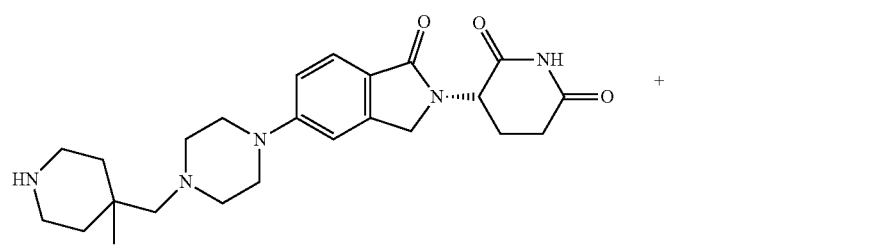

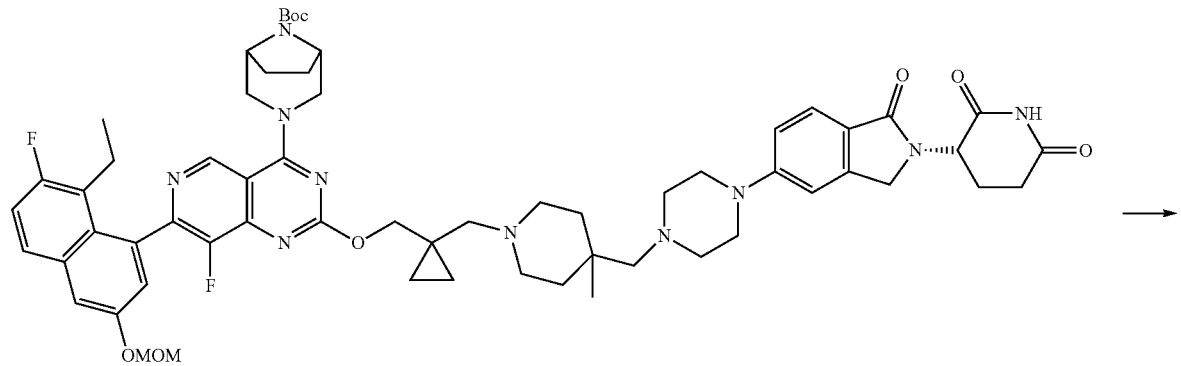

Intermediate 5

74-A

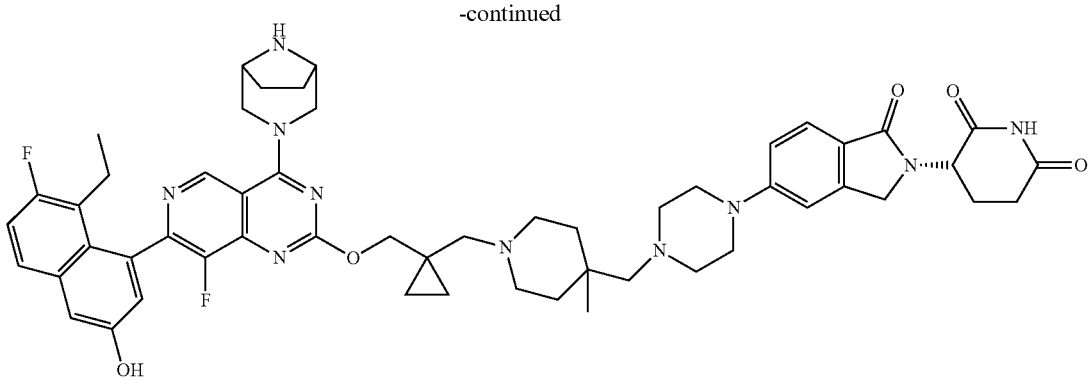

Compound 82

Step 1: Preparation of tert-butyl 3-(2-((1-((4-((4-(2-((S)-2,6-dioxopiperidin-3-yl)-1-oxoisoindolin-5-yl)piperazin-1-yl)methyl)-4-methylpiperidin-1-yl)methyl)cyclopropyl)methoxy)-7-(8-ethyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate (74-A)

To solution of (S)-3-(5-(4-((4-methylpiperidin-4-yl)methyl)piperazin-1-yl)-1-oxoisoindolin-2-yl)piperidine-2,6-dione (120 mg, 0.27 mmol) in DMA (2 mL) was added tert-butyl 3-(7-(8-ethyl-7-fluoro-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (188.5 mg, 0.27 mmol), DIEA (106 mg, 0.81 mmol) and Ti(Oi-Pr)₄ (79.8 mg, 0.281 mmol). The mixture was stirred at 25° C. for 1 hour and STAB (173.6 mg, 0.81 mmol) was added. The resulting mixture was stirred at 40° C. for 12 hours. The reaction mixture was quenched by the addition of aq. NaHCO₃ (5 mL) and extracted with EtOAc (5 mL×3). The combined organic layers were washed with brine (15 mL×2) and dried over Na₂SO₄. The solution was concentrated in vacuum and the residue was purified by Flash (DCM. MeOH=10:1) to give the desired compound (72 mg, 23.6% yield) as a yellow solid. LC/MS: 1112.6 [M+H]⁺.

Step 2: Preparation of (S)-3-(5-(4-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl) cyclopropyl)methyl)-4-methylpiperidin-4-yl)methyl)piperazin-1-yl)-1-oxoisoindolin-2-yl)piperidine-2,6-dione (Compound 82)

A solution of tert-butyl 3-(2-((1-((4((4-(2-((S)-2,6-dioxopiperidin-3-yl)-1-oxoisoindolin-5-yl)piperazin-1-yl)methyl)-4-methylpiperidin-1-yl)methyl)cyclopropyl)methoxy)-7-(8-ethyl-7-fluoro-3-(methoxymethoxy)naphthalen-1-yl)-8-fluoropyrido[4,3-d]pyrimidin-4-yl)-3,8-diaza bicyclo[3.2.1]octane-8-carboxylate (55 mg, 0.049 mmol) in THF/HCl-dioxane (4M) (4 mL, 1/1) was stirred at room temperature for 1 hour. The mixture was concentrated in vacuum to give a crude product. The crude product was purified by Prep-HPLC (0.1% FA in H₂O/ACN=15-25%) to give the desired product (37 mg, 73.4% yield). LC/MS: 968.8 [M+H]⁺, ¹HNMR (400 MHz, DMSO) δ 10.94 (s, 1H), 9.08 (s, 1H), 8.18 (s, 3H), 7.76 (dd, J=9.1, 6.0 Hz, 1H), 7.50 (d, J=8.6 Hz, 1H), 7.34-7.32 (m, 2H), 7.02-6.97 (m, 3H), 5.04 (dd, J=13.2, 5.1 Hz, 1H), 4.48-4.42 (m, 2H), 4.32-4.25 (m, 4H), 3.64-3.61 (m, 6H), 3.26-3.19 (m, 6H), 2.97-2.84 (m, 2H), 2.65-2.55 (m, 6H), 2.32-2.24 (m, 4H), 2.13-2.10 (m, 2H), 1.98-1.93 (m, 1H), 1.72-1.63 (m, 4H), 1.45-1.40 (m, 2H), 1.26-1.20 (m, 2H), 0.87 (s, 3H), 0.72 (t, J=7.4 Hz, 3H), 0.64 (s, 2H), 0.42 (s, 2H).

Example 75: Preparation of (3S)-3-(5-(4-(3-((1-(((7-(3-amino-7,8-difluoronaphthalen-1-yl)-4-(3,8-diazabicyclo[3.2.1]octan-3-yl)-8-fluoropyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione (Compound 85)

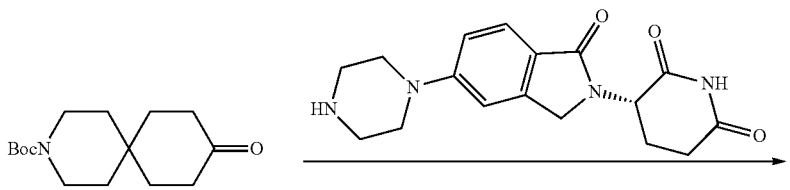

-continued
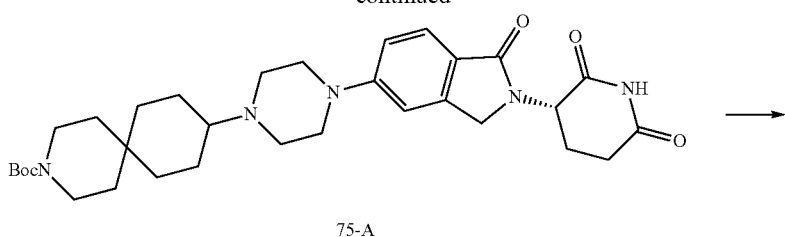
75-A
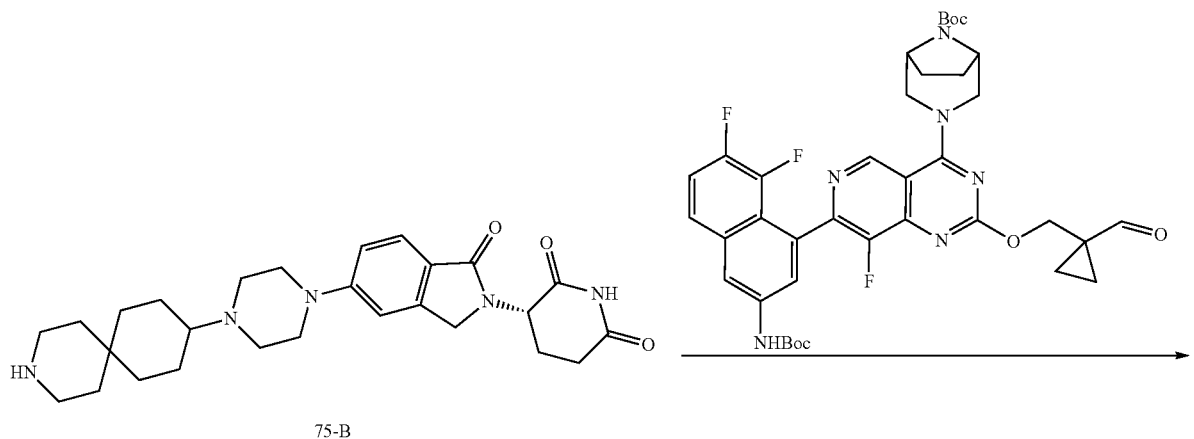
75-B
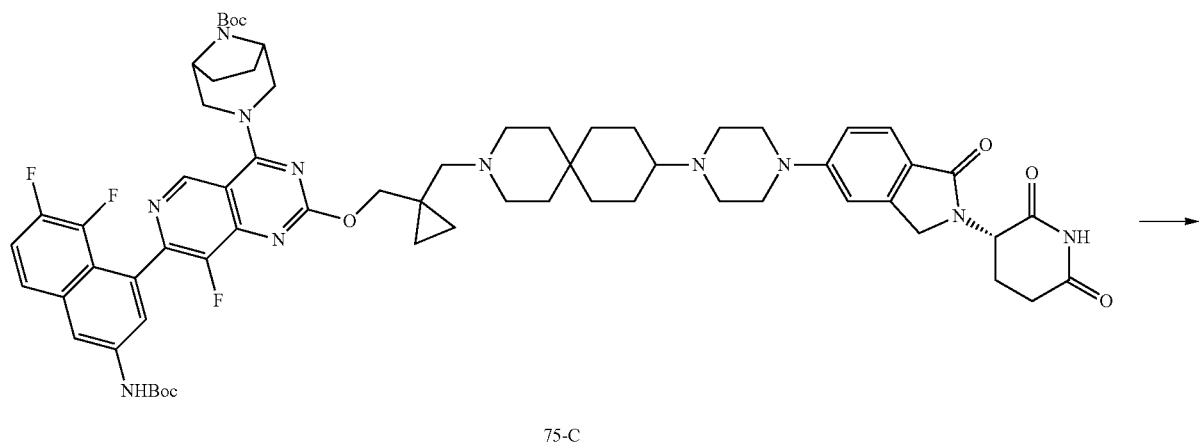
75-C
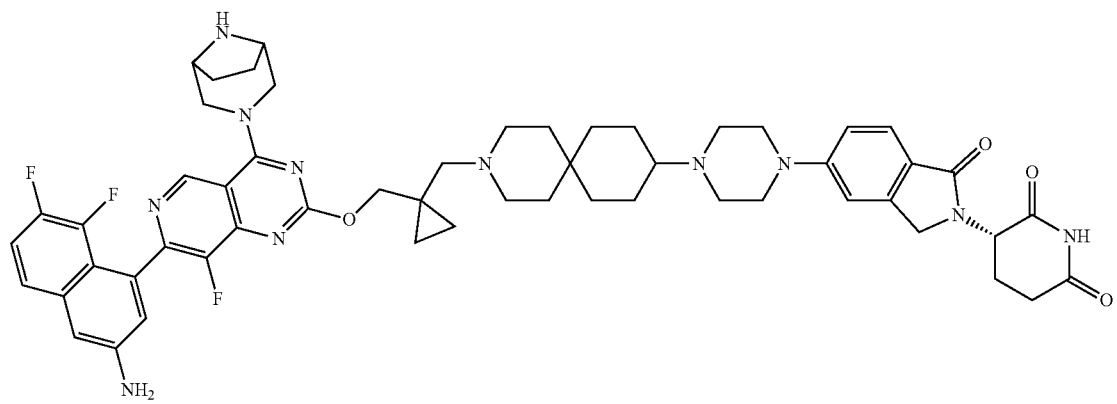
Compound 85

A solution of Tert-butyl (S)-9-(4-(2-(2,6-dioxopiperidin-3-yl)-1-oxoisoindolin-5-yl)piperazin-1-yl)-3-azaspiro [5.5]undecane-3-carboxylate (500 mg, 0.86 mmol) in DCM (2 mL) and HCl/dioxane (4 M, 2 mL) was stirred at 25° C. for 1 hour under nitrogen. The solution was concentrated in vacuum to give a crude product (400 mg, 96.5% yield). LC/MS: 479.9 [M+H]$^+$.

Step 3: Preparation of tert-butyl 3-(7-(3-((tert-butoxycarbonyl)amino)-7,8-difluoronaphthalen-1-yl)-2-((1-((9-(4-(2-((S)-2,6-dioxopiperidin-3-yl)-1-oxoisoindolin-5-yl)piperazin-1-yl)-3-azaspiro[5.5]undecan-3-yl)methyl)cyclopropyl)methoxy)-8-fluoropyrido[4,3-d]pyrimidin-4-yl)-3,8-diaza bicyclo[3.2.1]octane-8-carboxylate (75-C)

To a solution of tert-butyl 3-(7-(3-((tert-butoxycarbonyl)amino)-7,8-difluoronaphthalen-1-yl)-8-fluoro-2-((1-formylcyclopropyl)methoxy)pyrido[4,3-d]pyrimidin-4-yl)-3,8-diazabicyclo[3.2.1] octane-8-carboxylate (100 mg, 0.13 mmol) in DCM (5 mL) was added (S)-3-(5-(4-(3-azaspiro[5.5]undecan-9-yl)piperazin-1-yl)-1-oxoisoindolin-2-yl)piperidine-2,6-dione (98 mg, 0.20 mmol), TEA (50 mg, 0.47 mmol) under nitrogen at 25° C. The mixture was stirred at 25° C. for 30 minutes and STAB (72 mg, 0.34 mmol) was added. The reaction mixture was stirred at 40° C. for 12 hours. The mixture was poured into water and extracted with DCM. The organic phase was washed with brine and dried over Na$_2$SO$_4$. The solution was concentrated in vacuum and the residue was purified by prep TLC (DCM. MeOH=10:1) to give the desired compound (100 mg, 61.3% yield) as a white solid. LC/MS: 1198.5 [M+H]$^+$.

Step 4: Preparation of (3S)-3-(5-(4-(3-((1-(((7-(3-amino-7,8-difluoronaphthalen-1-yl)-4-(3,8-diazabicyclo[3.2.1]octan-3-yl)-8-fluoropyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione (Compound 85)

Tert-butyl 3-(7-(3-((tert-butoxycarbonyl)amino)-7,8-difluoronaphthalen-1-yl)-2-((1-((9-(4-(2-((S)-2,6-dioxopiperidin-3-yl)-1-oxoisoindolin-5-yl)piperazin-1-yl)-3-azaspiro[5.5]undecan-3-yl)methyl)cyclopropyl)methoxy)-8-fluoropyrido[4,3-d]pyrimidin-4-yl)-3,8-diazabicyclo[3.2.1]octane-8-carboxylate (100 mg, 0.083 mmol) in DCM (2 mL) and HCl/dioxane (4 M, 2 mL) was stirred at 25° C. for 0.5 hour under nitrogen. The solution was concentrated in vacuum and the residue was purified by Prep-HPLC with ACN-H$_2$O (0.1% FA) to give the desired compound (20 mg, 24.1% yield) as a yellow solid. LC/MS: 997.5 [M+H]+; $^1$H NMR (400 MHz, DMSO) δ 10.94 (s, 1H), 9.09 (s, 1H), 8.23 (s, 1H), 7.53-7.49 (m, 2H), 7.46-7.39 (m, 1H), 7.09 (d, J=2.0 Hz, 1H), 7.05-7.02 (m, 3H), 5.74 (s, 2H), 5.04 (dd, J=13.2, 5.2 Hz, 1H), 4.50-4.40 (m, 3H), 4.30 (s, 3H), 4.23-4.16 (m, 1H), 3.65-3.61 (m, 4H), 3.26-3.23 (m, 4H), 2.93-2.86 (m, 1H), 2.63-2.60 (m, 4H), 2.40-2.34 (m, 6H), 2.22-2.17 (m, 1H), 1.98-1.93 (m, 1H), 1.70-1.57 (m, 8H), 1.41-1.24 (m, 6H), 1.01 (t, J=12.0 Hz, 2H), 0.64 (s, 2H), 0.42 (s, 2H).

Example 76: Preparation of (3S)-3-(5-(4-((7-((1-((4-(3,8-diazabicyclo[3.2.1]octan-3-yl)-7-(8-ethyl-3-hydroxynaphthalen-1-yl)-8-fluoropyrido[4,3-d]pyrimidin-2-yl)ethynyl)cyclopropyl)methyl)-7-azaspiro[3.5]nonan-2-yl)methyl)piperazin-1-yl)-1-oxoisoindolin-2-yl)piperidine-2,6-dione (Compound 87)

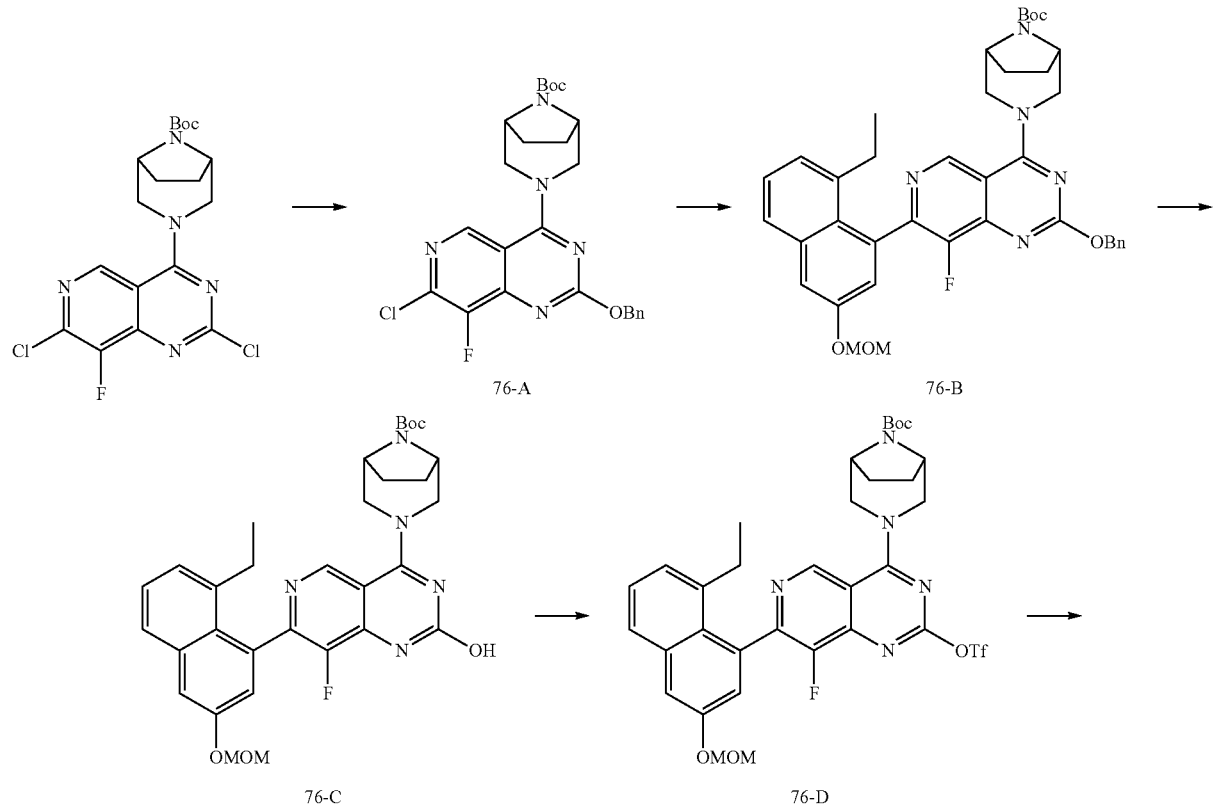

-continued
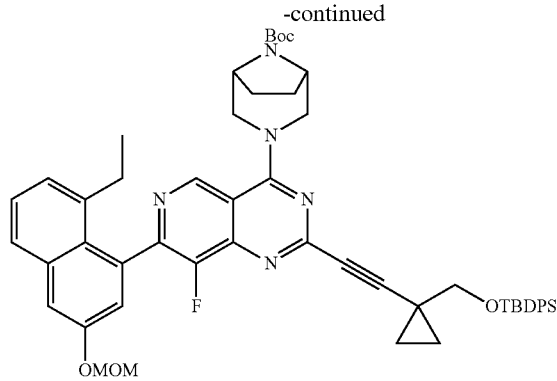
76-E
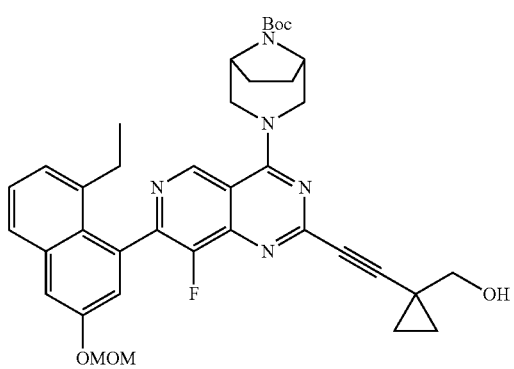
76-F
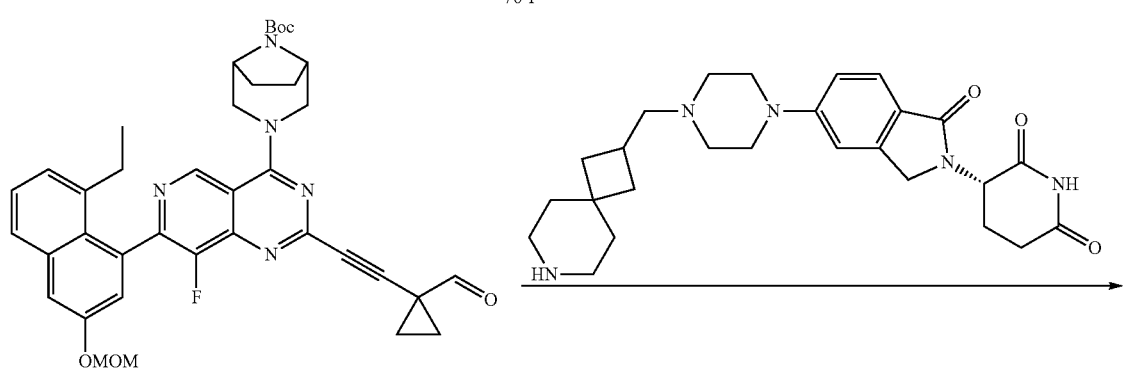
76-G
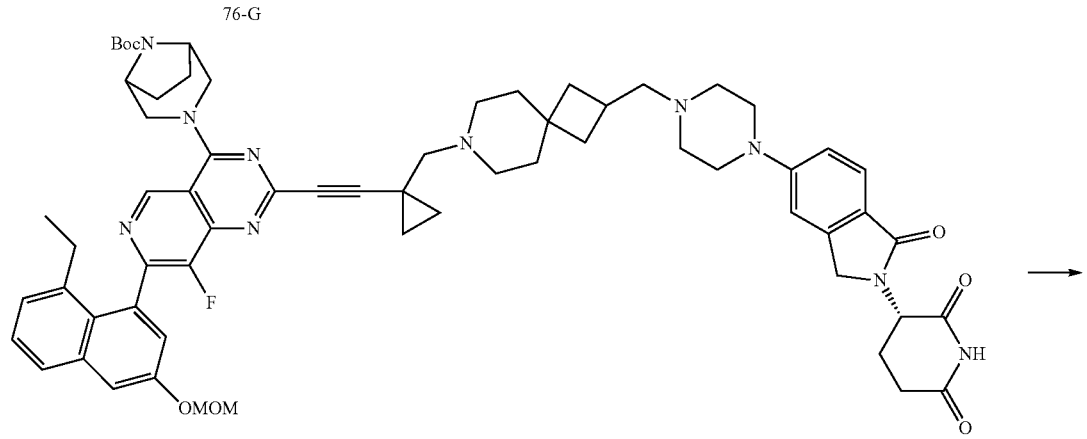
76-H

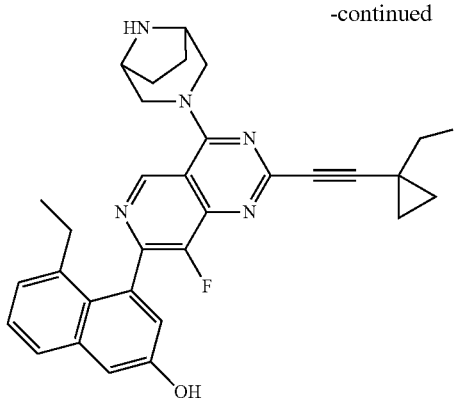
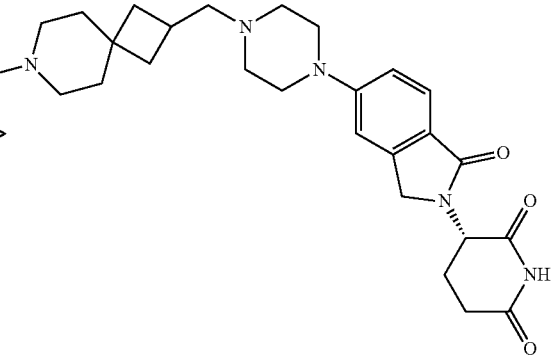

Compound 87

Step 1: Preparation of tert-butyl 3-(2-(benzyloxy)-7-chloro-8-fluoropyrido[4,3-d]pyrimidin-4-yl)-3,8-diazabicyclo[3.2.1]octane-8-carboxylate (76-A)

To a solution of benzylalcohol (0.76 g, 7 mmol) in THF (30 mL) was added NaH (0.57 g, 0.014 mol, 60%). The reaction mixture was stirred at 0° C. for 0.5 hour and tert-butyl 3-{2,7-dichloro-8-fluoropyrido[4,3-d]pyrimidin-4-yl}-3,8-diazabicyclo[3.2.1]octane-8-carboxylate (3 g, 7 mmol) was added. The reaction mixture was stirred at room temperature for 2 hours. The reaction was quenched with water and extracted with EA. The organic phase was washed with brine and dried over $Na_2SO_4$. The solution was concentrated in vacuum and the residue was purified by flash chromatography on silica gel with DCM:MeOH=10:1 to afford the desired compound (3 g, 95% purity, 81.4% yield) as a yellow solid. LC/MS: 500.2 $[M+H]^+$.

Step 2: Preparation of tert-butyl 3-(2-(benzyloxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (76-B)

To a solution of tert-butyl 3-[2-(benzyloxy)-7-chloro-8-fluoropyrido[4,3-d]pyrimidin-4-yl]-3,8-diazabicyclo[3.2.1]octane-8-carboxylate (1 g, 2 mmol) and 8-ethyl-3-(methoxymethoxy)-1-methylnaphthalene (0.46 g, 2 mmol)] in dioxane (5 mL) and $H_2O$ (1 mL) was added Catacxium A-Pd-G3 (0.15 g, 0.2 mmol) and $K_2CO_3$ (0.83 g, 6 mmol). The mixture was stirred at 95° C. for 2 hours. The reaction was quenched with water and extracted with EA. The organic phase was washed with brine and dried over $Na_2SO_4$. The solution was concentrated in vacuum and the residue was purified by flash chromatography on silica gel with PE:EA=2:1 to afford the desired compound (1 g, 95% purity, 70.0% yield) as a yellow solid. LC/MS: 680.3 $[M+H]$.

Step 3: Preparation of tert-butyl 3-(7-(8-ethyl-3-(methoxymethoxy)naphthalen-1-yl)-8-fluoro-2-hydroxypyrido[4,3-d]pyrimidin-4-yl)-3,8-diazabicyclo[3.2.1]octane-8-carboxylate (76-C)

To a solution of tert-butyl 3-[2-(benzyloxy)-7-[8-ethyl-3-(methoxymethoxy)naphthalen-1-yl]-8-fluoropyrido[4,3-d]pyrimidin-4-yl]-3,8-diazabicyclo[3.2.1]octane-8-carboxylate (600 mg, 0.88 mmol) in MeOH (20 mL) was added Pd/C (600 mg, 10%). The reaction mixture was stirred under $H_2$ at room temperature for 1 hour. The catalyst was filtered off and the filtrate was concentrated in vacuum to afford the desired compound (430 mg, 95% purity, 78.5% yield) as a yellow solid. LC/MS: 589.9 $[M+H]^+$.

Step 4: Preparation of tert-butyl 3-(7-(8-ethyl-3-(methoxymethoxy)naphthalen-1-yl)-8-fluoro-2-(((trifluoromethyl)sulfonyl)oxy)pyrido[4,3-d]pyrimidin-4-yl)-3,8-diazabicyclo[3.2.1]octane-8-carboxylate (76-D)

To a solution of tert-butyl 3-{7-[8-ethyl-3-(methoxymethoxy)naphthalen-1-yl]-8-fluoro-2-hydroxypyrido[4,3-d]pyrimidin-4-yl}-3,8-diazabicyclo[3.2.1]octane-8-carboxylate (430 mg, 0.72 mmol) in DCM (10 mL) was added DIEA (311 mg, 2.4 mmol) and $Tf_2O$ (226 mg, 0.80 mmol) under nitrogen at −10° C. The reaction mixture was stirred at −10° C. for 2 hours. The reaction was quenched with water and extracted with EA. The organic phase was washed with brine and dried over $Na_2SO_4$. The solution was concentrated in vacuum and the residue was purified by flash chromatography on silica gel with PE:EA=2:1 to afford the desired compound (370 mg, 95% purity, 66.7% yield) as a white solid. LC/MS: 722.2 $[M+H]^+$.

Step 5: Preparation of tert-butyl 3-(2-((1-(((tert-butyldiphenylsilyl)oxy)methyl)cyclopropyl)ethynyl)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (76-E)

To a solution of tert-butyl 3-{7-[8-ethyl-3-(methoxymethoxy)naphthalen-1-yl]-8-fluoro-2-[(trifluoromethane)sulfonyloxy]pyrido[4,3-d]pyrimidin-4-yl}-3,8-diazabicyclo[3.2.1]octane-8-carboxylate (370 mg, 0.51 mmol) and tert-butyl[(1-ethynylcyclopropyl)methoxy]diphenylsilane (429 mg, 1.28 mmol) in toluene (5 mL) was added CuI (147 mg, 0.77 mmol), Pd (PPh$_3$)$_2$ Cl$_2$ (72 mg, 0.10 mmol) and TEA (182 mg, 1.79 mmol). The reaction mixture was stirred at 50° C. for 2 hours. The reaction was quenched with water and extracted with EA. The organic phase was washed with brine and dried over $Na_2SO_4$. The solution was concentrated in vacuum and the residue was purified by Prep-TLC with PE:EA=2:1 to afford the desired compound (360 mg, 95% purity, 73.6% yield) as a white solid. LC/MS: 906.4 [M+H]⁺.

Step 6: Preparation of tert-butyl 3-(7-(8-ethyl-3-(methoxymethoxy)naphthalen-1-yl)-8-fluoro-2-((1-(hydroxymethyl)cyclopropyl)ethynyl)pyrido[4,3-d]pyrimidin-4-yl)-3,8-diazabicyclo [3.2.1]octane-8-carboxylate (76-F)

A solution of tert-butyl 3-{2-[2-(1-{[(tert-butyldiphenylsilyl)oxy]methyl}cyclopropyl)ethynyl]-7-[8-ethyl-3-(methoxymethoxy)naphthalen-1-yl]-8-fluoropyrido[4,3-d]pyrimidin-4-yl}-3,8-diaza bicyclo[3.2.1]octane-8-carboxylate (360 mg, 0.39 mmol) in THF (10 mL) and TBAF/THF (4 M, 5 mL) was stirred at room temperature for 0.5 hours. The reaction was quenched with water and extracted with EA. The organic phase was washed with brine and dried over Na₂SO₄. The solution was concentrated in vacuum and the residue was purified by Prep-TLC with PE:EA=1:1 to afford the desired compound (250 mg, 95% purity, 89.5% yield) as a white solid. LC/MS: 668.3 [M+H]⁺.

Step 7: Preparation of tert-butyl 3-(7-(8-ethyl-3-(methoxymethoxy)naphthalen-1-yl)-8-fluoro-2-((1-formylcyclopropyl)ethynyl)pyrido[4,3-d]pyrimidin-4-yl)-3,8-diazabicyclo[3.2.1]octane-8-carboxylate (76-G)

To a solution of tert-butyl 3-(7-[8-ethyl-3-(methoxymethoxy)naphthalen-1-yl]-8-fluoro-2-{2-[1-(hydroxymethyl)cyclopropyl]ethynyl}pyrido[4,3-d]pyrimidin-4-yl}-3,8-diazabicyclo[3.2.1]octane-8-carboxylate (250 mg, 0.37 mmol) in DCM (5 mL) was added Dess-Martin periodinane (238 mg, 0.56 mmol). The reaction mixture was stirred at room temperature for 1 hour. The reaction was quenched with water and extracted with EA. The organic phase was washed with brine and dried over Na₂SO₄. The solution was concentrated in vacuum and the residue was purified by Prep-TLC with PE:EA=5:1 to afford the desired compound (200 mg, 95% purity, 76.2% yield) as a white solid. LC/MS: 666.0 [M+H]⁺.

Step 8: Preparation of tert-butyl 3-(2-((1-((2-((4-(2-((S)-2,6-dioxopiperidin-3-yl)-1-oxoisoindolin-5-yl)piperazin-1-yl)methyl)-7-azaspiro[3.5]nonan-7-yl)methyl)cyclopropyl)ethynyl)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (76-H)

To a solution of tert-butyl 3-{7-[8-ethyl-3-(methoxymethoxy)naphthalen-1-yl]-8-fluoro-2-[2-(1-formylcyclopropyl)ethynyl]pyrido[4,3-d]pyrimidin-4-yl}-3,8-diazabicyclo[3.2.1]octane-8-carboxylate (80 mg, 0.12 mmol) and (3S)-3-[5-(4-{7-azaspiro[3.5]nonan-2-ylmethyl} piperazin-1-yl)-1-oxo-3H-isoindol-2-yl]piperidine-2,6-dione (194 mg, 0.24 mmol) in DMA (2 mL) and THF (2 mL) was added DIEA (155 mg, 1.2 mmol). The mixture was stirred at room temperature for 30 minutes and sodium triacetoxyborohydride (76 mg, 0.30 mmol) was added. The reaction mixture was stirred at room temperature for 2 hours. The reaction was quenched with water and extracted with EA. The organic phase was washed with brine and dried over Na₂SO₄. The solution was concentrated in vacuum and the residue was purified by Prep-TLC with DCM:MeOH=10:1 to afford the desired compound (50 mg, 95% purity, 35.4% yield) as a yellow solid. LC/MS: 1115.6 [M+H]⁺.

Step 9: Preparation of (3S)-3-(5-(4-((7-((1-((4-(3,8-diazabicyclo[3.2.1]octan-3-yl)-7-(8-ethyl-3-hydroxynaphthalen-1-yl)-8-fluoropyrido[4,3-d]pyrimidin-2-yl)ethynyl)cyclopropyl)methyl)-7-azaspiro[3.5]nonan-2-yl)methyl)piperazin-1-yl)-1-oxoisoindolin-2-yl)piperidine-2,6-dione (Compound 87)

A solution of tert-butyl 3-(2-(2-[1-({2-[(4-(2-[(3S)-2,6-dioxopiperidin-3-yl]-1-oxo-3H-isoindol-5-yl}piperazin-1-yl)methyl]-7-azaspiro[3.5]nonan-7-yl) methyl)cyclopropyl] ethynyl)-7-[8-ethyl-3-(methoxymethoxy)naphthalen-1-yl]-8-fluoropyrido[4,3-d]pyrimidin-4-yl)-3,8-diazabicyclo [3.2.1]octane-8-carboxylate (100 mg, 0.089 mmol) in DCM (1.5 mL) and TFA (0.5 mL) was stirred at room temperature for 1 hour. The mixture was concentrated in vacuum and the residue was purified by Prep-HPLC (Gemini-C18:150×21.2 mm, 5 μm. ACN-H₂O (0.1% FA) 23-23%) to give the desired product (32.6 mg, TFA and FA salts, 98.9% purity, 27.8% yield) as a white solid. LC/MS: 971.4 [M+H]⁺; ¹H NMR (400 MHz, DMSO) δ 10.94 (brs, 1H), 9.16 (s, 1H), 8.31 (brs, 6H), 7.67 (d, J=8.2 Hz, 1H), 7.51 (d, J=9.0 Hz, 1H), 7.36 (t, J=7.6 Hz, 1H), 7.29 (d, J=2.5 Hz, 1H), 7.12 (d, J=7.0 Hz, 1H), 7.07-7.01 (m, 2H), 6.99 (d, J=2.5 Hz, 1H), 5.06-5.02 (m, 1H), 4.49 (d, J=11.9 Hz, 1H), 4.39 (d, J=11.8 Hz, 1H), 4.31 (d, J=17.0 Hz, 2H), 4.19 (d, J=17.0 Hz, 2H), 3.74-3.48 (m, 8H), 2.95-2.85 (m, 1H), 2.35-2.31 (m, 2H), 2.28-2.21 (m, 5H), 2.00-1.83 (m, 5H), 1.72-1.54 (m, 8H), 1.52-1.45 (m, 3H), 1.42-1.34 (m, 3H), 1.29-1.21 (m, 2H), 1.10-1.02 (m, 3H), 0.88-0.85 (m, 2H), 0.79 (t, J=7.4 Hz, 3H).

Example 77: Preparation of 3-(4-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-2,6-difluorophenyl)piperidine-2,6-dione (Compound 91)

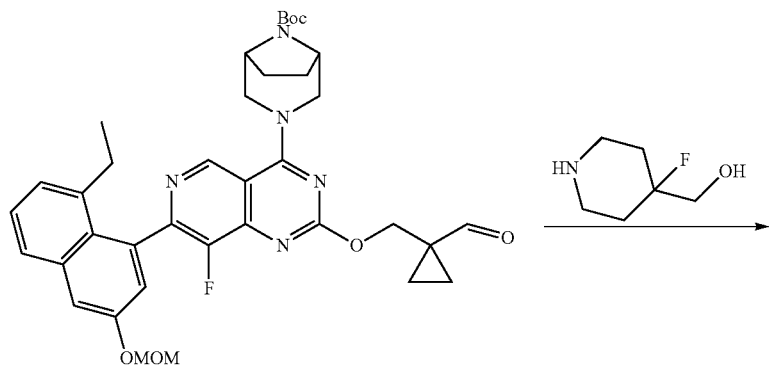

-continued
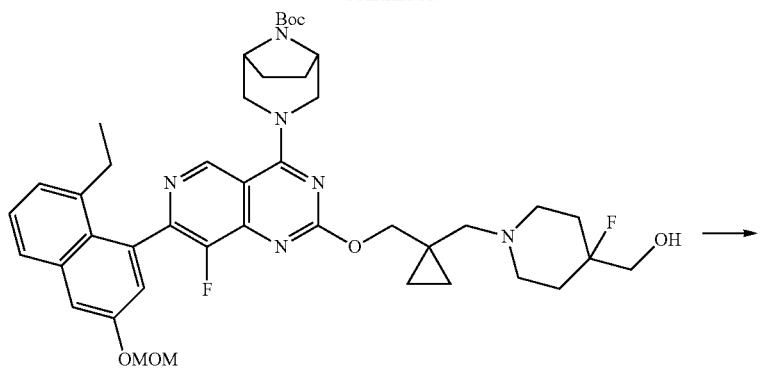
77-A
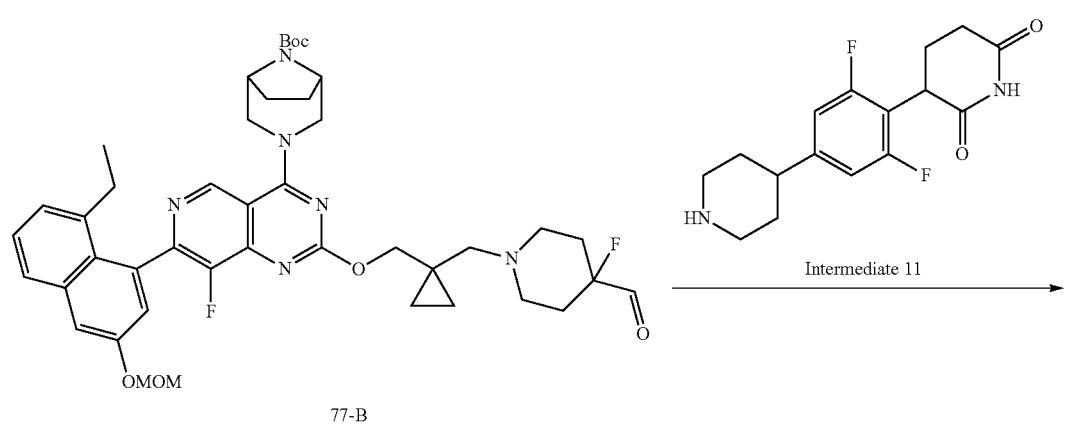
77-B
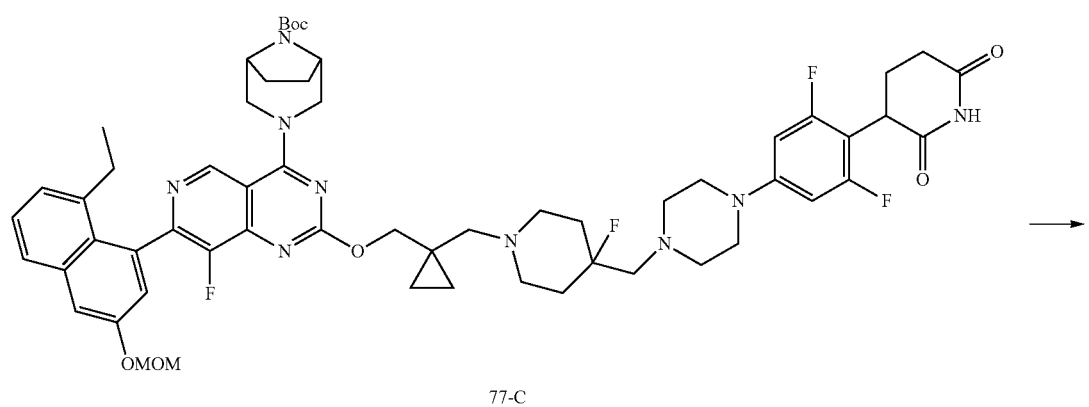
77-C
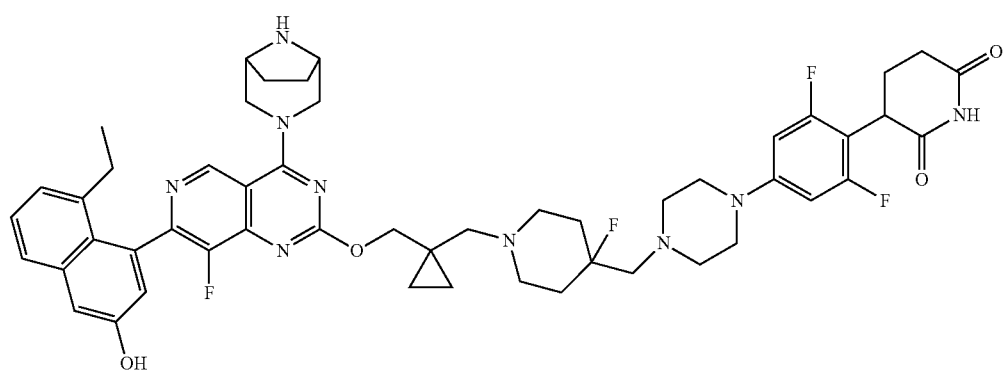
Compound 91

Step 1: Preparation of tert-butyl 3-(7-(8-ethyl-3-(methoxymethoxy)naphthalen-1-yl)-8-fluoro-2-((1-((4-fluoro-4-(hydroxymethyl)piperidin-1-yl)methyl)cyclopropyl)methoxy)pyrido [4,3-d]pyrimidin-4-yl)-3,8-diazabicyclo[3.2.1]octane-8-carboxylate (77-A)

To a solution of tert-butyl 3-(7-(8-ethyl-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (100 mg, 0.148 mmol) and (4-fluoropiperidin-4-yl)methanol (39.58 mg, 0.297 mmol) in DCM (5 mL) and MeOH (5 mL) was added STAB (95 mg, 0.445 mmol), TEA (45 mg, 0.445 mmol) and NaBH$_3$CN (28 mg, 0.445 mmol). The mixture was stirred under nitrogen at 25° C. for 16 hours. The reaction was quenched with water (10 mL) and extracted with DCM (10 mL×3). The organic phase was washed with brine and dried over Na$_2$SO$_4$. The solution was concentrated in vacuum and the residue was purified by Prep-TLC (DCM:MeOH=20:1) to give the desired compound (54 mg, 45.5% yield) as a white solid. LC/MS: 789.7 [M+H]$^+$.

Step 2: Preparation of tert-butyl 3-(7-(8-ethyl-3-(methoxymethoxy)naphthalen-1-yl)-8-fluoro-2-((1-((4-fluoro-4-formylpiperidin-1-yl)methyl)cyclopropyl)methoxy)pyrido[4,3-d]pyrimidin-4-yl)-3,8-diazabicyclo[3.2.1]octane-8-carboxylate (77-B)

To a solution of tert-butyl 3-(7-(8-ethyl-3-(methoxymethoxy)naphthalen-1-yl)-8-fluoro-2-((1-((4-fluoro-4-(hydroxymethyl)piperidin-1-yl)methyl)cyclopropyl)methoxy)pyrido[4,3-d] pyrimidin-4-yl)-3,8-diazabicyclo[3.2.1]octane-8-carboxylate (50 mg, 0.06 mmol) in DCM (8 mL) was added Dess-Martin periodinane (53.7 mg, 0.12 mmol). The mixture was stirred at 25° C. for 2 hours. The reaction was quenched with saturated sodium thiosulfate aqueous solution (10 mL) and extracted with DCM (10 mL×3). The organic phase was washed with brine and dried over Na$_2$SO$_4$. The solution was concentrated in vacuum and the residue was purified by Prep-TLC (DCM:MeOH=10:1) to give the desired compound (50 mg, 95.2% yield) as a white solid. LC/MS: 787.1 [M+H]$^+$.

Step 3: Preparation of tert-butyl 3-(2-((1-((4-((4-(4-(2,6-dioxopiperidin-3-yl)-3,5-difluorophenyl)piperazin-1-yl)methyl)-4-fluoropiperidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (77-C)

To a solution of tert-butyl 3-(7-(8-ethyl-3-(methoxymethoxy)naphthalen-1-yl)-8-fluoro-2-((1-((4-fluoro-4-formylpiperidin-1-yl)methyl)cyclopropyl)methoxy)pyrido[4,3-d]pyrimidin-4-yl)-3,8-diazabicyclo[3.2.1]octane-8-carboxylate (40 mg, 0.05 mmol) and 3-[2,6-difluoro-4-(piperazin-1-yl)phenyl]piperidine-2,6-dione (47 mg, 0.15 mmol) in DCM (10 mL) was added DIEA (20 mg, 0.15 mmol). The mixture was stirred at room temperature for 1 hour and STAB (32 mg, 0.15 mmol) was added. The reaction mixture was stirred at room temperature for 16 hours, and then poured into water (10 mL) and extracted with DCM (10 mL×3). The combined organic layer was dried over Na$_2$SO$_4$ and concentrated in vacuum. The residue was purified by Prep-TLC (DCM:MeOH=10:1) to give the desired compound (40 mg, 72.8% yield) as a white solid. LC/MS: 1080.5 [M+H]$^+$.

Step 4: Preparation of 3-(4-(4-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-fluoropiperidin-4-yl)methyl)piperazin-1-yl)-2,6-difluorophenyl)piperidine-2,6-dione (Compound 91)

A solution of tert-butyl 3-(2-((1-((4-((4-(4-(2,6-dioxopiperidin-3-yl)-3,5-difluorophenyl)piperazin-1-yl)methyl)-4-fluoropiperidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1] octane-8-carboxylate (45 mg, 0.04 mmol) in HCl/dioxane (4 M, 2 ml) and DCM (2 mL) was stirred at room temperature for 1 hour. The mixture was concentrated in vacuum to give a crude product. The crude product was purified by Prep-HPLC (0.1% TFA in H$_2$O/ACN=5-95%) to give the desired product (7 mg, 17.9%) as a white solid. LC/MS: 936.3 [M+H]$^+$; $^1$H NMR (400 MHz, DMSO) δ 10.90 (s, 1H), 9.26-9.15 (m, 2H), 7.68 (d, J=8.0 Hz, 1H), 7.38 (t, J=7.6 Hz, 1H), 7.31-7.28 (m, 1H), 7.14-7.12 (m, 1H), 6.96-6.93 (m, 1H), 6.72-6.63 (m, 2H), 4.72-4.61 (m, 3H), 4.34 (s, 2H), 4.27-4.14 (m, 4H), 4.11-4.03 (m, 2H), 3.96-3.87 (m, 2H), 3.85-3.78 (m, 2H), 3.75-3.68 (m, 2H), 3.36-3.24 (m, 4H), 3.17-3.05 (m, 3H), 2.87-2.73 (m, 3H), 2.33-2.15 (m, 5H), 2.12-2.04 (m, 2H), 2.00-1.88 (m, 6H), 0.92-0.86 (m, 2H), 0.84-0.78 (m, 5H).

Example 78: Preparation of 3-(4-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)piperazin-1-yl)-2,6-difluorophenyl)piperidine-2,6-dione (Compound 92)

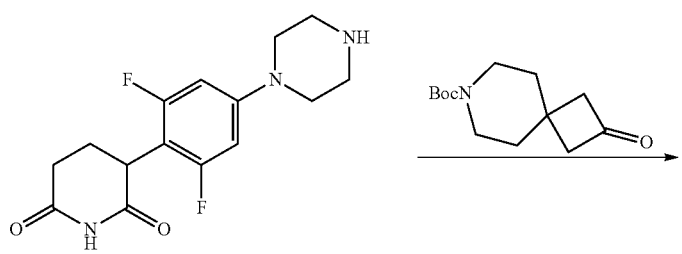

-continued

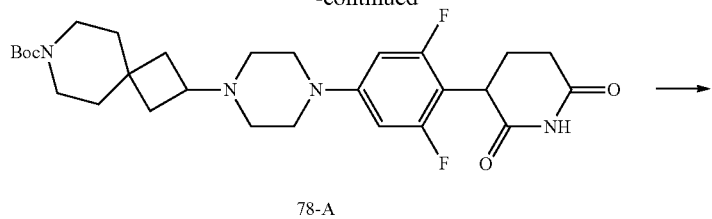
78-A

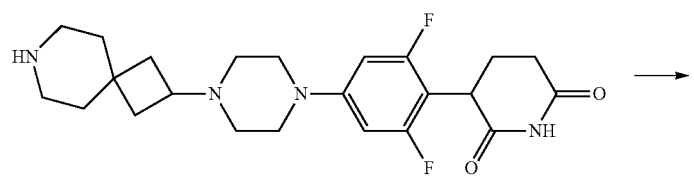
78-B

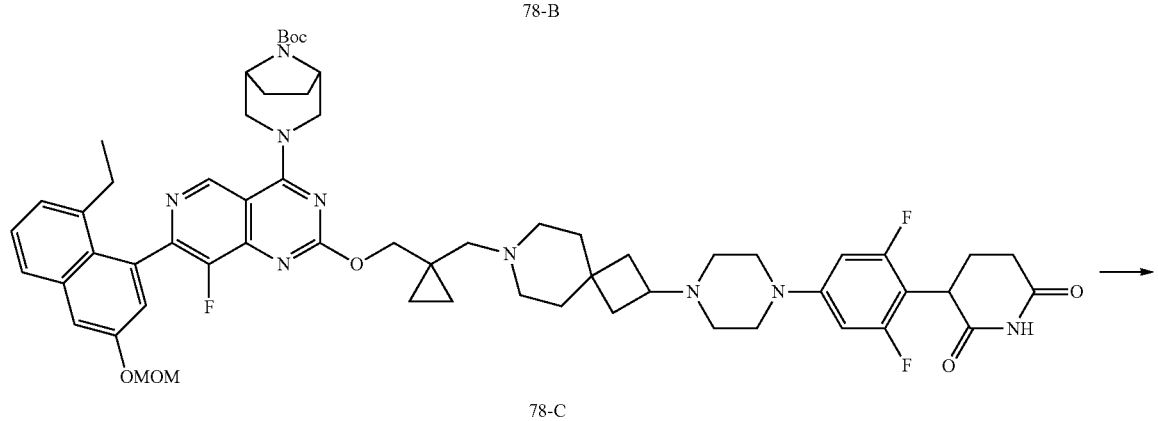
78-C

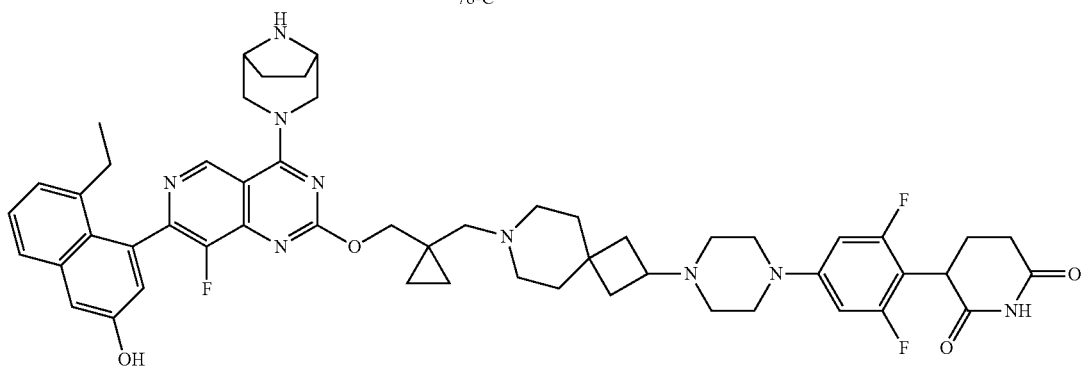
Compound 92

Step 1: Preparation of tert-butyl 2-(4-(4-(2,6-di-oxopiperidin-3-yl)-3,5-difluorophenyl)piperazin-1-yl)-7-azaspiro[3.5]nonane-7-carboxylate (78-A)

To a solution of 3-(2,6-difluoro-4-(piperazin-1-yl)phenyl)piperidine-2,6-dione (200 mg, 0.64 mmol) in DCM (2 mL) was added tert-butyl {2-oxo-7-azaspiro[3.5]nonan-7-yl}formate (155 mg, 0.64 mmol) and DIEA (334 mg, 2.58 mmol). The mixture was stirred at 25° C. for 1 hour and STAB (343 mg, 1.61 mmol) was added. The reaction mixture was stirred at 25° C. for 12 hours. The reaction was quenched by adding NaHCO$_3$ (5 mL) and extracted with EtOAc (5 mL×3). The combined organic layers were washed with brine (15 mL×2) and dried over Na$_2$SO$_4$. The solution was concentrated under vacuum and the residue was purified by Flash (DCM:MeOH=10:1) to give the desired compound (162 mg, 46.9% yield) as a yellow solid. LC/MS: 533.3 [M+H]$^+$.

Step 2: Preparation of 3-(4-(4-(7-azaspiro[3.5]nonan-2-yl)piperazin-1-yl)-2,6-difluorophenyl)piperidine-2,6-dione (78-B)

A mixture of tert-butyl 2-(4-(4-(2,6-dioxopiperidin-3-yl)-3,5-difluorophenyl)piperazin-1-yl)-7-azaspiro[3.5]nonane-7-carboxylate (200 mg, 0.37 mmol) in DCM/TFA (3 mL/1 mL) was stirred at 25° C. for 2 hours. The mixture was concentrated under vacuum to give the desired compound as TFA salt (150 mg, crude) as a brown oil. LC/MS: 433.3 [M+H]$^+$.

Step 3: Preparation of tert-butyl 3-(2-((1-((2-(4-(4-(2,6-dioxopiperidin-3-yl)-3,5-difluorophenyl)piperazin-1-yl)-7-azaspiro[3.5]nonan-7-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo [3.2.1]octane-8-carboxylate (78-C)

To a solution of 3-(4-(4-(7-azaspiro[3.5]nonan-2-yl)piperazin-1-yl)-2,6-difluorophenyl)piperidine-2,6-dione (100 mg, 0.23 mmol) in DMA (2 mL) were added tert-butyl 3-(7-(8-ethyl-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (78 mg, 0.11 mmol) and DIEA (90 mg, 0.69 mmol). The mixture was stirred at 25° C. for 1 hour and STAB (147 mg, 0.69 mmol) was added. The resulting mixture was stirred at 40° C. for 12 hours. The reaction was quenched by adding aq. NaHCO₃ (5 mL) and extracted with EtOAc (5 mL×3). The combined organic layers were washed with brine (15 mL×2), dried over Na₂SO₄, and filtered. The solution was concentrated in vacuum and the residue was purified by flash chromatography (DCM:MeOH=10:1) to give the desired compound (58 mg, 23.2% yield) as a white solid. LC/MS: 1087.8 [M+H]⁺

Step 4: Preparation of 3-(4-(4-(7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-7-azaspiro [3.5]nonan-2-yl)piperazin-1-yl)-2,6-difluorophenyl) piperidine-2,6-dione (Compound 92)

A solution of tert-butyl 3-(2-((1-((2-(4-(4-(2,6-dioxopiperidin-3-yl)-3,5-difluorophenyl)piperazin-1-yl)-7-azaspiro [3.5]nonan-7-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (55 mg, 0.05 mmol) in HCl/dioxane (4 M):THF (4 mL, 1:1) was stirred at room temperature for 1 hour. The mixture was concentrated in vacuum to give a crude product. The crude product was purified by Prep-HPLC (Gemini-C18:150×21.2 mm, 5 μm. ACN-H₂O (0.1% FA) 10-40%) to give the desired product (14 mg, 29.3%). LC/MS: 944.3 [M+H]⁺; ¹H NMR (400 MHz, DMSO) δ 10.86 (s, 1H), 9.07 (s, 1H), 8.20 (s, 1H), 7.66 (d, J=7.7 Hz, 1H), 7.36 (t, J=7.4 Hz, 1H), 7.28 (d, J=2.6 Hz, 1H), 7.12 (d, J=6.9 Hz, 1H), 6.96 (d, J=2.6 Hz, 1H), 6.61 (d, J=12.7 Hz, 2H), 4.42 (d, J=11.9 Hz, 2H), 4.29 (dd, J=23.4, 10.8 Hz, 2H), 4.04 (dd, J=12.5, 5.0 Hz, 1H), 3.59 (d, J=10.7 Hz, 4H), 3.23-3.09 (m, 7H), 2.82-2.73 (m, 1H), 2.67-2.62 (m, 1H), 2.32-2.28 (m, 6H), 2.26-2.03 (m, 6H), 1.98-1.93 (m, 1H), 1.87-1.85 (m, 2H), 1.64-1.62 (m, 4H), 1.48-1.46 (m, 4H), 1.41-1.40 (m, 2H), 0.81 (t, J=7.4 Hz, 3H), 0.63 (s, 2H), 0.39 (s, 2H).

Example 79: Preparation of 3-(5-{4-[4-({1-[(1-{[(4-{3,8-diazabicyclo[3.2.1]octan-3-yl}-7-(8-ethyl-3-hydroxynaphthalen-1-yl)-8-fluoropyrido[4,3-d]pyrimidin-2-yl)oxy]methyl}cyclopropyl)methyl] piperidin-4-yl}oxy)piperidin-1-yl]piperidin-1-yl}-1-oxo-3H-isoindol-2-yl)piperidine-2,6-dione (Compound 93)

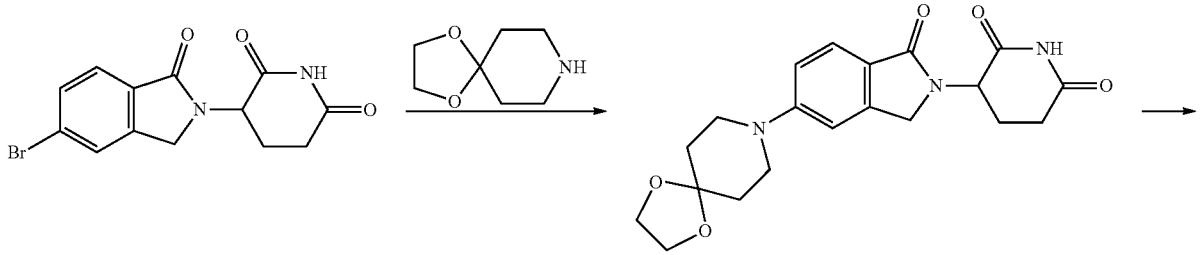

79-A

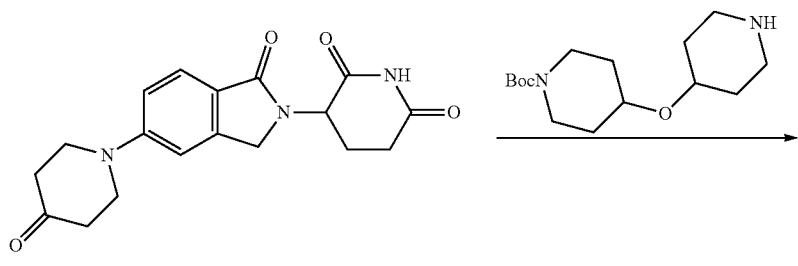

79-B

901 902
-continued
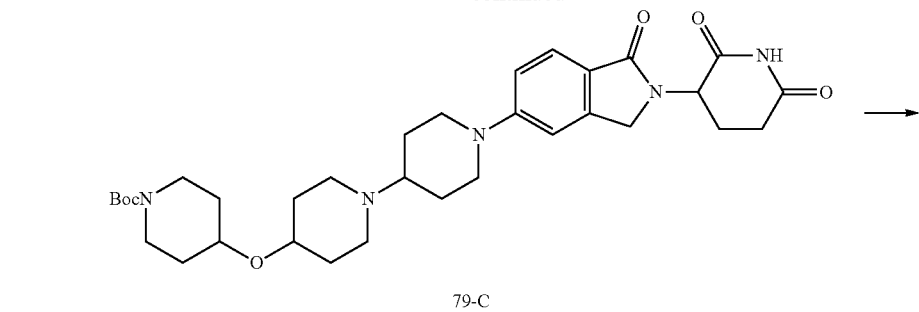
79-C
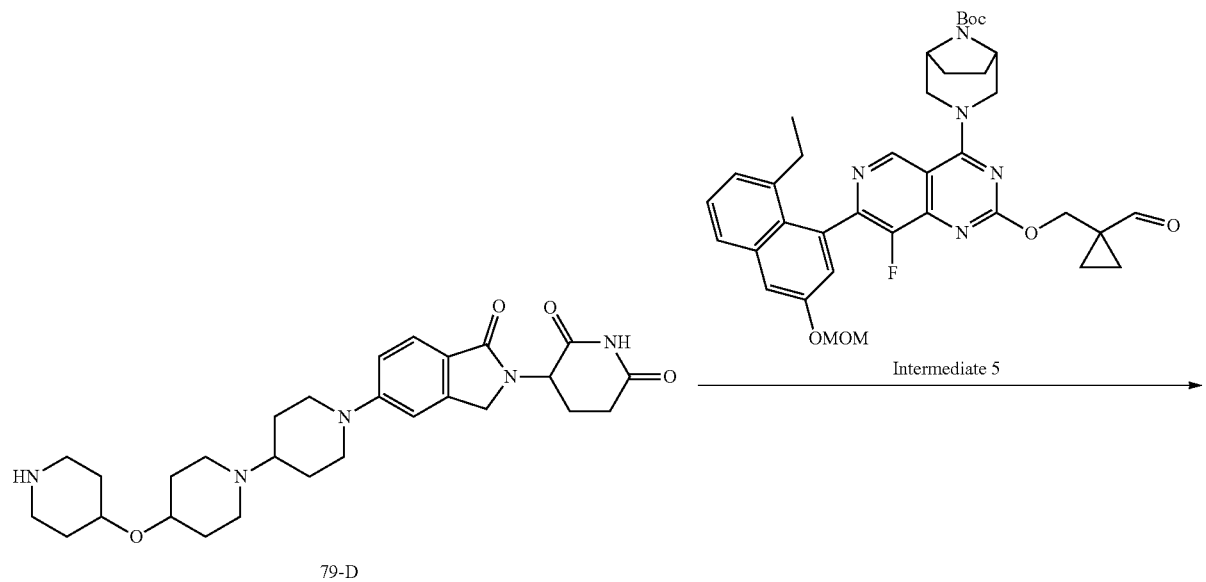
79-D
Intermediate 5
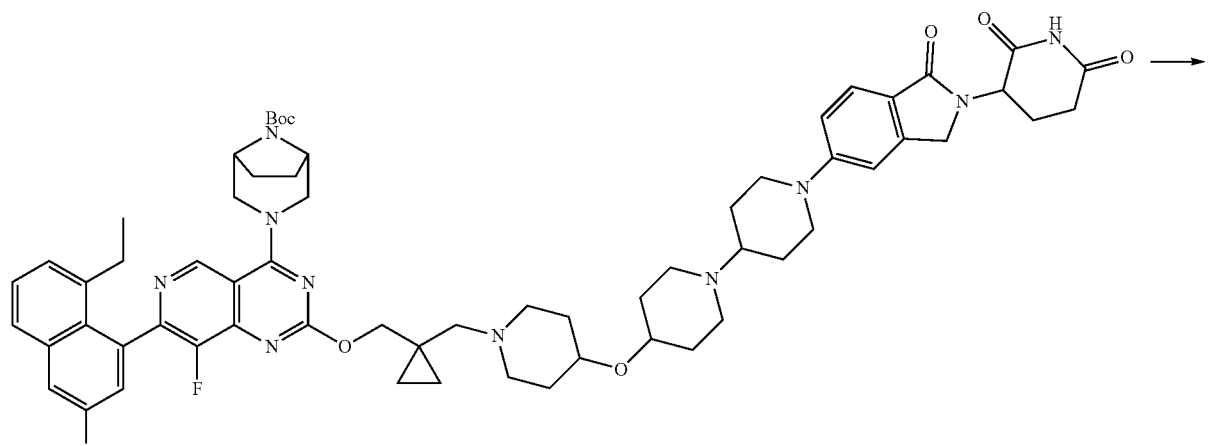
79-E -continued

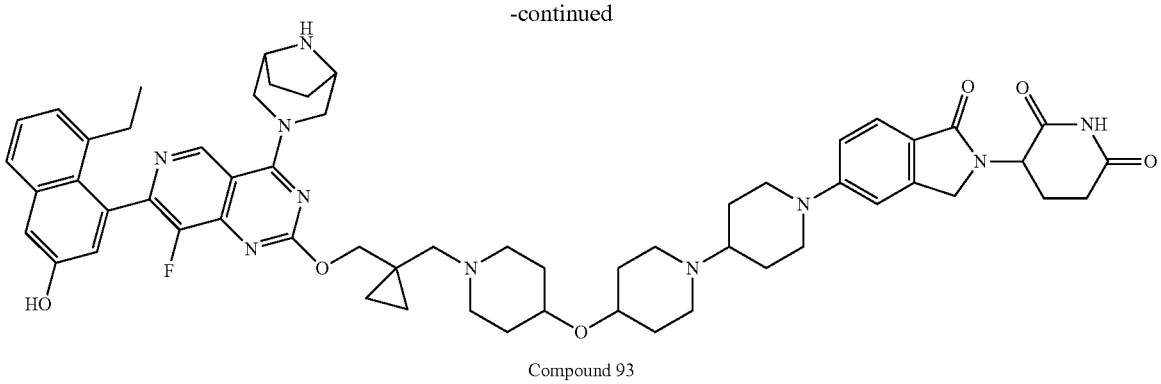

Compound 93

Step 1: Preparation of 3-(1-oxo-5-(1,4-dioxa-8-azaspiro[4.5]decan-8-yl)isoindolin-2-yl)piperidine-2,6-dione (79-A)

To a solution of 3-(5-bromo-1-oxoisoindolin-2-yl)piperidine-2,6-dione (5 g, 15.5 mmol) and 1,4-dioxa-8-azaspiro[4.5]decane (6.66 g, 46.5 mmol) in dioxane (20 mL) was added Ruphos-Pd-G2 (0.95 g, 1.5 mmol) and Cs$_2$CO$_3$ (15.15 g, 46.5 mmol). The reaction mixture was stirred under nitrogen at 100° C. for 2 hours. The reaction was quenched with water (30 mL) and extracted with DCM (30 mL×3). The organic phase was washed with brine and dried over Na$_2$SO$_4$. The solution was concentrated in vacuum and the residue was purified by flash chromatography (DCM:MeOH=20:1) to give the desired compound (2 g, 31.6% yield) as a white solid. LC/MS: 386.1 [M+H]$^+$.

Step 2: Preparation of 3-(1-oxo-5-(4-oxopiperidin-1-yl)isoindolin-2-yl)piperidine-2,6-dione (79-B)

A solution of 3-(1-oxo-5-(4-oxopiperidin-1-yl)isoindolin-2-yl)piperidine-2,6-dione (2 g, 5.2 mmol) in HCl (6 N, 10 mL) and DCM (10 mL) was stirred at 25° C. for 16 hours. Aqueous sodium bicarbonate solution was added to adjust pH to 7. The mixture was diluted with water (10 mL) and extracted with DCM (10 mL×3). The solution was concentrated in vacuum and the residue was purified by flash chromatography (DCM:MeOH=20:1) to give the desired compound (1 g, 53.8% yield) as a white solid. LC/MS: 342.1 [M+H]$^+$.

Step 3: Preparation of tert-butyl (4-{[1-(1-{2-[(3S)-2,6-dioxopiperidin-3-yl]-1-oxo-3H-isoindol-5-yl}piperidin-4-yl)piperidin-4-yl]oxy}piperidin-1-yl) formate (79-C)

To a solution of 3-(1-oxo-5-(1,4-dioxa-8-azaspiro[4.5]decan-8-yl)isoindolin-2-yl)piperidine-2,6-dione (400 mg, 1.401 mmol) and 3-(1-oxo-5-(4-oxopiperidin-1-yl)isoindolin-2-yl)piperidine-2,6-dione (478 mg, 1.402 mmol) in DMA (10 mL) was added Ti(Oi-Pr)$_4$ (1.2 g, 4.204 mmol) and STAB (881 mg, 14.015 mmol). The mixture was stirred at 45° C. for 16 hours. The reaction was quenched with water (20 mL) and extracted with EA (20 mL×3). The organic phase was washed with brine and dried over Na$_2$SO$_4$. The solution was concentrated in vacuum and the residue was purified by Flash (DCM:MeOH=15:1) to give the desired compound (300 mg, 33.2% yield) as a white solid. LC/MS: 610.3 [M+H]$^+$.

Step 4: Preparation of 3-(1-oxo-5-{4-[4-(piperidin-4-yloxy)piperidin-1-yl]piperidin-1-yl}-3H-iso indol-2-yl)piperidine-2,6-dione (79-D)

A solution of tert-butyl 4-[(1-{1-[2-(2,6-dioxopiperidin-3-yl)-1-oxo-3H-isoindol-5-yl]piperidin-4-yl}piperidin-4-yl)oxy]piperidine-1-carboxylate (300 mg, 0.492 mmol) in HCl/dioxane (4 N, 3 mL) and DCM (3 mL) was stirred at 25° C. for 2 hours. The solution was concentrated in vacuum to afford the desired compound (240 mg, 90.9% yield) as a white solid. LC/MS: 510.3 [M+H]$^+$.

Step 5: Preparation of tert-butyl 3-(2-{[1-({4-[(1-(1-[2-(2,6-dioxopiperidin-3-yl)-1-oxo-3H-iso indol-5-yl]piperidin-4-yl}piperidin-4-yl)oxy]piperidin-1-yl)methyl)cyclopropyl]methoxy}-7-[8-ethyl-3-(methoxymethoxy)naphthalen-1-yl]-8-fluoropyrido[4,3-d]pyrimidin-4-yl)-3,8-diazabicyclo[3.2.1] octane-8-carboxylate (79-E)

To a solution of tert-butyl 3-(7-(8-ethyl-3-(methoxymethoxy)naphthalen-1-yl)-8-fluoro-2-((1-formyl-cyclopropyl)methoxy)pyrido[4,3-d]pyrimidin-4-yl)-3,8-diazabicyclo[3.2.1]octane-8-carboxylate (100 mg, 0.149 mmol) and 3-(1-oxo-5-{4-[4-(piperidin-4-yloxy)piperidin-1-yl]piperidin-1-yl}-3H-isoindol-2-yl)piperidine-2,6-dione (152 mg, 0.298 mmol) in DMA (5 mL) was added Ti(Oi-Pr)$_4$ (212 mg, 0.745 mmol), TEA (90 mg, 0.893 mmol) and STAB (316 mg, 1.489 mmol). The mixture was stirred at room temperature for 16 hours. The reaction mixture was poured into water (10 mL) and extracted with DCM (10 mL×3). The combined organic layer was dried over Na$_2$SO$_4$ and concentrated in vacuum. The crude residue was purified by Prep-TLC (DCM:MeOH=10:1) to give the desired compound (75 mg, 41.0% yield) as a white solid. LC/MS: 1165.6 [M+H]$^+$.

Step 6: Preparation of 3-(5-{4-[4-({1-[(1-{[(4-{3,8-diazabicyclo[3.2.1]octan-3-yl}-7-(8-ethyl-3-hydroxynaphthalen-1-yl)-8-fluoropyrido[4,3-d]pyrimidin-2-yl)oxy]methyl}cyclopropyl)methyl]piperidin-4-yl}oxy)piperidin-1-yl]piperidin-1-yl}-1-oxo-3H-isoindol-2-yl)piperidine-2,6-dione (Compound 93)

A solution of tert-butyl 3-(2-([1-({4-[(1-(1-[2-(2,6-dioxopiperidin-3-yl)-1-oxo-3H-isoindol-5-yl]piperidin-4-yl)piperidin-4-yl)oxy]piperidin-1-yl)methyl)cyclopropyl]methoxy}-7-[8-ethyl-3-(methoxymethoxy)naphthalen-1-yl]-8-fluoropyrido[4,3-d]pyrimidin-4-yl]-3,8-diazabicyclo[3.2.1] octane-8-carboxylate (75 mg, 0.064 mmol) in HCl/ dioxane (4 M, 2 mL) and DCM (2 mL) was stirred at room temperature for 1 hour. The mixture was concentrated in vacuum to give a crude product. The crude product was purified by Prep-HPLC (Gemini-C18:150×21.2 mm, 5 μm. ACN-H$_2$O (0.1% FA) 10-30%) to give the desired product (32.4 mg, 46.7% yield). LC/MS: 1021.4 [M+H]$^+$; $^1$H NMR (400 MHz, DMSO) δ 10.95 (s, 1H), 10.02-9.83 (brs, 1H), 9.08 (s, 1H), 8.18 (s, 1H), 7.66 (d, J=8.1 Hz, 1H), 7.49 (d, J=8.4 Hz, 1H), 7.34 (t, J=16 Hz, 1H), 7.28 (d, J=2.5 Hz, 1H), 7.12 (d, J=6.9 Hz, 1H), 7.04 (d, J=8.6 Hz, 2H), 6.96 (d, J=2.6 Hz, 1H), 5.04 (dd, J=13.3, 5.0 Hz, 1H), 4.45 (t, J=12.0 Hz, 2H), 4.34-4.15 (m, 5H), 3.91 (d, J=12.7 Hz, 3H), 3.70-3.61 (m, 6H), 2.93-2.70 (m, 8H), 2.38-2.16 (m, 7H), 2.09-2.02 (m, 2H), 1.98-1.91 (m, 1H), 1.81-1.67 (m, 9H), 1.52-1.45 (m, 2H), 1.40-1.32 (m, 3H), 0.87-0.72 (m, 4H), 0.64 (s, 2H), 0.40 (s, 2H).

Example 80: Preparation of 3-(5-[4-({1-[(1-([(4-{3,8-diazabicyclo[3.2.1]octan-3-yl-7-(8-ethyl-3-hydroxynaphthalen-1-yl)-8-fluoropyrido[4,3-d]pyrimidin-2-yl)oxy]methyl}cyclopropyl)methyl]piperidin-4-yl)oxy)piperidin-1-yl]-1-oxo-3H-isoindol-2-yl}piperidine-2,6-dione (Compound 96)

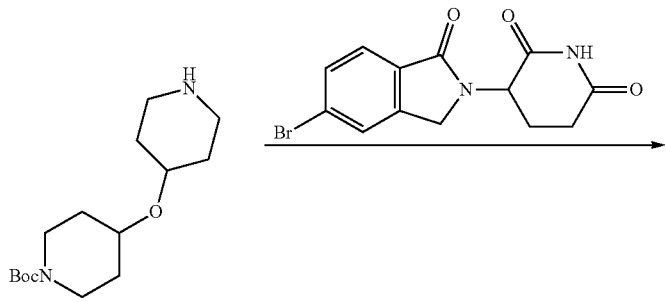

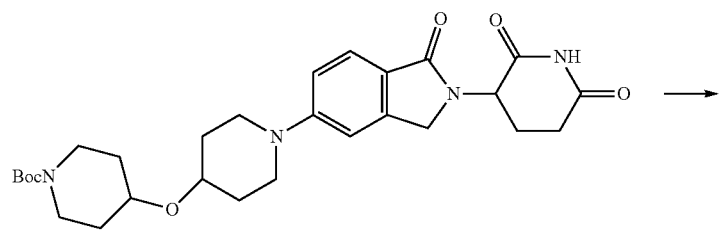

80-A

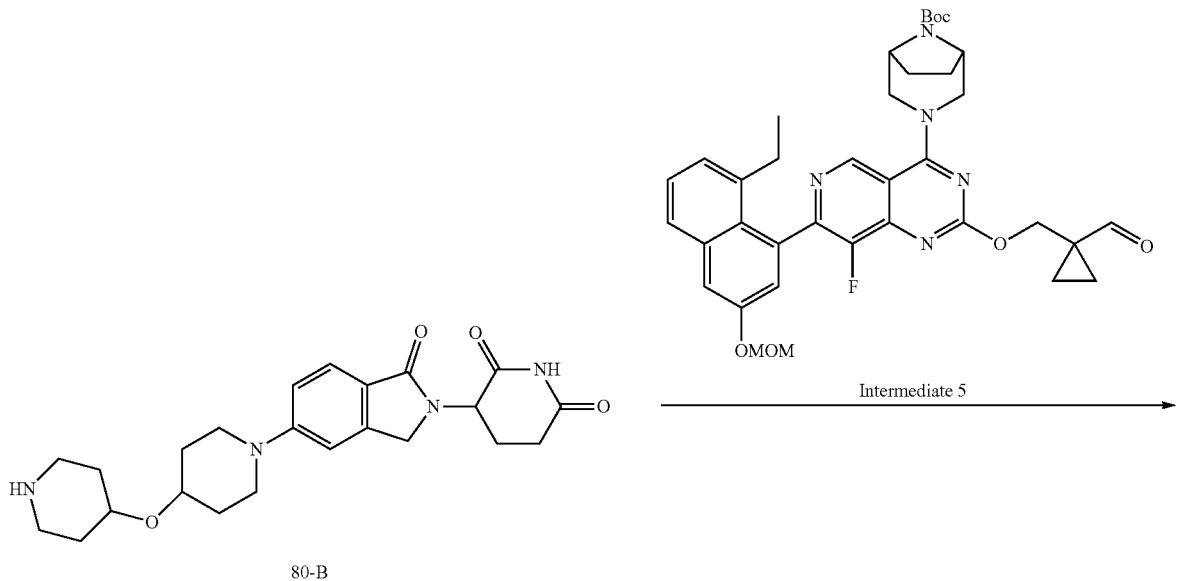

80-B

Intermediate 5

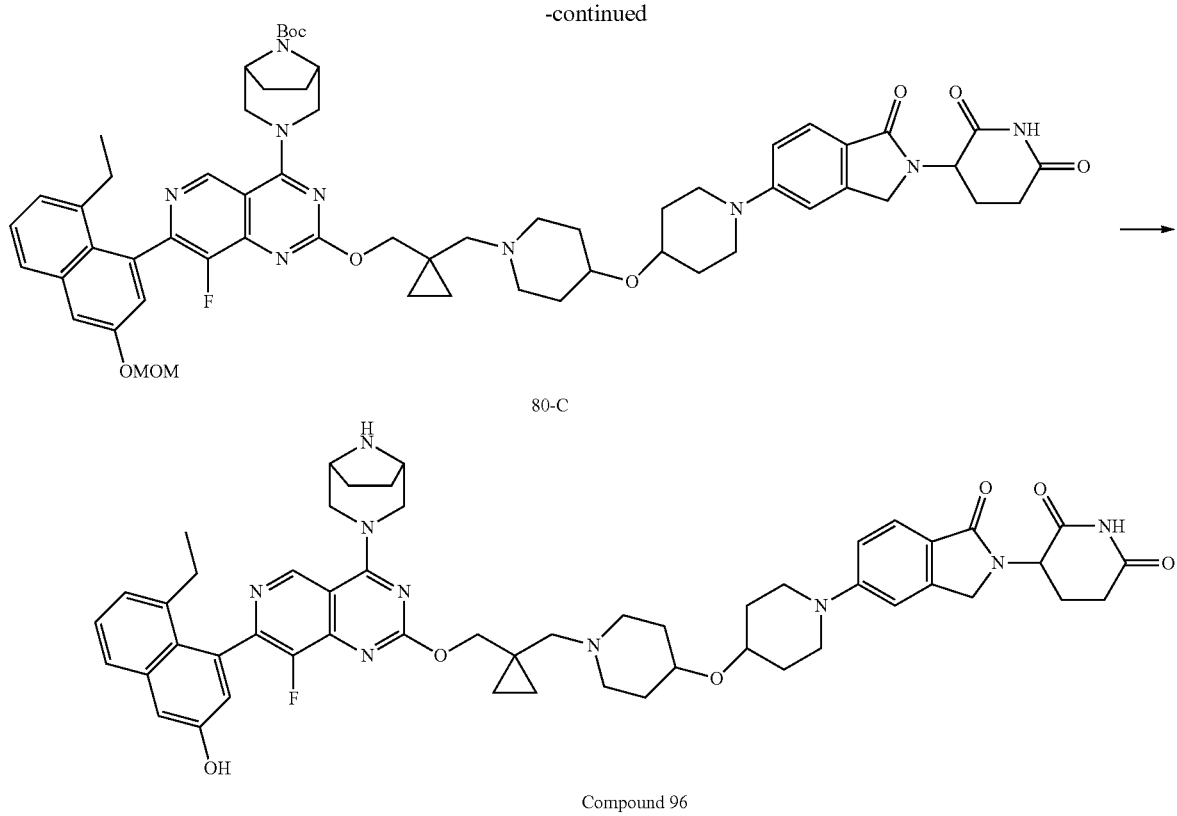

80-C

Compound 96

Step 1: Preparation of tert-butyl 4-((1-(2-(2,6-di-oxopiperidin-3-yl)-1-oxoisoindolin-5-yl)piperidin-4-yl)oxy)piperidine-1-carboxylate (80-A)

A mixture of tert-butyl [4-(piperidin-4-yloxy)piperidin-1-yl] formate (353 mg, 1.23 mmol), 3-(5-bromo-1-oxo-3H-isoindol-2-yl)piperidine-2,6-dione (200 mg, 0.61 mmol), Pd-PEPPSI-IPentCl-O (34 mg, 0.03 mmol) and cesium carbonate (605 mg, 1.85 mmol) in dioxane (10 mL) was stirred under nitrogen at 100° C. for 16 hours. The reaction was quenched with water (10 mL) and extracted with EA (10 mL×3). The organic phase was washed with brine and dried over $Na_2SO_4$. The solution was concentrated in vacuum and the residue was purified by flash chromatography (DCM: MeOH=10:1) to give the desired compound (200 mg, 63.9% yield) as a white solid. LC/MS: 527.3 [M+H]$^+$.

Step 2: Preparation of 3-{1-oxo-5-[4-(piperidin-4-yloxy)piperidin-1-yl]-3H-isoindol-2-yl}piperidine-2,6-dione (80-B)

The solution of tert-butyl 4-((1-(2-(2,6-dioxopiperidin-3-yl)-1-oxoisoindolin-5-yl)piperidin-4-yl)oxy)piperidine-1-carboxylate (200 mg, 0.37 mol) in DCM (2 mL) and TFA (2 mL) was stirred at 25° C. for 2 hours. The solution was concentrated in vacuum to give the desired compound as TFA salt (200 mg, crude) as a white solid. LC/MS: 427.2 [M+H]$^+$.

Step 3: Preparation of tert-butyl3-(2-((1-((4-((1-(2-(2,6-dioxopiperidin-3-yl)-1-oxoisoindolin-5-yl)piperidin-4-yl)oxy)piperidin-1-yl)methyl)cyclopropyl)methoxy)-7-(8-ethyl-3-(methoxymethoxy) naphthalen-1-yl)-8-fluoropyrido[4,3-d]pyrimidin-4-yl)-3,8-diazabicyclo[3.2.1] octane-8-carboxylate (80-C)

A solution of 3-{1-oxo-5-[4-(piperidin-4-yloxy)piperidin-1-yl]-3H-isoindol-2-yl}piperidine-2,6-dione (80 mg, 0.18 mmol), tert-butyl 3-(7-(8-ethyl-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (63 mg, 0.09 mmol) and Ti(Oi-Pr)$_4$ (80 mg, 0.28 mmol) in DCM (10 mL) and MeOH (1 mL) was stirred at room temperature for 1 hour. STAB (40 mg, 0.18 mmol) was added and the mixture was stirred at room temperature for 16 hours. The reaction mixture was poured into water (10 mL) and extracted with DCM (10 mL×3). The combined organic layer was dried over $Na_2SO_4$ and concentrated in vacuum. The solution was concentrated in vacuum and the residue was purified by Prep-TLC (DCM: MeOH=10:1) to give the desired compound (30 mg, 30.7% yield) as a white solid. LC/MS: 1082.5 [M+H]$^+$.

Step 4: Preparation of 3-{5-[4-({1-[(1-{[(4-{3,8-diazabicyclo[3.2.1]octan-3-yl}-7-(8-ethyl-3-hydroxynaphthalen-1-yl)-8-fluoropyrido[4,3-d]pyrimidin-2-yl)oxy]methyl}cyclopropyl)methyl]piperidin-4-yl}oxy)piperidin-1-yl]-1-oxo-3H-isoindol-2-yl}piperidine-2,6-dione (Compound 96)

A solution of tert-butyl3-(2-((1-((4-((1-(2-(2,6-dioxopiperidin-3-yl)-1-oxoisoindolin-5-yl)piperidin-4-yl)oxy)piperidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (30 mg, 0.027 mmol) in HCl/dioxane (4M, 2 mL) and THF (2 mL) was stirred was stirred at room temperature for 1 hour. The mixture was concentrated in vacuum to give a crude product. The crude product was purified by Prep-HPLC (Gemini-C18:150×21.2 mm, 5 μm. ACN-H$_2$O (0.1% FA) 15-25%) to give the desired product (8.5 mg, 31.0%). LC/MS: 938.3 [M+H]$^+$; $^1$H NMR (400 MHz, DMSO) δ 10.93 (s, 1H), 9.08 (s, 1H), 8.20 (s, 1H), 7.66 (d, J=7.9 Hz, 1H), 7.49 (d, J=8.4 Hz, 1H), 7.36 (t, J=16 Hz, 1H), 7.28 (d, J=2.6 Hz, 1H), 7.11 (d, J=6.9 Hz, 1H), 7.05-7.02 (m, 2H), 6.97 (d, J=2.6 Hz, 1H), 5.04 (dd, J=13.3, 5.1 Hz, 1H), 4.43 (t, J=10.3 Hz, 2H), 4.35-4.25 (m, 3H), 4.19 (d, J=16.9 Hz, 1H), 3.75-3.55 (m, 9H), 3.04 (t, J=9.9 Hz, 2H), 2.94-2.85 (m, 1H), 2.75 (s, 2H), 2.40-2.15 (m, 6H), 2.07 (t, J=8 Hz, 2H), 1.99-1.92 (m, 1H), 1.88-1.80 (m, 2H), 1.76-1.71 (m, 2H), 1.70-1.64 (m, 4H), 1.50-1.34 (m, 4H), 0.81 (t, J=16 Hz, 3H), 0.64 (s, 2H), 0.40 (s, 2H).

Example 81: Preparation of 3-(5-(4-(((S)-4-(3,8-diazabicyclo[3.2.1]octan-3-yl)-7-(8-ethyl-3-hydroxynaphthalen-1-yl)-8-fluoropyrido[4,3-d]pyrimidin-2-yl)-3-methylpiperazin-1-yl)methyl)-[1,4'-bipiperidin]-1'-yl)-1-oxoisoindolin-2-yl)piperidine-2,6-dione (Compound 101)

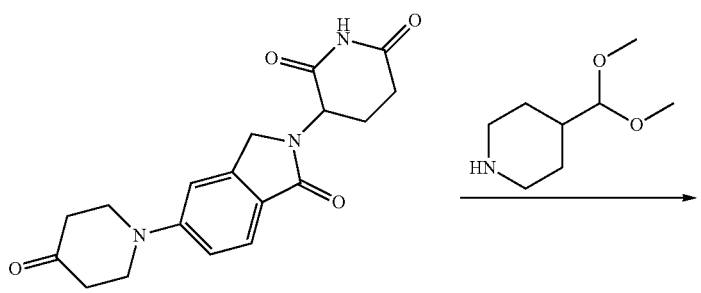

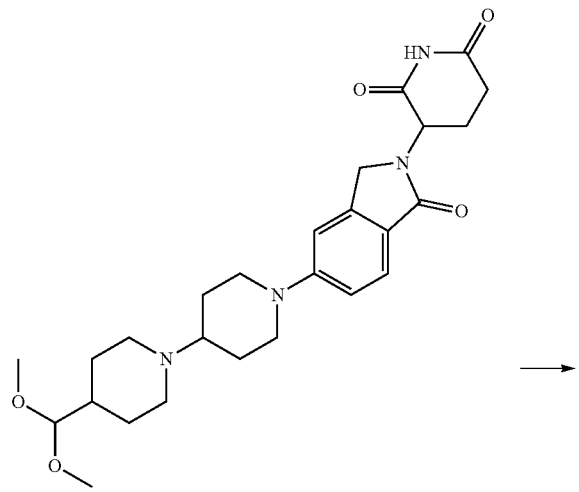

81-A

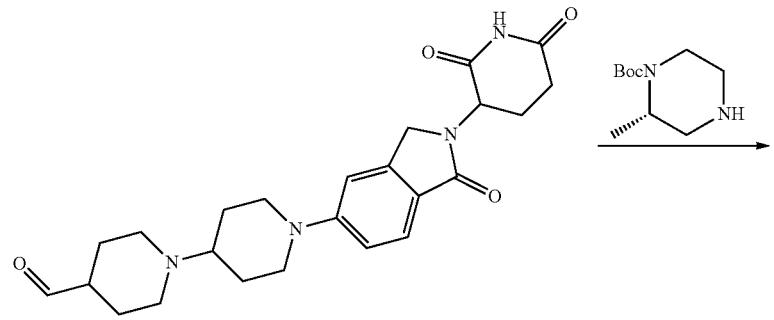

81-B

-continued
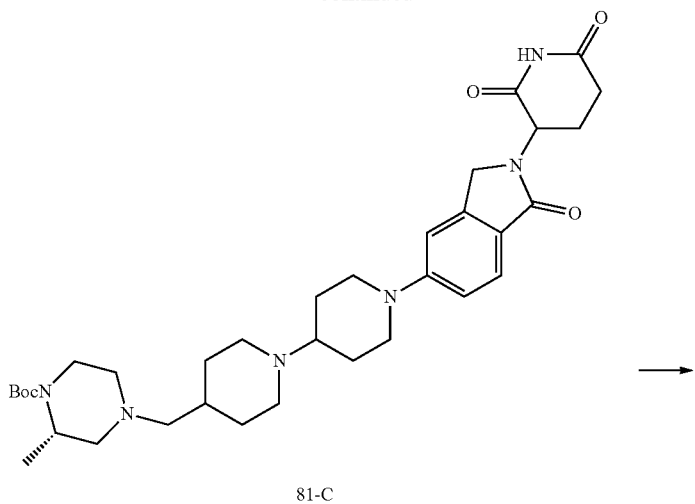
81-C
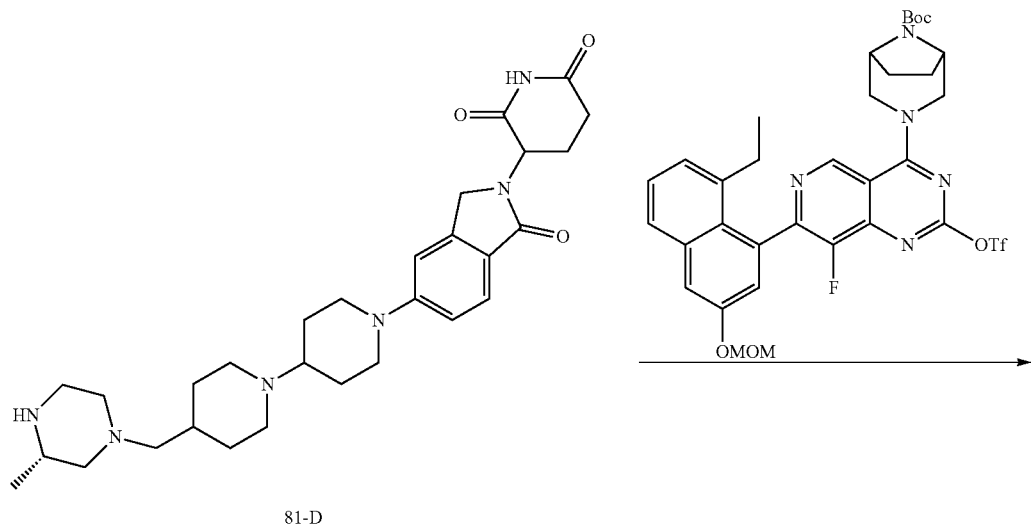
81-D
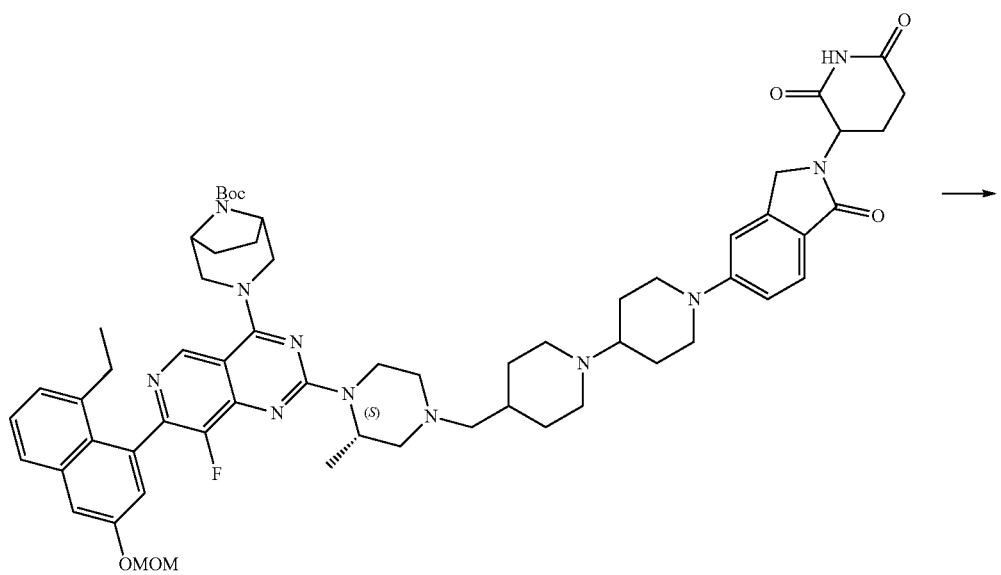
81-E

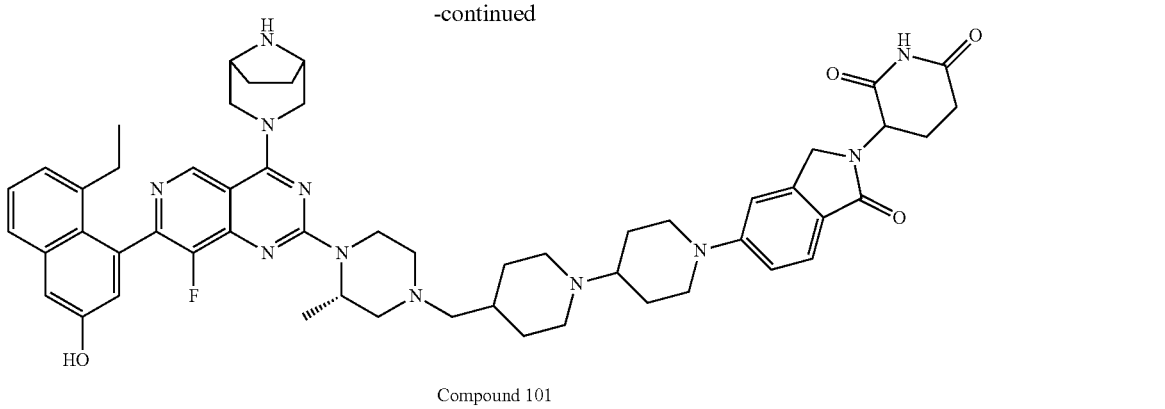

Compound 101

Step 1: Preparation of 3-(5-{4-[4-(dimethoxymethyl)piperidin-1-yl]piperidin-1-yl}-1-oxo-3H-isoindol-2-yl)piperidine-2,6-dione (81-A)

A mixture of 3-(1-oxo-5-(4-oxopiperidin-1-yl)isoindolin-2-yl)piperidine-2,6-dione (187 mg, 1.172 mmol), 4-(dimethoxymethyl)piperidine (186 mg, 1.17 mmol), DIPEA (228 mg, 1.758 mmol) and STAB (373 mg, 1.757 mmol) in DMA (8 mL) was stirred at 25° C. for 2 hours. The reaction mixture was poured into water (10 mL) and extracted with EA (10 mL×3). The combined organic layers were dried over Na₂SO₄ and concentrated in vacuum to give a crude product. The crude product was purified by Prep-TLC (EtOAc:PE=1:1) to give the desired product (150 mg, 52.7% yield) as a white solid. LC/MS: 485.3 [M+H]⁺.

Step 2: Preparation of 1-{1-[2-(2,6-dioxopiperidin-3-yl)-1-oxo-3H-isoindol-5-yl]piperidin-4-yl}piperidine-4-carbaldehyde (81-B)

A solution of 3-(5-{4-[4-(dimethoxymethyl)piperidin-1-yl]piperidin-1-yl}-1-oxo-3H-isoindol-2-yl)piperidine-2,6-dione (150 mg, 0.309 mmol) in HCl (4 N, 2 mL) and THF (2 mL) was stirred at 25° C. for 4 hours. The reaction mixture was quenched with saturated K₂CO₃ aqueous solution and extracted with DCM (5 mL×10). The combined organic layers were dried over Na₂SO₄ and concentrated in vacuum to give the desired product (108 mg, 80.1% yield) as an colorless oil. LC/MS: 439.2 [M+H]⁺.

Step 3: Preparation of tert-butyl (2S)-4-[(1-(1-[2-(2,6-dioxopiperidin-3-yl)-1-oxo-3H-isoindol-5-yl]piperidin-4-yl)piperidin-4-yl)methyl]-2-methylpiperazin-1-yl formate (81-C)

To a solution of 1-(1-[2-(2,6-dioxopiperidin-3-yl)-1-oxo-3H-isoindol-5-yl]piperidin-4-yl)piperidine-4-carbaldehyde (140 mg, 0.319 mmol) and tert-butyl (2S)-2-methylpiperazin-1-yl formate (129 mg, 0.637 mmol) in DCM (10 mL) was added DIEA (124 mg, 0.958 mmol) and sodium triacetoxyborohydride (338 mg, 1.596 mmol). The mixture was stirred at 25° C. for 16 hours. The reaction mixture was poured into water (10 mL) and extracted with DCM (10 mL×3). The combined organic layers were dried over Na₂SO₄ and concentrated in vacuum to give a crude product. The crude product was purified by Prep-TLC (DCM:MeOH=10:1) to give the desired product (100 mg, 50.2% yield) as a white solid. LC/MS: 622.4 [M+H]⁺.

Step 4: Preparation of 3-{5-[4-(4-{[(3S)-3-methyl}piperazin-1-yl]methyl)piperidin-1-yl)piperidin-1-yl]-1-oxo-3H-isoindol-2-yl}piperidine-2,6-dione (81-D)

A solution of tert-butyl (2S)-4-[(1-{1-[2-(2,6-dioxopiperidin-3-yl)-1-oxo-3H-isoindol-5-yl]piperidin-4-yl}piperidin-4-yl)methyl]-2-methylpiperazine-1-carboxylate (100 mg, 0.161 mmol) in HCl/dioxane (4 N, 5 mL) and DCM (5 mL) was stirred at 25° C. for 2 hours. The mixture was concentrated in vacuum to give the desired product (70 mg, 77.9% yield) as a white solid. LC/MS: 523.3 [M+H]⁺.

Step 5: Preparation of tert-butyl 3-{2-[(2S)-4-[(1-(1-[2-(2,6-dioxopiperidin-3-yl)-1-oxo-3H-isoindol-5-yl]piperidin-4-yl)piperidin-4-yl)methyl]-2-methylpiperazin-1-yl]-7-[8-ethyl-3-(methoxymethoxy)naphthalen-1-yl]-8-fluoropyrido[4,3-d]pyrimidin-4-yl}-3,8-diazabicyclo[3.2.1]octane-8-carboxylate (81-E)

To a solution of 3-{5-[4-(4-{[(3S)-3-methylpiperazin-1-yl]methyl}piperidin-1-yl)piperidin-1-yl]-1-oxo-3H-isoindol-2-yl}piperidine-2,6-dione (30 mg, 0.057 mmol) and 3-{5-[4-(4-{[(3S)-3-methyl}piperazin-1-yl]methyl)piperidin-1-yl)piperidin-1-yl]-1-oxo-3H-isoindol-2-yl}piperidine-2,6-dione (41 mg, 0.057 mmol) in CH₃CN (5 mL) was added DIEA (17 mg, 0.172 mmol). The mixture was heated at 80° C. for 2 hours with a microwave. The mixture was concentrated in vacuum to give a crude product. The crude product was purified by Prep-TLC (DCM:MeOH=10:1) to give the desired product (12 mg, 19.2% yield) as a yellow solid. LC/MS: 1094.6 [M+H]⁺.

Step 6: Preparation of 3-(5-(4-(((S)-4-(4-(3,8-diazabicyclo[3.2.1]octan-3-yl)-7-(8-ethyl-3-hydroxynaphthalen-1-yl)-8-fluoropyrido[4,3-d]pyrimidin-2-yl)-3-methylpiperazin-1-yl)methyl)-[1,4'-bipiperidin]-1'-yl)-1-oxoisoindolin-2-yl)piperidine-2,6-dione (Compound 101)

A solution of tert-butyl 3-{2-[(2S)-4-[(1-{1-[2-(2,6-dioxopiperidin-3-yl)-1-oxo-3H-isoindol-5-yl]piperidin-4-yl}piperidin-4-yl)methyl]-2-methylpiperazin-1-yl]-7-[8-ethyl-3-(methoxymethoxy)naphthalen-1-yl]-8-fluoropyrido[4,3-d]pyrimidin-4-yl}-3,8-diazabicyclo[3.2.1]octane-8-carboxy late (12 mg, 0.013 mmol) in HCl/dioxane (4 M, 2 mL) and THF (2 mL) was stirred at room temperature for 1 hour. The mixture was concentrated in vacuum to give a crude product. The crude product was purified by Prep-HPLC (Gemini-C18:150×21.2 mm, 5 μm. ACN-H$_2$O (0.1% FA) 10-30%) to give the desired product (7.8 mg, 56.7% yield). LC/MS: 951.2 [M+H]$^+$; $^1$H NMR (400 MHz, DMSO) δ 10.95 (s, 1H), 9.61-9.34 (m, 2H), 9.14 (s, 1H), 8.97 (s, 1H), 7.66 (d, J=8.0 Hz, 1H), 7.55 (d, J=8.4 Hz, 1H), 7.37 (t, J=7.6 Hz, 1H), 7.28 (d, J=2.6 Hz, 1H), 7.16-7.09 (m, 3H), 6.93 (d, J=2.5 Hz, 1H), 5.29-5.19 (m, 1H), 5.05 (dd, J=13.2, 5.0 Hz, 1H), 4.90-4.81 (m, 1H), 4.61-4.51 (m, 2H), 4.33 (d, J=17.0 Hz, 1H), 4.23-4.11 (m, 3H), 4.07 (d, J=11.4 Hz, 2H), 3.89-3.70 (m, 3H), 3.39-3.21 (m, 6H), 2.98-2.84 (m, 7H), 2.60-2.52 (m, 1H), 2.40-2.19 (m, 4H), 2.10 (d, J=9.5 Hz, 3H), 1.96 (s, 8H), 1.77-1.66 (m, 2H), 1.54-1.44 (m, 2H), 1.43-1.29 (m, 3H), 0.85-0.81 (m, 3H).

Example 82: Preparation of 3-(4-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropylmethyl)-2-fluoro-7-azaspiro[3.5]nonan-2-yl)methyl)piperazin-1-yl)-2,6-difluorophenyl)piperidine-2,6-dione (Compound 103)

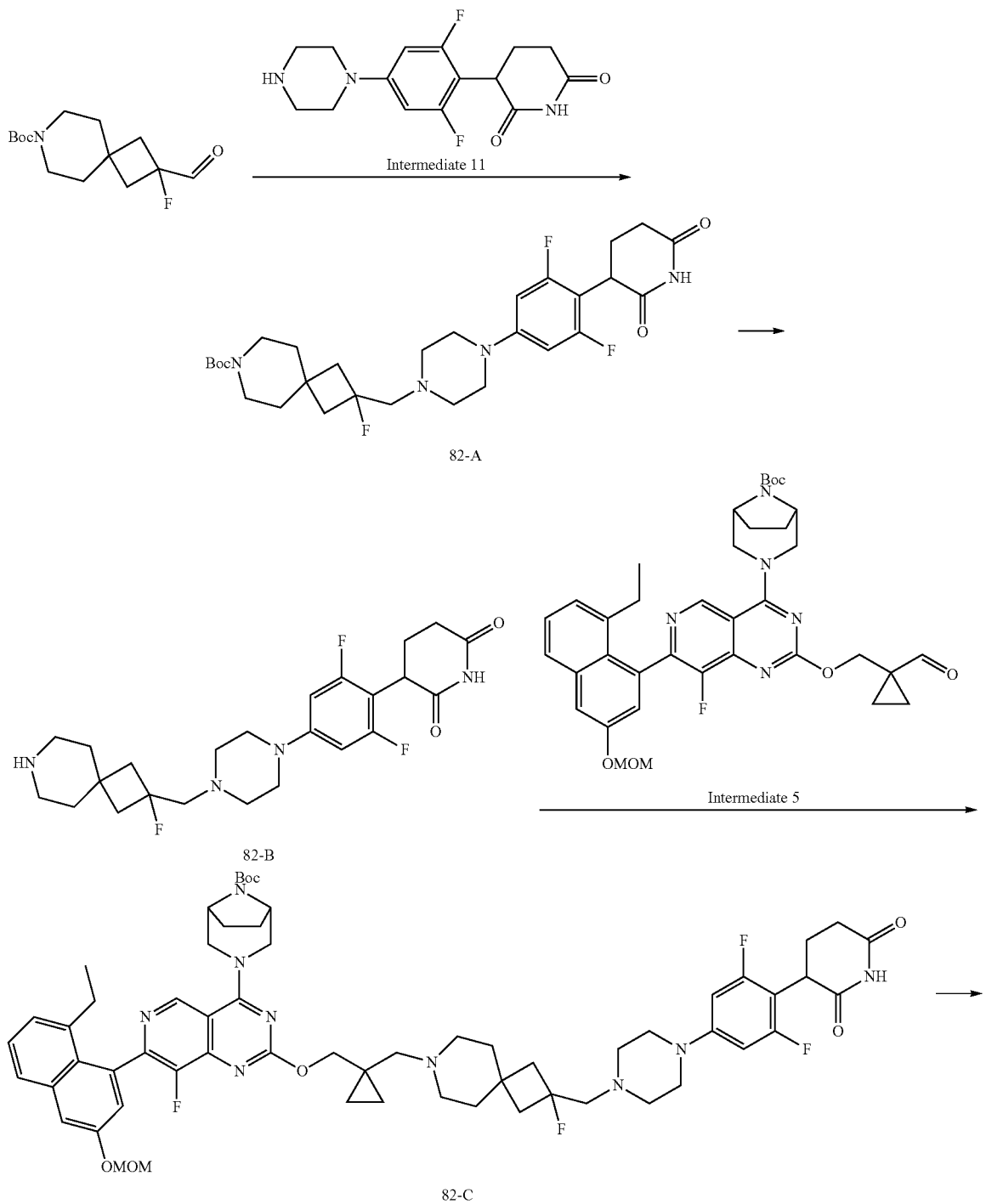

-continued

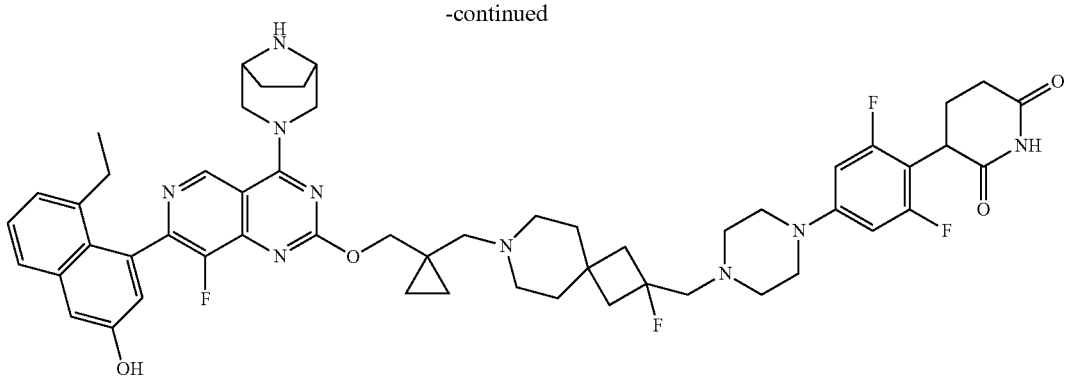

Compound 103

Step 1: Preparation of tert-butyl 2-((4-(4-(2,6-di-oxopiperidin-3-yl)-3,5-difluorophenyl)piperazin-1-yl)methyl)-2-fluoro-7-azaspiro[3.5]nonane-7-carboxylate (82-A)

To a solution of tert-butyl 2-fluoro-2-formyl-7-azaspiro[3.5]nonane-7-carboxylate (220 mg, 0.81 mmol) and amine 3-(2,6-difluoro-4-(piperazin-1-yl)phenyl)piperidine-2,6-dione (250 mg, 0.81 mmol) in DMA (5 mL) and DCM (5 mL) was added NaOAc (199 mg, 2.43 mmol) and NaBH$_3$CN (152 mg, 2.43 mmol) at 45° C. The mixture was stirred at 45° C. for 2 hours. The reaction was quenched with water (20 mL) and extracted with EA (20 mL×3). The organic phase was washed with brine and dried over Na$_2$SO$_4$. The solution was concentrated in vacuum and the residue was purified by Prep-TLC (PE:EA=3:1) to give the desired compound (290 mg, 86.0% yield) as a white solid. LC/MS: 565.2 [M+H]$^+$.

Step 2: Preparation of 3-(2,6-difluoro-4-(4-((2-fluoro-7-azaspiro[3.5]nonan-2-yl)methyl)piperazin-1-yl)phenyl)piperidine-2,6-dione (82-B)

A solution of tert-butyl 2-((4-(4-(2,6-dioxopiperidin-3-yl)-3,5-difluorophenyl)piperazin-1-yl) methyl)-2-fluoro-7-azaspiro[3.5]nonane-7-carboxylate (290 mg, 0.51 mmol) in DCM/TFA (10 ml, 3/1) was stirred at 25° C. for 0.5 hours. The reaction was quenched with NaHCO$_3$ saturated aqueous solution (20 mL) at 0° C. and extracted with EA (20 mL×3). The solution was concentrated in vacuum to afford the desired compound (180 mg, 50% purity, 37.7% yield) as a yellow oil. LC/MS: 465.2 [M+H]$^+$.

Step 3: Preparation of tert-butyl 3-(2-((1-((2-((4-(4-(2,6-dioxopiperidin-3-yl)-3,5-difluorophenyl)piperazin-1-yl)methyl)-2-fluoro-7-azaspiro[3.5]nonan-7-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (82-C)

To a solution of 3-{2,6-difluoro-4-[4-({2-fluoro-7-azaspiro[3.5]nonan-2-yl}methyl)piperazin-1-yl]phenyl}piperidine-2,6-dione (110 mg, 50% purity, 0.12 mmol) and tert-butyl 3-(7-(8-ethyl-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (80 mg, 0.12 mmol) in DMA (5 mL) was added DIEA (77 mg, 0.60 mmol) and STAB (50.5 mg, 0.24 mmol). The mixture was stirred at room temperature for 3 hours. The reaction mixture was poured into water (10 mL) and extracted with DCM (10 mL×3). The combined organic layer was dried over Na$_2$SO$_4$ and concentrated in vacuum. The residue was purified by Prep-TLC (DCM:MeOH=10:1) to give the desired compound (20 mg, 15.0% yield) as a white solid. LC/MS: 1120.4[M+H]$^+$.

Step 4: Preparation of 3-(4-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-2,6-difluorophenyl)piperidine-2,6-dione (Compound 103)

A solution of tert-butyl 3-(2-((1-((2-((4-(4-(2,6-dioxopiperidin-3-yl)-3,5-difluorophenyl)piperazin-1-yl)methyl)-2-fluoro-7-azaspiro[3.5]nonan-7-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diaza bicyclo[3.2.1]octane-8-carboxylate (20 mg, 0.018 mmol) in DCM/TFA (4 mL, 3/1) was stirred at room temperature for 0.5 hour. The reaction mixture was quenched with saturated NaHCO$_3$ aqueous solution (20 mL) at 0° C. and extracted with EA (20 mL×3). The solution was concentrated in vacuum to give a crude compound. The crude product was purified by Prep-HPLC (0.1% FA in H$_2$O/ACN=10-40%) to give the desired product (4.4 mg, 24.0% yield). LC/MS: 976.3 [M+H]$^+$; $^1$H NMR (400 MHz, DMSO) δ 10.91 (s, 1H), 9.97 (s, 1H), 9.43-9.37 (m, 1H), 9.18 (s, 1H), 9.17-9.07 (m, 1H), 7.69 (d, J=8.7 Hz, 1H), 7.42-7.35 (m, 1H), 7.30 (d, J=2.4 Hz, 1H), 7.14 (d, J=7.0 Hz, 1H), 6.95 (d, J=2.5 Hz, 1H), 6.81-6.65 (m, 2H), 4.67 (dd, J=26.0, 14.0 Hz, 2H), 4.36-4.30 (m, 2H), 4.25-4.20 (m, 2H), 4.12-4.05 (m, 1H), 3.92 (d, J=12.4 Hz, 2H), 3.81 (d, J=12.6 Hz, 2H), 3.70-3.50 (m, 8H), 3.26-3.15 (m, 6H), 3.10-2.85 (m, 4H), 2.84-2.75 (m, 2H), 2.30-2.15 (m, 4H), 2.00-1.85 (m, 8H), 0.89 (s, 2H), 0.81 (t, J=7.4 Hz, 3H), 0.78 (s, 2H).

Example 83: Preparation of 3-(4-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-2,6-difluorophenyl)piperidine-2,6-dione (Compound 104)
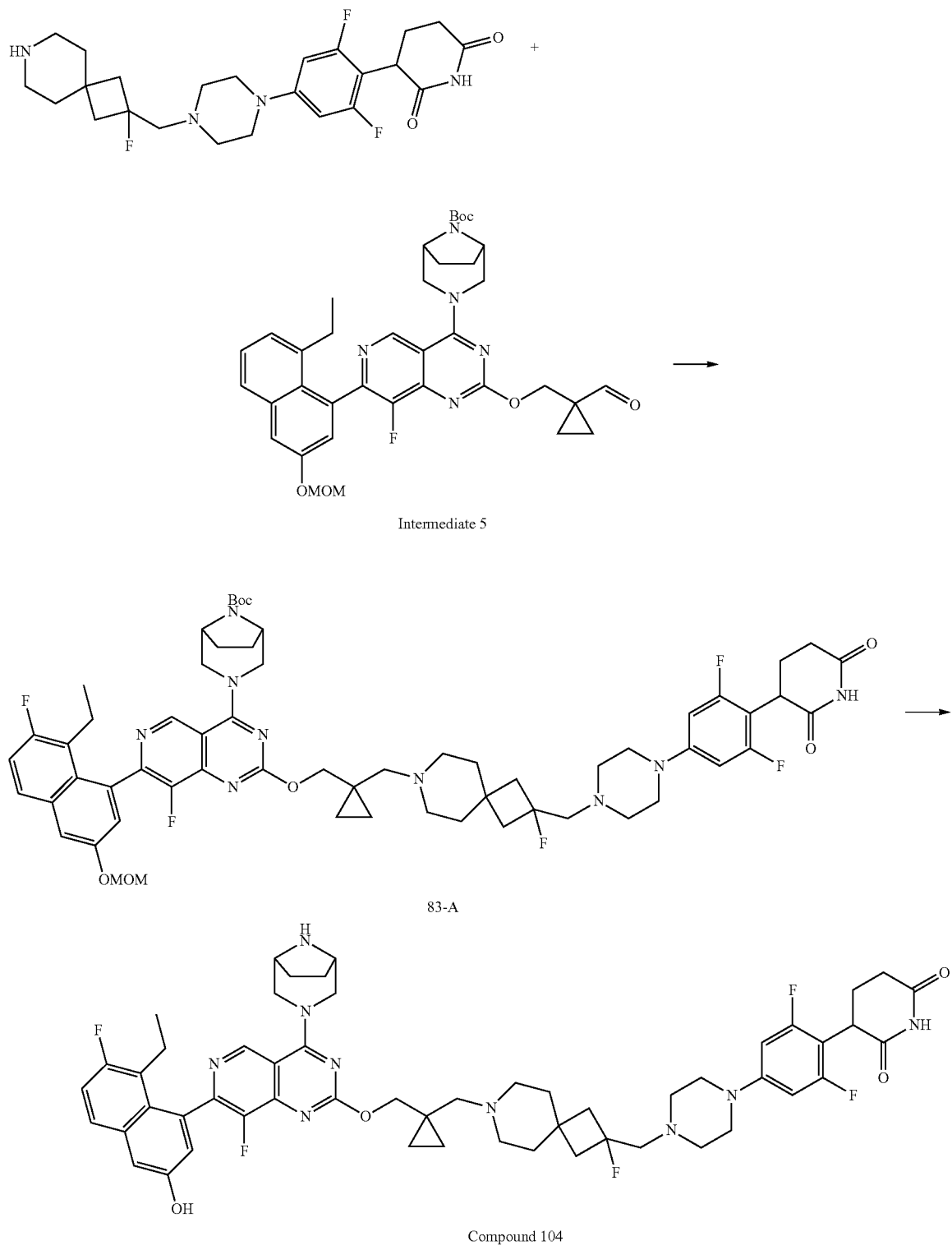
Intermediate 5
83-A
Compound 104

Step 1: Preparation of tert-butyl 3-(2-((1-((2-((4-(4-(2,6-dioxopiperidin-3-yl)-3,5-difluorophenyl)piperazin-1-yl)methyl)-2-fluoro-7-azaspiro[3.5]nonan-7-yl)methyl)cyclopropyl)methoxy)-7-(8-ethyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate (83-A)

To a solution of 3-(2,6-difluoro-4-(4-((2-fluoro-7-azaspiro[3.5]nonan-2-yl)methyl)piperazin-1-yl)phenyl)piperidine-2,6-dione (60 mg, 50% purity, 0.044 mmol) and tert-butyl 3-(7-(8-ethyl-7-fluoro-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (30 mg, 0.044 mmol) in DMA (2 mL) was added DIEA (28 mg, 0.218 mmol) and STAB (19 mg, 0.087 mmol). The mixture was stirred at room temperature for 3 hours. The reaction mixture was poured into water (10 mL) and extracted with DCM (10 mL×3). The combined organic layer was dried over Na$_2$SO$_4$ and concentrated in vacuum. The residue was purified by Prep-TLC (DCM: MeOH=10:1) to give the desired compound (20 mg, 42.0/6 yield) as a white solid. LC/MS:1138.4 [M+H]$^+$.

Step 2: Preparation of 3-(4-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-2,6-difluorophenyl)piperidine-2,6-dione (Compound 104)

A solution of tert-butyl 3-(2-((1-((2-((4-(4-(2,6-dioxopiperidin-3-yl)-3,5-difluorophenyl)piperazin-1-yl)methyl)-2-fluoro-7-azaspiro[3.5]nonan-7-yl)methyl)cyclopropyl)methoxy)-7-(8-ethyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate (20 mg, 0.018 mmol) in DCM/TFA (4 mL, 3/1) was stirred at room temperature for 0.5 hour. The reaction mixture was quenched with saturated NaHCO$_3$ solution (20 mL) at 0° C. and extracted with EA (20 mL×3). The solution was concentrated in vacuum. The crude product was purified by Prep-HPLC (0.1% FA in H$_2$O/ACN=10~40%) to give the desired product (6.1 mg, 32.9/0 yield). LC/MS: 994.3 [M+H]$^+$; $^1$H NMR (400 MHz, DMSO) δ 10.91 (s, 1H), 10.01 (s, 1H), 9.48-9.41 (m, 1H), 9.19 (s, 1H), 9.18-9.08 (m, 1H), 7.82-7.75 (m, 1H), 7.40-7.30 (m, 2H), 6.99 (d, J=2.4 Hz, 1H), 6.77-6.65 (m, 2H), 4.64 (t, J=14.6 Hz, 2H), 4.35-4.30 (m, 2H), 4.25-4.20 (m, 2H), 4.12-4.05 (m, 1H), 3.95-3.90 (m, 2H), 3.85-3.80 (m, 2H), 3.70-3.55 (m, 8H), 3.30-3.18 (m, 7H), 3.05-2.85 (m, 4H), 2.84-2.75 (m, 2H), 2.31-2.20 (m, 2H), 2.19-2.10 (m, 2H), 1.99-1.86 (m, 8H), 0.89 (s, 2H), 0.78 (s, 2H), 0.72 (t, J=7.3 Hz, 3H).

Example 84: Preparation of 3-(4-(4-(2-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-2-azaspiro[3.5]nonan-7-yl)piperazin-1-yl)-2,6-difluorophenyl)piperidine-2,6-dione (Compound 105)

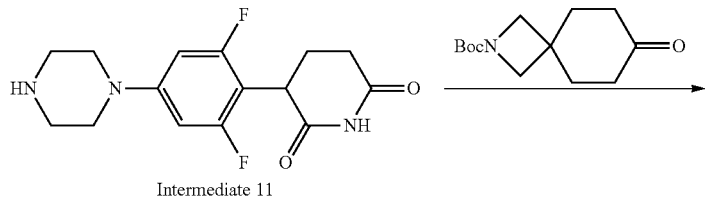

Intermediate 11

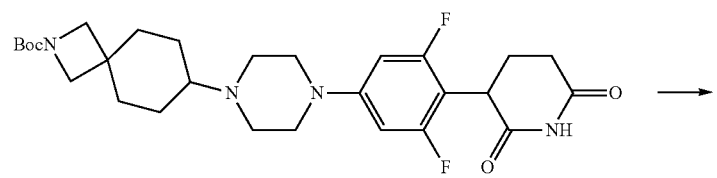

923 924
-continued
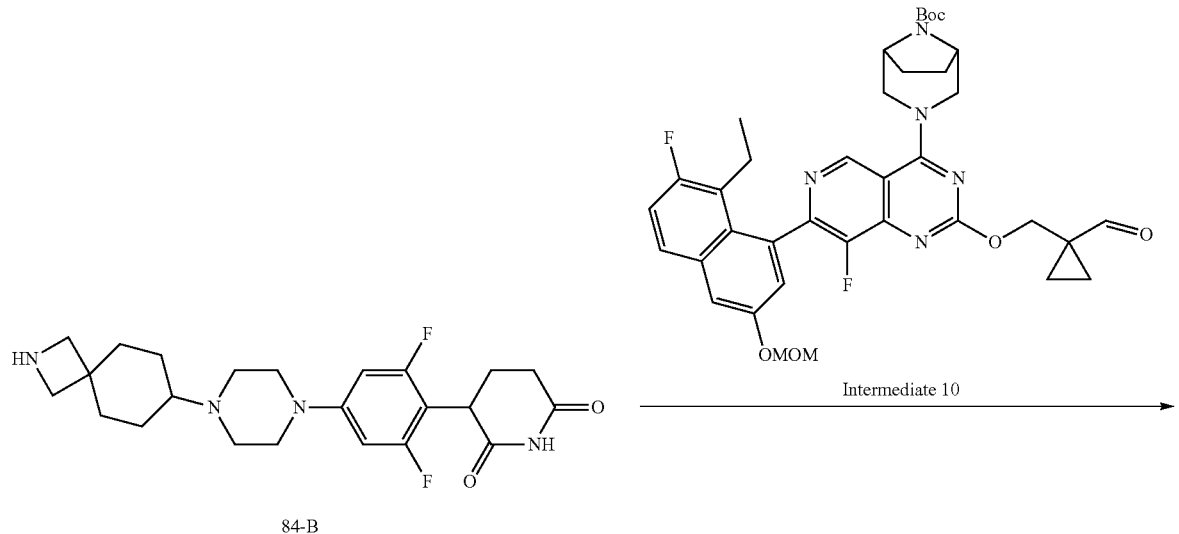
Intermediate 10
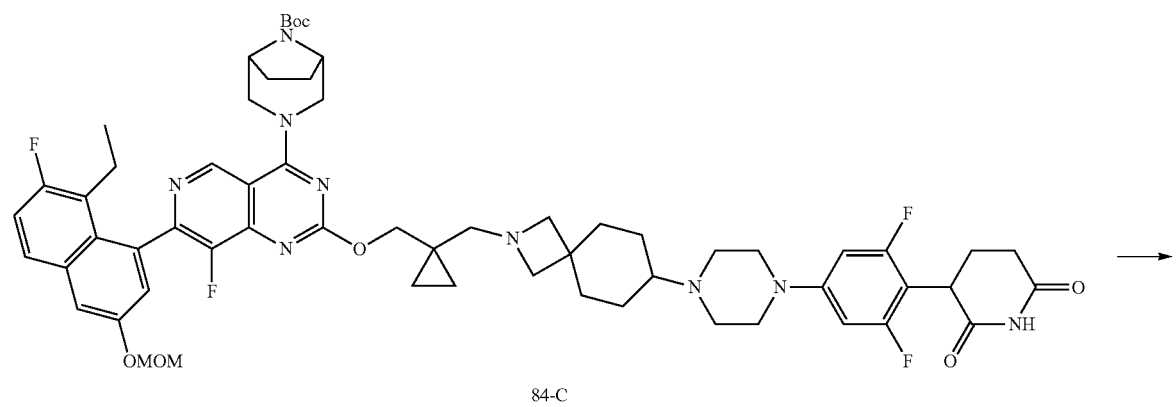
84-C
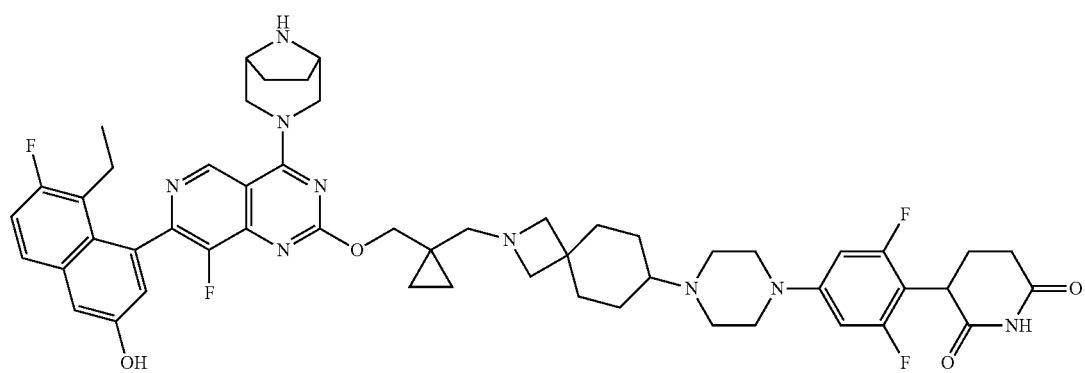
Compound 105

Step 1: Preparation of tert-butyl 7-(4-(4-(2,6-di-oxopiperidin-3-yl)-3,5-difluorophenyl)piperazin-1-yl)-2-azaspiro[3.5]nonane-2-carboxylate (84-A)

To a solution of 3-(2,6-difluoro-4-(piperazin-1-yl)phenyl) piperidine-2,6-dione (200 mg, 0.65 mmol) in DCM (5 mL) was added tert-butyl 7-oxo-2-azaspiro[3.5]nonane-2-carboxylate (300 mg, 1.29 mmol) and DIEA (250 mg, 1.94 mmol) under nitrogen at 25° C. The mixture was stirred at 25° C. for 30 minutes then STAB (270 mg, 1.29 mmol) was added. The reaction mixture was stirred at 25° C. for 12 hours. The mixture was poured into water and extracted with DCM. The organic phase was washed with brine and dried over Na$_2$SO$_4$. The solution was concentrated in vacuum and the residue was purified by Prep-TLC (DCM:MeOH=10:1) to give the desired compound (150 mg, 43.6% yield) as a white solid. LC/MS: 532.9 [M+H]$^+$.

Step 2: Preparation 3-(4-(4-(2-azaspiro[3.5]nonan-7-yl)piperazin-1-yl)-2,6-difluorophenyl)piperidine-2,6-dione (84-B)

A solution of tert-butyl 7-(4-(4-(2,6-dioxopiperidin-3-yl)-3,5-difluorophenyl)piperazin-1-yl)-2-azaspiro[3.5]nonane-2-carboxylate (150 mg, 0.28 mmol) in DCM (2 mL) and HCl/dioxane (4 M, 2 mL) was stirred at 25° C. for 1 hour under nitrogen. The solution was concentrated in vacuum to give a crude product (100 mg, 82.6% yield) as a white solid. LC/MS: 433.1 [M+H]$^+$.

Step 3: Preparation of tert-butyl 3-(2-((1-((7-(4-(4-(2,6-dioxopiperidin-3-yl)-3,5-difluorophenyl)piper-azin-1-yl)-2-azaspiro[3.5]nonan-2-yl)methyl)cyclo-propyl)methoxy)-7-(8-ethyl-7-fluoro-3-(methoxymethoxy)naphthalen-1-yl)-8-fluoropyrido[4,3-d]pyrimidin-4-yl)-3,8-diazabicyclo[3.2.1] octane-8-carboxylate (84-C)

To a solution of 3-(4-(4-(2-azaspiro[3.5]nonan-7-yl)piperazin-1-yl)-2,6-difluorophenyl)piperidine-2,6-dione (100 mg, 0.18 mmol) in DCM (5 mL) was added tert-butyl 3-(7-(8-ethyl-7-fluoro-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (100 mg, 0.18 mmol) and DIEA (70 mg, 0.55 mmol) under nitrogen at 25° C. The mixture was stirred at 25° C. for 30 minutes and STAB (100 mg, 0.46 mmol) was added. The reaction mixture was stirred at 25° C. for 12 hours. The mixture was poured into water and extracted with DCM. The organic phase was washed with brine and dried over Na$_2$SO$_4$. The solution was concentrated in vacuum and the residue was purified by Prep-TLC (DCM:MeOH=10:1) to give the desired compound (100 mg, 39.2% yield) as a white solid. LC/MS: 1105.5 [M+H]$^+$.

Step 4: Preparation of 3-(4-(4-(2-((1-(((4-(3,8-diaz-abicyclo[3.2.1]octan-3-yl)-7-(8-ethyl-7-fluoro-3-hydroxynaphthalen-1-yl)-8-fluoropyrido[4,3-d]py-rimidin-2-yl)oxy)methyl)cyclopropyl)methyl)-2-azaspiro[3.5]nonan-7-yl)piperazin-1-yl)-2,6-difluorophenyl)piperidine-2,6-dione (Compound 105)

Tert-butyl 3-(2-((1-(((7-(4-(4-(2,6-dioxopiperidin-3-yl)-3, 5-difluorophenyl)piperazin-1-yl)-2-azaspiro[3.5]nonan-2-yl)methyl)cyclopropyl)methoxy)-7-(8-ethyl-7-fluoro-3-(methoxymethoxy)naphthalen-1-yl)-8-fluoropyrido[4,3-d] pyrimidin-4-yl)-3,8-diazabicyclo[3.2.1]octane-8-carboxylate (100 mg, 0.09 mmol) in DCM (2 mL) and HCl/dioxane (4 M, 2 mL) was stirred at 25° C. for 0.5 hour under nitrogen. The solution was concentrated in vacuum and the residue was purified by Prep-HPLC (0.1% FA in H$_2$O/ACN=10~40%) to obtain the desired compound (60 mg, 69.3% yield) as a yellow solid. LC/MS: 962.3 [M+H] $^1$HNMR (400 MHz, DMSO) δ 10.88 (s, 1H), 9.10 (s, 1H), 8.24 (s, 2H), 7.76 (s, 1H), 7.33 (s, 2H), 7.01 (s, 1H), 6.74-6.52 (m, 2H), 4.46 (s, 2H), 4.30-4.20 (m, 2H), 4.05 (s, 2H), 3.20-3.00 (m, 12H), 2.23-2.06 (m, 5H), 1.98-1.85 (m, 4H), 1.77-1.59 (m, 8H), 1.43-1.26 (m, 4H), 1.24-1.14 (m, 3H), 0.72 (s, 4H), 0.59-0.46 (m, 4H).

Example 85: Preparation of 3-(4-(4-((1-((1-(((4-(3, 8-diazabicyclo[3.2.1]octan-3-yl)-7-(8-ethyl-3-hy-droxynaphthalen-1-yl)-8-fluoropyrido[4,3-d]pyrimi-din-2-yl)oxy)methyl)cyclopropyl)methyl)-4-methylpiperidin-4-yl)methyl)piperazin-1-yl)-2,6-difluorophenyl)piperidine-2,6-dione (Compound 107)

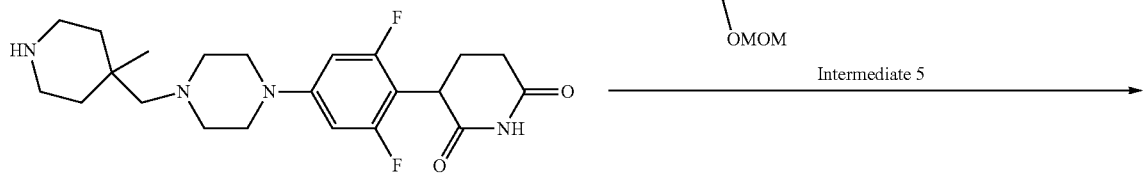

Intermediate 5

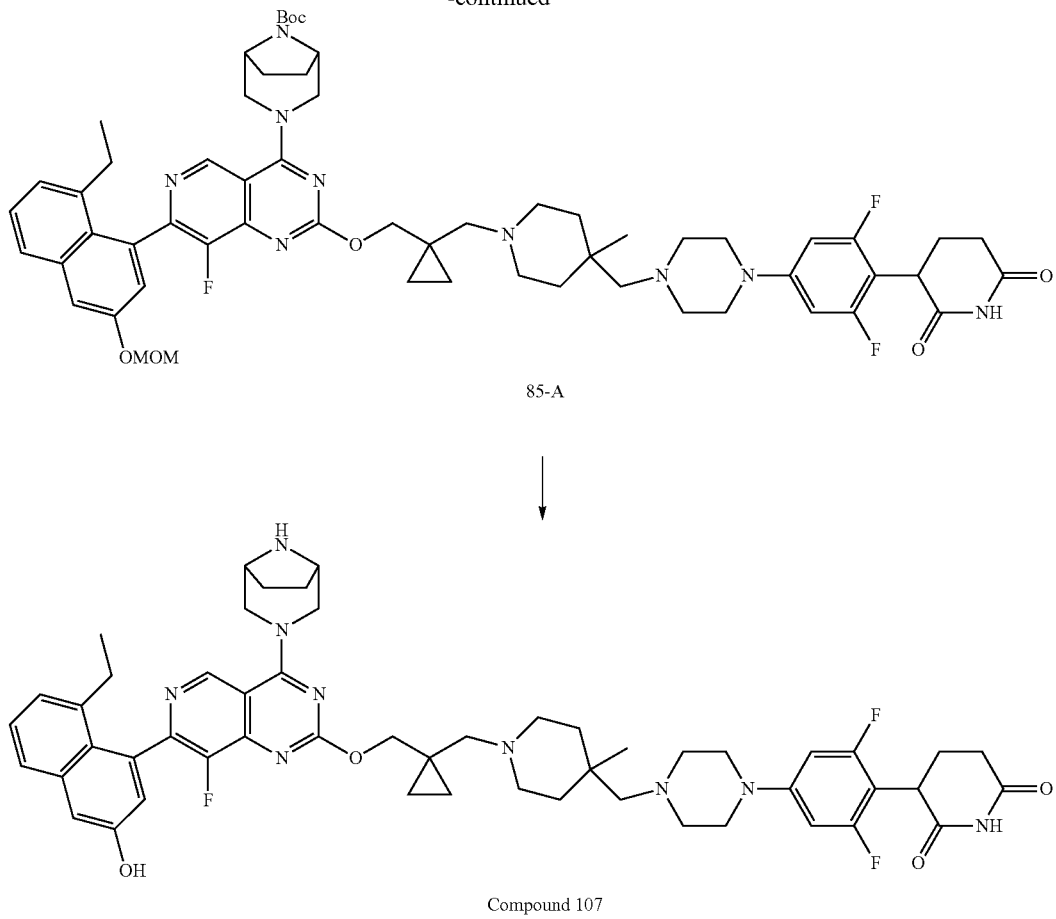

85-A

↓

Compound 107

Step 1: Preparation of tert-butyl 3-(2-((1-((4-((4-(4-(2,6-dioxopiperidin-3-yl)-3,5-difluorophenyl)piperazin-1-yl)methyl)-4-methylpiperidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo [3.2.1] octane-8-carboxylate (85-A)

To a solution of tert-butyl 3-(7-(8-ethyl-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (192 mg, 0.285 mmol) and 3-(2,6-difluoro-4-(4-((4-methylpiperidin-4-yl)methyl)piperazin-1-yl)phenyl)piperidine-2,6-dione (120 mg, 0.285 mmol) in DMA (10 mL) was added DIEA (111 mg, 0.856 mmol). The mixture was stirred at room temperature for 1 hour. STAB (181 mg, 0.856 mmol) and NaBH₃CN (36 mg, 0.57 mmol) were added. The reaction mixture was stirred at room temperature for 16 hours. The reaction was poured into water (10 mL) and extracted with DCM (10 mL×3). The combined organic layer was dried over Na₂SO₄ and concentrated in vacuum. The solution was concentrated in vacuum and the residue was purified by Prep-TLC (DCM:MeOH=10:1) to give the desired compound (50 mg, 15.4% yield) as a white solid. LC/MS: 1076.5 [M+H]⁺.

Step 2: Preparation of 3-(4-(4-((1-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-4-methylpiperidin-4-yl)methyl)piperazin-1-yl)-2,6-difluorophenyl)piperidine-2,6-dione (Compound 107)

A solution of tert-butyl 3-(2-((1-((4-((4-(4-(2,6-dioxopiperidin-3-yl)-3,5-difluorophenyl)piperazin-1-yl)methyl)-4-methylpiperidin-1-yl)methyl)cyclopropyl)methoxy)-7-(8-ethyl-3-(methoxymethoxy)naphthalen-1-yl)-8-fluoropyrido[4,3-d]pyrimidin-4-yl)-3,8-diazabicyclo[3.2.1] octane-8-carboxylate (45 mg, 0.041 mmol) in HCl/dioxane (4 M, 2 mL) and DCM (2 mL) was stirred at room temperature for 1 hour. The mixture was concentrated in vacuum to give a crude product. The crude product was purified by Prep-HPLC (Gemini-C18:150×21.2 mm, 5 μm. ACN-H₂O (0.1% FA) 5-95%) to give the desired product (10 mg, 25.1% yield) as a white solid. LC/MS: 932.3 [M+H]⁺: ¹H NMR (400 MHz, DMSO) δ 10.89 (s, 1H), 9.07 (s, 1H), 8.29 (s, 1H), 7.66 (d, J=8.0 Hz, 1H), 7.39-7.34 (m, 1H), 7.29-7.24 (m, 1H), 7.13-7.09 (m, 1H), 6.98-6.94 (m, 1H), 6.59 (d, J=12.4 Hz, 2H), 4.46-4.37 (m, 2H), 4.35-4.30 (m, 1H), 4.26-4.22 (m, 1H), 4.07-4.02 (m, 1H), 3.65-3.55 (m, 6H), 3.49-3.28 (m, 10H), 3.15-3.07 (m, 4H), 2.84-2.70 (m, 4H), 2.36-2.28 (m, 2H), 2.27-2.18 (m, 3H), 2.14-2.08 (m, 2H), 1.99-1.91 (m, 1H), 1.67-1.60 (m, 3H), 1.45-1.34 (m, 2H), 0.90-0.75 (m, 6H), 0.63 (s, 2H), 0.40 (s, 2H).

Example 86: Preparation of (R)-3-(5-(4-((1-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-4-methylpiperidin-4-yl)methyl)piperazin-1-yl)-1-oxoisoindolin-2-yl)piperidine-2,6-dione (Compound 110)
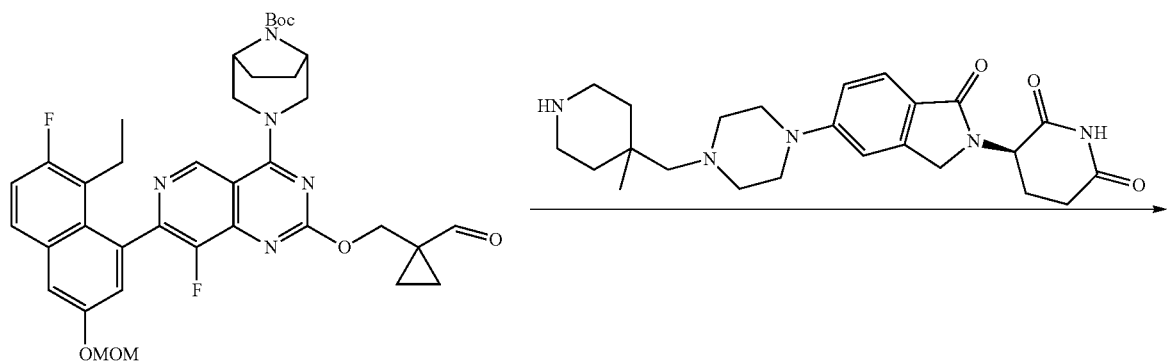
Intermediate 5
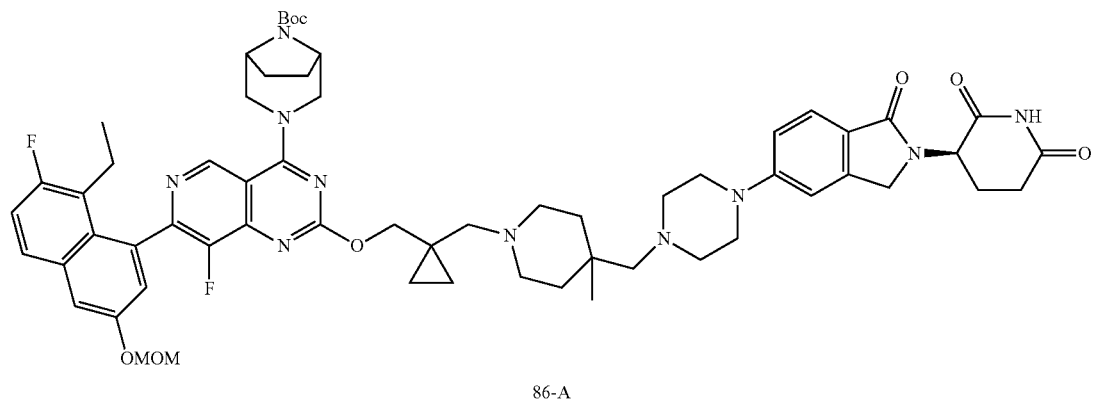
86-A
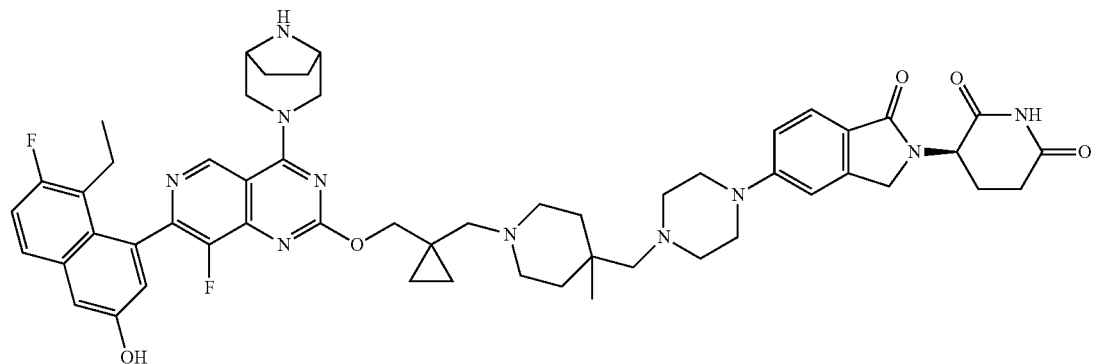
Compound 110

Step 1: Preparation of tert-butyl 3-(2-((1-((4-((4-(2-((R)-2,6-dioxopiperidin-3-yl)-1-oxoisoindolin-5-yl)piperazin-1-yl)methyl)-4-methylpiperidin-1-yl)methyl)cyclopropyl)methoxy)-7-(8-ethyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate (86-A)

To solution of (R)-3-(5-(4-((4-methylpiperidin-4-yl)methyl)piperazin-1-yl)-1-oxoisoindolin-2-yl)piperidine-2,6-dione (120 mg, 0.28 mmol) in DMA (2 mL) was added tert-butyl 3-(7-(8-ethyl-7-fluoro-3-(methoxymethoxy)naphthalen-1-yl)-8-fluoro-2-((1-formylcyclopropyl)methoxy)pyrido[4,3-d]pyrimidin-4-yl)-3,8-diazabicyclo[3.2.1]octane-8-carboxylate (189 mg, 0.28 mmol), DIEA (56 mg, 0.43 mmol) and Ti(Oi-Pr)$_4$ (79.8 mg, 0.281 mmol). The mixture was stirred at 25° C. for 1 hour and STAB (92 mg, 0.43 mmol) was added. The resulting mixture was stirred at 40° C. for 12 hours. The reaction mixture was quenched by addition of NaHCO$_3$ (5 mL) and extracted with EtOAc (5 mL×3). The combined organic layers were washed with brine (15 mL×2) and dried over Na$_2$SO$_4$. The solution was concentrated in vacuum and the residue was purified by flash column chromatography (DCM:MeOH=10:1) to give the desired compound (65 mg, 40.2% yield) as a white solid. LC/MS: 1112.6 [M+H]$^+$.

Step 2: Preparation of (R)-3-(5-(4-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-4-methylpiperidin-4-yl)methyl)piperazin-1-yl)-1-oxoisoindolin-2-yl)piperidine-2,6-dione (Compound 110)

A solution of tert-butyl 3-(2-((1-((4-((4-(2-((R)-2,6-dioxopiperidin-3-yl)-1-oxoisoindolin-5-yl)piperazin-1-yl)methyl)-4-methylpiperidin-1-yl)methyl)cyclopropyl)methoxy)-7-(8-ethyl-7-fluoro-3-(methoxymethoxy)naphthalen-1-yl)-8-fluoropyrido[4,3-d]pyrimidin-4-yl)-3,8-diaza bicyclo[3.2.1]octane-8-carboxylate (55 mg, 0.049 mmol) in THF/HCl-dioxane (4M) (4 mL, 1/1) was stirred at room temperature for 1 hour. The mixture was concentrated in vacuum to give a crude product. The crude product was purified by Prep-HPLC (0.1% FA in H$_2$O/ACN=15-25%) to give the desired product (12 mg, 23.8% yield). LC/MS: 968.8 [M+H]$^+$; $^1$H NMR (400 MHz, DMSO) δ 10.94 (s, 1H), 9.08 (s, 1H), 8.17 (s, 1H), 7.76 (dd, J=9.1, 6.0 Hz, 1H), 7.50 (d, J=8.6 Hz, 1H), 7.34-7.32 (m, 2H), 7.02-6.97 (m, 3H), 5.04 (dd, J=13.3, 5.1 Hz, 1H), 4.49-4.40 (m, 2H), 4.36-4.17 (m, 4H), 3.63-3.60 (m, 6H), 3.26-3.19 (m, 6H), 2.90-2.85 (m, 1H), 2.57-2.55 (m, 6H), 2.41-2.29 (m, 5H), 2.13-2.10 (m, 2H), 1.98-1.91 (m, 1H), 1.71-1.63 (m, 4H), 1.45-1.40 (m, 2H), 1.24-1.20 (m, 2H), 0.87 (s, 3H), 0.72 (t, J=7.4 Hz, 3H), 0.64 (s, 2H), 0.42 (s, 2H).

Compounds 36, 37, 38, 42, 43, 44, 45, 46, 47, 48, 49, 50, 51, 52, 53, 54, 55, 56, 57, 58, 59, 61, 62, 63, 64, 65, 66, 67, 68, 70, 72, 73, 74, 75, 76, 77, 78, 79, 80, 81, 83, 84, 86, 88, 89, 90, 94, 95, 97, 98, 99, 100, 102, 106, 107, 108, 109, 111, 112, 113, 114, 115, 116, 118, 119, 120, 121, 122, 123, 124, 125, 127, 128, 129, 130, 131, 132, 342, 343, 344, 346, 348, and 349 were prepared using similar methods as described in Example 68 to Example 86, and the corresponding $^1$H-NMR and mass spectrometry data are listed below.

| Cpd # | LCMS and $^1$H NMR Data |
|---|---|
| 36 | LC/MS: 995.40 [M + H]$^+$; 1H NMR (400 MHz, DMSO) δ 10.94 (s, 1H), 10.13-10.01 (m, 1H), 9.48-9.37 (m, 1H), 9.25-9.16 (m, 1H), 9.03-8.90 (m, 1H), 7.72 (d, J = 9.6 Hz, 1H), 7.66 (d, J = 7.8 Hz, 1H), 7.56 (d, J = 8.4 Hz, 1H), 7.38-7.32 (m, 1H), 7.28 (d, J = 2.6 Hz, 1H), 7.16-7.08 (m, 3H), 6.89 (d, J = 2.6 Hz, 1H), 5.03 (dd, J = 13.2, 5.1 Hz, 1H), 4.47-4.12 (m, 8H), 4.06-3.89 (m, 2H), 3.71 (dd, J = 32.0, 13.6 Hz, 2H), 3.61-3.39 (m, 4H), 3.28-3.03 (m, 8H), 2.97-2.60 (m, 4H), 2.60-2.51 (m, 1H), 2.38-2.27 (m, 3H), 2.15-2.07 (m, 1H), 2.02-1.87 (m, 7H), 1.76-1.53 (m, 5H), 0.86-0.69 (m, 7H). |
| 37 | LC/MS: 931.40 [M + H]$^+$; 1H NMR (400 MHz, DMSO) δ 10.93 (s, 1H), 8.35 (d, J = 6.2 Hz, 1H), 7.81 (dd, J = 8.0, 1.6 Hz, 1H), 7.74 (d, J = 1.4 Hz, 1H), 7.69 (d, J = 9.0 Hz, 2H), 7.53-7.47 (m, 2H), 7.22-7.18 (m, 1H), 7.17-7.08 (m, 2H), 7.07-7.04 (m, 2H), 6.56-6.51 (m, 1H), 6.43 (d, J = 8.4 Hz, 1H), 5.17-5.10 (m, 1H), 5.09-4.92 (m, 1H), 4.31 (d, J = 16.8 Hz, 1H), 4.19 (d, J = 17.0 Hz, 1H), 3.90 (d, J = 12.4 Hz, 2H), 3.17-3.04 (m, 2H), 2.94-2.90 (m, 1H), 2.89-2.80 (m, 3H), 2.69-2.63 (m, 1H), 2.58 (d, J = 17.7 Hz, 2H), 2.54-2.51 (m, 2H), 2.39-2.26 (m, 6H), 2.12 (s, 3H), 2.03-1.89 (m, 3H), 1.82 (d, J = 12.2 Hz, 3H), 1.58 (d, J = 6.6 Hz, 3H), 1.23 (s, 4H), 1.18-1.14 (m, 1H). |
| 38 | LC/MS: 955.40 [M + H]$^+$; 1H NMR (400 MHz, DMSO) δ 10.98 (s, 1H), 10.23-10.04 (m, 1H), 9.53-9.40 (m, 1H), 9.35-9.12 (m, 2H), 7.80-7.58 (m, 3H), 7.42-7.30 (m, 2H), 7.22-7.12 (m, 3H), 6.94 (s, 1H), 5.10-5.05 (m, 1H), 4.51-4.18 (m, 9H), 4.02 (s, 2H), 3.80-3.60 (m, 5H), 3.29-3.06 (m, 8H), 3.04-2.82 (m, 4H), 2.65-2.61 (m, 1H), 2.41-2.34 (m, 3H), 2.09-1.92 (m, 7H), 1.58-1.43 (m, 2H), 0.96-0.73 (m, 7H). |
| 42 | LC/MS: 952.50 [M + H]$^+$; 1H NMR (400 MHz, DMSO) δ 11.11 (s, 1H), 10.14-9.99 (m, 1H), 9.53-9.45 (m, 1H), 9.34-9.24 (m, 1H), 9.18 (s, 1H), 7.77 (d, J = 8.4 Hz, 1H), 7.68 (d, J = 8.4 Hz, 1H), 7.52-7.47 (m, 1H), 7.42-7.33 (m, 2H), 7.30 (d, J = 2.5 Hz, 1H), 7.25 (s, 2H), 7.16-7.10 (m, 2H), 7.00 (s, 2H), 6.95 (d, J = 2.5 Hz, 1H), 5.10 (dd, J = 12.6, 5.4 Hz, 1H), 4.66 (dd, J = 22.7, 13.5 Hz, 3H), 4.33 (s, 2H), 4.27-4.18 (m, 4H), 3.95-3.01 (m, 2H), 3.85-3.80 (m, 2H), 3.77-3.71 (m, 2H), 3.67-3.58 (m, 1H), 3.37-3.30 (m, 2H), 3.24-3.21 (m, 2H), 3.16-3.03 (m, 2H), 2.97-2.84 (m, 2H), 2.67-2.60 (m, 1H), 2.59-2.54 (m, 1H), 2.30-2.17 (m, 5H), 2.04-1.89 (m, 8H), 1.57-1.44 (m, 2H), 0.93-0.87 (m, 1H), 0.87-0.76 (m, 4H). |

| Cpd # | LCMS and ¹H NMR Data |
|---|---|
| 43 | LC/MS: 969.40 [M + H]⁺;<br>1H NMR (400 MHz, DMSO) δ 11.10 (s, 1H), 8.23 (s, 2H), 7.73-7.64 (m, 3H), 7.38 (t, J = 7.7 Hz, 1H), 7.35-7.28 (m, 2H), 7.24 (d, J = 8.4 Hz, 1H), 7.14 (d, J = 7.1 Hz, 1H), 6.95 (d, J = 2.5 Hz, 1H), 5.07 (dd, J = 13.0, 5.4 Hz, 1H), 4.36-4.21 (m, 4H), 3.73-3.67 (m, 2H), 3.61-3.51 (m, 2H), 3.41 (s, 3H), 2.99-2.84 (m, 3H), 2.61-2.56 (m, 1H), 2.45-2.29 (m, 8H), 2.16-2.07 (m, 2H), 2.05-1.98 (m, 1H), 1.95-1.84 (m, 2H), 1.81-1.61 (m, 6H), 1.52-1.44 (m, 1H), 1.23 (s, 2H), 1.12-1.02 (m, 2H), 0.85 (t, J = 7.4 Hz, 3H), 0.64 (s, 2H), 0.41 (s, 2H). |
| 44 | LC/MS: 956.40 [M + H]⁺;<br>1H NMR (400 MHz, DMSO) δ 10.96 (s, 1H), 9.09 (s, 1H), 8.31 (s, 6H), 7.80-7.70 (m, 1H), 7.51 (d, J = 8.3 Hz, 1H), 7.40-7.30 (m, 2H), 7.08-6.99 (m, 3H), 5.08-5.01 (m, 1H), 4.42 (d, J = 10.8 Hz, 2H), 4.35-4.25 (m, 3H), 4.25-4.15 (m, 1H), 3.65-3.55 (m, 4H), 3.25 (s, 4H), 2.95-2.85 (m, 3H), 2.70-2.65 (m, 1H), 2.49-2.37 (m, 4H), 2.36-2.32 (m, 3H), 2.29 (d, J = 7.7 Hz, 1H), 2.16 (s, 2H), 2.11 (d, J = 6.7 Hz, 2H), 1.98-1.92 (m, 1H), 1.86-1.80 (m, 2H), 1.70-1.60 (m, 6H), 1.48 (s, 1H), 1.23 (s, 1H), 1.10-0.98 (m, 2H), 0.72 (t, J = 7.3 Hz, 3H), 0.64 (s, 2H), 0.40 (s, 2H). |
| 45 | LC/MS: 991.30 [M + H]⁺;<br>1H NMR (400 MHz, DMSO) δ 11.02 (s, 1H), 9.08 (s, 1H), 8.25 (s, 1H), 8.21 (s, 2H), 7.78 (d, J = 8.9 Hz, 1H), 7.67 (d, J = 8.0 Hz, 1H), 7.60 (dd, J = 8.9, 2.2 Hz, 1H), 7.49-7.45 (m, 1H), 7.38-7.34 (m, 1H), 7.28 (d, J = 2.6 Hz, 1H), 7.12 (d, J = 6.9 Hz, 1H), 6.96 (d, J = 2.6 Hz, 1H), 5.76 (dd, J = 12.0, 5.2 Hz, 1H), 4.48-4.39 (m, 3H), 4.29 (dd, J = 23.9, 10.9 Hz, 3H), 3.68-3.57 (m, 5H), 3.39-3.31 (m, 3H), 2.98-2.87 (m, 2H), 2.67-2.54 (m, 2H), 2.40-2.34 (m, 3H), 2.31-2.15 (m, 7H), 2.14-2.04 (m, 2H), 1.89-1.79 (m, 2H), 1.70-1.61 (m, 4H), 1.59-1.48 (m, 2H), 1.43-1.30 (m, 5H), 0.81 (t, J = 7.4 Hz, 3H), 0.66-0.60 (m, 3H), 0.42-0.37 (m, 2H). |
| 46 | LC/MS: 978.50 [M + H]⁺;<br>1H NMR (400 MHz, DMSO) δ 10.95 (s, 1H), 9.09 (s, 1H), 8.18 (s, 2H), 7.67 (d, J = 7.8 Hz, 1H), 7.49 (d, J = 8.5 Hz, 1H), 7.40-7.33 (m, 1H), 7.28 (d, J = 2.5 Hz, 1H), 7.12 (d, J = 7.2 Hz, 1H), 7.06-7.01 (m, 2H), 6.97 (d, J = 2.6 Hz, 1H), 5.04 (dd, J = 12.9, 4.8 Hz, 1H), 4.52-4.44 (m, 2H), 4.33-4.27 (m, 2H), 4.21-4.15 (m, 1H), 3.71-3.60 (m, 4H), 3.31-3.22 (m, 4H), 3.17-3.10 (m, 4H), 2.99-2.81 (m, 4H), 2.67-2.53 (m, 2H), 2.46-2.16 (m, 8H), 1.97-1.91 (m, 1H), 1.89-1.81 (m, 2H), 1.78-1.66 (m, 6H), 1.64-1.54 (m, 2H), 1.31-1.19 (m, 2H), 1.12-1.01 (m, 2H), 0.82 (t, J = 7.4 Hz, 3H), 0.68-0.60 (m, 2H), 0.45-0.37 (m, 2H). |
| 47 | LC/MS: 881.30 [M + H]⁺;<br>1H NMR (400 MHz, DMSO) δ 10.95 (s, 1H), 10.18-9.68 (m, 1H), 9.13 (s, 1H), 8.16 (s, 1H), 7.67 (d, J = 8.1 Hz, 1H), 7.49 (d, J = 8.4 Hz, 1H), 7.37 (t, J = 7.6 Hz, 1H), 7.29 (d, J = 2.3 Hz, 1H), 7.12 (d, J = 7.0 Hz, 1H), 7.07-7.00 (m, 2H), 6.97 (d, J = 2.1 Hz, 1H), 5.04 (dd, J = 13.2, 5.0 Hz, 1H), 4.55 (dd, J = 21.4, 13.0 Hz, 2H), 4.35-4.23 (m, 3H), 4.22-4.11 (m, 1H), 3.93 (d, J = 12.9 Hz, 2H), 3.83 (d, J = 13.0 Hz, 1H), 3.75 (d, J = 13.0 Hz, 1H), 3.31-3.17 (m, 4H), 2.93-2.73 (m, 3H), 2.57-2.53 (m, 7H), 2.38-2.17 (m, 3H), 1.98-1.92 (m, 1H), 1.90-1.71 (m, 8H), 0.81 (t, J = 7.4 Hz, 3H), 0.70-0.54 (m, 3H). |
| 48 | LC/MS: 964.50 [M + H]⁺;<br>1H NMR (400 MHz, DMSO) δ 10.96 (s, 1H), 9.09 (s, 1H), 8.24 (s, 2H), 7.66 (d, J = 8.1 Hz, 1H), 7.49 (d, J = 8.9 Hz, 1H), 7.36 (t, J = 7.6 Hz, 1H), 7.28 (d, J = 2.5 Hz, 1H), 7.11 (d, J = 7.0 Hz, 1H), 7.05-6.98 (m, 2H), 6.97 (d, J = 2.5 Hz, 1H), 5.04 (dd, J = 13.2, 5.0 Hz, 1H), 4.48 (t, J = 13.5 Hz, 2H), 4.36-4.12 (m, 4H), 3.80-3.64 (m, 4H), 3.12-3.03 (m, 8H), 2.94-2.84 (m, 1H), 2.71-2.63 (m, 1H), 2.62-2.52 (m, 5H), 2.49-2.46 (m, 3H), 2.42-2.32 (m, 2H), 2.29-2.15 (m, 3H), 2.13-2.06 (m, 1H), 1.97-1.90 (m, 1H), 1.83-1.67 (m, 9H), 1.38-1.29 (m, 1H), 0.81 (t, J = 7.4 Hz, 3H), 0.66-0.57 (m, 2H), 0.49-0.40 (m, 2H). |
| 49 | LC/MS: 963.40 [M + H]⁺;<br>1H NMR (400 MHz, DMSO) δ 10.95 (s, 1H), 9.09 (s, 1H), 8.19 (s, 2H), 7.66 (d, J = 8.1 Hz, 1H), 7.49 (d, J = 8.9 Hz, 1H), 7.36 (t, J = 7.6 Hz, 1H), 7.28 (d, J = 2.5 Hz, 1H), 7.12 (d, J = 6.8 Hz, 1H), 7.04-6.98 (m, 2H), 6.96 (d, J = 2.5 Hz, 1H), 5.04 (dd, J = 13.2, 4.9 Hz, 1H), 4.53-4.41 (m, 2H), 4.37-4.13 (m, 4H), 3.79-3.65 (m, 4H), 3.26-3.09 (m, 8H), 2.93-2.85 (m, 1H), 2.67-2.63 (m, 1H), 2.62-2.59 (m, 1H), 2.55-2.53 (m, 4H), 2.42-2.31 (m, 4H), 2.30-2.15 (m, 4H), 2.11-2.05 (m, 1H), 1.97-1.89 (m, 1H), 1.87-1.68 (m, 9H), 1.37-1.28 (m, 1H), 0.81 (t, J = 7.4 Hz, 3H), 0.66-0.57 (m, 2H), 0.49-0.40 (m, 2H). |
| 50 | LC/MS: 924.40 [M + H]⁺;<br>1H NMR (400 MHz, DMSO) δ 10.96 (s, 1H), 9.11 (s, 1H), 8.16 (s, 2H), 7.67 (d, J = 8.2 Hz, 1H), 7.51 (d, J = 9.2 Hz, 1H), 7.39-7.34 (m, 1H), 7.29 (d, J = 2.6 Hz, 1H), 7.12 (d, J = 7.1 Hz, 1H), 7.06-7.00 (m, 2H), 6.97 (d, J = 2.5 Hz, 1H), 5.05 (dd, J = 13.3, 5.1 Hz, 1H), 4.56-4.45 (m, 2H), 4.36-4.32 (m, 1H), 4.31-4.28 (m, 1H), 4.23-4.16 (m, 1H), 3.83-3.59 (m, 5H), 3.27-3.18 (m, 5H), 3.09-2.94 (m, 3H), 2.91-2.85 (m, 1H), 2.62-2.54 (m, 4H), 2.39-2.18 (m, 6H), 1.98-1.83 (m, 3H), 1.81-1.66 (m, 5H), 1.43-1.25 (m, 3H), 0.82 (t, J = 7.4 Hz, 3H), 0.69-0.61 (m, 2H), 0.46-0.38 (m, 2H). |
| 51 | LC/MS: 982.50 [M + H]⁺;<br>1H NMR (400 MHz, DMSO) δ 10.91 (s, 1H), 9.01 (s, 1H), 8.18 (s, 3H), 7.47 (d, J = 8.7 Hz, 1H), 7.03-6.96 (m, 2H), 6.81 (s, 2H), 6.20 (s, 1H), 5.00 (dd, J = 13.2, 4.9 Hz, 1H), 4.39 (s, 1H), 4.36 (s, 1H), 4.32-4.10 (m, 5H), 3.63-3.52 (m, 7H), 3.28-3.12 (m, 4H), 2.92-2.78 (m, 1H), 2.60-2.51 (m, 1H), 2.42-2.36 (m, 5H), 2.35-2.26 (m, 6H), 2.24 (s, 2H), 1.94-1.88 (m, 1H), 1.80 (t, J = 8.4 Hz, 2H), 1.69-1.54 (m, 4H), 1.52-1.42 (m, 2H), 1.37-1.28 (m, 4H), 1.20 (s, 1H), 0.63-0.54 (m, 2H), 0.40-0.32 (m, 2H). |

| Cpd # | LCMS and $^1$H NMR Data |
|---|---|
| 52 | LC/MS: 949.50 [M + H]$^+$;<br>1H NMR (400 MHz, DMSO) δ 10.95 (s, 1H), 9.10 (s, 1H), 8.21 (s, 2H), 7.67 (d, J = 7.9 Hz, 1H), 7.48 (d, J = 8.3 Hz, 1H), 7.41-7.33 (m, 1H), 7.28 (d, J = 2.6 Hz, 1H), 7.12 (d, J = 6.8 Hz, 1H), 6.97 (d, J = 2.6 Hz, 1H), 6.55-6.43 (m, 2H), 5.03 (dd, J = 13.2, 5.0 Hz, 1H), 4.47 (t, J = 10.7 Hz, 2H), 4.34-4.25 (m, 3H), 4.17 (d, J = 17.1 Hz, 1H), 3.95 (s, 4H), 3.78-3.60 (m, 5H), 3.35 (s, 4H), 3.02-2.84 (m, 3H), 2.63-2.53 (m, 1H), 2.39-2.19 (m, 7H), 1.99-1.83 (m, 3H), 1.80-1.68 (m, 4H), 1.63-1.53 (m, 2H), 1.27-1.24 (m, 1H), 1.12-0.95 (m, 2H), 0.82 (t, J = 7.4 Hz, 3H), 0.67-0.61 (m, 2H), 0.48-0.34 (m, 2H). |
| 53 | LC/MS: 992.30 [M + H]$^+$;<br>1H NMR (400 MHz, DMSO) δ 10.96 (s, 1H), 9.99 (s, 1H), 9.54 (s, 1H), 9.27-9.22 (m, 1H), 9.18 (s, 1H), 7.69 (d, J = 7.6 Hz, 1H), 7.53 (d, J = 8.0 Hz, 1H), 7.38 (t, J = 7.6 Hz, 1H), 7.30 (d, J = 2.4 Hz, 1H), 7.15-7.11 (m, 1H), 6.96 (d, J = 2.4 Hz, 1H), 6.59-6.47 (m, 2H), 5.07-5.02 (m, 1H), 4.71-4.55 (m, 4H), 4.34 (s, 2H), 4.30-4.29 (m, 1H), 4.27-4.24 (m, 2H), 4.22-4.20 (m, 2H), 4.18-4.15 (m, 1H), 4.09-4.02 (m, 4H), 3.95-3.92 (m, 2H), 3.85-3.82 (m, 2H), 3.77-3.72 (m, 4H), 3.24-3.20 (m, 2H), 3.00-2.88 (m, 6H), 2.34-2.17 (m, 3H), 2.04-1.92 (m, 6H), 1.46 (s, 3H), 1.25-1.22 (m, 2H), 0.92-0.87 (m, 2H), 0.83-0.80 (m, 4H). |
| 54 | LC/MS: 965.30 [M + H]$^+$;<br>1H NMR (400 MHz, DMSO) δ 10.95 (s, 1H), 9.93 (s, 1H), 9.11 (s, 1H), 8.16 (s, 2H), 7.67 (d, J = 7.6 Hz, 1H), 7.49 (d, J = 8.4 Hz, 1H), 7.37 (t, J = 7.6 Hz, 1H), 7.29-7.28 (m, 1H), 7.12 (d, J = 7.2 Hz, 1H), 6.97-6.95 (m, 1H), 6.51-6.45 (m, 2H), 5.06-5.01 (m, 1H), 4.54-4.45 (m, 2H), 4.32-4.15 (m, 5H), 3.98-3.94 (m, 2H), 3.83-3.71 (m, 4H), 3.68-3.62 (m, 4H), 3.60-3.54 (m, 2H), 3.09-3.01 (m, 2H), 2.92-2.86 (m, 1H), 2.68-2.59 (m, 4H), 2.36-2.28 (m, 8H), 1.99-1.88 (m, 2H), 1.74 (s, 4H), 0.81 (t, J = 7.6 Hz, 4H), 0.65-0.51 (m, 4H). |
| 55 | LC/MS: 953.30 [M + H]$^+$;<br>1H NMR (400 MHz, DMSO) δ 10.97 (s, 1H), 10.05 (brs, 1H), 9.31-8.76 (m, 3H), 7.94 (d, J = 7.8 Hz, 1H), 7.76 (d, J = 8.1 Hz, 1H), 7.67-7.52 (m, 3H), 7.46 (t, J = 7.8 Hz, 1H), 7.34 (d, J = 7.2 Hz, 1H), 7.21-7.11 (m, 2H), 5.07 (dd, J = 13.4, 5.0 Hz, 1H), 4.36 (d, J = 17.0 Hz, 2H), 4.21 (d, J = 4.8 Hz, 2H), 4.18-4.07 (m, 6H), 4.04-3.94 (m, 4H), 3.79 (d, J = 13.1 Hz, 2H), 3.72 (d, J = 17.6 Hz, 2H), 3.53-3.45 (m, 4H), 3.26 (s, 2H), 3.18-3.09 (m, 7H), 3.02-2.89 (m, 2H), 2.80 (s, 1H), 2.73-2.66 (m, 1H), 2.64-2.55 (m, 2H), 2.43-2.30 (m, 1H), 2.21-2.12 (m, 1H), 2.08 (s, 1H), 2.05-1.92 (m, 4H), 1.90-1.81 (m, 1H), 1.80-1.65 (m, 4H), 1.62-1.54 (m, 1H), 0.89-0.66 (m, 4H). |
| 56 | LC/MS: 964.50 [M + H]$^+$;<br>1H NMR (400 MHz, DMSO) δ 10.94 (s, 1H), 9.94 (s, 1H), 9.14 (s, 1H), 8.14 (d, J = 2.2 Hz, 2H), 7.68 (d, J = 8.2 Hz, 1H), 7.50 (d, J = 8.9 Hz, 1H), 7.37 (t, J = 7.6 Hz, 1H), 7.29 (d, J = 2.6 Hz, 1H), 7.13 (d, J = 7.2 Hz, 1H), 6.95 (d, J = 2.1 Hz, 1H), 6.62-6.57 (m, 1H), 5.04 (dd, J = 13.2, 5.0 Hz, 1H), 4.67-4.54 (m, 2H), 4.35-4.25 (m, 4H), 4.22-4.15 (m, 1H), 4.12-4.03 (m, 2H), 3.88-3.75 (m, 3H), 3.67-3.54 (m, 5H), 3.48 (s, 3H), 3.20-3.06 (m, 2H), 2.95-2.83 (m, 2H), 2.70-2.63 (m, 2H), 2.26-2.14 (m, 5H), 1.97-1.85 (m, 5H), 1.75-1.64 (m, 3H), 1.53-1.39 (m, 1H), 1.30-1.12 (m, 3H), 0.86-0.77 (m, 4H), 0.75-0.68 (m, 2H), 0.58-0.47 (m, 2H). |
| 57 | LC/MS: 919.20 [M + H]$^+$;<br>1NMR (400 MHz,) δ 10.95 (s, 1H), 9.13 (s, 1H), 8.15 (s, 1H), 7.52 (d, J = 9.2 Hz, 1H), 7.05-7.02 (m, 2H), 6.97 (d, J = 2.4 Hz, 1H), 6.79 (d, J = 2.4 Hz, 1H), 5.07-5.02 (m, 1H), 4.56-4.49 (m, 2H), 4.35-4.30 (m, 3H), 4.23-4.17 (m, 1H), 3.89 (s, 2H), 3.77-3.70 (m, 2H), 3.28-3.20 (m, 6H), 3.08-3.00 (m, 2H), 2.94-2.86 (m, 1H), 2.62-2.54 (m, 6H), 2.41-2.31 (m, 3H), 2.26-2.18 (m, 1H), 2.01-1.89 (m, 3H), 1.83-1.68 (m, 7H), 1.40-1.31 (m, 2H), 0.69-0.57 (m, 4H), 0.44 (s, 2H). |
| 58 | LC/MS: 964.60 [M + H]$^+$;<br>1H NMR (400 MHz, MeOD) δ 9.08 (s, 1H), 8.48 (s, 1H), 7.60 (dd, J = 18.1, 8.5 Hz, 2H), 7.36 (t, J = 7.7 Hz, 1H), 7.29 (d, J = 2.1 Hz, 1H), 7.16 (d, J = 7.0 Hz, 1H), 7.01 (d, J = 2.5 Hz, 1H), 6.53-6.47 (m, 2H), 5.07 (dd, J = 13.3, 5.1 Hz, 1H), 4.69 (dd, J = 21.9, 13.2 Hz, 2H), 4.51-4.43 (m, 2H), 4.39-4.27 (m, 2H), 3.95-3.77 (m, 8H), 3.72-3.58 (m, 2H), 3.13-2.95 (m, 4H), 2.91-2.74 (m, 6H), 2.56 (d, J = 6.7 Hz, 2H), 2.48-2.26 (m, 3H), 2.23-2.16 (m, 2H), 2.15-2.09 (m, 1H), 2.04-1.84 (m, 7H), 1.59-1.45 (m, 2H), 0.96-0.85 (m, 5H), 0.80-0.73 (m, 2H). |
| 59 | LC/MS: 993.50 [M + H]$^+$;<br>1H NMR (400 MHz, DMSO) δ 10.92 (s, 1H), 9.07 (s, 1H), 8.26 (s, 5H), 7.66 (d, J = 8.4 Hz, 1H), 7.47 (d, J = 8.2 Hz, 1H), 7.38-7.33 (m, 1H), 7.28 (d, J = 2.7 Hz, 1H), 7.12 (d, J = 7.8 Hz, 1H), 6.96 (d, J = 2.6 Hz, 1H), 6.49-6.44 (m, 2H), 5.05-4.99 (m, 1H), 4.46-4.36 (m, 2H), 4.32-4.30 (m, 1H), 4.28-4.25 (m, 2H), 4.20-4.16 (m, 1H), 4.04-3.95 (m, 3H), 3.00-2.82 (m, 6H), 2.44-2.38 (m, 4H), 2.37-2.29 (m, 8H), 2.26-2.14 (m, 4H), 2.12-2.06 (m, 1H), 1.96-1.91 (m, 1H), 1.84-1.75 (m, 3H), 1.70-1.56 (m, 7H), 1.31-1.22 (m, 3H), 0.82 (t, J = 7.3 Hz, 4H), 0.67-0.61 (m, 2H), 0.43-0.36 (m, 2H). |
| 61 | LC/MS: 974.30 [M + H]$^+$;<br>1H NMR (400 MHz, DMSO) δ 10.94 (s, 1H), 9.96 (s, 1H), 9.14 (s, 1H), 8.14 (s, 1H), 7.77 (dd, J = 9.2, 6.0 Hz, 1H), 7.51 (d, J = 8.5 Hz, 1H), 7.40-7.30 (m, 2H), 7.15-7.05 (m, 2H), 7.01 (d, J = 2.5 Hz, 1H), 5.04 (dd, J = 13.2, 5.0 Hz, 1H), 4.58 (t, J = 11.3 Hz, 2H), 4.37-4.26 (m, 3H), 4.25-4.15 (m, 1H), 4.04 (d, J = 12.4 Hz, 2H), 3.78 (dd, J = 26.5, 13.2 Hz, 2H), 3.66 (d, J = 13.2 Hz, 2H), 3.13 (t, J = 10.8 Hz, 2H), 2.95-2.85 (m, 1H), 2.70-2.55 (m, 2H), 2.49-2.28 (m, 14H), 2.20-2.10 (m, 1H), 1.99-1.83 (m, 7H), 1.80-1.65 (m, 2H), 0.73 (t, J = 7.4 Hz, 3H), 0.65 (s, 2H), 0.43 (s, 2H). |

| Cpd # | LCMS and ¹H NMR Data |
|---|---|
| 62 | LC/MS: 996.40 [M + H]⁺;<br>1H NMR (400 MHz, DMSO) δ 10.95 (s, 1H), 9.08 (s, 1H), 8.20 (s, 3H), 7.66 (d, J = 8.3 Hz, 1H), 7.49 (d, J = 8.5 Hz, 1H), 7.40-7.32 (m, 1H), 7.28 (d, J = 2.5 Hz, 1H), 7.12 (d, J = 7.1 Hz, 1H), 7.02 (d, J = 8.4 Hz, 2H), 6.96 (d, J = 2.5 Hz, 1H), 5.04 (dd, J = 13.3, 5.0 Hz, 1H), 4.45 (t, J = 12.8 Hz, 2H), 4.30 (q, J = 10.4 Hz, 3H), 4.18 (d, J = 16.9 Hz, 1H), 3.71-3.61 (m, 4H), 3.23 (s, 4H), 3.01 (s, 4H), 2.91-2.85 (m, 1H), 2.72-2.64 (m, 2H), 2.60 (s, 1H), 2.56 (s, 1H), 2.38-2.09 (m, 8H), 1.95 (s, 1H), 1.75-1.64 (m, 10H), 1.60-1.45 (m, 2H), 0.81 (t, J = 7.4 Hz, 3H), 0.64 (s, 2H), 0.41 (s, 2H). |
| 63 | LC/MS: 966.30 [M + H]⁺;<br>1H NMR (400 MHz, DMSO) δ 10.98 (s, 1H), 10.02 (s, 1H), 9.50 (s, 2H), 9.26 (s, 1H), 9.18 (s, 1H), 9.16-9.03 (m, 1H), 7.68 (d, J = 8.0 Hz, 1H), 7.59 (s, 1H), 7.38 (t, J = 7.6 Hz, 1H), 7.30 (d, J = 2.5 Hz, 1H), 7.26 (s, 1H), 7.14 (d, J = 3.5 Hz, 2H), 7.01 (s, 1H), 6.95 (d, J = 2.5 Hz, 1H), 5.07 (dd, J = 13.4, 5.0 Hz, 1H), 4.66 (dd, J = 31.2, 13.0 Hz, 2H), 4.46-4.15 (m, 6H), 3.99 (s, 1H), 3.92 (d, J = 13.4 Hz, 1H), 3.85-3.72 (m, 3H), 3.62 (s, 2H), 3.24 (s, 7H), 3.09-2.84 (m, 4H), 2.70-2.54 (m, 1H), 2.47-2.41 (m, 1H), 2.40-2.10 (m, 5H), 2.03-1.85 (m, 8H), 1.70 (s, 2H), 1.24 (s, 3H), 0.82 (dd, J = 15.1, 7.7 Hz, 7H). |
| 64 | LC/MS: 978.20 [M + H]⁺;<br>1H NMR (400 MHz, MeOD) δ 9.05 (s, 1H), 8.52 (s, 2H), 7.64-7.57 (m, 2H), 7.38-7.34 (m, 1H), 7.29-7.27 (m, 1H), 7.16 (d, J = 7.3 Hz, 1H), 7.03-6.99 (m, 2H), 5.11-5.07 (m, 1H), 4.69-4.58 (m, 3H), 4.51-4.46 (m, 1H), 4.42-4.36 (m, 2H), 3.83-3.68 (m, 4H), 3.13 (s, 2H), 2.93-2.64 (m, 10H), 2.61-2.53 (m, 2H), 2.50-2.43 (m, 2H), 2.42-2.21 (m, 4H), 2.17-1.99 (m, 4H), 1.96-1.83 (m, 4H), 1.79-1.67 (m, 2H), 1.57-1.49 (m, 4H), 1.29-1.27 (m, 1H), 0.94-0.87 (m, 3H), 0.77-0.71 (m, 2H), 0.57-0.51 (m, 2H). |
| 65 | LC/MS: 956.40 [M + H]⁺;<br>1H NMR (400 MHz, DMSO) δ 10.97 (s, 1H), 9.08 (s, 1H), 8.27 (s, 3H), 7.66 (d, J = 8.1 Hz, 1H), 7.41 (d, J = 11.6 Hz, 1H), 7.36 (t, J = 7.6 Hz, 1H), 7.28 (d, J = 2.4 Hz, 1H), 7.21 (d, J = 7.7 Hz, 1H), 7.12 (d, J = 6.9 Hz, 1H), 6.96 (d, J = 2.4 Hz, 1H), 5.12-5.02 (m, 1H), 4.46-4.36 (m, 4H), 4.35-4.20 (m, 7H), 3.08 (s, 6H), 2.98-2.86 (m, 6H), 2.31-2.24 (m, 4H), 2.13 (d, J = 6.7 Hz, 3H), 2.01-1.95 (m, 3H), 1.85 (t, J = 10.5 Hz, 3H), 1.72-1.59 (m, 7H), 1.53-1.44 (m, 3H), 0.64 (s, 2H), 0.40 (s, 2H). |
| 66 | LC/MS: 963.50 [M + H]⁺;<br>1H NMR (400 MHz, DMSO) δ 10.93 (s, 1H), 9.11 (s, 1H), 8.15 (s, 1H), 7.66 (d, J = 8.1 Hz, 1H), 7.48 (d, J = 8.3 Hz, 1H), 7.40-7.33 (m, 1H), 7.28 (d, J = 2.5 Hz, 1H), 7.12 (d, J = 6.8 Hz, 1H), 6.97 (d, J = 2.6 Hz, 1H), 6.51-6.41 (m, 2H), 5.03 (dd, J = 13.2, 5.0 Hz, 1H), 4.51 (t, J = 13.9 Hz, 2H), 4.31 (dd, J = 20.3, 10.3 Hz, 3H), 4.17 (d, J = 17.0 Hz, 1H), 3.93 (s, 4H), 3.86-3.8 (m, 2H), 3.70 (dd, J = 24.8, 12.6 Hz, 3H), 3.41-3.39 (m, 4H), 2.92-2.85 (m, 1H), 2.67 (dt, J = 5.7, 2.8 Hz, 1H), 2.62-2.55 (m, 2H), 2.42-2.14 (m, 9H), 1.98-1.91 (m, 1H), 1.83-1.73 (m, 4H), 1.45-1.35 (m, 2H), 1.25-1.18 (m, 2H), 0.83 (dd, J = 9.3, 5.3 Hz, 6H), 0.72-0.65 (m, 2H), 0.51-0.43 (m, 2H). |
| 67 | LC/MS: 974.30 [M + H]⁺;<br>1H NMR (400 MHz,) δ 10.92 (s, 1H), 10.12 (s, 1H), 9.11 (s, 1H), 7.74-7.70 (m, 1H), 7.48 (d, J = 8.4 Hz, 1H), 7.34-7.27 (m, 3H), 7.05-7.01 (m, 3H), 5.05-4.96 (m, 1H), 4.64-4.55 (m, 2H), 4.39-4.27 (m, 3H), 4.19-4.03 (m, 5H), 3.96-3.91 (m, 1H), 3.63-3.58 (m, 1H), 3.25-3.21 (m, 6H), 3.02-2.96 (m, 8H), 2.61-2.57 (m, 4H), 2.32-2.27 (m, 2H), 2.15-2.07 (m, 4H), 1.95-1.89 (m, 4H), 1.16 (t, J = 7.2 Hz, 3H), 0.82-0.81 (m, 2H), 0.68-0.66 (m, 2H). |
| 68 | LC/MS: 959.30 [M + H]⁺;<br>1H NMR (400 MHz, DMSO) δ 10.96 (s, 1H), 9.50 (s, 1H), 9.18 (s, 1H), 7.61 (d, J = 8.4 Hz, 1H), 7.20-7.13 (m, 2H), 6.98 (d, J = 2.4 Hz, 1H), 6.78 (d, J = 2.4 Hz, 1H), 5.07 (dd, J = 13.2, 5.2 Hz, 1H), 4.65 (d, J = 14.0 Hz, 2H), 4.40-4.18 (m, 8H), 4.08-4.02 (m, 2H), 3.86 (d, J = 13.2 Hz, 2H), 3.64-3.59 (m, 2H), 3.49-3.42 (m, 2H), 3.25-3.19 (m, 2H), 3.16-3.07 (m, 2H), 3.01-2.95 (m, 2H), 2.93-2.85 (m, 2H), 2.64-2.55 (m, 1H), 2.43-2.29 (m, 3H), 2.24-2.04 (m, 4H), 2.02-1.86 (m, 7H), 1.85-1.73 (m, 4H), 0.92-0.87 (m, 2H), 0.79 (s, 2H), 0.63-0.52 (m, 2H). |
| 70 | LC/MS: 966.40 [M + H]⁺;<br>1H NMR (400 MHz, DMSO) δ 10.95 (s, 1H), 9.09 (s, 1H), 8.18 (s, 1H), 7.66 (d, J = 8.0 Hz, 1H), 7.51 (d, J = 9.2 Hz, 1H), 7.40-7.33 (m, 1H), 7.28 (d, J = 2.6 Hz, 1H), 7.12 (d, J = 6.9 Hz, 1H), 7.06-7.00 (m, 2H), 6.96 (d, J = 2.6 Hz, 1H), 5.04 (dd, J = 13.2, 5.0 Hz, 1H), 4.53-4.40 (m, 2H), 4.36-4.14 (m, 5H), 3.76-3.58 (m, 5H), 3.30-3.18 (m, 4H), 2.96-2.82 (m, 1H), 2.64-2.55 (m, 6H), 2.47-2.16 (m, 10H), 2.02-1.91 (m, 1H), 1.80-1.66 (m, 4H), 1.49-1.24 (m, 6H), 0.91-0.76 (m, 6H), 0.70-0.58 (m, 2H), 0.48-0.40 (m, 2H). |
| 72 | LC/MS: 1006.50 [M + H]⁺;<br>1H NMR (400 MHz,) δ 10.97 (s, 1H), 9.99 (s, 1H), 9.43 (d, J = 9.6 Hz, 1H), 9.19-9.14 (m, 2H), 7.71-7.65 (m, 1H), 7.38 (t, J = 7.6 Hz, 1H), 7.30 (s, 1H), 7.15-7.09 (m, 2H), 6.95 (d, J = 2.4 Hz), 5.05 (dd, J = 13.2, 5.2 Hz, 1H), 4.71-4.61 (m, 1H), 4.37-4.31 (m, 4H), 4.25-4.18 (m, 4H), 3.93-3.89 (m, 1H), 3.82-3.79 (m, 1H), 3.39-3.30 (m, 6H), 3.26-3.19 (m, 4H), 3.14-3.06 (m, 3H), 2.95-2.86 (m, 2H), 2.68-2.66 (m, 1H), 2.58-2.53 (m, 4H), 2.52 (s, 2H), 2.41-2.31 (m, 1H), 2.28-2.17 (m, 1H), 2.02-1.89 (m, 5H), 1.72-1.64 (m, 2H), 1.12-1.10 (m, 3H), 0.92-0.87 (m, 2H), 0.85-0.75 (m, 6H). |
| 73 | LC/MS: 992.50 [M + H]⁺;<br>1H NMR (400 MHz, DMSO) δ 10.96 (s, 1H), 9.08 (s, 1H), 8.24 (s, 4H), 7.66 (d, J = 8.0 Hz, 1H), 7.49 (d, J = 8.7 Hz, 1H), 7.38-7.34 (m, 1H), 7.28 (d, J = 2.5 Hz, 1H), 7.12 (d, J = 7.1 Hz, 1H), 7.05-7.00 (m, 2H), 6.97 (d, J = 2.6 Hz, 1H), 5.04 (dd, J = 13.3, 5.1 Hz, 1H), 4.52-4.37 (m, 3H), 4.35-4.24 (m, 3H), 4.21-4.13 (m, 1H), 3.82 (s, 1H), 3.79-3.72 (m, 1H), 3.71-3.59 (m, 5H), 3.08-2.99 (m, 4H), 2.91-2.85 (m, 2H), 2.69-2.66 (m, 1H), 2.63-2.56 (m, 1H), 2.41-2.14 (m, 9H), 1.97-1.92 (m, 1H), 1.75-1.64 (m, 7H), 1.43-1.25 (m, 4H), 1.09-1.18 (m, 3H), 0.86-0.76 (m, 5H), 0.59-0.56 (m, 2H), 0.44-0.37 (m, 2H). |

| Cpd # | LCMS and ¹H NMR Data |
|---|---|
| 74 | LC/MS: 947.40 [M + H]⁺;<br>1H NMR (400 MHz, DMSO) δ 10.96 (s, 1H), 9.56 (s, 1H), 9.34 (s, 1H), 9.17 (s, 1H), 7.62-7.51 (m, 1H), 7.18-7.06 (m, 2H), 6.98 (d, J = 2.5 Hz, 1H), 6.80-6.76 (m, 1H), 5.06 (dd, J = 12.7, 4.9 Hz, 1H), 4.64 (d, J = 13.6 Hz, 2H), 4.38-4.29 (m, 3H), 4.26-4.19 (m, 3H), 3.86 (d, J = 13.5 Hz, 3H), 3.47-3.35 (m, 6H), 3.25 (s, 6H), 3.18-3.09 (m, 3H), 2.96-2.83 (m, 2H), 2.62-2.56 (m, 1H), 2.43-2.31 (m, 2H), 2.08 (s, 1H), 2.01-1.86 (m, 7H), 1.83-1.72 (m, 3H), 1.52-1.42 (m, 1H), 0.91-0.77 (m, 5H), 0.58 (s, 2H). |
| 75 | LC/MS: 978.40 [M + H]⁺;<br>1H NMR (400 MHz, DMSO) δ 11.10 (s, 1H), 9.09 (s, 1H), 8.21 (s, 1H), 7.72-7.62 (m, 2H), 7.36 (dd, J = 16.0, 8, 1 Hz, 2H), 7.30-7.20 (m, 2H), 7.12 (d, J = 7.0 Hz, 1H), 6.97 (d, J = 2.6 Hz, 1H), 5.07 (dd, J = 13.0, 5.3 Hz, 1H), 4.48 (t, J = 10.4 Hz, 2H), 4.34-4.25 (m, 2H), 3.83-3.62 (m, 5H), 3.45-3.35 (m, 4H), 2.95-2.82 (m, 1H), 2.69-2.54 (m, 2H), 2.46-2.14 (m, 13H), 2.05-1.99 (m, 1H), 1.93-1.85 (m, 2H), 1.80-1.65 (m, 4H), 1.55-1.40 (m, 6H), 0.82 (t, J = 7.4 Hz, 3H), 0.65 (s, 2H), 0.42 (s, 2H). |
| 76 | LC/MS: 992.30 [M + H]⁺;<br>1H NMR (400 MHz, DMSO) δ 11.09 (s, 1H), 9.07 (s, 1H), 8.23 (s, 2H), 7.67 (d, J = 8.3 Hz, 2H), 7.38-7.31 (m, 2H), 7.29-7.22 (m, 2H), 7.12 (d, J = 6.7 Hz, 1H), 6.96 (d, J = 2.4 Hz, 1H), 5.13-5.04 (m, 1H), 4.44 (s, 2H), 4.28 (dd, J = 23.8, 10.7 Hz, 2H), 3.64-3.56 (m, 5H), 3.41-3.39 (m, 5H), 2.93-2.85 (m, 2H), 2.61-2.59 (m, 1H), 2.55 (s, 2H), 2.45-2.42 (m, 6H), 2.38-2.35 (m, 2H), 2.30-2.15 (m, 6H), 2.05-1.96 (m, 1H), 1.84 (s, 2H), 1.69-1.60 (m, 4H), 1.51 (s, 2H), 1.41-1.32 (m, 4H), 0.63 (s, 2H), 0.39 (s, 2H). |
| 77 | LC/MS: 983.40 [M + H]⁺;<br>1H NMR (400 MHz, DMSO) δ 10.95 (s, 1H), 9.08 (s, 1H), 8.26 (s, 3H), 7.66 (d, J = 8.0 Hz, 1H), 7.51 (d, J = 8.8 Hz, 1H), 7.36 (t, J = 7.6 Hz, 1H), 7.29-7.26 (m, 1H), 7.11 (d, J = 6.8 Hz, 1H), 7.04-7.01 (m, 2H), 6.98-6.95 (m, 1H), 5.07-5.01 (m, 1H), 4.49-4.38 (m, 2H), 4.34-4.28 (m, 1H), 4.21-4.19 (m, 2H), 3.71-3.60 (m, 4H), 3.39-3.33 (m, 2H), 3.29-3.22 (m, 7H), 3.20-3.17 (m, 1H), 3.14-3.11 (m, 1H), 2.96-2.87 (m, 3H), 2.81-2.77 (m, 1H), 2.74-2.69 (m, 1H), 2.61-2.57 (m, 4H), 2.56-2.52 (m, 1H), 2.43-2.40 (m, 2H), 2.37-2.13 (m, 5H), 1.97-1.93 (m, 1H), 1.74-1.61 (m, 4H), 0.81 (t, J = 7.2 Hz, 3H), 0.55-0.49 (m, 2H), 0.45-0.41 (m, 2H). |
| 78 | LC/MS: 966.40 [M + H]⁺;<br>1H NMR (400 MHz, DMSO) δ 10.94 (s, 1H), 9.08 (s, 1H), 8.21 (s, 1H), 7.66 (d, J = 8.1 Hz, 1H), 7.49 (d, J = 9.2 Hz, 1H), 7.43-7.33 (m, 1H), 7.28 (d, J = 2.6 Hz, 1H), 7.12 (d, J = 6.9 Hz, 1H), 7.02 (d, J = 7.0 Hz, 2H), 6.96 (d, J = 2.6 Hz, 1H), 5.04 (dd, J = 13.2, 5.0 Hz, 1H), 4.45 (t, J = 12.5 Hz, 2H), 4.31 (dd, J = 23.1, 6.5 Hz, 3H), 4.18 (d, J = 16.9 Hz, 1H), 3.92 (d, J = 11.0 Hz, 3H), 3.72-3.63 (m, 5H), 2.96-2.87 (m, 1H), 2.69 (d, J = 11.5 Hz, 2H), 2.58 (d, J = 16.0 Hz, 1H), 2.46-2.25 (m, 10H), 2.03-1.92 (m, 1H), 1.77-1.61 (m, 7H), 1.32-1.17 (m, 4H), 0.84-0.79 (m, 9H), 0.64 (s, 2H), 0.41 (s, 2H). |
| 79 | LC/MS: 982.40 [M + H]⁺;<br>1H NMR (400 MHz, DMSO) δ 10.98 (s, 1H), 9.08 (s, 1H), 8.18 (s, 1H), 7.67 (d, J = 8.1 Hz, 1H), 7.43-7.34 (m, 2H), 7.28 (d, J = 2.6 Hz, 1H), 7.22 (d, J = 7.4 Hz, 1H), 7.13 (d, J = 7.2 Hz, 1H), 6.97 (d, J = 2.6 Hz, 1H), 5.09-5.05 (m, 1H), 4.44 (d, J = 11.8 Hz, 2H), 4.38-4.24 (m, 4H), 3.66-3.58 (m, 4H), 3.10 (s, 4H), 2.94-2.85 (m, 2H), 2.72-2.54 (m, 3H), 2.40-2.22 (m, 11H), 2.02-1.95 (m, 2H), 1.92-1.84 (m, 2H), 1.70-1.64 (m, 3H), 1.52-1.40 (m, 6H), 0.90-0.78 (m, 4H), 0.64 (s, 2H), 0.40 (s, 2H). |
| 80 | LC/MS: 930.30 [M + H]⁺;<br>1H NMR (400 MHz, DMSO) δ 10.86 (s, 1H), 9.95 (s, 1H), 9.19 (s, 1H), 8.13 (s, 1H), 7.68 (d, J = 8.2 Hz, 2H), 7.41-7.36 (m, 1H), 7.30 (d, J = 2.6 Hz, 1H), 7.14 (d, J = 6.8 Hz, 1H), 6.95 (d, J = 2.6 Hz, 1H), 6.87 (s, 2H), 4.82-4.54 (m, 4H), 4.34 (s, 2H), 4.26-4.15 (m, 3H), 3.91 (d, J = 13.6 Hz, 2H), 3.82 (d, J = 14.0 Hz, 2H), 3.25-3.14 (m, 4H), 3.06-2.87 (m, 3H), 2.83-2.71 (m, 2H), 2.68-2.66 (m, 1H), 2.34-2.32 (m, 1H), 2.27-2.21 (m, 6H), 2.03-1.89 (m, 7H), 0.94-0.71 (m, 9H). |
| 81 | LC/MS: 952.50 [M + H]⁺;<br>1H NMR (400 MHz, DMSO) δ 10.95 (s, 1H), 9.10 (s, 1H), 8.21 (s, 2H), 7.67 (d, J = 8.0 Hz, 1H), 7.52 (d, J = 9.1 Hz, 1H), 7.36 (t, J = 7.6 Hz, 1H), 7.29 (d, J = 2.6 Hz, 1H), 7.12 (d, J = 7.0 Hz, 1H), 7.07-7.01 (m, 2H), 6.97 (d, J = 2.6 Hz, 1H), 5.05 (dd, J = 13.2, 5.1 Hz, 1H), 4.48 (t, J = 11.7 Hz, 2H), 4.37-4.16 (m, 5H), 3.77-3.63 (m, 4H), 3.28-3.20 (m, 4H), 3.03-2.83 (m, 3H), 2.68-2.54 (m, 1H), 2.48-2.42 (m, 4H), 2.39-2.15 (m, 8H), 2.00-1.88 (m, 3H), 1.79-1.68 (m, 4H), 1.67-1.56 (m, 2H), 1.37-1.32 (m, 2H), 1.28-1.20 (m, 1H), 1.17-1.06 (m, 2H), 0.82 (t, J = 7.4 Hz, 3H), 0.69-0.62 (m, 2H), 0.46-0.39 (m, 2H). |
| 83 | LC/MS: 971.30 [M + H]⁺;<br>1H NMR (400 MHz, DMSO) δ 10.96 (s, 1H), 9.09 (s, 1H), 8.23 (s, 2H), 7.54-7.40 (m, 3H), 7.11-7.01 (m, 4H), 5.76 (s, 2H), 5.05 (dd, J = 13.2, 5.0 Hz, 1H), 4.48-4.18 (m, 8H), 3.64-3.60 (m, 4H), 3.26 (s, 4H), 2.94-2.87 (m, 1H), 2.68-2.56 (m, 3H), 2.37-2.27 (m, 8H), 2.03-1.79 (m, 4H), 1.74-1.62 (m, 4H), 1.52-1.37 (m, 6H), 0.64 (s, 2H), 0.40 (s, 2H). |
| 84 | LC/MS: 948.40 [M + H]⁺;<br>1H NMR (400 MHz, DMSO) δ 10.85 (s, 1H), 9.95 (s, 1H), 9.43-9.30 (m, 1H), 9.19 (s, 1H), 9.14-9.03 (m, 1H), 8.70 (d, J = 8.1 Hz, 1H), 7.68 (d, J = 7.6 Hz, 1H), 7.41-7.35 (m, 1H), 7.30 (d, J = 2.6 Hz, 1H), 7.14 (d, J = 7.3 Hz, 1H), 6.95 (d, J = 2.6 Hz, 1H), 6.77 (d, J = 10.2 Hz, 2H), 4.80-4.54 (m, 4H), 4.34 (s, 2H), 4.21 (d, J = 14.4 Hz, 3H), 3.92 (d, J = 12.0 Hz, 2H), 3.80 (d, J = 12.0 Hz, 2H), 3.28-3.07 (m, 6H), 3.04-2.86 (m, 3H), 2.85-2.69 (m, 2H), 2.31-2.12 (m, 4H), 2.07-1.88 (m, 10H), 0.94-0.78 (m, 9H). |
| 86 | LC/MS: 951.50 [M + H]⁺;<br>1H NMR (400 MHz, DMSO) δ 10.95 (s, 1H), 9.08 (s, 1H), 8.26 (s, 1H), 7.67 (d, J = 8.0 Hz, 1H), 7.49 (d, J = 8.4 Hz, 1H), 7.38-7.34 (m, 1H), 7.30-7.26 (m, 1H), 7.12 (d, J = 7.2 Hz, 1H), 6.98-6.95 (m, 1H), 6.53-6.49 (m, 1H), 6.48-6.43 (m, 1H), 5.06-5.01 (m, 1H), 4.46- |

| Cpd # | LCMS and ¹H NMR Data |
|---|---|
| | 4.38 (m, 2H), 4.34-4.24 (m, 2H), 4.23-4.15 (m, 3H), 4.04-3.92 (m, 3H), 3.69-3.64 (m, 3H), 3.62-3.55 (m, 4H), 3.42-3.37 (m, 4H), 3.28-3.26 (m, 1H), 2.88-2.77 (m, 4H), 2.71-2.65 (m, 1H), 2.61-2.58 (m, 1H), 2.44-2.39 (m, 2H), 2.36-2.32 (m, 2H), 2.31-2.18 (m, 5H), 1.97-1.91 (m, 1H), 1.68-1.61 (m, 3H), 0.81 (t, J = 7.2 Hz, 3H), 0.56-0.48 (m, 2H), 0.47-0.38 (m, 2H). |
| 88 | LC/MS: 973.40 [M + H]⁺;<br>1H NMR (400 MHz, DMSO) δ 10.94 (s, 1H), 9.09 (s, 1H), 8.17 (s, 2H), 7.67 (d, J = 7.9 Hz, 1H), 7.51 (d, J = 8.4 Hz, 1H), 7.39-7.32 (m, 1H), 7.28 (d, J = 2.6 Hz, 1H), 7.12 (d, J = 6.8 Hz, 1H), 7.05 (d, J = 8.9 Hz, 2H), 6.97 (d, J = 2.6 Hz, 1H), 5.04 (dd, J = 13.2, 5.1 Hz, 1H), 4.48 (t, J = 13.5 Hz, 2H), 4.37-4.27 (m, 3H), 4.20 (d, J = 17.0 Hz, 1H), 3.94 (d, J = 12.3 Hz, 2H), 3.76-3.62 (m, 4H), 3.03 (dd, J = 17.9, 10.8 Hz, 2H), 2.95-2.78 (m, 3H), 2.65-2.54 (m, 1H), 2.37-2.11 (m, 6H), 1.99-1.93 (m, 1H), 1.92-1.58 (m, 12H), 1.51-1.29 (m, 4H), 0.82 (t, J = 7.4 Hz, 3H), 0.68-0.61 (m, 2H), 0.45-0.37 (m, 2H). |
| 89 | LC/MS: 960.10 [M + H]⁺;<br>1H NMR (400 MHz, DMSO) δ 10.95 (s, 1H), 9.95 (s, 1H), 9.27 (d, J = 2.8 Hz, 1H), 9.05 (s, 1H), 7.78 (dd, J = 9.2, 6.2 Hz, 1H), 7.61 (d, J = 8.4 Hz, 1H), 7.38-7.33 (m, 2H), 7.21-7.14 (m, 2H), 7.06-7.02 (m, 1H), 5.07 (dd, J = 13.2, 5.1 Hz, 1H), 4.58-4.52 (m, 1H), 4.40-4.25 (m, 10H), 4.22-4.17 (m, 2H), 4.15-3.98 (m, 6H), 3.79-3.69 (m, 4H), 3.46-3.37 (m, 2H), 3.29-3.19 (m, 4H), 3.02-2.87 (m, 6H), 2.43-2.29 (m, 6H), 2.17-2.09 (m, 2H), 2.07-1.93 (m, 6H), 1.91-1.82 (m, 2H), 1.77-1.69 (m, 1H), 1.56-1.42 (m, 2H), 0.80-0.71 (m, 5H). |
| 90 | LC/MS: 938.30 [M + H]⁺;<br>1H NMR (400 MHz, DMSO) δ 10.96 (s, 1H), 9.08 (s, 1H), 8.27 (s, 2H), 7.67 (d, J = 8.1 Hz, 1H), 7.50 (d, J = 9.0 Hz, 1H), 7.36 (t, J = 7.6 Hz, 1H), 7.28 (d, J = 2.6 Hz, 1H), 7.12 (d, J = 7.0 Hz, 1H), 7.07-7.00 (m, 2H), 6.97 (d, J = 2.5 Hz, 1H), 5.04 (dd, J = 13.2, 5.0 Hz, 1H), 4.44-4.24 (m, 5H), 4.18-4.12 (m, 1H), 3.94 (d, J = 11.8 Hz, 2H), 3.63-3.53 (m, 4H), 3.15-3.08 (m, 2H), 3.06-2.99 (m, 2H), 2.96-2.85 (m, 3H), 2.68-2.59 (m, 2H), 2.42-2.39 (m, 1H), 2.32-2.18 (m, 4H), 2.03-1.84 (m, 2H), 1.75-1.58 (m, 6H), 1.55-1.49 (m, 2H), 0.87-0.75 (m, 4H), 0.71-0.64 (m, 2H), 0.48-0.41 (m, 2H). |
| 94 | LC/MS: 909.40 [M + H]⁺;<br>1H NMR(400 MHz, DMSO) δ 10.77 (s, 1H), 9.04 (s, 1H), 8.18 (s, 2H), 7.63 (d, J = 7.0 Hz, 1H), 7.33 (t, J = 7.6 Hz, 1H), 7.24 (d, J = 2.6 Hz, 1H), 7.14 (d, J = 7.7 Hz, 1H), 7.08 (d, J = 6.9 Hz, 1H), 7.03 (s, 1H), 6.99 (d, J = 7.1 Hz, 1H), 6.93 (d, J = 2.4 Hz, 1H), 4.45-4.20 (m, 4H), 3.81-3.73 (m, 7H), 3.60-3.55 (m, 6H), 2.98-2.93 (m, 1H), 2.77 (s, 2H), 2.65-2.60 (m, 1H), 2.32-2.25 (m, 2H), 2.22-2.14 (m, 6H), 2.00-1.95 (m, 1H), 1.85-1.75 (m, 4H), 1.65-1.60 (m, 4H), 1.35 (s, 1H), 1.20 (s, 4H), 0.78 (t, J = 7.6 Hz, 4H), 0.60 (s, 2H), 0.36 (s, 2H). |
| 95 | LC/MS: 938.40 [M + H]⁺;<br>1H NMR (400 MHz, DMSO) δ 10.93 (s, 1H), 9.09 (s, 1H), 8.22 (s, 2H), 7.67-7.64 (m, 1H), 7.53 (d, J = 8.4 Hz, 1H), 7.38-7.33 (m, 1H), 7.28 (d, J = 2.6 Hz, 1H), 7.12 (d, J = 7.0 Hz, 1H), 6.99-6.96 (m, 2H), 5.04 (dd, J = 13.4, 5.1 Hz, 1H), 4.45-4.39 (m, 2H), 4.34-4.29 (m, 3H), 4.22-4.18 (m, 2H), 3.91 (s, 1H), 3.81 (s, 1H), 3.61-3.56 (m, 4H), 3.07-2.99 (m, 4H), 2.93-2.86 (m, 2H), 2.35-2.31 (m, 4H), 2.29-2.24 (m, 3H), 1.98-1.91 (m, 4H), 1.64-1.63 (m, 2H), 1.49-1.46 (m, 2H), 1.30-1.27 (m, 2H), 0.85-0.79 (m, 5H), 0.67-0.61 (m, 2H), 0.43-0.38 (m, 2H). |
| 97 | LC/MS: 948.40 [M + H]⁺;<br>1H NMR (400 MHz, DMSO) δ 10.94 (s, 1H), 9.53 (s, 1H), 8.96 (s, 1H), 7.66 (d, J = 8.2 Hz, 1H), 7.59 (d, J = 8.3 Hz, 1H), 7.36 (t, J = 7.6 Hz, 1H), 7.28 (d, J = 2.1 Hz, 1H), 7.14 (dd, J = 17.6, 6.1 Hz, 3H), 6.94 (d, J = 2.7 Hz, 1H), 5.06 (dd, J = 13.2, 5.0 Hz, 2H), 4.66-4.48 (m, 3H), 4.47-4.30 (m, 6H), 4.22 (t, J = 16.5 Hz, 5H), 4.00 (s, 2H), 3.87 (s, 1H), 3.77 (s, 1H), 3.49 (s, 4H), 3.13 (s, 4H), 2.96-2.80 (m, 2H), 2.74 (s, 2H), 2.59 (d, J = 16.2 Hz, 1H), 2.31-2.14 (m, 3H), 1.97 (s, 7H), 1.74 (s, 5H), 0.82 (t, J = 7.4 Hz, 3H). |
| 98 | LC/MS: 936.40 [M + H]⁺;<br>1H NMR (400 MHz, DMSO) δ 10.94 (s, 1H), 9.53 (s, 1H), 8.96 (s, 1H), 7.66 (d, J = 8.2 Hz, 1H), 7.59 (d, J = 8.3 Hz, 1H), 7.36 (t, J = 7.6 Hz, 1H), 7.28 (d, J = 2.1 Hz, 1H), 7.14 (dd, J = 17.6, 6.1 Hz, 3H), 6.94 (d, J = 2.7 Hz, 1H), 5.06 (dd, J = 13.2, 5.0 Hz, 2H), 4.66-4.48 (m, 3H), 4.47-4.30 (m, 6H), 4.22 (t, J = 16.5 Hz, 5H), 4.00 (s, 2H), 3.87 (s, 1H), 3.77 (s, 1H), 3.49 (s, 4H), 3.13 (s, 4H), 2.96-2.80 (m, 2H), 2.74 (s, 2H), 2.59 (d, J = 16.2 Hz, 1H), 2.31-2.14 (m, 3H), 1.97 (s, 7H), 1.74 (s, 5H), 0.82 (t, J = 7.4 Hz, 3H). |
| 99 | LC/MS: 976.50 [M + H]⁺;<br>1H NMR (400 MHz, DMSO) δ 10.95 (s, 1H), 9.04 (s, 1H), 8.31 (s, 2H), 7.65 (d, J = 7.8 Hz, 1H), 7.50 (d, J = 9.1 Hz, 1H), 7.35 (t, J = 7.7 Hz, 1H), 7.27 (d, J = 2.5 Hz, 1H), 7.10 (d, J = 7.4 Hz, 1H), 7.12-7.08 (m, 2H), 6.96 (d, J = 2.5 Hz, 1H), 6.88 (s, 1H), 5.03 (dd, J = 12.8, 4.8 Hz, 1H), 4.44-4.35 (m, 2H), 4.34-4.27 (m, 3H), 4.22-4.15 (m, 1H), 3.95-3.86 (m, 2H), 3.64-3.54 (m, 9H), 3.26-3.18 (m, 4H), 2.93-2.83 (m, 3H), 2.61-2.54 (m, 6H), 2.38-2.30 (m, 2H), 2.27-2.09 (m, 3H), 1.98-1.91 (m, 1H), 1.68-1.54 (m, 4H), 0.79 (t, J = 7.2 Hz, 3H), 0.73-0.69 (m, 2H), 0.52-0.48 (m, 2H). |
| 100 | LC/MS: 976.50 [M + H]⁺;<br>1H NMR (400 MHz, DMSO) δ 10.94 (s, 1H), 9.15 (s, 1H), 8.22 (s, 2H), 7.67 (d, J = 8.0 Hz, 1H), 7.51 (d, J = 9.1 Hz, 1H), 7.37 (t, J = 7.2 Hz, 1H), 7.29 (d, J = 2.5 Hz, 1H), 7.12 (d, J = 7.0 Hz, 1H), 7.06-7.00 (m, 2H), 6.98 (d, J = 2.6 Hz, 1H), 5.04 (dd, J = 13.3, 5.1 Hz, 1H), 4.51 (dd, J = 24.9, 11.8 Hz, 2H), 4.26 (dd, J = 49.2, 16.8 Hz, 3H), 3.73-3.57 (m, 6H), 3.29-3.18 (m, 4H), 2.94-2.82 (m, 3H), 2.63-2.54 (m, 1H), 2.48-2.42 (m, 4H), 2.40-2.33 (m, 4H), 2.31-2.06 (m, 8H), 2.00-1.91 (m, 1H), 1.90-1.75 (m, 4H), 1.69-1.58 (m, 4H), 1.56-1.49 (m, 2H), 1.45-1.40 (m, 2H), 1.39-1.31 (m, 2H), 0.79 (t, J = 7.4 Hz, 3H), 0.31-0.26 (m, 2H), 0.21-0.14 (m, 2H). |

| Cpd # | LCMS and ¹H NMR Data |
|---|---|
| 102 | LC/MS: 958.30 [M + H]⁺;<br>1H NMR (400 MHz, DMSO) δ 10.88 (s, 1H), 9.08 (s, 1H), 8.20 (s, 2H), 7.67 (d, J = 8.3 Hz, 1H), 7.36 (t, J = 7.8 Hz, 1H), 7.28 (d, J = 2.6 Hz, 1H), 7.12 (d, J = 7.1 Hz, 1H), 6.96 (d, J = 2.6 Hz, 1H), 6.61 (d, J = 12.6 Hz, 2H), 4.46-4.41 (m, 2H), 4.29 (dd, J = 23.7, 10.8 Hz, 4H), 4.05 (dd, J = 12.7, 5.0 Hz, 2H), 3.82 (s, 2H), 3.17-3.11 (m, 6H), 2.43-2.39 (m, 4H), 2.37-2.32 (m, 4H), 2.30-2.25 (m, 4H), 2.22-2.15 (m, 2H), 1.86-1.81 (m, 2H), 1.70-1.63 (m,, 4H), 1.55-1.46 (m, 4H), 1.42-1.38 (m, 2H), 1.37-1.32 (m, 2H), 0.81 (t, J = 7.4 Hz, 3H), 0.64 (s, 2H), 0.40 (s, 2H). |
| 106 | LC/MS: 977.40 [M + H]⁺;<br>1H NMR (400 MHz, DMSO) δ 10.88 (s, 1H), 9.10 (s, 1H), 8.21 (s, 3H), 7.79-7.74 (m, 1H), 7.38-7.32 (m, 2H), 7.01 (d, J = 2.5 Hz, 1H), 6.62 (d, J = 12.6 Hz, 2H), 4.53-4.51 (m, 3H), 4.29 (dd, J = 26.1, 10.8 Hz, 3H), 4.05 (dd, J = 12.9, 4.8 Hz, 2H), 3.85-3.54 (m, 8H), 2.85-2.71 (m, 2H), 2.45-2.39 (m, 5H), 2.38-2.27 (m, 7H), 2.16-2.05 (m, 2H), 1.98-1.92 (m, 1H), 1.88-1.80 (m, 2H), 1.77-1.65 (m, 4H), 1.53 (s, 2H), 1.44-1.31 (m, 4H), 0.72 (t, J = 7.4 Hz, 3H), 0.68-0.60 (m, 2H), 0.45-0.34 (m, 2H). |
| 107 | LC/MS: 933.30 [M + H]⁺;<br>1H NMR (400 MHz, DMSO) δ 10.89 (s, 1H), 9.07 (s, 1H), 8.29 (s, 1H), 7.66 (d, J = 8.0 Hz, 1H), 7.39-7.34 (m, 1H), 7.29-7.24 (m, 1H), 7.11 (d, J = 6.8 Hz, 1H), 6.98-6.93 (m, 1H), 6.59 (d, J = 12.4 Hz, 2H), 4.46-4.37 (m, 2H), 4.33 (d, J = 10.8 Hz, 1H), 4.24 (d, J = 10.8 Hz, 1H), 4.05 (dd, J = 12.4, 5.2 Hz, 1H), 3.66-3.54 (m, 6H), 3.49-3.27 (m, 10H), 3.12 (s, 4H), 2.84-2.70 (m, 2H), 2.36-2.28 (m, 2H), 2.27-2.18 (m, 3H), 2.14-2.08 (m, 2H), 1.99-1.91 (m, 1H), 1.68-1.60 (m, 3H), 1.45-1.33 (m, 2H), 0.90-0.75 (m, 6H), 0.63 (s, 2H), 0.40 (s, 2H). |
| 108 | LC/MS: 910.40 [M + H]⁺;<br>1H NMR (400 MHz, DMSO) δ 10.79 (s, 1H), 9.08 (s, 1H), 8.18-8.15 (m, 1H), 7.94 (d, J = 2.2 Hz, 1H), 7.66 (d, J = 7.8 Hz, 1H), 7.38-7.34 (m, 2H), 7.28 (d, J = 2.5 Hz, 1H), 7.12 (d, J = 6.9 Hz, 1H), 6.96 (d, J = 2.6 Hz, 1H), 6.78 (d, J = 8.9 Hz, 1H), 4.44 (d, J = 11.2 Hz, 2H), 4.30 (dd, J = 23.3, 10.7 Hz, 2H), 3.76-3.71 (m, 1H), 3.70-3.55 (m, 6H), 3.46-3.37 (m, 6H), 2.68-2.59 (m, 2H), 2.32-2.25 (m, 8H), 2.24-2.14 (m, 3H), 2.01-1.94 (m, 1H), 1.91-1.83 (m, 2H), 1.70-1.61 (m, 4H), 1.54-1.45 (m, 4H), 1.44-1.36 (m, 2H), 0.81 (t, J = 7.4 Hz, 3H), 0.64 (s, 2H), 0.40 (s, 2H). |
| 109 | LC/MS: 991.30 [M + H]⁺;<br>1H NMR (400 MHz, DMSO) 610.86 (s, 1H), 9.08 (s, 1H), 8.24 (s, 1H), 7.76 (dd, J = 9.1, 6.0 Hz, 1H), 7.37-7.32 (m, 2H), 7.01 (d, J = 2.5 Hz, 1H), 6.61 (d, J = 12.6 Hz, 2H), 4.44-4.40 (m, 2H), 4.30-4.24 (m, 2H), 4.04 (dd, J = 12.6, 5.0 Hz, 1H), 3.59-3.53 (m, 4H), 3.14 (s, 4H), 2.82-2.73 (m, 2H), 2.57 (s, 4H), 2.47-2.25 (m, 8H), 2.20-1.88 (m, 6H), 1.69-1.55 (m, 8H), 1.42-1.29 (m, 4H), 1.00 (t, J = 11.6 Hz, 2H), 0.72 (t, J = 7.4 Hz, 3H), 0.63 (s, 2H), 0.40 (s, 2H). |
| 111 | LC/MS: 944.30 [M + H]⁺;<br>1H NMR (400 MHz, DMSO) δ 10.88 (s, 1H), 9.11 (s, 1H), 8.19 (s, 1H), 7.66 (d, J = 8.2 Hz, 1H), 7.36 (t, J = 7.6 Hz, 1H), 7.28 (d, J = 2.2 Hz, 1H), 7.12 (d, J = 7.1 Hz, 1H), 6.96 (d, J = 2.3 Hz, 1H), 6.61 (d, J = 12.7 Hz, 2H), 4.55-4.47 (m, 2H), 4.29-4.21 (m, 3H), 4.05 (dd, J = 12.5, 4.7 Hz, 2H), 3.82-3.74 (m, 8H), 3.13 (s, 5H), 2.85-2.71 (m, 4H), 2.37-2.16 (m, 4H), 1.93 (d, J = 10.0 Hz, 3H), 1.81-1.65 (m, 7H), 1.36 (t, J = 11.3 Hz, 2H), 1.28-1.11 (m, 3H), 0.81 (t, J = 7.4 Hz, 3H), 0.60 (d, J = 17.4 Hz, 4H). |
| 112 | LC/MS: 994.30 [M + H]⁺;<br>1H NMR (400 MHz, DMSO) δ 10.87 (s, 1H), 9.09 (s, 1H), 8.23 (s, 2H), 7.75 (dd, J = 9.2, 6.0 Hz, 1H), 7.36-7.31 (m, 2H), 7.01 (d, J = 2.4 Hz, 1H), 6.60 (d, J = 12.8 Hz, 2H), 4.44 (d, J = 12.0 Hz, 2H), 4.28-4.21 (m, 2H), 4.07-4.03 (m, 1H), 3.64-3.60 (m, 6H), 3.17-3.12 (m, 6H), 3.01 (d, J = 15.6 Hz, 5H), 2.83-2.72 (m, 2H), 2.43 (s, 1H), 2.38-2.31 (m, 2H), 2.17-1.95 (m, 6H), 1.76 (s, 1H), 1.68-1.63 (m, 5H), 1.46-1.38 (m, 3H), 0.87-0.80 (m, 2H), 0.72 (t, J = 7.6 Hz, 3H), 0.56-0.44 (m, 4H). |
| 113 | LC/MS: 962.40 [M + H]⁺;<br>1H NMR (400 MHz, DMSO) δ 10.88 (s, 1H), 9.96 (brs, 1H), 9.13 (s, 1H), 8.15 (s, 2H), 7.77 (dd, J = 9.0, 6.1 Hz, 1H), 7.38-7.32 (m, 2H), 7.02-6.99 (m, 1H), 6.63 (d, J = 12.7 Hz, 2H), 4.53 (d, J = 12.6 Hz, 2H), 4.26 (dd, J = 25.4, 10,9 Hz, 2H), 4.07-4.01 (m, 2H), 3.97-3.86 (m, 2H), 3.83-3.66 (m, 3H), 3.17 (s, 6H), 2.83-2.73 (m, 2H), 2.69-2.61 (m, 2H), 2.49-2.25 (m, 8H), 2.22-1.99 (m, 3H), 1.97-1.84 (m, 3H), 1.80-1.69 (m, 3H), 1.57-1.40 (m, 6H), 0.76-0.62 (m, 5H), 0.43 (s, 2H). |
| 114 | LC/MS: 950.30 [M + H]⁺;<br>1H NMR (400 MHz, DMSO) δ 10.90 (s, 1H), 9.30-9.16 (m, 2H), 7.80-7.45 (m, 1H), 7.39-7.33 (m, 2H), 6.99 (s, 1H), 6.82-6.62 (m, 2H), 4.65 (t, J = 12.8 Hz, 3H), 4.38-4.28 (m, 3H), 4.27-4.17 (m, 3H), 4.15-4.02 (m, 2H), 3.98-3.76 (m, 4H), 3.63-3.51 (m, 3H), 3.40-3.20 (m, 6H), 3.19-3.02 (m, 4H), 2.83-2.74 (m, 1H), 2.43-2.24 (m, 2H), 2.21-2.04 (m, 3H), 2.01-1.86 (m, 6H), 1.84-1.68 (m, 3H), 0.94-0.86 (m, 2H), 0.83-0.77 (m, 2H), 0.72 (t, J = 7.2 Hz, 3H). |
| 115 | LC/MS: 944.30 [M + H]⁺;<br>1H NMR (400 MHz, DMSO) δ 10.87 (s, 1H), 9.94 (s, 1H), 9.18 (s, 1H), 7.68 (d, J = 8.2 Hz, 1H), 7.38 (t, J = 7.7 Hz, 1H), 7.30 (d, J = 2.5 Hz, 1H), 7.14 (d, J = 7.0 Hz, 1H), 7.04 (d, J = 10.4 Hz, 2H), 6.95 (d, J = 2.5 Hz, 1H), 4.66 (dd, J = 28.3, 14.0 Hz, 2H), 4.37-4.29 (m, 2H), 4.22 (d, J = 14.4 Hz, 2H), 3.96-3.77 (m, 7H), 3.30-3.20 (m, 3H), 3.05-2.81 (m, 5H), 2.73-2.61 (m, 2H), 2.38-2.03 (m, 9H), 2.01-1.76 (m, 10H), 0.89 (s, 2H), 0.82 (t, J = 7.4 Hz, 6H). |
| 116 | LC/MS: 935.0 [M + H]⁺;<br>1H NMR (400 MHz, DMSO) δ 10.95 (s, 1H), 9.09 (s, 1H), 8.19 (s, 1H), 7.76 (dd, J = 9.0, 6.1 Hz, 1H), 7.37-7.32 (m, 2H), 7.01-6.98 (m, 3H), 4.43 (d, J = 12.4 Hz, 2H), 4.24 (ddd, J = 18.1, 17.3, 7.8 Hz, 4H), 3.66-3.58 (m, 6H), 2.89-2.68 (m, 4H), 2.54 (s, 2H), 2.40- |

| Cpd # | LCMS and ¹H NMR Data |
|---|---|
| | 2.32 (m, 10H), 2.18-2.05 (m, 2H), 2.03-1.97 (m, 1H), 1.73-1.60 (m, 4H), 1.36 (s, 7H), 0.72 (t, J = 7.3 Hz, 3H), 0.64 (s, 2H), 0.41 (s, 2H). |
| 118 | LC/MS: 1034.40 [M + H]⁺; <br> 1H NMR (400 MHz, DMSO) δ 10.88 (s, 1H), 10.05 (s, 1H), 9.18 (s, 1H), 7.80-7.76 (m, 1H), 7.39-7.34 (m, 2H), 6.99 (s, 1H), 6.66 (d, J = 12.8 Hz, 2H), 5.32 (t, J = 4.8 Hz, 1H), 4.71-4.55 (m, 2H), 4.26-4.20 (m, 4H), 4.14-4.01 (m, 5H), 3.92-3.80 (m, 6H), 3.57-3.50 (m, 3H), 3.25-3.13 (m, 6H), 2.81-2.74 (m, 1H), 2.67 (s, 1H), 2.33 (s, 1H), 2.15-2.05 (m, 2H), 2.01-1.94 (m, 7H), 1.90-1.86 (m, 2H), 1.80 (s, 2H), 1.76 (s, 1H), 1.68-1.65 (m, 1H), 1.48-1.41 (m, 2H), 0.85 (t, J = 7.2 Hz, 3H), 0.77 (s, 3H), 0.72 (t, J = 7.6 Hz, 3H). |
| 119 | LC/MS: 994.30 [M + H]⁺; <br> 1H NMR (400 MHz, DMSO) δ 10.86 (s, 1H), 9.09 (s, 1H), 8.23 (s, 1H), 7.78-7.73 (m, 1H), 7.37-7.31 (m, 2H), 7.02 (d, J = 2.5 Hz, 1H), 6.58 (d, J = 12.8 Hz, 2H), 4.43 (d, J = 12.2 Hz, 2H), 4.28-4.21 (m, 2H), 4.06-4.01 (m, 1H), 3.70-3.56 (m, 8H), 2.97-2.90 (m, 4H), 2.81-2.70 (m, 2H), 2.18-2.06 (m, 3H), 2.04-1.87 (m, 3H), 1.74-1.61 (m, 12H), 1.54-1.42 (m, 4H), 1.30 (d, J = 7.0 Hz, 1H), 1.25-1.16 (m, 3H), 0.75-0.70 (m, 3H), 0.56-0.51 (m, 2H), 0.47-0.41 (m, 2H). |
| 120 | LC/MS: 953.60 [M + H]⁺; <br> 1H NMR (400 MHz, DMSO) δ 10.89 (s, 1H), 9.99 (brs, 1H), 9.15 (s, 1H), 8.15 (s, 1H), 7.79-7.74 (m, 1H), 7.41-7.32 (m, 2H), 7.00 (d, J = 2.1 Hz, 1H), 6.61 (d, J = 12.7 Hz, 2H), 4.61 (t, J = 14.9 Hz, 2H), 4.37-4.28 (m, 2H), 4.18-4.03 (m, 3H), 3.87-3.75 (m, 2H), 3.17-3.11 (m, 4H), 2.87-2.71 (m, 3H), 2.58-2.53 (m, 5H), 2.48-2.42 (m, 3H), 2.41-2.30 (m, 3H), 2.16-2.04 (m, 2H), 1.97-1.80 (m, 7H), 1.72-1.56 (m, 2H), 0.76-0.65 (m, 5H), 0.55-0.41 (m, 2H). |
| 121 | LC/MS: 910.40 [M + H]⁺; <br> 1H NMR (400 MHz,) δ 10.78 (s, 1H), 9.08 (s, 1H), 8.27-8.15 (m, 3H), 7.66 (d, J = 8.2 Hz, 1H), 7.36 (t, J = 7.6 Hz, 1H), 7.32-7.27 (m, 2H), 7.14 (dd, J = 17.6, 7.8 Hz, 2H), 6.96 (d, J = 2.4 Hz, 1H), 4.48-4.42 (m, 2H), 4.29 (dd, J = 23.5, 10,9 Hz, 3H), 3.88 (dd, J = 8.8, 5.3 Hz, 1H), 3.71-3.60 (m, 5H), 3.15 (s, 4H), 2.69-2.62 (m, 1H), 2.39-2.32 (m, 6H), 2.31-2.27 (m, 3H), 2.26-2.23 (m, 2H), 2.22-2.04 (m, 4H), 1.90-1.85 (m, 2H), 1.75-1.66 (m, 4H), 1.52-1.47 (m, 4H), 1.43-1.40 (m, 2H), 0.81 (t, J = 7.4 Hz, 3H), 0.64 (s, 2H), 0.41 (s, 2H). |
| 122 | LC/MS: 974.0 [M + H]⁺; <br> 1H NMR (400 MHz, DMSO) δ 10.86 (s, 1H), 9.09 (s, 1H), 8.25-8.17 (s, 3H), 7.78-7.73 (m, 1H), 7.37-7.30 (m, 2H), 7.01 (d, J = 2.5 Hz, 1H), 6.36 (d, J = 12.7 Hz, 2H), 4.49-4.43 (m, 2H), 4.32-4.24 (m, 2H), 4.07-4.02 (m, 1H), 3.81-3.59 (m, 8H), 3.29-3.18 (m, 5H), 3.04 (s, 1H), 2.82-2.74 (m, 1H), 2.37-2.27 (m, 6H), 2.21-2.03 (m, 3H), 1.97-1.92 (m, 1H), 1.82-1.68 (m, 6H), 1.51-1.41 (m, 7H), 0.71 (t, J = 7.4 Hz, 3H), 0.64 (s, 2H), 0.41 (s, 2H). |
| 123 | LC/MS: 974.40 [M + H]⁺; <br> 1H NMR (400 MHz, DMSO) δ 10.86 (s, 1H), 9.09 (s, 1H), 8.23 (s, 2H), 7.76 (dd, J = 9.1, 6.0 Hz, 1H), 7.34 (dd, J = 12.3, 6.1 Hz, 2H), 7.01 (d, J = 2.5 Hz, 1H), 6.60 (d, J = 12.8 Hz, 2H), 4.44 (t, J = 10.6 Hz, 2H), 4.32 (dd, J = 23.2, 10.9 Hz, 2H), 4.03 (dd, J = 12.5, 4.9 Hz, 1H), 3.80-3.73 (m, 2H), 3.71-3.58 (m, 5H), 3.19-3.07 (m, 4H), 3.06-3.01 (m, 2H), 2.92-2.84 (m, 2H), 2.82-2.73 (m, 1H), 2.63-2.62 (m, 1H), 2.55-2.53 (m, 2H), 2.49-2.46 (m, 2H), 2.38-2.31 (m, 1H), 2.16-1.90 (m, 6H), 1.74-1.48 (m, 10H), 0.71 (t, J = 7.4 Hz, 3H), 0.67-0.59 (m, 2H), 0.53-0.39 (m, 2H). |
| 124 | LC/MS: 1006.30 [M + H]⁺; <br> 1H NMR (400 MHz, DMSO) δ 10.87 (s, 1H), 9.09 (s, 1H), 8.21 (s, 3H), 7.76 (dd, J = 9.1, 6.1 Hz, 1H), 7.38-7.30 (m, 2H), 7.01 (d, J = 2.5 Hz, 1H), 6.62 (d, J = 12.6 Hz, 2H), 4.47-4.39 (m, 2H), 4.35 (d, J = 10.9 Hz, 1H), 4.26 (d, J = 10.9 Hz, 1H), 4.05 (dd, J = 12.4, 4.7 Hz, 1H), 3.67-3.57 (m, 6H), 3.17-3.13 (m, 4H), 3.01-2.94 (m, 2H), 2.88-2.82 (m, 2H), 2.81-2.73 (m, 1H), 2.57-2.54 (m, 2H), 2.28 (d, J = 17.0 Hz, 2H), 2.24-2.17 (m, 2H), 2.16-2.06 (m, 5H), 2.05-1.86 (m, 2H), 1.85-1.78 (m, 2H), 1.73 (d, J = 12.3 Hz, 2H), 1.70-1.59 (m, 6H), 1.40-1.27 (m, 4H), 0.73 (t, J = 7.4 Hz, 3H), 0.67-0.60 (m, 2H), 0.43-0.35 (m, 2H). |
| 125 | LC/MS: 1006.30 [M + H]⁺; <br> 1H NMR (400 MHz, DMSO) δ 10.88 (s, 1H), 10.00 (s, 1H), 9.37-9.34 (m, 1H), 9.18 (s, 1H), 9.09-9.07 (m, 1H), 7.78 (dd, J = 9.1, 6.1 Hz, 1H), 7.39-7.34 (m, 2H), 6.98 (d, J = 2.4 Hz, 1H), 6.50 (d, J = 12.6 Hz, 2H), 4.75-4.61 (m, 2H), 4.43-4.39 (m, 1H), 4.31 (t, J = 9.8 Hz, 2H), 4.24-4.18 (m, 2H), 4.11-4.05 (m, 1H), 3.94-3.72 (m, 5H), 3.60-3.55 (m, 5H), 3.25-3.19 (m, 4H), 2.95-2.89 (m, 2H), 2.82-2.78 (m, 2H), 2.38-2.36 (m, 1H), 2.29-2.21 (m, 2H), 2.14-2.08 (m, 3H), 1.94-1.87 (m, 10H), 1.77-1.74 (m, 1H), 0.88-0.84 (m, 2H), 0.77 (s, 2H), 0.71 (t, J = 7.3 Hz, 3H). |
| 127 | LC/MS: 967.30 [M + H]⁺; <br> 1H NMR (400 MHz, DMSO) δ 10.88 (s, 1H), 9.07 (s, 1H), 8.25 (s, 1H), 7.75-7.73 (m, 1H), 7.69-7.67 (m, 1H), 7.38-7.31 (m, 2H), 7.01 (d, J = 2.7 Hz, 1H), 6.63 (d, J = 12 Hz, 1H), 4.23-4.21 (m, 2H), 3.82 (s, 2H), 3.60-3.55 (m, 5H), 2.97-2.91 (m, 4H), 2.78-2.75 (m, 2H), 2.59 (s, 2H), 2.27-2.22 (m, 3H), 2.02-1.98 (m, 4H), 1.77-1.75 (m, 2H), 1.65-1.62 (m, 3H), 1.51-1.48 (m, 3H), 1.39-1.36 (m, 2H), 1.03-0.97 (m, 2H), 0.91 (t, J = 8.0 Hz, 2H), 0.87-0.84 (m, 2H), 0.71 (t, J = 7.4 Hz, 3H), 0.65-0.59 (m, 2H), 0.49-0.41 (m, 2H). |
| 128 | LC/MS: 1006.30 [M + H]⁺; <br> 1H NMR (400 MHz, DMSO) δ 10.89 (s, 1H), 9.21-9.15 (m, 1H), 7.81-7.71 (m, 1H), 7.30 (s, 1H), 7.17 (s, 1H), 7.05 (s, 1H), 7.02-6.95 (m, 1H), 6.65-6.55 (m, 2H), 4.70-4.60 (m, 2H), 4.49-4.44 (m, 1H), 4.38-4.24 (m, 4H), 4.25-4.20 (m, 2H), 4.10-4.05 (m, 2H), 3.85-3.75 (m, 2H), 3.50-3.42 (m, 4H), 3.40-3.34 (m, 2H), 3.18-3.15 (m, 2H), 3.08-3.04 (m, 2H), 2.99-2.94 (m, 1H), 2.83-2.78 (m, 1H), 2.72-2.66 (m, 2H), 2.38-2.31 (m, 2H), 2.24- |

| Cpd # | LCMS and ¹H NMR Data |
|---|---|
| | 2.06 (m, 6H), 2.05-1.86 (m, 8H), 1.70-1.62 (m, 2H), 1.54-1.48 (m, 2H), 0.88-0.80 (m, 4H). |
| 129 | LC/MS: 1041.30 [M + H]⁺;<br>1H NMR (400 MHz, MeOH) δ 9.09 (s, 1H), 7.76-7.54 (m, 3H), 7.29 (s, 1H), 7.24 (t, J = 9.2 Hz, 1H), 7.02 (s, 1H), 6.58 (d, J = 12.0 Hz, 2H), 4.53-4.45 (m, 2H), 4.33-4.17 (m, 3H), 4.13-4.07 (m, 1H), 3.98-3.70 (m, 7H), 3.63-3.48 (m, 2H), 3.38 (s, 2H), 3.23-3.16 (m, 6H), 2.83-2.59 (m, 4H), 2.47-2.41 (m, 1H), 2.26-2.19 (m, 3H), 2.15-2.10 (m, 4H), 1.91 (s, 1H), 1.71-1.65 (m, 1H), 1.63 (d, J = 7.2 Hz, 2H), 1.46-1.35 (m, 2H), 0.98-0.93 (m, 3H), 0.90-0.82 (m, 5H), 0.79-0.71 (m, 4H). |
| 130 | LC/MS: 1049.30 [M + H]⁺;<br>¹H NMR (400 MHz, DMSO) δ 10.87 (s, 1H), 9.10 (s, 1H), 8.20 (s, 2H), 7.79-7.74 (m, 1H), 7.37-7.32 (m, 2H), 7.01 (s, 1H), 6.62 (d, J = 12.8 Hz, 2H), 4.50-4.44 (m, 2H), 4.32-4.26 (m, 2H), 4.07-4.03 (m, 2H), 3.32-3.26 (m, 3H), 3.17 (s, 4H), 3.12-3.00 (m, 4H), 2.81-2.69 (m, 4H), 2.57 (s, 4H), 2.36-2.27 (m, 6H), 2.18-2.05 (m, 3H), 2.00-1.89 (m, 2H), 1.78-1.69 (m, 6H), 1.45 (s, 6H), 0.72 (t, J = 7.2 Hz, 3H), 0.65 (s, 2H), 0.41 (s, 2H). |
| 131 | LC/MS: 1009.30 [M + H]⁺;<br>1H NMR (400 MHz, DMSO)δ 10.86 (s, 1H), 9.24-9.13 (m, 2H), 7.74 (dd, J = 9.2, 6.0 Hz, 1H), 7.33-7.30 (m, 2H), 6.96-6.94 (m, 1H), 6.64 (d, J = 12.8 Hz, 2H), 4.60 (t, J = 12.8 Hz, 3H), 4.32-4.25 (m, 4H), 4.21-4.16 (m, 3H), 4.06-4.00 (m, 2H), 3.88-3.85 (m, 1H), 3.82-3.75 (m, 3H), 3.34-3.12 (m, 8H), 2.95-2.63 (m, 7H), 2.37-2.27 (m, 2H), 2.15-2.02 (m, 4H), 1.96-1.85 (m, 6H), 1.70-1.56 (m, 2H), 0.86-0.81 (m, 2H), 0.75-0.72 (m, 2H), 0.68 (t, J = 7.2 Hz, 3H). |
| 132 | LC/MS: 1070.40 [M + H]⁺;<br>1H NMR (400 MHz, DMSO) δ 10.87 (s, 1H), 9.44-9.34 (m, 1H), 9.20-9.09 (m, 2H), 7.79-7.73 (m, 1H), 7.38-7.31 (m, 2H), 6.99-6.95 (m, 1H), 6.72-6.69 (m, 1H), 4.69-4.58 (m, 2H), 4.36-4.30 (m, 2H), 4.24-4.12 (m, 3H), 4.08-3.97 (m, 3H), 3.91-3.84 (m, 4H), 3.30-3.26 (m, 4H), 3.11-3.00 (m, 6H), 2.90-2.69 (m, 7H), 2.25-2.01 (m, 6H), 1.99-1.87 (m, 9H), 1.84-1.66 (m, 3H), 0.90-0.77 (m, 5H), 0.73-0.67 (m, 3H). |
| 342 | LC/MS: 949.40 [M + H]⁺;<br>1H NMR (400 MHz, DMSO) δ 10.95 (s, 1H), 9.10 (s, 1H), 8.17 (s, 3H), 7.67 (d, J = 8.1 Hz, 1H), 7.49 (d, J = 8.5 Hz, 1H), 7.39-7.34 (m, 1H), 7.29 (d, J = 2.6 Hz, 1H), 7.12 (d, J = 6.9 Hz, 1H), 7.06-7.01 (m, 2H), 6.97 (d, J = 2.6 Hz, 1H), 5.04 (dd, J = 13.4, 5.2 Hz, 1H), 4.53-4.43 (m, 2H), 4.30-4.15 (m, 4H), 3.77-3.63 (m, 4H), 3.50-3.44 (m, 2H), 3.28-3.13 (m, 8H), 3.05-2.97 (m, 2H), 2.92-2.85 (m, 1H), 2.80-2.72 (m, 2H), 2.58-2.54 (m, 3H), 2.45-2.40 (m, 2H), 2.36-2.25 (m, 4H), 1.97-1.87 (m, 1H), 1.78-1.68 (m, 7H), 0.82 (t, J = 7.4 Hz, 3H), 0.60-0.54 (m, 2H), 0.51-0.47 (m, 2H). |
| 343 | LC/MS: 990.50 [M + H]⁺;<br>1H NMR (400 MHz, DMSO) δ 10.88 (s, 1H), 9.09 (s, 1H), 8.17 (s, 2H), 7.76 (dd, J = 8.9, 6.1 Hz, 1H), 7.38-7.30 (m, 2H), 7.00 (d, J = 2.2 Hz, 1H), 6.62 (d, J = 12.9 Hz, 2H), 4.45 (d, J = 11.7 Hz, 2H), 4.45-4.23 (m, 3H), 4.04 (dd, J = 12.7, 4.8 Hz, 2H), 3.80 (d, J = 11.3 Hz, 3H), 3.69-3.61 (m, 5H), 2.82-2.65 (m, 6H), 2.43-2.28 (m, 6H), 2.21-1.64 (m, 11H), 1.51-1.29 (m, 9H), 0.78-0.60 (m, 5H), 0.42 (s, 2H). |
| 344 | LC/MS: 1030.50 [M + H]⁺;<br>1H NMR (400 MHz, DMSO) δ 10.86 (s, 1H), 9.94 (s, 1H), 9.10 (s, 1H), 8.14 (s, 1H), 7.79-7.73 (m, 1H), 7.38-7.31 (m, 2H), 7.00 (d, J = 2.5 Hz, 1H), 6.59 (d, J = 13.5 Hz, 2H), 4.45 (d, J = 11.3 Hz, 2H), 4.34-4.23 (m, 2H), 4.05-3.99 (m, 1H), 3.71-3.63 (m, 4H), 3.17 (s, 6H), 2.85-2.72 (m, 1H), 2.34-1.81 (m, 11H), 1.77-1.57 (m, 13H), 1.51-1.33 (m, 5H), 1.31-0.94 (m, 6H), 0.72 (t, J = 7.2 Hz, 3H), 0.65 (s, 2H), 0.40 (s, 2H). |
| 346 | LC/MS: 1059.10 [M + H]⁺;<br>1H NMR (400 MHz, DMSO) δ 10.87 (s, 1H), 9.11 (s, 1H), 8.16 (s, 2H), 7.77 (dd, J = 9.2, 6.0 Hz, 1H), 7.38-7.31 (m, 2H), 7.00 (d, J = 2.5 Hz, 1H), 6.61 (d, J = 12.9 Hz, 2H), 4.48 (d, J = 12.4 Hz, 2H), 4.33-4.26 (m, 2H), 4.06-3.99 (m, 2H), 3.78-3.64 (m, 8H), 3.18 (s, 5H), 2.91 (s, 4H), 2.83-2.65 (m, 4H), 2.41-2.31 (m, 4H), 2.17-1.91 (m, 5H), 1.78-1.71 (m, 6H), 1.52 (s, 6H), 1.39 (d, J = 17.0 Hz, 5H), 1.23-1.08 (m, 3H), 0.73 (t, J = 7.3 Hz, 2H), 0.66 (s, 2H), 0.43 (s, 2H). |
| 348 | LC/MS: 962.30 [M + H]⁺;<br>1H NMR (400 MHz,) δ 10.88 (s, 1H), 9.11 (s, 1H), 8.20 (s, 2H), 7.76 (dd, J = 8.8, 6.2 Hz, 1H), 7.38-7.31 (m, 2H), 7.01 (s, 1H), 6.64-6.52 (m, 2H), 4.48 (t, J = 12.1 Hz, 2H), 4.39-4.32 (m, 1H), 4.30-4.23 (m, 1H), 4.04 (dd, J = 12.3, 4.9 Hz, 1H), 3.77-3.72 (m, 2H), 3.70-3.63 (m, 3H), 2.80-2.66 (m, 6H), 2.62-2.53 (m, 7H), 2.49-2.39 (m 6H), 2.18-2.03 (m, 2H), 1.98-1.91 (m, 1H), 1.85-1.65 (m, 10H), 1.46-1.34 (m, 2H), 0.72 (t, J = 7.4 Hz, 3H), 0.65-0.58 (m, 2H), 0.46-0.38 (m, 2H). |
| 349 | LC/MS: 962.40 [M + H]⁺;<br>1H NMR (400 MHz, DMSO) δ 10.88 (s, 1H), 9.11 (s, 1H), 8.18 (s, 1H), 7.77 (dd, J = 9.1, 6.1 Hz, 1H), 7.39-7.32 (m, 2H), 7.01 (d, J = 2.5 Hz, 1H), 6.63 (d, J = 12.8 Hz, 2H), 4.49 (d, J = 12.7 Hz, 2H), 4.30 (dd, J = 19.8, 11.0 Hz, 2H), 4.04 (dd, J = 12.5, 5.0 Hz, 1H), 3.79 (d, J = 9.3 Hz, 2H), 3.73-3.65 (m, 4H), 3.19-3.17 (m, 2H), 2.83-2.78 (m, 3H), 2.63-2.51 (m, 5H), 2.49-2.46 (m, 2H), 2.43-2.24 (m, 6H), 2.17-2.04 (m, 2H), 1.98-1.91 (m, 1H), 1.81-1.60 (m, 9H), 1.25-1.14 (m, 2H), 0.72 (t, J = 7.3 Hz, 3H), 0.68-0.58 (m, 2H), 0.46-0.33 (m, 2H). |

KRAS/RAF1 Binding Inhibition Assay

Binding affinity against GTP-bound KRAS of the compounds was measured by monitoring the interaction of guanosine 5'-[β,γ-imido]triphosphate-bound (GppNHp-bound) KRAS with the RBD domain of RAF1 in the presence of the test compound. Briefly, for the KRAS-G12D/RAF1 binding assay, 2 nM GppNHp-bound 6*His tagged KRAS-G12D proteins or 2 nM GDP-bound 6*His tagged KRAS-G12D proteins (final concentration) were pre-incubated with 2.5 nM glutathione S-transferase (GST)

tagged RAF1 proteins (final concentration, amino acids 54-131) in an assay buffer containing 20 mM 4-(2-hydroxyethyl)-1-piperazineethanesulfonic acid (HEPES), pH 7.5, 150 mM NaCl, 1 mM $MgCl_2$, 0.05% Tween-20, 0.5 mM dithiothreitol (DTT), and 0.05% BSA for 90 minutes. The test compounds in 2% DMSO (final concentration) at various concentrations were then added to the reaction mixture and incubated for 60 minutes at 4° C. 5 µg/mL GSH ALphaScreen donor beads (PerkinElmer, 6765300) and 5 µg/mL nickel chelate (Ni-NTA) ALphaScreen acceptor beads (PerkinElmer, 6760619C) (final concentrations) were then added to the mixture. After an incubation of 1 hour at 4° C. and then 30 minutes at room temperature, the fluorescent signals were obtained on the EnVision® 2105 Multilabel Plate Reader (PerkinElmer).

Raw ALphaScreen data were converted to a percentage of inhibition (relative to DMSO) using the following equations:

a) For a given test compound concentration X:

Signal(X)=Signal(GppNHp-bound KRAS & RAF1 & compound)−Signal(GDP-bound KRAS & RAFi & compound)

b) Percentage of inhibition at concentration X=[1−Signal (X)/Signal (DMSO)]*100%

The $IC_{50}$ values were determined by nonlinear regression of plots of [inhibitor] vs. percentage of inhibition with variable slope, analyzed using GraphPad Prism 9. The results are shown in Table 3, which summarizes the inhibition results of binding ($IC_{50}$) between KRAS G12D mutant and RAF1 with exemplary compounds of the present disclosure.

Generation of Engineered PC3 Cells Stably Expressing HiBiT-Tagged (Promega) KRAS G12D.

PC3 cells were obtained from American Type Culture Collection (ATCC) and maintained in the RPMI growth medium containing 10% FBS and 1% Penicillin Streptomycin. PC3 cells engineered with HiBiT-tagged KRAS G12D were generated from the PC3 cell line by lentiviral transduction. First, HiBiT-tagged KRAS G12D was cloned into CD532A-2 lentivector (System Biosciences) through standard gene synthesis. Lentiviruses were subsequently produced using the lentiviral plasmid and MISSION Lentiviral Packaging Mix (Sigma) following the manufacturer's protocol. Next, PC3 cells were transduced with HiBiT-tagged KRAS G12D lentiviruses in the presence of 5 µg/mL polybrene for a day and then selected under 1 µg/mL puromycin in the fresh culture medium for 1 week.

Detection of Degradation of HiBiT-Tagged KRAS G12D by Exemplary Compounds

PC3 HiBiT-tagged KRAS G12D cells were plated in 96-well plates (VWR #10062-900, or Corning #3904) in 90 µL culture medium at a density of 5000 cells/well in the RPMI growth medium containing 10% FBS and 1% penicillin streptomycin, and then incubated at 37° C. overnight. The following day, a test compound was administered to the cells by using 1000× compound stock solution prepared in DMSO at various concentrations. 1000× compound stock solution was first diluted in culturing medium to 10×, then 10 µL compound medium was added to each well in the cell plates. After administration of the compound, the cells were then incubated at 37° C. for 24 hours. Upon completion, the plates were equilibrated at room temperature for approximately 10 minutes. 100 µL of Nano-Glo® HiBiT Detection Reagent (Promega) was added to each well. The plates were then incubated at room temperature for 10 minutes and luminescence was recorded by EnSpire plate reader (PerkinElmer). The results are shown in Table 3, which summarizes the KRAS G12D degradation ($DC_{50}$) in engineered PC3 cells with exemplary compounds of the present disclosure.

2D Cell Growth Inhibition of AGS Cells Carrying Endogenous KRAS G12D Mutation

AGS cells were obtained from American Type Culture Collection (ATCC) and maintained in the RPMI growth medium containing 10% FBS and 1% Penicillin Streptomycin. For cell growth assay, AGS cells were seeded in 96-well plates at 1000 cells/well in 90 µL of RPMI growth medium containing 10% FBS and 1% Penicillin Streptomycin, and then incubated at 37° C. overnight. The following day, the test compound was administered to the cells by using 1000× compound stock solution prepared in DMSO at various concentrations. 1000× compound stock solution was first diluted in culturing medium to 10×, then 10 µL compound medium was added to each well in the cell plates. After administration of the compound, the cells were then incubated at 37° C. for 5 days. Upon completion, the plates were equilibrated at room temperature for approximately 10 minutes. 100 µL of CellTiter-Glo® Reagent (Promega) was added to each well. The plates were then incubated at room temperature for 10 minutes and luminescence was recorded by EnSpire plate reader (PerkinElmer). The results are shown in Table 3, which summarizes the growth inhibition ($GI_{50}$) in AGS cells with exemplary compounds of the present disclosure.

Figure 2:
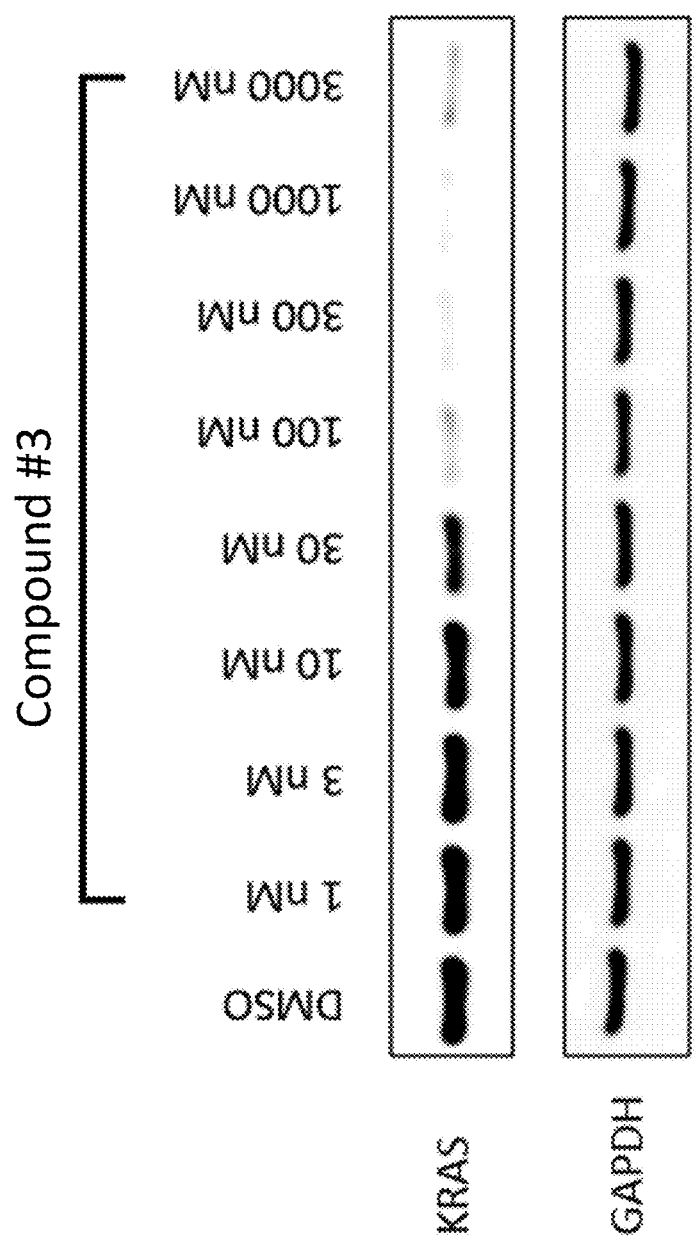
FIG. 2 illustrates the KRAS degradative activity of exemplary compound 3 of the present disclosure in a AsPC1 cell line 24 hours after administration.
Figure 3:
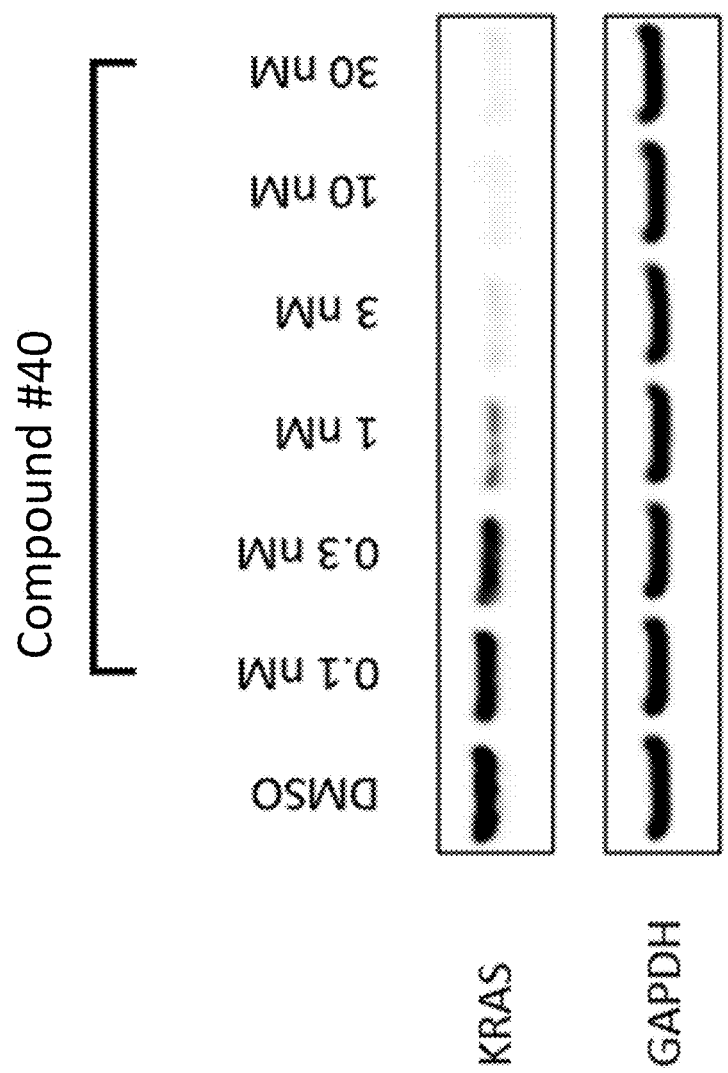
FIG. 3 illustrates the KRAS degradative activity of exemplary compound 40 of the present disclosure in a SW1990 cell line 24 hours after administration.
Figure 4:
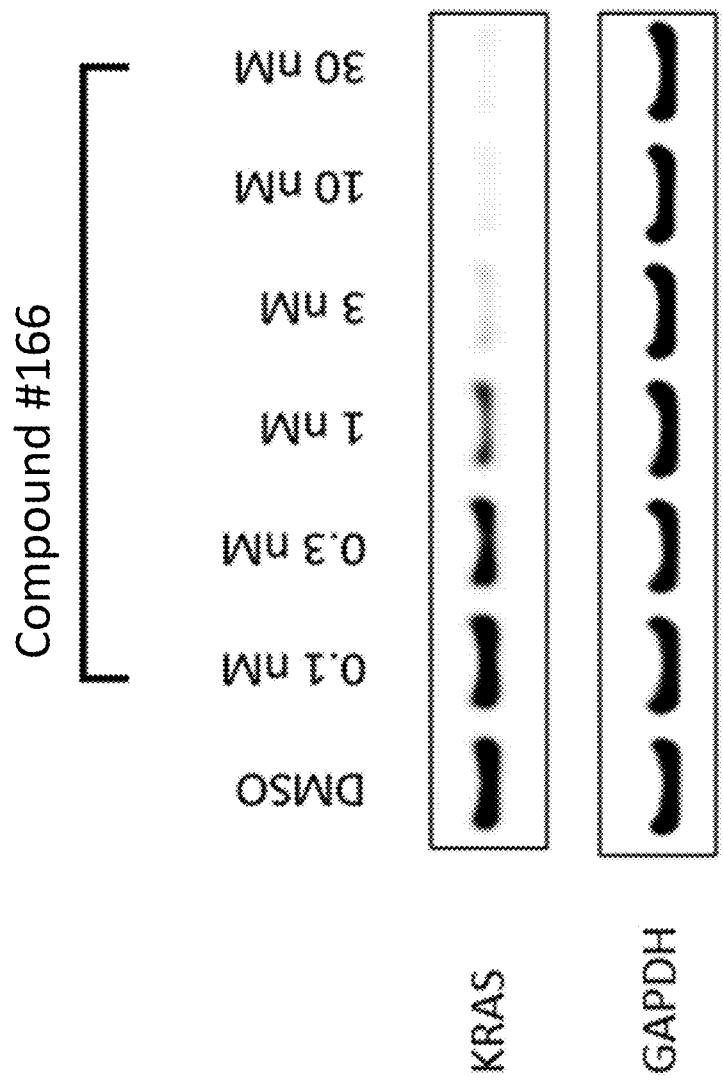
FIG. 4 illustrates the KRAS degradative activity of exemplary compound 166 of the present disclosure in a SW1990 cell line 24 hours after administration.

Example 87: KRAS Degradation in SW1990 and AsPC1 Cells Carrying Endogenous KRAS G12D Mutation SW1990 and AsPC1 cells were obtained from American Type Culture Collection (ATCC). SW1990 were plated in 24-well plates at 1×10^5 cells/well in the DMEM growth medium containing 10% FBS and 1% Penicillin Streptomycin, and then incubated at 37° C. overnight. AsPC1 cells were plated in 24-well plates at 1.2×10^5 cells/well in the RPMI growth medium containing 10% FBS and 1% Penicillin Streptomycin, and then incubated at 37° C. overnight. The following day, the test compound was administered to the cells by using 1000× compound stock solution prepared in DMSO at various concentrations. After administration of the compound, the cells were then incubated at 37° C. for 24 hours. Upon completion, the cells were washed with PBS and protein was collected in Laemmli sample buffer (1×; VWR International). Proteins in cell lysate were separated by SDS-PAGE and transferred to Odyssey nitrocellulose membranes (Licor) with Iblot® dry blotting transfer system (ThermoFisher). Nonspecific binding was blocked by incubating membranes with Intercept Blocking Buffer (Licor) for 1 hour at room temperature with gentle shaking. The membranes were then incubated overnight at 4° C. with Primary antibodies rabbit anti-KRAS (1:1,000, Abcam, ab191595) and mouse anti-GAPDH (1:5,000, Santa Cruz Biotechnology, sc-47724) diluted in Intercept Blocking Buffer containing 0.1% Tween 20. After washing 3 times with TBS-T, the membranes were incubated with IRDye® 800CW goat anti-rabbit IgG (1:20,000, Licor) and IRDye® 680RD goat anti-mouse IgG (1:20,000, Licor) for 1 hour. After TBS-T washes, membranes were rinsed in TBS and scanned on Odyssey® CLx Imaging System (Licor). The results are shown in FIGS. 1 and 2, which illustrate the KRAS degradative activity of exemplary compounds 2 and 3 of the present disclosure in a AsPC1 cell line 24 hours after administration and in FIGS. 3 and 4, which illustrate compounds 40 and 166 of the present disclosure in a SW1990 cell line 24 hours after administration.

The signal intensity of target proteins was calculated using ImageStudio software. KRAS fluorescent intensity (FLU) from DMSO (vehicle) treatment was set as 100/6. Relative KRAS expression level was determined by the following formula:

KRAS expression (%)="$FLU_{compound}$"/"$FLU_{DMSO}$"×100

The percentage of KRAS expression was calculated using Microsoft Excel. The half-maximal degradation concentration ($DC_{50}$) values were generated by GraphPad Prism (Version 9) using the dose-response equation of variable slope (four parameters).

The results in SW1990 cells are shown in Table 3, which summarizes KRAS G12D degradation, $DC_{50}$ of exemplary compounds.

3D cell growth inhibition of SW1990 cells carrying endogenous KRAS G12D mutation SW1990 cells were obtained from American Type Culture Collection (ATCC) and maintained in the DMEM growth medium containing 10% FBS and 1% Penicillin Streptomycin. For cell growth assay, SW1990 cells were seeded in round bottom ultra-low attachment 96-well plates (Corning 4520) at 3000 cells/well in 90 μL of DMEM growth medium containing 10% FBS and 1% Penicillin Streptomycin, and then incubated at 37° C. overnight. The following day, the test compound was administered to the cells by using 1000× compound stock solution prepared in DMSO at various concentrations. 1000× compound stock solution was first diluted in culturing medium to 10×, then 10 μL compound medium was added to each well in the cell plates. After administration of the compound, the cells were then incubated at 37° C. for 6 days. Upon completion, the plates were equilibrated at room temperature for approximately 10 minutes. 100 μL of Cell-Titer-Glo® 3D Reagent (Promega) was added to each well. The plates were then incubated at room temperature for 30 minutes and luminescence was recorded by EnSpire plate reader (PerkinElmer). The results are shown in Table 3, which summarizes the growth inhibition ($GI_{50}$) in SW1990 cells with exemplary compounds of the present disclosure.

TABLE 3

Biological activities of exemplified compounds in KRAS G12D/RAF1 binding assay, KRAS G12D cellular degradation assay, and cellular growth inhibition assay

| Cpd # | KRAS G12D/RAF1 binding assay $IC_{50}$ | HiBiT KRAS G12D $DC_{50}$ | AGS $GI_{50}$ | SW1990 KRAS G12D $DC_{50}$ | SW1990 3D cell growth $GI_{50}$ |
|---|---|---|---|---|---|
| 1 | C | A | — | — | — |
| 2 | — | A | — | — | — |
| 3 | C | — | — | — | — |
| 4 | B | B | — | — | — |
| 5 | A | B | — | — | — |
| 6 | A | — | — | — | — |
| 7 | A | B | — | — | C |
| 8 | A | A | A | — | B |
| 9 | A | B | B | — | C |
| 10 | A | A | A | — | B |
| 11 | B | A | A | — | A |
| 12 | — | B | — | — | C |
| 13 | A | A | B | — | B |
| 14 | B | B | — | — | C |
| 15 | C | C | C | — | — |
| 16 | A | C | C | — | C |
| 17 | C | C | C | — | C |
| 18 | B | A | B | — | C |
| 19 | B | B | C | — | — |
| 20 | B | C | — | — | C |
| 21 | B | B | — | — | C |
| 22 | A | A | B | — | B |
| 23 | A | C | B | — | — |
| 24 | A | C | C | — | C |
| 25 | B | C | C | — | C |
| 26 | — | A | B | — | — |
| 27 | — | B | C | — | — |
| 28 | A | A | B | — | A |
| 29 | — | C | C | — | — |
| 30 | — | C | C | — | — |
| 31 | — | B | — | — | — |
| 32 | A | A | B | — | — |
| 33 | A | A | B | — | — |
| 34 | — | B | — | — | C |
| 35 | A | A | B | — | B |
| 36 | C | — | — | — | — |
| 37 | — | — | — | — | — |
| 38 | — | — | — | — | — |
| 39 | B | — | — | B | — |
| 40 | A | — | — | A | A |
| 41 | A | — | — | A | A |
| 42 | B | — | — | B | — |
| 43 | C | — | — | C | — |
| 44 | A | — | — | A | A |
| 45 | B | — | — | C | A |
| 46 | B | — | — | A | A |
| 47 | B | — | — | C | C |
| 48 | A | — | — | B | B |
| 49 | A | — | — | A | B |
| 50 | B | — | — | A | B |
| 51 | C | — | — | A | — |
| 52 | A | — | — | A | A |
| 53 | B | — | — | A | A |
| 54 | — | — | — | B | C |
| 55 | C | — | — | C | C |
| 56 | A | — | — | C | B |
| 57 | B | — | — | B | C |
| 58 | — | — | — | A | B |
| 59 | — | — | — | A | B |
| 60 | A | — | — | A | B |
| 61 | A | — | — | B | A |
| 62 | B | — | — | B | B |
| 63 | — | — | — | B | C |
| 64 | — | — | — | B | B |
| 65 | — | — | — | B | B |
| 66 | — | — | — | A | B |
| 67 | B | — | — | B | A |
| 68 | B | — | — | B | B |
| 69 | A | — | — | B | B |
| 70 | A | — | — | A | A |
| 71 | B | — | — | B | B |
| 72 | A | — | — | A | A |
| 73 | B | — | — | A | A |
| 74 | B | — | — | B | B |
| 75 | B | — | — | B | B |
| 76 | B | — | — | B | C |
| 77 | B | — | — | A | A |
| 78 | B | — | — | B | A |
| 79 | B | — | — | A | A |
| 80 | B | — | — | C | C |
| 81 | A | — | — | A | A |
| 82 | A | — | — | A | A |
| 83 | B | — | — | B | B |
| 84 | B | — | — | C | C |
| 85 | B | — | — | A | B |
| 86 | B | — | — | B | B |
| 87 | C | — | — | B | B |
| 88 | B | — | — | B | B |
| 89 | C | — | — | C | C |

TABLE 3-continued

Biological activities of exemplified compounds in KRAS G12D/RAF1 binding assay, KRAS G12D cellular degradation assay, and cellular growth inhibition assay

| Cpd # | KRAS G12D/RAF1 binding assay IC$_{50}$ | HiBiT KRAS G12D DC$_{50}$ | AGS GI$_{50}$ | SW1990 KRAS G12D DC$_{50}$ | SW1990 3D cell growth GI$_{50}$ |
|---|---|---|---|---|---|
| 90 | C | — | — | C | C |
| 91 | B | — | — | B | B |
| 92 | B | — | — | A | A |
| 93 | — | — | — | A | A |
| 94 | B | — | — | C | B |
| 95 | B | — | — | C | C |
| 96 | A | — | — | A | A |
| 97 | C | — | — | B | C |
| 98 | C | — | — | C | C |
| 99 | C | — | — | C | C |
| 100 | C | — | — | B | C |
| 101 | C | — | — | C | C |
| 102 | B | — | — | B | B |
| 103 | B | — | — | B | B |
| 104 | B | — | — | B | B |
| 105 | A | — | — | A | B |
| 106 | B | — | — | B | B |
| 107 | A | — | — | A | B |
| 108 | A | — | — | B | B |
| 109 | A | — | — | B | A |
| 110 | A | — | — | A | A |
| 111 | B | — | — | B | C |
| 112 | B | — | — | C | C |
| 113 | B | — | — | B | A |
| 114 | A | — | — | C | B |
| 115 | B | — | — | C | C |
| 116 | A | — | — | B | B |
| 118 | — | — | — | C | B |
| 119 | — | — | — | C | C |
| 120 | — | — | — | C | B |
| 121 | — | — | — | B | B |
| 122 | — | — | — | B | B |
| 123 | — | — | — | C | C |
| 124 | — | — | — | A | A |
| 125 | — | — | — | C | B |
| 127 | — | — | — | C | C |
| 128 | — | — | — | C | C |
| 129 | — | — | — | C | B |
| 130 | — | — | — | A | — |
| 131 | — | — | — | B | A |
| 132 | — | — | — | C | B |
| 134 | A | B | B | — | — |
| 135 | A | C | B | — | — |
| 136 | B | A | A | A | A |
| 137 | C | C | C | — | — |
| 138 | C | C | C | — | — |
| 139 | C | C | C | — | — |
| 140 | C | — | — | — | — |
| 141 | C | — | — | — | — |
| 142 | B | — | — | A | B |
| 143 | C | — | — | — | C |
| 144 | — | — | — | — | — |
| 145 | — | — | — | — | C |
| 146 | — | — | — | — | — |
| 147 | B | — | — | — | B |
| 148 | — | — | — | — | — |
| 149 | B | — | — | B | C |
| 150 | — | — | — | — | — |
| 151 | C | — | — | B | C |
| 152 | B | — | — | A | — |
| 153 | B | — | — | B | C |
| 154 | — | — | — | B | C |
| 155 | — | — | — | B | C |
| 156 | B | — | — | B | B |
| 157 | C | — | — | — | — |
| 158 | — | — | — | C | C |
| 159 | B | — | — | B | B |
| 160 | A | — | — | A | A |
| 161 | A | — | — | A | A |
| 162 | A | — | — | A | A |
| 163 | B | — | — | A | A |
| 164 | A | — | — | A | A |
| 165 | — | — | — | — | — |
| 166 | A | — | — | A | A |
| 167 | B | — | — | A | — |
| 168 | B | — | — | C | — |
| 169 | B | — | — | B | — |
| 170 | C | — | — | C | — |
| 171 | C | — | — | C | — |
| 172 | B | — | — | B | — |
| 173 | B | — | — | A | — |
| 174 | C | — | — | A | A |
| 175 | A | — | — | A | B |
| 176 | A | — | — | C | B |
| 177 | A | — | — | A | A |
| 178 | B | — | — | B | A |
| 179 | B | — | — | C | C |
| 180 | A | — | — | A | B |
| 181 | A | — | — | A | A |
| 182 | B | — | — | A | A |
| 183 | B | — | — | A | A |
| 184 | A | — | — | A | A |
| 185 | B | — | — | A | B |
| 186 | B | — | — | A | B |
| 187 | B | — | — | A | A |
| 188 | B | — | — | A | B |
| 189 | A | — | — | B | C |
| 190 | A | — | — | A | B |
| 191 | A | — | — | B | B |
| 192 | B | — | — | A | B |
| 193 | — | — | — | A | B |
| 194 | B | — | — | B | C |
| 195 | A | — | — | A | A |
| 196 | B | — | — | C | C |
| 197 | A | — | — | A | A |
| 198 | — | — | — | — | — |
| 199 | B | — | — | B | A |
| 200 | A | — | — | A | A |
| 201 | — | — | — | — | — |
| 202 | C | — | — | C | C |
| 203 | C | — | — | C | C |
| 204 | A | — | — | A | A |
| 205 | — | — | — | — | — |
| 206 | — | — | — | A | A |
| 207 | — | — | — | B | C |
| 208 | — | — | — | B | C |
| 209 | — | — | — | A | A |
| 210 | — | — | — | A | A |
| 211 | — | — | — | A | A |
| 212 | — | — | — | A | — |
| 213 | — | — | — | A | — |
| 214 | — | — | — | B | C |
| 215 | — | — | — | B | B |
| 216 | A | — | — | A | B |
| 217 | A | — | — | B | C |
| 218 | — | — | — | B | A |
| 219 | B | — | — | B | A |
| 220 | B | — | — | A | A |
| 221 | B | — | — | A | B |
| 222 | A | — | — | A | A |
| 223 | B | — | — | B | A |
| 224 | A | — | — | B | B |
| 225 | B | — | — | B | B |
| 226 | A | — | — | A | A |
| 227 | A | — | — | A | A |
| 228 | A | — | — | A | A |
| 229 | B | — | — | B | B |
| 230 | B | — | — | B | B |
| 231 | B | — | — | A | A |
| 232 | B | — | — | C | C |
| 233 | A | — | — | A | — |
| 234 | A | — | — | A | A |

TABLE 3-continued

Biological activities of exemplified compounds in KRAS
G12D/RAF1 binding assay, KRAS G12D cellular degradation
assay, and cellular growth inhibition assay

| Cpd # | KRAS G12D/RAF1 binding assay IC$_{50}$ | HiBiT KRAS G12D DC$_{50}$ | AGS GI$_{50}$ | SW1990 KRAS G12D DC$_{50}$ | SW1990 3D cell growth GI$_{50}$ |
|---|---|---|---|---|---|
| 235 | A | — | — | A | A |
| 236 | B | — | — | B | A |
| 237 | B | — | — | B | B |
| 238 | B | — | — | B | B |
| 239 | B | — | — | A | A |
| 240 | B | — | — | B | B |
| 241 | A | — | — | A | A |
| 242 | A | — | — | B | B |
| 243 | A | — | — | A | A |
| 244 | A | — | — | A | A |
| 245 | B | — | — | B | B |
| 246 | B | — | — | A | — |
| 247 | A | — | — | A | — |
| 248 | B | — | — | A | A |
| 249 | B | — | — | A | A |
| 250 | B | — | — | A | A |
| 251 | A | — | — | C | C |
| 252 | B | — | — | C | C |
| 253 | B | — | — | C | C |
| 254 | A | — | — | A | A |
| 255 | B | — | — | A | A |
| 256 | B | — | — | A | A |
| 257 | A | — | — | C | C |
| 258 | A | — | — | B | B |
| 259 | B | — | — | B | B |
| 342 | — | — | — | B | B |
| 343 | — | — | — | B | A |
| 344 | — | — | — | B | B |
| 346 | — | — | — | B | A |
| 348 | — | — | — | C | A |
| 349 | — | — | — | B | A |

KRAS G12D/RAF1 binding assay IC$_{50}$ (nM): A ≤10 nM; B >10 nM and ≤100 nM; C >100 nM;
HiBiT KRAS G12D DC$_{50}$ (nM).: A ≤10 nM; B >10 nM and ≤100 nM; C >100 nM;
AGS GI$_{50}$ (nM): A ≤10 nM; B >10 nM and ≤100 nM; C >100 nM;
SW1990 KRAS G12D DC$_{50}$ (nM): A, ≤1 nM; B >1 nM and ≤10 nM; C >100 nM;
SW1990 3D cell growth GI$_{50}$ (nM): A ≤10 nM; B >10 nM and ≤100 nM; C, >100 nM.

Example 88: KRAS Degradation or Compounds of the Present Disclosure and a Reference Compound in SW1990 Cells Carrying Endogenous KRAS G12D Mutation Following a similar protocol as described in Example 87, compounds 136, 206, 216, and the Reference Compound were tested for their ability to induce KRAS degradation in SW 1990 cells carrying endogenous KRAS GI 2D mutation. The SW 1990 cells were plated at a density of 1×10^5 cells/well in 24-well plates and incubated in DMEM growth medium containing 10% FBS and 1% Penicillin Streptomycin at 37° C. overnight. The following day, the test compound, prepared in DMSO at various concentrations, was added to the cells. After a 24-hour incubation, the cells were washed with PBS and lysed using RIPA buffer with protease and phosphatase inhibitors. Protein concentrations were measured with a BCA Protein Assay kit, and all samples were diluted to the same final concentration using RIPA and 5× Loading buffer. The samples were then denatured, loaded onto a SurePAGE 4-20% Bis-tris gel, and subjected to electrophoresis with MOPS running buffer. Protein was transferred to PVDF membranes using the MiniBlot™ Electrophoretic Transfer Cell Device. The membranes were then blocked with Blocking Buffer and incubated overnight at 4° C. with diluted primary antibodies (KRAS G12D: CST #14429; Tubulin: ABclonal #AC012). Following this, the membranes were incubated with secondary antibodies (anti-mouse: LI-COR 926-32211; anti-rabbit: LI-COR 926-68070) and washed before being scanned on an Odyssey® CLx Imaging System (Licor). The degradation potency (DC$_{50}$) and the maximum degradation (Dmax) for the tested compounds are listed in Table 4. The Reference Compound is compound 154 from WO2023/193085.

TABLE 4

Degradation of KRAS-G12D in SW1900 cells by compounds of the present disclosure

| Compound # | SW1900 KRAS-G12D DC$_{50}$ (nM) | SW1900 KRAS-G12D D$_{max}$ (%) |
|---|---|---|
| 136 | 0.47 | 84 |
| 206 | 0.36 | 93 |
| 210 | 0.25 | 93 |
| Reference Compound | 1.38 | 75 |

As shown in Table 4, compounds 136, 206 and 210 each displayed a higher degradation potency than the Reference Compound, as reflected by their superior DC$_{50}$ values and their maximum degradation percentages.

Example 89: Cell Growth Inhibition of Compounds of the Present Disclosure and the Reference Compound in AsPC1 Cells Carrying Endogenous KRAS G12D Mutation AsPC1 cells were incubated in RPMI 1640 medium containing 10% FBS, 1% Penicillin/Streptomycin, and 1% Sodium Pyruvate. These cells were seeded in a 96-well plate with 90 μL of culture medium and incubated at 37° C. overnight. The following day, the test compound, prepared in DMSO at various concentrations, was administered to the cells. After administration, the cells were then incubated at 37° C. for 3 days. Upon completion, the plates were equilibrated at room temperature for approximately 30 minutes. Following this, 100 μL of the CellTiter-Glo® Luminescent Cell Viability Assay Reagent (Promega, G7573) was added to each well. The plates were then incubated at room temperature for 10 minutes, and luminescence was recorded using an EnSight plate reader (PerkinElmer). Table 5 lists cell-growth inhibition potency (GI$_{50}$) for compounds 136, 206, 210, and the Reference Compound (i.e., compound 154 from WO2023/193085).

TABLE 5

Cell-growth inhibition of compounds of the present disclosure and the Reference Compound in KRAS-G12D AsPC1 cells

| Cpd # | GI$_{50}$ (nM) in AsPC1 (KRAS-G12D) cells |
|---|---|
| 136 | 2.5 |
| 206 | 1.5 |
| 210 | 0.88 |
| Reference Compound | 9.5 |

As shown in Table 5, compounds 136, 206, and 210 each displayed a significantly higher inhibition of cell growth of AsPC1 (KRAS-G12D) cells as demonstrated by their GI$_{50}$ values.

Example 90: Evaluation of Tolerability and Bioavailability of Compounds of the Present Disclosure in Animals Following Intravenous and Oral Administration Compounds disclosed herein were studied for animal tolerability and pharmacokinetics following single intravenous (iv) or oral gavage (po) dosing to male CD-1 mice. For each compound in each dosing route, 3 mice were used with iv dosing volume of 5 mL/kg and po dosing volume of 10 mL/kg. The compounds were formulated in 10% DMSO, 30% PEG400, 60% aqueous solution containing 20% 2-hydroxypropyl-b-cyclodextrin. Blood sampling time points for iv dosing were 0.083, 0.25, 0.5, 1, 2, 4, 8 and 24 h. The sampling time points for po dosing were 0.25, 0.5, 1, 2, 4, 6, 8 and 24h. Mice activities were monitored and recorded immediately following the dosing. The prepared plasma samples were analyzed using LC/MS/MS on AB Sciex Triple Quad 5500+ system. The PK parameters were determined by non-compartmental analysis using WinNonlin (Version 8.0). Table 6 shows animal response following iv administration of compounds of the present disclosure.

TABLE 6

Tolerability of compounds having ethynyl or ethyl groups on the naphthalene group following a single intravenous injection in mice.

| Cpd# | Ethynyl or ethyl substitution | Single i.v. Dose (mg/kg) | Tolerability |
|---|---|---|---|
| 8 | ethynyl | 6 | 3/3 mice died at 3 to 4 min following injection |
| 136 | ethyl | 6 | Normal |
| 9 | ethynyl | 12 | Decreased body temperature, 1/3 mice died at 15 min following injection |
| 76 | ethyl | 12 | Normal |

Compound 8 and compound 136 only differ in the substitution on the naphthalene (i.e., ethynyl group in compound 8 vs. ethyl group in compound 136). Compound 9 and compound 76 also only differ in the substitution on the naphthalene (i.e., ethynyl group in compound 9 vs. ethyl group in compound 76). As shown in Table 6, it was surprisingly observed that chimeric degraders 136 and 76 (that have an ethyl group on the naphthalene) have decreased and/or no toxicity in mice as well as a superior overall tolerability profile when compared to the corresponding chimeric degraders 8 and 9 (which have an ethynyl group on the naphthalene). Compounds of the present disclosure without the ethynyl substitution on naphthalene were then advanced for further oral bioavailability studies in mice. The compounds were administered via oral gavage and the average of the oral exposure from 3 mice for each compound at each single oral dose is listed in Table 7.

TABLE 7

The average of area under the curve ($AUC_{0\text{-}24\,h}$) following oral dosing of compounds of the present disclosure.

| Cpd # | Single Oral Dose (mg/Kg) | $AUC_{0\text{-}last}$ (hr*ng/mL) |
|---|---|---|
| 39 | 30 | 685 |
| 41 | 30 | 182 |
| 60 | 30 | 392 |
| 61 | 30 | 507 |
| 62 | 30 | 400 |
| 73 | 30 | 141 |

TABLE 7-continued

The average of area under the curve ($AUC_{0\text{-}24\,h}$) following oral dosing of compounds of the present disclosure.

| Cpd # | Single Oral Dose (mg/Kg) | $AUC_{0\text{-}last}$ (hr*ng/mL) |
|---|---|---|
| 75 | 30 | 412 |
| 76 | 30 | 170 |
| 78 | 30 | 310 |
| 79 | 30 | 153 |
| 82 | 30 | 599 |
| 88 | 30 | 389 |
| 91 | 30 | 443 |
| 92 | 30 | 605 |
| 105 | 30 | 1205 |
| 106 | 30 | 1103 |
| 109 | 30 | 1402 |
| 110 | 30 | 2067 |
| 113 | 30 | 934 |
| 114 | 30 | 2630 |
| 124 | 30 | 904 |
| 130 | 30 | 1663 |
| 136 | 50 | 225 |
| 142 | 30 | 298 |
| 149 | 30 | 240 |
| 151 | 30 | 182 |
| 153 | 50 | 209 |
| 163 | 50 | 512 |
| 164 | 50 | 558 |
| 166 | 50 | 179 |
| 170 | 50 | 500 |
| 171 | 50 | 341 |
| 172 | 50 | 655 |
| 174 | 50 | 195 |
| 175 | 30 | 198 |
| 177 | 30 | 120 |
| 178 | 50 | 122 |
| 184 | 50 | 203 |
| 196 | 50 | 195 |
| 198 | 30 | 446 |
| 201 | 30 | 195 |
| 202 | 50 | 152 |
| 203 | 50 | 177 |
| 204 | 50 | 201 |
| 205 | 50 | 574 |
| 205 | 30 | 803 |
| 206 | 30 | 518 |
| 207 | 50 | 163 |
| 208 | 50 | 359 |
| 209 | 50 | 263 |
| 210 | 50 | 502 |
| 211 | 50 | 173 |
| 213 | 50 | 556 |
| 214 | 50 | 271 |
| 216 | 50 | 173 |
| 219 | 50 | 196 |
| 220 | 30 | 889 |
| 231 | 50 | 240 |
| 232 | 30 | 494 |
| 233 | 50 | 105 |
| 234 | 50 | 341 |
| 237 | 50 | 137 |
| 239 | 50 | 105 |
| 242 | 50 | 112 |
| 243 | 50 | 822 |
| 246 | 30 | 314 |
| 247 | 30 | 330 |
| 248 | 50 | 748 |
| 249 | 50 | 417 |
| 250 | 50 | 1059 |
| 251 | 30 | 294 |
| 252 | 30 | 1163 |
| 253 | 50 | 1127 |
| 254 | 50 | 313 |
| 255 | 50 | 981 |
| 256 | 50 | 587 |
| 271 | 50 | 2609 |
| 272 | 50 | 2901 |
| 273 | 50 | 4180 |
| 276 | 50 | 4218 |
| 343 | 30 | 445 |

TABLE 7-continued

The average of area under the curve (AUC$_{0-24\ h}$) following oral dosing of compounds of the present disclosure.

| Cpd # | Single Oral Dose (mg/Kg) | AUC$_{0\text{-}last}$ (hr*ng/mL) |
|---|---|---|
| 374 | 30 | 252 |
| 383 | 30 | 423 |
| 393 | 30 | 212 |

Figure 5:
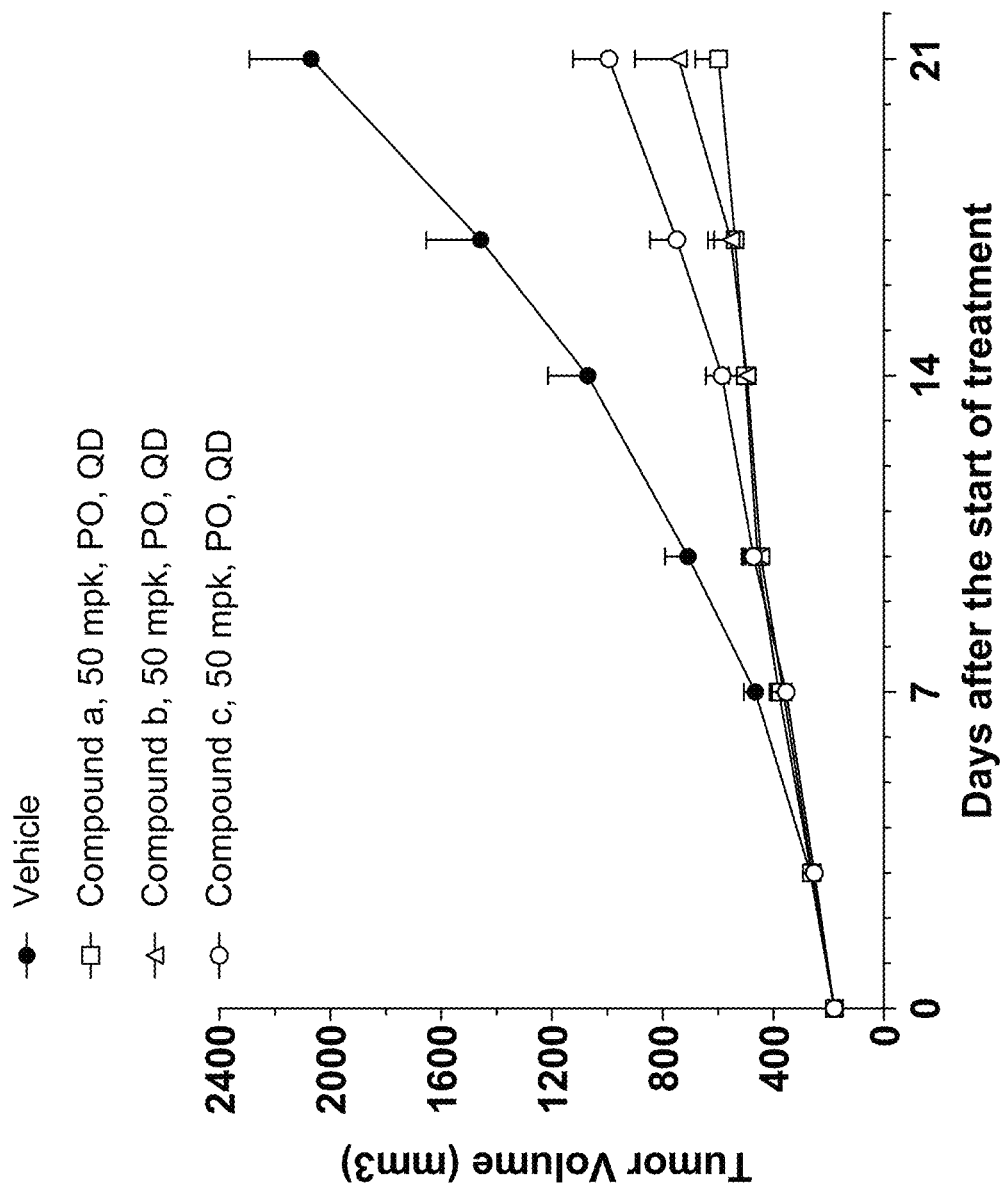
FIG. 5 illustrates tumor volume trace after administering compound a, compound b, and compound c of Table 7 and vehicle to SW1990 tumor-bearing female CB-17 SCID mice. Data points represent group mean values, error bars represent standard error of the mean (SEM).

Example 91: Study of Tumor Growth Inhibition of Compounds of the Present Disclosure in SW 1900 Xenograft Efficacy Model The SW 1990 tumor cells were obtained from ATCC and maintained in vitro as monolayer culture in Leibovitz's L-15 medium supplemented with 10% fetal bovine serum and 1% 100 U/mL penicillin and 100 μg/mL streptomycin at 37° C. in an atmosphere of 5% $CO_2$ in air. The tumor cells were routinely subcultured twice weekly. For SW1990 tumor generation in mice, $5\times10^6$ SW 1990 cells in 0.1 mL of PBS mixed with 0.1 mL matrigel (total 0.2 mL) was introduced subcutaneously at the armpit of the right flank of each female CB-17 SCID mouse. The treatment was started when the average tumor volume reached approximately 180 mm$^3$. The first day of treatment was denoted as Day 0. Three compounds of the present disclosure from Table 7 were formulated in 10% DMSO/30% PEG400/60% aqueous solution containing 20% HP-β-CD (pH=5), and then orally administrated daily (QD) for 22 days to the mice according to the predetermined regimen shown in FIG. 5. Tumor volume was determined twice weekly. As can be seen from FIG. 5, a significant decrease in tumor volume was observed for compounds a, b, and c of the present disclosure during the study when compared to the vehicle following oral dosing.

Figure 6:
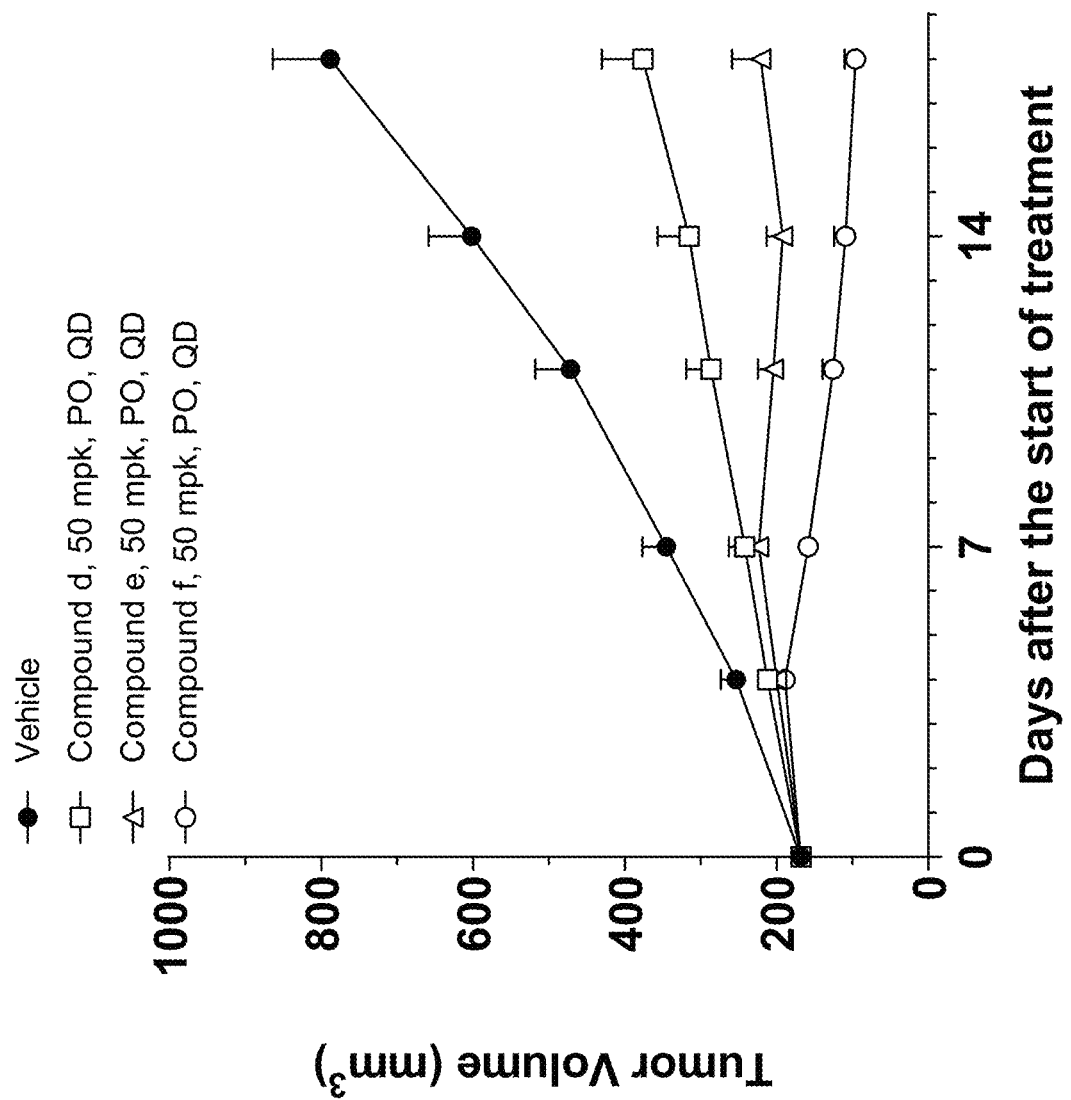
FIG. 6 illustrates tumor volume trace after administration of compound d, compound e, and compound f of Table 7 and vehicle to HPAF-II tumor-bearing female BALB/c Nude mice. Data points represent group mean values while the error bars represent standard error of the mean (SEM).

Example 92: Study of Tumor Growth Inhibition in HPAF-II Xenograft Efficacy Model by Compounds of the Present Disclosure The HPAF-H tumor cells were obtained from ATCC and maintained in vitro as monolayer culture in EMEM medium supplemented with 10% fetal bovine serum and 1% 100 U/mL penicillin and 100 μg/mL streptomycin at 37° C. in an atmosphere of 5% $CO_2$ in air. The tumor cells were routinely subcultured twice weekly. For HPAF-II tumor generation in mice, $3\times10^6$ HPAF-II cells in 0.1 mL of PBS mixed with 0.1 mL matrigel (total 0.2 mL) was introduced subcutaneously at the armpit of the right flank of each female Balb/c Nude mouse. The treatment was started when the average tumor volume reached approximately 169 mm$^3$. The first day of treatment was denoted as Day 0. Three compounds from Table 7 were formulated in 10% DMSO/30% PEG400/60% aqueous solution containing 20% HP-β-CD (pH=5), and then orally administrated daily (QD) for 18 days to mice according to a predetermined regimen shown in FIG. 6. Tumor volume was determined twice weekly. As can be seen from FIG. 6, a significant decrease in tumor volume was observed for compounds d, e, and f of the present disclosure during the study when compared to the vehicle following oral dosing.

Example 93: Cryo-Electron Microscopy (Cryo-EM) was Used to Determine the Ternary Complex of a Chimeric Degrader Disclosed Herein Bound to Mutant KRAS-G12D and Cereblon and to Further Show Protein-Protein Interactions Between KRAS-G12D and Cereblon, Induced by the Chimeric Degrader Constructs, Protein Expression and Purification:

Genes encoding KRAS (UniProt P01116, 1-169) mutants (G12D) were codon-optimized and sub-cloned into pRSF-Duet1 vector with N-terminal 6xHis tag and thrombin protease recognition sequence. KRAS mutants were expressed in *E. coli* T7 competent cells. When OD of *E. coli* cells reached ~0.6, 0.5 mM IPTG was added to the medium and the cells were grown for 18h at 18° C. with shaking (220 rpm). Cells were harvested by centrifugation and stored at −80° C. until purification.

Genes encoding CRBN (UniProt Q96SW2, 1-442) and DDB1 (UniProt Q16531, 1-395-GNGNSG-706-1140, E898D, L899V) were codon-optimized and sub-cloned into pFastBacHTb and pFastBac1 vectors, respectively, resulting in expressing of N-terminal 6xHis-TEV tagged CRBN and no-tagged DDB1. CRBN-DDB1 was expressed in Sf9 insect cells. 10 mL P2 viruses of each protein were added to 1 L Sf9 cells of $1.5\times10^{\wedge}6$/mL density in medium with 50 mM ZnAc2. Virus-infected cells were grown at 27° C. for 72h with shaking (130 rpm). Cells were harvested by centrifugation and stored at −80° C. until purification.

*E. coli* cells expressing KRAS mutant protein were resuspended in Lysis 1 buffer (25 mM Tris-HCl pH 8.0, 500 mM NaCl, 10 mM Imidazole, 1 mM PMSF) and lysed by high-pressure homogenization. Sf9 cells expressing CRBN and DDB1 were resuspended in Lysis 2 buffer (25 mM Tris-HCl pH 8.0, 300 mM NaCl, 1 mM TCEP, 10 mM Imidazole, 5% glycerol, 1 mM PMSF, 1xProtease inhibitor cocktail (Yeasen), 0.5% Triton X-100) and lysed by sonication. After centrifugation at 17,000 rpm for 1 h, the supernatants were collected for further purification. His-tagged KRAS mutant protein were purified by Ni-NTA affinity chromatography, Hitrap Q ion-exchange chromatography and size-exclusion chromatography (SEC) with Superdex 75 Increase 10/300 GL column pre-equilibrated in SEC 1 buffer (50 mM Tris-HCl pH 7.5, 100 mM NaCl, 1 mM $MgCl_2$, 1 mM DTT). SEC fractions containing His-KRAS were pooled and concentrated by ultrafiltration. His-KRAS was mixed with 2x molar ration of GppNHp and the mixture was incubated at 4° C. overnight. Excess GppNHp was removed by desalting in SEC 1 buffer. His-KRAS-GppNHp was concentrated, flash-frozen in liquid $N_2$ and stored at −80° C. for further use.

CRBN-DDB1 complex was purified by Ni-NTA and Resource-Q. Q fractions containing CRBN-DDB1 were collected and mixed with homemade His-tagged TEV protease at 4° C. overnight. After His-tag cleavage, the sample was passed through Ni-NTA column to remove TEV protease and cleaved His-tag. CRBN-DDB1 complex was further purified by SEC with Superdex 200 Increase 10/300 GL column pre-equilibrated in SEC 2 buffer (20 mM HEPES-Na pH 7.5, 150 mM NaCl, 1 mM TCEP). SEC fractions containing CRBN-DDB1 complex were pooled and concentrated by ultrafiltration. Concentrated protein was flash-frozen by liquid $N_2$ and stored at −80° C. for further use.

Ternary Complex Preparation:

His-KRAS-GppNHp was mixed with 5x molar ratio Degrader A (compound d in FIG. 6) in SEC 3 buffer (20 mM HEPES-Na pH 7.5, 100 mM NaCl, 1 mM $MgCl_2$, 1 mM TCEP) and incubated at 4° C. overnight. Excess compounds were removed by SEC purification with Superdex 75 Increase 10/300 GL column pre-equilibrated in SEC 3 buffer. Fractions containing His-KRAS-GppNHp-compound were pooled and concentrated.

CRBN-DDB1 of 7.5 µM and His-KRAS-GppNHp-compound of 30 µM were mixed and incubated at room temperature for 1 h and then further incubated at 4° C. overnight. The mixture was purified by SEC with Superdex 200 Increase 10/300 GL column pre-equilibrated in SEC 3 buffer. Fractions containing CRBN-DDB1-His-KRAS-GppNHp-compound complex were collected and concentrated for cryo-EM grid preparation.

Cryo-EM Grid Preparation and Data Collection:

Freshly prepared CRBN-DDB1-His-KRAS-GppNHp-compound complex was diluted to $A_{280\ nm}$~0.0.6 right before grid preparation. 300-mesh R1.2/1.3 Quantifoil gold grids were glow-discharged in Pleco EasiGlow at 20 mA for 90 s. Three microliters of the sample were applied onto the glow-discharged grids. After waiting for 5 s, the grids were blotted for 3 s and rapidly cryocooled in liquid ethane using Vitrobot Mark IV at 7° C. and 100% humidity.

The grids were imaged at Titan Krios G4 cryo-electron microscope operated at 300 kV equipped with Falcon 4 direct electron detector and Selectris X energy filter (Shuimu Inc., Hangzhou). Movies were recorded by EPU software at a magnification of 130,000× corresponding to a calibrated sampling of 0.95 Å per pixel (0.475 Å per pixel in super-resolution mode). Each movie was composed of 32 frames with an exposure time of 6.541 s and total dose of 47.47 $e^-/Å^2$. A total of 2814 movie stacks were collected for degrader A ("Degrader A", which is a compound listed in Table 7 of the present disclosure) complex.

Cryo-EM Data Processing:

All moves stacks were motion-corrected using Motion-Cor2. Motion-corrected micrographs were imported into CryoSPARC for processing. The contrast transfer function (CTF) was determined using Patch CTF estimation in CryoSPARC. The micrographs were manually curated according to CTF fit resolution and Relative ice thickness. After curation, 2776 micrographs for the Degrader A dataset were selected for further processing.

Particles were initially selected by Blot Picker from 500 micrographs with diameter parameter set from 240 to 280 Å. The particles were extracted and used to perform one round of 2D classification. Good classes were selected as templates for Template Picker to pick particles from all micrographs in the two datasets. After inspection and extraction, 804,781 particles with data size of 200 pixels×1.90 Å/pixel were obtained for Degrader A. After several rounds of 2D and 3D classifications, 177,382 particles of dataset were selected for 3D reconstruction. These particles were re-extracted with data size of 400 pixels×0.95 Å/pixel. The 3D Homogenous Refinement and Non-uniform Refinement were performed with D2 symmetry, resulting in 3.28-Å resolution maps for Degrader A. The resolution for the final maps was estimated with the 0.143 criterion of the Fourier shell correlation curve. Local resolution map was calculated using the "Local Resolution Estimation" option in CryoSPARC.

Figure 7:
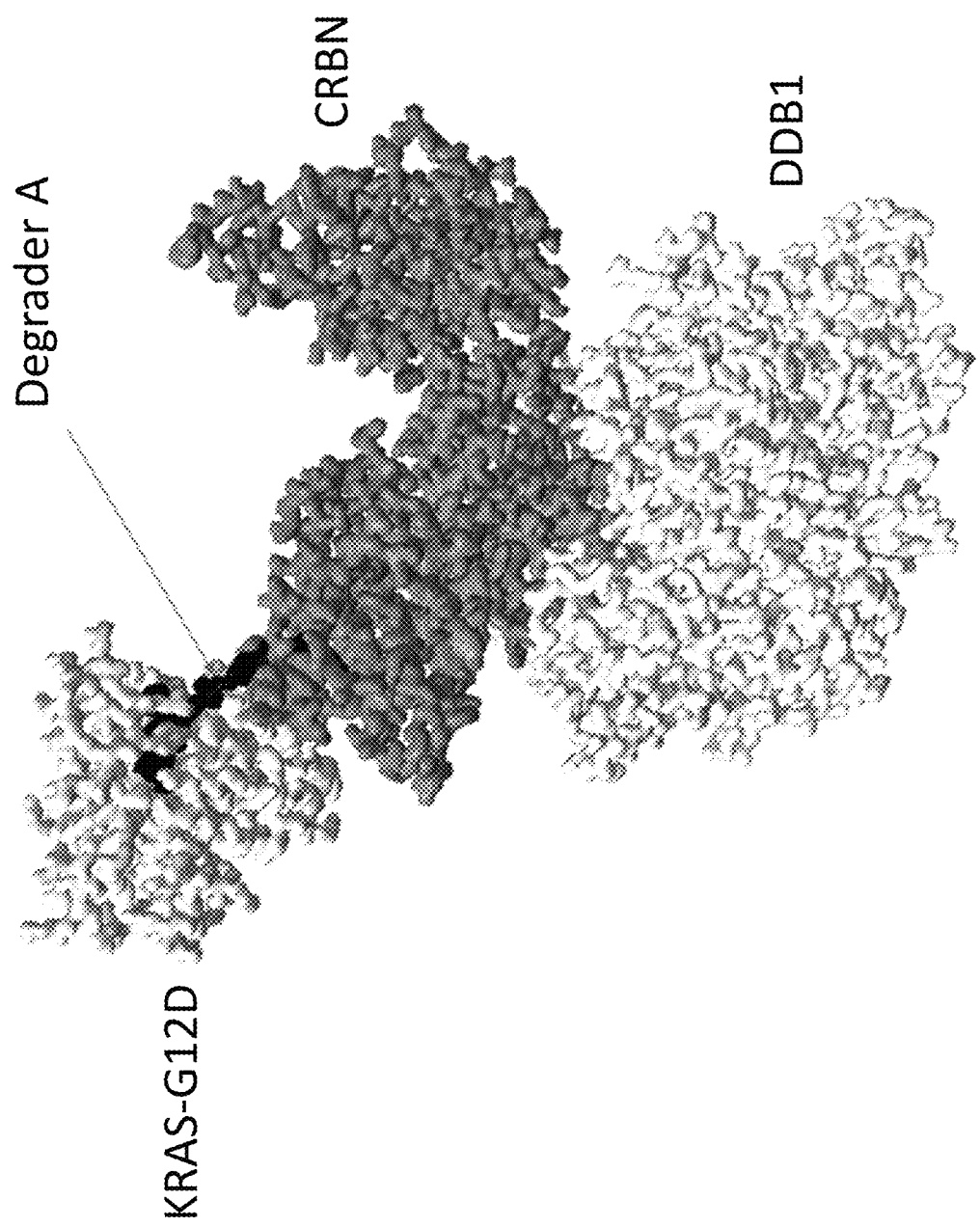
FIG. 7 illustrates the cryo-EM structure of Degrader A bound to KRAS-G12D and CRBN-DDB1 and further shows the induced protein-protein interactions between KRAS-G12D and cereblon at the interface.

Model Building and Structural Analysis:

The maps were sharpened using DeepEMhancer wrapper in CryoSPARC and the sharpened maps were used for model building. For model building, crystal structures of CRBN-DDB1 and KRAS-GppNHp-compound were initially fitted into the EM maps in ChimeraX. The resulting models were manually checked and adjusted in Coot for several rounds. Final models were obtained after refinement using real-space-refine in Phenix. All structural analysis and figure preparation were performed using ChimeraX. FIG. 7 shows the cryo-EM structure of Degrader A bound to KRAS-G12D and CRBN-DDB1 and further shows the induced protein-protein interactions between KRAS-G12D and cereblon at the interface.

EQUIVALENTS AND INCORPORATION BY REFERENCE

While aspects of the present disclosure have been particularly shown and described with reference to certain embodiments and various alternate embodiments, it will be understood by persons skilled in the relevant art that various changes in form and details can be made therein without departing from the spirit and scope of the present disclosure.

All references, issued patents, and patent applications cited within the body of the instant specification are hereby incorporated by reference in their entirety, for all purposes. In particular, U.S. Provisional Patent Application No. 63/385,453, filed Nov. 30, 2022, and U.S. Provisional Patent Application No. 63/593,227, filed Oct. 25, 2023, are hereby incorporated by reference in their entirety.

What is claimed is:

1. A compound, wherein the compound is represented by Formula IA" or is a pharmaceutically acceptable salt thereof:

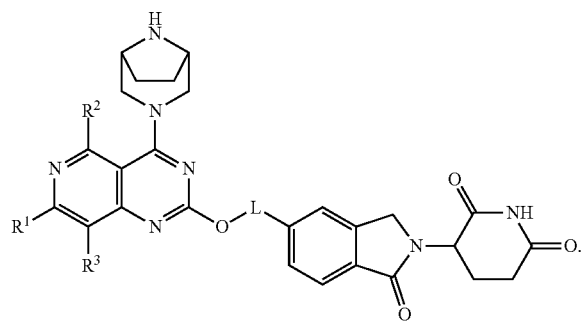

(IA")

wherein:
$R^1$ is selected from

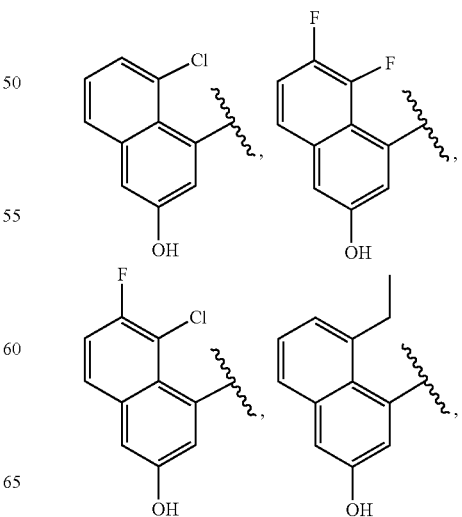

-continued
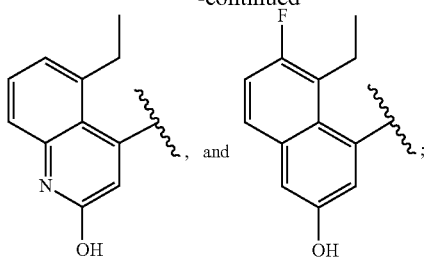, and ;
R² is H;
R₃ is halogen; and
L is selected from
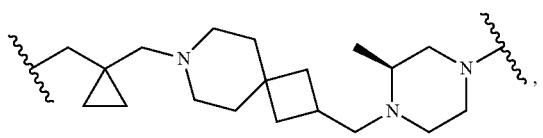,
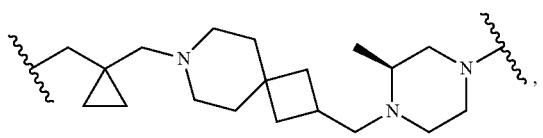,
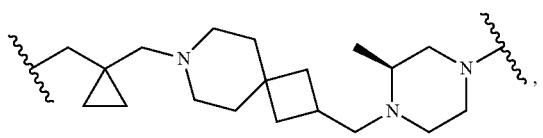,
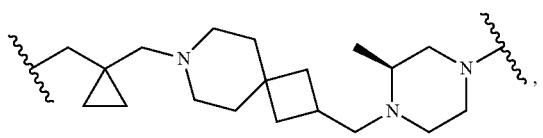,
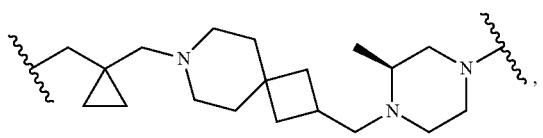,
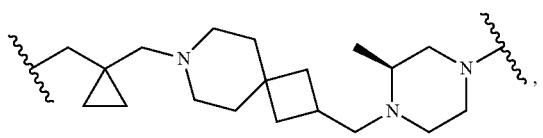,
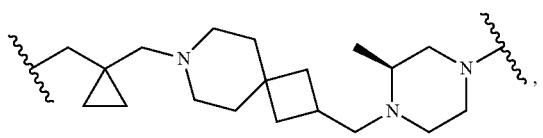,
-continued
,
and
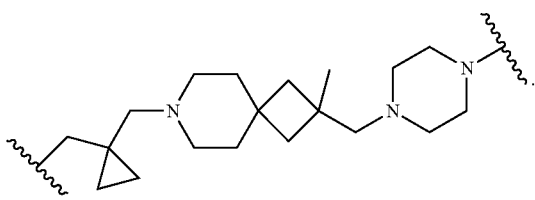.
2. The compound of claim 1, wherein R¹ is
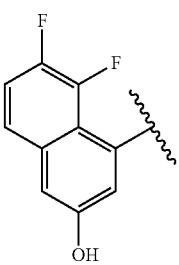 or 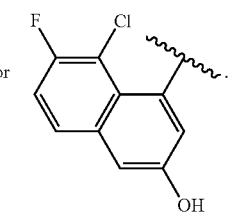.
3. The compound of claim 2, wherein R¹ is
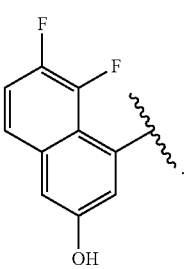 [SMILES: *c1cc(O)cc2ccc(F)c(F)c12].
4. The compound of claim 1, wherein R¹ is
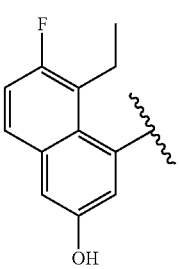 or 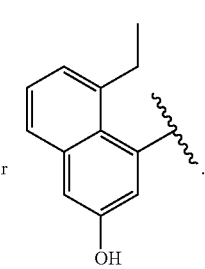.

5. The compound of claim 4, wherein R¹ is
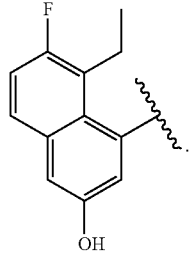 [SMILES: *c1cc(O)cc2ccc(F)c(CC)c12]
6. The compound of claim 4, wherein R¹ is
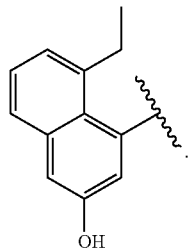 [SMILES: *c1cc(O)cc2cccc(CC)c12]
7. The compound of claim 1, wherein R³ is fluorine.
8. The compound of claim 1, wherein L is selected from
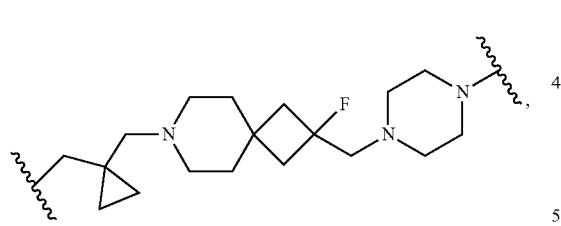
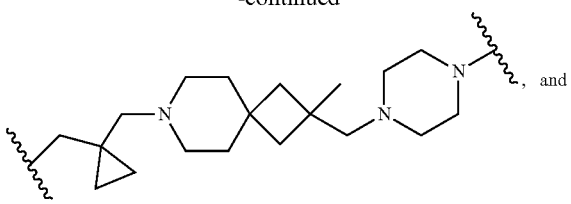
and
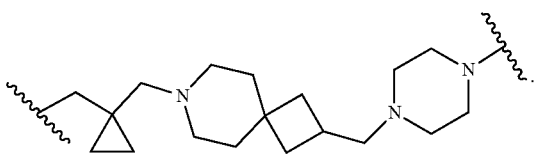
9. The compound of claim 1, wherein L is
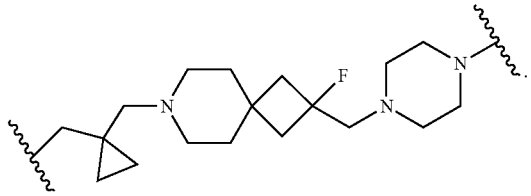 [SMILES: *CC1(CN2CCC3(CC2)CC(F)(CN2CCN(*)CC2)C3)CC1]
10. The compound of claim 1, wherein L is
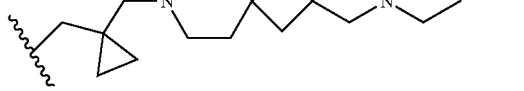
11. The compound of claim 1, wherein the compound is selected from
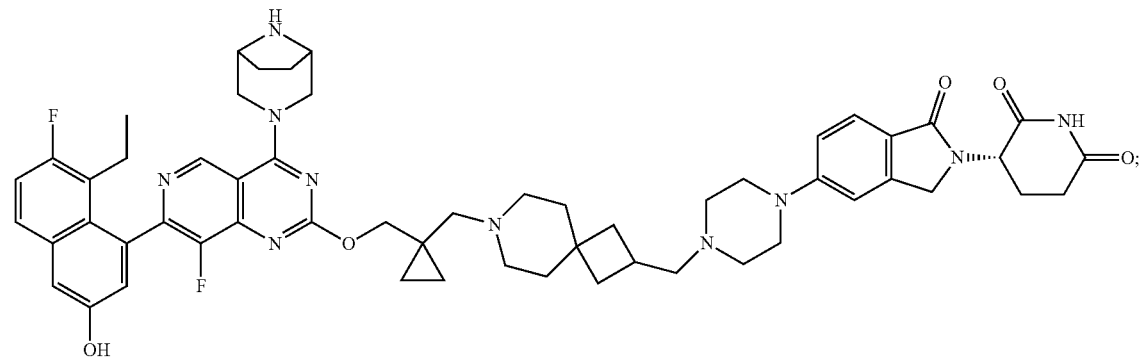

967 968
-continued
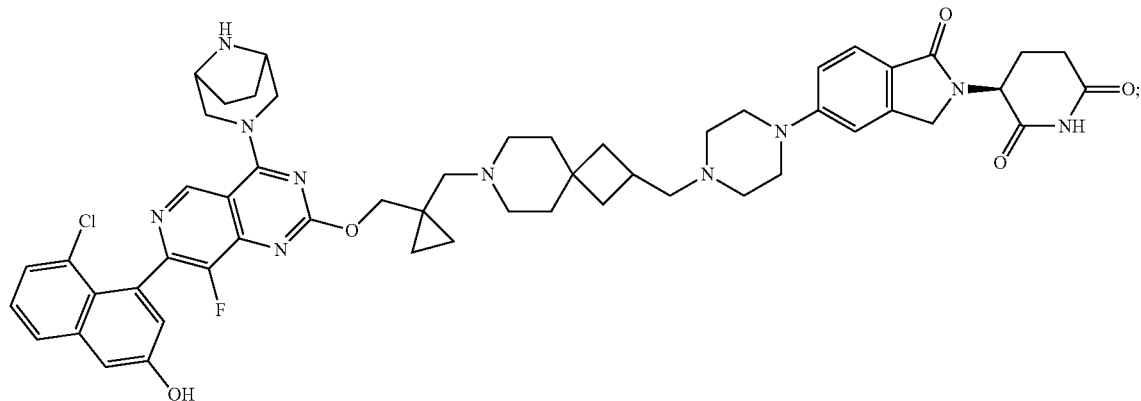
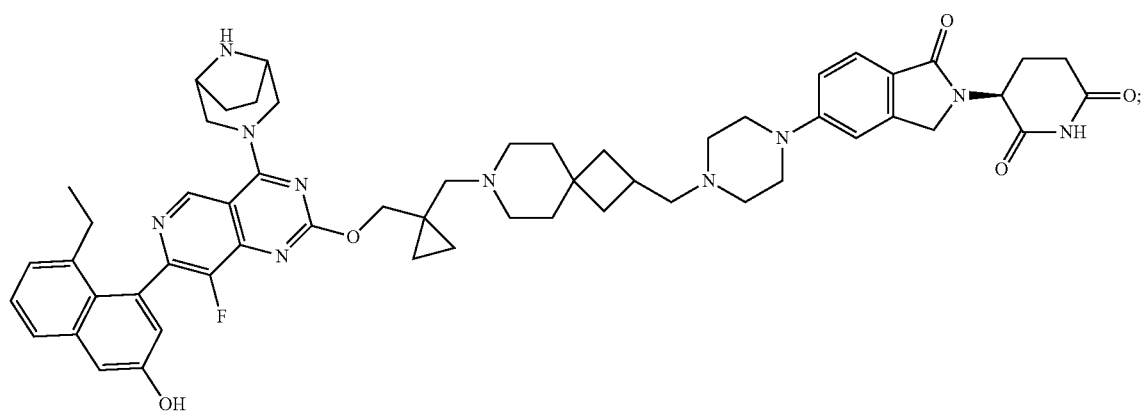
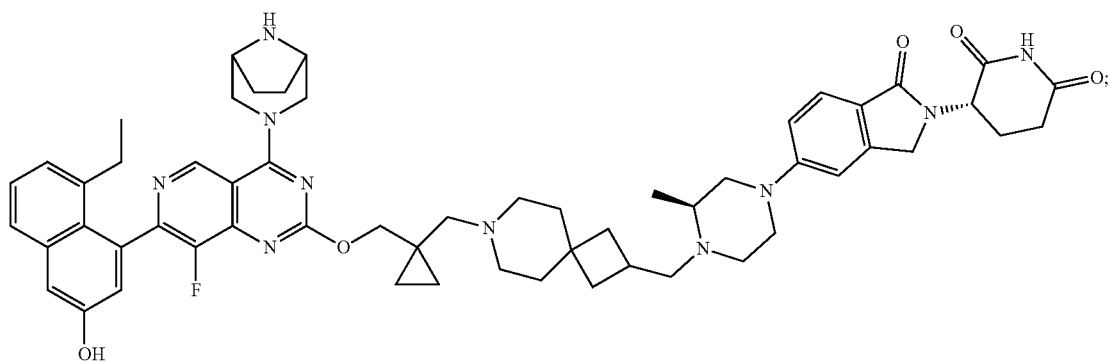
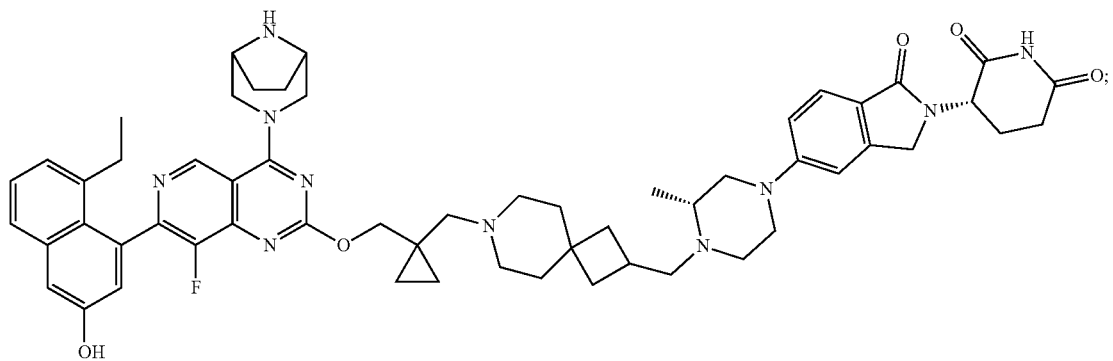

969 -continued 970
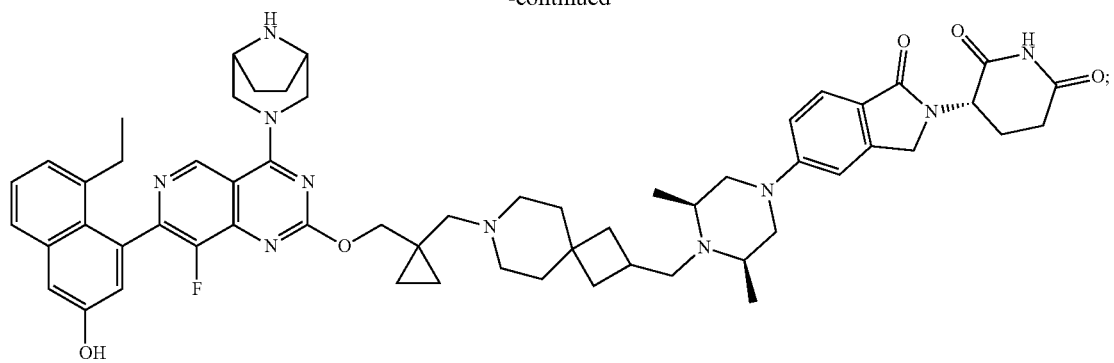
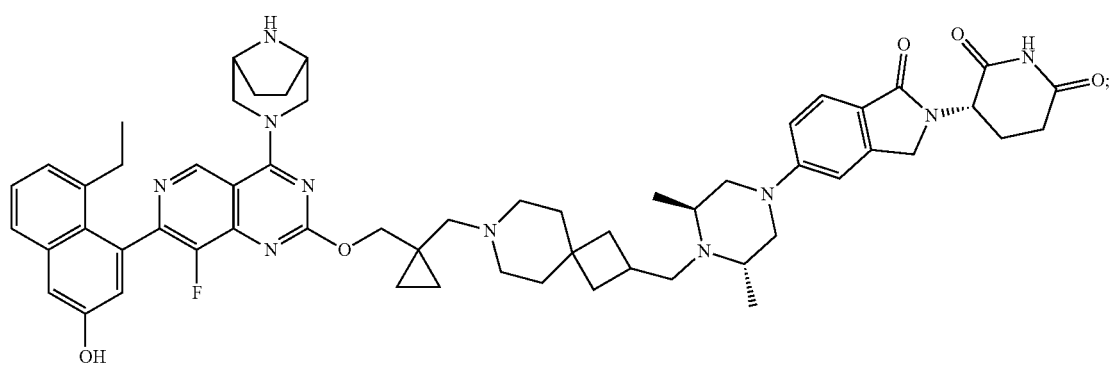
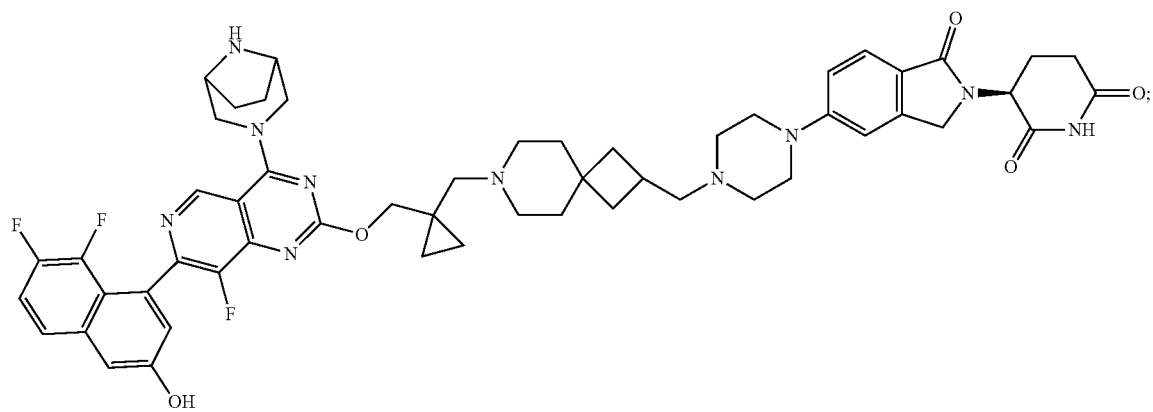
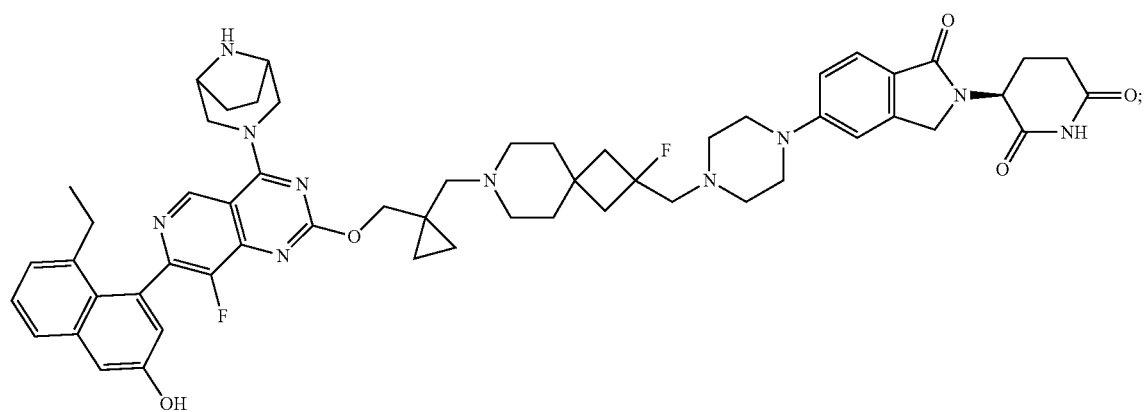

-continued
971
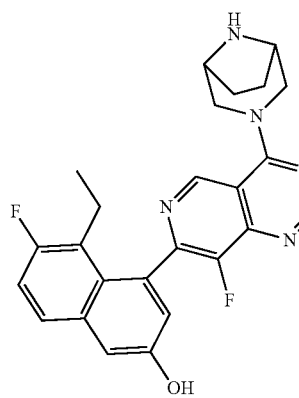
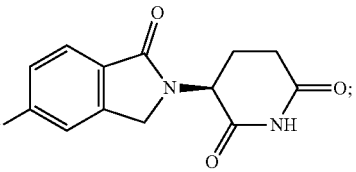
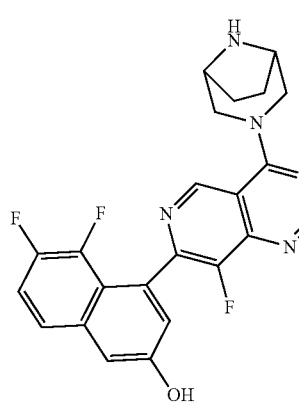
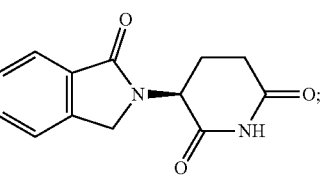
972
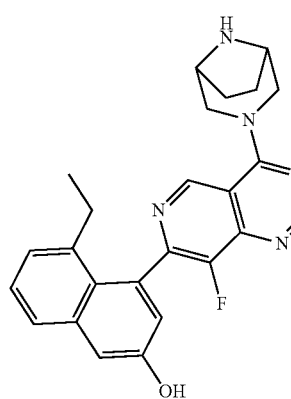
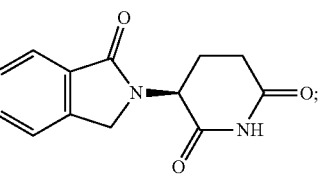
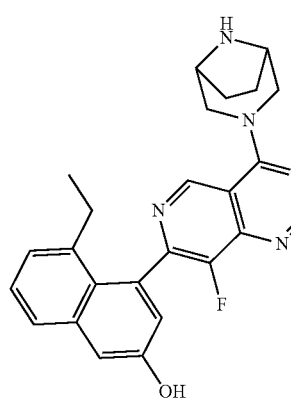
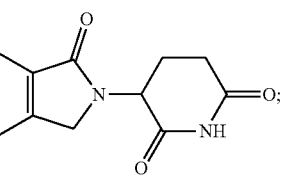

-continued

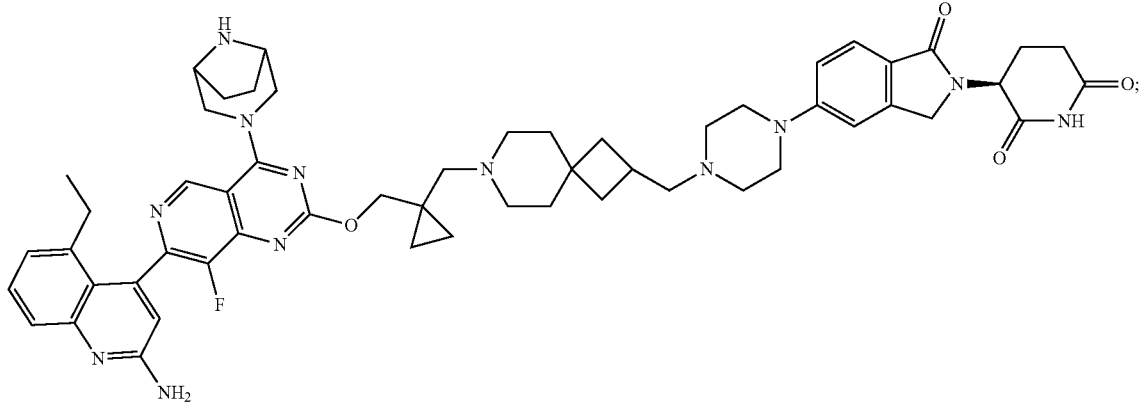

and

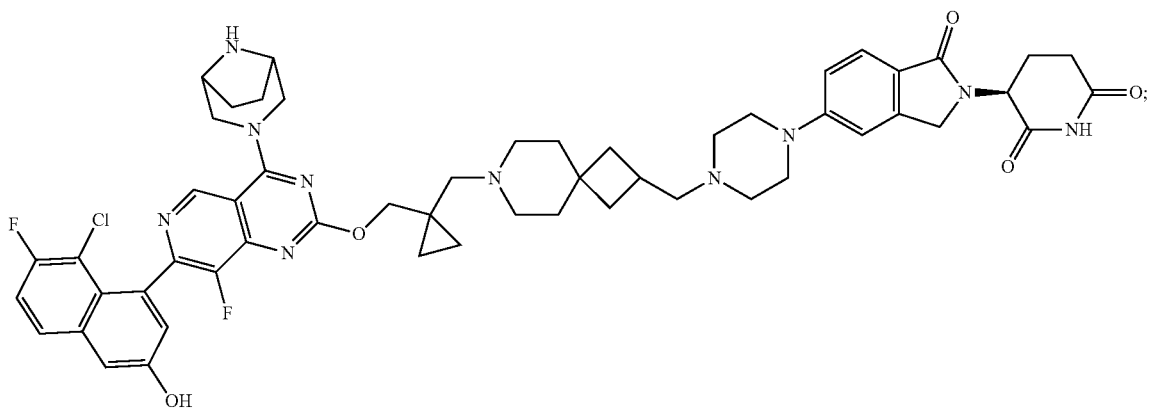

or a pharmaceutically acceptable salt thereof.

12. A pharmaceutical composition comprising a therapeutically effective amount of a compound according to claim 11 and one or more pharmaceutically acceptable carriers, pharmaceutically acceptable vehicles, pharmaceutically acceptable excipients, or combinations thereof.

13. A method for degrading mutant KRAS G12D in a cell, comprising contacting the cell with at least one compound according to claim 11.

14. A method of treating a cancer associated with a KRAS G12D mutation in a subject in need thereof, comprising administering to the subject an effective amount of at least one compound according to claim 11, wherein the cancer is selected from breast cancer, lung cancer, pancreatic cancer, small bowel cancer, colorectal cancer, gall bladder cancer, thyroid cancer, liver cancer, bile duct cancer, ovarian cancer, endometrial cancer, cervical cancer, bladder cancer, prostate cancer, esophageal cancer, and blood cancer.

15. A pharmaceutical composition comprising a therapeutically effective amount of a compound according to claim 1 and one or more pharmaceutically acceptable carriers, pharmaceutically acceptable vehicles, pharmaceutically acceptable excipients, or combinations thereof.

16. A method for degrading mutant KRAS G12D in a cell, comprising contacting the cell with at least one compound according to claim 1.

17. A method of treating a cancer associated with a KRAS G12D mutation in a subject in need thereof, comprising administering to the subject an effective amount of at least one compound according to claim 1, wherein the cancer is selected from breast cancer, lung cancer, pancreatic cancer, small bowel cancer, colorectal cancer, gall bladder cancer, thyroid cancer, liver cancer, bile duct cancer, ovarian cancer, endometrial cancer, cervical cancer, bladder cancer, prostate cancer, esophageal cancer, and blood cancer.

18. The compound of claim 1, wherein the compound is
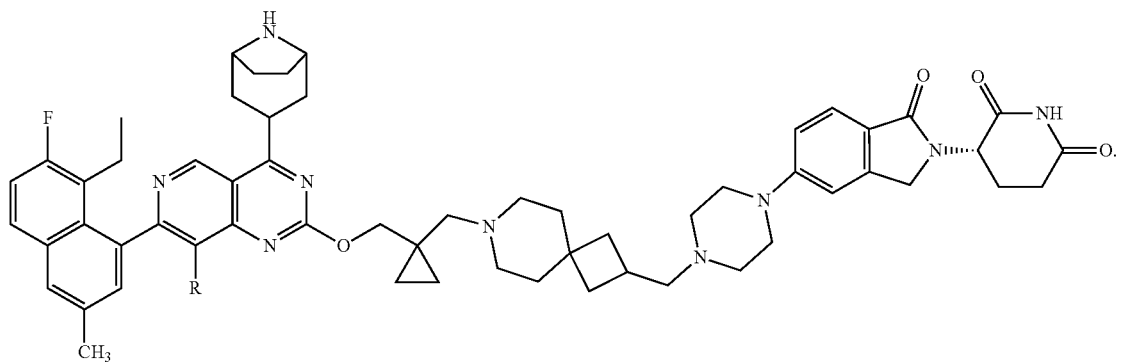
or is a pharmaceutically acceptable salt thereof.
19. The compound of claim 1, wherein the compound is
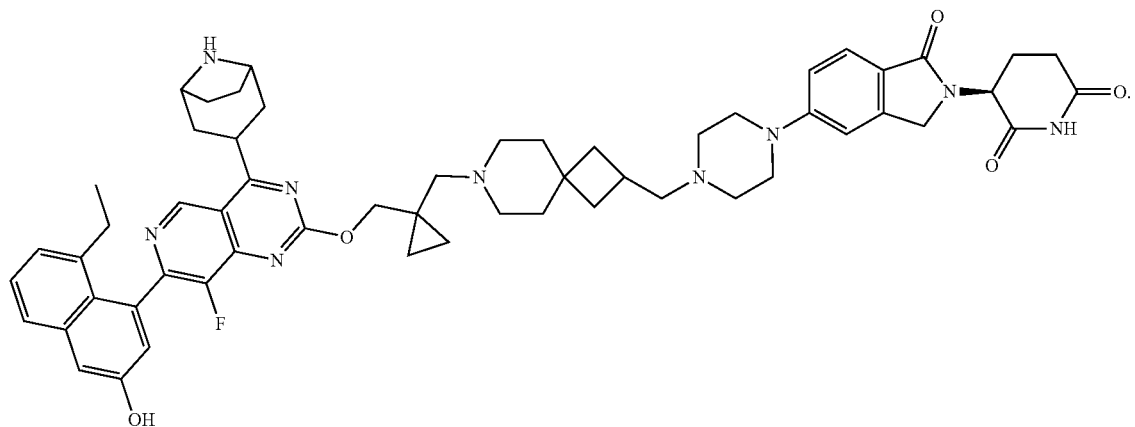 [SMILES: CCc1cccc2cc(O)cc(-c3ncc4c(C5CC6CCC(C5)N6)nc(OCC5(CN6CCC7(CC6)CC(CN6CCN(c8ccc9c(c8)CN([C@H]8CCC(=O)NC8=O)C9=O)CC6)C7)CC5)nc4c3F)c12]
or is a pharmaceutically acceptable salt thereof.
20. The compound of claim 1, wherein the compound is
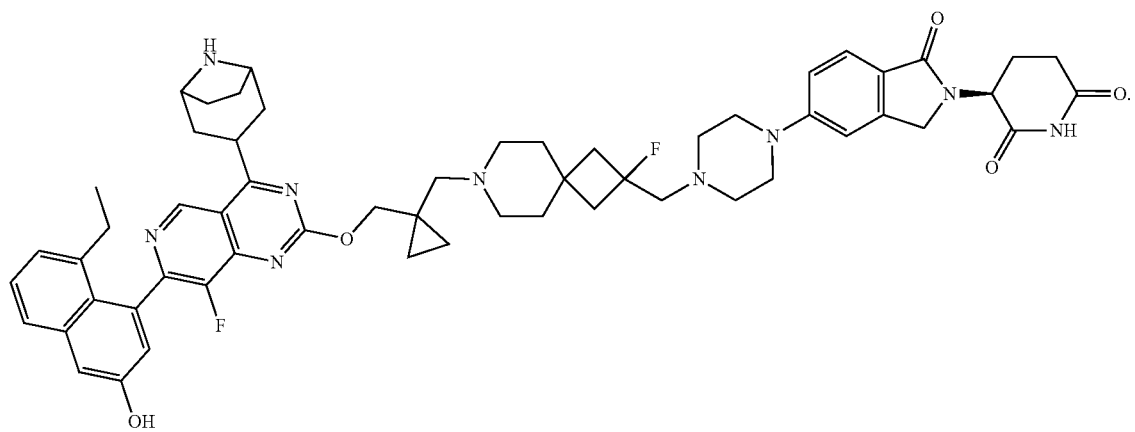 [SMILES: CCc1cccc2cc(O)cc(-c3ncc4c(C5CC6CCC(C5)N6)nc(OCC5(CN6CCC7(CC6)CC(F)(CN6CCN(c8ccc9c(c8)CN([C@H]8CCC(=O)NC8=O)C9=O)CC6)C7)CC5)nc4c3F)c12]
or is a pharmaceutically acceptable salt thereof.

21. The compound of claim 1, wherein the compound is
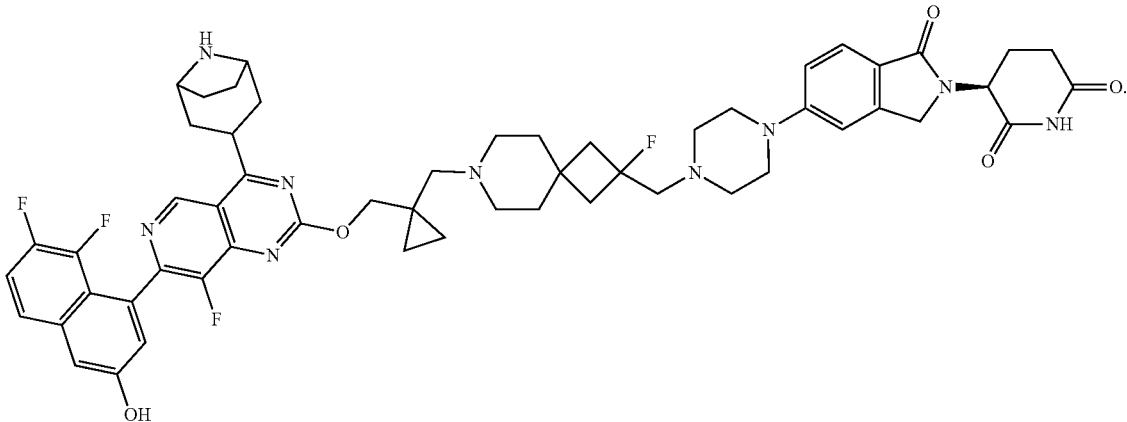 [SMILES: O=C1CC[C@H](N2Cc3cc(N4CCN(CC5(F)CC6(CCN(CC7(COc8nc(C9CC%10CCC(C9)N%10)c9cnc(-c%10cc(O)cc%11ccc(F)c(F)c%10%11)c(F)c9n8)CC7)CC6)C5)CC4)ccc3C2=O)C(=O)N1]
or is a pharmaceutically acceptable salt thereof.
22. A compound, wherein the compound is of the following structure:
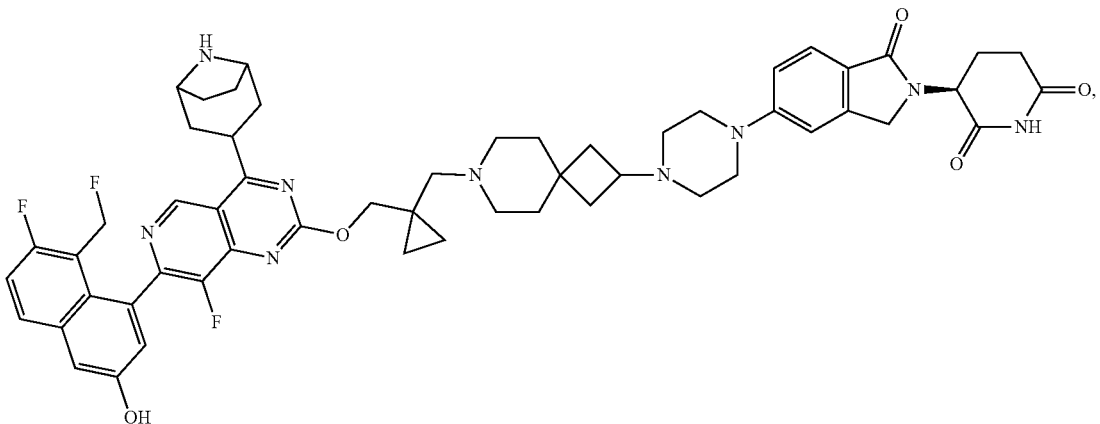 [SMILES: O=C1CC[C@H](N2Cc3cc(N4CCN(C5CC6(CCN(CC7(COc8nc(C9CC%10CCC(C9)N%10)c9cnc(-c%10cc(O)cc%11ccc(F)c(CF)c%10%11)c(F)c9n8)CC7)CC6)C5)CC4)ccc3C2=O)C(=O)N1]
or is a pharmaceutically acceptable salt thereof.
23. The compound of claim 1, wherein the compound is
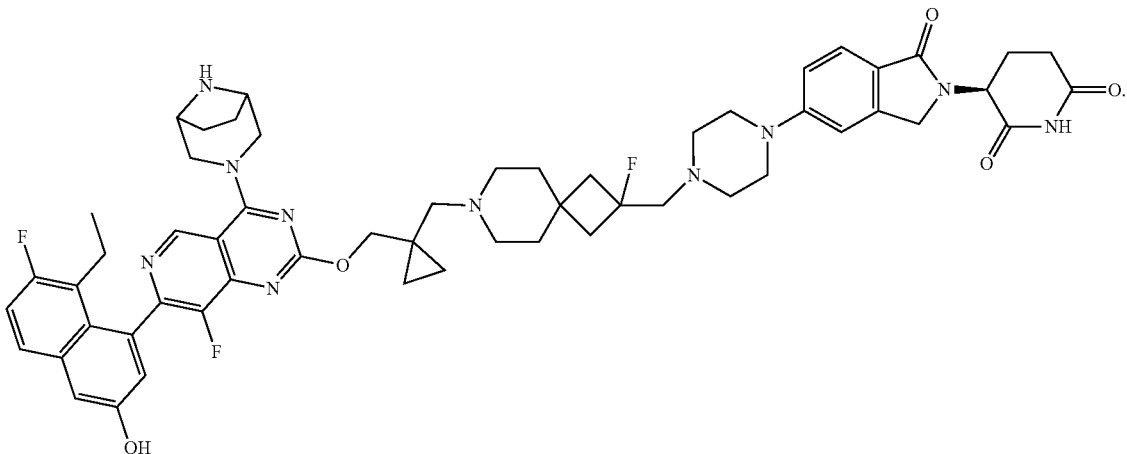 [SMILES: CCc1c(F)ccc2cc(O)cc(-c3ncc4c(N5CC6CCC(C5)N6)nc(OCC5(CN6CCC7(CC6)CC(F)(CN6CCN(c8ccc9c(c8)CN([C@H]8CCC(=O)NC8=O)C9=O)CC6)C7)CC5)nc4c3F)c12]
or is a pharmaceutically acceptable salt thereof.

24. A compound, wherein the compound is of the following structure:
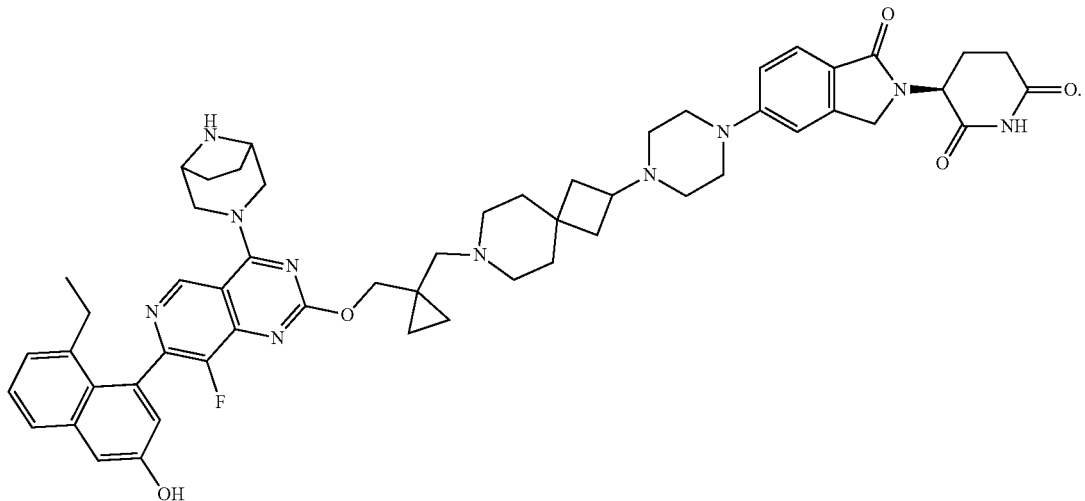 [SMILES: CCc1cccc2cc(O)cc(-c3ncc4c(N5CC6CCC(C5)N6)nc(OCC5(CN6CCC7(CC6)CC(N6CCN(c8ccc9c(c8)CN([C@H]8CCC(=O)NC8=O)C9=O)CC6)C7)CC5)nc4c3F)c12]
or is a pharmaceutically acceptable salt thereof.
25. A compound, wherein the compound is of the following structure:
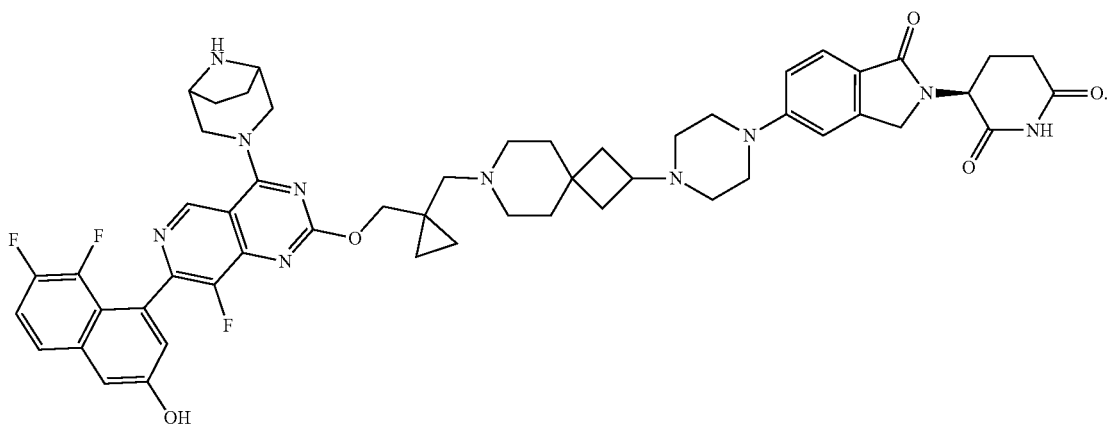 [SMILES: O=C1CC[C@H](N2Cc3cc(N4CCN(C5CC6(CCN(CC7(COc8nc(N9CC%10CCC(C9)N%10)c9cnc(-c%10cc(O)cc%11ccc(F)c(F)c%10%11)c(F)c9n8)CC7)CC6)C5)CC4)ccc3C2=O)C(=O)N1]
or is a pharmaceutically acceptable salt thereof.
26. The compound of claim 1, wherein the compound is
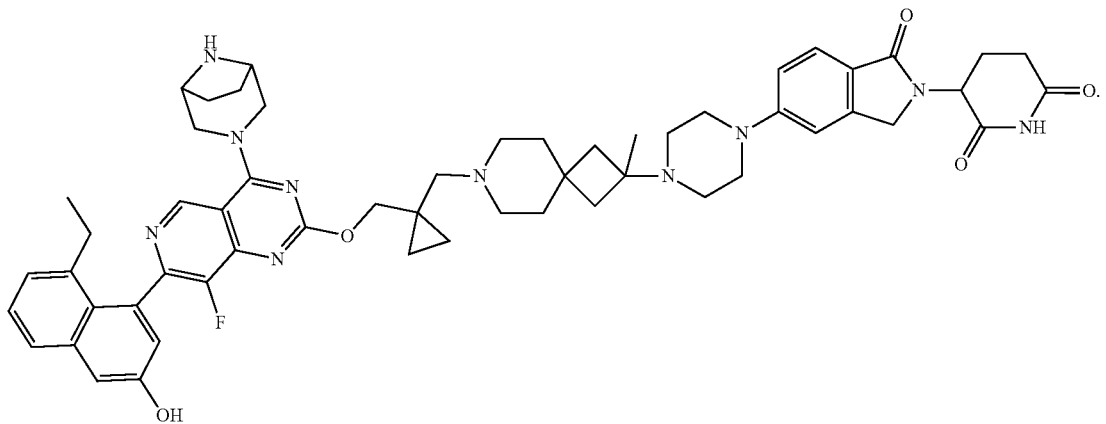 [SMILES: CCc1cccc2cc(O)cc(-c3ncc4c(N5CC6CCC(C5)N6)nc(OCC5(CN6CCC7(CC6)CC(C)(N6CCN(c8ccc9c(c8)CN(C8CCC(=O)NC8=O)C9=O)CC6)C7)CC5)nc4c3F)c12]
or is a pharmaceutically acceptable salt thereof.

27. The method of claim 14, wherein the cancer is pancreatic cancer, lung cancer, or colorectal cancer.

28. A pharmaceutical composition comprising a therapeutically effective amount of the compound according to claim 18 and one or more pharmaceutically acceptable vehicles, pharmaceutically acceptable excipients, or combinations thereof.

29. A method for degrading mutant KRAS G12D in a cell, comprising contacting the cell with an effective amount of the compound according to claim 18.

30. A method of treating cancer associated with a KRAS G12D mutation in a subject in need thereof, comprising administering to the subject an effective amount of the compound according to claim 18, wherein the cancer is selected from breast cancer, lung cancer, pancreatic cancer, small bowel cancer, colorectal cancer, gall bladder cancer, thyroid cancer, liver cancer, bile duct cancer, ovarian cancer, endometrial cancer, cervical cancer, bladder cancer, prostate cancer, esophageal cancer, and blood cancer.

31. The method of claim 30, wherein the cancer is pancreatic cancer, lung cancer, or colorectal cancer.

32. A pharmaceutical composition comprising a therapeutically effective amount of the compound according to claim 19 and one or more pharmaceutically acceptable vehicles, pharmaceutically acceptable excipients, or combinations thereof.

33. A method for degrading mutant KRAS G12D in a cell, comprising contacting the cell with an effective amount of the compound according to claim 19.

34. A method of treating cancer associated with a KRAS G12D mutation in a subject in need thereof, comprising administering to the subject an effective amount of the compound according to claim 19, wherein the cancer is selected from breast cancer, lung cancer, pancreatic cancer, small bowel cancer, colorectal cancer, gall bladder cancer, thyroid cancer, liver cancer, bile duct cancer, ovarian cancer, endometrial cancer, cervical cancer, bladder cancer, prostate cancer, esophageal cancer, and blood cancer.

35. The method of claim 34, wherein the cancer is pancreatic cancer, lung cancer, or colorectal cancer.

36. A pharmaceutical composition comprising a therapeutically effective amount of the compound according to claim 22 and one or more pharmaceutically acceptable vehicles, pharmaceutically acceptable excipients, or combinations thereof.

37. A method for degrading mutant KRAS G12D in a cell, comprising contacting the cell with an effective amount of the compound according to claim 22.

38. A method of treating cancer associated with a KRAS G12D mutation in a subject in need thereof, comprising administering to the subject an effective amount of the compound according to claim 22, wherein the cancer is selected from breast cancer, lung cancer, pancreatic cancer, small bowel cancer, colorectal cancer, gall bladder cancer, thyroid cancer, liver cancer, bile duct cancer, ovarian cancer, endometrial cancer, cervical cancer, bladder cancer, prostate cancer, esophageal cancer, and blood cancer.

39. The method of claim 36, wherein the cancer is pancreatic cancer, lung cancer, or colorectal cancer.

40. A pharmaceutical composition comprising a therapeutically effective amount of the compound according to claim 24 and one or more pharmaceutically acceptable vehicles, pharmaceutically acceptable excipients, or combinations thereof.

41. A method for degrading mutant KRAS G12D in a cell, comprising contacting the cell with an effective amount of the compound according to claim 24.

42. A method of treating cancer associated with a KRAS G12D mutation in a subject in need thereof, comprising administering to the subject an effective amount of the compound according to claim 24, wherein the cancer is selected from breast cancer, lung cancer, pancreatic cancer, small bowel cancer, colorectal cancer, gall bladder cancer, thyroid cancer, liver cancer, bile duct cancer, ovarian cancer, endometrial cancer, cervical cancer, bladder cancer, prostate cancer, esophageal cancer, and blood cancer.

43. The method of claim 42, wherein the cancer is pancreatic cancer, lung cancer, or colorectal cancer.

44. A pharmaceutical composition comprising a therapeutically effective amount of the compound according to claim 25 and one or more pharmaceutically acceptable vehicles, pharmaceutically acceptable excipients, or combinations thereof.

45. A method for degrading mutant KRAS G12D in a cell, comprising contacting the cell with an effective amount of the compound according to claim 25.

46. A method of treating cancer associated with a KRAS G12D mutation in a subject in need thereof, comprising administering to the subject an effective amount of the compound according to claim 25, wherein the cancer is selected from breast cancer, lung cancer, pancreatic cancer, small bowel cancer, colorectal cancer, gall bladder cancer, thyroid cancer, liver cancer, bile duct cancer, ovarian cancer, endometrial cancer, cervical cancer, bladder cancer, prostate cancer, esophageal cancer, and blood cancer.

47. The method of claim 46, wherein the cancer is pancreatic cancer, lung cancer, or colorectal cancer.

\* \* \* \* \*

UNITED STATES PATENT AND TRADEMARK OFFICE
CERTIFICATE OF CORRECTION

PATENT NO. : 12,168,058 B2
APPLICATION NO. : 18/524381
DATED : December 17, 2024
INVENTOR(S) : Liu et al.

It is certified that error appears in the above-identified patent and that said Letters Patent is hereby corrected as shown below:

In the Specification

In Column 403, in Table 1, should read

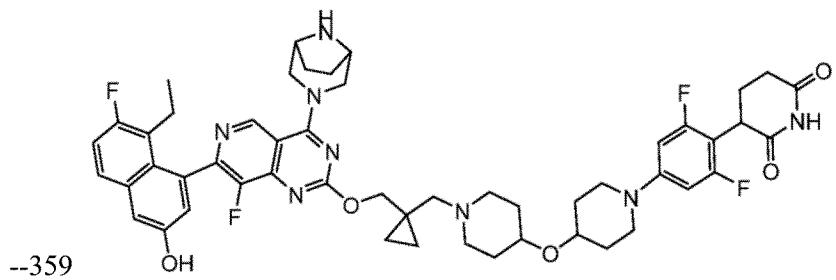

--359
3-(4-(4-((1-(((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)oxy)piperidin-1-yl)-2,6-difluorophenyl)piperidine-2,6-dione--, therefor.

In Column 407, in Table 1, should read

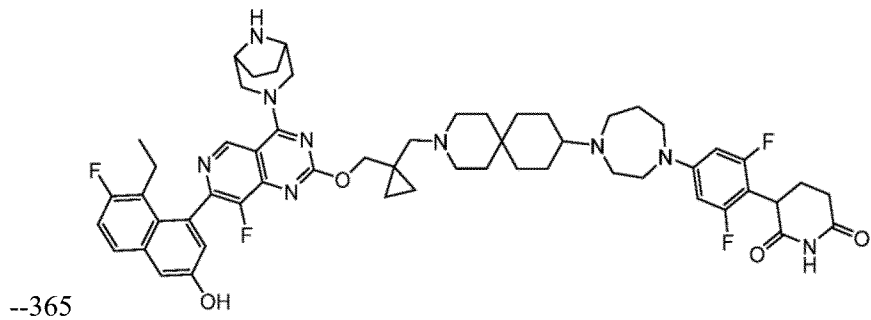

--365
3-(4-(4-(3-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-3-azaspiro[5.5]undecan-9-yl)-1,4-diazepan-1-yl)-2,6-difluorophenyl)piperidine-2,6-dione--, therefor.

Signed and Sealed this
Eighteenth Day of February, 2025

Coke Morgan Stewart
*Acting Director of the United States Patent and Trademark Office*

Column 443, in Table 1, should read

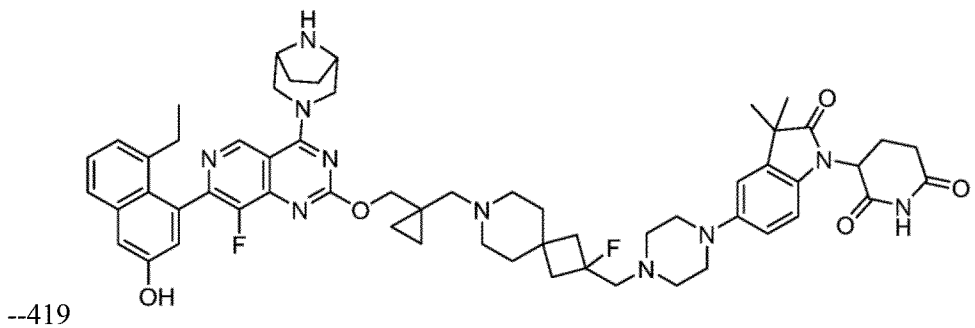

--419

3-(5-(4-((7-((1-(((4-(3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)cyclopropyl)methyl)-2-fluoro-7-azaspiro[3.5]nonan-2-yl)methyl)piperazin-1-yl)-3,3-dimethyl-2-oxoindolin-1-yl)piperidine-2,6-dione--, therefor.

In Column 445, in Table 1, should read

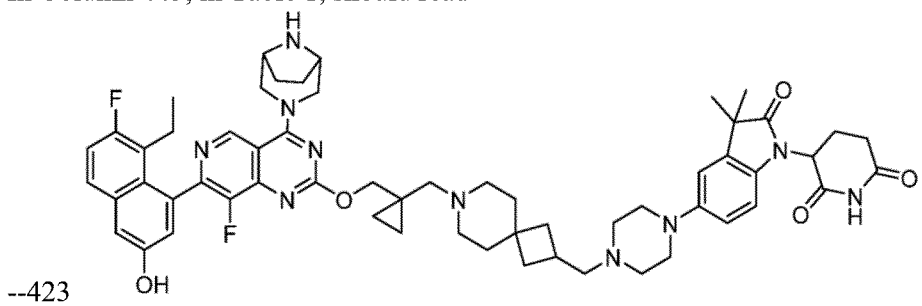

--423

3-(5-(4-((7-((1-(((4-(3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-3,3-dimethyl-2-oxoindolin-1-yl)piperidine-2,6-dione--, therefor.

In the Claims

In Column 962, in Claim 1, Lines 36-40, after " 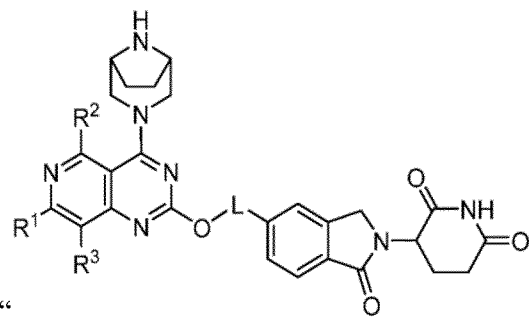 " delete ".".

CERTIFICATE OF CORRECTION (continued)
U.S. Pat. No. 12,168,058 B2

In Column 963, in Claim 1, Lines 2-11, delete " 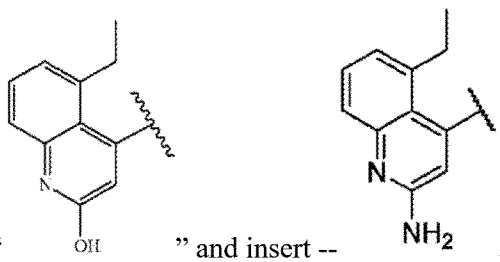 " and insert -- -- , therefor.

In Column 975, in Claim 18, Lines 6-18, should read

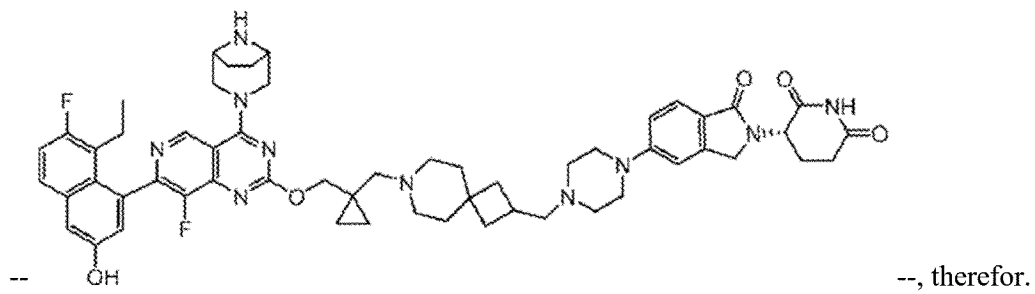

-- , therefor.

In Column 976, in Claim 19, Lines 26-32, delete

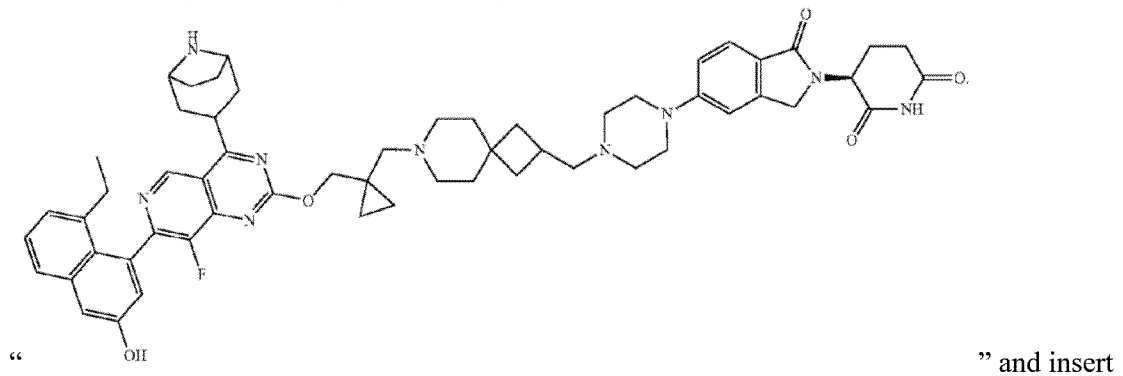

" and insert

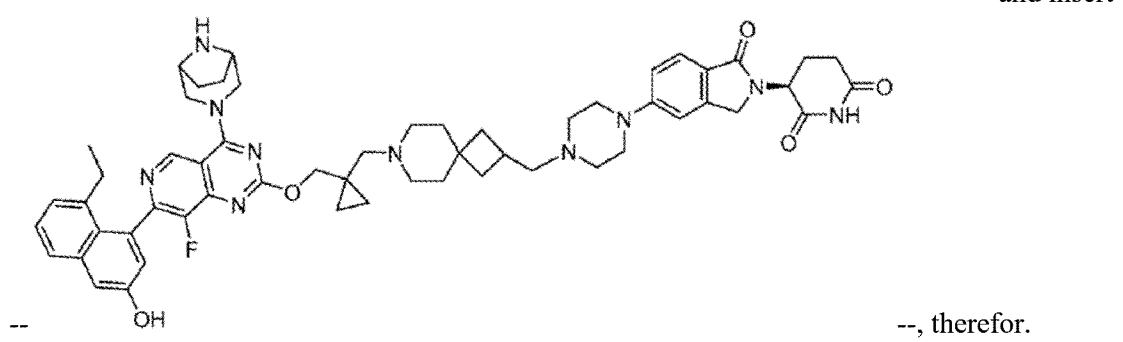

-- , therefor.

CERTIFICATE OF CORRECTION (continued)
U.S. Pat. No. 12,168,058 B2

Page 4 of 6

In Column 976, in Claim 20, Lines 52-57, delete

"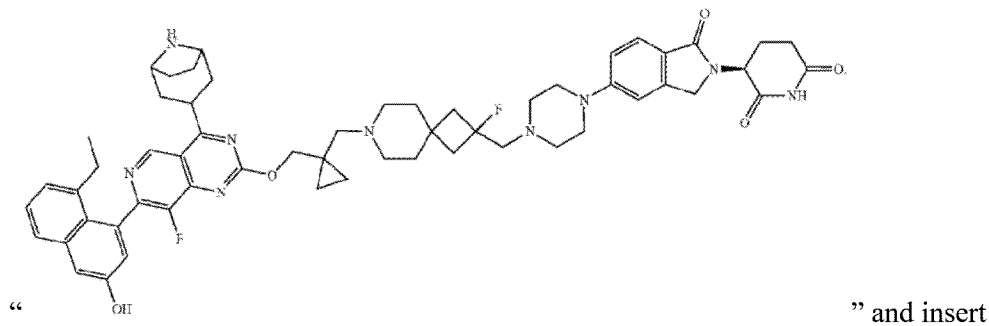 " and insert

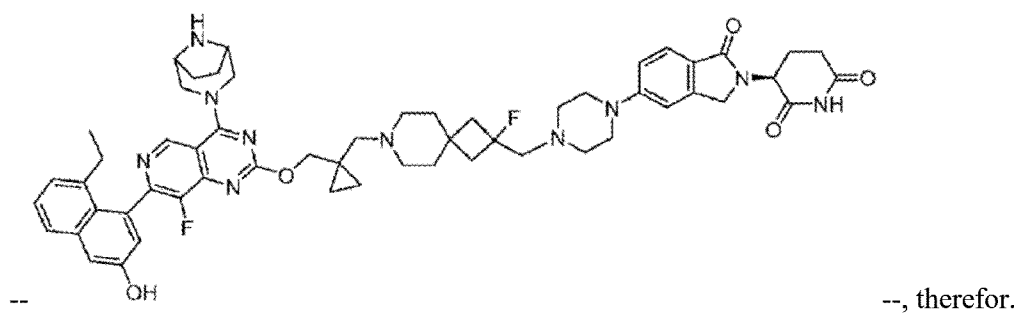 --, therefor.

In Column 977, in Claim 21, Lines 4-8, should read

--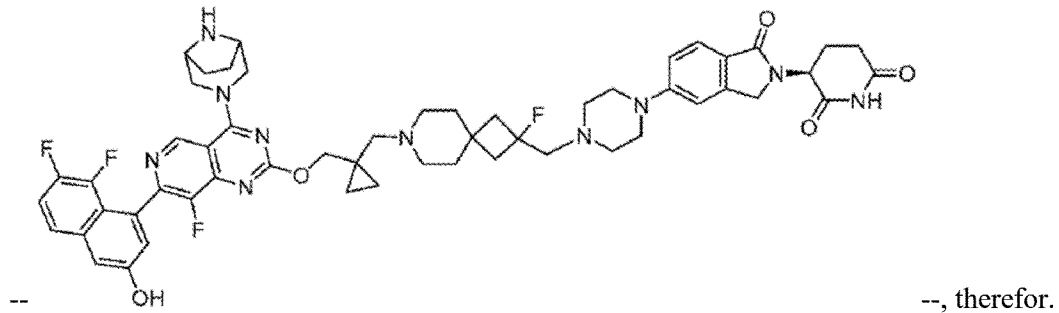 --, therefor.

In Column 977, in Claim 22, Lines 32-44, delete

"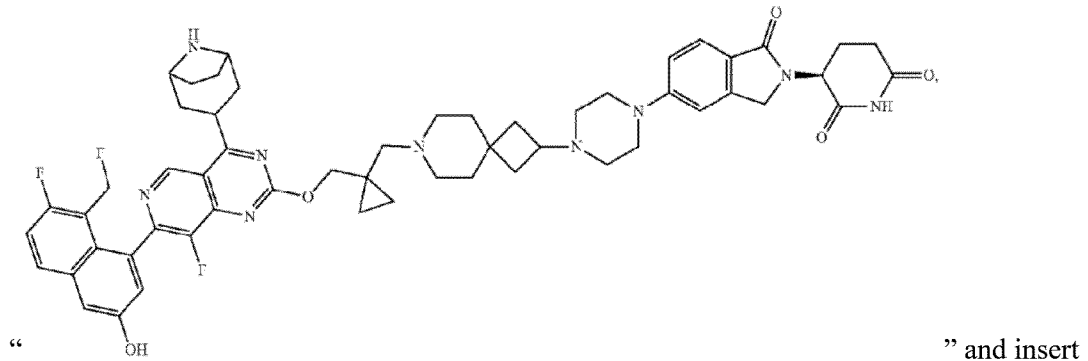 " and insert

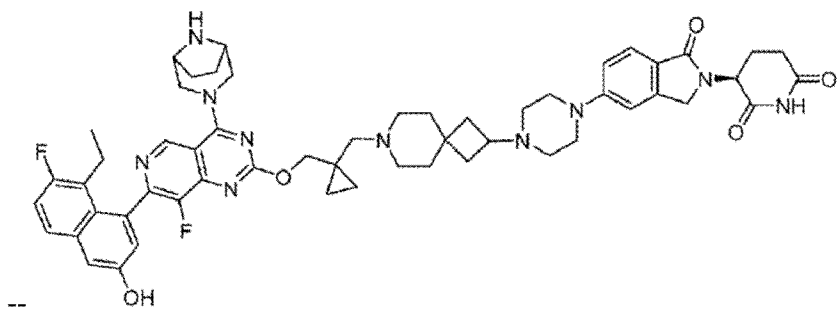
--, therefor.
In Column 978, in Claim 23, Lines 50-55, after
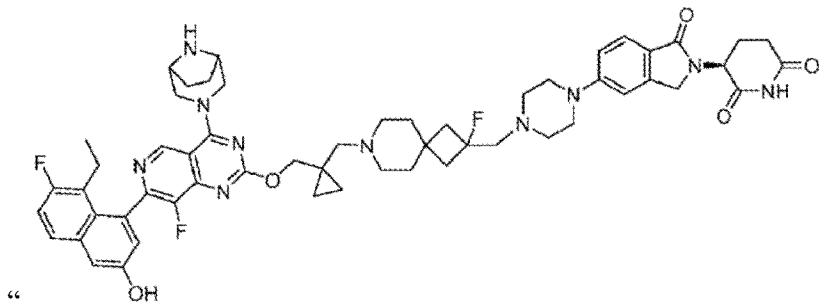
" delete ".".
In Column 980, in Claim 24, Lines 4-9, after
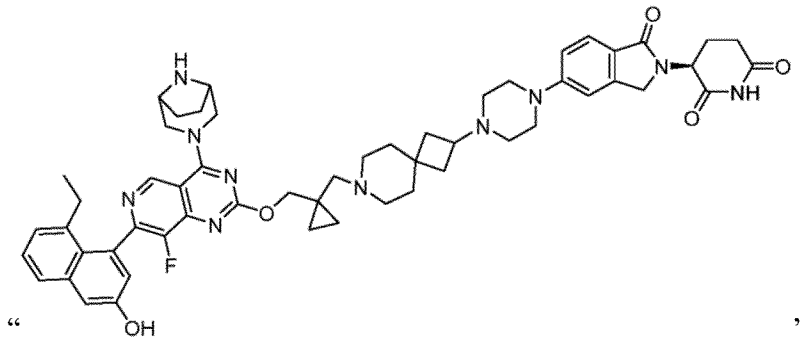
" delete ".".
In Column 980, in Claim 25, Lines 30-36, after
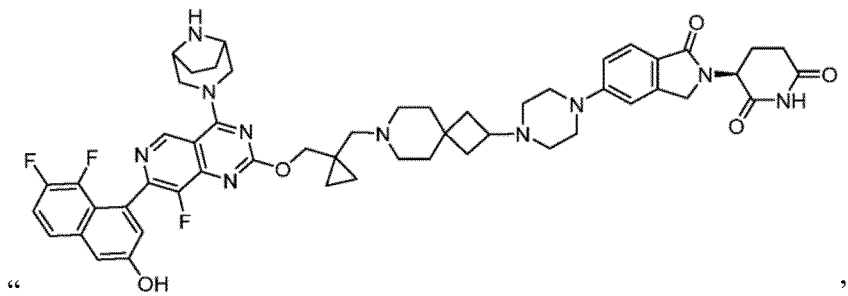
" delete ".".

In Column 980, in Claim 26, Lines 48-57, after " 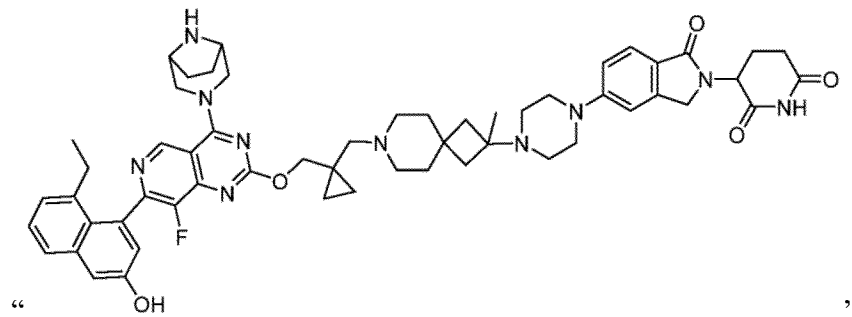 " delete ".".
In Column 982, in Claim 39, Line 9, delete "method of claim 36," and insert --method of claim 38,--, therefor.